US012269818B2

(12) United States Patent
Clark et al.

(10) Patent No.: US 12,269,818 B2
(45) **Date of Patent: *Apr. 8, 2025**

(54) ANALOGS OF XANOMELINE

(71) Applicant: Terran Biosciences Inc., New York, NY (US)

(72) Inventors: Samuel Clark, Miami, FL (US); Matthew Duncton, Las Vegas, NV (US)

(73) Assignee: Terran Biosciences Inc., Miami Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,450

(22) Filed: Feb. 16, 2024

(65) Prior Publication Data

US 2024/0368149 A1 Nov. 7, 2024

Related U.S. Application Data

(60) Provisional application No. 63/523,619, filed on Jun. 27, 2023, provisional application No. 63/461,543, filed on Apr. 24, 2023.

(51) Int. Cl.
*C07D 417/04* (2006.01)

(52) U.S. Cl.
CPC .................................. *C07D 417/04* (2013.01)

(58) Field of Classification Search
CPC .................................................... C07D 417/04
See application file for complete search history.

(56) References Cited

U.S. PATENT DOCUMENTS

| | | | |
|---|---|---|---|
| 5,043,345 A | 8/1991 | Sauerberg et al. | |
| 5,545,638 A | 8/1996 | Greenwood | |
| 5,750,541 A | 5/1998 | Bymaster et al. | |
| 6,043,258 A | 3/2000 | Bymaster et al. | |
| 6,083,957 A | 7/2000 | Olesen et al. | |
| 9,670,200 B2 | 6/2017 | Almarsson et al. | |
| 10,265,311 B2 | 4/2019 | Elenko et al. | |
| 10,933,020 B2 | 3/2021 | Betancourt et al. | |
| 2020/0323839 A1 | 10/2020 | Elenko et al. | |
| 2021/0145810 A1 | 5/2021 | Monn et al. | |
| 2022/0144817 A1* | 5/2022 | Bennett .................. | A61K 31/46 |

FOREIGN PATENT DOCUMENTS

| | | | |
|---|---|---|---|
| WO | WO-9429303 | A1 | 12/1994 |
| WO | WO-2020172516 | A1 | 8/2020 |
| WO | WO-2022052936 | A1 | 3/2022 |
| WO | WO-2022182733 | A1 | 9/2022 |
| WO | WO-2024226691 | A1 | 10/2024 |

OTHER PUBLICATIONS

Albert, D.H., et al.; "Ex vivo inhibition of beta-thromboglobulin release following administration to man of ABT-299, a novel prodrug of a potent platelet activating factor antagonist," Inflammation Research; 46(7):272-277 (1997).

Kane, B.E., et al.; "Synthesis and evaluation of xanomeline analogs—probing the wash-resistant phenomenon at the M1 muscarinic acetylcholine receptor," Bioorg Med Chem .; 16(3):1376-1392 (2008).

Maspero, M., et al.; "Tacrine-xanomeline and tacrine-iperoxo hybrid ligands: Synthesis and biological evaluation at acetylcholinesterase and M1 muscarinic acetylcholine receptors," Bioorganic Chemistry, 96:103633, pp. 1-13; doi: 10.1016/j.bioorg.2020.103633 (2020).

Matera, C., et al.; "Novel Xanomeline-Containing Bitopic Ligands of Muscarinic Acetylcholine Receptors: Design, Synthesis and FRET Investigation," Molecules, 28(5):2407, pp. 1-24, doi: 10.3390/molecules28052407 (2023).

Pubchem SID 272884427: 1,2,5,6-Tetrahydro-1-methyl-3-[4-hexyloxy-1,2,5-thiadiazole-3- yllpyridine 1-oxide. Pubchem Deposit Date: Dec. 15, 2015 [retrieved online Sep. 4, 2024] URL: https://pubchem.ncbi.nlm.nih.gov/substance/272884427; 3 pages.

Ring, B.J., et al.; "Flavin-containing monooxygenase-mediated N-oxidation of the M(1)-muscarinic agonist xanomeline," Drug Metabolism and Disposition, 27(10): 1099-1103 (1999).

Sauerberg, P., et al.; "Novel functional M1 selective muscarinic agonists. Synthesis and structure-activity relationships of 3-(1,2,5-thiadiazolyl)-1,2,5,6-tetrahydro-1-methylpyridines," Journal of Medicinal Chemistry, 35(12):2274-2283 (1992).

Sunagawa, M., et al.; "New anti-MRSA and anti-VRE carbapenems; synthesis and structure-activity relationships of 1beta-methyl-2-(thiazol-2-ylthio)carbapenems," The Journal of Antibiotics (Tokyo), 55(8):722-757; doi: 10.7164/antibiotics.55.722 (2002).

Volpato, D.; "Bitopic Ligands and their molecular fragments for the study of the M1 Muscarinic Receptor," University of Wuerzburg, Thesis; 285 pages [retrieved online Sep. 4, 2024]URL: https://opus.bibliothek.uni-wuerzburg.de/opus4-wuerzburg/frontdoor/deliver/index/docld/24881/file/PhD_Thesis_Daniela_Volpato.pdf (2021).

* cited by examiner

*Primary Examiner* — Rebecca L Anderson
(74) *Attorney, Agent, or Firm* — COOLEY LLP; Heidi A. Erlacher; Eric A. Owens

(57) ABSTRACT

Disclosed herein are xanomeline analogs, as well as methods for making and using the analogs to, for example, treat neuropsychiatric disorders.

42 Claims, 98 Drawing Sheets

ANALOGS OF XANOMELINE

CROSS-REFERENCE TO RELATED APPLICATIONS

This application claims priority to U.S. Provisional Application No. 63/523,619, filed on Jun. 27, 2023 and U.S. Provisional Application No. 63/461,543, filed on Apr. 24, 2023, which are incorporated herein by reference in their entirety.

FIELD OF THE INVENTION

The present disclosure relates to analogs of xanomeline including analogs intended to act as prodrugs of xanomeline and methods for using such analogs to treat neuropsychiatric disorders.

BACKGROUND OF THE INVENTION

Schizophrenia and related neuropsychiatric diseases are among the leading causes of disability worldwide. Despite recent advances, there remains a need for new therapeutics to support treatment of debilitating neuropsychiatric diseases such as schizophrenia.

Recently, xanomeline has received renewed interest for the treatment of schizophrenia and other disorders. Disclosed herein are analogs and prodrugs of xanomeline with improved properties and potential combinations with trospium or combinations with analogs of trospium or combinations with prodrugs of trospium.

BRIEF SUMMARY OF THE INVENTION

Disclosed herein are analogs of xanomeline, such as a compound of Formula (Ia), Formula (Ia):

(Ia)

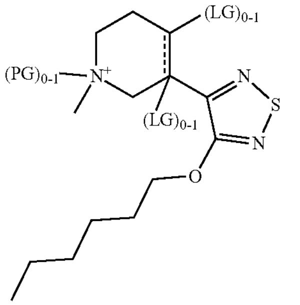

(Ia) Wherein PG is an optional progroup that forms an N-oxide, or has the formula —$(CR^1R^2)$—$OR^3$; LG is an optional leaving group, provided that only one LG is present in Formula (Ia). Also disclosed are methods for using the disclosed xanomeline analogs, such as in a method for treating a neuropsychiatric disorder.

The foregoing and other objects, features, and advantages of the invention will become more apparent from the following detailed description, with reference to the accompanying figures.

DETAILED DESCRIPTION

I. Terms

Figure 1:
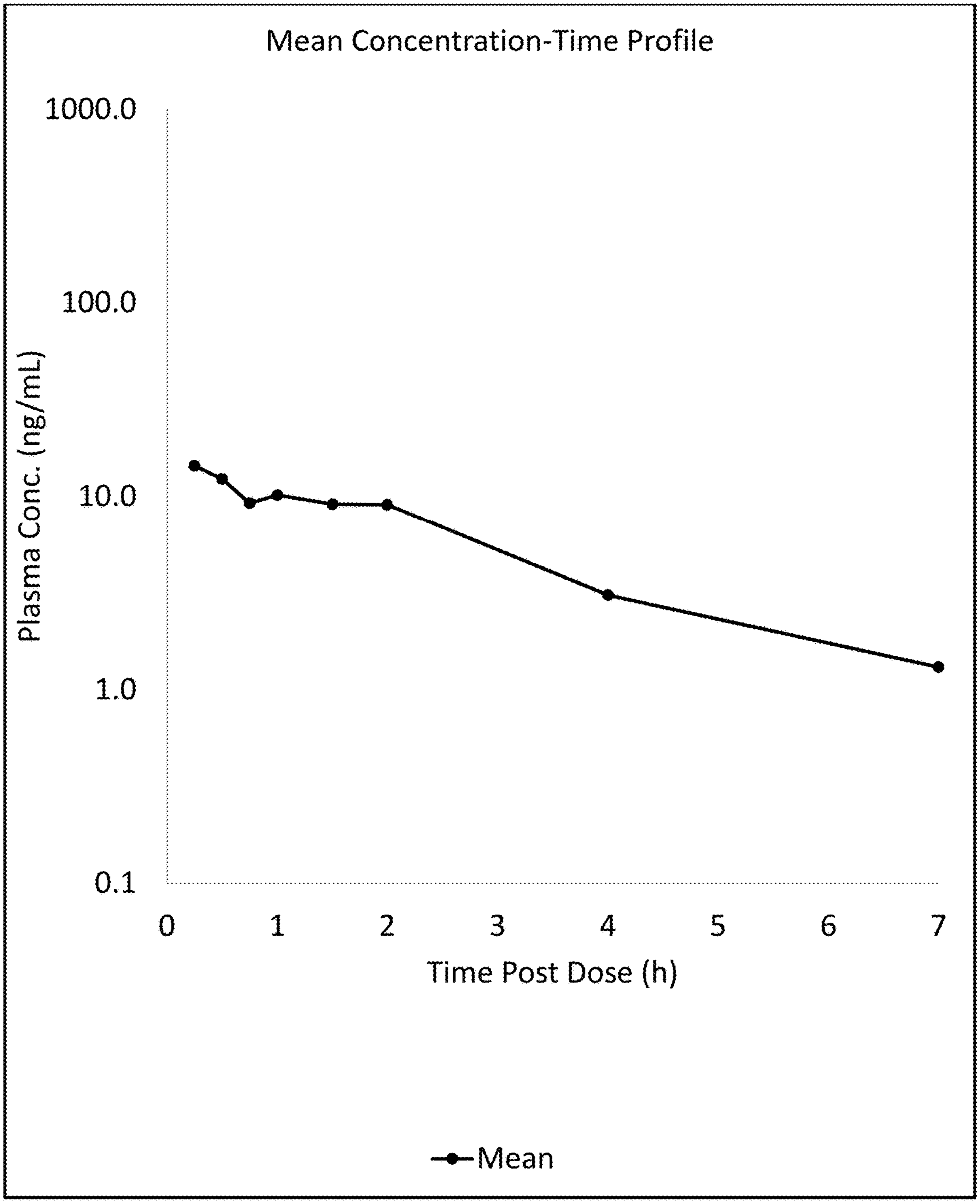
FIG. 1 shows mean concentration-time profiles of xanomeline following SC dosing of xanomeline (1 mg/kg of xanomeline) to male Sprague Dawley (SD) rats.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

"Administering" refers to any suitable mode of administration, including, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Subject" refers to an animal, such as a mammal, including, but not limited to, primates (e.g., humans), cows, sheep, goats, horses, dogs, cats, rabbits, rats, mice and the like. In certain embodiments, the subject is a human subject.

"Therapeutically effective amount" or "therapeutically sufficient amount" or "effective or sufficient amount" refers to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

"Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

"Combination therapy" refers to a method of treating a disease or disorder, wherein two or more different pharmaceutical agents are administered in overlapping regimens so that the subject is simultaneously exposed to both agents. For example, the compounds of the invention can be used in combination with other pharmaceutically active compounds. The compounds of the invention can be administered simultaneously (as a single preparation or separate preparation) or sequentially to the other drug therapy. In general, a combination therapy envisions administration of two or more drugs during a single cycle or course of therapy.

"Neurotrophic factors" refers to a family of soluble peptides or proteins which support the survival, growth, and differentiation of developing and mature neurons.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT2_A$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an ECso with respect to $5HT_{2A}$ activity of no more than about 100 mM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

"Composition" refers to a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention. "Xanomeline" refers to the compound 3-(4-hexyloxy-1,2,5-thiadiazol-3-yl)-1-methyl-5,6-dihydro-2H-pyridine, or 3-(hexyloxy)-4-(1-methyl-1,2,5,6-tetrahydropyridin-3-yl)-1,2,5-thiadiazole. The compound may also be referred to as hexyloxy-TZTP, LY-246,708, LY-246708, Lumeron, Memcor, NNC 11-0232, or Kar-XT.

Xanomeline has the formula:

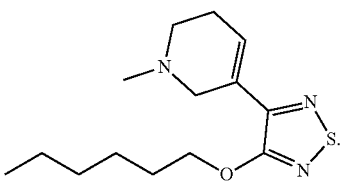 [SMILES: CCCCCCOc1nsnc1C1=CCCN(C)C1]

Compounds herein can include all stereoisomers, enantiomers, diastereomers, mixtures, racemates, atropisomers, and tautomers thereof.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocycloalkyl groups, heteroaryl groups, cycloalkyl groups, acyl groups, acyloxy groups, carbamate groups, amide groups, ureido groups, epoxy groups, and ester groups.

Non-limiting examples of alkyl groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Alkyl groups can include branched and unbranched alkyl groups. Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxyethyl, 1,2-difluoroethyl, and 3-carboxypropyl.

Non-limiting examples of cycloalkyl groups include cyclopropyl, cyclobutyl, cyclopentyl, cyclohexyl, cycloheptyl, and cyclooctyl groups. Cycloalkyl groups also include fused-, bridged-, and spiro-bicycles and higher fused-, bridged-, and spiro-systems. A cycloalkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl groups include straight, branched, and cyclic alkenyl groups. The olefin or olefins of an alkenyl group can be, for example, E, Z, cis, trans, terminal, or exo-methylene. An alkenyl group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl groups include straight, branched, and cyclic alkynyl groups. The triple bond of an alkynyl group can be internal or terminal. An alkynyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinimide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

The term "acyl" refers to the groups HC(O)—, alkyl-C(O)—, cycloalkyl-C(O)—, cycloalkenyl-C(O)—, aryl-C(O)—, heteroaryl-C(O)— and heterocyclyl-C(O)— where alkyl, cycloalkyl, cycloalkenyl, aryl, heteroaryl, and heterocyclyl are as described herein. By way of example acyl groups include acetyl and benzoyl groups.

"Alkyl" refers to an optionally substituted straight-chain, or optionally substituted branched-chain saturated hydrocarbon having from one to about ten carbon atoms, or from one to six carbon atoms, wherein an $sp^3$-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl, and hexyl, and longer alkyl groups, such as heptyl, octyl, and the like. Whenever it appears herein, a numerical range such as "$C_{1-6}$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{2-20}$ alkyl, $C_{7-15}$ alkyl, $C_{1-10}$ alkyl, a $C_{1-9}$ alkyl, a $C_{1-8}$ alkyl, a $C_{1-7}$ alkyl, a $C_{1-6}$ alkyl, a $C_{1-5}$ alkyl, a $C_{1-4}$ alkyl, a $C_{1-3}$ alkyl, a $C_{1-2}$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkenyl" refers to an optionally substituted straight-chain, or optionally substituted branched-chain hydrocarbon having one or more carbon-carbon double-bonds and having from two to about ten carbon atoms, more preferably two to about six carbon atoms, wherein an $sp^2$-hybridized carbon of the alkenyl residue is attached to the rest of the molecule by a single bond. The group may be in either the cis or trans conformation about the double bond(s), and should be understood to include both isomers. Examples include, but are not limited to, ethenyl (—$CH{=}CH_2$), 1-propenyl (—$CH_2CH{=}CH_2$), isopropenyl [—$C(CH_3){=}CH_2$], butenyl, 1,3-butadienyl, and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms, or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —$CF_3$, —OH, —OMe, —$NH_2$, or —$NO_2$. In some embodiments, an alkenyl is optionally substituted with oxo, halogen, —CN, —$CF_3$, —OH, or —OMe. In some embodiments, the alkenyl is optionally substituted with halogen.

"Alkynyl" refers to an optionally substituted straight-chain or optionally substituted branched-chain hydrocarbon having one or more carbon-carbon triple-bonds and having from two to about ten carbon atoms, more preferably from two to about six carbon atoms. Examples include, but are not limited to, ethynyl, 2-propynyl, 2-butynyl, 1,3-butadiynyl, and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms, or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, —OMe, —$NH_2$, or —$NO_2$. In some embodiments, an alkynyl is optionally substituted with oxo, halogen, —CN, —$CF_3$, —OH, or —OMe. In some embodiments, the alkynyl is optionally substituted with halogen.

"Alkoxy" refers to a radical of the formula —$OR^a$ where $R^a$ is an alkyl radical as defined. Non-limiting examples of alkoxy groups include methoxy, ethoxy, propoxy, isopropoxy, and isobutoxy. In some embodiments, alkoxy is $C_1$-$C_6$ alkoxy. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Hydroxyalkyl include, for example, aminomethyl, aminoethyl, aminopropyl, aminobutyl, or aminopentyl. In some embodiments, the hydroxyalkyl is aminomethyl.

"Aryl" refers to a radical derived from a hydrocarbon ring system comprising hydrogen, 6 to 30 carbon atoms, and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, —OMe, —$NH_2$, or —$NO_2$. In some embodiments, an aryl is optionally substituted with halogen, methyl, ethyl, —CN, —$CF_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom), bridged, or spiro ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo [3.3.0]octane, bicyclo[4.3.0] nonane, cis-decalin, trans-decalin, bicyclo[2.1.1]hexane, bicyclo[2.2.1]heptane, bicyclo[2.2.2]octane, bicyclo[3.2.2] nonane, and bicyclo[3.3.2]decane, and 7,7-dimethyl-bicyclo [2.2.1]heptanyl. Partially saturated cycloalkyls include, for example, cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Haloalkyl" refers to an alkyl radical, as defined above, that is substituted by one or more halogens. In some embodiments, the alkyl is substituted with one, two, or three halogens. In some embodiments, the alkyl is substituted with one, two, three, four, five, or six halogens. Haloalkyl include, for example, trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl is trifluoromethyl. In some embodiments, haloalkyl is $C_1$-$C_6$ haloalkyl.

"Halo" or "halogen" refers to bromo, chloro, fluoro, or iodo. In some embodiments, halogen is fluoro or chloro. In some embodiments, halogen is fluoro.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, $—CH_2OCH_3$, $—CH_2CH_2OCH_3$, $—CH_2CH_2OCH_2CH_2OCH_3$, or $—CH(CH_3)OCH_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, $—CF_3$, —OH, —OMe, $—NH_2$, or $—NO_2$. In some embodiments, a heteroalkyl is optionally substituted with oxo, halogen, methyl, ethyl, —CN, $—CF_3$, —OH, or —OMe. In some embodiments, the heteroalkyl is optionally substituted with halogen.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous, and sulfur. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized.

Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the cycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. In some embodiments, heterocycloalkyl is aziridinyl, azetidinyl, morpholinyl, piperidinyl, piperazinyl, oxetanyl, tetrahydrofuryl, tetrahydropyranyl, or thiomorpholinyl. The term heterocycloalkyl also includes all ring forms of the carbohydrates, including but not limited to, the monosaccharides, the disaccharides, and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, $—CF_3$, —OH, —OMe, $—NH_2$, or $—NO_2$. In some embodiments, a heterocycloalkyl is optionally substituted with oxo, halogen, methyl, ethyl, —CN, $—CF_3$, —OH, or —OMe. In some embodiments, the heterocycloalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous, and sulfur, and at least one aromatic ring. he heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). In some embodiments, heteroaryl is imidazolyl, indazolyl, indolyl, pyrrolyl, pyrazolyl, pyridinyl, pyrazinyl, pyrimidinyl, pyridazinyl, triazolyl, or tetrazolyl. Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, $—CF_3$, —OH, —OMe, $—NH_2$, or $—NO_2$. In some embodiments, a heteroaryl is optionally substituted with halogen, methyl, ethyl, —CN, —$CF_3$, —OH, or —OMe. In some embodiments, the heteroaryl is optionally substituted with halogen.

Certain compounds according to Formula (I) disclosed herein are isotopically enriched, meaning that they have an isotope present in greater than its natural abundance at one or more position. The term "isotopic enrichment factor" as used herein means the ratio between the isotopic abundance and the natural abundance of a specified isotope. In a compound of this disclosure, when a particular position is designated as having a particular isotope, such as deuterium, it is understood that the abundance of deuterium at that position is substantially greater than the natural abundance of deuterium, which is about 0.015% (on a mol/mol basis). A position designated as a particular isotope will have a minimum isotopic enrichment factor of at least 3000 (45% incorporation of the indicated isotope). Thus, isotopically enriched compounds disclosed herein having deuterium will have a minimum isotopic enrichment factor of at least 3000 (45% deuterium incorporation) at each atom designated as deuterium in the compound. Such compounds may be referred to herein as "deuterated" compounds. In one embodiment, deuterated compounds disclosed herein have an isotopic enrichment factor for each designated atom of at least 3500 (52.5%), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, the present disclosure provides a deuterated analogue of any compound disclosed herein. A deuterated analogue can include a compound herein where one or more $^1H$ atoms is replaced with a deuterium atom.

II. Compounds

Disclosed herein are analogs of xanomeline. In one embodiment the disclosed analogs function as prodrugs of xanomeline, releasing xanomeline as an active metabolite under suitable conditions, such as physiological conditions following administration of the analog to a subject.

In one embodiment, the analogs of xanomeline disclosed herein have Formula (Ia):

(Ia)

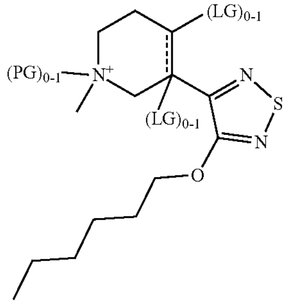

wherein PG is an optional progroup that together with the nitrogen atom to which it is attached forms an N-oxide, or has the formula —$(CR^1R^2)$—$OR^3$;

LG is an optional leaving group, provided that only one LG is present in Formula (Ia). In one embodiment, LG is an oxygen atom, that together with the adjacent LG substituted carbon atoms forms an epoxide ring.

When PG is present, it is attached to a quaternary nitrogen atom. Accordingly, a counterion also is present in such PG-substituted compounds (not illustrated in Formula (Ia)). Examples of suitable counterions include anionic counterions, including monovalent and divalent anions. As understood by those of ordinary skill in the art, when the counterion is divalent it is present in a 1:2 stoichiometry with the molecule of Formula (Ia). Suitable counterions include halides, phosphates, sulfates, sulfonates, carboxylates, hydroxides and the like.

In certain embodiments, compounds of Formula (Ia) are represented by Formula (Ib):

(Ib)

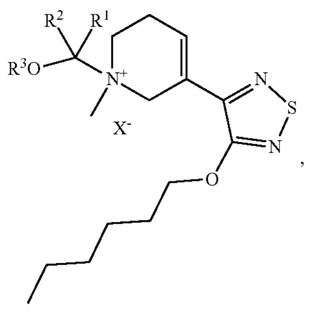

wherein $R^1$ and $R^2$ are independently selected from hydrogen and $C_{1-6}$ alkyl;

$R^3$ is selected from —$C(O)OR^4$, —$C(O)R^5$, —$Si(R^6)_3$, —$CH(R^7)OR^8$, —$CH(R^7)NR^aC(O)R^d$, —$CH(R^7)NR^cR^c$, —$CH(R^7)NR^aC(O)OR^d$, —$CH(R^7)OC(O)NR^eR^e$; —$CH(R^7)OC(O)R^7$, and —$P(O)OR^{10}(OR^{10})$, $R^4$ is independently selected from —$C(R^7)_2$—$OC(O)C(R^7)_2NR^cR^c$, —$C(R^7)_2$—$OC(O)C(R^7)_3$, —$CH(R^7)R^x$, —$CH(R^7)OCH(R^7)R^x$, —$(CH_2)_m$—$R^b$, —$(CHR^a)_m$—$R^b$, —$(CR^aR^a)_m$—$R^b$, alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl is unsubstituted or substituted with one or more $R^4$;

m is independently for each occurrence 2 or 3;

$R^x$ is

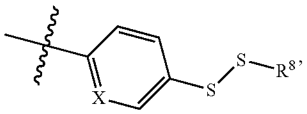

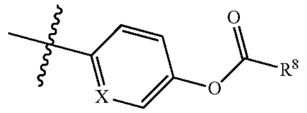

X is N or CH;

each $R^a$ is, for each occurrence, independently selected from the group consisting of hydrogen, $(C_{1-6})$ alkyl and $(C_{3-8})$ cycloalkyl;

each $R^b$ is independently selected from the group consisting of —S—S—$(CHR^a)_m$—$NR^cR^c$, —$OSi(R^d)_3$, —$OC(O)R^d$, —$OC(O)R^9$;

each $R^c$ is independently $R^a$, or, alternatively, two $R^c$ are taken together with the nitrogen atom to which they are bonded to form a 4 to 8-membered cycloheteroalkyl, which may optionally include one or more of the same or different additional heteroatoms and which may optionally be substituted with one or more of the same or different groups selected from oxo, —$CH_2OR^a$, —$C(O)R^a$ and $R^d$ groups;

each $R^d$ is independently selected from ($C_{1-6}$) alkyl, 5-membered heteroaryl, 6-membered heteroaryl and 6-membered aryl, each optionally substituted with each optionally substituted with 1, 2 or 3 groups selected from halogen, $C_{14}$ alkyl, and —$OR^a$;

with respect to the group —$NR^eR^e$; each $R^e$ is $R^a$, wherein at least one of the $R^a$ groups is substituted with at least one group selected from —$OC_{1-6}$ alkyl, —$OC(O)C_{1-6}$ alkyl, —OH, —$SC_{1-6}$ alkyl, and —SH;

$R^5$ is —$Si(R^d)_3$, —$C(R^8)_2$—$NR^cR^c$ or —$C(R^5)_2$—$C(R^7)_2$—$R^y$ alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl is unsubstituted or substituted with one or more $R^A$;

$R^6$ is alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl is unsubstituted or substituted with one or more $R^A$;

$R^7$ is independently hydrogen, alkyl, alkenyl, haloalkyl, heteroalkyl, cycloalkyl, heterocyclylalkyl wherein alkyl, heteroalkyl, cycloalkyl, heterocyclylalkyl is unsubstituted or substituted with one or more —$OR^a$, —$NR^cR^c$, —$C(O)OR^a$, —$N(R^a)C(O)OR^a$, $R^y$ is

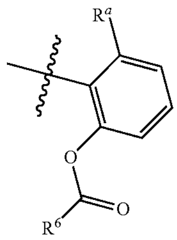

;

$R^8$ is —$Si(R^d)_3$, or $CH(R^5)OC(O)NHR^f$;

$R^f$ is —$Si(R^d)_3$, —$C(R^5)_2$—$NR^cR^c$ or —$C(R^5)_2$—$C(R^5)_2$—$R^y$;

$R^9$ is a $C_{6-15}$ alkylene or alkenylene chain;

each $R^{10}$ is independently selected from hydrogen, —$(CH_2)_n$—$R^g$, —$(CHR^a)_n$—$R^g$, and —$(CR^aR^a)_n$—$R^g$, alkyl, alkenyl, heteroalkyl, cycloalkyl, heterocyclylalkyl, aryl, or heteroaryl, wherein alkyl, heteroalkyl, cycloalkyl, heterocyclylalkyl, aryl, and heteroaryl is unsubstituted or substituted with one or more $R^B$;

n is independently for each occurrence 2 or 3;

each $R^9$ is independently —OH, —$NH_2$, —$N(R^{11})C(O)R^7$, —$N(R^{11})C(O)OR^{12}$, —$OC(O)R^{13}$, —$OC(O)OR^{14}$, —$OC(O)NR^cR^c$;

each $R^A$ is independently alkyl, heteroalkyl, cycloalkyl, heterocyclylalkyl, aryl, heteroaryl, halogen, an amino acid side chain, —$OR^{11}$, —$C(O)OR^{12}$, —$N(R^{13})C(O)OR^{14}$, —$N(R^{13})C(O)R^{14}$, —$C(O)R^{14}$, —$OC(O)R^{15}$, —$OC(O)OR^{16}$, —$OP(O)OR^{17}[N(R^{18})R^{19}]$, —$N(R^{18})R^{19}$, —$C(O)N(R^{18})R^{19}$, —$OC(O)N(R^{18})R^{19}$, or —$OP(O)OR^{10}(OR^{10})$, wherein alkyl, heteroalkyl, cycloalkyl, heterocyclylalkyl, aryl, or heteroaryl is unsubstituted or substituted with one or more alkyl, aryl, halogen, —S—$R^{13}$, —$OR^{13}$, —$NR(R^{18})R^{19}$, —$C(O)R^{14}$, —$OC(O)R^{15}$, —$OC(O)OR^{16}$, or —$OC(O)N(R^{18})R^{19}$;

each of $R^{11}$, $R^{12}$, $R^{13}$, $R^{14}$, $R^{15}$, $R^{16}$, or $R^{17}$ is independently hydrogen, alkyl, alkenyl, heteroalkyl, cycloalkyl, heterocyclylalkyl, aryl, or heteroaryl, wherein alkyl, heteroalkyl, cycloalkyl, heterocyclylalkyl, aryl, and heteroaryl is unsubstituted or substituted with one or more $R^B$;

each of $R^{18}$ and $R^{19}$ is independently hydrogen, alkyl, alkenyl, heteroalkyl, cycloalkyl, heterocyclylalkyl, aryl, or heteroaryl, wherein alkyl, heteroalkyl, cycloalkyl, heterocyclylalkyl, aryl, or heteroaryl is unsubstituted or substituted with one or more $R^B$; or $R^{18}$ and $R^{19}$ together with the atom to which they are attached form a heterocyclylalkyl ring or heteroaryl ring, each of which is unsubstituted or substituted with one or more $R^B$;

each $R^B$ is independently halogen, amino, cyano, hydroxyl, alkyl, alkenyl, heteroalkyl, cycloalkyl, heterocyclylalkyl, aryl, heteroaryl, arylalkyl, —$OC(O)R^{18}$, —$C(O)R^{18}$, —$C(O)OR^{18}$, $NHC(O)OR^{18}$, or heteroarylalkyl, wherein cycloalkyl, heterocyclylalkyl, aryl, or heteroaryl is unsubstituted or substituted with one or more halogen, amino, cyano, hydroxyl, alkyl, acetyl, or benzoyl, and $X^-$ is a pharmaceutically acceptable counterion.

In some embodiments, compounds of Formulas (Ia) and (Ib) have Formula (Ic):

(Ic)

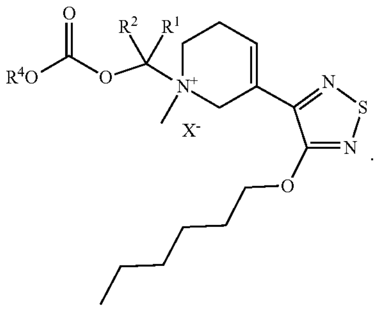

.

In some embodiments, compounds of Formulas (Ia) and (Ib) have Formula (Id):

(Id)

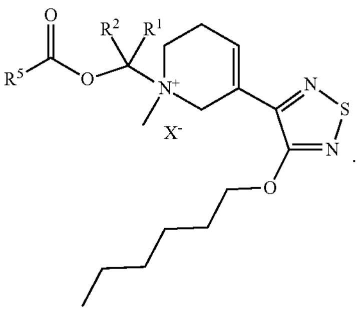

.

In some embodiments, compounds of Formulas (Ia) and (Ib) have Formula (Ie):

(Ie)

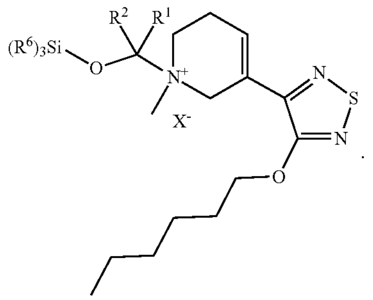

In some embodiments of Formula (Ia), compounds disclosed herein have Formula (If) or (Ig):

(If)

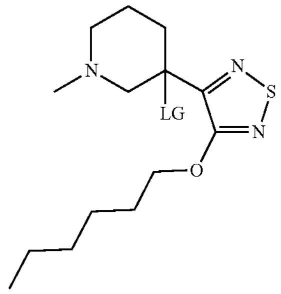

(Ig)

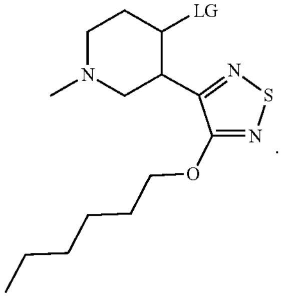

With reference to Formulas (If) and (Ig), an elimination reaction yields xanomeline.

In some embodiments of Formula (Ia), the LG groups comprise an epoxide, such that in one embodiment compounds of Formula (Ia) have Formula (Ih):

(Ih)

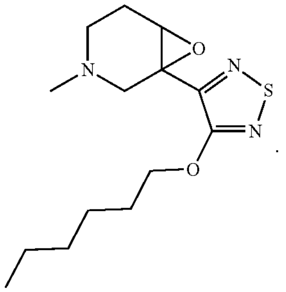

In some embodiments, compounds of Formula (Ia) are N-oxide compounds of Formulas (Ii) and/or (Ij):

(Ii)

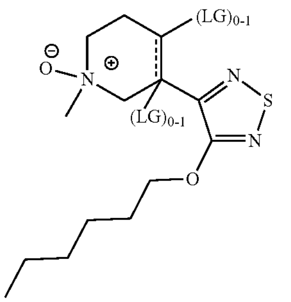

(Ij)

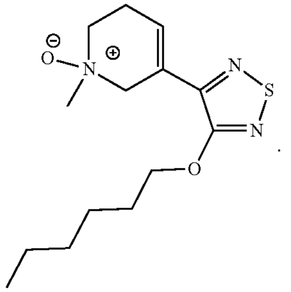

In some embodiments, the present disclosure provides compounds of Formulas (Ia), (Ib), (Ic), (Id), (Ie), (If), (Ig) (Ih), (Ii), and (Ij) that are isotopically enriched. In one embodiment, a compound of Formulas (Ia), (Ib), (Ic), (Id), (Ie), (If), (Ig), (Ih), (Ii), and/or (Ij) is enriched in deuterium.

In some embodiments, the disclosed xanomeline analogs have Formula (I), (II), (III), (IV), (V), (VI), (VII), (VIII), (IX), (X), (XI), (XII), (XIII), (XIV), or (XV):

(I)

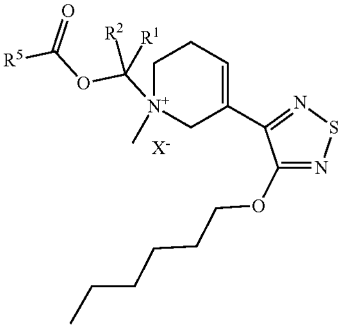

-continued

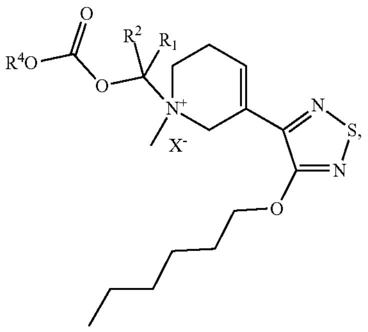

X = Cl, Br, I, $CH_3CO_2$, $PhCO_2$, $MeSO_3$, $CF_3SO_3$, $PhSO_3$, $H_2PO_4$
$R^1$, $R^2$ = H, Me, Et, iPr in any combination
$R^4$ and $R^5$ = $C_1$-$C_{20}$ alkyl, $C_1$-$C_{20}$ substituted alkyl, $C_3$-$C_{20}$ cycloalkyl, $C_3$-$C_{20}$ substituted cycloalkyl, aryl, heteroaryl (II)

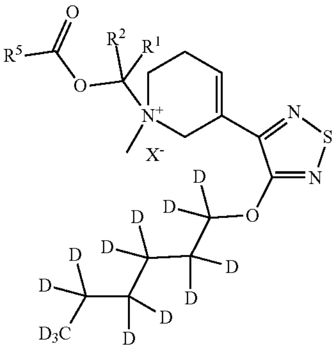

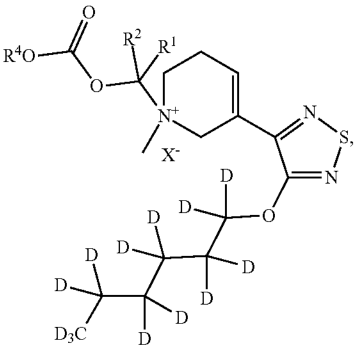

X = Cl, Br, I, $CH_3CO_2$, $PhCO_2$, $MeSO_3$, $CF_3SO_3$, $PhSO_3$, $H_2PO_4$
$R^1$, $R^2$ = H, Me, Et, iPr in any combination
$R^4$ and $R^5$ = $C_1$-$C_{20}$ alkyl, $C_1$-$C_{20}$ substituted alkyl, $C_3$-$C_{20}$ cycloalkyl, $C_3$-$C_{20}$ substituted cycloalkyl, aryl, heteroaryl -continued (III)

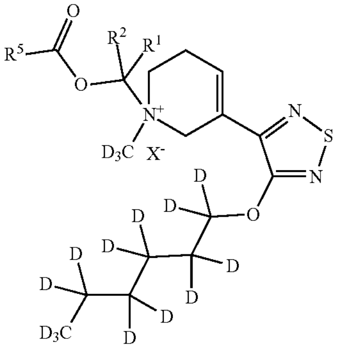

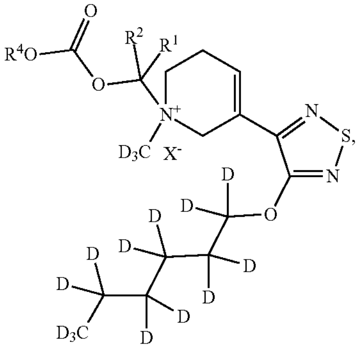

X = Cl, Br, I, $CH_3CO_2$, $PhCO_2$, $MeSO_3$, $CF_3SO_3$, $PhSO_3$, $H_2PO_4$
$R^1$, $R^2$ = H, Me, Et, iPr in any combination
$R^4$ and $R^5$ = $C_1$-$C_{20}$ alkyl, $C_1$-$C_{20}$ substituted alkyl, $C_3$-$C_{20}$ cycloalkyl, $C_3$-$C_{20}$ substituted cycloalkyl, aryl, heteroaryl (IV)

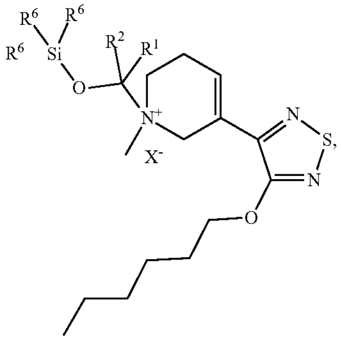

X = Cl, Br, I, $CH_3CO_2$, $PhCO_2$, $MeSO_3$,$CF_3SO_3$, $PhSO_3$, $H_2PO_4$
$R^1$, $R^2$ = H, Me, Et, iPr in any combination
$R^6$ = Me, Et, iPr, tBu, Ph in any combination -continued (V)

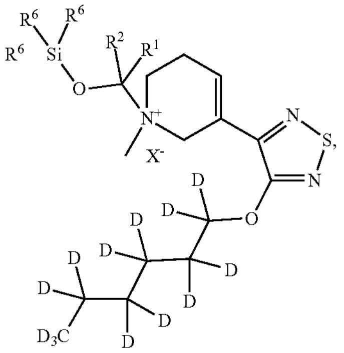

X = Cl, Br, I, $CH_3CO_2$, $PhCO_2$, $MeSO_3$, $CF_3SO_3$, $PhSO_3$, $H_2PO_4$
$R^1$, $R^2$ = H, Me, Et, iPr in any combination
$R^6$ = Me, Et, iPr, tBu, Ph in any combination (VI)

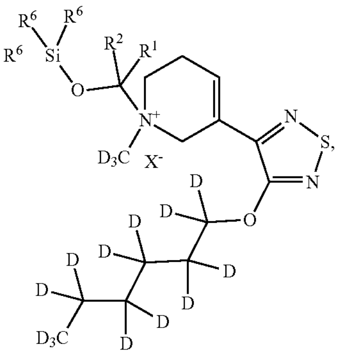

X = Cl, Br, I, $CH_3CO_2$, $PhCO_2$, $MeSO_3$, $CF_3SO_3$, $PhSO_3$, $H_2PO_4$
$R^1$, $R^2$ = H, Me, Et, iPr in any combination
$R^6$ = Me, Et, iPr, tBu, Ph in any combination (VII)

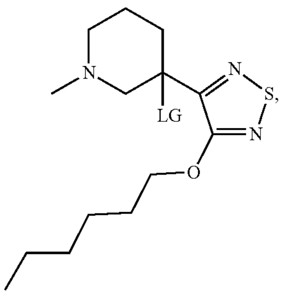

LG = Cl, Br, I, OH, OMe, OAc (VIII)

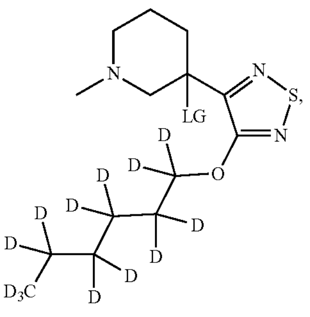

LG = Cl, Br, I, OH, OMe, OAc

-continued (IX)

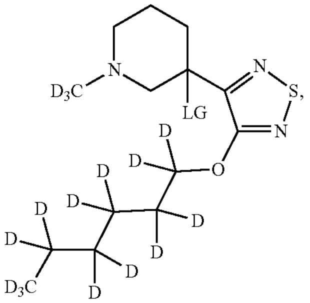

LG = Cl, Br, I, OH, OMe, OAc (X)

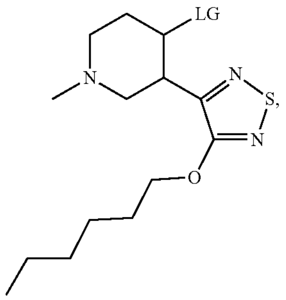

LG = Cl, Br, I, OH, OMe, OAc (XI)

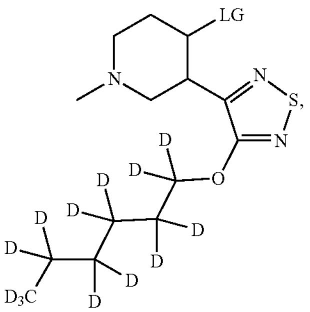

LG = Cl, Br, I, OH, OMe, OAc (XII)

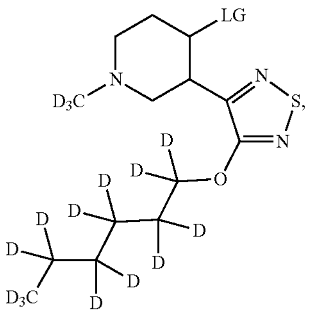

LG = Cl, Br, I, OH, OMe, OAc

-continued (XIII)

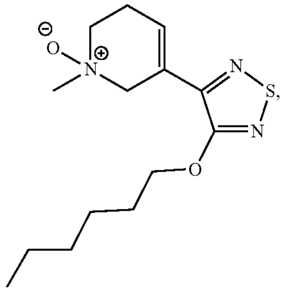

(XIV)

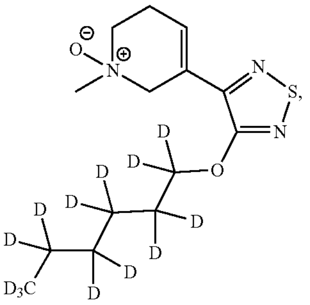

(XV)

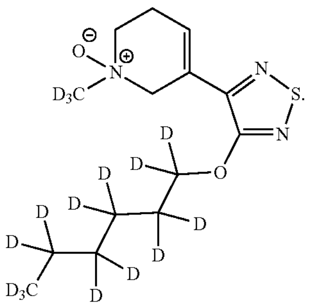

In some embodiments of the Formulas above, including Formulas (Ia), (Ib), (Ic), (Id), (Ie), (I), (II), (III), (IV), (V) and (VI), $R^1$ and $R^2$ are hydrogen. In some embodiments of the Formulas above, at least one of $R^1$ and $R^2$ is other than hydrogen, such as in compounds wherein at least one of $R^1$ and $R^2$ is $C_{1-6}$ alkyl. In some embodiments of Formulas (Ia), (Ib), (Ic), (Id), (Ie), (I), (II), (III), (IV), (V) and (VI), $R^1$ and $R^2$ are the same. In some embodiments, $R^1$ and $R^2$ are different, such in compounds wherein one of $R^1$ and $R^2$ is hydrogen, and the other is $C_{1-6}$ alkyl. When $R^1$ and $R^2$ are different, the carbon to which they are bonded is chiral. Chiral compounds are provided herein in racemic and optically active forms. Certain embodiments of chiral compounds disclosed herein are specifically illustrated herein, such as in Table 1. Where such compounds are illustrated, all stereoisomers are specifically contemplated. For example, where the compound illustrated has the S-configuration at a chiral carbon, the opposite or R-configuration of that carbon atom also is contemplated herein.

In some embodiments of the Formulas above, including Formulas (Ia), (Ib), (Ic), (Id), (le), (I), (II), (III), (IV), (V) and (VI), $R^4$ and $R^5$ or $R^6$ each are alkyl, such as branched or unbranched alkyl. In some embodiments, the alkyl or branched alkyl is unsubstituted.

In some embodiments of Formulas (Ia), (Ib), (Ic), (Id), (I), (II) and (III), $R^4$ or $R^5$ are unsubstituted alkyl. In some embodiments, $R^4$ or $R^5$ are $C_{1-6}$ alkyl, such as methyl, ethyl, propyl, butyl, sec-butyl or t-butyl. In some embodiments, $R^4$ or $R^5$ is $C_8$ alkyl, $C_{10}$ alkyl, $C_{12}$ alkyl, $C_{14}$ alkyl or $C_{15}$ alkyl.

In some embodiments (Ia), (Ib), (Ic), (Id), (I), (II) and (III), $R^4$ or $R^5$ are substituted alkyl.

In some embodiments, $R^4$ or $R^5$ are haloalkyl, such as perhaloalkyl.

In some embodiments, $X^-$ is halo, carboxylate, sulfonate, pamoate, or phosphate.

In some embodiments, $X^-$ is halo, or pamoate.

In some embodiments, $X^-$ is halo.

In some embodiments, $X^-$ is pamoate.

In some embodiments, $X^-$ is chloro.

Selected compounds of the disclosure, including compounds intended to act as prodrugs of xanomeline, are provided in TABLE 1.

TABLE 1

| Cpd No. | Structure |
|---|---|
| 1 | 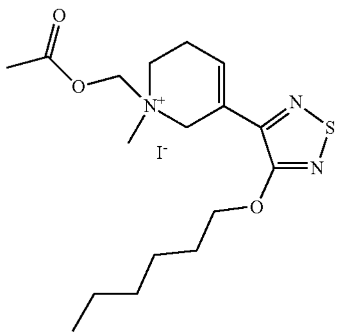 [SMILES: CCCCCCOc1nsnc1C1=CCC[N+](C)(COC(C)=O)C1 ; [I-]] |

TABLE 1-continued
| Cpd No. | Structure |
| --- | --- |
| 2 | 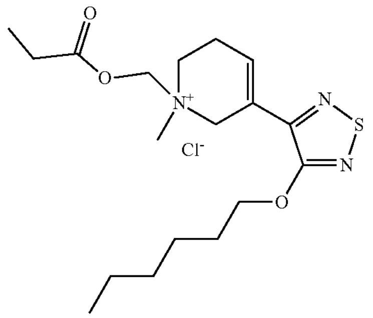 [SMILES: CCCCCCOc1nsnc1C1=CCC[N+](C)(COC(=O)CC)C1 ; [Cl-]] |
| 3 | 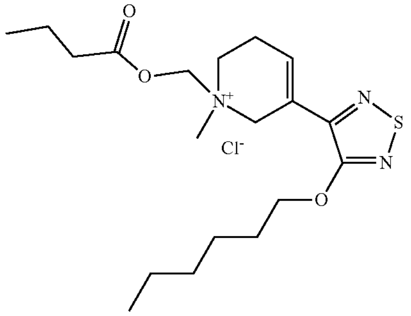 [SMILES: CCCCCCOc1nsnc1C1=CCC[N+](C)(COC(=O)CCC)C1 ; [Cl-]] |
| 4 | 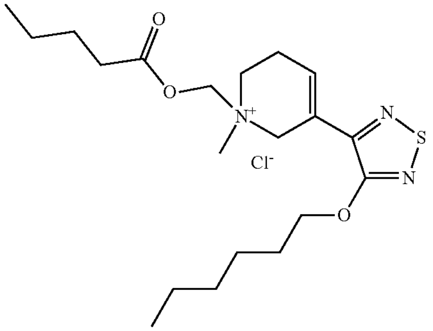 [SMILES: CCCCCCOc1nsnc1C1=CCC[N+](C)(COC(=O)CCCC)C1 ; [Cl-]] |
| 5 | 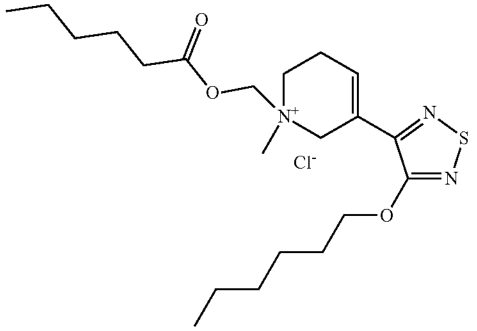 [SMILES: CCCCCCOc1nsnc1C1=CCC[N+](C)(COC(=O)CCCCC)C1 ; [Cl-]] |

TABLE 1-continued
| Cpd No. | Structure |
| --- | --- |
| 6 | 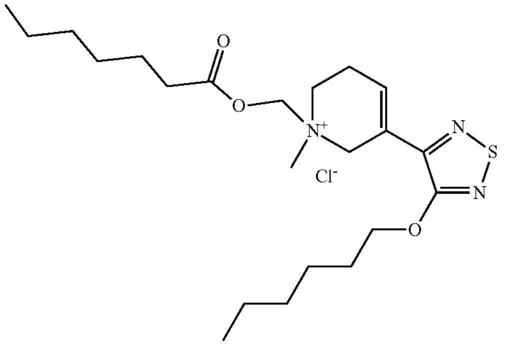 [SMILES: CCCCCCOc1nsnc1C1=CCC[N+](C)(COC(=O)CCCCCC)C1 ; [Cl-]] |
| 7 | 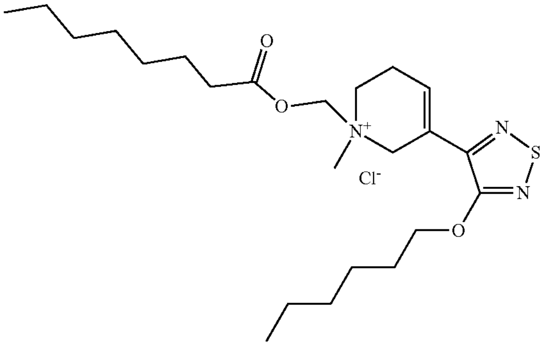 [SMILES: CCCCCCCC(=O)OC[N+]1(C)CCC=C(c2nsnc2OCCCCCC)C1 ; [Cl-]] |
| 8 | 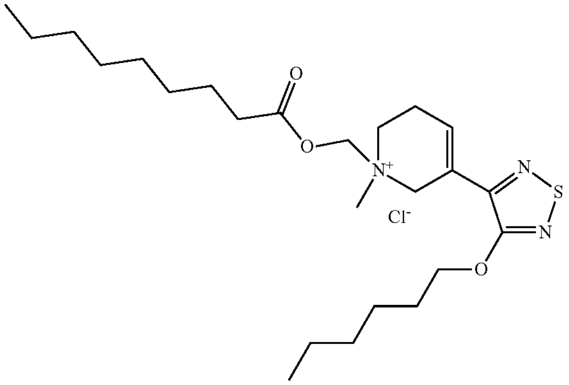 [SMILES: CCCCCCCCC(=O)OC[N+]1(C)CCC=C(c2nsnc2OCCCCCC)C1 ; [Cl-]] |
| 9 | 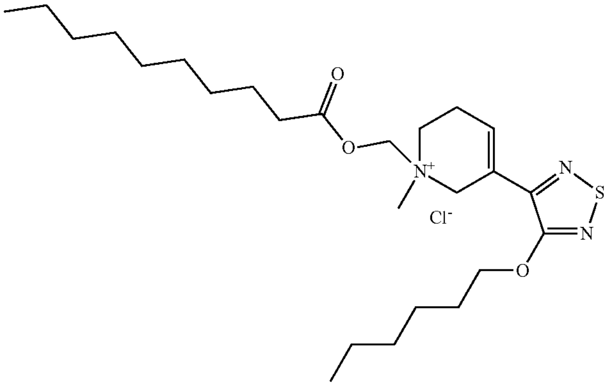 [SMILES: CCCCCCCCCC(=O)OC[N+]1(C)CCC=C(c2nsnc2OCCCCCC)C1 ; [Cl-]] |

TABLE 1-continued
| Cpd No. | Structure |
| --- | --- |
| 10 | 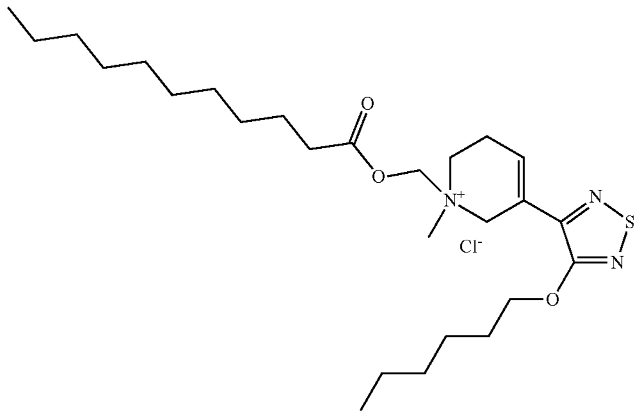 [SMILES: CCCCCCCCCCC(=O)OC[N+]1(C)CCC=C(c2nsnc2OCCCCCC)C1 ; [Cl-]] |
| 11 | 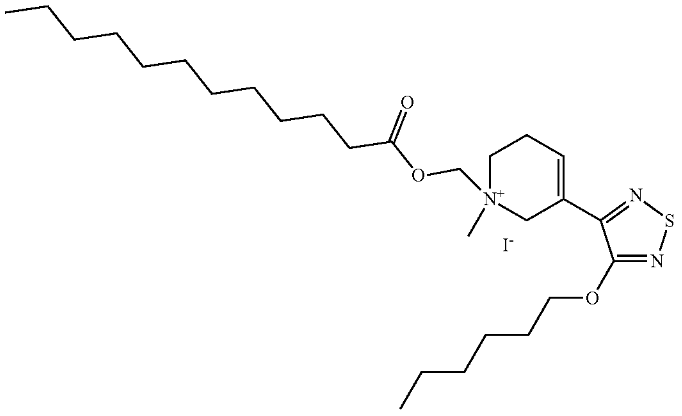 [SMILES: CCCCCCCCCCCC(=O)OC[N+]1(C)CCC=C(c2nsnc2OCCCCCC)C1 ; [I-]] |
| 12 | 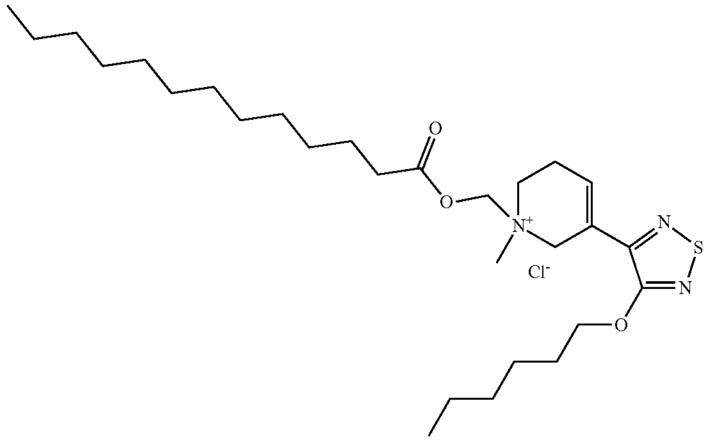 [SMILES: CCCCCCCCCCCCC(=O)OC[N+]1(C)CCC=C(c2nsnc2OCCCCCC)C1 ; [Cl-]] |

TABLE 1-continued
| Cpd No. | Structure |
| --- | --- |
| 13 | 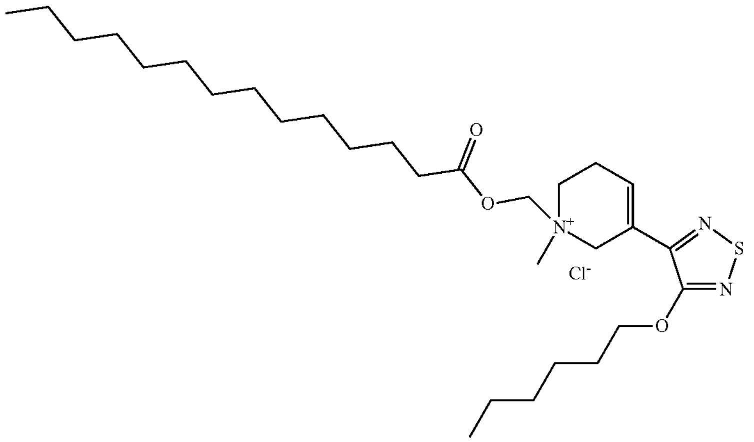 [SMILES: CCCCCCCCCCCCCC(=O)OC[N+]1(C)CCC=C(c2nsnc2OCCCCCC)C1 ; [Cl-]] |
| 14 | 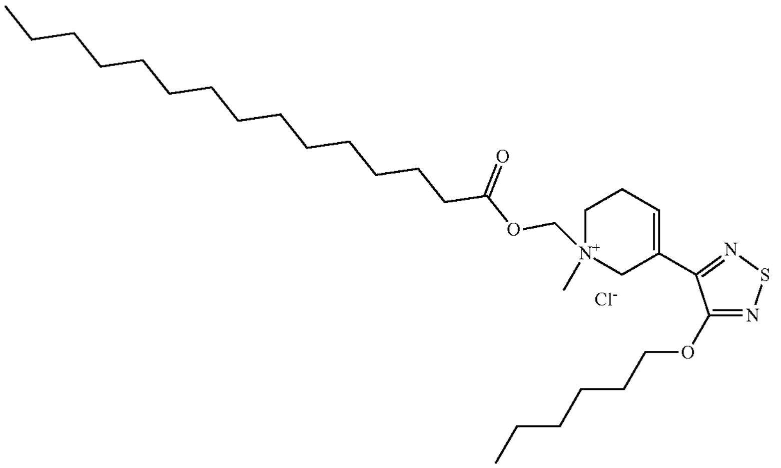 [SMILES: CCCCCCCCCCCCCCC(=O)OC[N+]1(C)CCC=C(c2nsnc2OCCCCCC)C1 ; [Cl-]] |
| 15 | 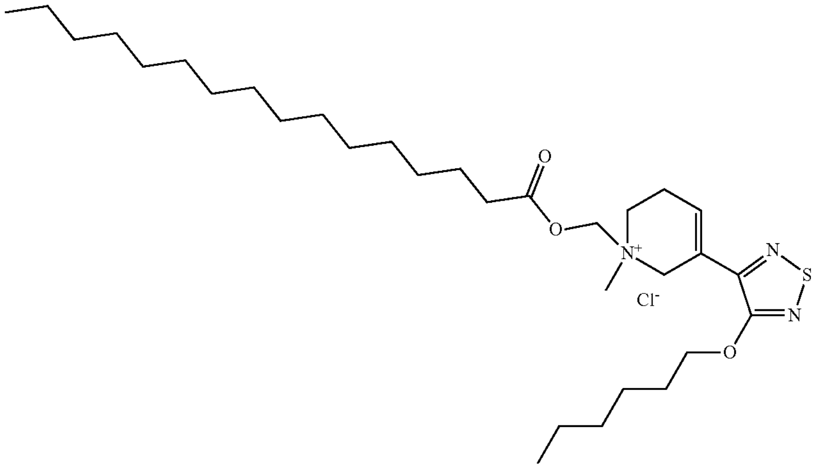 [SMILES: CCCCCCCCCCCCCCCC(=O)OC[N+]1(C)CCC=C(c2nsnc2OCCCCCC)C1 ; [Cl-]] |

TABLE 1-continued
| Cpd No. | Structure |
|---|---|
| 16 | 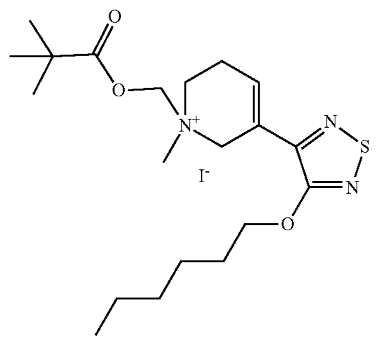 [SMILES: CCCCCCOc1nsnc1C1=CCC[N+](C)(COC(=O)C(C)(C)C)C1 ; [I-]] |
| 17 | 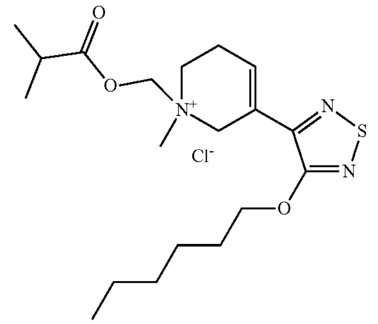 [SMILES: CCCCCCOc1nsnc1C1=CCC[N+](C)(COC(=O)C(C)C)C1 ; [Cl-]] |
| 18 | 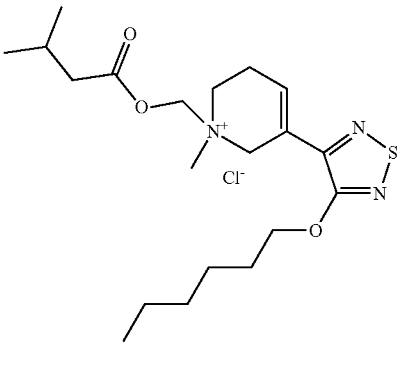 [SMILES: CCCCCCOc1nsnc1C1=CCC[N+](C)(COC(=O)CC(C)C)C1 ; [Cl-]] |
| 19 | 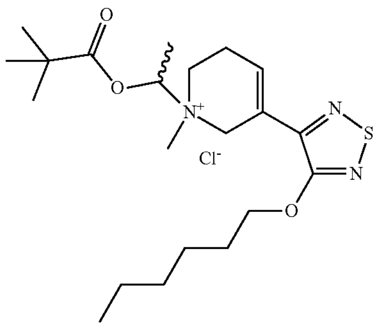 [SMILES: CCCCCCOc1nsnc1C1=CCC[N+](C)(C(C)OC(=O)C(C)(C)C)C1 ; [Cl-]] |

TABLE 1-continued
| Cpd No. | Structure |
| --- | --- |
| 20 | 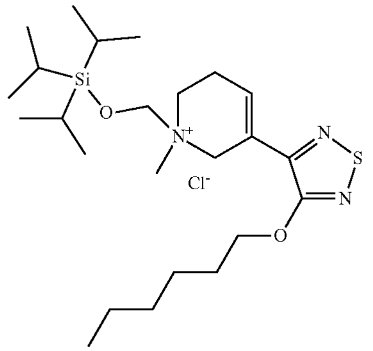 [SMILES: CCCCCCOc1nsnc1C1=CCC[N+](C)(CO[Si](C(C)C)(C(C)C)C(C)C)C1 ; [Cl-]] |
| 21 | 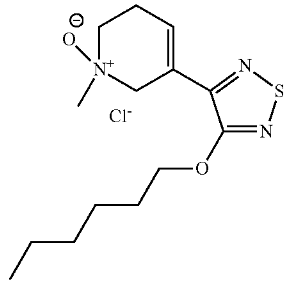 [SMILES: CCCCCCOc1nsnc1C1=CCC[N+](C)([O-])C1 ; [Cl-]] |
| 22 | 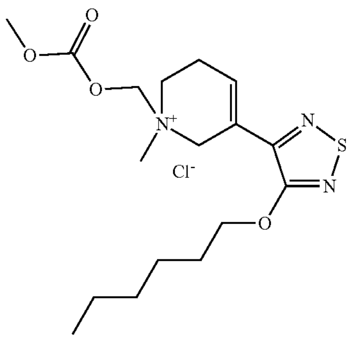 [SMILES: CCCCCCOc1nsnc1C1=CCC[N+](C)(COC(=O)OC)C1 ; [Cl-]] |
| 23 | 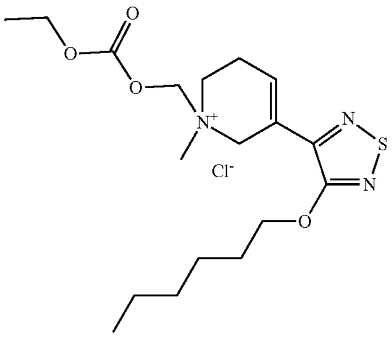 [SMILES: CCCCCCOc1nsnc1C1=CCC[N+](C)(COC(=O)OCC)C1 ; [Cl-]] |

TABLE 1-continued
| Cpd No. | Structure |
| --- | --- |
| 24 | 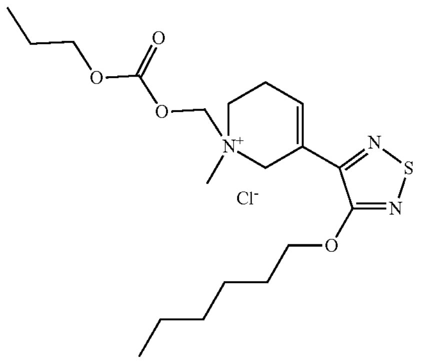 [SMILES: CCCCCCOc1nsnc1C1=CCC[N+](C)(COC(=O)OCCC)C1 ; [Cl-]] |
| 25 | 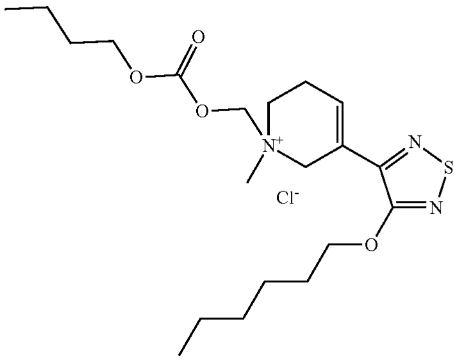 [SMILES: CCCCCCOc1nsnc1C1=CCC[N+](C)(COC(=O)OCCCC)C1 ; [Cl-]] |
| 26 | 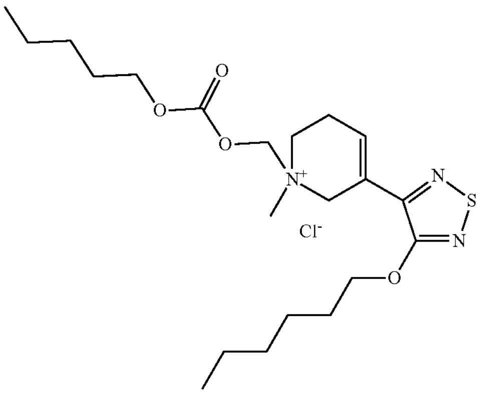 [SMILES: CCCCCCOc1nsnc1C1=CCC[N+](C)(COC(=O)OCCCCC)C1 ; [Cl-]] |
| 27 | 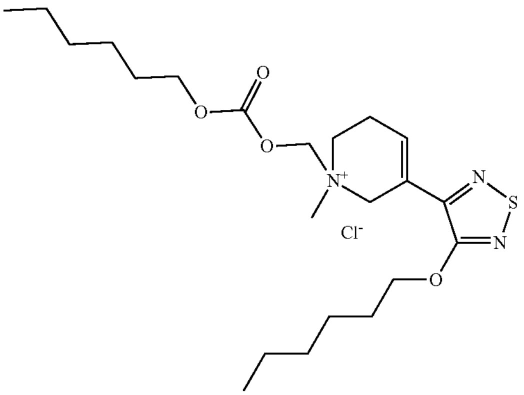 [SMILES: CCCCCCOC(=O)OC[N+]1(C)CCC=C(c2nsnc2OCCCCCC)C1 ; [Cl-]] |

TABLE 1-continued
| Cpd No. | Structure |
|---|---|
| 28 | 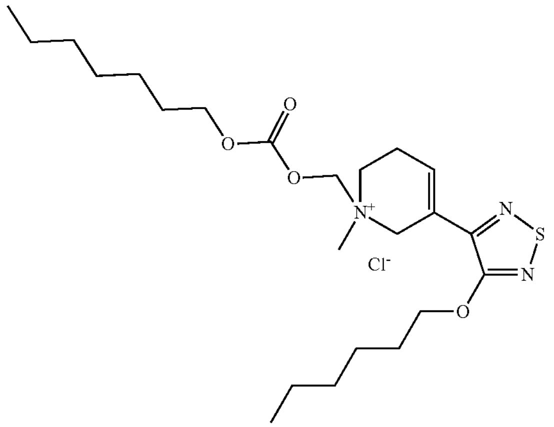 [SMILES: CCCCCCCOC(=O)OC[N+]1(C)CCC=C(c2nsnc2OCCCCCC)C1 ; [Cl-]] |
| 29 | 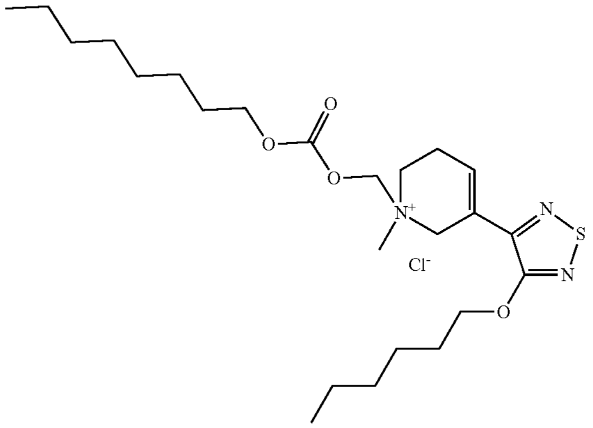 [SMILES: CCCCCCCCOC(=O)OC[N+]1(C)CCC=C(c2nsnc2OCCCCCC)C1 ; [Cl-]] |
| 30 | 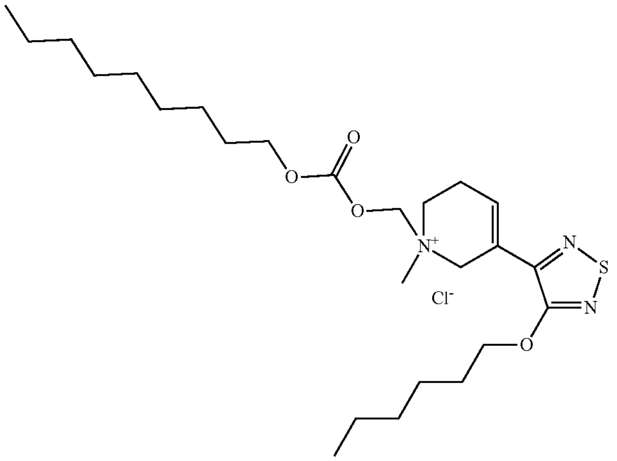 [SMILES: CCCCCCCCCOC(=O)OC[N+]1(C)CCC=C(c2nsnc2OCCCCCC)C1 ; [Cl-]] |

TABLE 1-continued
| Cpd No. | Structure |
|---|---|
| 31 | 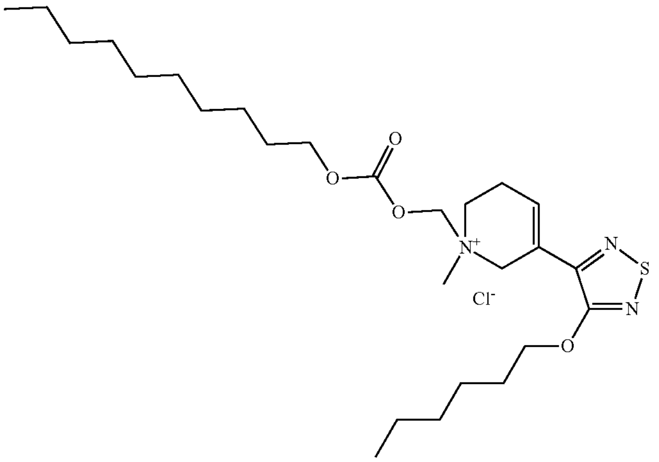 [SMILES: CCCCCCCCCCOC(=O)OC[N+]1(C)CCC=C(c2nsnc2OCCCCCC)C1 ; [Cl-]] |
| 32 | 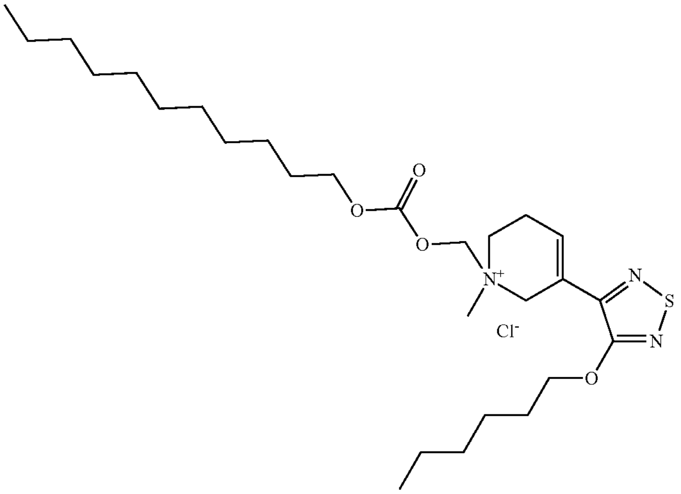 [SMILES: CCCCCCCCCCCOC(=O)OC[N+]1(C)CCC=C(c2nsnc2OCCCCCC)C1 ; [Cl-]] |
| 33 | 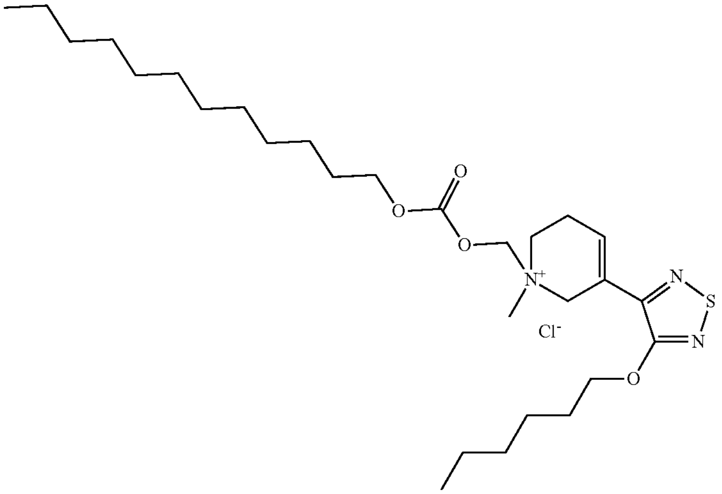 [SMILES: CCCCCCCCCCCCOC(=O)OC[N+]1(C)CCC=C(c2nsnc2OCCCCCC)C1 ; [Cl-]] |

TABLE 1-continued
| Cpd No. | Structure |
|---|---|
| 34 | 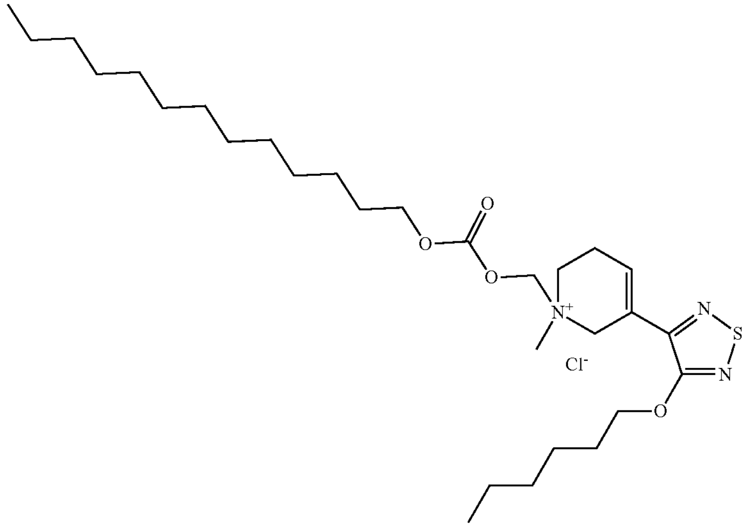 [SMILES: CCCCCCCCCCCCCOC(=O)OC[N+]1(C)CCC=C(c2nsnc2OCCCCCC)C1 ; [Cl-]] |
| 35 | 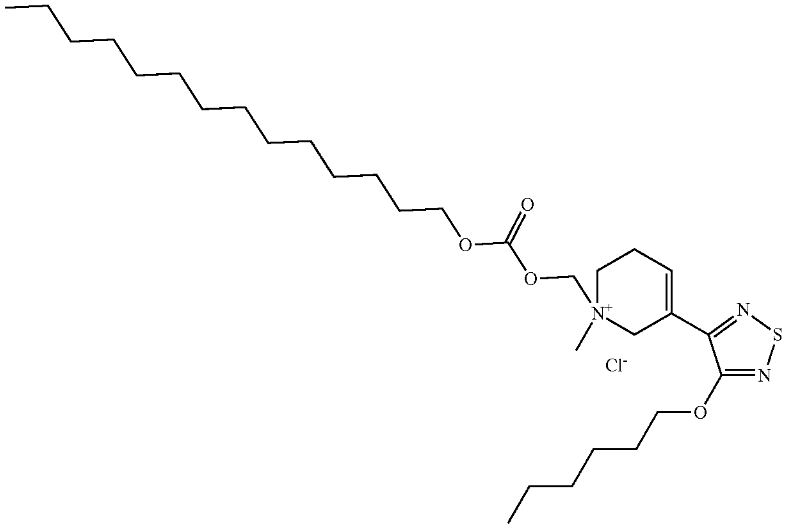 [SMILES: CCCCCCCCCCCCCCOC(=O)OC[N+]1(C)CCC=C(c2nsnc2OCCCCCC)C1 ; [Cl-]] |
| 36 | 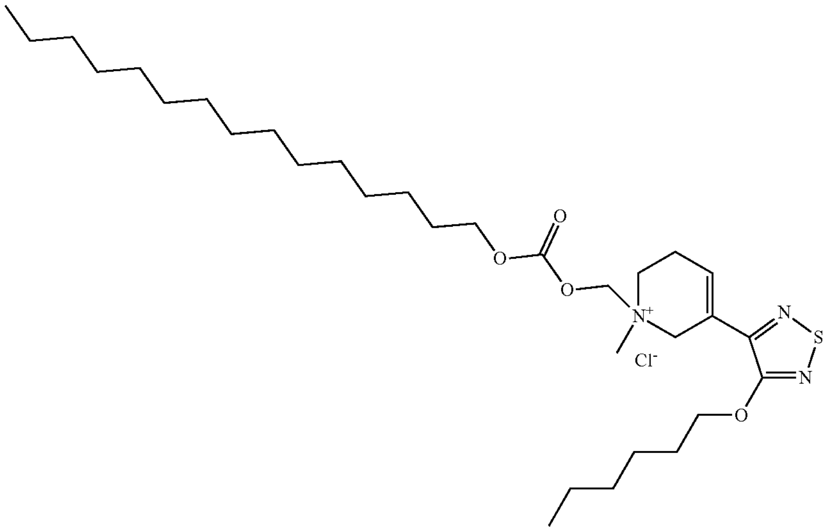 [SMILES: CCCCCCCCCCCCCCCOC(=O)OC[N+]1(C)CCC=C(c2nsnc2OCCCCCC)C1 ; [Cl-]] |

TABLE 1-continued
| Cpd No. | Structure |
|---|---|
| 37 | 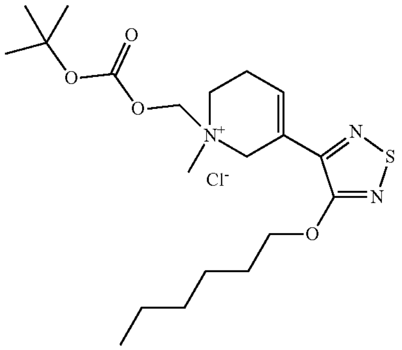 [SMILES: CCCCCCOc1nsnc1C1=CCC[N+](C)(COC(=O)OC(C)(C)C)C1 ; [Cl-]] |
| 38 | 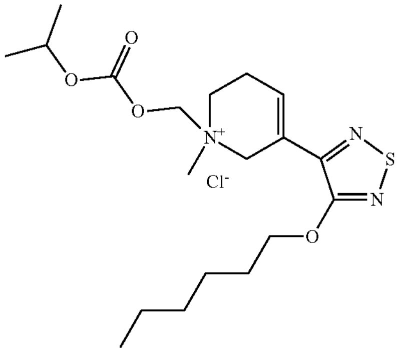 [SMILES: CCCCCCOc1nsnc1C1=CCC[N+](C)(COC(=O)OC(C)C)C1 ; [Cl-]] |
| 39 | 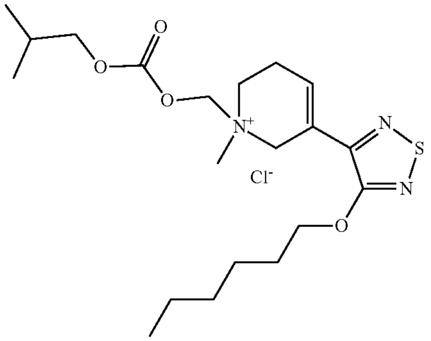 [SMILES: CCCCCCOc1nsnc1C1=CCC[N+](C)(COC(=O)OCC(C)C)C1 ; [Cl-]] |
| 40 | 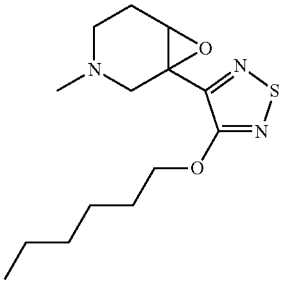 [SMILES: CCCCCCOc1nsnc1C12CN(C)CCC1O2] |

TABLE 1-continued
| Cpd No. | Structure |
| --- | --- |
| 41 | 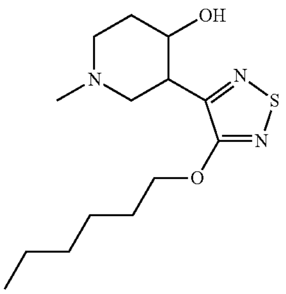 [SMILES: CCCCCCOc1nsnc1C1CN(C)CCC1O] |
| 42 | 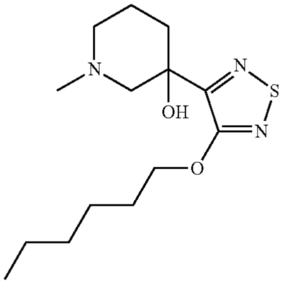 [SMILES: CCCCCCOc1nsnc1C1(O)CCCN(C)C1] |
| 43 | 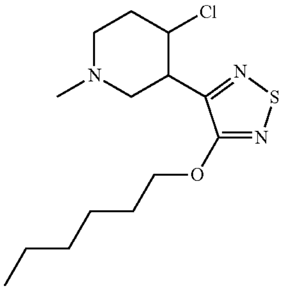 [SMILES: CCCCCCOc1nsnc1C1CN(C)CCC1Cl] |
| 44 | 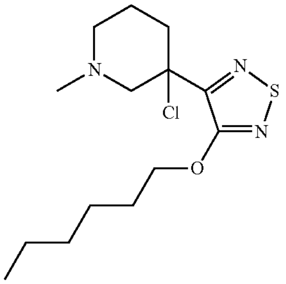 [SMILES: CCCCCCOc1nsnc1C1(Cl)CCCN(C)C1] |
| 45 | 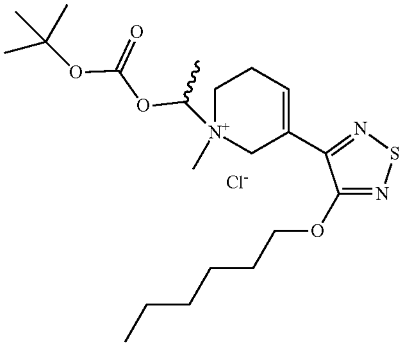 [SMILES: CCCCCCOc1nsnc1C1=CCC[N+](C)(C(C)OC(=O)OC(C)(C)C)C1 ; [Cl-]] |

TABLE 1-continued
| Cpd No. | Structure |
| --- | --- |
| 46 | 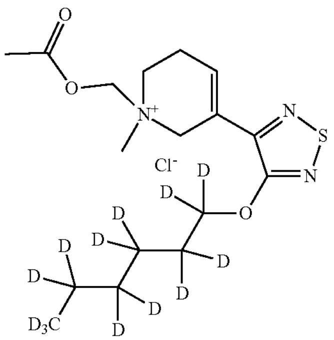 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(C)=O)C1 ; [Cl-]] |
| 47 | 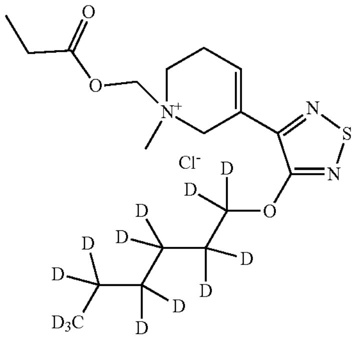 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CC)C1 ; [Cl-]] |
| 48 | 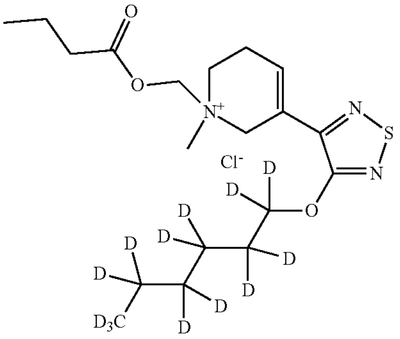 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCC)C1 ; [Cl-]] |
| 49 | 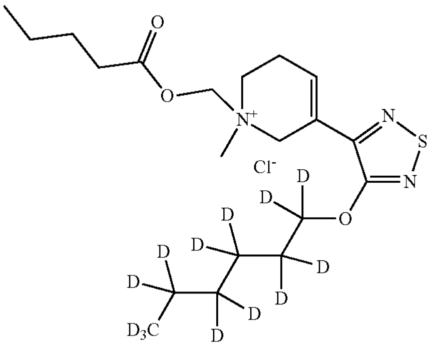 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCC)C1 ; [Cl-]] |

TABLE 1-continued
| Cpd No. | Structure |
| --- | --- |
| 50 | 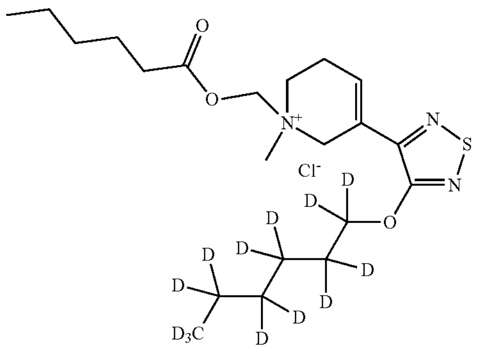 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCC)C1 ; [Cl-]] |
| 51 | 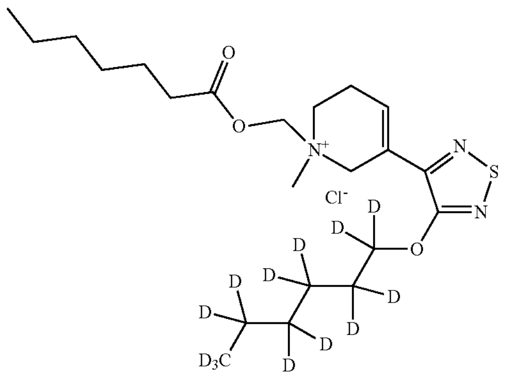 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCC)C1 ; [Cl-]] |
| 52 | 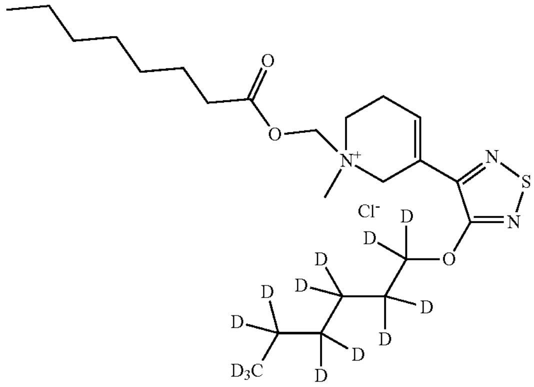 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCC)C1 ; [Cl-]] |
| 53 | 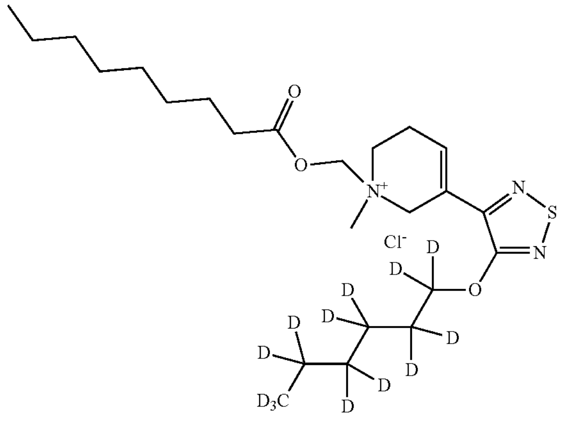 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCC)C1 ; [Cl-]] |

TABLE 1-continued
| Cpd No. | Structure |
|---|---|
| 54 | 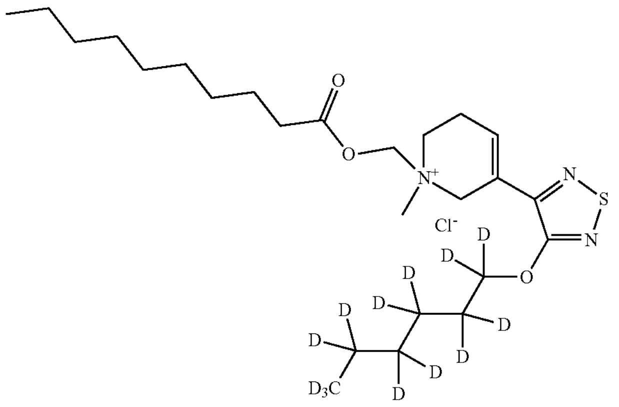 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCC)C1 ; [Cl-]] |
| 55 | 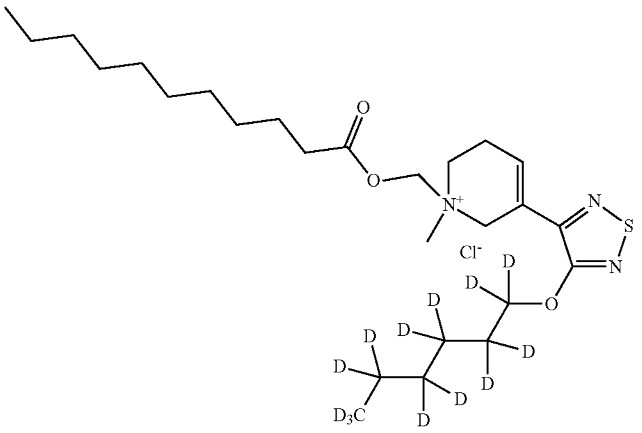 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCC)C1 ; [Cl-]] |
| 56 | 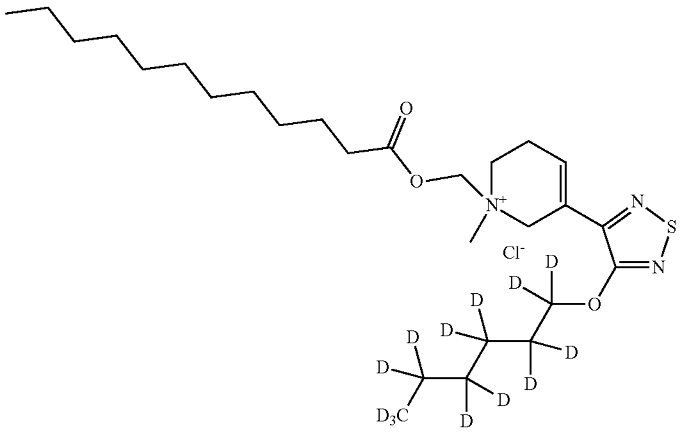 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCCC)C1 ; [Cl-]] |

TABLE 1-continued
| Cpd No. | Structure |
|---|---|
| 57 | 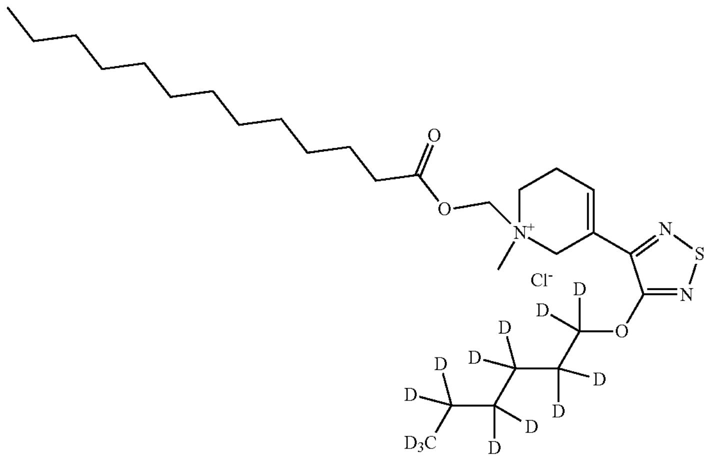 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCCCC)C1 ; [Cl-]] |
| 58 | 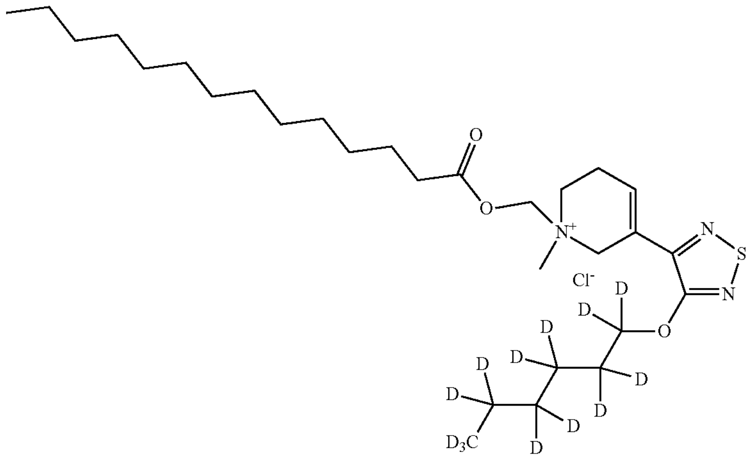 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCCCCC)C1 ; [Cl-]] |
| 59 | 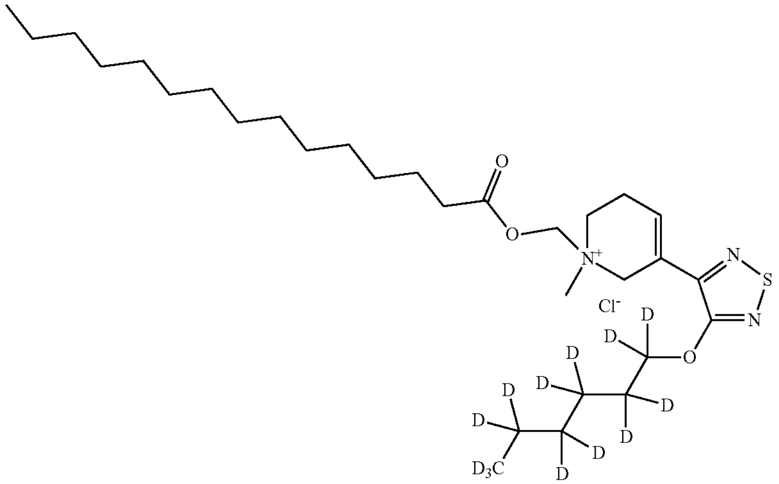 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCCCCCC)C1 ; [Cl-]] |

TABLE 1-continued
| Cpd No. | Structure |
|---|---|
| 60 | 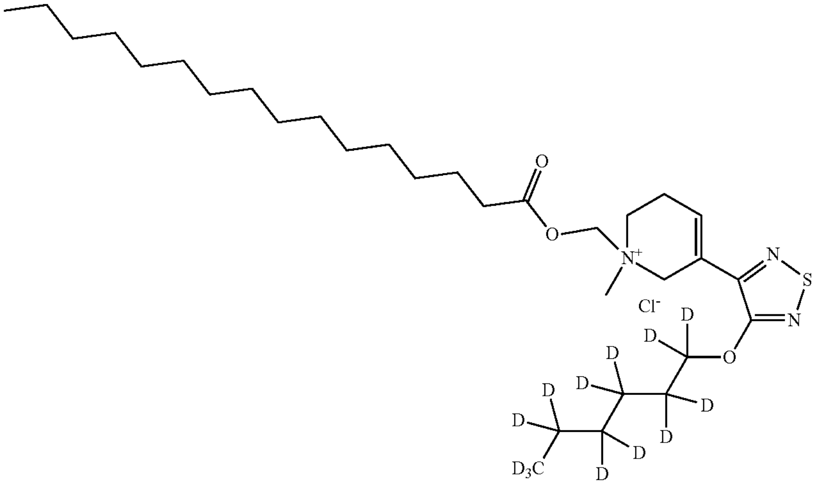 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCCCCCCC)C1 ; [Cl-]] |
| 61 | 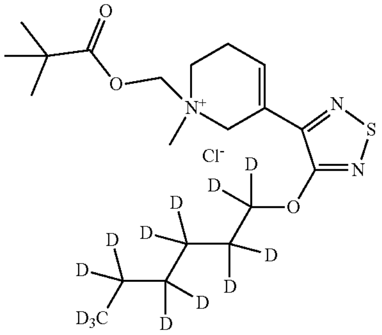 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)C(C)(C)C)C1 ; [Cl-]] |
| 62 | 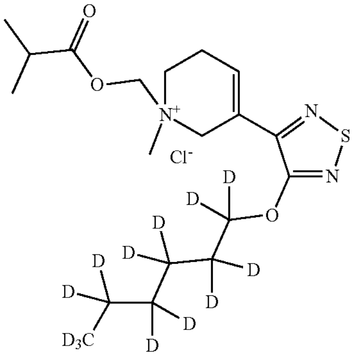 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)C(C)C)C1 ; [Cl-]] |
| 63 | 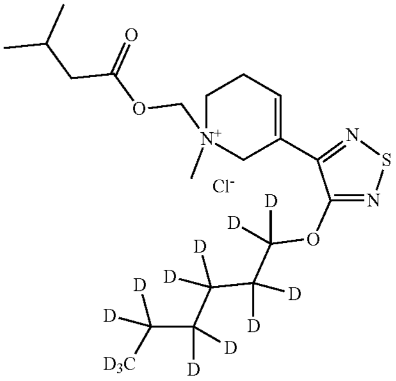 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CC(C)C)C1 ; [Cl-]] |

TABLE 1-continued
| Cpd No. | Structure |
|---|---|
| 64 | 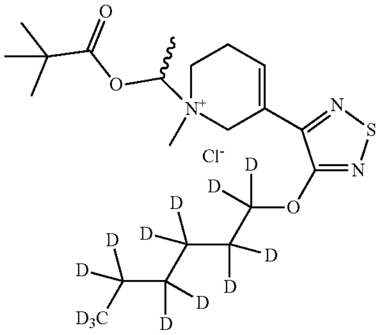 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)C(C)(C)C)C1 ; [Cl-]] |
| 65 | 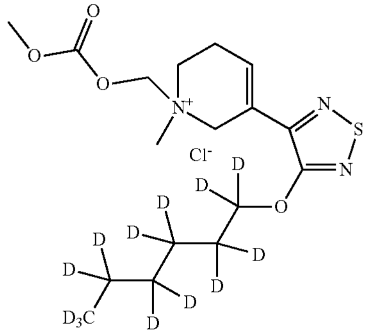 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC)C1 ; [Cl-]] |
| 66 | 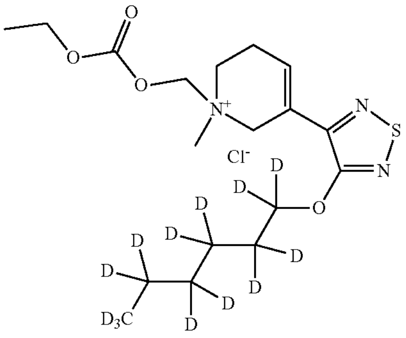 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCC)C1 ; [Cl-]] |
| 67 | 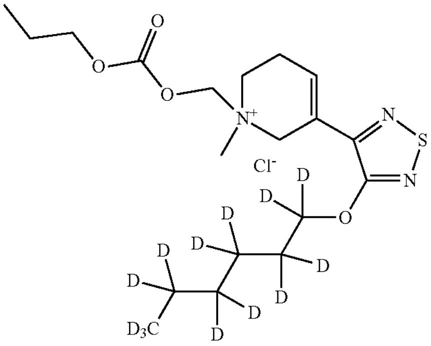 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCC)C1 ; [Cl-]] |

TABLE 1-continued
| Cpd No. | Structure |
| --- | --- |
| 68 | 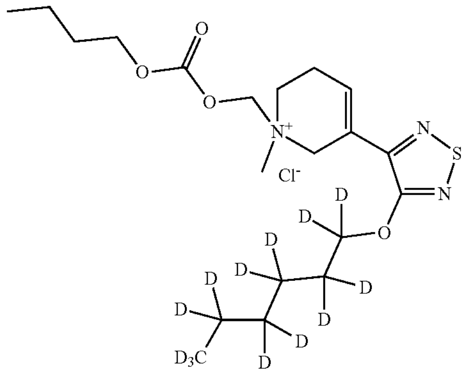 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCC)C1 ; [Cl-]] |
| 69 | 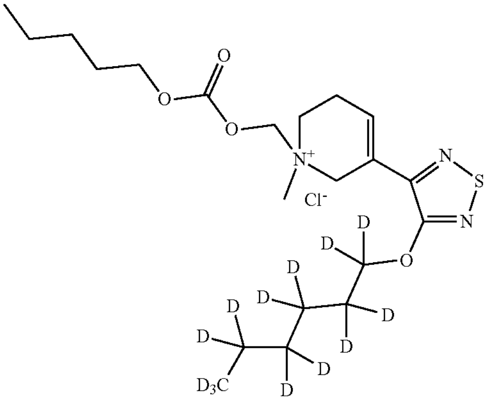 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCC)C1 ; [Cl-]] |
| 70 | 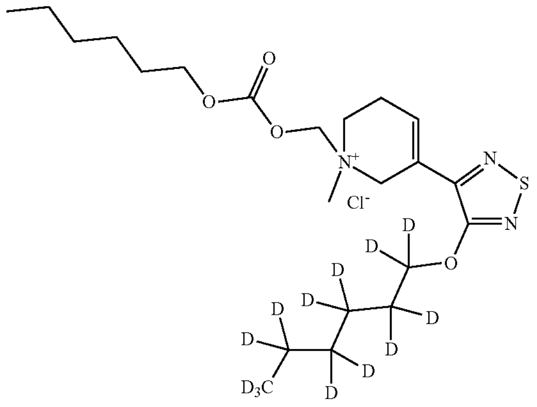 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCC)C1 ; [Cl-]] |
| 71 | 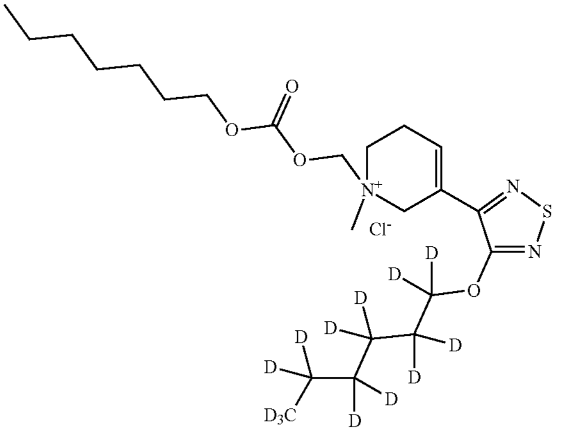 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCCC)C1 ; [Cl-]] |

TABLE 1-continued
| Cpd No. | Structure |
| --- | --- |
| 72 | 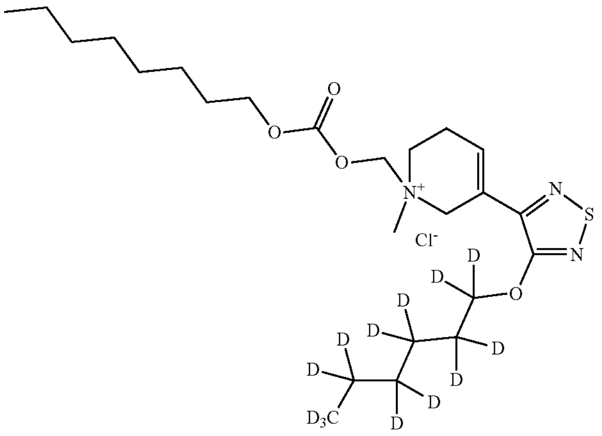 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCCCC)C1 ; [Cl-]] |
| 73 | 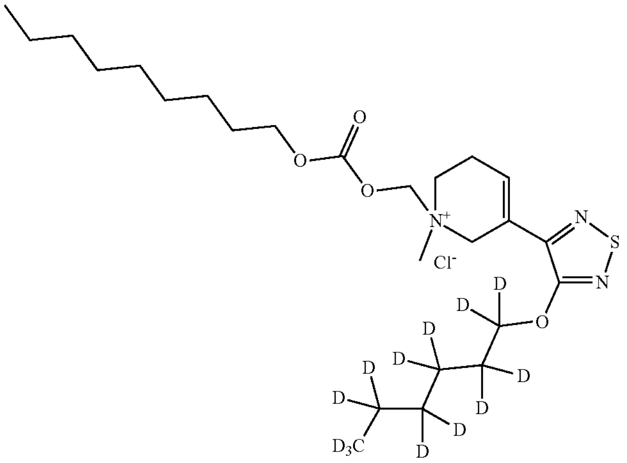 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCCCCC)C1 ; [Cl-]] |
| 74 | 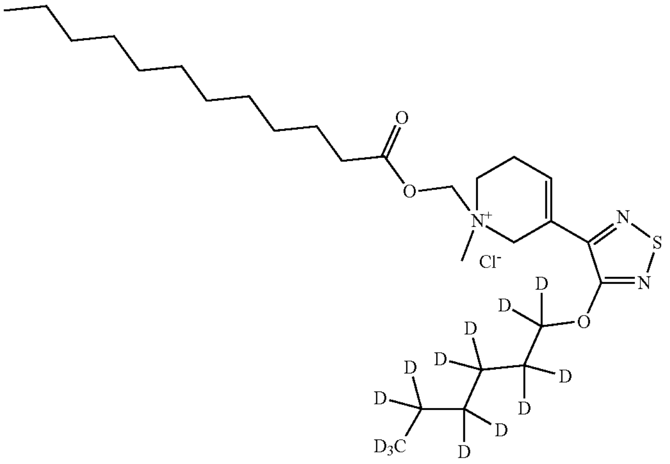 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCCC)C1 ; [Cl-]] |

TABLE 1-continued
| Cpd No. | Structure |
|---|---|
| 75 | 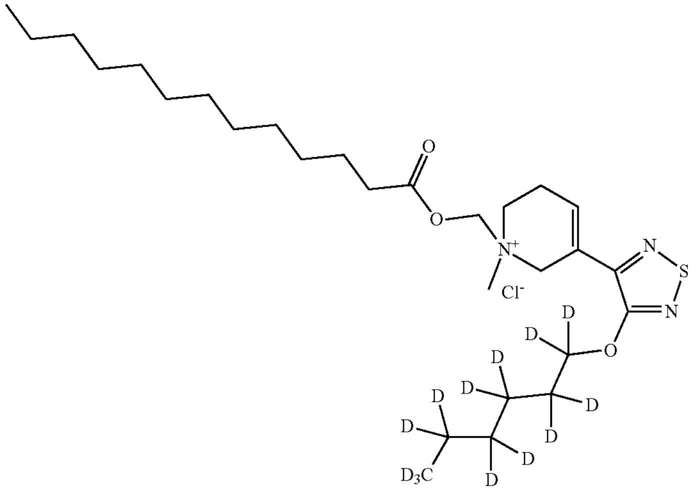 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCCCC)C1 ; [Cl-]] |
| 76 | 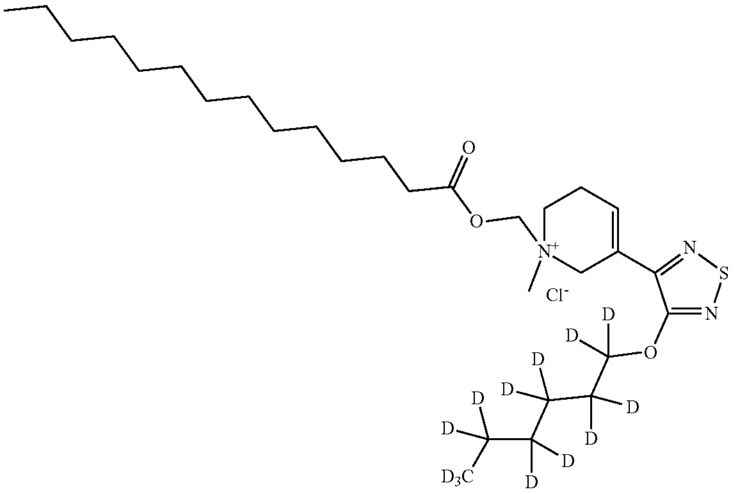 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCCCCCC)C1 ; [Cl-]] |
| 77 | 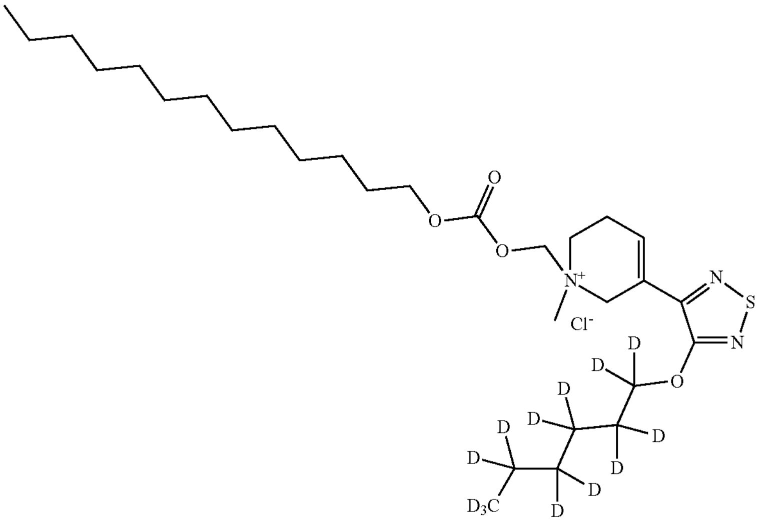 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCCCCCCCCC)C1 ; [Cl-]] |

TABLE 1-continued
| Cpd No. | Structure |
| --- | --- |
| 78 | 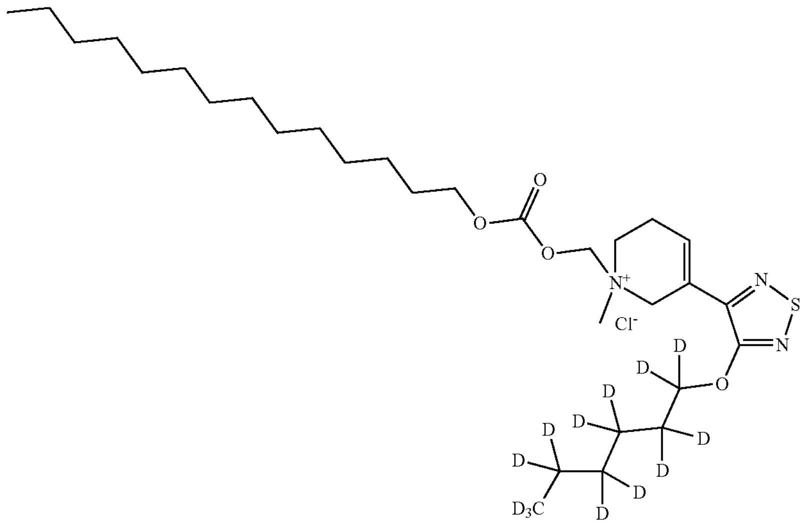 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCCCCCCCCCC)C1 ; [Cl-]] |
| 79 | 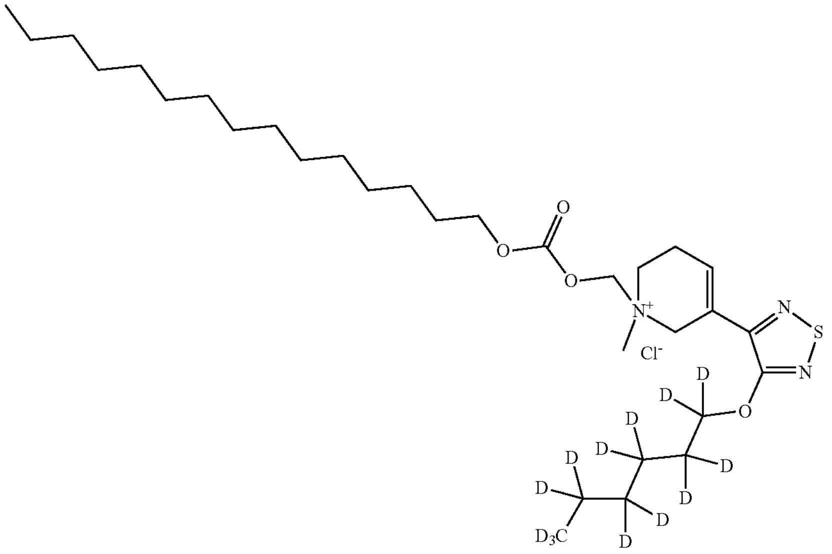 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCCCCCCCCCCC)C1 ; [Cl-]] |
| 80 | 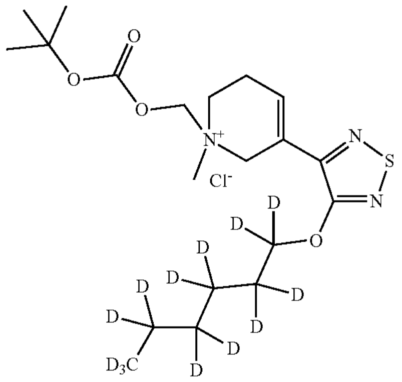 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC(C)(C)C)C1 ; [Cl-]] |

TABLE 1-continued
| Cpd No. | Structure |
|---|---|
| 81 | 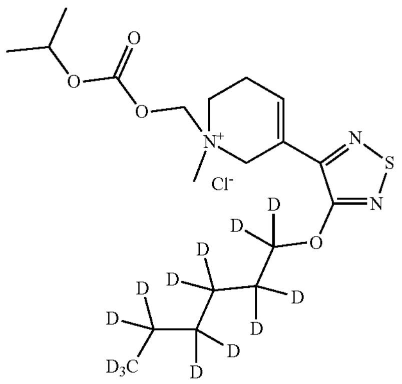 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC(C)C)C1 ; [Cl-]] |
| 82 | 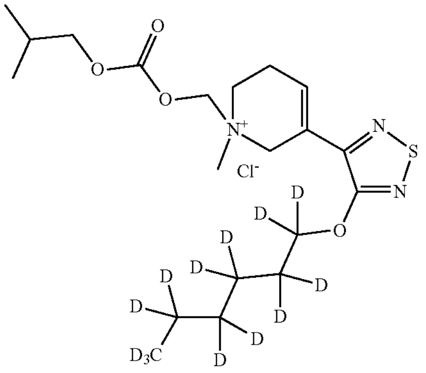 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCC(C)C)C1 ; [Cl-]] |
| 83 | 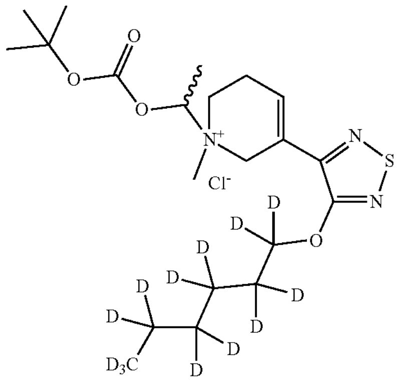 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC(C)(C)C)C1 ; [Cl-]] |
| 84 | 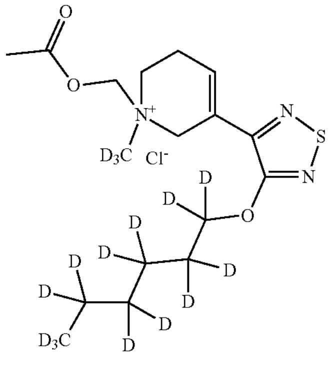 [SMILES: [2H]C([2H])([2H])C([2H])([2H])C([2H])([2H])C([2H])([2H])C([2H])([2H])C([2H])([2H])Oc1nsnc1C1=CCC[N+](COC(C)=O)(C([2H])([2H])[2H])C1 ; [Cl-]] |

TABLE 1-continued
| Cpd No. | Structure |
| --- | --- |
| 85 | 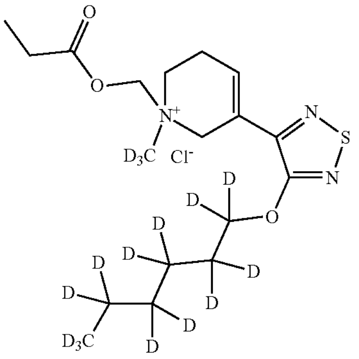 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CC)(C([2H])([2H])[2H])C1 ; [Cl-]] |
| 86 | 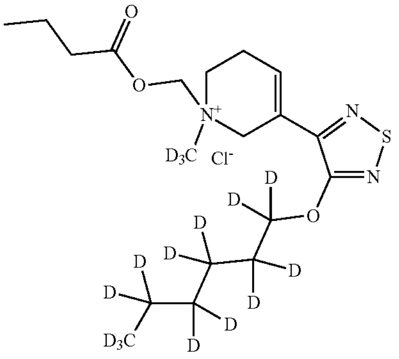 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCC)(C([2H])([2H])[2H])C1 ; [Cl-]] |
| 87 | 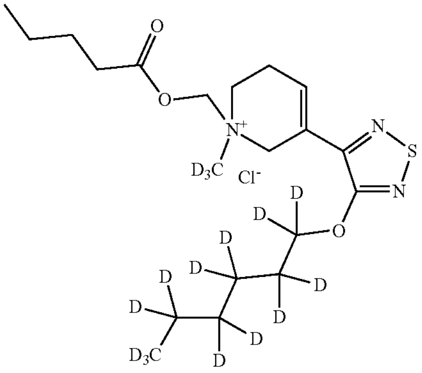 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCC)(C([2H])([2H])[2H])C1 ; [Cl-]] |
| 88 | 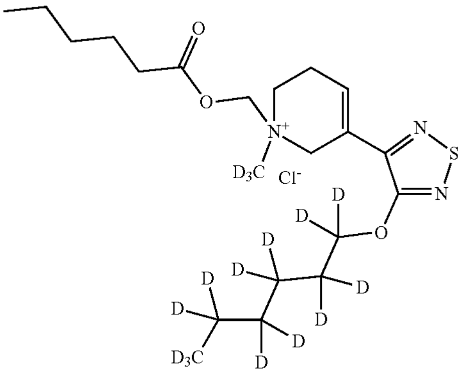 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCC)(C([2H])([2H])[2H])C1 ; [Cl-]] |

TABLE 1-continued
| Cpd No. | Structure |
| --- | --- |
| 89 | 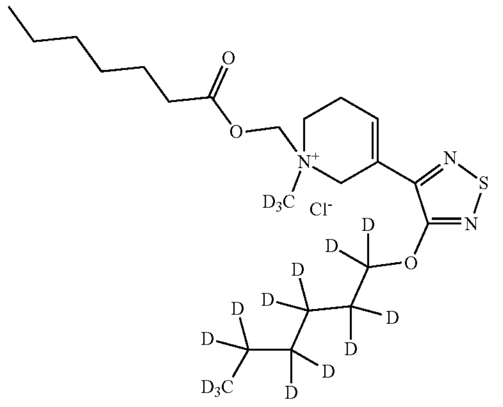 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCC)(C([2H])([2H])[2H])C1 ; [Cl-]] |
| 90 | 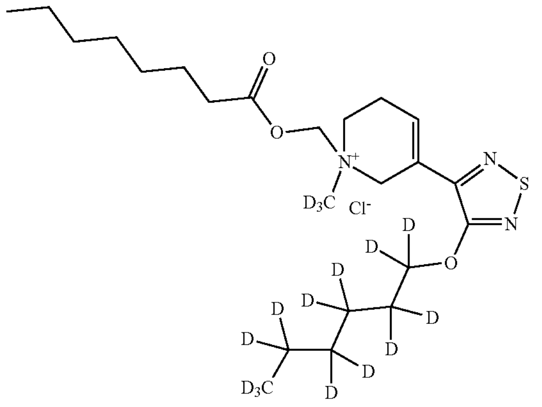 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCC)(C([2H])([2H])[2H])C1 ; [Cl-]] |
| 91 | 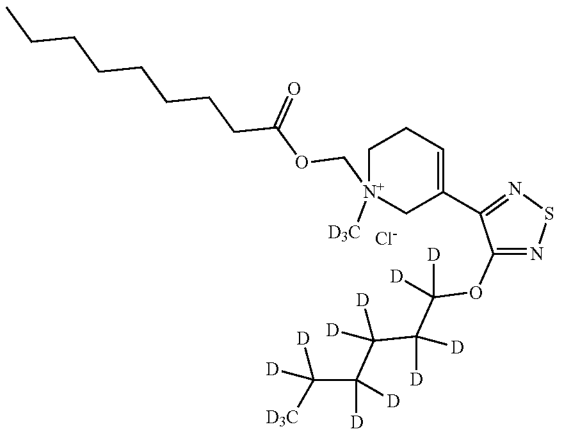 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCC)(C([2H])([2H])[2H])C1 ; [Cl-]] |

TABLE 1-continued
| Cpd No. | Structure |
| --- | --- |
| 92 | 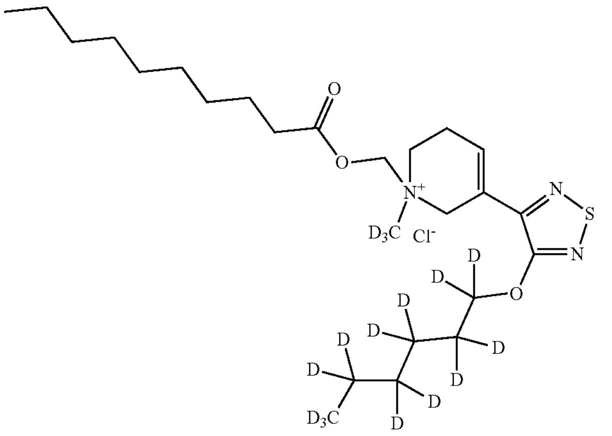 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCC)(C([2H])([2H])[2H])C1 ; [Cl-]] |
| 93 | 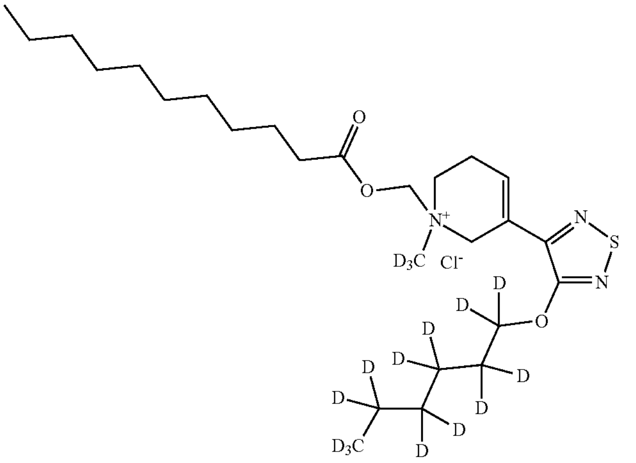 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCC)(C([2H])([2H])[2H])C1 ; [Cl-]] |
| 94 | 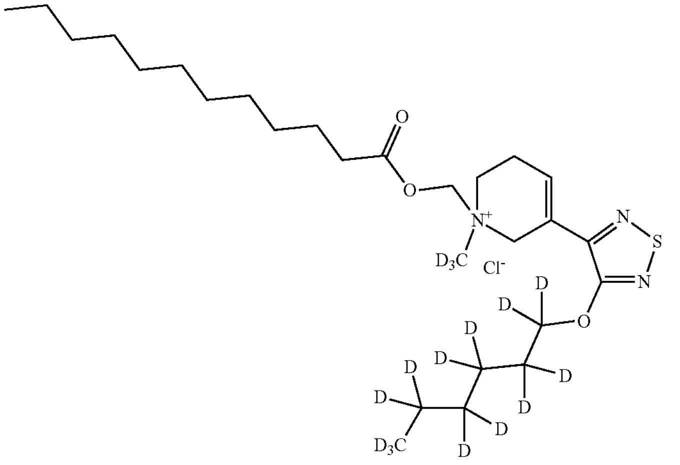 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCCC)(C([2H])([2H])[2H])C1 ; [Cl-]] |

TABLE 1-continued
| Cpd No. | Structure |
|---|---|
| 95 | 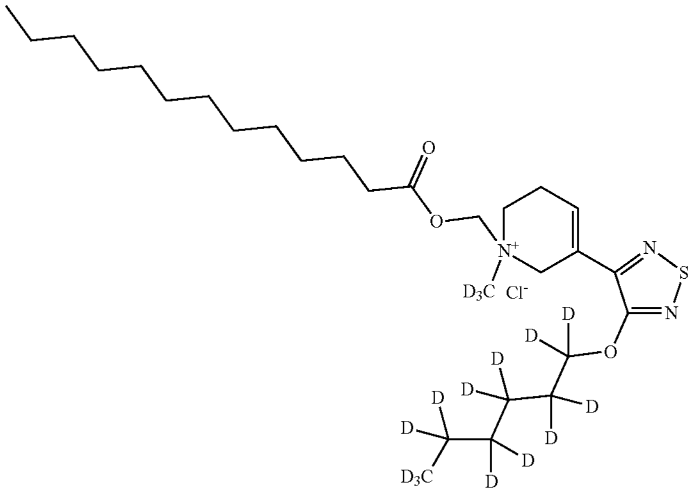 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCCCC)(C([2H])([2H])[2H])C1 ; [Cl-]] |
| 96 | 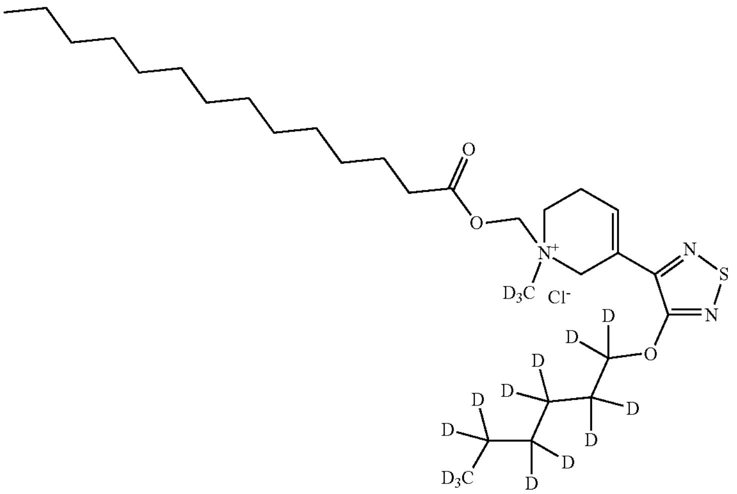 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCCCCC)(C([2H])([2H])[2H])C1 ; [Cl-]] |
| 97 | 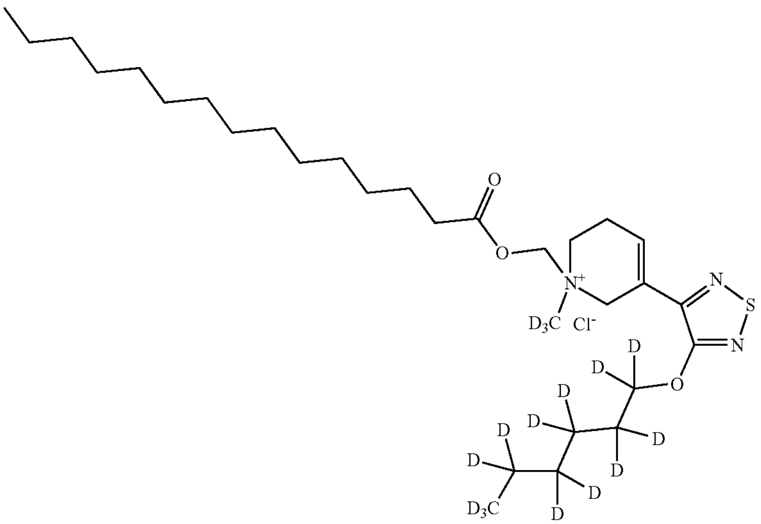 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCCCCCC)(C([2H])([2H])[2H])C1 ; [Cl-]] |

TABLE 1-continued
| Cpd No. | Structure |
| --- | --- |
| 98 | 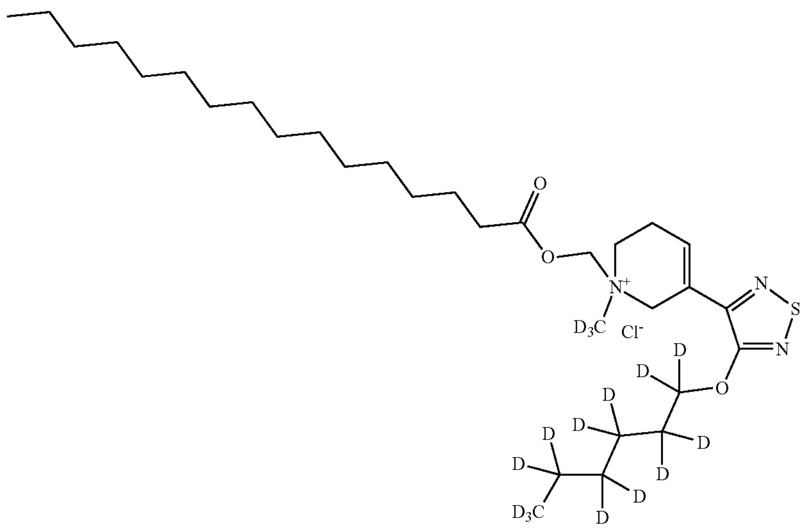 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCCCCCCC)(C([2H])([2H])[2H])C1 ; [Cl-]] |
| 99 | 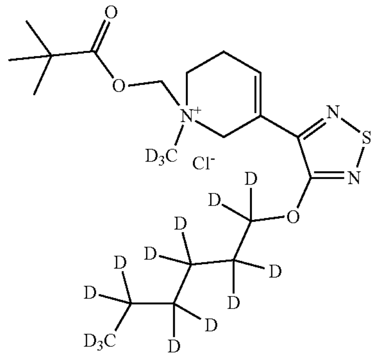 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)C(C)(C)C)(C([2H])([2H])[2H])C1 ; [Cl-]] |
| 100 | 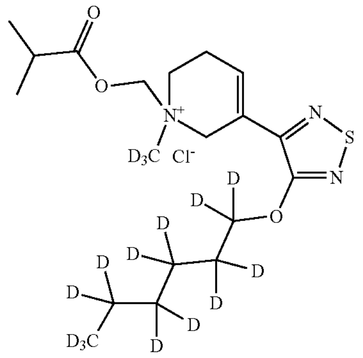 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)C(C)C)(C([2H])([2H])[2H])C1 ; [Cl-]] |

TABLE 1-continued
| Cpd No. | Structure |
| --- | --- |
| 101 | 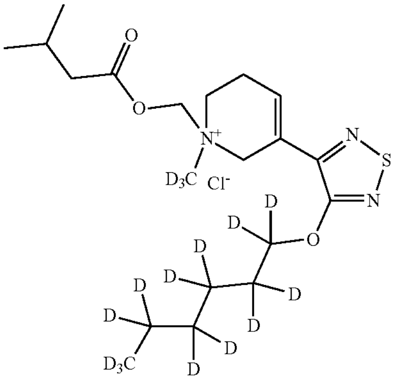 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CC(C)C)(C([2H])([2H])[2H])C1 ; [Cl-]] |
| 102 | 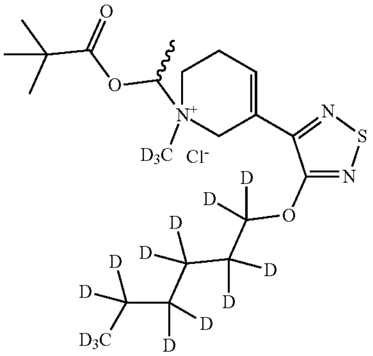 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)C(C)(C)C)(C([2H])([2H])[2H])C1 ; [Cl-]] |
| 103 | 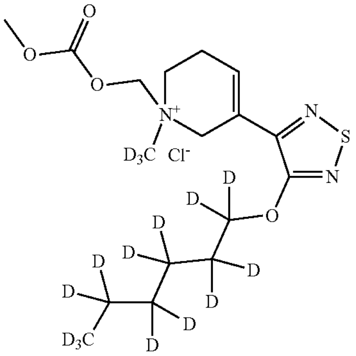 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC)(C([2H])([2H])[2H])C1 ; [Cl-]] |
| 104 | 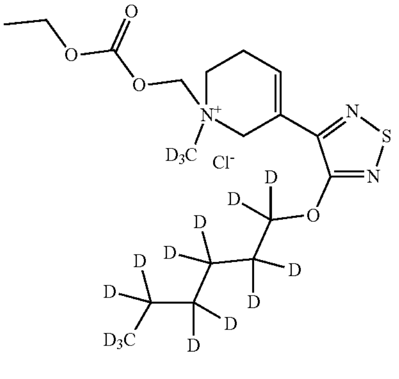 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCC)(C([2H])([2H])[2H])C1 ; [Cl-]] |

TABLE 1-continued
| Cpd No. | Structure |
|---|---|
| 105 | 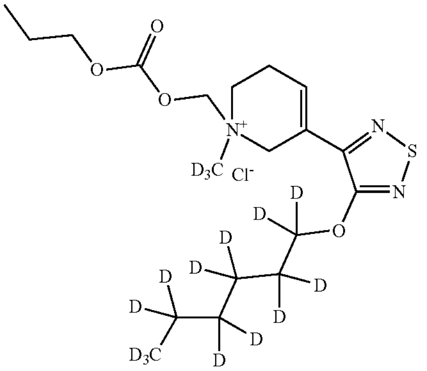 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCC)(C([2H])([2H])[2H])C1 ; [Cl-]] |
| 106 | 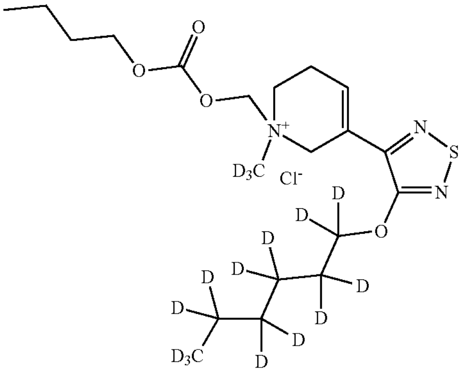 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCCC)(C([2H])([2H])[2H])C1 ; [Cl-]] |
| 107 | 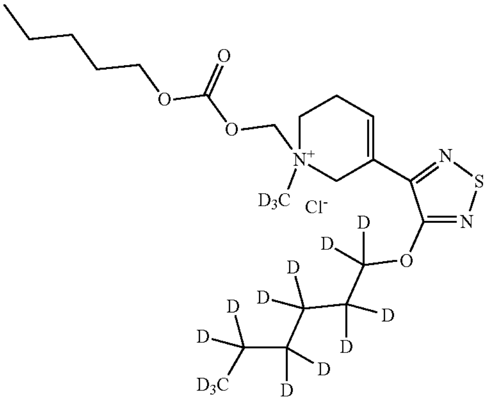 |
| 108 | 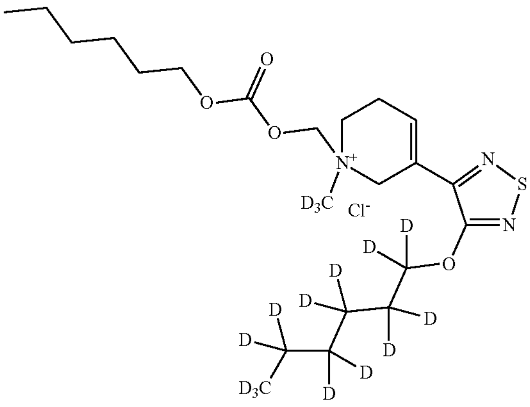 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCCCCC)(C([2H])([2H])[2H])C1 ; [Cl-]] |

TABLE 1-continued
| Cpd No. | Structure |
| --- | --- |
| 109 | 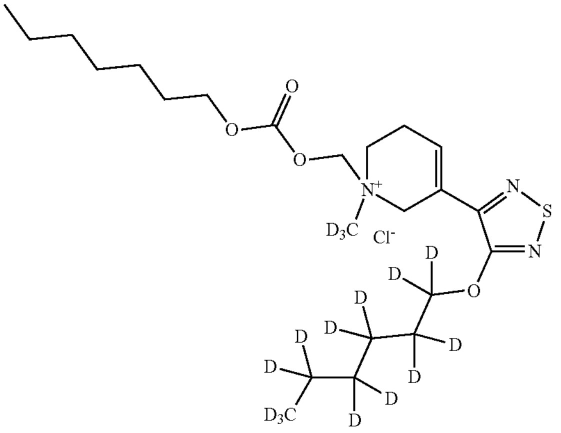 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCCCCCC)(C([2H])([2H])[2H])C1 ; [Cl-]] |
| 110 | 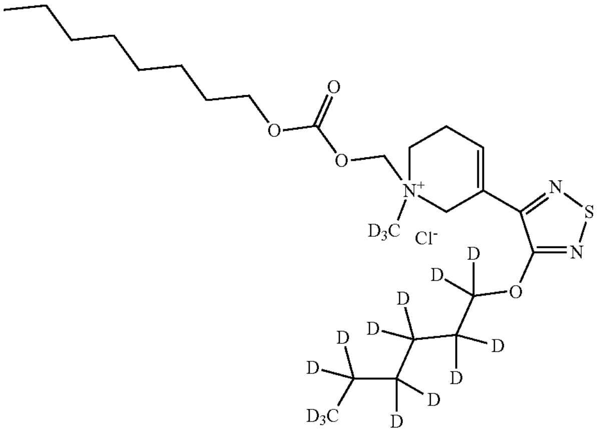 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCCCCCCC)(C([2H])([2H])[2H])C1 ; [Cl-]] |
| 111 | 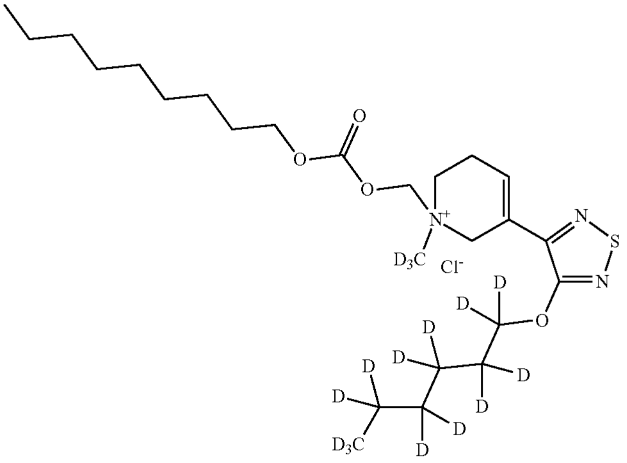 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCCCCCCCC)(C([2H])([2H])[2H])C1 ; [Cl-]] |

TABLE 1-continued
| Cpd No. | Structure |
|---|---|
| 112 | 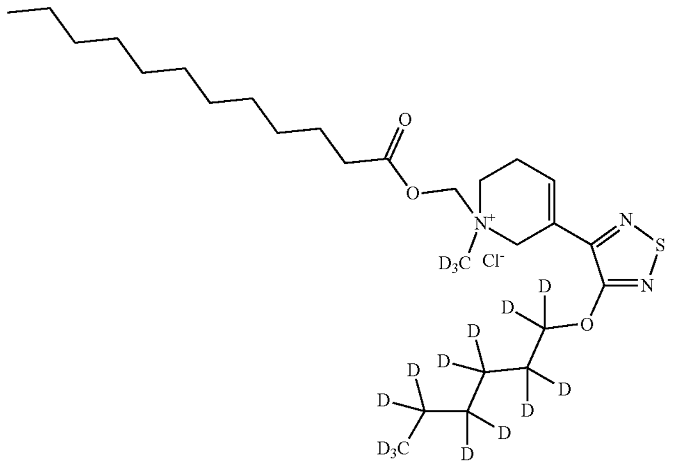 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCCC)(C([2H])([2H])[2H])C1 ; [Cl-]] |
| 113 | 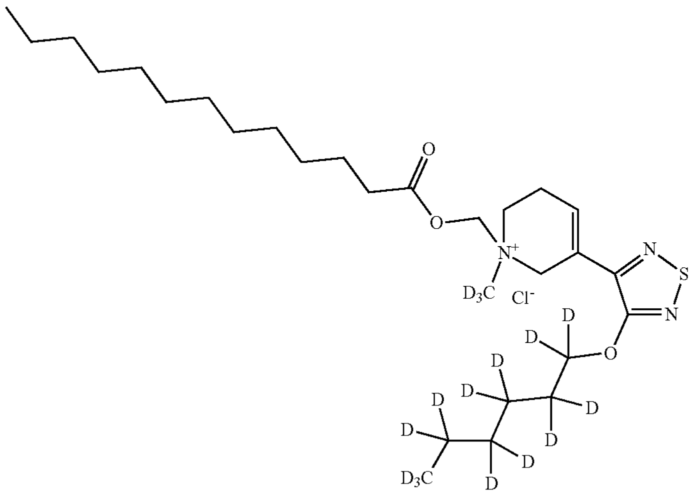 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCCCC)(C([2H])([2H])[2H])C1 ; [Cl-]] |
| 114 | 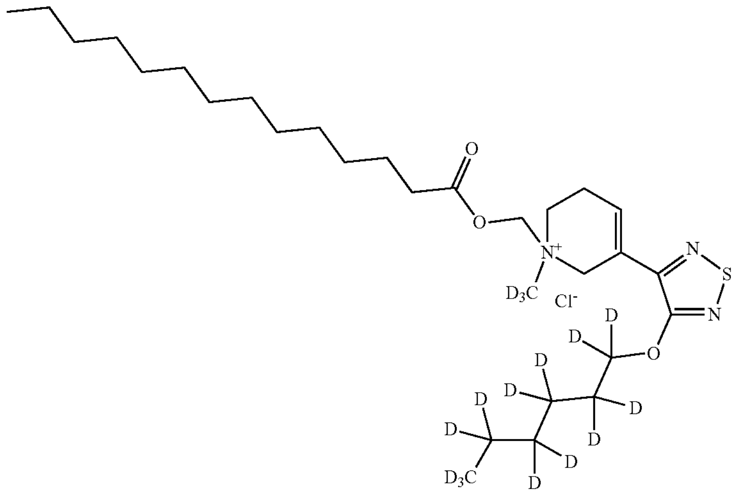 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCCCCCCCC)(C([2H])([2H])[2H])C1 ; [Cl-]] |

TABLE 1-continued
| Cpd No. | Structure |
|---|---|
| 115 | 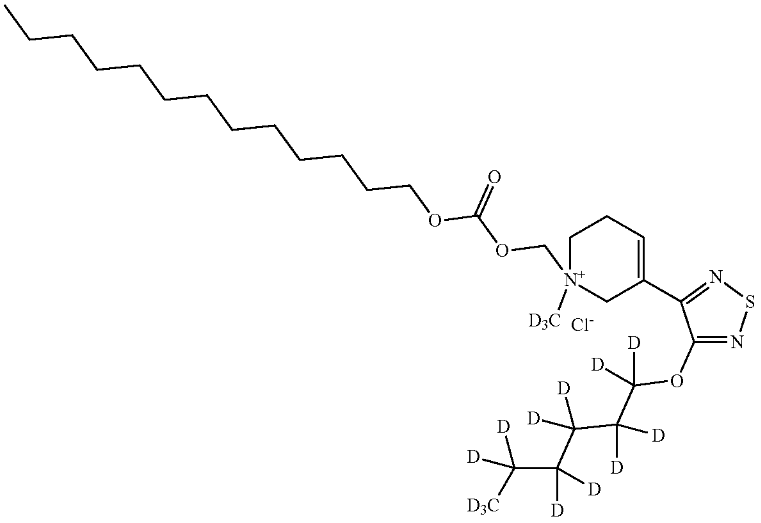 |
| 116 | 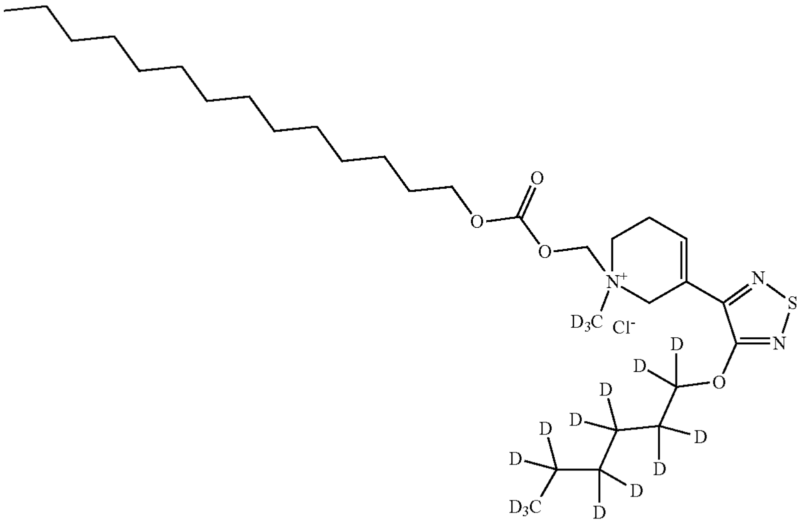 |
| 117 | 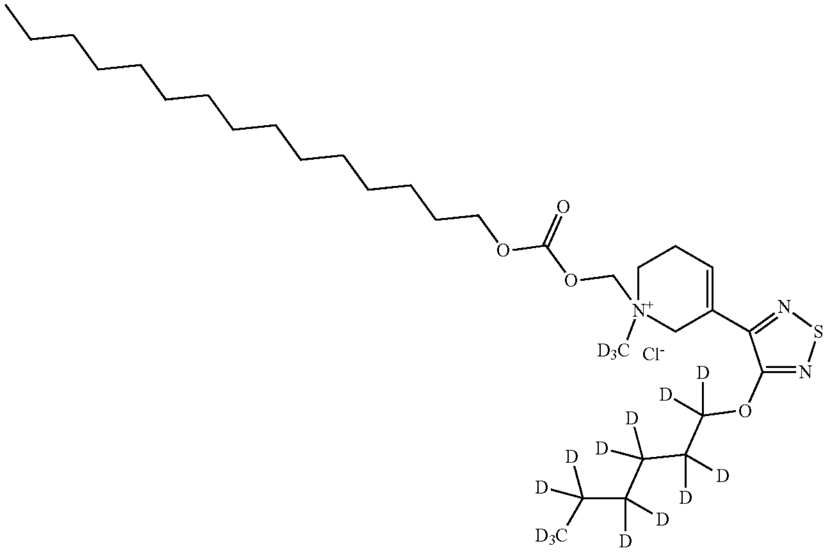 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCCCCCCCCCCCCCC)(C([2H])([2H])[2H])C1 ; [Cl-]] |

TABLE 1-continued
| Cpd No. | Structure |
| --- | --- |
| 118 | 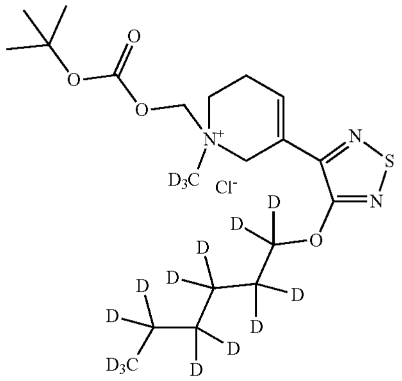 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC(C)(C)C)(C([2H])([2H])[2H])C1 ; [Cl-]] |
| 119 | 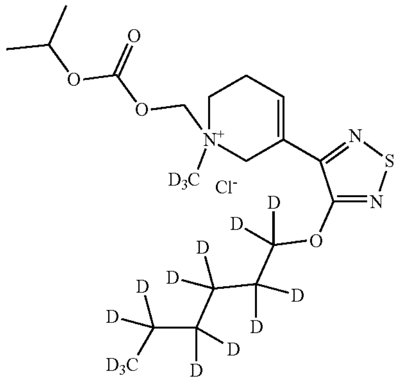 |
| 120 | 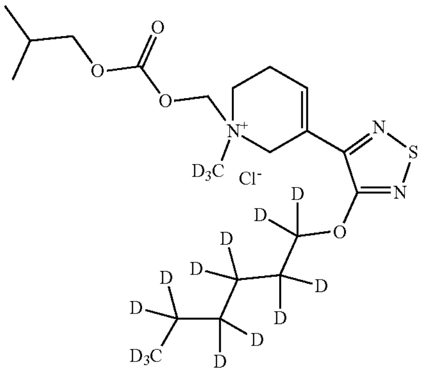 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCC(C)C)(C([2H])([2H])[2H])C1 ; [Cl-]] |
| 121 | 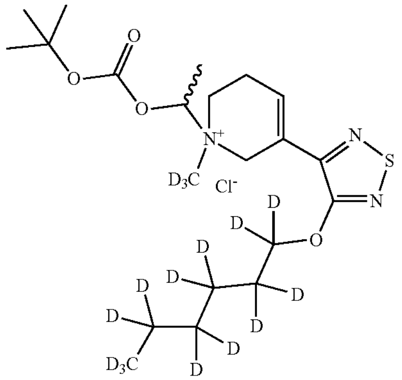 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC(C)(C)C)(C([2H])([2H])[2H])C1 ; [Cl-]] |

TABLE 1-continued
| Cpd No. | Structure |
| --- | --- |
| 122 | 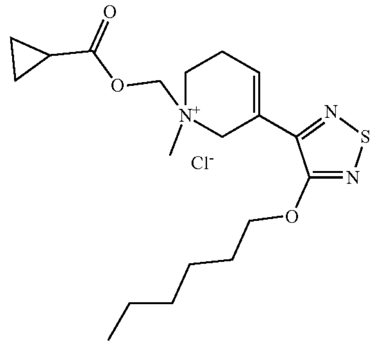 [SMILES: CCCCCCOc1nsnc1C1=CCC[N+](C)(COC(=O)C2CC2)C1 ; [Cl-]] |
| 123 | 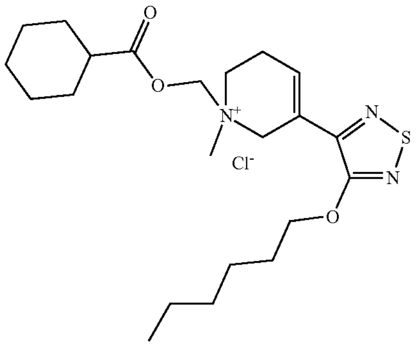 [SMILES: CCCCCCOc1nsnc1C1=CCC[N+](C)(COC(=O)C2CCCCC2)C1 ; [Cl-]] |
| 124 | 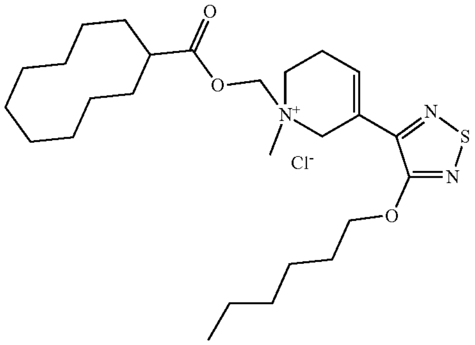 [SMILES: CCCCCCOc1nsnc1C1=CCC[N+](C)(COC(=O)C2CCCCCCCCC2)C1 ; [Cl-]] |
| 125 | 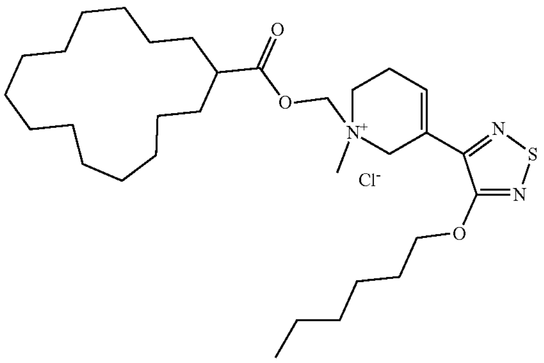 [SMILES: CCCCCCOc1nsnc1C1=CCC[N+](C)(COC(=O)C2CCCCCCCCCCCCCC2)C1 ; [Cl-]] |

TABLE 1-continued
| Cpd No. | Structure |
| --- | --- |
| 126 | 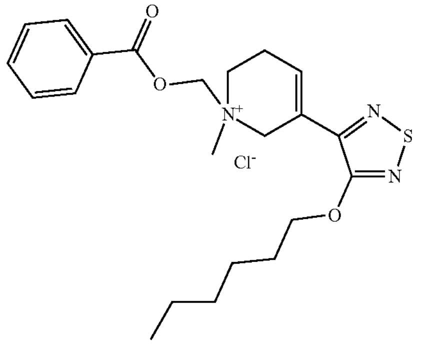 [SMILES: CCCCCCOc1nsnc1C1=CCC[N+](C)(COC(=O)c2ccccc2)C1 ; [Cl-]] |
| 127 | 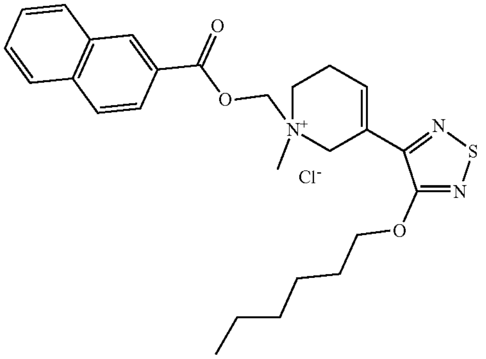 [SMILES: CCCCCCOc1nsnc1C1=CCC[N+](C)(COC(=O)c2ccc3ccccc3c2)C1 ; [Cl-]] |
| 128 | 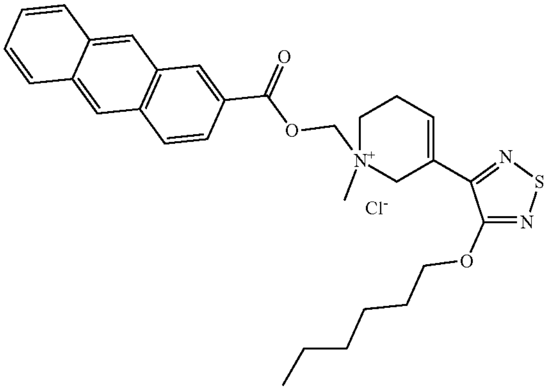 [SMILES: CCCCCCOc1nsnc1C1=CCC[N+](C)(COC(=O)c2ccc3cc4ccccc4cc3c2)C1 ; [Cl-]] |
| 129 | 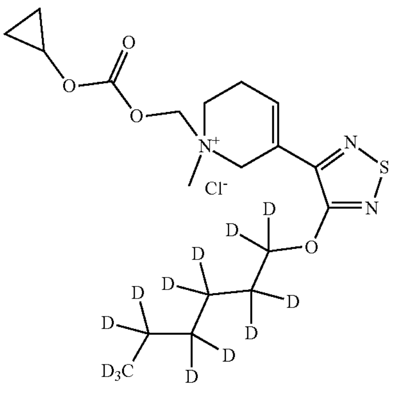 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC2CC2)C1 ; [Cl-]] |

TABLE 1-continued
| Cpd No. | Structure |
|---|---|
| 130 | 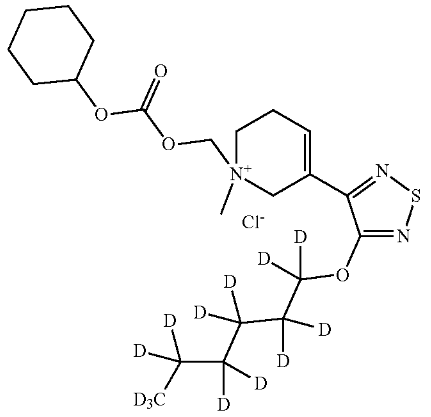 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC2CCCCC2)C1 ; [Cl-]] |
| 131 | 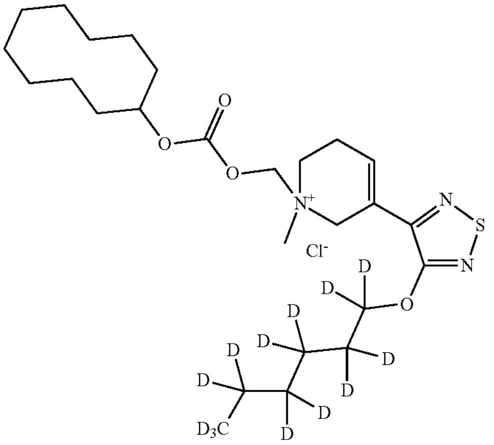 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC2CCCCCCCCC2)C1 ; [Cl-]] |
| 132 | 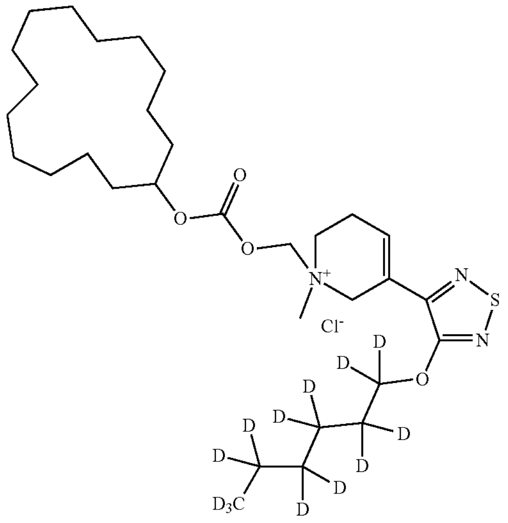 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC2CCCCCCCCCCCCCC2)C1 ; [Cl-]] |

TABLE 1-continued
| Cpd No. | Structure |
|---|---|
| 133 | 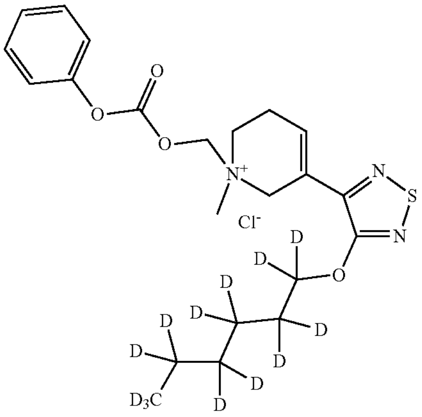 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)Oc2ccccc2)C1 ; [Cl-]] |
| 134 | 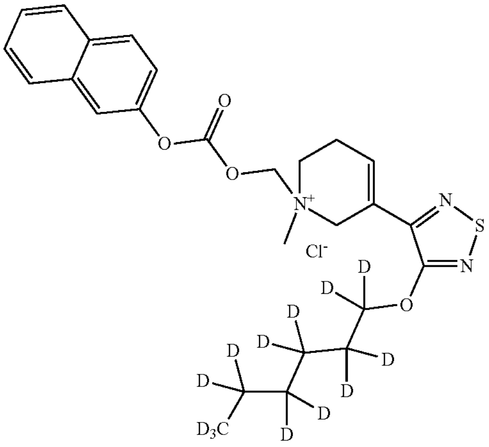 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)Oc2ccc3ccccc3c2)C1 ; [Cl-]] |
| 135 | 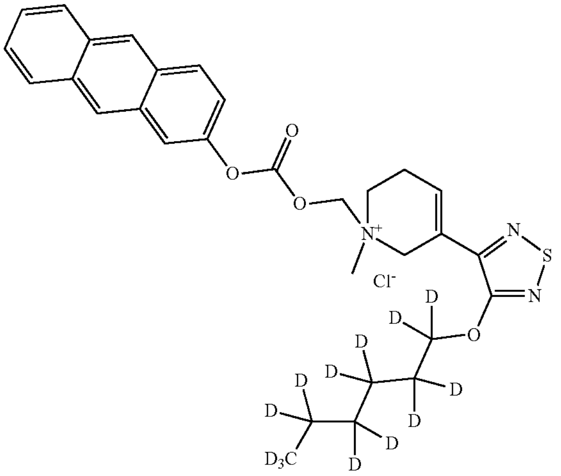 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)Oc2ccc3cc4ccccc4cc3c2)C1 ; [Cl-]] |

TABLE 1-continued
| Cpd No. | Structure |
|---|---|
| 136 | 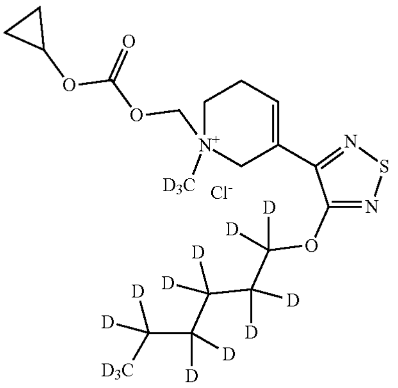 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC2CC2)(C([2H])([2H])[2H])C1 ; [Cl-]] |
| 137 | 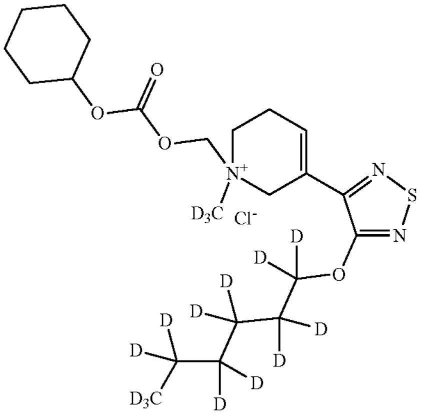 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC2CCCCC2)(C([2H])([2H])[2H])C1 ; [Cl-]] |
| 138 | 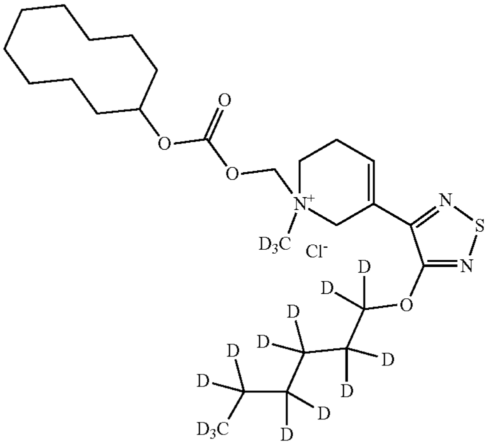 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC2CCCCCCCCC2)(C([2H])([2H])[2H])C1 ; [Cl-]] |

TABLE 1-continued
| Cpd No. | Structure |
|---|---|
| 139 | 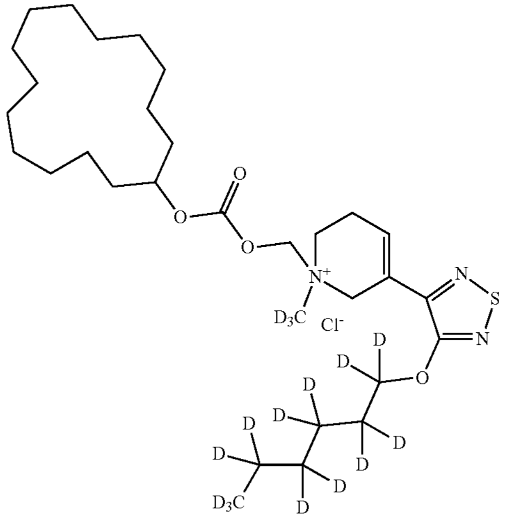 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC2CCCCCCCCCCCCCC2)(C([2H])([2H])[2H])C1 ; [Cl-]] |
| 140 | 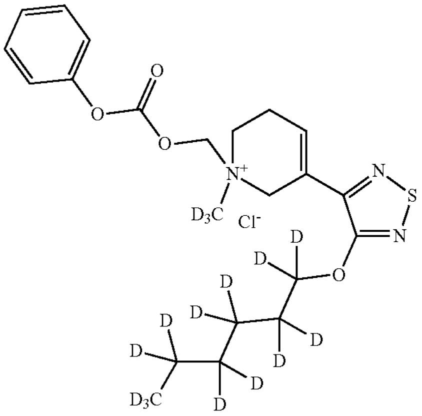 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)Oc2ccccc2)(C([2H])([2H])[2H])C1 ; [Cl-]] |
| 141 | 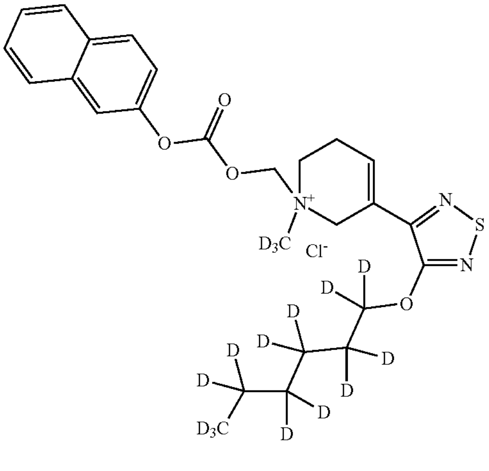 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)Oc2ccc3ccccc3c2)(C([2H])([2H])[2H])C1 ; [Cl-]] |

TABLE 1-continued
| Cpd No. | Structure |
|---|---|
| 142 | 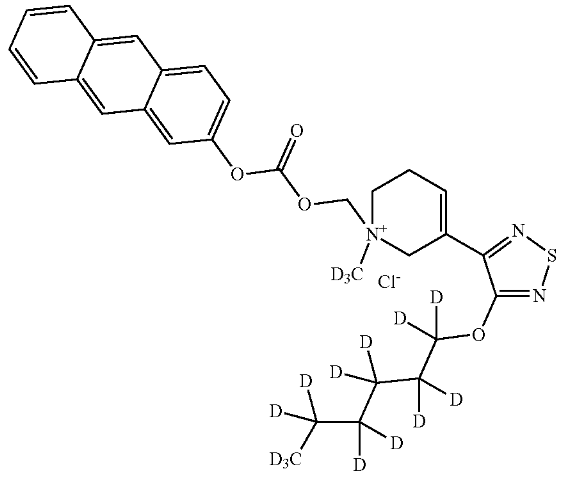 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)Oc2ccc3cc4ccccc4cc3c2)(C([2H])([2H])[2H])C1 ; [Cl-]] |
| 143 | 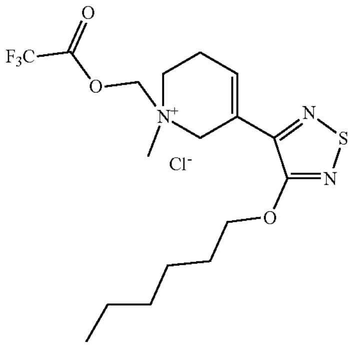 [SMILES: CCCCCCOc1nsnc1C1=CCC[N+](C)(COC(=O)C(F)(F)F)C1 ; [Cl-]] |
| 144 | 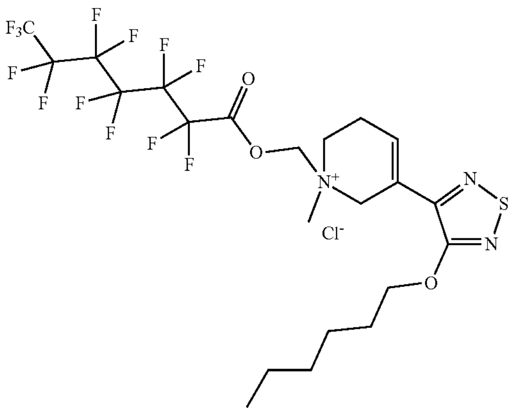 [SMILES: CCCCCCOc1nsnc1C1=CCC[N+](C)(COC(=O)C(F)(F)C(F)(F)C(F)(F)C(F)(F)C(F)(F)C(F)(F)F)C1 ; [Cl-]] |

TABLE 1-continued
| Cpd No. | Structure |
| --- | --- |
| 145 | 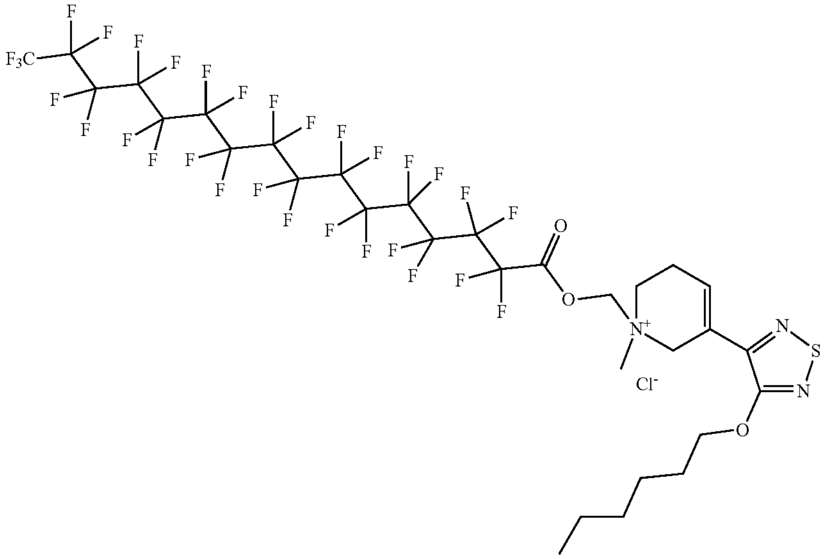 [SMILES: CCCCCCOc1nsnc1C1=CCC[N+](C)(COC(=O)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)C1 ; [Cl-]] |
| 146 | 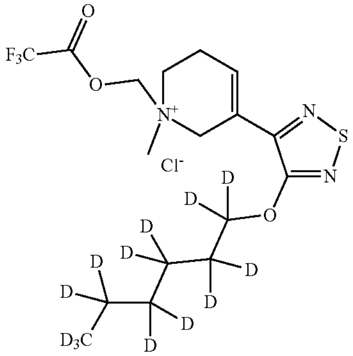 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)C(F)(F)F)C1 ; [Cl-]] |
| 147 | 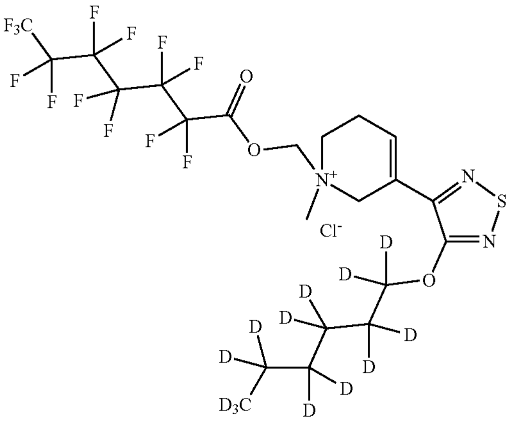 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)C(F)(F)C(F)(F)C(F)(F)C(F)(F)C(F)(F)C(F)(F)F)C1 ; [Cl-]] |

TABLE 1-continued
| Cpd No. | Structure |
| --- | --- |
| 148 | 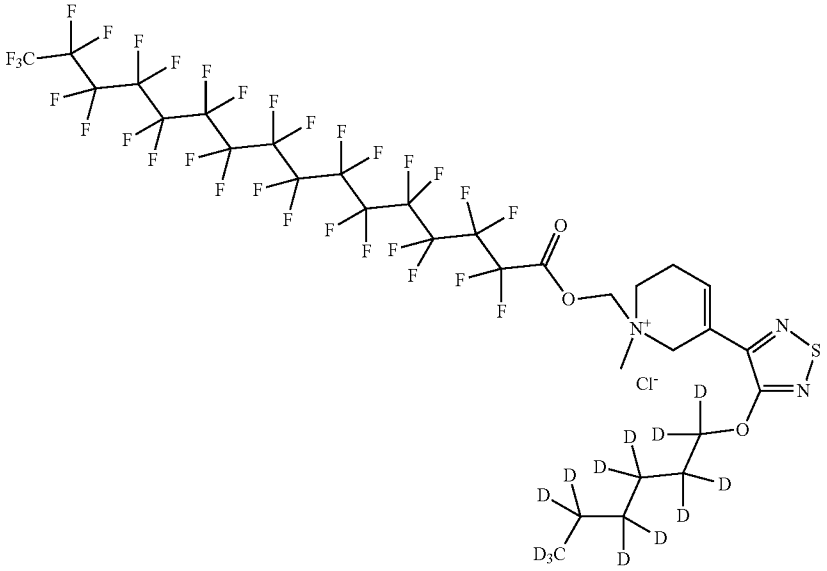 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)C1 ; [Cl-]] |
| 149 | 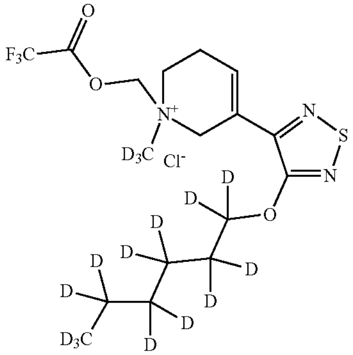 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)C(F)(F)F)(C([2H])([2H])[2H])C1 ; [Cl-]] |
| 150 | 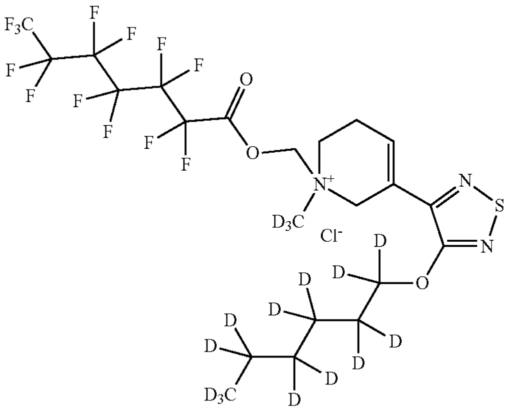 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)C(F)(F)C(F)(F)C(F)(F)C(F)(F)C(F)(F)C(F)(F)F)(C([2H])([2H])[2H])C1 ; [Cl-]] |

TABLE 1-continued
| Cpd No. | Structure |
| --- | --- |
| 151 | 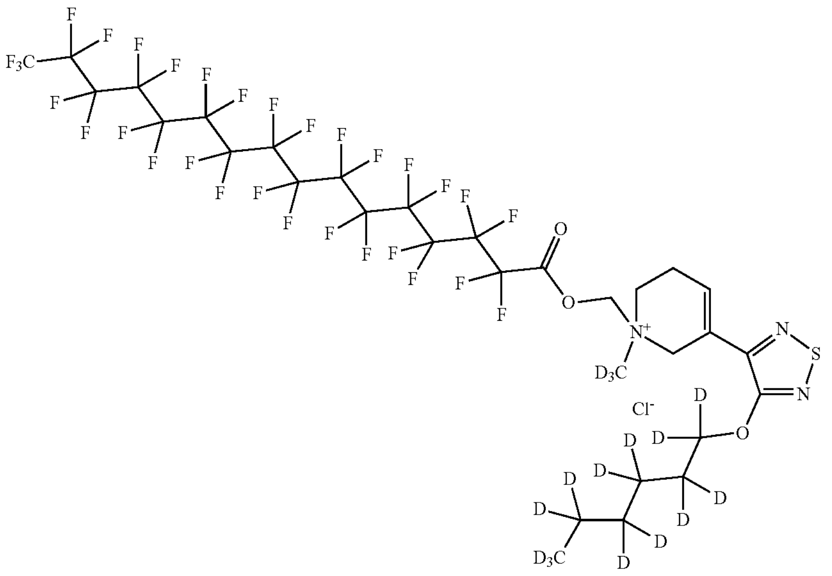 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)(C([2H])([2H])[2H])C1 ; [Cl-]] |
| 152 | 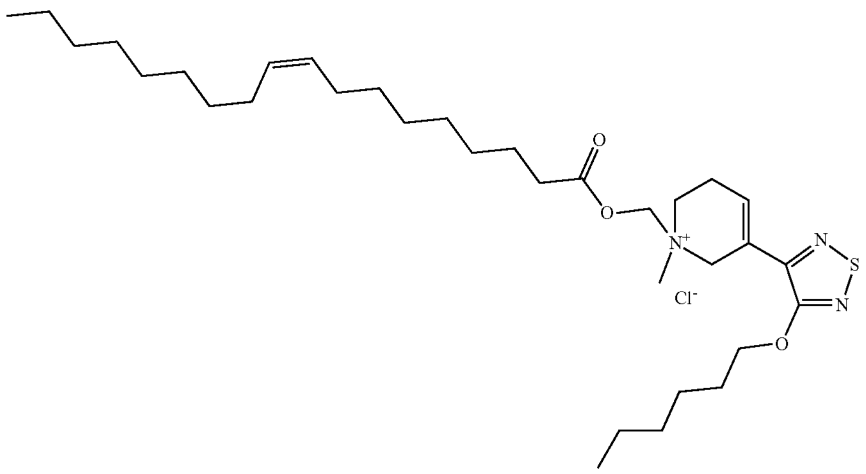 [SMILES: CCCCCCCC/C=C\CCCCCCCC(=O)OC[N+]1(C)CCC=C(c2nsnc2OCCCCCC)C1 ; [Cl-]] |
| 153 | 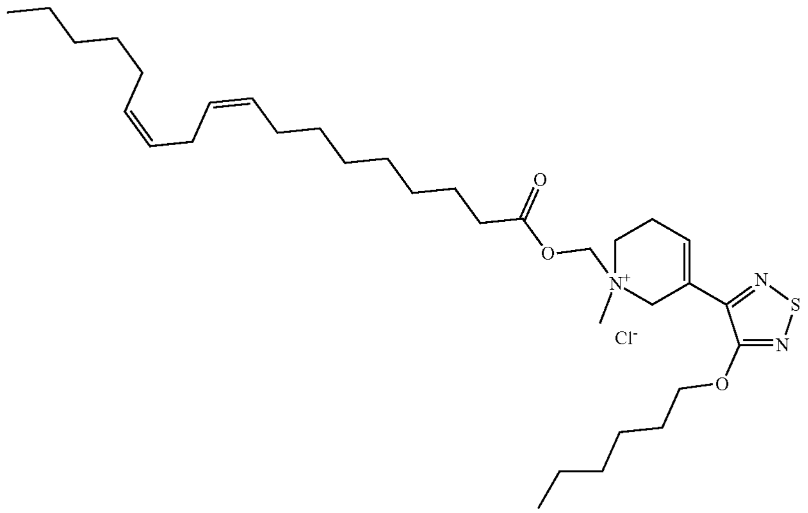 [SMILES: CCCCC/C=C\C/C=C\CCCCCCCC(=O)OC[N+]1(C)CCC=C(c2nsnc2OCCCCCC)C1 ; [Cl-]] |

TABLE 1-continued
| Cpd No. | Structure |
| --- | --- |
| 154 | 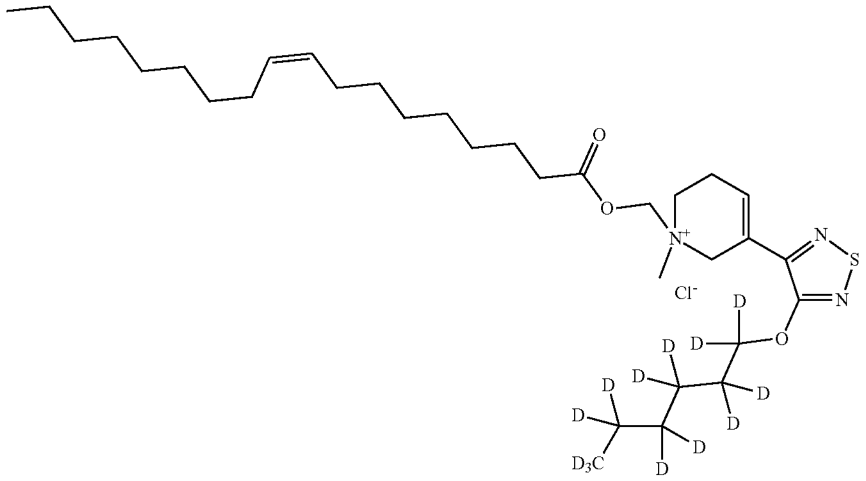 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCC/C=C\CCCCCCCC)C1 ; [Cl-]] |
| 155 | 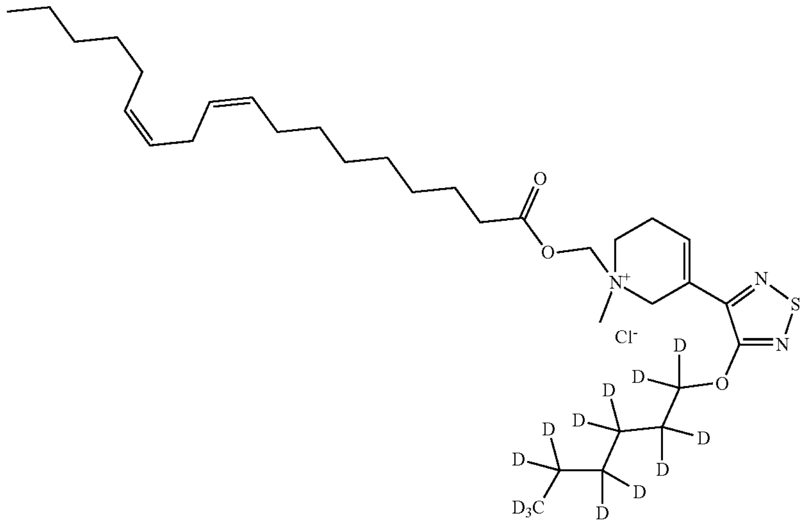 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCC/C=C\C/C=C\CCCCC)C1 ; [Cl-]] |
| 156 | 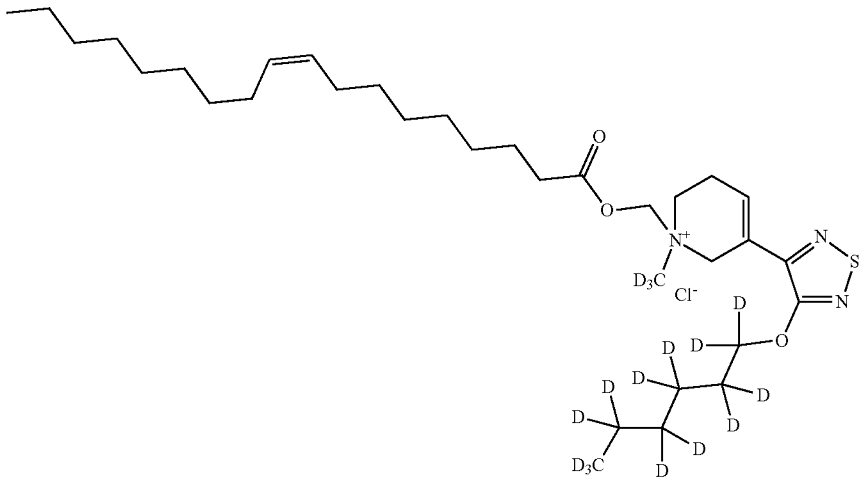 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCC/C=C\CCCCCCCC)(C([2H])([2H])[2H])C1 ; [Cl-]] |

TABLE 1-continued
| Cpd No. | Structure |
| --- | --- |
| 157 | 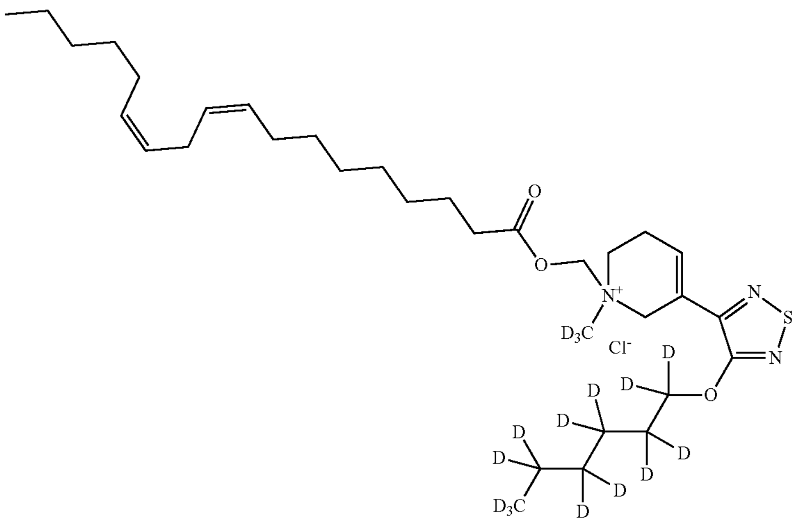 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)CCCCCCC/C=C\C/C=C\CCCCC)(C([2H])([2H])[2H])C1 ; [Cl-]] |
| 158 | 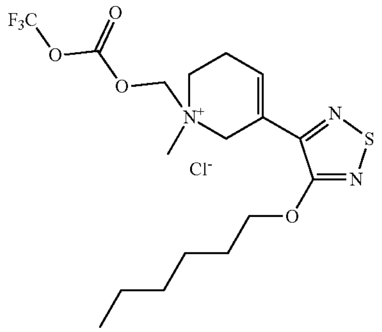 [SMILES: CCCCCCOc1nsnc1C1=CCC[N+](C)(COC(=O)OC(F)(F)F)C1 ; [Cl-]] |
| 159 | 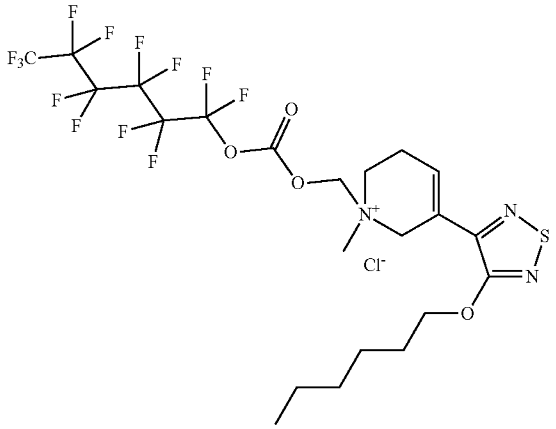 [SMILES: CCCCCCOc1nsnc1C1=CCC[N+](C)(COC(=O)OC(F)(F)C(F)(F)C(F)(F)C(F)(F)C(F)(F)C(F)(F)F)C1 ; [Cl-]] |

TABLE 1-continued
| Cpd No. | Structure |
|---|---|
| 160 | 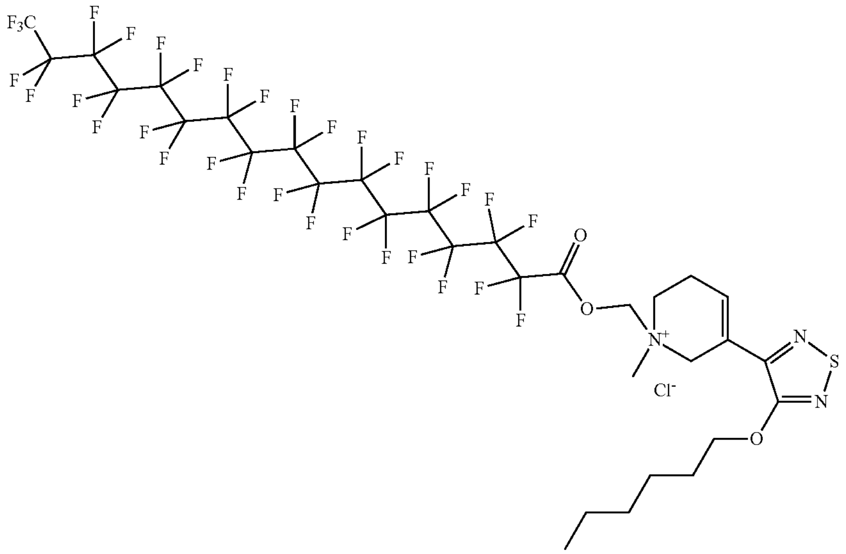 [SMILES: CCCCCCOc1nsnc1C1=CCC[N+](C)(COC(=O)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)C1 ; [Cl-]] |
| 161 | 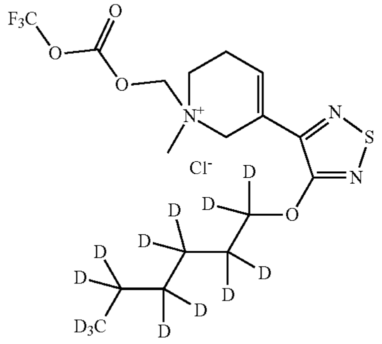 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC(F)(F)F)C1 ; [Cl-]] |
| 162 | 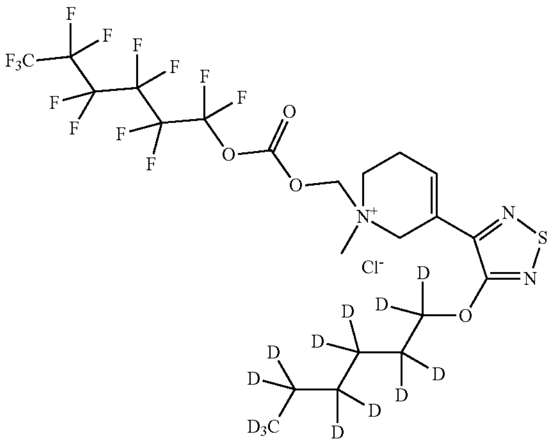 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC(F)(F)C(F)(F)C(F)(F)C(F)(F)C(F)(F)C(F)(F)F)C1 ; [Cl-]] |

TABLE 1-continued
| Cpd No. | Structure |
| --- | --- |
| 163 | 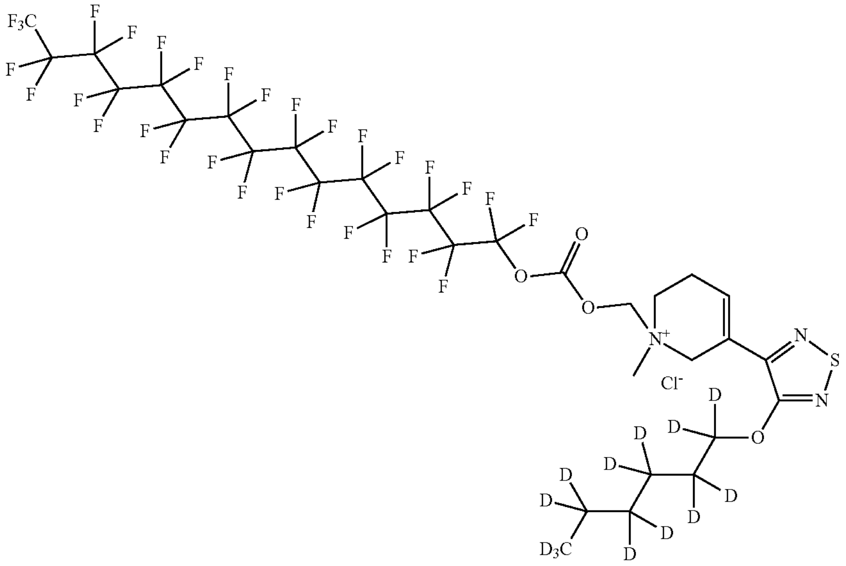 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)C1 ; [Cl-]] |
| 164 | 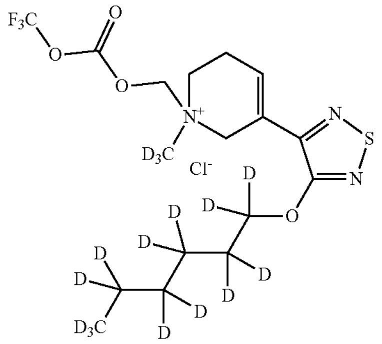 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC(F)(F)F)(C([2H])([2H])[2H])C1 ; [Cl-]] |
| 165 | 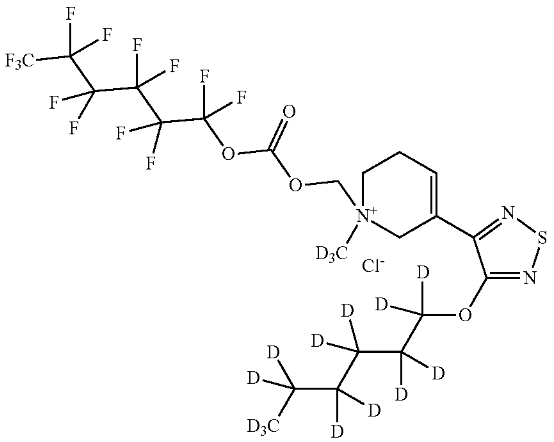 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC(F)(F)C(F)(F)C(F)(F)C(F)(F)C(F)(F)C(F)(F)F)(C([2H])([2H])[2H])C1 ; [Cl-]] |

TABLE 1-continued
| Cpd No. | Structure |
| --- | --- |
| 166 | 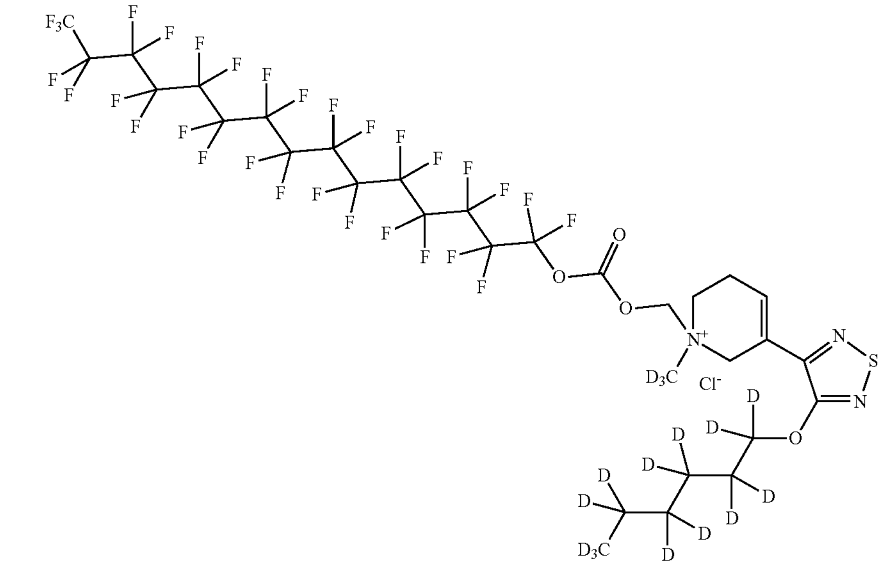 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)(C([2H])([2H])[2H])C1 ; [Cl-]] |
| 167 | 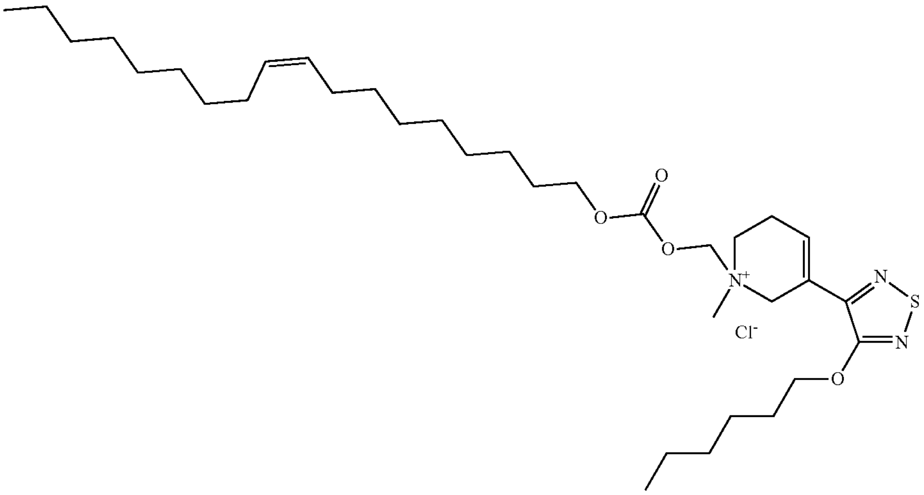 [SMILES: CCCCCCCC/C=C\CCCCCCCCOC(=O)OC[N+]1(C)CCC=C(c2nsnc2OCCCCCC)C1 ; [Cl-]] |
| 168 | 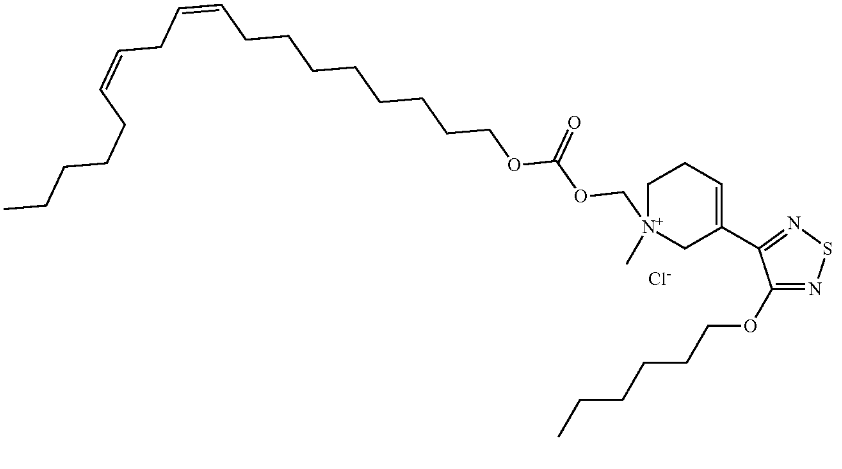 [SMILES: CCCCC/C=C\C/C=C\CCCCCCCCOC(=O)OC[N+]1(C)CCC=C(c2nsnc2OCCCCCC)C1 ; [Cl-]] |

TABLE 1-continued
| Cpd No. | Structure |
| --- | --- |
| 169 | 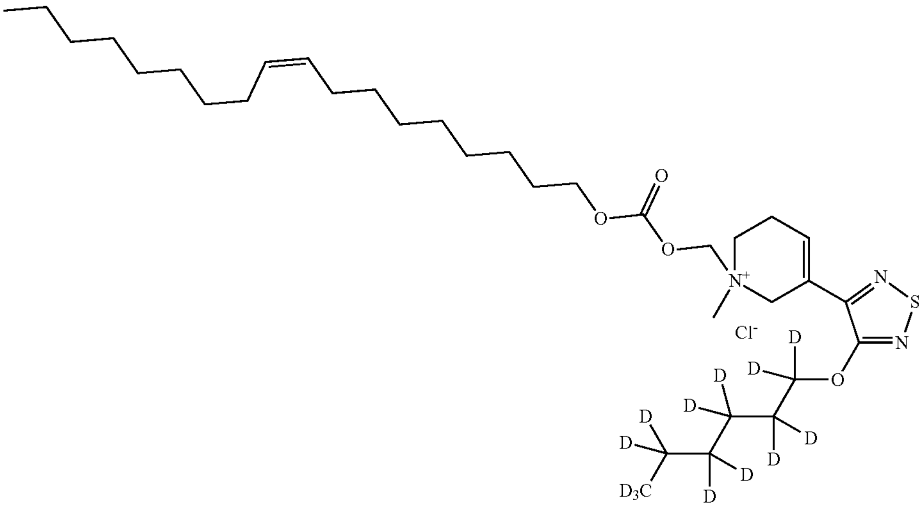 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCCCC/C=C\CCCCCCCC)C1 ; [Cl-]] |
| 170 | 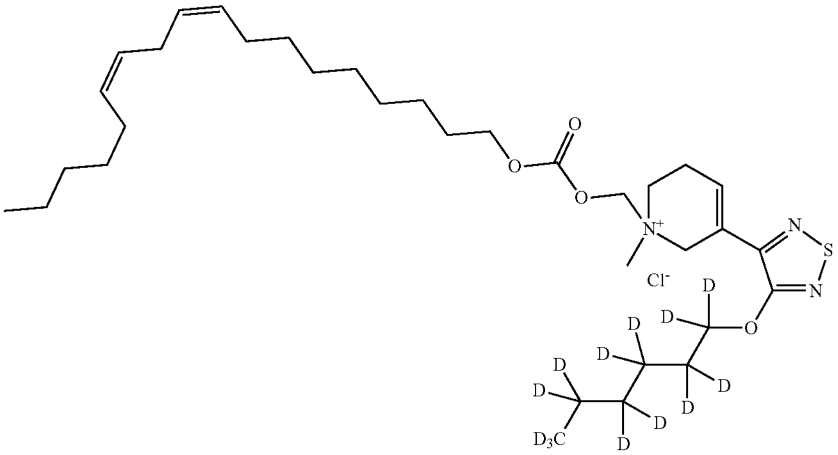 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)OCCCCCCCC/C=C\C/C=C\CCCCC)C1 ; [Cl-]] |
| 171 | 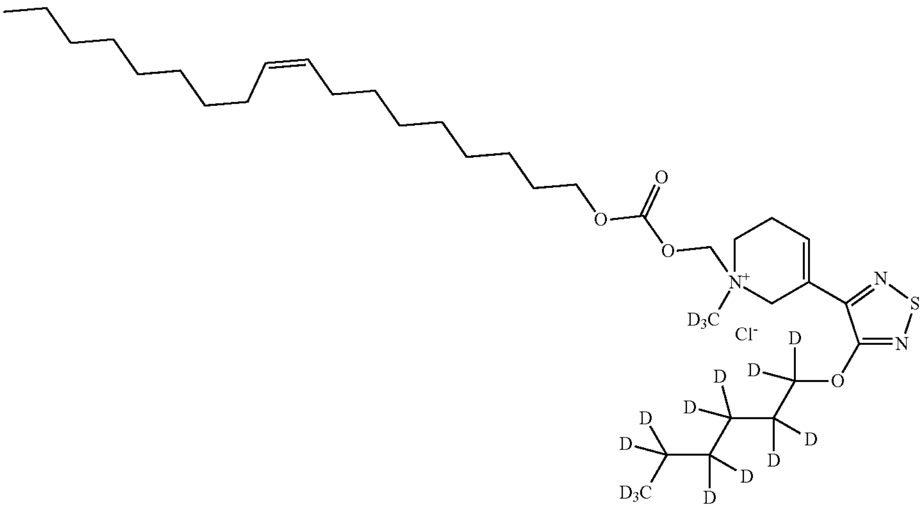 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCCCCCCC/C=C\CCCCCCCC)(C([2H])([2H])[2H])C1 ; [Cl-]] |

TABLE 1-continued
| Cpd No. | Structure |
| --- | --- |
| 172 | 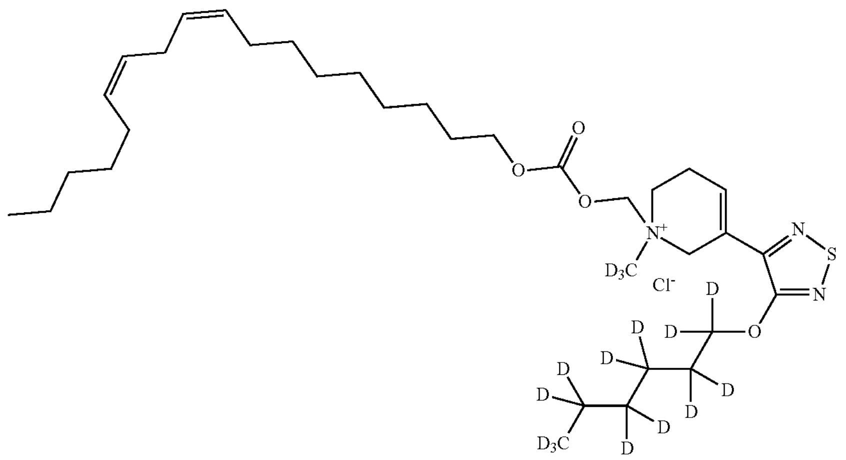 [SMILES: [2H]C([2H])([2H])C([2H])([2H])C([2H])([2H])C([2H])([2H])C([2H])([2H])C([2H])([2H])Oc1nsnc1C1=CCC[N+](COC(=O)OCCCCCCCC/C=C\C/C=C\CCCCC)(C([2H])([2H])[2H])C1 ; [Cl-]] |
| 173 | 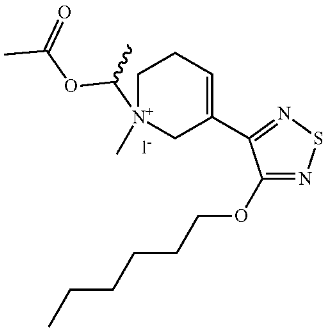 |
| 174 | 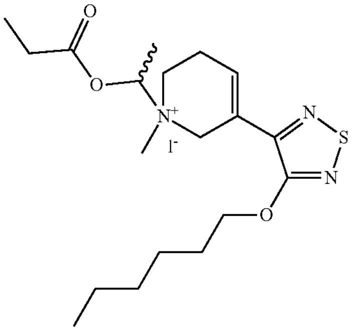 |
| 175 | 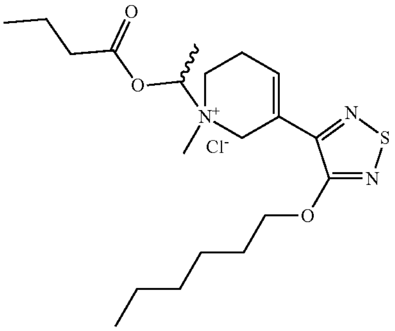 [SMILES: CCCCCCOc1nsnc1C1=CCC[N+](C)(C(C)OC(=O)CCC)C1 ; [Cl-]] |

TABLE 1-continued
| Cpd No. | Structure |
|---|---|
| 176 | 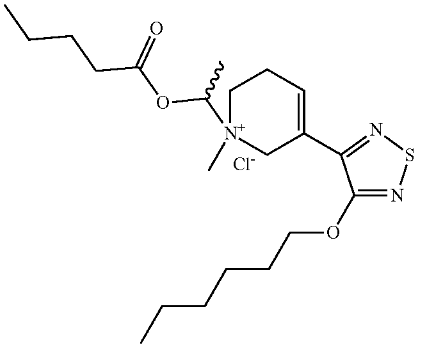 [SMILES: CCCCCCOc1nsnc1C1=CCC[N+](C)(C(C)OC(=O)CCCC)C1 ; [Cl-]] |
| 177 | 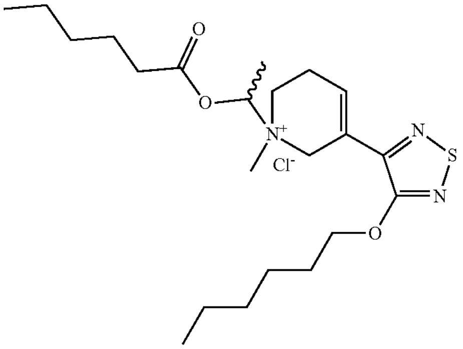 [SMILES: CCCCCCOc1nsnc1C1=CCC[N+](C)(C(C)OC(=O)CCCCC)C1 ; [Cl-]] |
| 178 | 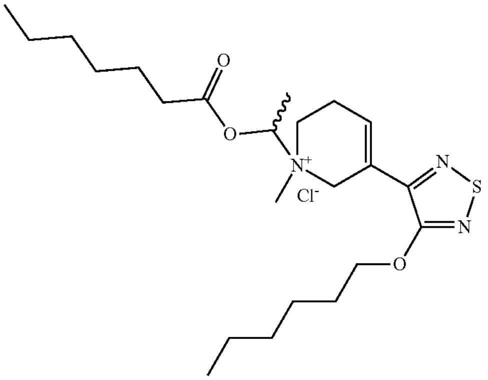 [SMILES: CCCCCCOc1nsnc1C1=CCC[N+](C)(C(C)OC(=O)CCCCCC)C1 ; [Cl-]] |
| 179 | 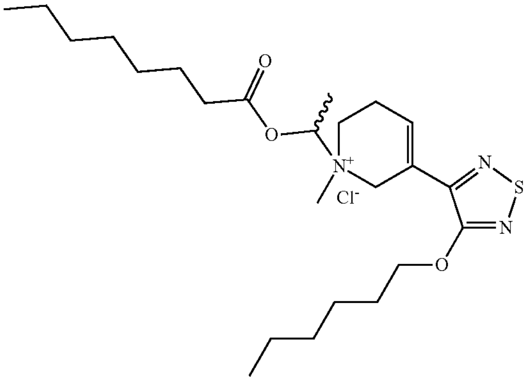 [SMILES: CCCCCCCC(=O)OC(C)[N+]1(C)CCC=C(c2nsnc2OCCCCCC)C1 ; [Cl-]] |

TABLE 1-continued
| Cpd No. | Structure |
| --- | --- |
| 180 | 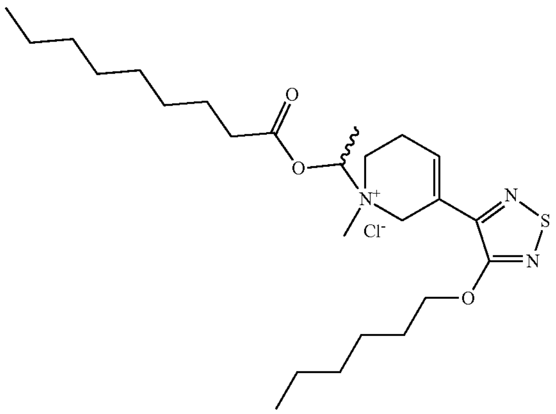 [SMILES: CCCCCCCCC(=O)OC(C)[N+]1(C)CCC=C(c2nsnc2OCCCCCC)C1 ; [Cl-]] |
| 181 | 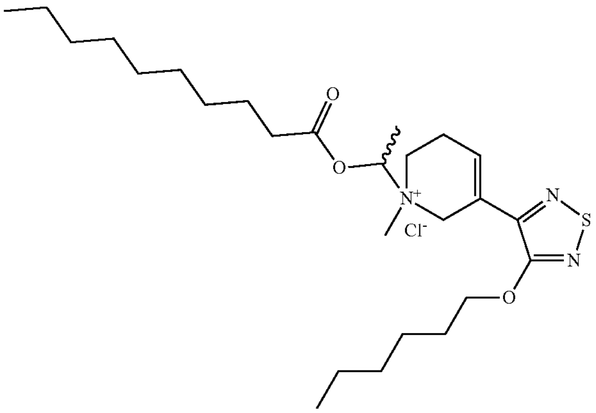 [SMILES: CCCCCCCCCC(=O)OC(C)[N+]1(C)CCC=C(c2nsnc2OCCCCCC)C1 ; [Cl-]] |
| 182 | 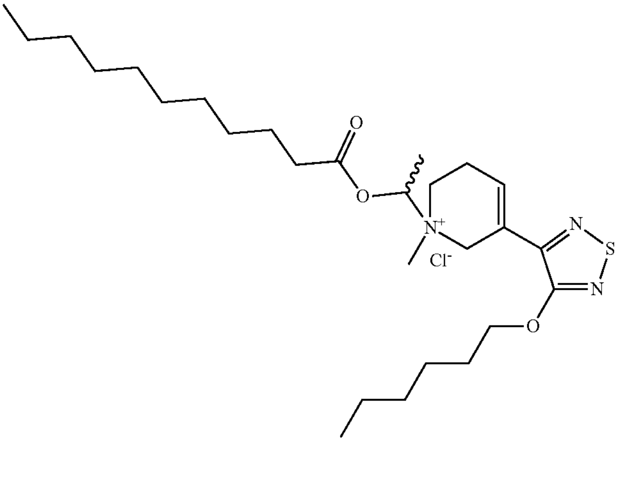 [SMILES: CCCCCCCCCCC(=O)OC(C)[N+]1(C)CCC=C(c2nsnc2OCCCCCC)C1 ; [Cl-]] |

TABLE 1-continued
| Cpd No. | Structure |
|---|---|
| 183 | 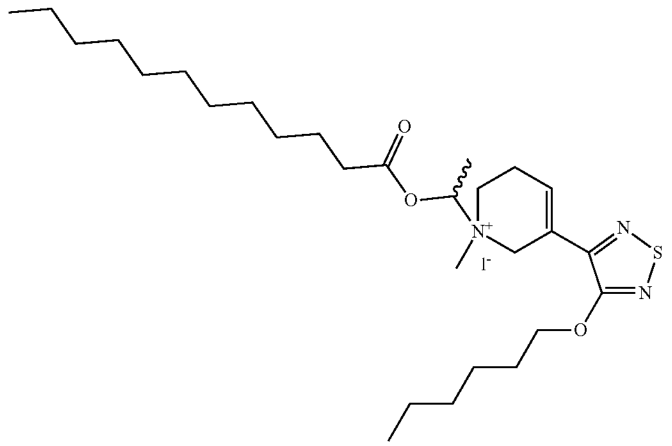 |
| 184 | 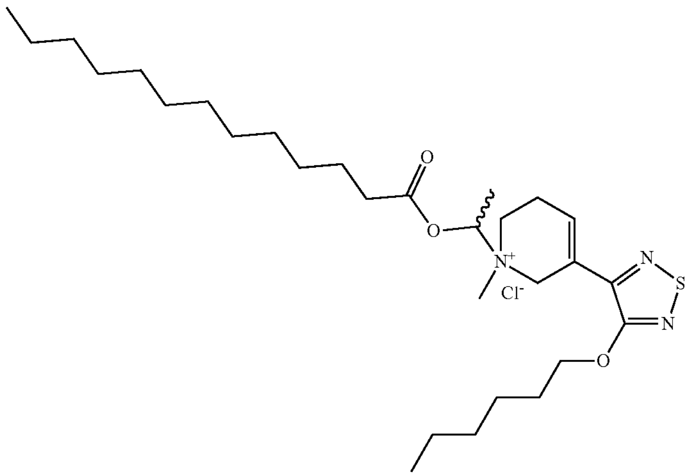 [SMILES: CCCCCCCCCCCCC(=O)OC(C)[N+]1(C)CCC=C(c2nsnc2OCCCCCC)C1 ; [Cl-]] |
| 185 | 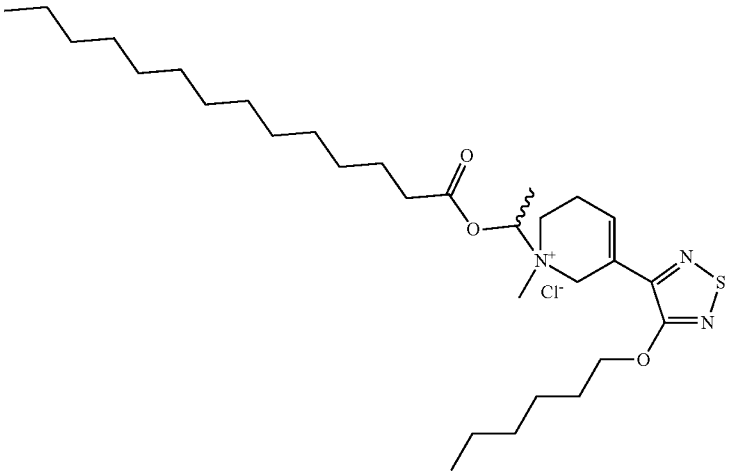 [SMILES: CCCCCCCCCCCCCC(=O)OC(C)[N+]1(C)CCC=C(c2nsnc2OCCCCCC)C1 ; [Cl-]] |

TABLE 1-continued
| Cpd No. | Structure |
|---|---|
| 186 | 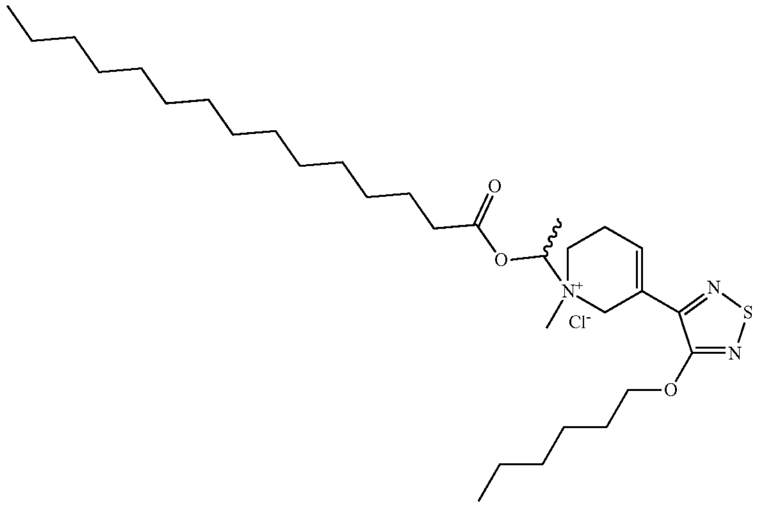 [SMILES: CCCCCCCCCCCCCCC(=O)OC(C)[N+]1(C)CCC=C(c2nsnc2OCCCCCC)C1 ; [Cl-]] |
| 187 | 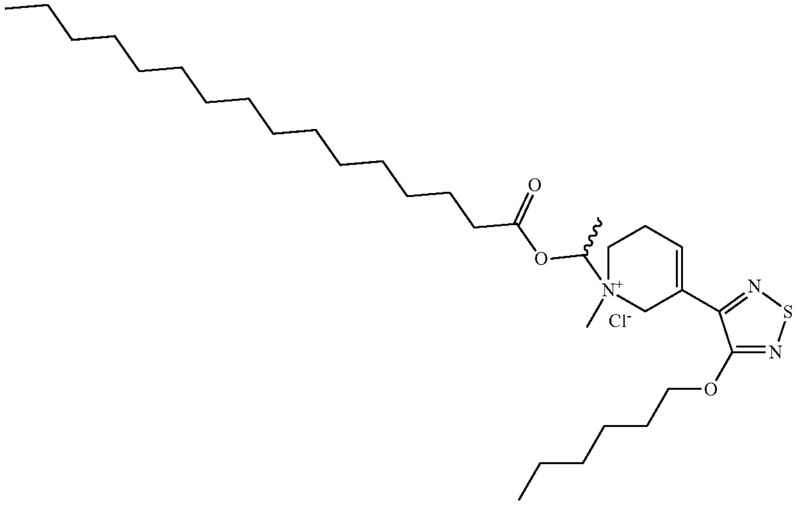 [SMILES: CCCCCCCCCCCCCCCC(=O)OC(C)[N+]1(C)CCC=C(c2nsnc2OCCCCCC)C1 ; [Cl-]] |
| 188 | 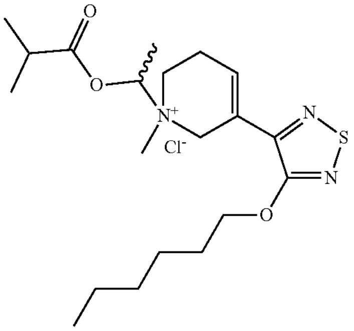 [SMILES: CCCCCCOc1nsnc1C1=CCC[N+](C)(C(C)OC(=O)C(C)C)C1 ; [Cl-]] |

TABLE 1-continued
| Cpd No. | Structure |
|---|---|
| 189 | 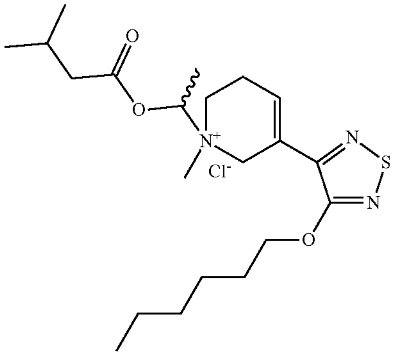 [SMILES: CCCCCCOc1nsnc1C1=CCC[N+](C)(C(C)OC(=O)CC(C)C)C1 ; [Cl-]] |
| 190 | 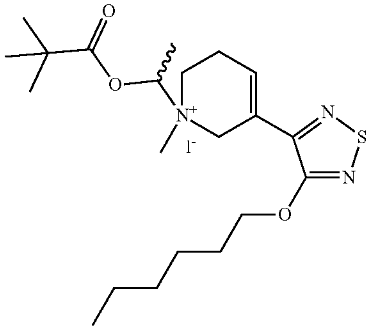 |
| 191 | 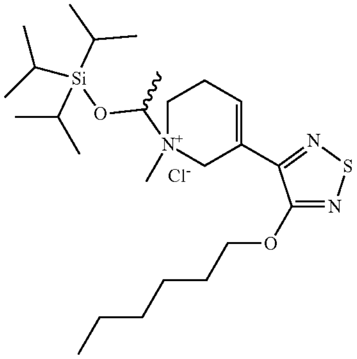 [SMILES: CCCCCCOc1nsnc1C1=CCC[N+](C)(C(C)O[Si](C(C)C)(C(C)C)C(C)C)C1 ; [Cl-]] |
| 192 | 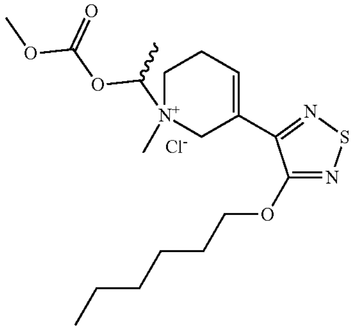 [SMILES: CCCCCCOc1nsnc1C1=CCC[N+](C)(C(C)OC(=O)OC)C1 ; [Cl-]] |

TABLE 1-continued
| Cpd No. | Structure |
| --- | --- |
| 193 | 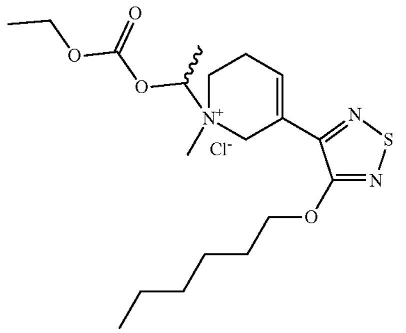 [SMILES: CCCCCCOc1nsnc1C1=CCC[N+](C)(C(C)OC(=O)OCC)C1 ; [Cl-]] |
| 194 | 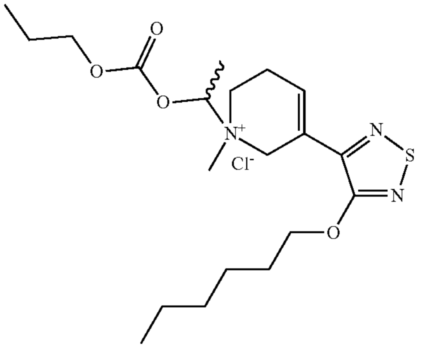 [SMILES: CCCCCCOc1nsnc1C1=CCC[N+](C)(C(C)OC(=O)OCCC)C1 ; [Cl-]] |
| 195 | 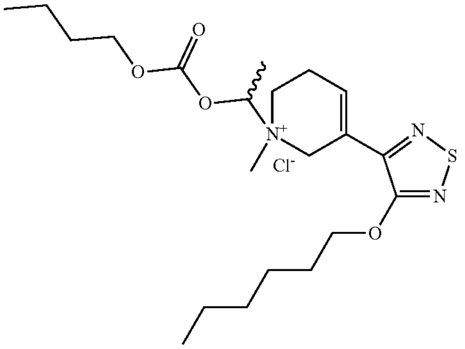 |
| 196 | 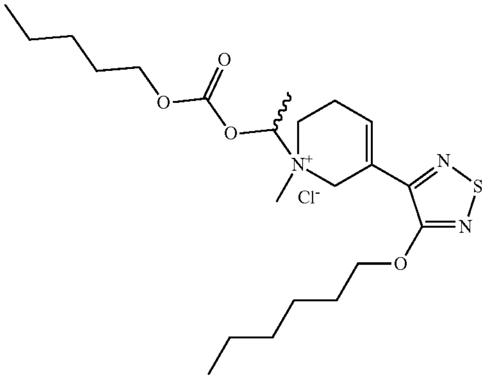 |

TABLE 1-continued
| Cpd No. | Structure |
| --- | --- |
| 197 | 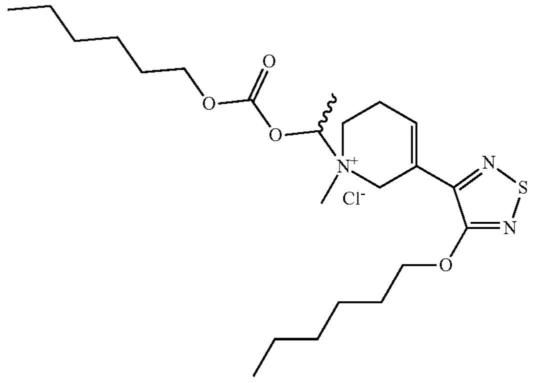 |
| 198 | 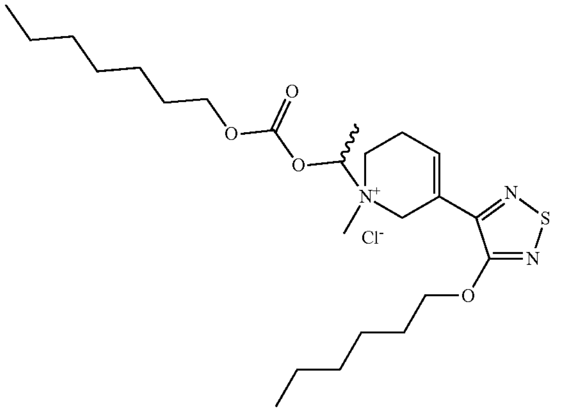 [SMILES: CCCCCCCOC(=O)OC(C)[N+]1(C)CCC=C(c2nsnc2OCCCCCC)C1 ; [Cl-]] |
| 199 | 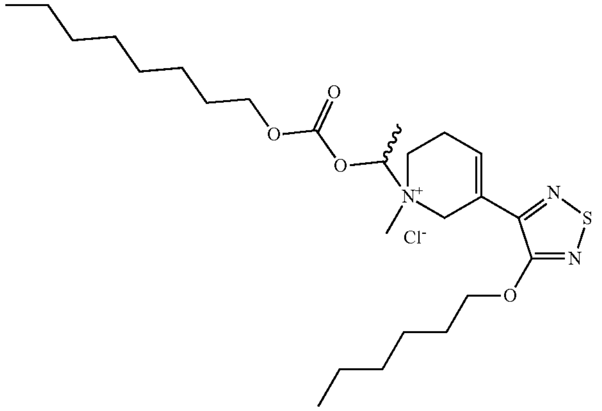 [SMILES: CCCCCCCCOC(=O)OC(C)[N+]1(C)CCC=C(c2nsnc2OCCCCCC)C1 ; [Cl-]] |

TABLE 1-continued
| Cpd No. | Structure |
| --- | --- |
| 200 | 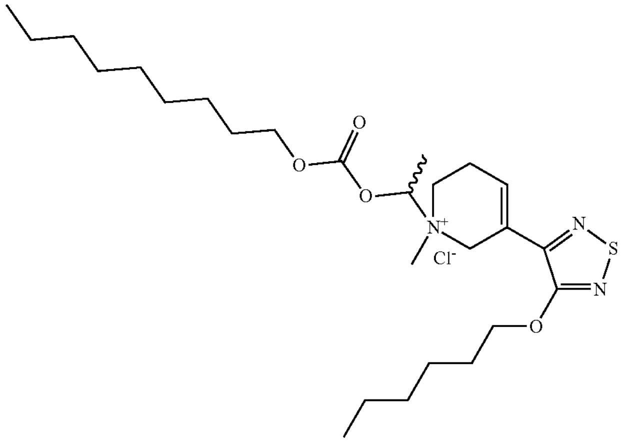 |
| 201 | 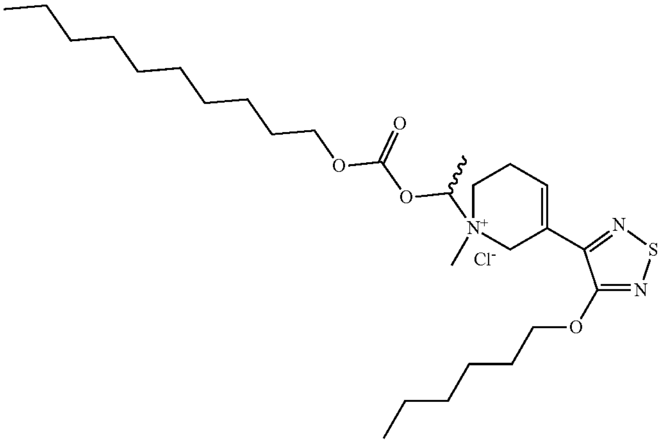 [SMILES: CCCCCCCCCCOC(=O)OC(C)[N+]1(C)CCC=C(c2nsnc2OCCCCCC)C1 ; [Cl-]] |
| 202 | 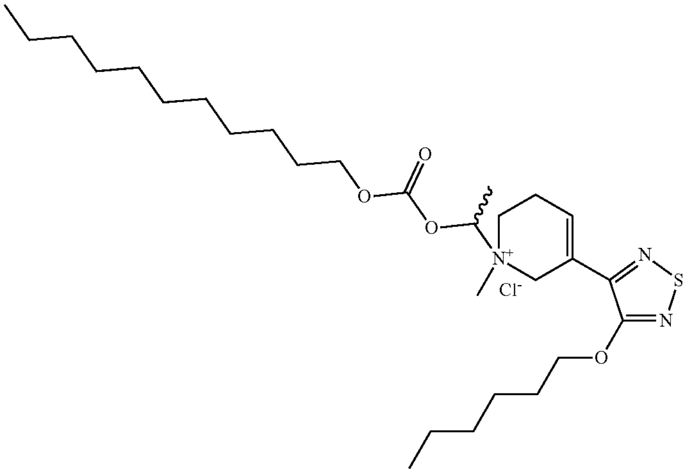 [SMILES: CCCCCCCCCCCOC(=O)OC(C)[N+]1(C)CCC=C(c2nsnc2OCCCCCC)C1 ; [Cl-]] |

TABLE 1-continued
| Cpd No. | Structure |
| --- | --- |
| 203 | 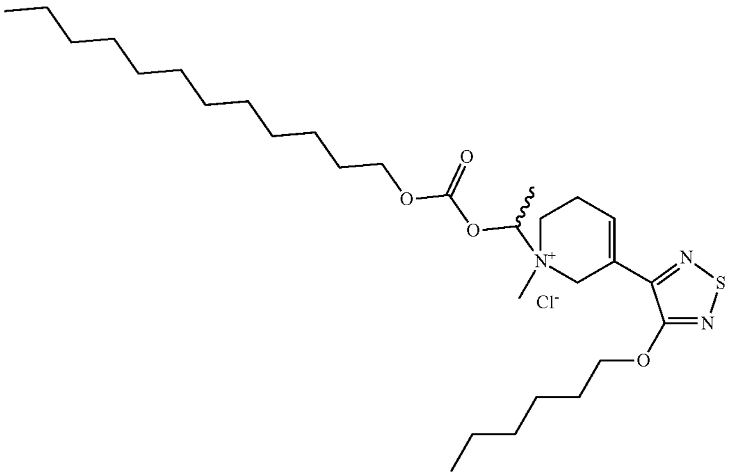 [SMILES: CCCCCCCCCCCCOC(=O)OC(C)[N+]1(C)CCC=C(c2nsnc2OCCCCCC)C1 ; [Cl-]] |
| 204 | 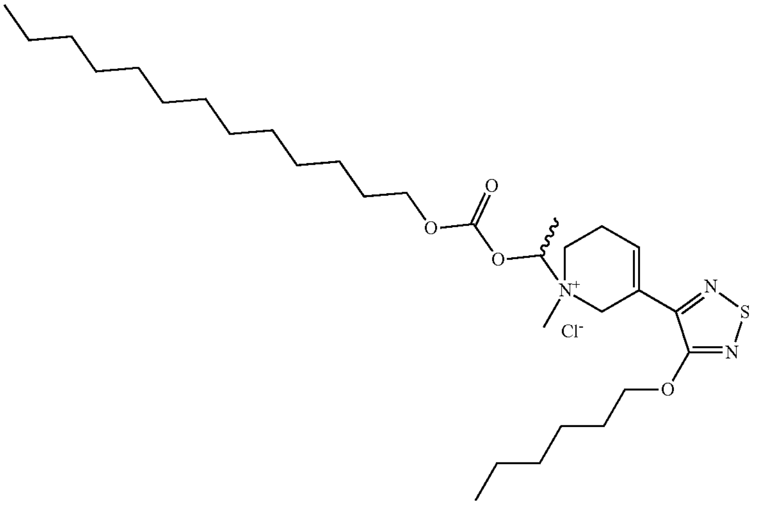 [SMILES: CCCCCCCCCCCCCOC(=O)OC(C)[N+]1(C)CCC=C(c2nsnc2OCCCCCC)C1 ; [Cl-]] |
| 205 | 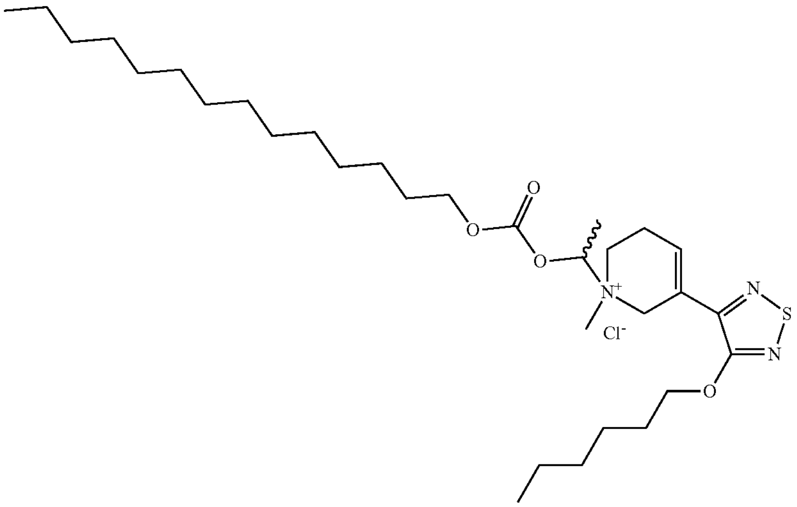 [SMILES: CCCCCCCCCCCCCCOC(=O)OC(C)[N+]1(C)CCC=C(c2nsnc2OCCCCCC)C1 ; [Cl-]] |

TABLE 1-continued
| Cpd No. | Structure |
|---|---|
| 206 | 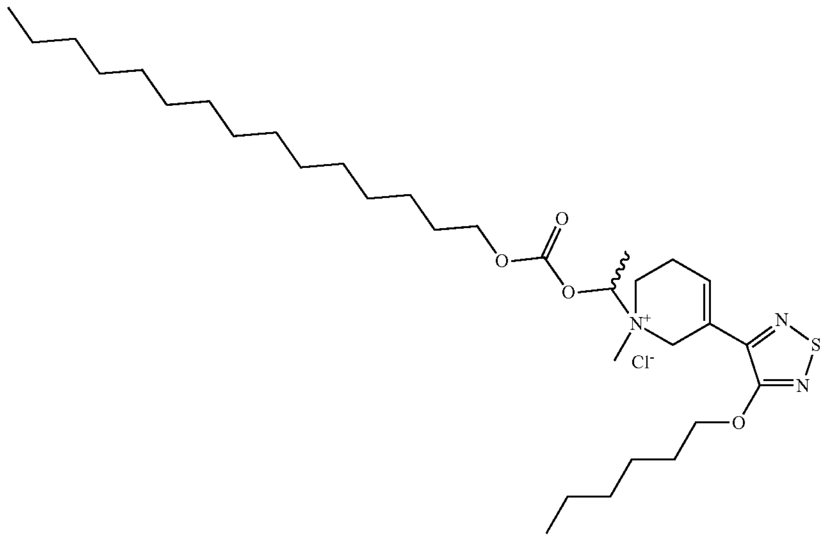 [SMILES: CCCCCCCCCCCCCCCOC(=O)OC(C)[N+]1(C)CCC=C(c2nsnc2OCCCCCC)C1 ; [Cl-]] |
| 207 | 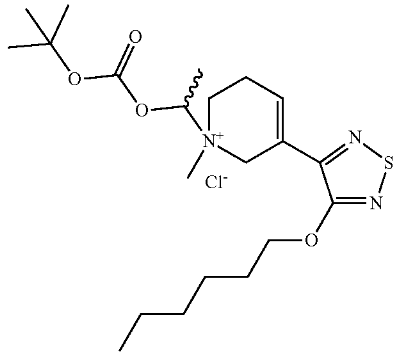 [SMILES: CCCCCCOc1nsnc1C1=CCC[N+](C)(C(C)OC(=O)OC(C)(C)C)C1 ; [Cl-]] |
| 208 | 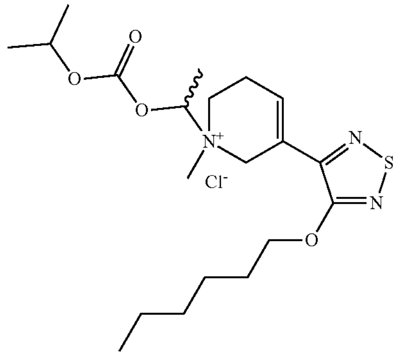 [SMILES: CCCCCCOc1nsnc1C1=CCC[N+](C)(C(C)OC(=O)OC(C)C)C1 ; [Cl-]] |
| 209 | 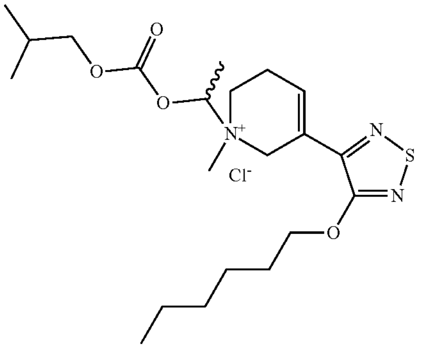 [SMILES: CCCCCCOc1nsnc1C1=CCC[N+](C)(C(C)OC(=O)OCC(C)C)C1 ; [Cl-]] |

TABLE 1-continued
| Cpd No. | Structure |
| --- | --- |
| 210 | 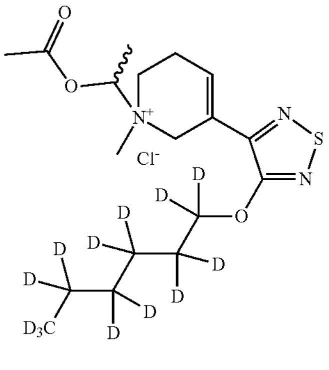 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(C)=O)C1 ; [Cl-]] |
| 211 | 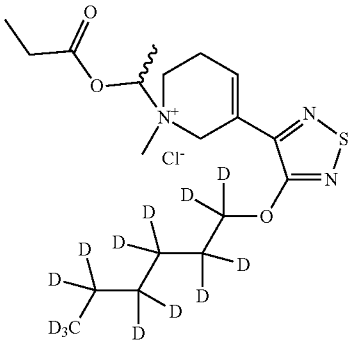 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CC)C1 ; [Cl-]] |
| 212 | 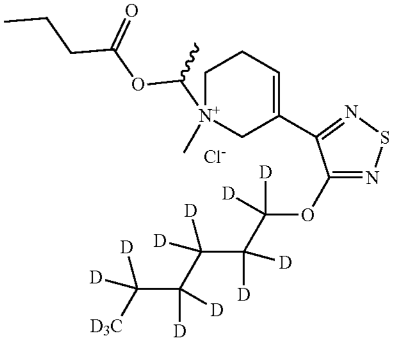 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCC)C1 ; [Cl-]] |
| 213 | 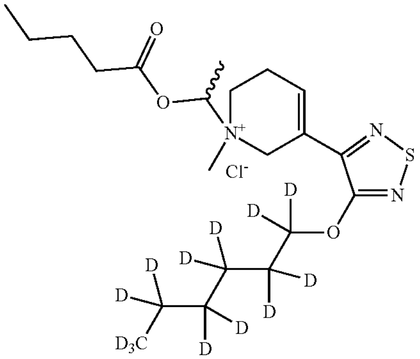 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCC)C1 ; [Cl-]] |

TABLE 1-continued
| Cpd No. | Structure |
|---|---|
| 214 | 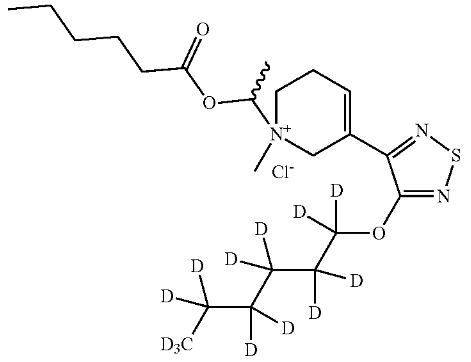 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCC)C1 ; [Cl-]] |
| 215 | 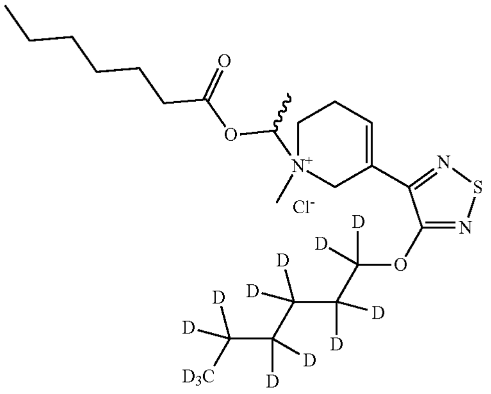 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCC)C1 ; [Cl-]] |
| 216 | 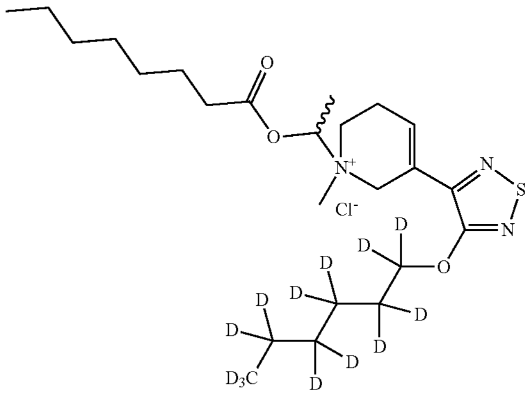 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCC)C1 ; [Cl-]] |
| 217 | 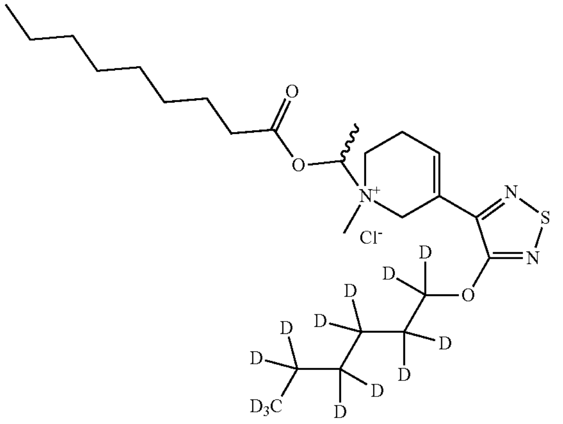 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCCC)C1 ; [Cl-]] |

TABLE 1-continued
| Cpd No. | Structure |
| --- | --- |
| 218 | 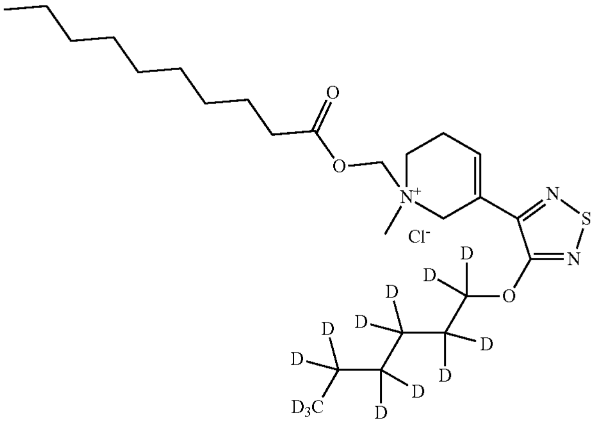 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)CCCCCCCCC)C1 ; [Cl-]] |
| 219 | 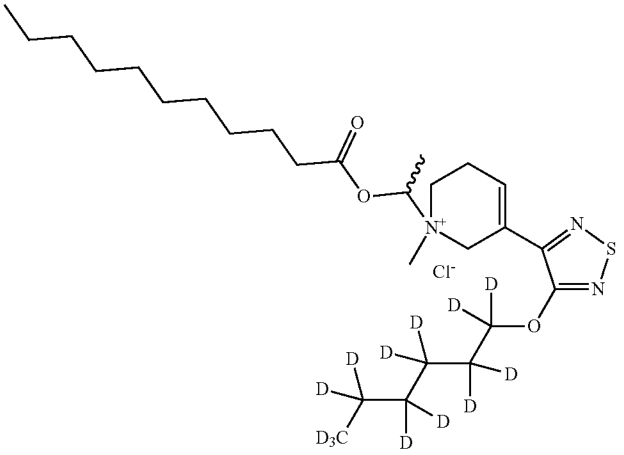 |
| 220 | 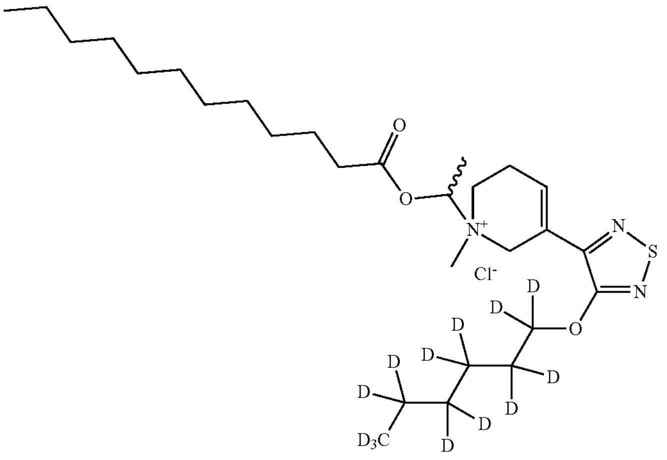 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCCCCCC)C1 ; [Cl-]] |

TABLE 1-continued
| Cpd No. | Structure |
| --- | --- |
| 221 | 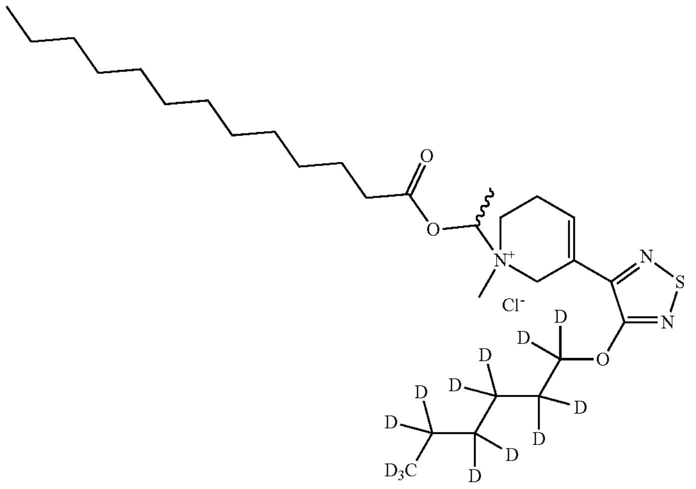 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCCCCCCC)C1 ; [Cl-]] |
| 222 | 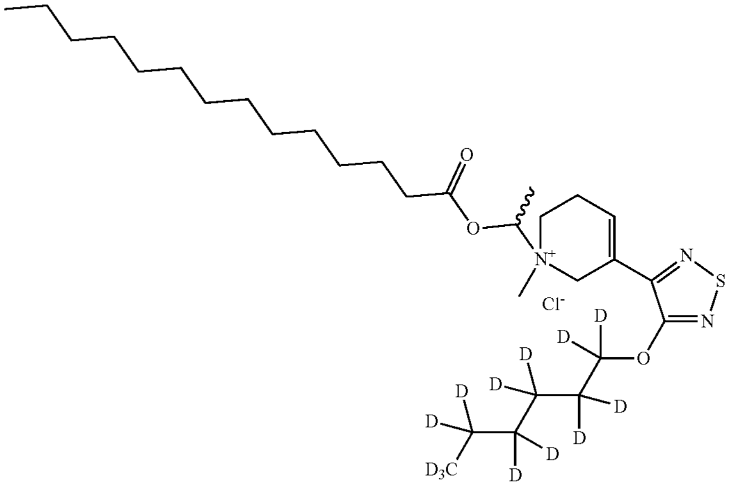 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCCCCCCCC)C1 ; [Cl-]] |
| 223 | 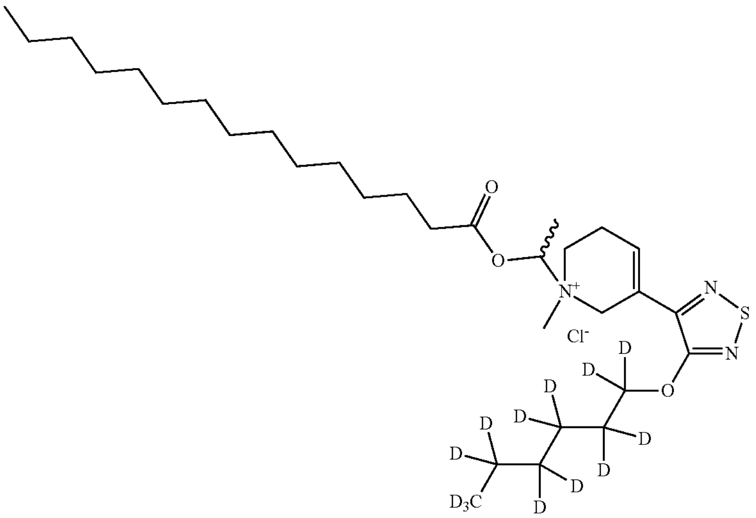 |

TABLE 1-continued
| Cpd No. | Structure |
|---|---|
| 224 | 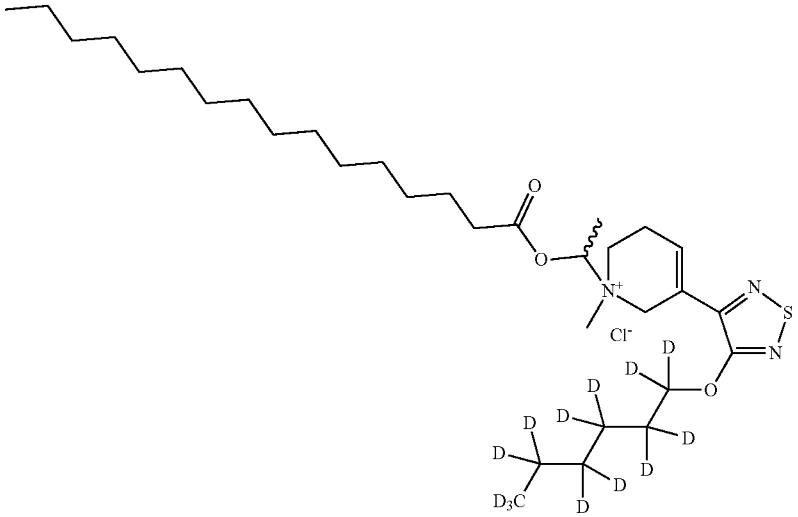 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCCCCCCCCCC)C1 ; [Cl-]] |
| 225 | 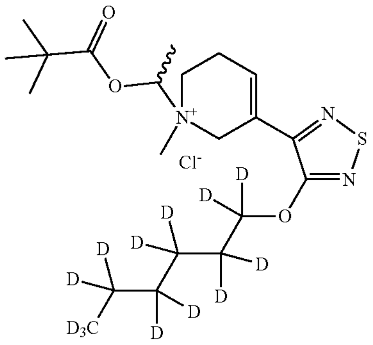 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)C(C)(C)C)C1 ; [Cl-]] |
| 226 | 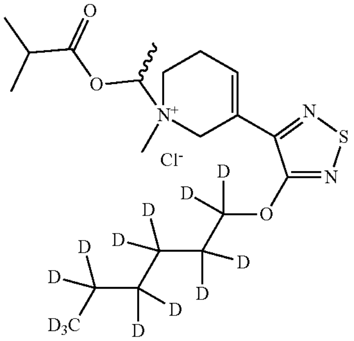 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)C(C)C)C1 ; [Cl-]] |
| 227 | 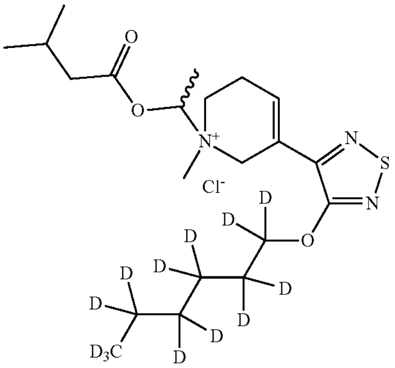 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CC(C)C)C1 ; [Cl-]] |

TABLE 1-continued
| Cpd No. | Structure |
|---|---|
| 228 | 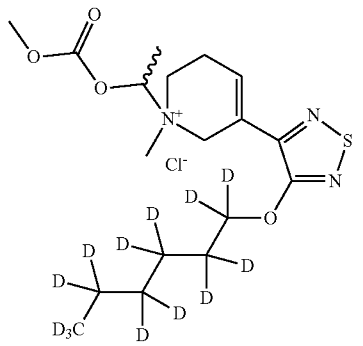 |
| 229 | 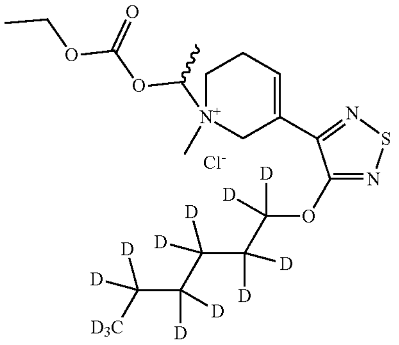 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCC)C1 ; [Cl-]] |
| 230 | 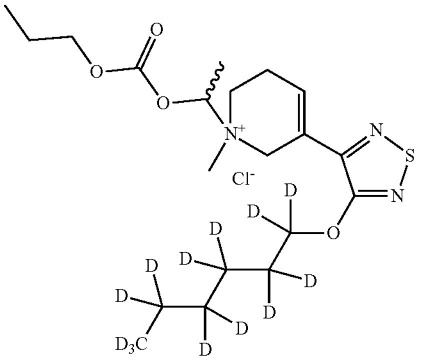 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCC)C1 ; [Cl-]] |
| 231 | 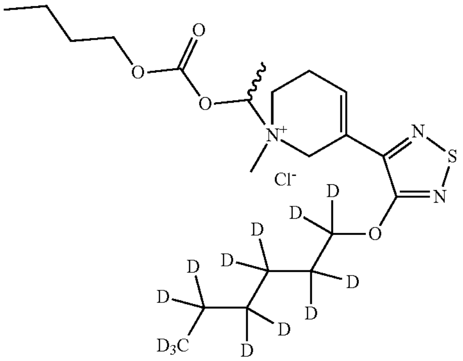 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCC)C1 ; [Cl-]] |

TABLE 1-continued
| Cpd No. | Structure |
|---|---|
| 232 | 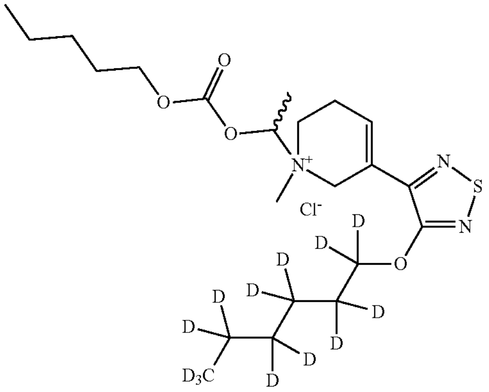 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCC)C1 ; [Cl-]] |
| 233 | 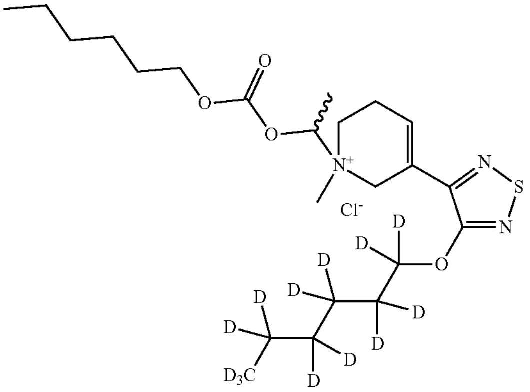 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCCC)C1 ; [Cl-]] |
| 234 | 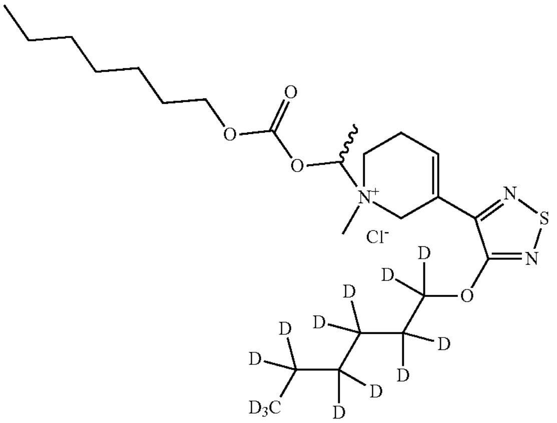 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCCCC)C1 ; [Cl-]] |

TABLE 1-continued
| Cpd No. | Structure |
| --- | --- |
| 235 | 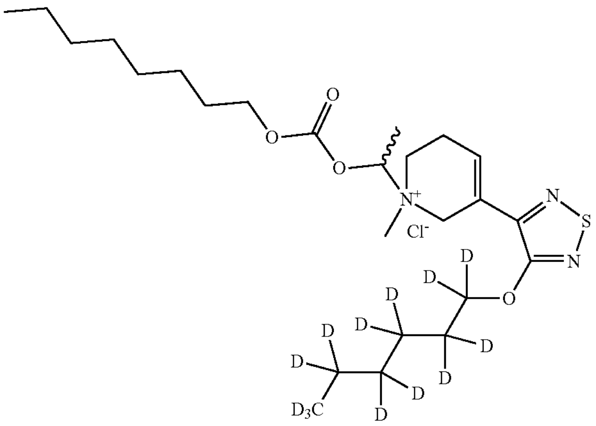 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCCCCC)C1 ; [Cl-]] |
| 236 | 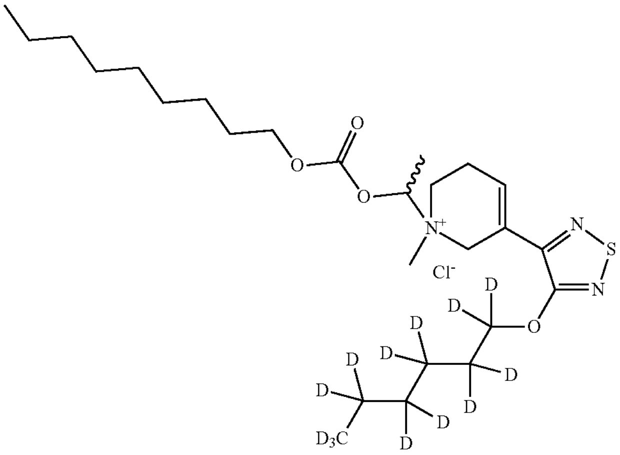 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCCCCCC)C1 ; [Cl-]] |
| 237 | 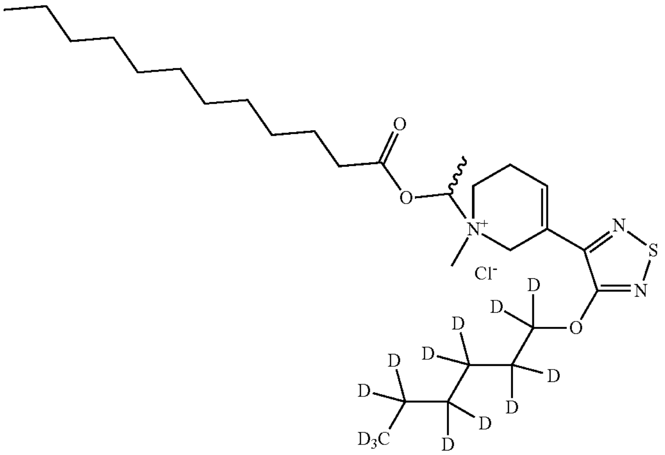 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCCCCCC)C1 ; [Cl-]] |

TABLE 1-continued
| Cpd No. | Structure |
|---|---|
| 238 | 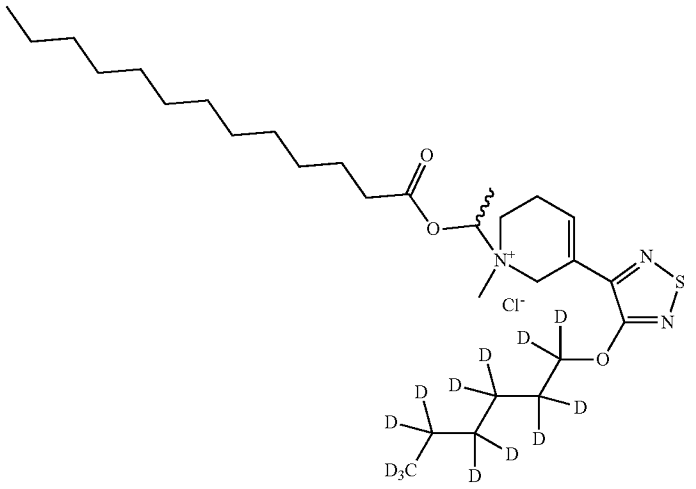 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCCCCCCC)C1 ; [Cl-]] |
| 239 | 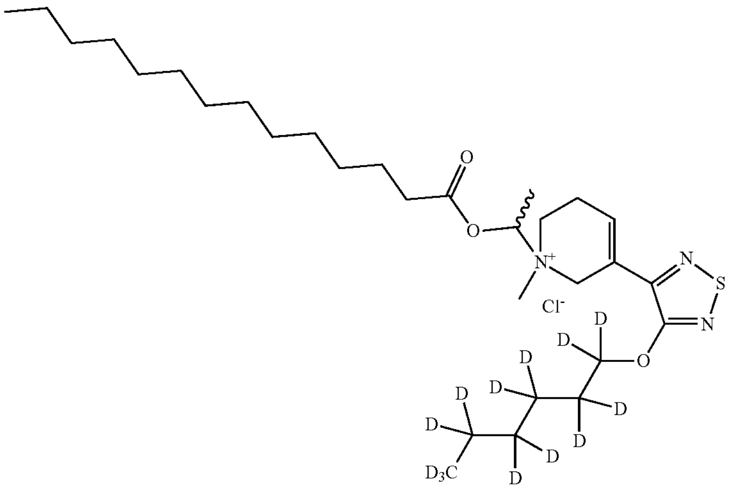 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCCCCCCCC)C1 ; [Cl-]] |
| 240 | 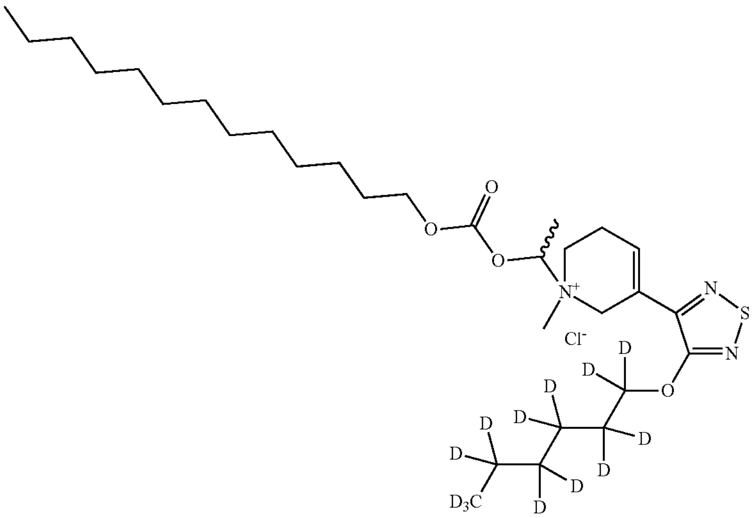 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCCCCCCCCCC)C1 ; [Cl-]] |

TABLE 1-continued
| Cpd No. | Structure |
|---|---|
| 241 | 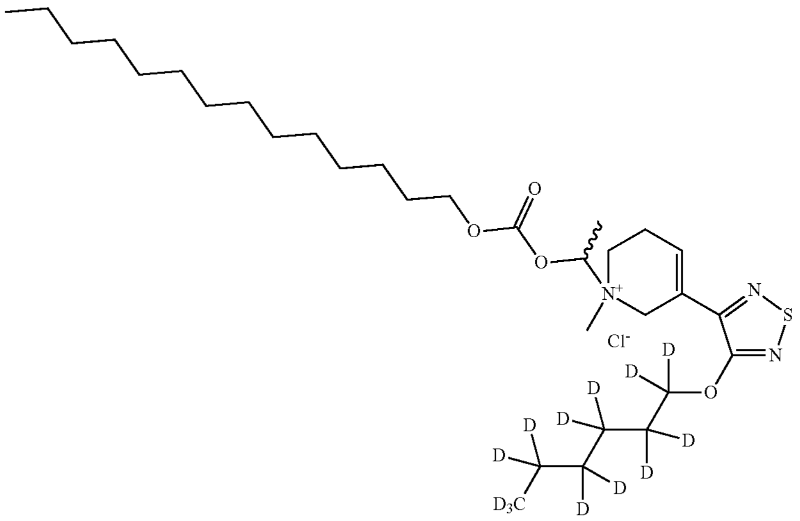 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCCCCCCCCCCC)C1 ; [Cl-]] |
| 242 | 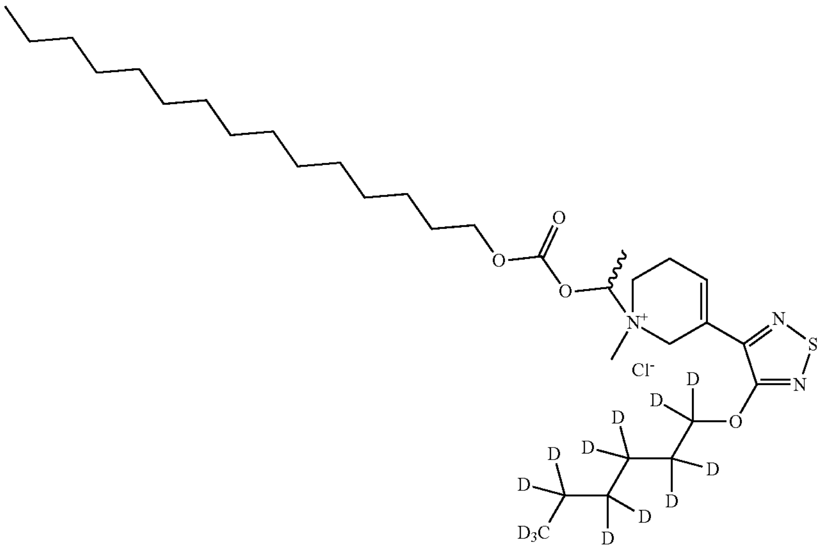 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCCCCCCCCCCCC)C1 ; [Cl-]] |
| 243 | 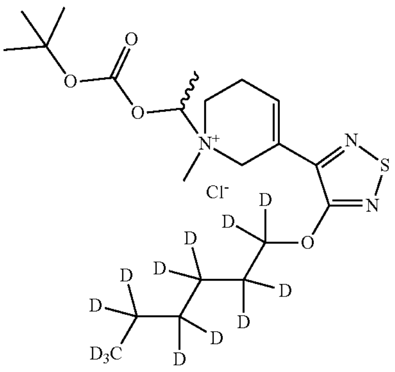 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC(C)(C)C)C1 ; [Cl-]] |

TABLE 1-continued
| Cpd No. | Structure |
| --- | --- |
| 244 | 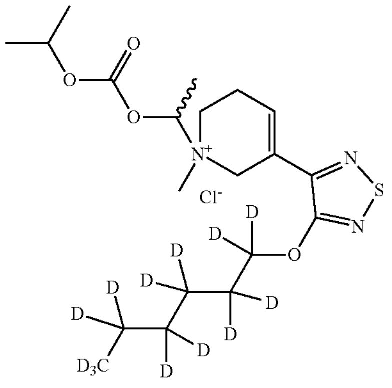 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC(C)C)C1 ; [Cl-]] |
| 245 | 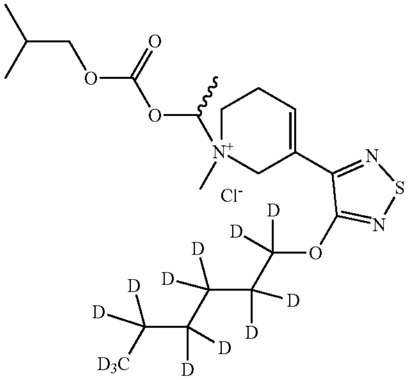 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCC(C)C)C1 ; [Cl-]] |
| 246 | 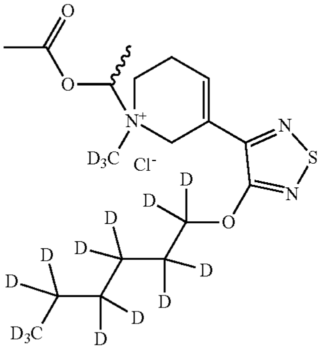 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(C)=O)(C([2H])([2H])[2H])C1 ; [Cl-]] |
| 247 | 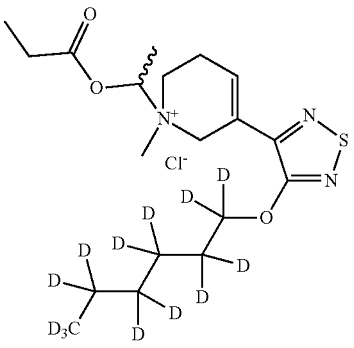 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CC)C1 ; [Cl-]] |

TABLE 1-continued
| Cpd No. | Structure |
| --- | --- |
| 248 | 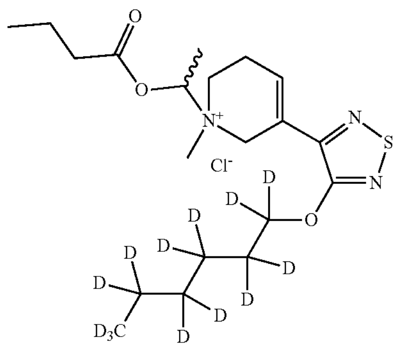 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCC)C1 ; [Cl-]] |
| 249 | 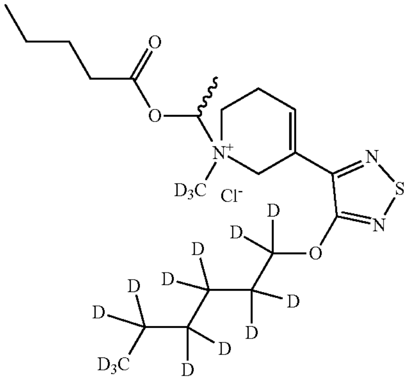 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCC)(C([2H])([2H])[2H])C1 ; [Cl-]] |
| 250 | 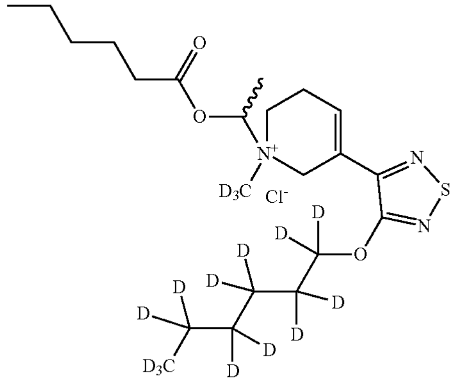 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCC)(C([2H])([2H])[2H])C1 ; [Cl-]] |
| 251 | 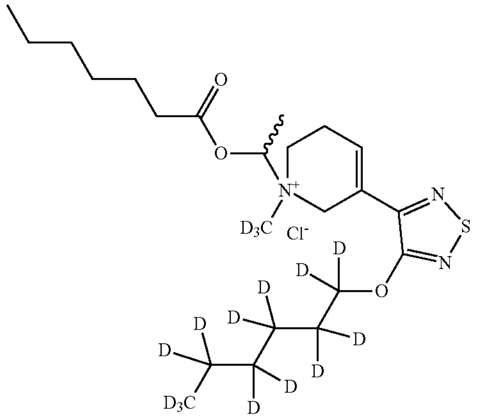 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCC)(C([2H])([2H])[2H])C1 ; [Cl-]] |

TABLE 1-continued
| Cpd No. | Structure |
| --- | --- |
| 252 | 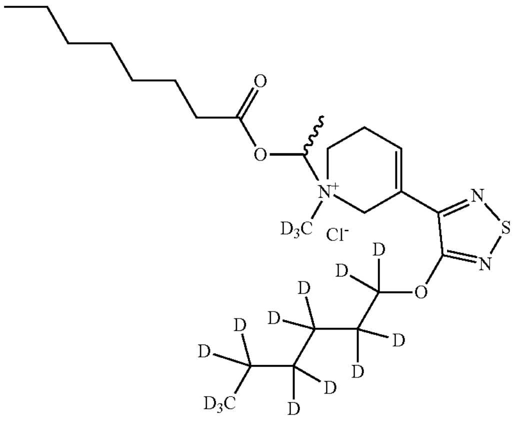 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCC)(C([2H])([2H])[2H])C1 ; [Cl-]] |
| 253 | 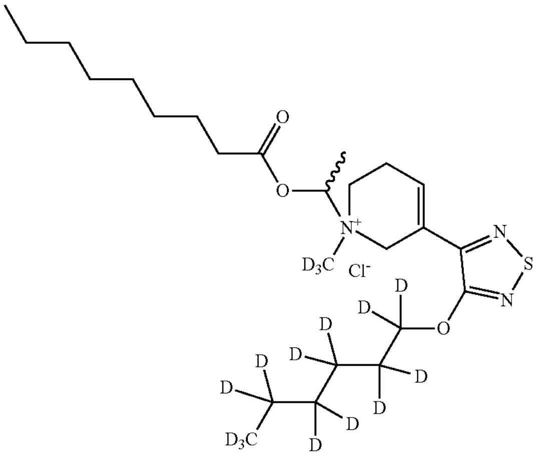 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCC)(C([2H])([2H])[2H])C1 ; [Cl-]] |
| 254 | 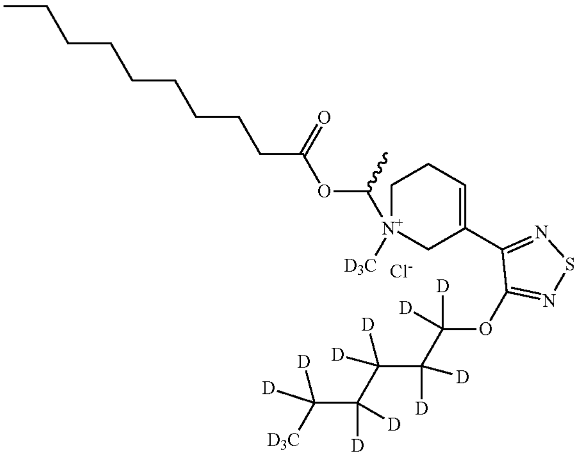 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCC)(C([2H])([2H])[2H])C1 ; [Cl-]] |

TABLE 1-continued
| Cpd No. | Structure |
|---|---|
| 255 | 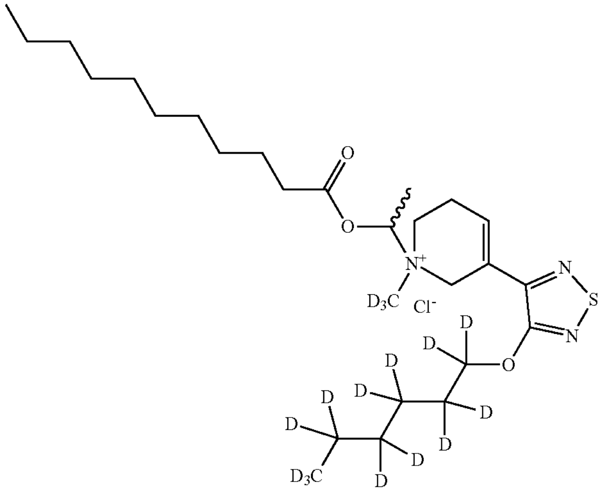 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCC)(C([2H])([2H])[2H])C1 ; [Cl-]] |
| 256 | 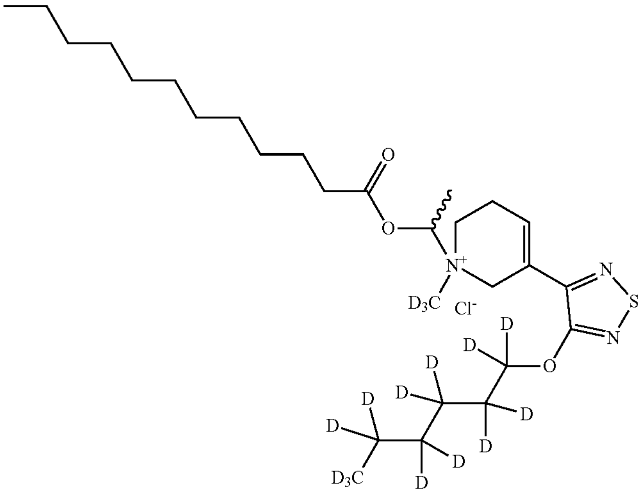 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCCC)(C([2H])([2H])[2H])C1 ; [Cl-]] |
| 257 | 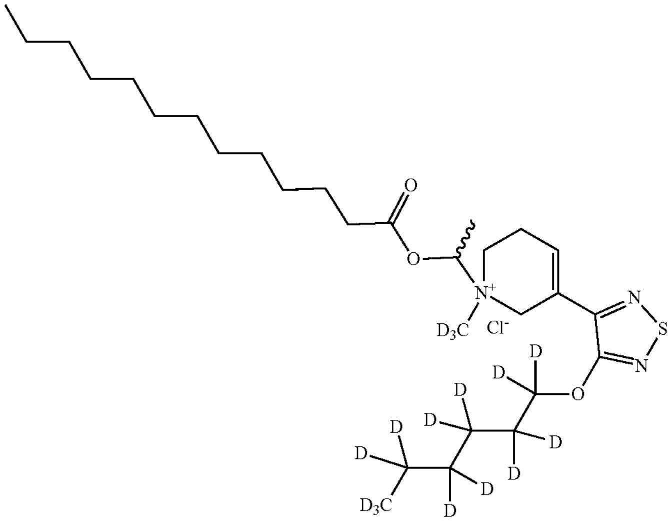 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCCCC)(C([2H])([2H])[2H])C1 ; [Cl-]] |

TABLE 1-continued
| Cpd No. | Structure |
|---|---|
| 258 | 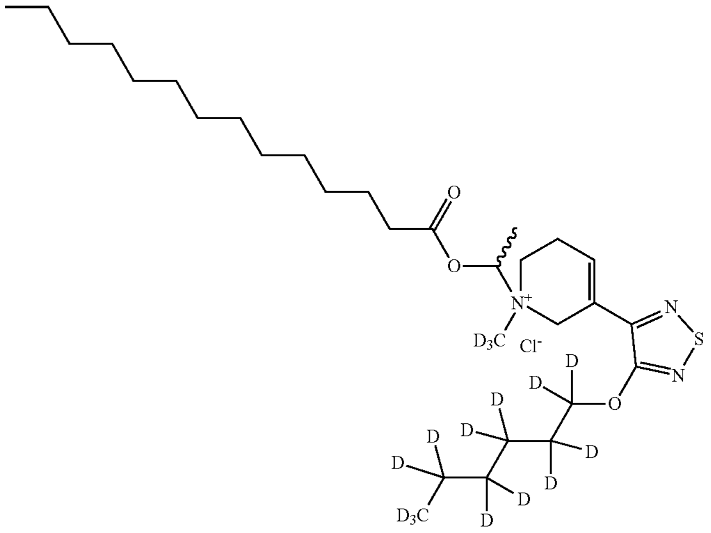 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCCCCC)(C([2H])([2H])[2H])C1 ; [Cl-]] |
| 259 | 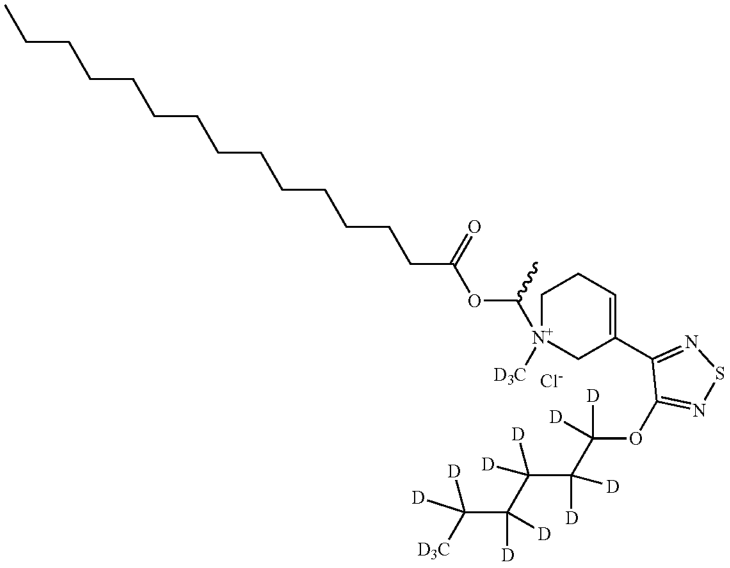 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCCCCCC)(C([2H])([2H])[2H])C1 ; [Cl-]] |

TABLE 1-continued
| Cpd No. | Structure |
|---|---|
| 260 | 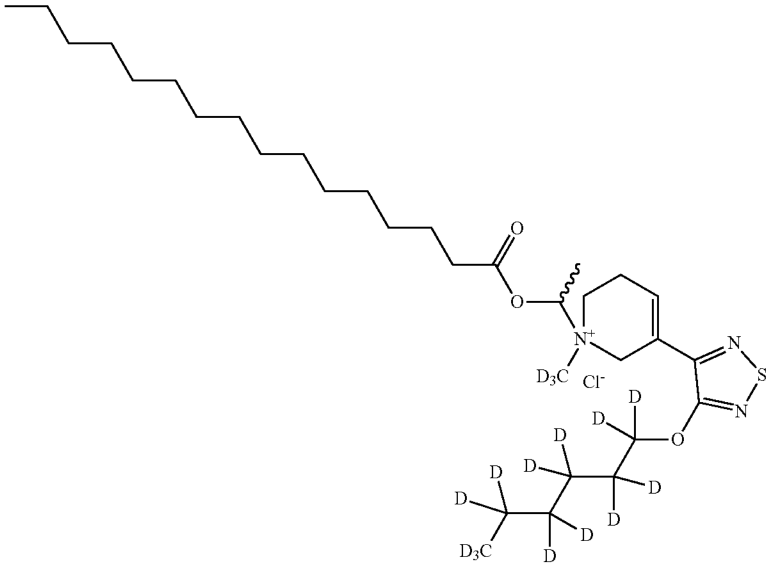 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCCCCCCC)(C([2H])([2H])[2H])C1 ; [Cl-]] |
| 261 | 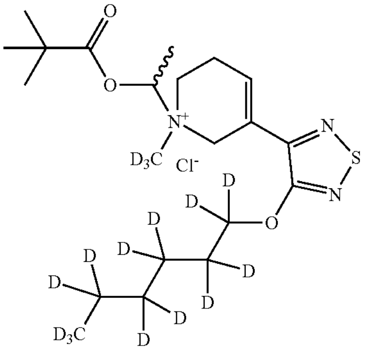 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)C(C)(C)C)(C([2H])([2H])[2H])C1 ; [Cl-]] |
| 262 | 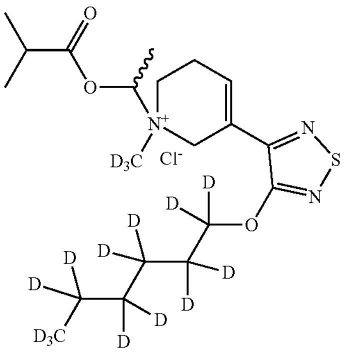 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)C(C)C)(C([2H])([2H])[2H])C1 ; [Cl-]] |

TABLE 1-continued
| Cpd No. | Structure |
| --- | --- |
| 263 | 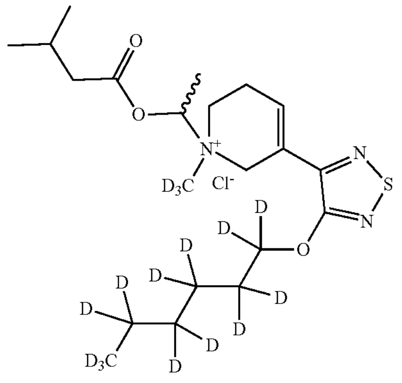 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CC(C)C)(C([2H])([2H])[2H])C1 ; [Cl-]] |
| 264 | 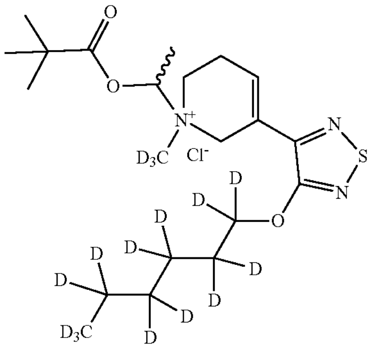 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)C(C)(C)C)(C([2H])([2H])[2H])C1 ; [Cl-]] |
| 265 | 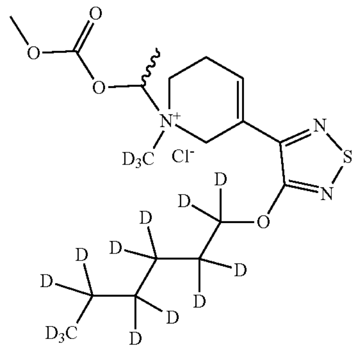 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC)(C([2H])([2H])[2H])C1 ; [Cl-]] |
| 266 | 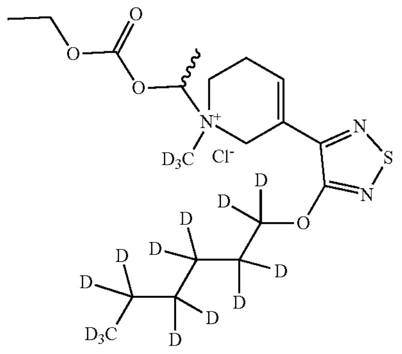 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCC)(C([2H])([2H])[2H])C1 ; [Cl-]] |

TABLE 1-continued
| Cpd No. | Structure |
|---|---|
| 267 | 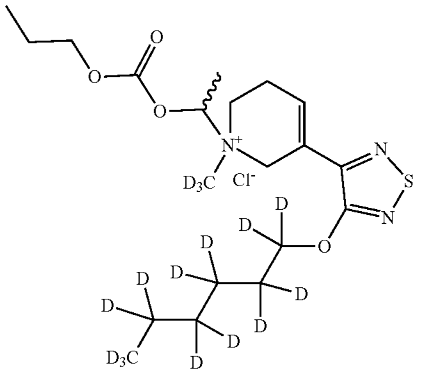 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCC)(C([2H])([2H])[2H])C1 ; [Cl-]] |
| 268 | 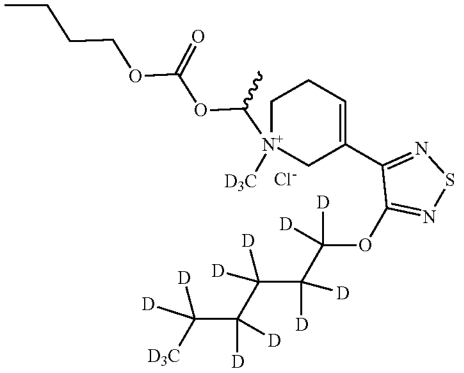 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCC)(C([2H])([2H])[2H])C1 ; [Cl-]] |
| 269 | 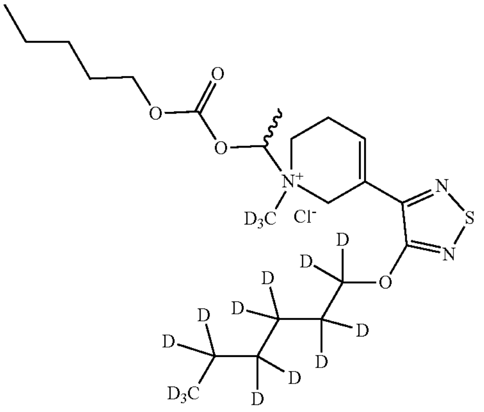 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCCC)(C([2H])([2H])[2H])C1 ; [Cl-]] |
| 270 | 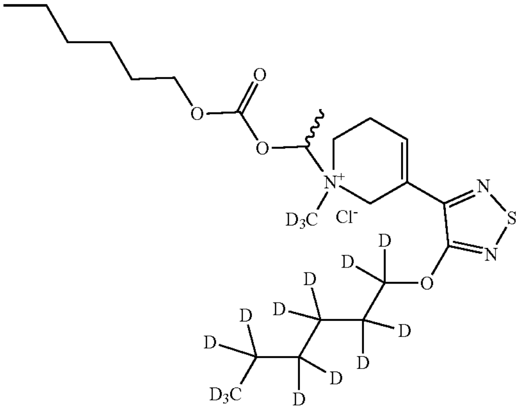 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCCCC)(C([2H])([2H])[2H])C1 ; [Cl-]] |

TABLE 1-continued
| Cpd No. | Structure |
| --- | --- |
| 271 | 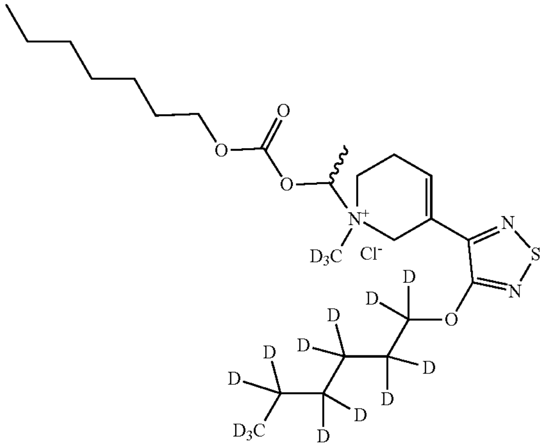 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCCCCC)(C([2H])([2H])[2H])C1 ; [Cl-]] |
| 272 | 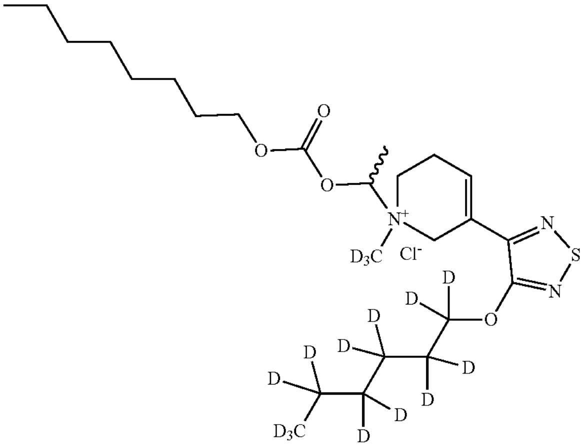 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCCCCCC)(C([2H])([2H])[2H])C1 ; [Cl-]] |
| 273 | 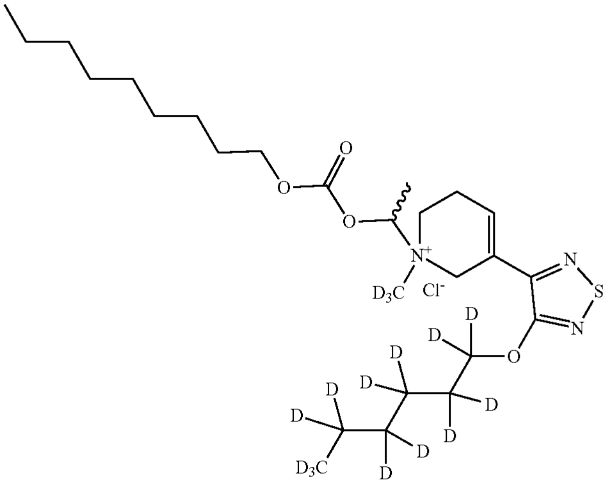 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCCCCCCC)(C([2H])([2H])[2H])C1 ; [Cl-]] |

TABLE 1-continued
| Cpd No. | Structure |
| --- | --- |
| 274 | 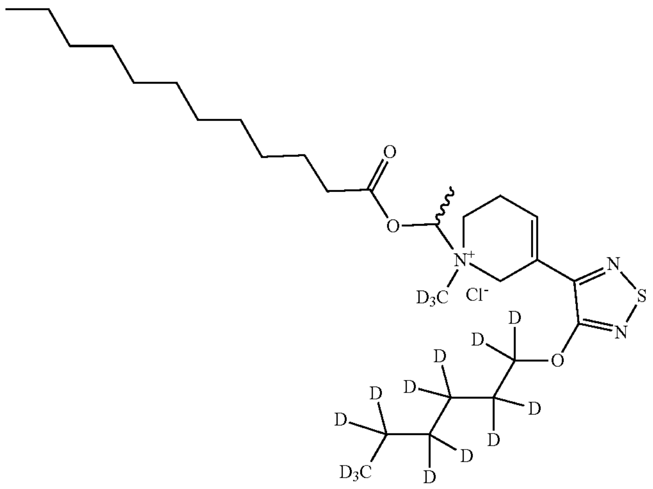 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCCC)(C([2H])([2H])[2H])C1 ; [Cl-]] |
| 275 | 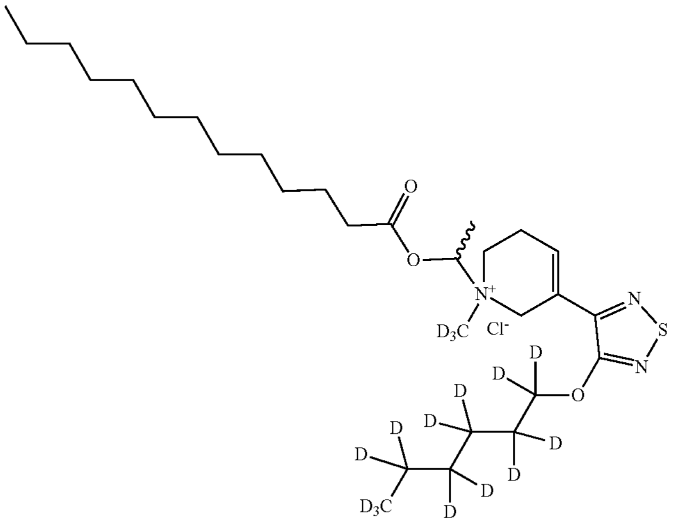 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCCCC)(C([2H])([2H])[2H])C1 ; [Cl-]] |
| 276 | 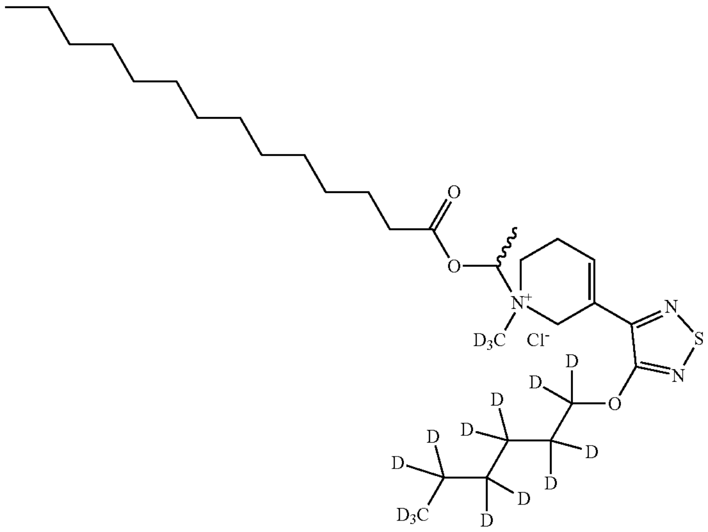 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCCCCCCCC)(C([2H])([2H])[2H])C1 ; [Cl-]] |

TABLE 1-continued
| Cpd No. | Structure |
| --- | --- |
| 277 | 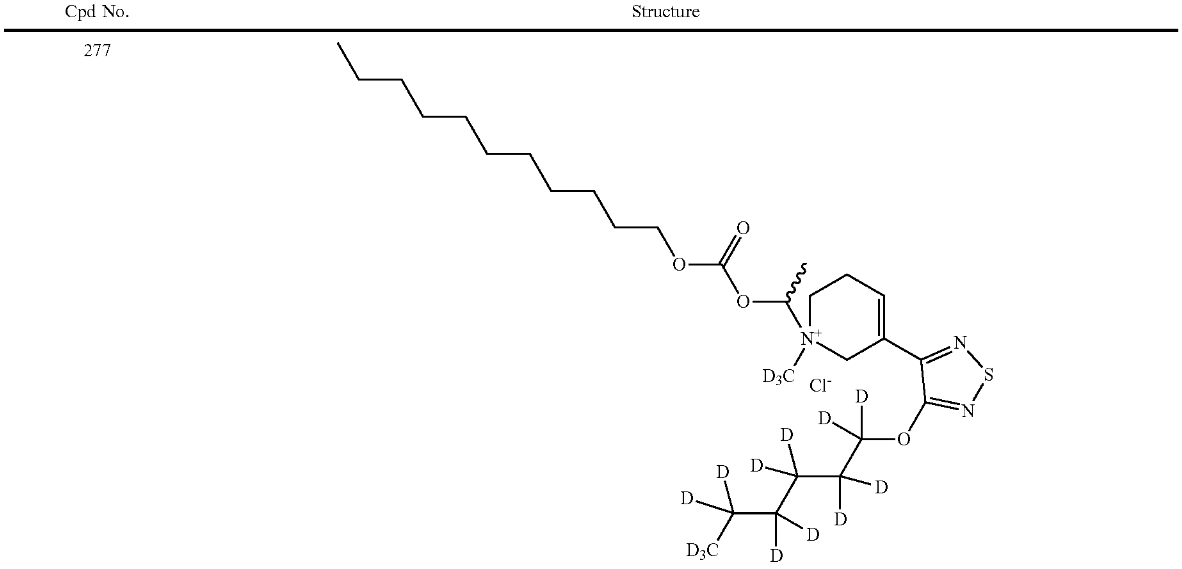 |
| 278 | 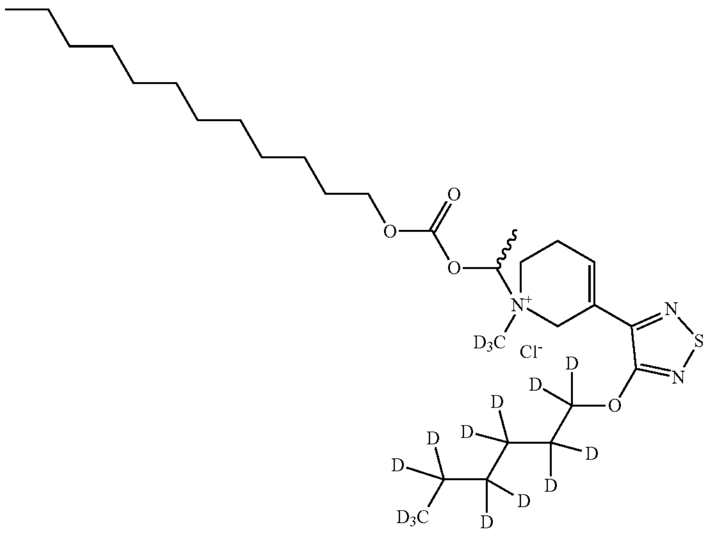 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCCCCCCCCCC)(C([2H])([2H])[2H])C1 ; [Cl-]] |
| 279 | 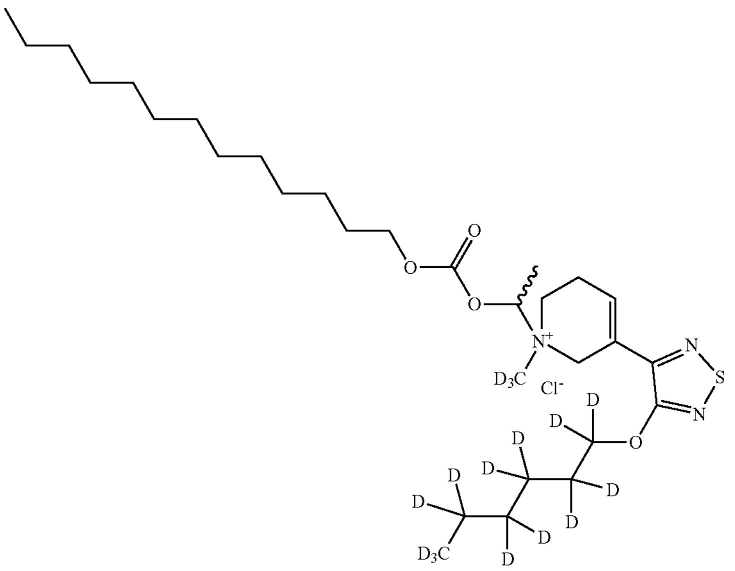 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCCCCCCCCCCC)(C([2H])([2H])[2H])C1 ; [Cl-]] |

TABLE 1-continued
| Cpd No. | Structure |
|---|---|
| 280 | 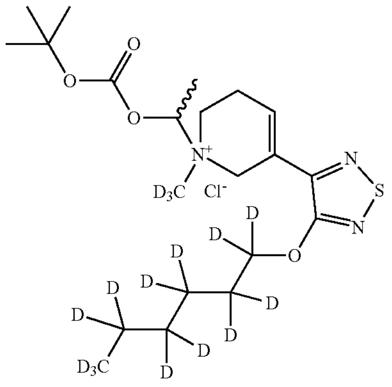 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC(C)(C)C)(C([2H])([2H])[2H])C1 ; [Cl-]] |
| 281 | 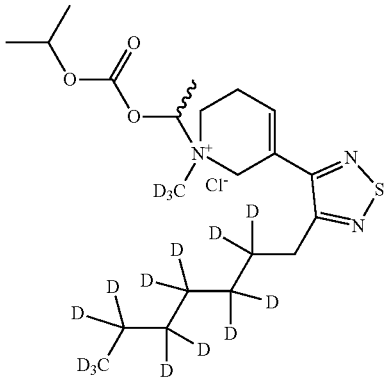 [SMILES: [2H]C([2H])([2H])C([2H])([2H])C([2H])([2H])C([2H])([2H])C([2H])([2H])C([2H])([2H])Cc1nsnc1C1=CCC[N+](C(C)OC(=O)OC(C)C)(C([2H])([2H])[2H])C1 ; [Cl-]] |
| 282 | 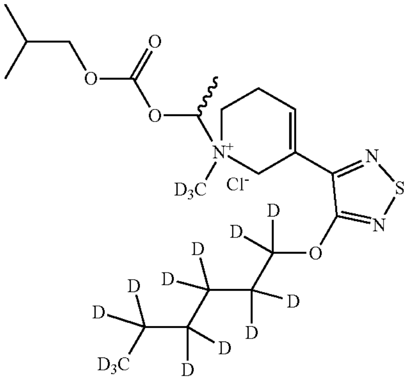 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCC(C)C)(C([2H])([2H])[2H])C1 ; [Cl-]] |
| 283 | 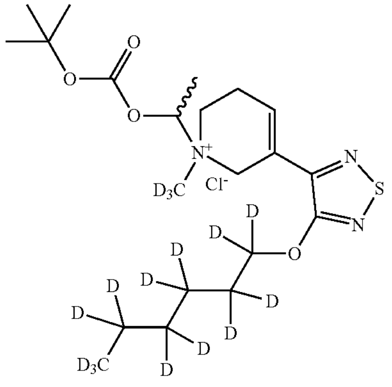 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC(C)(C)C)(C([2H])([2H])[2H])C1 ; [Cl-]] |

TABLE 1-continued
| Cpd No. | Structure |
| --- | --- |
| 284 | 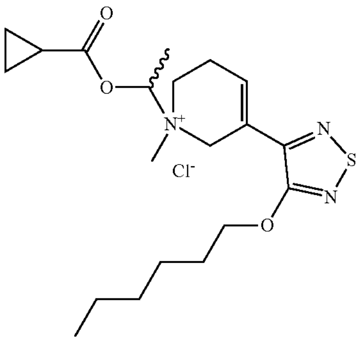 [SMILES: CCCCCCOc1nsnc1C1=CCC[N+](C)(C(C)OC(=O)C2CC2)C1 ; [Cl-]] |
| 285 | 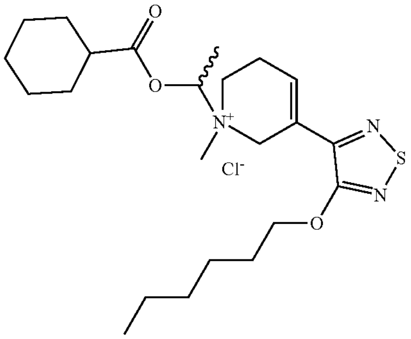 [SMILES: CCCCCCOc1nsnc1C1=CCC[N+](C)(C(C)OC(=O)C2CCCCC2)C1 ; [Cl-]] |
| 286 | 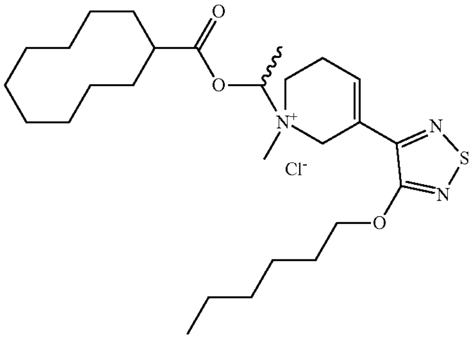 [SMILES: CCCCCCOc1nsnc1C1=CCC[N+](C)(C(C)OC(=O)C2CCCCCCCCC2)C1 ; [Cl-]] |
| 287 | 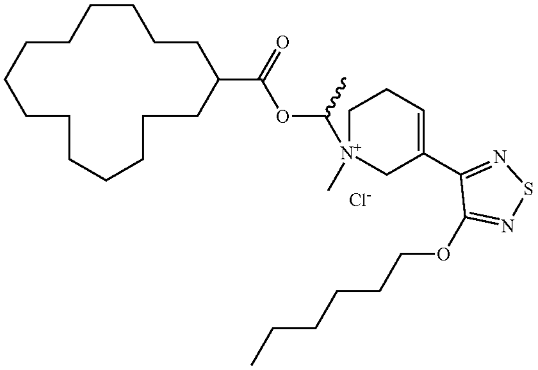 [SMILES: CCCCCCOc1nsnc1C1=CCC[N+](C)(C(C)OC(=O)C2CCCCCCCCCCCCCC2)C1 ; [Cl-]] |

TABLE 1-continued
| Cpd No. | Structure |
| --- | --- |
| 288 | 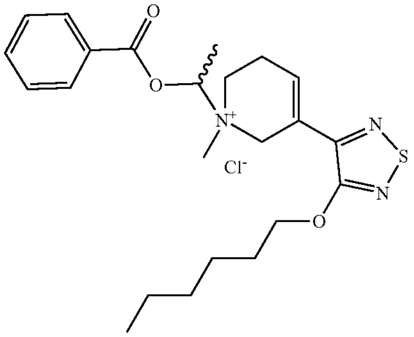 [SMILES: CCCCCCOc1nsnc1C1=CCC[N+](C)(C(C)OC(=O)c2ccccc2)C1 ; [Cl-]] |
| 289 | 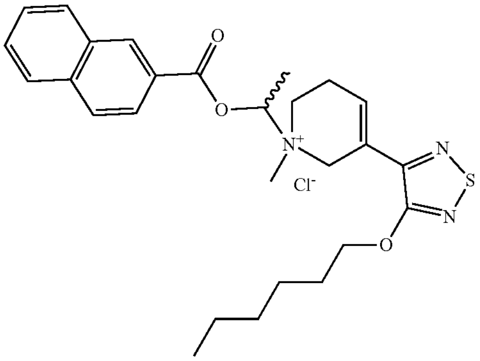 [SMILES: CCCCCCOc1nsnc1C1=CCC[N+](C)(C(C)OC(=O)c2ccc3ccccc3c2)C1 ; [Cl-]] |
| 290 | 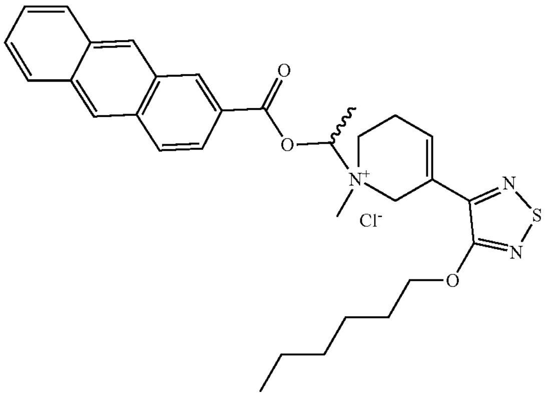 [SMILES: CCCCCCOc1nsnc1C1=CCC[N+](C)(C(C)OC(=O)c2ccc3cc4ccccc4cc3c2)C1 ; [Cl-]] |
| 291 | 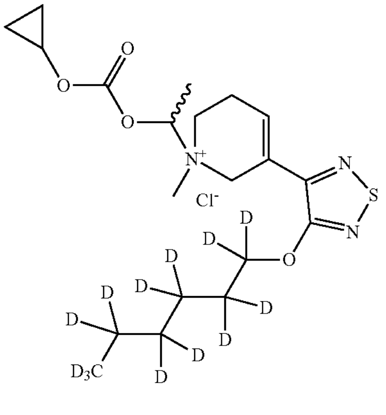 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC2CC2)C1 ; [Cl-]] |

TABLE 1-continued
| Cpd No. | Structure |
| --- | --- |
| 292 | 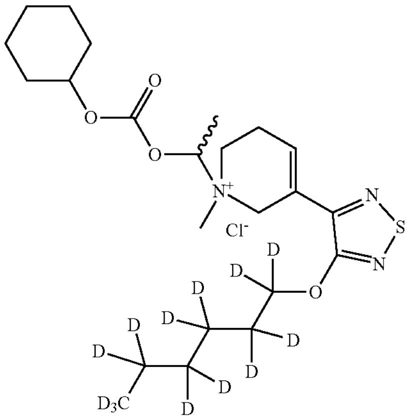 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC2CCCCC2)C1 ; [Cl-]] |
| 293 | 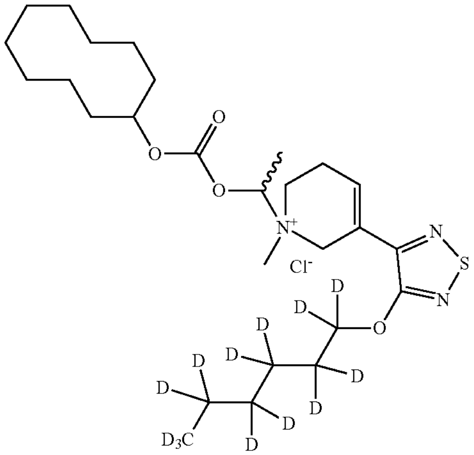 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC2CCCCCCCCC2)C1 ; [Cl-]] |
| 294 | 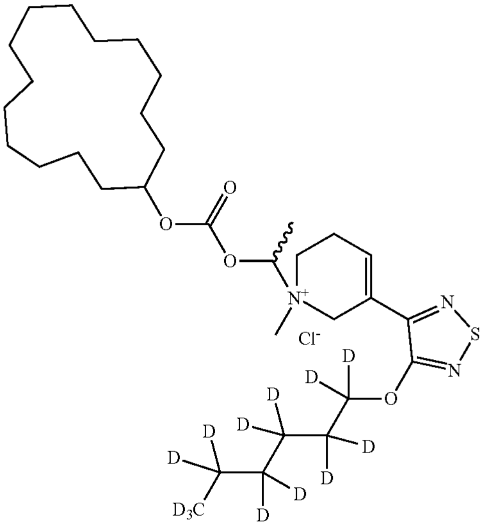 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC2CCCCCCCCCCCCCC2)C1 ; [Cl-]] |

TABLE 1-continued
| Cpd No. | Structure |
|---|---|
| 295 | 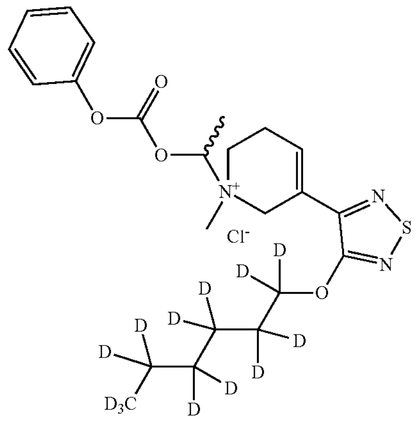 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)Oc2ccccc2)C1 ; [Cl-]] |
| 296 | 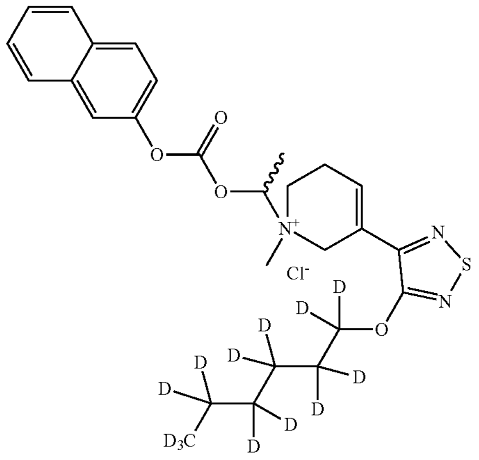 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)Oc2ccc3ccccc3c2)C1 ; [Cl-]] |
| 297 | 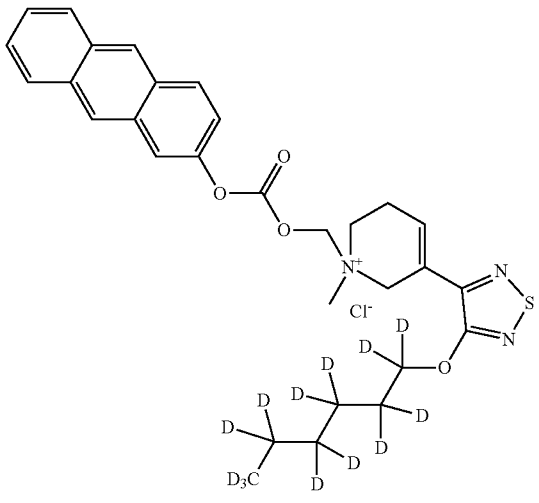 [SMILES: [2H]C([2H])([2H])C([2H])([2H])C([2H])([2H])C([2H])([2H])C([2H])([2H])C([2H])([2H])Oc1nsnc1C1=CCC[N+](C)(COC(=O)Oc2ccc3cc4ccccc4cc3c2)C1 ; [Cl-]] |

TABLE 1-continued
| Cpd No. | Structure |
| --- | --- |
| 298 | 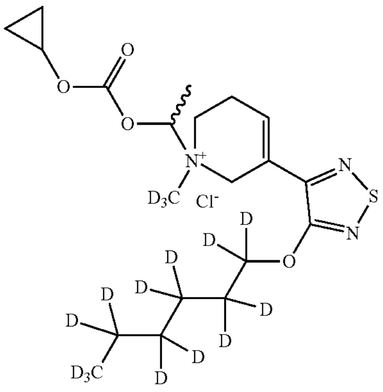 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC2CC2)(C([2H])([2H])[2H])C1 ; [Cl-]] |
| 299 | 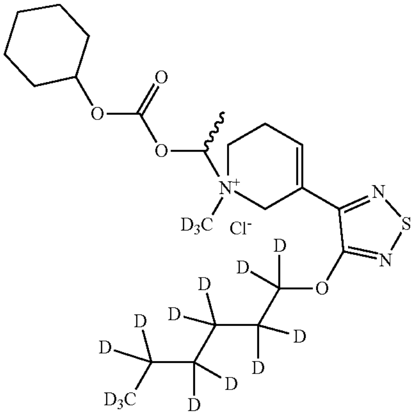 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC2CCCCC2)(C([2H])([2H])[2H])C1 ; [Cl-]] |
| 300 | 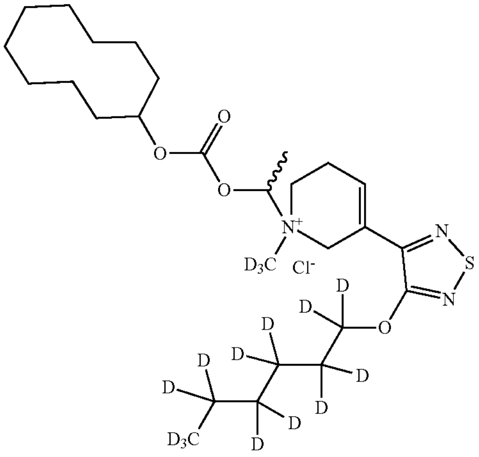 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC2CCCCCCCCC2)(C([2H])([2H])[2H])C1 ; [Cl-]] |

TABLE 1-continued
| Cpd No. | Structure |
| --- | --- |
| 301 | 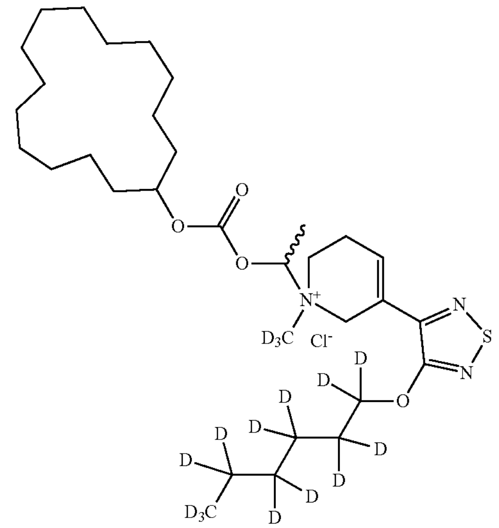 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC2CCCCCCCCCCCCCC2)(C([2H])([2H])[2H])C1 ; [Cl-]] |
| 302 | 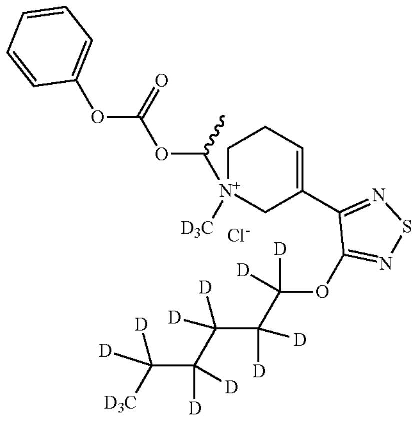 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)Oc2ccccc2)(C([2H])([2H])[2H])C1 ; [Cl-]] |
| 303 | 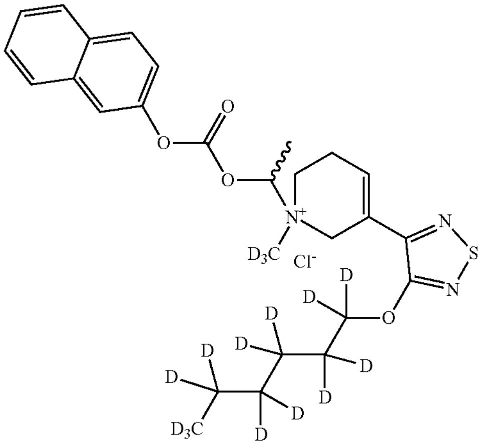 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)Oc2ccc3ccccc3c2)(C([2H])([2H])[2H])C1 ; [Cl-]] |

TABLE 1-continued
| Cpd No. | Structure |
| --- | --- |
| 304 | 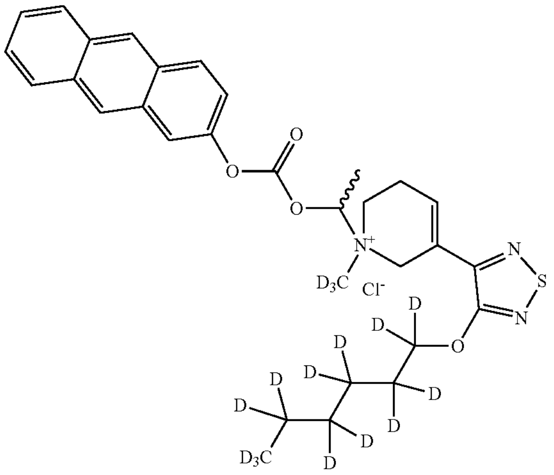 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)Oc2ccc3cc4ccccc4cc3c2)(C([2H])([2H])[2H])C1 ; [Cl-]] |
| 305 | 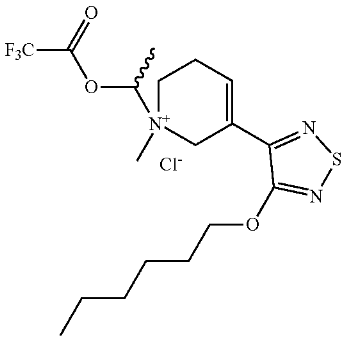 [SMILES: CCCCCCOc1nsnc1C1=CCC[N+](C)(C(C)OC(=O)C(F)(F)F)C1 ; [Cl-]] |
| 306 | 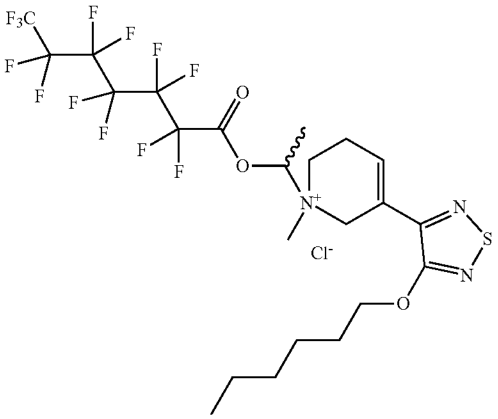 [SMILES: CCCCCCOc1nsnc1C1=CCC[N+](C)(C(C)OC(=O)C(F)(F)C(F)(F)C(F)(F)C(F)(F)C(F)(F)C(F)(F)F)C1 ; [Cl-]] |

TABLE 1-continued
| Cpd No. | Structure |
|---|---|
| 307 | 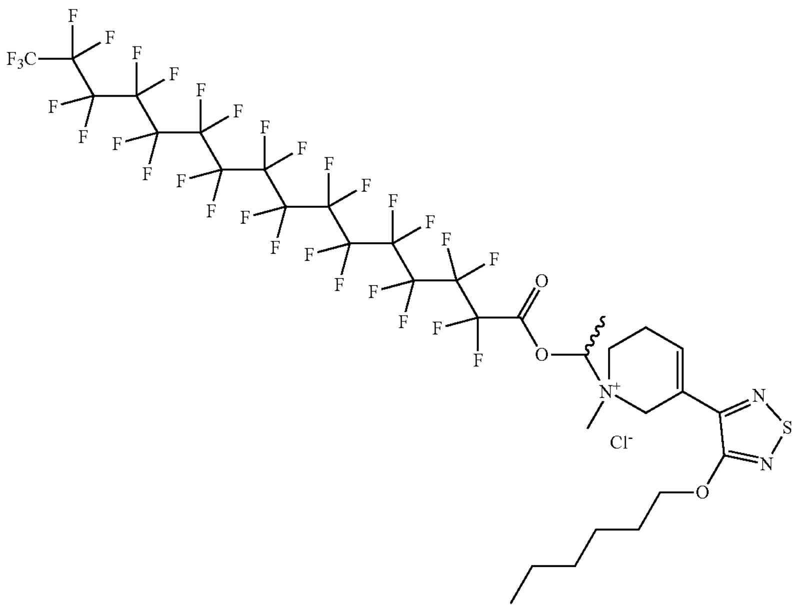 [SMILES: CCCCCCOc1nsnc1C1=CCC[N+](C)(C(C)OC(=O)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)C1 ; [Cl-]] |
| 308 | 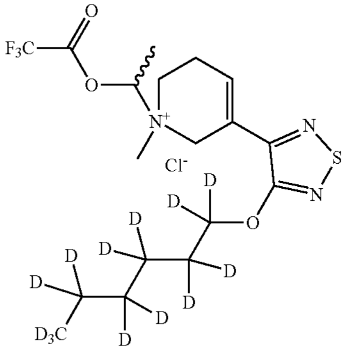 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)C(F)(F)F)C1 ; [Cl-]] |
| 309 | 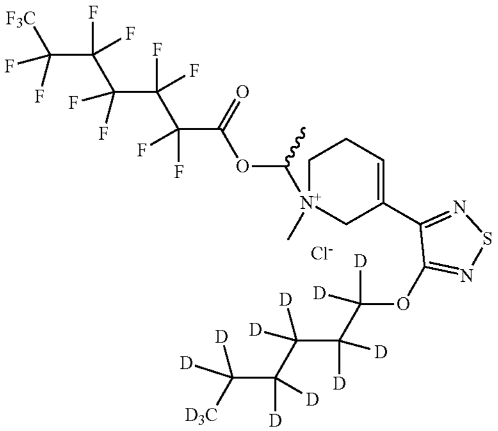 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)C(F)(F)C(F)(F)C(F)(F)C(F)(F)C(F)(F)C(F)(F)F)C1 ; [Cl-]] |

TABLE 1-continued
| Cpd No. | Structure |
| --- | --- |
| 310 | 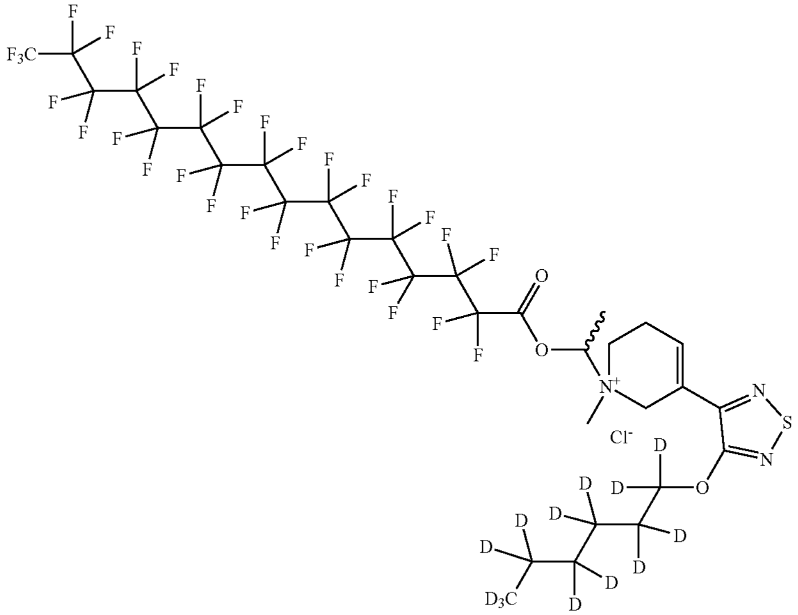 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)C1 ; [Cl-]] |
| 311 | 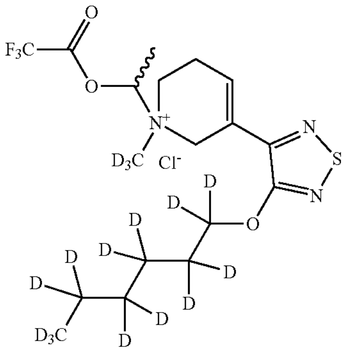 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)C(F)(F)F)(C([2H])([2H])[2H])C1 ; [Cl-]] |
| 312 | 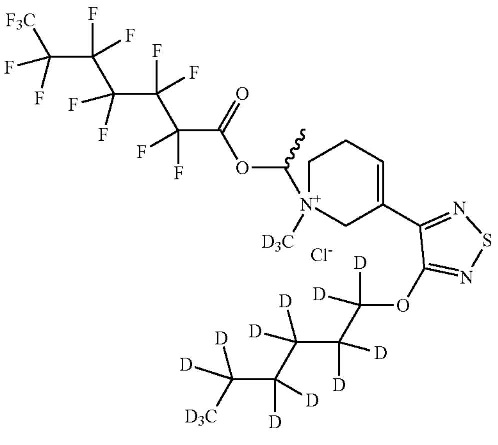 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)C(F)(F)C(F)(F)C(F)(F)C(F)(F)C(F)(F)C(F)(F)F)(C([2H])([2H])[2H])C1 ; [Cl-]] |

TABLE 1-continued
| Cpd No. | Structure |
| --- | --- |
| 313 | 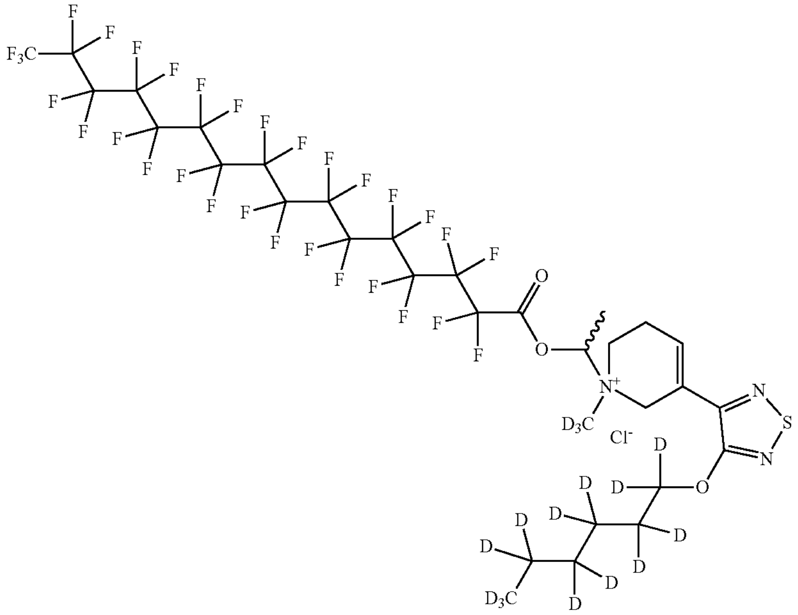 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)(C([2H])([2H])[2H])C1 ; [Cl-]] |
| 314 | 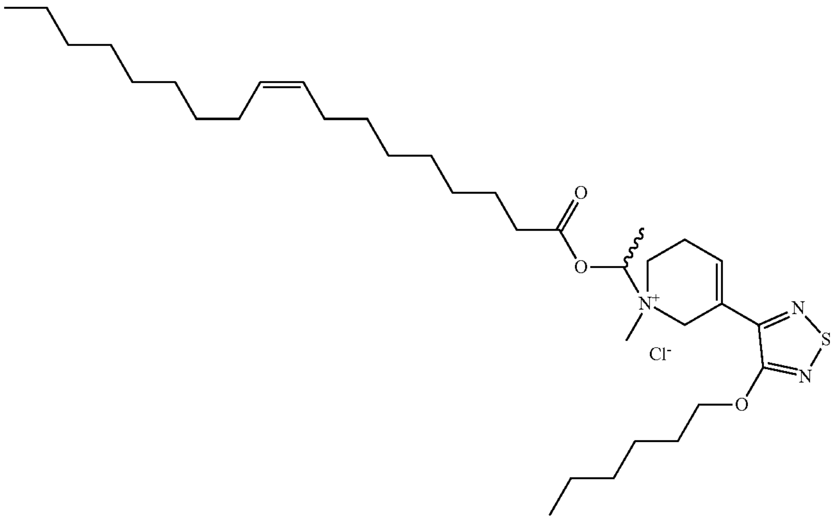 [SMILES: CCCCCCCC/C=C\CCCCCCCC(=O)OC(C)[N+]1(C)CCC=C(c2nsnc2OCCCCCC)C1 ; [Cl-]] |

TABLE 1-continued
| Cpd No. | Structure |
|---|---|
| 315 | 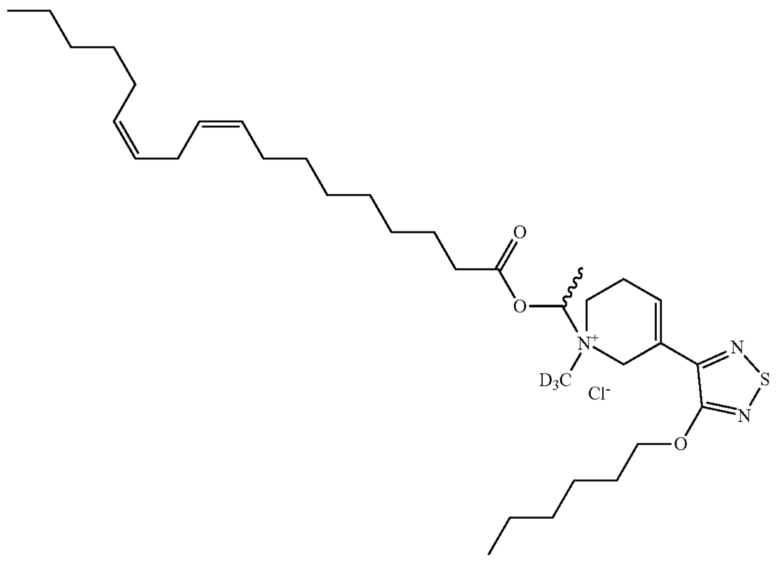 [SMILES: [2H]C([2H])([2H])[N+]1(C(C)OC(=O)CCCCCCC/C=C\C/C=C\CCCCC)CCC=C(c2nsnc2OCCCCCC)C1 ; [Cl-]] |
| 316 | 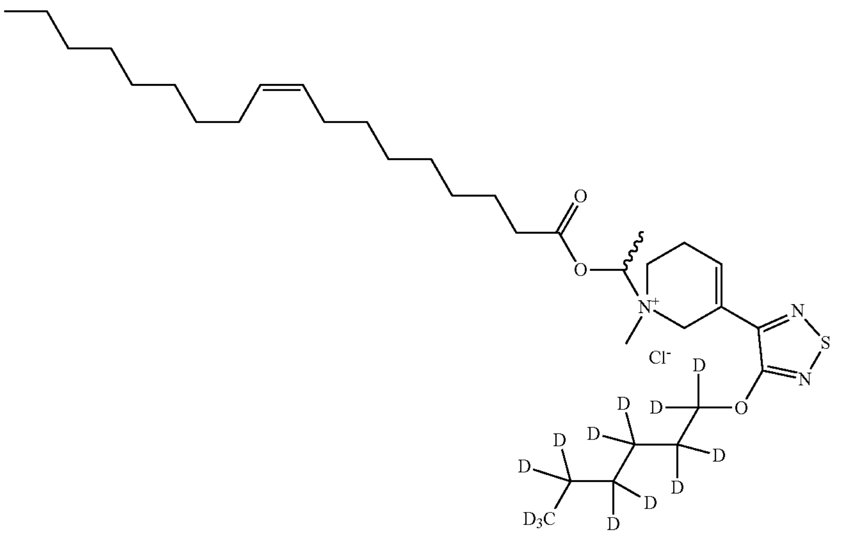 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCC/C=C\CCCCCCCC)C1 ; [Cl-]] |

TABLE 1-continued
| Cpd No. | Structure |
| --- | --- |
| 317 | 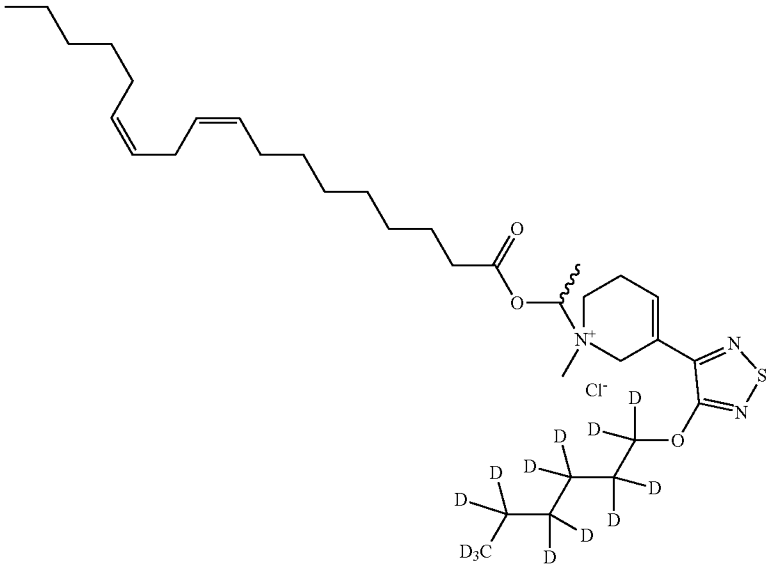 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)CCCCCCC/C=C\C/C=C\CCCCC)C1 ; [Cl-]] |
| 318 | 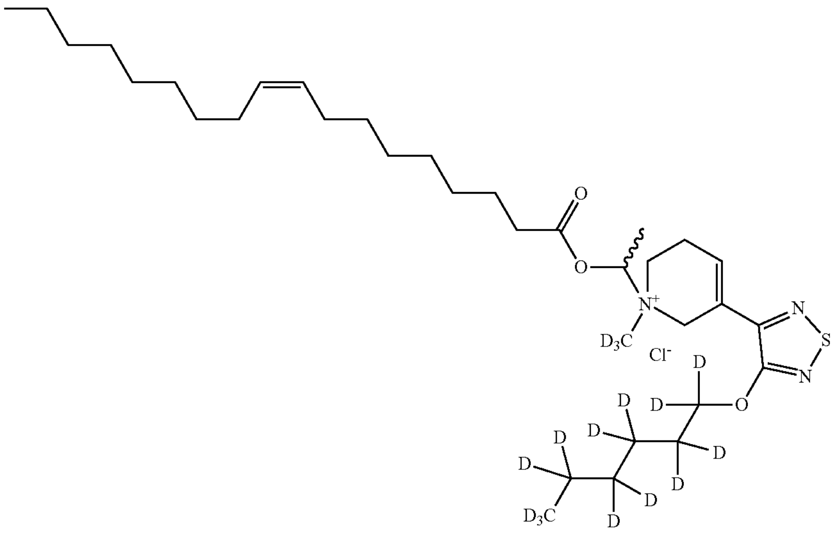 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCC/C=C\CCCCCCCC)(C([2H])([2H])[2H])C1 ; [Cl-]] |

TABLE 1-continued
| Cpd No. | Structure |
| --- | --- |
| 319 | 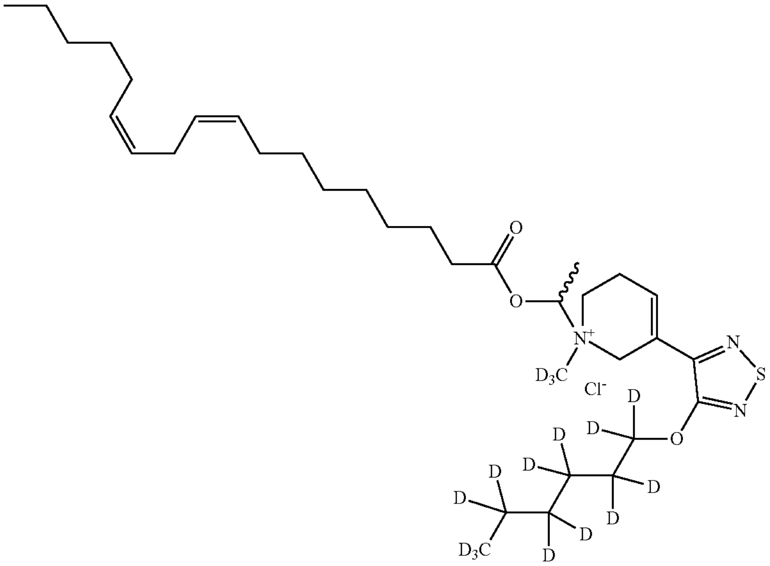 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)CCCCCCC/C=C\C/C=C\CCCCC)(C([2H])([2H])[2H])C1 ; [Cl-]] |
| 320 | 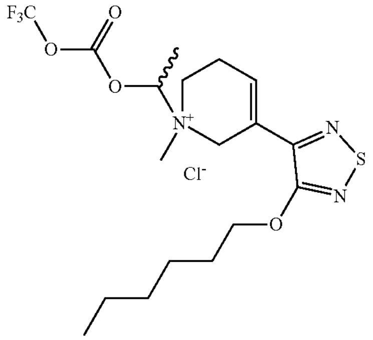 [SMILES: CCCCCCOc1nsnc1C1=CCC[N+](C)(C(C)OC(=O)OC(F)(F)F)C1 ; [Cl-]] |
| 321 | 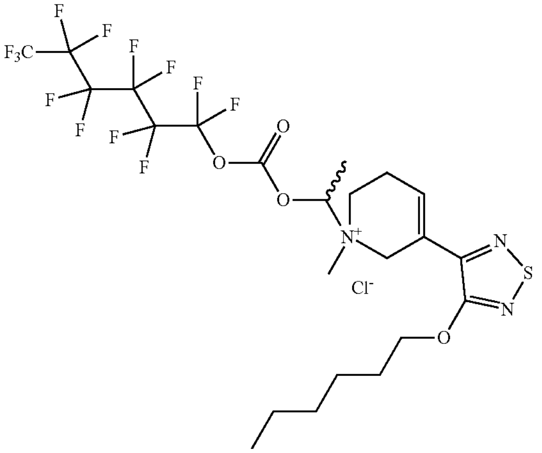 [SMILES: CCCCCCOc1nsnc1C1=CCC[N+](C)(C(C)OC(=O)OC(F)(F)C(F)(F)C(F)(F)C(F)(F)C(F)(F)C(F)(F)F)C1 ; [Cl-]] |

TABLE 1-continued
| Cpd No. | Structure |
| --- | --- |
| 322 | 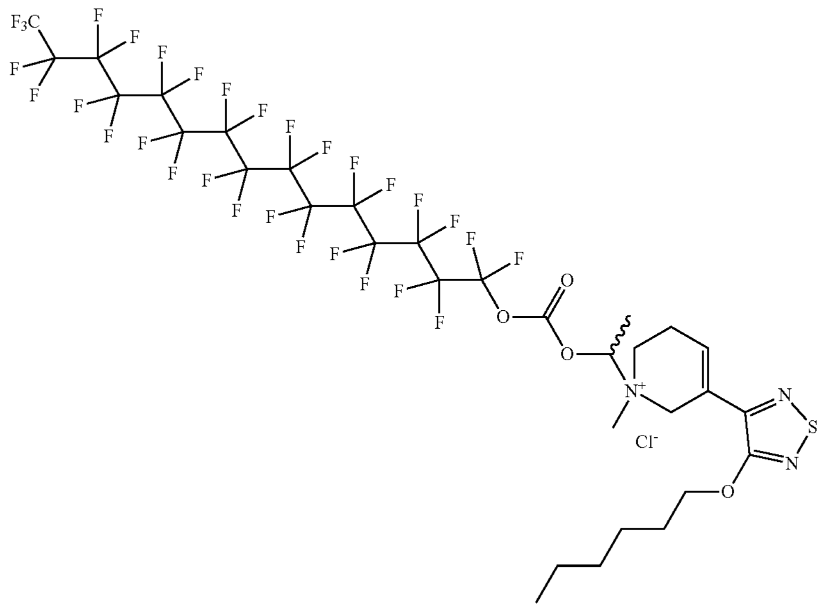 [SMILES: CCCCCCOc1nsnc1C1=CCC[N+](C)(C(C)OC(=O)OC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)C1 ; [Cl-]] |
| 323 | 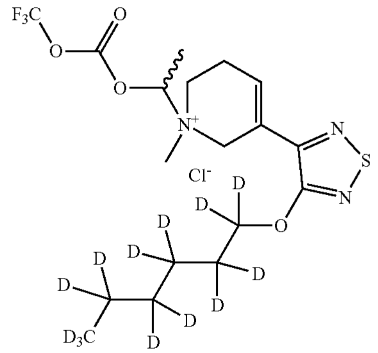 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC(F)(F)F)C1 ; [Cl-]] |
| 324 | 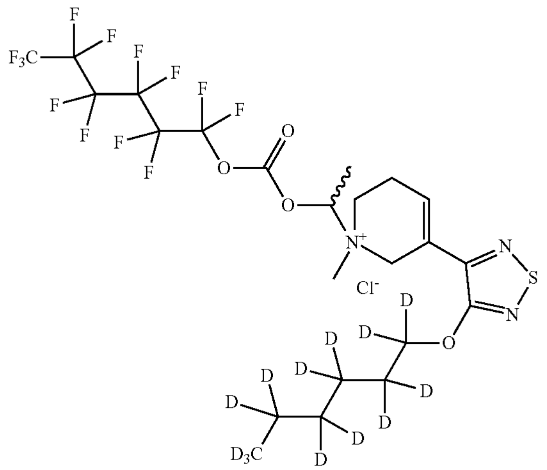 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC(F)(F)C(F)(F)C(F)(F)C(F)(F)C(F)(F)C(F)(F)F)C1 ; [Cl-]] |

TABLE 1-continued
| Cpd No. | Structure |
| --- | --- |
| 325 | 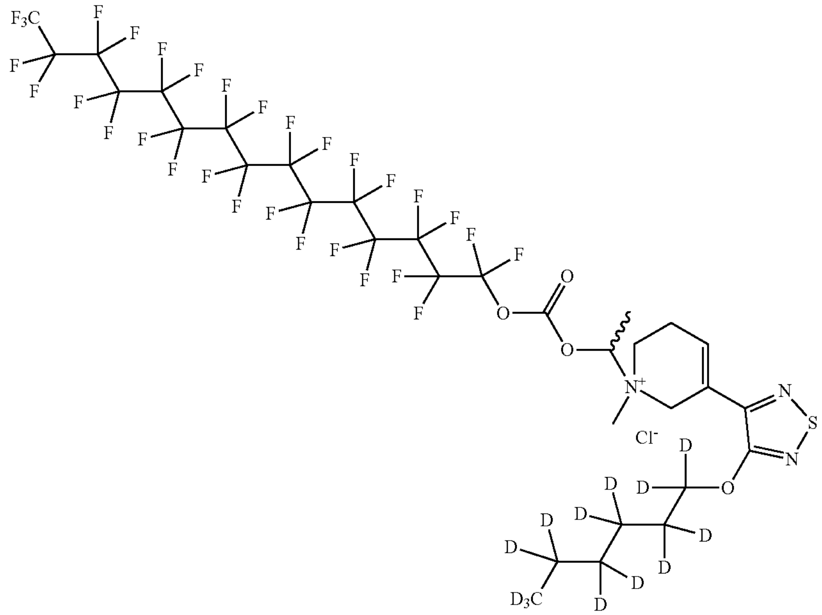 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)C1 ; [Cl-]] |
| 326 | 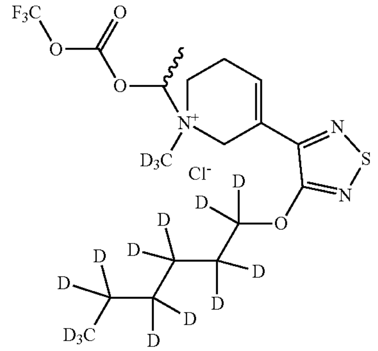 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC(F)(F)F)(C([2H])([2H])[2H])C1 ; [Cl-]] |
| 327 | 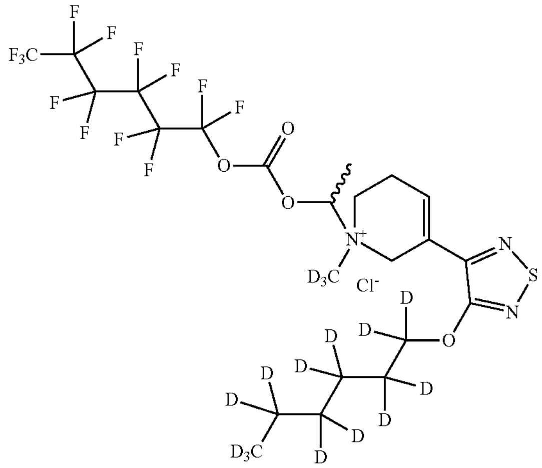 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC(F)(F)C(F)(F)C(F)(F)C(F)(F)C(F)(F)C(F)(F)F)(C([2H])([2H])[2H])C1 ; [Cl-]] |

TABLE 1-continued
| Cpd No. | Structure |
| --- | --- |
| 328 | 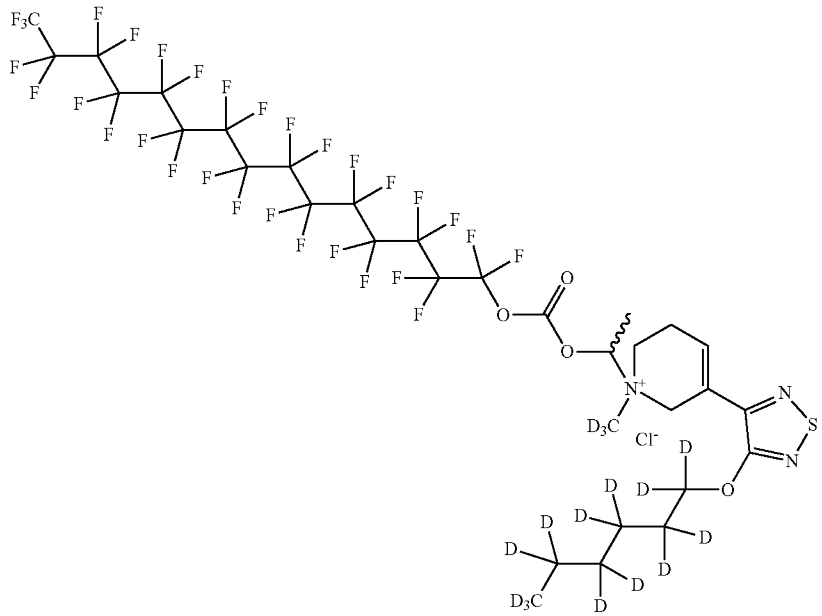 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)(C([2H])([2H])[2H])C1 ; [Cl-]] |
| 329 | 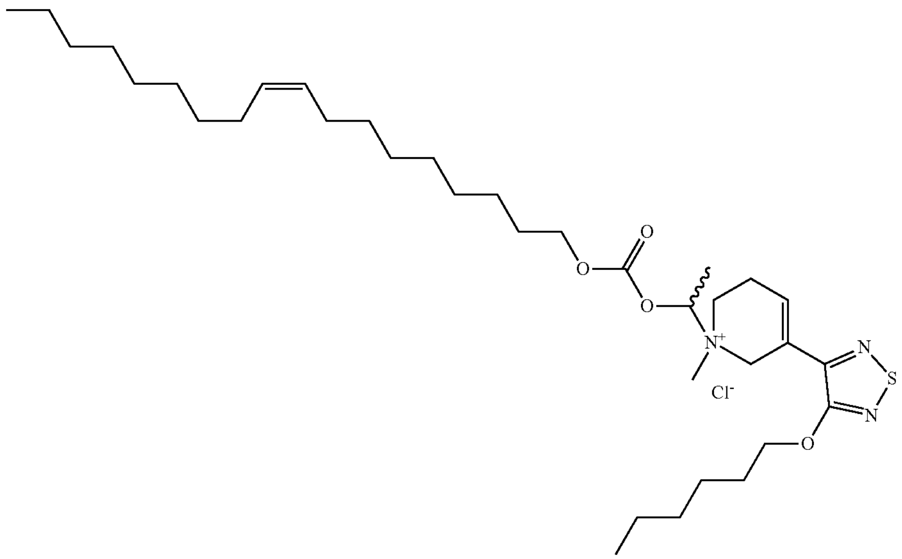 [SMILES: CCCCCCCC/C=C\CCCCCCCCOC(=O)OC(C)[N+]1(C)CCC=C(c2nsnc2OCCCCCC)C1 ; [Cl-]] |

TABLE 1-continued
| Cpd No. | Structure |
| --- | --- |
| 330 | 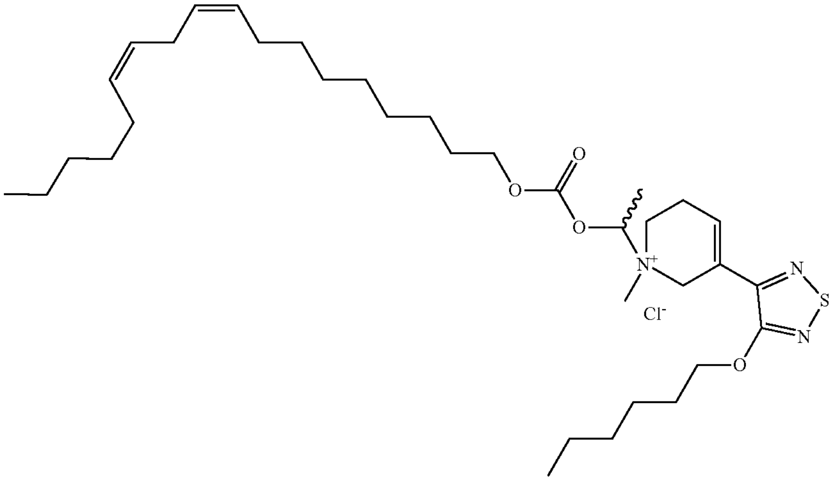 [SMILES: CCCCC/C=C\C/C=C\CCCCCCCCOC(=O)OC(C)[N+]1(C)CCC=C(c2nsnc2OCCCCCC)C1 ; [Cl-]] |
| 331 | 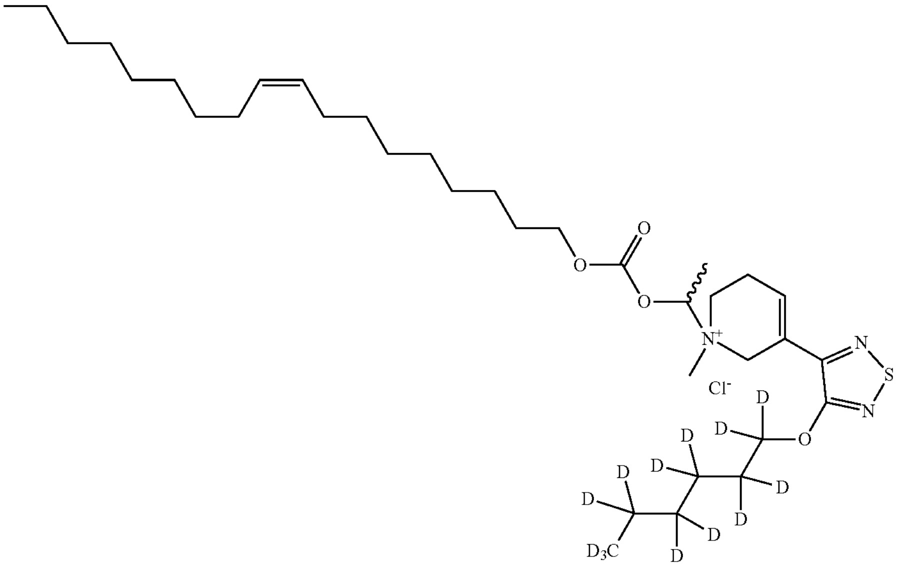 [SMILES: [2H]C([2H])([2H])C([2H])([2H])C([2H])([2H])C([2H])([2H])C([2H])([2H])C([2H])([2H])Oc1nsnc1C1=CCC[N+](C)(C(C)OC(=O)OCCCCCCCC/C=C\CCCCCCCC)C1 ; [Cl-]] |
| 332 | 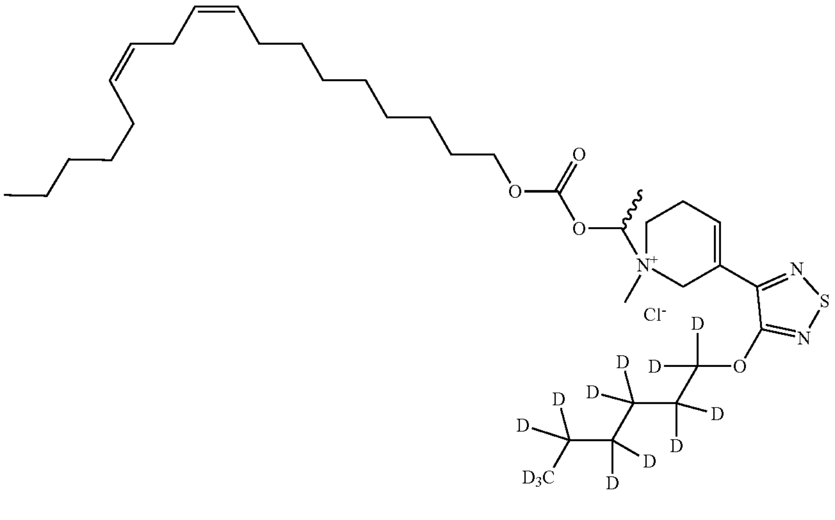 |

TABLE 1-continued
| Cpd No. | Structure |
|---|---|
| 333 | 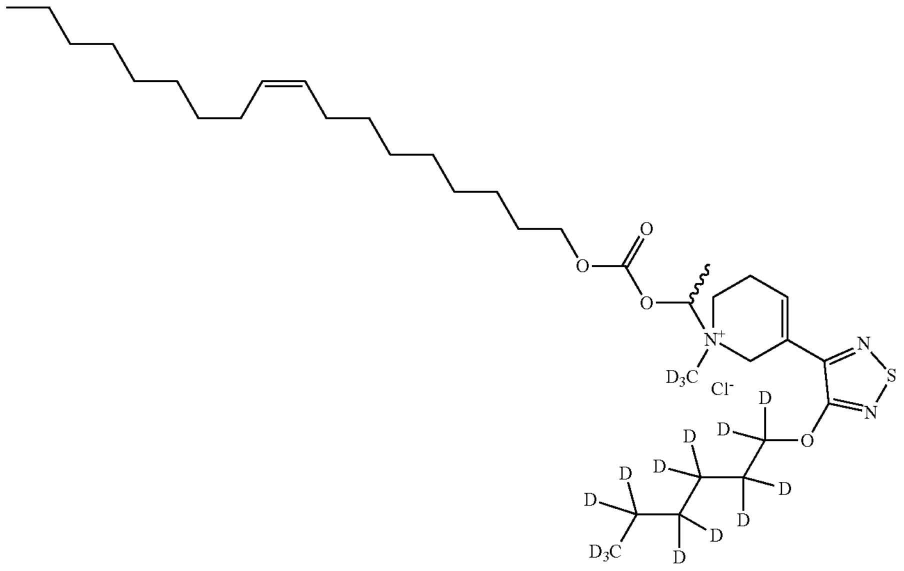 |
| 334 | 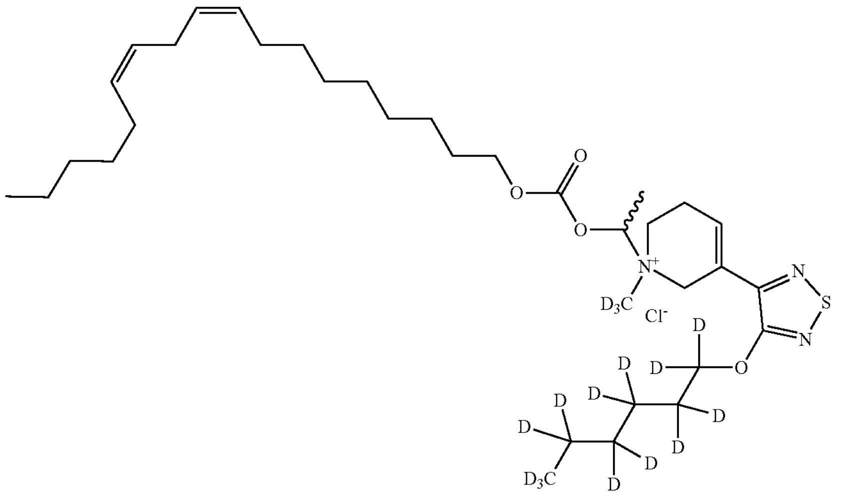 [SMILES: [2H]C([2H])([2H])C([2H])([2H])C([2H])([2H])C([2H])([2H])C([2H])([2H])C([2H])([2H])Oc1nsnc1C1=CCC[N+](C(C)OC(=O)OCCCCCCCC/C=C\C/C=C\CCCCC)(C([2H])([2H])[2H])C1 ; [Cl-]] |
| 335 | 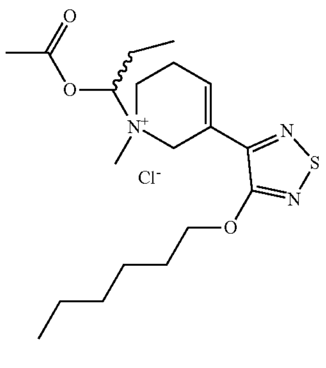 [SMILES: CCCCCCOc1nsnc1C1=CCC[N+](C)(C(CC)OC(C)=O)C1 ; [Cl-]] |

TABLE 1-continued
| Cpd No. | Structure |
|---|---|
| 336 | 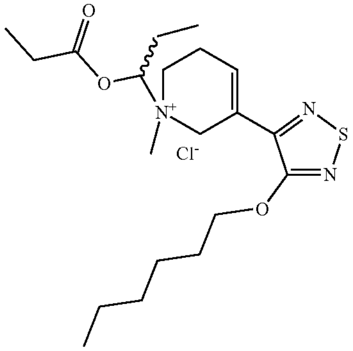 [SMILES: CCCCCCOc1nsnc1C1=CCC[N+](C)(C(CC)OC(=O)CC)C1 ; [Cl-]] |
| 337 | 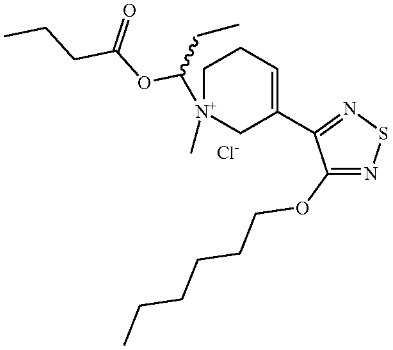 [SMILES: CCCCCCOc1nsnc1C1=CCC[N+](C)(C(CC)OC(=O)CCC)C1 ; [Cl-]] |
| 338 | 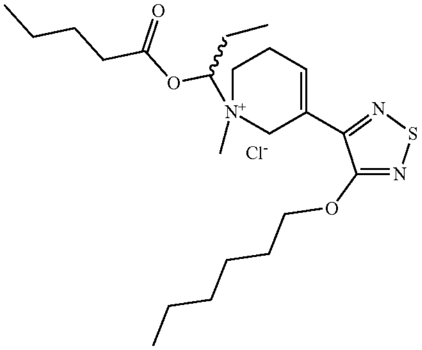 [SMILES: CCCCCCOc1nsnc1C1=CCC[N+](C)(C(CC)OC(=O)CCCC)C1 ; [Cl-]] |
| 339 | 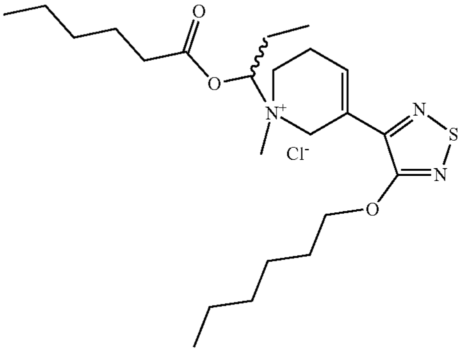 [SMILES: CCCCCCOc1nsnc1C1=CCC[N+](C)(C(CC)OC(=O)CCCCC)C1 ; [Cl-]] |

TABLE 1-continued
| Cpd No. | Structure |
|---|---|
| 340 | 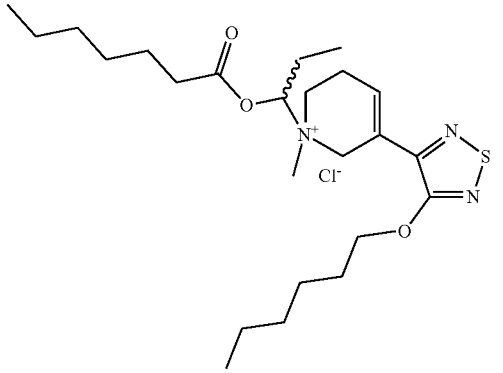 [SMILES: CCCCCCOc1nsnc1C1=CCC[N+](C)(C(CC)OC(=O)CCCCCC)C1 ; [Cl-]] |
| 341 | 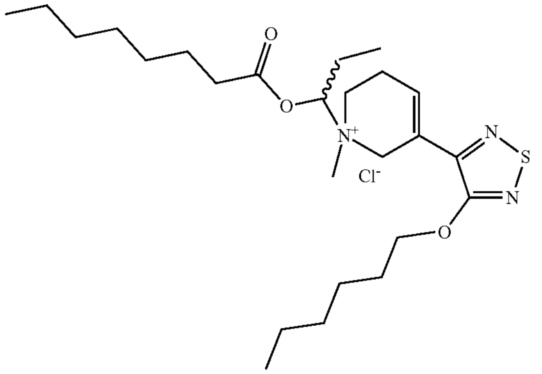 [SMILES: CCCCCCCC(=O)OC(CC)[N+]1(C)CCC=C(c2nsnc2OCCCCCC)C1 ; [Cl-]] |
| 342 | 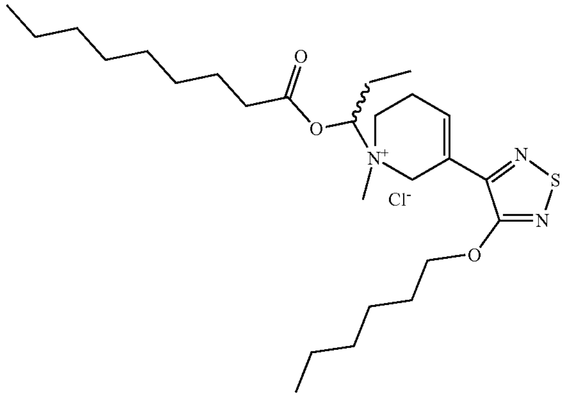 [SMILES: CCCCCCCCC(=O)OC(CC)[N+]1(C)CCC=C(c2nsnc2OCCCCCC)C1 ; [Cl-]] |
| 343 | 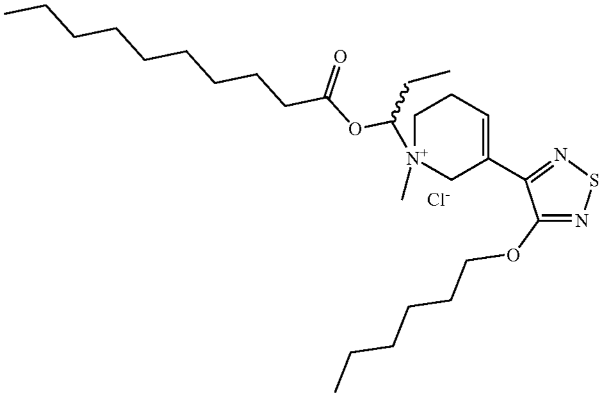 [SMILES: CCCCCCCCCC(=O)OC(CC)[N+]1(C)CCC=C(c2nsnc2OCCCCCC)C1 ; [Cl-]] |

TABLE 1-continued
| Cpd No. | Structure |
|---|---|
| 344 | 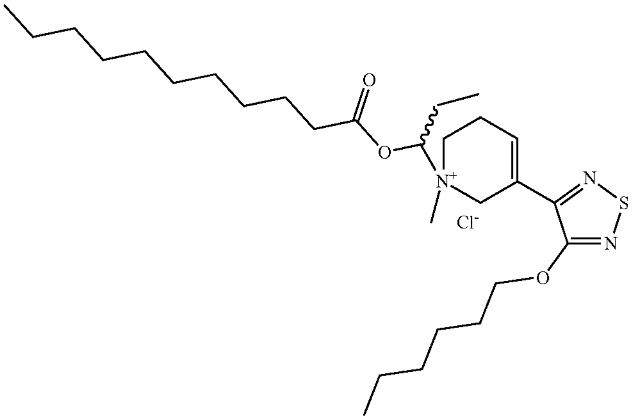 [SMILES: CCCCCCCCCCC(=O)OC(CC)[N+]1(C)CCC=C(c2nsnc2OCCCCCC)C1 ; [Cl-]] |
| 345 | 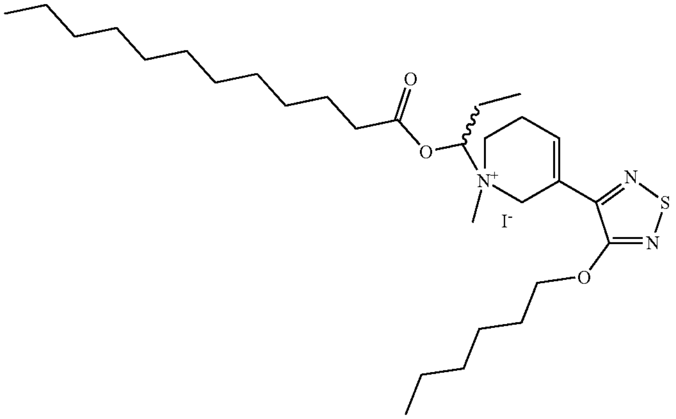 |
| 346 | 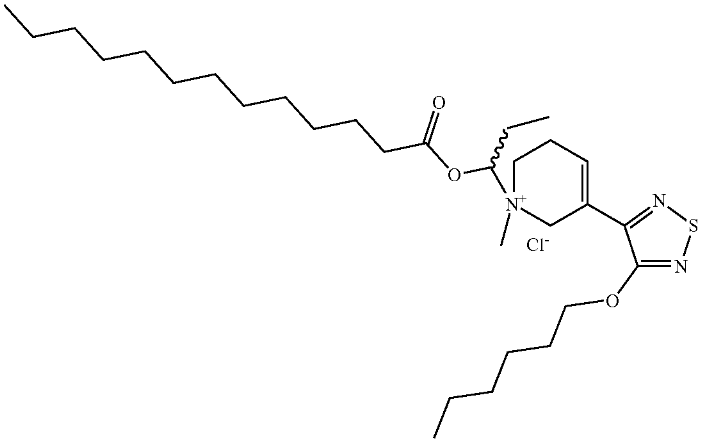 |

TABLE 1-continued
| Cpd No. | Structure |
| --- | --- |
| 347 | 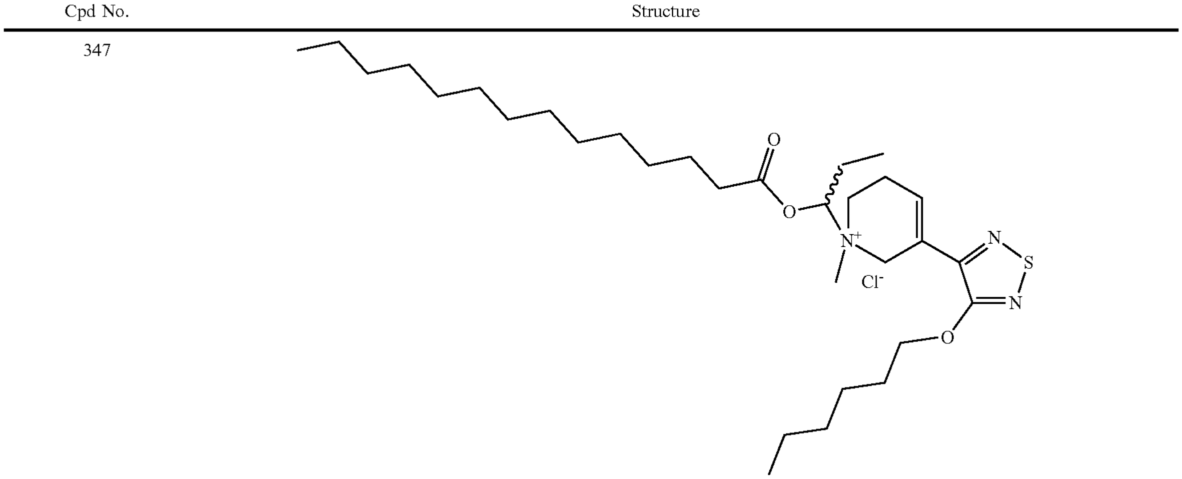 |
| 348 | 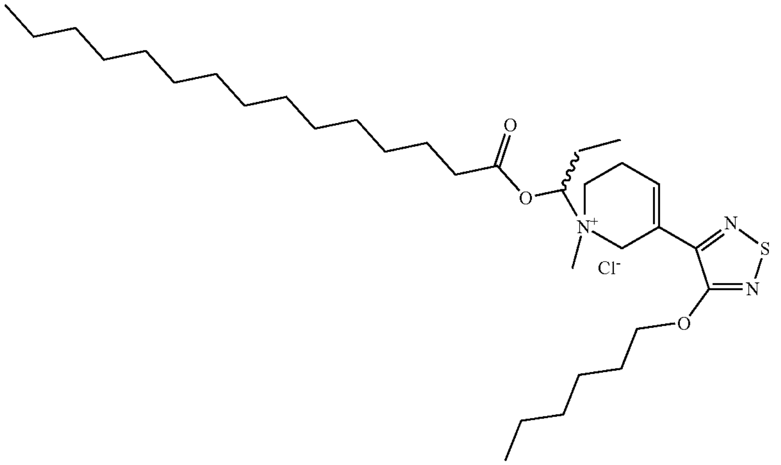 [SMILES: CCCCCCCCCCCCCCC(=O)OC(CC)[N+]1(C)CCC=C(c2nsnc2OCCCCCC)C1 ; [Cl-]] |
| 349 | 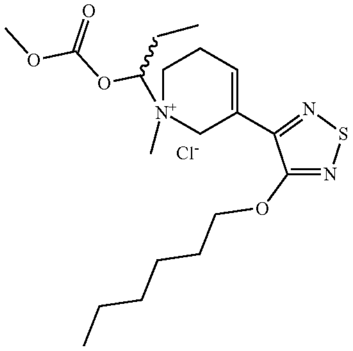 [SMILES: CCCCCCOc1nsnc1C1=CCC[N+](C)(C(CC)OC(=O)OC)C1 ; [Cl-]] |
| 350 | 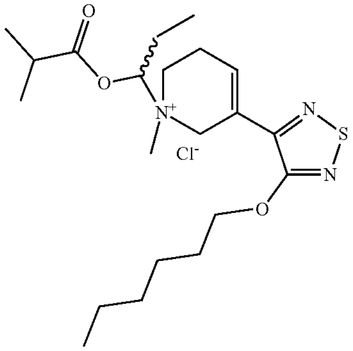 [SMILES: CCCCCCOc1nsnc1C1=CCC[N+](C)(C(CC)OC(=O)C(C)C)C1 ; [Cl-]] |

TABLE 1-continued
| Cpd No. | Structure |
|---|---|
| 351 | 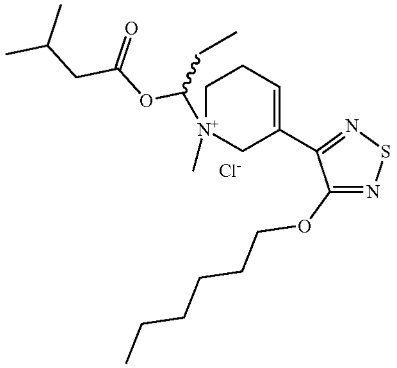 [SMILES: CCCCCCOc1nsnc1C1=CCC[N+](C)(C(CC)OC(=O)CC(C)C)C1 ; [Cl-]] |
| 352 | 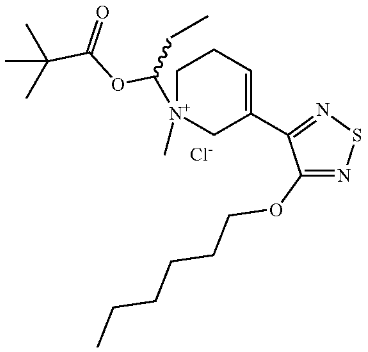 [SMILES: CCCCCCOc1nsnc1C1=CCC[N+](C)(C(CC)OC(=O)C(C)(C)C)C1 ; [Cl-]] |
| 353 | 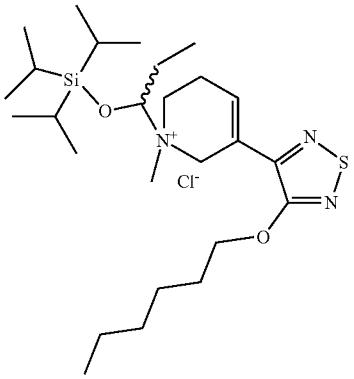 [SMILES: CCCCCCOc1nsnc1C1=CCC[N+](C)(C(CC)O[Si](C(C)C)(C(C)C)C(C)C)C1 ; [Cl-]] |
| 354 | 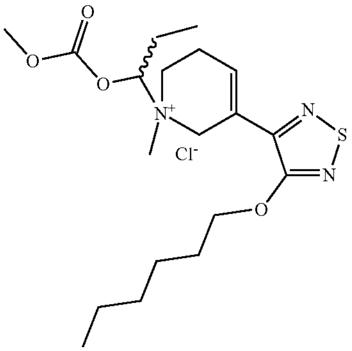 [SMILES: CCCCCCOc1nsnc1C1=CCC[N+](C)(C(CC)OC(=O)OC)C1 ; [Cl-]] |

TABLE 1-continued
| Cpd No. | Structure |
| --- | --- |
| 355 | 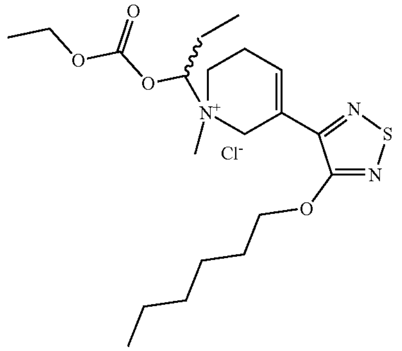 [SMILES: CCCCCCOc1nsnc1C1=CCC[N+](C)(C(CC)OC(=O)OCC)C1 ; [Cl-]] |
| 356 | 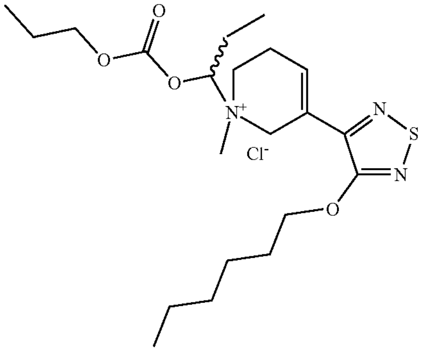 [SMILES: CCCCCCOc1nsnc1C1=CCC[N+](C)(C(CC)OC(=O)OCCC)C1 ; [Cl-]] |
| 357 | 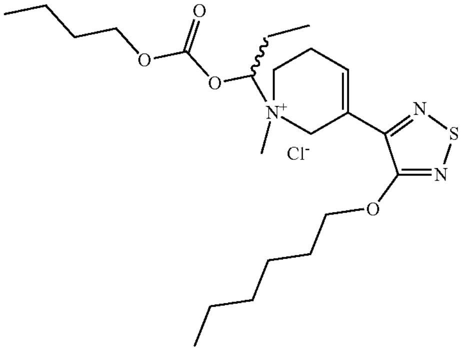 [SMILES: CCCCCCOc1nsnc1C1=CCC[N+](C)(C(CC)OC(=O)OCCCC)C1 ; [Cl-]] |
| 358 | 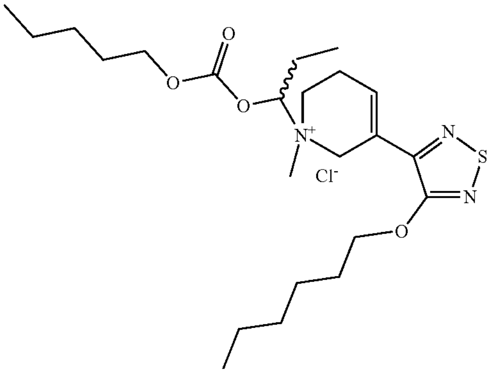 [SMILES: CCCCCCOc1nsnc1C1=CCC[N+](C)(C(CC)OC(=O)OCCCCC)C1 ; [Cl-]] |

TABLE 1-continued
| Cpd No. | Structure |
|---|---|
| 359 | 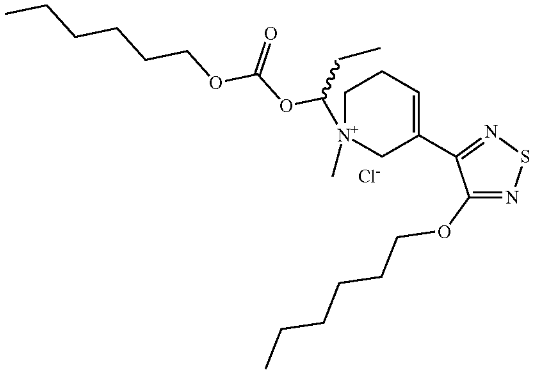 [SMILES: CCCCCCOC(=O)OC(CC)[N+]1(C)CCC=C(c2nsnc2OCCCCCC)C1 ; [Cl-]] |
| 360 | 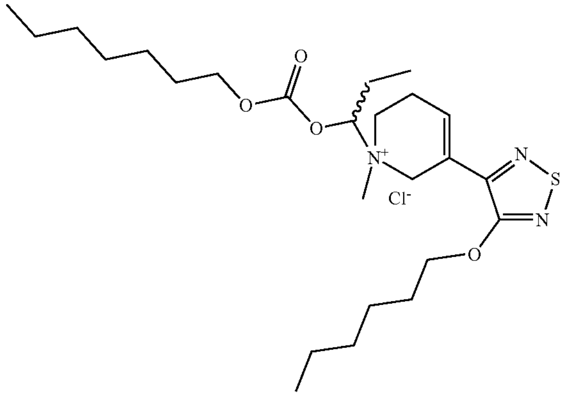 |
| 361 | 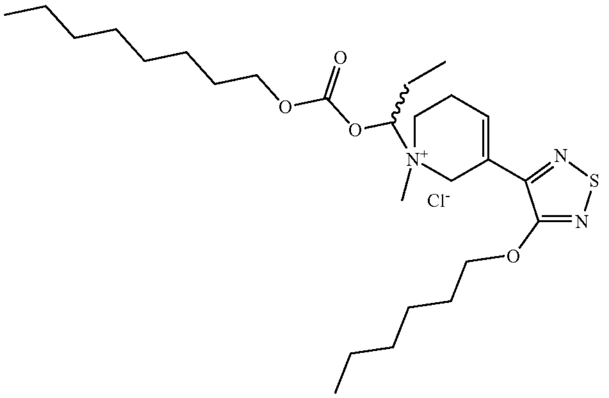 [SMILES: CCCCCCCCOC(=O)OC(CC)[N+]1(C)CCC=C(c2nsnc2OCCCCCC)C1 ; [Cl-]] |
| 362 | 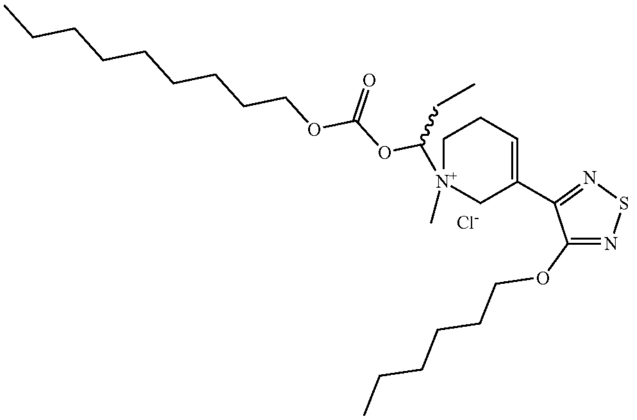 [SMILES: CCCCCCCCCOC(=O)OC(CC)[N+]1(C)CCC=C(c2nsnc2OCCCCCC)C1 ; [Cl-]] |

TABLE 1-continued
| Cpd No. | Structure |
| --- | --- |
| 363 | 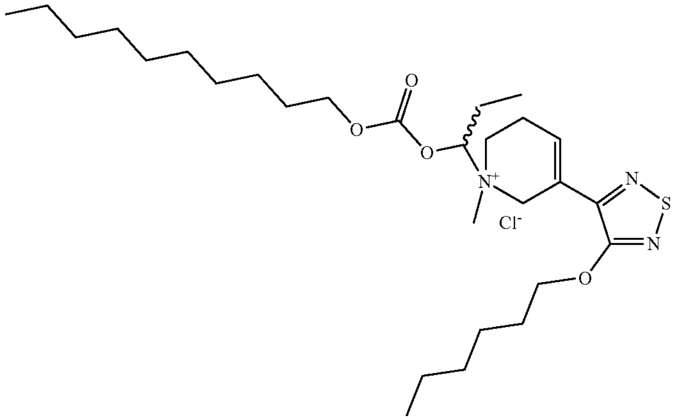 [SMILES: CCCCCCCCCCOC(=O)OC(CC)[N+]1(C)CCC=C(c2nsnc2OCCCCCC)C1 ; [Cl-]] |
| 364 | 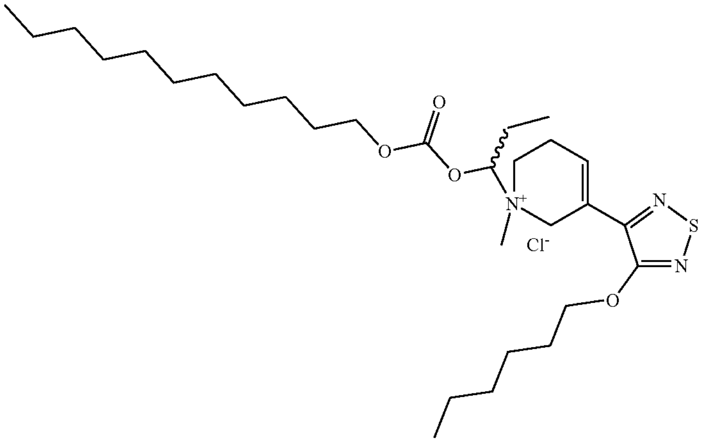 |
| 365 | 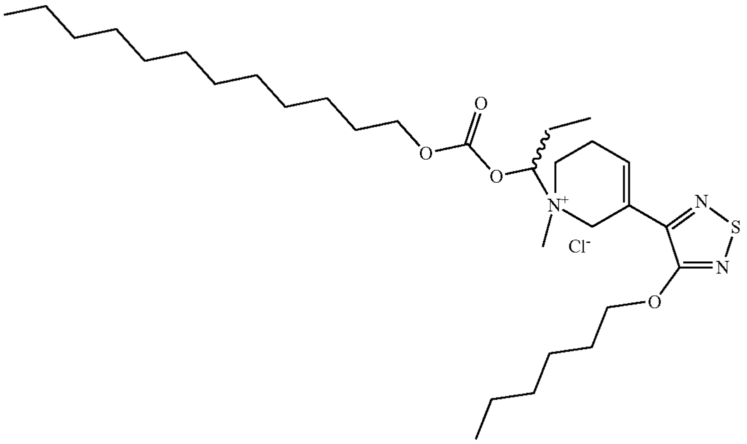 |

TABLE 1-continued
| Cpd No. | Structure |
|---|---|
| 366 | 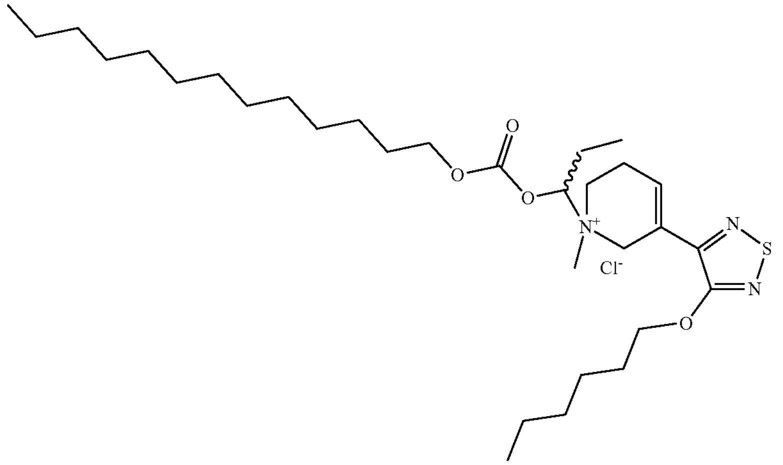 [SMILES: CCCCCCCCCCCCCOC(=O)OC(CC)[N+]1(C)CCC=C(c2nsnc2OCCCCCC)C1 ; [Cl-]] |
| 367 | 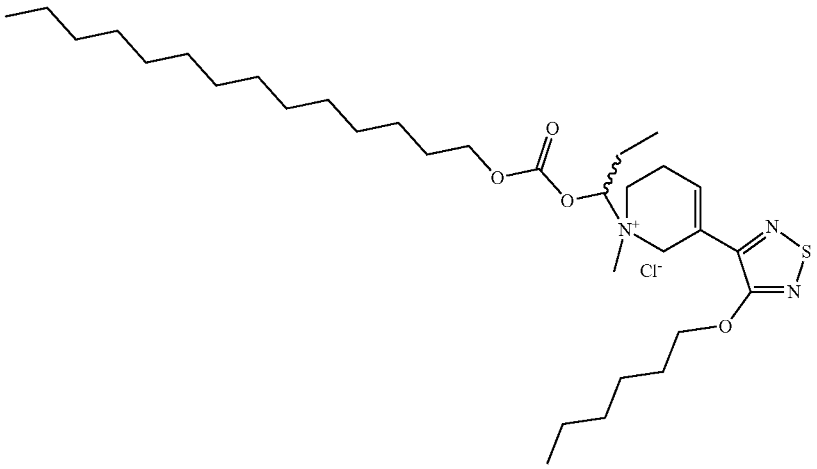 [SMILES: CCCCCCCCCCCCCCOC(=O)OC(CC)[N+]1(C)CCC=C(c2nsnc2OCCCCCC)C1 ; [Cl-]] |
| 368 | 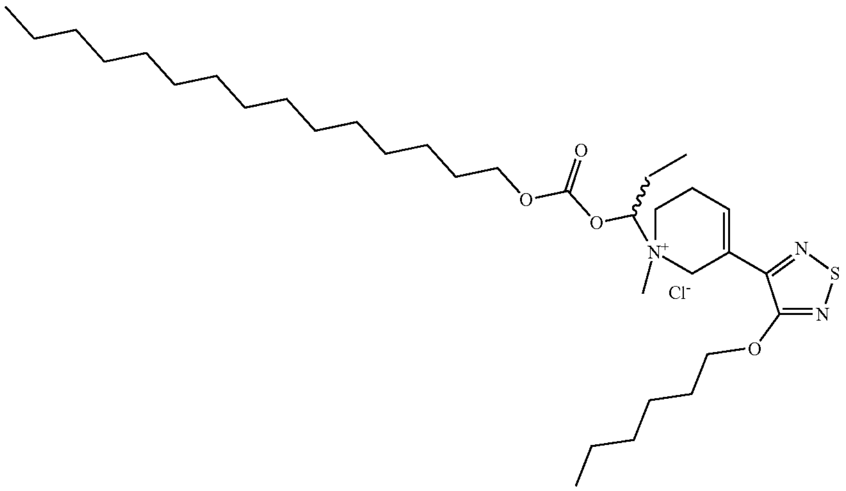 [SMILES: CCCCCCCCCCCCCCCOC(=O)OC(CC)[N+]1(C)CCC=C(c2nsnc2OCCCCCC)C1 ; [Cl-]] |

TABLE 1-continued
| Cpd No. | Structure |
| --- | --- |
| 369 | 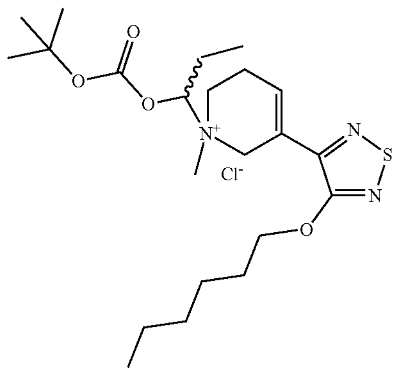 [SMILES: CCCCCCOc1nsnc1C1=CCC[N+](C)(C(CC)OC(=O)OC(C)(C)C)C1 ; [Cl-]] |
| 370 | 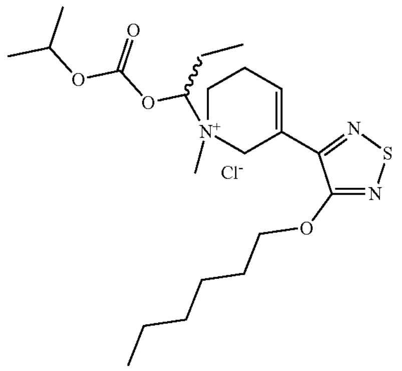 [SMILES: CCCCCCOc1nsnc1C1=CCC[N+](C)(C(CC)OC(=O)OC(C)C)C1 ; [Cl-]] |
| 371 | 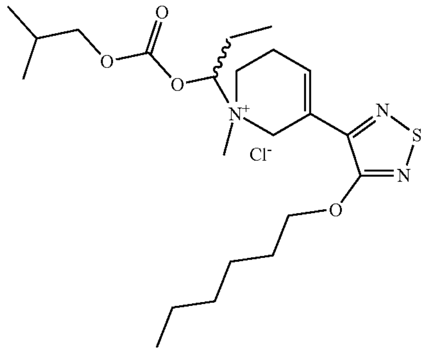 [SMILES: CCCCCCOc1nsnc1C1=CCC[N+](C)(C(CC)OC(=O)OCC(C)C)C1 ; [Cl-]] |
| 372 | 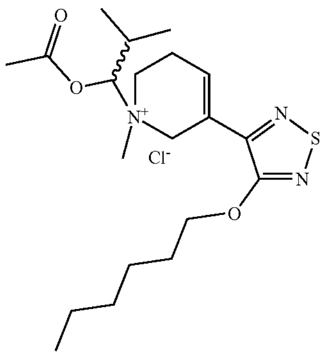 [SMILES: CCCCCCOc1nsnc1C1=CCC[N+](C)(C(OC(C)=O)C(C)C)C1 ; [Cl-]] |

TABLE 1-continued
| Cpd No. | Structure |
| --- | --- |
| 373 | 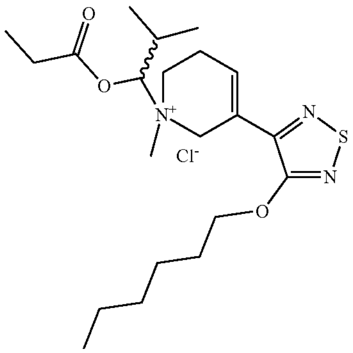 [SMILES: CCCCCCOc1nsnc1C1=CCC[N+](C)(C(OC(=O)CC)C(C)C)C1 ; [Cl-]] |
| 374 | 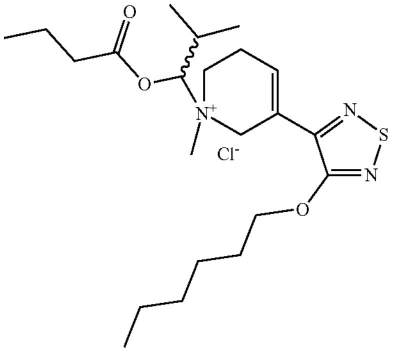 [SMILES: CCCCCCOc1nsnc1C1=CCC[N+](C)(C(OC(=O)CCC)C(C)C)C1 ; [Cl-]] |
| 375 | 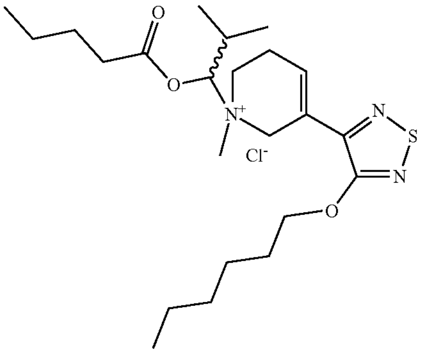 [SMILES: CCCCCCOc1nsnc1C1=CCC[N+](C)(C(OC(=O)CCCC)C(C)C)C1 ; [Cl-]] |
| 376 | 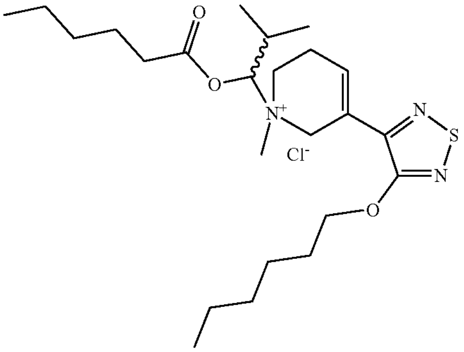 [SMILES: CCCCCCOc1nsnc1C1=CCC[N+](C)(C(OC(=O)CCCCC)C(C)C)C1 ; [Cl-]] |

TABLE 1-continued
| Cpd No. | Structure |
| --- | --- |
| 377 | 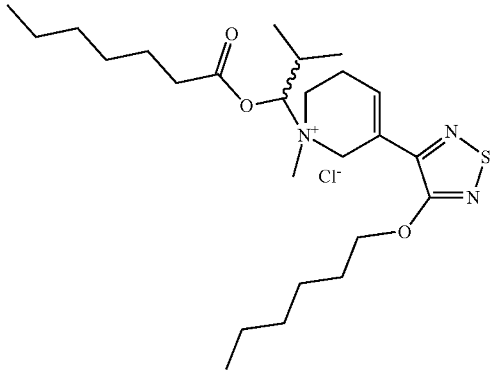 [SMILES: CCCCCCOc1nsnc1C1=CCC[N+](C)(C(OC(=O)CCCCCC)C(C)C)C1 ; [Cl-]] |
| 378 | 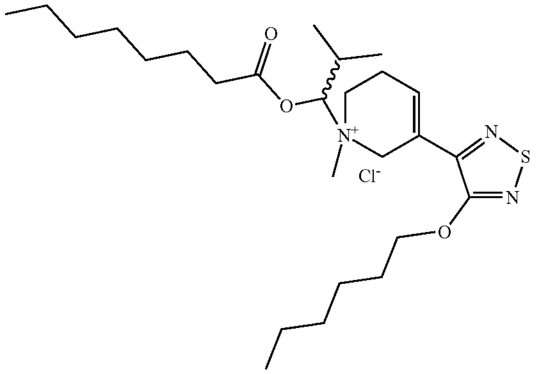 [SMILES: CCCCCCCC(=O)OC(C(C)C)[N+]1(C)CCC=C(c2nsnc2OCCCCCC)C1 ; [Cl-]] |
| 379 | 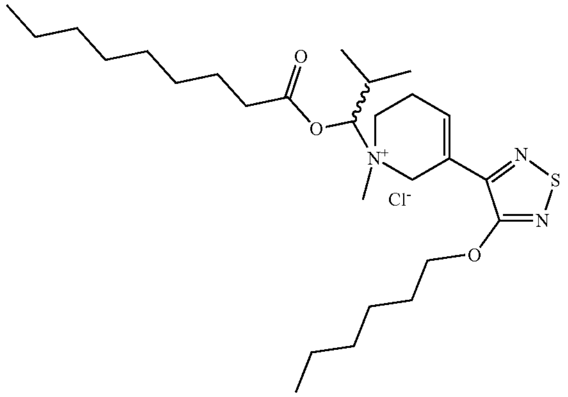 [SMILES: CCCCCCCCC(=O)OC(C(C)C)[N+]1(C)CCC=C(c2nsnc2OCCCCCC)C1 ; [Cl-]] |
| 380 | 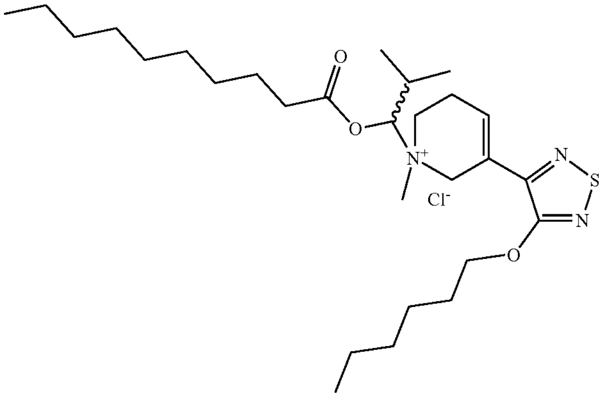 [SMILES: CCCCCCCCCC(=O)OC(C(C)C)[N+]1(C)CCC=C(c2nsnc2OCCCCCC)C1 ; [Cl-]] |

TABLE 1-continued
| Cpd No. | Structure |
| --- | --- |
| 381 | 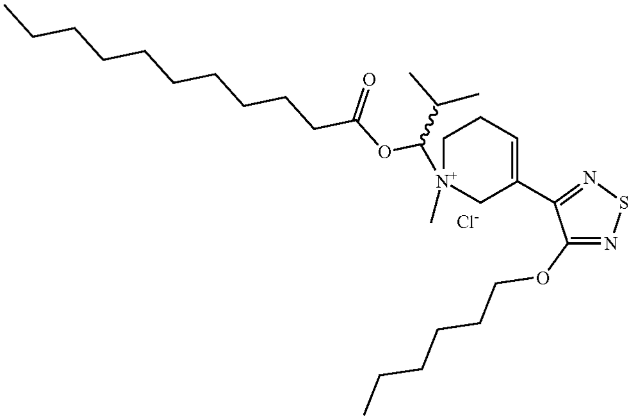 [SMILES: CCCCCCCCCCC(=O)OC(C(C)C)[N+]1(C)CCC=C(c2nsnc2OCCCCCC)C1 ; [Cl-]] |
| 382 | 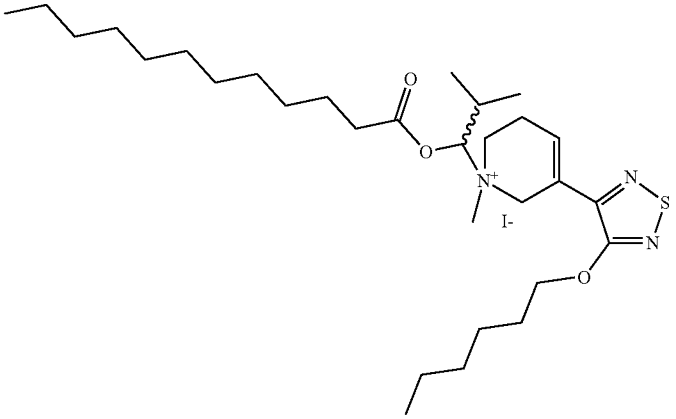 [SMILES: CCCCCCCCCCCC(=O)OC(C(C)C)[N+]1(C)CCC=C(c2nsnc2OCCCCCC)C1 ; [I-]] |
| 383 | 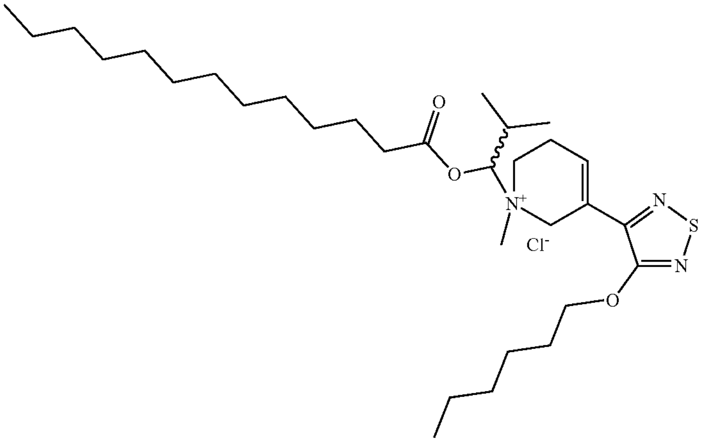 [SMILES: CCCCCCCCCCCCC(=O)OC(C(C)C)[N+]1(C)CCC=C(c2nsnc2OCCCCCC)C1 ; [Cl-]] |

TABLE 1-continued
| Cpd No. | Structure |
|---|---|
| 384 | 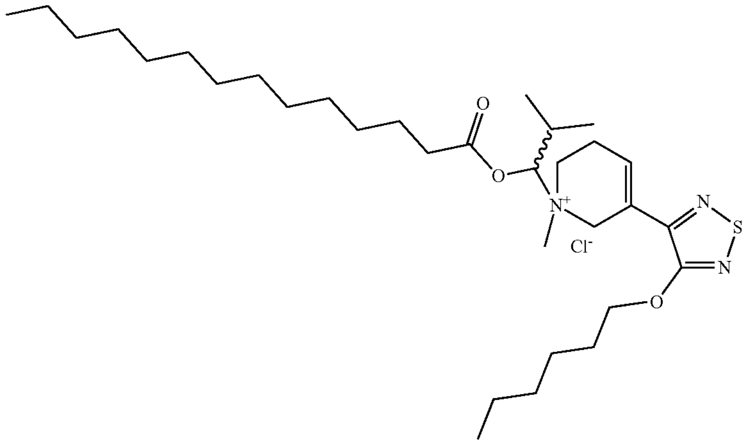 [SMILES: CCCCCCCCCCCCCC(=O)OC(C(C)C)[N+]1(C)CCC=C(c2nsnc2OCCCCCC)C1 ; [Cl-]] |
| 385 | 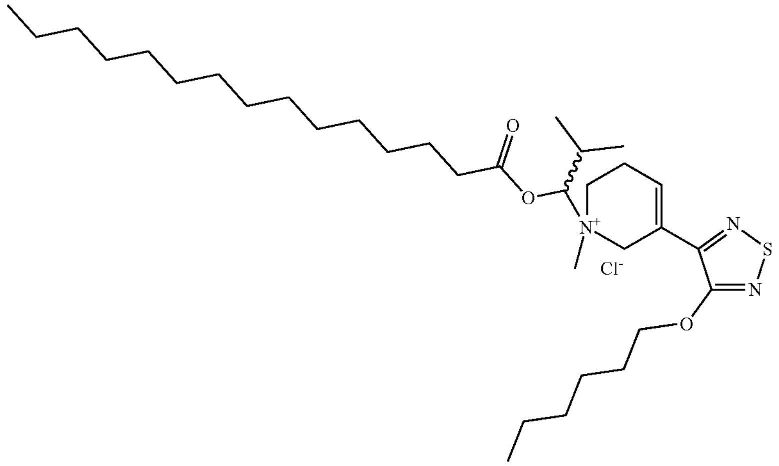 [SMILES: CCCCCCCCCCCCCCC(=O)OC(C(C)C)[N+]1(C)CCC=C(c2nsnc2OCCCCCC)C1 ; [Cl-]] |
| 386 | 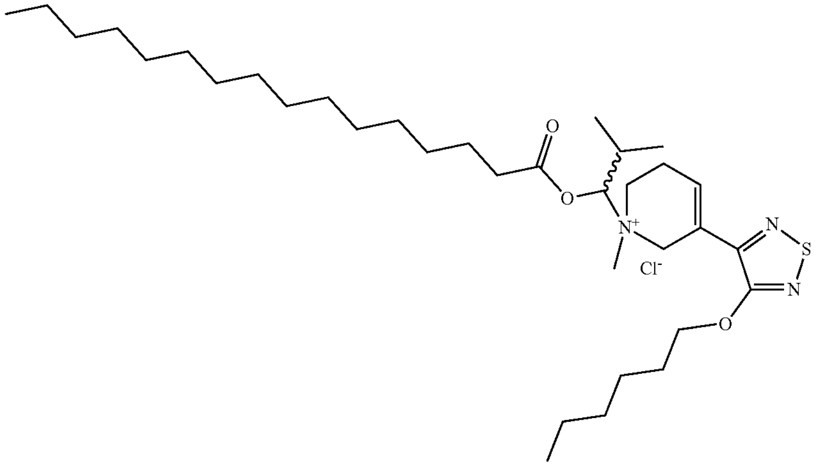 [SMILES: CCCCCCCCCCCCCCCC(=O)OC(C(C)C)[N+]1(C)CCC=C(c2nsnc2OCCCCCC)C1 ; [Cl-]] |

TABLE 1-continued
| Cpd No. | Structure |
|---|---|
| 387 | 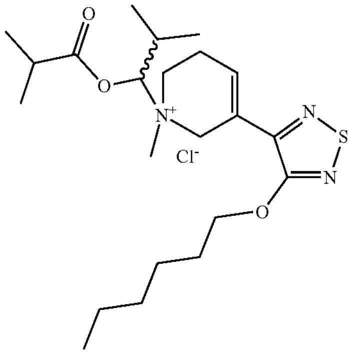 [SMILES: CCCCCCOc1nsnc1C1=CCC[N+](C)(C(OC(=O)C(C)C)C(C)C)C1 ; [Cl-]] |
| 388 | 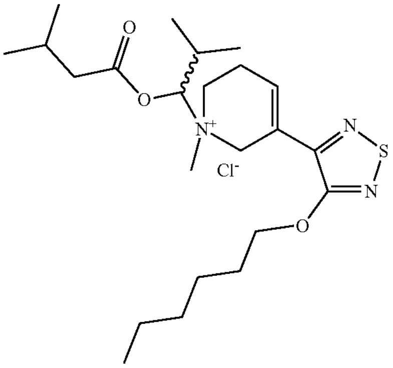 [SMILES: CCCCCCOc1nsnc1C1=CCC[N+](C)(C(OC(=O)CC(C)C)C(C)C)C1 ; [Cl-]] |
| 389 | 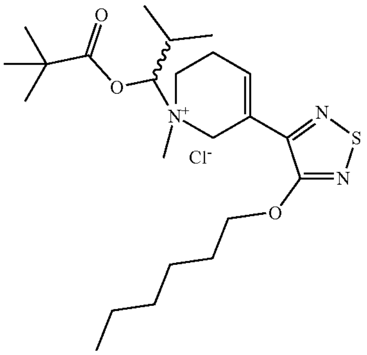 [SMILES: CCCCCCOc1nsnc1C1=CCC[N+](C)(C(OC(=O)C(C)(C)C)C(C)C)C1 ; [Cl-]] |
| 390 | 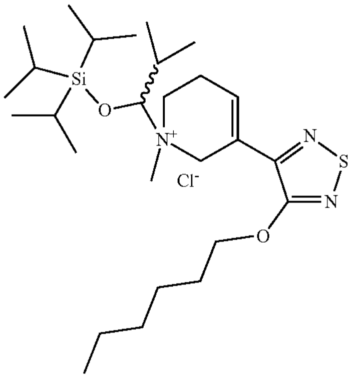 [SMILES: CCCCCCOc1nsnc1C1=CCC[N+](C)(C(O[Si](C(C)C)(C(C)C)C(C)C)C(C)C)C1 ; [Cl-]] |

TABLE 1-continued
| Cpd No. | Structure |
| --- | --- |
| 391 | 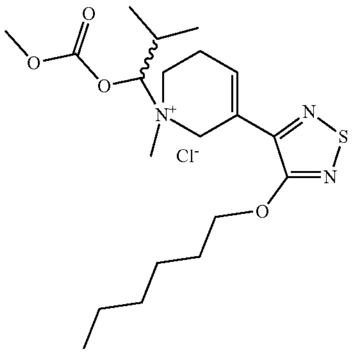 [SMILES: CCCCCCOc1nsnc1C1=CCC[N+](C)(C(OC(=O)OC)C(C)C)C1 ; [Cl-]] |
| 392 | 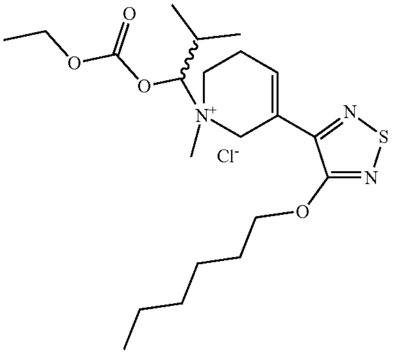 [SMILES: CCCCCCOc1nsnc1C1=CCC[N+](C)(C(OC(=O)OCC)C(C)C)C1 ; [Cl-]] |
| 393 | 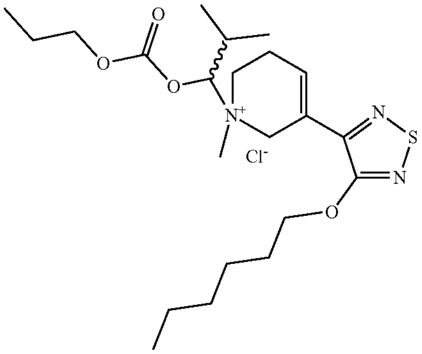 [SMILES: CCCCCCOc1nsnc1C1=CCC[N+](C)(C(OC(=O)OCCC)C(C)C)C1 ; [Cl-]] |
| 394 | 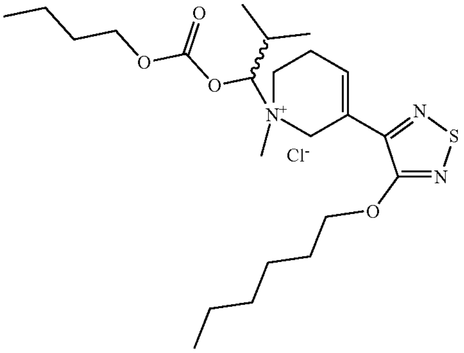 [SMILES: CCCCCCOc1nsnc1C1=CCC[N+](C)(C(OC(=O)OCCCC)C(C)C)C1 ; [Cl-]] |

TABLE 1-continued
| Cpd No. | Structure |
| --- | --- |
| 395 | 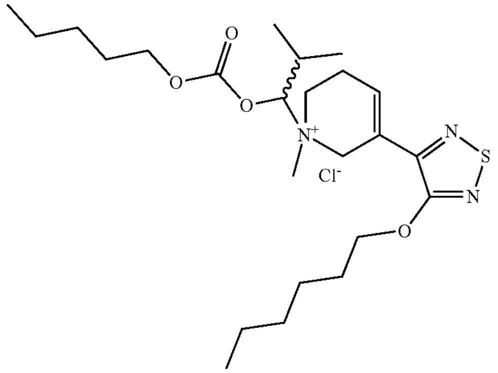 [SMILES: CCCCCCOc1nsnc1C1=CCC[N+](C)(C(OC(=O)OCCCCC)C(C)C)C1 ; [Cl-]] |
| 396 | 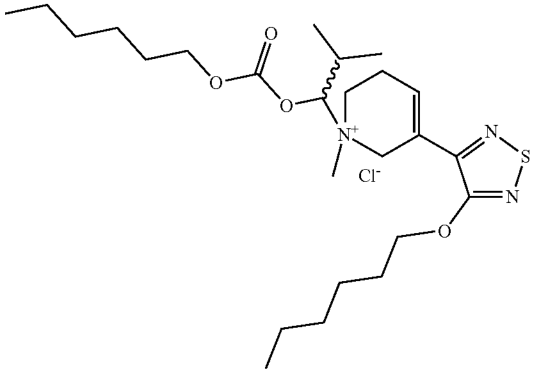 [SMILES: CCCCCCOC(=O)OC(C(C)C)[N+]1(C)CCC=C(c2nsnc2OCCCCCC)C1 ; [Cl-]] |
| 397 | 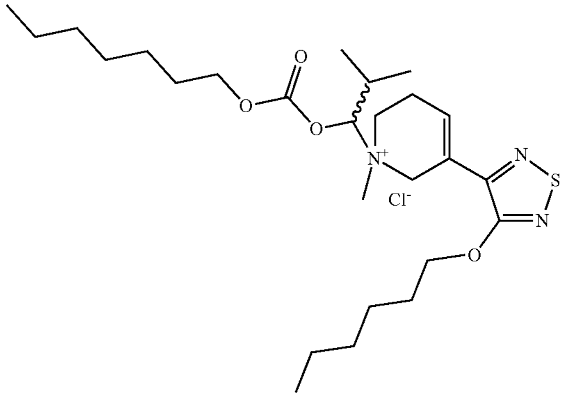 [SMILES: CCCCCCCOC(=O)OC(C(C)C)[N+]1(C)CCC=C(c2nsnc2OCCCCCC)C1 ; [Cl-]] |
| 398 | 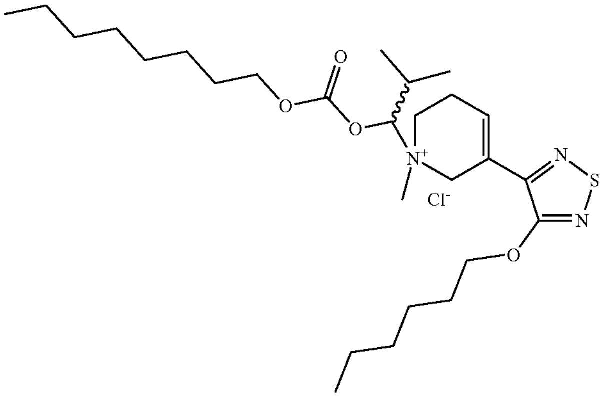 [SMILES: CCCCCCCCOC(=O)OC(C(C)C)[N+]1(C)CCC=C(c2nsnc2OCCCCCC)C1 ; [Cl-]] |

TABLE 1-continued
| Cpd No. | Structure |
|---|---|
| 399 | 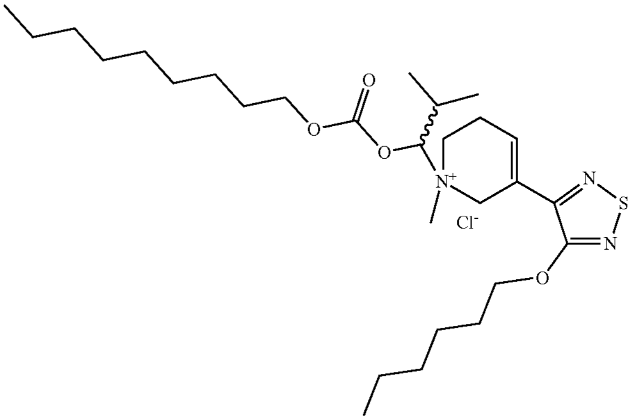 [SMILES: CCCCCCCCCOC(=O)OC(C(C)C)[N+]1(C)CCC=C(c2nsnc2OCCCCCC)C1 ; [Cl-]] |
| 400 | 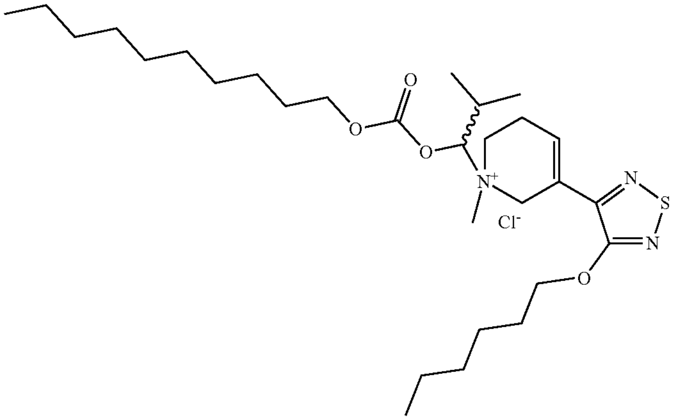 [SMILES: CCCCCCCCCCOC(=O)OC(C(C)C)[N+]1(C)CCC=C(c2nsnc2OCCCCCC)C1 ; [Cl-]] |
| 401 | 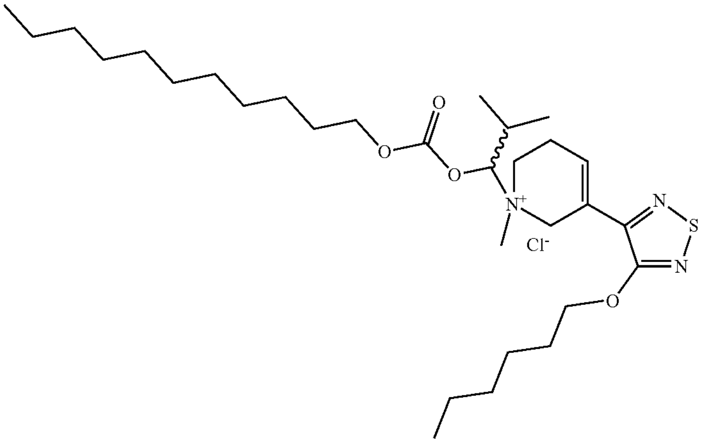 [SMILES: CCCCCCCCCCCOC(=O)OC(C(C)C)[N+]1(C)CCC=C(c2nsnc2OCCCCCC)C1 ; [Cl-]] |

TABLE 1-continued
| Cpd No. | Structure |
|---|---|
| 402 | 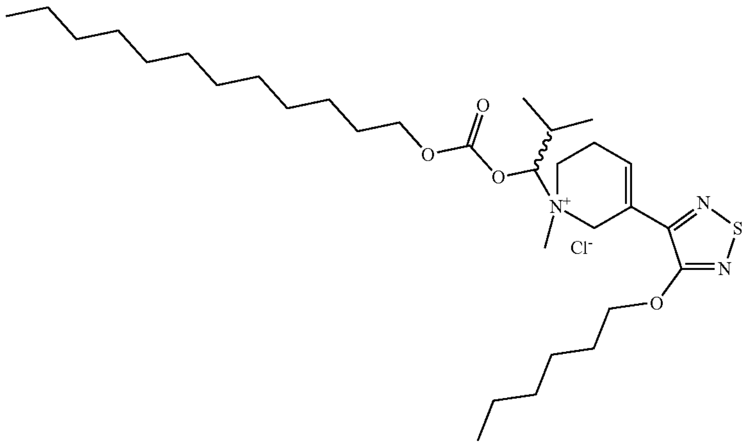 [SMILES: CCCCCCCCCCCCOC(=O)OC(C(C)C)[N+]1(C)CCC=C(c2nsnc2OCCCCCC)C1 ; [Cl-]] |
| 403 | 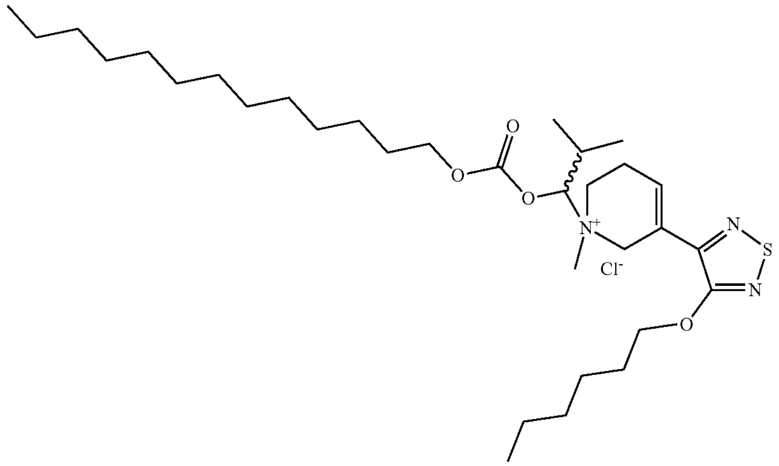 [SMILES: CCCCCCCCCCCCCOC(=O)OC(C(C)C)[N+]1(C)CCC=C(c2nsnc2OCCCCCC)C1 ; [Cl-]] |
| 404 | 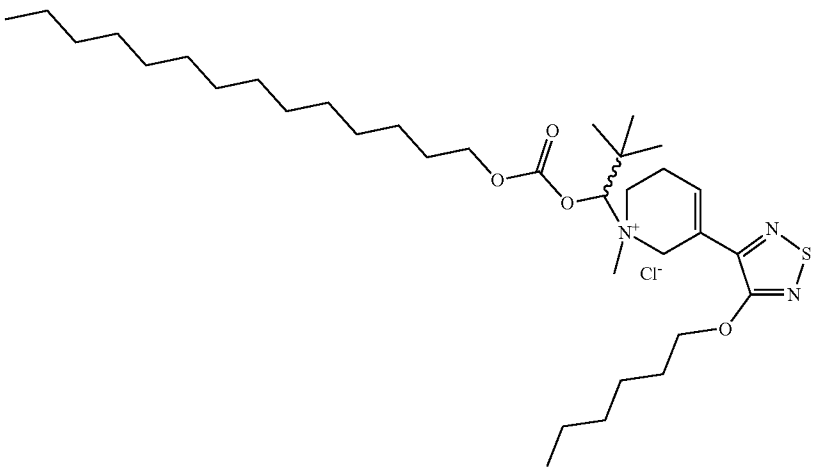 |

TABLE 1-continued
| Cpd No. | Structure |
|---|---|
| 405 | 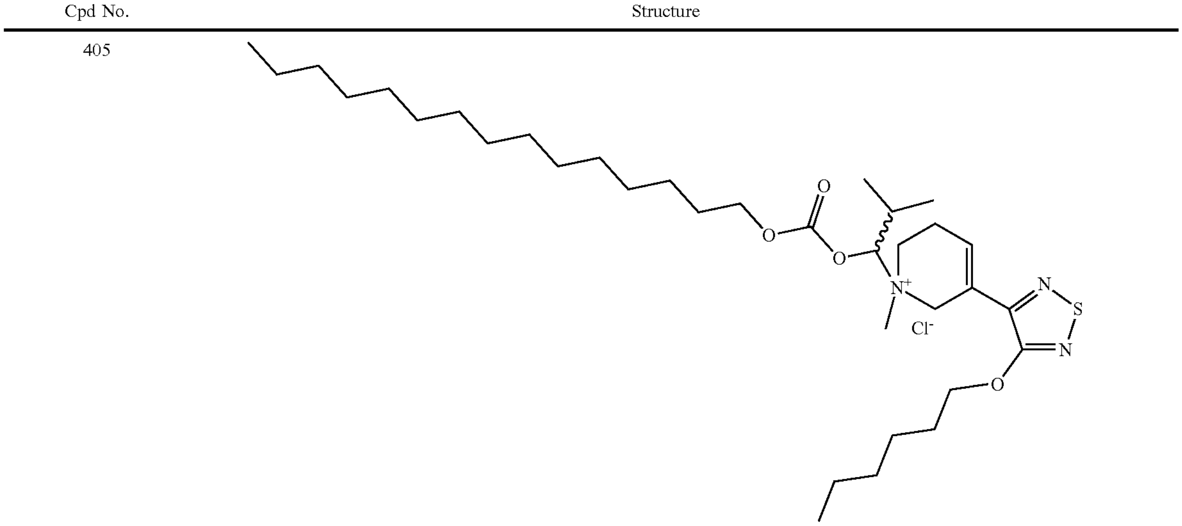 |
| 406 | 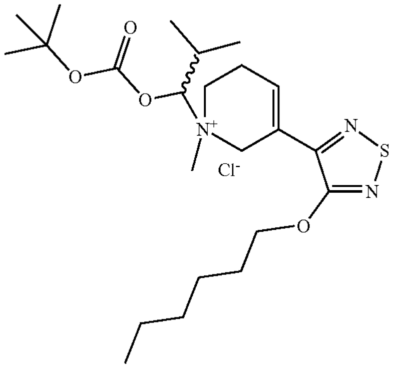 [SMILES: CCCCCCOc1nsnc1C1=CCC[N+](C)(C(OC(=O)OC(C)(C)C)C(C)C)C1 ; [Cl-]] |
| 407 | 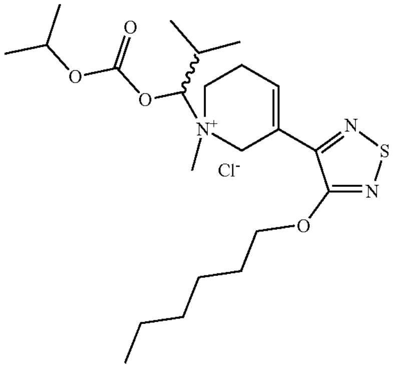 [SMILES: CCCCCCOc1nsnc1C1=CCC[N+](C)(C(OC(=O)OC(C)C)C(C)C)C1 ; [Cl-]] |
| 408 | 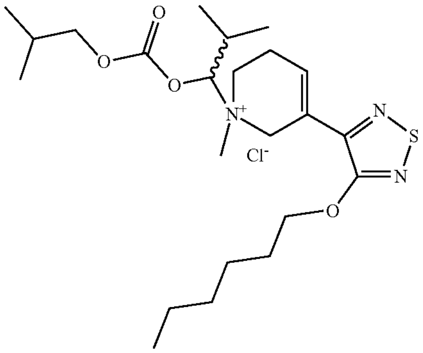 [SMILES: CCCCCCOc1nsnc1C1=CCC[N+](C)(C(OC(=O)OCC(C)C)C(C)C)C1 ; [Cl-]] |

TABLE 1-continued
| Cpd No. | Structure |
|---|---|
| 409 | 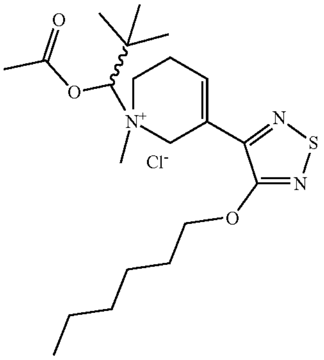 [SMILES: CCCCCCOc1nsnc1C1=CCC[N+](C)(C(OC(C)=O)C(C)(C)C)C1 ; [Cl-]] |
| 410 | 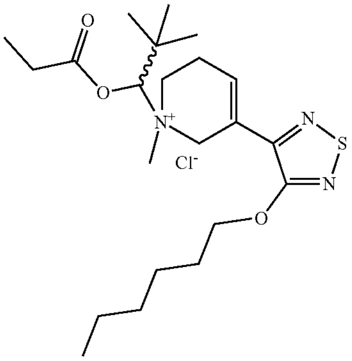 [SMILES: CCCCCCOc1nsnc1C1=CCC[N+](C)(C(OC(=O)CC)C(C)(C)C)C1 ; [Cl-]] |
| 411 | 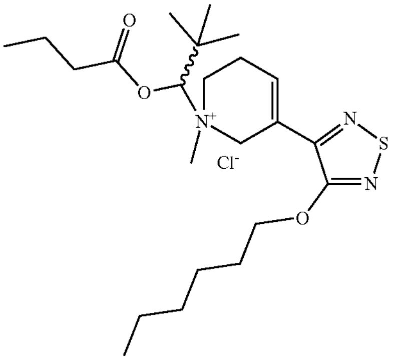 [SMILES: CCCCCCOc1nsnc1C1=CCC[N+](C)(C(OC(=O)CCC)C(C)(C)C)C1 ; [Cl-]] |
| 412 | 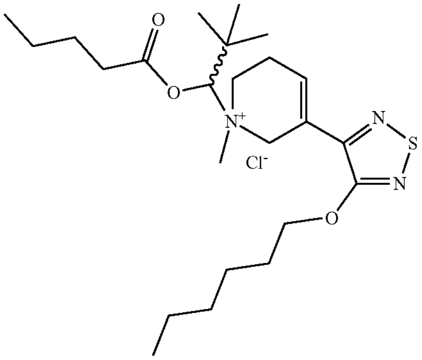 [SMILES: CCCCCCOc1nsnc1C1=CCC[N+](C)(C(OC(=O)CCCC)C(C)(C)C)C1 ; [Cl-]] |

TABLE 1-continued
| Cpd No. | Structure |
|---|---|
| 413 | 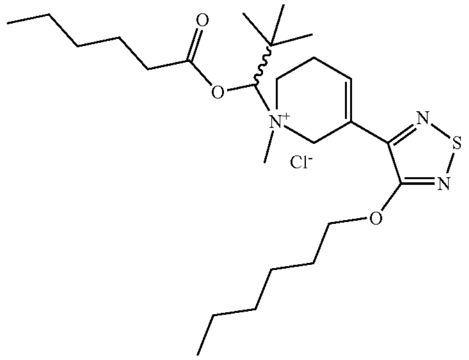 [SMILES: CCCCCCOc1nsnc1C1=CCC[N+](C)(C(OC(=O)CCCCC)C(C)(C)C)C1 ; [Cl-]] |
| 414 | 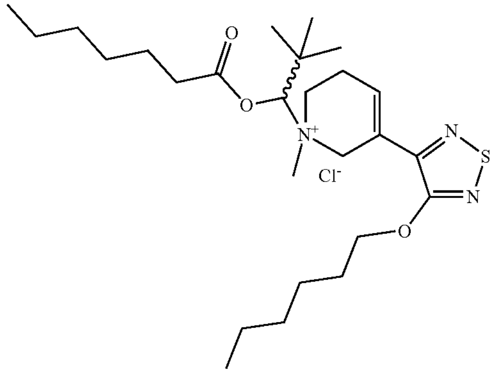 [SMILES: CCCCCCOc1nsnc1C1=CCC[N+](C)(C(OC(=O)CCCCCC)C(C)(C)C)C1 ; [Cl-]] |
| 415 | 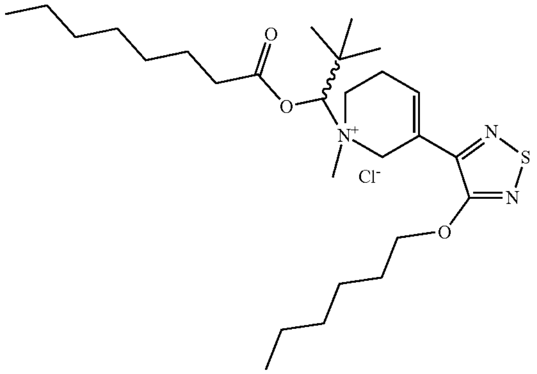 [SMILES: CCCCCCCC(=O)OC(C(C)(C)C)[N+]1(C)CCC=C(c2nsnc2OCCCCCC)C1 ; [Cl-]] |
| 416 | 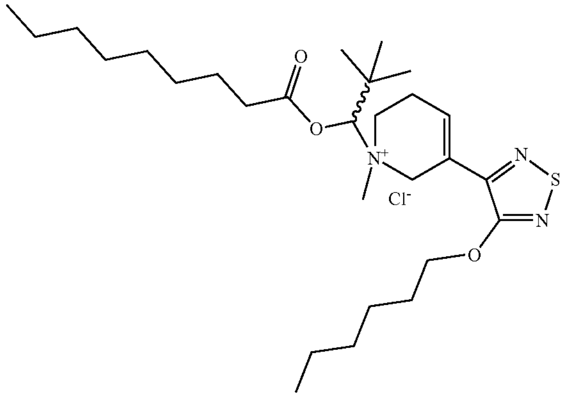 [SMILES: CCCCCCCCC(=O)OC(C(C)(C)C)[N+]1(C)CCC=C(c2nsnc2OCCCCCC)C1 ; [Cl-]] |

TABLE 1-continued
| Cpd No. | Structure |
|---|---|
| 417 | 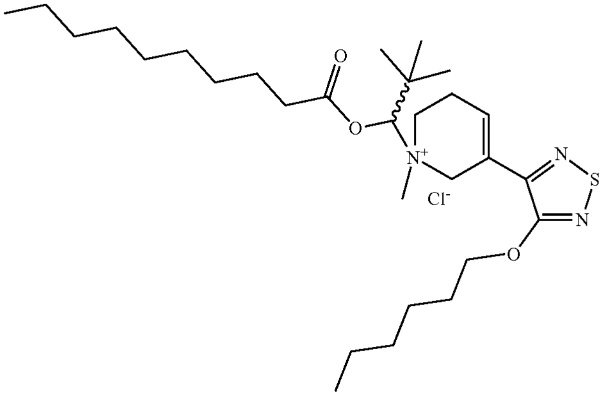 [SMILES: CCCCCCCCCC(=O)OC(C(C)(C)C)[N+]1(C)CCC=C(c2nsnc2OCCCCCC)C1 ; [Cl-]] |
| 418 | 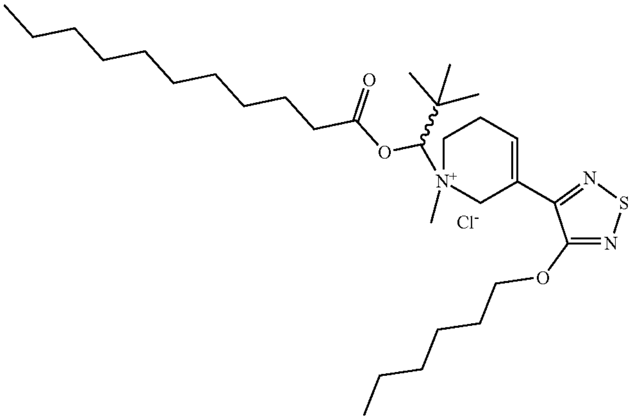 [SMILES: CCCCCCCCCCC(=O)OC(C(C)(C)C)[N+]1(C)CCC=C(c2nsnc2OCCCCCC)C1 ; [Cl-]] |
| 419 | 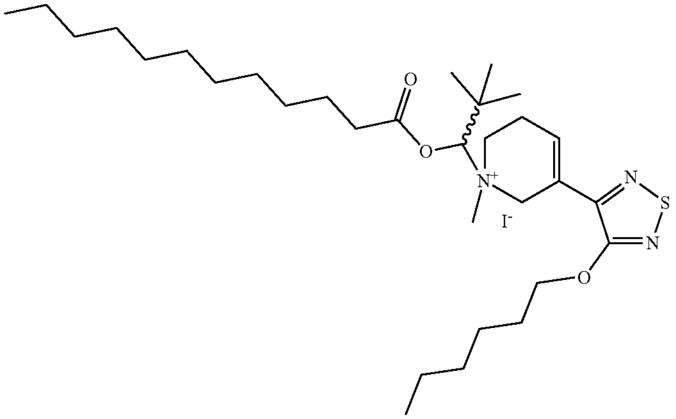 [SMILES: CCCCCCCCCCCC(=O)OC(C(C)(C)C)[N+]1(C)CCC=C(c2nsnc2OCCCCCC)C1 ; [I-]] |

TABLE 1-continued
| Cpd No. | Structure |
| --- | --- |
| 420 | 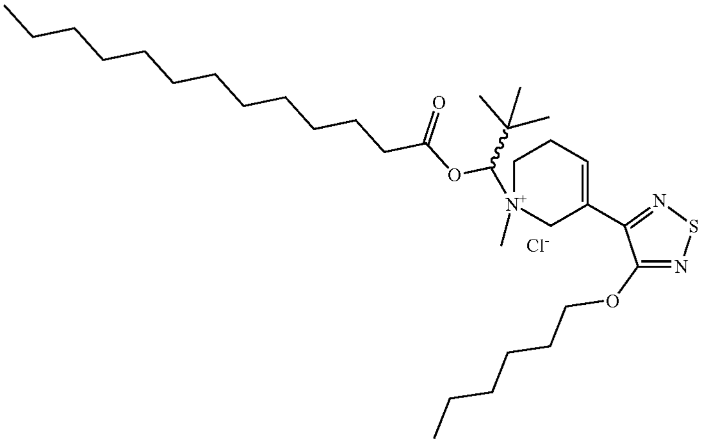 [SMILES: CCCCCCCCCCCCC(=O)OC(C(C)(C)C)[N+]1(C)CCC=C(c2nsnc2OCCCCCC)C1 ; [Cl-]] |
| 421 | 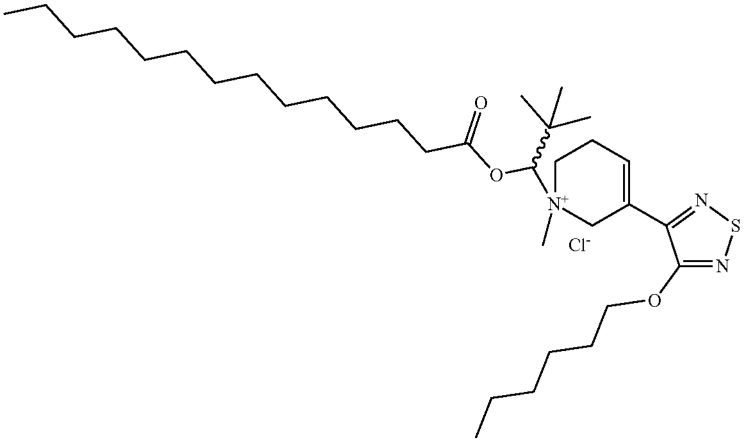 [SMILES: CCCCCCCCCCCCCC(=O)OC(C(C)(C)C)[N+]1(C)CCC=C(c2nsnc2OCCCCCC)C1 ; [Cl-]] |
| 422 | 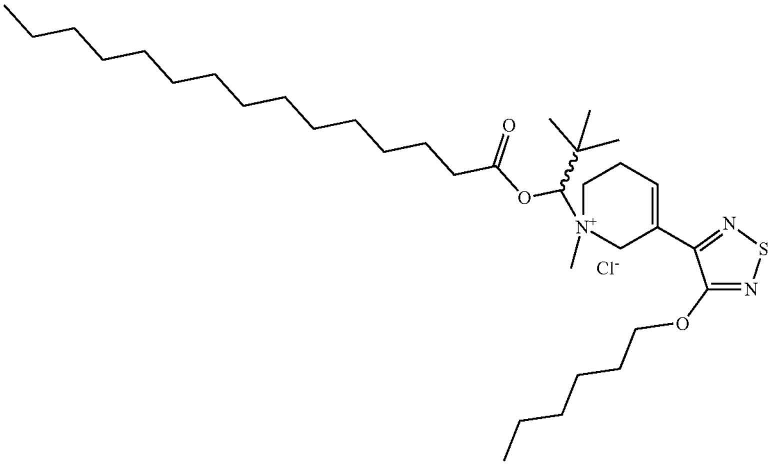 [SMILES: CCCCCCCCCCCCCCC(=O)OC(C(C)(C)C)[N+]1(C)CCC=C(c2nsnc2OCCCCCC)C1 ; [Cl-]] |

TABLE 1-continued
| Cpd No. | Structure |
|---|---|
| 423 | 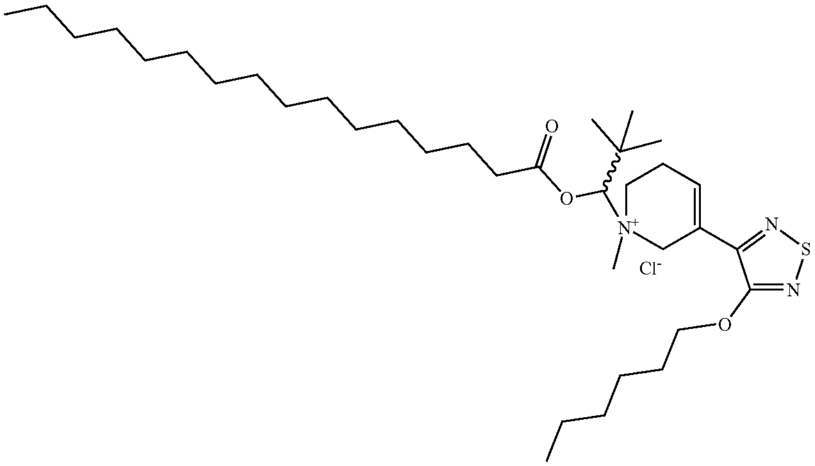 [SMILES: CCCCCCCCCCCCCCCC(=O)OC(C(C)(C)C)[N+]1(C)CCC=C(c2nsnc2OCCCCCC)C1 ; [Cl-]] |
| 424 | 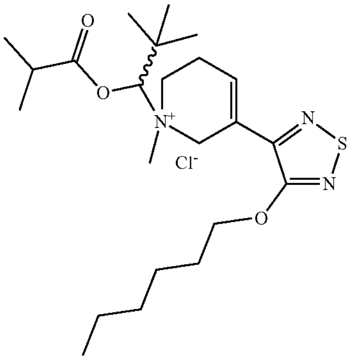 [SMILES: CCCCCCOc1nsnc1C1=CCC[N+](C)(C(OC(=O)C(C)C)C(C)(C)C)C1 ; [Cl-]] |
| 425 | 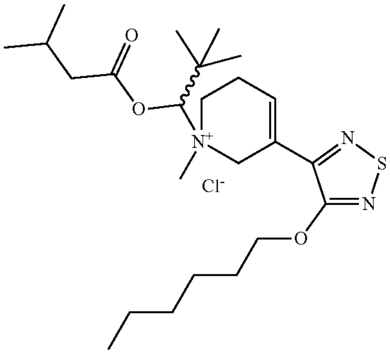 [SMILES: CCCCCCOc1nsnc1C1=CCC[N+](C)(C(OC(=O)CC(C)C)C(C)(C)C)C1 ; [Cl-]] |
| 426 | 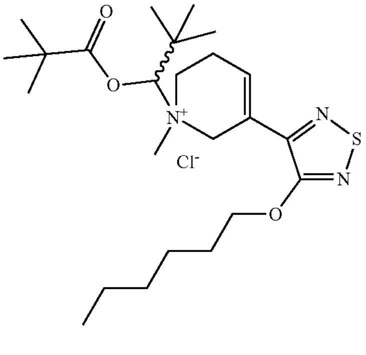 [SMILES: CCCCCCOc1nsnc1C1=CCC[N+](C)(C(OC(=O)C(C)(C)C)C(C)(C)C)C1 ; [Cl-]] |

TABLE 1-continued
| Cpd No. | Structure |
|---|---|
| 427 | 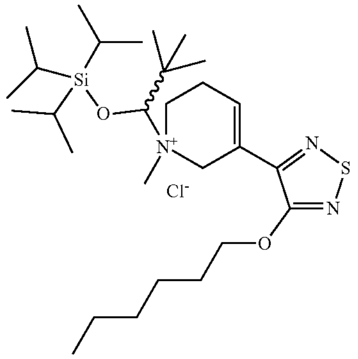 [SMILES: CCCCCCOc1nsnc1C1=CCC[N+](C)(C(O[Si](C(C)C)(C(C)C)C(C)C)C(C)(C)C)C1 ; [Cl-]] |
| 428 | 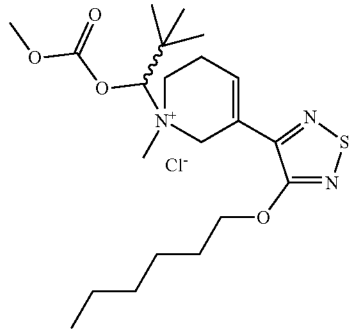 [SMILES: CCCCCCOc1nsnc1C1=CCC[N+](C)(C(OC(=O)OC)C(C)(C)C)C1 ; [Cl-]] |
| 429 | 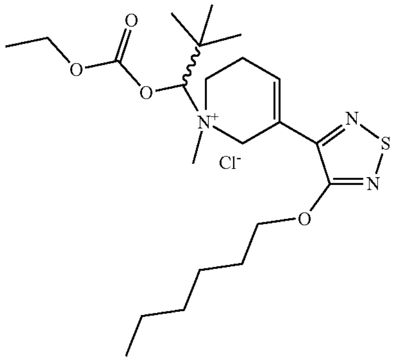 [SMILES: CCCCCCOc1nsnc1C1=CCC[N+](C)(C(OC(=O)OCC)C(C)(C)C)C1 ; [Cl-]] |
| 430 | 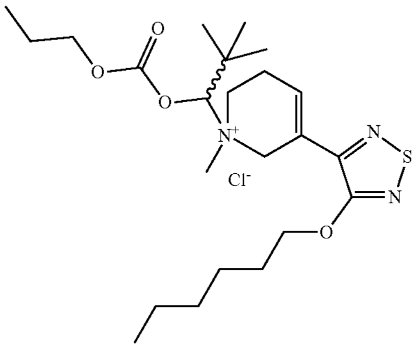 [SMILES: CCCCCCOc1nsnc1C1=CCC[N+](C)(C(OC(=O)OCCC)C(C)(C)C)C1 ; [Cl-]] |

TABLE 1-continued
| Cpd No. | Structure |
|---|---|
| 431 | 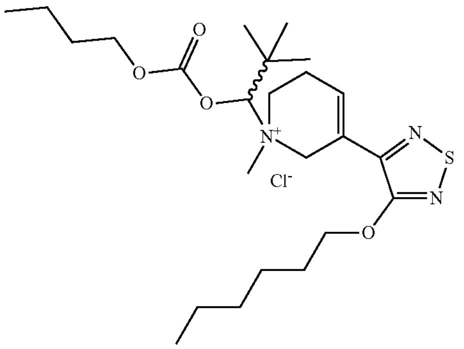 [SMILES: CCCCCCOc1nsnc1C1=CCC[N+](C)(C(OC(=O)OCCCC)C(C)(C)C)C1 ; [Cl-]] |
| 432 | 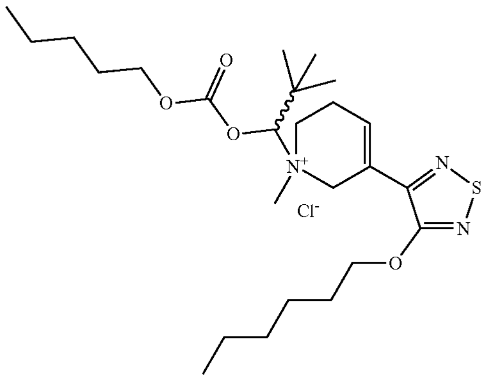 [SMILES: CCCCCCOc1nsnc1C1=CCC[N+](C)(C(OC(=O)OCCCCC)C(C)(C)C)C1 ; [Cl-]] |
| 433 | 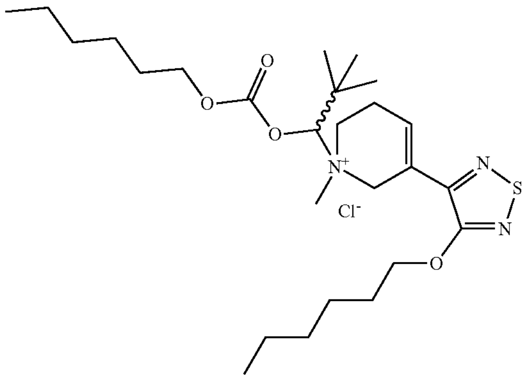 [SMILES: CCCCCCOC(=O)OC(C(C)(C)C)[N+]1(C)CCC=C(c2nsnc2OCCCCCC)C1 ; [Cl-]] |
| 434 | 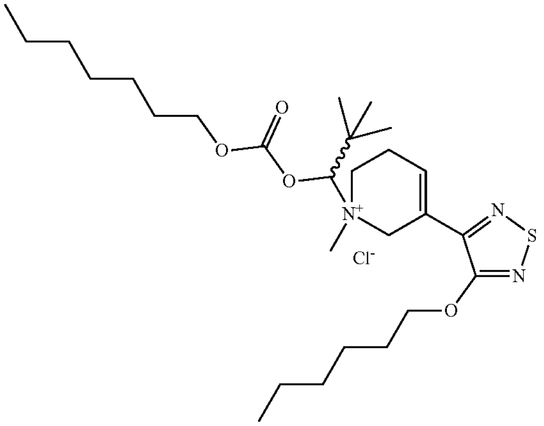 [SMILES: CCCCCCCOC(=O)OC(C(C)(C)C)[N+]1(C)CCC=C(c2nsnc2OCCCCCC)C1 ; [Cl-]] |

TABLE 1-continued
| Cpd No. | Structure |
|---|---|
| 435 | 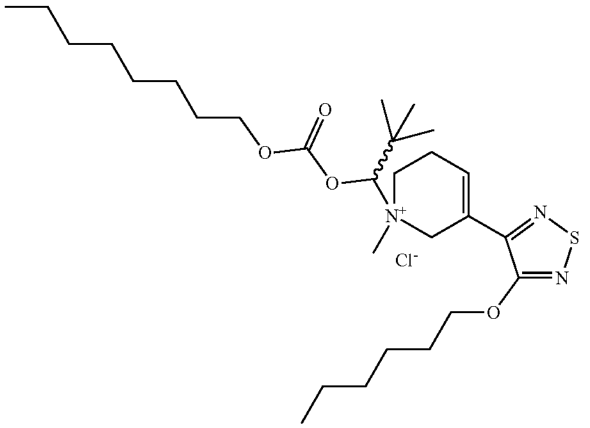 [SMILES: CCCCCCCCOC(=O)OC(C(C)(C)C)[N+]1(C)CCC=C(c2nsnc2OCCCCCC)C1 ; [Cl-]] |
| 436 | 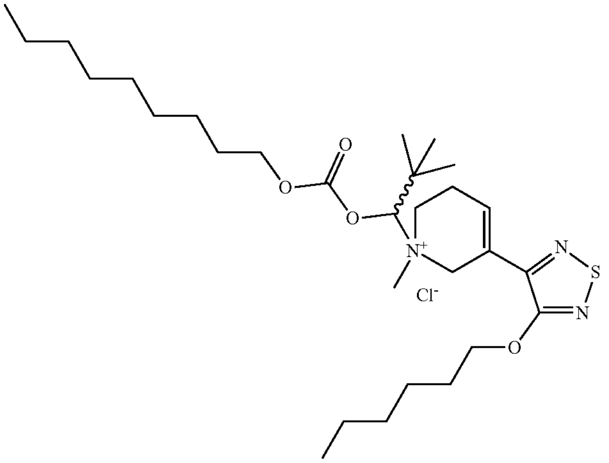 [SMILES: CCCCCCCCCOC(=O)OC(C(C)(C)C)[N+]1(C)CCC=C(c2nsnc2OCCCCCC)C1 ; [Cl-]] |
| 437 | 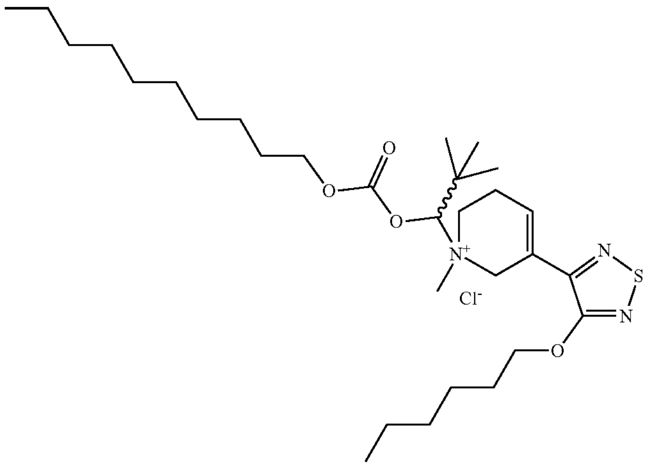 [SMILES: CCCCCCCCCCOC(=O)OC(C(C)(C)C)[N+]1(C)CCC=C(c2nsnc2OCCCCCC)C1 ; [Cl-]] |

TABLE 1-continued
| Cpd No. | Structure |
| --- | --- |
| 438 | 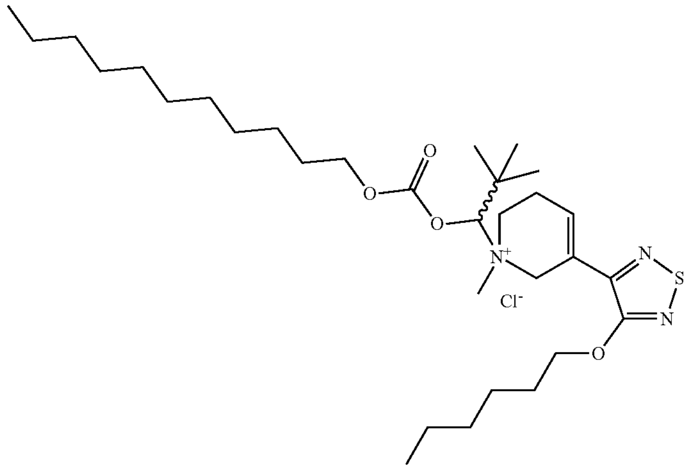 [SMILES: CCCCCCCCCCCOC(=O)OC(C(C)(C)C)[N+]1(C)CCC=C(c2nsnc2OCCCCCC)C1 ; [Cl-]] |
| 439 | 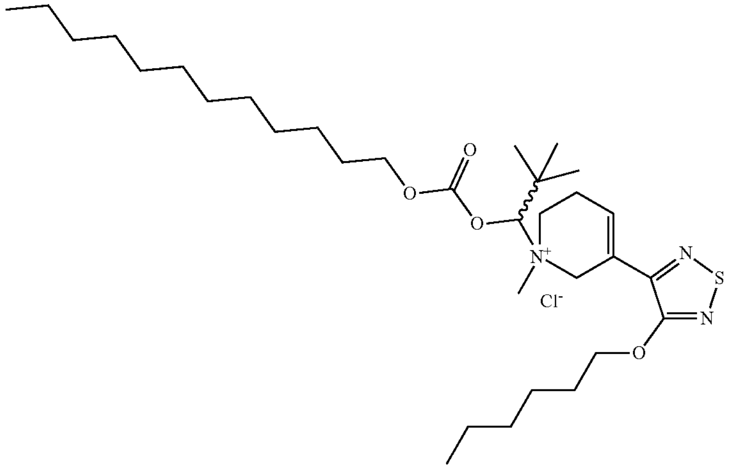 [SMILES: CCCCCCCCCCCCOC(=O)OC(C(C)(C)C)[N+]1(C)CCC=C(c2nsnc2OCCCCCC)C1 ; [Cl-]] |
| 440 | 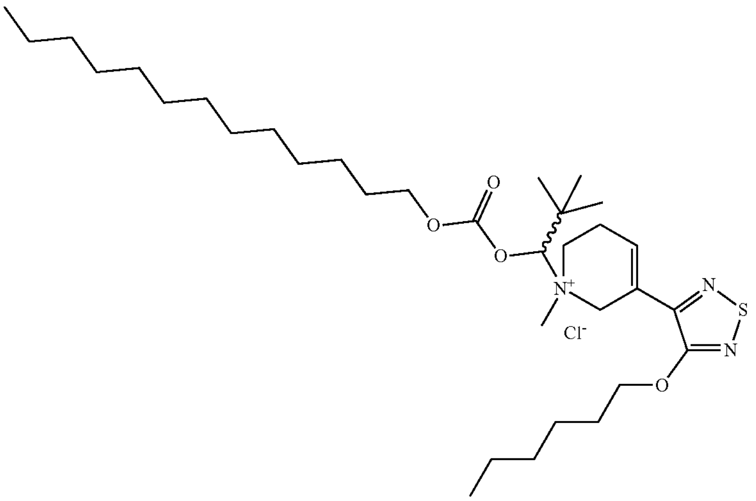 [SMILES: CCCCCCCCCCCCCOC(=O)OC(C(C)(C)C)[N+]1(C)CCC=C(c2nsnc2OCCCCCC)C1 ; [Cl-]] |

TABLE 1-continued
| Cpd No. | Structure |
|---|---|
| 441 | 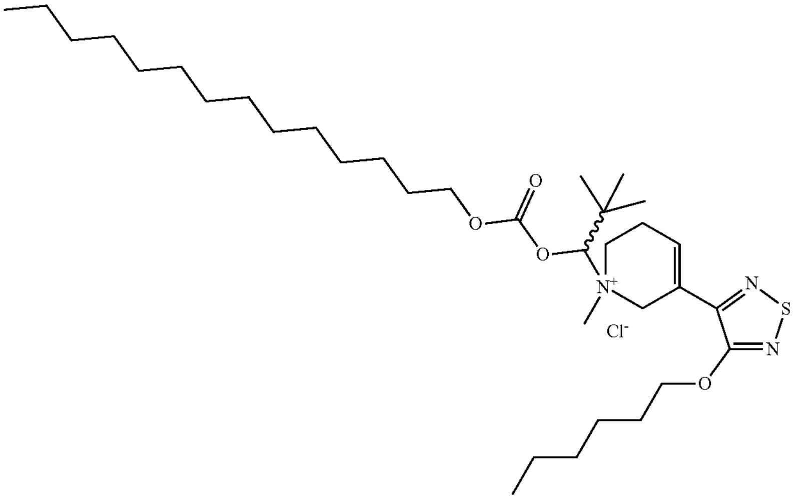 [SMILES: CCCCCCCCCCCCCCOC(=O)OC(C(C)(C)C)[N+]1(C)CCC=C(c2nsnc2OCCCCCC)C1 ; [Cl-]] |
| 442 | 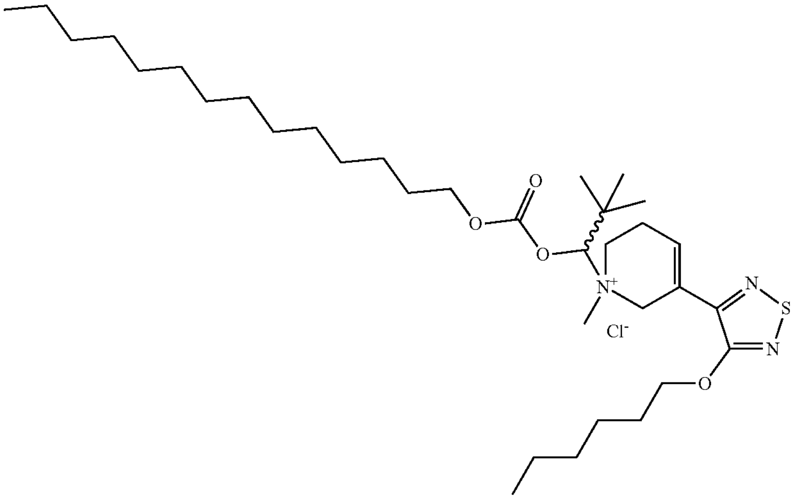 [SMILES: CCCCCCCCCCCCCCOC(=O)OC(C(C)(C)C)[N+]1(C)CCC=C(c2nsnc2OCCCCCC)C1 ; [Cl-]] |
| 443 | 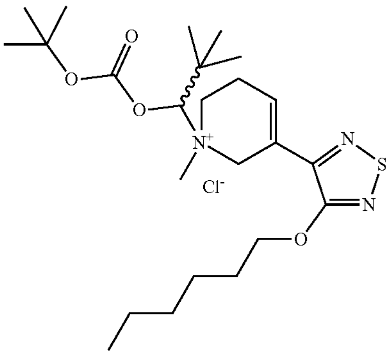 [SMILES: CCCCCCOc1nsnc1C1=CCC[N+](C)(C(OC(=O)OC(C)(C)C)C(C)(C)C)C1 ; [Cl-]] |

TABLE 1-continued
| Cpd No. | Structure |
| --- | --- |
| 444 | 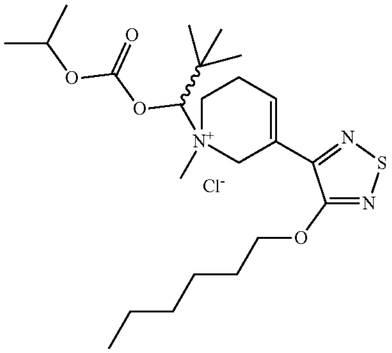 [SMILES: CCCCCCOc1nsnc1C1=CCC[N+](C)(C(OC(=O)OC(C)C)C(C)(C)C)C1 ; [Cl-]] |
| 445 | 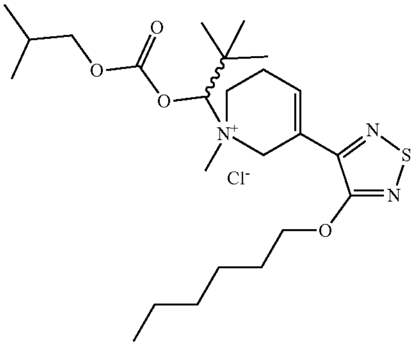 [SMILES: CCCCCCOc1nsnc1C1=CCC[N+](C)(C(OC(=O)OCC(C)C)C(C)(C)C)C1 ; [Cl-]] |
| 446 | 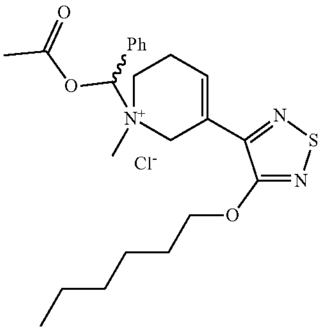 [SMILES: CCCCCCOc1nsnc1C1=CCC[N+](C)(C(OC(C)=O)c2ccccc2)C1 ; [Cl-]] |
| 447 | 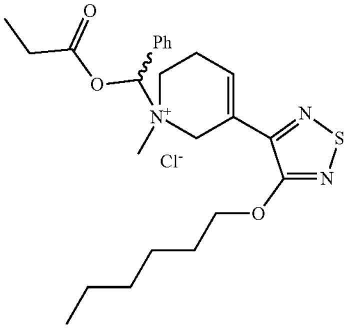 [SMILES: CCCCCCOc1nsnc1C1=CCC[N+](C)(C(OC(=O)CC)c2ccccc2)C1 ; [Cl-]] |

TABLE 1-continued
| Cpd No. | Structure |
| --- | --- |
| 448 | 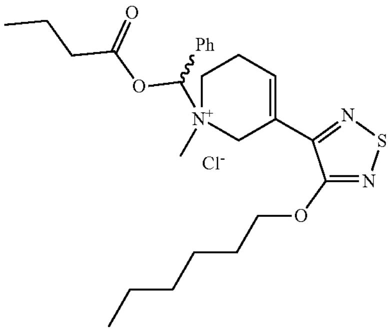 [SMILES: CCCCCCOc1nsnc1C1=CCC[N+](C)(C(OC(=O)CCC)c2ccccc2)C1 ; [Cl-]] |
| 449 | 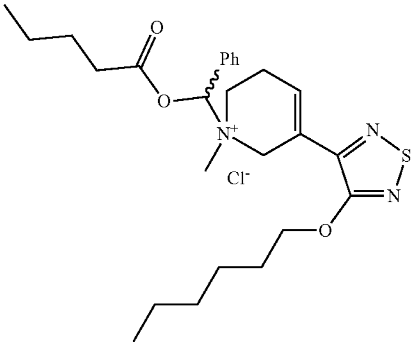 [SMILES: CCCCCCOc1nsnc1C1=CCC[N+](C)(C(OC(=O)CCCC)c2ccccc2)C1 ; [Cl-]] |
| 450 | 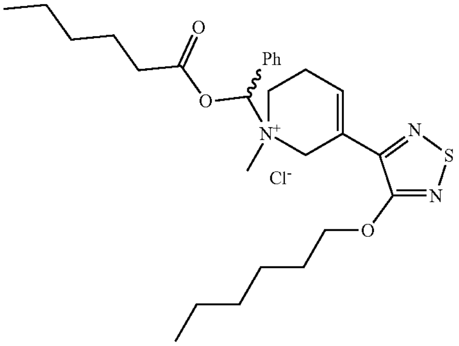 [SMILES: CCCCCCOc1nsnc1C1=CCC[N+](C)(C(OC(=O)CCCCC)c2ccccc2)C1 ; [Cl-]] |
| 451 | 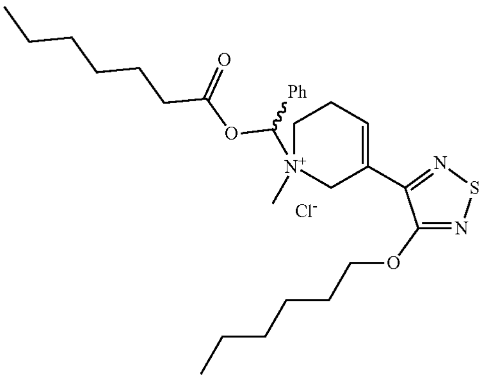 |

TABLE 1-continued
| Cpd No. | Structure |
|---|---|
| 452 | 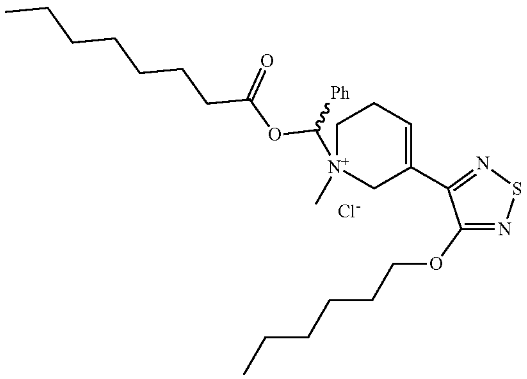 |
| 453 | 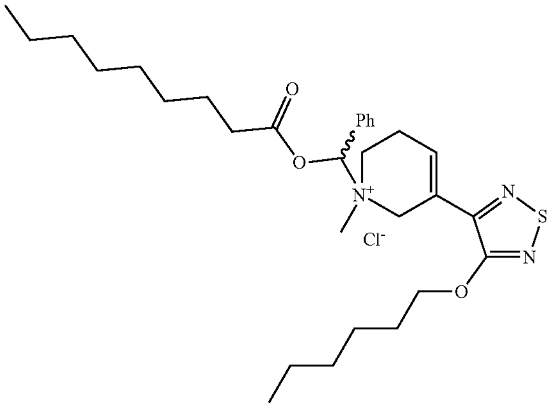 [SMILES: CCCCCCCCC(=O)OC(c1ccccc1)[N+]1(C)CCC=C(c2nsnc2OCCCCCC)C1 ; [Cl-]] |
| 454 | 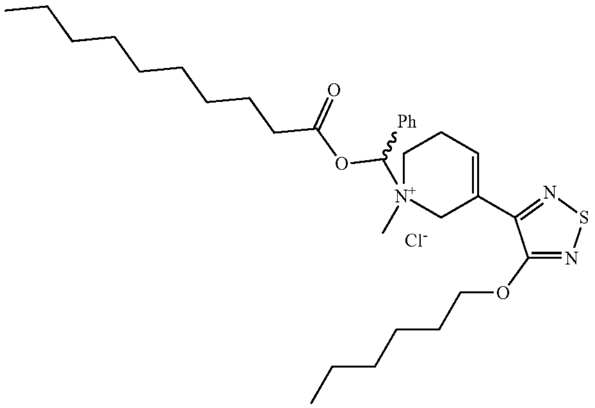 [SMILES: CCCCCCCCCC(=O)OC(c1ccccc1)[N+]1(C)CCC=C(c2nsnc2OCCCCCC)C1 ; [Cl-]] |

TABLE 1-continued
| Cpd No. | Structure |
|---|---|
| 455 | 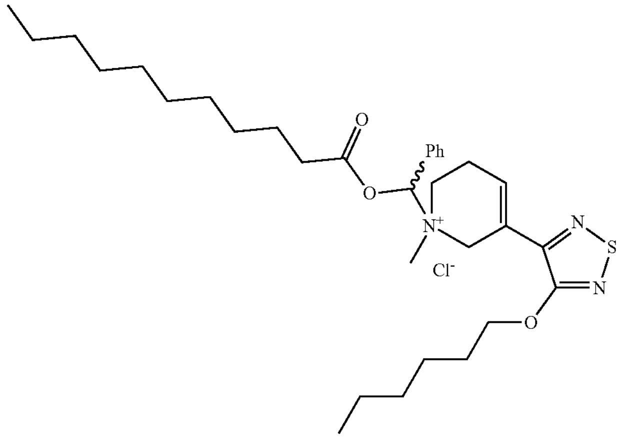 [SMILES: CCCCCCCCCCC(=O)OC(c1ccccc1)[N+]1(C)CCC=C(c2nsnc2OCCCCCC)C1 ; [Cl-]] |
| 456 | 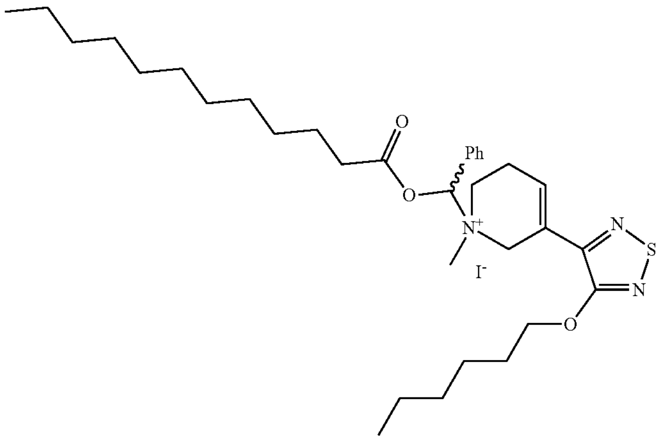 [SMILES: CCCCCCCCCCCC(=O)OC(c1ccccc1)[N+]1(C)CCC=C(c2nsnc2OCCCCCC)C1 ; [I-]] |
| 457 | 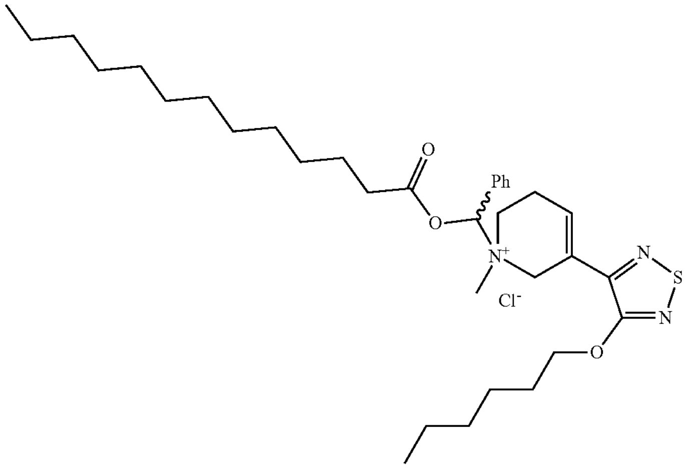 [SMILES: CCCCCCCCCCCCC(=O)OC(c1ccccc1)[N+]1(C)CCC=C(c2nsnc2OCCCCCC)C1 ; [Cl-]] |

TABLE 1-continued
| Cpd No. | Structure |
| --- | --- |
| 458 | 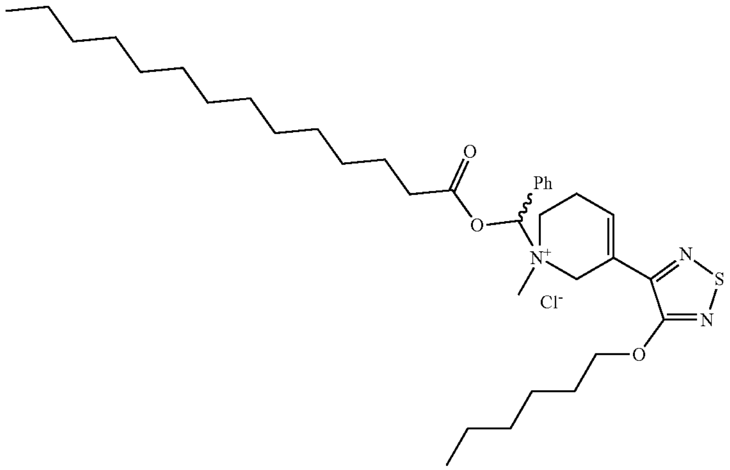 [SMILES: CCCCCCCCCCCCCC(=O)OC(c1ccccc1)[N+]1(C)CCC=C(c2nsnc2OCCCCCC)C1 ; [Cl-]] |
| 459 | 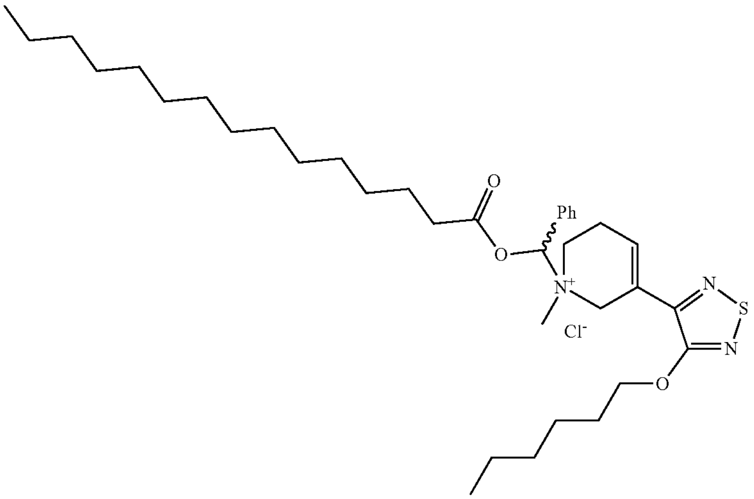 [SMILES: CCCCCCCCCCCCCCC(=O)OC(c1ccccc1)[N+]1(C)CCC=C(c2nsnc2OCCCCCC)C1 ; [Cl-]] |
| 460 | 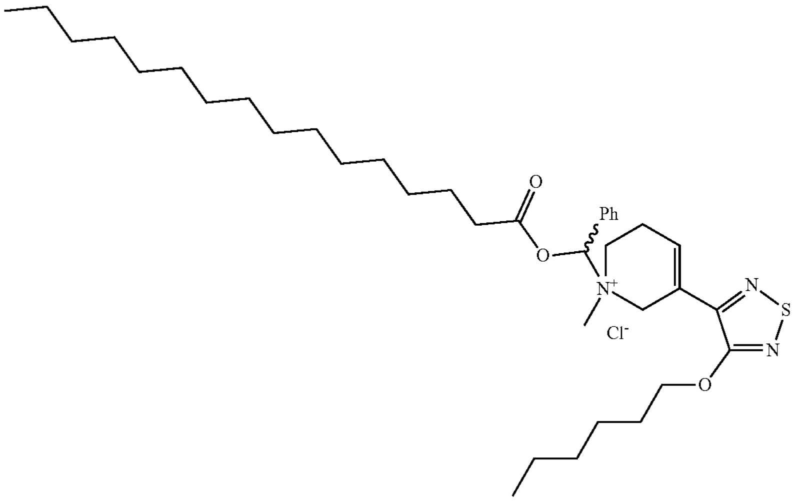 [SMILES: CCCCCCCCCCCCCCCC(=O)OC(c1ccccc1)[N+]1(C)CCC=C(c2nsnc2OCCCCCC)C1 ; [Cl-]] |

TABLE 1-continued
| Cpd No. | Structure |
|---|---|
| 461 | 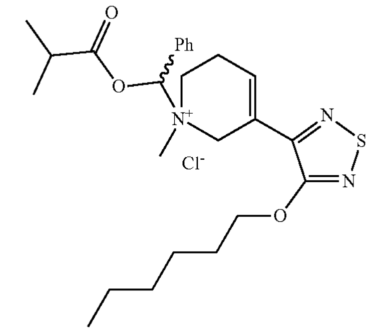 [SMILES: CCCCCCOc1nsnc1C1=CCC[N+](C)(C(OC(=O)C(C)C)c2ccccc2)C1 ; [Cl-]] |
| 462 | 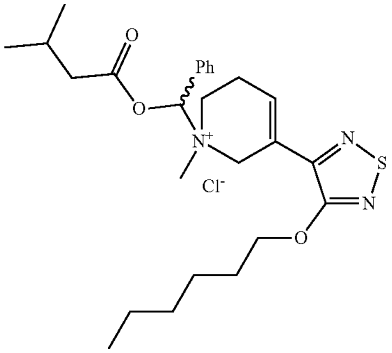 [SMILES: CCCCCCOc1nsnc1C1=CCC[N+](C)(C(OC(=O)CC(C)C)c2ccccc2)C1 ; [Cl-]] |
| 463 | 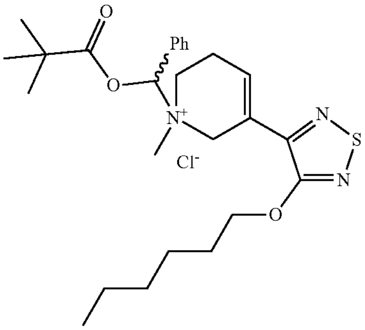 [SMILES: CCCCCCOc1nsnc1C1=CCC[N+](C)(C(OC(=O)C(C)(C)C)c2ccccc2)C1 ; [Cl-]] |
| 464 | 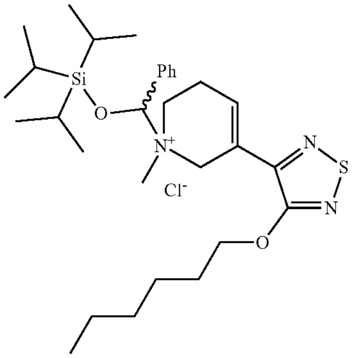 [SMILES: CCCCCCOc1nsnc1C1=CCC[N+](C)(C(O[Si](C(C)C)(C(C)C)C(C)C)c2ccccc2)C1 ; [Cl-]] |

TABLE 1-continued
| Cpd No. | Structure |
|---|---|
| 465 | 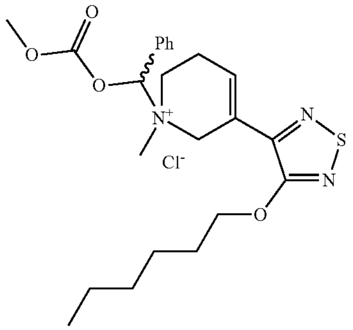 [SMILES: CCCCCCOc1nsnc1C1=CCC[N+](C)(C(OC(=O)OC)c2ccccc2)C1 ; [Cl-]] |
| 466 | 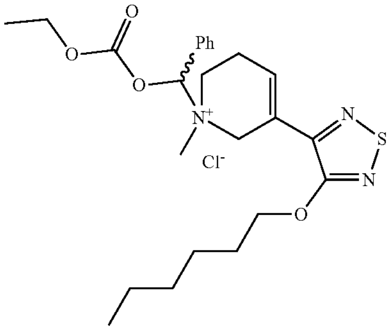 [SMILES: CCCCCCOc1nsnc1C1=CCC[N+](C)(C(OC(=O)OCC)c2ccccc2)C1 ; [Cl-]] |
| 467 | 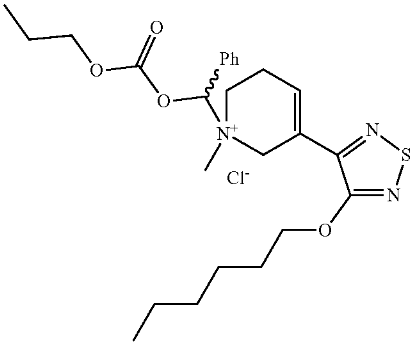 [SMILES: CCCCCCOc1nsnc1C1=CCC[N+](C)(C(OC(=O)OCCC)c2ccccc2)C1 ; [Cl-]] |
| 468 | 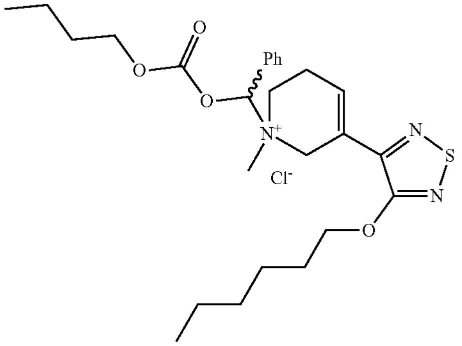 |

TABLE 1-continued
| Cpd No. | Structure |
| --- | --- |
| 469 | 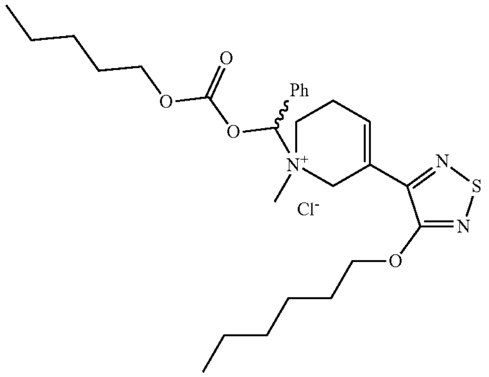 [SMILES: CCCCCCOc1nsnc1C1=CCC[N+](C)(C(OC(=O)OCCCCC)c2ccccc2)C1 ; [Cl-]] |
| 470 | 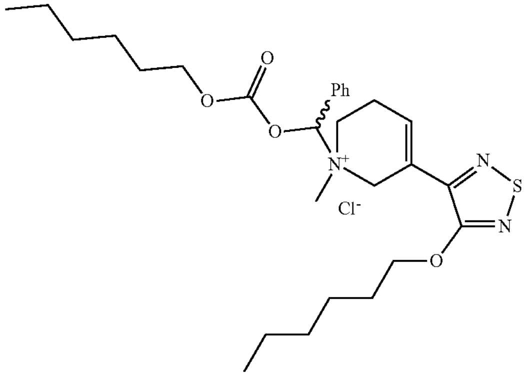 [SMILES: CCCCCCOC(=O)OC(c1ccccc1)[N+]1(C)CCC=C(c2nsnc2OCCCCCC)C1 ; [Cl-]] |
| 471 | 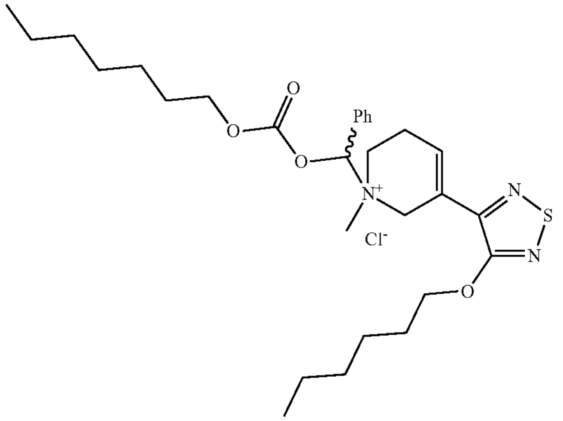 [SMILES: CCCCCCCOC(=O)OC(c1ccccc1)[N+]1(C)CCC=C(c2nsnc2OCCCCCC)C1 ; [Cl-]] |
| 472 | 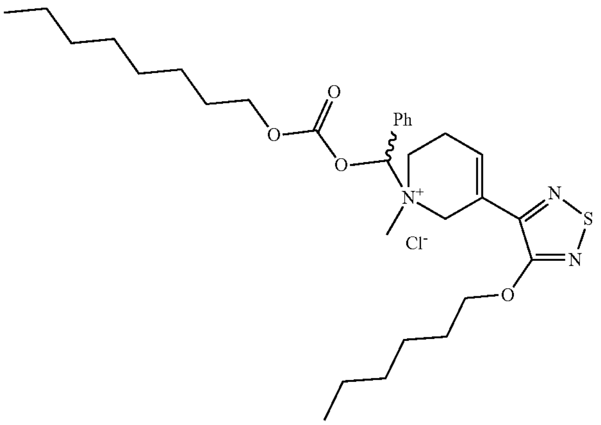 [SMILES: CCCCCCCCOC(=O)OC(c1ccccc1)[N+]1(C)CCC=C(c2nsnc2OCCCCCC)C1 ; [Cl-]] |

TABLE 1-continued
| Cpd No. | Structure |
|---|---|
| 473 | 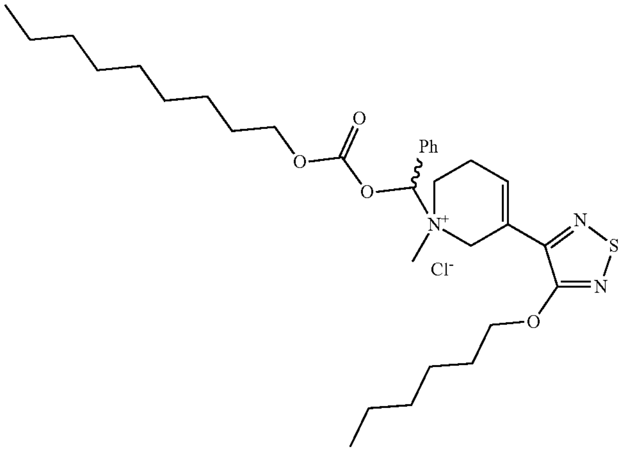 [SMILES: CCCCCCCCCOC(=O)OC(c1ccccc1)[N+]1(C)CCC=C(c2nsnc2OCCCCCC)C1 ; [Cl-]] |
| 474 | 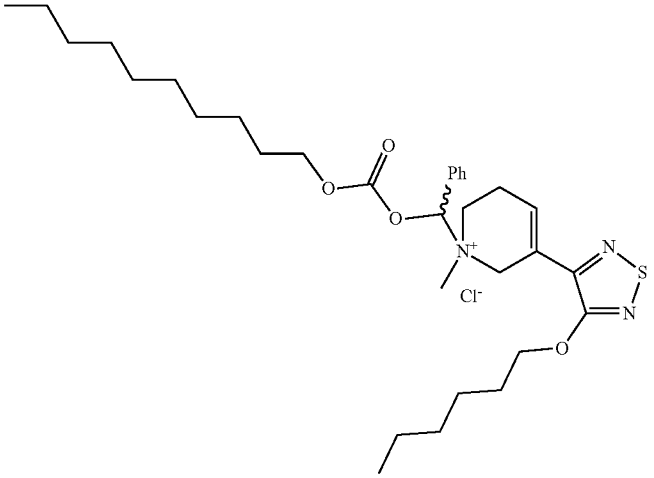 [SMILES: CCCCCCCCCCOC(=O)OC(c1ccccc1)[N+]1(C)CCC=C(c2nsnc2OCCCCCC)C1 ; [Cl-]] |
| 475 | 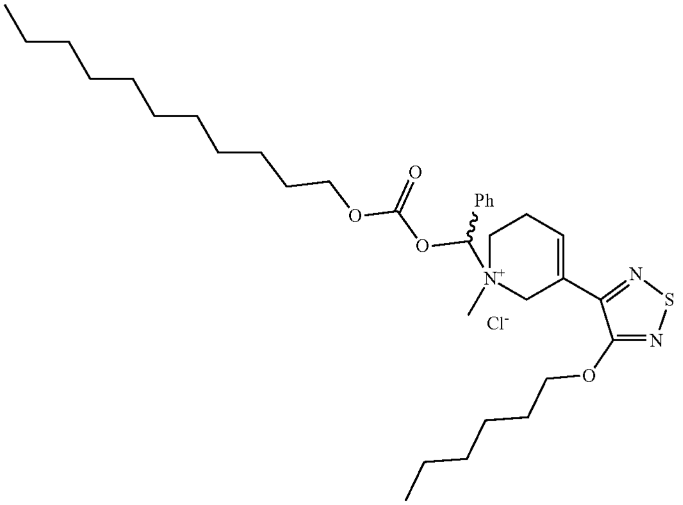 [SMILES: CCCCCCCCCCCOC(=O)OC(c1ccccc1)[N+]1(C)CCC=C(c2nsnc2OCCCCCC)C1 ; [Cl-]] |

TABLE 1-continued
| Cpd No. | Structure |
|---|---|
| 476 | 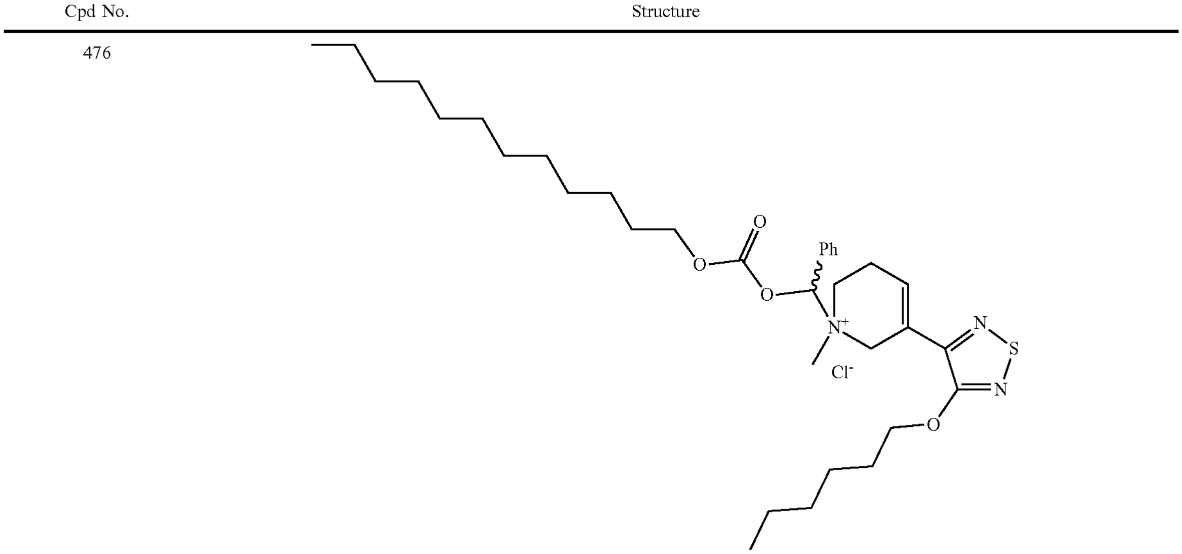 |
| 477 | 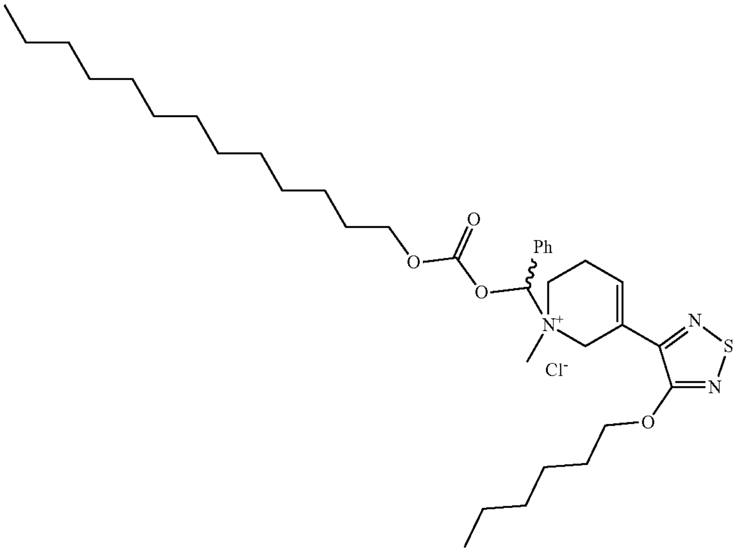 [SMILES: CCCCCCCCCCCCCOC(=O)OC(c1ccccc1)[N+]1(C)CCC=C(c2nsnc2OCCCCCC)C1 ; [Cl-]] |
| 478 | 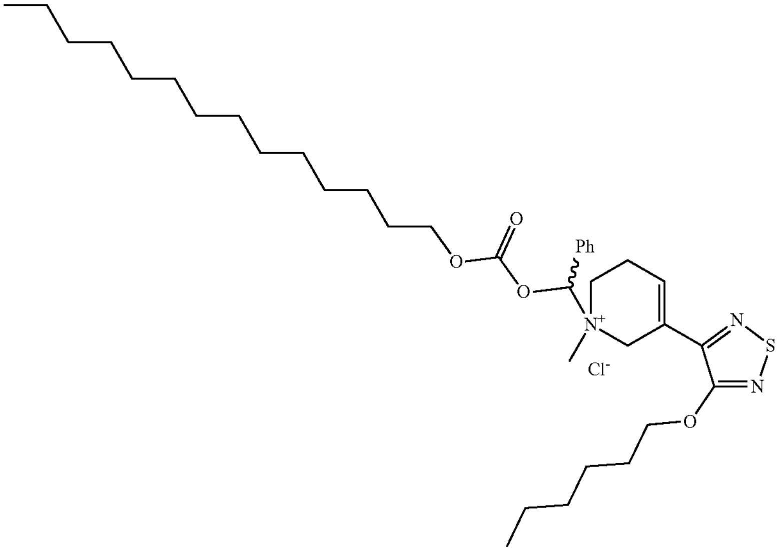 [SMILES: CCCCCCCCCCCCCCOC(=O)OC(c1ccccc1)[N+]1(C)CCC=C(c2nsnc2OCCCCCC)C1 ; [Cl-]] |

TABLE 1-continued
| Cpd No. | Structure |
|---|---|
| 479 | 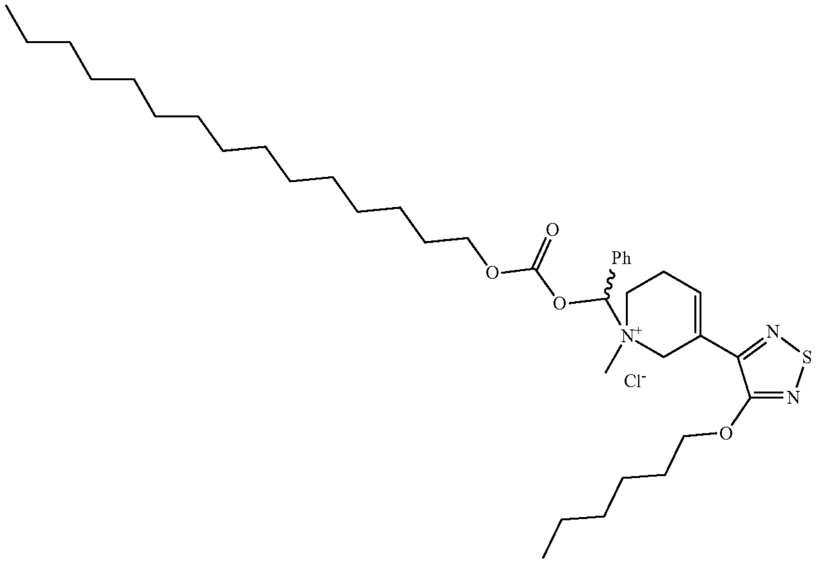 [SMILES: CCCCCCCCCCCCCCCOC(=O)OC(c1ccccc1)[N+]1(C)CCC=C(c2nsnc2OCCCCCC)C1 ; [Cl-]] |
| 480 | 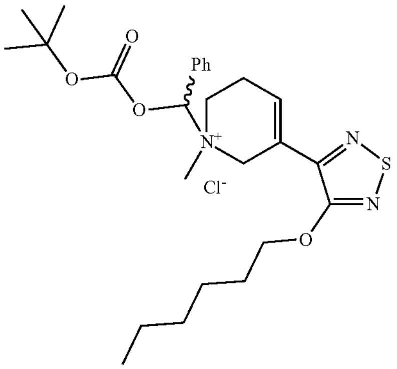 [SMILES: CCCCCCOc1nsnc1C1=CCC[N+](C)(C(OC(=O)OC(C)(C)C)c2ccccc2)C1 ; [Cl-]] |
| 481 | 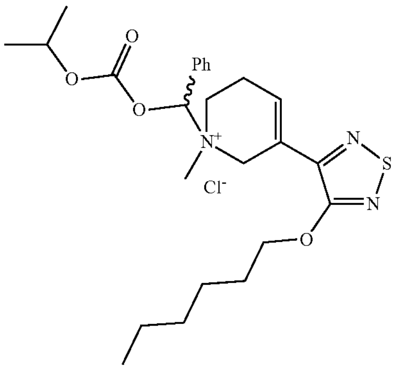 [SMILES: CCCCCCOc1nsnc1C1=CCC[N+](C)(C(OC(=O)OC(C)C)c2ccccc2)C1 ; [Cl-]] |

TABLE 1-continued
| Cpd No. | Structure |
| --- | --- |
| 482 | 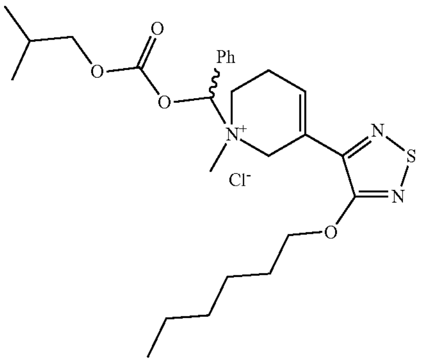 [SMILES: CCCCCCOc1nsnc1C1=CCC[N+](C)(C(OC(=O)OCC(C)C)c2ccccc2)C1 ; [Cl-]] |
| 483 | 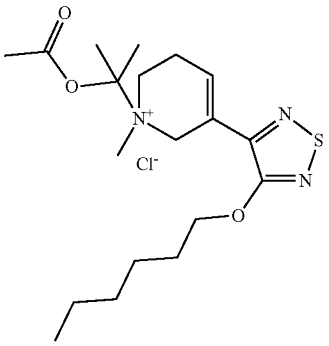 [SMILES: CCCCCCOc1nsnc1C1=CCC[N+](C)(C(C)(C)OC(C)=O)C1 ; [Cl-]] |
| 484 | 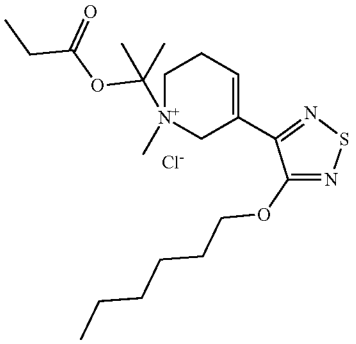 [SMILES: CCCCCCOc1nsnc1C1=CCC[N+](C)(C(C)(C)OC(=O)CC)C1 ; [Cl-]] |
| 485 | 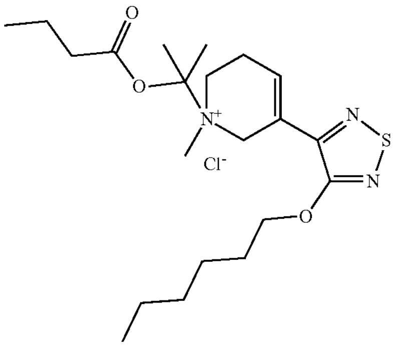 [SMILES: CCCCCCOc1nsnc1C1=CCC[N+](C)(C(C)(C)OC(=O)CCC)C1 ; [Cl-]] |

TABLE 1-continued
| Cpd No. | Structure |
|---|---|
| 486 | 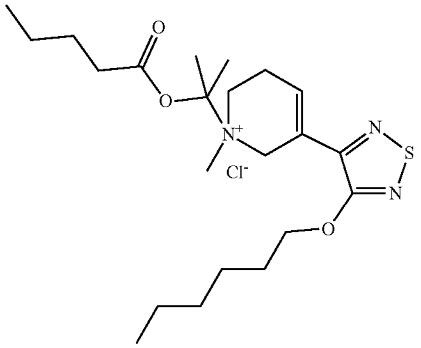 [SMILES: CCCCCCOc1nsnc1C1=CCC[N+](C)(C(C)(C)OC(=O)CCCC)C1 ; [Cl-]] |
| 487 | 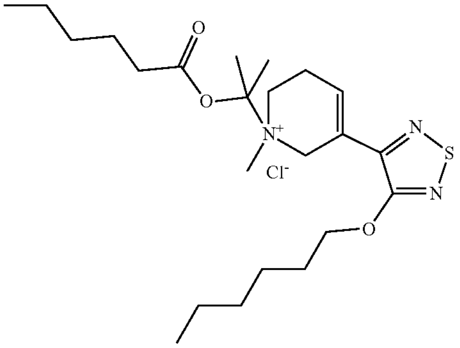 [SMILES: CCCCCCOc1nsnc1C1=CCC[N+](C)(C(C)(C)OC(=O)CCCCC)C1 ; [Cl-]] |
| 488 | 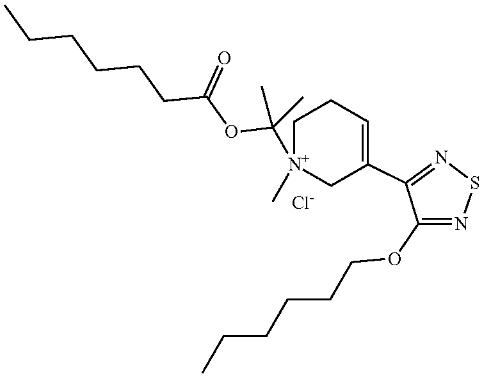 [SMILES: CCCCCCOc1nsnc1C1=CCC[N+](C)(C(C)(C)OC(=O)CCCCCC)C1 ; [Cl-]] |
| 489 | 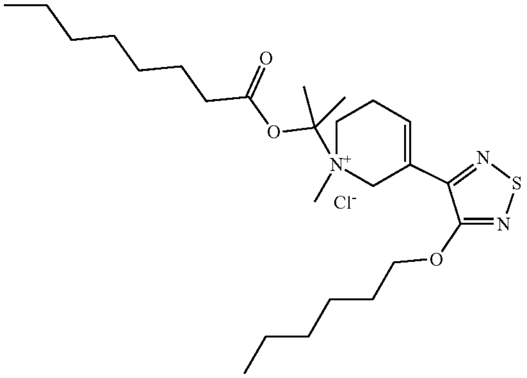 [SMILES: CCCCCCCC(=O)OC(C)(C)[N+]1(C)CCC=C(c2nsnc2OCCCCCC)C1 ; [Cl-]] |

TABLE 1-continued
| Cpd No. | Structure |
| --- | --- |
| 490 | 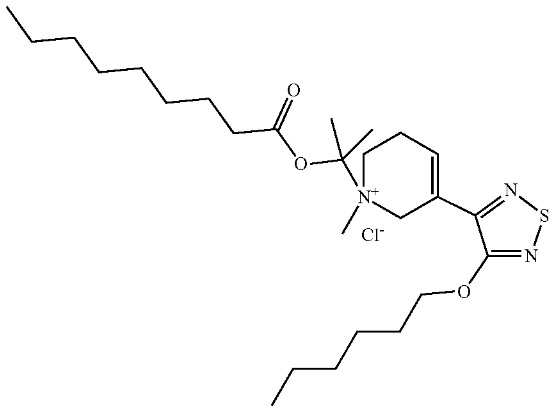 [SMILES: CCCCCCCCC(=O)OC(C)(C)[N+]1(C)CCC=C(c2nsnc2OCCCCCC)C1 ; [Cl-]] |
| 491 | 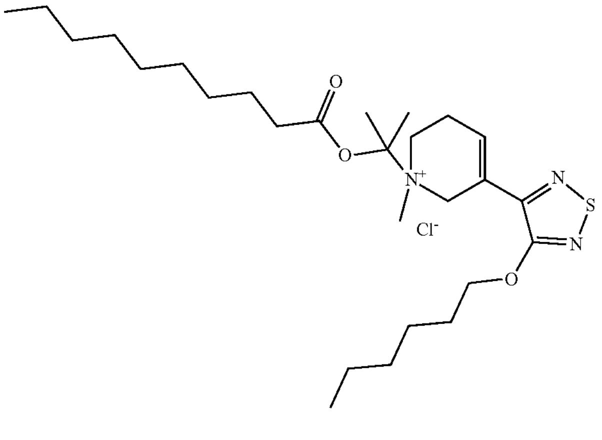 [SMILES: CCCCCCCCCC(=O)OC(C)(C)[N+]1(C)CCC=C(c2nsnc2OCCCCCC)C1 ; [Cl-]] |
| 492 | 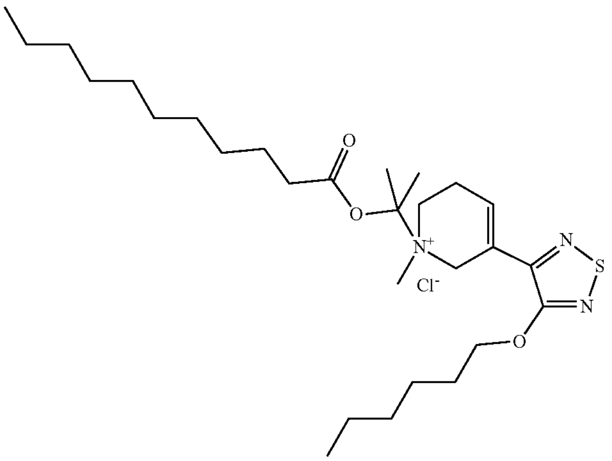 [SMILES: CCCCCCCCCCC(=O)OC(C)(C)[N+]1(C)CCC=C(c2nsnc2OCCCCCC)C1 ; [Cl-]] |

TABLE 1-continued
| Cpd No. | Structure |
| --- | --- |
| 493 | 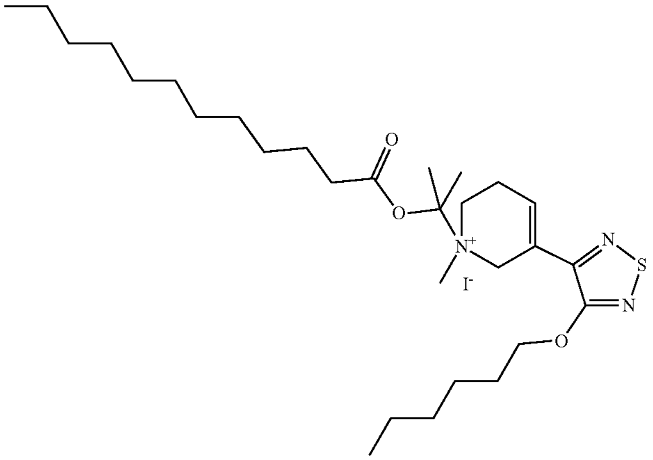 [SMILES: CCCCCCCCCCCC(=O)OC(C)(C)[N+]1(C)CCC=C(c2nsnc2OCCCCCC)C1 ; [I-]] |
| 494 | 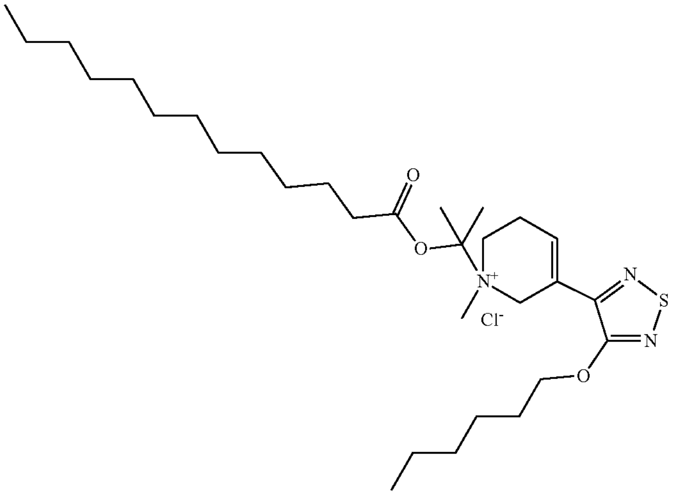 [SMILES: CCCCCCCCCCCCC(=O)OC(C)(C)[N+]1(C)CCC=C(c2nsnc2OCCCCCC)C1 ; [Cl-]] |
| 495 | 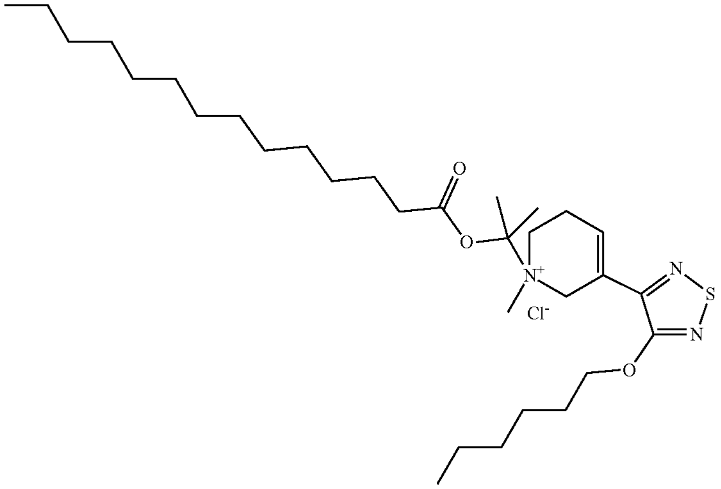 [SMILES: CCCCCCCCCCCCCC(=O)OC(C)(C)[N+]1(C)CCC=C(c2nsnc2OCCCCCC)C1 ; [Cl-]] |

TABLE 1-continued
| Cpd No. | Structure |
|---|---|
| 496 | 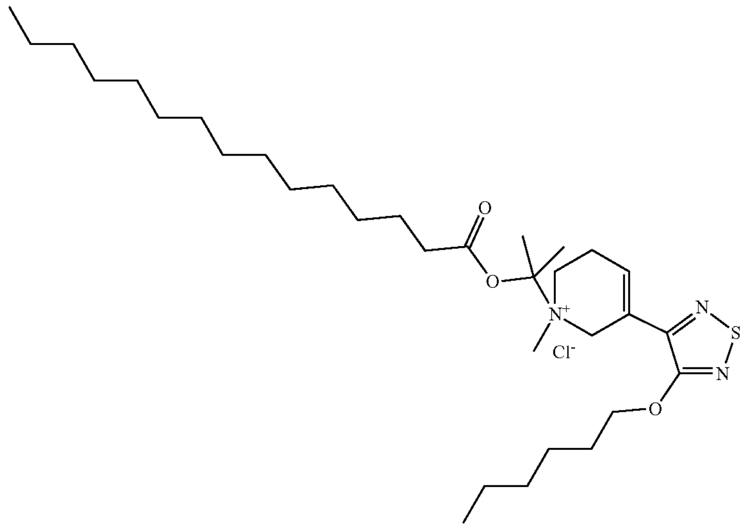 [SMILES: CCCCCCCCCCCCCCC(=O)OC(C)(C)[N+]1(C)CCC=C(c2nsnc2OCCCCCC)C1 ; [Cl-]] |
| 497 | 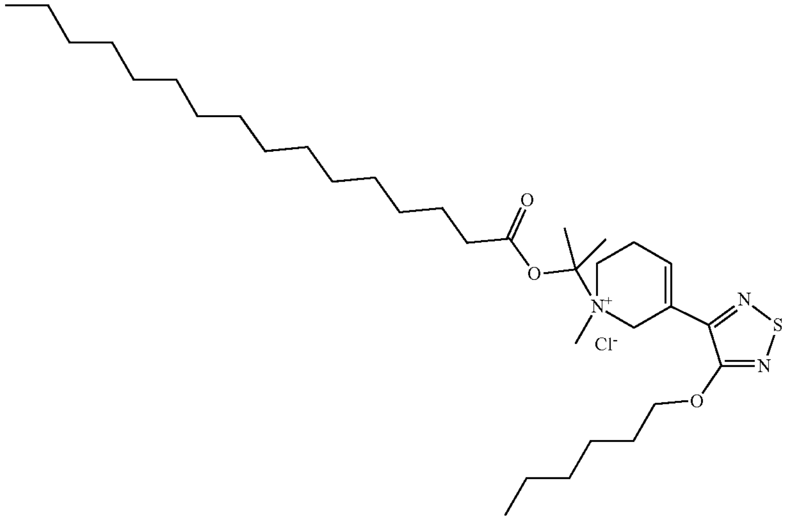 [SMILES: CCCCCCCCCCCCCCCC(=O)OC(C)(C)[N+]1(C)CCC=C(c2nsnc2OCCCCCC)C1 ; [Cl-]] |
| 498 | 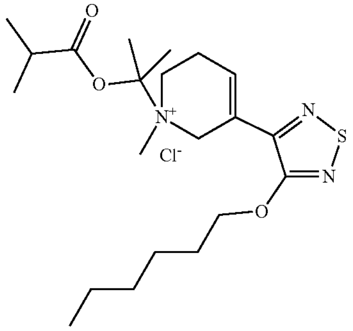 [SMILES: CCCCCCOc1nsnc1C1=CCC[N+](C)(C(C)(C)OC(=O)C(C)C)C1 ; [Cl-]] |

TABLE 1-continued
| Cpd No. | Structure |
| --- | --- |
| 499 | 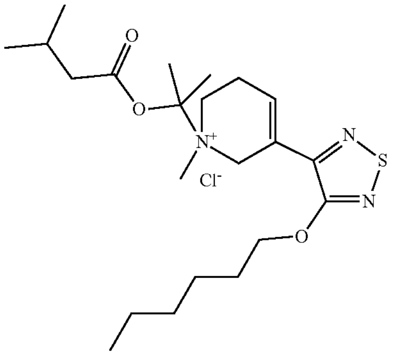 [SMILES: CCCCCCOc1nsnc1C1=CCC[N+](C)(C(C)(C)OC(=O)CC(C)C)C1 ; [Cl-]] |
| 500 | 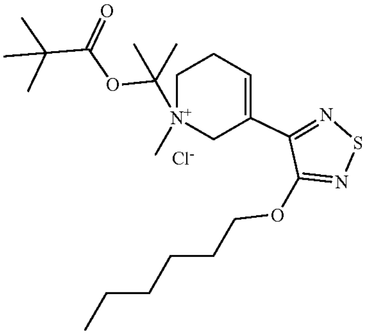 [SMILES: CCCCCCOc1nsnc1C1=CCC[N+](C)(C(C)(C)OC(=O)C(C)(C)C)C1 ; [Cl-]] |
| 501 | 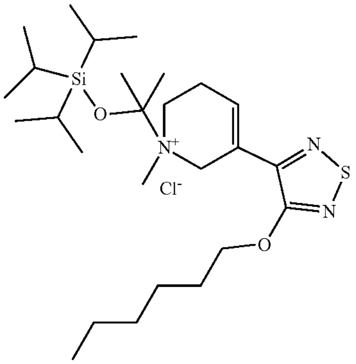 [SMILES: CCCCCCOc1nsnc1C1=CCC[N+](C)(C(C)(C)O[Si](C(C)C)(C(C)C)C(C)C)C1 ; [Cl-]] |
| 502 | 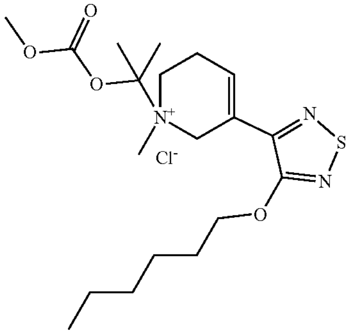 [SMILES: CCCCCCOc1nsnc1C1=CCC[N+](C)(C(C)(C)OC(=O)OC)C1 ; [Cl-]] |

TABLE 1-continued
| Cpd No. | Structure |
|---|---|
| 503 | 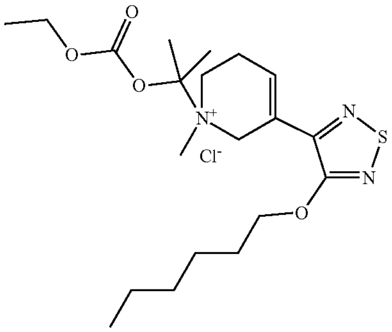 [SMILES: CCCCCCOc1nsnc1C1=CCC[N+](C)(C(C)(C)OC(=O)OCC)C1 ; [Cl-]] |
| 504 | 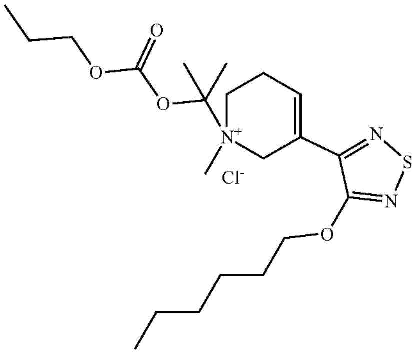 [SMILES: CCCCCCOc1nsnc1C1=CCC[N+](C)(C(C)(C)OC(=O)OCCC)C1 ; [Cl-]] |
| 505 | 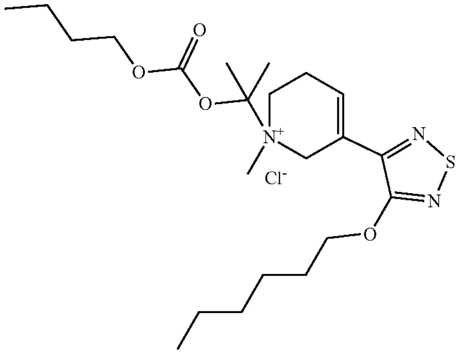 [SMILES: CCCCCCOc1nsnc1C1=CCC[N+](C)(C(C)(C)OC(=O)OCCCC)C1 ; [Cl-]] |
| 506 | 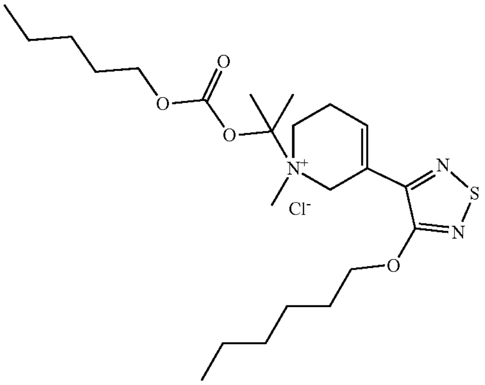 [SMILES: CCCCCCOc1nsnc1C1=CCC[N+](C)(C(C)(C)OC(=O)OCCCCC)C1 ; [Cl-]] |

TABLE 1-continued
| Cpd No. | Structure |
| --- | --- |
| 507 | 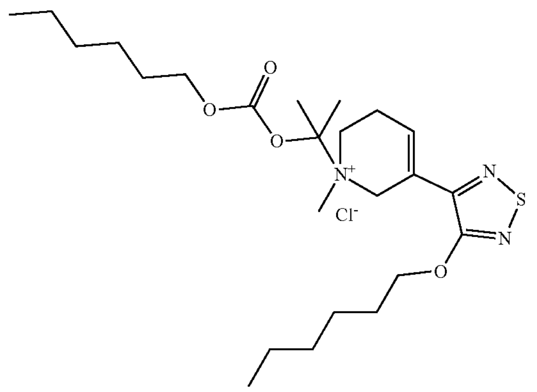 [SMILES: CCCCCCOC(=O)OC(C)(C)[N+]1(C)CCC=C(c2nsnc2OCCCCCC)C1 ; [Cl-]] |
| 508 | 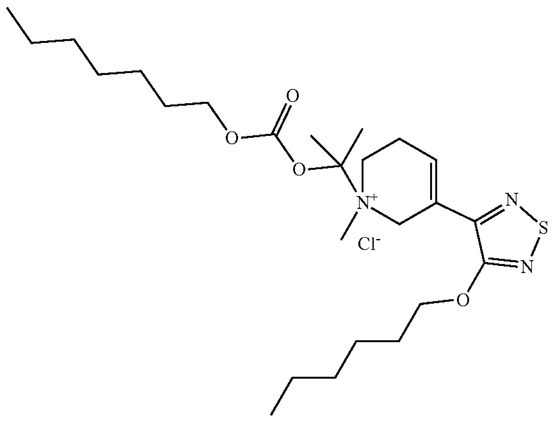 [SMILES: CCCCCCCOC(=O)OC(C)(C)[N+]1(C)CCC=C(c2nsnc2OCCCCCC)C1 ; [Cl-]] |
| 509 | 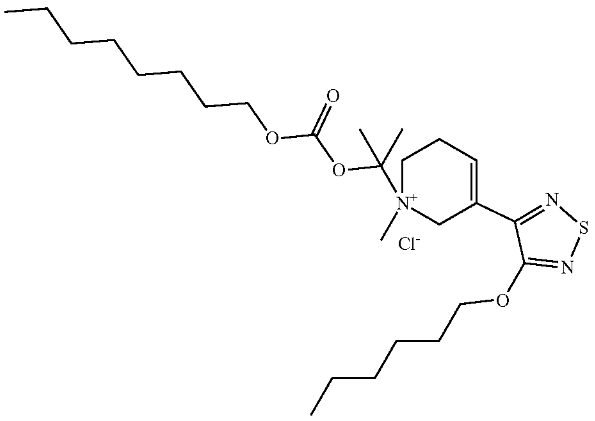 [SMILES: CCCCCCCCOC(=O)OC(C)(C)[N+]1(C)CCC=C(c2nsnc2OCCCCCC)C1 ; [Cl-]] |

TABLE 1-continued
| Cpd No. | Structure |
| --- | --- |
| 510 | 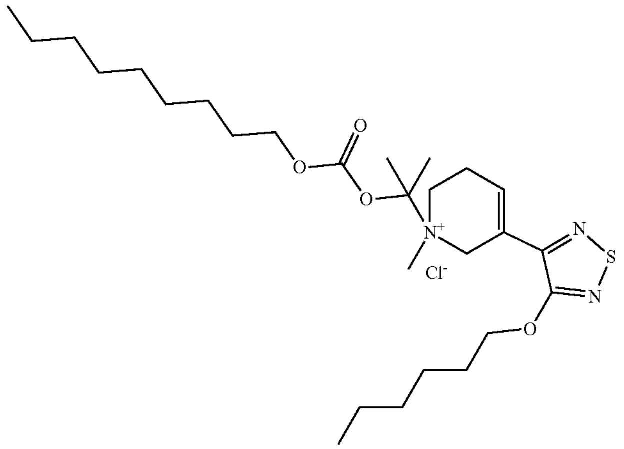 [SMILES: CCCCCCCCCOC(=O)OC(C)(C)[N+]1(C)CCC=C(c2nsnc2OCCCCCC)C1 ; [Cl-]] |
| 511 | 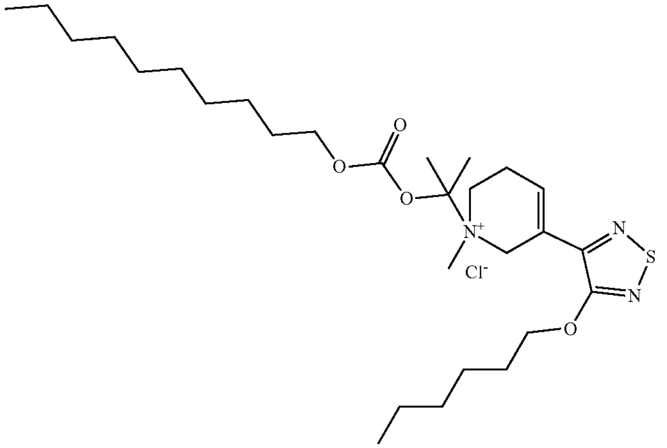 [SMILES: CCCCCCCCCCOC(=O)OC(C)(C)[N+]1(C)CCC=C(c2nsnc2OCCCCCC)C1 ; [Cl-]] |
| 512 | 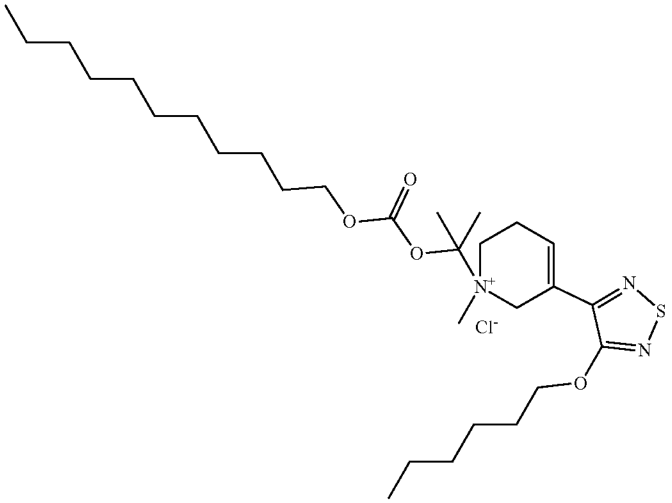 [SMILES: CCCCCCCCCCCOC(=O)OC(C)(C)[N+]1(C)CCC=C(c2nsnc2OCCCCCC)C1 ; [Cl-]] |

TABLE 1-continued
| Cpd No. | Structure |
| --- | --- |
| 513 | 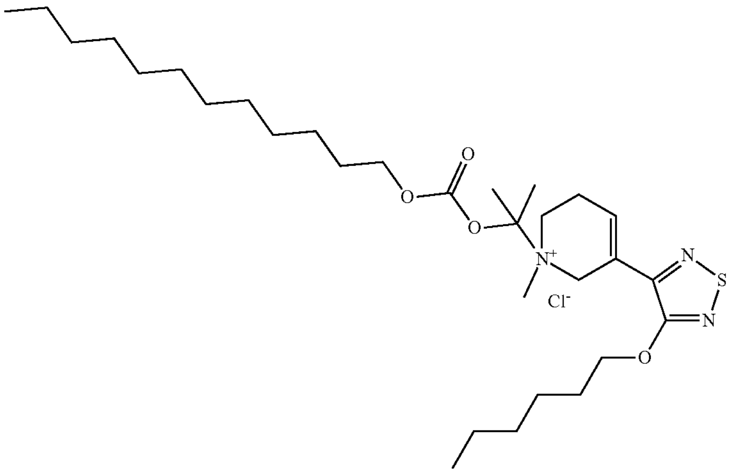 [SMILES: CCCCCCCCCCCCOC(=O)OC(C)(C)[N+]1(C)CCC=C(c2nsnc2OCCCCCC)C1 ; [Cl-]] |
| 514 | 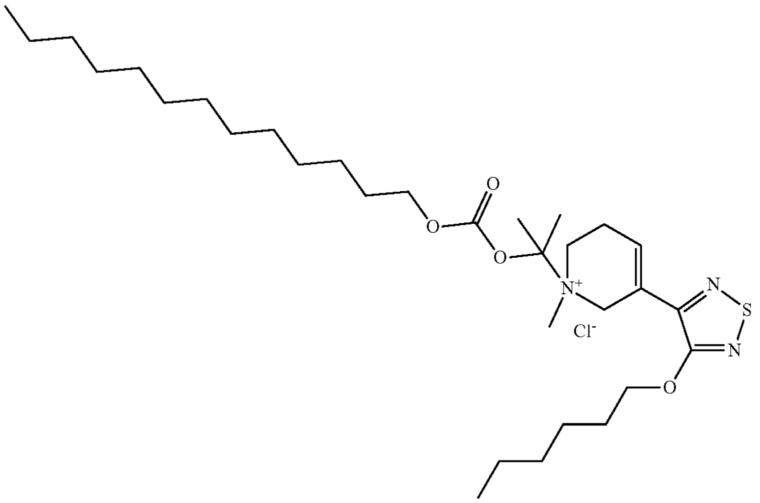 [SMILES: CCCCCCCCCCCCCOC(=O)OC(C)(C)[N+]1(C)CCC=C(c2nsnc2OCCCCCC)C1 ; [Cl-]] |
| 515 | 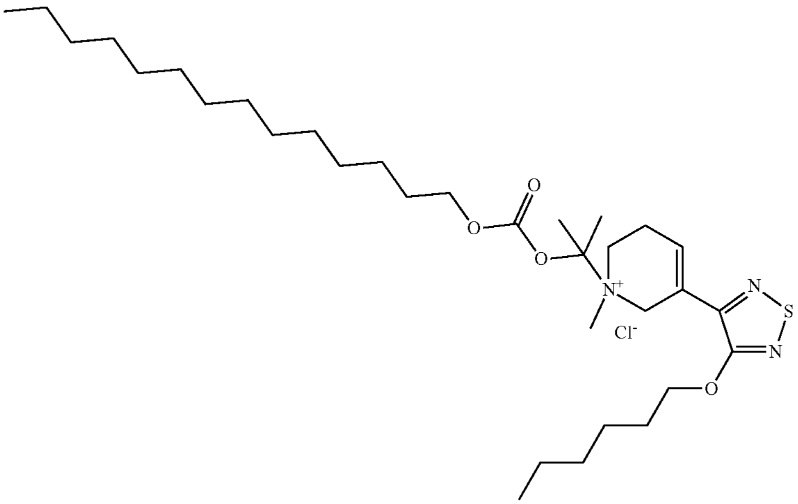 [SMILES: CCCCCCCCCCCCCCOC(=O)OC(C)(C)[N+]1(C)CCC=C(c2nsnc2OCCCCCC)C1 ; [Cl-]] |

TABLE 1-continued
| Cpd No. | Structure |
| --- | --- |
| 516 | 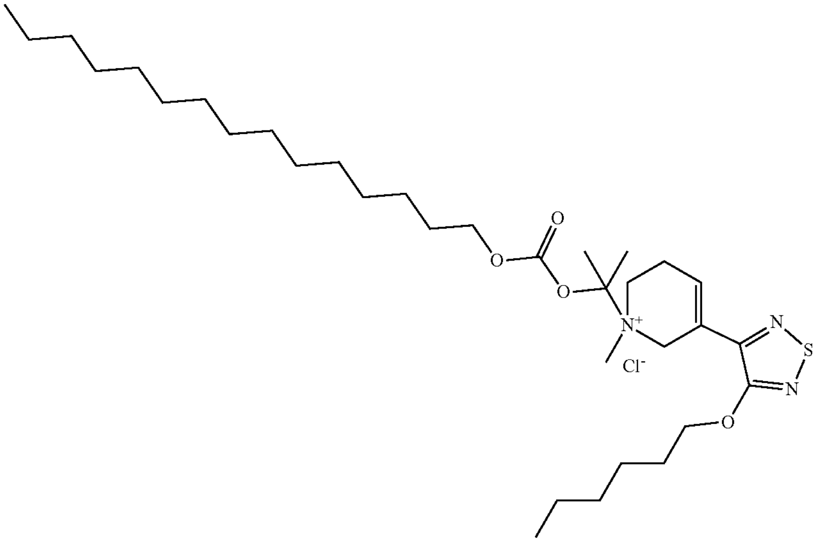 [SMILES: CCCCCCCCCCCCCCCOC(=O)OC(C)(C)[N+]1(C)CCC=C(c2nsnc2OCCCCCC)C1 ; [Cl-]] |
| 517 | 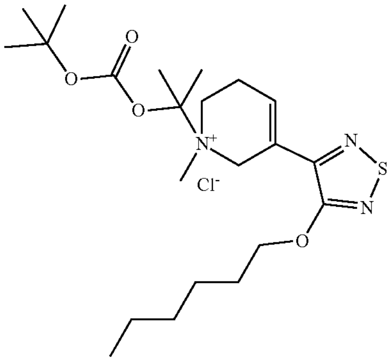 [SMILES: CCCCCCOc1nsnc1C1=CCC[N+](C)(C(C)(C)OC(=O)OC(C)(C)C)C1 ; [Cl-]] |
| 518 | 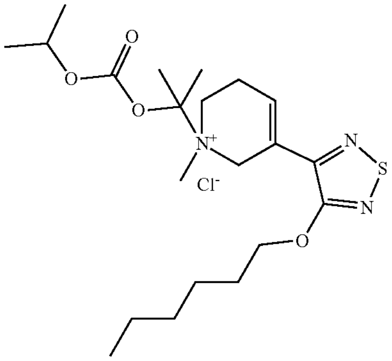 [SMILES: CCCCCCOc1nsnc1C1=CCC[N+](C)(C(C)(C)OC(=O)OC(C)C)C1 ; [Cl-]] |

TABLE 1-continued
| Cpd No. | Structure |
|---|---|
| 519 | 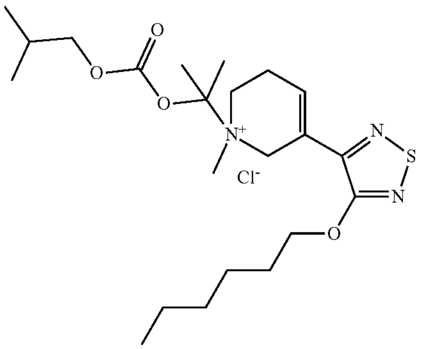 [SMILES: CCCCCCOc1nsnc1C1=CCC[N+](C)(C(C)(C)OC(=O)OCC(C)C)C1 ; [Cl-]] |
| 520 | 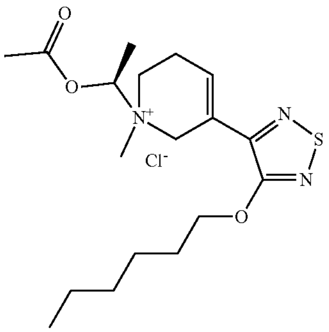 [SMILES: CCCCCCOc1nsnc1C1=CCC[N+](C)([C@H](C)OC(C)=O)C1 ; [Cl-]] |
| 521 | 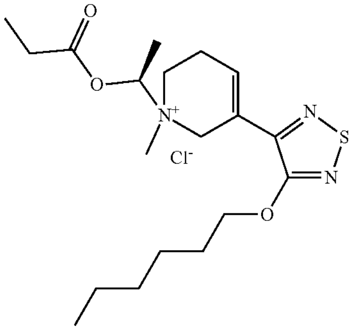 [SMILES: CCCCCCOc1nsnc1C1=CCC[N+](C)([C@H](C)OC(=O)CC)C1 ; [Cl-]] |
| 522 | 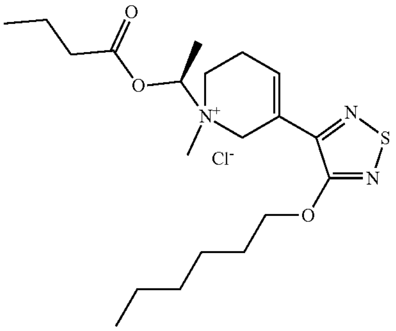 [SMILES: CCCCCCOc1nsnc1C1=CCC[N+](C)([C@H](C)OC(=O)CCC)C1 ; [Cl-]] |

TABLE 1-continued
| Cpd No. | Structure |
|---|---|
| 523 | 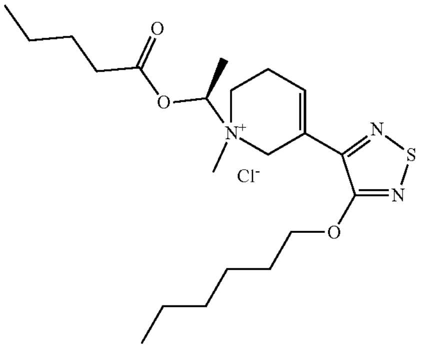 [SMILES: CCCCCCOc1nsnc1C1=CCC[N+](C)([C@H](C)OC(=O)CCCC)C1 ; [Cl-]] |
| 524 | 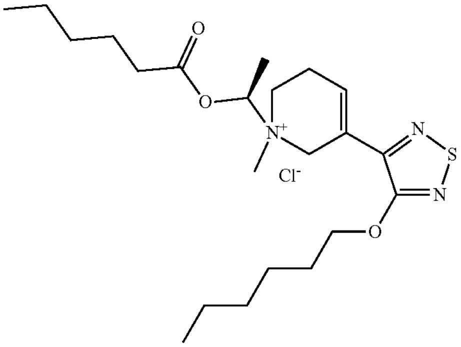 [SMILES: CCCCCCOc1nsnc1C1=CCC[N+](C)([C@H](C)OC(=O)CCCCC)C1 ; [Cl-]] |
| 525 | 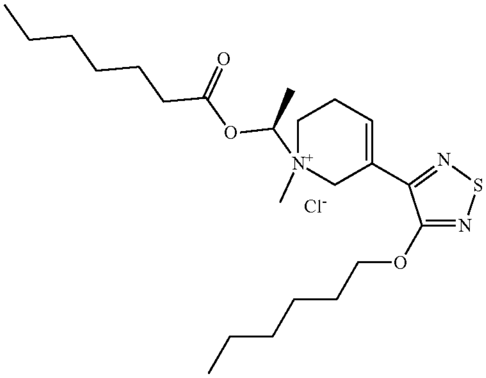 [SMILES: CCCCCCOc1nsnc1C1=CCC[N+](C)([C@H](C)OC(=O)CCCCCC)C1 ; [Cl-]] |
| 526 | 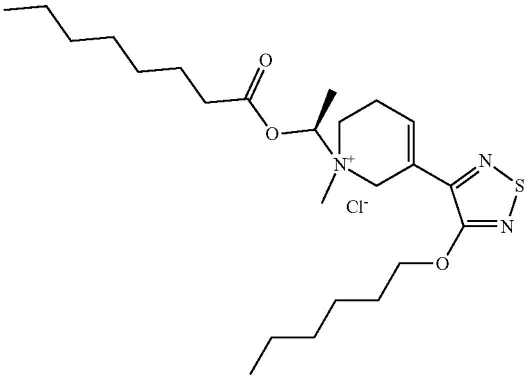 [SMILES: CCCCCCCC(=O)O[C@@H](C)[N+]1(C)CCC=C(c2nsnc2OCCCCCC)C1 ; [Cl-]] |

TABLE 1-continued
| Cpd No. | Structure |
|---|---|
| 527 | 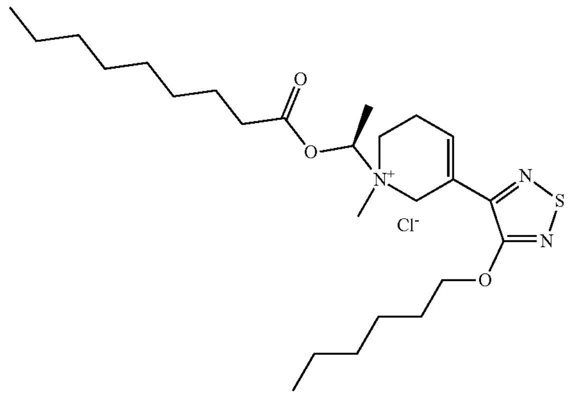 [SMILES: CCCCCCCCC(=O)O[C@@H](C)[N+]1(C)CCC=C(c2nsnc2OCCCCCC)C1 ; [Cl-]] |
| 528 | 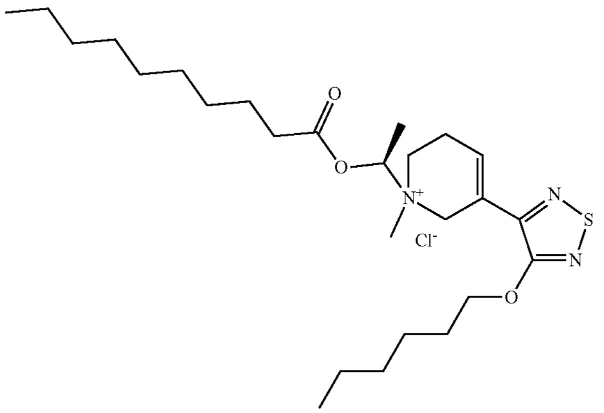 [SMILES: CCCCCCCCCC(=O)O[C@@H](C)[N+]1(C)CCC=C(c2nsnc2OCCCCCC)C1 ; [Cl-]] |
| 529 | 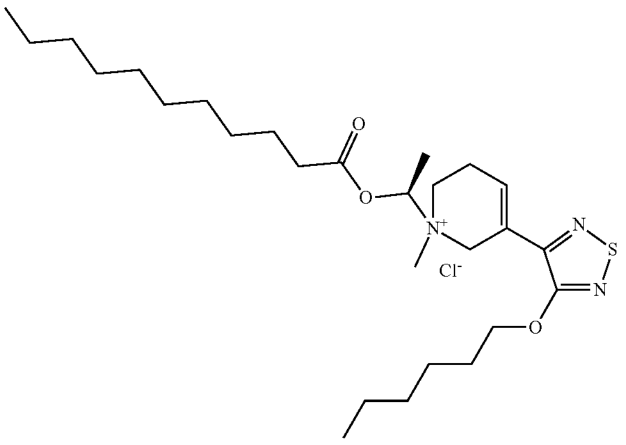 [SMILES: CCCCCCCCCCC(=O)O[C@@H](C)[N+]1(C)CCC=C(c2nsnc2OCCCCCC)C1 ; [Cl-]] |

TABLE 1-continued
| Cpd No. | Structure |
|---|---|
| 530 | 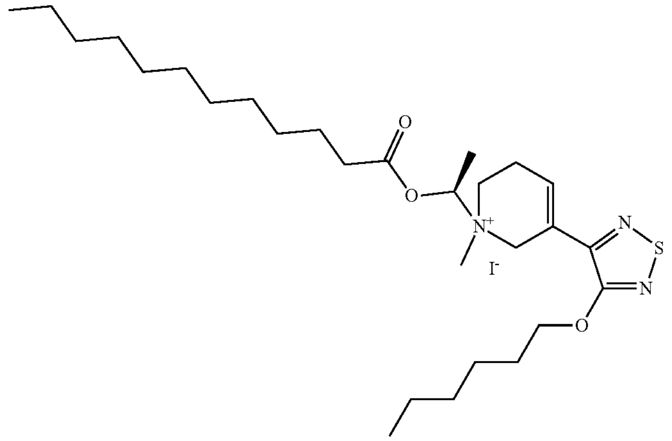 [SMILES: CCCCCCCCCCCC(=O)O[C@@H](C)[N+]1(C)CCC=C(c2nsnc2OCCCCCC)C1 ; [I-]] |
| 531 | 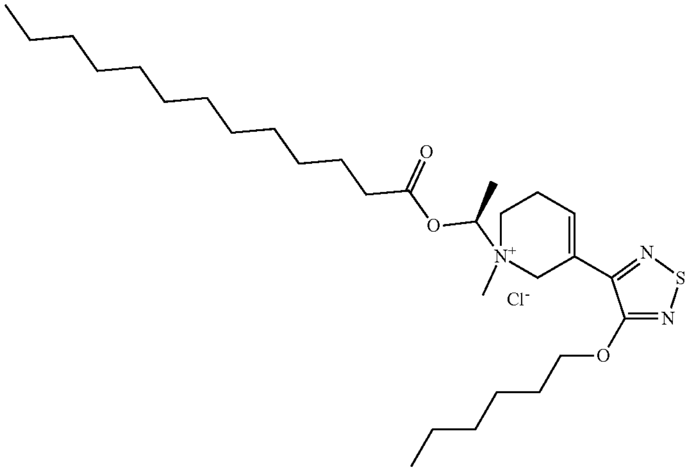 [SMILES: CCCCCCCCCCCCC(=O)O[C@@H](C)[N+]1(C)CCC=C(c2nsnc2OCCCCCC)C1 ; [Cl-]] |
| 532 | 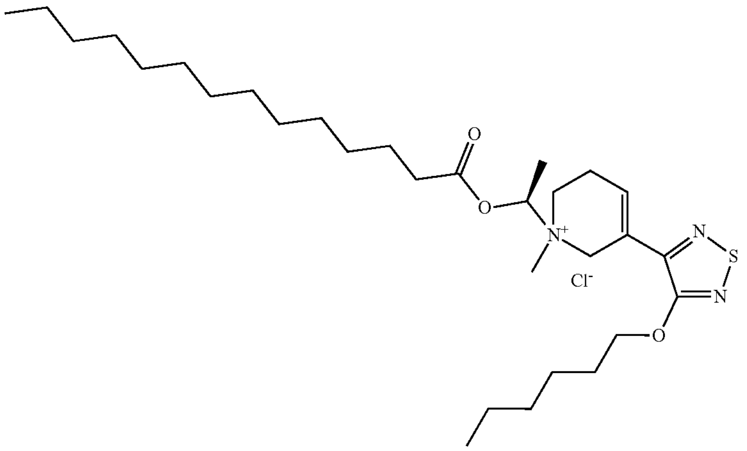 [SMILES: CCCCCCCCCCCCCC(=O)O[C@@H](C)[N+]1(C)CCC=C(c2nsnc2OCCCCCC)C1 ; [Cl-]] |

TABLE 1-continued
| Cpd No. | Structure |
| --- | --- |
| 533 | 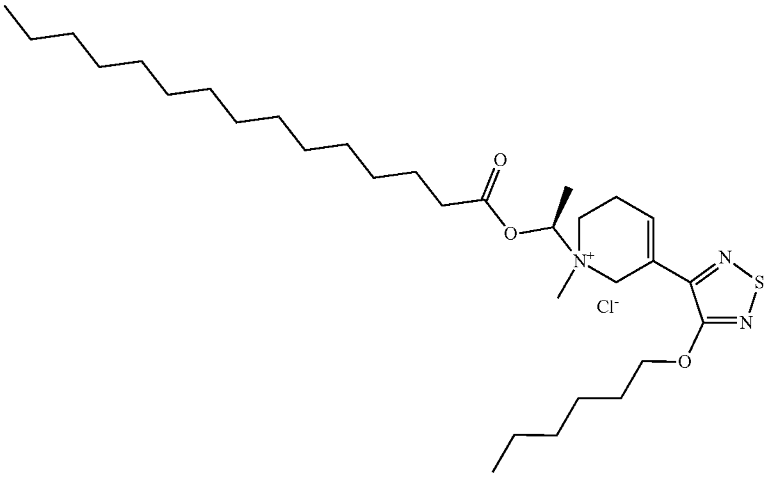 [SMILES: CCCCCCCCCCCCCCC(=O)O[C@@H](C)[N+]1(C)CCC=C(c2nsnc2OCCCCCC)C1 ; [Cl-]] |
| 534 | 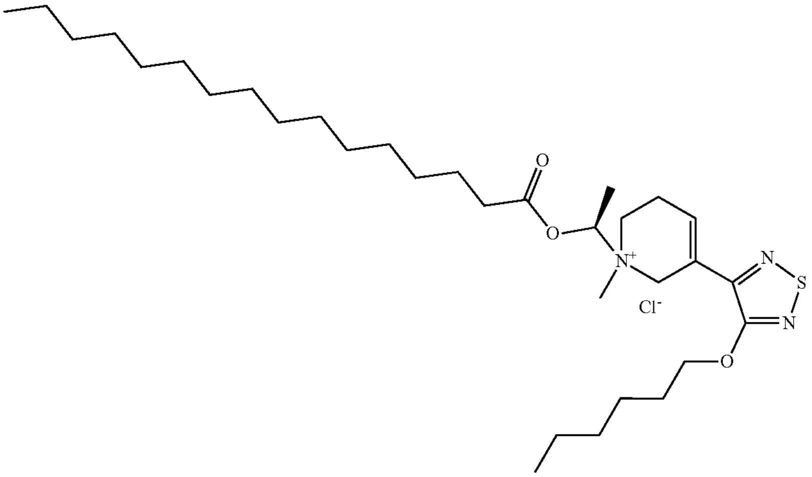 [SMILES: CCCCCCCCCCCCCCCC(=O)O[C@@H](C)[N+]1(C)CCC=C(c2nsnc2OCCCCCC)C1 ; [Cl-]] |
| 535 | 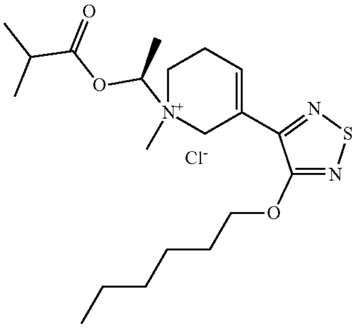 [SMILES: CCCCCCOc1nsnc1C1=CCC[N+](C)([C@H](C)OC(=O)C(C)C)C1 ; [Cl-]] |

TABLE 1-continued
| Cpd No. | Structure |
| --- | --- |
| 536 | 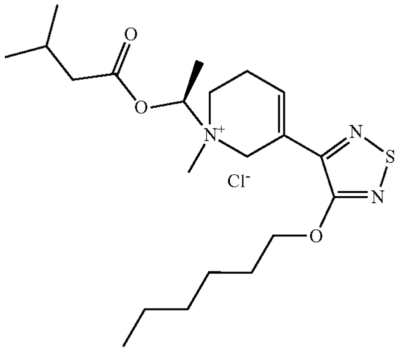 [SMILES: CCCCCCOc1nsnc1C1=CCC[N+](C)([C@H](C)OC(=O)CC(C)C)C1 ; [Cl-]] |
| 537 | 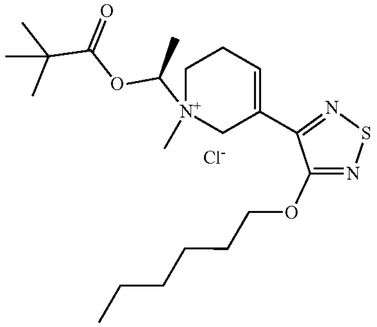 [SMILES: CCCCCCOc1nsnc1C1=CCC[N+](C)([C@H](C)OC(=O)C(C)(C)C)C1 ; [Cl-]] |
| 538 | 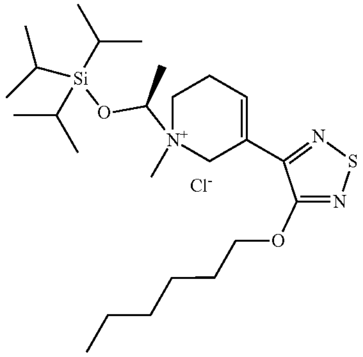 [SMILES: CCCCCCOc1nsnc1C1=CCC[N+](C)([C@H](C)O[Si](C(C)C)(C(C)C)C(C)C)C1 ; [Cl-]] |
| 539 | 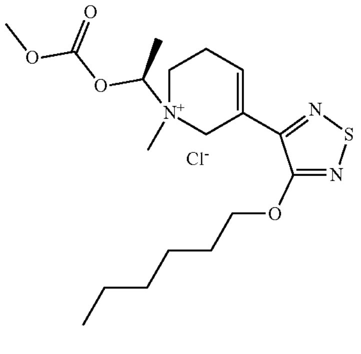 [SMILES: CCCCCCOc1nsnc1C1=CCC[N+](C)([C@H](C)OC(=O)OC)C1 ; [Cl-]] |

TABLE 1-continued
| Cpd No. | Structure |
|---|---|
| 540 | 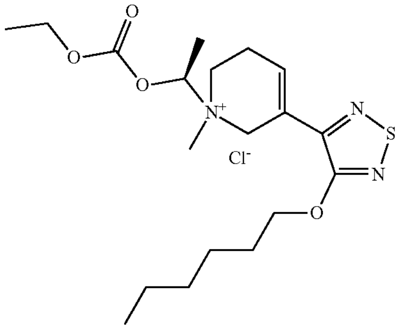 [SMILES: CCCCCCOc1nsnc1C1=CCC[N+](C)([C@H](C)OC(=O)OCC)C1 ; [Cl-]] |
| 541 | 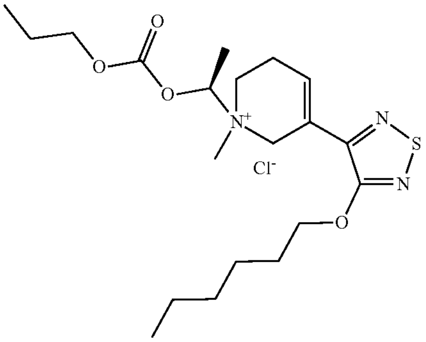 [SMILES: CCCCCCOc1nsnc1C1=CCC[N+](C)([C@H](C)OC(=O)OCCC)C1 ; [Cl-]] |
| 542 | 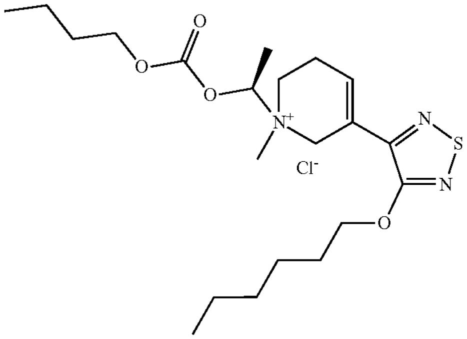 [SMILES: CCCCCCOc1nsnc1C1=CCC[N+](C)([C@H](C)OC(=O)OCCCC)C1 ; [Cl-]] |
| 543 | 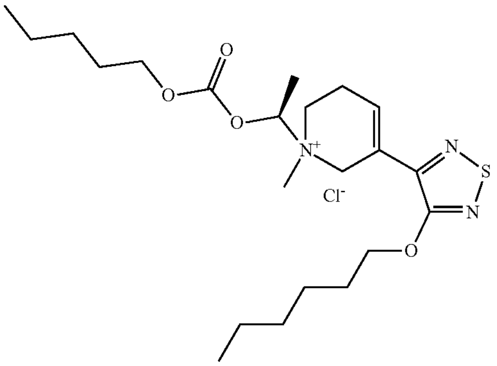 [SMILES: CCCCCCOc1nsnc1C1=CCC[N+](C)([C@H](C)OC(=O)OCCCCC)C1 ; [Cl-]] |

TABLE 1-continued
| Cpd No. | Structure |
|---|---|
| 544 | 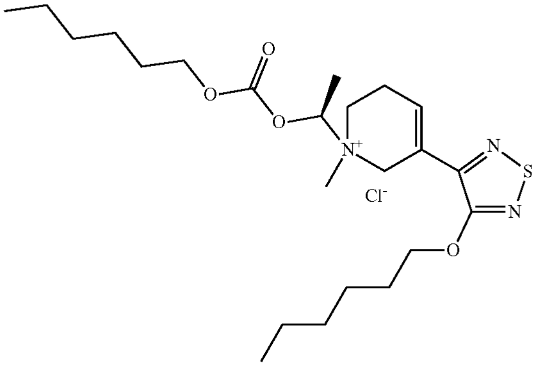 [SMILES: CCCCCCOC(=O)O[C@@H](C)[N+]1(C)CCC=C(c2nsnc2OCCCCCC)C1 ; [Cl-]] |
| 545 | 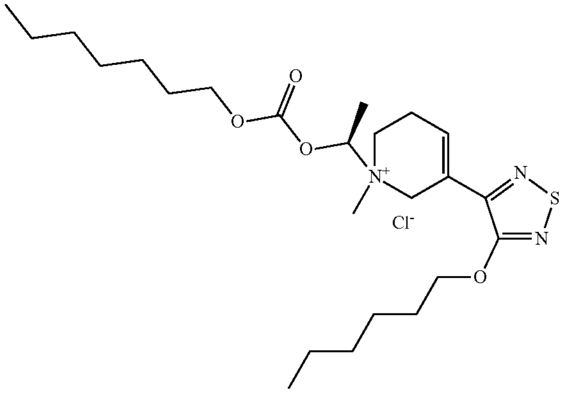 [SMILES: CCCCCCCOC(=O)O[C@@H](C)[N+]1(C)CCC=C(c2nsnc2OCCCCCC)C1 ; [Cl-]] |
| 546 | 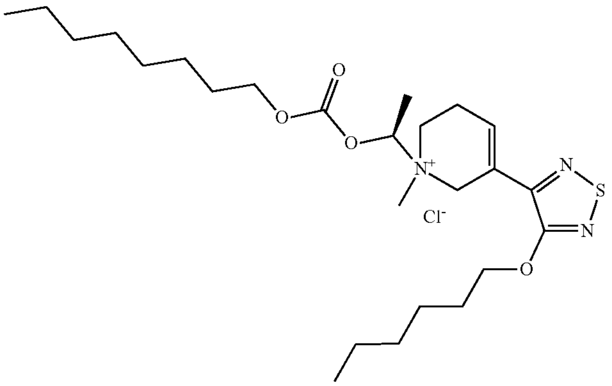 [SMILES: CCCCCCCCOC(=O)O[C@@H](C)[N+]1(C)CCC=C(c2nsnc2OCCCCCC)C1 ; [Cl-]] |
| 547 | 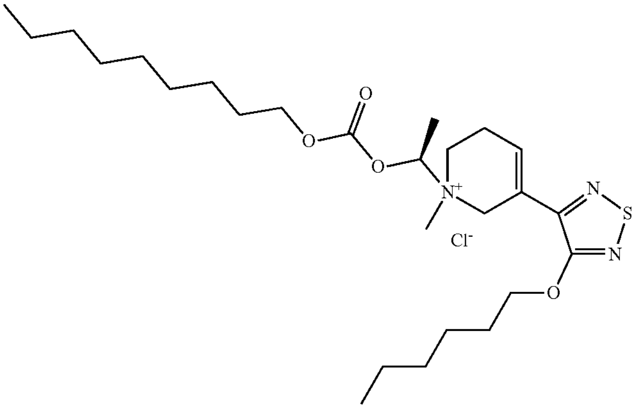 [SMILES: CCCCCCCCCOC(=O)O[C@@H](C)[N+]1(C)CCC=C(c2nsnc2OCCCCCC)C1 ; [Cl-]] |

TABLE 1-continued
| Cpd No. | Structure |
|---|---|
| 548 | 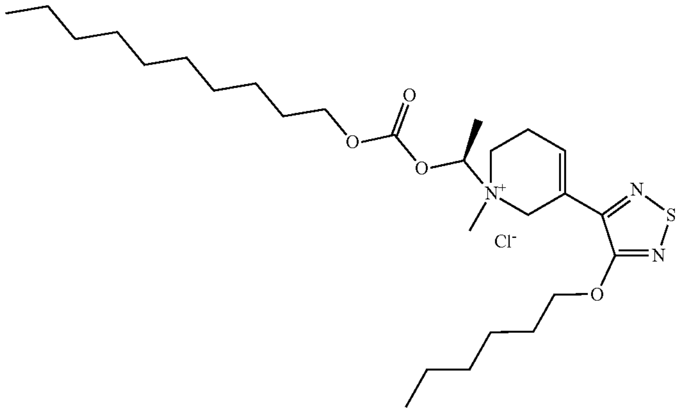 [SMILES: CCCCCCCCCCOC(=O)O[C@@H](C)[N+]1(C)CCC=C(c2nsnc2OCCCCCC)C1 ; [Cl-]] |
| 549 | 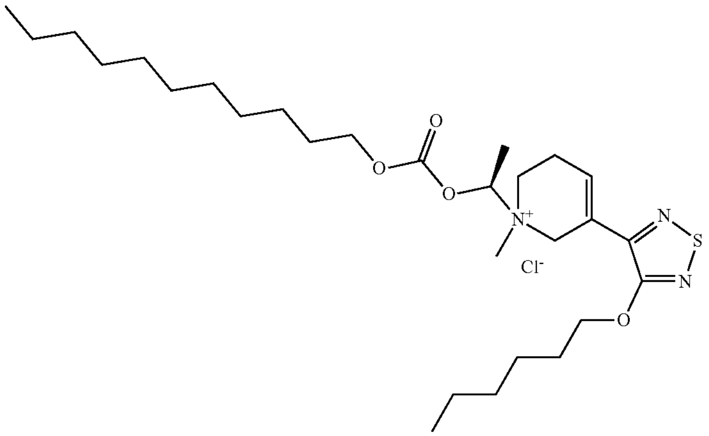 [SMILES: CCCCCCCCCCCOC(=O)O[C@@H](C)[N+]1(C)CCC=C(c2nsnc2OCCCCCC)C1 ; [Cl-]] |
| 550 | 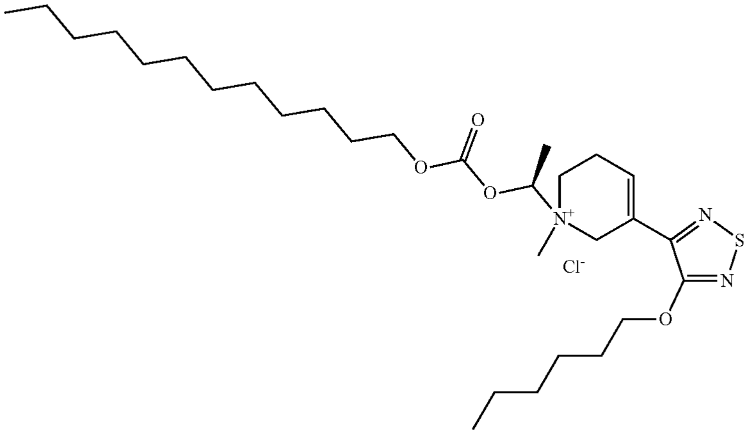 [SMILES: CCCCCCCCCCCCOC(=O)O[C@@H](C)[N+]1(C)CCC=C(c2nsnc2OCCCCCC)C1 ; [Cl-]] |

TABLE 1-continued
| Cpd No. | Structure |
|---|---|
| 551 | 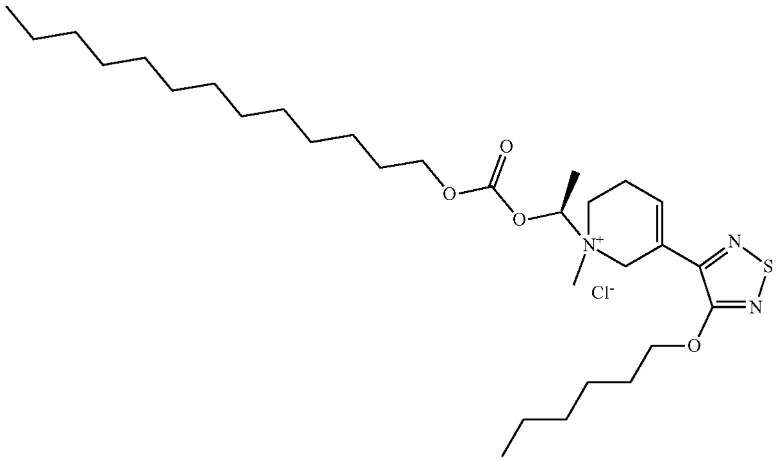 [SMILES: CCCCCCCCCCCCCOC(=O)O[C@@H](C)[N+]1(C)CCC=C(c2nsnc2OCCCCCC)C1 ; [Cl-]] |
| 552 | 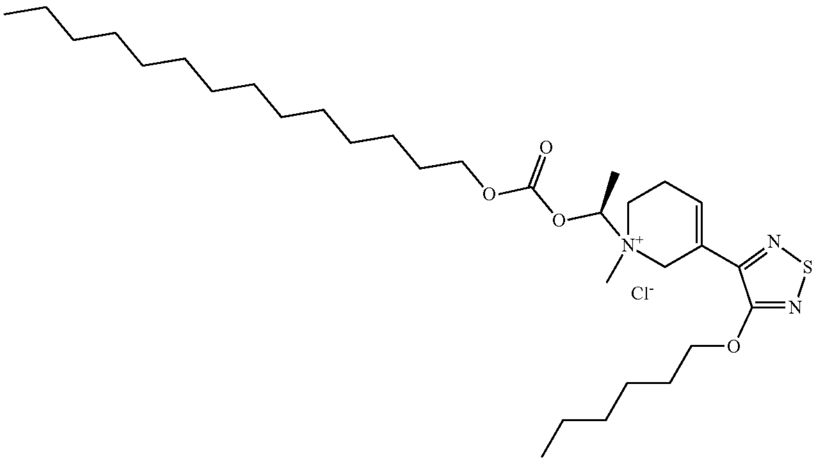 [SMILES: CCCCCCCCCCCCCCOC(=O)O[C@@H](C)[N+]1(C)CCC=C(c2nsnc2OCCCCCC)C1 ; [Cl-]] |
| 553 | 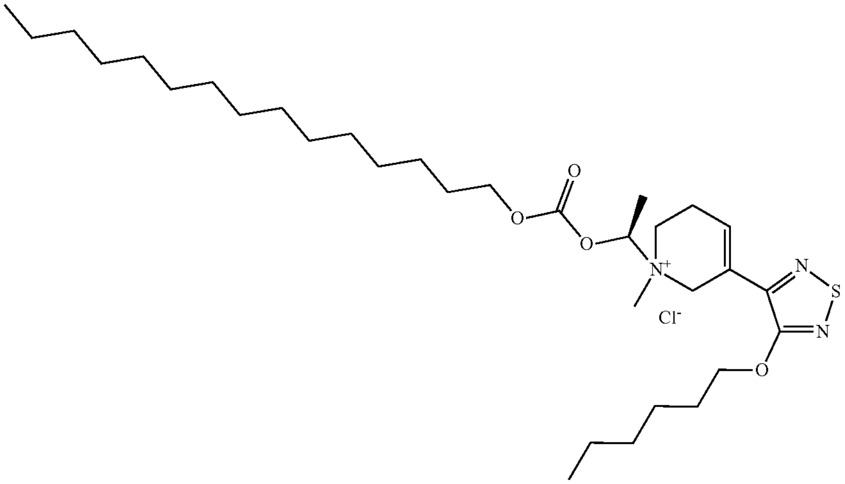 [SMILES: CCCCCCCCCCCCCCCOC(=O)O[C@@H](C)[N+]1(C)CCC=C(c2nsnc2OCCCCCC)C1 ; [Cl-]] |

TABLE 1-continued
| Cpd No. | Structure |
|---|---|
| 554 | 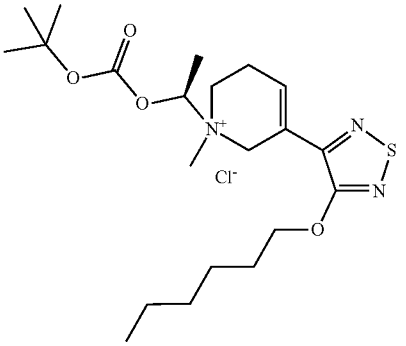 [SMILES: CCCCCCOc1nsnc1C1=CCC[N+](C)([C@H](C)OC(=O)OC(C)(C)C)C1 ; [Cl-]] |
| 555 | 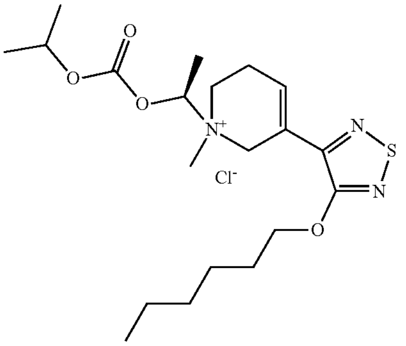 [SMILES: CCCCCCOc1nsnc1C1=CCC[N+](C)([C@H](C)OC(=O)OC(C)C)C1 ; [Cl-]] |
| 556 | 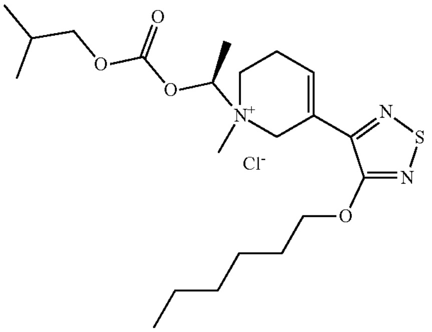 [SMILES: CCCCCCOc1nsnc1C1=CCC[N+](C)([C@H](C)OC(=O)OCC(C)C)C1 ; [Cl-]] |
| 557 | 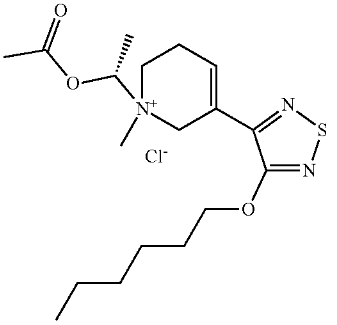 [SMILES: CCCCCCOc1nsnc1C1=CCC[N+](C)([C@@H](C)OC(C)=O)C1 ; [Cl-]] |

TABLE 1-continued
| Cpd No. | Structure |
| --- | --- |
| 558 | 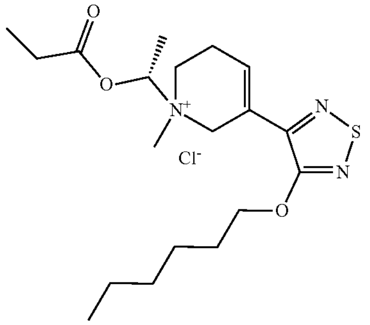 [SMILES: CCCCCCOc1nsnc1C1=CCC[N+](C)([C@@H](C)OC(=O)CC)C1 ; [Cl-]] |
| 559 | 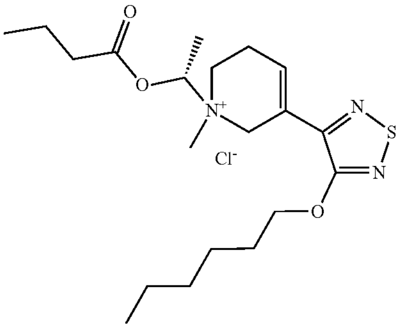 [SMILES: CCCCCCOc1nsnc1C1=CCC[N+](C)([C@@H](C)OC(=O)CCC)C1 ; [Cl-]] |
| 560 | 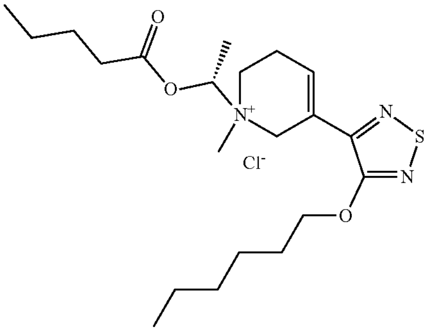 [SMILES: CCCCCCOc1nsnc1C1=CCC[N+](C)([C@@H](C)OC(=O)CCCC)C1 ; [Cl-]] |
| 561 | 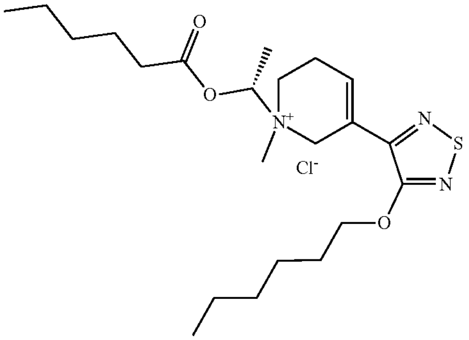 [SMILES: CCCCCCOc1nsnc1C1=CCC[N+](C)([C@@H](C)OC(=O)CCCCC)C1 ; [Cl-]] |

TABLE 1-continued
| Cpd No. | Structure |
|---|---|
| 562 | 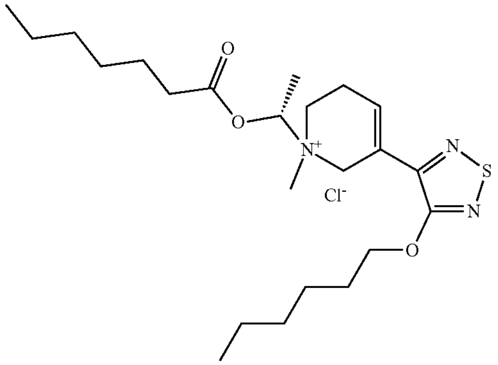 [SMILES: CCCCCCOc1nsnc1C1=CCC[N+](C)([C@@H](C)OC(=O)CCCCCC)C1 ; [Cl-]] |
| 563 | 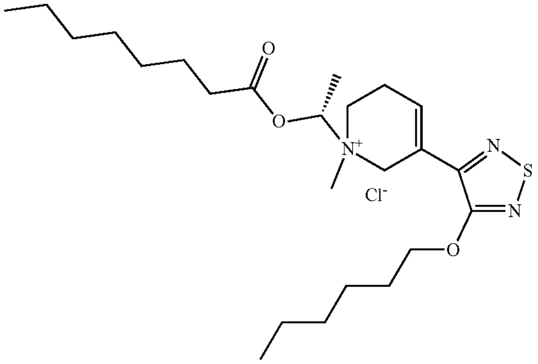 [SMILES: CCCCCCCC(=O)O[C@H](C)[N+]1(C)CCC=C(c2nsnc2OCCCCCC)C1 ; [Cl-]] |
| 564 | 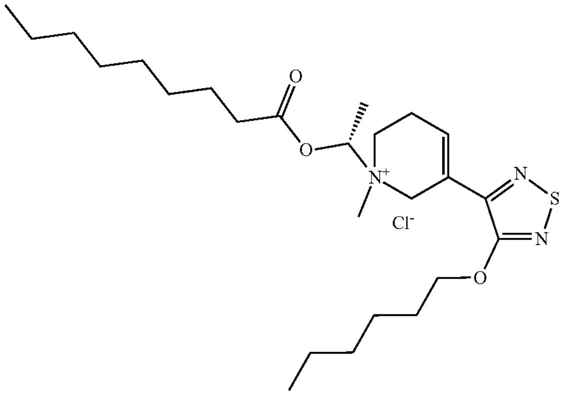 [SMILES: CCCCCCCCC(=O)O[C@H](C)[N+]1(C)CCC=C(c2nsnc2OCCCCCC)C1 ; [Cl-]] |
| 565 | 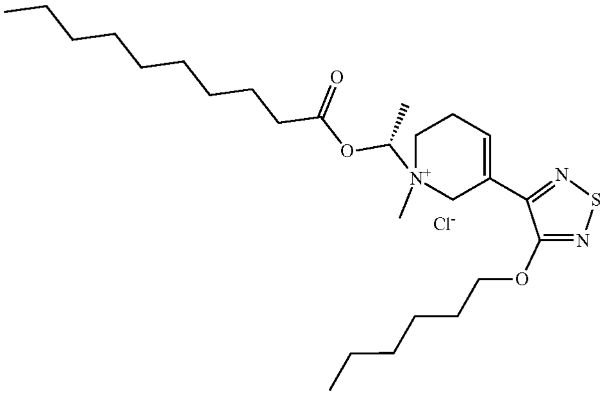 [SMILES: CCCCCCCCCC(=O)O[C@H](C)[N+]1(C)CCC=C(c2nsnc2OCCCCCC)C1 ; [Cl-]] |

TABLE 1-continued
| Cpd No. | Structure |
|---|---|
| 566 | 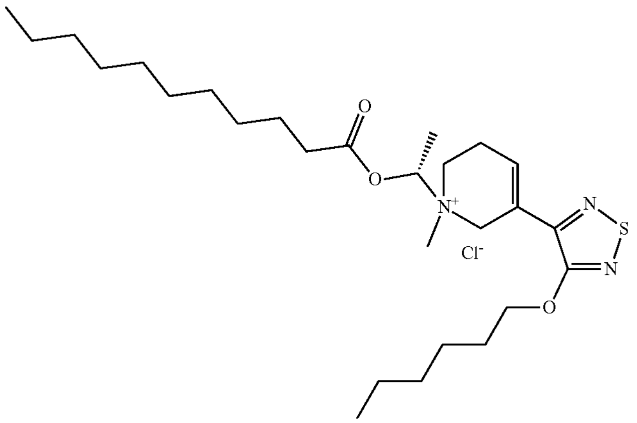 [SMILES: CCCCCCCCCCC(=O)O[C@H](C)[N+]1(C)CCC=C(c2nsnc2OCCCCCC)C1 ; [Cl-]] |
| 567 | 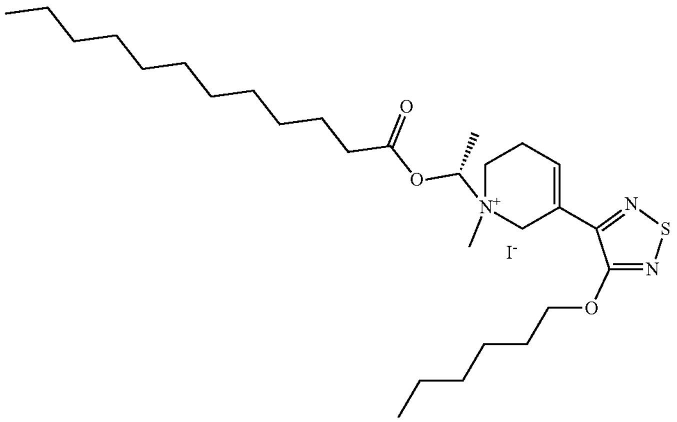 [SMILES: CCCCCCCCCCCC(=O)O[C@H](C)[N+]1(C)CCC=C(c2nsnc2OCCCCCC)C1 ; [I-]] |
| 568 | 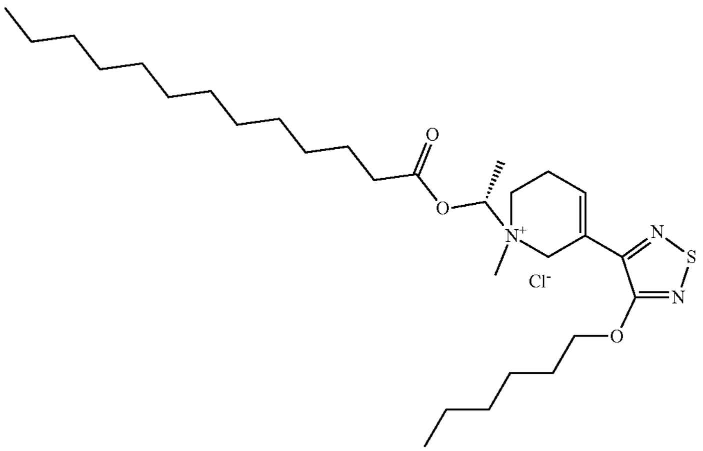 [SMILES: CCCCCCCCCCCCC(=O)O[C@H](C)[N+]1(C)CCC=C(c2nsnc2OCCCCCC)C1 ; [Cl-]] |

TABLE 1-continued
| Cpd No. | Structure |
| --- | --- |
| 569 | 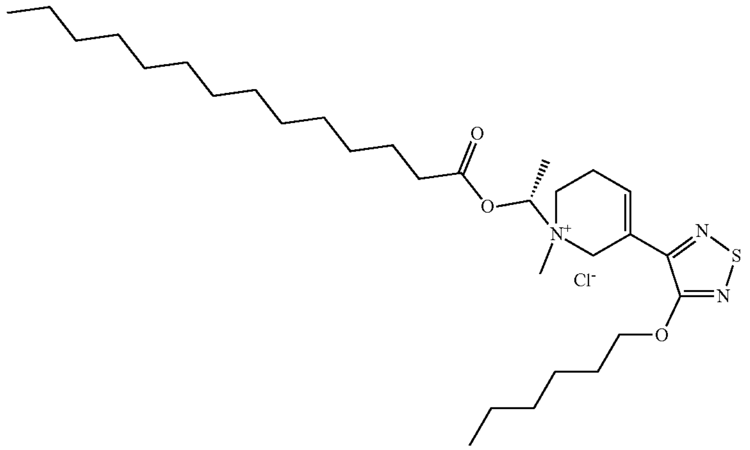 [SMILES: CCCCCCCCCCCCCC(=O)O[C@H](C)[N+]1(C)CCC=C(c2nsnc2OCCCCCC)C1 ; [Cl-]] |
| 570 | 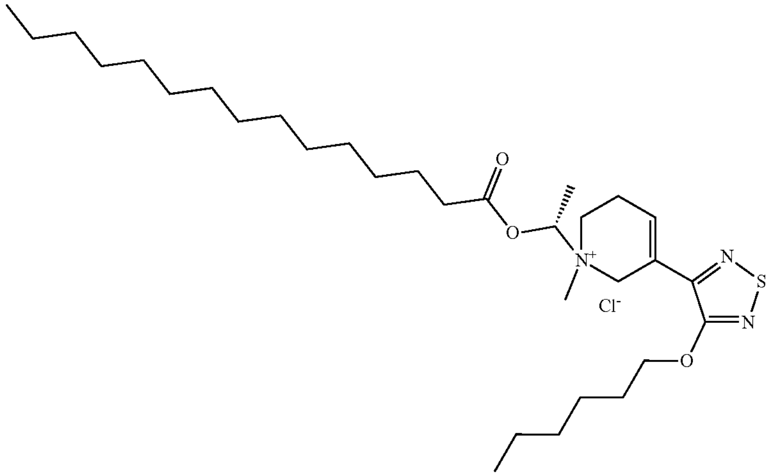 [SMILES: CCCCCCCCCCCCCCC(=O)O[C@H](C)[N+]1(C)CCC=C(c2nsnc2OCCCCCC)C1 ; [Cl-]] |
| 571 | 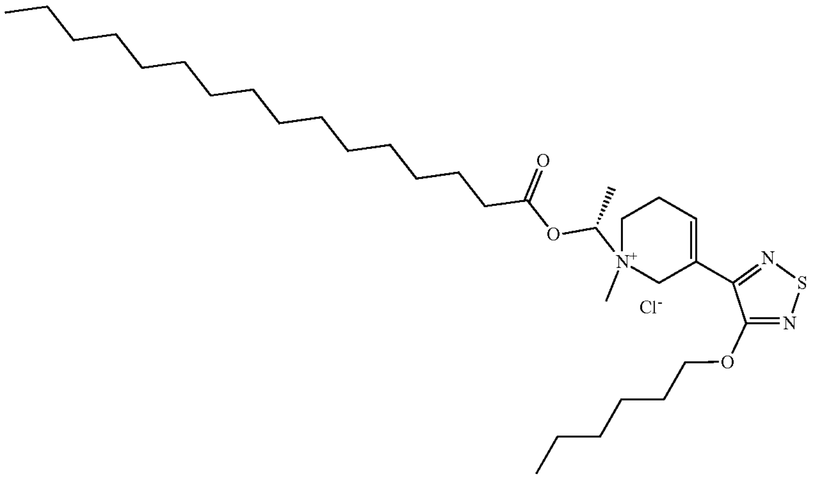 [SMILES: CCCCCCCCCCCCCCCC(=O)O[C@H](C)[N+]1(C)CCC=C(c2nsnc2OCCCCCC)C1 ; [Cl-]] |

TABLE 1-continued
| Cpd No. | Structure |
|---|---|
| 572 | 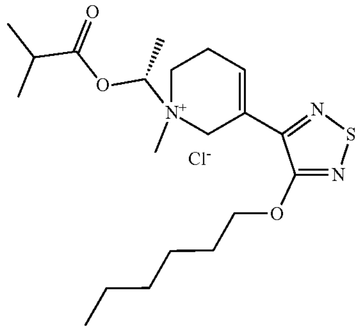 [SMILES: CCCCCCOc1nsnc1C1=CCC[N+](C)([C@@H](C)OC(=O)C(C)C)C1 ; [Cl-]] |
| 573 | 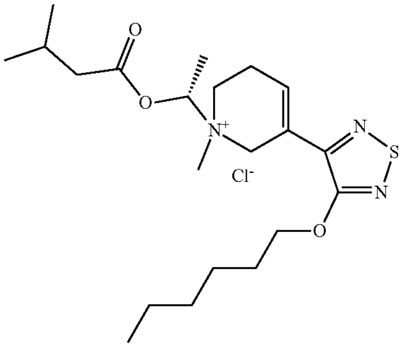 [SMILES: CCCCCCOc1nsnc1C1=CCC[N+](C)([C@@H](C)OC(=O)CC(C)C)C1 ; [Cl-]] |
| 574 | 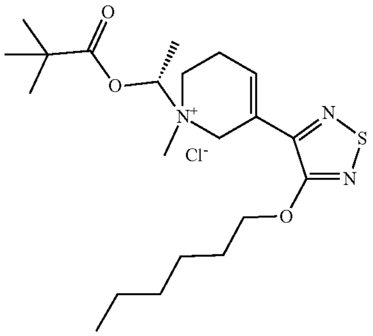 [SMILES: CCCCCCOc1nsnc1C1=CCC[N+](C)([C@@H](C)OC(=O)C(C)(C)C)C1 ; [Cl-]] |
| 575 | 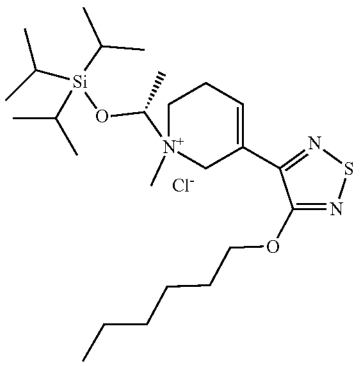 [SMILES: CCCCCCOc1nsnc1C1=CCC[N+](C)([C@@H](C)O[Si](C(C)C)(C(C)C)C(C)C)C1 ; [Cl-]] |

TABLE 1-continued
| Cpd No. | Structure |
| --- | --- |
| 576 | 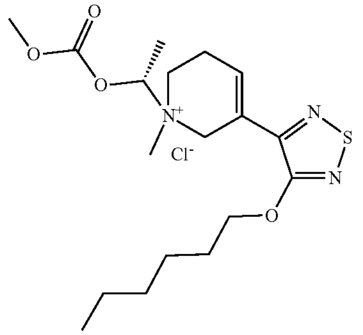 [SMILES: CCCCCCOc1nsnc1C1=CCC[N+](C)([C@@H](C)OC(=O)OC)C1 ; [Cl-]] |
| 577 | 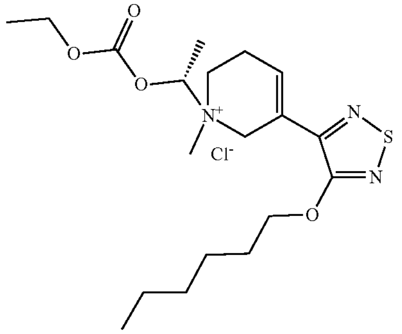 [SMILES: CCCCCCOc1nsnc1C1=CCC[N+](C)([C@@H](C)OC(=O)OCC)C1 ; [Cl-]] |
| 578 | 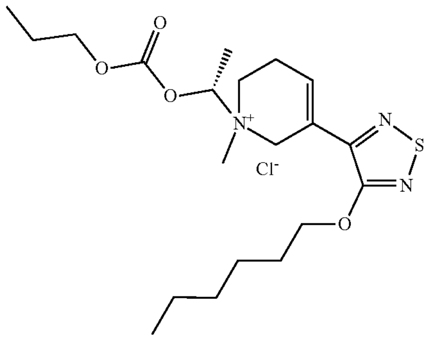 [SMILES: CCCCCCOc1nsnc1C1=CCC[N+](C)([C@@H](C)OC(=O)OCCC)C1 ; [Cl-]] |
| 579 | 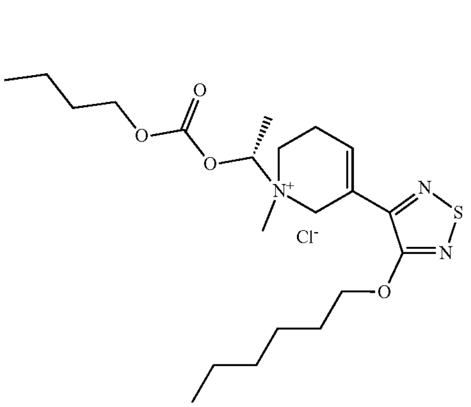 [SMILES: CCCCCCOc1nsnc1C1=CCC[N+](C)([C@@H](C)OC(=O)OCCCC)C1 ; [Cl-]] |

TABLE 1-continued
| Cpd No. | Structure |
|---|---|
| 580 | 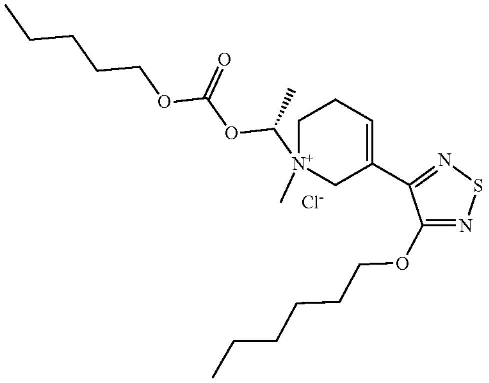 [SMILES: CCCCCCOc1nsnc1C1=CCC[N+](C)([C@@H](C)OC(=O)OCCCCC)C1 ; [Cl-]] |
| 581 | 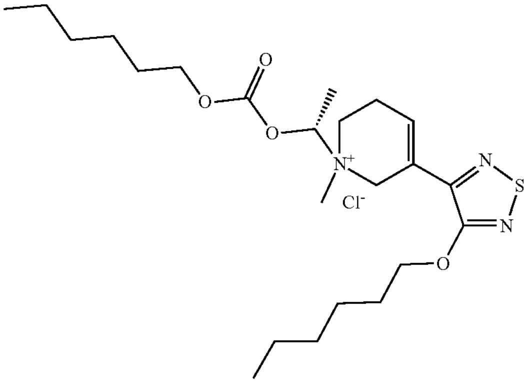 [SMILES: CCCCCCOC(=O)O[C@H](C)[N+]1(C)CCC=C(c2nsnc2OCCCCCC)C1 ; [Cl-]] |
| 582 | 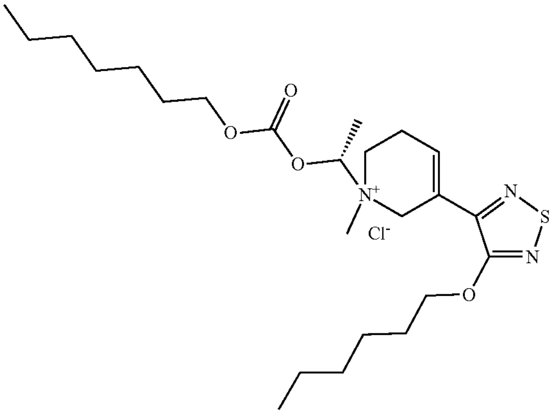 [SMILES: CCCCCCCOC(=O)O[C@H](C)[N+]1(C)CCC=C(c2nsnc2OCCCCCC)C1 ; [Cl-]] |
| 583 | 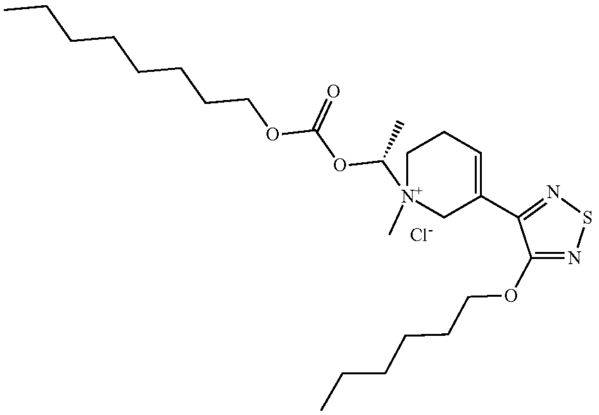 [SMILES: CCCCCCCCOC(=O)O[C@H](C)[N+]1(C)CCC=C(c2nsnc2OCCCCCC)C1 ; [Cl-]] |

TABLE 1-continued
| Cpd No. | Structure |
| --- | --- |
| 584 | 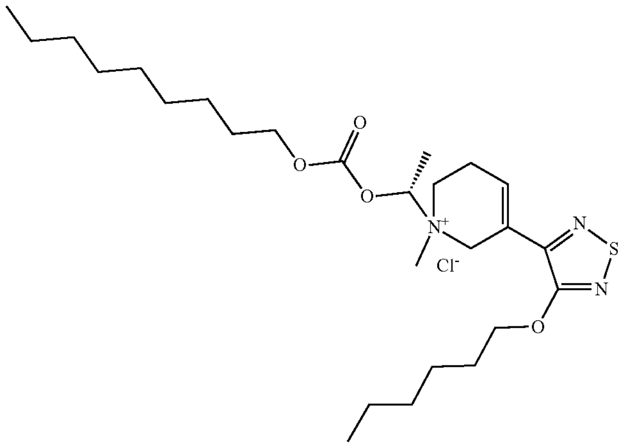 [SMILES: CCCCCCCCCOC(=O)O[C@H](C)[N+]1(C)CCC=C(c2nsnc2OCCCCCC)C1 ; [Cl-]] |
| 585 | 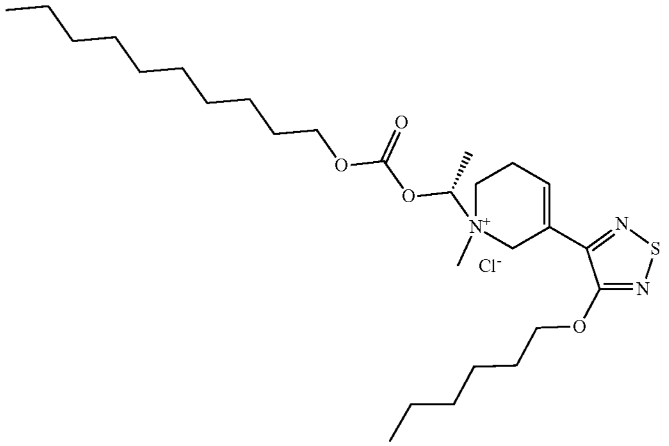 [SMILES: CCCCCCCCCCOC(=O)O[C@H](C)[N+]1(C)CCC=C(c2nsnc2OCCCCCC)C1 ; [Cl-]] |
| 586 | 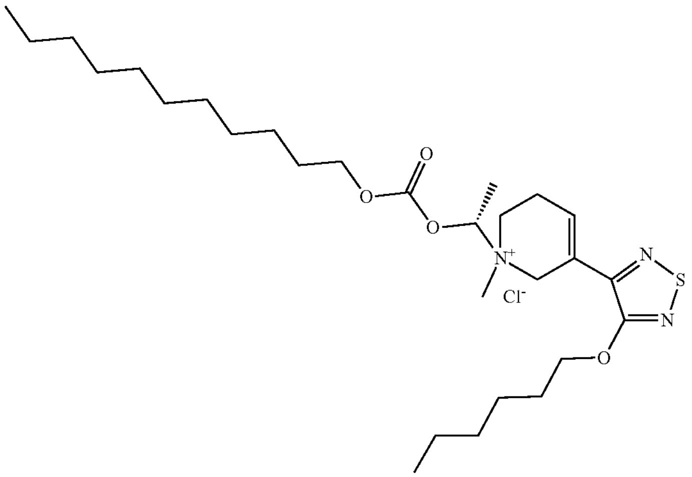 [SMILES: CCCCCCCCCCCOC(=O)O[C@H](C)[N+]1(C)CCC=C(c2nsnc2OCCCCCC)C1 ; [Cl-]] |

TABLE 1-continued
| Cpd No. | Structure |
|---|---|
| 587 | 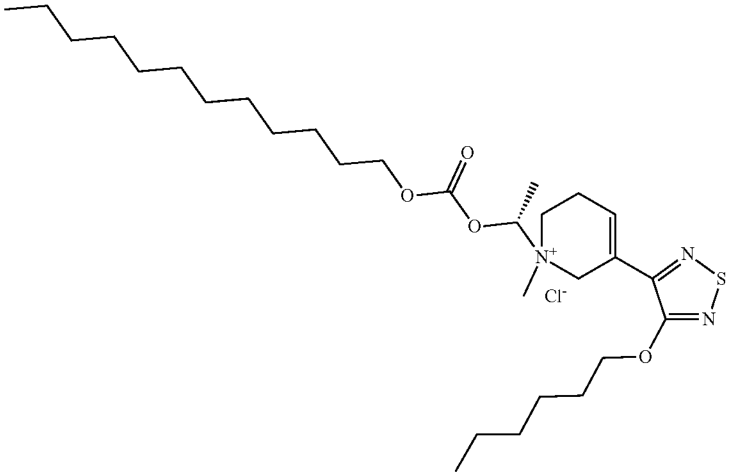 [SMILES: CCCCCCCCCCCCOC(=O)O[C@H](C)[N+]1(C)CCC=C(c2nsnc2OCCCCCC)C1 ; [Cl-]] |
| 588 | 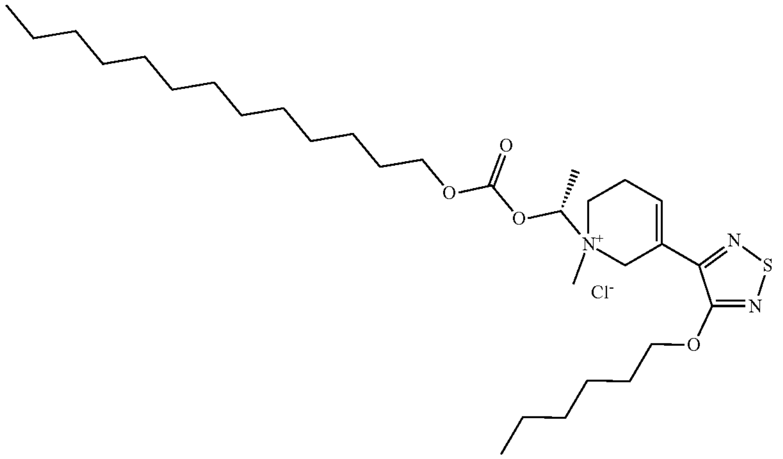 [SMILES: CCCCCCCCCCCCCOC(=O)O[C@H](C)[N+]1(C)CCC=C(c2nsnc2OCCCCCC)C1 ; [Cl-]] |
| 589 | 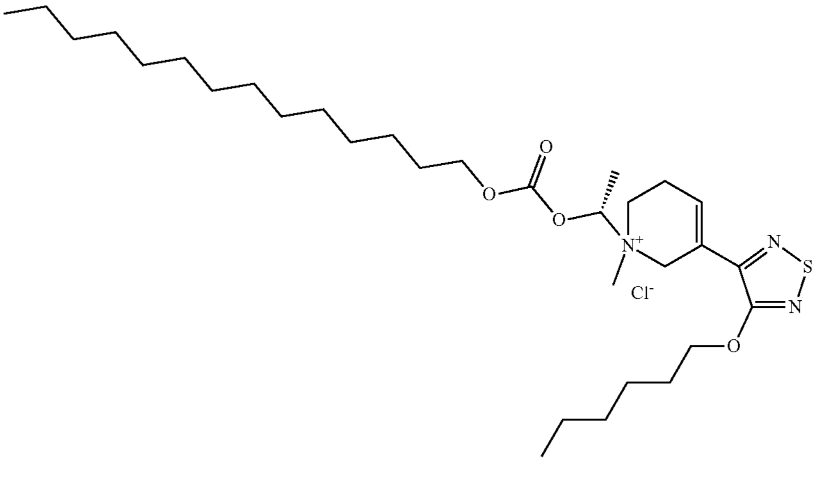 [SMILES: CCCCCCCCCCCCCCOC(=O)O[C@H](C)[N+]1(C)CCC=C(c2nsnc2OCCCCCC)C1 ; [Cl-]] |

TABLE 1-continued
| Cpd No. | Structure |
| --- | --- |
| 590 | 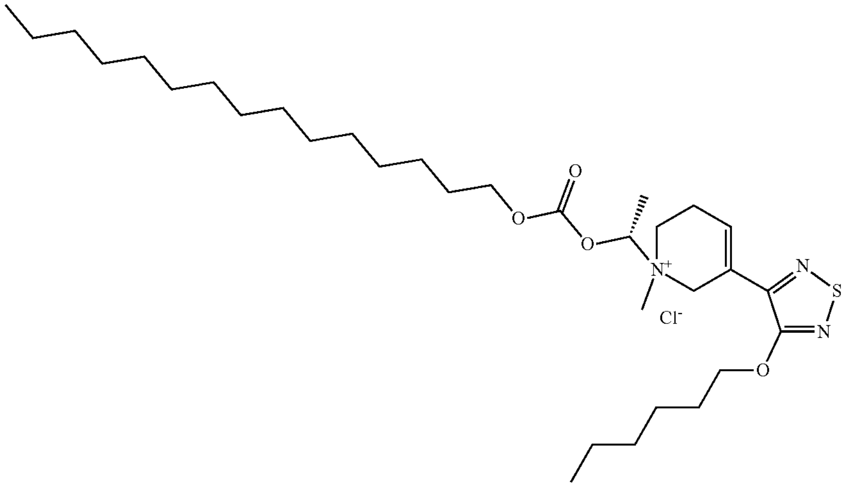 [SMILES: CCCCCCCCCCCCCCCOC(=O)O[C@H](C)[N+]1(C)CCC=C(c2nsnc2OCCCCCC)C1 ; [Cl-]] |
| 591 | 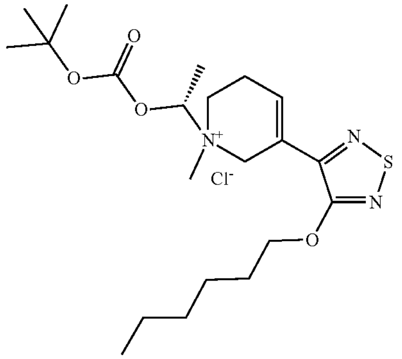 [SMILES: CCCCCCOc1nsnc1C1=CCC[N+](C)([C@@H](C)OC(=O)OC(C)(C)C)C1 ; [Cl-]] |
| 592 | 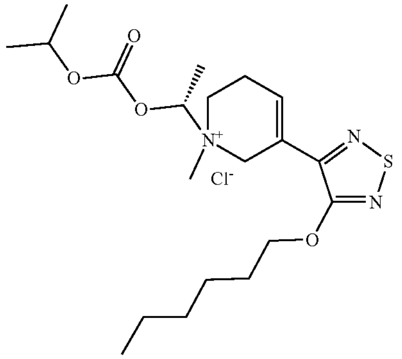 [SMILES: CCCCCCOc1nsnc1C1=CCC[N+](C)([C@@H](C)OC(=O)OC(C)C)C1 ; [Cl-]] |
| 593 | 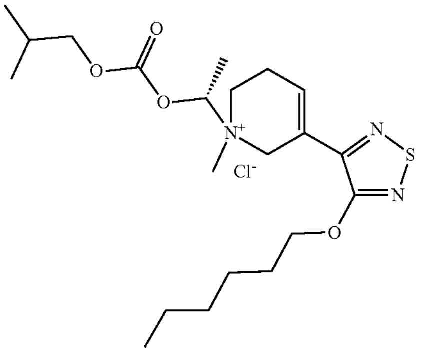 [SMILES: CCCCCCOc1nsnc1C1=CCC[N+](C)([C@@H](C)OC(=O)OCC(C)C)C1 ; [Cl-]] |

TABLE 1-continued
| Cpd No. | Structure |
|---|---|
| 594 | 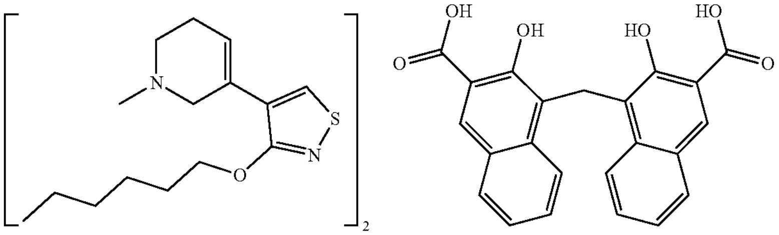 |
| 595 | 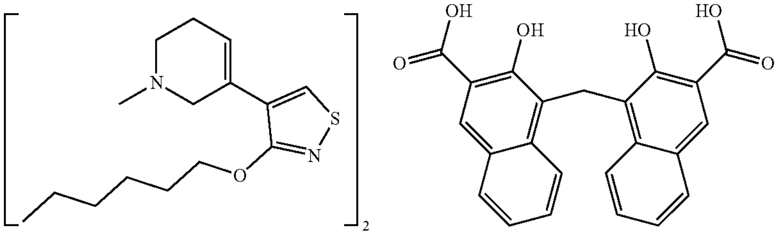 |
| 596 | 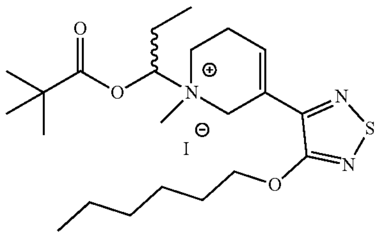 [SMILES: CCCCCCOc1nsnc1C1=CCC[N+](C)(C(CC)OC(=O)C(C)(C)C)C1 ; [I-]] |
| 597 | 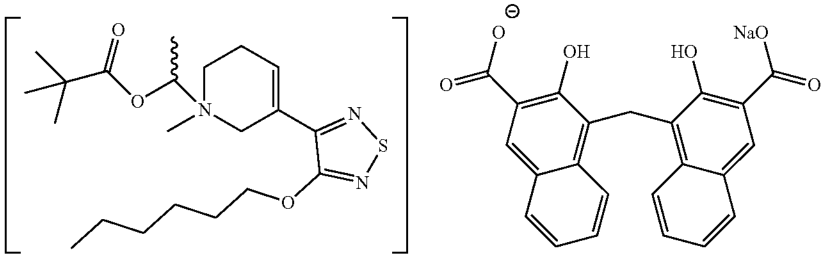 |
| 598 | 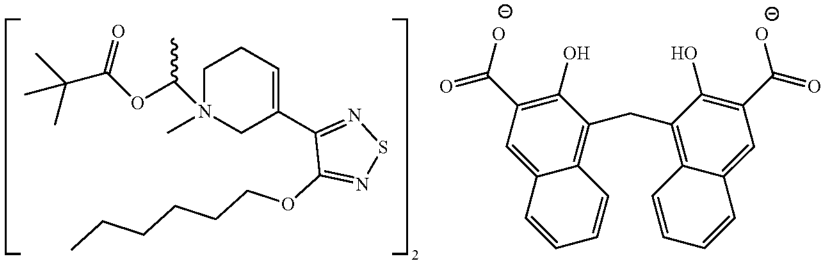 |
| 599 | 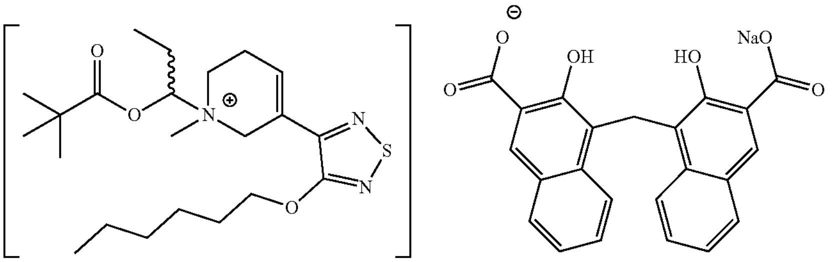 |

TABLE 1-continued
| Cpd No. | Structure |
| --- | --- |
| 600 | 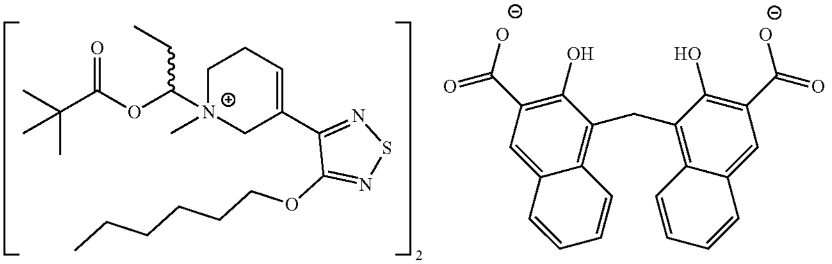 |
| 601 | 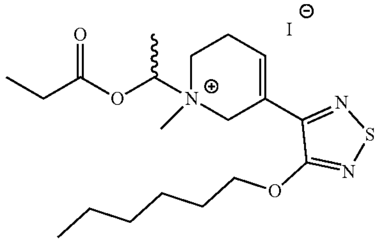 [SMILES: [I-] ; CCCCCCOc1nsnc1C1=CCC[N+](C)(C(C)OC(=O)CC)C1] |
| 602 | 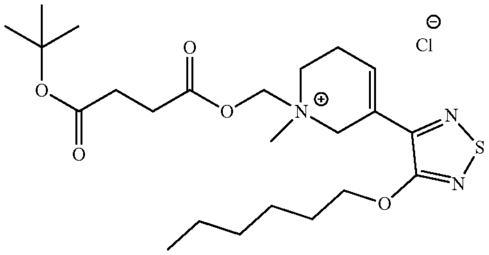 [SMILES: CCCCCCOc1nsnc1C1=CCC[N+](C)(COC(=O)CCC(=O)OC(C)(C)C)C1 ; [Cl-]] |
| 603 | 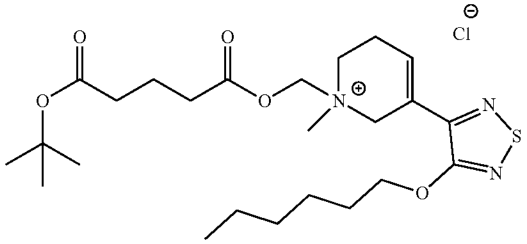 [SMILES: [Cl-] ; CCCCCCOc1nsnc1C1=CCC[N+](C)(COC(=O)CCCC(=O)OC(C)(C)C)C1] |
| 604 | 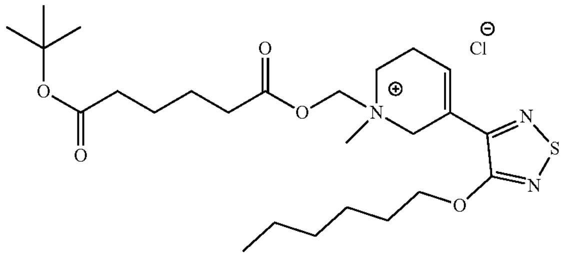 [SMILES: CCCCCCOc1nsnc1C1=CCC[N+](C)(COC(=O)CCCCC(=O)OC(C)(C)C)C1 ; [Cl-]] |
| 605 | 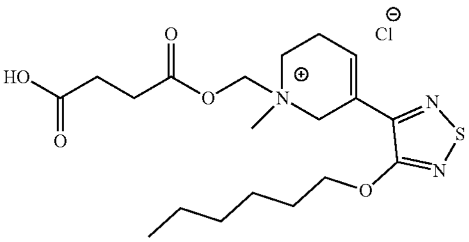 [SMILES: [Cl-] ; CCCCCCOc1nsnc1C1=CCC[N+](C)(COC(=O)CCC(=O)O)C1] |

TABLE 1-continued
| Cpd No. | Structure |
|---|---|
| 606 | 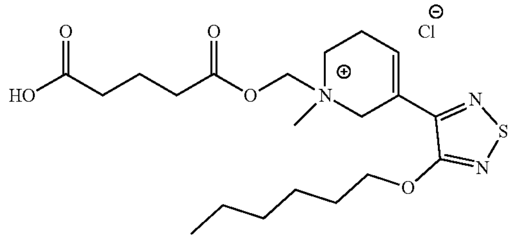 [SMILES: [Cl-] ; CCCCCCOc1nsnc1C1=CCC[N+](C)(COC(=O)CCCC(=O)O)C1] |
| 607 | 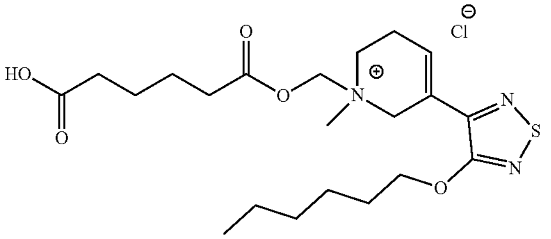 [SMILES: [Cl-] ; CCCCCCOc1nsnc1C1=CCC[N+](C)(COC(=O)CCCCC(=O)O)C1] |
| 608 | 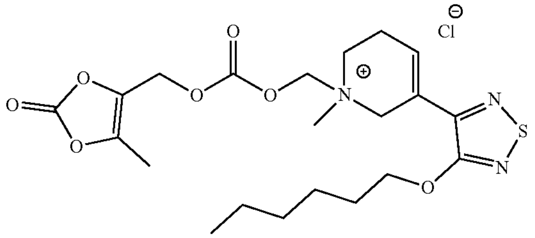 [SMILES: [Cl-] ; CCCCCCOc1nsnc1C1=CCC[N+](C)(COC(=O)OCc2oc(=O)oc2C)C1] |
| 609 | 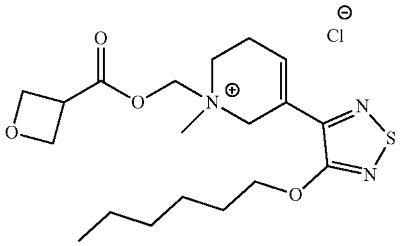 [SMILES: [Cl-] ; CCCCCCOc1nsnc1C1=CCC[N+](C)(COC(=O)C2COC2)C1] |
| 610 | 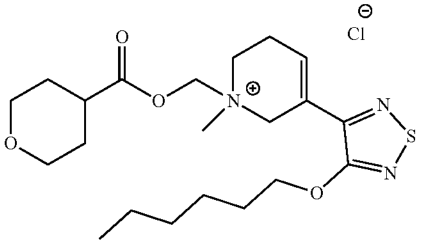 [SMILES: [Cl-] ; CCCCCCOc1nsnc1C1=CCC[N+](C)(COC(=O)C2CCOCC2)C1] |
| 611 | 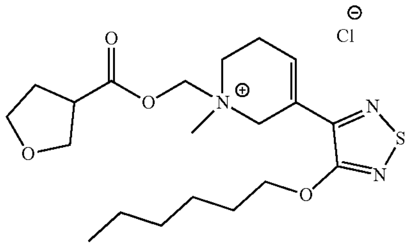 [SMILES: [Cl-] ; CCCCCCOc1nsnc1C1=CCC[N+](C)(COC(=O)C2CCOC2)C1] |

TABLE 1-continued
| Cpd No. | Structure |
| --- | --- |
| 612 | 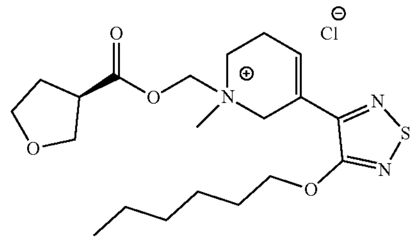 [SMILES: [Cl-] ; CCCCCCOc1nsnc1C1=CCC[N+](C)(COC(=O)[C@@H]2CCOC2)C1] |
| 613 | 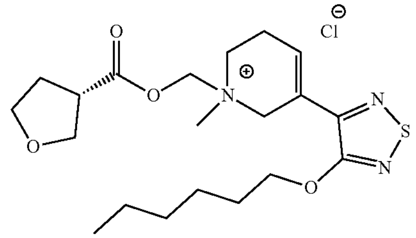 [SMILES: [Cl-] ; CCCCCCOc1nsnc1C1=CCC[N+](C)(COC(=O)[C@H]2CCOC2)C1] |
| 614 | 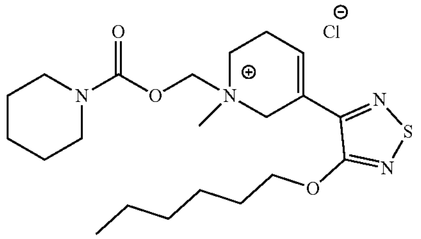 [SMILES: [Cl-] ; CCCCCCOc1nsnc1C1=CCC[N+](C)(COC(=O)N2CCCCC2)C1] |
| 615 | 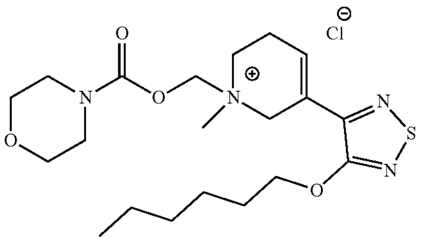 [SMILES: [Cl-] ; CCCCCCOc1nsnc1C1=CCC[N+](C)(COC(=O)N2CCOCC2)C1] |
| 616 | 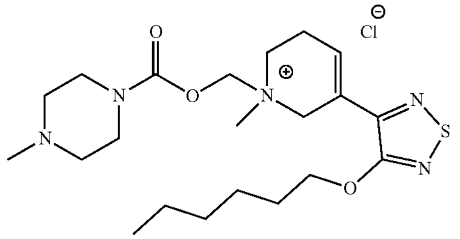 [SMILES: [Cl-] ; CCCCCCOc1nsnc1C1=CCC[N+](C)(COC(=O)N2CCN(C)CC2)C1] |
| 617 | 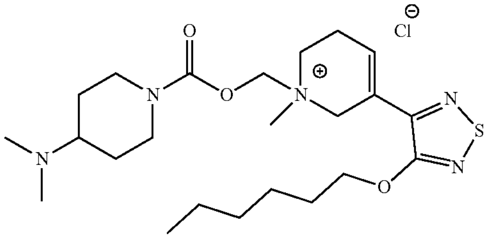 [SMILES: [Cl-] ; CCCCCCOc1nsnc1C1=CCC[N+](C)(COC(=O)N2CCC(N(C)C)CC2)C1] |

TABLE 1-continued
| Cpd No. | Structure |
|---|---|
| 618 | 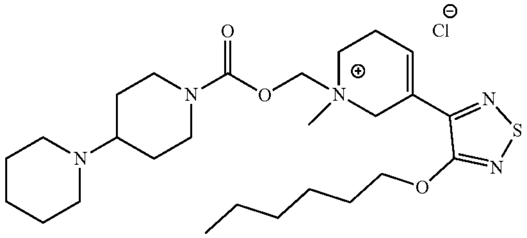 [SMILES: [Cl-] ; CCCCCCOc1nsnc1C1=CCC[N+](C)(COC(=O)N2CCC(N3CCCCC3)CC2)C1] |
| 619 | 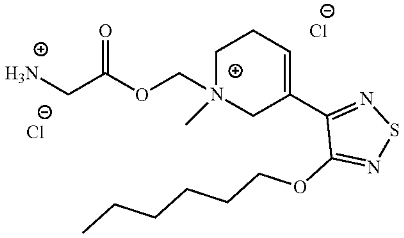 [SMILES: [Cl-] ; CCCCCCOc1nsnc1C1=CCC[N+](C)(COC(=O)C[NH3+])C1 ; [Cl-]] |
| 620 | 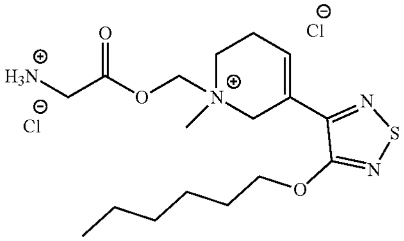 [SMILES: [Cl-] ; [Cl-] ; CCCCCCOc1nsnc1C1=CCC[N+](C)(COC(=O)C[NH3+])C1] |
| 621 | 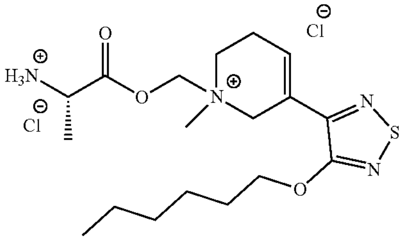 [SMILES: [Cl-] ; [Cl-] ; CCCCCCOc1nsnc1C1=CCC[N+](C)(COC(=O)[C@H](C)[NH3+])C1]<br>L-amino acid |
| 622 | 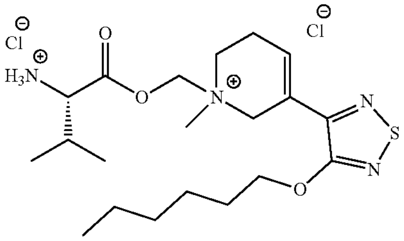 [SMILES: [Cl-] ; [Cl-] ; CCCCCCOc1nsnc1C1=CCC[N+](C)(COC(=O)[C@@H]([NH3+])C(C)C)C1]<br>L-amino acid |
| 623 | 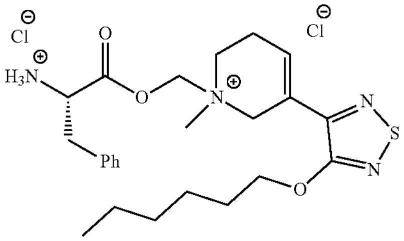 [SMILES: [Cl-] ; [Cl-] ; CCCCCCOc1nsnc1C1=CCC[N+](C)(COC(=O)[C@@H]([NH3+])Cc2ccccc2)C1] |

TABLE 1-continued
| Cpd No. | Structure |
|---|---|
| | L-amino acid |
| 624 | 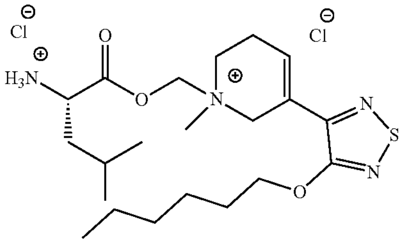 |
| | L-amino acid |
| 625 | 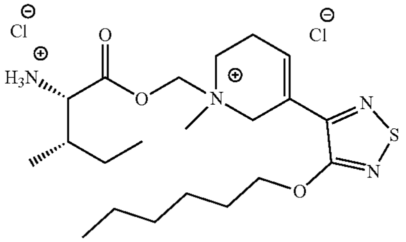 |
| | L-amino acid |
| 626 | 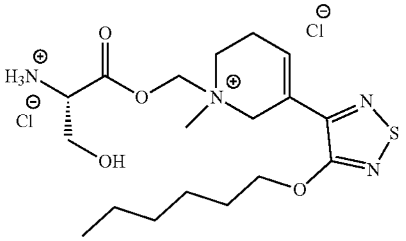 [SMILES: [Cl-] ; [Cl-] ; CCCCCCOc1nsnc1C1=CCC[N+](C)(COC(=O)[C@@H]([NH3+])CO)C1] |
| | L-amino acid |
| 627 | 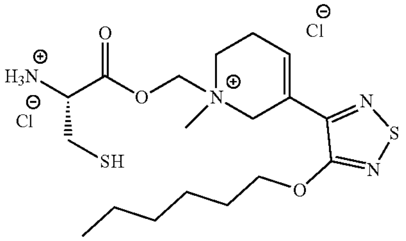 |
| | L-amino acid |
| 628 | 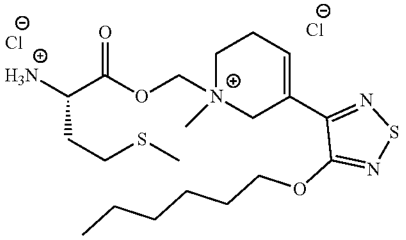 [SMILES: [Cl-] ; [Cl-] ; CCCCCCOc1nsnc1C1=CCC[N+](C)(COC(=O)[C@@H]([NH3+])CCSC)C1] |
| | L-amino acid |

TABLE 1-continued
| Cpd No. | Structure |
|---|---|
| 629 | 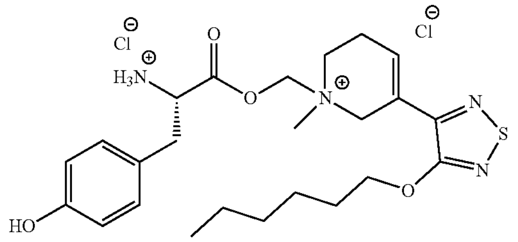 [SMILES: [Cl-] ; CCCCCCOc1nsnc1C1=CCC[N+](C)(COC(=O)[C@@H]([NH3+])Cc2ccc(O)cc2)C1 ; [Cl-]]<br>L-amino acid |
| 630 | 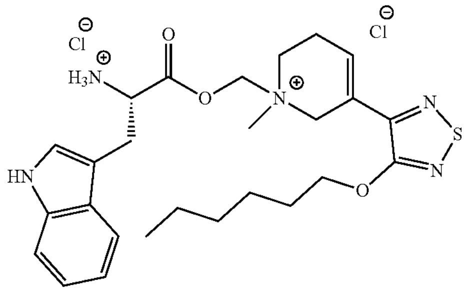 [SMILES: [Cl-] ; CCCCCCOc1nsnc1C1=CCC[N+](C)(COC(=O)[C@@H]([NH3+])Cc2c[nH]c3ccccc23)C1 ; [Cl-]]<br>L-amino acid |
| 631 | 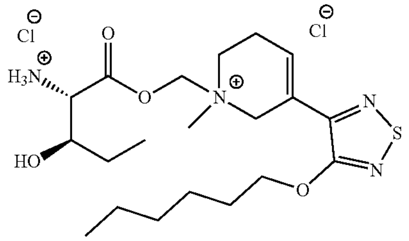 [SMILES: [Cl-] ; [Cl-] ; CCCCCCOc1nsnc1C1=CCC[N+](C)(COC(=O)[C@@H]([NH3+])[C@H](O)CC)C1]<br>L-amino acid |
| 632 | 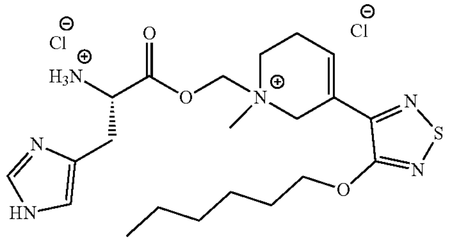 [SMILES: [Cl-] ; CCCCCCOc1nsnc1C1=CCC[N+](C)(COC(=O)[C@@H]([NH3+])Cc2c[nH]cn2)C1 ; [Cl-]]<br>L-amino acid |
| 633 | 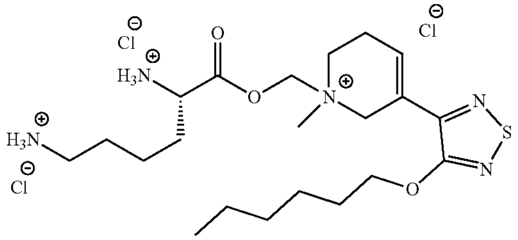 [SMILES: [Cl-] ; [Cl-] ; CCCCCCOc1nsnc1C1=CCC[N+](C)(COC(=O)[C@@H]([NH3+])CCCC[NH3+])C1 ; [Cl-]]<br>L-amino acid |

TABLE 1-continued
| Cpd No. | Structure |
|---|---|
| 634 | 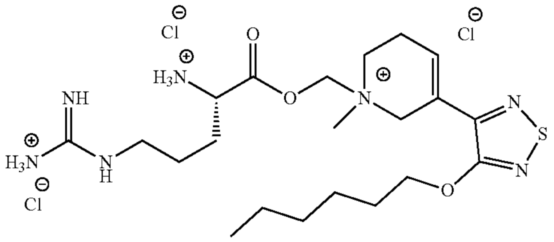 [SMILES: [Cl-] ; [Cl-] ; Cl ; CCCCCCOc1nsnc1C1=CCC[N+](C)(COC(=O)[C@@H]([NH3+])CCCNC(=N)[NH3+])C1] L-amino acid |
| 635 | 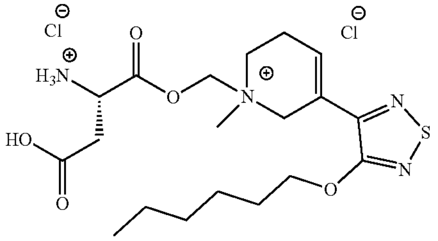 [SMILES: [Cl-] ; [Cl-] ; CCCCCCOc1nsnc1C1=CCC[N+](C)(COC(=O)[C@@H]([NH3+])CC(=O)O)C1] L-amino acid |
| 636 | 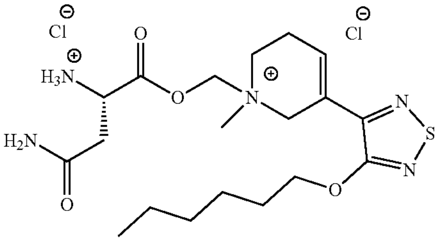 [SMILES: [Cl-] ; [Cl-] ; CCCCCCOc1nsnc1C1=CCC[N+](C)(COC(=O)[C@@H]([NH3+])CC(N)=O)C1] L-amino acid |
| 637 | 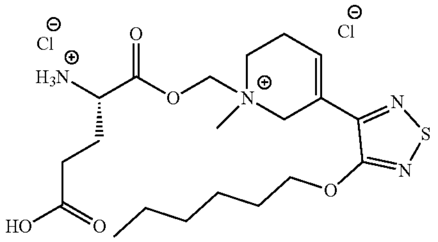 [SMILES: [Cl-] ; CCCCCCOc1nsnc1C1=CCC[N+](C)(COC(=O)[C@@H]([NH3+])CCC(=O)O)C1 ; [Cl-]] L-amino acid |
| 638 | 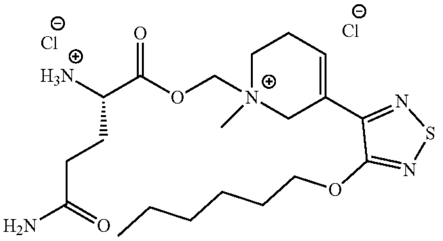 [SMILES: [Cl-] ; CCCCCCOc1nsnc1C1=CCC[N+](C)(COC(=O)[C@@H]([NH3+])CCC(N)=O)C1 ; [Cl-]] L-amino acid |

TABLE 1-continued
| Cpd No. | Structure |
| --- | --- |
| 639 | 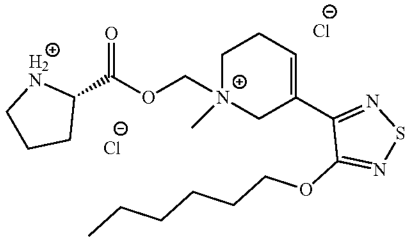<br>L-amino acid |
| 640 | 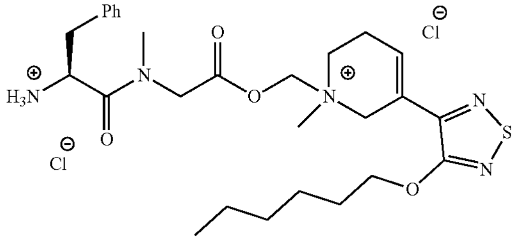 [SMILES: CCCCCCOc1nsnc1C1=CCC[N+](C)(COC(=O)CN(C)C(=O)[C@@H]([NH3+])Cc2ccccc2)C1 ; [Cl-] ; [Cl-]] |
| 641 | 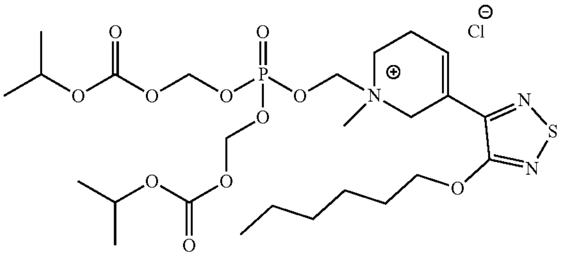 [SMILES: [Cl-] ; CCCCCCOc1nsnc1C1=CCC[N+](C)(COP(=O)(OCOC(=O)OC(C)C)OCOC(=O)OC(C)C)C1] |
| 642 | 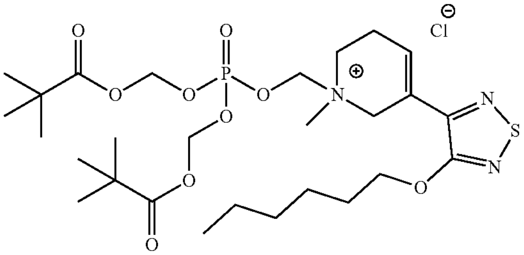 [SMILES: [Cl-] ; CCCCCCOc1nsnc1C1=CCC[N+](C)(COP(=O)(OCOC(=O)C(C)(C)C)OCOC(=O)C(C)(C)C)C1] |
| 643 | 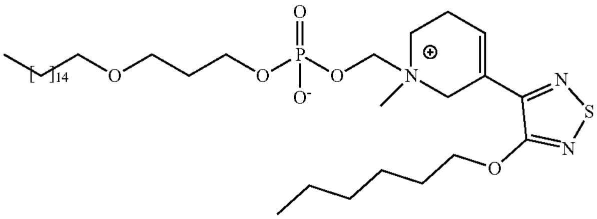 |
| 644 | 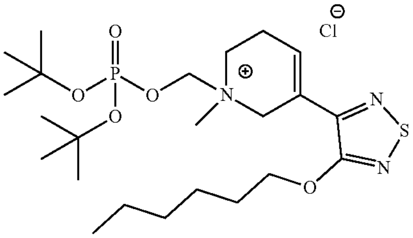 [SMILES: [Cl-] ; CCCCCCOc1nsnc1C1=CCC[N+](C)(COP(=O)(OC(C)(C)C)OC(C)(C)C)C1] |

TABLE 1-continued
| Cpd No. | Structure |
| --- | --- |
| 645 | 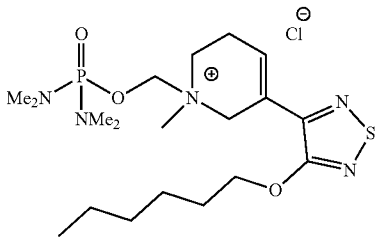 [SMILES: [Cl-] ; CCCCCCOc1nsnc1C1=CCC[N+](C)(COP(=O)(N(C)C)N(C)C)C1] |
| 646 | 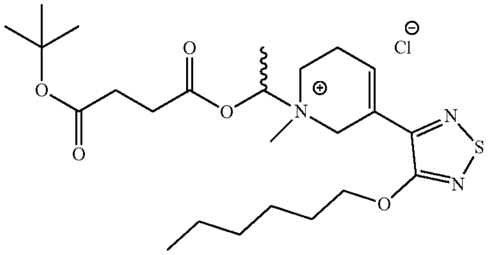 [SMILES: CCCCCCOc1nsnc1C1=CCC[N+](C)(C(C)OC(=O)CCC(=O)OC(C)(C)C)C1 ; [Cl-]] |
| 647 | 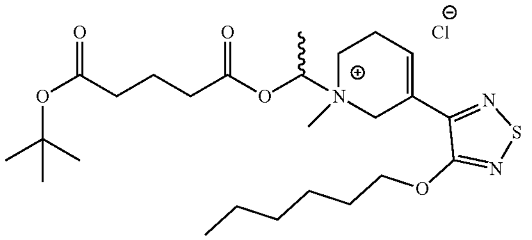 [SMILES: [Cl-] ; CCCCCCOc1nsnc1C1=CCC[N+](C)(C(C)OC(=O)CCCC(=O)OC(C)(C)C)C1] |
| 648 | 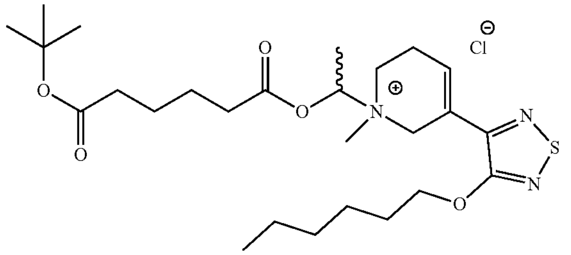 [SMILES: CCCCCCOc1nsnc1C1=CCC[N+](C)(C(C)OC(=O)CCCCC(=O)OC(C)(C)C)C1 ; [Cl-]] |
| 649 | 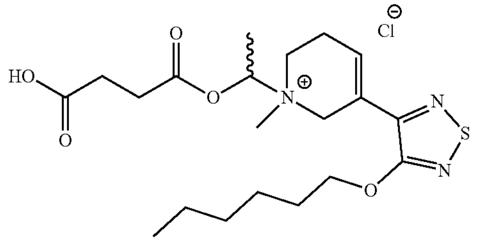 [SMILES: [Cl-] ; CCCCCCOc1nsnc1C1=CCC[N+](C)(C(C)OC(=O)CCC(=O)O)C1] |
| 650 | 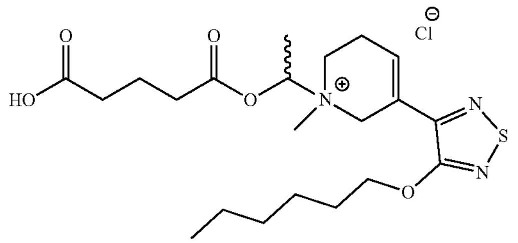 [SMILES: [Cl-] ; CCCCCCOc1nsnc1C1=CCC[N+](C)(C(C)OC(=O)CCCC(=O)O)C1] |

TABLE 1-continued
| Cpd No. | Structure |
| --- | --- |
| 651 | 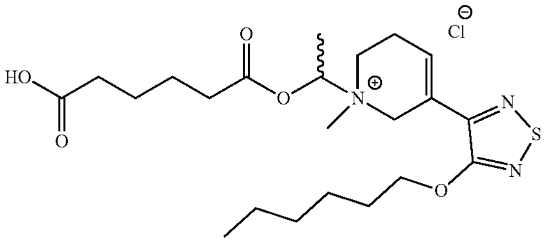 [SMILES: [Cl-] ; CCCCCCOc1nsnc1C1=CCC[N+](C)(C(C)OC(=O)CCCCC(=O)O)C1] |
| 652 | 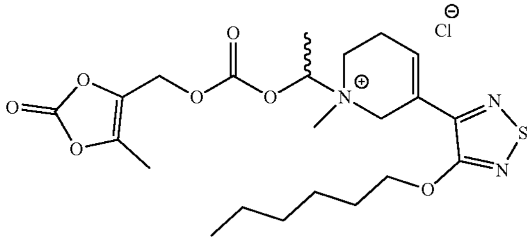 [SMILES: [Cl-] ; CCCCCCOc1nsnc1C1=CCC[N+](C)(C(C)OC(=O)OCc2oc(=O)oc2C)C1] |
| 653 | 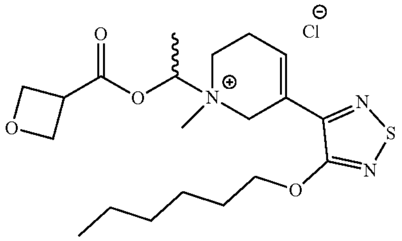 [SMILES: [Cl-] ; CCCCCCOc1nsnc1C1=CCC[N+](C)(C(C)OC(=O)C2COC2)C1] |
| 654 | 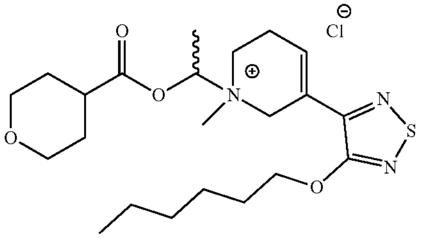 [SMILES: [Cl-] ; CCCCCCOc1nsnc1C1=CCC[N+](C)(C(C)OC(=O)C2CCOCC2)C1] |
| 655 | 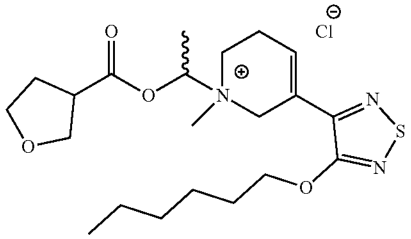 [SMILES: [Cl-] ; CCCCCCOc1nsnc1C1=CCC[N+](C)(C(C)OC(=O)C2CCOC2)C1] |
| 656 | 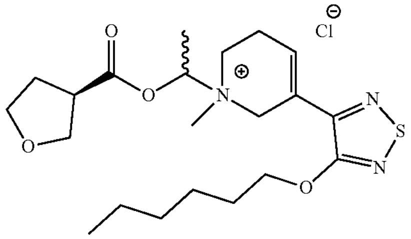 [SMILES: [Cl-] ; CCCCCCOc1nsnc1C1=CCC[N+](C)(C(C)OC(=O)[C@@H]2CCOC2)C1] |

TABLE 1-continued
| Cpd No. | Structure |
|---|---|
| 657 | 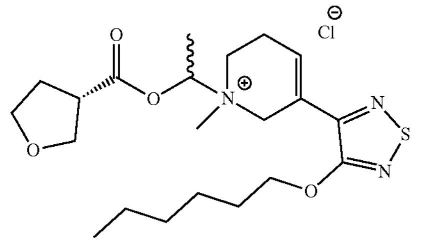 [SMILES: [Cl-] ; CCCCCCOc1nsnc1C1=CCC[N+](C)(C(C)OC(=O)[C@H]2CCOC2)C1] |
| 658 | 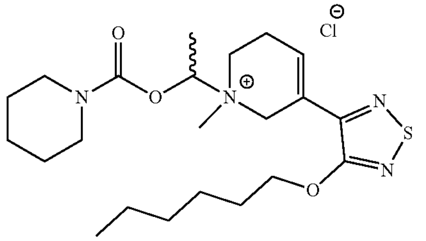 [SMILES: [Cl-] ; CCCCCCOc1nsnc1C1=CCC[N+](C)(C(C)OC(=O)N2CCCCC2)C1] |
| 659 | 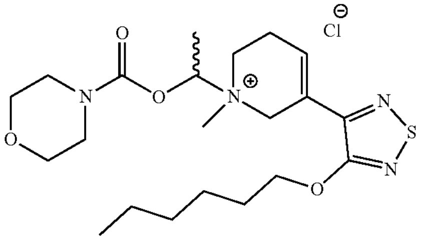 [SMILES: [Cl-] ; CCCCCCOc1nsnc1C1=CCC[N+](C)(C(C)OC(=O)N2CCOCC2)C1] |
| 660 | 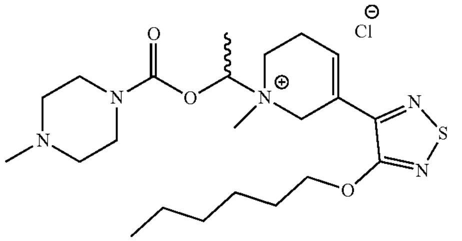 [SMILES: [Cl-] ; CCCCCCOc1nsnc1C1=CCC[N+](C)(C(C)OC(=O)N2CCN(C)CC2)C1] |
| 661 | 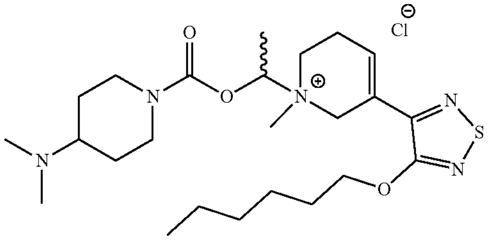 [SMILES: [Cl-] ; CCCCCCOc1nsnc1C1=CCC[N+](C)(C(C)OC(=O)N2CCC(N(C)C)CC2)C1] |
| 662 | 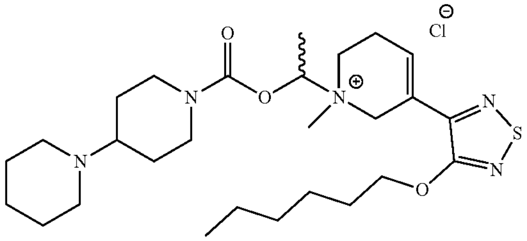 [SMILES: [Cl-] ; CCCCCCOc1nsnc1C1=CCC[N+](C)(C(C)OC(=O)N2CCC(N3CCCCC3)CC2)C1] |

TABLE 1-continued
| Cpd No. | Structure |
| --- | --- |
| 663 | 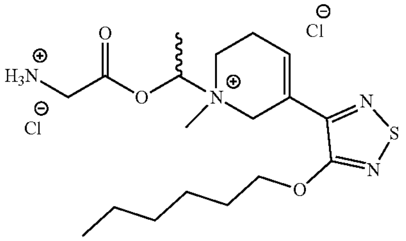 [SMILES: [Cl-] ; [Cl-] ; CCCCCCOc1nsnc1C1=CCC[N+](C)(C(C)OC(=O)C[NH3+])C1] |
| 664 | 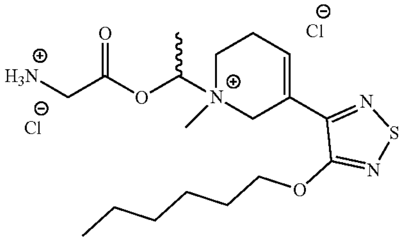 [SMILES: [Cl-] ; [Cl-] ; CCCCCCOc1nsnc1C1=CCC[N+](C)(C(C)OC(=O)C[NH3+])C1] |
| 665 | 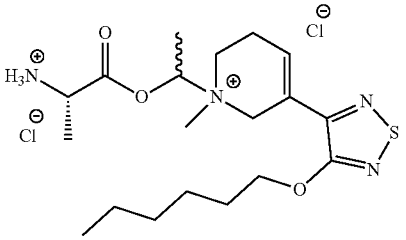 [SMILES: [Cl-] ; [Cl-] ; CCCCCCOc1nsnc1C1=CCC[N+](C)(C(C)OC(=O)[C@H](C)[NH3+])C1] L-amino acid |
| 666 | 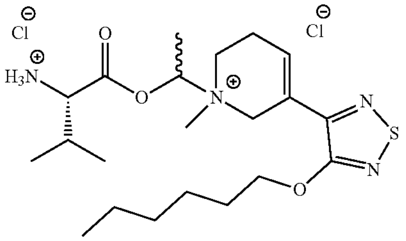 [SMILES: [Cl-] ; [Cl-] ; CCCCCCOc1nsnc1C1=CCC[N+](C)(C(C)OC(=O)[C@@H]([NH3+])C(C)C)C1] L-amino acid |
| 667 | 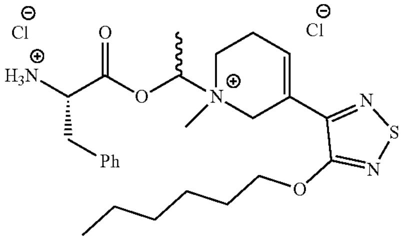 [SMILES: [Cl-] ; [Cl-] ; CCCCCCOc1nsnc1C1=CCC[N+](C)(C(C)OC(=O)[C@@H]([NH3+])Cc2ccccc2)C1] L-amino acid |

TABLE 1-continued
| Cpd No. | Structure |
|---|---|
| 668 | 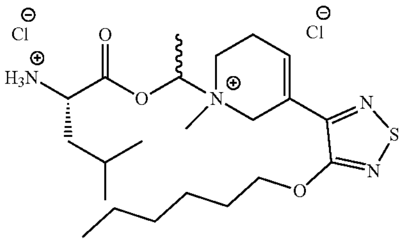 [SMILES: [Cl-] ; [Cl-] ; CCCCCCOc1nsnc1C1=CCC[N+](C)(C(C)OC(=O)[C@@H]([NH3+])CC(C)C)C1]<br>L-amino acid |
| 669 | 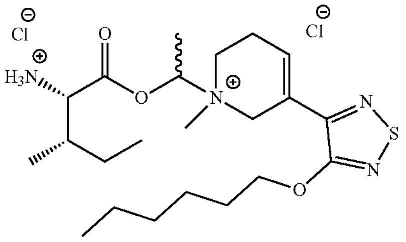 [SMILES: [Cl-] ; [Cl-] ; CCCCCCOc1nsnc1C1=CCC[N+](C)(C(C)OC(=O)[C@@H]([NH3+])[C@@H](C)CC)C1]<br>L-amino acid |
| 670 | 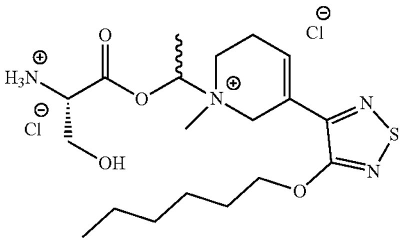 [SMILES: [Cl-] ; [Cl-] ; CCCCCCOc1nsnc1C1=CCC[N+](C)(C(C)OC(=O)[C@@H]([NH3+])CO)C1]<br>L-amino acid |
| 671 | 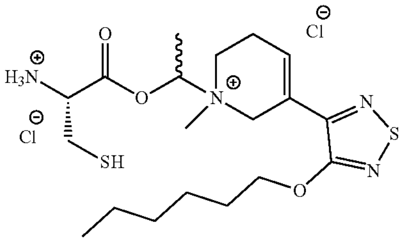 [SMILES: [Cl-] ; [Cl-] ; CCCCCCOc1nsnc1C1=CCC[N+](C)(C(C)OC(=O)[C@@H]([NH3+])CS)C1]<br>L-amino acid |
| 672 | 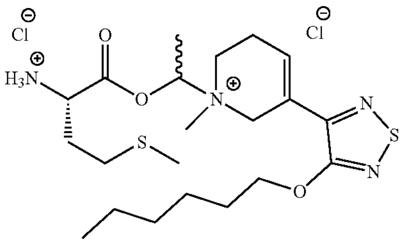 [SMILES: [Cl-] ; [Cl-] ; CCCCCCOc1nsnc1C1=CCC[N+](C)(C(C)OC(=O)[C@@H]([NH3+])CCSC)C1]<br>L-amino acid |

TABLE 1-continued
| Cpd No. | Structure |
| --- | --- |
| 673 | 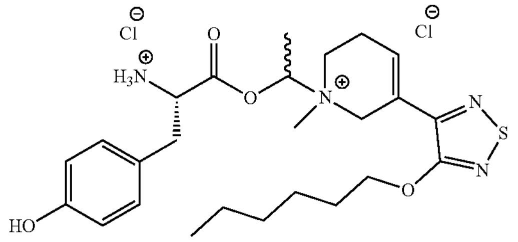 [SMILES: [Cl-] ; [Cl-] ; CCCCCCOc1nsnc1C1=CCC[N+](C)(C(C)OC(=O)[C@@H]([NH3+])Cc2ccc(O)cc2)C1]<br>L-amino acid |
| 674 | 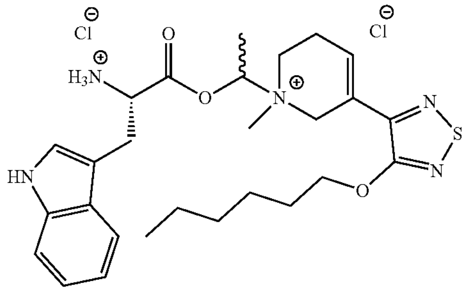 [SMILES: [Cl-] ; [Cl-] ; CCCCCCOc1nsnc1C1=CCC[N+](C)(C(C)OC(=O)[C@@H]([NH3+])Cc2c[nH]c3ccccc23)C1]<br>L-amino acid |
| 675 | 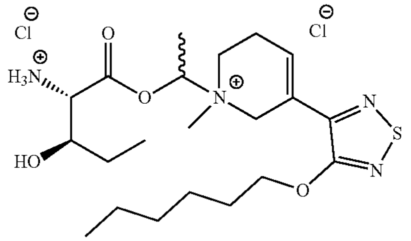 [SMILES: [Cl-] ; [Cl-] ; CCCCCCOc1nsnc1C1=CCC[N+](C)(C(C)OC(=O)[C@@H]([NH3+])[C@H](O)CC)C1]<br>L-amino acid |
| 676 | 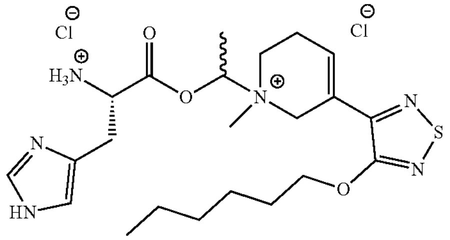 [SMILES: [Cl-] ; [Cl-] ; CCCCCCOc1nsnc1C1=CCC[N+](C)(C(C)OC(=O)[C@@H]([NH3+])Cc2c[nH]cn2)C1]<br>L-amino acid |
| 677 | 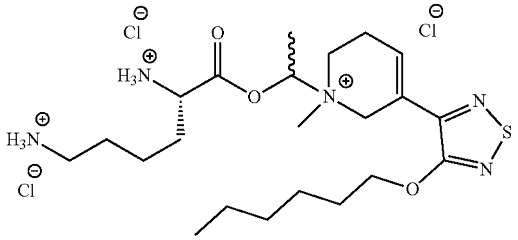 [SMILES: [Cl-] ; [Cl-] ; [Cl-] ; CCCCCCOc1nsnc1C1=CCC[N+](C)(C(C)OC(=O)[C@@H]([NH3+])CCCC[NH3+])C1]<br>L-amino acid |

TABLE 1-continued
| Cpd No. | Structure |
| --- | --- |
| 678 | 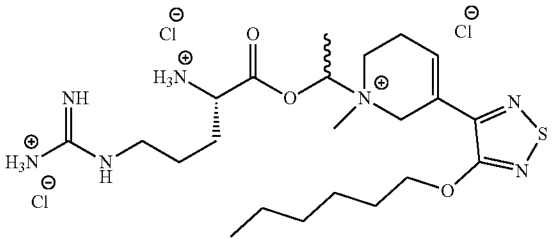 [SMILES: [Cl-] ; [Cl-] ; CCCCCCOc1nsnc1C1=CCC[N+](C)(C(C)OC(=O)[C@@H]([NH3+])CCCNC(=N)[NH3+])C1 ; [Cl-]]<br>L-amino acid |
| 679 | 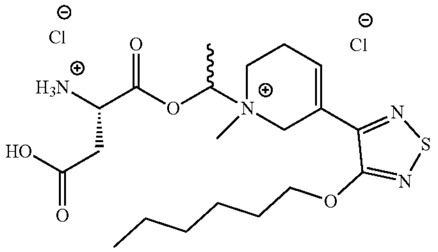 [SMILES: [Cl-] ; CCCCCCOc1nsnc1C1=CCC[N+](C)(C(C)OC(=O)[C@@H]([NH3+])CC(=O)O)C1 ; [Cl-]]<br>L-amino acid |
| 680 | 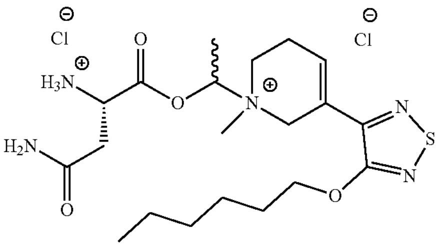 [SMILES: [Cl-] ; CCCCCCOc1nsnc1C1=CCC[N+](C)(C(C)OC(=O)[C@@H]([NH3+])CC(N)=O)C1 ; [Cl-]]<br>L-amino acid |
| 681 | 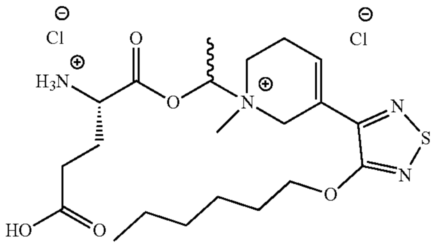 [SMILES: [Cl-] ; CCCCCCOc1nsnc1C1=CCC[N+](C)(C(C)OC(=O)[C@@H]([NH3+])CCC(=O)O)C1 ; [Cl-]]<br>L-amino acid |
| 682 | 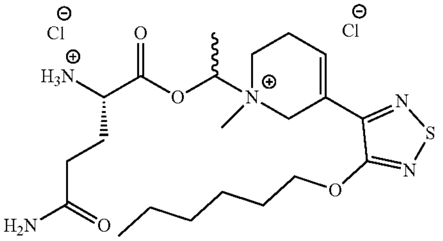 [SMILES: [Cl-] ; [Cl-] ; CCCCCCOc1nsnc1C1=CCC[N+](C)(C(C)OC(=O)[C@@H]([NH3+])CCC(N)=O)C1]<br>L-amino acid |

TABLE 1-continued
| Cpd No. | Structure |
| --- | --- |
| 683 | 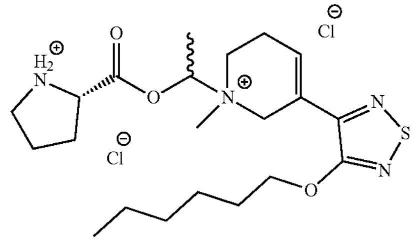<br>L-amino acid |
| 684 | 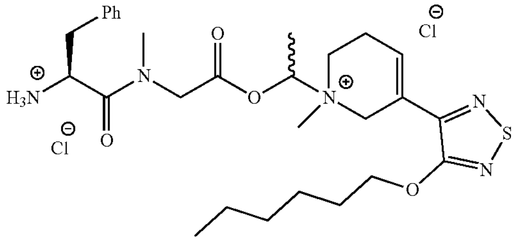 [SMILES: CCCCCCOc1nsnc1C1=CCC[N+](C)(C(C)OC(=O)CN(C)C(=O)[C@@H]([NH3+])Cc2ccccc2)C1 ; [Cl-] ; [Cl-]] |
| 685 | 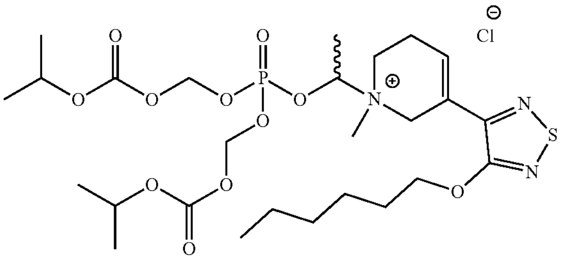 [SMILES: CCCCCCOc1nsnc1C1=CCC[N+](C)(C(C)OP(=O)(OCOC(=O)OC(C)C)OCOC(=O)OC(C)C)C1 ; [Cl-]] |
| 686 | 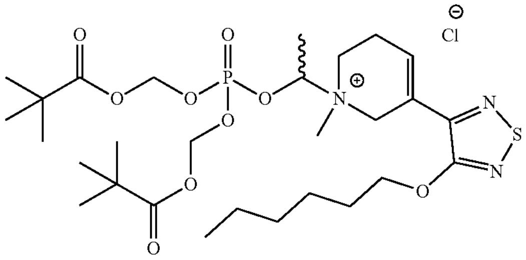 [SMILES: CCCCCCOc1nsnc1C1=CCC[N+](C)(C(C)OP(=O)(OCOC(=O)C(C)(C)C)OCOC(=O)C(C)(C)C)C1 ; [Cl-]] |
| 687 | 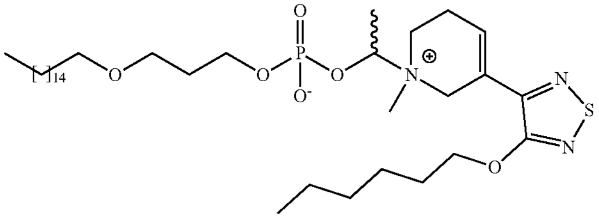 [SMILES: CCCCCCOc1nsnc1C1=CCC[N+](C)(C(C)OP(=O)([O-])OCCCOCCC)C1] |
| 688 | 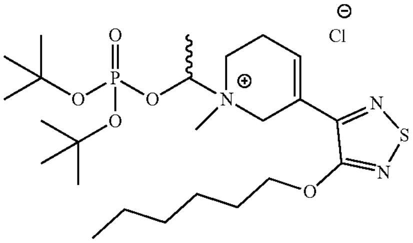 [SMILES: CCCCCCOc1nsnc1C1=CCC[N+](C)(C(C)OP(=O)(OC(C)(C)C)OC(C)(C)C)C1 ; [Cl-]] |

TABLE 1-continued
| Cpd No. | Structure |
| --- | --- |
| 689 | 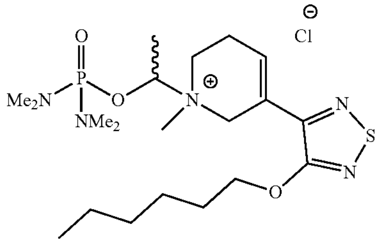 [SMILES: CCCCCCOc1nsnc1C1=CCC[N+](C)(C(C)OP(=O)(N(C)C)N(C)C)C1 ; [Cl-]] |
| 690 | 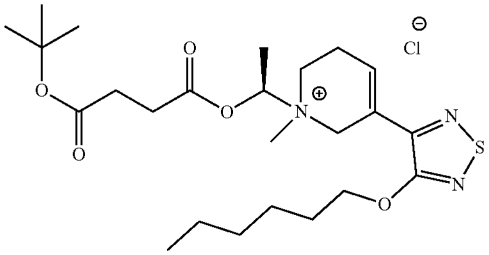 [SMILES: CCCCCCOc1nsnc1C1=CCC[N+](C)([C@H](C)OC(=O)CCC(=O)OC(C)(C)C)C1 ; [Cl-]] |
| 691 | 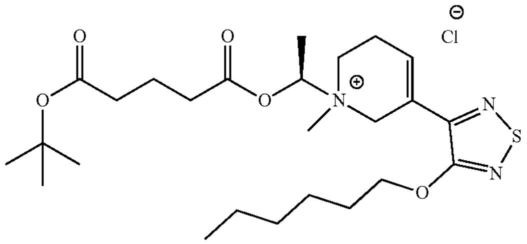 [SMILES: CCCCCCOc1nsnc1C1=CCC[N+](C)([C@H](C)OC(=O)CCCC(=O)OC(C)(C)C)C1 ; [Cl-]] |
| 692 | 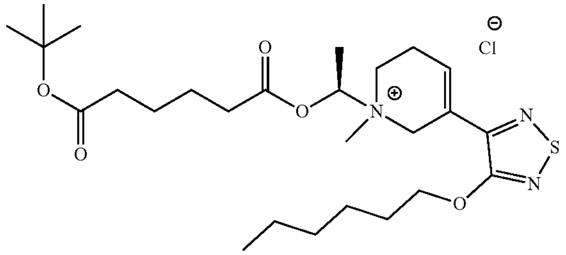 [SMILES: CCCCCCOc1nsnc1C1=CCC[N+](C)([C@H](C)OC(=O)CCCCC(=O)OC(C)(C)C)C1 ; [Cl-]] |
| 693 | 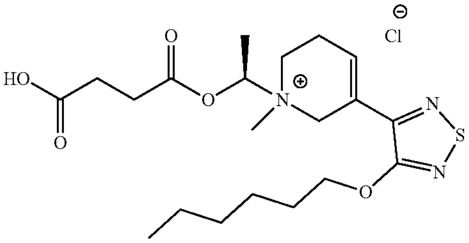 [SMILES: CCCCCCOc1nsnc1C1=CCC[N+](C)([C@H](C)OC(=O)CCC(=O)O)C1 ; [Cl-]] |
| 694 | 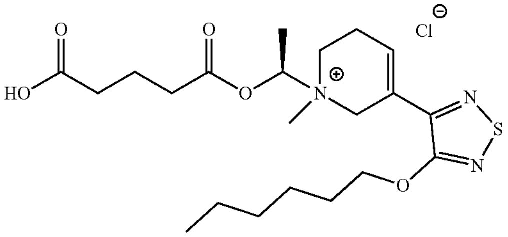 [SMILES: CCCCCCOc1nsnc1C1=CCC[N+](C)([C@H](C)OC(=O)CCCC(=O)O)C1 ; [Cl-]] |

TABLE 1-continued
| Cpd No. | Structure |
|---|---|
| 695 | 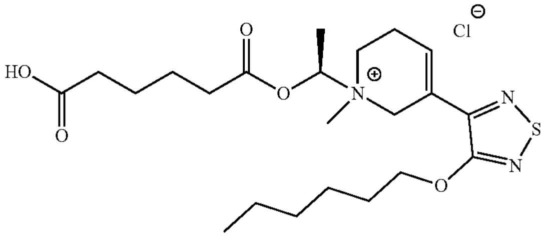 [SMILES: CCCCCCOc1nsnc1C1=CCC[N+](C)([C@H](C)OC(=O)CCCCC(=O)O)C1 ; [Cl-]] |
| 696 | 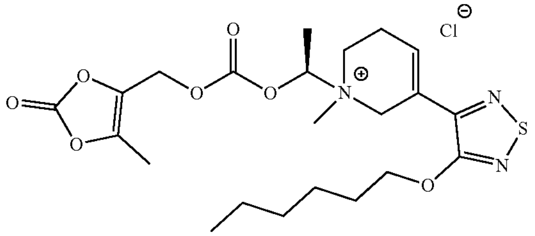 [SMILES: CCCCCCOc1nsnc1C1=CCC[N+](C)([C@H](C)OC(=O)OCc2oc(=O)oc2C)C1 ; [Cl-]] |
| 697 | 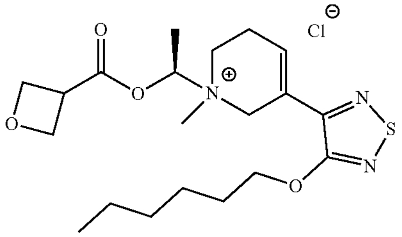 [SMILES: CCCCCCOc1nsnc1C1=CCC[N+](C)([C@H](C)OC(=O)C2COC2)C1 ; [Cl-]] |
| 698 | 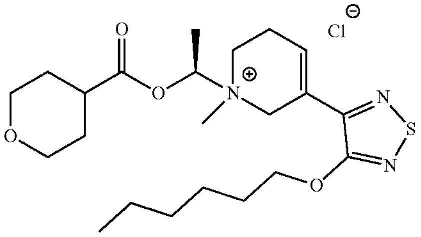 [SMILES: CCCCCCOc1nsnc1C1=CCC[N+](C)([C@H](C)OC(=O)C2CCOCC2)C1 ; [Cl-]] |
| 699 | 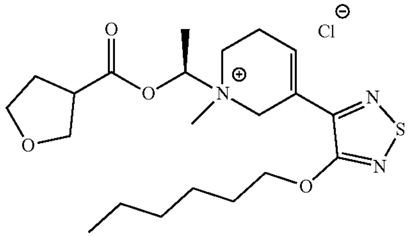 [SMILES: CCCCCCOc1nsnc1C1=CCC[N+](C)([C@H](C)OC(=O)C2CCOC2)C1 ; [Cl-]] |
| 700 | 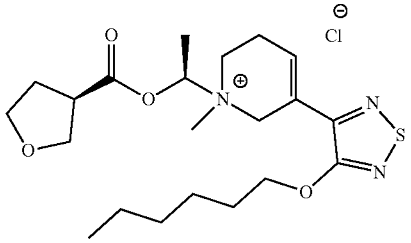 [SMILES: CCCCCCOc1nsnc1C1=CCC[N+](C)([C@H](C)OC(=O)[C@@H]2CCOC2)C1 ; [Cl-]] |

TABLE 1-continued
| Cpd No. | Structure |
|---|---|
| 701 | 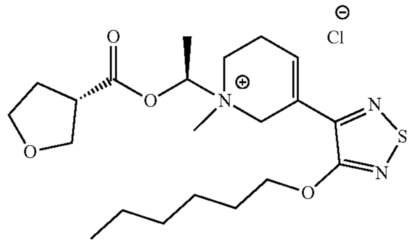 [SMILES: CCCCCCOc1nsnc1C1=CCC[N+](C)([C@H](C)OC(=O)[C@H]2CCOC2)C1 ; [Cl-]] |
| 702 | 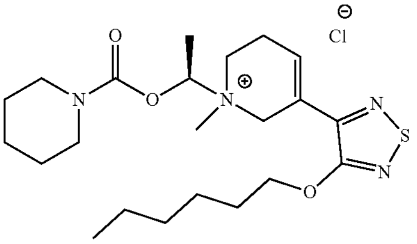 [SMILES: CCCCCCOc1nsnc1C1=CCC[N+](C)([C@H](C)OC(=O)N2CCCCC2)C1 ; [Cl-]] |
| 703 | 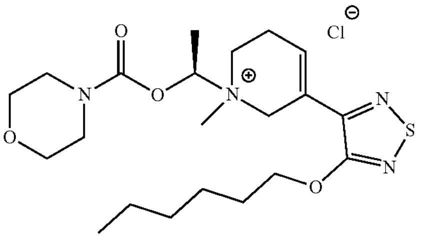 |
| 704 | 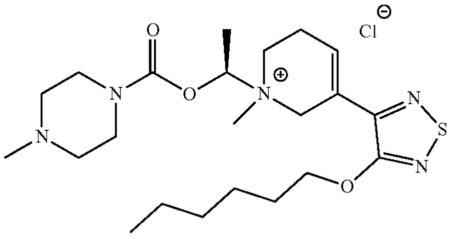 [SMILES: CCCCCCOc1nsnc1C1=CCC[N+](C)([C@H](C)OC(=O)N2CCN(C)CC2)C1 ; [Cl-]] |
| 705 | 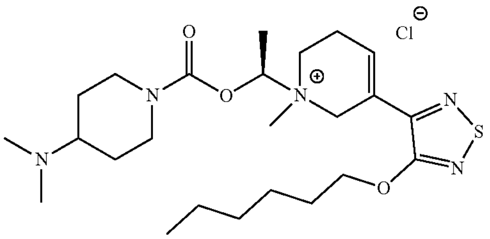 [SMILES: CCCCCCOc1nsnc1C1=CCC[N+](C)([C@H](C)OC(=O)N2CCC(N(C)C)CC2)C1 ; [Cl-]] |
| 706 | 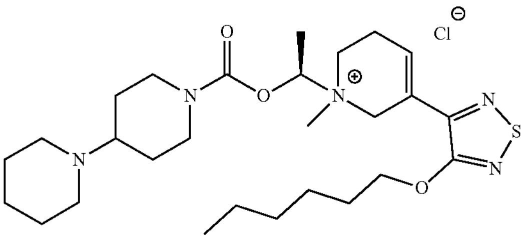 [SMILES: CCCCCCOc1nsnc1C1=CCC[N+](C)([C@H](C)OC(=O)N2CCC(N3CCCCC3)CC2)C1 ; [Cl-]] |

TABLE 1-continued
| Cpd No. | Structure |
|---|---|
| 707 | 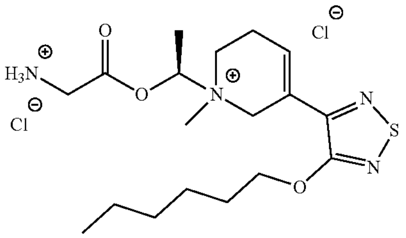 [SMILES: [Cl-] ; CCCCCCOc1nsnc1C1=CCC[N+](C)([C@H](C)OC(=O)C[NH3+])C1 ; [Cl-]] |
| 708 | 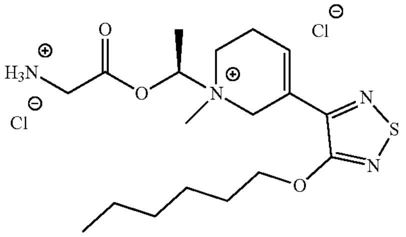 [SMILES: [Cl-] ; CCCCCCOc1nsnc1C1=CCC[N+](C)([C@H](C)OC(=O)C[NH3+])C1 ; [Cl-]] |
| 709 | 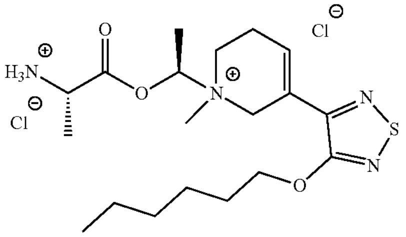 [SMILES: [Cl-] ; CCCCCCOc1nsnc1C1=CCC[N+](C)([C@H](C)OC(=O)[C@H](C)[NH3+])C1 ; [Cl-]]<br>L-amino acid |
| 710 | 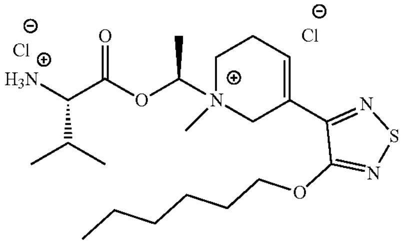 [SMILES: [Cl-] ; [Cl-] ; CCCCCCOc1nsnc1C1=CCC[N+](C)([C@H](C)OC(=O)[C@@H]([NH3+])C(C)C)C1]<br>L-amino acid |
| 711 | 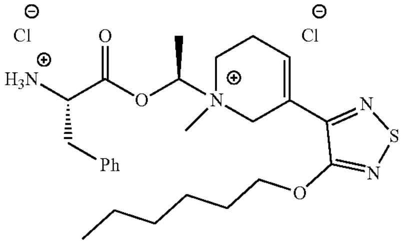 [SMILES: [Cl-] ; [Cl-] ; CCCCCCOc1nsnc1C1=CCC[N+](C)([C@H](C)OC(=O)[C@@H]([NH3+])Cc2ccccc2)C1]<br>L-amino acid |

TABLE 1-continued
| Cpd No. | Structure |
|---|---|
| 712 | 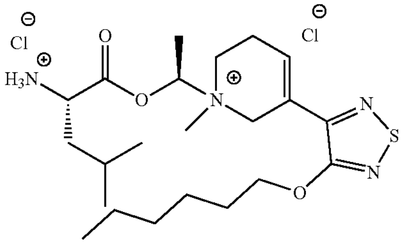 [SMILES: [Cl-] ; [Cl-] ; CCCCCCOc1nsnc1C1=CCC[N+](C)([C@H](C)OC(=O)[C@@H]([NH3+])CC(C)C)C1]<br>L-amino acid |
| 713 | 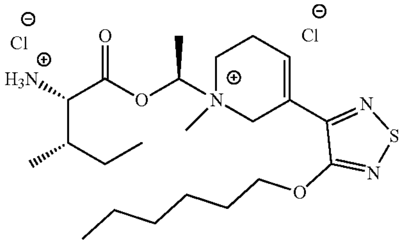 [SMILES: [Cl-] ; [Cl-] ; CCCCCCOc1nsnc1C1=CCC[N+](C)([C@H](C)OC(=O)[C@@H]([NH3+])[C@@H](C)CC)C1]<br>L-amino acid |
| 714 | 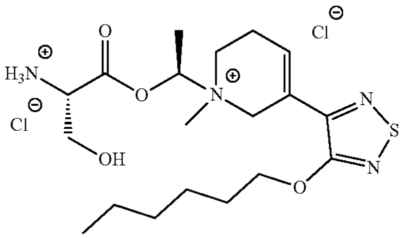 [SMILES: [Cl-] ; CCCCCCOc1nsnc1C1=CCC[N+](C)([C@H](C)OC(=O)[C@@H]([NH3+])CO)C1 ; [Cl-]]<br>L-amino acid |
| 715 | 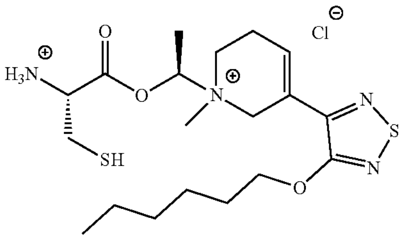 [SMILES: CCCCCCOc1nsnc1C1=CCC[N+](C)([C@H](C)OC(=O)[C@@H]([NH3+])CS)C1 ; [Cl-]]<br>L-amino acid |
| 716 | 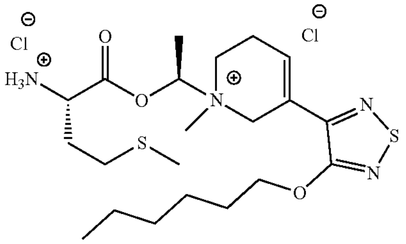 [SMILES: [Cl-] ; [Cl-] ; CCCCCCOc1nsnc1C1=CCC[N+](C)([C@H](C)OC(=O)[C@@H]([NH3+])CCSC)C1]<br>L-amino acid |

TABLE 1-continued
| Cpd No. | Structure |
| --- | --- |
| 717 | 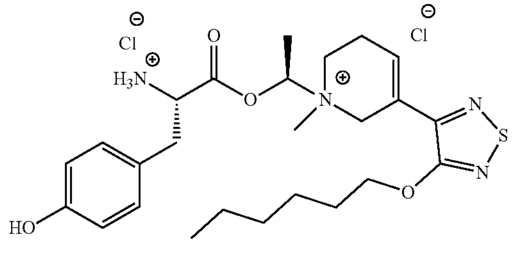 [SMILES: [Cl-] ; CCCCCCOc1nsnc1C1=CCC[N+](C)([C@H](C)OC(=O)[C@@H]([NH3+])Cc2ccc(O)cc2)C1 ; [Cl-]] L-amino acid |
| 718 | 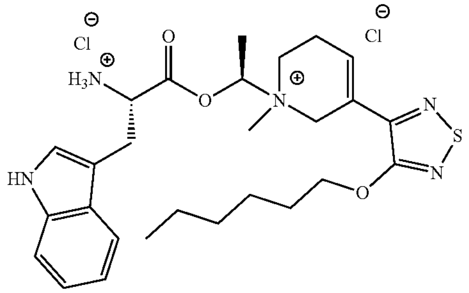 [SMILES: [Cl-] ; CCCCCCOc1nsnc1C1=CCC[N+](C)([C@H](C)OC(=O)[C@@H]([NH3+])Cc2c[nH]c3ccccc23)C1 ; [Cl-]] L-amino acid |
| 719 | 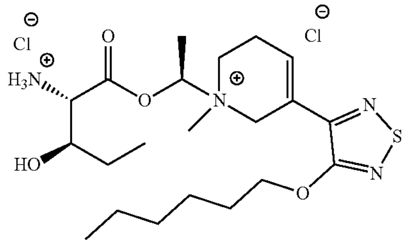 [SMILES: [Cl-] ; [Cl-] ; CCCCCCOc1nsnc1C1=CCC[N+](C)([C@H](C)OC(=O)[C@@H]([NH3+])[C@H](O)CC)C1] L-amino acid |
| 720 | 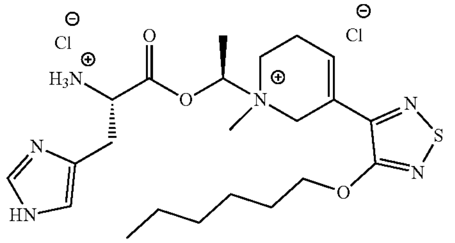 [SMILES: [Cl-] ; CCCCCCOc1nsnc1C1=CCC[N+](C)([C@H](C)OC(=O)[C@@H]([NH3+])Cc2c[nH]cn2)C1 ; [Cl-]] L-amino acid |
| 721 | 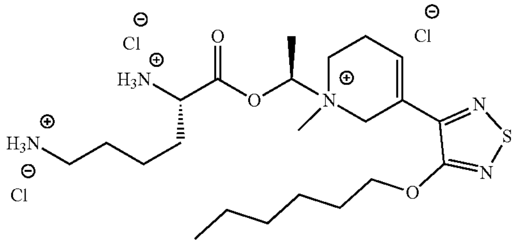 [SMILES: [Cl-] ; Cl ; CCCCCCOc1nsnc1C1=CCC[N+](C)([C@H](C)OC(=O)[C@@H]([NH3+])CCCCN)C1 ; [Cl-]] L-amino acid |

TABLE 1-continued
| Cpd No. | Structure |
|---|---|
| 723 | 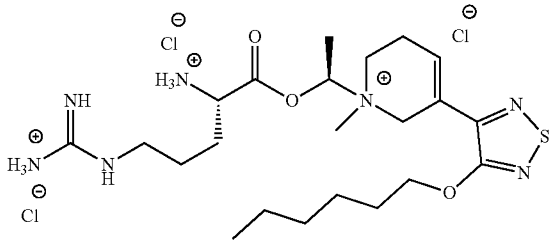 [SMILES: [Cl-] ; [Cl-] ; CCCCCCOc1nsnc1C1=CCC[N+](C)([C@H](C)OC(=O)[C@@H]([NH3+])CCCNC(=N)[NH3+])C1 ; [Cl-]] L-amino acid |
| 724 | 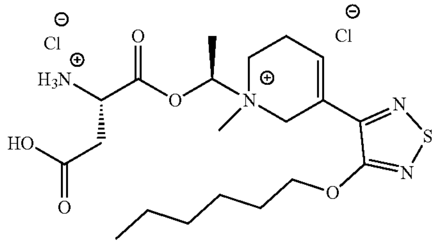 [SMILES: [Cl-] ; CCCCCCOc1nsnc1C1=CCC[N+](C)([C@H](C)OC(=O)[C@@H]([NH3+])CC(=O)O)C1 ; [Cl-]] L-amino acid |
| 725 | 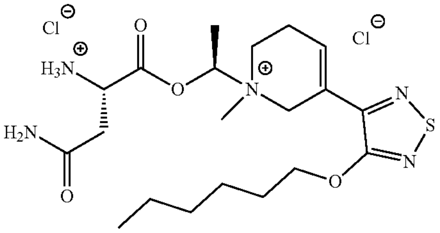 L-amino acid |
| 726 | 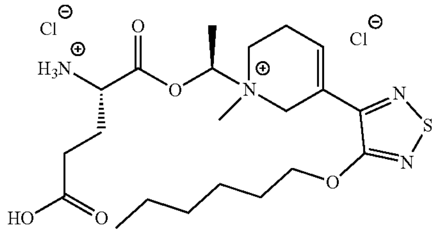 L-amino acid |
| 727 | 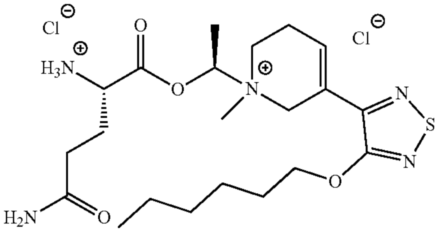 L-amino acid |

TABLE 1-continued
| Cpd No. | Structure |
|---|---|
| 728 | 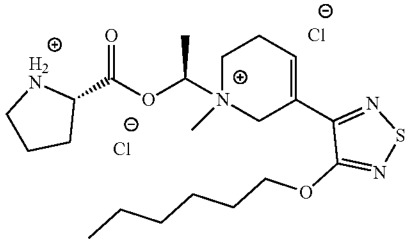 L-amino acid |
| 729 | 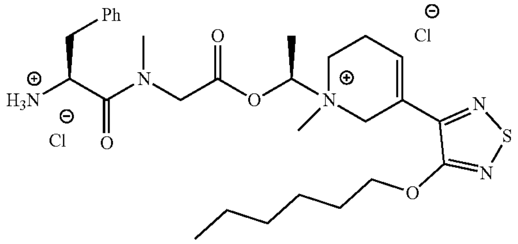 [SMILES: CCCCCCOc1nsnc1C1=CCC[N+](C)([C@H](C)OC(=O)CN(C)C(=O)[C@@H]([NH3+])Cc2ccccc2)C1 ; [Cl-] ; [Cl-]] |
| 730 | 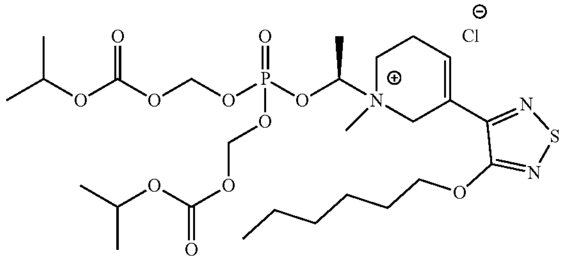 [SMILES: [Cl-] ; CCCCCCOc1nsnc1C1=CCC[N+](C)([C@H](C)OP(=O)(OCOC(=O)OC(C)C)OCOC(=O)OC(C)C)C1] |
| 731 | 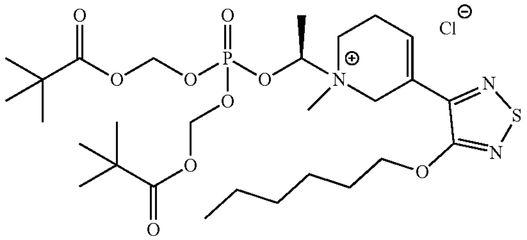 [SMILES: CCCCCCOc1nsnc1C1=CCC[N+](C)([C@H](C)OP(=O)(OCOC(=O)C(C)(C)C)OCOC(=O)C(C)(C)C)C1 ; [Cl-]] |
| 732 | 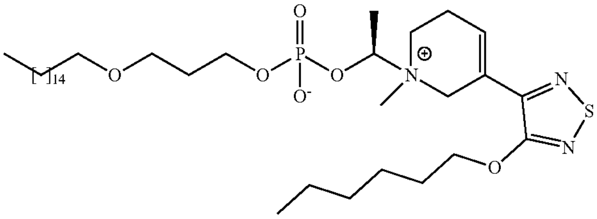 [SMILES: CCCCCCOc1nsnc1C1=CCC[N+](C)([C@H](C)OP(=O)([O-])OCCCOCCC)C1] |
| 733 | 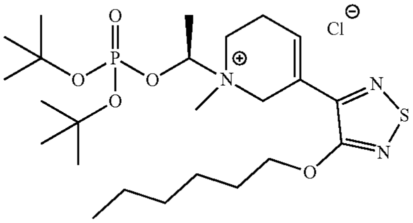 [SMILES: CCCCCCOc1nsnc1C1=CCC[N+](C)([C@H](C)OP(=O)(OC(C)(C)C)OC(C)(C)C)C1 ; [Cl-]] |

TABLE 1-continued
| Cpd No. | Structure |
|---|---|
| 734 | 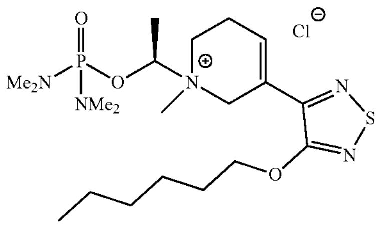 [SMILES: CCCCCCOc1nsnc1C1=CCC[N+](C)([C@H](C)OP(=O)(N(C)C)N(C)C)C1 ; [Cl-]] |
| 735 | 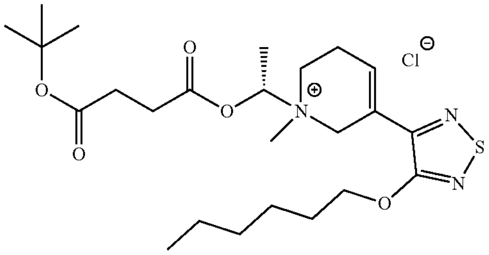 [SMILES: CCCCCCOc1nsnc1C1=CCC[N+](C)([C@@H](C)OC(=O)CCC(=O)OC(C)(C)C)C1 ; [Cl-]] |
| 736 | 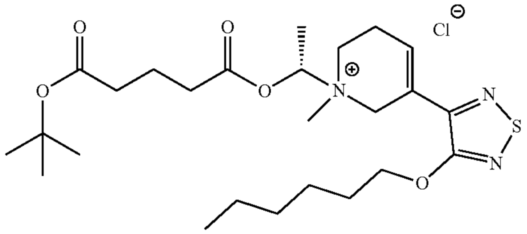 [SMILES: CCCCCCOc1nsnc1C1=CCC[N+](C)([C@@H](C)OC(=O)CCCC(=O)OC(C)(C)C)C1 ; [Cl-]] |
| 737 | 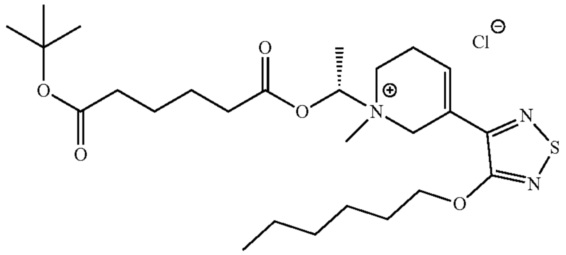 [SMILES: CCCCCCOc1nsnc1C1=CCC[N+](C)([C@@H](C)OC(=O)CCCCC(=O)OC(C)(C)C)C1 ; [Cl-]] |
| 738 | 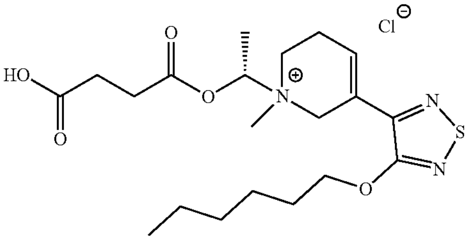 [SMILES: [Cl-] ; CCCCCCOc1nsnc1C1=CCC[N+](C)([C@@H](C)OC(=O)CCC(=O)O)C1] |
| 739 | 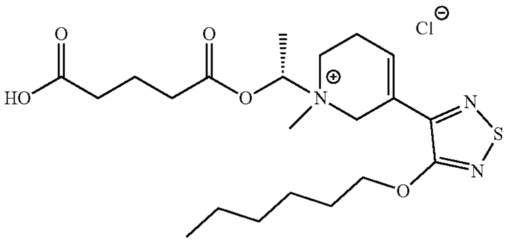 [SMILES: [Cl-] ; CCCCCCOc1nsnc1C1=CCC[N+](C)([C@@H](C)OC(=O)CCCC(=O)O)C1] |

TABLE 1-continued
| Cpd No. | Structure |
|---|---|
| 740 | 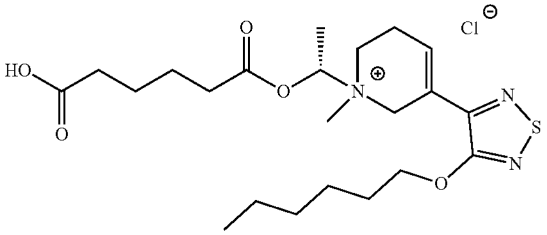 [SMILES: CCCCCCOc1nsnc1C1=CCC[N+](C)([C@@H](C)OC(=O)CCCCC(=O)O)C1 ; [Cl-]] |
| 741 | 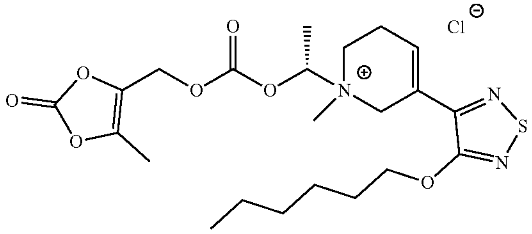 [SMILES: CCCCCCOc1nsnc1C1=CCC[N+](C)([C@@H](C)OC(=O)OCc2oc(=O)oc2C)C1 ; [Cl-]] |
| 742 | 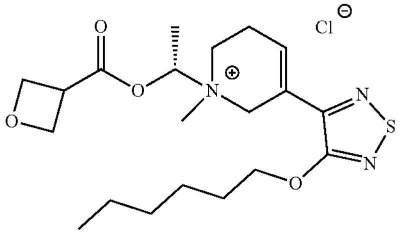 [SMILES: CCCCCCOc1nsnc1C1=CCC[N+](C)([C@@H](C)OC(=O)C2COC2)C1 ; [Cl-]] |
| 743 | 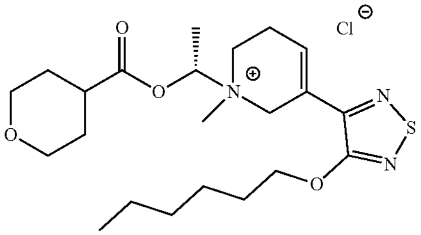 [SMILES: CCCCCCOc1nsnc1C1=CCC[N+](C)([C@@H](C)OC(=O)C2CCOCC2)C1 ; [Cl-]] |
| 744 | 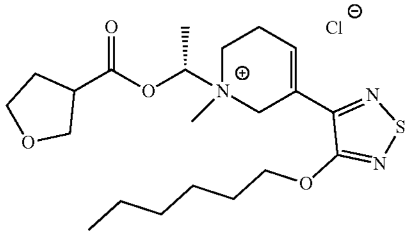 [SMILES: CCCCCCOc1nsnc1C1=CCC[N+](C)([C@@H](C)OC(=O)C2CCOC2)C1 ; [Cl-]] |
| 745 | 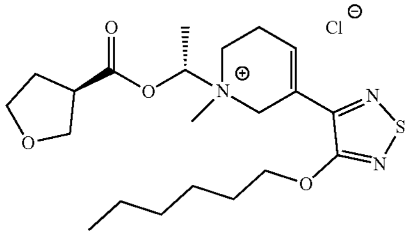 [SMILES: CCCCCCOc1nsnc1C1=CCC[N+](C)([C@@H](C)OC(=O)[C@@H]2CCOC2)C1 ; [Cl-]] |

TABLE 1-continued
| Cpd No. | Structure |
|---|---|
| 746 | 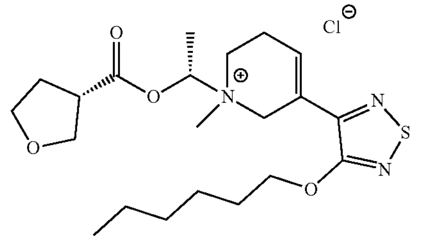 [SMILES: [Cl-] ; CCCCCCOc1nsnc1C1=CCC[N+](C)([C@@H](C)OC(=O)[C@H]2CCOC2)C1] |
| 747 | 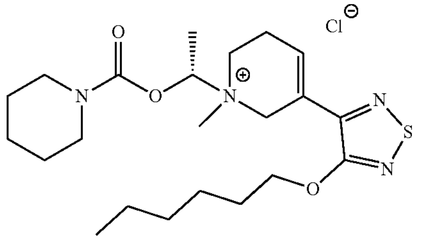 [SMILES: [Cl-] ; CCCCCCOc1nsnc1C1=CCC[N+](C)([C@@H](C)OC(=O)N2CCCCC2)C1] |
| 748 | 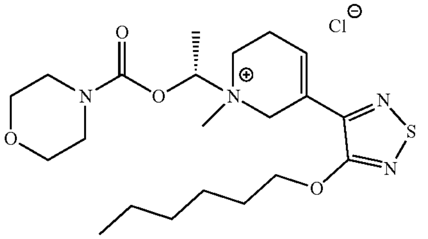 [SMILES: [Cl-] ; CCCCCCOc1nsnc1C1=CCC[N+](C)([C@@H](C)OC(=O)N2CCOCC2)C1] |
| 749 | 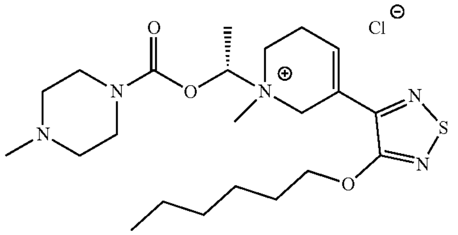 [SMILES: CCCCCCOc1nsnc1C1=CCC[N+](C)([C@@H](C)OC(=O)N2CCN(C)CC2)C1 ; [Cl-]] |
| 750 | 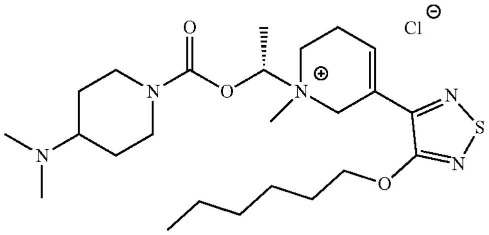 [SMILES: CCCCCCOc1nsnc1C1=CCC[N+](C)([C@@H](C)OC(=O)N2CCC(N(C)C)CC2)C1 ; [Cl-]] |
| 751 | 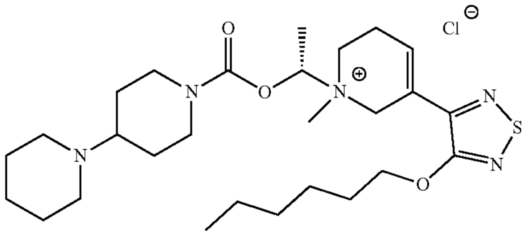 [SMILES: CCCCCCOc1nsnc1C1=CCC[N+](C)([C@@H](C)OC(=O)N2CCC(N3CCCCC3)CC2)C1 ; [Cl-]] |

TABLE 1-continued
| Cpd No. | Structure |
| --- | --- |
| 752 | 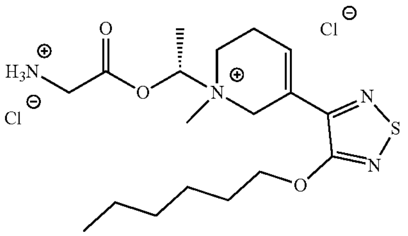 [SMILES: [Cl-] ; CCCCCCOc1nsnc1C1=CCC[N+](C)([C@@H](C)OC(=O)C[NH3+])C1 ; [Cl-]] |
| 753 | 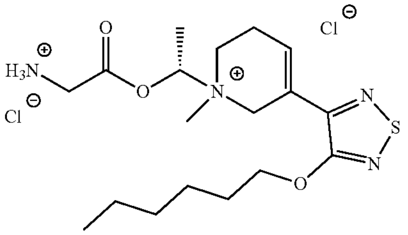 [SMILES: [Cl-] ; CCCCCCOc1nsnc1C1=CCC[N+](C)([C@@H](C)OC(=O)C[NH3+])C1 ; [Cl-]] |
| 754 | 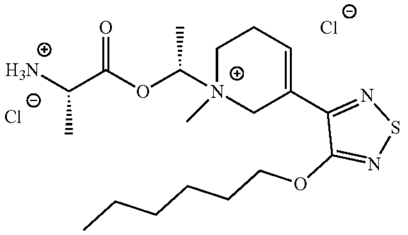 [SMILES: [Cl-] ; CCCCCCOc1nsnc1C1=CCC[N+](C)([C@@H](C)OC(=O)[C@H](C)[NH3+])C1 ; [Cl-]]<br>L-amino acid |
| 755 | 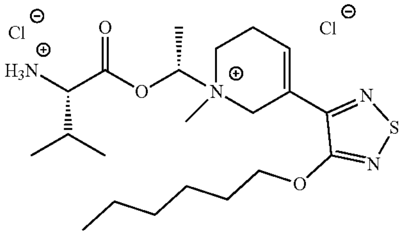 [SMILES: [Cl-] ; CCCCCCOc1nsnc1C1=CCC[N+](C)([C@@H](C)OC(=O)[C@@H]([NH3+])C(C)C)C1 ; [Cl-]]<br>L-amino acid |
| 756 | 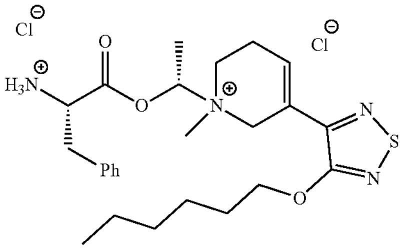<br>L-amino acid |
L-amino acid TABLE 1-continued
| Cpd No. | Structure |
|---|---|
| 757 | 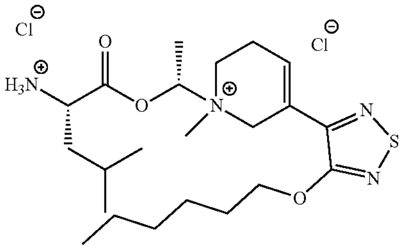<br>L-amino acid |
| 758 | 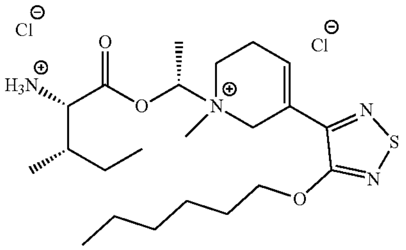<br>L-amino acid |
| 759 | 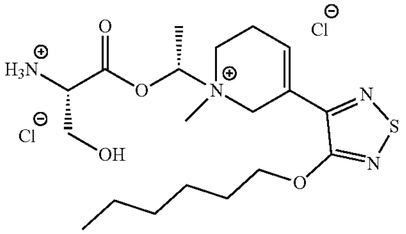<br>L-amino acid |
| 760 | 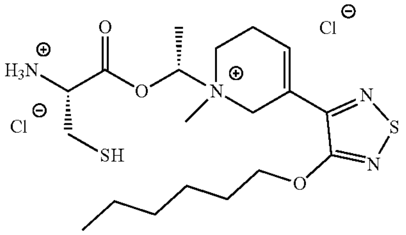 [SMILES: [Cl-] ; CCCCCCOc1nsnc1C1=CCC[N+](C)([C@@H](C)OC(=O)[C@@H]([NH3+])CS)C1 ; [Cl-]]<br>L-amino acid |
| 761 | 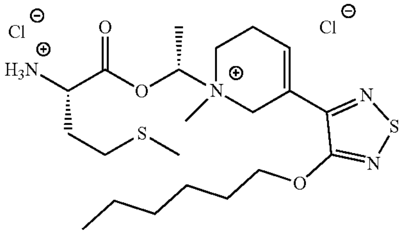 [SMILES: [Cl-] ; CCCCCCOc1nsnc1C1=CCC[N+](C)([C@@H](C)OC(=O)[C@@H]([NH3+])CCSC)C1 ; [Cl-]]<br>L-amino acid |

TABLE 1-continued
| Cpd No. | Structure |
|---|---|
| 762 | 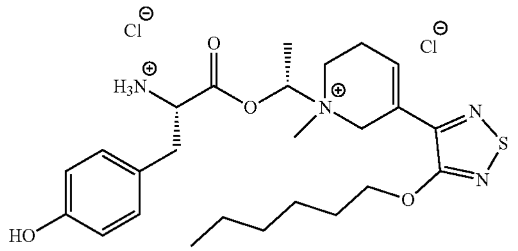 L-amino acid |
| 763 | 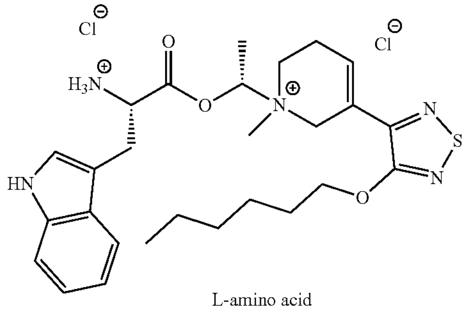 [SMILES: [Cl-] ; CCCCCCOc1nsnc1C1=CCC[N+](C)([C@@H](C)OC(=O)[C@@H]([NH3+])Cc2c[nH]c3ccccc23)C1 ; [Cl-]] L-amino acid |
| 764 | 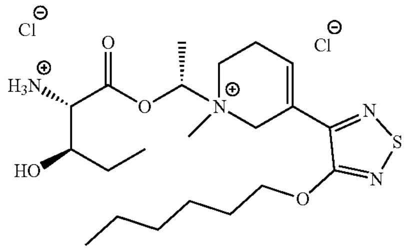 L-amino acid |
| 765 | 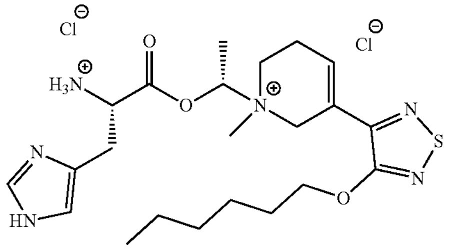 L-amino acid |
| 766 | 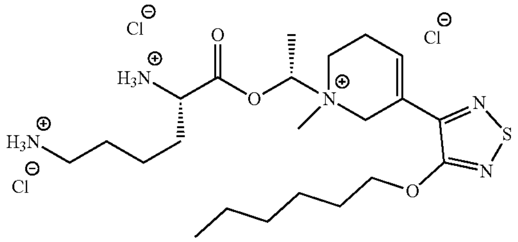 L-amino acid |

TABLE 1-continued
| Cpd No. | Structure |
| --- | --- |
| 767 | 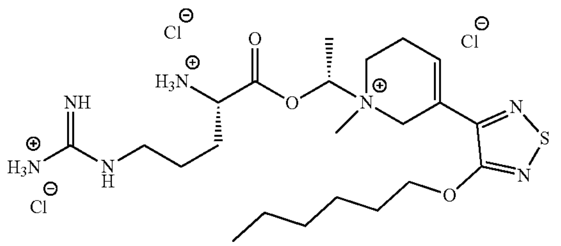 L-amino acid |
| 768 | 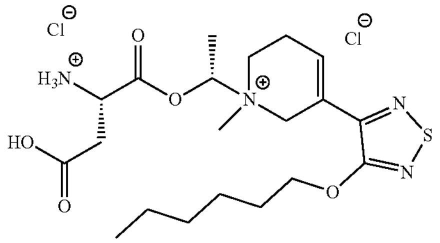 L-amino acid |
| 769 | 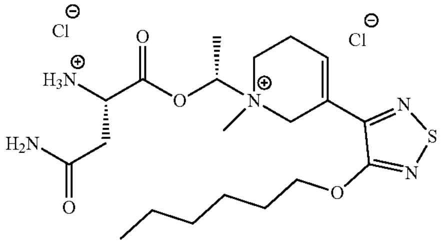 L-amino acid |
| 770 | 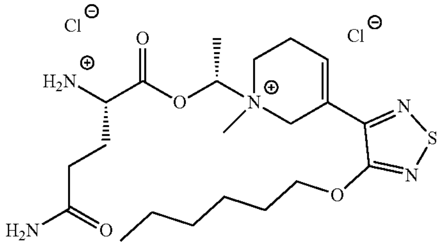 L-amino acid |
| 771 | 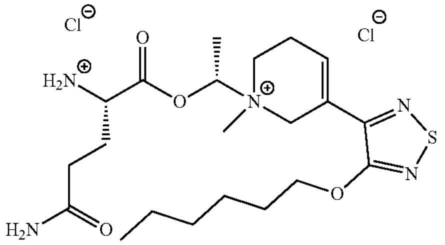 L-amino acid |

TABLE 1-continued
| Cpd No. | Structure |
|---|---|
| 772 | 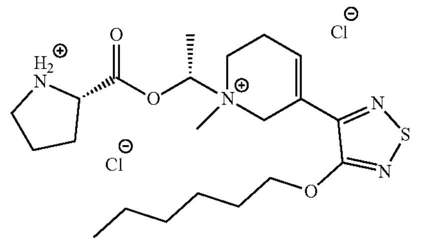 L-amino acid |
| 773 | 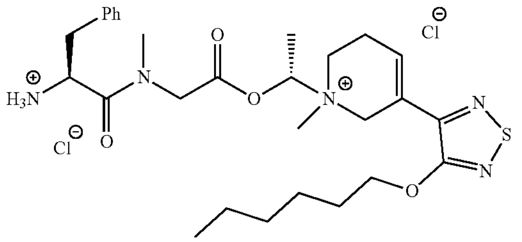 [SMILES: CCCCCCOc1nsnc1C1=CCC[N+](C)([C@@H](C)OC(=O)CN(C)C(=O)[C@@H]([NH3+])Cc2ccccc2)C1 ; [Cl-] ; [Cl-]] |
| 774 | 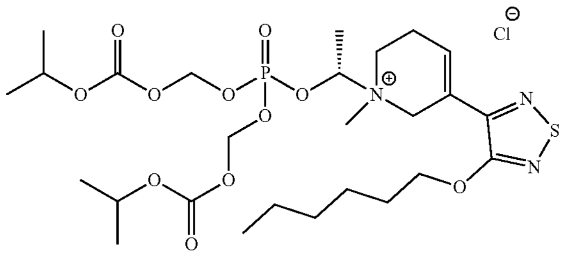 [SMILES: CCCCCCOc1nsnc1C1=CCC[N+](C)([C@@H](C)OP(=O)(OCOC(=O)OC(C)C)OCOC(=O)OC(C)C)C1 ; [Cl-]] |
| 775 | 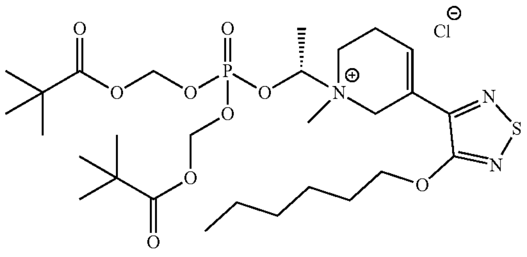 [SMILES: CCCCCCOc1nsnc1C1=CCC[N+](C)([C@@H](C)OP(=O)(OCOC(=O)C(C)(C)C)OCOC(=O)C(C)(C)C)C1 ; [Cl-]] |
| 776 | 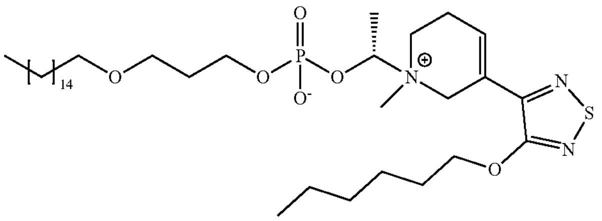 |
| 777 | 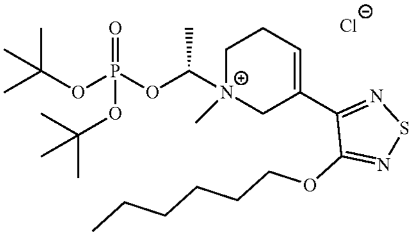 [SMILES: [Cl-] ; CCCCCCOc1nsnc1C1=CCC[N+](C)([C@@H](C)OP(=O)(OC(C)(C)C)OC(C)(C)C)C1] |

TABLE 1-continued
| Cpd No. | Structure |
|---|---|
| 778 | 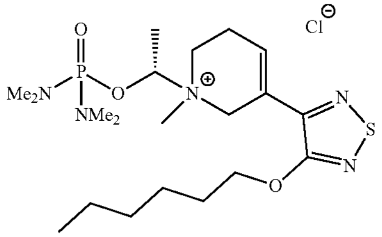 [SMILES: [Cl-] ; CCCCCCOc1nsnc1C1=CCC[N+](C)([C@@H](C)OP(=O)(N(C)C)N(C)C)C1] |
| 779 | 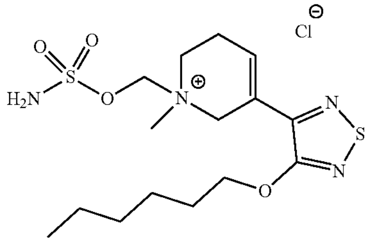 [SMILES: [Cl-] ; CCCCCCOc1nsnc1C1=CCC[N+](C)(COS(N)(=O)=O)C1] |
| 780 | 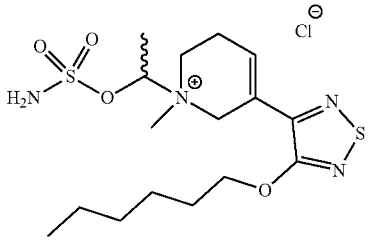 [SMILES: [Cl-] ; CCCCCCOc1nsnc1C1=CCC[N+](C)(C(C)OS(N)(=O)=O)C1] |
| 781 | 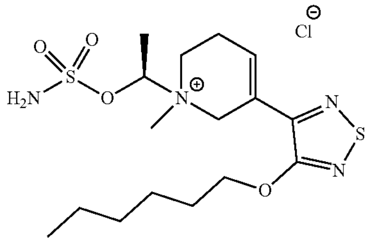 [SMILES: [Cl-] ; CCCCCCOc1nsnc1C1=CCC[N+](C)([C@H](C)OS(N)(=O)=O)C1] |
| 782 | 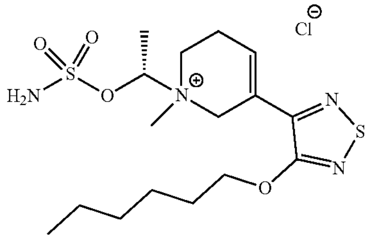 [SMILES: [Cl-] ; CCCCCCOc1nsnc1C1=CCC[N+](C)([C@@H](C)OS(N)(=O)=O)C1] |
| 783 | 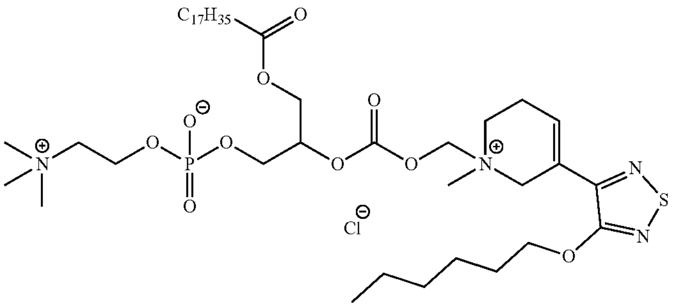 |

TABLE 1-continued
| Cpd No. | Structure |
|---|---|
| 784 | 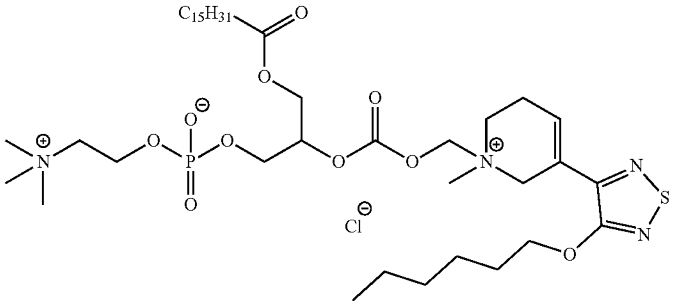 |
| 785 | 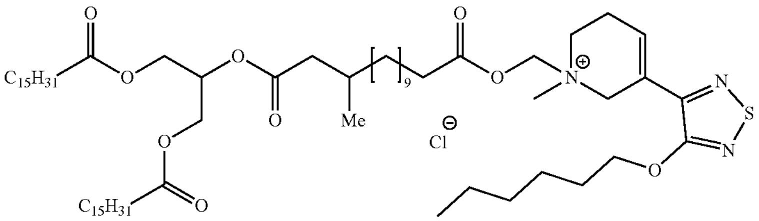 |
| 786 | 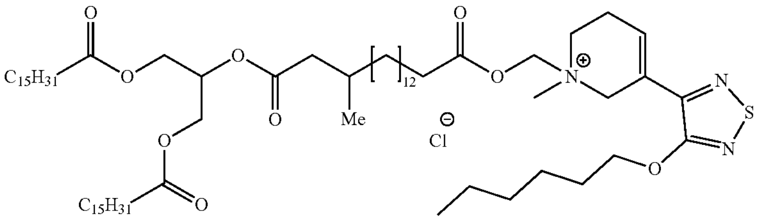 |
| 787 | 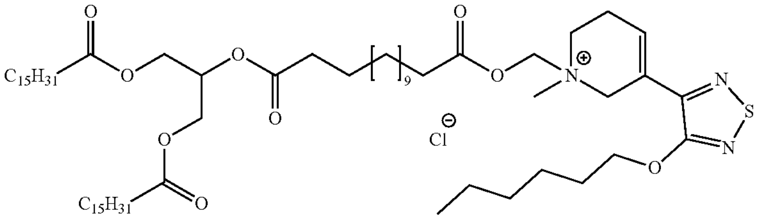 |
| 788 | 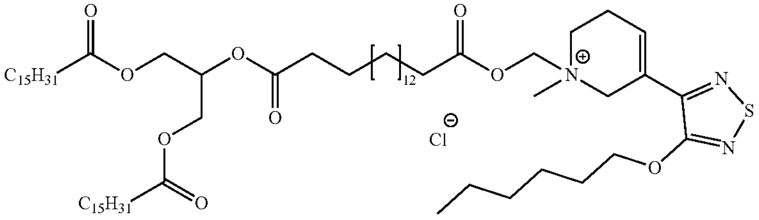 |
| 789 | 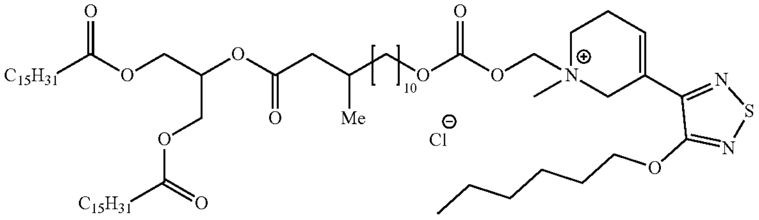 |

TABLE 1-continued
| Cpd No. | Structure |
|---|---|
| 790 | 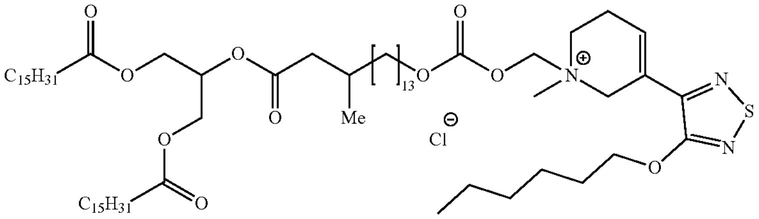 |
| 791 | 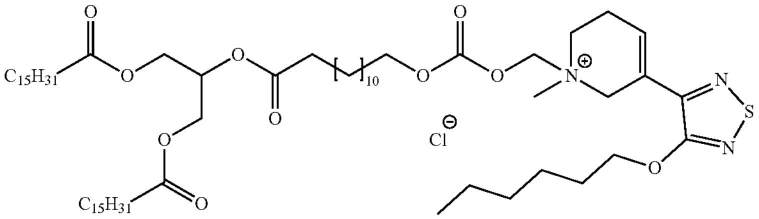 |
| 792 | 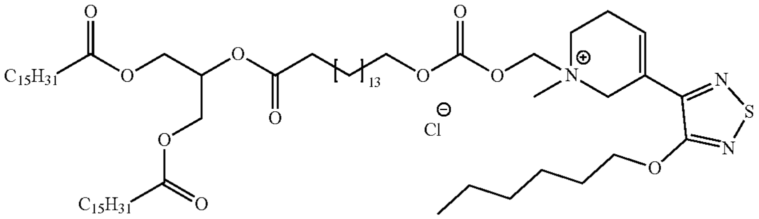 |
| 793 | 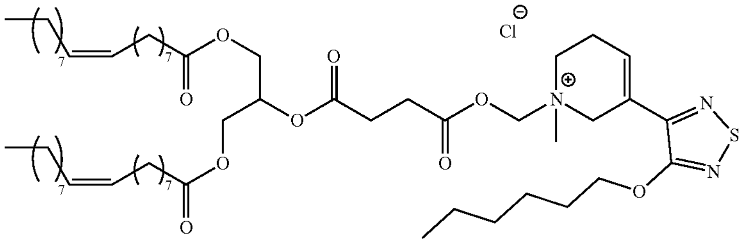 |
| 794 | 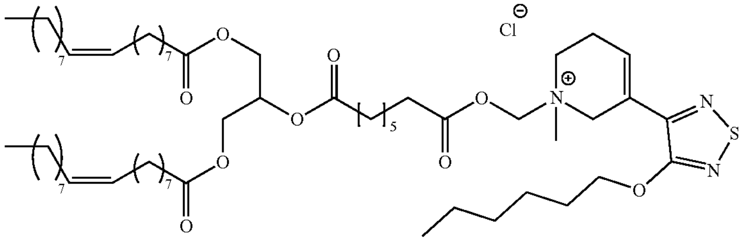 |
| 795 | 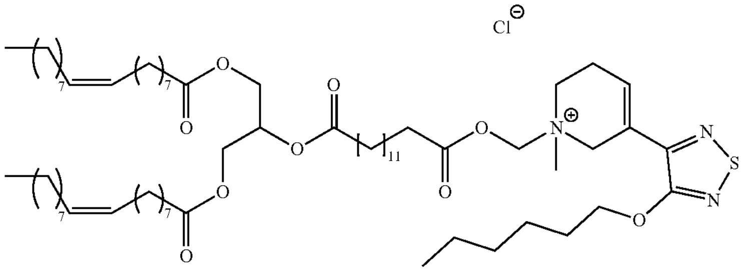 |

TABLE 1-continued
| Cpd No. | Structure |
| --- | --- |
| 796 | 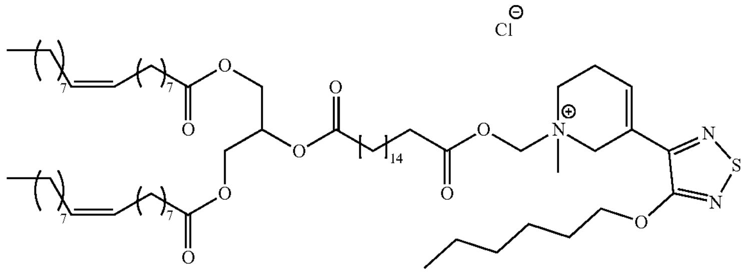 |
| 797 | 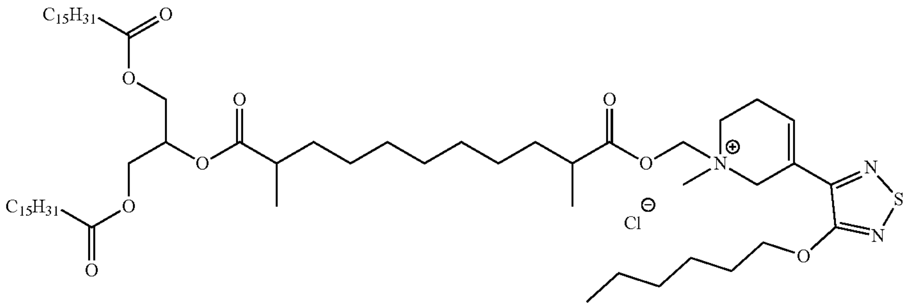 [SMILES: "C15H31" ; CCCCCCOc1nsnc1C1=CCC[N+](C)(COC(=O)C(C)CCCCCCCC(C)C(=O)OC(COC=O)COC=O)C1 ; "C15H31" ; [Cl-]] |
| 798 | 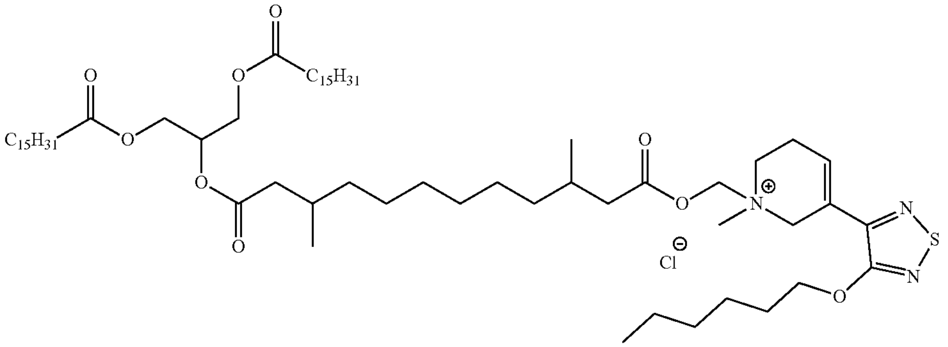 |
| 799 | 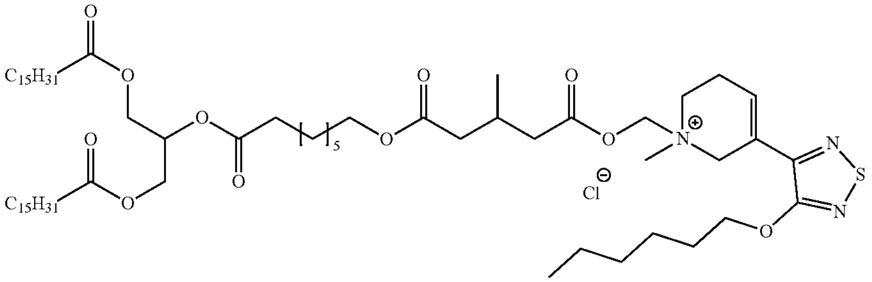 |
| 800 | 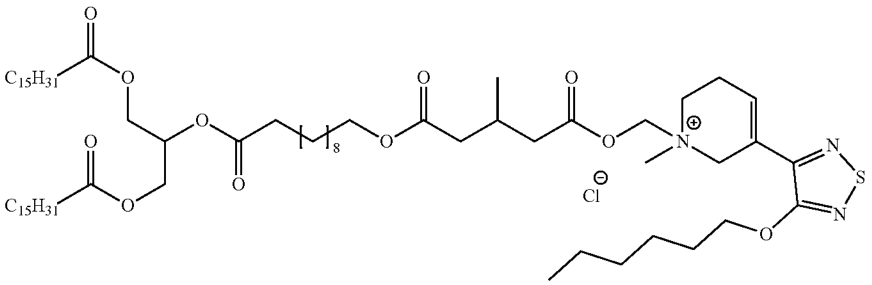 |

TABLE 1-continued
| Cpd No. | Structure |
|---|---|
| 801 | 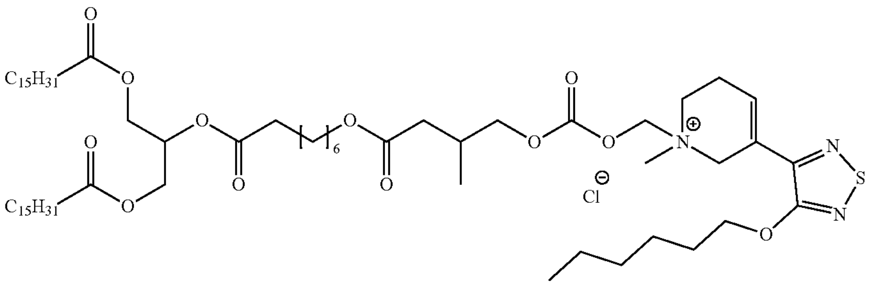 |
| 802 | 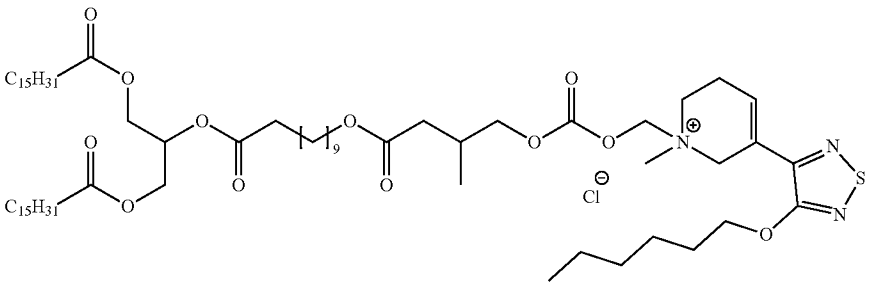 |
| 803 | 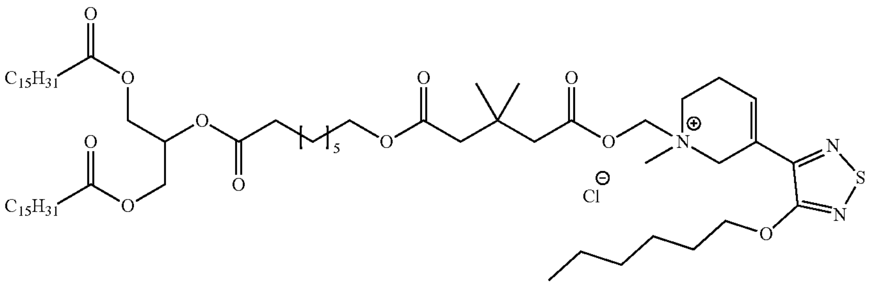 |
| 804 | 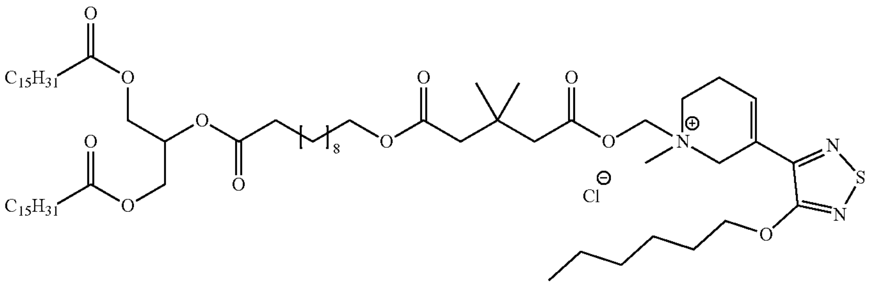 |
| 805 | 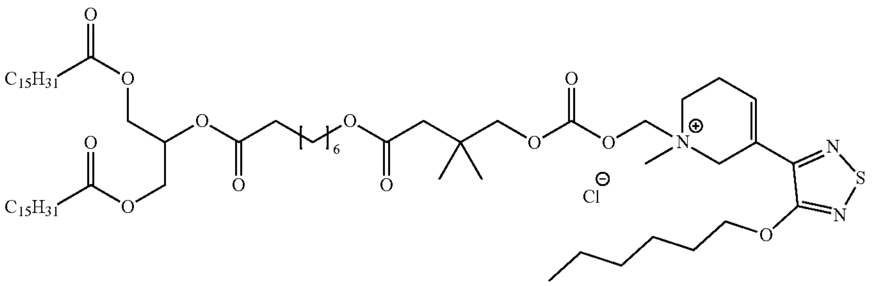 |

TABLE 1-continued
| Cpd No. | Structure |
|---|---|
| 806 | 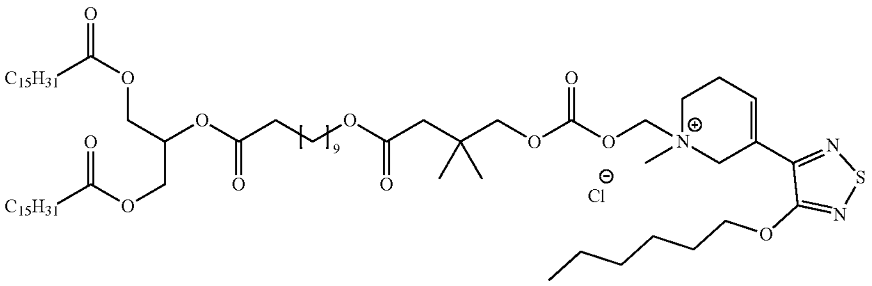 |
| 807 | 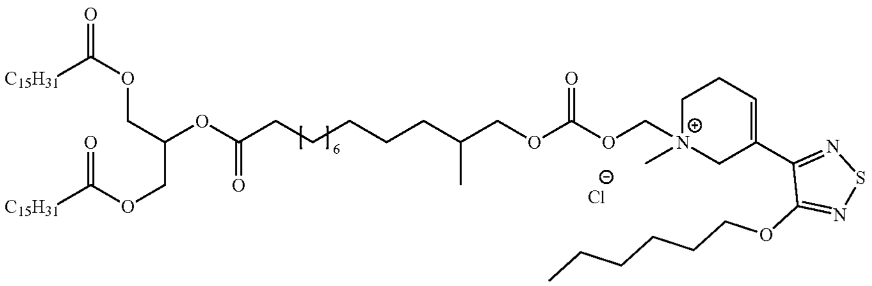 |
| 808 | 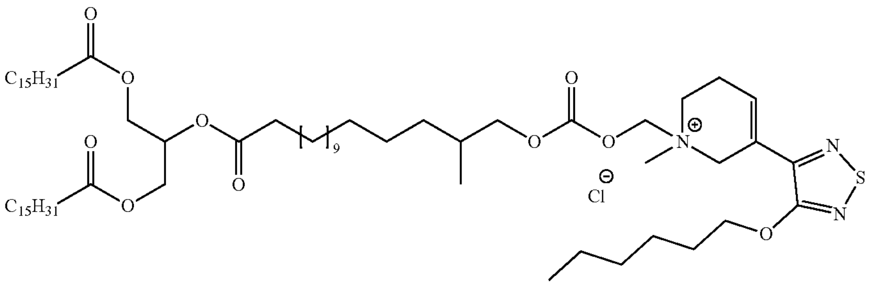 |
| 809 | 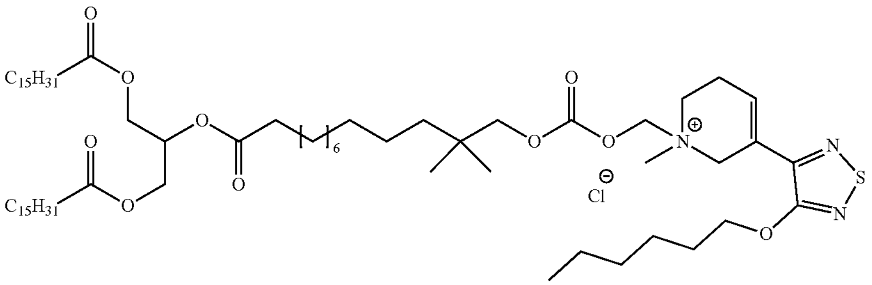 |
| 810 | 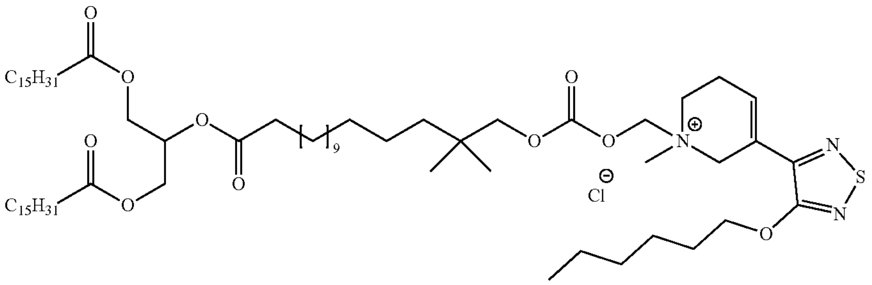 |

TABLE 1-continued
| Cpd No. | Structure |
| --- | --- |
| 811 | 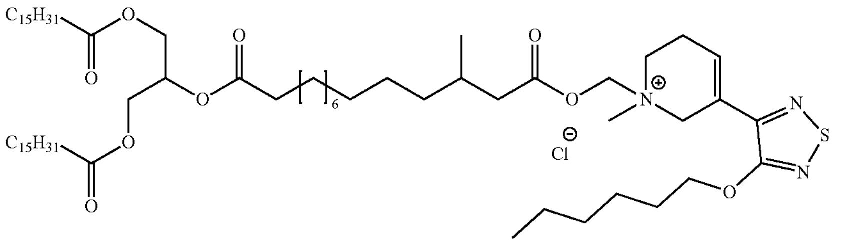 |
| 812 | 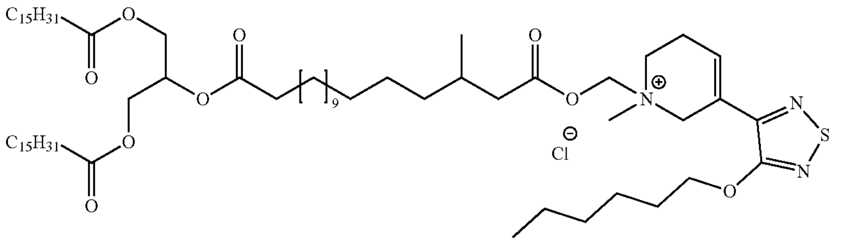 |
| 813 | 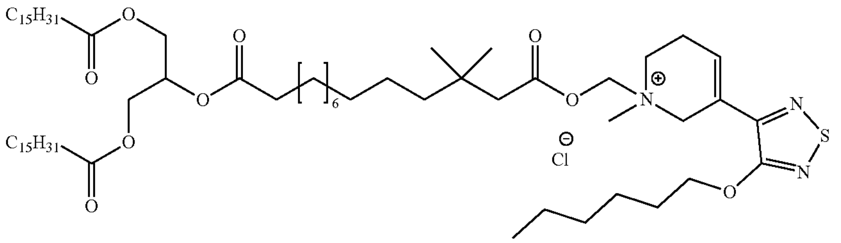 |
| 814 | 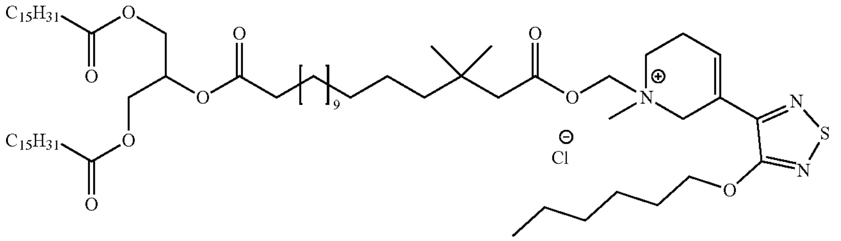 |
| 815 | 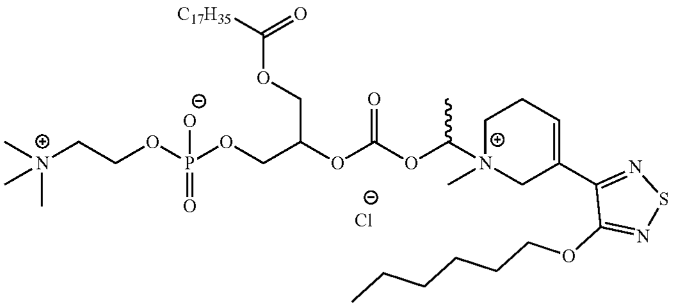 |
| 816 | 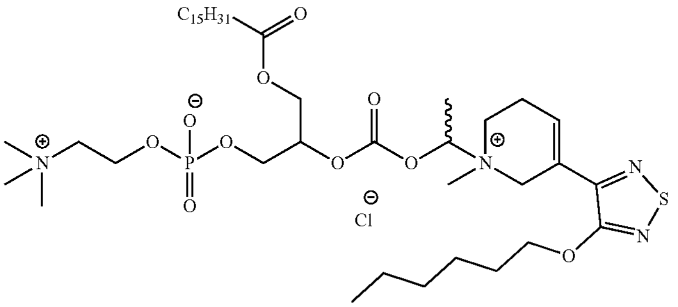 |

TABLE 1-continued
| Cpd No. | Structure |
|---|---|
| 817 | 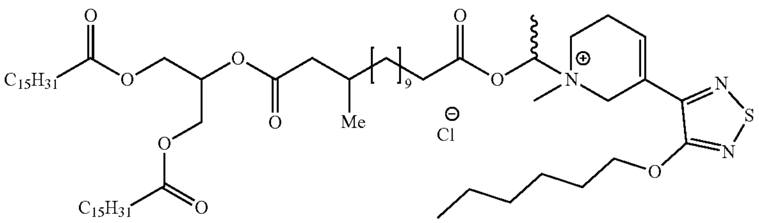 |
| 818 | 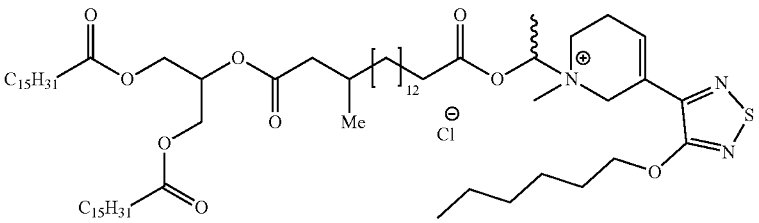 |
| 819 | 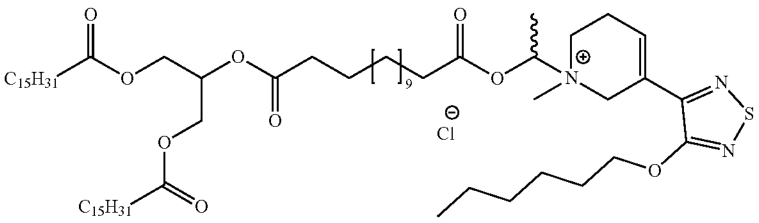 |
| 820 | 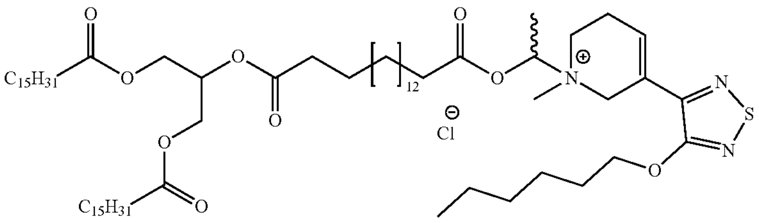 |
| 821 | 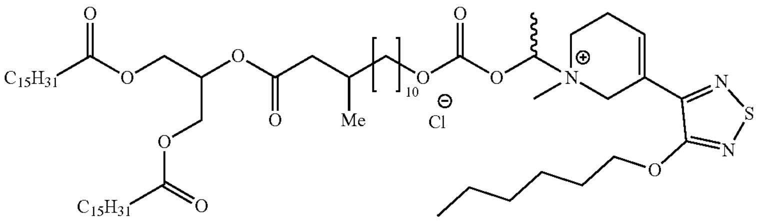 |
| 822 | 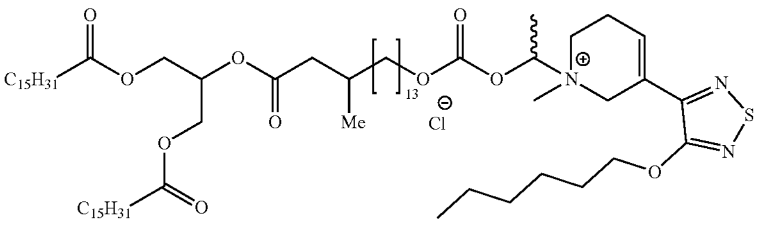 |

TABLE 1-continued
| Cpd No. | Structure |
| --- | --- |
| 823 | 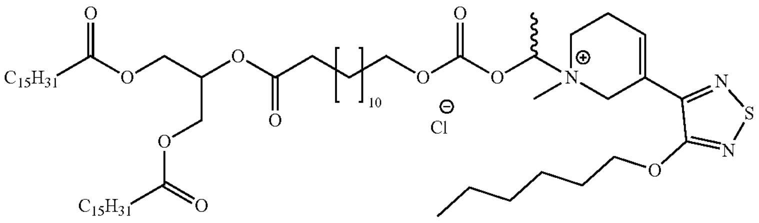 |
| 824 | 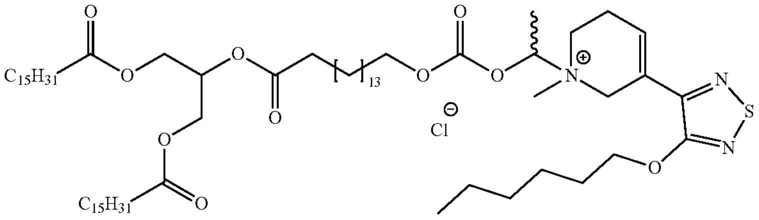 |
| 825 | 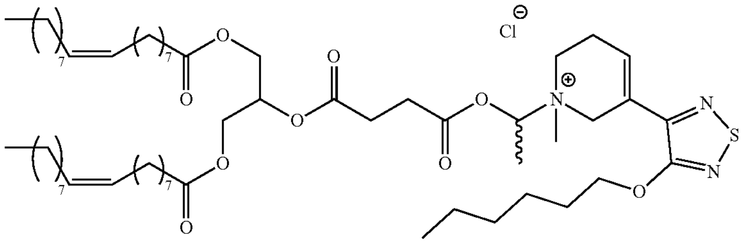 |
| 826 | 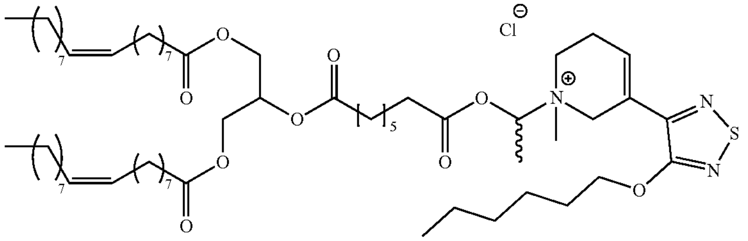 |
| 827 | 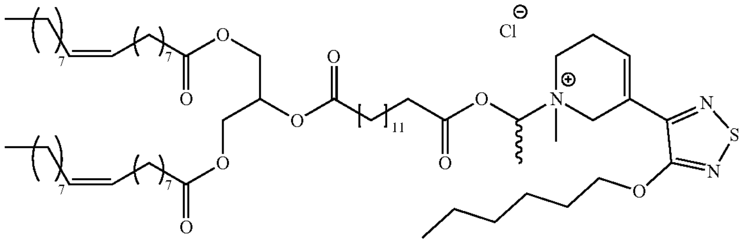 |
| 828 | 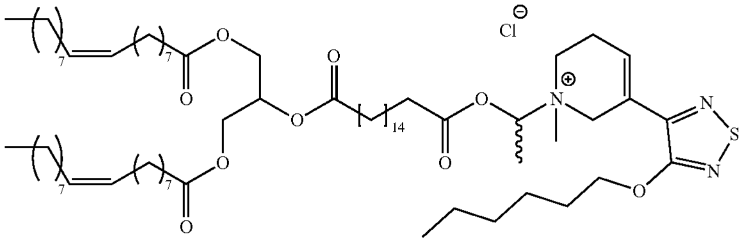 |

TABLE 1-continued
| Cpd No. | Structure |
|---|---|
| 829 | 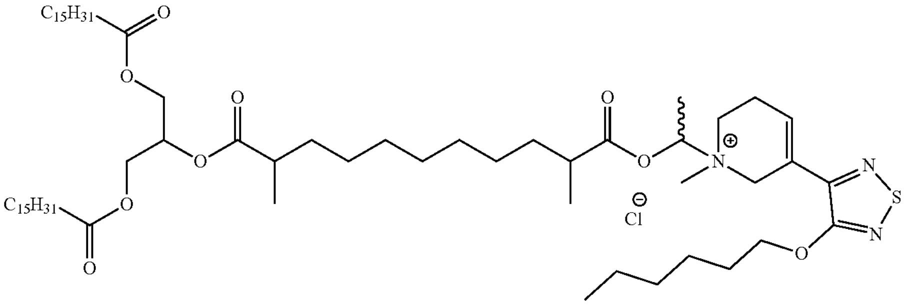 |
| 830 | 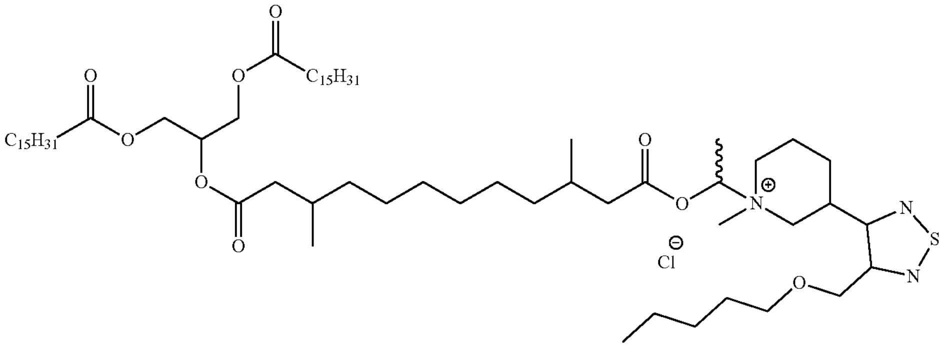 |
| 831 | 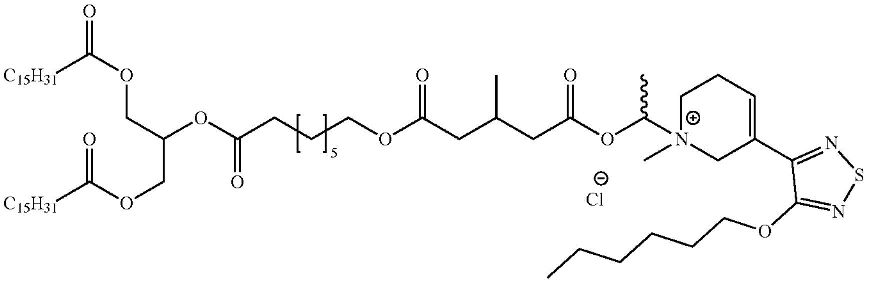 |
| 832 | 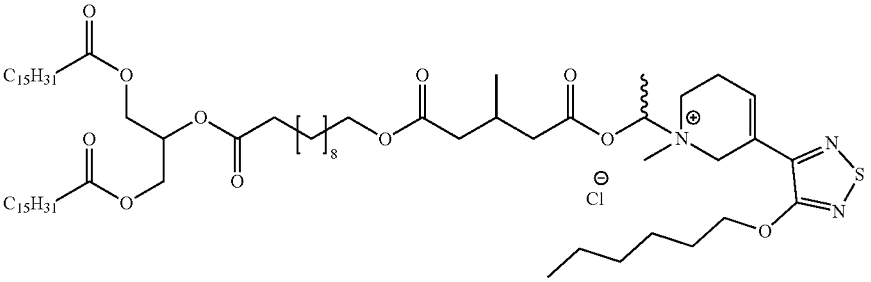 |
| 833 | 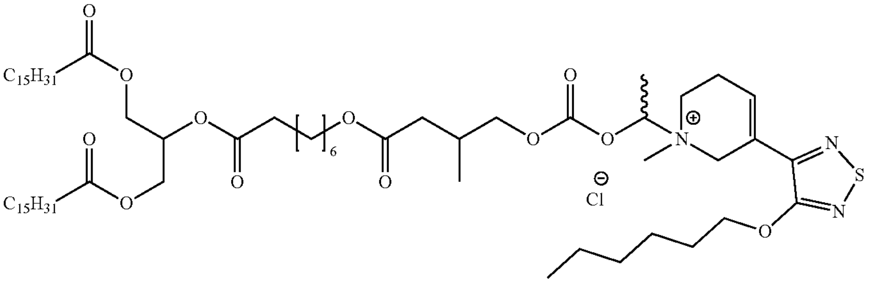 |

TABLE 1-continued
| Cpd No. | Structure |
|---|---|
| 834 | 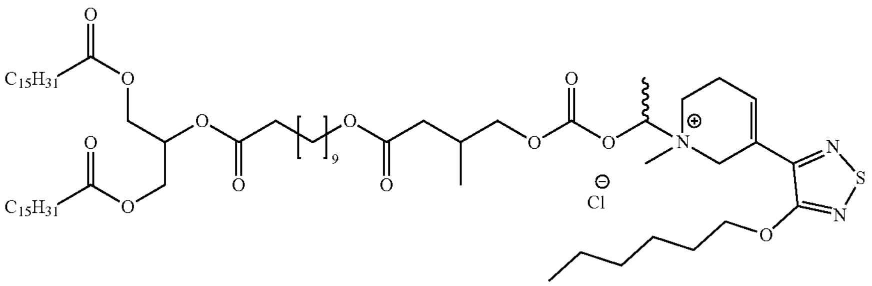 |
| 835 | 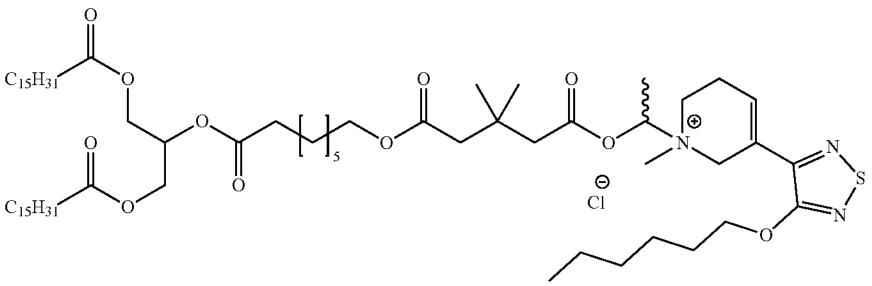 |
| 836 | 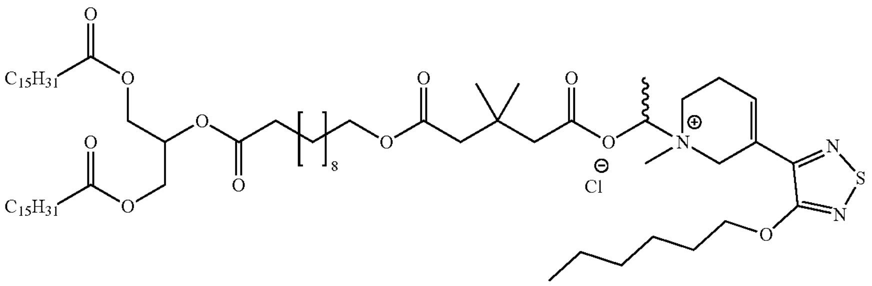 |
| 837 | 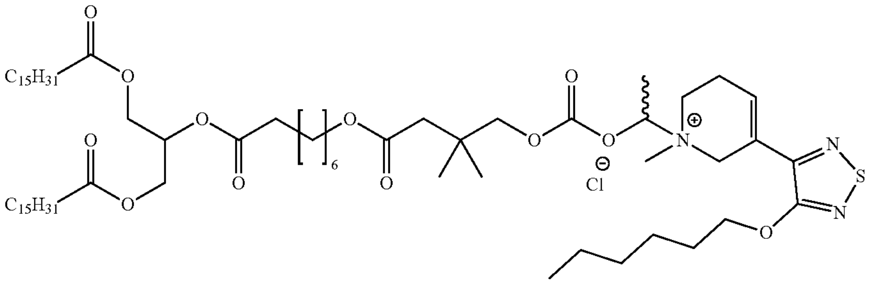 |
| 838 | 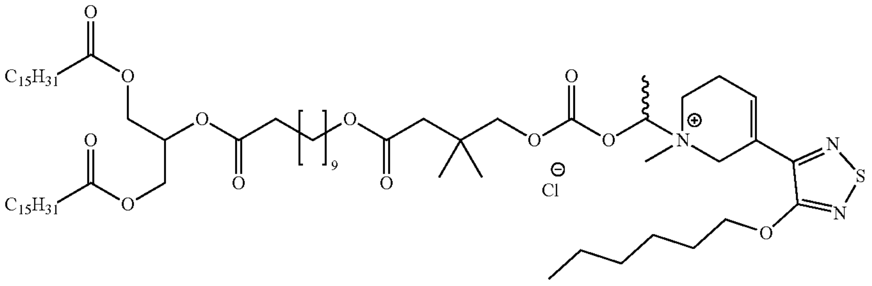 |

TABLE 1-continued
| Cpd No. | Structure |
| --- | --- |
| 839 | 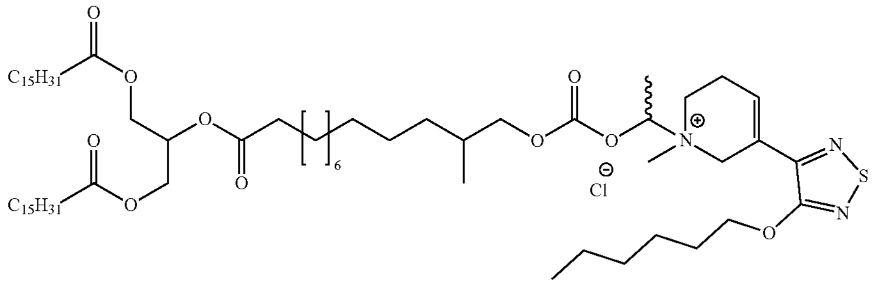 |
| 840 | 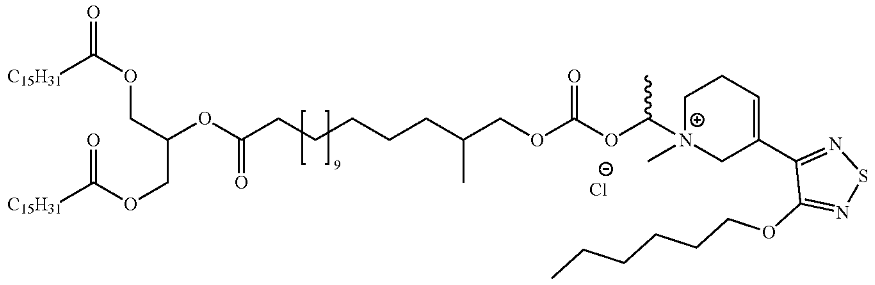 |
| 841 | 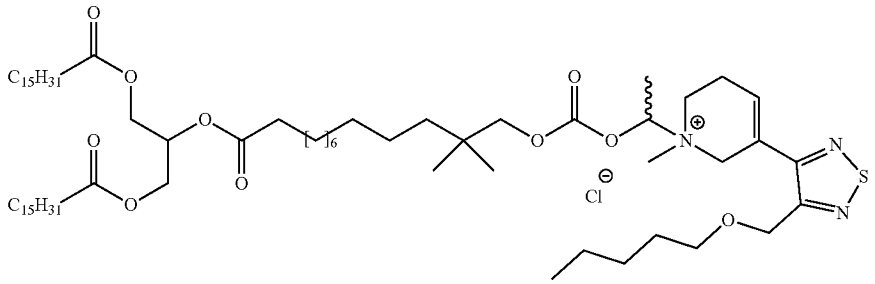 |
| 842 | 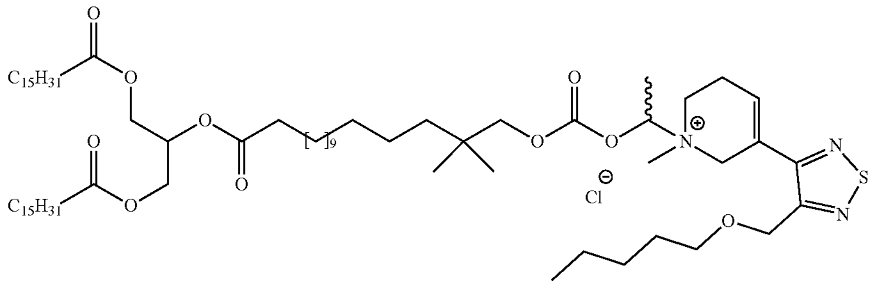 |
| 843 | 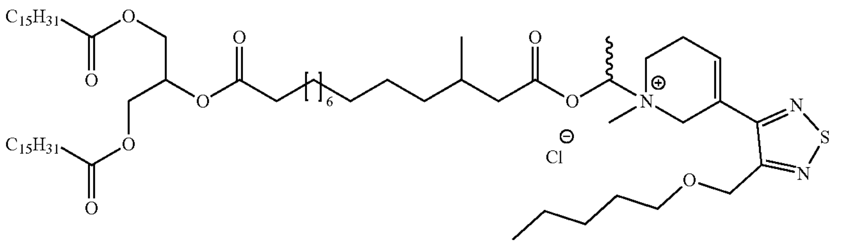 |

TABLE 1-continued
| Cpd No. | Structure |
|---|---|
| 844 | 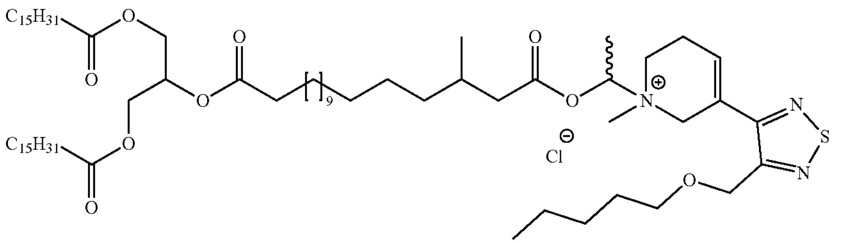 |
| 845 | 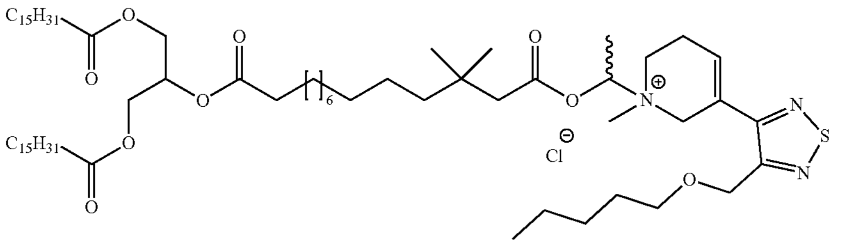 |
| 846 | 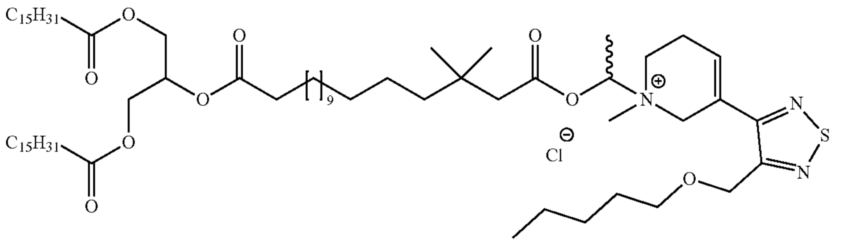 |
| 847 | 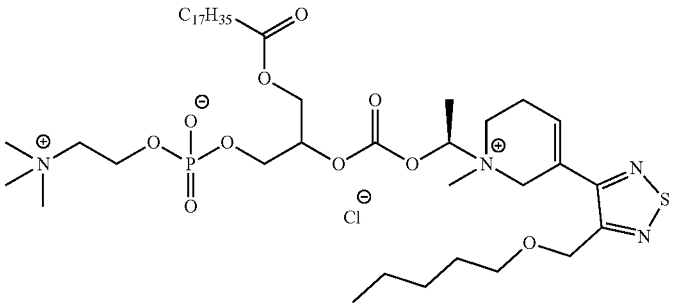 |
| 848 | 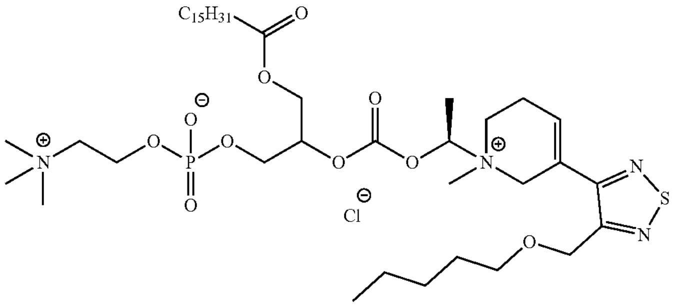 |
| 849 | 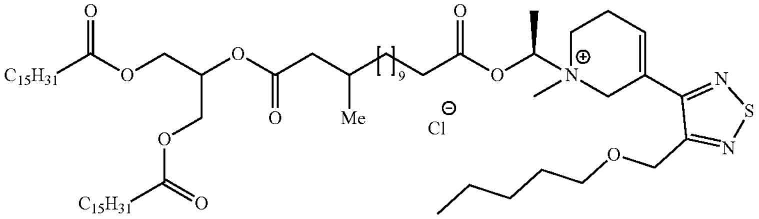 |

TABLE 1-continued
| Cpd No. | Structure |
|---|---|
| 850 | 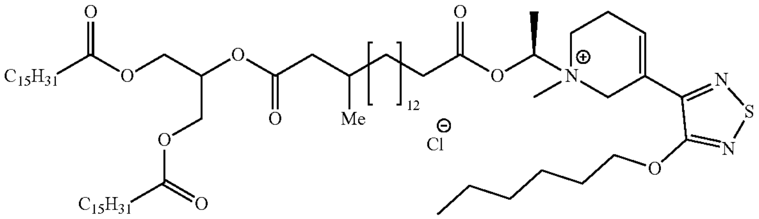 |
| 851 | 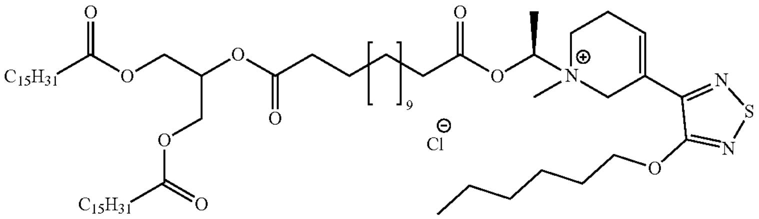 |
| 852 | 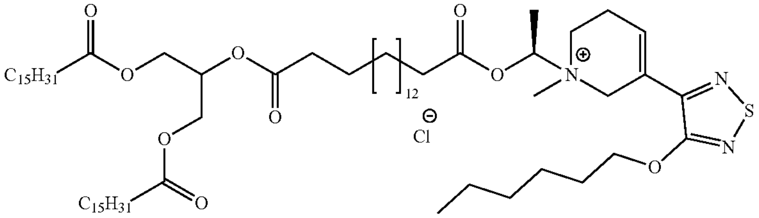 |
| 853 | 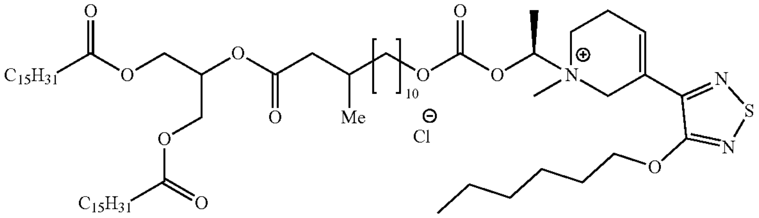 |
| 854 | 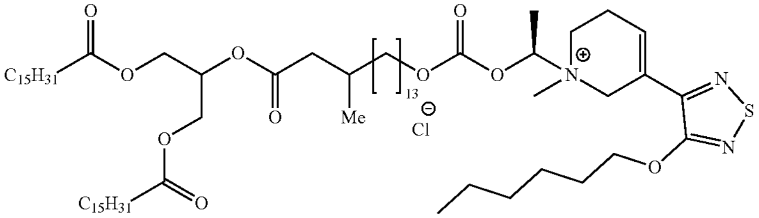 |
| 855 | 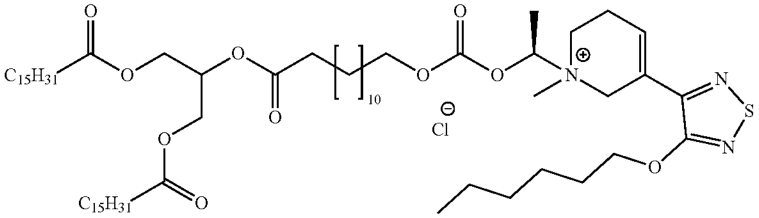 |
| 856 | 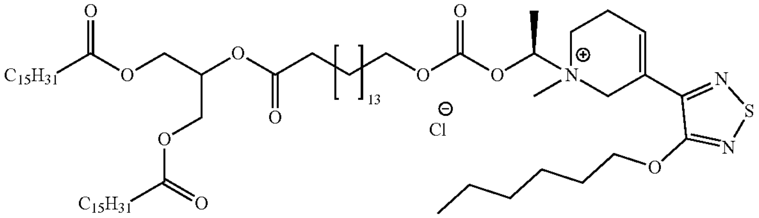 |

TABLE 1-continued
| Cpd No. | Structure |
|---|---|
| 857 | 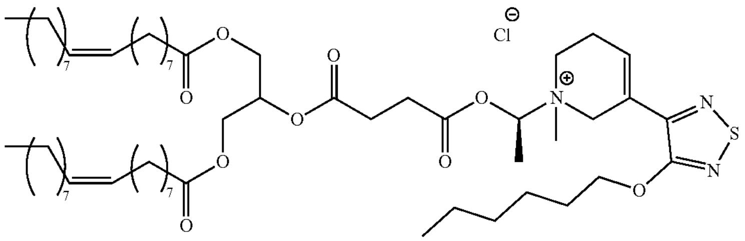 |
| 858 | 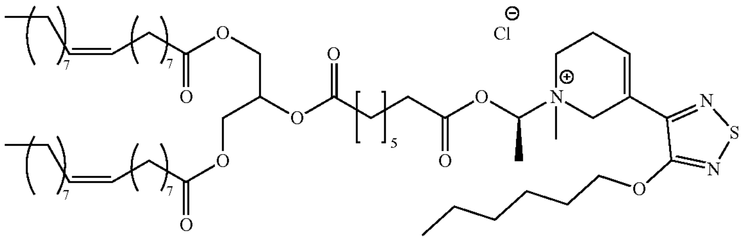 |
| 859 | 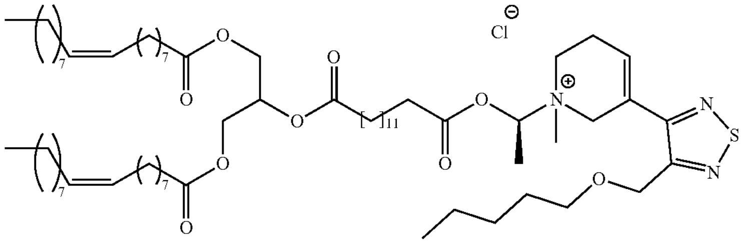 |
| 860 | 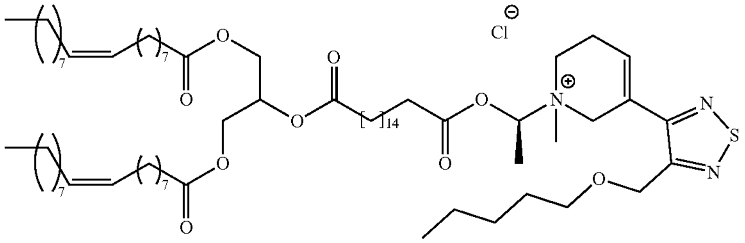 |
| 861 | 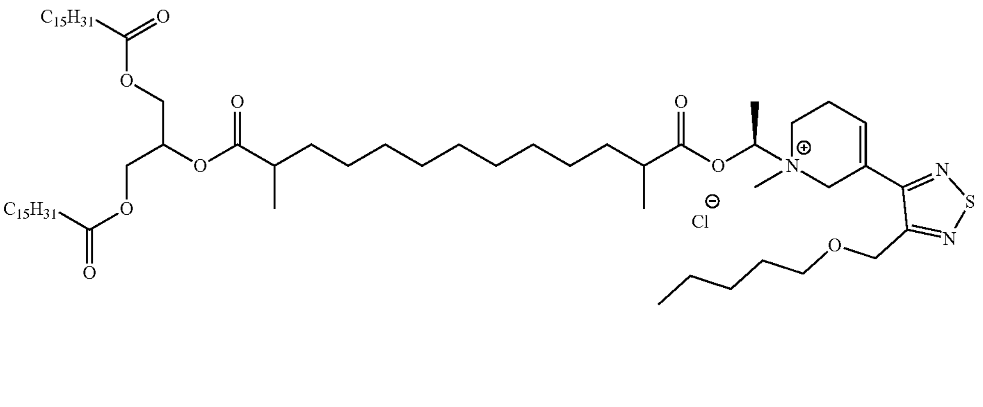 |

TABLE 1-continued
| Cpd No. | Structure |
| --- | --- |
| 862 | 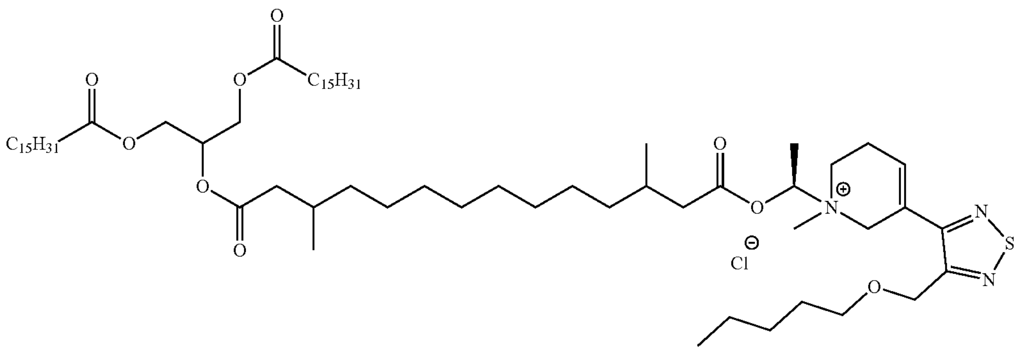 |
| 863 | 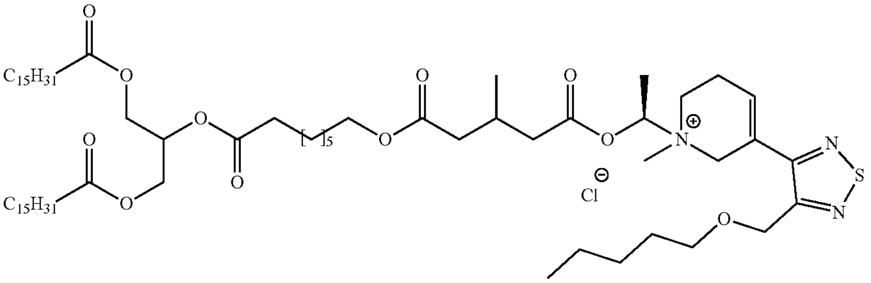 |
| 864 | 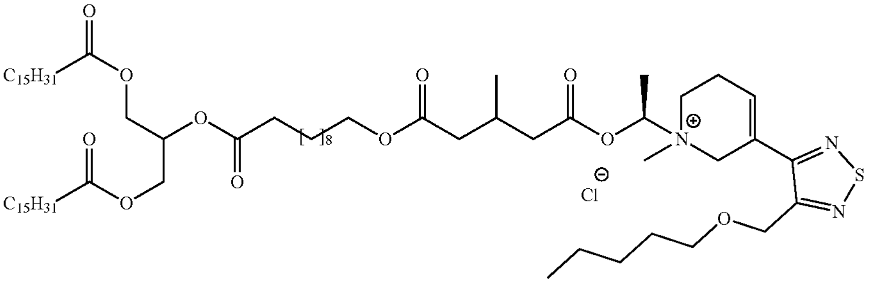 |
| 865 | 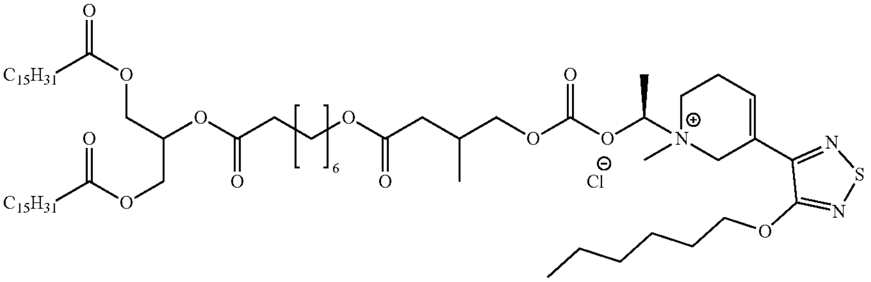 |
| 866 | 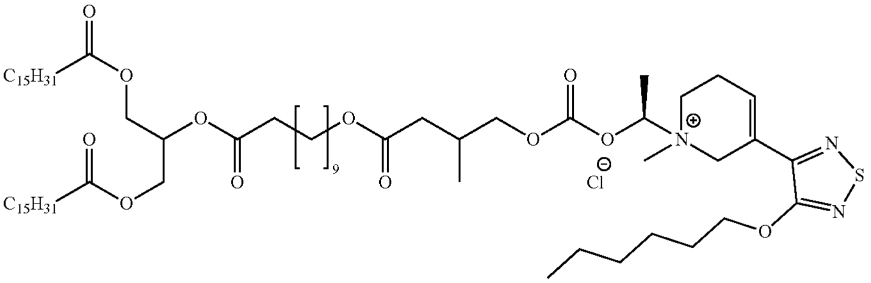 |

TABLE 1-continued
| Cpd No. | Structure |
|---|---|
| 867 | 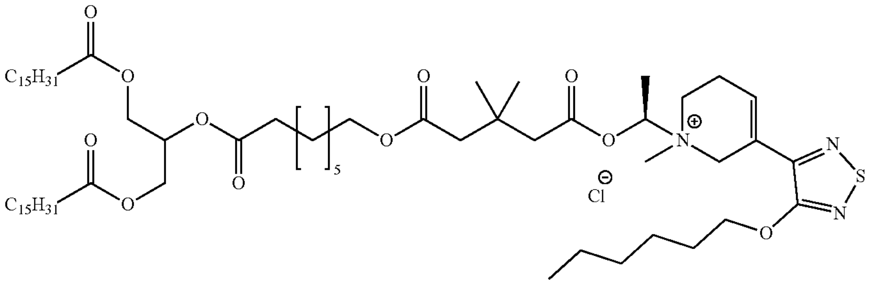 |
| 868 | 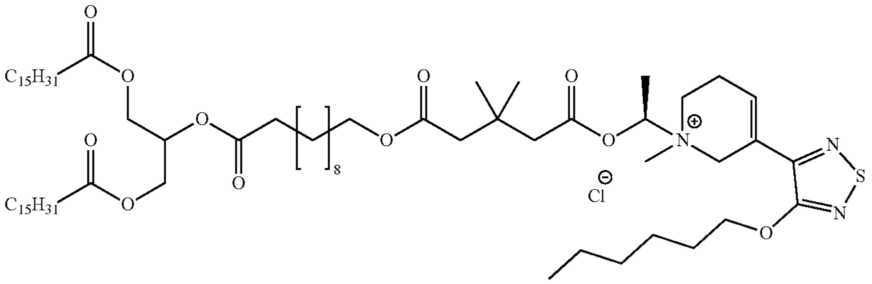 |
| 869 | 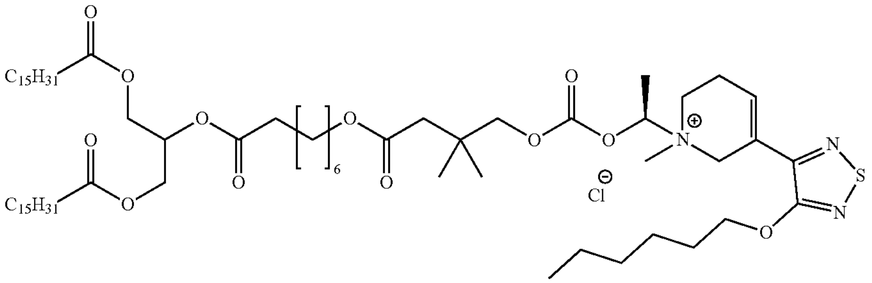 |
| 870 | 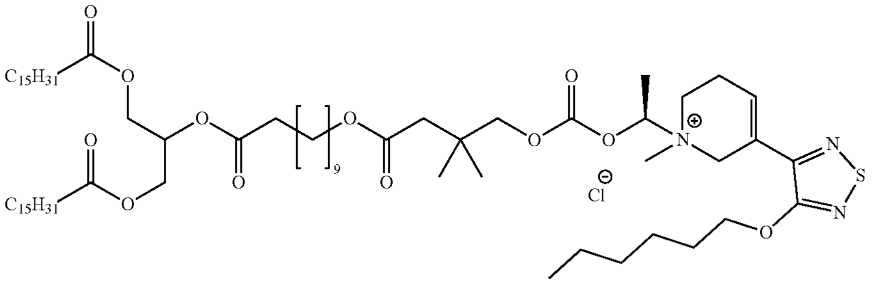 |
| 871 | 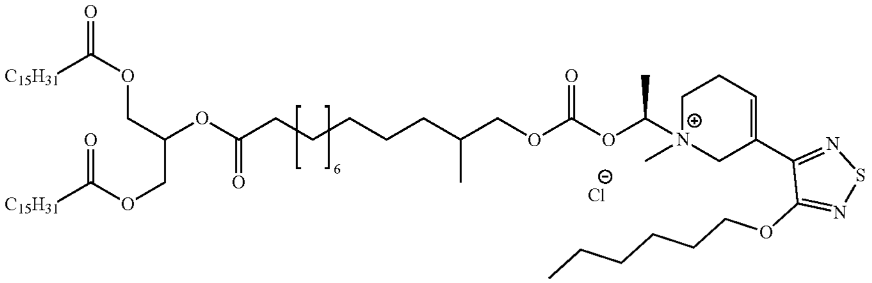 |

TABLE 1-continued
| Cpd No. | Structure |
|---|---|
| 872 | 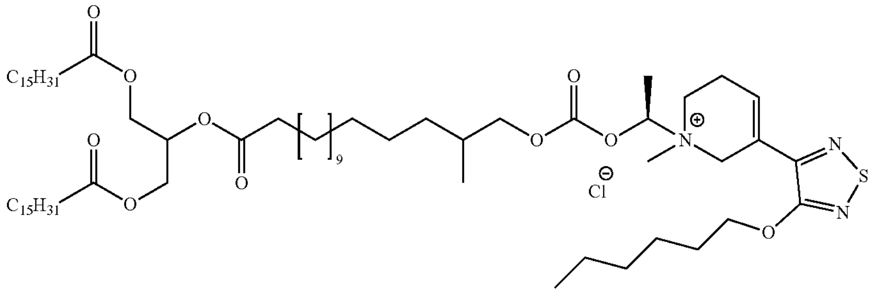 |
| 873 | 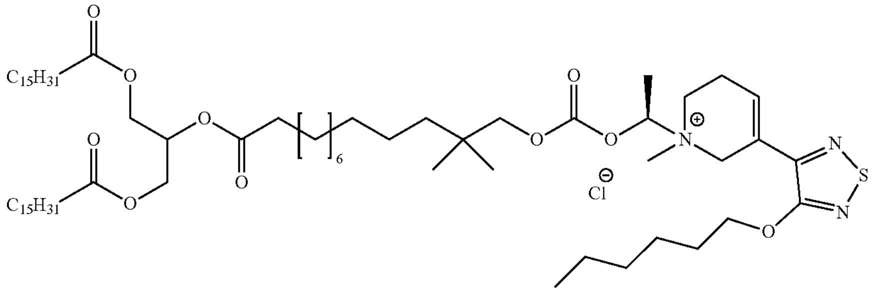 |
| 874 | 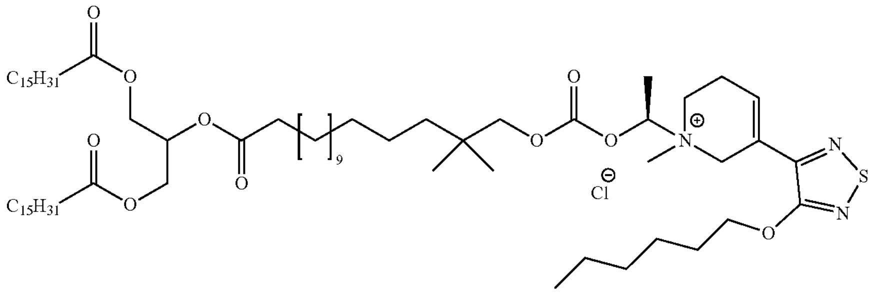 |
| 875 | 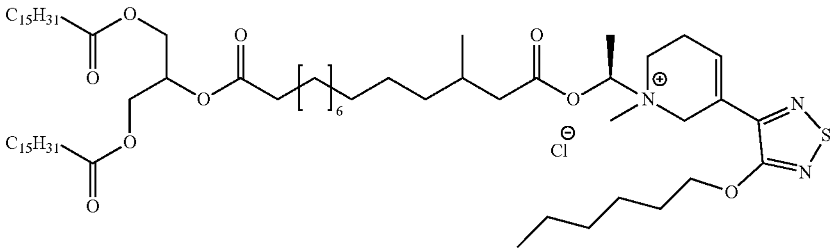 |
| 876 | 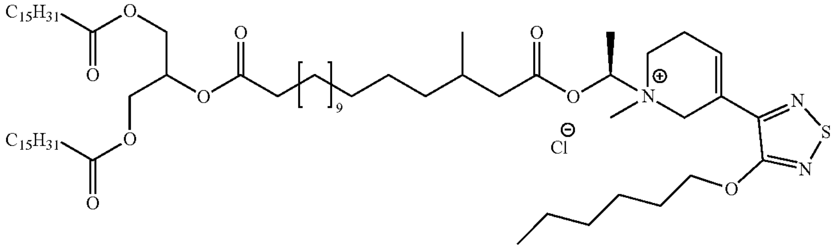 |

TABLE 1-continued
| Cpd No. | Structure |
| --- | --- |
| 877 | 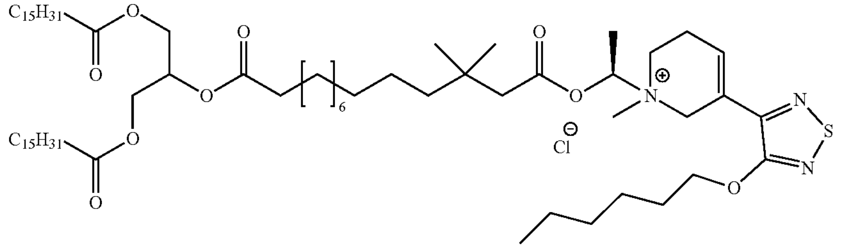 |
| 878 | 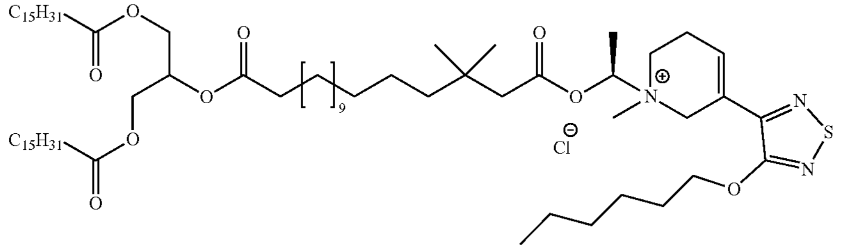 |
| 879 | 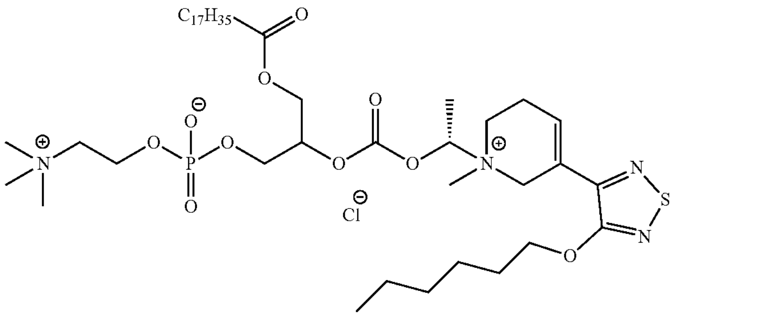 |
| 880 | 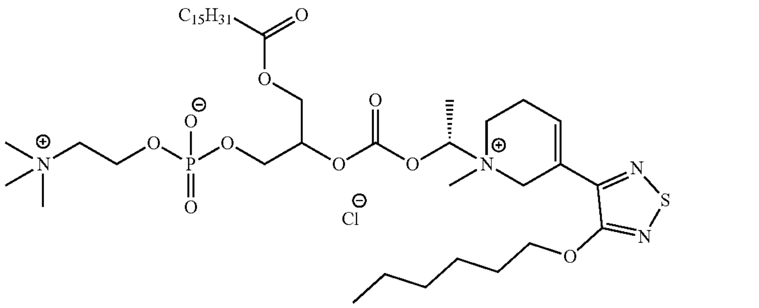 |
| 881 | 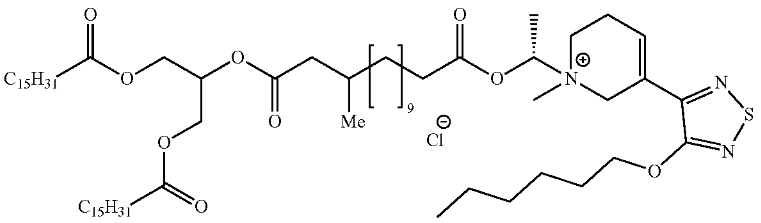 |
| 882 | 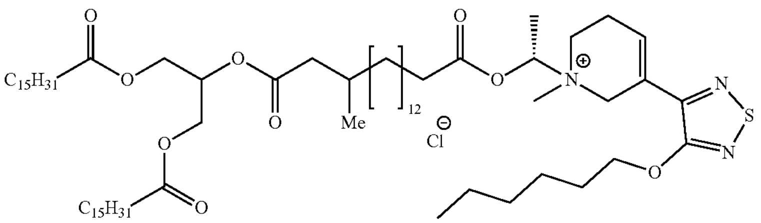 |

TABLE 1-continued
| Cpd No. | Structure |
| --- | --- |
| 883 | 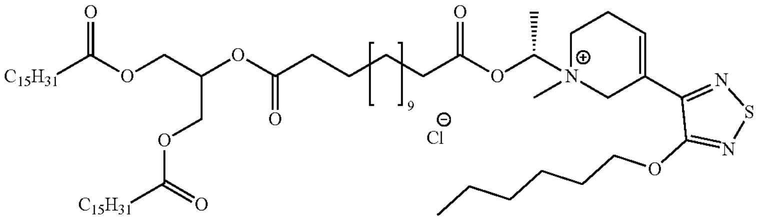 |
| 884 | 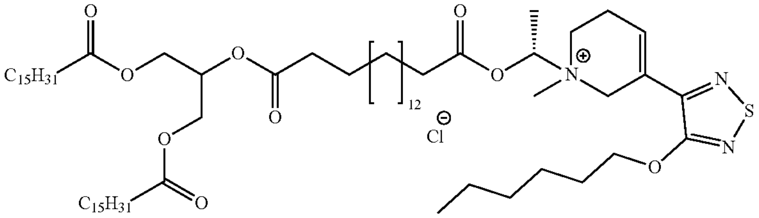 |
| 885 | 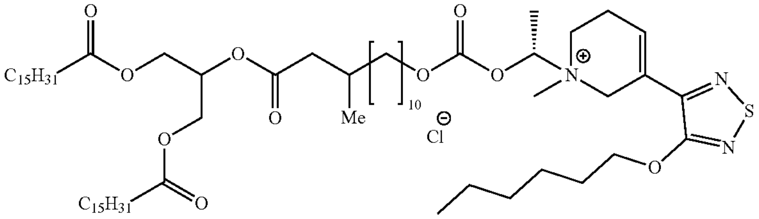 |
| 886 | 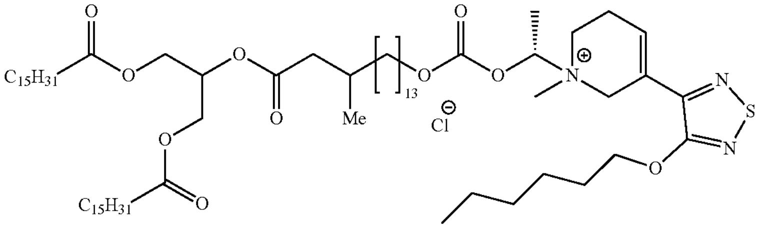 |
| 887 | 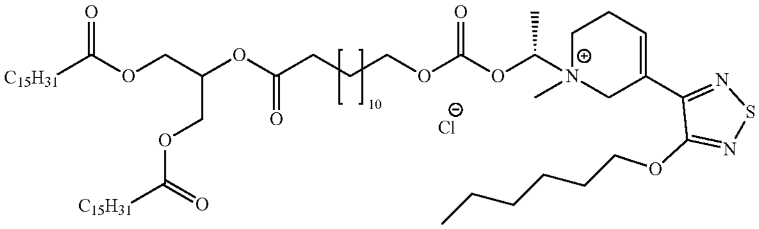 |
| 888 | 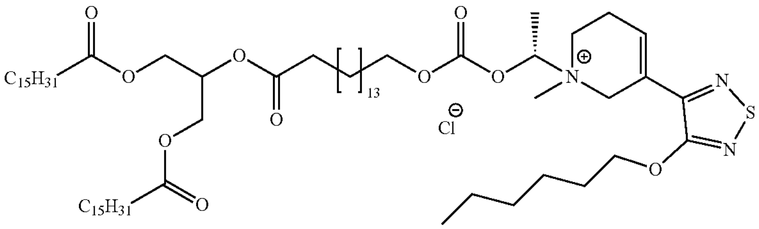 |

TABLE 1-continued
| Cpd No. | Structure |
|---|---|
| 889 | 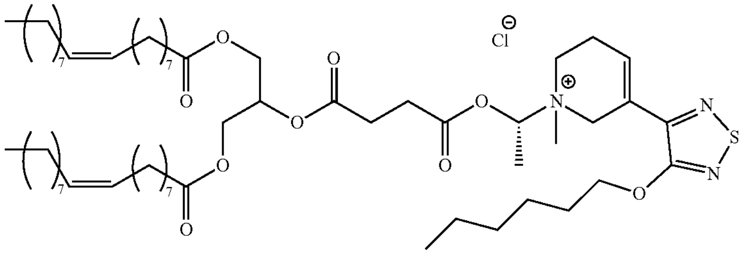 |
| 890 | 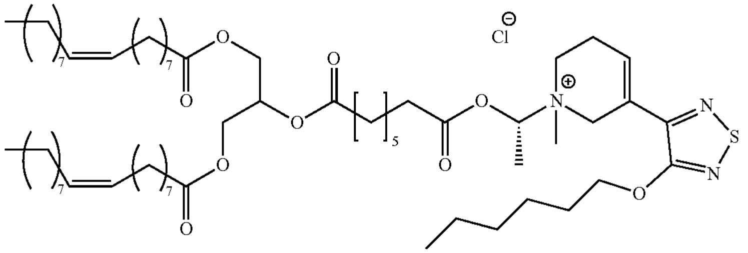 |
| 891 | 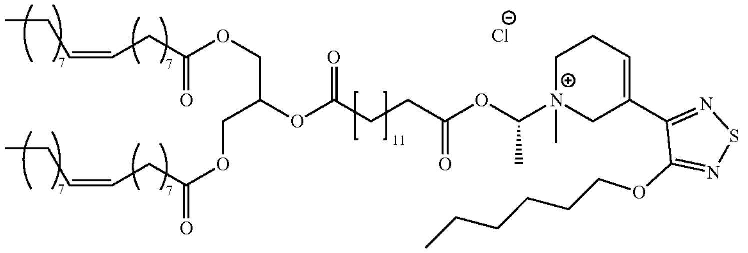 |
| 892 | 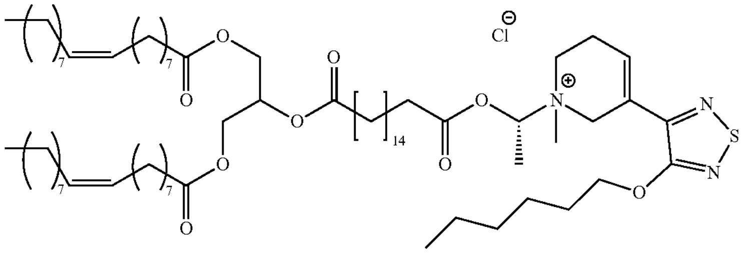 |
| 893 | 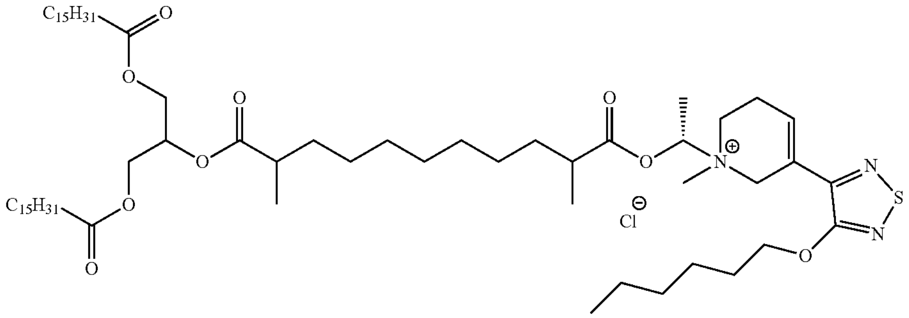 |

TABLE 1-continued
| Cpd No. | Structure |
|---|---|
| 894 | 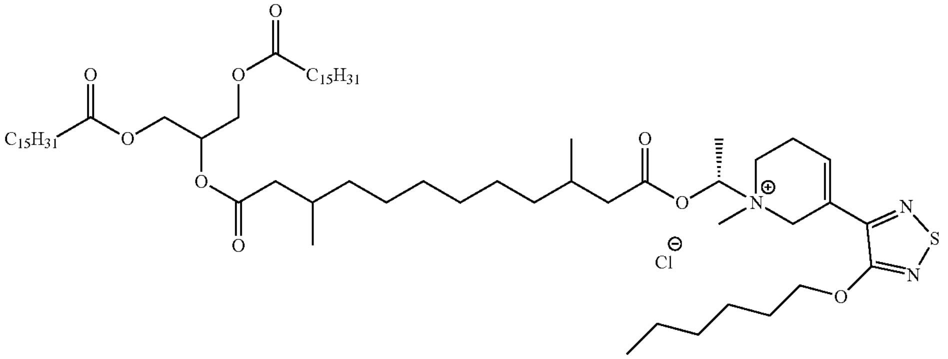 |
| 895 | 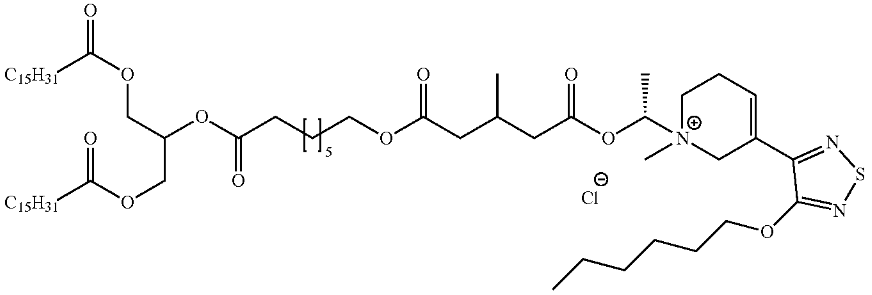 |
| 896 | 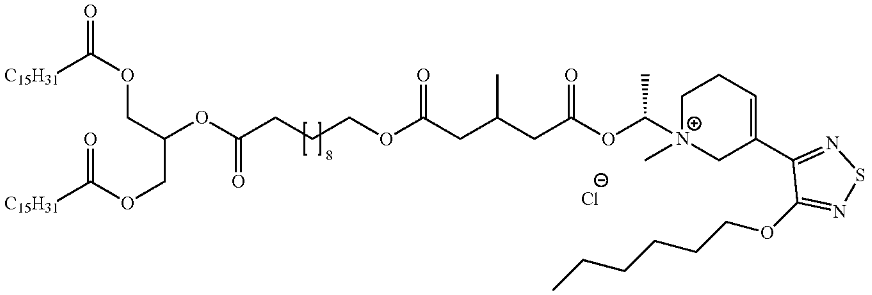 |
| 897 | 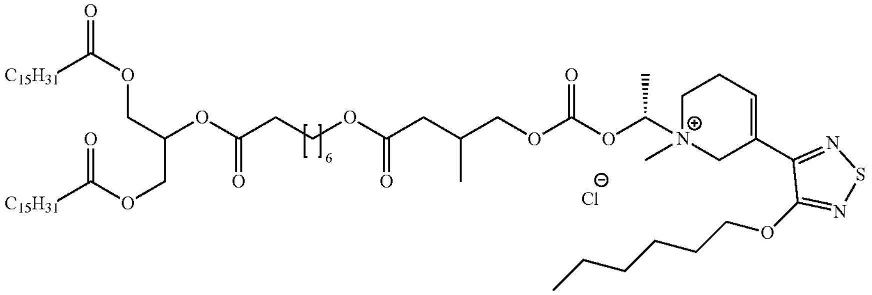 |
| 898 | 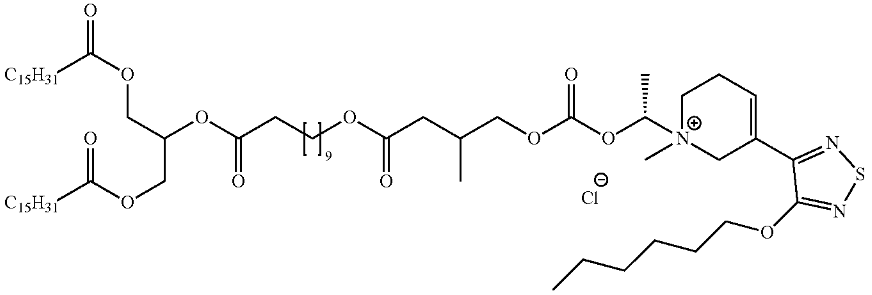 |

TABLE 1-continued
| Cpd No. | Structure |
|---|---|
| 899 | 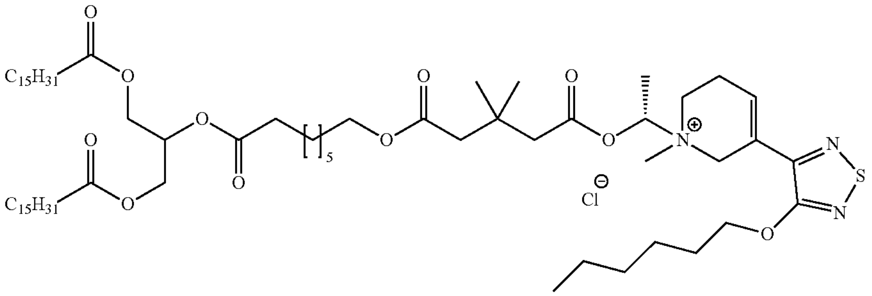 |
| 900 | 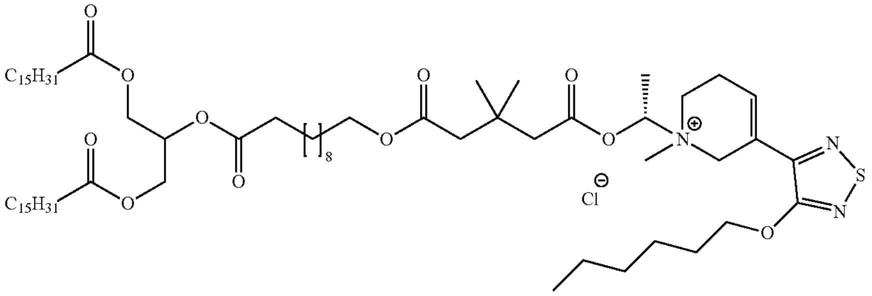 |
| 901 | 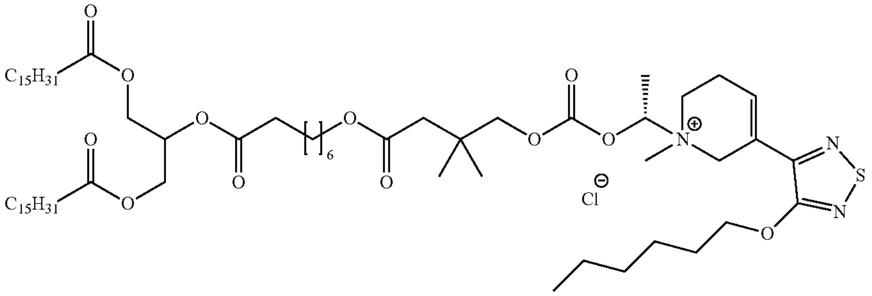 |
| 902 | 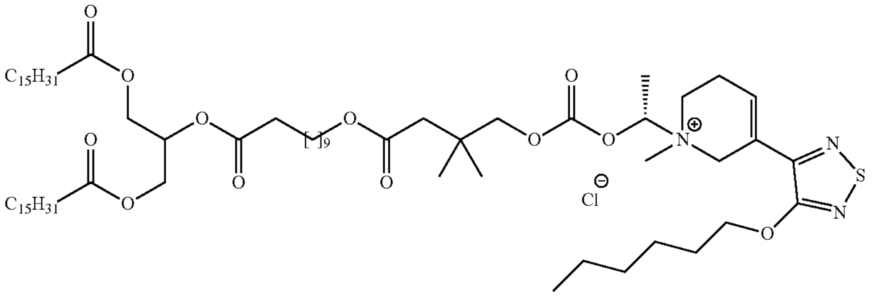 |
| 903 | 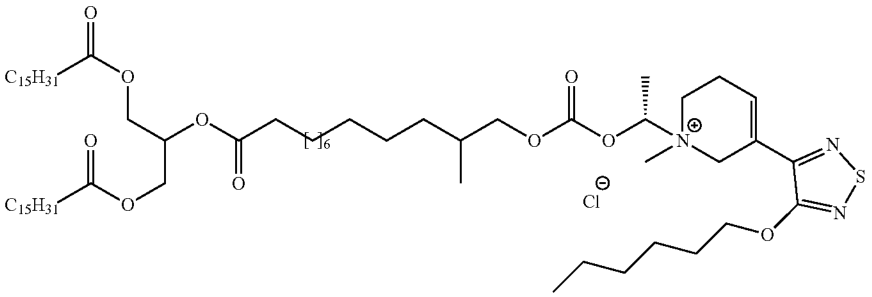 |

TABLE 1-continued
| Cpd No. | Structure |
|---|---|
| 904 | 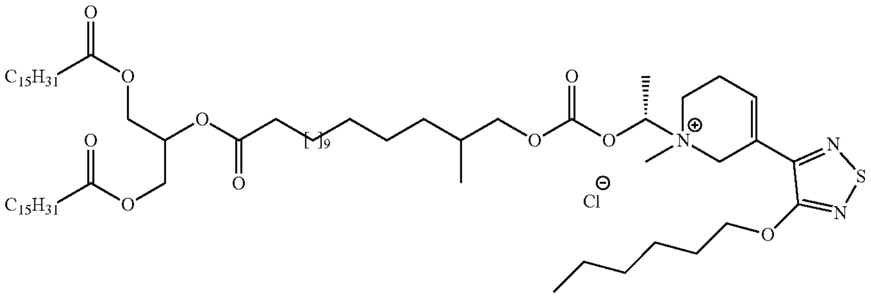 |
| 905 | 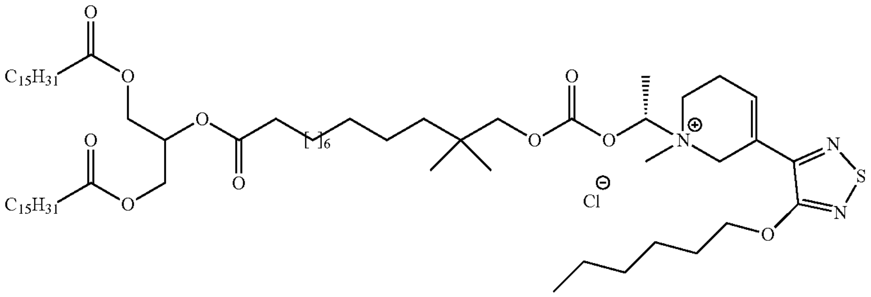 |
| 906 | 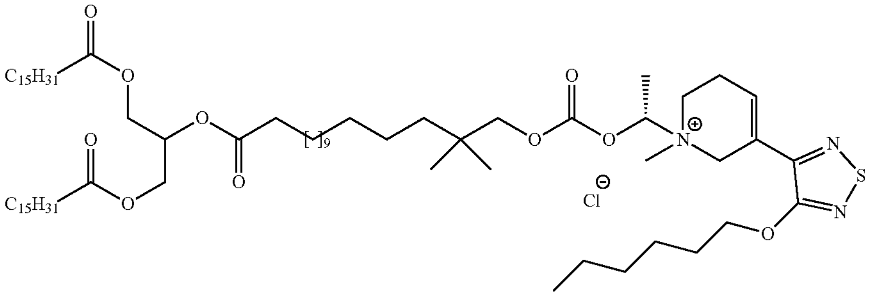 |
| 907 | 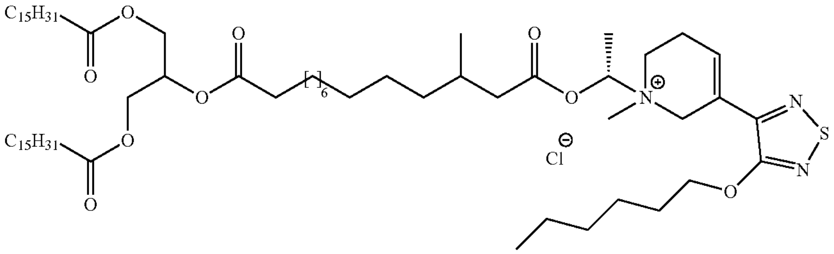 |
| 908 | 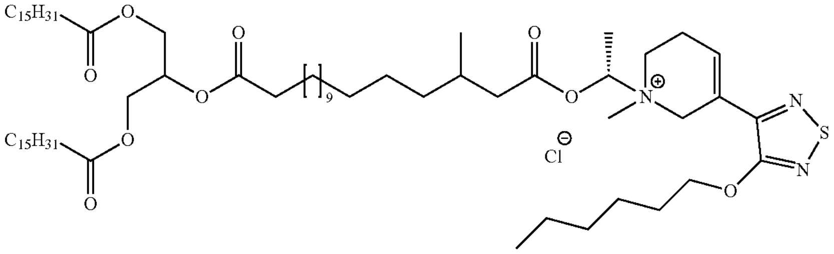 |

TABLE 1-continued
| Cpd No. | Structure |
|---|---|
| 909 | 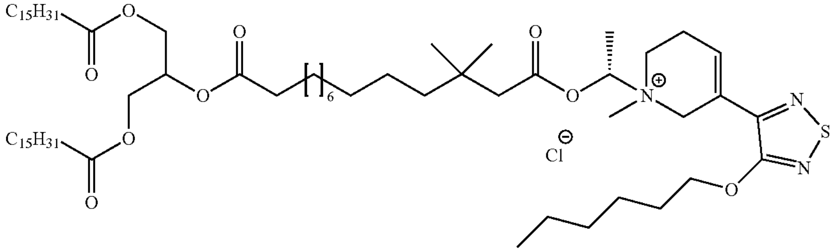 |
| 910 | 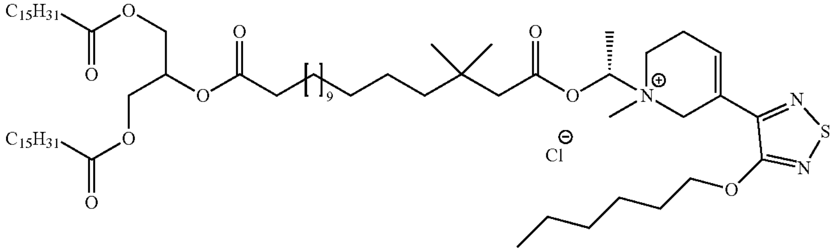 |
| 911 | 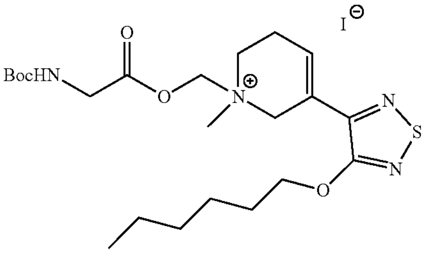 [SMILES: [I-] ; CCCCCCOc1nsnc1C1=CCC[N+](C)(COC(=O)CNC(=O)OC(C)(C)C)C1] |
| 912 | 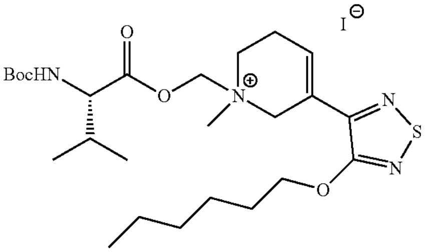 [SMILES: [I-] ; CCCCCCOc1nsnc1C1=CCC[N+](C)(COC(=O)[C@@H](NC(=O)OC(C)(C)C)C(C)C)C1] |
| 913 | 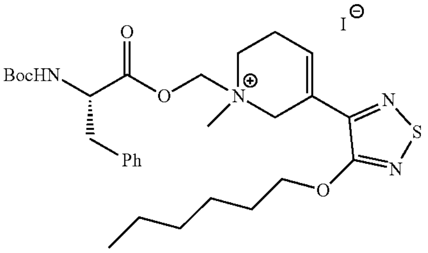 [SMILES: [I-] ; CCCCCCOc1nsnc1C1=CCC[N+](C)(COC(=O)[C@H](Cc2ccccc2)NC(=O)OC(C)(C)C)C1] |
| 914 | 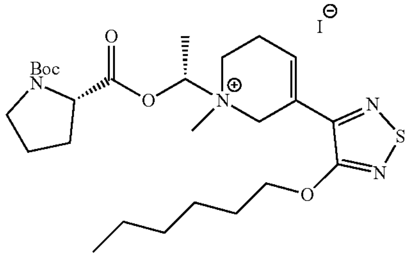<br>L-amino acid |

TABLE 1-continued
| Cpd No. | Structure |
|---|---|
| 915 | 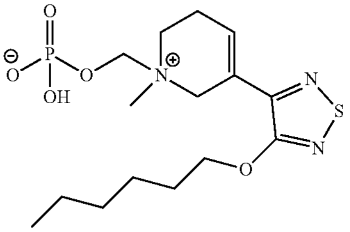 [SMILES: CCCCCCOc1nsnc1C1=CCC[N+](C)(COP(=O)([O-])O)C1] |
| 916 | 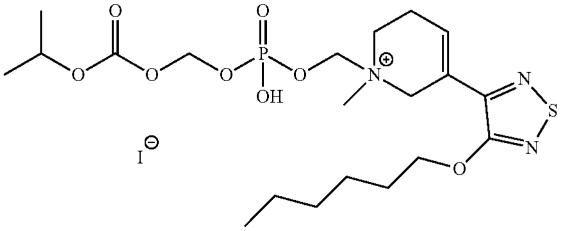 [SMILES: CCCCCCOc1nsnc1C1=CCC[N+](C)(COP(=O)(O)OCOC(=O)OC(C)C)C1 ; [I-]] |
| 917 | 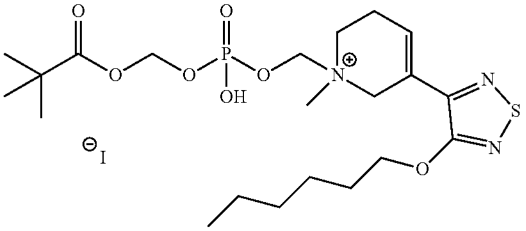 [SMILES: CCCCCCOc1nsnc1C1=CCC[N+](C)(COP(=O)(O)OCOC(=O)C(C)(C)C)C1 ; [I-]] |
| 918 | 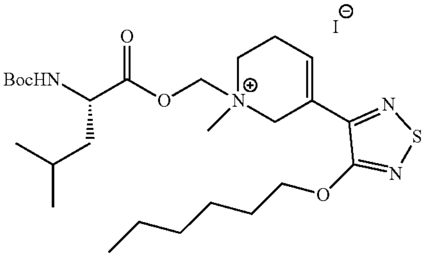 [SMILES: [I-] ; CCCCCCOc1nsnc1C1=CCC[N+](C)(COC(=O)[C@H](CC(C)C)NC(=O)OC(C)(C)C)C1] |
| 919 | 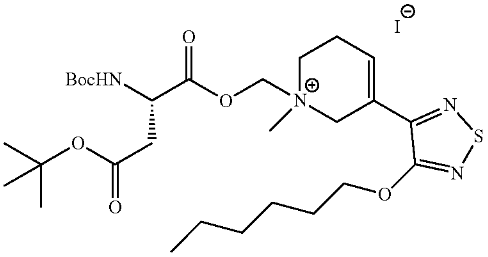 [SMILES: [I-] ; CCCCCCOc1nsnc1C1=CCC[N+](C)(COC(=O)[C@H](CC(=O)OC(C)(C)C)NC(=O)OC(C)(C)C)C1] |
| 920 | 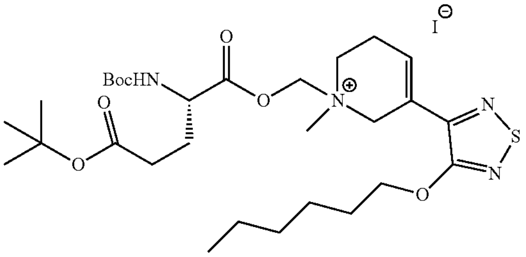 [SMILES: [I-] ; CCCCCCOc1nsnc1C1=CCC[N+](C)(COC(=O)[C@H](CCC(=O)OC(C)(C)C)NC(=O)OC(C)(C)C)C1] |

TABLE 1-continued
| Cpd No. | Structure |
|---|---|
| 921 | 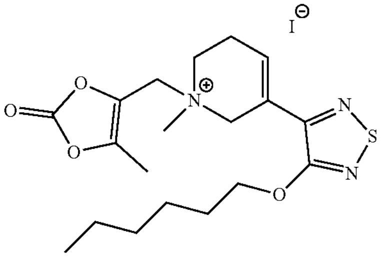 [SMILES: [I-] ; CCCCCCOc1nsnc1C1=CCC[N+](C)(Cc2oc(=O)oc2C)C1] |
| 922 | 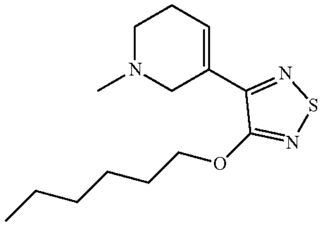<br>Xanomeline |
In some embodiments, a compound disclosed in TABLE 1 is administered in combination with an analog of trospium chloride, including compounds disclosed in TABLE 2. The compounds disclosed in TABLE 2 include compounds intended to act as prodrugs of Trospium.
TABLE 2
| Cpd No. | Structure |
|---|---|
| 1 | 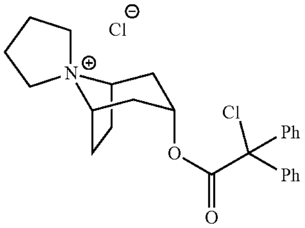 [SMILES: O=C(OC1CC2CCC(C1)[N+]21CCCC1)C(Cl)(c1ccccc1)c1ccccc1 ; [Cl-]] |
| 2 | 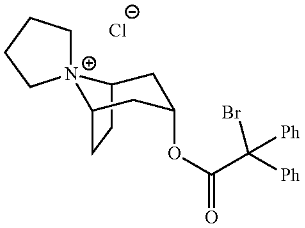 [SMILES: O=C(OC1CC2CCC(C1)[N+]21CCCC1)C(Br)(c1ccccc1)c1ccccc1 ; [Cl-]] |
| 3 | 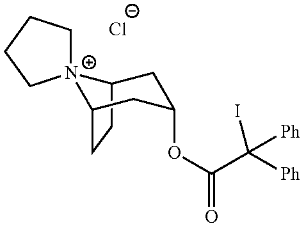 [SMILES: O=C(OC1CC2CCC(C1)[N+]21CCCC1)C(I)(c1ccccc1)c1ccccc1 ; [Cl-]] |

TABLE 2-continued
| Cpd No. | Structure |
| --- | --- |
| 4 | 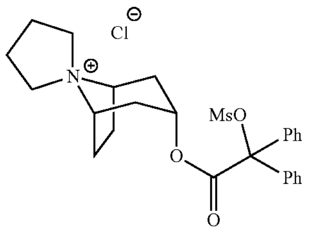 [SMILES: CS(=O)(=O)OC(C(=O)OC1CC2CCC(C1)[N+]21CCCC1)(c1ccccc1)c1ccccc1 ; [Cl-]] |
| 5 | 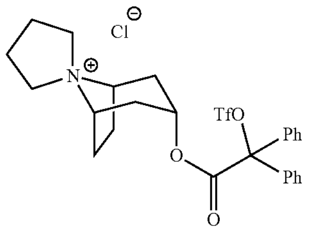 [SMILES: O=C(OC1CC2CCC(C1)[N+]21CCCC1)C(OS(=O)(=O)C(F)(F)F)(c1ccccc1)c1ccccc1 ; [Cl-]] |
| 6 | 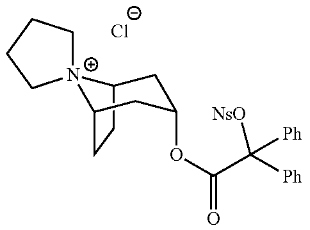 |
| 7 | 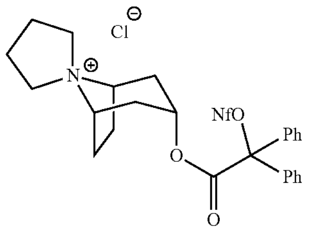 |
| 8 | 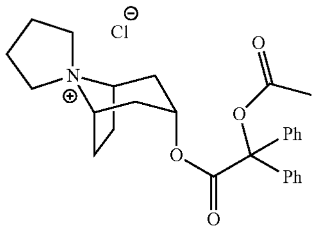 [SMILES: CC(=O)OC(C(=O)OC1CC2CCC(C1)[N+]21CCCC1)(c1ccccc1)c1ccccc1 ; [Cl-]] |
| 9 | 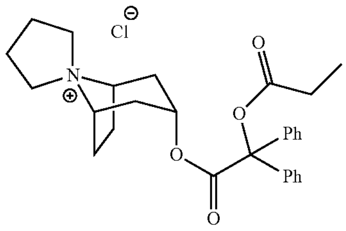 [SMILES: CCC(=O)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 10 | 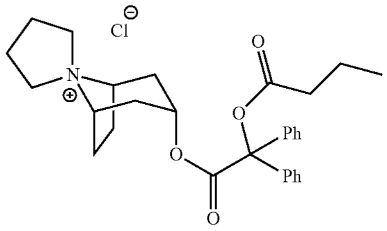 [SMILES: CCCC(=O)OC(C(=O)OC1CC2CCC(C1)[N+]21CCCC1)(c1ccccc1)c1ccccc1 ; [Cl-]] |
| 11 | 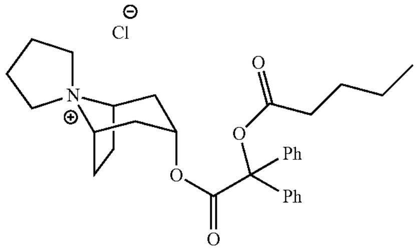 [SMILES: [Cl-] ; CCCCC(=O)OC(C(=O)OC1CC2CCC(C1)[N+]21CCCC1)(c1ccccc1)c1ccccc1] |
| 12 | 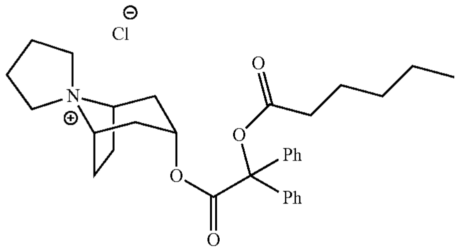 [SMILES: [Cl-] ; CCCCCC(=O)OC(C(=O)OC1CC2CCC(C1)[N+]21CCCC1)(c1ccccc1)c1ccccc1] |
| 13 | 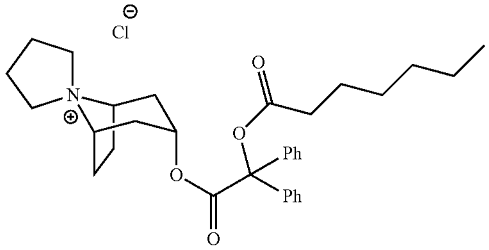 [SMILES: [Cl-] ; CCCCCCC(=O)OC(C(=O)OC1CC2CCC(C1)[N+]21CCCC1)(c1ccccc1)c1ccccc1] |
| 14 | 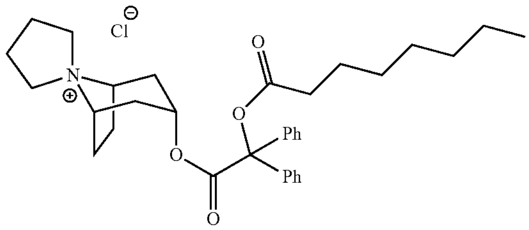 [SMILES: CCCCCCCC(=O)OC(C(=O)OC1CC2CCC(C1)[N+]21CCCC1)(c1ccccc1)c1ccccc1 ; [Cl-]] |
| 15 | 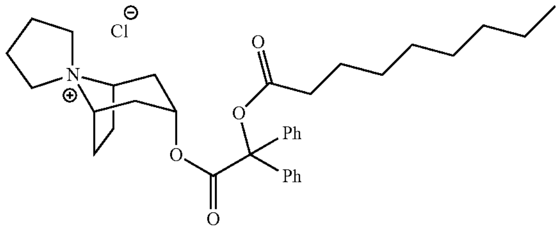 [SMILES: CCCCCCCCC(=O)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 16 | 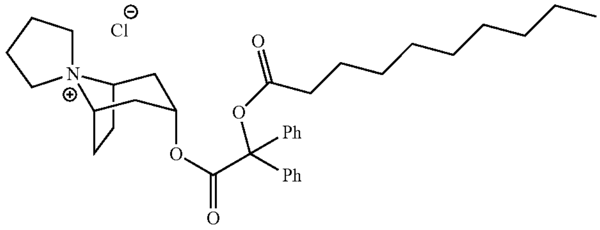 [SMILES: CCCCCCCCCC(=O)OC(C(=O)OC1CC2CCC(C1)[N+]21CCCC1)(c1ccccc1)c1ccccc1 ; [Cl-]] |
| 17 | 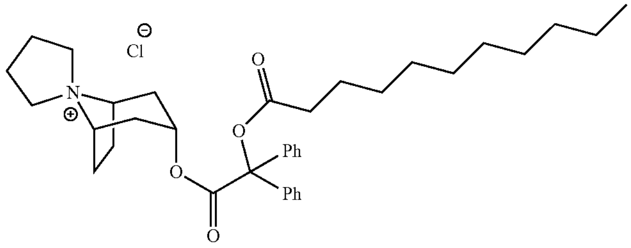 [SMILES: CCCCCCCCCCC(=O)OC(C(=O)OC1CC2CCC(C1)[N+]21CCCC1)(c1ccccc1)c1ccccc1 ; [Cl-]] |
| 18 | 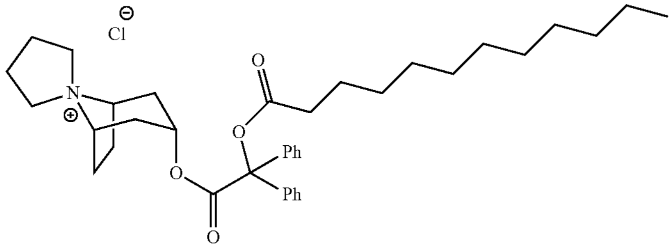 [SMILES: CCCCCCCCCCCC(=O)OC(C(=O)OC1CC2CCC(C1)[N+]21CCCC1)(c1ccccc1)c1ccccc1 ; [Cl-]] |
| 19 | 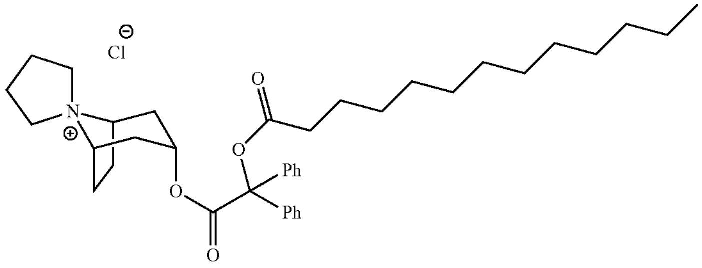 [SMILES: CCCCCCCCCCCCC(=O)OC(C(=O)OC1CC2CCC(C1)[N+]21CCCC1)(c1ccccc1)c1ccccc1 ; [Cl-]] |
| 20 | 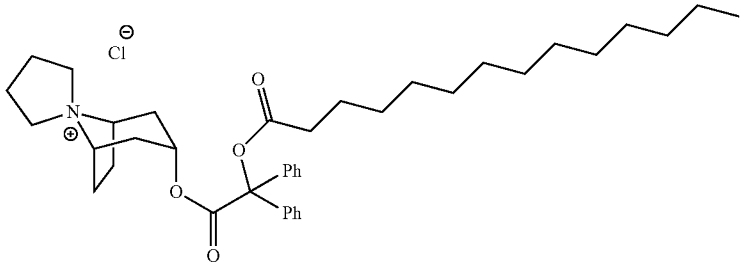 [SMILES: CCCCCCCCCCCCCC(=O)OC(C(=O)OC1CC2CCC(C1)[N+]21CCCC1)(c1ccccc1)c1ccccc1 ; [Cl-]] |
| 21 | 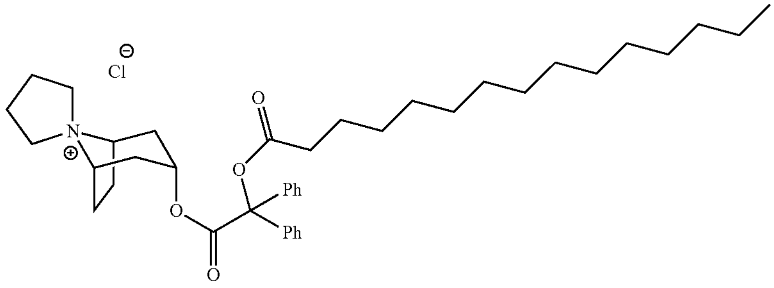 [SMILES: CCCCCCCCCCCCCCC(=O)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 22 | 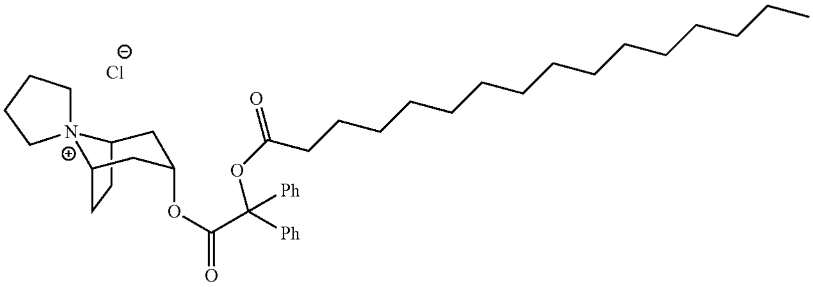 |
| 23 | 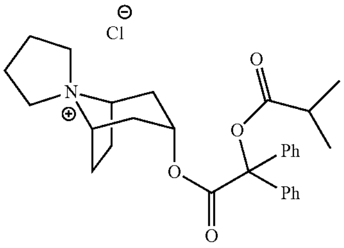 [SMILES: [Cl-] ; CC(C)C(=O)OC(C(=O)OC1CC2CCC(C1)[N+]21CCCC1)(c1ccccc1)c1ccccc1] |
| 24 | 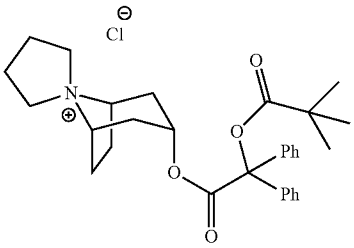 [SMILES: [Cl-] ; CC(C)(C)C(=O)OC(C(=O)OC1CC2CCC(C1)[N+]21CCCC1)(c1ccccc1)c1ccccc1] |
| 25 | 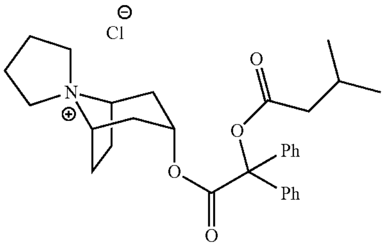 [SMILES: [Cl-] ; CC(C)CC(=O)OC(C(=O)OC1CC2CCC(C1)[N+]21CCCC1)(c1ccccc1)c1ccccc1] |
| 26 | 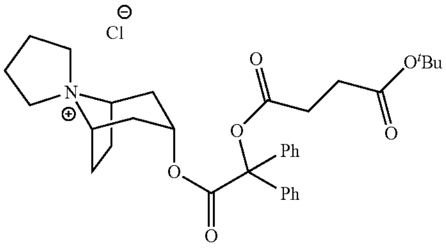 [SMILES: [Cl-] ; CC(C)(C)OC(=O)CCC(=O)OC(C(=O)OC1CC2CCC(C1)[N+]21CCCC1)(c1ccccc1)c1ccccc1] |
| 27 | 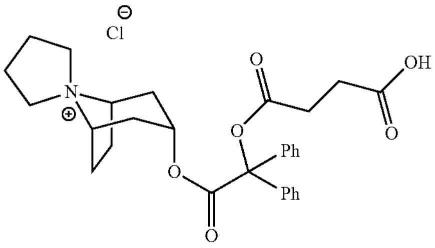 [SMILES: [Cl-] ; O=C(O)CCC(=O)OC(C(=O)OC1CC2CCC(C1)[N+]21CCCC1)(c1ccccc1)c1ccccc1] |

TABLE 2-continued
| Cpd No. | Structure |
|---|---|
| 28 | 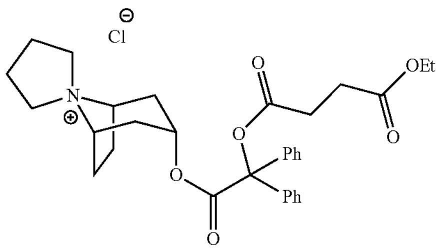 [SMILES: [Cl-] ; CCOC(=O)CCC(=O)OC(C(=O)OC1CC2CCC(C1)[N+]21CCCC1)(c1ccccc1)c1ccccc1] |
| 29 | 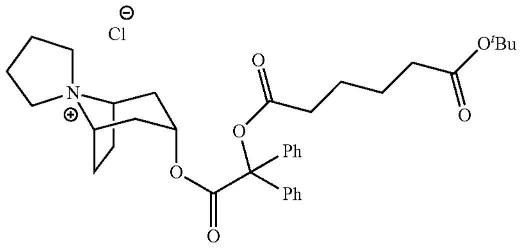 [SMILES: [Cl-] ; CC(C)(C)OC(=O)CCCCC(=O)OC(C(=O)OC1CC2CCC(C1)[N+]21CCCC1)(c1ccccc1)c1ccccc1] |
| 30 | 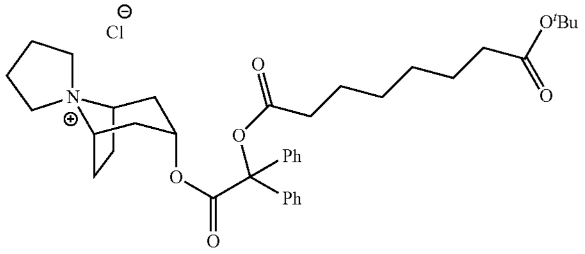 [SMILES: CC(C)(C)OC(=O)CCCCCCC(=O)OC(C(=O)OC1CC2CCC(C1)[N+]21CCCC1)(c1ccccc1)c1ccccc1 ; [Cl-]] |
| 31 | 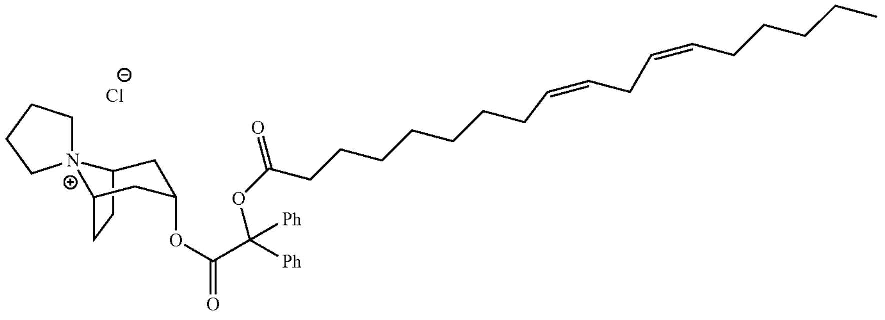 [SMILES: CCCCC/C=C\C/C=C\CCCCCCCC(=O)OC(C(=O)OC1CC2CCC(C1)[N+]21CCCC1)(c1ccccc1)c1ccccc1 ; [Cl-]] |
| 32 | 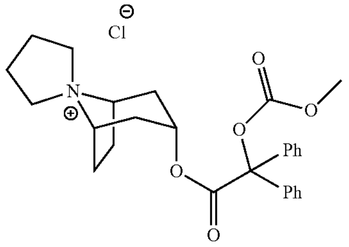 [SMILES: [Cl-] ; COC(=O)OC(C(=O)OC1CC2CCC(C1)[N+]21CCCC1)(c1ccccc1)c1ccccc1] |

TABLE 2-continued
| Cpd No. | Structure |
|---|---|
| 33 | 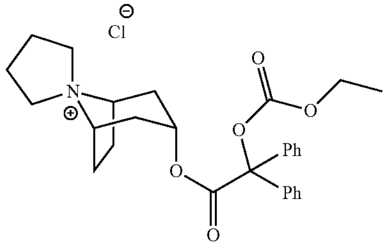 [SMILES: [Cl-] ; CCOC(=O)OC(C(=O)OC1CC2CCC(C1)[N+]21CCCC1)(c1ccccc1)c1ccccc1] |
| 34 | 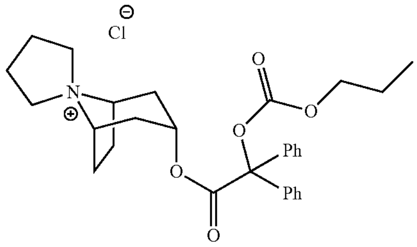 [SMILES: [Cl-] ; CCCOC(=O)OC(C(=O)OC1CC2CCC(C1)[N+]21CCCC1)(c1ccccc1)c1ccccc1] |
| 35 | 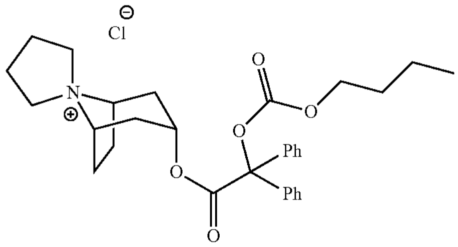 [SMILES: [Cl-] ; CCCCOC(=O)OC(C(=O)OC1CC2CCC(C1)[N+]21CCCC1)(c1ccccc1)c1ccccc1] |
| 36 | 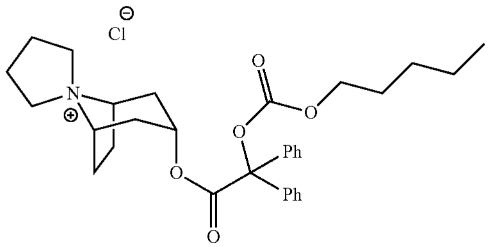 [SMILES: [Cl-] ; CCCCCOC(=O)OC(C(=O)OC1CC2CCC(C1)[N+]21CCCC1)(c1ccccc1)c1ccccc1] |
| 37 | 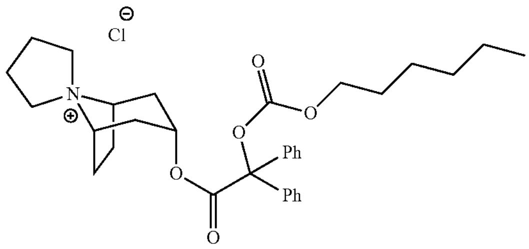 [SMILES: [Cl-] ; CCCCCCOC(=O)OC(C(=O)OC1CC2CCC(C1)[N+]21CCCC1)(c1ccccc1)c1ccccc1] |
| 38 | 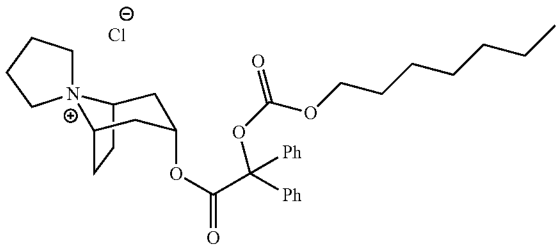 [SMILES: CCCCCCCOC(=O)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 39 | 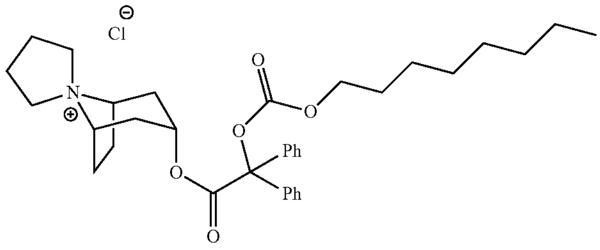 [SMILES: CCCCCCCCOC(=O)OC(C(=O)OC1CC2CCC(C1)[N+]21CCCC1)(c1ccccc1)c1ccccc1 ; [Cl-]] |
| 40 | 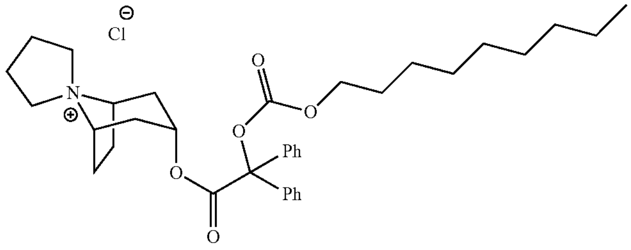 [SMILES: CCCCCCCCCOC(=O)OC(C(=O)OC1CC2CCC(C1)[N+]21CCCC1)(c1ccccc1)c1ccccc1 ; [Cl-]] |
| 41 | 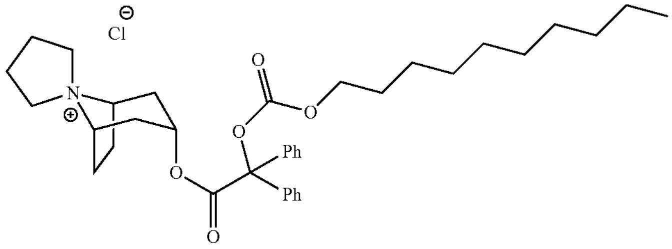 [SMILES: CCCCCCCCCCOC(=O)OC(C(=O)OC1CC2CCC(C1)[N+]21CCCC1)(c1ccccc1)c1ccccc1 ; [Cl-]] |
| 42 | 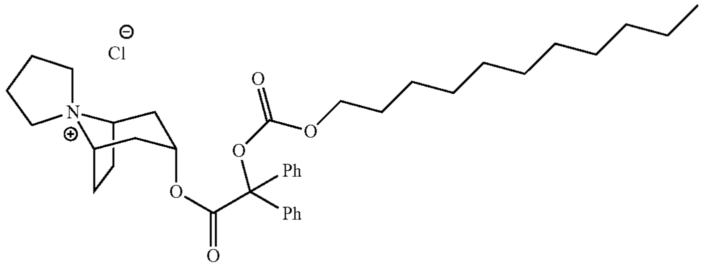 |
| 43 | 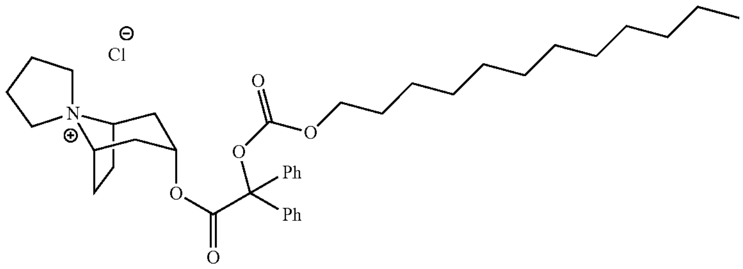 |

TABLE 2-continued
| Cpd No. | Structure |
|---|---|
| 44 | 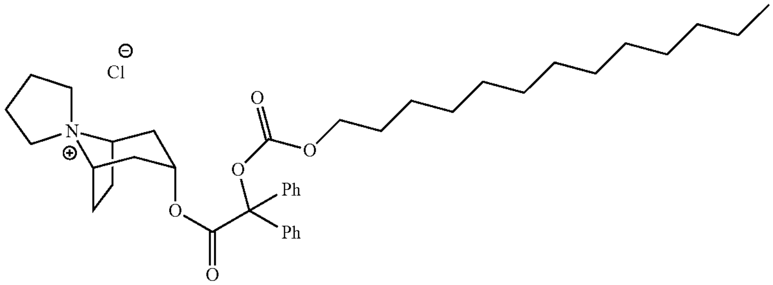 |
| 45 | 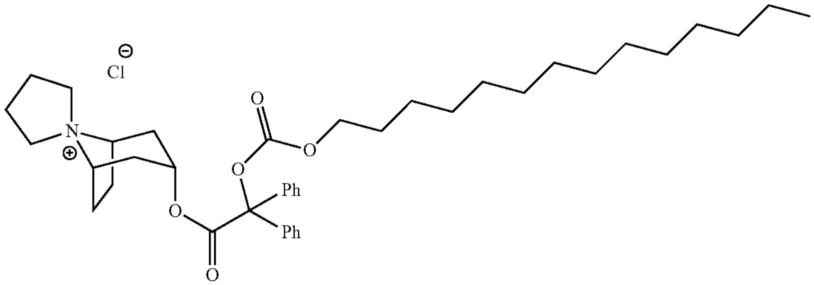 |
| 46 | 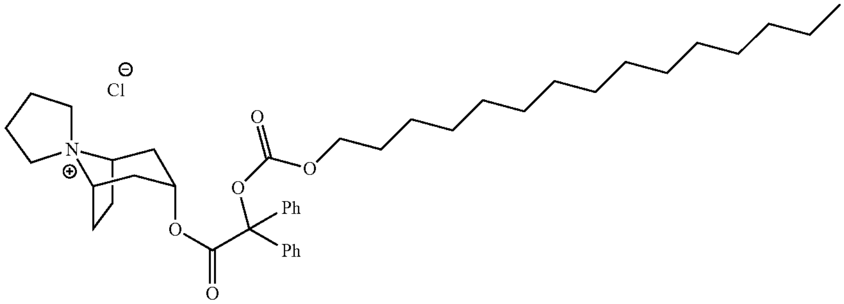 [SMILES: CCCCCCCCCCCCCCCOC(=O)OC(C(=O)OC1CC2CCC(C1)[N+]21CCCC1)(c1ccccc1)c1ccccc1 ; [Cl-]] |
| 47 | 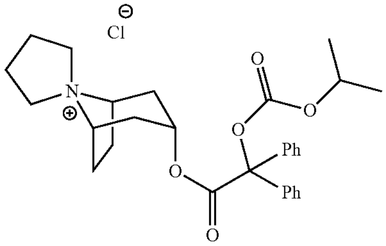 [SMILES: [Cl-] ; CC(C)OC(=O)OC(C(=O)OC1CC2CCC(C1)[N+]21CCCC1)(c1ccccc1)c1ccccc1] |
| 48 | 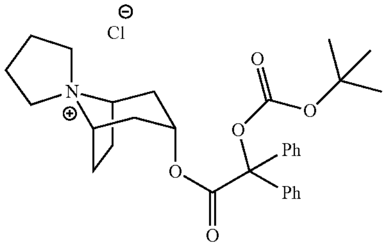 [SMILES: [Cl-] ; CC(C)(C)OC(=O)OC(C(=O)OC1CC2CCC(C1)[N+]21CCCC1)(c1ccccc1)c1ccccc1] |

TABLE 2-continued
| Cpd No. | Structure |
|---|---|
| 49 | 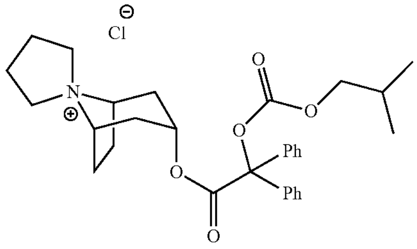 [SMILES: [Cl-] ; CC(C)COC(=O)OC(C(=O)OC1CC2CCC(C1)[N+]21CCCC1)(c1ccccc1)c1ccccc1] |
| 50 | 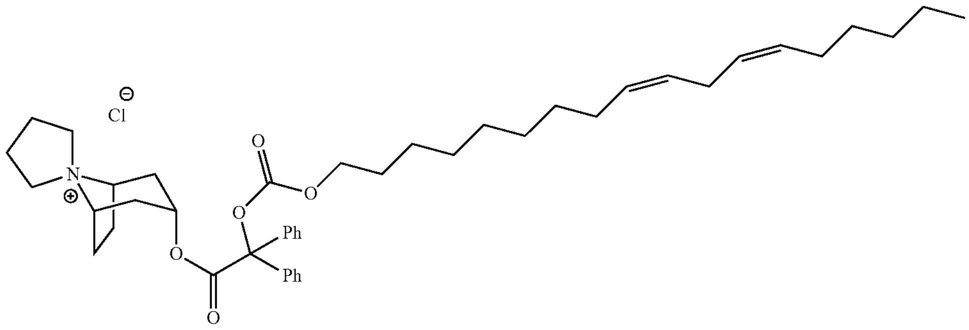 [SMILES: CCCCC/C=C\C/C=C\CCCCCCCCOC(=O)OC(C(=O)OC1CC2CCC(C1)[N+]21CCCC1)(c1ccccc1)c1ccccc1 ; [Cl-]] |
| 51 | 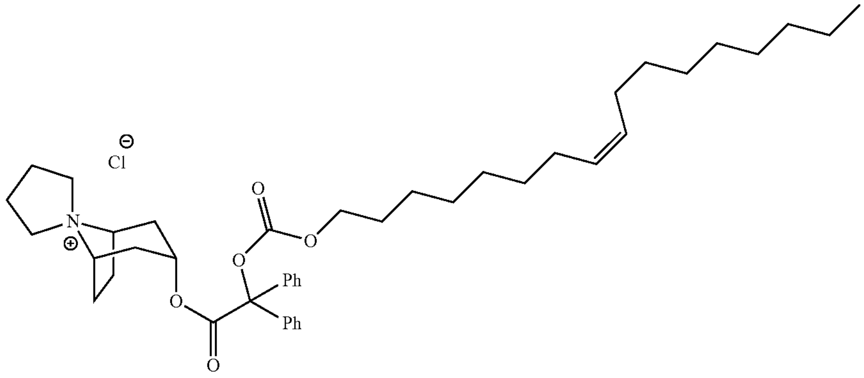 [SMILES: CCCCCCCC/C=C\CCCCCCCOC(=O)OC(C(=O)OC1CC2CCC(C1)[N+]21CCCC1)(c1ccccc1)c1ccccc1 ; [Cl-]] |
| 52 | 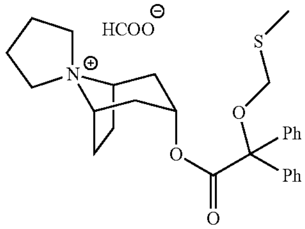 |
| 53 | 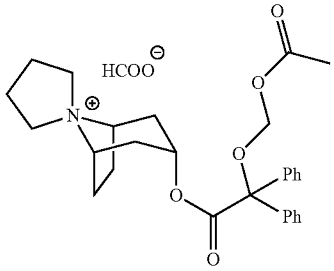 |

TABLE 2-continued
| Cpd No. | Structure |
|---|---|
| 54 | 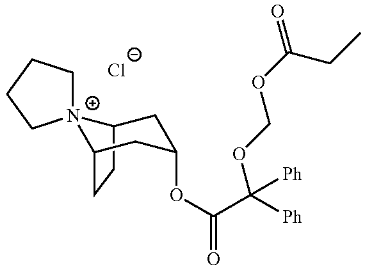 [SMILES: CCC(=O)OCOC(C(=O)OC1CC2CCC(C1)[N+]21CCCC1)(c1ccccc1)c1ccccc1 ; [Cl-]] |
| 55 | 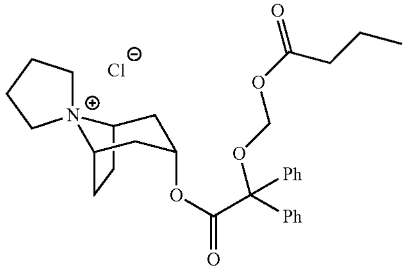 [SMILES: CCCC(=O)OCOC(C(=O)OC1CC2CCC(C1)[N+]21CCCC1)(c1ccccc1)c1ccccc1 ; [Cl-]] |
| 56 | 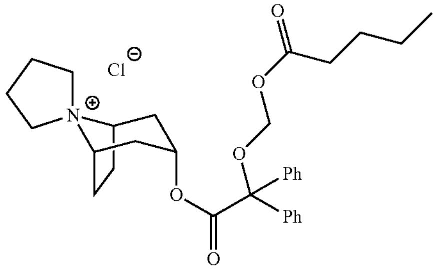 [SMILES: CCCCC(=O)OCOC(C(=O)OC1CC2CCC(C1)[N+]21CCCC1)(c1ccccc1)c1ccccc1 ; [Cl-]] |
| 57 | 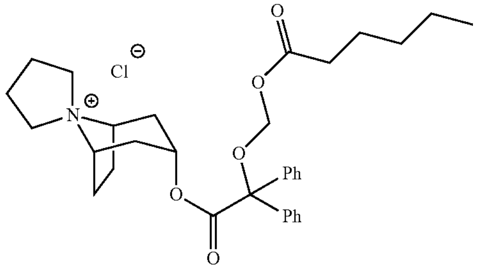 [SMILES: CCCCCC(=O)OCOC(C(=O)OC1CC2CCC(C1)[N+]21CCCC1)(c1ccccc1)c1ccccc1 ; [Cl-]] |
| 58 | 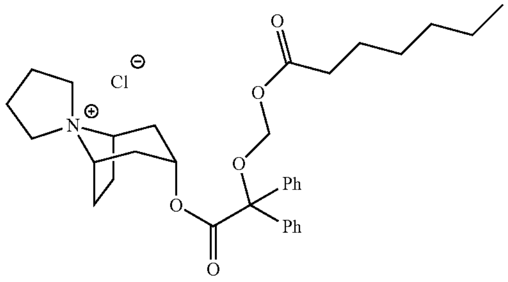 [SMILES: CCCCCCC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 59 | 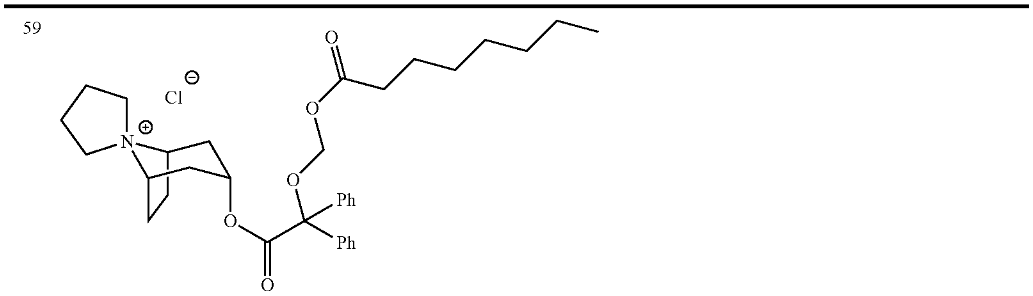 |
| 60 | 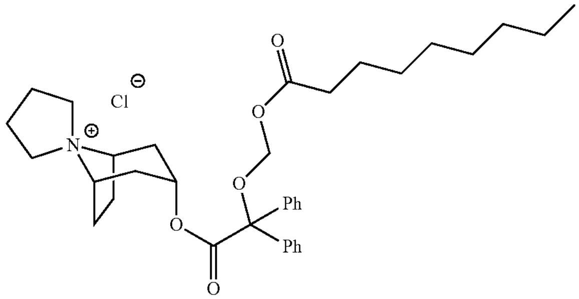 [SMILES: CCCCCCCCC(=O)OCOC(C(=O)OC1CC2CCC(C1)[N+]21CCCC1)(c1ccccc1)c1ccccc1 ; [Cl-]] |
| 61 | 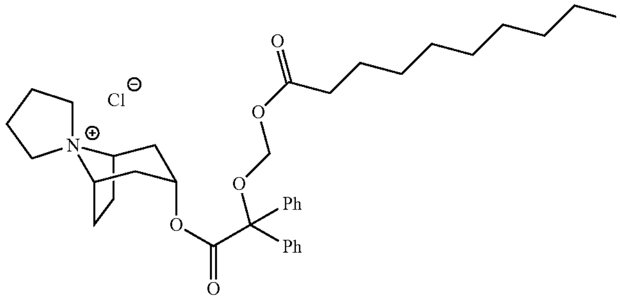 [SMILES: CCCCCCCCCC(=O)OCOC(C(=O)OC1CC2CCC(C1)[N+]21CCCC1)(c1ccccc1)c1ccccc1 ; [Cl-]] |
| 62 | 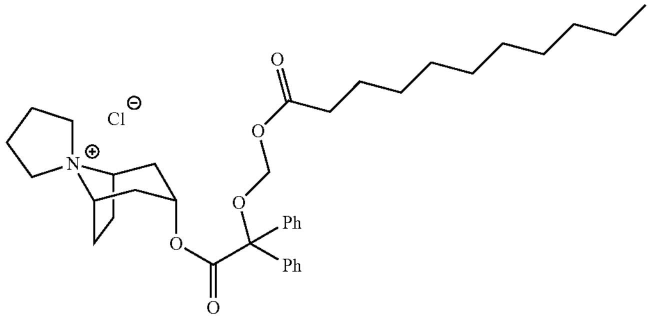 [SMILES: CCCCCCCCCCC(=O)OCOC(C(=O)OC1CC2CCC(C1)[N+]21CCCC1)(c1ccccc1)c1ccccc1 ; [Cl-]] |
| 63 | 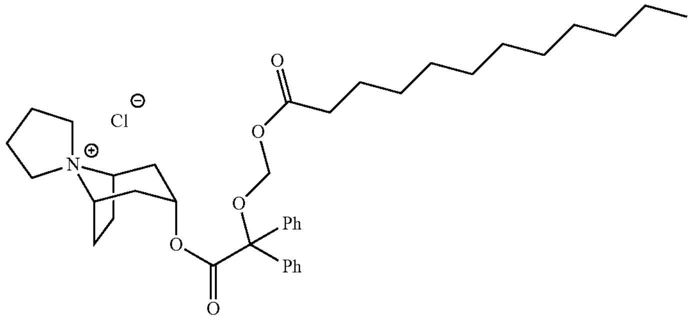 [SMILES: CCCCCCCCCCCC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 64 | 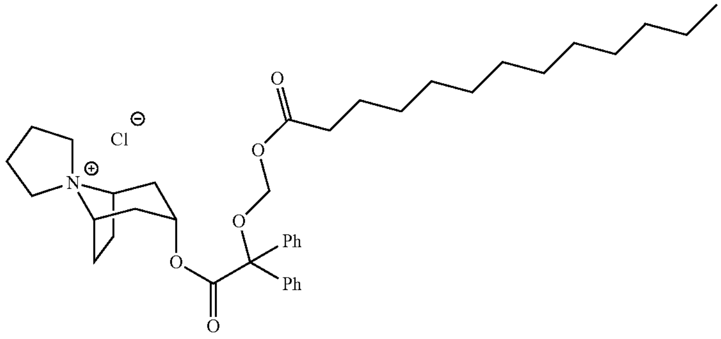 [SMILES: CCCCCCCCCCCCC(=O)OCOC(C(=O)OC1CC2CCC(C1)[N+]21CCCC1)(c1ccccc1)c1ccccc1 ; [Cl-]] |
| 65 | 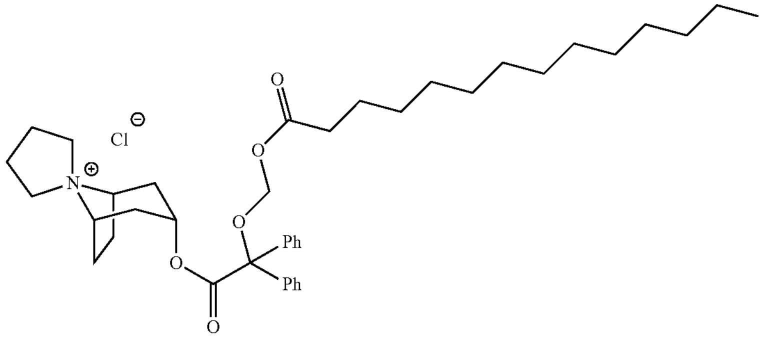 [SMILES: CCCCCCCCCCCCCC(=O)OCOC(C(=O)OC1CC2CCC(C1)[N+]21CCCC1)(c1ccccc1)c1ccccc1 ; [Cl-]] |
| 66 | 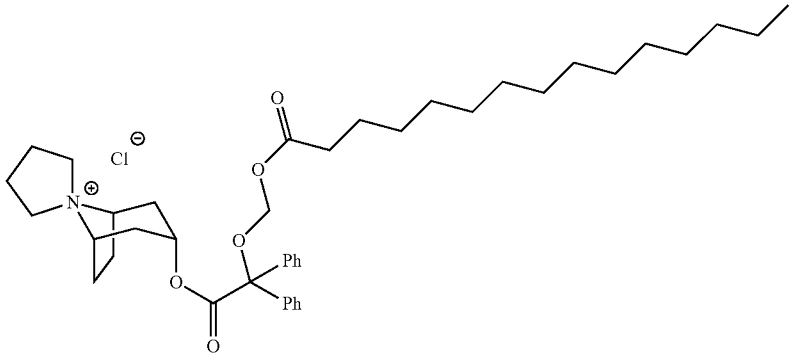 [SMILES: CCCCCCCCCCCCCCC(=O)OCOC(C(=O)OC1CC2CCC(C1)[N+]21CCCC1)(c1ccccc1)c1ccccc1 ; [Cl-]] |
| 67 | 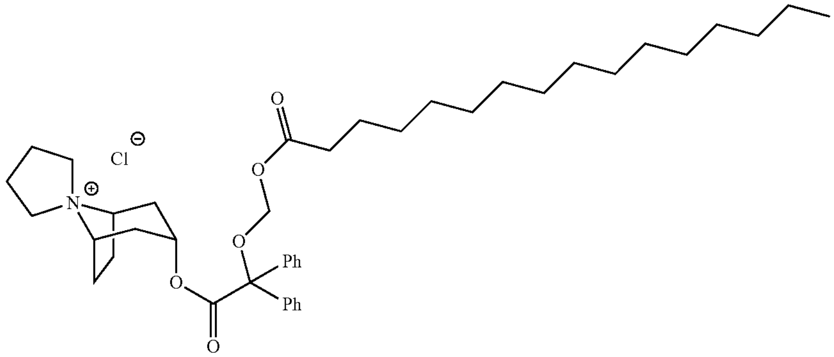 [SMILES: CCCCCCCCCCCCCCCC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 68 | 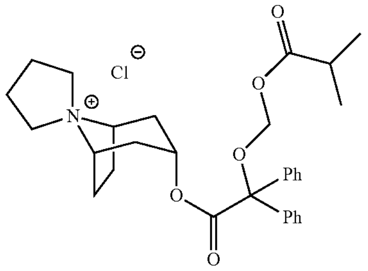 [SMILES: CC(C)C(=O)OCOC(C(=O)OC1CC2CCC(C1)[N+]21CCCC1)(c1ccccc1)c1ccccc1 ; [Cl-]] |
| 69 | 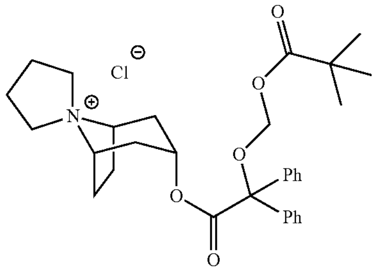 [SMILES: CC(C)(C)C(=O)OCOC(C(=O)OC1CC2CCC(C1)[N+]21CCCC1)(c1ccccc1)c1ccccc1 ; [Cl-]] |
| 70 | 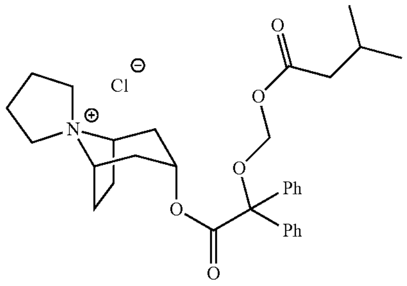 [SMILES: CC(C)CC(=O)OCOC(C(=O)OC1CC2CCC(C1)[N+]21CCCC1)(c1ccccc1)c1ccccc1 ; [Cl-]] |
| 71 | 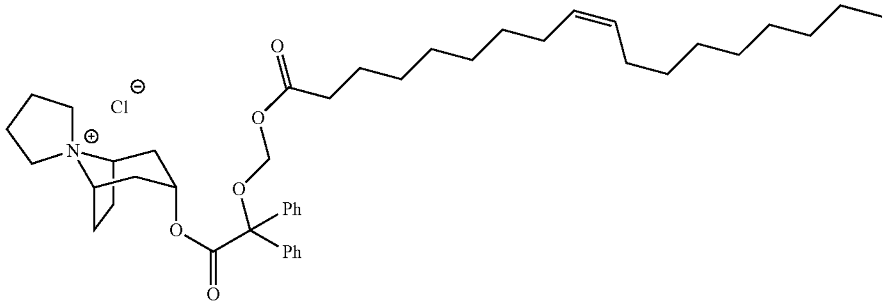 [SMILES: CCCCCCCC/C=C\CCCCCCCC(=O)OCOC(C(=O)OC1CC2CCC(C1)[N+]21CCCC1)(c1ccccc1)c1ccccc1 ; [Cl-]] |
| 72 | 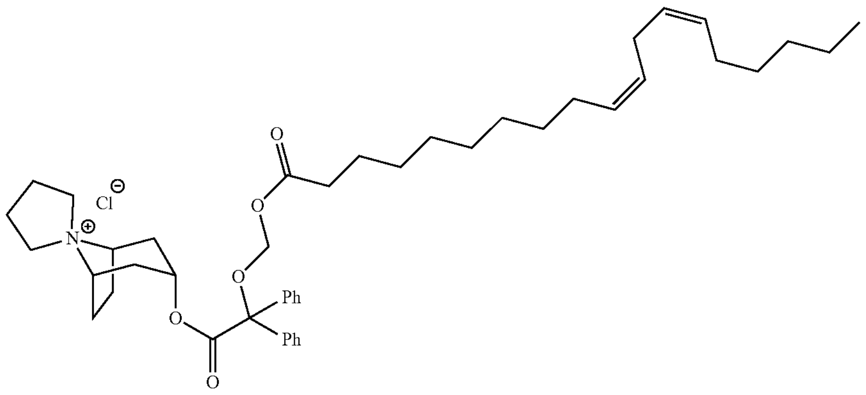 [SMILES: CCCCC/C=C\C/C=C\CCCCCCCCC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 73 | 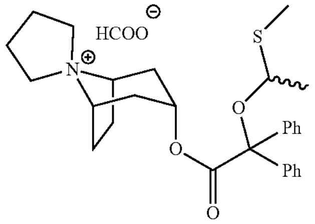 |
| 74 | 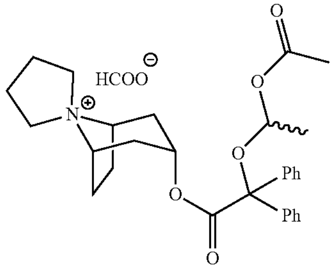 |
| 75 | 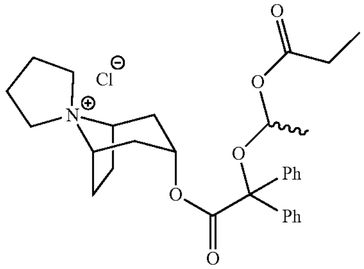 |
| 76 | 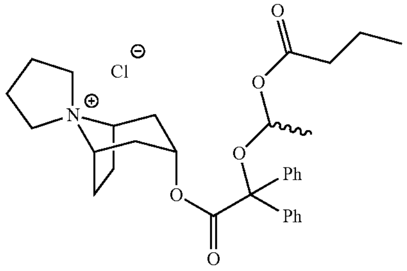 [SMILES: CCCC(=O)OC(C)OC(C(=O)OC1CC2CCC(C1)[N+]21CCCC1)(c1ccccc1)c1ccccc1 ; [Cl-]] |
| 77 | 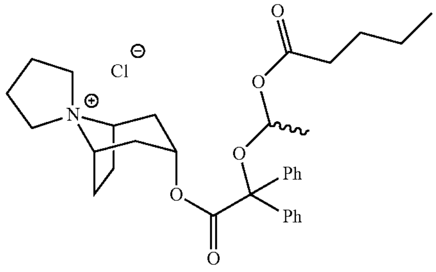 [SMILES: CCCCC(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 78 | 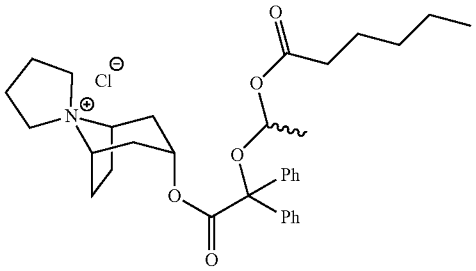 [SMILES: CCCCCC(=O)OC(C)OC(C(=O)OC1CC2CCC(C1)[N+]21CCCC1)(c1ccccc1)c1ccccc1 ; [Cl-]] |
| 79 | 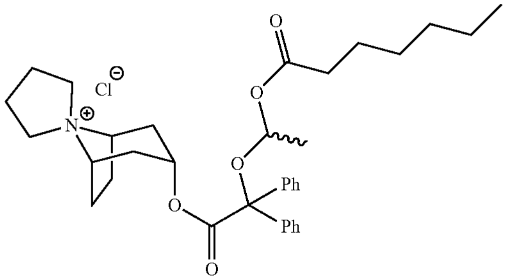 [SMILES: CCCCCCC(=O)OC(C)OC(C(=O)OC1CC2CCC(C1)[N+]21CCCC1)(c1ccccc1)c1ccccc1 ; [Cl-]] |
| 80 | 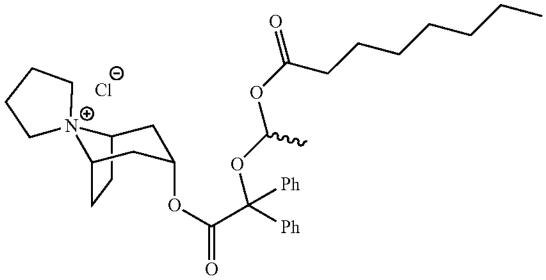 [SMILES: CCCCCCCC(=O)OC(C)OC(C(=O)OC1CC2CCC(C1)[N+]21CCCC1)(c1ccccc1)c1ccccc1 ; [Cl-]] |
| 81 | 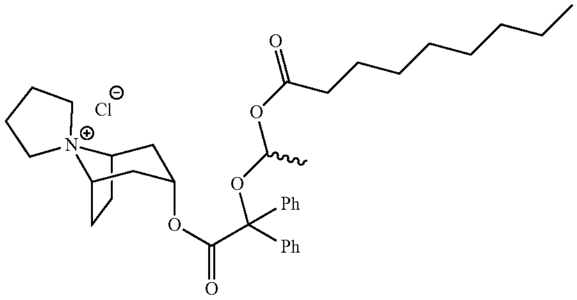 [SMILES: CCCCCCCCC(=O)OC(C)OC(C(=O)OC1CC2CCC(C1)[N+]21CCCC1)(c1ccccc1)c1ccccc1 ; [Cl-]] |
| 82 | 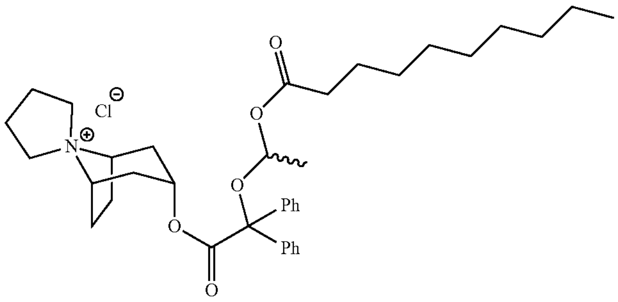 |

TABLE 2-continued
| Cpd No. | Structure |
|---|---|
| 83 | 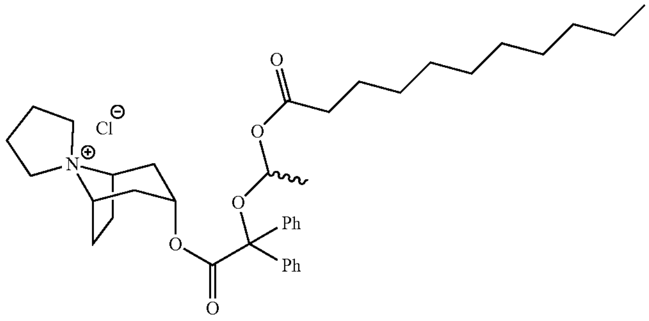 [SMILES: CCCCCCCCCCC(=O)OC(C)OC(C(=O)OC1CC2CCC(C1)[N+]21CCCC1)(c1ccccc1)c1ccccc1 ; [Cl-]] |
| 84 | 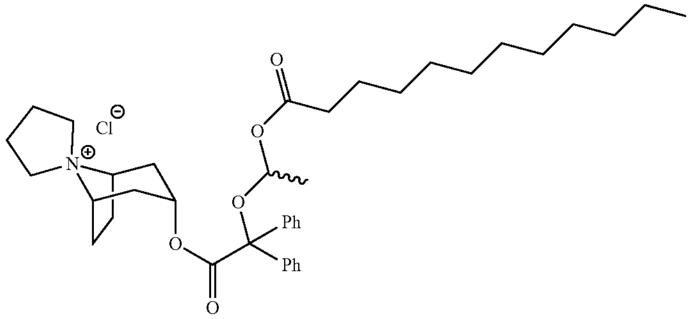 [SMILES: CCCCCCCCCCCC(=O)OC(C)OC(C(=O)OC1CC2CCC(C1)[N+]21CCCC1)(c1ccccc1)c1ccccc1 ; [Cl-]] |
| 85 | 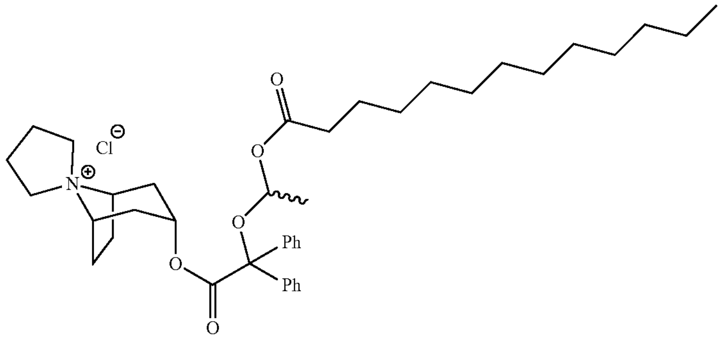 [SMILES: CCCCCCCCCCCCC(=O)OC(C)OC(C(=O)OC1CC2CCC(C1)[N+]21CCCC1)(c1ccccc1)c1ccccc1 ; [Cl-]] |
| 86 | 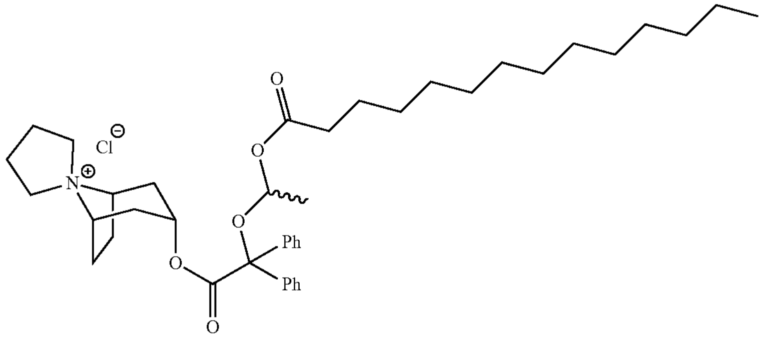 |

TABLE 2-continued
| Cpd No. | Structure |
|---|---|
| 87 | 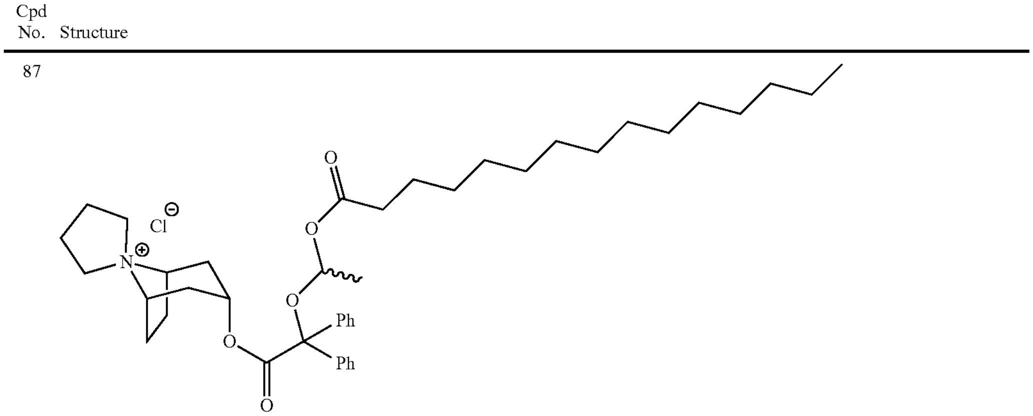 |
| 88 | 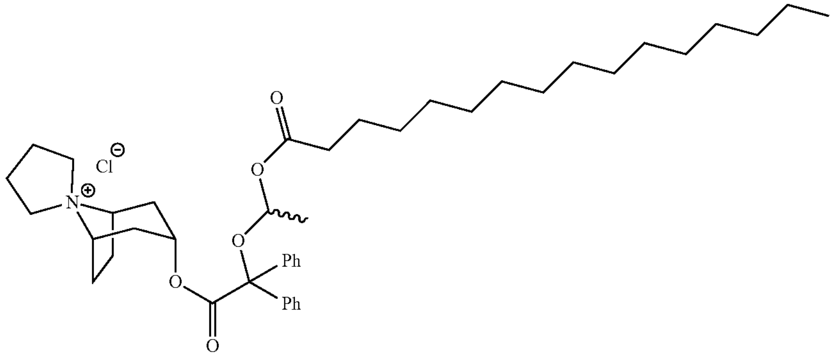 |
| 89 | 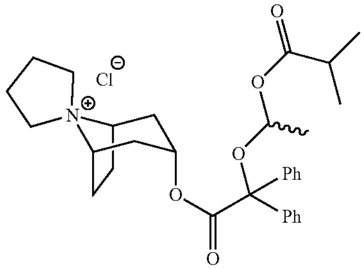 [SMILES: CC(OC(=O)C(C)C)OC(C(=O)OC1CC2CCC(C1)[N+]21CCCC1)(c1ccccc1)c1ccccc1 ; [Cl-]] |
| 90 | 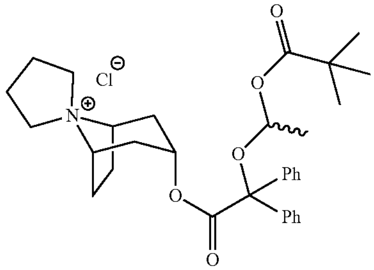 [SMILES: CC(OC(=O)C(C)(C)C)OC(C(=O)OC1CC2CCC(C1)[N+]21CCCC1)(c1ccccc1)c1ccccc1 ; [Cl-]] |
| 91 | 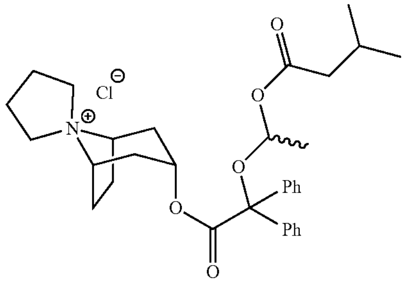 [SMILES: CC(C)CC(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 92 | 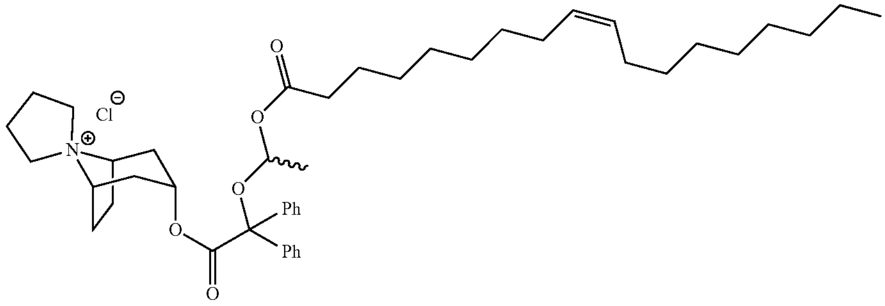 |
| 93 | 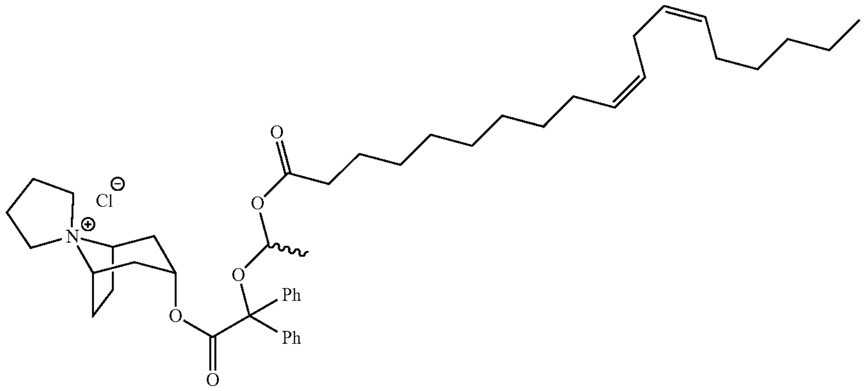 [SMILES: CCCCC/C=C\C/C=C\CCCCCCCCC(=O)OC(C)OC(C(=O)OC1CC2CCC(C1)[N+]21CCCC1)(c1ccccc1)c1ccccc1 ; [Cl-]] |
| 94 | 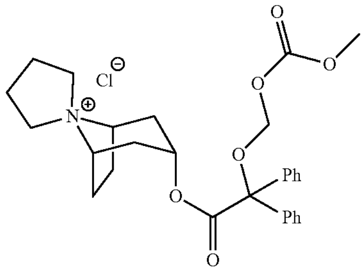 [SMILES: COC(=O)OCOC(C(=O)OC1CC2CCC(C1)[N+]21CCCC1)(c1ccccc1)c1ccccc1 ; [Cl-]] |
| 95 | 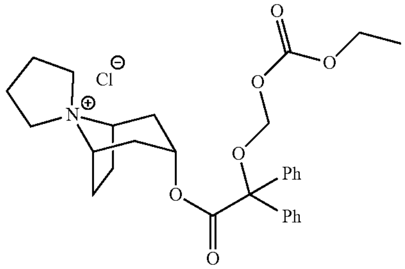 [SMILES: CCOC(=O)OCOC(C(=O)OC1CC2CCC(C1)[N+]21CCCC1)(c1ccccc1)c1ccccc1 ; [Cl-]] |
| 96 | 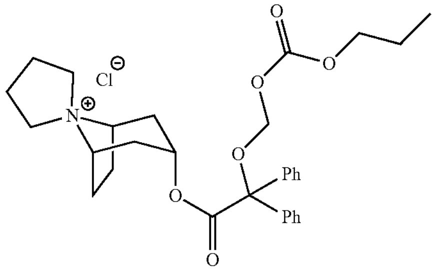 [SMILES: CCCOC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
| --- | --- |
| 97 | 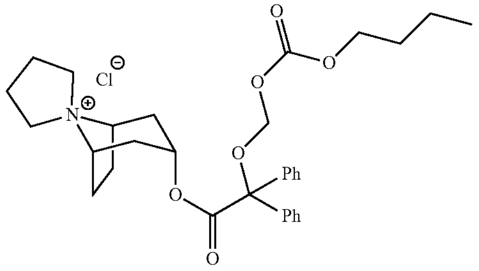 [SMILES: CCCCOC(=O)OCOC(C(=O)OC1CC2CCC(C1)[N+]21CCCC1)(c1ccccc1)c1ccccc1 ; [Cl-]] |
| 98 | 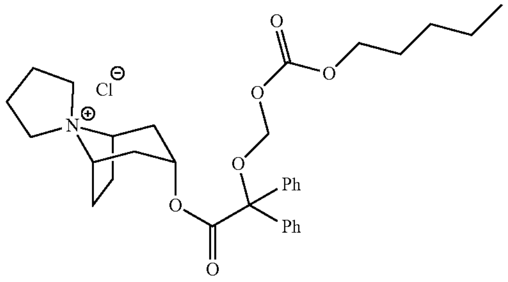 [SMILES: CCCCCOC(=O)OCOC(C(=O)OC1CC2CCC(C1)[N+]21CCCC1)(c1ccccc1)c1ccccc1 ; [Cl-]] |
| 99 | 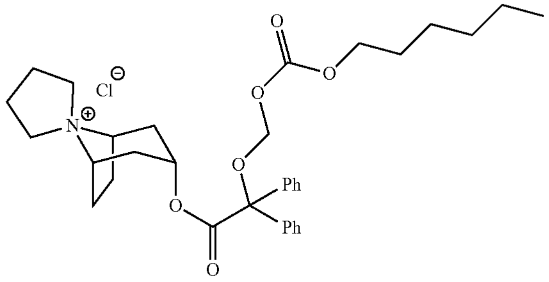 [SMILES: CCCCCCOC(=O)OCOC(C(=O)OC1CC2CCC(C1)[N+]21CCCC1)(c1ccccc1)c1ccccc1 ; [Cl-]] |
| 100 | 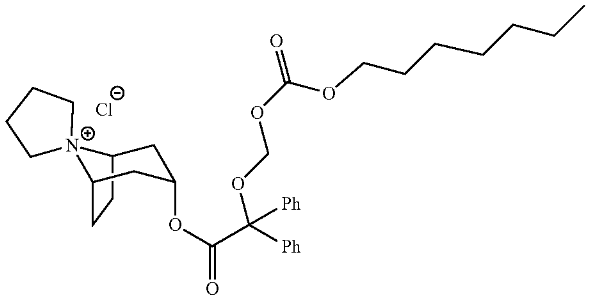 [SMILES: CCCCCCCOC(=O)OCOC(C(=O)OC1CC2CCC(C1)[N+]21CCCC1)(c1ccccc1)c1ccccc1 ; [Cl-]] |
| 101 | 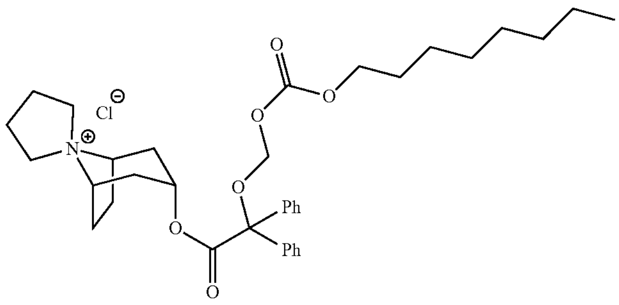 [SMILES: CCCCCCCCOC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 102 | 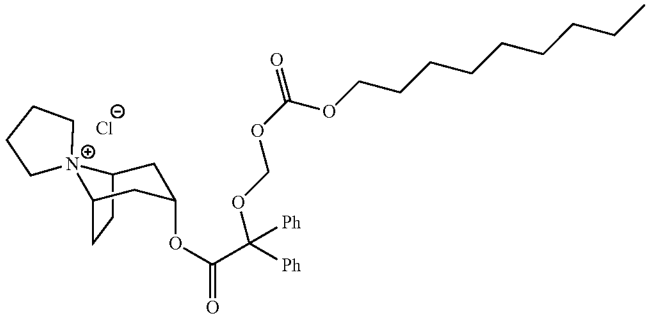 [SMILES: CCCCCCCCCOC(=O)OCOC(C(=O)OC1CC2CCC(C1)[N+]21CCCC1)(c1ccccc1)c1ccccc1 ; [Cl-]] |
| 103 | 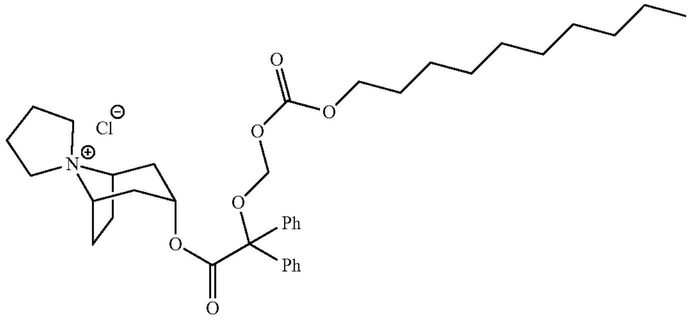 [SMILES: CCCCCCCCCCOC(=O)OCOC(C(=O)OC1CC2CCC(C1)[N+]21CCCC1)(c1ccccc1)c1ccccc1 ; [Cl-]] |
| 104 | 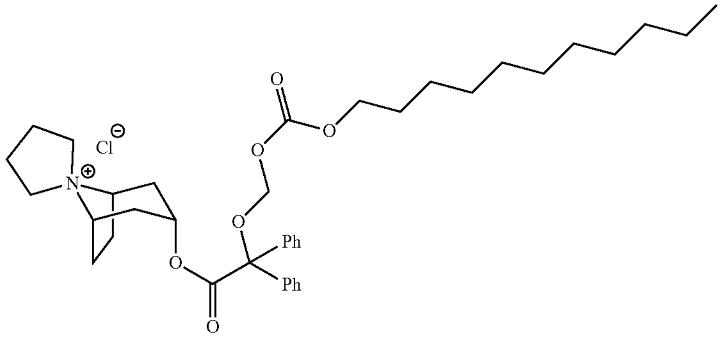 [SMILES: CCCCCCCCCCCOC(=O)OCOC(C(=O)OC1CC2CCC(C1)[N+]21CCCC1)(c1ccccc1)c1ccccc1 ; [Cl-]] |
| 105 | 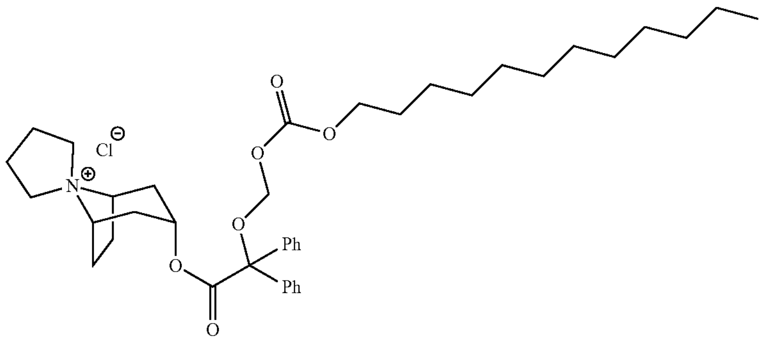 [SMILES: CCCCCCCCCCCCOC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 106 | 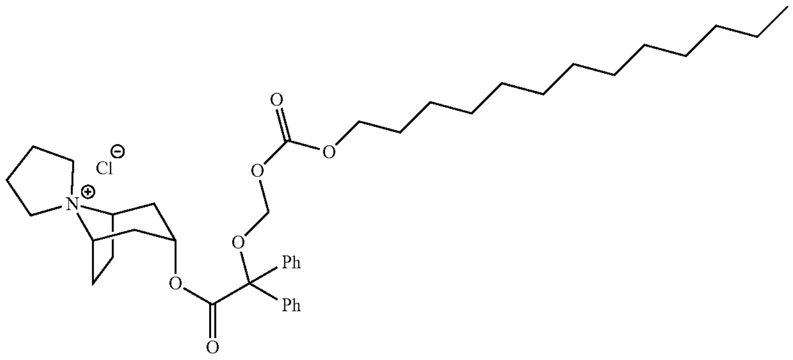 [SMILES: CCCCCCCCCCCCCOC(=O)OCOC(C(=O)OC1CC2CCC(C1)[N+]21CCCC1)(c1ccccc1)c1ccccc1 ; [Cl-]] |
| 107 | 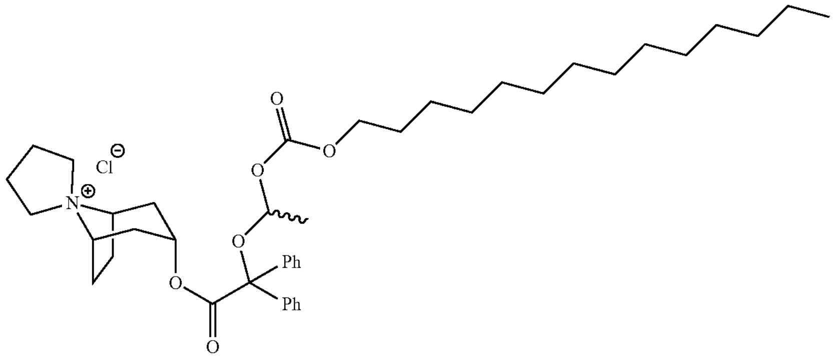 [SMILES: CCCCCCCCCCCCCCOC(=O)OC(C)OC(C(=O)OC1CC2CCC(C1)[N+]21CCCC1)(c1ccccc1)c1ccccc1 ; [Cl-]] |
| 108 | 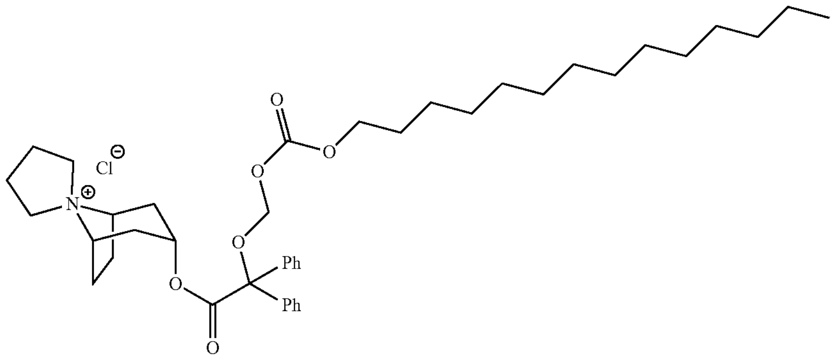 [SMILES: CCCCCCCCCCCCCCOC(=O)OCOC(C(=O)OC1CC2CCC(C1)[N+]21CCCC1)(c1ccccc1)c1ccccc1 ; [Cl-]] |
| 109 | 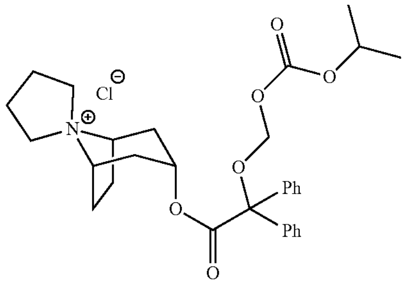 [SMILES: CC(C)OC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 110 | 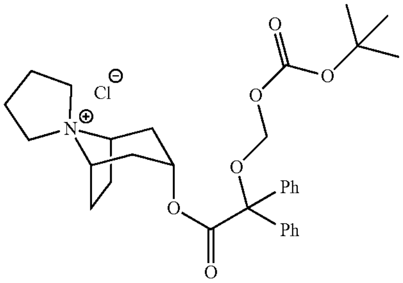 [SMILES: CC(C)(C)OC(=O)OCOC(C(=O)OC1CC2CCC(C1)[N+]21CCCC1)(c1ccccc1)c1ccccc1 ; [Cl-]] |
| 111 | 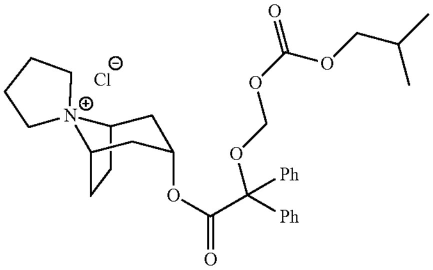 [SMILES: CC(C)COC(=O)OCOC(C(=O)OC1CC2CCC(C1)[N+]21CCCC1)(c1ccccc1)c1ccccc1 ; [Cl-]] |
| 112 | 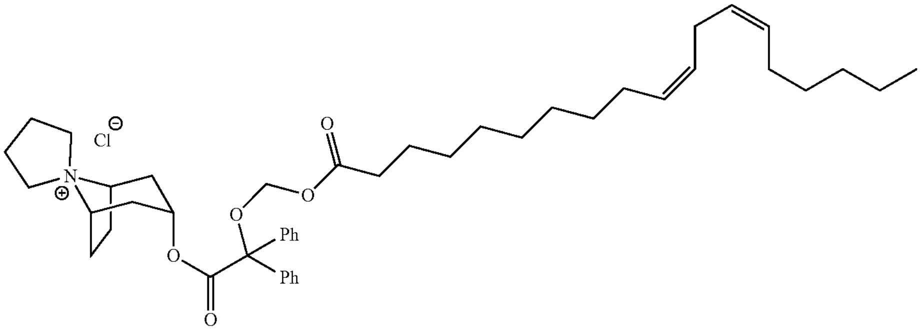 [SMILES: CCCCC/C=C\C/C=C\CCCCCCCCC(=O)OCOC(C(=O)OC1CC2CCC(C1)[N+]21CCCC1)(c1ccccc1)c1ccccc1 ; [Cl-]] |
| 113 | 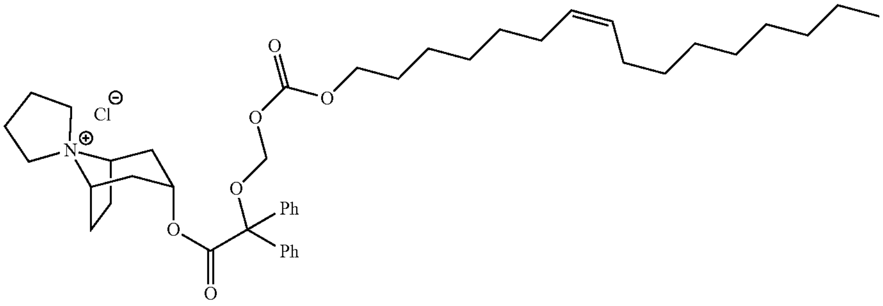 [SMILES: CCCCCCCC/C=C\CCCCCCOC(=O)OCOC(C(=O)OC1CC2CCC(C1)[N+]21CCCC1)(c1ccccc1)c1ccccc1 ; [Cl-]] |
| 114 | 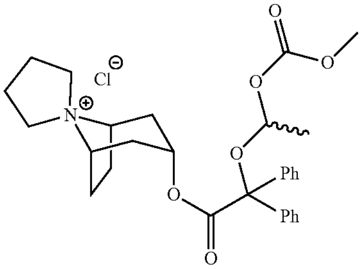 [SMILES: COC(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 115 | 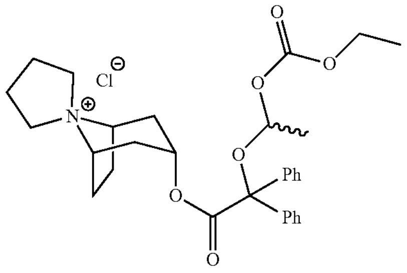 [SMILES: CCOC(=O)OC(C)OC(C(=O)OC1CC2CCC(C1)[N+]21CCCC1)(c1ccccc1)c1ccccc1 ; [Cl-]] |
| 116 | 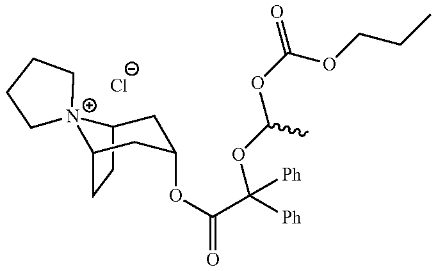 [SMILES: CCCOC(=O)OC(C)OC(C(=O)OC1CC2CCC(C1)[N+]21CCCC1)(c1ccccc1)c1ccccc1 ; [Cl-]] |
| 117 | 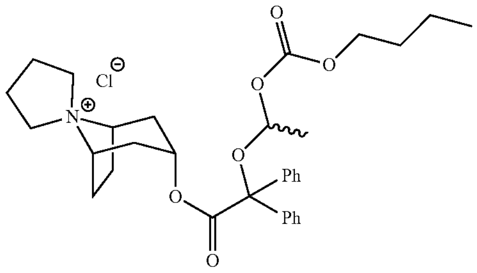 [SMILES: CCCCOC(=O)OC(C)OC(C(=O)OC1CC2CCC(C1)[N+]21CCCC1)(c1ccccc1)c1ccccc1 ; [Cl-]] |
| 118 | 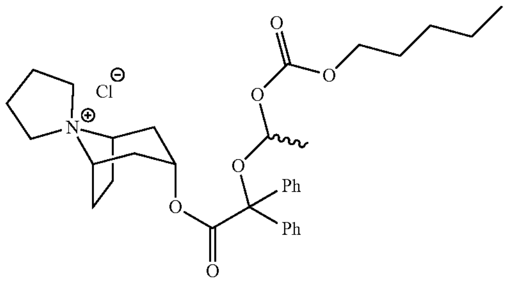 [SMILES: CCCCCOC(=O)OC(C)OC(C(=O)OC1CC2CCC(C1)[N+]21CCCC1)(c1ccccc1)c1ccccc1 ; [Cl-]] |
| 119 | 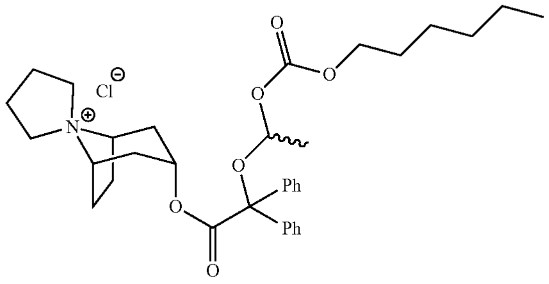 [SMILES: CCCCCCOC(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
| --- | --- |
| 120 | 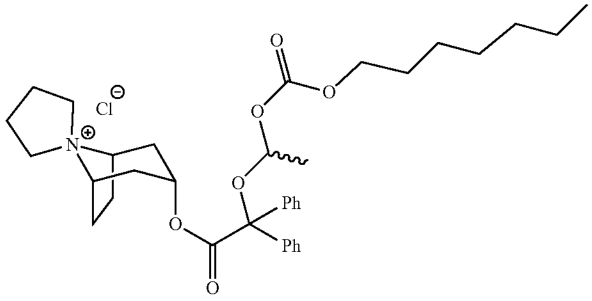 [SMILES: CCCCCCCOC(=O)OC(C)OC(C(=O)OC1CC2CCC(C1)[N+]21CCCC1)(c1ccccc1)c1ccccc1 ; [Cl-]] |
| 121 | 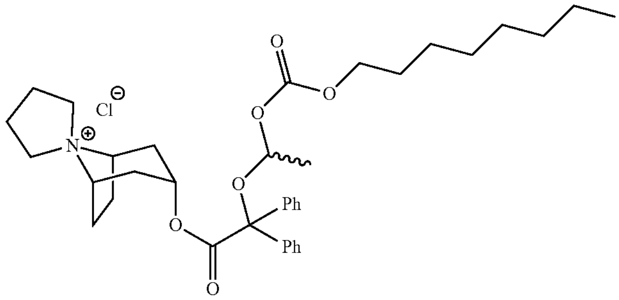 [SMILES: CCCCCCCCOC(=O)OC(C)OC(C(=O)OC1CC2CCC(C1)[N+]21CCCC1)(c1ccccc1)c1ccccc1 ; [Cl-]] |
| 122 | 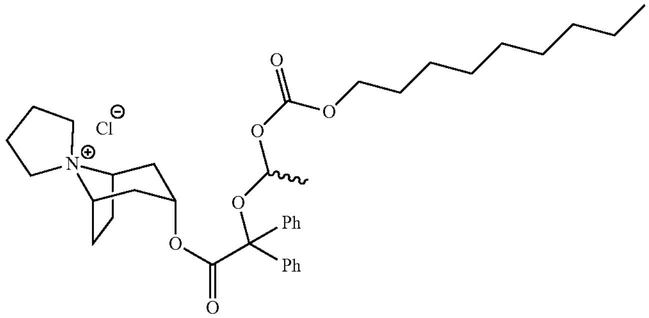 |
| 123 | 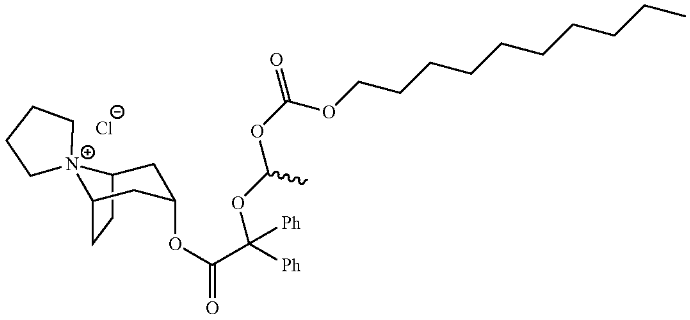 [SMILES: CCCCCCCCCCOC(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 124 | 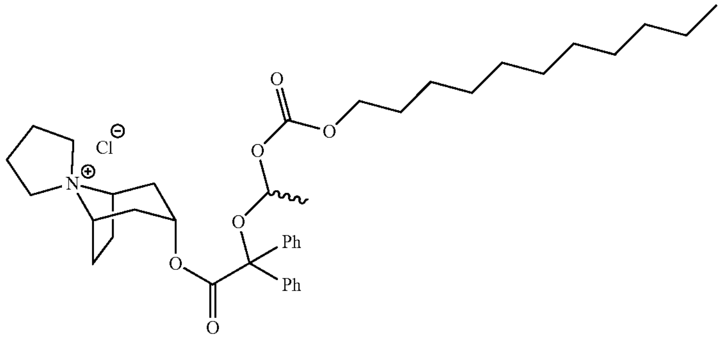 |
| 125 | 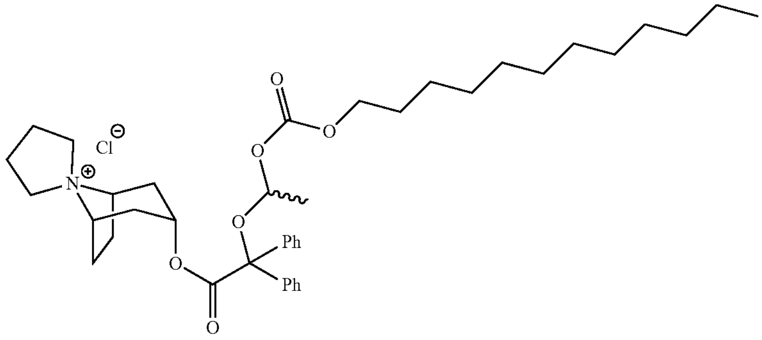 [SMILES: CCCCCCCCCCCCOC(=O)OC(C)OC(C(=O)OC1CC2CCC(C1)[N+]21CCCC1)(c1ccccc1)c1ccccc1 ; [Cl-]] |
| 126 | 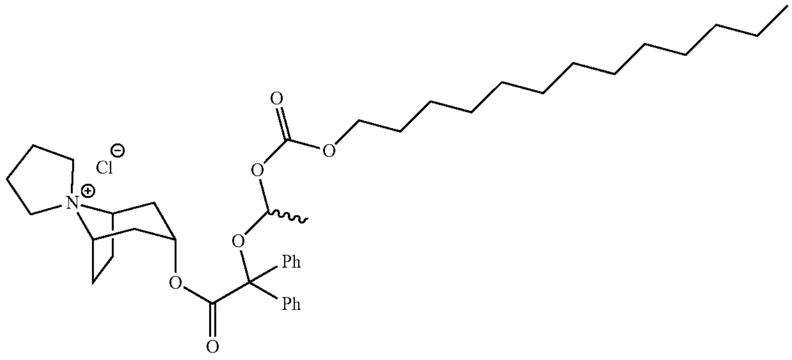 [SMILES: CCCCCCCCCCCCCOC(=O)OC(C)OC(C(=O)OC1CC2CCC(C1)[N+]21CCCC1)(c1ccccc1)c1ccccc1 ; [Cl-]] |
| 127 | 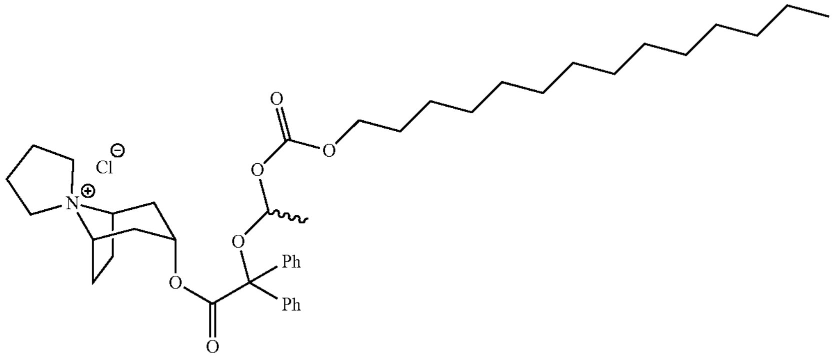 [SMILES: CCCCCCCCCCCCCCOC(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 128 | 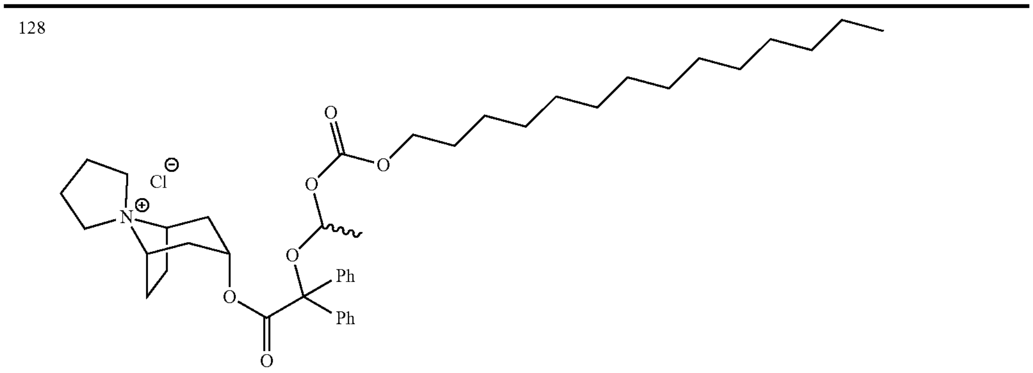 |
| 129 | 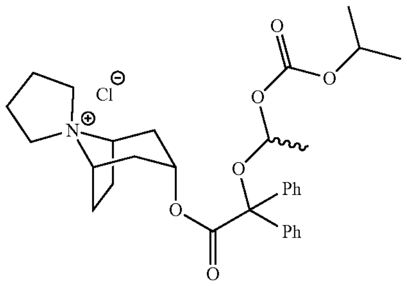 [SMILES: CC(C)OC(=O)OC(C)OC(C(=O)OC1CC2CCC(C1)[N+]21CCCC1)(c1ccccc1)c1ccccc1 ; [Cl-]] |
| 130 | 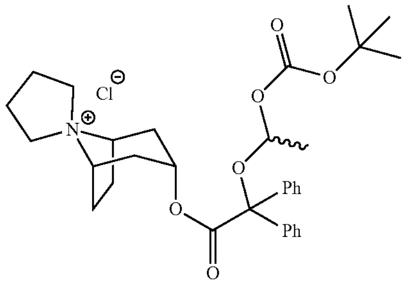 [SMILES: CC(OC(=O)OC(C)(C)C)OC(C(=O)OC1CC2CCC(C1)[N+]21CCCC1)(c1ccccc1)c1ccccc1 ; [Cl-]] |
| 131 | 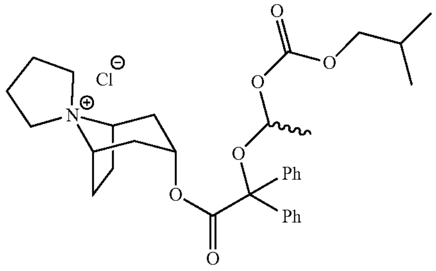 [SMILES: CC(C)COC(=O)OC(C)OC(C(=O)OC1CC2CCC(C1)[N+]21CCCC1)(c1ccccc1)c1ccccc1 ; [Cl-]] |
| 132 | 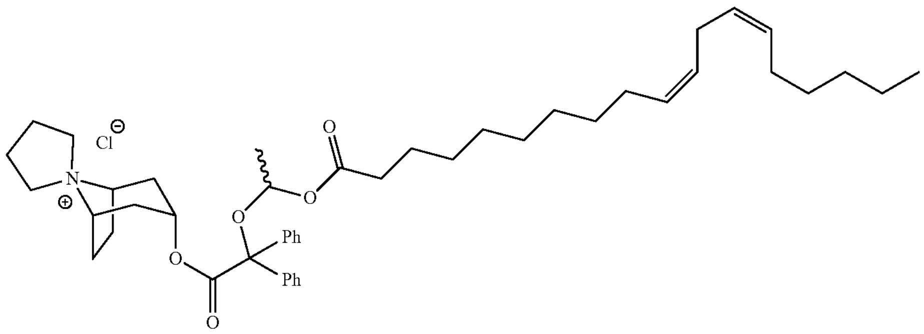 [SMILES: CCCCC/C=C\C/C=C\CCCCCCCCC(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
| --- | --- |
| 133 | 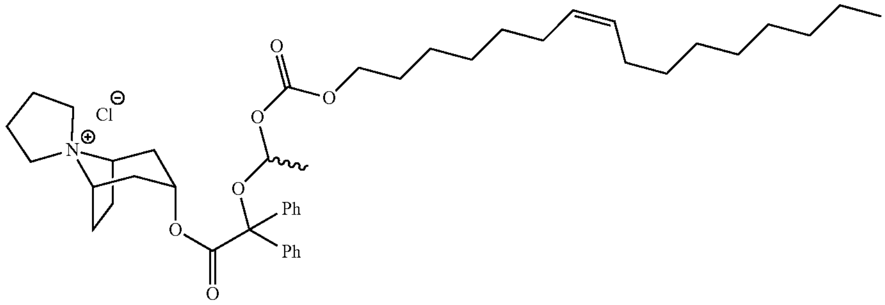 [SMILES: CCCCCCCC/C=C\CCCCCCOC(=O)OC(C)OC(C(=O)OC1CC2CCC(C1)[N+]21CCCC1)(c1ccccc1)c1ccccc1 ; [Cl-]] |
| 134 | 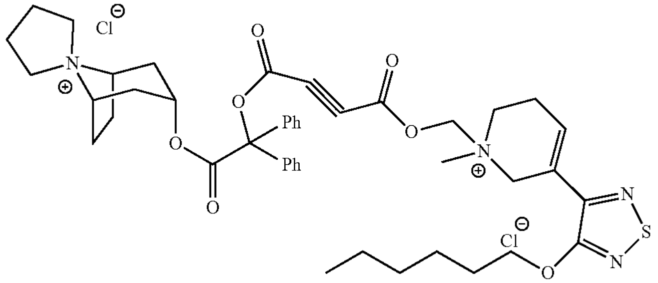 [SMILES: CCCCCCOc1nsnc1C1=CCC[N+](C)(COC(=O)C#CC(=O)OC(C(=O)OC2CC3CCC(C2)[N+]32CCCC2)(c2ccccc2)c2ccccc2)C1 ; [Cl-] ; [Cl-]] |
| 135 | 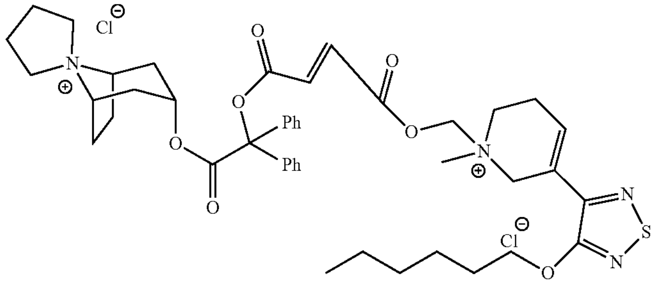 [SMILES: CCCCCCOc1nsnc1C1=CCC[N+](C)(COC(=O)/C=C/C(=O)OC(C(=O)OC2CC3CCC(C2)[N+]32CCCC2)(c2ccccc2)c2ccccc2)C1 ; [Cl-] ; [Cl-]] |
| 136 | 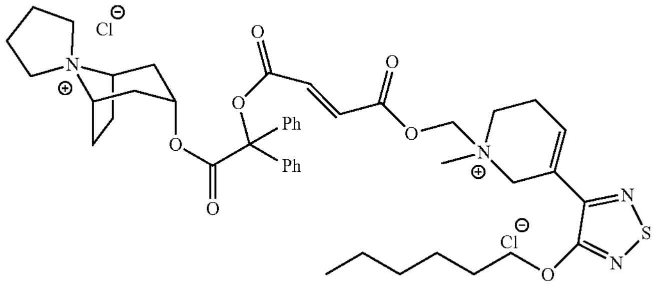 [SMILES: CCCCCCOc1nsnc1C1=CCC[N+](C)(COC(=O)/C=C/C(=O)OC(C(=O)OC2CC3CCC(C2)[N+]32CCCC2)(c2ccccc2)c2ccccc2)C1 ; [Cl-] ; [Cl-]] |
| 137 | 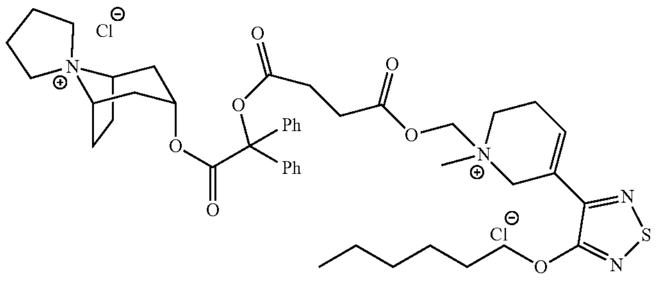 [SMILES: CCCCCCOc1nsnc1C1=CCC[N+](C)(COC(=O)CCC(=O)OC(C(=O)OC2CC3CCC(C2)[N+]32CCCC2)(c2ccccc2)c2ccccc2)C1 ; [Cl-] ; [Cl-]] |

TABLE 2-continued
| Cpd No. | Structure |
|---|---|
| 138 | 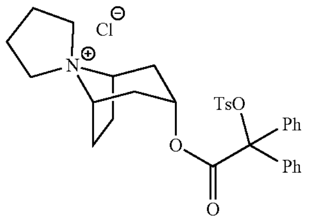 [SMILES: Cc1ccc(S(=O)(=O)OC(C(=O)OC2CC3CCC(C2)[N+]32CCCC2)(c2ccccc2)c2ccccc2)cc1 ; [Cl-]] |
| 139 | 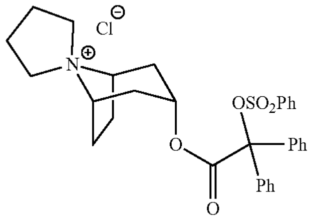 |
| 140 | 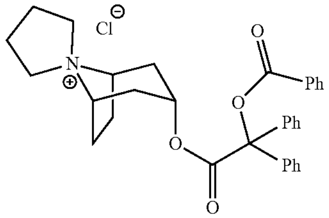 [SMILES: O=C(OC(C(=O)OC1CC2CCC(C1)[N+]21CCCC1)(c1ccccc1)c1ccccc1)c1ccccc1 ; [Cl-]] |
| 141 | 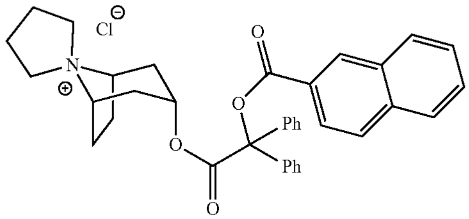 [SMILES: O=C(OC(C(=O)OC1CC2CCC(C1)[N+]21CCCC1)(c1ccccc1)c1ccccc1)c1ccc2ccccc2c1 ; [Cl-]] |
| 142 | 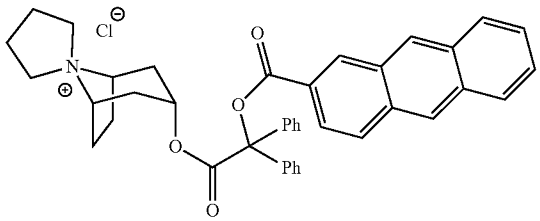 [SMILES: O=C(OC(C(=O)OC1CC2CCC(C1)[N+]21CCCC1)(c1ccccc1)c1ccccc1)c1ccc2cc3ccccc3cc2c1 ; [Cl-]] |
| 143 | 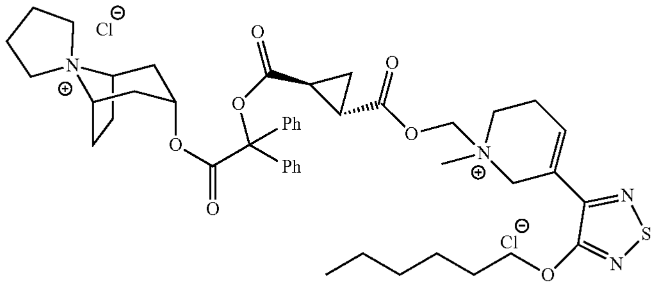 [SMILES: CCCCCCOc1nsnc1C1=CCC[N+](C)(COC(=O)[C@H]2C[C@@H]2C(=O)OC(C(=O)OC2CC3CCC(C2)[N+]32CCCC2)(c2ccccc2)c2ccccc2)C1 ; [Cl-] ; [Cl-]] |

TABLE 2-continued
| Cpd No. | Structure |
|---|---|
| 144 | 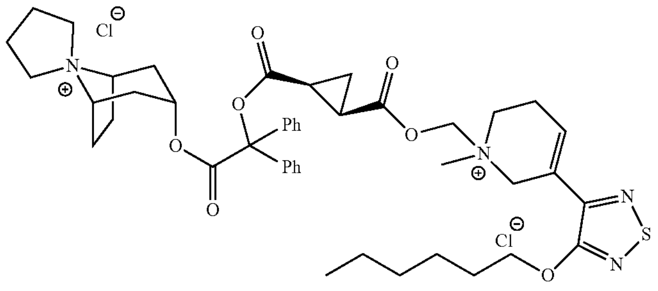 [SMILES: CCCCCCOc1nsnc1C1=CCC[N+](C)(COC(=O)[C@@H]2C[C@@H]2C(=O)OC(C(=O)OC2CC3CCC(C2)[N+]32CCCC2)(c2ccccc2)c2ccccc2)C1 ; [Cl-] ; [Cl-]] |
| 145 | 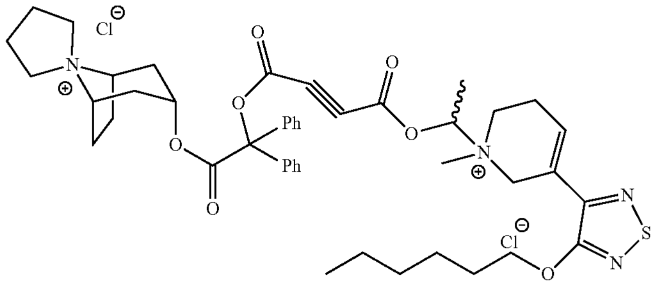 [SMILES: CCCCCCOc1nsnc1C1=CCC[N+](C)(C(C)OC(=O)C#CC(=O)OC(C(=O)OC2CC3CCC(C2)[N+]32CCCC2)(c2ccccc2)c2ccccc2)C1 ; [Cl-] ; [Cl-]] |
| 146 | 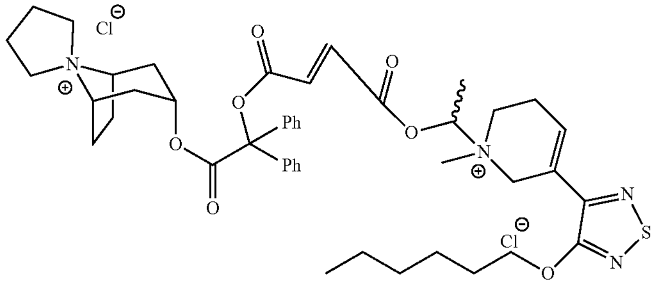 [SMILES: CCCCCCOc1nsnc1C1=CCC[N+](C)(C(C)OC(=O)/C=C/C(=O)OC(C(=O)OC2CC3CCC(C2)[N+]32CCCC2)(c2ccccc2)c2ccccc2)C1 ; [Cl-] ; [Cl-]] |
| 147 | 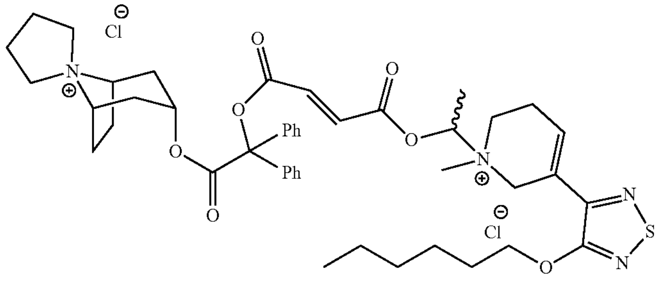 [SMILES: CCCCCCOc1nsnc1C1=CCC[N+](C)(C(C)OC(=O)/C=C/C(=O)OC(C(=O)OC2CC3CCC(C2)[N+]32CCCC2)(c2ccccc2)c2ccccc2)C1 ; [Cl-] ; [Cl-]] |
| 148 | 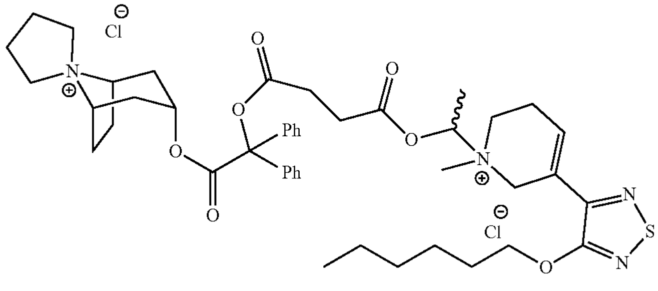 [SMILES: CCCCCCOc1nsnc1C1=CCC[N+](C)(C(C)OC(=O)CCC(=O)OC(C(=O)OC2CC3CCC(C2)[N+]32CCCC2)(c2ccccc2)c2ccccc2)C1 ; [Cl-] ; [Cl-]] |

TABLE 2-continued
| Cpd No. | Structure |
|---|---|
| 149 | 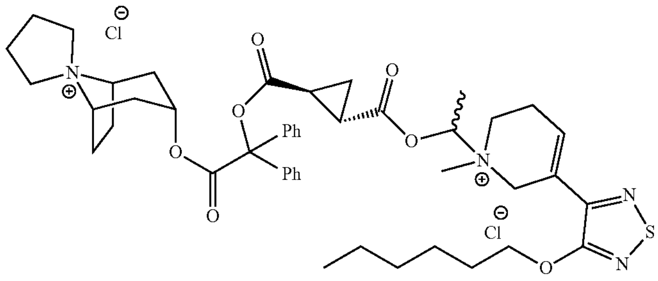 [SMILES: CCCCCCOc1nsnc1C1=CCC[N+](C)(C(C)OC(=O)[C@H]2C[C@@H]2C(=O)OC(C(=O)OC2CC3CCC(C2)[N+]32CCCC2)(c2ccccc2)c2ccccc2)C1 ; [Cl-] ; [Cl-]] |
| 150 | 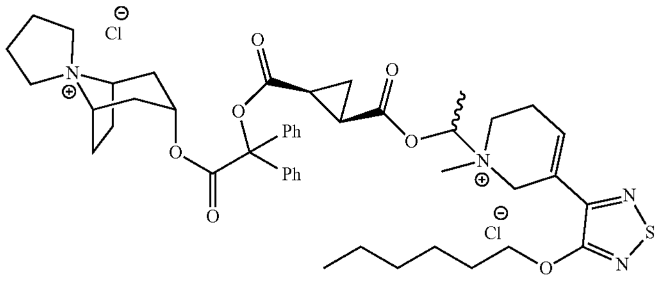 [SMILES: CCCCCCOc1nsnc1C1=CCC[N+](C)(C(C)OC(=O)[C@@H]2C[C@@H]2C(=O)OC(C(=O)OC2CC3CCC(C2)[N+]32CCCC2)(c2ccccc2)c2ccccc2)C1 ; [Cl-] ; [Cl-]] |
| 151 | 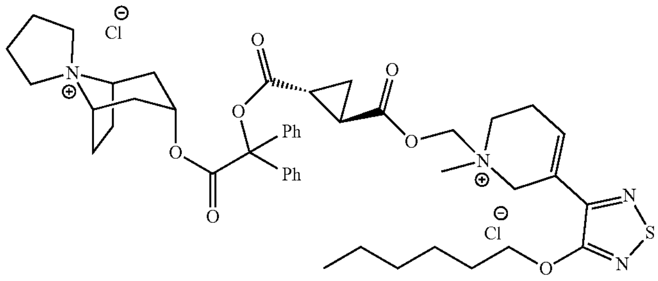 [SMILES: CCCCCCOc1nsnc1C1=CCC[N+](C)(COC(=O)[C@@H]2C[C@H]2C(=O)OC(C(=O)OC2CC3CCC(C2)[N+]32CCCC2)(c2ccccc2)c2ccccc2)C1 ; [Cl-] ; [Cl-]] |
| 152 | 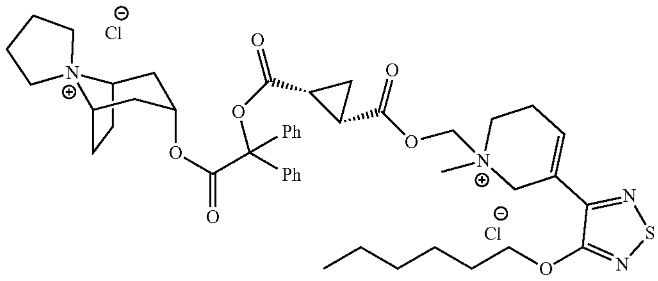 [SMILES: CCCCCCOc1nsnc1C1=CCC[N+](C)(COC(=O)[C@H]2C[C@H]2C(=O)OC(C(=O)OC2CC3CCC(C2)[N+]32CCCC2)(c2ccccc2)c2ccccc2)C1 ; [Cl-] ; [Cl-]] |
| 153 | 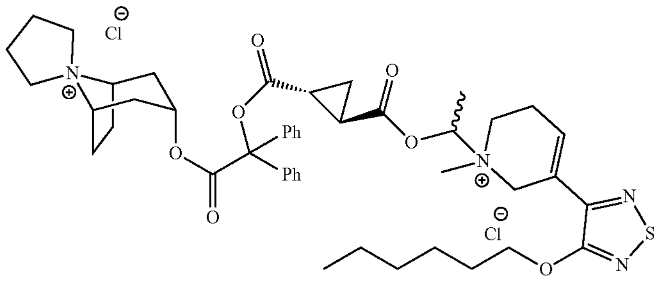 [SMILES: CCCCCCOc1nsnc1C1=CCC[N+](C)(C(C)OC(=O)[C@@H]2C[C@H]2C(=O)OC(C(=O)OC2CC3CCC(C2)[N+]32CCCC2)(c2ccccc2)c2ccccc2)C1 ; [Cl-] ; [Cl-]] |

TABLE 2-continued
| Cpd No. | Structure |
| --- | --- |
| 154 | 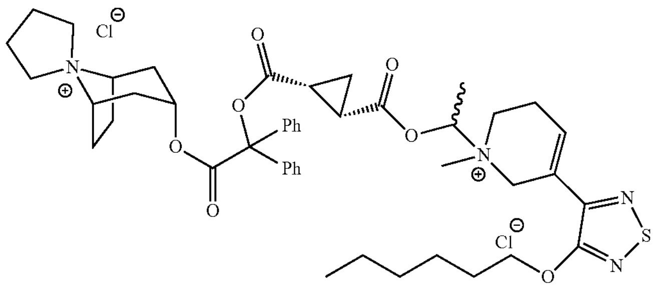 [SMILES: CCCCCCOc1nsnc1C1=CCC[N+](C)(C(C)OC(=O)[C@H]2C[C@H]2C(=O)OC(C(=O)OC2CC3CCC(C2)[N+]32CCCC2)(c2ccccc2)c2ccccc2)C1 ; [Cl-] ; [Cl-]] |
| 155 | 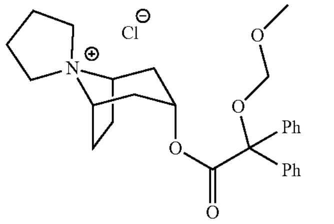 |
| 156 | 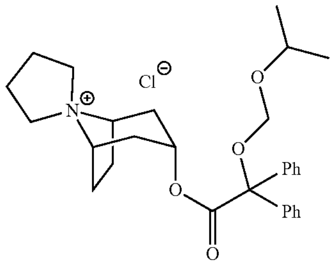 [SMILES: CC(C)OCOC(C(=O)OC1CC2CCC(C1)[N+]21CCCC1)(c1ccccc1)c1ccccc1 ; [Cl-]] |
| 157 | 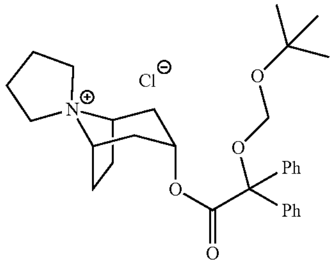 [SMILES: CC(C)(C)OCOC(C(=O)OC1CC2CCC(C1)[N+]21CCCC1)(c1ccccc1)c1ccccc1 ; [Cl-]] |
| 158 | 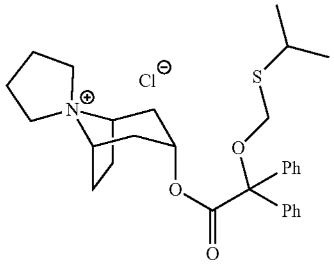 [SMILES: CC(C)SCOC(C(=O)OC1CC2CCC(C1)[N+]21CCCC1)(c1ccccc1)c1ccccc1 ; [Cl-]] |

TABLE 2-continued
| Cpd No. | Structure |
| --- | --- |
| 159 | 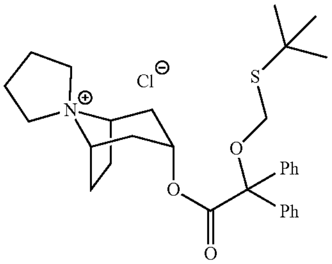 [SMILES: CC(C)(C)SCOC(C(=O)OC1CC2CCC(C1)[N+]21CCCC1)(c1ccccc1)c1ccccc1 ; [Cl-]] |
| 160 | 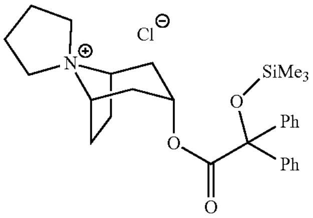 [SMILES: C[Si](C)(C)OC(C(=O)OC1CC2CCC(C1)[N+]21CCCC1)(c1ccccc1)c1ccccc1 ; [Cl-]] |
| 161 | 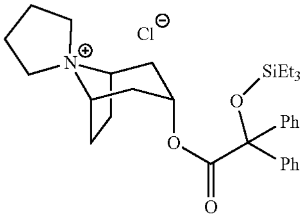 |
| 162 | 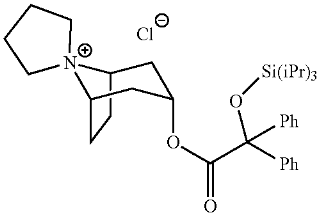 |
| 163 | 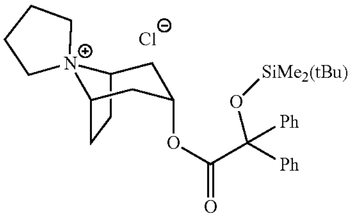 |
| 164 | 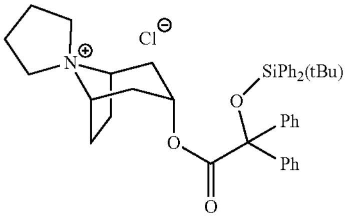 |

TABLE 2-continued
| Cpd No. | Structure |
|---|---|
| 165 | 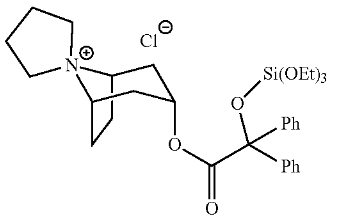 |
| 166 | 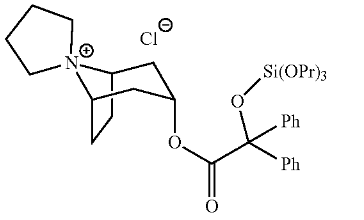 |
| 167 | 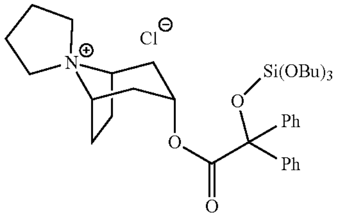 |
| 168 | 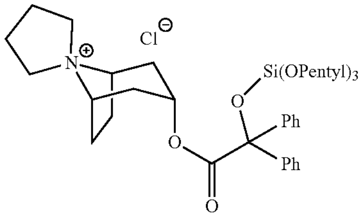 |
| 169 | 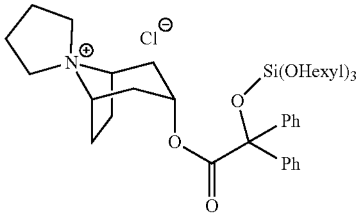 |
| 170 | 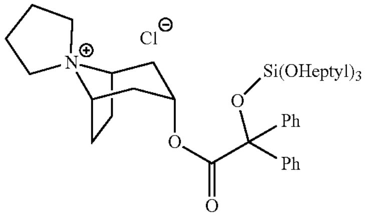 |
| 171 | 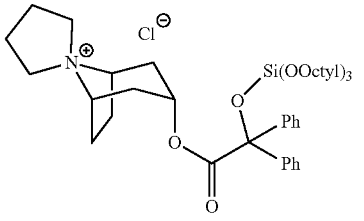 |

TABLE 2-continued
| Cpd No. | Structure |
|---|---|
| 172 | 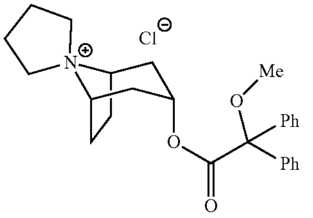 [SMILES: COC(C(=O)OC1CC2CCC(C1)[N+]21CCCC1)(c1ccccc1)c1ccccc1 ; [Cl-]] |
| 173 | 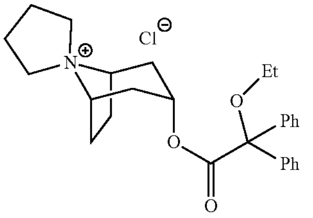 [SMILES: CCOC(C(=O)OC1CC2CCC(C1)[N+]21CCCC1)(c1ccccc1)c1ccccc1 ; [Cl-]] |
| 174 | 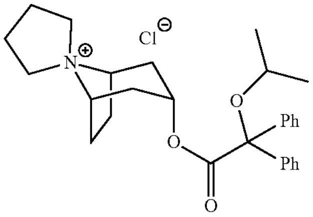 [SMILES: CC(C)OC(C(=O)OC1CC2CCC(C1)[N+]21CCCC1)(c1ccccc1)c1ccccc1 ; [Cl-]] |
| 175 | 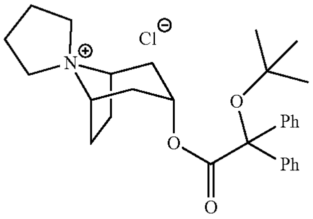 [SMILES: CC(C)(C)OC(C(=O)OC1CC2CCC(C1)[N+]21CCCC1)(c1ccccc1)c1ccccc1 ; [Cl-]] |
| 176 | 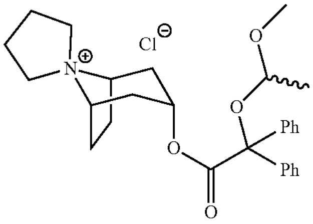 [SMILES: CSC(C)OC(C(=O)OC1CC2CCC(C1)[N+]21CCCC1)(c1ccccc1)c1ccccc1 ; [Cl-]] |
| 177 | 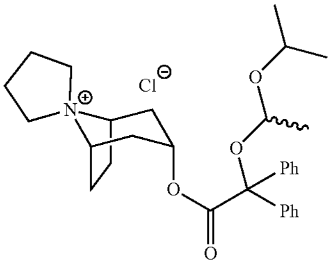 [SMILES: CC(C)SC(C)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 178 | 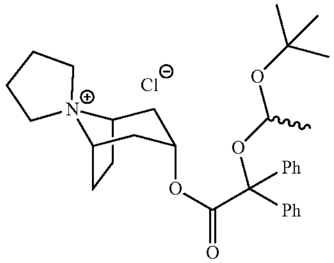 |
| 179 | 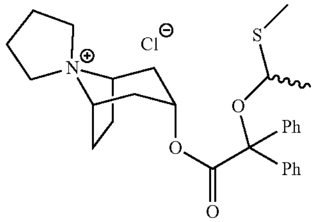 |
| 180 | 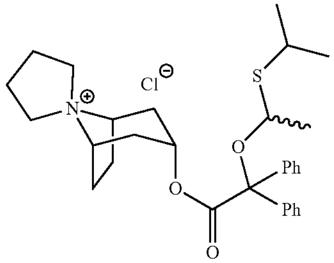 |
| 181 | 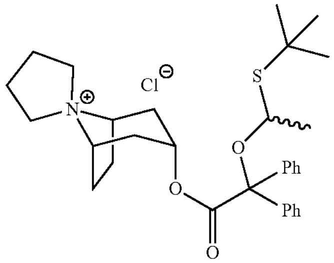 [SMILES: CC(OC(C(=O)OC1CC2CCC(C1)[N+]21CCCC1)(c1ccccc1)c1ccccc1)SC(C)(C)C ; [Cl-]] |
| 182 | 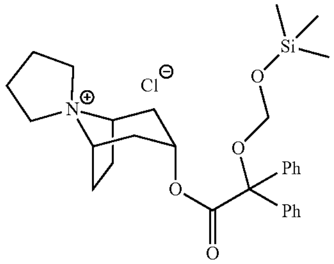 [SMILES: C[Si](C)(C)OCOC(C(=O)OC1CC2CCC(C1)[N+]21CCCC1)(c1ccccc1)c1ccccc1 ; [Cl-]] |
| 183 | 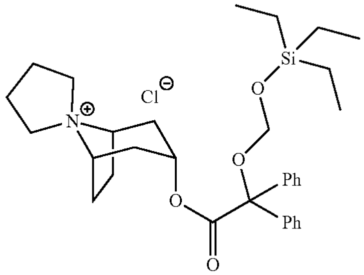 [SMILES: CC[Si](CC)(CC)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 184 | 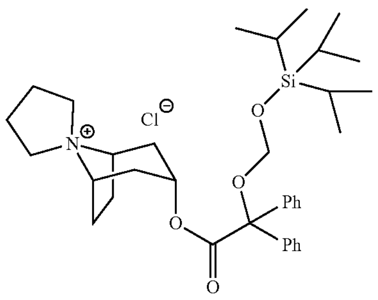 [SMILES: CC(C)[Si](OCOC(C(=O)OC1CC2CCC(C1)[N+]21CCCC1)(c1ccccc1)c1ccccc1)(C(C)C)C(C)C ; [Cl-]] |
| 185 | 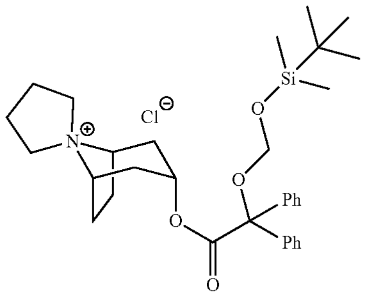 [SMILES: CC(C)(C)[Si](C)(C)OCOC(C(=O)OC1CC2CCC(C1)[N+]21CCCC1)(c1ccccc1)c1ccccc1 ; [Cl-]] |
| 186 | 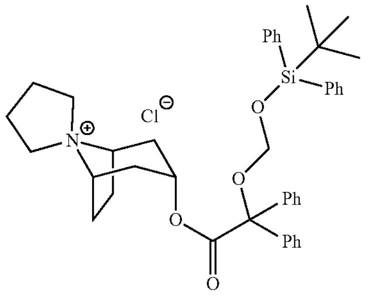 [SMILES: CC(C)(C)[Si](OCOC(C(=O)OC1CC2CCC(C1)[N+]21CCCC1)(c1ccccc1)c1ccccc1)(c1ccccc1)c1ccccc1 ; [Cl-]] |
| 187 | 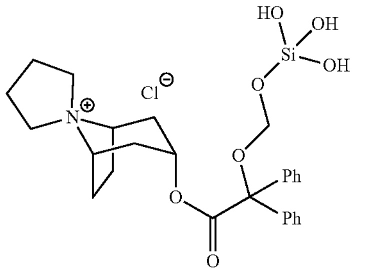 [SMILES: O=C(OC1CC2CCC(C1)[N+]21CCCC1)C(OCO[Si](O)(O)O)(c1ccccc1)c1ccccc1 ; [Cl-]] |
| 188 | 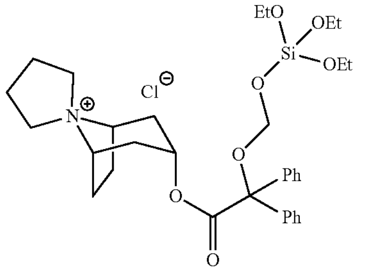 [SMILES: CCO[Si](OCC)(OCC)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 189 | 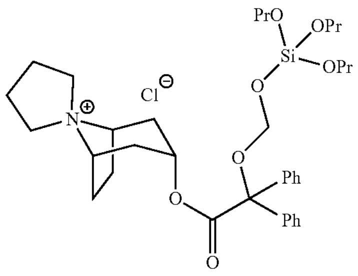 |
| 190 | 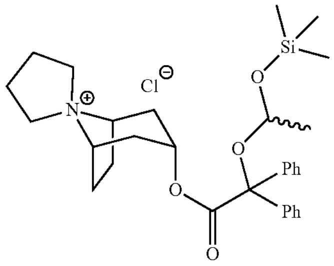 [SMILES: CC(OC(C(=O)OC1CC2CCC(C1)[N+]21CCCC1)(c1ccccc1)c1ccccc1)O[Si](C)(C)C ; [Cl-]] |
| 191 | 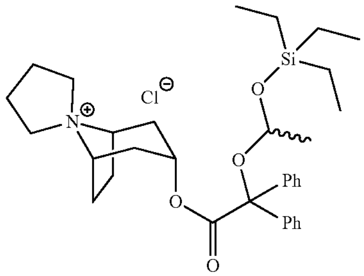 [SMILES: CC[Si](CC)(CC)OC(C)OC(C(=O)OC1CC2CCC(C1)[N+]21CCCC1)(c1ccccc1)c1ccccc1 ; [Cl-]] |
| 192 | 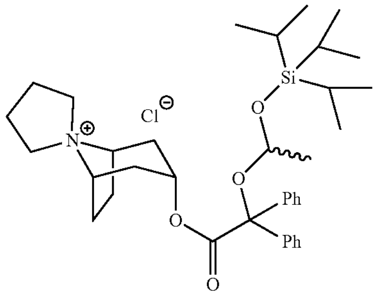 [SMILES: CC(OC(C(=O)OC1CC2CCC(C1)[N+]21CCCC1)(c1ccccc1)c1ccccc1)O[Si](C(C)C)(C(C)C)C(C)C ; [Cl-]] |
| 193 | 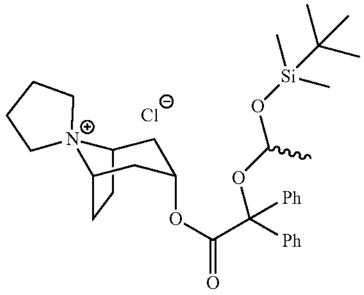 [SMILES: CC(OC(C(=O)OC1CC2CCC(C1)[N+]21CCCC1)(c1ccccc1)c1ccccc1)O[Si](C)(C)C(C)(C)C ; [Cl-]] |

TABLE 2-continued
| Cpd No. | Structure |
|---|---|
| 194 | 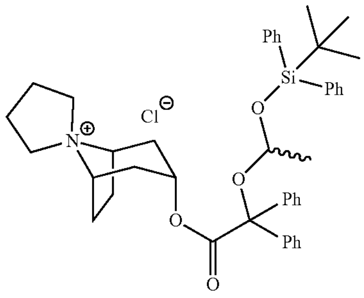 [SMILES: CC(OC(C(=O)OC1CC2CCC(C1)[N+]21CCCC1)(c1ccccc1)c1ccccc1)O[Si](c1ccccc1)(c1ccccc1)C(C)(C)C ; [Cl-]] |
| 195 | 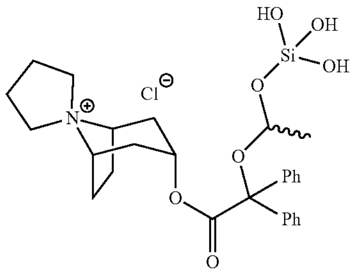 [SMILES: CC(OC(C(=O)OC1CC2CCC(C1)[N+]21CCCC1)(c1ccccc1)c1ccccc1)O[Si](O)(O)O ; [Cl-]] |
| 196 | 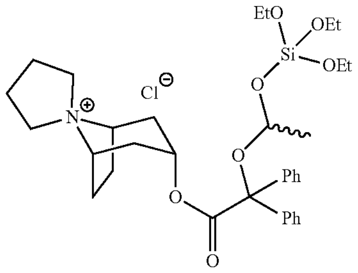 [SMILES: CCO[Si](OCC)(OCC)OC(C)OC(C(=O)OC1CC2CCC(C1)[N+]21CCCC1)(c1ccccc1)c1ccccc1 ; [Cl-]] |
| 197 | 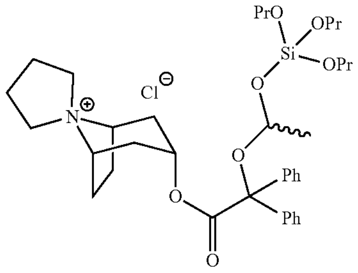 |
| 198 | 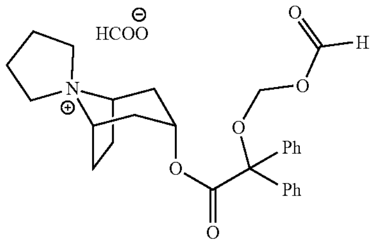 |

TABLE 2-continued
| Cpd No. | Structure |
|---|---|
| 199 | 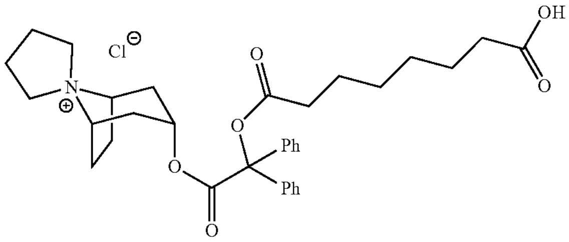 [SMILES: O=C(O)CCCCCCC(=O)OC(C(=O)OC1CC2CCC(C1)[N+]21CCCC1)(c1ccccc1)c1ccccc1 ; [Cl-]] |
| 200 | 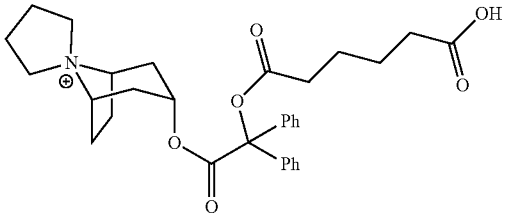 [SMILES: O=C(O)CCCCC(=O)OC(C(=O)OC1CC2CCC(C1)[N+]21CCCC1)(c1ccccc1)c1ccccc1] |
| 201 | 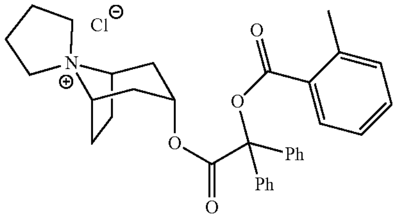 [SMILES: Cc1ccccc1C(=O)OC(C(=O)OC1CC2CCC(C1)[N+]21CCCC1)(c1ccccc1)c1ccccc1 ; [Cl-]] |
| 202 | 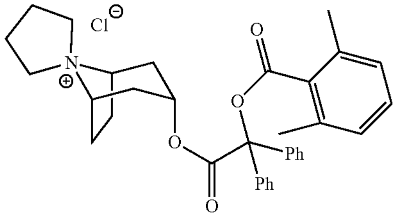 [SMILES: Cc1cccc(C)c1C(=O)OC(C(=O)OC1CC2CCC(C1)[N+]21CCCC1)(c1ccccc1)c1ccccc1 ; [Cl-]] |
| 203 | 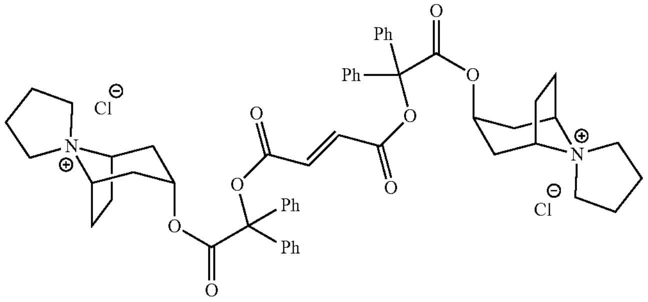 [SMILES: O=C(/C=C/C(=O)OC(C(=O)OC1CC2CCC(C1)[N+]21CCCC1)(c1ccccc1)c1ccccc1)OC(C(=O)OC1CC2CCC(C1)[N+]21CCCC1)(c1ccccc1)c1ccccc1 ; [Cl-] ; [Cl-]] |
| 204 | 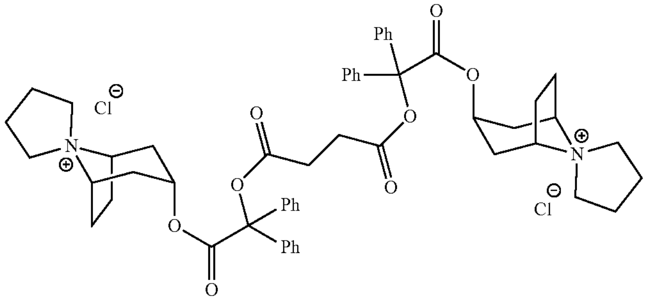 [SMILES: O=C(CCC(=O)OC(C(=O)OC1CC2CCC(C1)[N+]21CCCC1)(c1ccccc1)c1ccccc1)OC(C(=O)OC1CC2CCC(C1)[N+]21CCCC1)(c1ccccc1)c1ccccc1 ; [Cl-] ; [Cl-]] |

TABLE 2-continued
| Cpd No. | Structure |
|---|---|
| 205 | 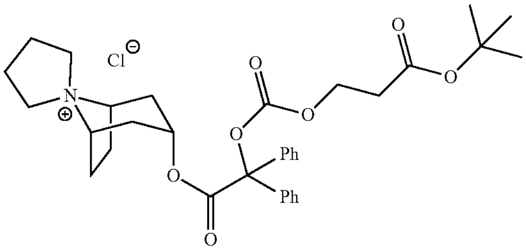 [SMILES: CC(C)(C)OC(=O)CCOC(=O)OC(C(=O)OC1CC2CCC(C1)[N+]21CCCC1)(c1ccccc1)c1ccccc1 ; [Cl-]] |
| 206 | 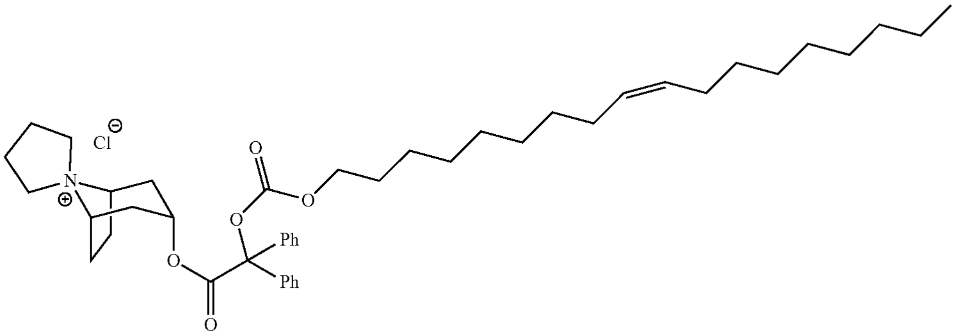 [SMILES: CCCCCCCC/C=C\CCCCCCCCOC(=O)OC(C(=O)OC1CC2CCC(C1)[N+]21CCCC1)(c1ccccc1)c1ccccc1 ; [Cl-]] |
| 207 | 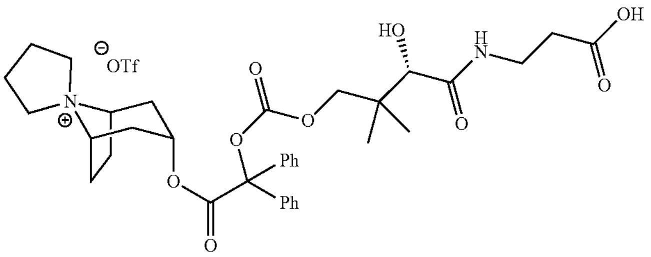 [SMILES: CC(C)(COC(=O)OC(C(=O)OC1CC2CCC(C1)[N+]21CCCC1)(c1ccccc1)c1ccccc1)[C@H](O)C(=O)NCCC(=O)O ; "OTf"] |
| 208 | 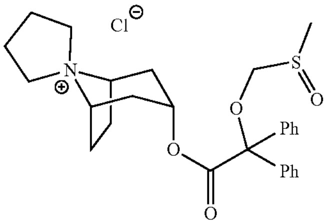 [SMILES: CS(=O)COC(C(=O)OC1CC2CCC(C1)[N+]21CCCC1)(c1ccccc1)c1ccccc1 ; [Cl-]] |
| 209 | 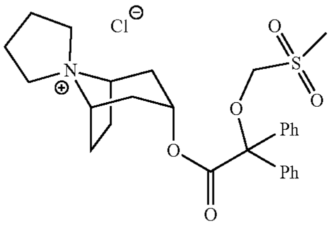 [SMILES: CS(=O)(=O)COC(C(=O)OC1CC2CCC(C1)[N+]21CCCC1)(c1ccccc1)c1ccccc1 ; [Cl-]] |
| 210 | 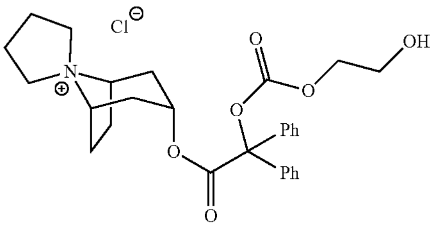 [SMILES: O=C(OCCO)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 211 | 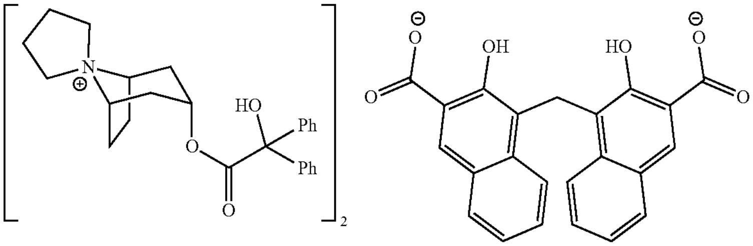 |
| 212 | 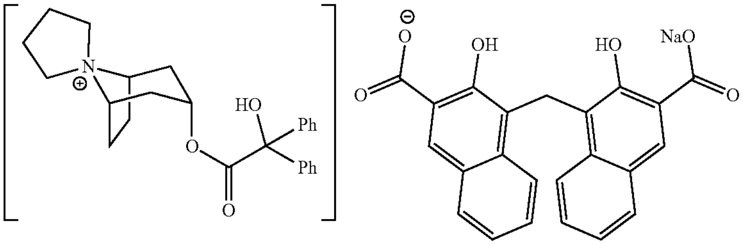 |
| 213 | 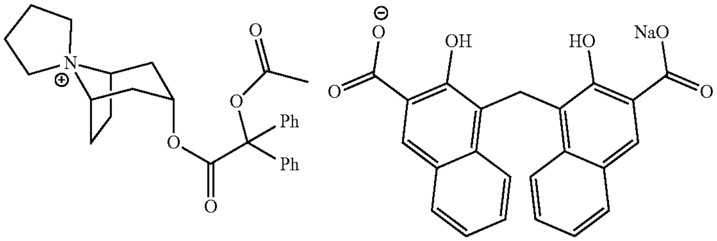 |
| 214 | 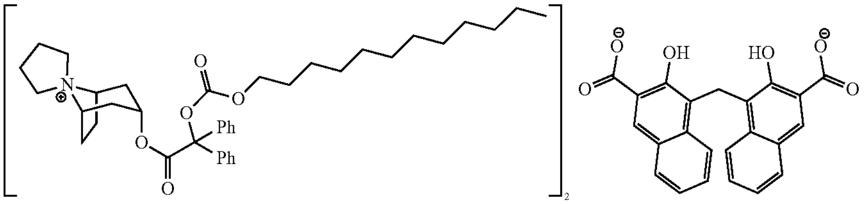 |
| 215 | 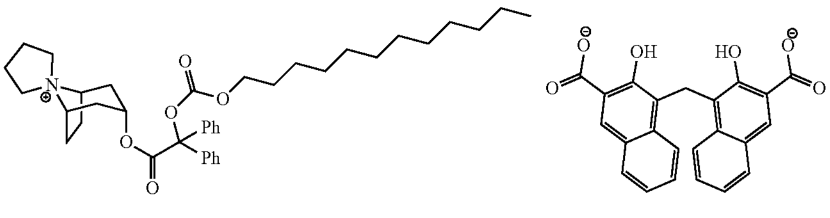 [SMILES: CCCCCCCCCCCCOC(=O)OC(C(=O)OC1CC2CCC(C1)[N+]21CCCC1)(c1ccccc1)c1ccccc1 ; O=C([O-])c1cc2ccccc2c(Cc2c(O)c(C(=O)[O-])cc3ccccc23)c1O] |
| 216 | 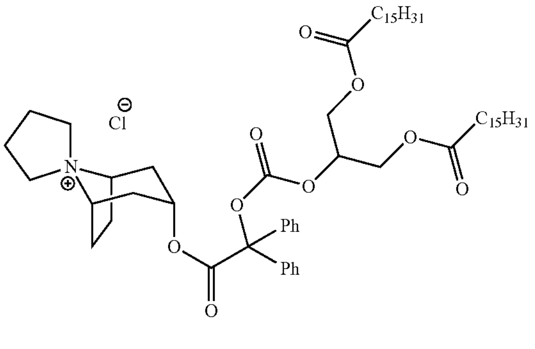 |

TABLE 2-continued
| Cpd No. | Structure |
|---|---|
| 217 | 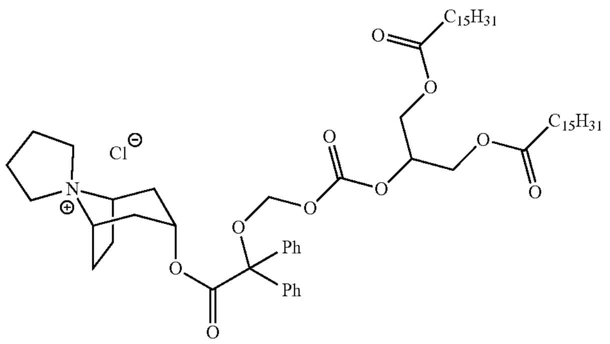 |
| 218 | 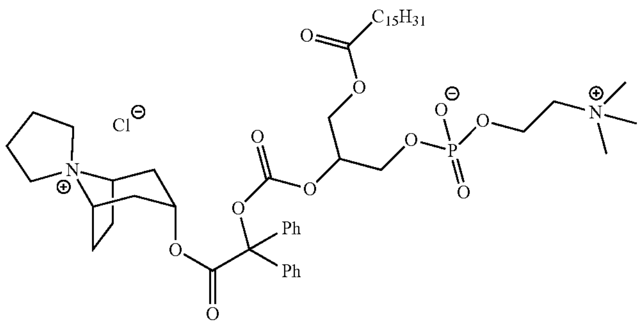 |
| 219 | 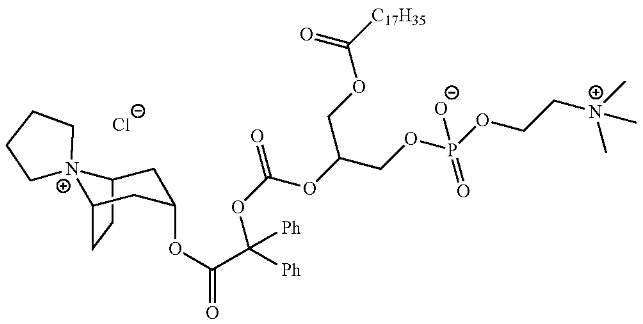 |
| 220 | 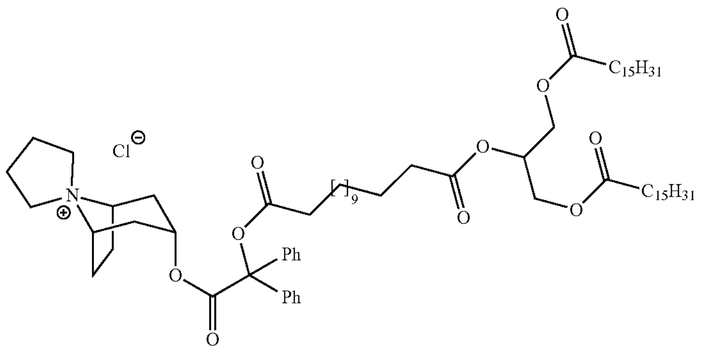 |

TABLE 2-continued
| Cpd No. | Structure |
|---|---|
| 221 | 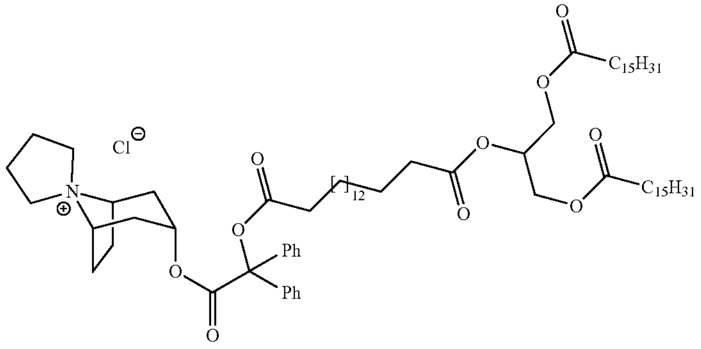 |
| 222 | 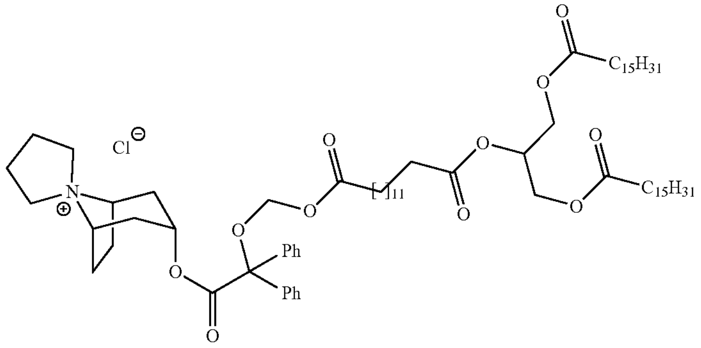 |
| 223 | 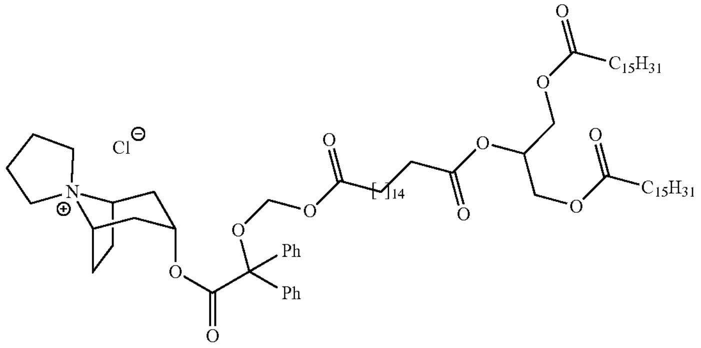 |
| 224 | 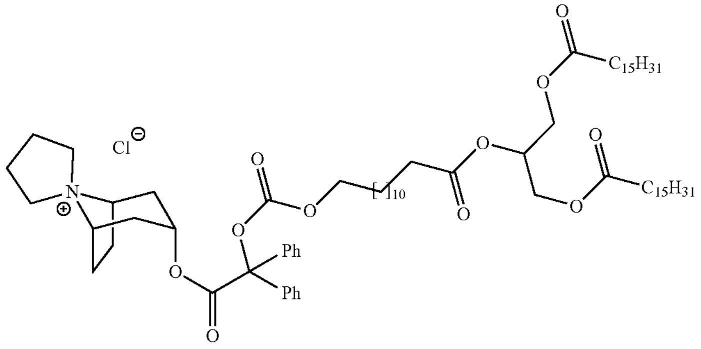 |

TABLE 2-continued
| Cpd No. | Structure |
|---|---|
| 225 | 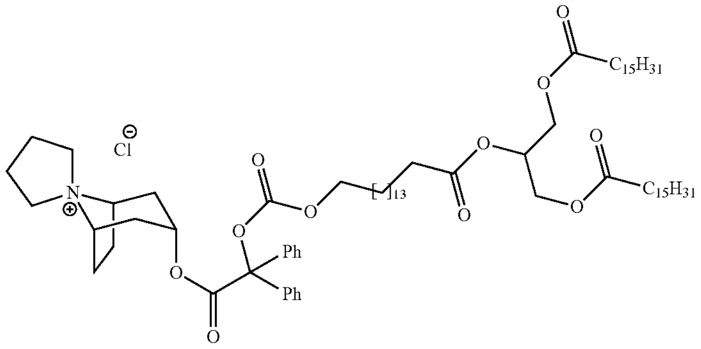 |
| 226 | 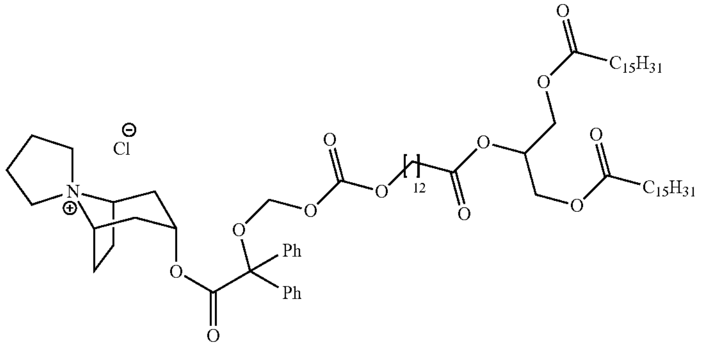 |
| 227 | 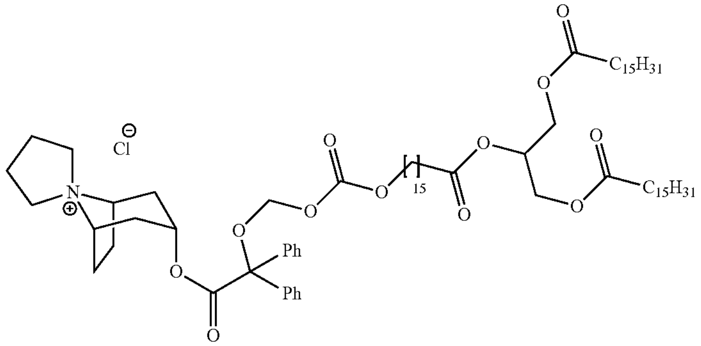 |
| 228 | 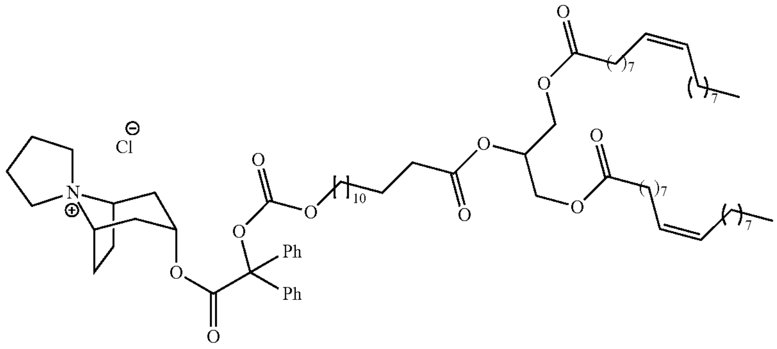 |

TABLE 2-continued
| Cpd No. | Structure |
|---|---|
| 229 | 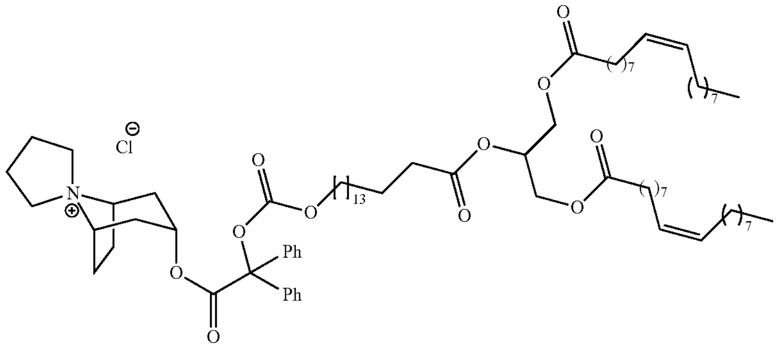 |
| 230 | 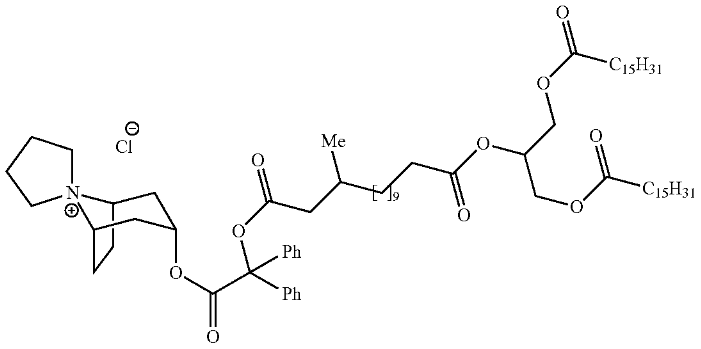 |
| 231 | 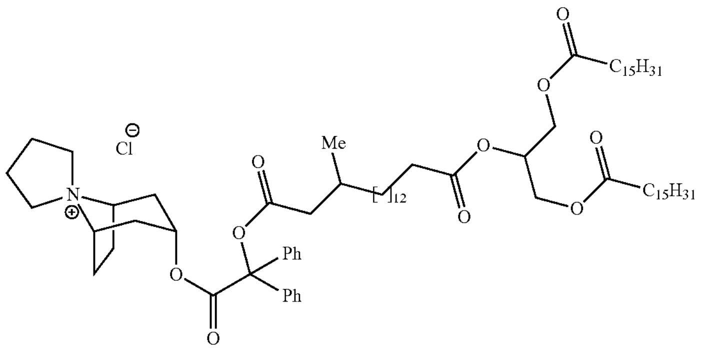 |
| 232 | 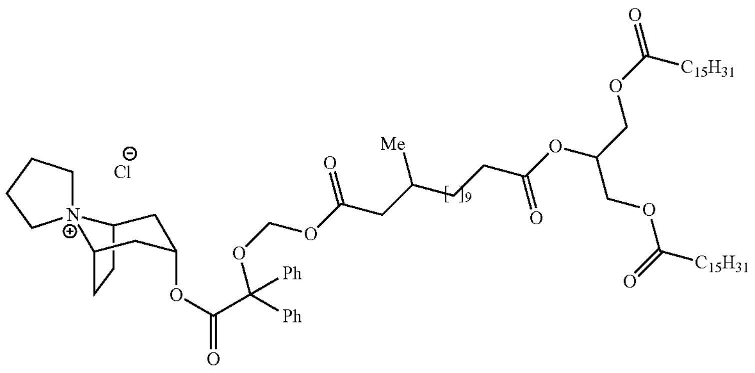 |

TABLE 2-continued
| Cpd No. | Structure |
|---|---|
| 233 | 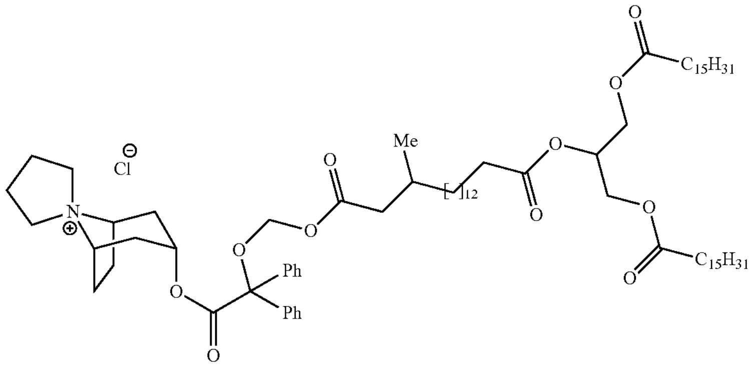 |
| 234 | 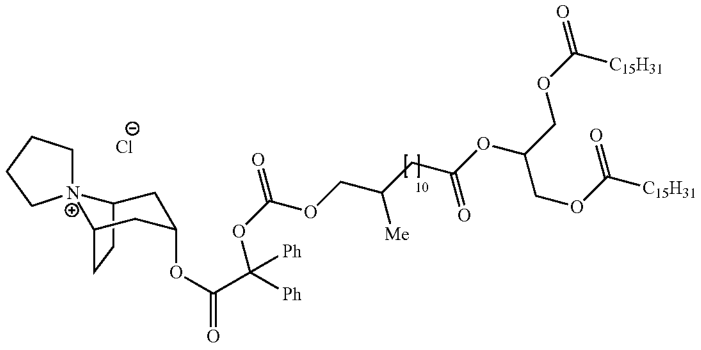 |
| 235 | 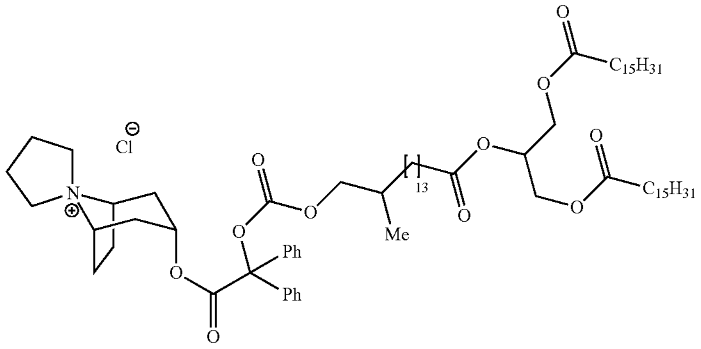 |
| 236 | 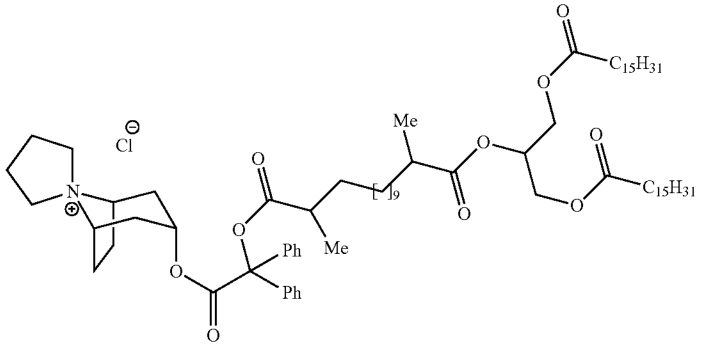 |

TABLE 2-continued
| Cpd No. | Structure |
|---|---|
| 237 | 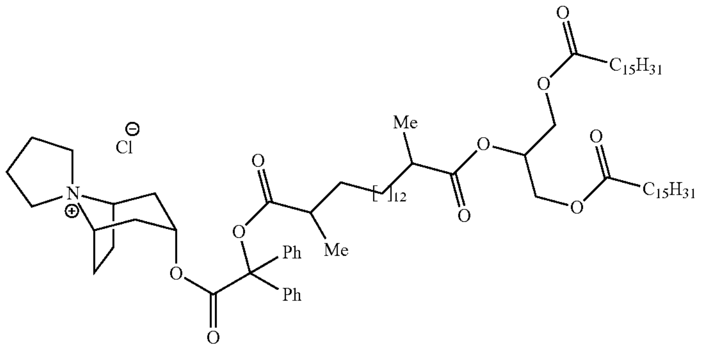 |
| 238 | 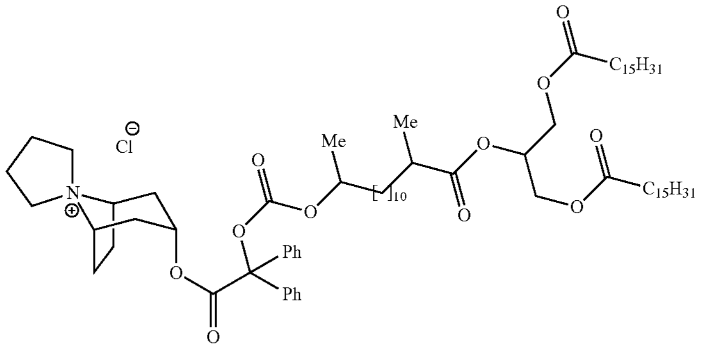 |
| 239 | 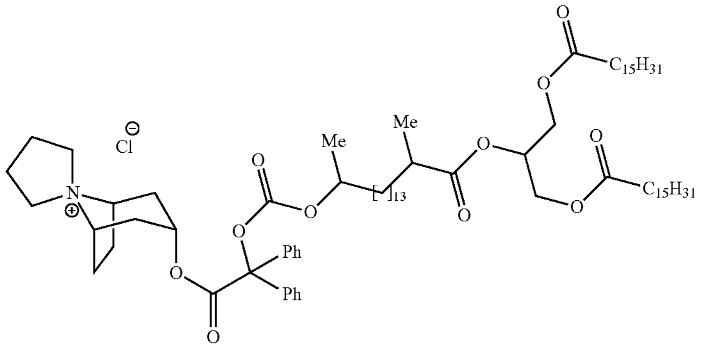 |
| 240 | 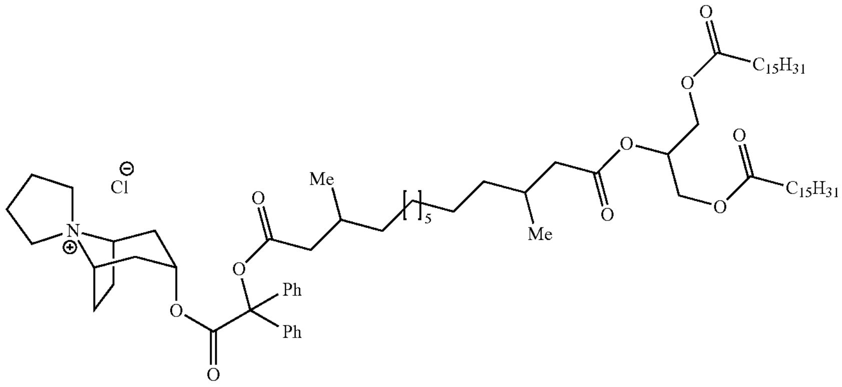 |

TABLE 2-continued
| Cpd No. | Structure |
|---|---|
| 241 | 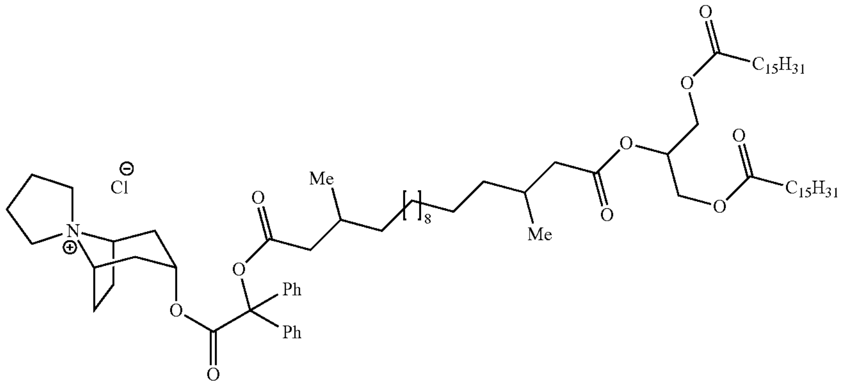 |
| 242 | 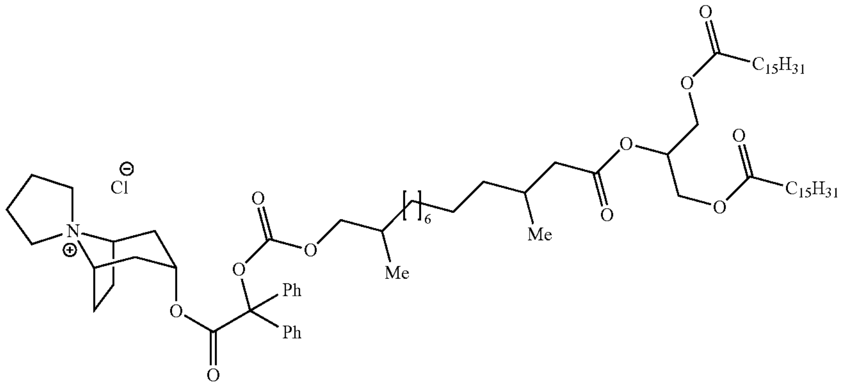 |
| 243 | 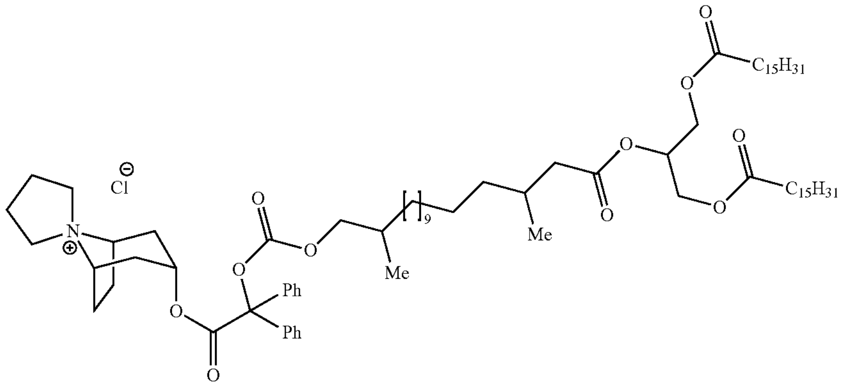 |
| 244 | 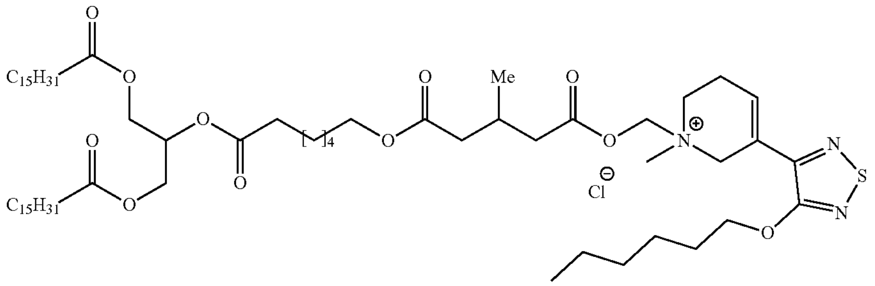 |

TABLE 2-continued
| Cpd No. | Structure |
|---|---|
| 245 | 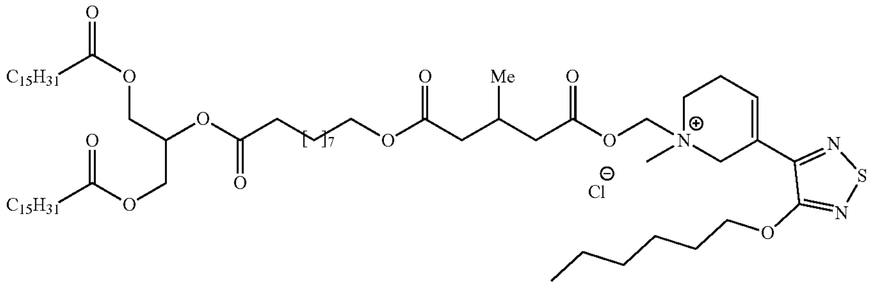 |
| 246 | 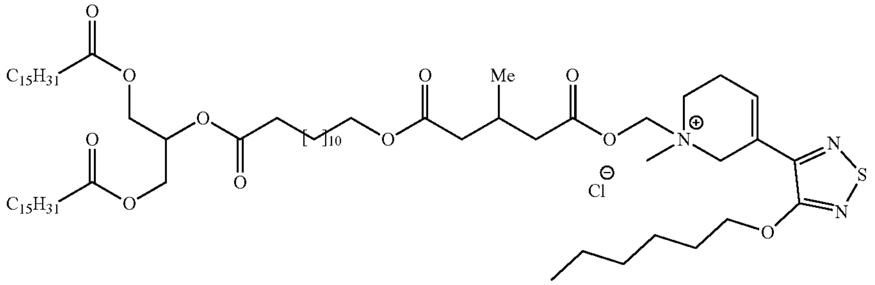 |
| 247 | 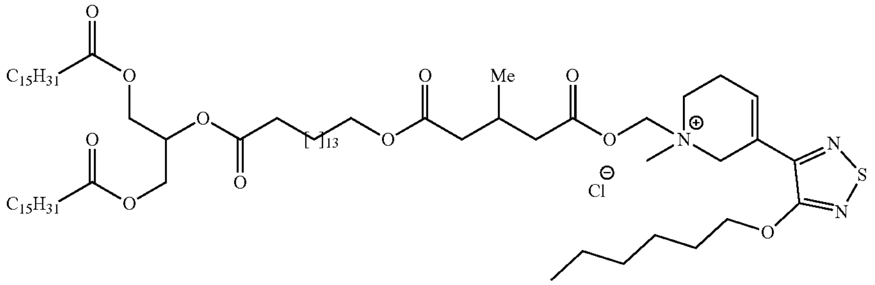 |
| 248 | 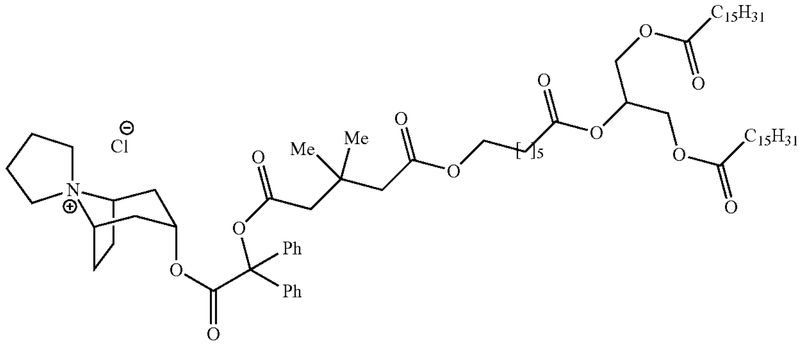 |
| 249 | 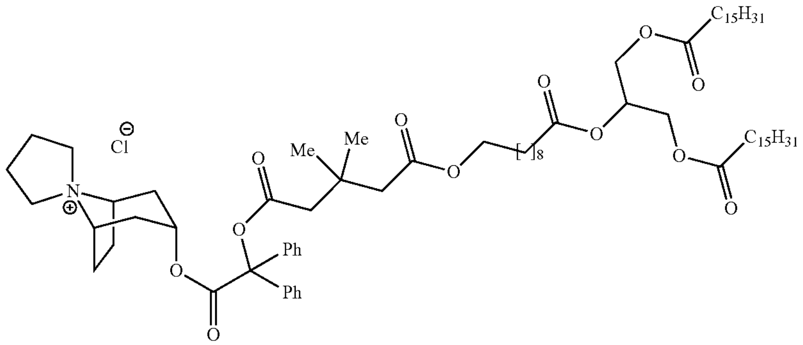 |

TABLE 2-continued
| Cpd No. | Structure |
|---|---|
| 250 | 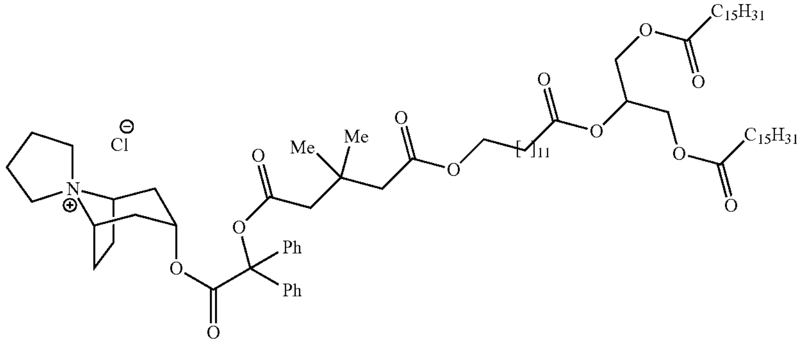 |
| 251 | 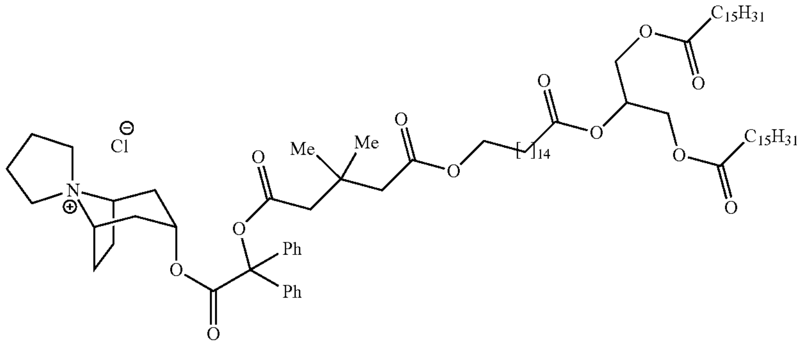 |
| 252 | 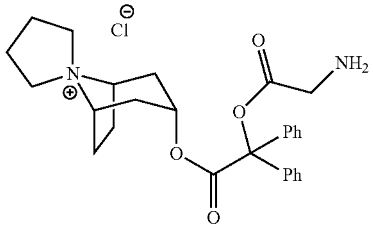 [SMILES: NCC(=O)OC(C(=O)OC1CC2CCC(C1)[N+]21CCCC1)(c1ccccc1)c1ccccc1 ; [Cl-]] |
| 253 | 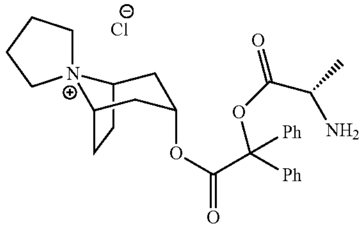 [SMILES: C[C@H](N)C(=O)OC(C(=O)OC1CC2CCC(C1)[N+]21CCCC1)(c1ccccc1)c1ccccc1 ; [Cl-]] |
| 254 | 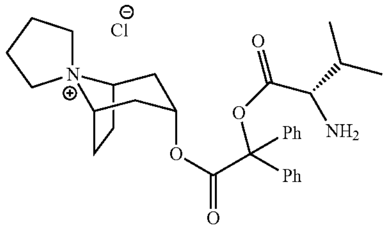 [SMILES: CC(C)[C@H](N)C(=O)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 255 | 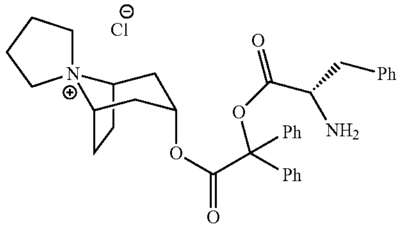 [SMILES: N[C@@H](Cc1ccccc1)C(=O)OC(C(=O)OC1CC2CCC(C1)[N+]21CCCC1)(c1ccccc1)c1ccccc1 ; [Cl-]] |
| 256 | 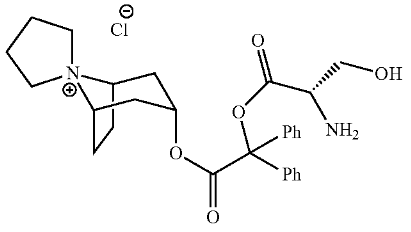 [SMILES: N[C@@H](CO)C(=O)OC(C(=O)OC1CC2CCC(C1)[N+]21CCCC1)(c1ccccc1)c1ccccc1 ; [Cl-]] |
| 257 | 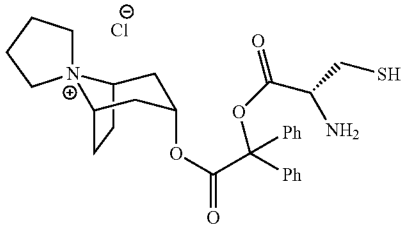 [SMILES: N[C@@H](CS)C(=O)OC(C(=O)OC1CC2CCC(C1)[N+]21CCCC1)(c1ccccc1)c1ccccc1 ; [Cl-]] |
| 258 | 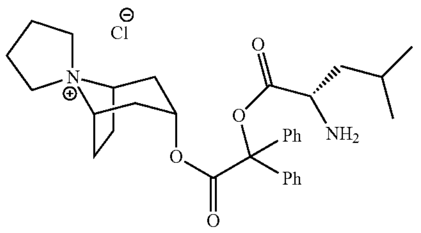 [SMILES: CC(C)C[C@H](N)C(=O)OC(C(=O)OC1CC2CCC(C1)[N+]21CCCC1)(c1ccccc1)c1ccccc1 ; [Cl-]] |
| 259 | 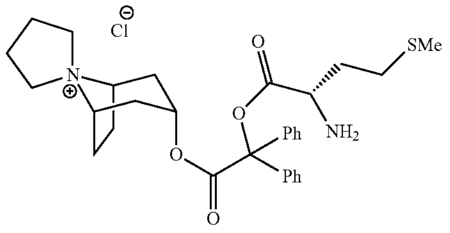 [SMILES: CSCC[C@H](N)C(=O)OC(C(=O)OC1CC2CCC(C1)[N+]21CCCC1)(c1ccccc1)c1ccccc1 ; [Cl-]] |
| 260 | 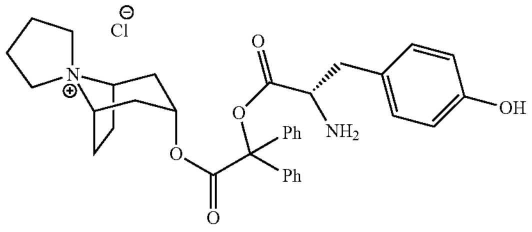 [SMILES: N[C@@H](Cc1ccc(O)cc1)C(=O)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 261 | 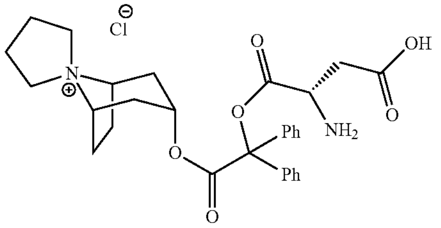 [SMILES: N[C@@H](CC(=O)O)C(=O)OC(C(=O)OC1CC2CCC(C1)[N+]21CCCC1)(c1ccccc1)c1ccccc1 ; [Cl-]] |
| 262 | 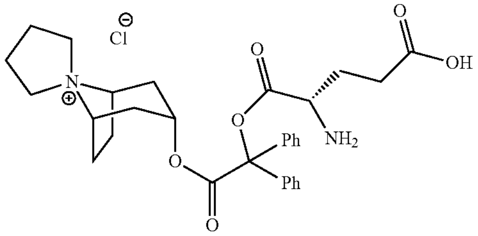 [SMILES: N[C@@H](CCC(=O)O)C(=O)OC(C(=O)OC1CC2CCC(C1)[N+]21CCCC1)(c1ccccc1)c1ccccc1 ; [Cl-]] |
| 263 | 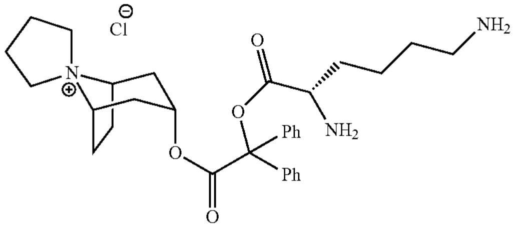 [SMILES: NCCCC[C@H](N)C(=O)OC(C(=O)OC1CC2CCC(C1)[N+]21CCCC1)(c1ccccc1)c1ccccc1 ; [Cl-]] |
| 264 | 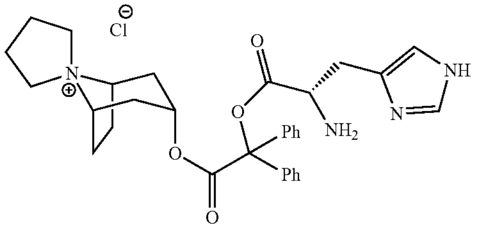 [SMILES: N[C@@H](Cc1c[nH]cn1)C(=O)OC(C(=O)OC1CC2CCC(C1)[N+]21CCCC1)(c1ccccc1)c1ccccc1 ; [Cl-]] |
| 265 | 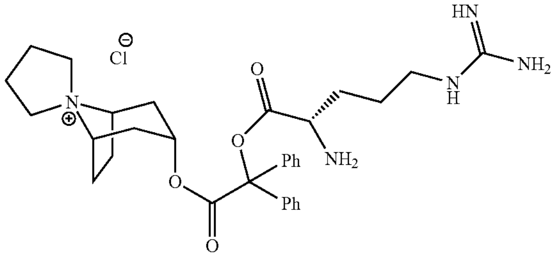 [SMILES: N=C(N)NCCC[C@H](N)C(=O)OC(C(=O)OC1CC2CCC(C1)[N+]21CCCC1)(c1ccccc1)c1ccccc1 ; [Cl-]] |
| 266 | 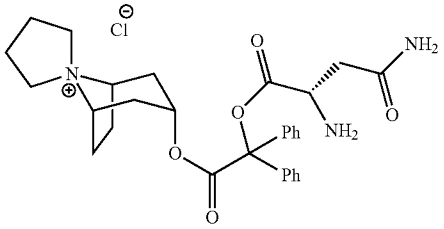 [SMILES: NC(=O)C[C@H](N)C(=O)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 267 | 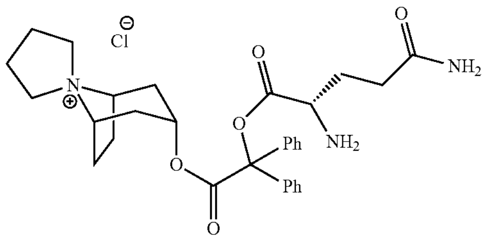 [SMILES: NC(=O)CC[C@H](N)C(=O)OC(C(=O)OC1CC2CCC(C1)[N+]21CCCC1)(c1ccccc1)c1ccccc1 ; [Cl-]] |
| 268 | 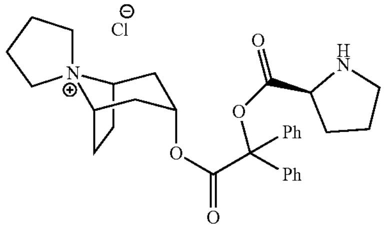 [SMILES: O=C(OC(C(=O)OC1CC2CCC(C1)[N+]21CCCC1)(c1ccccc1)c1ccccc1)[C@@H]1CCCN1 ; [Cl-]] |
| 269 | 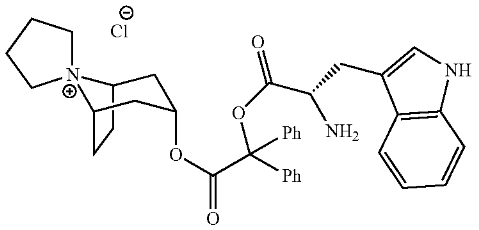 [SMILES: N[C@@H](Cc1c[nH]c2ccccc12)C(=O)OC(C(=O)OC1CC2CCC(C1)[N+]21CCCC1)(c1ccccc1)c1ccccc1 ; [Cl-]] |
| 270 | 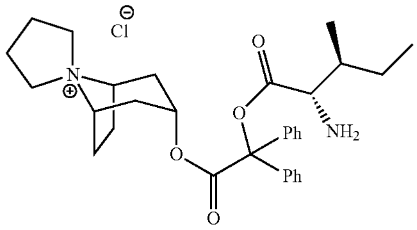 [SMILES: CC[C@H](C)[C@H](N)C(=O)OC(C(=O)OC1CC2CCC(C1)[N+]21CCCC1)(c1ccccc1)c1ccccc1 ; [Cl-]] |
| 271 | 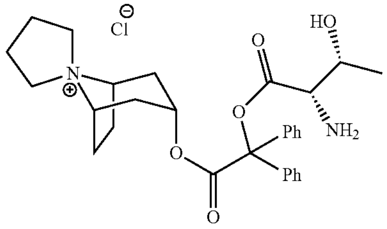 [SMILES: C[C@@H](O)[C@H](N)C(=O)OC(C(=O)OC1CC2CCC(C1)[N+]21CCCC1)(c1ccccc1)c1ccccc1 ; [Cl-]] |
| 272 | 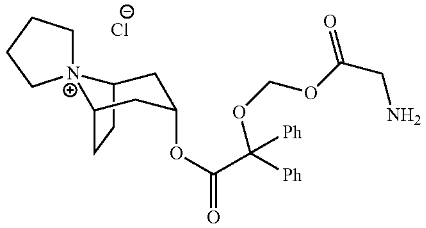 [SMILES: NCC(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 273 | 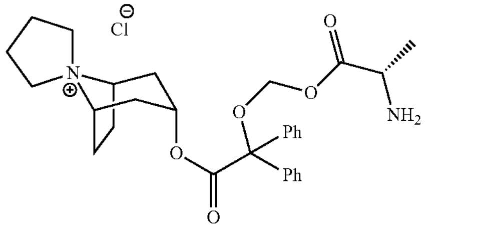 [SMILES: C[C@H](N)C(=O)OCOC(C(=O)OC1CC2CCC(C1)[N+]21CCCC1)(c1ccccc1)c1ccccc1 ; [Cl-]] |
| 274 | 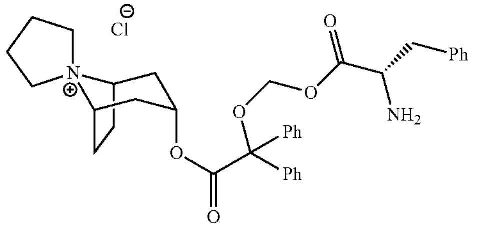 [SMILES: N[C@@H](Cc1ccccc1)C(=O)OCOC(C(=O)OC1CC2CCC(C1)[N+]21CCCC1)(c1ccccc1)c1ccccc1 ; [Cl-]] |
| 275 | 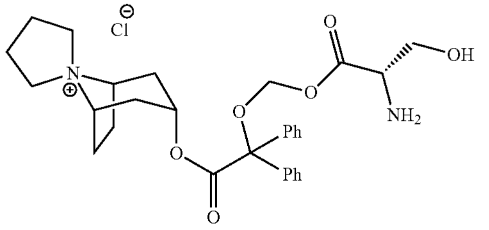 |
| 276 | 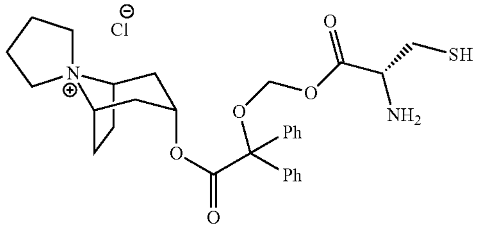 [SMILES: N[C@@H](CO)C(=O)OCOC(C(=O)OC1CC2CCC(C1)[N+]21CCCC1)(c1ccccc1)c1ccccc1 ; [Cl-]] |
| 277 | 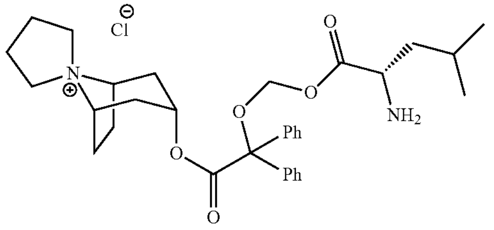 [SMILES: CC(C)C[C@H](N)C(=O)OCOC(C(=O)OC1CC2CCC(C1)[N+]21CCCC1)(c1ccccc1)c1ccccc1 ; [Cl-]] |
| 278 | 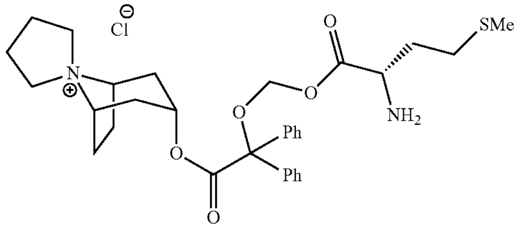 [SMILES: CSCC[C@H](N)C(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 279 | 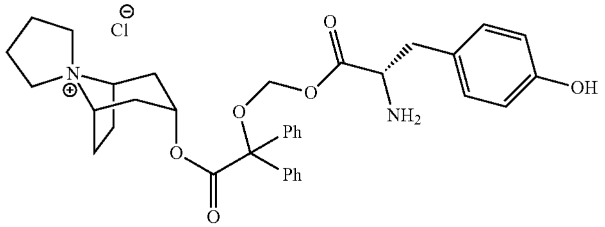 |
| 280 | 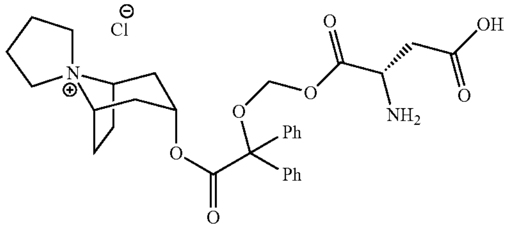 [SMILES: N[C@@H](CC(=O)O)C(=O)OCOC(C(=O)OC1CC2CCC(C1)[N+]21CCCC1)(c1ccccc1)c1ccccc1 ; [Cl-]] |
| 281 | 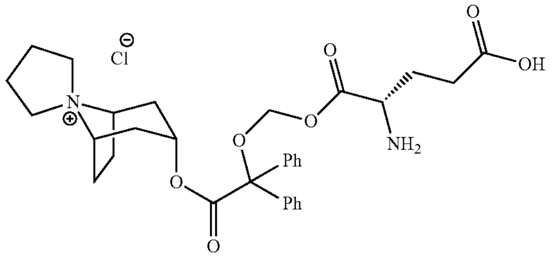 [SMILES: N[C@@H](CCC(=O)O)C(=O)OCOC(C(=O)OC1CC2CCC(C1)[N+]21CCCC1)(c1ccccc1)c1ccccc1 ; [Cl-]] |
| 282 | 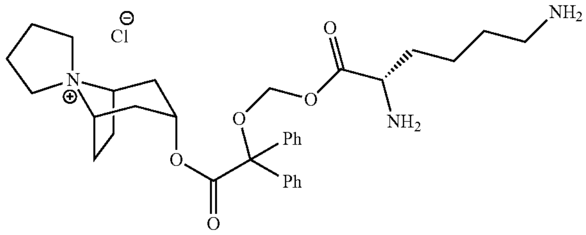 [SMILES: NCCCC[C@H](N)C(=O)OCOC(C(=O)OC1CC2CCC(C1)[N+]21CCCC1)(c1ccccc1)c1ccccc1 ; [Cl-]] |
| 283 | 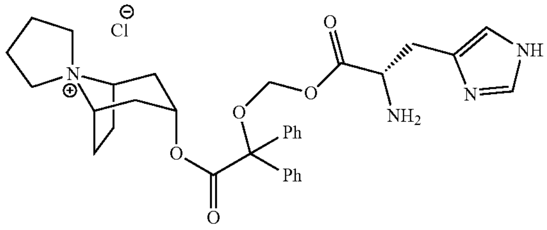 [SMILES: N[C@@H](Cc1c[nH]cn1)C(=O)OCOC(C(=O)OC1CC2CCC(C1)[N+]21CCCC1)(c1ccccc1)c1ccccc1 ; [Cl-]] |
| 284 | 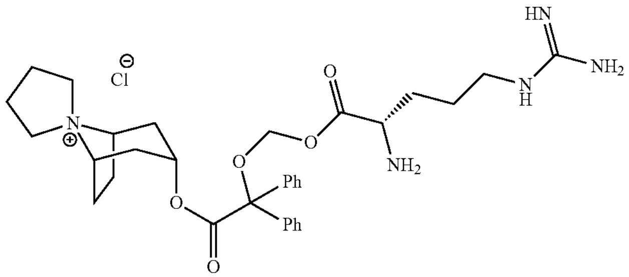 [SMILES: N=C(N)NCCC[C@H](N)C(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 285 | 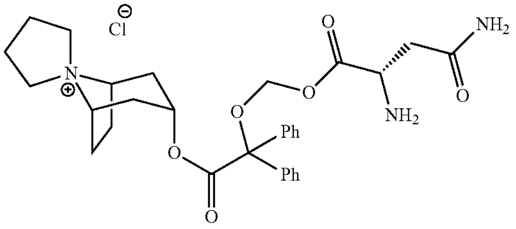 [SMILES: NC(=O)C[C@H](N)C(=O)OCOC(C(=O)OC1CC2CCC(C1)[N+]21CCCC1)(c1ccccc1)c1ccccc1 ; [Cl-]] |
| 286 | 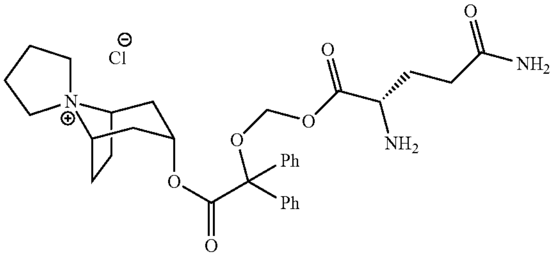 [SMILES: NC(=O)CC[C@H](N)C(=O)OCOC(C(=O)OC1CC2CCC(C1)[N+]21CCCC1)(c1ccccc1)c1ccccc1 ; [Cl-]] |
| 287 | 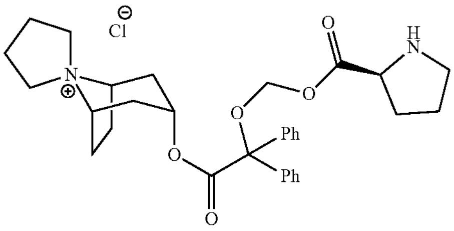 [SMILES: O=C(OCOC(C(=O)OC1CC2CCC(C1)[N+]21CCCC1)(c1ccccc1)c1ccccc1)[C@@H]1CCCN1 ; [Cl-]] |
| 288 | 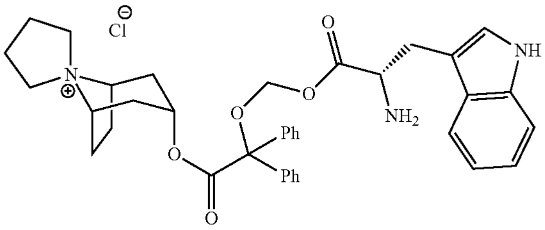 [SMILES: N[C@@H](Cc1c[nH]c2ccccc12)C(=O)OCOC(C(=O)OC1CC2CCC(C1)[N+]21CCCC1)(c1ccccc1)c1ccccc1 ; [Cl-]] |
| 289 | 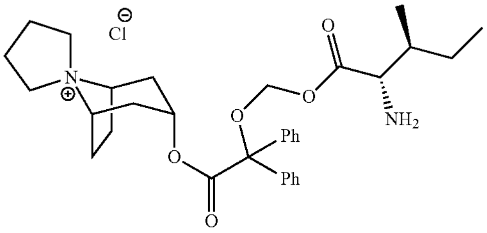 [SMILES: CC[C@H](C)[C@H](N)C(=O)OCOC(C(=O)OC1CC2CCC(C1)[N+]21CCCC1)(c1ccccc1)c1ccccc1 ; [Cl-]] |
| 290 | 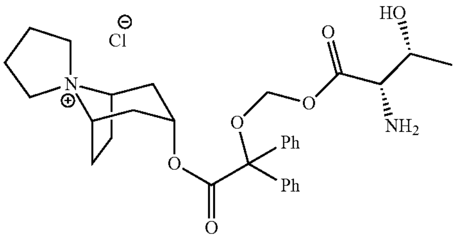 [SMILES: C[C@@H](O)[C@H](N)C(=O)OCOC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 291 | 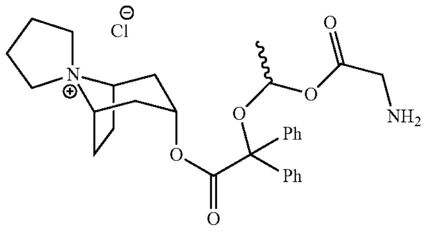 [SMILES: CC(OC(=O)CN)OC(C(=O)OC1CC2CCC(C1)[N+]21CCCC1)(c1ccccc1)c1ccccc1 ; [Cl-]] |
| 292 | 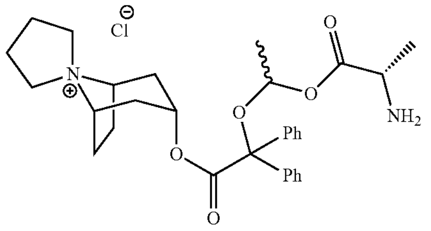 [SMILES: CC(OC(=O)[C@H](C)N)OC(C(=O)OC1CC2CCC(C1)[N+]21CCCC1)(c1ccccc1)c1ccccc1 ; [Cl-]] |
| 293 | 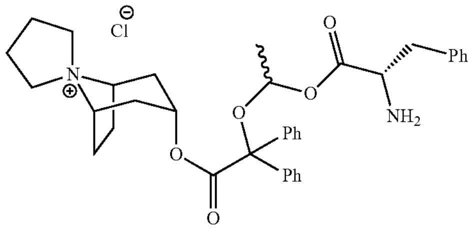 [SMILES: CC(OC(=O)[C@@H](N)Cc1ccccc1)OC(C(=O)OC1CC2CCC(C1)[N+]21CCCC1)(c1ccccc1)c1ccccc1 ; [Cl-]] |
| 294 | 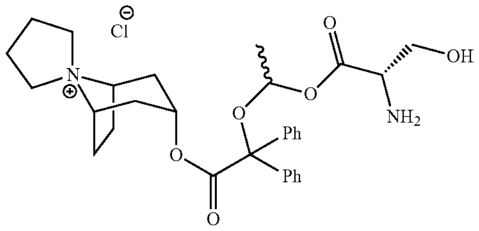 |
| 295 | 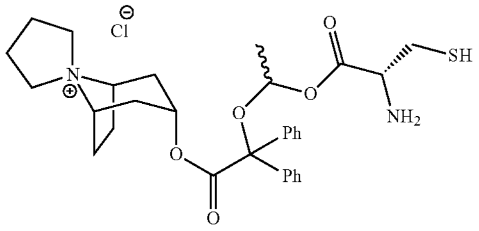 [SMILES: CC(OC(=O)[C@@H](N)CO)OC(C(=O)OC1CC2CCC(C1)[N+]21CCCC1)(c1ccccc1)c1ccccc1 ; [Cl-]] |
| 296 | 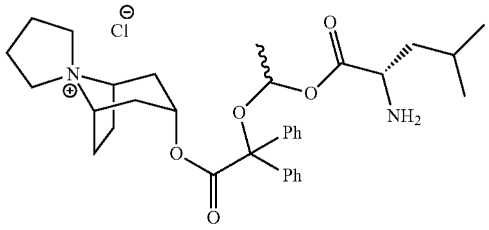 [SMILES: CC(C)C[C@H](N)C(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 297 | 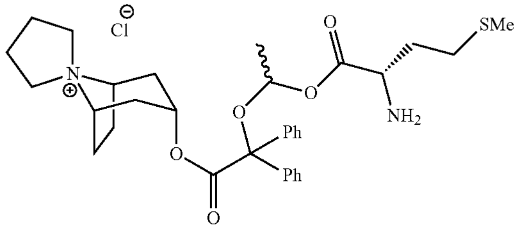 [SMILES: CSCC[C@H](N)C(=O)OC(C)OC(C(=O)OC1CC2CCC(C1)[N+]21CCCC1)(c1ccccc1)c1ccccc1 ; [Cl-]] |
| 298 | 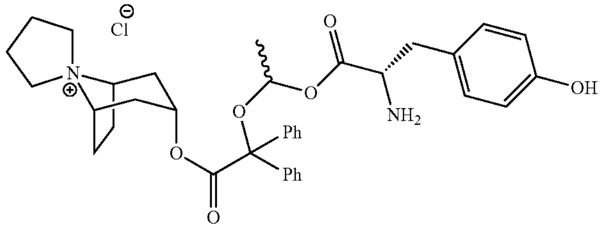 [SMILES: CC(OC(=O)[C@@H](N)Cc1ccc(O)cc1)OC(C(=O)OC1CC2CCC(C1)[N+]21CCCC1)(c1ccccc1)c1ccccc1 ; [Cl-]] |
| 299 | 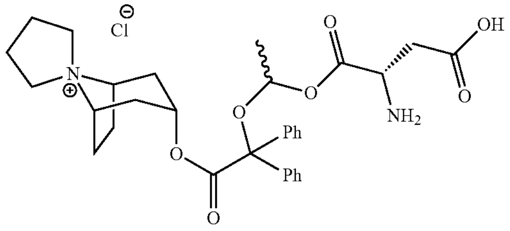 [SMILES: CC(OC(=O)[C@@H](N)CC(=O)O)OC(C(=O)OC1CC2CCC(C1)[N+]21CCCC1)(c1ccccc1)c1ccccc1 ; [Cl-]] |
| 300 | 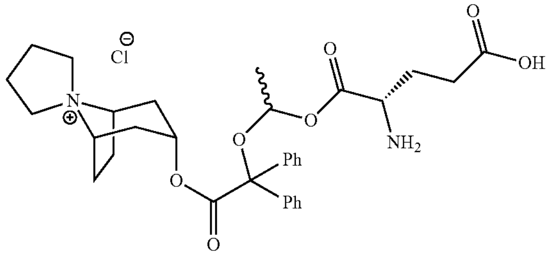 [SMILES: CC(OC(=O)[C@@H](N)CCC(=O)O)OC(C(=O)OC1CC2CCC(C1)[N+]21CCCC1)(c1ccccc1)c1ccccc1 ; [Cl-]] |
| 301 | 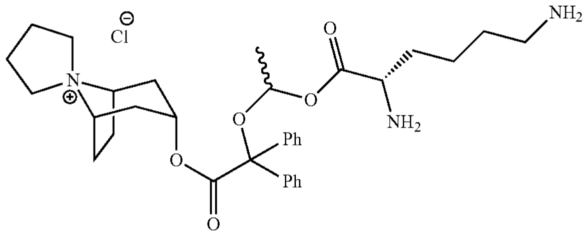 [SMILES: CC(OC(=O)[C@@H](N)CCCCN)OC(C(=O)OC1CC2CCC(C1)[N+]21CCCC1)(c1ccccc1)c1ccccc1 ; [Cl-]] |
| 302 | 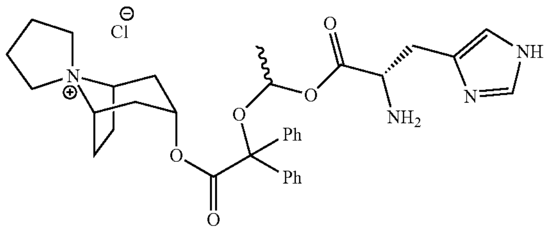 [SMILES: CC(OC(=O)[C@@H](N)Cc1c[nH]cn1)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 303 | 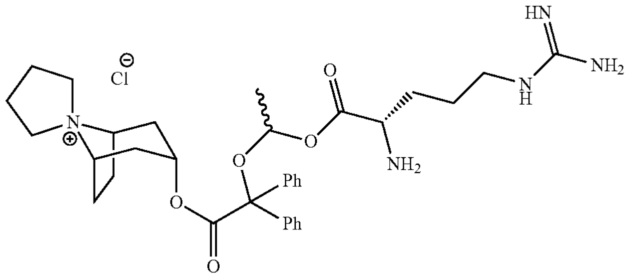 [SMILES: CC(OC(=O)[C@@H](N)CCCNC(=N)N)OC(C(=O)OC1CC2CCC(C1)[N+]21CCCC1)(c1ccccc1)c1ccccc1 ; [Cl-]] |
| 304 | 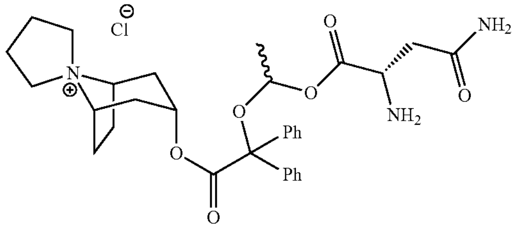 [SMILES: CC(OC(=O)[C@@H](N)CC(N)=O)OC(C(=O)OC1CC2CCC(C1)[N+]21CCCC1)(c1ccccc1)c1ccccc1 ; [Cl-]] |
| 305 | 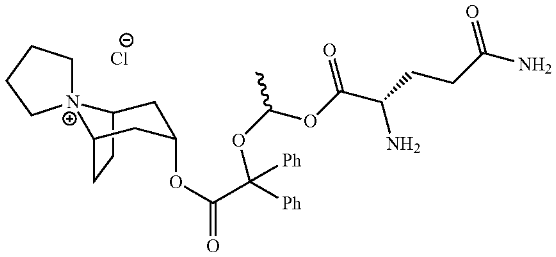 [SMILES: CC(OC(=O)[C@@H](N)CCC(N)=O)OC(C(=O)OC1CC2CCC(C1)[N+]21CCCC1)(c1ccccc1)c1ccccc1 ; [Cl-]] |
| 306 | 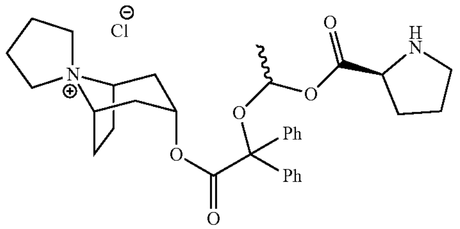 [SMILES: CC(OC(=O)[C@@H]1CCCN1)OC(C(=O)OC1CC2CCC(C1)[N+]21CCCC1)(c1ccccc1)c1ccccc1 ; [Cl-]] |
| 307 | 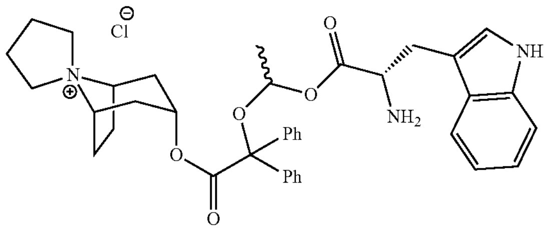 [SMILES: CC(OC(=O)[C@@H](N)Cc1c[nH]c2ccccc12)OC(C(=O)OC1CC2CCC(C1)[N+]21CCCC1)(c1ccccc1)c1ccccc1 ; [Cl-]] |
| 308 | 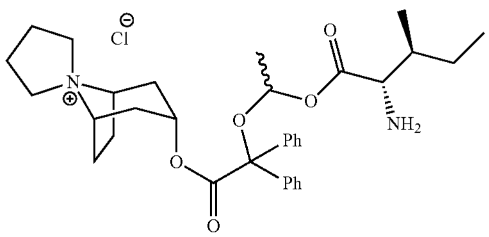 [SMILES: CC[C@H](C)[C@H](N)C(=O)OC(C)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 309 | 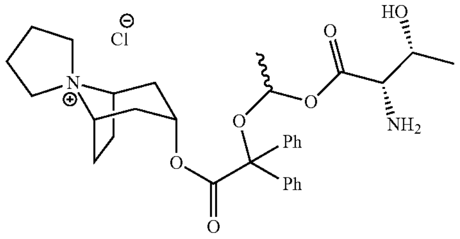 [SMILES: CC(OC(=O)[C@@H](N)[C@@H](C)O)OC(C(=O)OC1CC2CCC(C1)[N+]21CCCC1)(c1ccccc1)c1ccccc1 ; [Cl-]] |
| 310 | 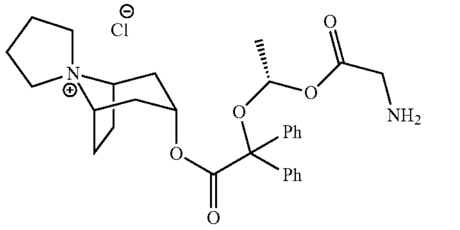 [SMILES: C[C@H](OC(=O)CN)OC(C(=O)OC1CC2CCC(C1)[N+]21CCCC1)(c1ccccc1)c1ccccc1 ; [Cl-]] |
| 311 | 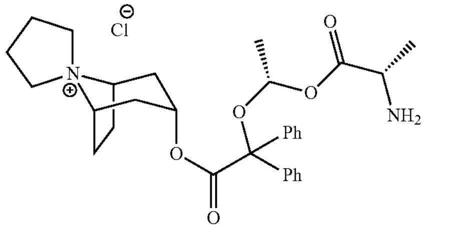 [SMILES: C[C@H](OC(=O)[C@H](C)N)OC(C(=O)OC1CC2CCC(C1)[N+]21CCCC1)(c1ccccc1)c1ccccc1 ; [Cl-]] |
| 312 | 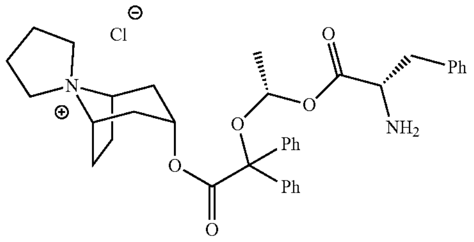 [SMILES: C[C@H](OC(=O)[C@@H](N)Cc1ccccc1)OC(C(=O)OC1CC2CCC(C1)[N+]21CCCC1)(c1ccccc1)c1ccccc1 ; [Cl-]] |
| 313 | 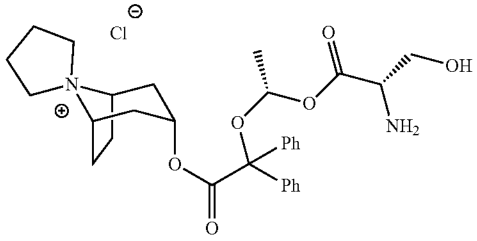 [SMILES: C[C@H](OC(=O)[C@@H](N)CO)OC(C(=O)OC1CC2CCC(C1)[N+]21CCCC1)(c1ccccc1)c1ccccc1 ; [Cl-]] |
| 314 | 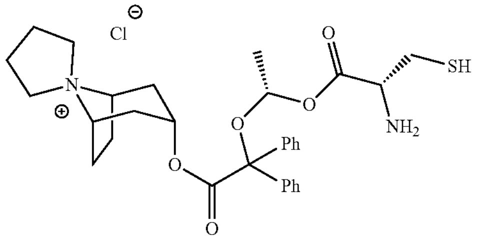 [SMILES: C[C@H](OC(=O)[C@@H](N)CS)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 315 | 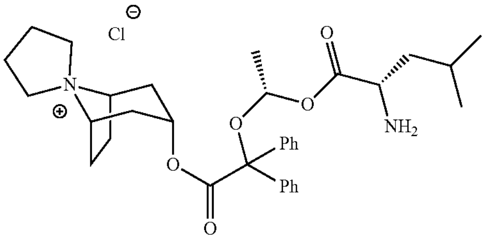 [SMILES: CC(C)C[C@H](N)C(=O)O[C@@H](C)OC(C(=O)OC1CC2CCC(C1)[N+]21CCCC1)(c1ccccc1)c1ccccc1 ; [Cl-]] |
| 316 | 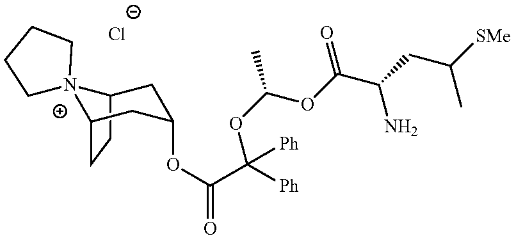 [SMILES: CSC(C)C[C@H](N)C(=O)O[C@@H](C)OC(C(=O)OC1CC2CCC(C1)[N+]21CCCC1)(c1ccccc1)c1ccccc1 ; [Cl-]] |
| 317 | 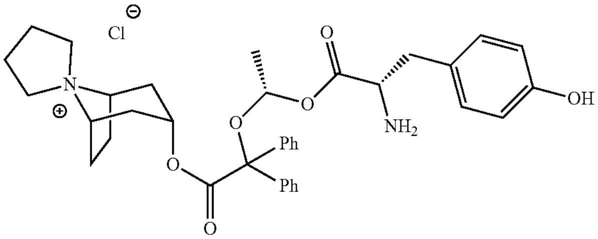 [SMILES: C[C@H](OC(=O)[C@@H](N)Cc1ccc(O)cc1)OC(C(=O)OC1CC2CCC(C1)[N+]21CCCC1)(c1ccccc1)c1ccccc1 ; [Cl-]] |
| 318 | 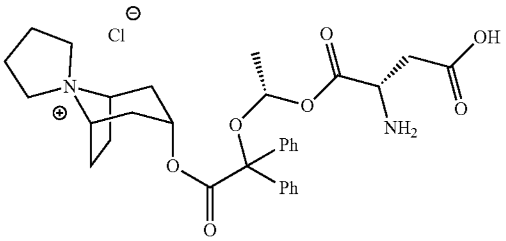 [SMILES: C[C@H](OC(=O)[C@@H](N)CC(=O)O)OC(C(=O)OC1CC2CCC(C1)[N+]21CCCC1)(c1ccccc1)c1ccccc1 ; [Cl-]] |
| 319 | 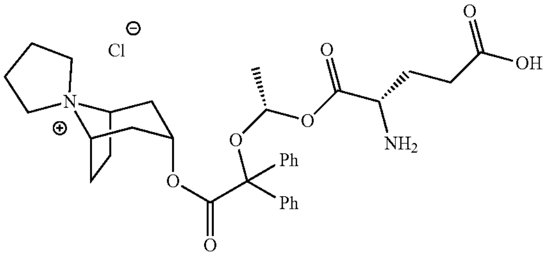 [SMILES: C[C@H](OC(=O)[C@@H](N)CCC(=O)O)OC(C(=O)OC1CC2CCC(C1)[N+]21CCCC1)(c1ccccc1)c1ccccc1 ; [Cl-]] |
| 320 | 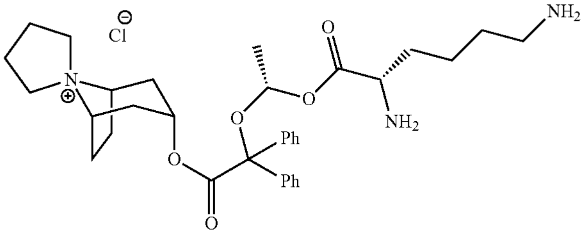 [SMILES: C[C@H](OC(=O)[C@@H](N)CCCCN)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 321 | 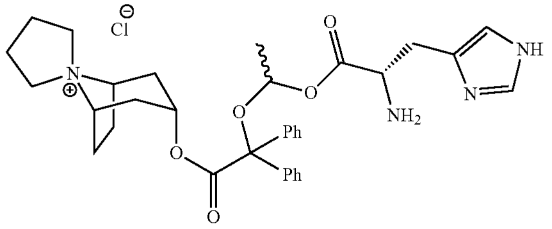 [SMILES: CC(OC(=O)[C@@H](N)Cc1c[nH]cn1)OC(C(=O)OC1CC2CCC(C1)[N+]21CCCC1)(c1ccccc1)c1ccccc1 ; [Cl-]] |
| 322 | 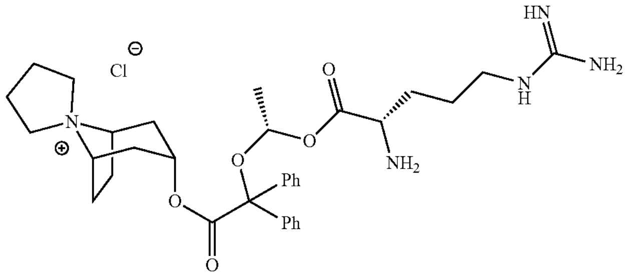 [SMILES: C[C@H](OC(=O)[C@@H](N)CCCNC(=N)N)OC(C(=O)OC1CC2CCC(C1)[N+]21CCCC1)(c1ccccc1)c1ccccc1 ; [Cl-]] |
| 323 | 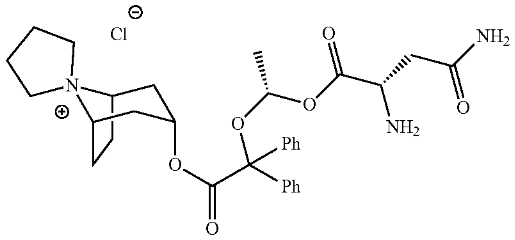 [SMILES: C[C@H](OC(=O)[C@@H](N)CC(N)=O)OC(C(=O)OC1CC2CCC(C1)[N+]21CCCC1)(c1ccccc1)c1ccccc1 ; [Cl-]] |
| 324 | 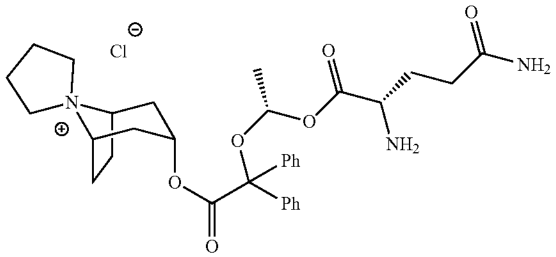 [SMILES: C[C@H](OC(=O)[C@@H](N)CCC(N)=O)OC(C(=O)OC1CC2CCC(C1)[N+]21CCCC1)(c1ccccc1)c1ccccc1 ; [Cl-]] |
| 325 | 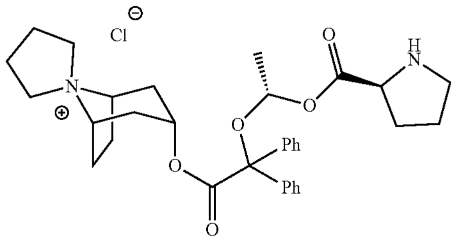 [SMILES: C[C@H](OC(=O)[C@@H]1CCCN1)OC(C(=O)OC1CC2CCC(C1)[N+]21CCCC1)(c1ccccc1)c1ccccc1 ; [Cl-]] |
| 326 | 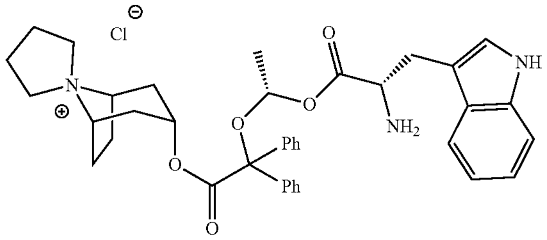 [SMILES: C[C@H](OC(=O)[C@@H](N)Cc1c[nH]c2ccccc12)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 327 | 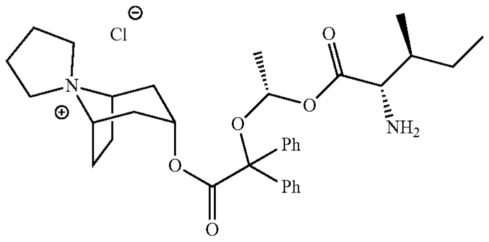 [SMILES: CC[C@H](C)[C@H](N)C(=O)O[C@@H](C)OC(C(=O)OC1CC2CCC(C1)[N+]21CCCC1)(c1ccccc1)c1ccccc1 ; [Cl-]] |
| 328 | 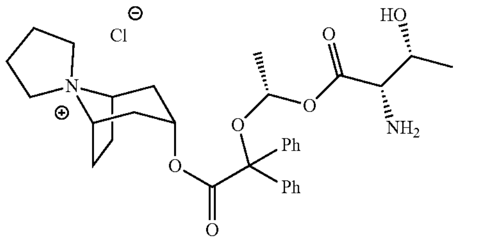 [SMILES: C[C@H](OC(=O)[C@@H](N)[C@@H](C)O)OC(C(=O)OC1CC2CCC(C1)[N+]21CCCC1)(c1ccccc1)c1ccccc1 ; [Cl-]] |
| 329 | 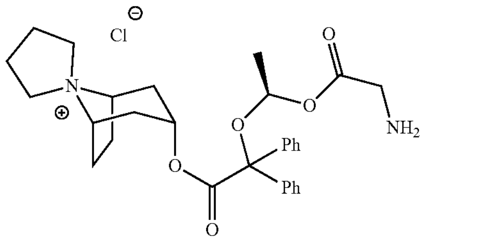 [SMILES: C[C@@H](OC(=O)CN)OC(C(=O)OC1CC2CCC(C1)[N+]21CCCC1)(c1ccccc1)c1ccccc1 ; [Cl-]] |
| 330 | 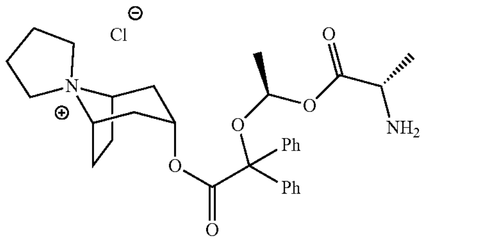 [SMILES: C[C@@H](OC(=O)[C@H](C)N)OC(C(=O)OC1CC2CCC(C1)[N+]21CCCC1)(c1ccccc1)c1ccccc1 ; [Cl-]] |
| 331 | 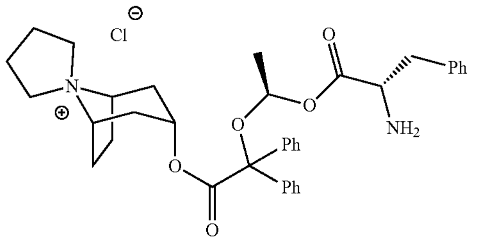 [SMILES: C[C@@H](OC(=O)[C@@H](N)Cc1ccccc1)OC(C(=O)OC1CC2CCC(C1)[N+]21CCCC1)(c1ccccc1)c1ccccc1 ; [Cl-]] |
| 332 | 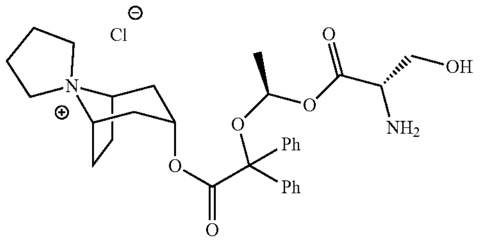 [SMILES: C[C@@H](OC(=O)[C@@H](N)CO)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 333 | 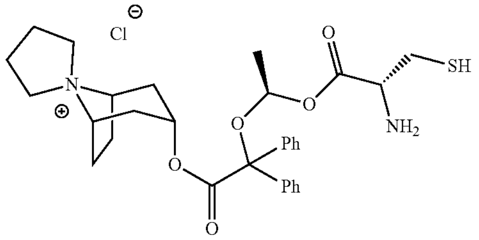 [SMILES: C[C@@H](OC(=O)[C@@H](N)CS)OC(C(=O)OC1CC2CCC(C1)[N+]21CCCC1)(c1ccccc1)c1ccccc1 ; [Cl-]] |
| 334 | 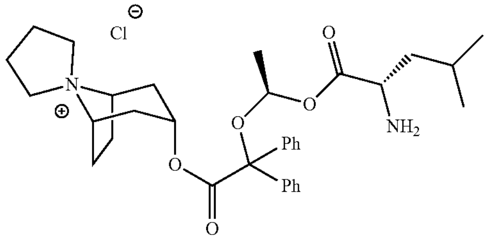 [SMILES: CC(C)C[C@H](N)C(=O)O[C@H](C)OC(C(=O)OC1CC2CCC(C1)[N+]21CCCC1)(c1ccccc1)c1ccccc1 ; [Cl-]] |
| 335 | 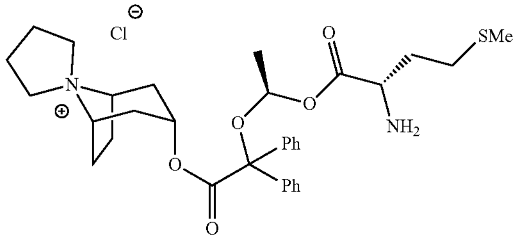 [SMILES: CSCC[C@H](N)C(=O)O[C@H](C)OC(C(=O)OC1CC2CCC(C1)[N+]21CCCC1)(c1ccccc1)c1ccccc1 ; [Cl-]] |
| 336 | 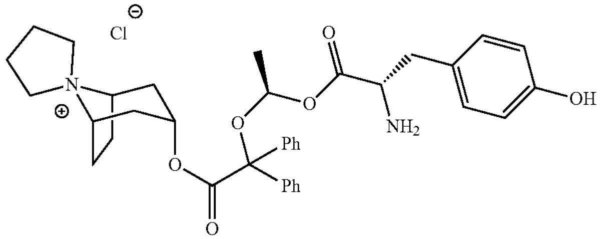 [SMILES: C[C@@H](OC(=O)[C@@H](N)Cc1ccc(O)cc1)OC(C(=O)OC1CC2CCC(C1)[N+]21CCCC1)(c1ccccc1)c1ccccc1 ; [Cl-]] |
| 337 | 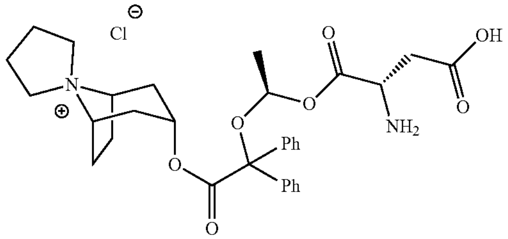 [SMILES: C[C@@H](OC(=O)[C@@H](N)CC(=O)O)OC(C(=O)OC1CC2CCC(C1)[N+]21CCCC1)(c1ccccc1)c1ccccc1 ; [Cl-]] |
| 338 | 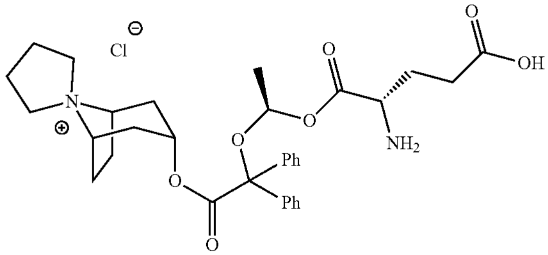 [SMILES: C[C@@H](OC(=O)[C@@H](N)CCC(=O)O)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 339 | 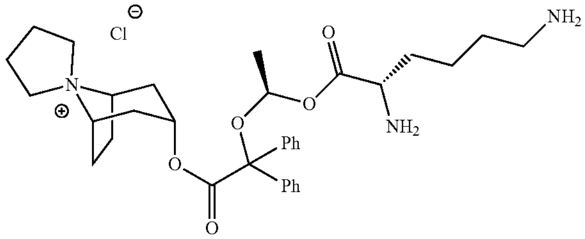 [SMILES: C[C@@H](OC(=O)[C@@H](N)CCCCN)OC(C(=O)OC1CC2CCC(C1)[N+]21CCCC1)(c1ccccc1)c1ccccc1 ; [Cl-]] |
| 340 | 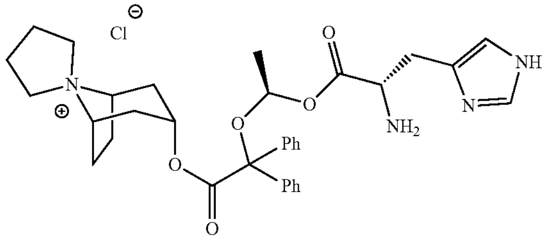 [SMILES: C[C@@H](OC(=O)[C@@H](N)Cc1c[nH]cn1)OC(C(=O)OC1CC2CCC(C1)[N+]21CCCC1)(c1ccccc1)c1ccccc1 ; [Cl-]] |
| 341 | 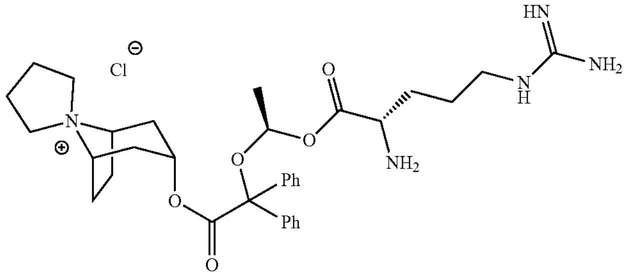 [SMILES: C[C@@H](OC(=O)[C@@H](N)CCCNC(=N)N)OC(C(=O)OC1CC2CCC(C1)[N+]21CCCC1)(c1ccccc1)c1ccccc1 ; [Cl-]] |
| 342 | 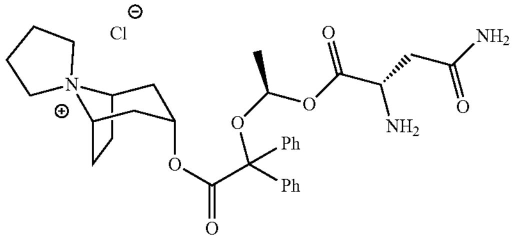 [SMILES: C[C@@H](OC(=O)[C@@H](N)CC(N)=O)OC(C(=O)OC1CC2CCC(C1)[N+]21CCCC1)(c1ccccc1)c1ccccc1 ; [Cl-]] |
| 343 | 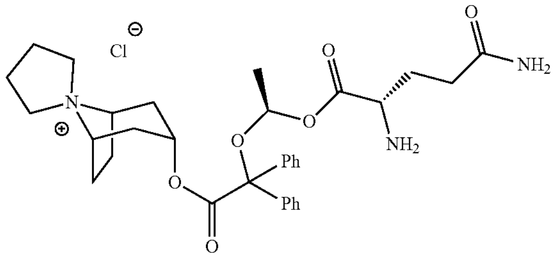 [SMILES: C[C@@H](OC(=O)[C@@H](N)CCC(N)=O)OC(C(=O)OC1CC2CCC(C1)[N+]21CCCC1)(c1ccccc1)c1ccccc1 ; [Cl-]] |
| 344 | 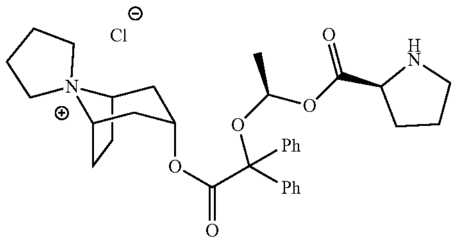 [SMILES: C[C@@H](OC(=O)[C@@H]1CCCN1)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 345 | 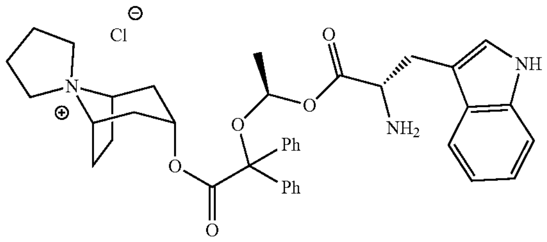 [SMILES: C[C@@H](OC(=O)[C@@H](N)Cc1c[nH]c2ccccc12)OC(C(=O)OC1CC2CCC(C1)[N+]21CCCC1)(c1ccccc1)c1ccccc1 ; [Cl-]] |
| 346 | 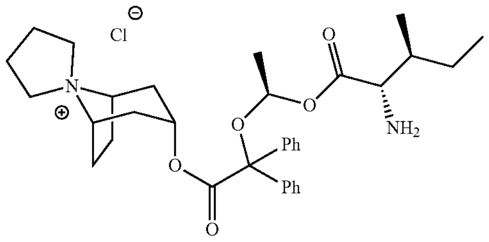 [SMILES: CC[C@H](C)[C@H](N)C(=O)O[C@H](C)OC(C(=O)OC1CC2CCC(C1)[N+]21CCCC1)(c1ccccc1)c1ccccc1 ; [Cl-]] |
| 347 | 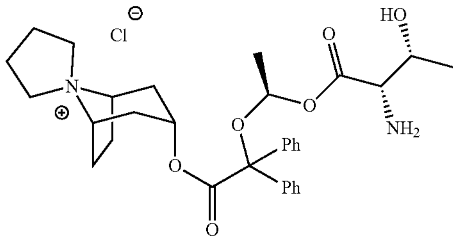 [SMILES: C[C@@H](OC(=O)[C@@H](N)[C@@H](C)O)OC(C(=O)OC1CC2CCC(C1)[N+]21CCCC1)(c1ccccc1)c1ccccc1 ; [Cl-]] |
| 348 | 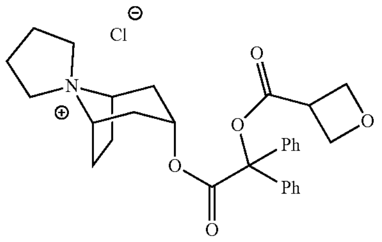 [SMILES: O=C(OC(C(=O)OC1CC2CCC(C1)[N+]21CCCC1)(c1ccccc1)c1ccccc1)C1COC1 ; [Cl-]] |
| 349 | 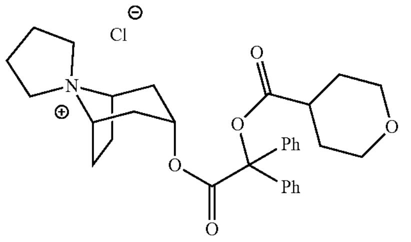 [SMILES: O=C(OC(C(=O)OC1CC2CCC(C1)[N+]21CCCC1)(c1ccccc1)c1ccccc1)C1CCOCC1 ; [Cl-]] |
| 350 | 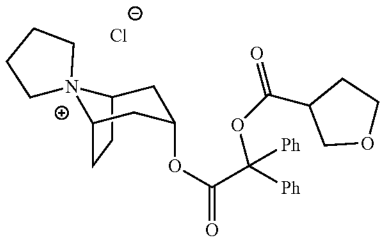 [SMILES: O=C(OC(C(=O)OC1CC2CCC(C1)[N+]21CCCC1)(c1ccccc1)c1ccccc1)C1CCOC1 ; [Cl-]] |

TABLE 2-continued
| Cpd No. | Structure |
|---|---|
| 351 | 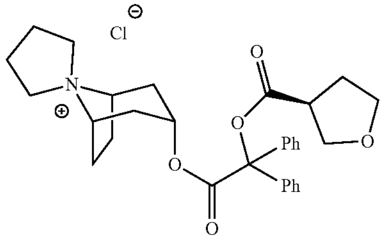 [SMILES: O=C(OC(C(=O)OC1CC2CCC(C1)[N+]21CCCC1)(c1ccccc1)c1ccccc1)[C@H]1CCOC1 ; [Cl-]] |
| 352 | 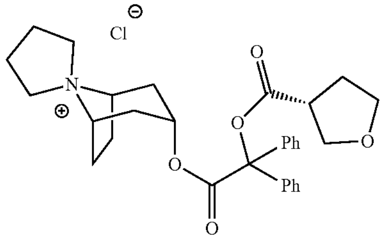 [SMILES: O=C(OC(C(=O)OC1CC2CCC(C1)[N+]21CCCC1)(c1ccccc1)c1ccccc1)[C@@H]1CCOC1 ; [Cl-]] |
| 353 | 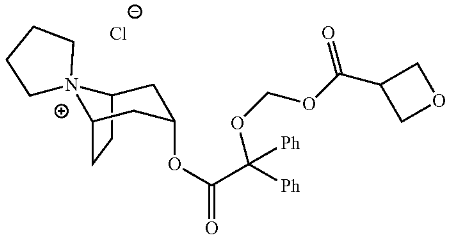 [SMILES: O=C(OCOC(C(=O)OC1CC2CCC(C1)[N+]21CCCC1)(c1ccccc1)c1ccccc1)C1COC1 ; [Cl-]] |
| 354 | 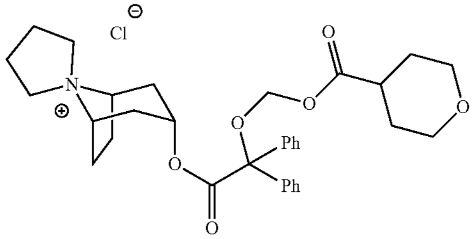 [SMILES: O=C(OCOC(C(=O)OC1CC2CCC(C1)[N+]21CCCC1)(c1ccccc1)c1ccccc1)C1CCOCC1 ; [Cl-]] |
| 355 | 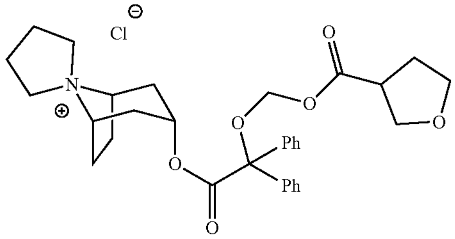 [SMILES: O=C(OCOC(C(=O)OC1CC2CCC(C1)[N+]21CCCC1)(c1ccccc1)c1ccccc1)C1CCOC1 ; [Cl-]] |
| 356 | 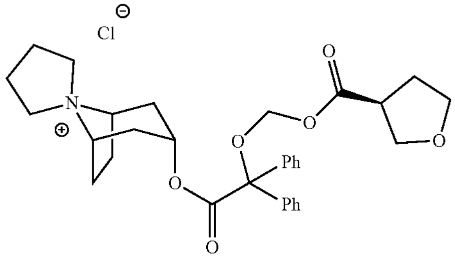 [SMILES: [Cl-] ; O=C(OCOC(C(=O)OC1CC2CCC(C1)[N+]21CCCC1)(c1ccccc1)c1ccccc1)[C@H]1CCOC1] |

TABLE 2-continued
| Cpd No. | Structure |
| --- | --- |
| 357 | 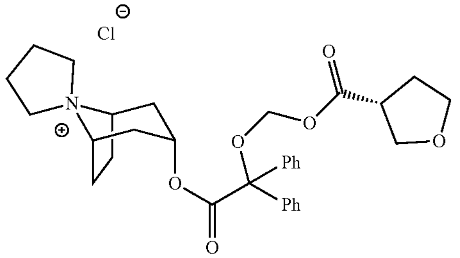 [SMILES: [Cl-] ; O=C(OCOC(C(=O)OC1CC2CCC(C1)[N+]21CCCC1)(c1ccccc1)c1ccccc1)[C@@H]1CCOC1] |
| 358 | 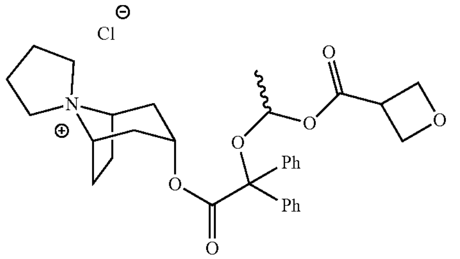 [SMILES: [Cl-] ; CC(OC(=O)C1COC1)OC(C(=O)OC1CC2CCC(C1)[N+]21CCCC1)(c1ccccc1)c1ccccc1] |
| 359 | 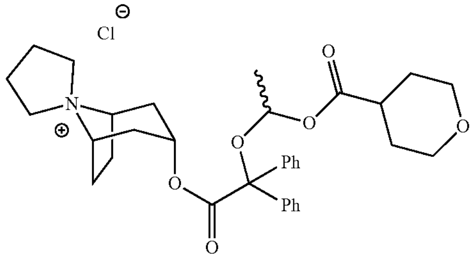 [SMILES: [Cl-] ; CC(OC(=O)C1CCOCC1)OC(C(=O)OC1CC2CCC(C1)[N+]21CCCC1)(c1ccccc1)c1ccccc1] |
| 360 | 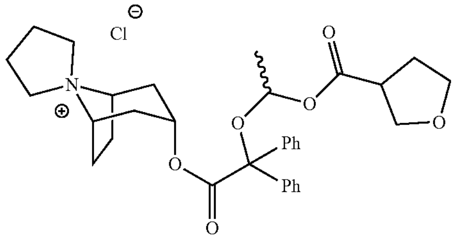 [SMILES: CC(OC(=O)C1CCOC1)OC(C(=O)OC1CC2CCC(C1)[N+]21CCCC1)(c1ccccc1)c1ccccc1 ; [Cl-]] |
| 361 | 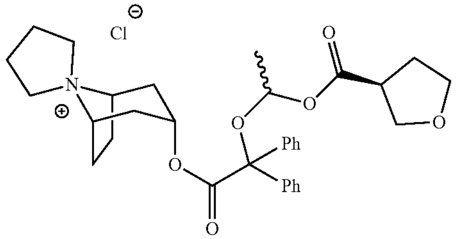 [SMILES: CC(OC(=O)[C@H]1CCOC1)OC(C(=O)OC1CC2CCC(C1)[N+]21CCCC1)(c1ccccc1)c1ccccc1 ; [Cl-]] |
| 362 | 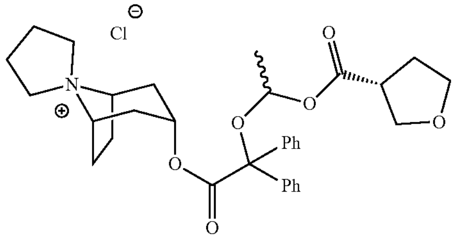 [SMILES: CC(OC(=O)[C@@H]1CCOC1)OC(C(=O)OC1CC2CCC(C1)[N+]21CCCC1)(c1ccccc1)c1ccccc1 ; [Cl-]] |

TABLE 2-continued
| Cpd No. | Structure |
| --- | --- |
| 363 | 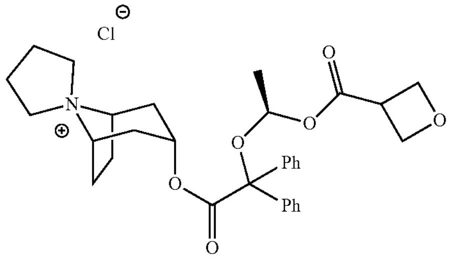 [SMILES: [Cl-] ; C[C@@H](OC(=O)C1COC1)OC(C(=O)OC1CC2CCC(C1)[N+]21CCCC1)(c1ccccc1)c1ccccc1] |
| 364 | 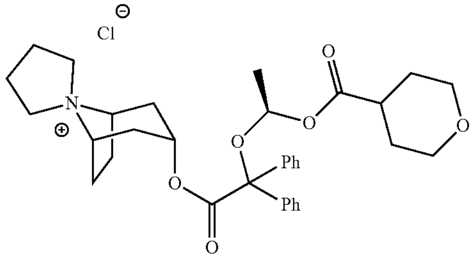 [SMILES: [Cl-] ; C[C@@H](OC(=O)C1CCOCC1)OC(C(=O)OC1CC2CCC(C1)[N+]21CCCC1)(c1ccccc1)c1ccccc1] |
| 365 | 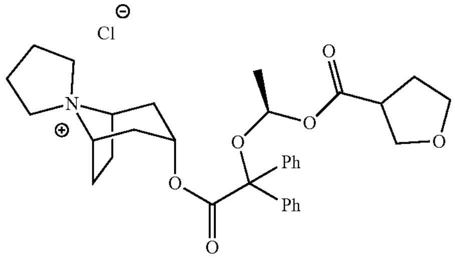 [SMILES: [Cl-] ; C[C@@H](OC(=O)C1CCOC1)OC(C(=O)OC1CC2CCC(C1)[N+]21CCCC1)(c1ccccc1)c1ccccc1] |
| 366 | 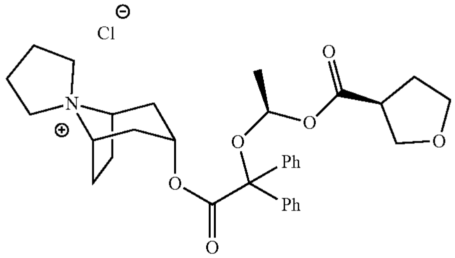 [SMILES: [Cl-] ; C[C@@H](OC(=O)[C@H]1CCOC1)OC(C(=O)OC1CC2CCC(C1)[N+]21CCCC1)(c1ccccc1)c1ccccc1] |
| 367 | 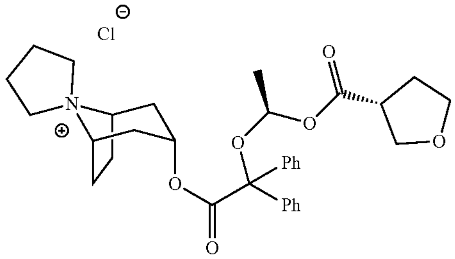 [SMILES: [Cl-] ; C[C@@H](OC(=O)[C@@H]1CCOC1)OC(C(=O)OC1CC2CCC(C1)[N+]21CCCC1)(c1ccccc1)c1ccccc1] |
| 368 | 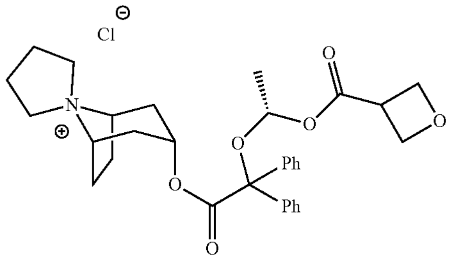 [SMILES: [Cl-] ; C[C@H](OC(=O)C1COC1)OC(C(=O)OC1CC2CCC(C1)[N+]21CCCC1)(c1ccccc1)c1ccccc1] |

TABLE 2-continued
| Cpd No. | Structure |
|---|---|
| 369 | 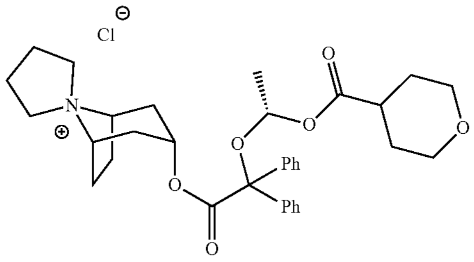 [SMILES: [Cl-] ; C[C@H](OC(=O)C1CCOCC1)OC(C(=O)OC1CC2CCC(C1)[N+]21CCCC1)(c1ccccc1)c1ccccc1] |
| 370 | 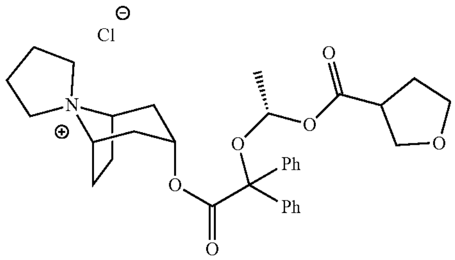 [SMILES: [Cl-] ; C[C@H](OC(=O)C1CCOC1)OC(C(=O)OC1CC2CCC(C1)[N+]21CCCC1)(c1ccccc1)c1ccccc1] |
| 371 | 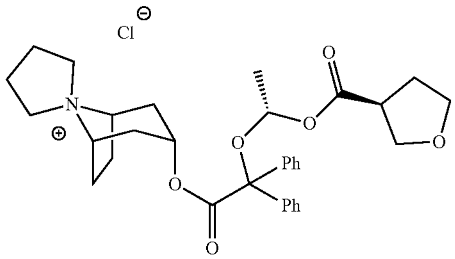 |
| 372 | 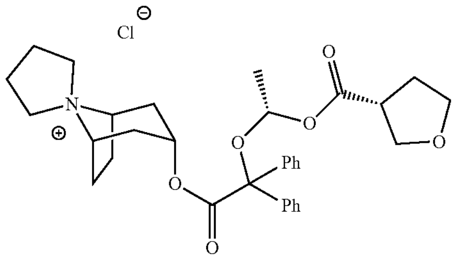 |
| 373 | 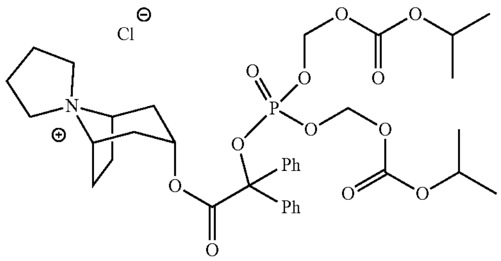 |

TABLE 2-continued
| Cpd No. | Structure |
| --- | --- |
| 374 | 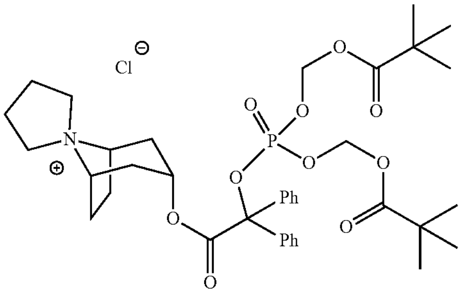 |
| 375 | 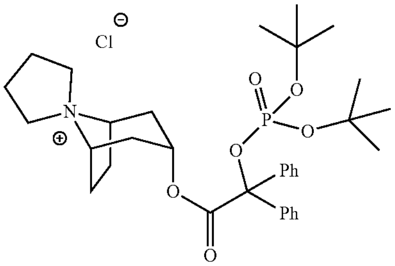 [SMILES: CC(C)(C)OP(=O)(OC(C)(C)C)OC(C(=O)OC1CC2CCC(C1)[N+]21CCCC1)(c1ccccc1)c1ccccc1 ; [Cl-]] |
| 376 | 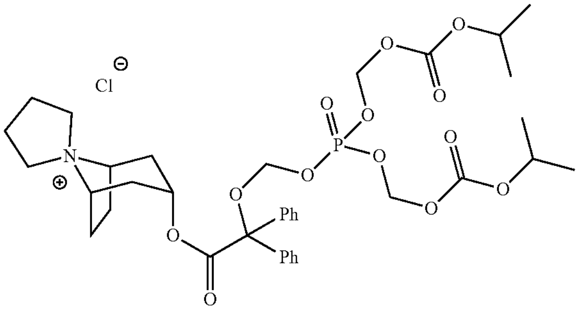 [SMILES: CC(C)OC(=O)OCOP(=O)(OCOC(=O)OC(C)C)OCOC(C(=O)OC1CC2CCC(C1)[N+]21CCCC1)(c1ccccc1)c1ccccc1 ; [Cl-]] |
| 377 | 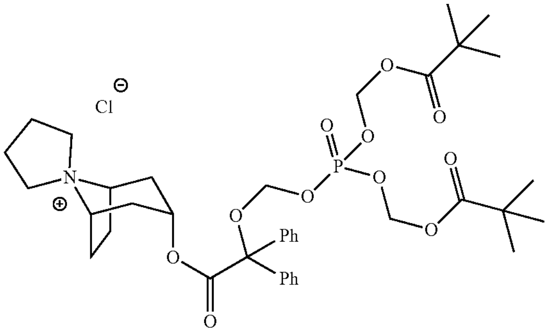 [SMILES: CC(C)(C)C(=O)OCOP(=O)(OCOC(=O)C(C)(C)C)OCOC(C(=O)OC1CC2CCC(C1)[N+]21CCCC1)(c1ccccc1)c1ccccc1 ; [Cl-]] |
| 378 | 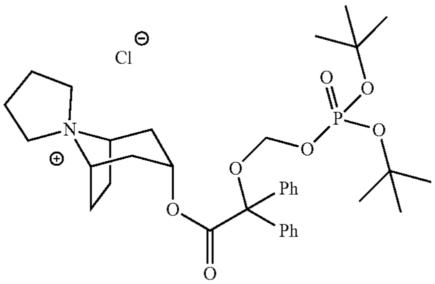 |

TABLE 2-continued
| Cpd No. | Structure |
|---|---|
| 379 | 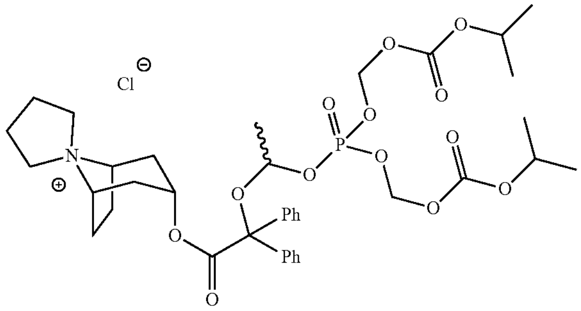 |
| 380 | 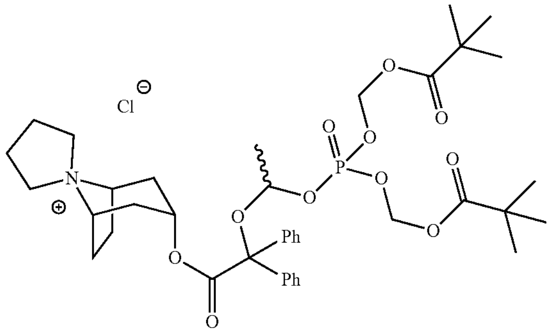 |
| 381 | 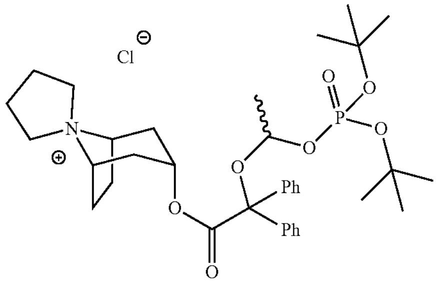 |
| 382 | 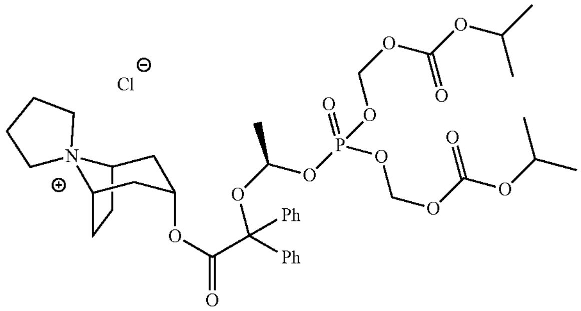 |

TABLE 2-continued
| Cpd No. | Structure |
|---|---|
| 383 | 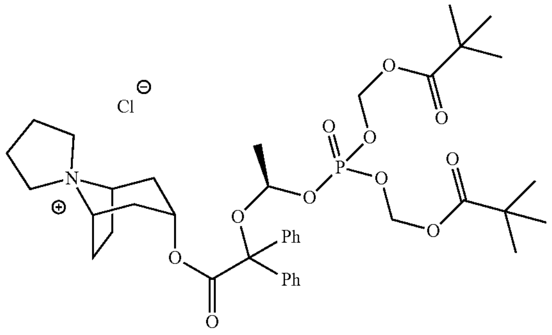 |
| 384 | 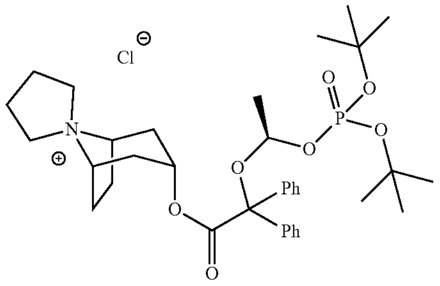 |
| 385 | 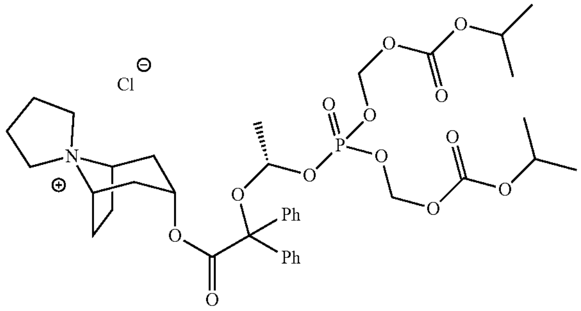 |
| 386 | 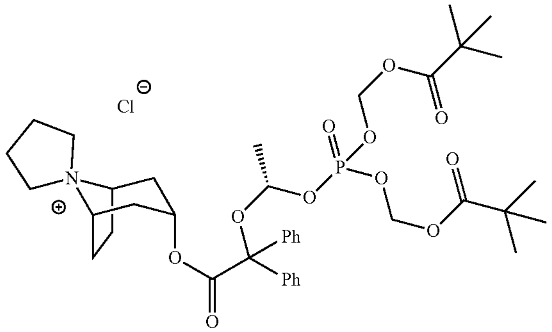 |
| 387 | 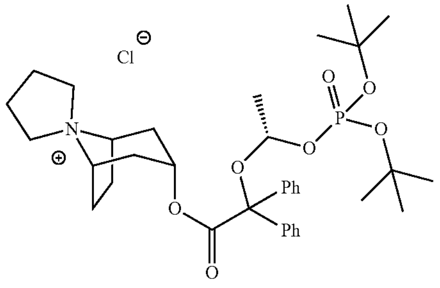 |

TABLE 2-continued
| Cpd No. | Structure |
|---|---|
| 388 | 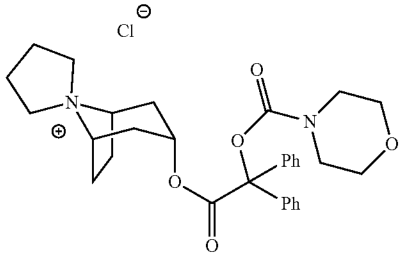 |
| 389 | 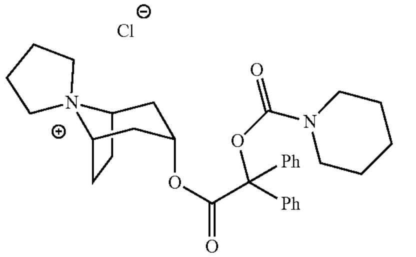 |
| 390 | 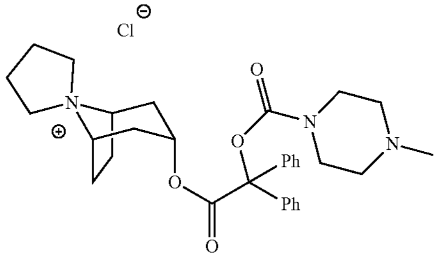 |
| 391 | 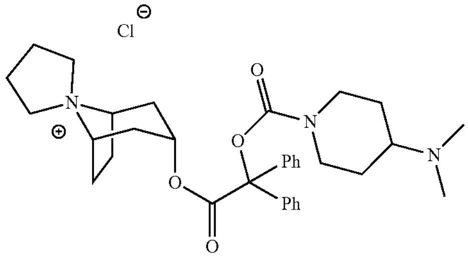 |
| 392 | 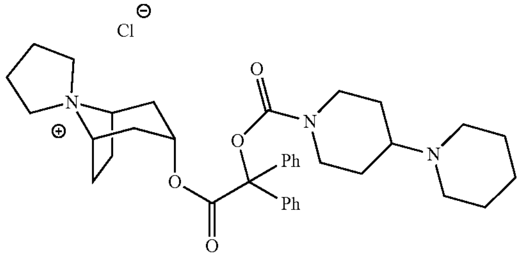 |
| 393 | 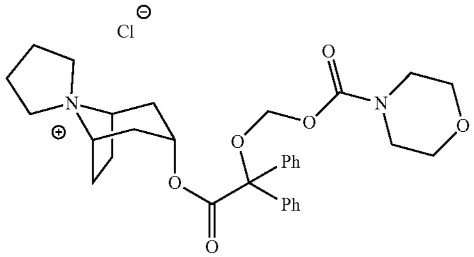 |

TABLE 2-continued
| Cpd No. | Structure |
|---|---|
| 394 | 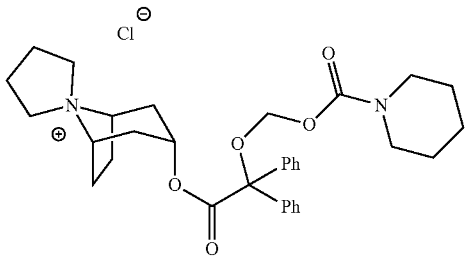 |
| 395 | 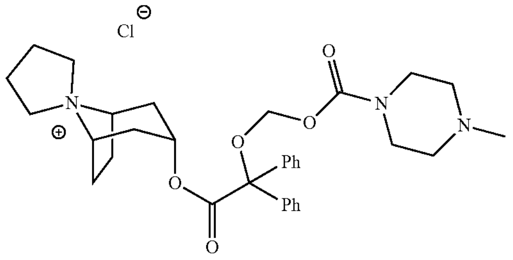 |
| 396 | 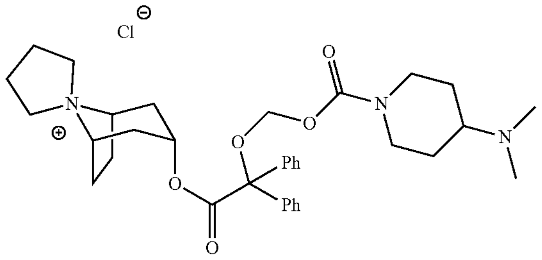 |
| 397 | 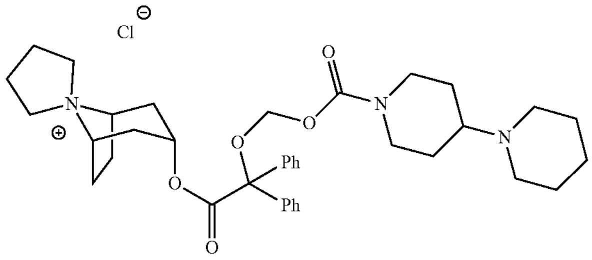 |
| 398 | 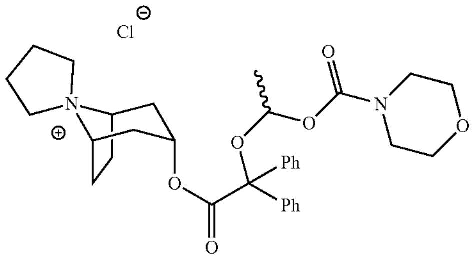 |

TABLE 2-continued
| Cpd No. | Structure |
|---|---|
| 399 | 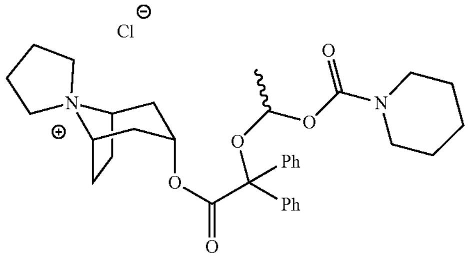 |
| 400 | 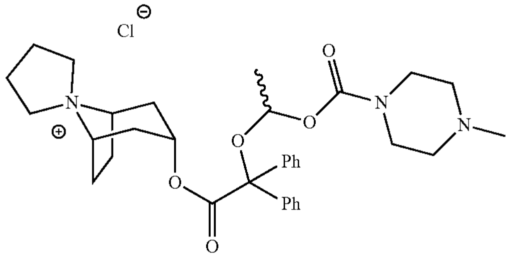 |
| 401 | 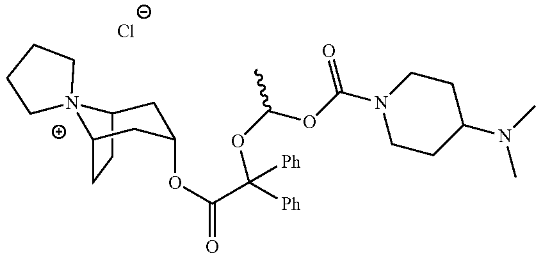 |
| 402 | 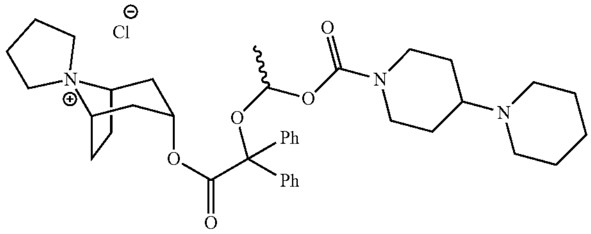 [SMILES: CC(OC(=O)N1CCC(N2CCCCC2)CC1)OC(C(=O)OC1CC2CCC(C1)[N+]21CCCC1)(c1ccccc1)c1ccccc1 ; [Cl-]] |
| 403 | 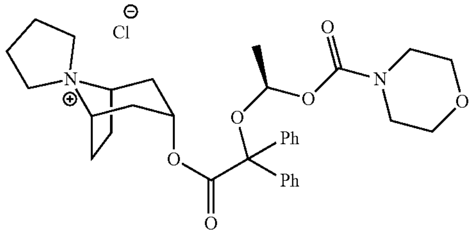 [SMILES: C[C@@H](OC(=O)N1CCOCC1)OC(C(=O)OC1CC2CCC(C1)[N+]21CCCC1)(c1ccccc1)c1ccccc1 ; [Cl-]] |
| 404 | 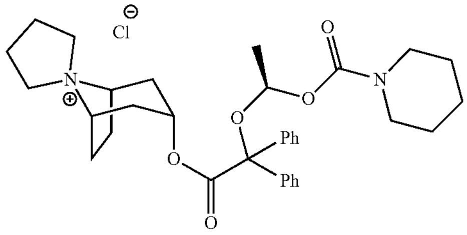 [SMILES: C[C@@H](OC(=O)N1CCCCC1)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 405 | 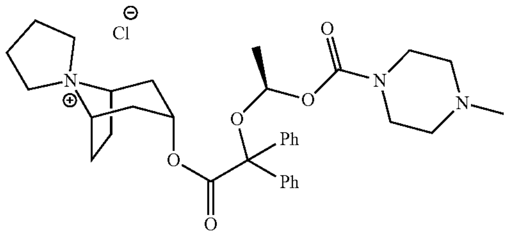 [SMILES: C[C@@H](OC(=O)N1CCN(C)CC1)OC(C(=O)OC1CC2CCC(C1)[N+]21CCCC1)(c1ccccc1)c1ccccc1 ; [Cl-]] |
| 406 | 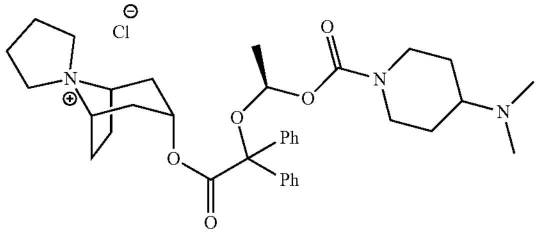 [SMILES: C[C@@H](OC(=O)N1CCC(N(C)C)CC1)OC(C(=O)OC1CC2CCC(C1)[N+]21CCCC1)(c1ccccc1)c1ccccc1 ; [Cl-]] |
| 407 | 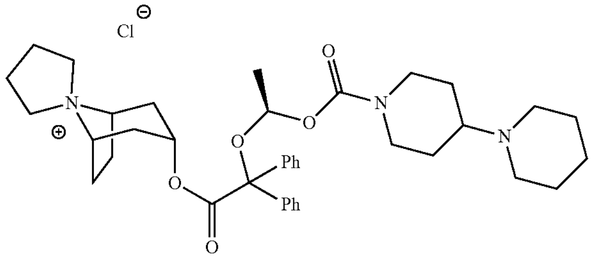 |
| 408 | 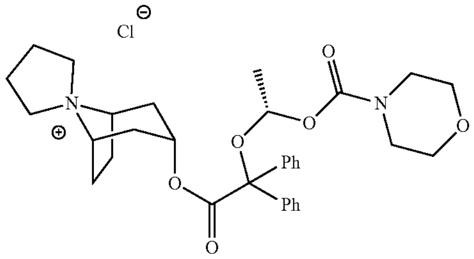 |
| 409 | 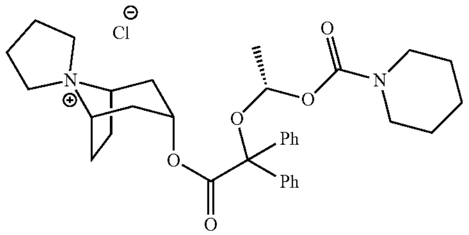 [SMILES: C[C@H](OC(=O)N1CCCCC1)OC(C(=O)OC1CC2CCC(C1)[N+]21CCCC1)(c1ccccc1)c1ccccc1 ; [Cl-]] |
| 410 | 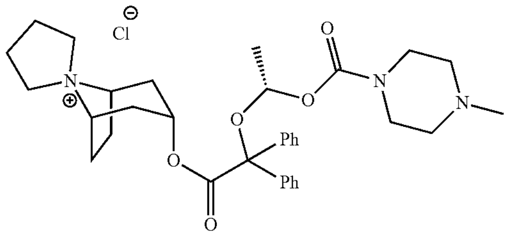 [SMILES: C[C@H](OC(=O)N1CCN(C)CC1)OC(C(=O)OC1CC2CCC(C1)[N+]21CCCC1)(c1ccccc1)c1ccccc1 ; [Cl-]] |

TABLE 2-continued
| Cpd No. | Structure |
|---|---|
| 411 | 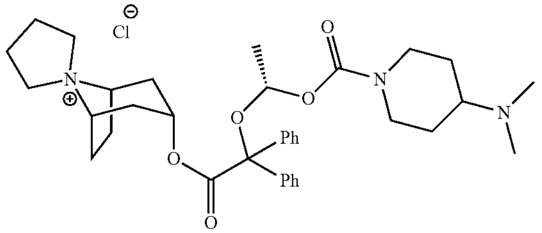 [SMILES: C[C@H](OC(=O)N1CCC(N(C)C)CC1)OC(C(=O)OC1CC2CCC(C1)[N+]21CCCC1)(c1ccccc1)c1ccccc1 ; [Cl-]] |
| 412 | 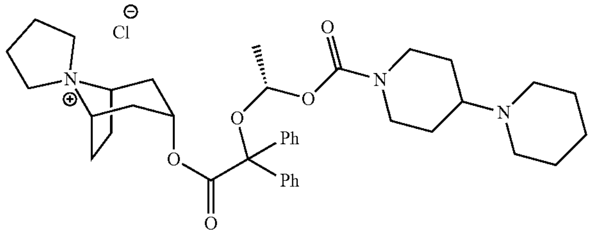 [SMILES: C[C@H](OC(=O)N1CCC(N2CCCCC2)CC1)OC(C(=O)OC1CC2CCC(C1)[N+]21CCCC1)(c1ccccc1)c1ccccc1 ; [Cl-]] |
| 413 | 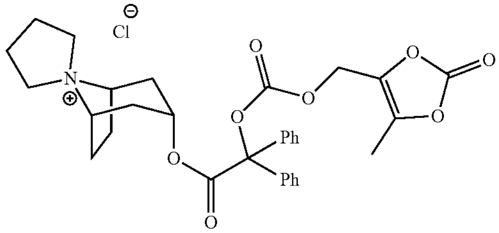 [SMILES: Cc1oc(=O)oc1COC(=O)OC(C(=O)OC1CC2CCC(C1)[N+]21CCCC1)(c1ccccc1)c1ccccc1 ; [Cl-]] |
| 414 | 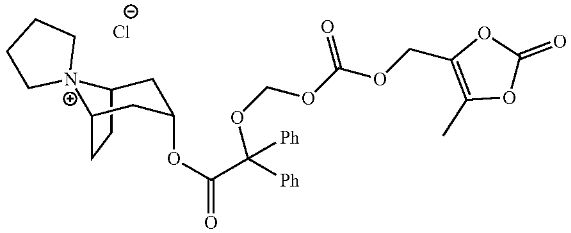 [SMILES: Cc1oc(=O)oc1COC(=O)OCOC(C(=O)OC1CC2CCC(C1)[N+]21CCCC1)(c1ccccc1)c1ccccc1 ; [Cl-]] |
| 415 | 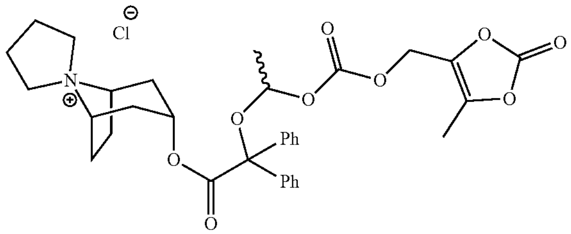 [SMILES: Cc1oc(=O)oc1COC(=O)OC(C)OC(C(=O)OC1CC2CCC(C1)[N+]21CCCC1)(c1ccccc1)c1ccccc1 ; [Cl-]] |
| 416 | 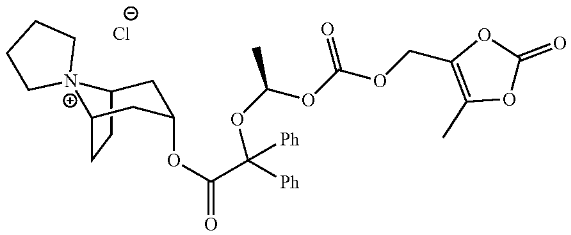 [SMILES: Cc1oc(=O)oc1COC(=O)O[C@H](C)OC(C(=O)OC1CC2CCC(C1)[N+]21CCCC1)(c1ccccc1)c1ccccc1 ; [Cl-]] |

TABLE 2-continued

| Cpd No. | Structure |
|---|---|
| 417 | 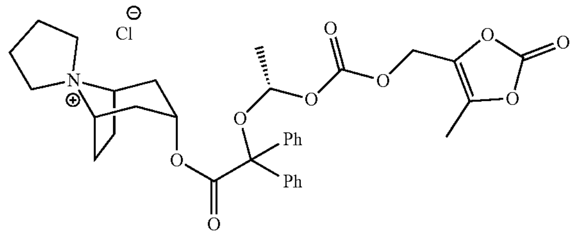 [SMILES: Cc1oc(=O)oc1COC(=O)O[C@@H](C)OC(C(=O)OC1CC2CCC(C1)[N+]21CCCC1)(c1ccccc1)c1ccccc1 ; [Cl-]] |
| 418 | 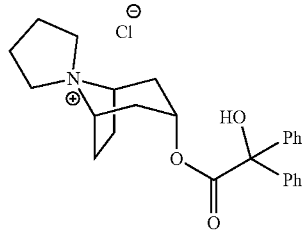 Trospium chloride |

The present disclosure provides for pharmaceutically acceptable salts of any compound described herein as well as the use of such salts. As is understood by those of skill in the art, any compound with an ionizable group, such as an acidic hydrogen, or a basic nitrogen, can be provided in the form of a salt, and pharmaceutically acceptable salt forms of such compounds are specifically contemplated herein. Pharmaceutically acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically acceptable salt is a metal salt. In some embodiments, a pharmaceutically acceptable salt is an ammonium salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the present disclosure. In some embodiments, the organic amine is trimethyl amine, triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, pyrazolidine, pyrazoline, pyridazine, pyrimidine, imidazole, or pyrazine.

In some embodiments, an ammonium salt is a triethyl amine salt, trimethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, a pyridazine salt, a pyrimidine salt, an imidazole salt, or a pyrazine salt.

Acid addition salts can arise from the addition of an acid to a compound of the present disclosure. In some embodiments, the acid is organic. In some embodiments, the acid is inorganic.

In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucuronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, xinafoic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, a xinafoate salt, or a maleate salt.

III. Pharmaceutical Compositions and Formulations

In some embodiments, the present invention provides a pharmaceutical composition comprising a compound of the present invention, such as a composition comprising a compound of any of Table 1, the Formulas illustrated above, including any of Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV), and a pharmaceutically acceptable excipient. Such compositions are suitable for administration to a subject, such as a human subject.

The presently disclosed pharmaceutical compositions can be prepared in a wide variety of oral, parenteral and topical dosage forms. Oral preparations include tablets, pills, powder, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. The compounds of the present disclosure can be formulated as a long acting injectable. The compounds of the present disclosure can be formulated as extended release oral formulations. The compounds of the present disclosure can be formulated as a slow release patch.

Also, the compositions described herein can be administered by inhalation, for example, intranasally. Additionally, the compositions of the present disclosure can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the compounds of the present invention.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethylcellulose, or sodium carboxymethylcellulose; and gums including 123escri and tragacanth; as well as proteins including, but not limited to, gelatin and collagen.

If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil,described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In some embodiments, the pharmaceutical compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present invention can be delivered by the use of liposomes which fuse with the cellular membrane or are endocytosed, for example, by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., A1-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

In some embodiments a compound listed in Table 1, or a pharmaceutically acceptable salt thereof, is a prodrug of xanomeline and is formulated with a compound listed in Table 2, or a pharmaceutically acceptable salt thereof which is a prodrug of trospium, in an extended release oral formulation, long acting injectable formulation, or patch formulation, to deliver about 250 mg of free base equivalents of a xanomeline and about 60 mg free base equivalents of trospium equivalents daily.

In some embodiments, a compound listed in Table 1 is formulated with a compound listed in Table 2 in an extended release oral formulation to deliver 200 mg of a xanomeline free base equivalents and 40 mg of trospium free base equivalents daily.

In some embodiments, a compound listed in Table 1 is formulated with a compound listed in Table 2 in an long acting injectable formulation, wherein the a compound listed in Table 1 is present between about 500 mg, or at about 1000 mg, about 1250 mg, about 1500 mg, about 1750 mg, about 2000 mg, about 2250 mg, about 2500 mg, or about 3000 mg, and the a compound listed in Table 2 is provided between about 100 mg, or at about 200 mg, or at about 300 mg, or at about 400 mg, or at about 500 mg, or at about 1000 mg, about 1250 mg, about 1500 mg, about 1750 mg, about 2000 mg, about 2250 mg, about 2500 mg, or about 3000 mg.

In some embodiments, a compound listed in Table 1 is coformulated with a compound listed in Table 2 in an patch, wherein the a compound listed in Table 1 is present between about 500 mg, or at about 1000 mg, about 1250 mg, about 1500 mg, about 1750 mg, about 2000 mg, about 2250 mg, about 2500 mg, or about 3000 mg, and the a compound listed in Table 2 is provided between about 100 mg, or at about 200 mg, or at about 300 mg, or at about 400 mg, or at about 500 mg, or at about 1000 mg, about 1250 mg, about 1500 mg, about 1750 mg, about 2000 mg, about 2250 mg, about 2500 mg, or about 3000 mg.

In some embodiments the extended release formulation contains less than 2.0% wt. % 3-[(4-hexyloxy)-1,2,5-thiadizaol-3-yl]-5-hydroyl-1-methylpyridin-1-ium.

In some embodiments the extended release formulation contains less than 1.5 wt. % 3-[(4-hexyloxy)-1,2,5-thiadizaol-3-yl]-5-hydroyl-1-methylpyridin-1-ium.

In some embodiments the extended release formulation contains less than 1.0% wt. % 3-[(4-hexyloxy)-1,2,5-thiadizaol-3-yl]-5-hydroyl-1-methylpyridin-1-ium.

In some embodiments the extended release formulation contains less than 0.5 wt. % 3-[(4-hexyloxy)-1,2,5-thiadizaol-3-yl]-5-hydroyl-1-methylpyridin-1-ium.

In some embodiments the extended release formulations described herein result in increase patient compliance with a medication schedule when compared to immediate release formulations of a compound listed in Table 1 and a compound listed in Table 2 taken twice daily oral.

In some embodiments the extended release formulations described herein are taken no more than once daily and result in a lower rate of medication discontinuation when compared to immediate release formulations of a compound listed in Table 1 and a compound listed in Table 2 taken twice daily oral.

In some embodiments the extended release formulations described herein are taken no more than once daily and result in a lower rate of side effects when compared to immediate release formulations of a compound listed in Table 1 and a compound listed in Table 2 taken twice daily oral.

In some embodiments the extended release formulations described herin are taken no more than once daily and result in a lower rate of side effects including but not limited to, dry mouth, headache, gastrointestinal side effects, nausea, vomiting, diarrhea, when compared to immediate release formulations of a compound listed in Table 1 and a compound listed in Table 2 taken orally twice daily.

In some embodiments a compound listed in Table 1 is formulated as an extended release formulation in a ratio with a compound listed in Table 2. In some embodiments the compound listed in Table 1 is present at a ratio range with a compound listed in Table 2 of between about 5 to 1 to 1 to 1, or at about a 5 to 1 ratio, or at about 4 to 1 ratio, or at about a 3 to 1 ratio, or at about a 2 to 1 ratio, or at about a 1.5 to 1 ratio.

In some embodiments a compound listed in Table 1 is formulated with a compound listed in Table 2 as a solid oral immediate release formulation.

In some embodiments a compound listed in Table 1 is formulated with a compound listed in Table 2 as a solid oral extended release formulation.

In one embodiment the solid oral extended release formulation has a composition comprising a core comprising (i) a compound listed in Table 1 and (ii) a compound listed in Table 2, and (iii) a coating that is 5% the weight of the core.

In one embodiment the solid oral extended release formulation has a composition comprising a core comprising (i) a compound listed in Table 1 and (ii) a compound listed in Table 2 and (iii) a coating that is 10% the weight of the core.

In one embodiment the solid oral extended release formulation has a composition comprising a core comprising (i) a compound listed in Table 1 and (ii) a compound listed in Table 2, and (iii) a coating that is 15% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 5% the weight of the core and where the individual beads comprised of a compound listed in Table 2 have a composition comprising (i) a core comprising a compound listed in Table 2 and (ii) a coating that is about 5% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 10% the weight of the core and where the individual beads comprised of a compound listed in Table 2 have a composition comprising (i) a core comprising a compound listed in Table 2 and (ii) a coating that is about 10% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 15% the weight of the core and where the individual beads comprised of a compound listed in Table 2 have a composition comprising (i) a core comprising a compound listed in Table 2 and (ii) a coating that is about 15% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 5% the weight of the core and where the individual beads comprised of a compound listed in Table 2 have a composition comprising (i) a core comprising a compound listed in Table 2 and (ii) a coating that is about 10% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 5% the weight of the core and where the individual beads comprised of a compound listed in Table 2 have a composition comprising (i) a core comprising a compound listed in Table 2 and (ii) a coating that is about 15% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 10% the weight of the core and where the individual beads comprised of a compound listed in Table 2 have a composition comprising (i) a core comprising a compound listed in Table 2 and (ii) a coating that is about 5% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 10% the weight of the core and where the individual beads comprised of a compound listed in Table 2 have a composition comprising (i) a core comprising a compound listed in Table 2 and (ii) a coating that is about 15% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 15% the weight of the core and where the individual beads comprised of a compound listed in Table 2 have a composition comprising (i) a core comprising a compound listed in Table 2 and (ii) a coating that is about 5% the weight of the core.

In one embodiment the oral extended release formulation is a capsule containing a plurality of a beads composed of a compound listed in Table 1, and a plurality of beads of a compound listed in Table 2, where the individual beads of a compound listed in Table 1 have a composition comprising (i) a core comprising a compound listed in Table 1 and (ii) a coating that is about 15% the weight of the core and where the individual beads comprised of a compound listed in Table 2 have a composition comprising (i) a core comprising a compound listed in Table 2 and (ii) a coating that is about 10% the weight of the core.

Plasticizer

In some embodiments, pharmaceutical compositions disclosed herein comprise a plasticizer. Plasticizers suitable for use in the pharmaceutical compositions of the present the disclosure include, but are not limited to, glycerin, polyethylene glycols, polyethylene glycol monomethyl ether, propylene glycol, and sorbitol sorbitan solution. Hydrophobic plasticizers suitable for the disclosure include, but are not limited to, acetyl tributyl citrate, acetyl triethyl citrate, castor oil, diacetylated monoglycerides, dibutyl sebacate, diethyl phthalate, triacetin, tributyl citrate, triethyl citrate, gelucire 39/01, and gelucire 43/01. In certain embodiments of the disclosure, the plasticizers include various polyethylene glycols, glycerin, and triethyl citrate.

Diluent

In some embodiments, pharmaceutical compositions disclosed herein comprise a diluent such as lactose, sucrose, D-mannitol, mannitol 100SD, starch, alginic acid, crystalline cellulose, e.g., microcrystalline cellulose, microcrystalline cellulose PH-102, silicified microcrystalline cellulose, and light silicic anhydride. In some embodiments, the diluent is microcrystalline cellulose.

Lubricant

In some embodiments, the pharmaceutical compositions disclosed herein comprise a lubricant. The lubricant the pharmaceutical composition from sticking, e.g., during storage. Exemplary and nonlimiting lubricants that may be used in the pharmaceutical compositions disclosed herein include sodium stearyl fumarate, glyceral behenate, magnesium stearate, calcium stearate, or talc. In some embodiments, the lubricant comprises about 0.1%, about 0.2%, about 0.3%, about 0.4%, about 0.5%, about 1%, about 1.5%, or about 2% of the composition by weight.

Suitable pharmaceutical excipients, as well as pharmaceutical necessities for use in pharmaceutical formulations, are described in Remington: Remington: The Science and Practice of Pharmacy, (23rd ed.) ed. A. Adejare., 2020, Academic Press, Philadelphia, PA, and in the USP44/NF39 (United States Pharmacopeia and the National Formulary) or corresponding European or Japanese reference documents.

Suitable excipients for formulating a long acting solid oral dosage of a compound listed in Table 1 and a compound listed in Table 2 include but are not limited to the following fillers, Lactose SD Fast Flo 316, Mannitol 100SD, Microcrystalline Cellulose (Avicel PH102), Dicalcium Phosphate Dihydrate(DI-TAB), and the following lubricants, Glyceryl Behenate COMPRITAL 888 ATO, Sodium stearyl fumarate, Magnesium stearate.

Suitable release control polymers for formulating a long acting solid oral dosage of a compound listed in Table 1 and a compound listed in Table 2 include but are not limited to HPMC (Methocel) K4M, Eudragit RS PO, Eudragit RL PO.

Suitable coatings for formulating a long acting solid oral dosage of a compound listed in Table 1 and a compound listed in Table 2 include but are not limited to Ethocel Standard 10 Premium Ethycellulose, Carbopol 71G NF Polymer.

Solvents suitable for formulation include but are not limited to, Acetonitrile (ACN), Methanol (MeOH), TEA, $NH_4OAc$, N-hexane, 2-propanol, Diethanolamine, HCOOH, Ethanol, Sodium hexane sulfonate Additional excipients include but are not limited to, Lactose monohydrate SDRY 316, Microcrystalline cellulose (Avicel PH102), HPMC (Methocel) K4M, Polyethylene oxide (Polyox 301), Kollidon SR, Mannitol (SD100), Croscarmellose Sodium (Ac-Di-Sol), Crospovidone (Kollidon CL), Colloidal Silicon dioxide (Aerosil 200), Magnesium Stearate, Magnesium stearate LIGAMED MF-2-V, Glycerol Behenate, Sodium stearyl fumarate, HPC (Klucel EXF), Glyceryl Behenate COMPRITAL 888 ATO, Dicalcium Phosphate Dihydrate(DI-TAB), Sodium Stearyl Fumarate, Eudragit RL PO, Eudragit RS PO, Ethocel Standard10FP Premium Ethycellulose, Carbopol 71G NF Polymer, Lactose SD Fast Flo 316, Hydroxypropyl Methylcellulose Methocel K4M Premium, HPC (Klucel EXF), Lactose Hydrate Mod. Spry Dry Fast Flo 316

Release Profiles

In one embodiment, the compositions are formulated such that the compound listed in Table 1 has an in vitro dissolution profile slower than that for an immediate release (IR) formulation. As used herein, the immediate release (IR) formulation for a compound listed in Table 1 means compositions of a compound listed in Table 1 that lack a release modifying structural element such as a matrix or coating.

In one embodiment, the compositions are formulated such that the compound listed in Table 2 has an in vitro dissolution profile slower than that for an immediate release (IR) formulation. As used herein, the immediate release (IR) formulation for a compound listed in Table 2 means compositions of a compound listed in Table 2 that lack a release modifying structural element such as a matrix or coating.

The compositions disclosed herein may exhibit plasma concentration curves having initial (e.g., from 2 hours after administration to 4 hours after administration) slopes less than 75%, 50%, 40%, 30%, 20%, or 10% of those for an IR formulation of the same dosage of a compound listed in Table 1. The precise slope for a given individual will vary to the quantity of a compound listed in Table 1 delivered, including, for example, whether the patient has eaten or not. For other doses, the slopes vary directly in relationship to dose.

The compositions disclosed herein may exhibit plasma concentration curves having initial (e.g., from 2 hours after administration to 4 hours after administration) slopes less than 75%, 50%, 40%, 30%, 20%, or 10% of those for an IR formulation of the same dosage of a compound listed in Table 2. The precise slope for a given individual will vary to the quantity of a compound listed in Table 2 delivered, including, for example, whether the patient has eaten or not. For other doses, the slopes vary directly in relationship to dose.

In some embodiments, at least 75%, 90%, 95%, 97%, 98%, 99%, or even 100% of the compound listed in Table 1 is provided in a modified or extended release dosage form and upon administration of the composition of a subject. Desirably, 99%, 98%, 95%, 90%, 85%, 70%, 50%, or 30% of the compound listed in Table 1 remains in an extended release dosage form within one hour of administration.

In some embodiments, at least 75%, 90%, 95%, 97%, 98%, 99%, or even 100% of the compound listed in Table 2 is provided in a modified or extended release dosage form and upon administration of the composition of a subject. Desirably, 99%, 98%, 95%, 90%, 85%, 70%, 50%, or 30% of the compound listed in Table 2 remains in an extended release dosage form within one hour of administration.

In some embodiments, the disclosure provides a pharmaceutical composition comprising (i) a modified release coating and/or matrix and (ii) a compound listed in Table 1, wherein a compound listed in Table 1 has an in vitro dissolution profile ranging between 0 and about 40% in four hours, 0 and about 80% in eight hours, 0 and about 95% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 2, wherein a compound listed in Table 2 has an in vitro dissolution profile ranging between 0 and about 40% in four hours, 0 and about 80% in eight hours, 0 and about 95% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1, wherein a compound listed in Table 1 has an in vitro dissolution profile between 0 and 15% in four hours, 0 and about 60% in eight hours, 0 and about 80% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 2, wherein a compound listed in Table 2 has an in vitro dissolution profile between 0 and 15% in four hours, 0 and about 60% in eight hours, 0 and about 80% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1, wherein a compound listed in Table 1 has an in vitro dissolution profile ranging between 0 and 5% in four hours, 0 and 15% in eight hours, 0 and 40% in twelve hours, and 0 and 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 2, wherein a compound listed in Table 2 has an in vitro dissolution profile ranging between 0 and 5% in four hours, 0 and 15% in eight hours, 0 and 40% in twelve hours, and 0 and 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1 and a compound listed in Table 2, wherein a compound listed in Table 1 has an in vitro dissolution profile ranging between 0 and about 40% in four hours, 0 and about 80% in eight hours, 0 and about 95% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1 and a compound listed in Table 2, wherein a compound listed in Table 2 has an in vitro dissolution profile ranging between 0 and about 40% in four hours, 0 and about 80% in eight hours, 0 and about 95% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1 and a compound listed in Table 2, wherein a compound listed in Table 1 has an in vitro dissolution profile between 0 and 15% in four hours, 0 and about 60% in eight hours, 0 and about 80% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1 and a compound listed in Table 2, wherein a compound listed in Table 2 has an in vitro dissolution profile between 0 and 15% in four hours, 0 and about 60% in eight hours, 0 and about 80% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1 and a compound listed in Table 2, wherein a compound listed in Table 1 has an in vitro dissolution profile ranging between 0 and 5% in four hours, 0 and 15% in eight hours, 0 and 40% in twelve hours, and 0 and 100% in twenty four hours, as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1 and a compound listed in Table 2, wherein a compound listed in Table 2 has an in vitro dissolution profile ranging between 0 and 5% in four hours, 0 and 15% in eight hours, 0 and 40% in twelve hours, and 0 and 100% in twenty four hours, as measured using a USP type II apparatus (paddle) at 50 RPM rotational speed in pH 1.2 HCl media.

In some embodiments, the pharmaceutical compositions provide a compound listed in Table 1 in vitro dissolution profile ranging between about 0 and about 1% at one hour, about 3% and about 4% at two hours, about 7% and about 8% at three hours, about 12% and 13% at four hours, about 52% and about 56% at eight hours, about 79% and 83% at twelve hours, between about 90% and about 96% at eighteen hours, and between about 94% and about 100% at 24 hours as measured using a USP type II apparatus (paddle) at 50 RPM rotational speed in pH 1.2 HCl media.

In some embodiments, the pharmaceutical compositions provide a compound listed in Table 2 in vitro dissolution profile ranging between about 0 and about 1% at one hour, about 3% and about 4% at two hours, about 7% and about 8% at three hours, about 12% and 13% at four hours, about 52% and about 56% at eight hours, about 79% and 83% at twelve hours, between about 90% and about 96% at eighteen hours, and between about 94% and about 100% at 24 hours as measured using a USP type II apparatus (paddle) at 50 RPM rotational speed in pH 1.2 HCl media.

In some embodiments, the pharmaceutical compositions provide a compound listed in Table 1 in vitro dissolution profile ranging between about 38% and about 40% at four hours, between about 76% and about 82% at eight hours, between about 92% and about 96% at twelve hours, between about 97% and 100% at eighteen hours, and 99% or more in twenty four hours as measured using a USP type II apparatus (paddle) at 50 RPM rotational speed in pH 1.2 HCl media.

In some embodiments, the pharmaceutical compositions provide a compound listed in Table 2 in vitro dissolution profile ranging between about 38% and about 40% at four hours, between about 76% and about 82% at eight hours, between about 92% and about 96% at twelve hours, between about 97% and 100% at eighteen hours, and 99% or more in twenty four hours as measured using a USP type II apparatus (paddle) at 50 RPM rotational speed in pH 1.2 HCl media.

In some embodiments, the pharmaceutical compositions provide a compound listed in Table 1 in vitro dissolution profile ranging between about 10% and about 11% at four hours, about 51% and about 56% at 8 hours, about 79% and 81% at twelve hours, about 93% and 96% in eighteen hours, and about 97% and 99% at twenty four hours as measured using a USP type II apparatus (paddle) at 50 RPM rotational speed in pH 1.2 HCl media.

In some embodiments, the pharmaceutical compositions provide a compound listed in Table 2 in vitro dissolution profile ranging between about 10% and about 11% at four hours, about 51% and about 56% at 8 hours, about 79% and 81% at twelve hours, about 93% and 96% in eighteen hours, and about 97% and 99% at twenty four hours as measured using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1, or a pharmaceutically acceptable salt thereof, wherein the composition has an in vitro dissolution profile of a compound listed in Table 1 ranging between 35% and 45% at four hours, 75% and 85% at eight hours, 90% and 95% at twelve hours, and about 100% at twenty four hours, as measured at 37° C. using a USP type II apparatus (paddle) at 50 RPM rotational speed in pH 1.2 HCl media, and (iii) a compound listed in Table 2, or a pharmaceutically acceptable salt thereof, wherein the composition has an in vitro dissolution profile of a compound listed in Table 2 ranging between 35% and 45% at four hours, 75% and 85% at eight hours, 90% and 95% at twelve hours, and about 100% at twenty four hours, as measured at 37° C. using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1, or a pharmaceutically acceptable salt thereof, wherein the composition has an in vitro dissolution profile of a compound listed in Table 1 ranging between 9% and 18% at four hours, 50% and 62% at eight hours, 78% and 85% at twelve hours, and about 100% at twenty four hours, as measured at 37° C. using a USP type II apparatus (paddle) at 50 RPM rotational speed in pH 1.2 HCl media, and (iii) a compound listed in Table 2, or a pharmaceutically acceptable salt thereof, wherein the composition has an in vitro dissolution profile of a compound listed in Table 2 ranging between 9% and 18% at four hours, 50% and 62% at eight hours, 78% and 85% at twelve hours, and about 100% at twenty four hours, as measured at 37° C. using a USP type II apparatus (paddle) at 50 RPM rotational speed in pH 1.2 HCl media.

In some embodiments, the disclosure provides a pharmaceutical composition comprising (i) a modified release coating and/or matrix and (ii) a compound listed in Table 1, or a pharmaceutically acceptable salt thereof, wherein the composition has an in vitro dissolution profile of a compound listed in Table 1 ranging between 2% and 4% at four hours, 13% and 16% at eight hours, 35% and 45% at twelve hours, 93% and 96% at twenty four hours, and about 100% at 36 hours, as measured at 37° C. using a USP type II apparatus (paddle) at 50 RPM rotational speed in pH 1.2 HCl media, and (iii) a compound listed in Table 2, or a pharmaceutically acceptable salt thereof, wherein the composition has an in vitro dissolution profile of a compound listed in Table 2 ranging between 2% and 4% at four hours, 13% and 16% at eight hours, 35% and 45% at twelve hours, 93% and 96% at twenty four hours, and about 100% at 36 hours, as measured at 37° C. using a USP type II apparatus (paddle) at 50 RPM rotational speed in pH 1.2 HCl media.

In some embodiments, the pharmaceutical compositions provide a compound listed in Table 1 in vitro dissolution ranging between 0% and 3% in four hours, between about 14% and about 15% in eight hours, between about 033% and about 43% in twelve hours, between about 83% and 84% in eighteen hours, between about 94% and about 95% in twenty four hours, between about 97% and about 98% in thirty hours, and between about 98% and about 99% in thirty hours as measured using a USP type II apparatus (paddle) at 50 RPM rotational speed in pH 1.2 HCl media.

In some embodiments, the pharmaceutical compositions provide a compound listed in Table 2 in vitro dissolution ranging between 0% and 3% in four hours, between about 14% and about 15% in eight hours, between about 033% and about 43% in twelve hours, between about 83% and 84% in eighteen hours, between about 94% and about 95% in twenty four hours, between about 97% and about 98% in thirty hours, and between about 98% and about 99% in thirty hours as measured using a USP type II apparatus (paddle) at 50 RPM rotational speed in pH 1.2 HCl media.

In some embodiments, the pharmaceutical compositions provide a compound listed in Table 1 in vitro dissolution ranging between 0% and about 1% in one hour, about 4% and about 6% in two hours, about 9% and about 11% in three hours, about 14% and about 18% in four hours, about 58% and about 68% in eight hours, about 82% and 89% in twelve hours, about 92% and about 98% in eighteen hours, and about 94% and 100% in twenty four hours as measured using a USP type II apparatus (paddle) at 50 RPM rotational speed in pH 1.2 HCl media.

In some embodiments, the pharmaceutical compositions provide a compound listed in Table 2 in vitro dissolution ranging between 0% and about 1% in one hour, about 4% and about 6% in two hours, about 9% and about 11% in three hours, about 14% and about 18% in four hours, about 58% and about 68% in eight hours, about 82% and 89% in twelve hours, about 92% and about 98% in eighteen hours, and about 94% and 100% in twenty four hours as measured using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between 0 and about 40% in four hours, 0 and about 80% in eight hours, 0 and about 95% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile between 0 and 15% in four hours, 0 and about 60% in eight hours, 0 and about 80% in twelve hours, and 0 and about 100% in twenty four hours, as measured using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between 0 and 5% in four hours, 0 and 15% in eight hours, 0 and 40% in twelve hours, and 0 and 100% in twenty four hours, as measured using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between about 0 and about 1% at one hour, about 3% and about 4% at two hours, about 7% and about 8% at three hours, about 12% and 13% at four hours, about 52% and about 56% at eight hours, about 79% and 83% at twelve hours, between about 90% and about 96% at eighteen hours, and between about 94% and about 100% at 24 hours as measured using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between about 38% and about 40% at four hours, between about 76% and about 82% at eight hours, between about 92% and about 96% at twelve hours, between about 97% and 100% at eighteen hours, and 99% or more in twenty four hours as measured using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between about 10% and about 11% at four hours, about 51% and about 56% at 8 hours, about 79% and 81% at twelve hours, about 93% and 96% in eighteen hours, and about 97% and 99% at twenty four hours as measured using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between 35% and 45% at four hours, 75% and 85% at eight hours, 90% and 95% at twelve hours, and about 100% at twenty four hours, as measured at 37° C. using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between 9% and 18% at four hours, 50% and 62% at eight hours, 78% and 85% at twelve hours, and about 100% at twenty four hours, as measured at 37° C. using a USP type II apparatus (paddle) at 50 RPM rotational speed in pH 1.2 HCl media; In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between 2% and 4% at four hours, 13% and 16% at eight hours, 35% and 45% at twelve hours, 93% and 96% at twenty four hours, and about 100% at 36 hours, as measured at 37° C. using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between 0% and 3% in four hours, between about 14% and about 15% in eight hours, between about 033% and about 43% in twelve hours, between about 83% and 84% in eighteen hours, between about 94% and about 95% in twenty four hours, between about 97% and about 98% in thirty hours, and between about 98% and about 99% in thirty hours as measured using a USP type II apparatus (paddle) at 50 RPM rotational speed in pH 1.2 HCl media.

In some embodiments, the disclosure provides a pharmaceutical composition comprising (i) a capsule containing a plurality of beads comprised of a compound listed in Table 1 and (ii) a plurality of beads comprised of a compound listed in Table 2; the plurality beads of a compound listed in Table 1 having a modified release coating and a core comprising a compound listed in Table 1, and the plurality of beads of a compound listed in Table 2 having a modified release coating and a core comprising a compound listed in Table 2, the a compound listed in Table 1 and a compound listed in Table 2 each having an in vitro dissolution profile ranging between 0% and about 1% in one hour, about 4% and about 6% in two hours, about 9% and about 11% in three hours, about 14% and about 18% in four hours, about 58% and about 68% in eight hours, about 82% and 89% in twelve hours, about 92% and about 98% in eighteen hours, and about 94% and 100% in twenty four hours as measured using a USP type II apparatus (paddle) at 50 RPM rotational speed in pH 1.2 HCl media.

IV. Administration

The compositions of the present invention can be administered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, and the like as is known to those of ordinary skill in the art. Suitable dosage ranges for the compounds disclosed herein include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg. In some embodiments, a compound disclosed herein, including those described in Table 1, is provided at a dose of from about 5 mg to about 500 mg, about 10 mg, about 25 mg, about 50 mg, about 75 mg, about 100 mg, about 150 mg, about 225 mg, or about 300 mg. In some embodiments, a compound listed in Table 1, or a pharmaceutically acceptable salt thereof, is formulated with a compound listed in Table 2 in an extended release oral formulation, wherein the a compound listed in Table 1 is present between about 5 mg to about 500 mg, or between about 10 mg to about 400 mg, or between about 20 mg to about 300 mg, or between about 50 mg to about 300 mg, or between about 75 mg to about 250 mg, or between about 100 mg to about 200 mg, or between about 150 mg to about 200 mg, or between about 175 mg to about 200 mg, or between about 200 mg to about 225 mg, or between about 225 mg to about 250 mg, or between about 250 mg to about 275 mg, or between about 275 mg to about 300 mg, or at about 10 mg, or at about 25 mg, or at about 50 mg, or at about 75 mg, or at about 100 mg, or at about 125 mg, or at about 150 mg, or at about 175 mg, or at about 200 mg, or at about 225 mg, or at about 250 mg, or at about 275 mg, or at about 300 mg, or at about 325 mg, or at about 350 mg, or at about 375 mg, or at about 400 mg, or at about 425 mg, or at about 450 mg, or at about 475 mg, or at about 500 mg, and a compound listed in Table 2, or a pharmaceutically acceptable salt thereof, is present between about 5 mg and about 250 mg, or between about 10 mg to about 400 mg, or between about 20 mg to about 300 mg, or between about 50 mg to about 300 mg, or between about 75 mg to about 250 mg, or between about 100 mg to about 200 mg, or between about 150 mg to about 200 mg, or between about 175 mg to about 200 mg, or between about 200 mg to about 225 mg, or between about 225 mg to about 250 mg, or between about 250 mg to about 275 mg, or between about 275 mg to about 300 mg, or at about 10 mg, or at about 25 mg, or at about 50 mg, or at about 75 mg, or at about 100 mg, or at about 125 mg, or at about 150 mg, or at about 175 mg, or at about 200 mg, or at about 225 mg, or at about 250 mg, or at about 275 mg, or at about 300 mg, or at about 325 mg, or at about 350 mg, or at about 375 mg, or at about 400 mg, or at about 425 mg, or at about 450 mg, or at about 475 mg, or at about 500 mg.

In some embodiments, a compound listed in Table 1, or a pharmaceutically acceptable salt thereof, is formulated with a compound listed in Table 2 as a long acting injectable formulation or a patch formulation, wherein the a compound listed in Table 1 is present between about 5 mg to about 5000 mg, or between about 5 mg to about 4500 mg, or between about 5 mg to about 4000 mg, or between about 5 mg to about 3500 mg, or between about 5 mg to about 3000 mg, or between about 5 mg to about 2500 mg, or between about 5 mg to about 2000 mg, or between about 5 mg to about 1500 mg, or between about 5 mg to about 1000 mg, or between about 5 mg to about 500 mg.

In some embodiments, a compound listed in Table 1, or a pharmaceutically acceptable salt thereof, is coformulated with a compound listed in Table 2, or a pharmaceutically acceptable salt thereof, in an extended release oral formulation, wherein the a compound listed in Table 1 is present at about 50 mg, or about 75 mg, or about 100 mg, or about 125 mg, or about 150 mg, or about 175 mg, or about 200 mg, or about 250 mg, or about 300 mg, or about 325 mg, or about 350 mg, or about 375 mg, or about 400 mg, and the compound listed in Table 2 is present at about 30 mg, or at about 40 mg, or at about 50 mg, or at about 60 mg, or at about 70 mg, or at about 80 mg, or at about 90 mg, or at about 100 mg, or at about 110 mg, or at about 120 mg, or at about 130 mg, or at about 140 mg, or at about 150 mg, or at about 160 mg, or at about 170 mg, or at about 180 mg, or at about 190 mg, or at about 200 mg.

The compounds disclosed herein can be administered at any suitable frequency, interval and duration. For example, the compounds can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

In some embodiments, a compound disclosed in Table 1 is administered in combination with a compound disclosed in Table 2. In some embodiments, a compound disclosed in Table 1 is provided at a dose of from about 5 mg to about 500 mg, about 10 mg, about 25 mg, about 50 mg, about 75 mg, about 100 mg, about 150 mg, about 225 mg, or about 300 mg, and a compound disclosed in Table 2 is provided at a dose of about 5 mg to about 500 mg, about 10 mg, about 20 mg, about 25 mg, about 30 mg, about 50 mg, about 75 mg, about 100 mg, about 150 mg, about 225 mg, or about 300 mg.

The compounds of the present invention can be co-administered with a second active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, such as by preparing a single pharmaceutical composition including both the compound of the present invention and a second active agent. In some embodiments, the compound of the present invention and the second active agent can be formulated separately.

The disclosed compounds and the second active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the second active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods disclosed herein.

The present disclosure advantageously provides pharmaceutical compositions of a compound listed in Table 1 and a compound listed in Table 2 that are suitable for once-daily administration. It is believed that compositions of a compound listed in Table 1 and a compound listed in Table 2 that are suitable for once-daily dosing provide a benefit relative to compositions of a compound listed in Table 1 and a compound listed in Table 2 that must be administered multiple times per day, at least because a compound listed in Table 1 and a compound listed in Table 2 may be used as a therapy for individuals who suffer from psychological disorders such as schizophrenia and may be unable or unwilling to comply with a multiple-times-daily dosing regimen.

The present disclosure advantageously provides pharmaceutical compositions of a compound listed in Table 1 and a compound listed in Table 2 that are suitable for once-monthly, or about once every two months, or about once every three months, injectable administration. It is believed that compositions of a compound listed in Table 1 and a compound listed in Table 2 that are suitable for once-monthly, or about once every two months, or about once every three months, injectable administration provide a benefit relative to compositions of a compound listed in Table 1 and a compound listed in Table 2 that must be administered multiple times per day, at least because a compound listed in Table 1 and a compound listed in Table 2 may be used as a therapy for individuals who suffer from psychological disorders such as schizophrenia and may be unable or unwilling to comply with a multiple-times-daily dosing regimen.

A compound listed in Table 1, or a pharmaceutically acceptable salt thereof, and a compound listed in Table 2, or a pharmaceutically acceptable salt thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e.by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound listed in Table 1 and a compound listed in Table 2 with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

In any of the above-mentioned pharmaceutical composition, process, method, use, medicament, and manufacturing features of the instant disclosure, any of the alternate embodiments of macromolecules of the present disclosure described herein also apply.

A compound listed in Table 1 or pharmaceutical compositions comprising a compound listed in Table 1 and a compound listed in Table 2, or pharmaceutical compositions comprising a compound listed in Table 1 or Table 2 may be administered to a subject by any route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray or powder); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intranasal; by implant of a depot or reservoir, for example, subcutaneously or intramuscularly.

The compositions of a compound listed in Table 1 and a compound listed in Table 2 disclosed herein can be administered at any suitable frequency, interval and duration. For example, the compounds can be administered once an hour, or two, three or more times an hour, once a day, or two, three, or more times per day, or once every 2, 3, 4, 5, 6, or 7 days, so as to provide the preferred dosage level. When the compound of the present disclosure is administered more than once a day, representative intervals include 5, 10, 15, 20, 30, 45 and 60 minutes, as well as 1, 2, 4,6, 8, 10, 12, 16, 20, and 24 hours. The compound of the present disclosure can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

V. Methods of Treatment

The compounds of the present invention, such as a compound of any of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and (XV), can be used for increasing neuronal plasticity. The compounds of the present invention can also be used to treat any brain disease. The compounds of the present invention can also be used for increasing at least one of translation, transcription or secretion of neurotrophic factors.

In some embodiments, a compound of the present invention, such as a compound of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV), is used to treat neurological diseases. In some embodiments, the compounds have, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, a compound of the present invention, such as a compound of Table 2, is used to treat diseases of the urinary tract including overactive bladder.

In some embodiments, a compound of the present invention is used for increasing neuronal plasticity. In some embodiments, the compounds described herein are used for treating a brain disorder. In some embodiments, the compounds described herein are used for increasing at least one of translation, transcription, or secretion of neurotrophic factors.

In some embodiments, the present invention provides a method of treating a disease, including administering to a subject in need thereof, a therapeutically effective amount of a compound of the present invention, such as a compound of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV). In some embodiments, the disease is a musculoskeletal pain disorder including fibromyalgia, muscle pain, joint stiffness, osteoarthritis, rheumatoid arthritis, muscle cramps. In some embodiments, the present invention provides a method of treating a disease of women's reproductive health including premenstrual dysphoric disorder (PMDD), premenstrual syndrome (PMS), post-partum depression, and menopause.

In some embodiments, a compound disclosed herein including in Table 1 is administered in combination with a compound disclosed in Table 2 to treat a patient with a psychotic illness including schizophrenia.

In some embodiments a compound disclosed herein including in Table 1 is administered in combination with a muscarinic receptor antagonist.

Muscarinic antagonists suitable for combination with a compound disclosed herein, including those described in Table 1 and Table 2, include without limitation, trospium ethylatropine, methylatropine, atropine, D/L-Hyoscyamine, Atropine methonitrate, Aclidinium bromide, Benztropine, Cyclopentolate, Diphenhydramine, Doxylamine, Dimenhydrinate, Dicyclomine, Darifenacin, Flavoxate, Glycopyrrolate, Hydroxyzine, Ipratropium, Mebeverine, Oxybutynin, Pirenzepine, Procyclidine, Solifenacin, Tropicamide, Tiotropium, Trihexyphenidyl/Benzhexol, Tolterodine In some embodiments a compound disclosed herein including in Table 1 is administered in combination with a muscarinic receptor antagonist where the muscarinic antagonist is an pan-antagonist muscarinic receptors.

In some embodiments a compound disclosed herein including in Table 1 is administered in combination with a peripherally restricted muscarinic receptor antagonist where the muscarinic antagonist does not cross the blood brain barrier.

In some embodiments a compound disclosed herein including in Table 1 is administered in combination with a nonselective muscarinic receptor antagonist.

In some embodiments a compound disclosed herein including in Table 1 is administered in combination with a muscarinic receptor antagonist where the muscarinic antagonist is an antagonist of the M1 and M4 receptors.

In some embodiments a compound disclosed herein including in Table 1 is administered in combination with a peripherally restricted muscarinic receptor antagonist that does not cross the blood brain barrier and where the muscarinic antagonist is an antagonist of the M1 and M4 receptors.

In some embodiments a compound disclosed herein including in Table 1 is administered in combination with a peripherally restricted muscarinic receptor antagonist that does not cross the blood brain barrier and where the muscarinic antagonist is an antagonist of the M1 receptor.

In some embodiments a compound disclosed herein including in Table 1 is administered in combination with a peripherally restricted muscarinic receptor antagonist that does not cross the blood brain barrier and where the muscarinic antagonist is an antagonist of the M4 receptor.

In some embodiments a compound disclosed herein including in Table 1 is administered in combination with a compound disclosed in Table 2 where the compounds are administered separately, sequentially, or simultaneously.

In some embodiments a compound disclosed in Table 1 is administered in combination with a compound disclosed in Table 2 wherein the compound disclosed in Table 1 is administered before the compound disclosed in Table 2.

In some embodiments a compound disclosed in Table 1 is administered in combination with a compound disclosed in Table 2 wherein the compound disclosed in Table 1 is administered at the same time as the compound disclosed in Table 2.

In some embodiments a compound disclosed in Table 1 is administered in combination with a compound disclosed in Table 2 wherein the compound disclosed in Table 1 is administered after the compound disclosed in Table 2.

In some embodiments a compound disclosed in Table 1 is administered in combination with a compound disclosed in Table 2 wherein the compounds are both formulated into a fixed dose combination.

In some embodiments a compound disclosed in Table 1 is administered in combination with a compound disclosed in Table 2 wherein the compounds are both formulated as a single long acting injectable drug.

In some embodiments a compound disclosed in Table 1 is administered in combination with a compound disclosed in Table 2 wherein the compounds are administered as a single injection.

In some embodiments a compound disclosed in Table 1 is administered in combination with a compound disclosed in Table 2 wherein the compounds are administered as separate injections.

In some embodiments a compound disclosed in Table 1 is administered in combination with a compound disclosed in Table 2 wherein the compounds are administered in a specific ratio.

In some embodiments, a compound disclosed herein including in Table 1 is administered in combination with a compound disclosed in Table 2. In some embodiments, a compound disclosed in Table 1 is provided at a dose of from about 5 mg to about 500 mg, about 10 mg, about 25 mg, about 50 mg, about 75 mg, about 100 mg, about 150 mg, about 225 mg, or about 300 mg, and a compound disclosed in Table 2 is provided at a dose of about 5 mg to about 500 mg, about 10 mg, about 20 mg, about 25 mg, about 30 mg, about 50 mg, about 75 mg, about 100 mg, about 150 mg, about 225 mg, or about 300 mg.

In some embodiments, a compound disclosed herein, including those described in Table 1 and Table 2, is administered simultaneous with a psychedelic compound. In some embodiments, a compound disclosed herein, including those described in Table 1 and Table 2, is co-administered in the same formulation as a psychedelic compound. In some embodiments, a compound disclosed herein, including those described in Table 1 and Table 2, is administered prior to a psychedelic compound, such as about 8 hours to about 30 minutes prior, or about three hours, or about two hours, or about one hour prior to administration of a psychedelic compound. In some embodiments, the compound disclosed herein, including those described in Table 1 and Table 2, is administered at most about one hour prior to the psychedelic compound. In some embodiments, the compound disclosed herein, including those described in Table 1 and Table 2, is administered at most about two hours prior to the psychedelic compound. In some embodiments, the compound disclosed herein, including those described in Table 1 and Table 2, is administered after a psychedelic compound, such as about one to about 30 minutes, or about 1 hour, or about 2 hours, or about 3 hours, or about 4 hours, or about 5 hours, or about 6 hours, or about 7 hours, or about 8 hours, or about 9 hours, or about 10 hours, or about 11 hours, or about 12 hours, after the administration of a psychedelic compound. Psychedelics suitable for combination with a compound disclosed herein, including those described in Table 1 and Table 2, include without limitation psilocybin, psilocin, baeocystin, norbaeocystin, LSD, lisurgide, ibogaine, mescaline (3,4,5-trimethoxy-phenethylamine), phenethylamine (PEA), carboxamindotryptamine, proscaline (2-(3,5-dimethoxy-4-propoxyphenyl)ethanamine), metaescaline (2-(3-ethoxy-4,5-dimethoxyphenyl)ethanamine), allylescaline (4-Allyloxy-3,5-dimethyloxy phenylethylamine), methallylescaline (4-Methallyloxy-3,5-dimethoxyphenethylamine), 3,4-Methylenedioxy-A (MDA), 3,4-methylenedioxy-N-ethylamphetamine (MDE), asymbescaline (3,4-Diethoxy-5-methoxyphenethylamine), mescaline-NBOMe, 1B-LSD, ETH-LAD, 1P-ETH-LAD, AL-LAD, LSZ, LSM-775, 1-(4-Bromofuro[2,3-f] [1]benzofuran-8-yl)propan-2-amine, 25I-NBOH, N-(2-Methoxybenzyl)-2-(3,4,5-trimethoxyphenyl) ethanamine, N-(2-hydroxybenzyl)-2,5-dimethoxy-4-iodo-phenethylamine, N-(2-hydroxybenzyl)-2,5-dimethoxy-4-chloro-phenethylamine, N-(2-hydroxybenzyl)-2,5-dimethoxy-4-bromo-phenethylamine, 4-Allyloxy-3,5-dimethyloxyphenylethylamine, N-(2-fluorobenzyl)-2,5-dimethoxy-4-iodo-phenethylamine, 2,5-dimethoxy-4-tert-butylthio-phenethylamine, 2,5-dimethoxy-4-propylthio-phenethylamine, 2,5-dimethoxy-4-propylphenethylamine, 2,5-dimethoxy-4-nitrophenethylamine, 2,5-dimethoxy-4-nitroamphetamine, 2,5-dimethoxy-4-methylphenethylamine, 2,5-dimethoxy-4-isopropylthio-phenethylamine, 2,5-dimethoxy-4-iodophenethylamine, 2,5-dimethoxy-4-iodoamphetamine, 2,5-dimethoxy-4-fluorophenethylamine, 2,5-dimethoxy-4-ethylthio-phenethylamine, 2,5-dimethoxy-4-ethylphenethylamine, 2,5-dimethoxy-4-cyclopropylmethylthio-phenethylamine, 2,5-dimethoxy-4-chlorophenethylamine, 2,5-dimethoxy-4-chloroamphetamine, 2,5-dimethoxy-4-bromoamphetamine, 2,5-dimethoxy-4-bromo-β-ketophenethylamine, 2,5-dimethoxy-4-(2-fluoroethylthio)-phenethylamine, 2-(4-propyl-2,5-dimethoxyphenyl)-N-[(2-methoxyphenyl)methyl] ethanamine, 2-(4-methyl-2,5-dimethoxyphenyl)-N-[(2-methoxyphenyl)methyl]ethanamine, 2-(4-iodo-2,5-dimethoxyphenyl)-N-[(2-methoxyphenyl)methyl] ethanamine, 2-(4-fluoro-2,5-dimethoxyphenyl)-N-[(2-methoxyphenyl)methyl]ethanamine, 2-(4-ethyl-2,5- dimethoxyphenyl)-N-[(2-methoxyphenyl)methyl] ethanamine, 2-(4-chloro-2,5-dimethoxyphenyl)-N-[(2-methoxyphenyl)methyl]ethanamine, 2-(4-bromo-2,5-dimethoxyphenyl)-N-[(2-methoxyphenyl)methyl]ethanamine, 2-Bromo-4,5-methylenedioxy-A (2-Br-4,5-MDA), 4-Bromo-3,5-dimethoxy-A (4-Br-3,5-DMA), 3,4-Dimethyl-2,5-dimethoxy-PEA (2C-G), 3,4-Trimethylene-2,5-dimethoxy-PEA (2C-G-3), 3,4-Trimethylene-2,5-dimethoxy-A (G-3), 3,4-Tetramethylene-2,5-dimethoxy-PEA (2C-G-4), 3,4-Tetramethylene-2,5-dimethoxy-A (G-4), 3,4-Norbornyl-2,5-dimethoxy-PEA (2C-G-5), 3,4-Norbornyl-2,5-dimethoxy-A (G-5), 1,4-Dimethoxynaphthyl-2-ethylamine (2C-G-N), 1,4-Dimethoxynaphthyl-2-isopropylamine (G-N), 2,5-Dimethoxy-PEA (2C-H), 4-Ethoxy-3,5-dimethoxy-A (3C-E), 4-Ethoxy-3,5-dimethoxy-PEA, 4-Benzyloxy-3,5-dimethoxy-A (3C-BZ), 4-Isopropoxy-2,5-dimethoxy-PEA (2C-O-4), 4-Methylseleno-2,5-dimethoxy-PEA (2C-SE), 4-Methylthio-2,5-dimethoxy-PEA (2C-T), 4-Isopropylthio-2,6-dimethoxy-PEA (psi-2C-T-4), 4-(2-Methoxyethylthio)-2,5-dimethoxy-PEA (2C-T-13), 4-Cyclopropylthio-2,5-dimethoxy-PEA (2C-T-15), 4-(s)-Butylthio-2,5-dimethoxy-PEA (2C-T-17), 4-Acetoxy-N-methyl-N-ethyltryptamine (4-AcO-MET), 4-Acetoxy-N-methyl-N-allyltryptamine (4-AcO-MALT), 4-Acetyloxy-N,N-diallyltryptamine (4-AcO-DALT), N,N,N-trimethyl-4-phosphoryloxytryptamine (aeruginascin), 4-Hydroxy-N,N,N-trimethyltryptamine, [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl]dihydrogen phosphate, [3-(2-trimethylaminoethyl)-1H-indol-4-yl] dihydrogen phosphate, and 4-hydroxy-N,N,N-trimethyltryptamine, 6-Allyl-N,N-diethyl-NL, N,N-Dibutyl-T, N,N-Diethyl-T, N,N-Diisopropyl-T, alpha-methyl-T, 5-Methyoxy-alpha-methyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy 1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N,N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T, Ibogaine, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, 2,N-Dimethyl-4,5-methylenedioxy-A, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, N-Isopropyl-4-methoxy-N-methyl-T, N-Isopropyl-5-methoxy-N-methyl-T, 5,6-Dimethyoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha Methyl-T, N-Ethyl-T, N-Methyl-T, 6-Propyl-N L, N,N-Tetramethylene-T, Tryptamine, 7-Methoxy-1-methyl-1,2,3,4-tetrahydro-C, alpha,N-Dimethyl-5-methoxy-T, alpha-Ethyl-3,4,5-trimethoxy-PEA (AEM), 4-Methylthio-2,5-dimethoxy-A (ALEPH), 4-Ethylthio-2,5-dimethoxy-A (ALEPH-2), 4-Isopropylthio-2,5-dimethoxy-A (ALEPH-4), 4-Phenylthio-2,5-dimethoxy-A (ALEPH-6), 4-Propylthio-2,5-dimethoxy-A (ALEPH-7), 2,5-Dimethoxy-alpha-ethyl-4-methyl-PEA (ARIADNE), 4-Butoxy-3,5-dimethoxy-PEA, 2,5-Dimethoxy-4,N-dimethyl-A (BEATRICE), 2,5-Bismethylthio-4-methyl-A (BIS-TOM), 4-Bromo-2,5,beta-trimethoxy-PEA (BOB), 2,5,beta-Trimethoxy-4-methyl-PEA (BOD), beta-Methoxy-3,4-methylenedioxy-PEA (BOH), 2,5-Dimethoxy-beta-hydroxy-4-methyl-PEA (BOHD), 3,4,5,beta-Tetramethoxy-PEA (BOM), 4-Cyclopropylmethoxy-3,5-dimethoxy-PEA (CPM), 4-Trideuteromethyl-3,5-dimethoxy-PEA (4-D), 3,4,5-trimethoxy-beta, beta-dideuterophenethylamine (beta-D), 4-Methyl-3,5-Dimethoxy-PEA, 2,4-Dimethoxy-A (2,4-DMA), 2,5-Dimethoxy-A (2,5-DMA), 3,4-Dimethoxy-A (3,4-DMA), 2-(2,5-Dimethoxy-4-methylphenyl)-cyclopropylamine (DMCPA), 3,4-Dimethoxy-beta-hydroxy-PEA (DME), 2,5-Dimethoxy-3,4-methylenedioxy-A (DMMDA), 2,3-Dimethoxy-4,5-methylenedioxy-A (DMMDA-2), 3,4-Dimethoxy-PEA (DMPEA), 2,5-dimethoxy-4-(n)-amylamphetamine (DOAM), 4-(2-Fluoroethyl)-2,5-dimethoxy-A (DOEF), 4-Ethyl-2,5-dimethoxy-A (DOET), 4-Methyl-2,6-dimethoxy-A (psi-DOM), 4-Propyl-2,5-dimethoxy-A (DOPR), 2,4,5-Triethoxy-A (EEE), 4-Diethoxy-5-methoxy-A (EEM), 2,5-Diethoxy-4-methoxy-A (EME), 2-Ethoxy-4,5-dimethoxy-A (EMM), N,alpha-diethyl-3,4-methylenedioxy-PEA (ETHYL-J), N-Ethyl-alpha-propyl-3,4-methylenedioxy-PEA (ETHYL-K), Benzofuran-2-methyl-5-methoxy-6-(2-aminopropane), Benzofuran-2,2-dimethyl-5-methoxy-6-(2-aminopropane), N-Hydroxy-N-methyl-3,4-methylenedioxy-A (FLEA), 3,4-Dimethyl-2,5-dimethoxy-A, 2,5-Dimethoxy-N-hydroxy-4-ethylthio-PEA (HOT-2), 2,5-Dimethoxy-N-hydroxy-4-(n)-propylthio-PEA (HOT-7), 2,5-Dimethoxy-N-hydroxy-4-(s)-butylthio-PEA (HOT-17), 2,5-Dimethoxy-N,N-dimethyl-4-iodo-A (IDNNA), 2,3,4-Trimethoxy-PEA (IM), 3,5-Dimethoxy-4-isopropoxy-PEA (IP), 5-Ethoxy-2-methoxy-4-methyl-A (IRIS), alpha-Ethyl-3,4-methylenedioxy-PEA, 3-Methoxy-4,5-methylenedioxy-PEA, 3-Methoxy-4,5-methylenedioxy-A (MMDA), 2-Methoxy-4,5-methylenedioxy-A (MMDA-2), 2-Methoxy-3,4-methylenedioxy-A (MMDA-3a), 4-Methoxy-2,3-methylenedioxy-A (MMDA-3b), 4-methoxyamphetamine, N-Allyl-3,4-methylenedioxy-A (MDAL), N-Butyl-3,4-methylenedioxy-A (MDBU), N-Benzyl-3,4-methylenedioxy-A (MDBZ), N-Cyclopropylmethyl-3,4-methylenedioxy-A (MDCPM), N,N-Dimethyl-3,4-methylenedioxy-A (MDDM), N-(2-Hydroxyethyl)-3,4-methylenedioxy-A, N-Isopropyl-3,4-methylenedioxy-A (MDIP), N-Methyl-3,4-ethylenedioxy-A (MDMC), N-Methoxy-3,4-methylenedioxy-A, N-(2-Methoxyethyl)-3,4-methylenedioxy-A, alpha,alpha,N-Trimethyl-3,4-methylenedioxy-PEA (MDMP), N-Hydroxy-3,4-methylenedioxy-A (MDOH), 3,4-Methylenedioxy-PEA, alpha,alpha-Dimethyl-3,4-methylenedioxy-PEA (MDPH), N-Propargyl-3,4-methylenedioxy-A (MDPL), N-Propyl-3,4-methylenedioxy-A (MDPR), 3,4-Dimethoxy-5-ethoxy-PEA (ME), 3-methoxy-4,5-Ethylenedioxy-A (MEDA), 2-Methoxy-4,5-diethoxy-A (MEE), 2,5-Dimethoxy-4-ethoxy-A (MEM), 3-Methoxy-4-ethoxy-PEA, 5-Bromo-2,4-dimethoxy-A, 5-Methylthio-2,4-dimethoxy-A, N-Methyl-2,5-dimethoxy-A, 4-Bromo-2,5-dimethoxy-N-methyl-A, N-Methyl-alpha-ethyl-3,4-methylenedioxy-PEA, N-Methyl-alpha-propyl-3,4-methylenedioxy-PEA, N-Methyl-4-methoxy-A, N-Methyl-2-methoxy-4,5-methylenedioxy-A, 2,4-Dimethoxy-5-ethoxy-A (MME), 3,4-Dimethoxy-5-propoxy-PEA (MP), 2,5-Dimethoxy-4-propoxy-A (MPM), 2-Methylthio-4,5-dimethoxy-A, 3,5-Dimethoxy-4-phenethyloxy-PEA (PE), 4-Propynyloxy-3,5-dimethoxy-PEA, 3,5-Diethoxy-4-methoxy-PEA, 3,4,5-Tetramethoxy-A, 4-Ethoxy-3-ethylthio-5-methoxy-PEA, 3-Ethoxy-4-ethylthio-5-methoxy-PEA, 3,4-Diethoxy-5-methylthio-PEA, 4-Thiobutoxy-3,5-dimethoxy-PEA, 4-Ethoxy-5-methoxy-3-methylthio-PEA (3-TE), 3,5-Dimethoxy-4- ethylthio-PEA (4-TE), 2-Methylthio-3,4-dimethoxy-PEA (2-TIM), 3-Methylthio-2,4-dimethoxy-PEA (3-TIM), 4-Methylthio-2,3-dimethoxy-PEA (4-TIM), 3-Methylthio-4,5-dimethoxy-PEA (3-TM), 4-Methylthio-3,5-dimethoxy-PEA (4-TM), 3,4,5-Trimethoxy-A (TMA), 2,4,5-Trimethoxy-A (TMA-2), 2,3,4-Trimethoxy-A (TMA-3), 2,3,5-Trimethoxy-A (TMA-4), 2,3,6-Trimethoxy-A (TMA-5), 2,4,6-Trimethoxy-A (TMA-6), 4,5-Dimethoxy-3-ethylthio-PEA (3-TME), 3-Ethoxy-5-methoxy-4-methylthio-PEA (4-TME), 3-Ethoxy-4-methoxy-5-methylthio-PEA (5-TME), 2-Methylthio-3,4-methylenedioxy-A, 4,5-Thiomethyleneoxy-2-methoxy-A, 2,4,5-Trimethoxy-PEA, 4-Ethyl-5-methoxy-2-methylthio-A (2-TOET), 4-Ethyl-2-methoxy-5-methylthio-A (5-TOET), 4-Ethyl-2-methoxy-5-methylthio-A (2-TOM), 2-Methoxy-4-methyl-5-methylthio-A (5-TOM), 2-Methoxy-4-methyl-5-methylsulfinyl-A (TOMSO), 4-Propylthio-3,5-dimethoxy-PEA (TP), 3,4,5-Triethoxy-PEA (TRIS), 3-Ethoxy-5-ethylthio-4-methoxy-PEA (3-TSB), 3,5-Diethoxy-4-methylthio-PEA (4-TSB), 4,5-Diethoxy-3-ethylthio-PEA (3-T-TRIS), 3,5-Diethoxy-4-ethylthio-PEA (4-T-TRIS), 2-(2-Chlorophenyl)-2-(methylamino)cyclohexanone (ketamine), 5-methoxy-2,3-dihydro-1H-inden-2-amine (MEAI), N-methyl-N-allyltryptamine (MALT),N-ethyl-N-propyltryptamine (EPT), 5-Methoxy-N,N-diallyltryptamine (5-MeO-DALT), 6-Methoxy-N,N-dimethyltryptamine (6-MeO-DMT), 6-fluoro-N,N,-dimethyltryptamine (6-Fluoro-DMT), N-methyl-N-propyltryptamine (MPT), N-Methyl-N-isopropyltryptamine (MiPT), N,N-Dimethyl-N-allyltryptamine (DMALT), 4-Acetoxy-N,N,N-trimethyltryptamine (4-AcO-TMT), 4-Acetoxy-N,N-dimethyl-N-ethyltryptamine (4-OAc-DMET), 4-Acetoxy-N,N-dimethyl-N-propyltryptamine (4-AcO-DMPT), N-(4-bromophenyl)adamantan-2-amine (bromantane), 3-(6-(4-fluoro-3-methoxyphenoxy)pyrimidin-4-yl)-5,5-dimethylimidazolidine-2,4-dione, N-(4-((2-fluorobenzyl)oxy)benzyl)-2-(trifluoromethyl)thiazole-4-carboxamide, 4-{trans-2-[4-(3-Fluorophenyl)pyrimidin-2-yl]cyclopropyl}benzenesulfonamide, sodium 6-methoxy-2-methyl-3-(3,4,5-trimethoxybenzoyl)benzofuran-7-yl phosphate, 1-ethyl-6-(indan-2-ylamino)-3-(morpholine-4-carbonyl)-1,8-naphthyridin-4-one, 4-((1S,3S)-3-(5-cyclopentyl-1,2,4-oxadiazol-3-yl)-2,2-dimethylcyclopropyl)benzenesulfonamide, (2S,5R)-5-(4-((1-(5-fluoro-2-(trifluoromethoxy)phenyl)-1H-tetrazol-5-yl)oxy)phenyl)pyrrolidine-2-carboxamide, N-(4-fluorophenethyl)-3-methylisoxazole-4-sulfonamide, (7-hydroxy-6-methoxy-2-methylbenzofuran-3-yl)(3,4,5-trimethoxyphenyl)methanone(7-hydroxy-6-methoxy-2-methylbenzofuran-3-yl)(3,4,5-trimethoxyphenyl)methanone, 6-((2,3-dihydro-1H-inden-2-yl)amino)-1-ethyl-3-(1-methyl-1H-imidazol-2-yl)-1,8-naphthyridin-4(1H)-one, 2-(2-(Allyloxy)-5-fluorophenyl)cyclopropyl)methanamine, 1,5-dimethyl-N-(2-(trifluoromethyl)pyridin-4-yl)-1H-indole-3-carboxamide, (2-(5-Fluoro-2-(2-fluoroethoxy)phenyl)cyclopropyl)methanamine, (2-(5-Chloro-2-(2-fluoroethoxy)phenyl)cyclopropyl)methanamine, (2-(5-Chloro-2-((2-fluoroallyl)oxy)phenyl)cyclopropyl)methanamine, 5,6-dimethoxy-2,3-dihydro-1H-inden-2-amine, N—N-disisopropyltryptamine-4-glutarate, 2-methoxy-7-methyl-5,6,7,8,9,10-hexahydropyrido[3',2':4,5]pyrrolo[2,3-d]azepine, 1-(5-methoxy-1H-indol-1-yl)-N,N,2-trimethylpropan-2-amine, 2-(5-methoxy-1H-pyrrolo[2,3-c]pyridin-1-yl)-N,N-dimethylethanamine, (R)—N,N-diethyl-1,3,4,5-tetrahydrobenzo[cd]indol-4-amine, (S)—N,N-diethyl-1,3,4,5-tetrahydrobenzo[cd]indol-4-amin, 2-(4-allyl-2,5-dimethoxyphenyl)ethanamine, N-Ethyl-2-(5-Fluoro-1H-Indol-3-YL)-N-Methylethan-1-Amine, (R)-2-(methylamino)-2-phenylcyclohexanone, (R)-2-(D3-methylamino)-2-phenylcyclohexanone, (S)-2-(methylamino)-2-phenylcyclohexanone, (S)-2-(D3-methylamino)-2-phenylcyclohexanone, (S)-3-(2,5-dimethoxy-4-(trifluoromethyl)phenyl)piperidine, 3-methylmethcathinone (3-MMC), 3-(2-(Bis(Methyl-D3)Amino)Ethyl-1,1,2,2-D4)-1H-Indol-4-YL(9Z,12Z)-Octadeca-9,12-Dienoate, (R)-3-((1-(Methyl-d3)Pyrolidin-2-YL)Methyl)-1H-Indol-4-OL, 5-(2-methylaminopropyl)benzofuran, 6-(2-methylaminopropyl)benzofuran, 2-chloro-N,N,-dimethyltryptamine,2-bromo-N,N,-dimethyltryptamine, 2-bromo-4-acetoxy-N,N-dimethyltryptamine, 2-chloro-4-methoxy-N,N,-dimethyltryptamine, 1-(3-(2-(dimethylamino)ethyl)-1H-indol-4-yl)-N-methylmethanesulfonamide, DMT-alpha,alpha-d2 (DMT-d2), psilocin-alpha, alpha-d2 (psilocin-d2), aeruginascin-alpha-alpha-d2 (aeruginascin-d2), razoxane, dexrazoxane, N-Allyl-3,4-methylenedioxy-amphetamine (MDAL), N-Butyl-3,4-methylenedioxyamphetamine (MDBU), N-Benzyl-3,4-methylenedioxyamphetamine (MDBZ), N-Cyclopropylmethyl-3,4-methylenedioxyamphetamine (MDCPM), N,N-Dimethyl-3,4-methylenedioxyamphetamine (MDDM), N-(2-Hydroxyethyl)-3,4-methylenedioxy amphetamine (MDHOET), N-Isopropyl-3,4-methylenedioxyamphetamine (MDIP), N-Methyl-3,4-ethylenedioxyamphetamine (MDMC), N-Methoxy-3,4-methylenedioxyamphetamine (MDMEO), N-(2-Methoxyethyl)-3,4-methylenedioxyamphetamine (MDMEOET), alpha,alpha,N-Trimethyl-3,4-methylenedioxyphenethylamine (MDMP), 3,4-Methylenedioxy-N-methylphentermine, N-Hydroxy-3,4-methylenedioxyamphetamine (MDOH), 3,4-Methylenedioxyphenethylamine (MDPEA), alpha,alpha-Dimethyl-3,4-methylenedioxyphenethylamine (MDPH; 3,4-methylenedioxyphentermine), N-Propargyl-3,4-methylenedioxyamphetamine (MDPL), 3,4-methylenedioxy-N-methyl-α-ethylphenylethylamine,3,4-Methylenedioxyamphetamine (MDA), Ethylone, (also known as 3,4-methylenedioxy-N ethylcathinone), and N-Propyl-3,4 methylenedioxyamphetamine (MDPR), or a pharmaceutically acceptable salt, solvate, metabolite, deuterated analogue, derivative, prodrug, or combinations thereof. In some embodiments, the psychedelic is selected from the group consisting of psilocybin, 4-Acetoxy-DMT, LSD, ALD-52, 1P-LSD, DMT, 5-MeO-DMT, 2C-B, ibogaine, MDMA, DOM, mescaline, R-MDMA, S-MDMA, MBDB, Methylone, R-methylone, S-methylone, MDEA, S-MDEA, N-Ethyl-2-(5-Fluoro-1H-Indol-3YL)-N-Methylethan-1-Amine, 4-OH-DiPT hemi-glutarate, 5,6-Dimethoxy-2-Aminoindane, 5-Methoxy-2-Aminoindane, 2-Br-LSD, MDAI, MDA, R-MDA, and S-MDA.

Methods for Increasing Neuronal Plasticity

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity by treating a subject with a compound of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV) can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present invention provides methods for increasing neuronal plasticity, comprising contacting a neuronal cell with a compound of the present invention, such as a compound of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV). In some embodiments, increasing neuronal plasticity improves a brain disorder described herein.

In some embodiments, a compound of the present invention is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neuronal plasticity of any compound of the present invention is a phenotypic assay, a dendritogenesis assay, a spinogenesis assay, a synaptogenesis assay, a Sholl analysis, a concentration-response experiment, a 5-$HT_{2A}$ agonist assay, a 5-$HT_{2A}$ antagonist assay, a 5-$HT_{2A}$ binding assay, or a 5-HT2A blocking experiment (e.g., ketanserin blocking experiments). In some embodiments, the experiment or assay to determine the hallucinogenic potential of any compound of the present invention is a mouse head-twitch response (HTR) assay. In some embodiments, the present invention provides a method for increasing neuronal plasticity, comprising contacting a neuronal cell with a compound of Table 1, Formulas (Ia), (Ib), (Ic), (Id), (Ie), (If), (Ig) (Lh), (Ii), (Ij), (I), (II), (III), (IV), (V), (VI), (VII), (VIII), (IX), (X), (XI), (XII), (XIII), (XIV), and/or (XV).

Methods of Treating a Brain Disorder

In some embodiments, the present invention provides a method of treating a disease, including administering to a subject in need thereof, a therapeutically effective amount of a compound of the present invention, such as a compound of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV). In some embodiments, the disease is a musculoskeletal pain disorder including fibromyalgia, muscle pain, joint stiffness, osteoarthritis, rheumatoid arthritis, muscle cramps. In some embodiments, the present invention provides a method of treating a disease of women's reproductive health including premenstrual dysphoric disorder (PMDD), premenstrual syndrome (PMS), post-partum depression, and menopause. In some embodiments, the present invention provides a method of treating a brain disorder, including administering to a subject in need thereof, a therapeutically effective amount of a compound of the present invention. In some embodiments, the present invention provides a method of treating a brain disorder with combination therapy, including administering to a subject in need thereof, a therapeutically effective amount of a compound of the present invention and at least one additional therapeutic agent.

In some embodiments, 5-$HT_{2A}$ modulators (e.g., 5-$HT_{2A}$ agonists) are used to treat a brain disorder. In some embodiments, the brain disorders comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound of the present invention, such as a compound of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV), is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder), depression, and anxiety.

In some embodiments, the present invention provides a method of treating a brain disorder, comprising administering to a subject in need thereof a therapeutically effective amount of a compound disclosed herein, such as a compound of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV).

In some embodiments, the brain disorder is a neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the brain disorder is a neurodegenerative disorder, Alzheimer's, or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the method further comprises administering one or more additional therapeutic agent that is lithium, olanzapine (Zyprexa), quetiapine (Seroquel), risperidone (Risperdal), ariprazole (Abilify), ziprasidone (Geodon), clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Parnate), diazepam (Valium), alprazolam (Xanax), or clonazepam (Klonopin).

In some embodiments the administration of a compound listed in Table 1 enhances the efficacy of the additional therapeutic agent. In some embodiments the administration of a compound listed in Table 1 results in a greater antipsychotic efficacy of the additional therapeutic agent as measured by a scale such as the PANSS, or BPRS, or SAPS or SANS. In some embodiments the administration of a compound listed in Table 1 results in a greater reduction in the positive, negative, or cognitive symptoms of schizophrenia than administration of the additional therapeutic agent alone as measured by a scale such as the PANSS, or BPRS, or SAPS or SANS. In some embodiments the administration of a compound listed in Table 1 results in a greater antidepressant efficacy of the additional therapeutic agent as measured by a scale such as the Montgomery-Asberg Depression Rating Scale (MADRS) or Hamilton Depression Rating Scale HDRS or HAM-D.

In certain embodiments of the method for treating a brain disorder disclosed herein with a compound according to Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV), a second therapeutic agent that is an empathogenic agent is administered. Examples of suitable empathogenic agents for use in combination with a compound according to Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV) are selected from the phenethylamines, such as 3,4-methylenedioxymethamphetamine (MDMA) and analogs thereof. Other suitable empathogenic agents for use in combination with the presently disclosed compounds include, without limitation:

N-Allyl-3,4-methylenedioxy-amphetamine (MDAL)
N-Butyl-3,4-methylenedioxyamphetamine (MDBU)
N-Benzyl-3,4-methylenedioxyamphetamine (MDBZ)
N-Cyclopropylmethyl-3,4-methylenedioxyamphetamine (MDCPM)
N,N-Dimethyl-3,4-methylenedioxyamphetamine (MDDM)
N-Ethyl-3,4-methylenedioxyamphetamine (MDE; MDEA)
N-(2-Hydroxyethyl)-3,4-methylenedioxy amphetamine (MDHOET)
N-Isopropyl-3,4-methylenedioxyamphetamine (MDIP)
N-Methyl-3,4-ethylenedioxyamphetamine (MDMC)
N-Methoxy-3,4-methylenedioxyamphetamine (MDMEO)
N-(2-Methoxyethyl)-3,4-methylenedioxyamphetamine (MDMEOET)
alpha,alpha,N-Trimethyl-3,4-methylenedioxyphenethylamine (MDMP;
3,4-Methylenedioxy-N-methylphentermine)
N-Hydroxy-3,4-methylenedioxyamphetamine (MDOH)
3,4-Methylenedioxyphenethylamine (MDPEA)
alpha,alpha-Dimethyl-3,4-methylenedioxyphenethylamine (MDPH; 3,4-methylenedioxyphentermine)
N-Propargyl-3,4-methylenedioxyamphetamine (MDPL)
Methylenedioxy-2-aminoindane (MDAI)
N-methyl-1,3-benzodioxolylbutanamine (MBDB)

3,4-methylenedioxy-N-methyl-α-ethylphenylethylamine
3,4-Methylenedioxyamphetamine (MDA)
Methylone (also known as 3,4-methylenedioxy-N-methylcathinone)
Ethylone, (also known as 3,4-methylenedioxy-N-ethylcathinone)
GHB or Gamma Hydroxybutyrate or sodium oxybate
N-Propyl-3,4-methylenedioxyamphetamine (MDPR), and the like.

In some embodiments, the compounds of the present invention are used in combination with the standard of care therapy for a neurological disease described herein. Non-limiting examples of the standard of care therapies, may include, for example, lithium, olanzapine, quetiapine, risperidone, ariprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Nonlimiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline. Additional examples of standard of care therapeutics are known to those of ordinary skill in the art.

Methods of Increasing at Least One of Translation, Transcription, or Secretion of Neurotrophic Factors Neurotrophic factors refers to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-HT2A modulators (e.g., 5-HT2A agonists) are used to increase at least one of translation, transcription, or secretion of neurotrophic factors. In some embodiments, a compound of the present invention, such as a compound of Formula I, is used to increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present invention provides a method for increasing at least one of translation, transcription or secretion of neurotrophic factors, comprising contacting a neuronal cell with a compound disclosed herein, such as a compound of Table 1, Formulas (Ia), (Ib), (Ic), (Id), (Ie), (If), (Ig) (Ih), (Ii), (Ij), (I), (II), (III), (IV), (V), (VI), (VII), (VIII), (IX), (X), (XI), (XII), (XIII), (XIV), and/or (XV).

Listings of Numbered Embodiments

1. A compound according to Formula (Ia):

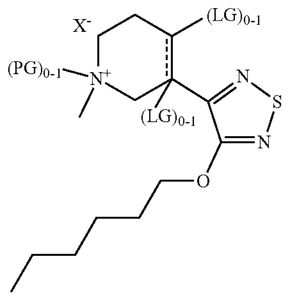

wherein PG is an optional progroup that together with the nitrogen atom to which it is attached forms an N-oxide, or has the formula —$(CR^1R^2)$—$OR^3$;

LG is an optional leaving group, provided that only one LG is present in the compound;

$R^3$ is selected from —$C(O)OR^4$, —$C(O)R^5$, —$Si(R^6)_3$, —$CH(R^7)OR^8$, —$CH(R^7)NR^aC(O)R^d$, —$CH(R^7)NR^cR^c$, —$CH(R^7)NR^aC(O)OR^d$, —$CH(R^7)OC(O)NR^cR^c$; —$CH(R^7)OC(O)R^7$, and —$P(O)OR^{10}(OR^{10})$;

$R^4$ is independently selected from —$C(R^7)_2$—$OC(O)C(R^7)_2NR^cR^c$, —$C(R^7)_2$—$OC(O)C(R^7)_3$, —$CH(R^7)R^X$, —$CH(R^7)OCH(R^7)R^X$, —$(CH_2)_m$—$R^b$, —$(CHR^a)_m$—$R^b$, —$(CR^aR^a)_m$—$R^b$, alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl is unsubstituted or substituted with one or more $R^A$;

m is independently for each occurrence 2 or 3;

$R^x$ is

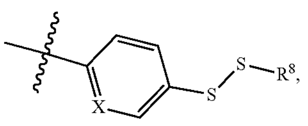

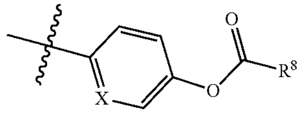

X is N or CH;

each $R^a$ is, for each occurrence, independently selected from the group consisting of hydrogen, $(C_{1-6})$ alkyl and $(C_{3-8})$ cycloalkyl;

each $R^b$ is independently selected from the group consisting of —S—S—$(CHR^a)_m$—$NR^cR^c$, —$OSi(R^d)_3$, —$OC(O)R^d$, —$OC(O)R^9$;

each $R^c$ is independently $R^a$, or, alternatively, two $R^c$ are taken together with the nitrogen atom to which they are bonded to form a 4 to 8-membered cycloheteroalkyl, which may optionally include one or more of the same or different additional heteroatoms and which may optionally be substituted with one or more of the same or different groups selected from oxo, —$CH_2OR^a$, —$C(O)R^a$ and $R^d$ groups;

each $R^d$ is independently selected from $(C_{1-6})$ alkyl, 5-membered heteroaryl, 6-membered heteroaryl and 6-membered aryl, each optionally substituted with each optionally substituted with 1, 2 or 3 groups selected from halogen, $C_{14}$ alkyl, and —$OR^a$;

with respect to the group —$NR^eR^e$; each $R^e$ is $R^a$, wherein at least one of the $R^a$ groups is substituted with at least one group selected from —$OC_{1-6}$ alkyl, —$OC(O)C_{1-6}$ alkyl, —OH, —$SC_{1-6}$ alkyl, and —SH;

$R^5$ is —$Si(R^d)_3$, —$C(R^5)_2$—$NR^cR^c$ or —$C(R^5)_2$—$C(R^7)_2$—$R^y$ alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl is unsubstituted or substituted with one or more $R^A$;

$R^6$ is alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl is unsubstituted or substituted with one or more $R^A$;

$R^7$ is independently hydrogen, alkyl, alkenyl, haloalkyl, heteroalkyl, cycloalkyl, heterocyclylalkyl wherein alkyl, heteroalkyl, cycloalkyl, heterocyclylalkyl is unsubstituted or substituted with one or more —$OR^a$, —$NR^cR^c$, —$C(O)OR^a$, —$N(R^a)C(O)OR^a$, $R^y$ is

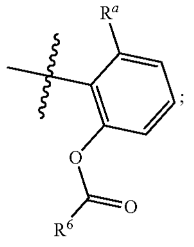

$R^8$ is —$Si(R^d)_3$, or $CH(R^5)OC(O)NHR^f$;

$R^f$ is —$Si(R^d)_3$, —$C(R^5)_2$—$NR^cR^c$ or —$C(R^5)_2$—$C(R^5)_2$—$R^y$;

$R^9$ is a $C_{6-15}$ alkylene or alkenylene chain;

each $R^{10}$ is independently selected from hydrogen, —$(CH_2)_n$—$R^g$, —$(CHR^a)_n$—$R^g$, and —$(CR^aR^a)_n$—$R^g$, alkyl, alkenyl, heteroalkyl, cycloalkyl, heterocyclylalkyl, aryl, or heteroaryl, wherein alkyl, heteroalkyl, cycloalkyl, heterocyclylalkyl, aryl, and heteroaryl is unsubstituted or substituted with one or more $R^B$;

n is independently for each occurrence 2 or 3;

each $R^9$ is independently —OH, —$NH_2$, —$N(R^{11})C(O)R^7$, —$N(R^{11})C(O)OR^{12}$, —$OC(O)R^{13}$, —$OC(O)OR^{14}$, —$OC(O)NR^cR^c$;

each $R^A$ is independently alkyl, heteroalkyl, cycloalkyl, heterocyclylalkyl, aryl, heteroaryl, halogen, an amino acid side chain, —$OR^{11}$, —$C(O)OR^{12}$, —$N(R^{13})C(O)OR^{14}$, —$N(R^{13})C(O)R^{14}$, —$C(O)R^{14}$, —$OC(O)R^{15}$, —$OC(O)OR^{16}$, —$OP(O)OR^{17}[N(R^{18})R^{19}]$, —$N(R^{18})R^{19}$, —$C(O)N(R^{18})R^{19}$, —$OC(O)N(R^{18})R^{19}$, or —$OP(O)OR^{10}(OR^{10})$, wherein alkyl, heteroalkyl, cycloalkyl, heterocyclylalkyl, aryl, or heteroaryl is unsubstituted or substituted with one or more alkyl, aryl, halogen, —S—$R^{13}$, —$OR^{13}$, —$NR(R^{18})R^{19}$, —$C(O)R^{14}$, —$OC(O)R^{15}$, —$OC(O)OR^{16}$, or —$OC(O)N(R^{18})R^{19}$;

each of $R^{11}$, R, $R^{13}$, $R^{14}$, $R^{15}$, $R^{16}$, or $R^{17}$ is independently hydrogen, alkyl, alkenyl, heteroalkyl, cycloalkyl, heterocyclylalkyl, aryl, or heteroaryl, wherein alkyl, heteroalkyl, cycloalkyl, heterocyclylalkyl, aryl, and heteroaryl is unsubstituted or substituted with one or more $R^B$;

each of $R^{18}$ and $R^{19}$ is independently hydrogen, alkyl, alkenyl, heteroalkyl, cycloalkyl, heterocyclylalkyl, aryl, or heteroaryl, wherein alkyl, heteroalkyl, cycloalkyl, heterocyclylalkyl, aryl, or heteroaryl is unsubstituted or substituted with one or more $R^B$; or $R^{18}$ and $R^{19}$ together with the atom to which they are attached form a heterocyclylalkyl ring or heteroaryl ring, each of which is unsubstituted or substituted with one or more $R^B$;

each $R^B$ is independently halogen, amino, cyano, hydroxyl, alkyl, alkenyl, heteroalkyl, cycloalkyl, heterocyclylalkyl, aryl, heteroaryl, arylalkyl, —$OC(O)R^{18}$, —$C(O)R^{18}$, —$C(O)OR^{18}$, $NHC(O)OR^{18}$, or heteroarylalkyl, wherein cycloalkyl, heterocyclylalkyl, aryl, or heteroaryl is unsubstituted or substituted with one or more halogen, amino, cyano, hydroxyl, alkyl, acetyl, or benzoyl, and $X^-$, when present, a pharmaceutically acceptable counterion.

2. The compound of embodiment 1, wherein the compound is isotopically enriched.

3. The compound of embodiment 1, having the formula:

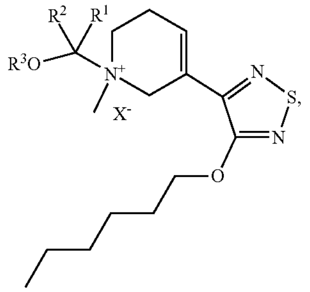

wherein $R^1$ and $R^2$ are independently selected from hydrogen and $C_{1-6}$ alkyl;

$R^3$ is selected from —$C(O)OR^4$, —$C(O)R^5$, —$Si(R^6)_3$;

$R^4$, $R^5$ and $R^6$; are independently selected from alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl is unsubstituted or substituted with one or more $R^A$;

each $R^A$ is independently alkyl, heteroalkyl, cycloalkyl, heterocyclylalkyl, aryl, heteroaryl, halogen, an amino acid side chain, —$OR^{11}$, —$C(O)OR^{12}$, —$N(R^{13})C(O)OR^{14}$, —$N(R^{13})C(O)R^{14}$, —$C(O)R^{14}$, —$OC(O)R^{15}$, —$OC(O)OR^{16}$, —$OP(O)OR^{17}[N(R^{18})R^{19}]$, —$N(R^{18})R^{19}$, —$C(O)N(R^{18})R^{19}$, —$OC(O)N(R^{18})R^{19}$, or —$OP(O)OR^{20}(OR^{21})$, wherein alkyl, heteroalkyl, cycloalkyl, heterocyclylalkyl, aryl, or heteroaryl is unsubstituted or substituted with one or more alkyl, aryl, halogen, —S—$R^{13}$, —$OR^{13}$, —$NR(R^{18})R^{19}$, —$C(O)R^{14}$, —$OC(O)R^{15}$, —$OC(O)OR^{16}$, or —$OC(O)N(R^{18})R^{19}$; each of $R^{11}$, $R^{12}$, $R^{13}$, $R^{14}$, $R^{15}$, $R^{16}$, or $R^{17}$ is independently hydrogen, alkyl, alkenyl, heteroalkyl, cycloalkyl, heterocyclylalkyl, aryl, or heteroaryl, wherein alkyl, heteroalkyl, cycloalkyl, heterocyclylalkyl, aryl, and heteroaryl is unsubstituted or substituted with one or more $R^B$;

each of $R^{18}$ and $R^{19}$ is independently hydrogen, alkyl, alkenyl, heteroalkyl, cycloalkyl, heterocyclylalkyl, aryl, or heteroaryl, wherein alkyl, heteroalkyl, cycloalkyl, heterocyclylalkyl, aryl, or heteroaryl is unsubstituted or substituted with one or more $R^B$; or $R^{18}$ and $R^{19}$ together with the atom to which they are attached form a heterocyclylalkyl ring or heteroaryl ring, each of which is unsubstituted or substituted with one or more $R^B$;

each $R^B$ is independently halogen, amino, cyano, hydroxyl, alkyl, alkenyl, heteroalkyl, cycloalkyl, heterocyclylalkyl, aryl, heteroaryl, arylalkyl, —$OC(O)R^{18}$, —$C(O)R^{18}$, —$C(O)OR^{18}$, $NHC(O)OR^{18}$, or heteroarylalkyl, wherein cycloalkyl, heterocyclylalkyl, aryl, or heteroaryl is unsubstituted or substituted with one or more halogen, amino, cyano, hydroxyl, alkyl, acetyl, or benzoyl, and $X^-$ is a pharmaceutically acceptable counterion.

4. The compound of embodiment 3, having the formula:

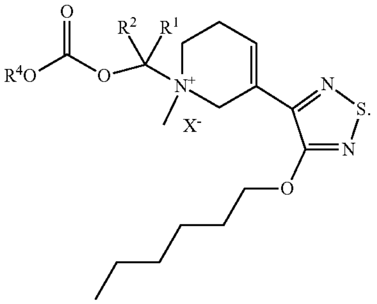

5. The compound of embodiment 4, having the formula

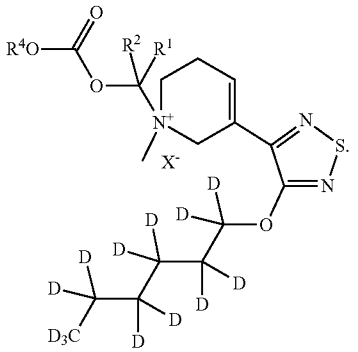

6. The compound of embodiment 4, having the formula

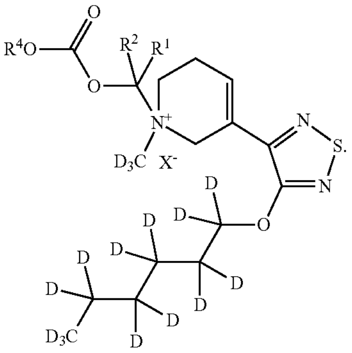

7. The compound of embodiment 3, having the formula:

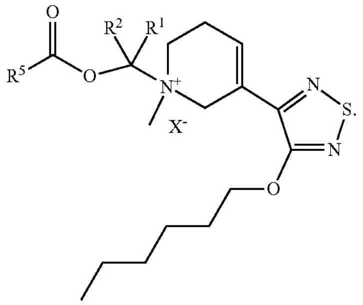

8. The compound of embodiment 7, having the formula

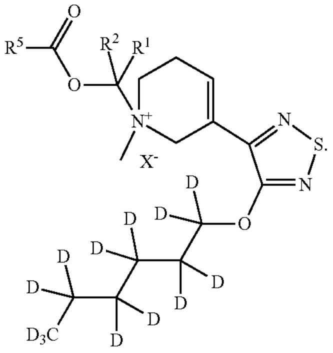

9. The compound of embodiment 7, having the formula

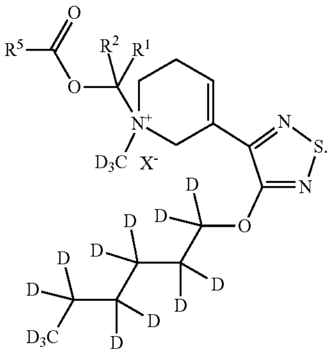

10. The compound of embodiment 3, having the formula:

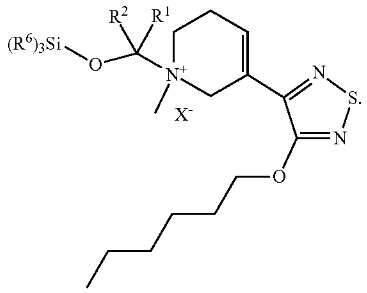

11. The compound of embodiment 10, having the formula

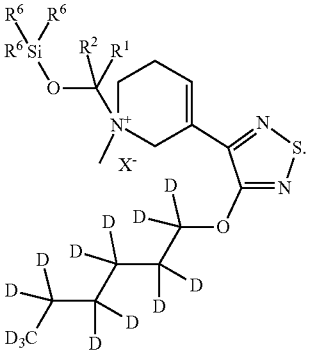

12. The compound of embodiment 10 having the formula

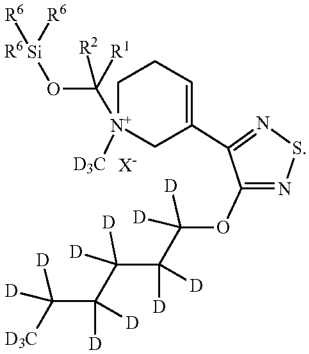

13. The compound of embodiment 1, wherein the compound has the formula:

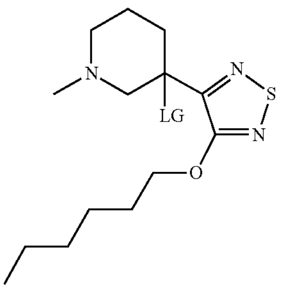

or

-continued

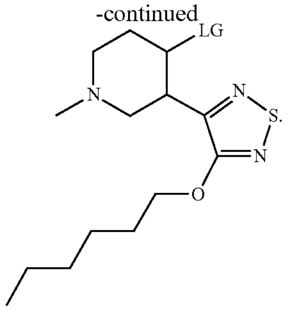

14. The compound of embodiment 13, wherein LG is selected from halo, —OH, and —OAc.

15. The compound of embodiment 1, wherein the compound has the formula:

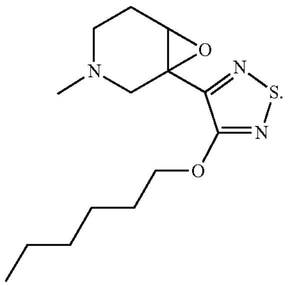 [SMILES: CCCCCCOc1nsnc1C12CN(C)CCC1O2]

16. The compound of embodiment 13, having the formula:

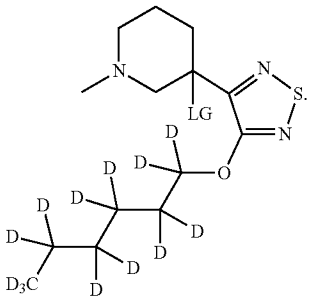

LG = Cl, Br, I, OH, OMe, OAc

17. The compound of embodiment 13, having the formula:

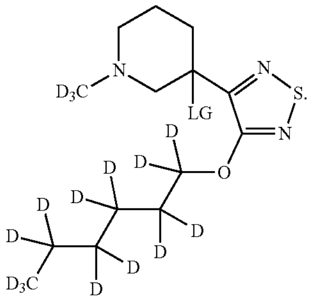

LG = Cl, Br, I, OH, OMe, OAc

18. The compound of embodiment 13, having the formula

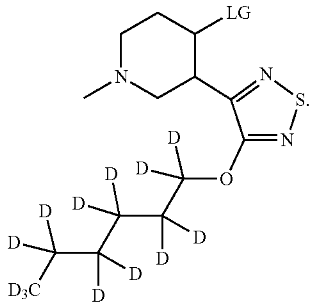

LG = Cl, Br, I, OH, OMe, OAc

19. The compound of embodiment 13, having the formula

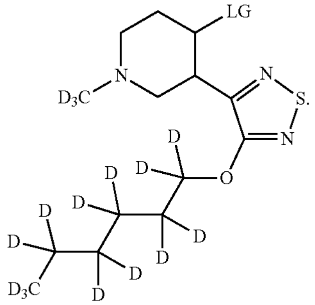

LG = Cl, Br, I, OH, OMe, OAc

20. The compound of embodiment 1, wherein the compound has the formula:

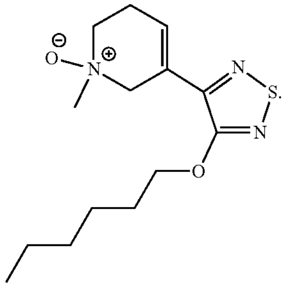 [SMILES: CCCCCCOc1nsnc1C1=CCC[N+](C)([O-])C1]

21. The compound of embodiment 20, having the formula

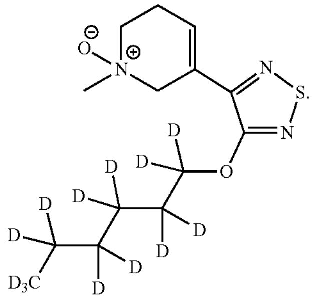 [SMILES: [2H]C([2H])([2H])C([2H])([2H])C([2H])([2H])C([2H])([2H])C([2H])([2H])C([2H])([2H])Oc1nsnc1C1=CCC[N+](C)([O-])C1]

22. The compound of embodiment 20, having the formula

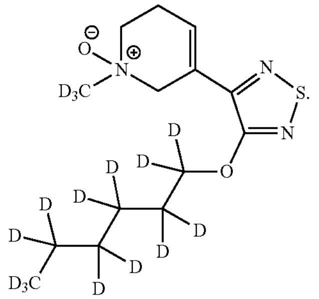 [SMILES: [2H]C([2H])([2H])C([2H])([2H])C([2H])([2H])C([2H])([2H])C([2H])([2H])C([2H])([2H])Oc1nsnc1C1=CCC[N+]([O-])(C([2H])([2H])[2H])C1]

23. A compound selected from the listing of compounds in Table 1.

24. A pharmaceutical composition, comprising a compound according to any one of embodiments 1-23, and a pharmaceutically acceptable carrier.

25. A method for treating a neuropsychiatric disorder in a subject in need thereof, comprising administering a compound of any one of embodiments 1-23, or the pharmaceutical composition of embodiment 224 to the subject.

A1. A compound according to the following formula:

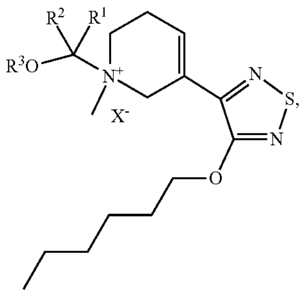

wherein:

$R^1$ and $R^2$ are independently selected from hydrogen and $C_{1-6}$ alkyl;

$R^3$ is —C(O)$R^5$;

$R^5$ is $C_{1-14}$ alkyl; and $X^-$ is a pharmaceutically acceptable counterion.

A2. The compound of embodiment A1, wherein $R^1$ is H.

A3. The compound of embodiment A1, wherein $R^2$ is $C_{1-2}$ alkyl

A4. The compound of embodiment A1, wherein $R^1$ is H, and $R^2$ is $C_{1-2}$ alkyl A5. The compound of embodiment A1, wherein $R^1$ is H and $R^2$ is H.

A6. The compound of embodiment A1, wherein $R^5$ is $C_{1-4}$ alkyl.

A7. The compound of embodiment A1, wherein $R^5$ is $C_{4-12}$ alkyl.

A8. The compound of embodiment A1, wherein $R^5$ is $C_4$ alkyl.

A9. The compound of embodiment A1, wherein $R^5$ is $C_7$ alkyl.

A10. The compound of embodiment A1, wherein $R^5$ is $C_{12}$ alkyl. A10. The compound of embodiment A1, wherein $R^1$ is H, and $R^5$ is $C_4$ alkyl.

A11. The compound of embodiment A1, wherein $R^2$ is $C_1$-2 alkyl, and $R^5$ is $C_4$ alkyl A12. The compound of embodiment A1, wherein $R^1$ is H, $R^2$ is H, and $R^5$ is $C_7$ alkyl or $C_{12}$ alkyl.

A13. The compound of embodiment A1, wherein $R^1$ is H, $R^2$ is $C_{1-2}$ alkyl, and $R^5$ is $C_4$ alkyl.

A14. The compound of embodiment A1, wherein the compound is selected from

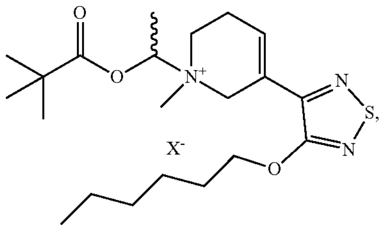

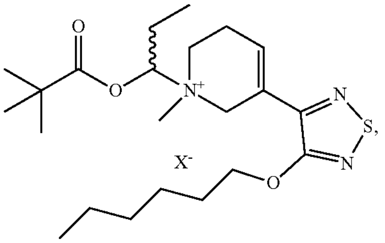

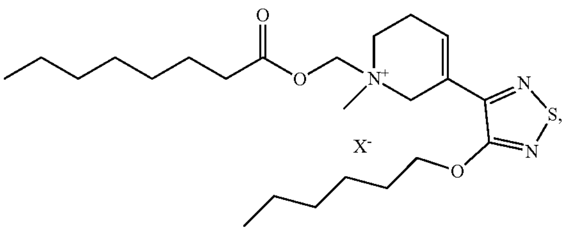

or

-continued

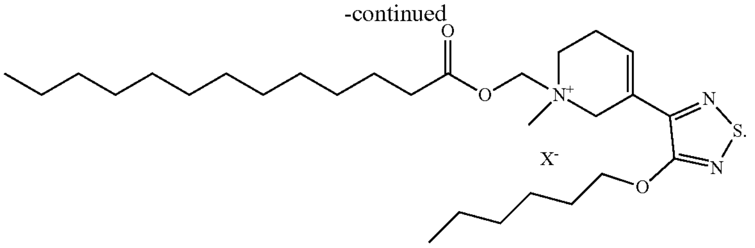

A15. A pharmaceutical composition comprising a compound of embodiment A14 and a pharmaceutically acceptable excipient.

A16. A method for treating a neuropsychiatric disease, comprising administering an effective amount of a compound of embodiment A14.

A17. A method for treating a neuropsychiatric disease, comprising administering an effective amount of the pharmaceutical composition of embodiment A14.

A18. The compound of embodiment A1, wherein the compound is selected from any one of the following:

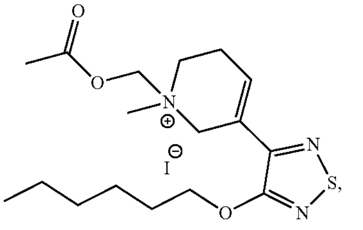

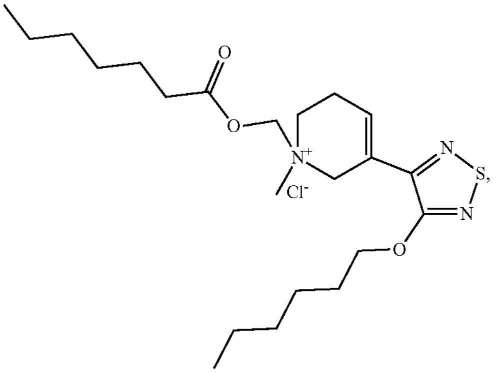

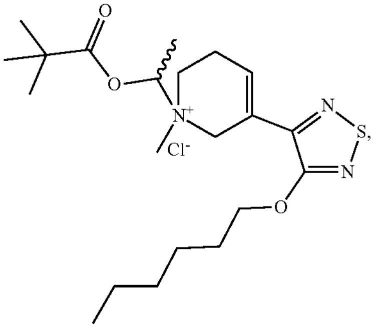

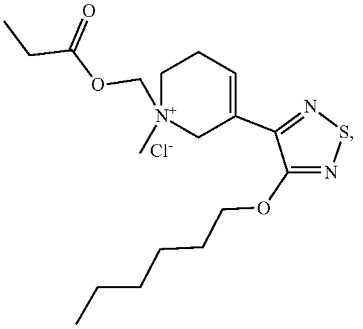

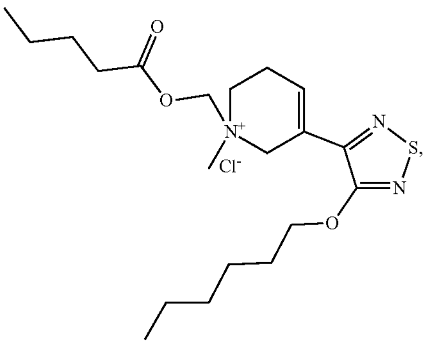

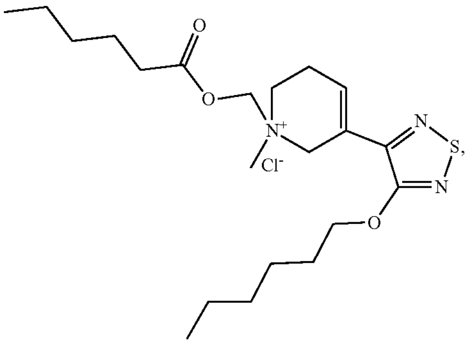

-continued
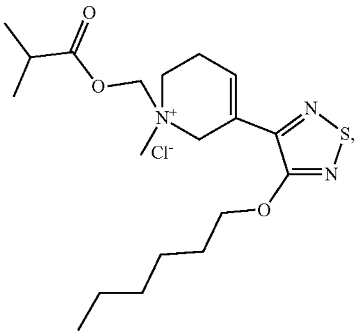
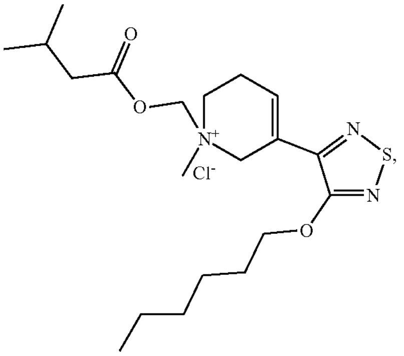
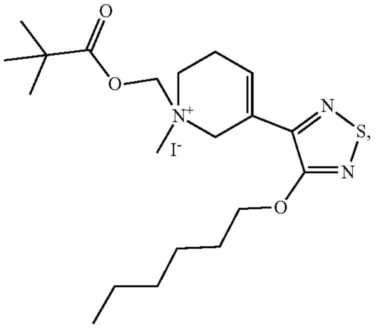
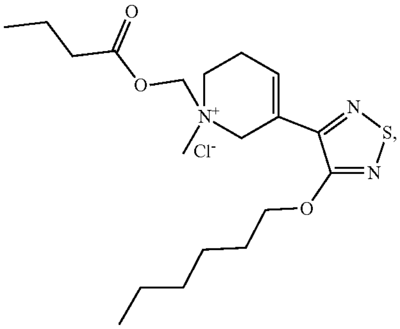
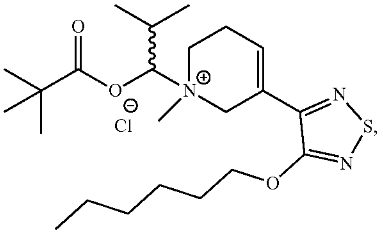
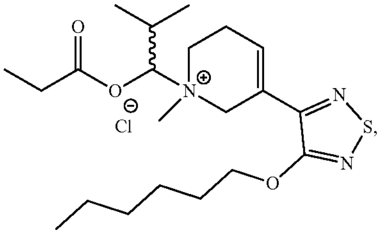
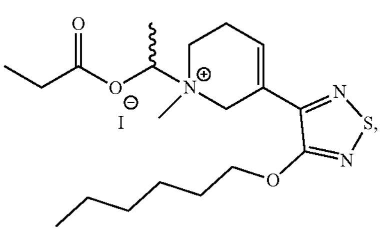
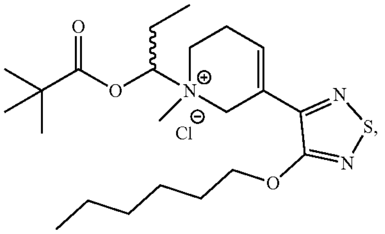
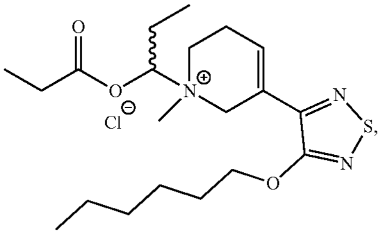
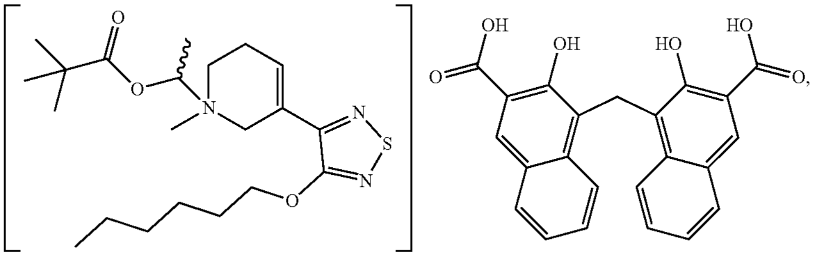

-continued

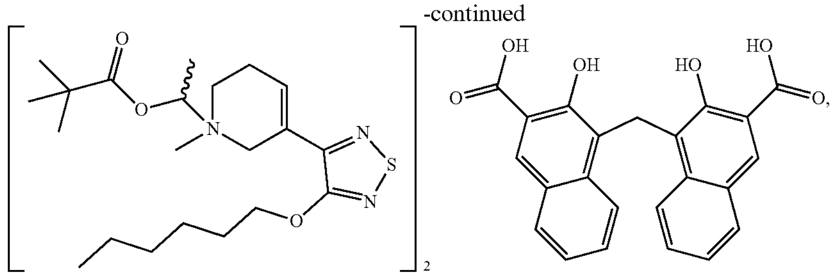

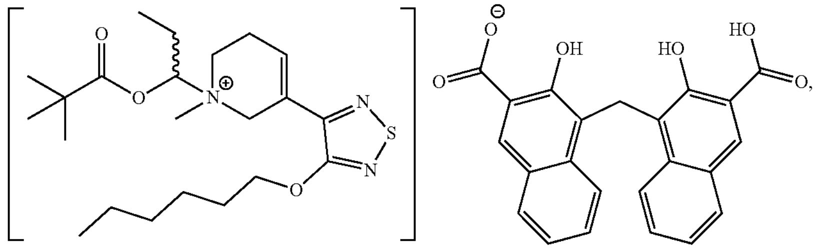

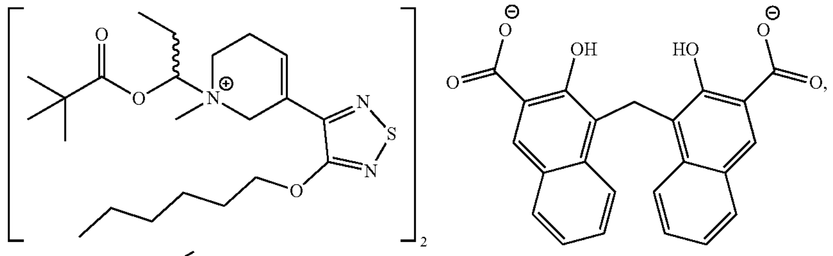

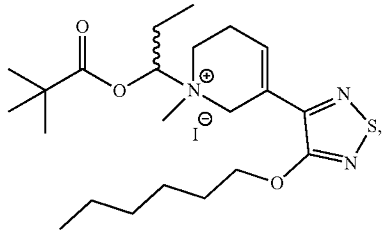

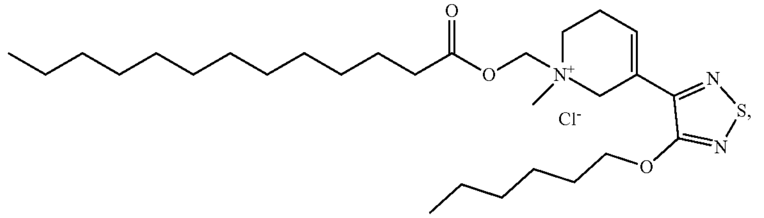

or

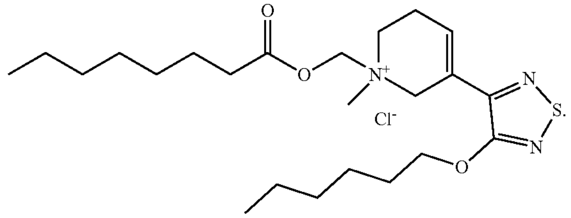

A19. A pharmaceutical composition comprising a compound of embodiment A18 and a pharmaceutically acceptable excipient.

A20. A method for treating a neuropsychiatric disease, comprising administering an effective amount of a compound of embodiment A18.

A21. A method for treating a neuropsychiatric disease, comprising administering an effective amount of the pharmaceutical composition of embodiment A19.

A22. The compound of embodiment A18, wherein the compound is

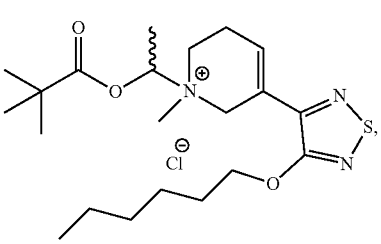,

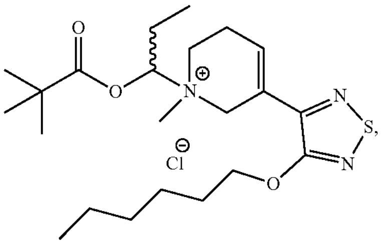,

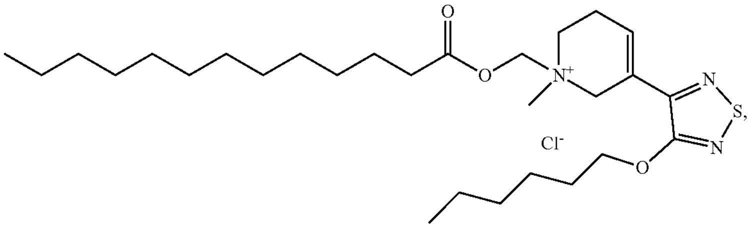, or

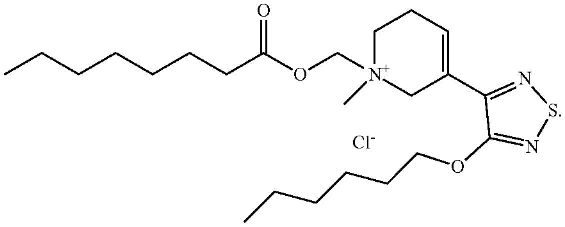.

A23. A pharmaceutical composition comprising a compound of embodiment A22 and a pharmaceutically acceptable excipient.

A24. A method for treating a neuropsychiatric disease, comprising administering an effective amount of a compound of embodiment A22.

A25. A method for treating a neuropsychiatric disease, comprising administering an effective amount of the pharmaceutical composition of embodiment A23.

A26. The compound of embodiment A18, wherein the compound is

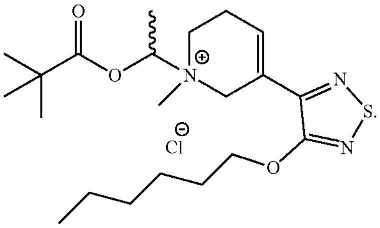 [SMILES: CCCCCCOc1nsnc1C1=CCC[N+](C)(C(C)OC(=O)C(C)(C)C)C1 ; [Cl-]].

A27. A pharmaceutical composition comprising a compound of embodiment A26 and a pharmaceutically acceptable excipient.

A28. A method for treating a neuropsychiatric disease, comprising administering an effective amount of a compound of embodiment A26.

A29. A method for treating a neuropsychiatric disease, comprising administering an effective amount of the pharmaceutical composition of embodiment A27.

A30. The compound of embodiment A18, wherein the compound is:

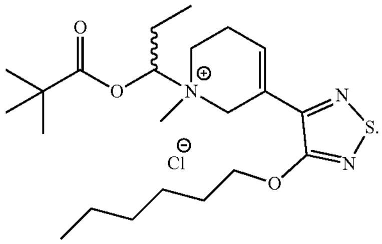 [SMILES: CCCCCCOc1nsnc1C1=CCC[N+](C)(C(CC)OC(=O)C(C)(C)C)C1 ; [Cl-]].

A31. A pharmaceutical composition comprising a compound of embodiment A30 and a pharmaceutically acceptable excipient.

A32. A method for treating a neuropsychiatric disease, comprising administering an effective amount of a compound of embodiment A30.

A33. A method for treating a neuropsychiatric disease, comprising administering an effective amount of the pharmaceutical composition of embodiment A31.

A34. The compound of embodiment A14, wherein the compound is:

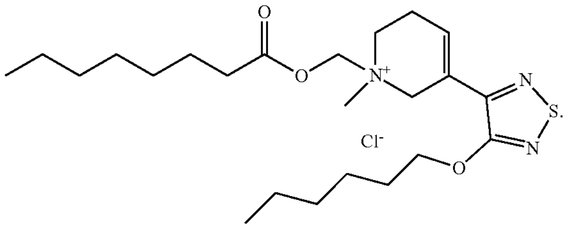 [SMILES: CCCCCCCC(=O)OC[N+]1(C)CCC=C(c2nsnc2OCCCCCC)C1 ; [Cl-]].

A35. A pharmaceutical composition comprising a compound of embodiment A34 and a pharmaceutically acceptable excipient.

A36. A method for treating a neuropsychiatric disease, comprising administering an effective amount of a compound of embodiment A34.

A37. A method for treating a neuropsychiatric disease, comprising administering an effective amount of the pharmaceutical composition of embodiment A35.

A38. The compound of embodiment A14, wherein the compound is:

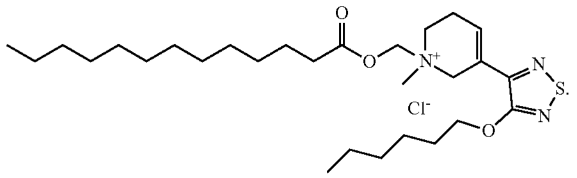 [SMILES: CCCCCCCCCCCCC(=O)OC[N+]1(C)CCC=C(c2nsnc2OCCCCCC)C1 ; [Cl-]]

A39. A pharmaceutical composition comprising a compound of embodiment A38 and a pharmaceutically acceptable excipient.

A40. A method for treating a neuropsychiatric disease, comprising administering an effective amount of a compound of embodiment A38.

A41. A method for treating a neuropsychiatric disease, comprising administering an effective amount of the pharmaceutical composition of embodiment A39.

EXAMPLES

Exemplary compounds disclosed herein are prepared from the isotopically enriched building blocks analogous to those used to synthesize the unenriched compounds.

A. Chemical Synthesis

General Method for the Preparation of Chloromethyl Esters

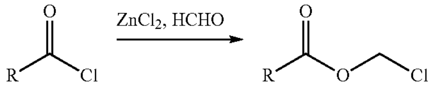

A mixture of acid chloride (1 equiv.), paraformaldehyde (1 equiv.) and $ZnCl_2$ (0.02 equiv.) was heated to 95° C. (oil bath temperature) and stirred for 6 h. The mixture was filtered hot and purified with a plug of silica gel eluting with hexane to give the desired compound.

Preparation of Chloromethyl Propanoate

Undertaken on a 16.6 mmol scale to give the product (1.70 g, 84%) as an oil. $^1$H NMR (400 MHz, $CDCl_3$) δ 5.71 (s, 2H), 2.42 (q, J=7.5 Hz, 2H), 1.18 (t, J=7.5 Hz, 3H).

Preparation of Chloromethyl Pentanoate

Undertaken on a 16.6 mmol scale to give the product (1.47 g, 59%) as an oil. $^1$H NMR (400 MHz, $CDCl_3$) δ 5.70 (s, 2H), 2.42-2.36 (m, 2H), 1.73-1.57 (m, 2H), 1.47-1.28 (m, 2H), 0.93 (t, J=7.3 Hz, 3H).

Preparation of Chloromethyl Hexanoate

Undertaken on a 14.9 mmol scale to give the product (1.80 g, 73%) as an oil. $^1$H NMR (400 MHz, $CDCl_3$) δ 5.70 (s, 2H), 2.38 (t, J=7.5 Hz, 2H), 1.72-1.57 (m, 2H), 1.37-1.29 (m, 4H), 0.94-0.83 (m, 3H).

Preparation of Chloromethyl Heptanoate

Undertaken on a 13.5 mmol scale to give the product (1.43 g, 60%) as an oil. $^1$H NMR (400 MHz, $CDCl_3$) δ 5.70 (s, 2H), 2.46-2.29 (m, 2H), 1.65 (dq, J=8.2, 7.3 Hz, 2H), 1.48-1.20 (m, 6H), 0.97-0.81 (m, 3H).

Preparation of Chloromethyl Octanoate

Undertaken on a 12.3 mmol scale to give the product (1.61 g, 68%) as an oil. $^1$H NMR (400 MHz, $CDCl_3$) δ 5.70 (s, 2H), 2.38 (t, J=7.6 Hz, 2H), 1.65 (p, J=7.6 Hz, 2H), 1.27-1.32 (m, 8H), 0.86-0.90 (m, 3H).

Preparation of Chloromethyl Nonanoate

Undertaken on a 11.3 mmol scale to give the product (1.51 g, 65%) as an oil. $^1$H NMR (400 MHz, $CDCl_3$) δ 5.70 (s, 2H), 2.38 (t, J=7.6 Hz, 2H), 1.65 (p, J=7.2 Hz, 2H), 1.30-1.27 (m, 10H), 0.88 (t, J=7.6 Hz, 3H).

Preparation of Chloromethyl Decanoate

Undertaken on a 10.5 mmol to give the product (1.36 g, 59%) as a solid. $^1$H NMR (400 MHz, $CDCl_3$) δ 5.70 (s, 2H), 2.38 (t, J=7.2 Hz, 2H), 1.69-1.61 (m, 2H), 1.40-1.18 (m, 12H), 0.88 (t, J=6.8 Hz, 3H).

Preparation of Chloromethyl Undecanoate

Undertaken on a 4.88 mmol scale to give the product (636 mg, 55%) as an oil. $^1$H NMR (400 MHz, $CDCl_3$) δ 5.70 (s, 2H), 2.38 (t, J=7.6 Hz, 2H), 1.65 (p, J=7.6 Hz, 2H), 1.26 (s, 14H), 0.88 (t, J=7.2 Hz, 3H).

Preparation of Chloromethyl Dodecanate

Undertaken on a 9.1 mmol scale to give the product (1.21 g, 54%) as an oil. $^1$H NMR (400 MHz, $CDCl_3$) δ 5.70 (s, 2H), 2.38 (t, J=7.5 Hz, 2H), 1.65 (p, J=7.5 Hz, 2H), 1.36-1.17 (m, 16H), 0.95-0.80 (m, 3H).

Preparation of Iodomethyl Dodecanate

A mixture of chloromethyl dodecanate (1.219 g, 4.90 mmol) and NaI (2.20 g, 14.7 mmol) in MeCN (10 mL) at rt was stirred in the dark for 18 h. The mixture was diluted with $H_2O$ (40 mL) and extracted with DCM (2×30 mL). The combined organic layers were washed with brine (30 mL), dried ($MgSO_4$), filtered and the filtrate was concentrated in vacuo to give the product (1.36 g) contaminated with 25% of the starting material. The product was again stirred with NaI (2.57 g, 17.1 mmol) in MeCN (7 mL) at the rt in the dark for 116 h. The mixture was diluted with $H_2O$ (40 mL) and extracted with DCM (2×30 mL). The combined organic layers were washed with brine (30 mL), dried ($MgSO_4$), filtered and the filtrate was concentrated in vacuo to give the product (1.29 g, 77%) as a solid. $^1$H NMR (400 MHz, $CDCl_3$) δ 5.91 (s, 2H), 2.32 (t, J=7.5 Hz, 2H), 1.63 (p, J=7.4 Hz, 2H), 1.28 (d, J=13.3 Hz, 16H), 0.97-0.80 (m, 3H).

Preparation of Chloromethyl Tridecanoate

Undertaken on an 8.81 mmol scale to give the product (1.28 g, 55%) as a solid. $^1$H NMR (400 MHz, $CDCl_3$) δ 5.70 (s, 2H), 2.38 (t, J=7.5 Hz, 2H), 1.65 (p, J=7.5 Hz, 2H), 1.36-1.21 (m, 18H), 0.91-0.84 (m, 3H).

Preparation of Chloromethyl Tetradecanoate

Undertaken on a 13.4 mmol scale to give the product (1.67 g, 45%) as a solid. $^1$H NMR (400 MHz, $CDCl_3$) δ 5.70 (s, 2H), 2.38 (t, J=7.5 Hz, 2H), 1.64 (h, J=7.5 Hz, 2H), 1.37-1.10 (m, 20H), 0.92-0.85 (m, 3H).

Preparation of Chloromethyl Pentadecanoate

Undertaken on a 9.25 mmol scale. Purified by column chromatography on silica gel (0 to 25% EtOAc in hexane) to give the product (1.24 g, 46%) as a solid. $^1$H NMR (400 MHz, $CDCl_3$) δ 5.70 (s, 2H), 2.38 (t, J=7.5 Hz, 2H), 1.65 (p, J=7.5 Hz, 2H), 1.36-1.15 (m, 22H), 0.90-0.86 (m, 3H).

Preparation of Chloromethyl Hexadecanoate

Undertaken on a 7.64 mmol scale to give the product (1.30 g, 56%) as a solid. $^1$H NMR (400 MHz, $CDCl_3$) δ 5.70 (s, 2H), 2.38 (t, J=7.5 Hz, 2H), 1.65 (p, J=7.5 Hz, 2H), 1.26 (s, 24H), 0.94-0.78 (m, 3H).

General Method of Preparation of Chloromethyl Carbonates

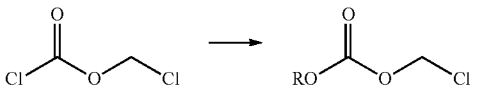

To a stirred mixture of chloromethyl chloroformate (10.5 mmol) in DCM (40 mL) at 0° C. was added a mixture of the alcohol (10.5 mmol) and pyridine (0.89 mL, 11 mmol) in DCM (11 mL) dropwise over 30 min. The mixture was warmed to rt and stirred for 20 h, then washed with 0.5 M HCl (20 mL), $H_2O$ (20 mL), saturated sodium bicarbonate solution (20 mL) and brine (20 mL). The organics were dried ($Na_2SO_4$), filtered and the filtrate was concentrated in vacuo to give the product.

Preparation of Chloromethyl Propyl Carbonate

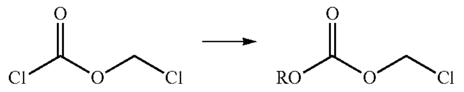

Undertaken on 25 mmol scale to give the product (1.1 g, 29%) as an oil. $^1H$ NMR (400 MHz, $CDCl_3$) δ 5.73 (s, 2H), 4.19 (q, J=6.8 Hz, 1H), 1.77-1.68 (p, J=6.8 Hz, 2H), 0.97 (t, J=7.6 Hz, 3H).

Preparation of Butyl Chloromethyl Carbonate

Undertaken on a 20.2 mmol scale to give the product (2.83 g, 89%) as an oil. $^1H$ NMR (400 MHz, $CDCl_3$) δ 5.73 (s, 2H), 4.23 (q, J=6.4 Hz, 1H), 1.72-1.65 (m, 2H), 1.46-1.38 (m, 2H), 0.95 (t, J=7.6 Hz, 3H).

Preparation of Chloromethyl Pentyl Carbonate

Undertaken on a 13.9 mmol scale to give the product (1.97 g, 79%) as an oil. $^1H$ NMR (400 MHz, $CDCl_3$) δ 5.73 (s, 2H), 4.22 (t, J=6.7 Hz, 2H), 1.80-1.63 (m, 2H), 1.36 (tt, J=9.1, 3.7 Hz, 4H), 1.00-0.83 (m, 3H).

Preparation of Chloromethyl Hexyl Carbonate

Undertaken on a 23.5 mmol scale to give the product (3.23 g, 85%) as an oil. $^1H$ NMR (400 MHz, $CDCl_3$) δ 5.72 (s, 2H), 4.22 (q, J=6.8 Hz, 1H), 1.73-1.66 (m, 2H), 1.41-1.27 (m, 7H), 0.91-0.87 (t, J=7.2 Hz, 3H).

Preparation of Chloromethyl Heptyl Carbonate

Undertaken on a 20.7 mmol scale to give the product (3.35 g, 93%) as an oil. $^1H$ NMR (400 MHz, $CDCl_3$) δ 5.73 (s, 2H), 4.22 (q, J=6.8 Hz, 1H), 1.73-1.66 (m, 2H), 1.41-1.24 (m, 8H), 0.90-0.88 (m, 3H).

Preparation of Chloromethyl Octyl Carbonate

Undertaken on a 11.5 mmol scale to give the product (2.32 g, 90%) as an oil. $^1H$ NMR (400 MHz, $CDCl_3$) δ 5.73 (s, 2H), 4.22 (q, J=6.8 Hz, 1H), 1.73-1.65 (m, 2H), 1.37-1.27 (m, 10H), 0.87 (t, J=6.8 Hz, 3H).

Preparation of Chloromethyl Nonyl Carbonate

Undertaken on a 10.5 mmol scale to give the product (2.26 g, 91%) as an oil. $^1H$ NMR (400 MHz, $CDCl_3$) δ 5.73 (s, 2H), 4.22 (t, J=6.7 Hz, 2H), 1.69 (dq, J=8.2, 6.7 Hz, 2H), 1.45-1.16 (m, 12H), 0.96-0.80 (m, 3H).

Preparation of Chloromethyl Decyl Carbonate

Purified by column chromatography on silica gel (0 to 3% EtOAc in hexane) to give the product (685 mg, 26%) as an oil. $^1H$ NMR (400 MHz, $CDCl_3$) δ 5.73 (s, 2H), 4.22 (t, J=6.7 Hz, 2H), 1.69 (dq, J=8.2, 6.7 Hz, 2H), 1.44-1.16 (m, 14H), 0.96-0.80 (m, 3H).

Preparation of Chloromethyl Undecyl Carbonate

Undertaken on a 11.5 mmol scale to give the product (1.76 g, 76%) as an oil. $^1H$ NMR (400 MHz, $CDCl_3$) δ 5.73 (s, 2H), 4.22 (q, J=6.4 Hz, 2H), 1.73-1.65 (m, 2H), 1.46-1.22 (m, 16H), 0.88 (t, J=6.8 Hz, 3H).

Preparation of Chloromethyl Dodecyl Carbonate

Undertaken on an 8.5 mmol scale to give the product (1.12 g, 50%) as an oil. $^1H$ NMR (400 MHz, $CDCl_3$) δ 5.73 (s, 2H), 4.22 (t, J=6.4 Hz, 2H), 1.73-1.65 (m, 2H), 1.46-1.22 (m, 18H), 0.88 (t, J=6.8 Hz, 3H).

Preparation of Chloromethyl Tridecyl Carbonate

Undertaken on a 9.98 mmol scale to give the product (2.78 g, 95%) as a solid. $^1H$ NMR (400 MHz, $CDCl_3$) δ 5.73 (s, 2H), 4.22 (t, J=6.7 Hz, 2H), 1.69 (dq, J=8.1, 6.7 Hz, 2H), 1.41-1.18 (m, 20H), 0.93-0.79 (m, 3H).

Preparation of Chloromethyl Tetradecyl Carbonate

Undertaken on a 7.0 mmol scale to give the product (1.77 g, 82%) as an oil. $^1H$ NMR (400 MHz, $CDCl_3$) δ 5.73 (s, 2H), 4.22 (q, J=6.8 Hz, 1H), 1.73-1.64 (m, 2H), 1.48-1.24 (m, 24H), 0.89-0.86 (m, 3H).

Preparation of Chloromethyl Pentadecyl Carbonate

Undertaken on a 6.57 mmol scale to give the product (1.96 g, 93%) as an oil. $^1H$ NMR (400 MHz, $CDCl_3$) δ 5.73 (s, 2H), 4.22 (q, J=6.8 Hz, 1H), 1.73-1.66 (m, 2H), 1.42-1.24 (m, 25H), 0.90-0.88 (m, 3H).

Preparation of Tert-Butyl Chloromethyl Carbonate

Undertaken on a 10.8 mmol scale to give the product (1.11 g, 26%) as an oil. $^1H$ NMR (400 MHz, $CDCl_3$) δ 5.69 (s, 2H), 1.52 (s, 9H).

Preparation of Chloromethyl Propan-2-Yl Carbonate

Undertaken on a 10.5 mmol scale to give the product (1.03 g, 64%) as an oil. $^1H$ NMR (400 MHz, $CDCl_3$) δ 5.72 (s, 2H), 4.96 (hept, J=6.3 Hz, 1H), 1.34 (d, J=6.3 Hz, 6H).

Preparation of Chloromethyl Isobutyl Carbonate

Undertaken on a 13.5 mmol to give the product (2.41 g, 72%) as an oil. $^1H$ NMR (400 MHz, $CDCl_3$) δ 5.73 (s, 2H), 4.01 (d, J=6.8 Hz, 2H), 2.06-1.1.96 (m, 1H), 0.96 (t, J=6.4 Hz, 6H).

General Method for the Synthesis of Acyloxymethyl Final Compounds (Unless Otherwise Stated)

To a stirred solution of 3-hexyloxy-4-(1-methyl-3,6-dihydro-2H-pyridin-5-yl)-1,2,5-thiadiazole [xanomeline] (0.36 mmol) in MeCN (1.5 mL) at rt was added the chloromethyl ester (0.71 mmol) in one portion. The reaction mixture was stirred at rt for 85 h, then concentrated in vacuo and the crude product was triturated with $Et_2O$. The precipitate was filtered, rinsed with a mixture of $Et_2O$/hexane (1:1) to give the product.

Example 1: Preparation of [5-(4-hexyloxy-1,2,5-thiadiazol-3-yl)-1-methyl-3,6-dihydro-2H-pyridin-1-ium-1-yl]methyl acetate iodide [Xanomeline methyl acetate iodide prodrug]

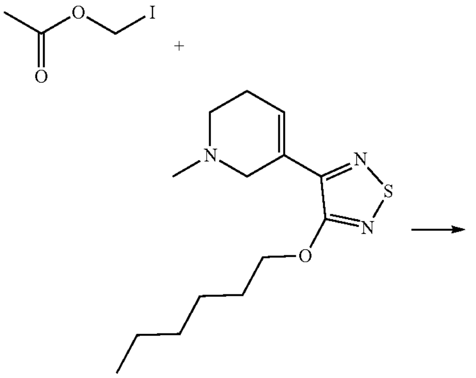

-continued

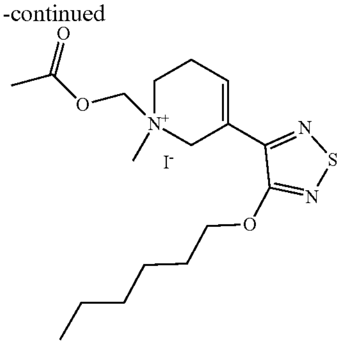

To a stirred solution of 3-hexyloxy-4-(1-methyl-3,6-dihydro-2H-pyridin-5-yl)-1,2,5-thiadiazole [xanomeline] (110 mg, 0.39 mmol) in MeCN (2 mL) at rt was added iodomethyl acetate (117 mg, 0.59 mmol) in one portion. The mixture was stirred at rt for 24 h, then concentrated in vacuo and the crude product was purified by preparative HPLC (eluent: 10% to 100% MeCN in $H_2O$ gradient) to afford the title compound (37 mg, 19%) as a solid. Retention time: 1.479 min; m/z=[M]+ calculated for $C_{17}H_{28}N_3O_3S$ 354.2; found 354.2; $^1H$ NMR (400 MHz, $CD_3OD$) δ 7.32 (tt,J=4.0, 1.7 Hz, 1H), 5.53-5.35 (m, 2H), 4.57 (q, J=2.2 Hz, 1H), 4.53 (t, J=6.6 Hz, 3H), 3.76-3.64 (m, 2H), 3.24 (s, 3H), 2.93-2.78 (m, 2H), 2.29 (s, 3H), 1.96-1.80 (m, 2H), 1.58-1.45 (m, 2H), 1.44-1.30 (m, 4H), 1.00-0.87 (m, 3H).

Example 2: Preparation of 1-methyl-5-[4-(hexyloxy)-1,2,5-thiadiazol-3-yl]-1-[(propanoyloxy)methyl]-1,2,3,6-tetrahydropyridin-1-ium chloride [Xanomeline methyl propionate chloride prodrug]

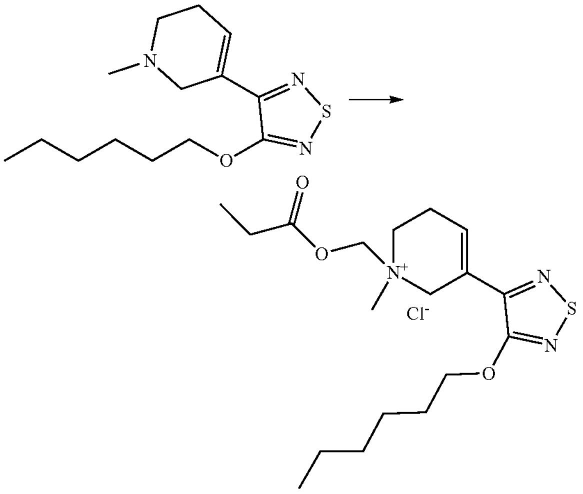

To a solution of xanomeline (130 mg, 0.462 mmol) in MeCN (3 mL) was added chloromethyl propionate (170 mg, 1.39 mmol) dropwise. The reaction mixture was stirred at 40° C. for 15h. The mixture was evaporated to dryness and the residue was triturated with $Et_2O$ and filtered to give the product as a solid. Both LCMS and NMR shows small impurities. Retention time: 1.43 min; m/z=$[M]^+$ calculated for $C_{18}H_{30}N_3O_3S$ 368.2; found 368; $^1H$ NMR (400 MHz, $CDCl_3$) δ 7.24 (s, 1H), 6.06-5.96 (m, 2H), 4.72-4.60 (m, 2H), 4.98-4.44 (m, 3H), 4.24-4.15 (m, 1H), 3.59 (s, 3H), 2.87 (bs, 2H), 2.60-2.53 (m, 2H), 1.88-1.81 (m, 2H), 1.47-1.34 (m, 6H), 1.22-1.18 (m, 3H), 0.95-0.93 (m, 3H).

Example 3: Preparation of [5-(4-hexyloxy-1,2,5-thiadiazol-3-yl)-1-methyl-3,6-dihydro-2H-pyridin-1-ium-1-yl]methyl butanoate chloride [Xanomeline methyl butanoate chloride prodrug] (Table 1 Compound 3)

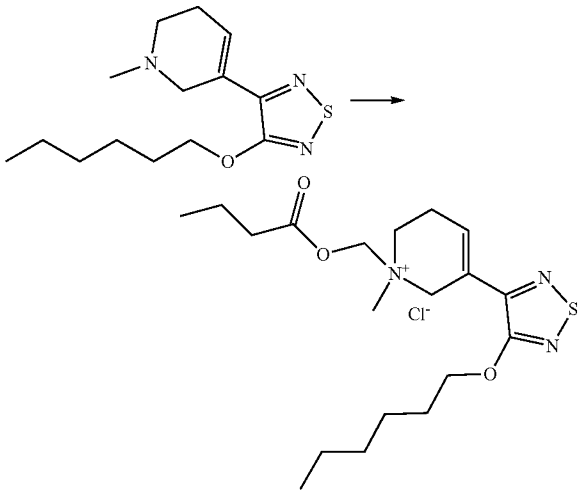

To a stirred solution of 3-hexyloxy-4-(1-methyl-3,6-dihydro-2H-pyridin-5-yl)-1,2,5-thiadiazole [xanomeline] (100 mg, 0.355 mmol) in MeCN (1 mL) was added chloromethyl butanoate (90 μL, 0.71 mmol) in one portion. The mixture was stirred at rt for 48 h, then concentrated in vacuo. The crude product was purified by reverse phase HPLC (eluent: 10-100% MeCN in $H_2O$) to afford the title compound (38 mg, 25%) as a solid. Retention time: 1.591 min; $^1H$ NMR (400 MHz, $CDCl_3$) δ 7.31-7.19 (m, 1H), 6.02 (d, J=8.5 Hz, 1H), 5.91 (d, J=8.5 Hz, 1H), 4.61-4.42 (m, 5H), 4.11 (dt, J=13.0, 6.9 Hz, 1H), 3.55 (s, 3H), 2.87 (s, 2H), 2.51 (t, J=7.4 Hz, 2H), 1.93-1.57 (m, 4H), 1.52-1.30 (m, 6H), 1.06-0.86 (m, 6H).

Example 4: Preparation of [5-(4-hexyloxy-1,2,5-thiadiazol-3-yl)-1-methyl-3,6-dihydro-2H-pyridin-1-ium-1-yl]methyl pentanoate chloride [Xanomeline methyl pentanoate chloride prodrug] (Table 1 Compound 4)

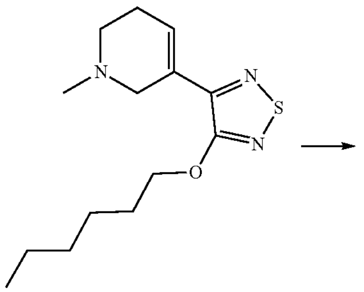

-continued

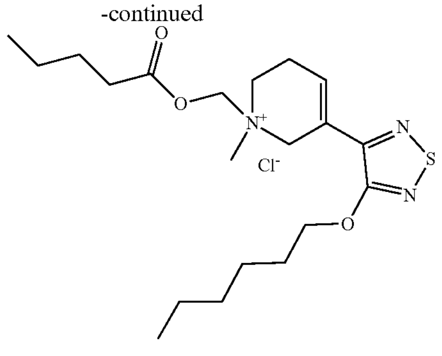

Reaction performed on 0.533 mmol of xanomeline. Purified by gradient column chromatography (0 to 15% MeOH in DCM) to give the product (133 mg, 58%) as a solid. Retention time 3.327 min; m/z=$[M]^+$ calculated for $C_{20}H_{34}N_3O_3S$ 396.2; Found 396.2; $^1H$ NMR (400 MHz, $CDCl_3$) δ 7.26-7.21 (m, 1H), 6.08-5.89 (m, 2H), 4.70-4.54 (m, 2H), 4.47 (t, J=6.8 Hz, 3H), 4.16 (dt, J=13.0, 6.7 Hz, 1H), 3.58 (s, 3H), 2.87 (s, 2H), 2.59-2.45 (m, 2H), 1.85 (dq, J=8.4, 6.8 Hz, 2H), 1.74-1.57 (m, 2H), 1.52-1.29 (m, 8H), 1.01-0.85 (m, 6H).

Example 5: Preparation of 1-[(hexanoyloxy)methyl]-1-methyl-5-[4-(hexyloxy-1,2,5-thiadiazol-3-yl)]-1,2,3,6-tetrahydropyridin-1-ium chloride aka [5-(4-hexyloxy-1,2,5-thiadiazol-3-yl)-1-methyl-3,6-dihydro-2H-pyridin-1-ium-1-yl]methyl hexanoate chloride [Xanomeline methyl hexanoate chloride prodrug] (Table 1 Compound 5)

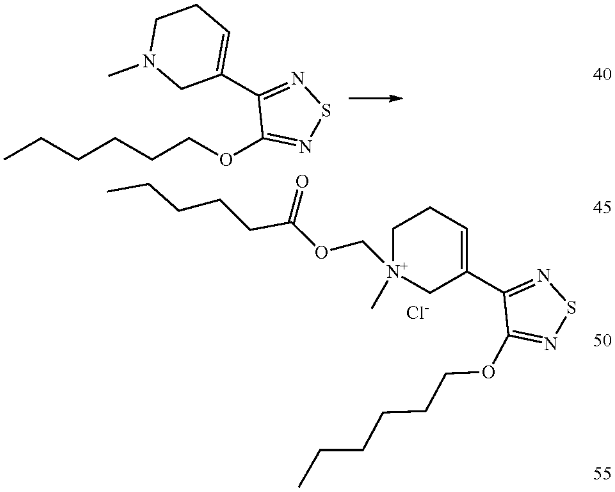

Reaction performed on 0.533 mmol of xanomeline. Purified by gradient column chromatography (0 to 15% MeOH in DCM) to give the product (166 mg, 70%) as a solid. Retention time 3.494 min; m/z=$[M]^+$ calculated for $C_{21}H_{36}N_3O_3S$ 410.2; Found 410.2; $^1H$ NMR (400 MHz, $CDCl_3$) δ 7.24 (td, J=4.0, 1.9 Hz, 1H), 6.08-5.89 (m, 2H), 4.70-4.55 (m, 3H), 4.47 (t, J=6.7 Hz, 2H), 4.16 (dt, J=13.0, 6.8 Hz, 1H), 3.58 (s, 3H), 2.87 (s, 2H), 2.52 (dd, J=7.9, 7.1 Hz, 2H), 1.85 (p, J=6.9 Hz, 2H), 1.75-1.59 (m, 2H), 1.54-1.24 (m, 10H), 0.99-0.84 (m, 6H).

Example 6: Preparation of [5-(4-hexyloxy-1,2,5-thiadiazol-3-yl)-1-methyl-3,6-dihydro-2H-pyridin-1-ium-1-yl]methyl heptanoate chloride [Xanomeline methyl heptanoate chloride prodrug] (Table 1 Compound 6)

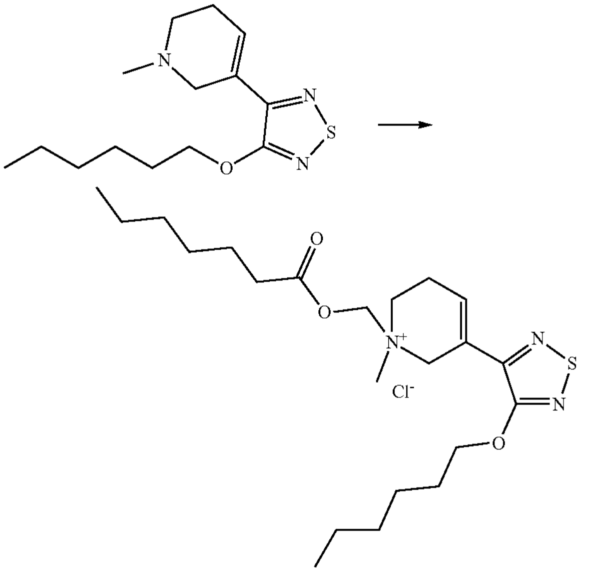

To a stirred solution of 3-hexyloxy-4-(1-methyl-3,6-dihydro-2H-pyridin-5-yl)-1,2,5-thiadiazole (150 mg, 0.53 mmol) in MeCN (2 mL) was added chloromethyl heptanoate (238 mg, 1.33 mmol) in one portion. The mixture was stirred at rt for 4 days and the precipitate was isolated by filtration and washed with cold MeCN (0.5 mL) to afford the product (79 mg, 32%) as a solid. Retention time: 1.674 min; m/z=$[M]^+$ calculated for $C_{22}H_{38}N_3O_3S$ 424.2; found 424.2; $^1H$ NMR (400 MHz, $CDCl_3$) δ 7.24 (d, J=4.2 Hz, 1H), 6.03 (d, J=8.6 Hz, 1H), 5.91 (d, J=8.6 Hz, 1H), 4.61-4.42 (m, 5H), 4.11 (dt, J=13.2, 6.8 Hz, 1H), 3.55 (s, 3H), 2.86 (s, 2H), 2.52 (t, J=7.5 Hz, 2H), 1.76 (m, 8H), 1.52-1.21 (m, 7H), 1.00-0.79 (m, 7H).

Example 7: Preparation of [5-(4-hexyloxy-1,2,5-thiadiazol-3-yl)-1-methyl-3,6-dihydro-2H-pyridin-1-ium-1-yl]methyl octanoate chloride [Xanomeline methyl octanoate chloride prodrug] (Table 1 Compound 7)

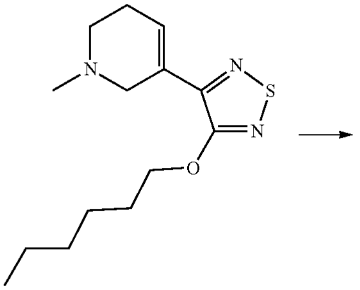

-continued

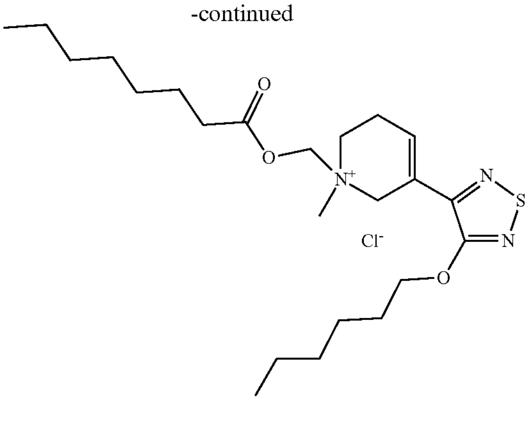

Reaction performed on 0.355 mmol of xanomeline to give the product (48 mg, 29%) as a solid. Retention time: 1.70 min; m/z=[M]$^+$ calculated for $C_{23}H_{40}N_3O_3S$ 438.3; found 438.2; $^1$H NMR (400 MHz, $CDCl_3$) δ 7.24 (br. s, 1H), 6.03 (d, J=8.4 Hz, 1H), 4.58 (br. s, 1H), 4.94-4.44 (m, 4H), 4.17-4.12 (m, 1H), 3.57 (s, 3H), 2.86 (br. s, 2H), 2.51 (t, J=7.2 Hz, 2H), 1.89-1.81 (m, 2H), 1.71-1.62 (m, 3H), 1.46-1.28 (m, 14H), 0.93-0.87 (m, 6H).

Example 8: Preparation of [5-(4-hexyloxy-1,2,5-thiadiazol-3-yl)-1-methyl-3,6-dihydro-2H-pyridin-1-ium-1-yl]methyl nonanoate chloride [Xanomeline methyl nonanoate chloride prodrug] (Table 1 Compound 8)

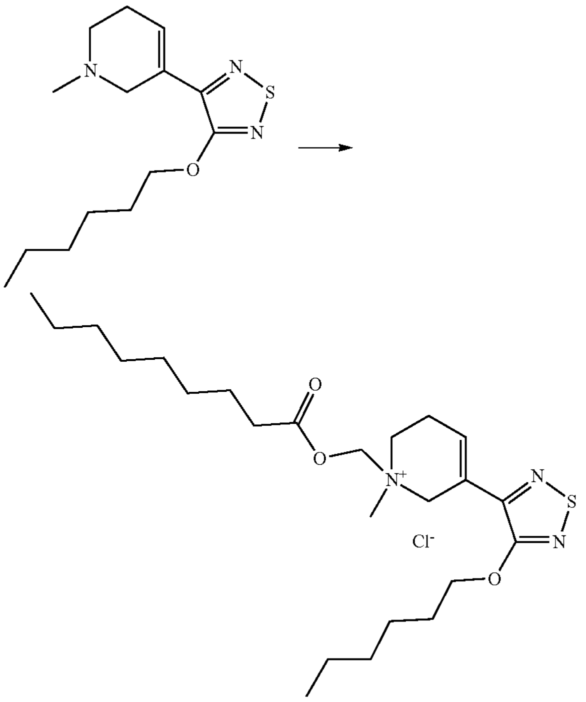

Reaction performed on 0.355 mmol of xanomeline to give the product (64 mg, 37%) as an oil. Retention time 1.74 min; m/z=[M]$^+$ calculated for $C_{24}H_{42}N_3O_3S$ 452.3; found 453.2; $^1$H NMR (400 MHz, $CDCl_3$) δ 7.24 (br. s, 1H), 6.02 (d, J=8.4 Hz, 1H), 5.94 (d, J=8.4 Hz, 1H), 4.64 (br. s, 2H), 4.59-4.45 (m, 3H), 4.18-4.12 (m, 1H), 3.58 (s, 3H), 2.86 (br. s, 2H), 2.51 (t, J=7.2 Hz, 2H), 1.89-1.81 (m, 2H), 1.68-1.62 (m, 2H), 1.46-1.26 (m, 16H), 0.93-0.86 (m, 6H).

Example 9: Preparation of [5-(4-hexyloxy-1,2,5-thiadiazol-3-yl)-1-methyl-3,6-dihydro-2H-pyridin-1-ium-1-yl]methyl decanoate chloride [Xanomeline methyl decanoate chloride prodrug] (Table 1 Compound 9)

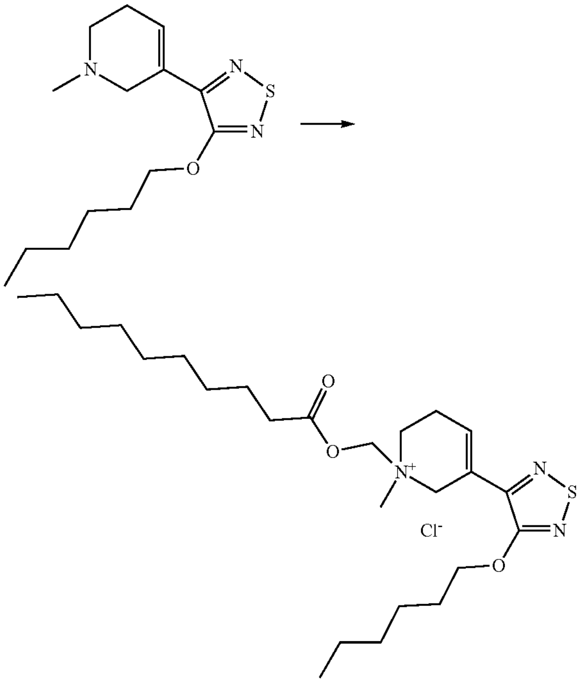

Reaction performed on 0.355 mmol of xanomeline to give the product (102 mg, 57%) as a solid. Retention time 1.79 min; m/z=[M]$^+$ calculated for $C_{25}H_{44}N_3O_3S$ 466.3; found 466.3; $^1$H NMR (400 MHz, $CDCl_3$) δ 7.24 (br. s, 1H), 6.02 (d, J=8.4 Hz, 1H), 5.92 (d, J=8.4 Hz, 1H), 4.57 (br. s, 2H), 4.49-4.46 (m, 3H), 4.17-4.10 (m, 1H), 3.56 (s, 3H), 2.86 (br. s, 2H), 2.51 (t, J=7.2 Hz, 2H), 1.89-1.81 (m, 2H), 1.68-1.62 (m, 2H), 1.46-1.26 (m, 18H), 0.93-0.86 (m, 6H).

Example 10: Preparation of [5-(4-hexyloxy-1,2,5-thiadiazol-3-yl)-1-methyl-3,6-dihydro-2H-pyridin-1-ium-1-yl]methyl undecanoate chloride [Xanomeline methyl undecanoate chloride prodrug] (Table 1 Compound 10)

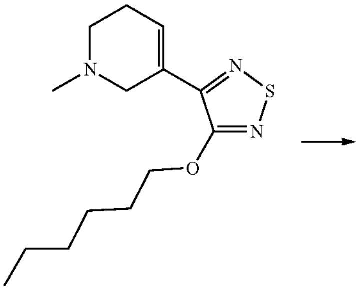

-continued

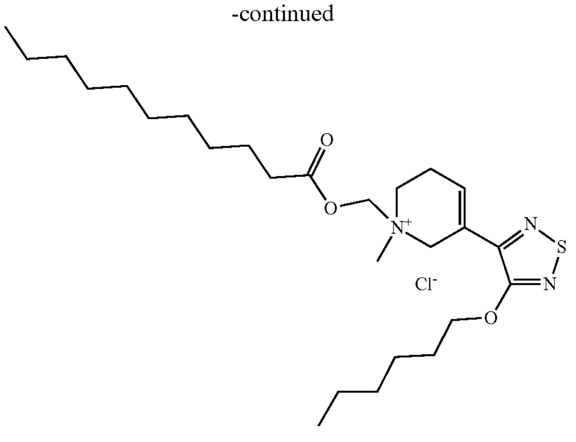

Reaction performed on 0.355 mmol of xanomeline to give the product (103 mg, 56%) as a solid. Retention time 1.84 min; m/z=$[M]^+$ calculated for $C_{26}H_{46}N_3O_3S$ 480.3; found 480.4; $^1H$ NMR (400 MHz, $CDCl_3$) δ 7.24 (br. s, 1H), 6.02 (d, J=8.4 Hz, 1H), 5.93 (d, J=8.4 Hz, 1H), 4.63 (br. s, 1H), 4.59-4.45 (m, 4H), 4.17-4.10 (m, 1H), 3.57 (s, 3H), 2.86 (br. s, 2H), 2.51 (t, J=7.2 Hz, 2H), 1.89-1.81 (m, 2H), 1.68-1.62 (m, 2H), 1.46-1.26 (m, 20H), 0.93-0.86 (m, 6H).

Example 11: Preparation of [5-(4-hexyloxy-1,2,5-thiadiazol-3-yl)-1-methyl-3,6-dihydro-2H-pyridin-1-ium-1-yl]methyl dodecanoate iodide [Xanomeline methyl dodecanoate iodide prodrug] (Table 1 Compound 11)

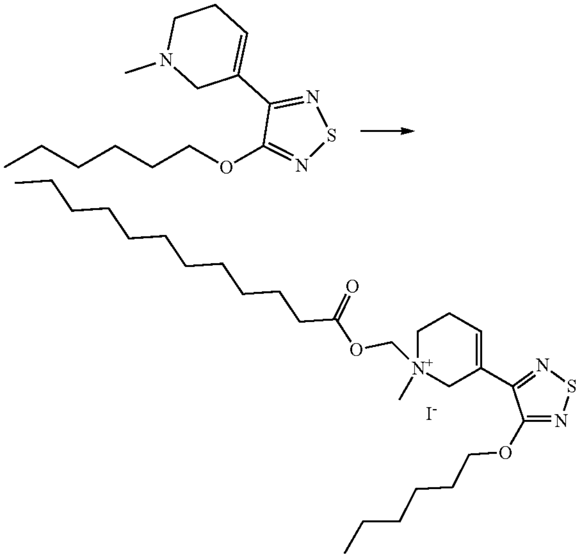

To a stirred mixture of 3-hexyloxy-4-(1-methyl-3,6-dihydro-2H-pyridin-5-yl)-1,2,5-thiadiazole (60 mg, 0.21 mmol) in MeCN (1 mL) was added iodomethyl dodecanoate (145 mg, 0.43 mmol) in one portion. The mixture was stirred at rt for 24 h, then concentrated in vacuo. The crude product was purified by column chromatography on silica gel (eluent: 2-15% MeOH in EtOAc) to afford the title compound (43 mg, 32%) as a viscous oil/semi-solid. Retention time: 1.881 min; m/z=$[M]^+$ calculated for $C_{27}H_{48}N_3O_3S$ 494.3 found 494.3; $^1H$ NMR (400 MHz, $CD_3OD$) δ 7.32 (tt, J=4.0, 1.7 Hz, 1H), 5.51 (d, J=8.8 Hz, 1H), 5.39 (d, J=8.9 Hz, 1H), 4.64-4.42 (m, 4H), 3.69 (td, J=6.4, 2.3 Hz, 2H), 3.23 (s, 3H), 2.93-2.79 (m, 2H), 2.60 (t, J=7.4 Hz, 2H), 1.88 (dq, J=7.9, 6.6 Hz, 2H), 1.69 (p, J=7.4 Hz, 2H), 1.57-1.21 (m, 22H), 1.01-0.81 (m, 6H).

Example 12: Preparation of 1-methyl-5-[4-(hexyloxy)-1,2,5-thiadiazol-3-yl]-1-[(tridecanoyloxy) methyl]-1,2,3,6-tetrahydropyridin-1-ium chloride [Xanomeline methyl decatriaoate chloride prodrug] (Table 1 Compound 12)

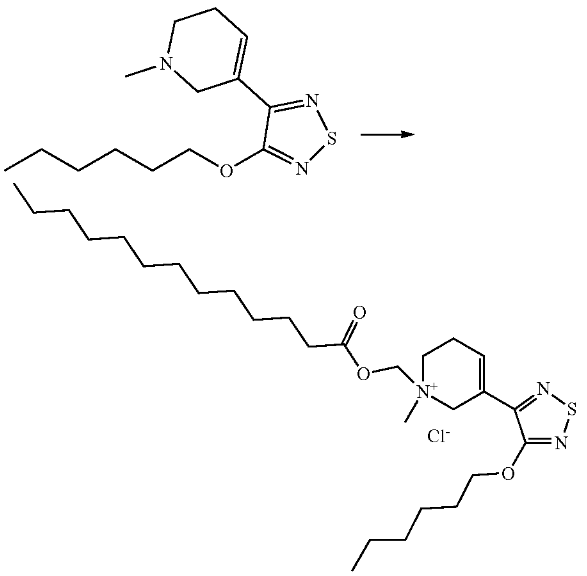

Reaction performed on 0.711 mmol of xanomeline and purified by gradient column chromatography (0 to 10% MeOH in DCM) to give the product (195 mg, 50%) as a solid. Retention time 1.845 min; m/z=$[M]^+$ calculated for $C_{28}H_{50}N_3O_3S$ 508.4; found 508.2; $^1H$ NMR (400 MHz, $CDCl_3$) δ 7.26-7.18 (m, 1H), 6.02 (d, J=8.5 Hz, 1H), 5.96 (d, J=8.4 Hz, 1H), 4.72-4.40 (m, 5H), 4.17 (dt, J=13.0, 6.7 Hz, 1H), 3.59 (s, 3H), 2.87 (t, J=5.4 Hz, 2H), 2.51 (t, J=7.5 Hz, 2H), 1.97-1.77 (m, 2H), 1.66 (p, J=7.4 Hz, 2H), 1.54-1.15 (m, 24H), 1.02-0.79 (m, 6H).

Example 13: Preparation of [5-(4-hexyloxy-1,2,5-thiadiazol-3-yl)-1-methyl-3,6-dihydro-2H-pyridin-1-ium-1-yl]methyl tetradecanoate chloride [Xanomeline methyl decatettaraoate chloride prodrug] (Table 1 Compound 13)

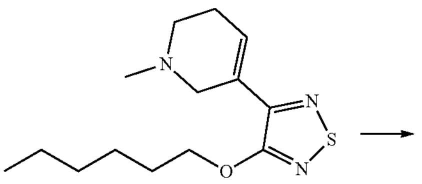

-continued

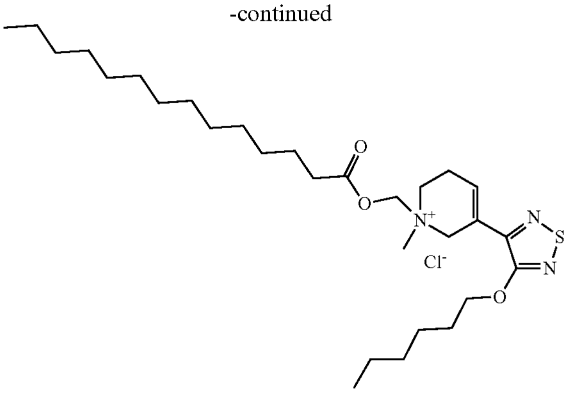

To a stirred solution of xanomeline (175 mg, 0.622 mmol) in MeCN (3 mL) at rt was added chloromethyl tetradecanoate (344 mg, 1.24 mmol) in one portion. The mixture was stirred at 45° C. for 48 h, allowed to cool to rt and the emerging precipitate was collected by filtration and air dried to afford the title compound (75 mg, 21%) as a solid. Retention time: 1.878 min; m/z=$[M]^+$ calculated for $C_{29}H_{52}N_3O_3S$ 522.4; found 522.3; $^1H$ NMR (400 MHz, DMSO-$d_6$) δ 7.24-7.13 (m, 1H), 5.45 (d, J=1.5 Hz, 2H), 4.55-4.39 (m, 4H), 3.63 (h, J=6.2 Hz, 2H), 3.14 (s, 3H), 2.78 (s, 2H), 2.56 (t, J=7.4 Hz, 2H), 1.82 (dt, J=14.2, 6.7 Hz, 2H), 1.57 (q, J=7.1 Hz, 2H), 1.43 (q, J=6.9 Hz, 2H), 1.37-1.10 (m, 24H), 0.95-0.79 (m, 6H).

Example 14: Preparation of 1-methyl-1[(pentadecanoyloxy)methyl]-5-[4-(hexyloxy-1,2,5-thiadiazol-3-yl)]-1,2,3,6-tetrahydropyridin-1-ium chloride [Xanomeline methyl pentadecanoate chloride prodrug] (Table 1 Compound 14)

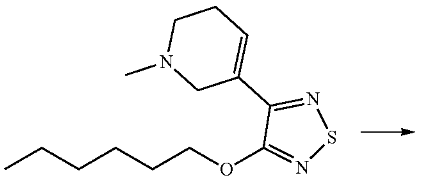

-continued

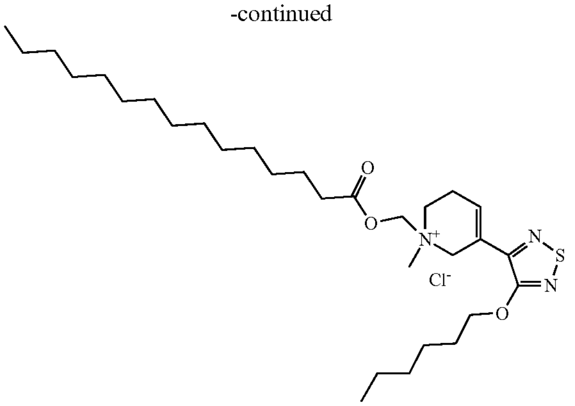

Reaction performed on 0.533 mmol of xanomeline and purified by gradient column chromatography on silica gel (0 to 10% MeOH in DCM) to give the product (46 mg, 15%) as a solid. Retention time 1.931 min; m/z=$[M]^+$ calculated for $C_{30}H_{54}N_3O_3S$ 536.4; found 536.3; $^1H$ NMR (400 MHz, $CDCl_3$) δ 7.26-7.18 (m, 1H), 6.03 (d, J=8.5 Hz, 1H), 5.95 (d, J=8.5 Hz, 1H), 4.69-4.41 (m, 5H), 4.15 (dt, J=13.0, 6.7 Hz, 1H), 3.58 (s, 3H), 2.86 (s, 2H), 2.51 (t, J=7.5 Hz, 2H), 1.93-1.58 (m, 6H), 1.54-1.16 (m, 26H), 0.99-0.81 (m, 6H).

Example 15: Preparation of [5-(4-hexyloxy-1,2,5-thiadiazol-3-yl)-1-methyl-3,6-dihydro-2H-pyridin-1-ium-1-yl]methyl hexadecanoate chloride [Xanomeline methyl hexadecanoate chloride prodrug] (Table 1 Compound 15)

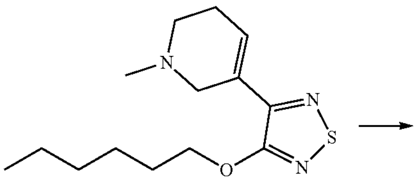

-continued

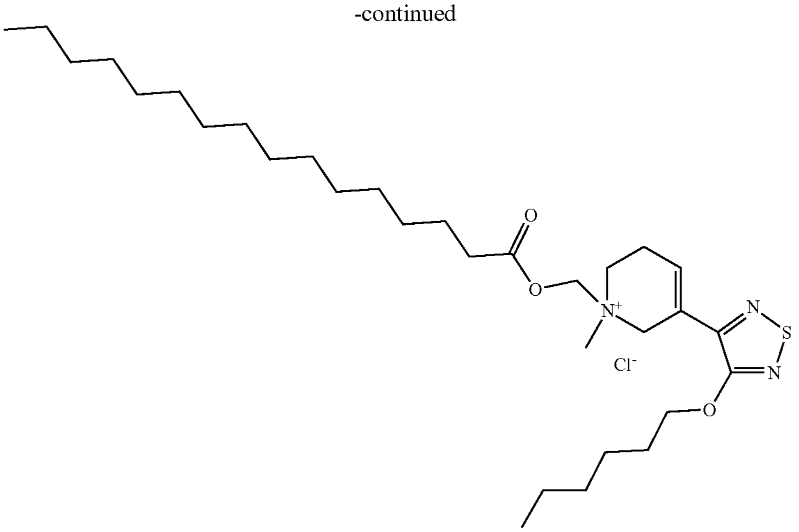

To a stirred mixture of 3-hexyloxy-4-(1-methyl-3,6-dihydro-2H-pyridin-5-yl)-1,2,5-thiadiazole [Xanomeline] (145 mg, 0.52 mmol) in MeCN (3 mL) at rt was added chloromethyl hexadecanoate (314 mg, 1.03 mmol) in one portion. The mixture was stirred at rt for 72 h, then concentrated in vacuo and the crude product was purified by column chromatography on silica gel (eluent: 1% to 20% MeOH in EtOAc gradient) to afford the title compound (61 mg, 20%) as a solid. Retention time: 5.610 min (10 minute LCMS method); m/z=$[M]^+$ calculated for $C_{31}H_{59}N_3O_3S$ 550.4; found 550.4; $^1H$ NMR (400 MHz, $CDCl_3$) δ 7.24 (d, J=4.1 Hz, 1H), 6.04 (d, J=8.6 Hz, 1H), 5.91 (d, J=8.6 Hz, 1H), 4.60-4.42 (m, 5H), 4.11 (dt, J=13.2, 6.9 Hz, 1H), 3.55 (s, 3H), 2.86 (s, 2H), 2.52 (t, J=7.5 Hz, 2H), 1.85 (p, J=6.9 Hz, 2H), 1.74-1.60 (m, 7H), 1.55-1.16 (m, 25H), 0.98-0.81 (m, 6H).

Example 16: Preparation of [5-(4-hexyloxy-1,2,5-thiadiazol-3-yl)-1-methyl-3,6-dihydro-2H-pyridin-1-ium-1-yl]methyl 2,2-dimethylpropanoate iodide [Xanomeline methyl "tert-butanoate" iodide prodrug] (Table 1 Compound 16)

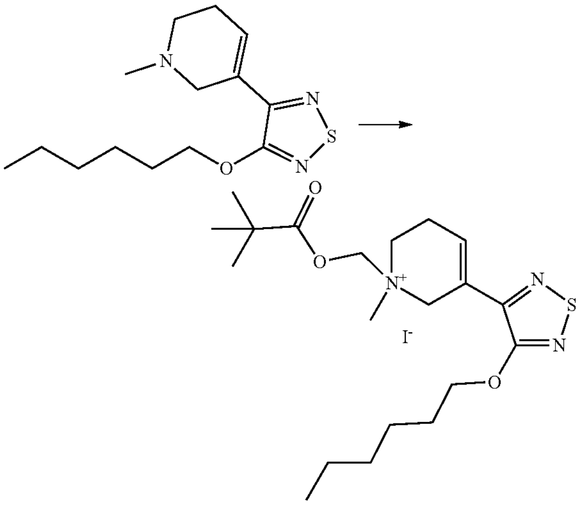

To a stirred mixture of 3-hexyloxy-4-(1-methyl-3,6-dihydro-2H-pyridin-5-yl)-1,2,5-thiadiazole [xanomeline] (50 mg, 0.18 mmol) in MeCN (1 mL) at rt was added iodomethyl 2,2-dimethylpropanoate (27.6 μL, 0.18 mmol) in one portion. The reaction mixture was stirred at rt for 20 h, and the resulting precipitate was isolated by filtration to afford the title compound (78 mg, 83%) as a semi-solid. Retention time: 1.550 min; m/z=$[M]^+$ calculated for $C_{20}H_{34}N_3O_3S$ 396.2; found 396.2; $^1H$ NMR (400 MHz, $CD_3OD$) δ 7.33 (tt, J=4.0, 1.8 Hz, 1H), 5.53 (d, J=8.8 Hz, 1H), 5.38 (d, J=8.8 Hz, 1H), 4.60-4.47 (m, 4H), 3.69 (t, J=6.3 Hz, 2H), 3.49 (q, J=7.0 Hz, 1H), 3.24 (s, 3H), 1.96-1.81 (m, 2H), 1.49 (q, J=7.3 Hz, 2H), 1.44-1.35 (m, 4H), 1.33 (s, 9H), 1.18 (t, J=7.0 Hz, 1H), 1.00-0.87 (m, 3H).

Example 17: Preparation of [5-(4-hexyloxy-1,2,5-thiadiazol-3-yl)-1-methyl-3,6-dihydro-2H-pyridin-1-ium-1-yl]methyl 2-methylpropanoate chloride [Xanomeline methyl isobutyrate chloride prodrug] (Table 1 Compound 17)

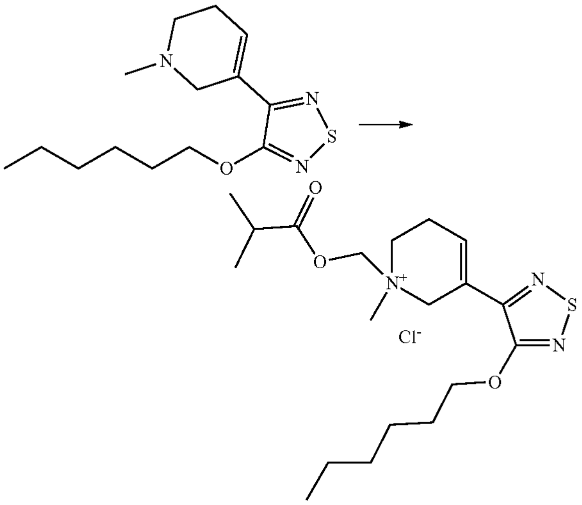

To a stirred mixture of 3-hexyloxy-4-(1-methyl-3,6-dihydro-2H-pyridin-5-yl)-1,2,5-thiadiazole [xanomeline] (70 mg, 0.25 mmol) in MeCN (1 mL) was added chloromethyl 2-methylpropanoate (62.9 μL, 0.5 mmol) in one portion. The mixture was stirred at rt for 72 h and concentrated in vacuo. The residue was purified by reverse phase HPLC (eluent: 10-100% MeCN in $H_2O$) to afford the product (53 mg, 51%) as a solid. Retention time: 1.535 min; m/z=$[M]^+$ calculated for $C_{19}H_{32}N_3O_3S$ 382.2 found 382.2; $^1H$ NMR (400 MHz, $CDCl_3$) δ 7.24 (d, J=4.1 Hz, 1H), 6.03 (d, J=8.6 Hz, 1H), 5.89 (d, J=8.6 Hz, 1H), 4.58-4.42 (m, 5H), 4.10 (dt, J=13.1, 6.9 Hz, 1H), 3.54 (s, 3H), 2.89-2.70 (m, 4H), 1.86 (p, J=6.8 Hz, 2H), 1.52-1.21 (m, 11H), 0.98-0.86 (m, 3H).

Example 18: Preparation of [5-(4-hexyloxy-1,2,5-thiadiazol-3-yl)-1-methyl-3,6-dihydro-2H-pyridin-1-ium-1-yl]methyl 3-methylbutanoate chloride [Xanomeline methyl neopentanoate chloride prodrug] (Table 1 Compound 18)

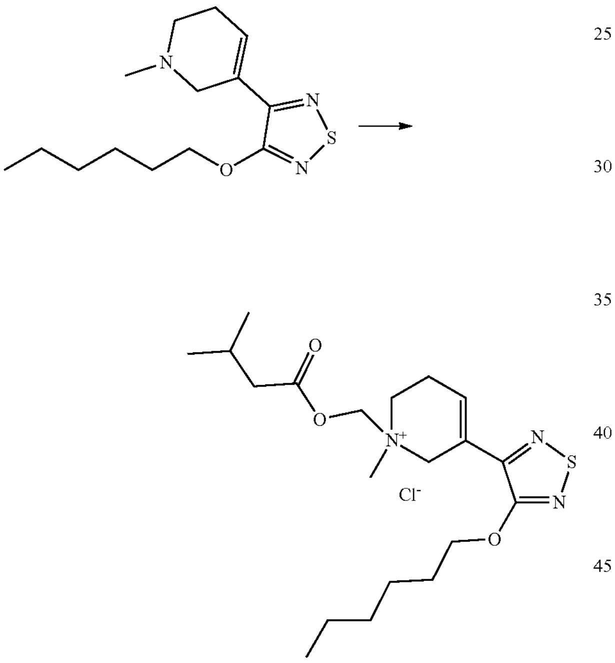

To a stirred mixture of 3-hexyloxy-4-(1-methyl-3,6-dihydro-2H-pyridin-5-yl)-1,2,5-thiadiazole [xanomeline] (150 mg, 0.53 mmol) in MeCN (1 mL) was added chloromethyl 3-methylbutanoate (82.7 μL, 1.07 mmol) in one portion. The mixture was stirred at rt for 48 h and concentrated in vacuo. The residue was purified by reverse phase HPLC (eluent: 10-100% MeCN in H2O) to afford the product (81 mg, 35%) as a solid. Retention time: 1.582 min; m/z=$[M]^+$ calculated for $C_{20}H_{34}N_3O_3S$ 396.2 found 396.2; 1H NMR (400 MHz, CDCl3) δ 7.25 (s, 1H), 6.01 (d, J=8.5 Hz, 1H), 5.89 (d, J=8.6 Hz, 1H), 4.60-4.42 (m, 5H), 4.11 (dt, J=13.1, 6.8 Hz, 1H), 3.55 (s, 3H), 2.87 (s, 2H), 2.41 (d, J=7.1 Hz, 2H), 2.14 (dp, J=13.7, 6.8 Hz, 1H), 1.85 (p, J=6.9 Hz, 2H), 1.52-1.30 (m, 6H), 1.01 (s, 3H), 0.99 (s, 3H), 0.96-0.86 (m, 3H).

Example 19: Preparation of 1-[5-(4-hexyloxy-1,2,5-thiadiazol-3-yl)-1-methyl-3,6-dihydro-2H-pyridin-1-ium-1-yl]ethyl 2,2-dimethylpropanoate chloride [Xanomeline oxyethyl pivalate chloride] (Table 1 Compound 19)

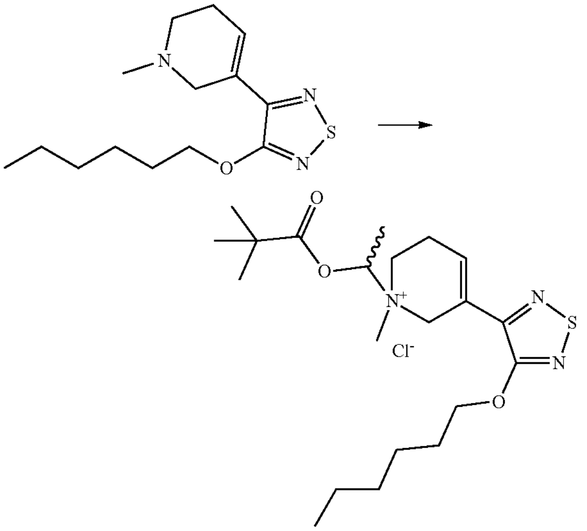

To a solution of 3-hexyloxy-4-(1-methyl-3,6-dihydro-2H-pyridin-5-yl)-1,2,5-thiadiazole [xanomeline] (150 mg, 0.53 mmol) in $CH_3CN$ (3 mL) was added 1-chloroethyl 2,2-dimethylpropanoate [CAS No: 40258-80-8] (135 μL, 1.07 mmol) and NaI (8.0 mg, 0.05 mmol), giving a complete solution. The mixture was sealed and heated under microwave irradiation to 50° C. and stirred at this temperature for 42 h (Biotage initiator microwave). The mixture was concentrated in vacuo and purified by reverse-phase HPLC (eluent: 10-100% MeCN in $H_2O$) to give the product (62 mg, 26%) as a solid. Retention time 1.571 min; m/z=$[M]^+$ calculated for $C_{21}H_{36}N_3O_3S$ 410.3; found 410.2; $^1H$ NMR (400 MHz, $CDCl_3$) δ 7.25 (s, 1H), 6.21-6.02 (m, 1H), 4.95-4.29 (m, 5H), 3.64-3.49 (m, 3H), 3.22-2.96 (m, 1H), 2.89-2.56 (m, 1H), 1.95-1.81 (m, 3H), 1.79 (d, J=5.9 Hz, 2H), 1.46 (p, J=6.6 Hz, 4H), 1.36 (dq, J=6.8, 3.8 Hz, 4H), 1.31 (s, 6H), 1.29 (s, 2H), 0.99-0.86 (m, 3H).

Example 20: Preparation of [5-(4-hexyloxy-1,2,5-thiadiazol-3-yl)-1-methyl-3,6-dihydro-2H-pyridin-1-ium-1-yl]methoxy-triisopropyl-silane chloride [Xanomeline methyl tri-isopropylsilyl ether chloride prodrug] (Table 1 Compound 20)

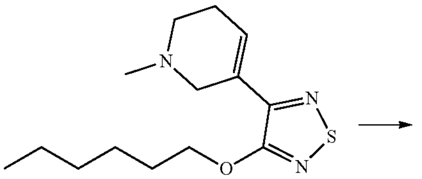

-continued

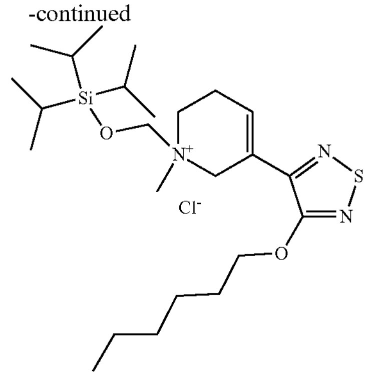

To a stirred solution of 3-hexyloxy-4-(1-methyl-3,6-dihydro-2H-pyridin-5-yl)-1,2,5-thiadiazole [xanomeline] (200 mg, 0.71 mmol) in MeCN (2 mL) was added chloromethoxy (triisopropyl)silane (317 mg, 1.42 mmol) in one portion. The mixture was stirred at rt for 48 h, then concentrated in vacuo and the crude product was purified by column chromatography on silica gel (eluent: 2-25% MeOH in EtOAc gradient) to afford the product (255 mg, 76%) as a solid. Retention time: 1.729 min; m/z=[M]$^+$ calculated for $C_{24}H_{46}N_3O_2SSi$ 468.3 found 468.2; $^1$H NMR (400 MHz, $CDCl_3$) δ 7.23 (s, 1H), 5.41 (d, J=6.1 Hz, 1H), 5.24 (d, J=6.1 Hz, 1H), 4.65 (d, J=16.3 Hz, 1H), 4.54-4.33 (m, 4H), 3.96 (dt, J=13.2, 6.9 Hz, 1H), 3.47 (s, 3H), 2.93-2.70 (m, 2H), 1.93-1.77 (m, 2H), 1.52-1.41 (m, 2H), 1.41-1.30 (m, 4H), 1.30-1.16 (m, 3H), 1.11 (dd, J=7.3, 3.1 Hz, 18H), 1.00-0.81 (m, 3H).

Example 21: Preparation of 3-hexyloxy-4-(1-methyl-1-oxido-3,6-dihydro-2H-pyridin-1-ium-5-yl)-1,2,5-thiadiazole [Xanomeline N-oxide prodrug] (Table 1 Compound 21)

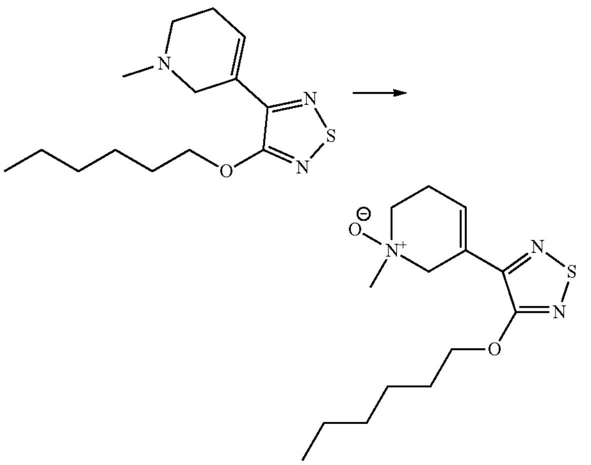

To a stirred mixture of 3-hexyloxy-4-(1-methyl-3,6-dihydro-2H-pyridin-5-yl)-1,2,5-thiadiazole [xanomeline] (50 mg, 0.18 mmol) in DCM (1.5 mL) at rt was added 3-chlorobenzenecarboperoxoic acid (mcpba) (36.8 mg, 0.213 mmol) portion-wise over 2 min. The mixture was stirred at rt overnight then concentrated in vacuo. The residue was taken up in EtOAc (100 mL) and washed with sodium bicarbanate solution (2×25 mL). The organic layer was concentrated in vacuo and the crude product was purified by column chromatography on silica gel (eluent: 2-15% MeOH in EtOAc) to give the product (30 mg, 56%) as a viscous oil. Retention time: 1.436 min; m/z=[M+H]$^+$ calculated for $C_{14}H_{23}N_3O_2S$ 298.1 found 298.2; $^1$H NMR (400 MHz, $CDCl_3$) δ 7.20 (ddt, J=5.4, 3.6, 1.7 Hz, 1H), 4.53-4.35 (m, 4H), 3.57-3.27 (m, 5H), 3.20 -2.99 (m, 1H), 2.62-2.34 (m, 1H), 1.84 (dq, J=7.9, 6.7 Hz, 2H), 1.54-1.26 (m, 6H), 1.00-0.85 (m, 3H).

General Method for the Synthesis of Alkoxycarbonyloxymethyl Final Compounds:

To a mixture of xanomeline (150 mg, 0.63 mmol) in MeCN (2 mL) was added dropwise chloromethyl alkyl carbonate (1.57 mmol, 2.5 eq). The mixture was heated at 50° C., or 60° C. and stirred for 15 h, then dry-loaded onto silica gel and purified using column chromatography on silica gel [Biotage system; 10 g cartridge, 2% MeOH in DCM (3 CVs), 2 to 20% MeOH in DCM (20 CVs), then 20% MeOH in DCM (10 CVS)]. The pure fractions were collected and evaporated to dryness to give the product as a solid.

Example 22: Preparation of ethyl [5-(4-hexyloxy-1,2,5-thiadiazol-3-yl)-1-methyl-3,6-dihydro-2H-pyridin-1-ium-1-yl]methyl carbonate chloride [Xanomeline methyl ethylcarbonate chloride prodrug] (Table 1 Compound 23)

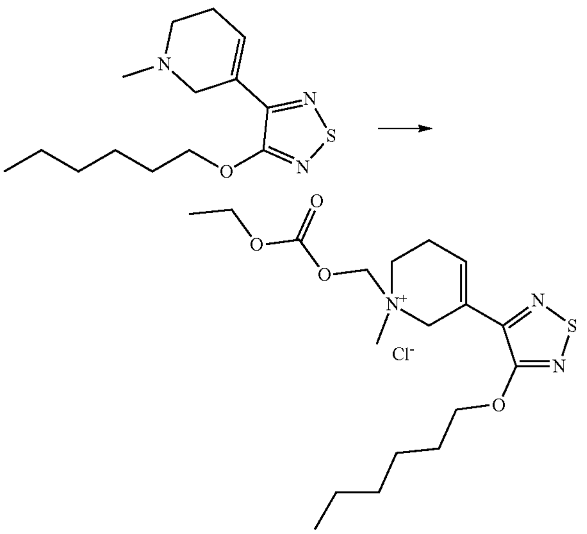

To a stirred solution of xanomeline (50 mg, 0.18 mmol) and MeCN (1 mL) at rt was added chloromethyl ethyl carbonate (49.2 mg, 0.36 mmol). The mixture was stirred at rt for 5 d, then concentrated in vacuo and the crude product was purified by reverse-phase HPLC (eluent 10-100% MeCN in $H_2O$ gradient) to afford the product (30 mg, 40%) as a solid. Retention time: 1.492 min; m/z=[M]$^+$ calculated for $C_{18}H_{30}N_3O_4S$ 384.2; found 384.2; $^1$H NMR (400 MHz, $CDCl_3$) δ 7.33-7.21 (m, 1H), 6.03-5.85 (m, 2H), 4.83-4.61 (m, 2H), 4.55-4.38 (m, 3H), 4.32 (q, J=7.1 Hz, 2H), 4.19 (dt, J=13.0, 6.7 Hz, 1H), 3.60 (s, 3H), 2.90 (s, 2H), 1.94-1.80 (m, 2H), 1.54-1.29 (m, 9H), 0.99-0.85 (m, 3H).

Example 23: Preparation of [5-(4-hexyloxy-1,2,5-thiadiazol-3-yl)-1-methyl-3,6-dihydro-2H-pyridin-1-ium-1-yl]methyl propyl carbonate chloride [Xanomeline methyl propylcarbonate chloride prodrug] (Table 1 Compound 24)

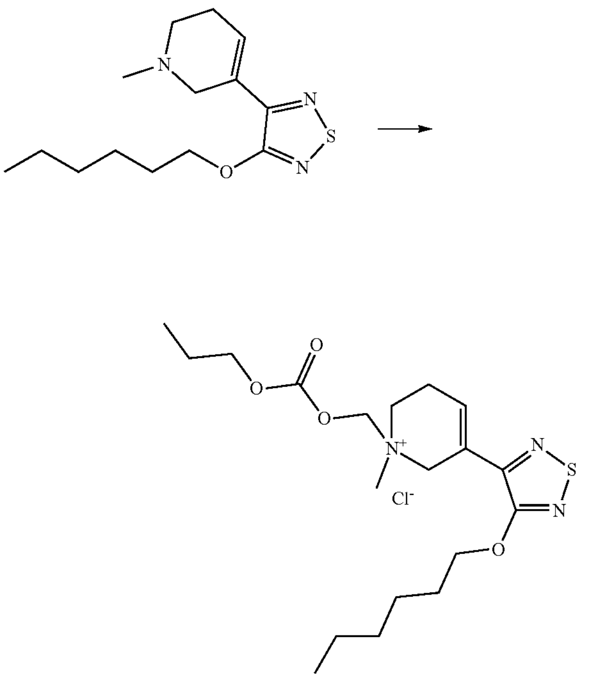

The reaction was carried out according to the general method using 0.15 g (0.63 mmol) of xanomeline. Product isolated (135 mg, 54%) as a solid. Retention time: 1.47 min; m/z=$[M]^+$ calculated for $C_{19}H_{32}N_3O_4S$ 398.2; found 398.2; $^1$H NMR (400 MHz, $CDCl_3$) δ 7.24 (t, J=4.3 Hz, 1H), 6.12 (d, J=8.4 Hz, 1H), 5.98 (d, J=8.4 Hz, 1H), 4.68 (q, J=16.4 Hz, 2H), 4.58-4.41 (m, 3H), 4.26-4.11 (m, 3H), 3.59 (s, 3H), 2.87 (s, 2H), 1.93-1.65 (m, 4H), 1.52-1.22 (m, 6H), 1.05-0.85 (m, 6H).

Example 24: Preparation of butyl [5-(4-hexyloxy-1,2,5-thiadiazol-3-yl)-1-methyl-3,6-dihydro-2H-pyridin-1-ium-1-yl]methyl carbonate chloride aka [5-(4-hexyloxy-1,2,5-thiadiazol-3-yl)-1-methyl-3,6-dihydro-2H-pyridin-1-ium-1-yl]methyl butyl carbonate chloride [Xanomeline methyl butylcarbonate chloride prodrug] (Table 1 Compound 25)

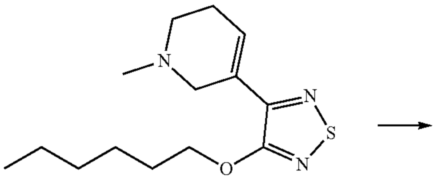

-continued

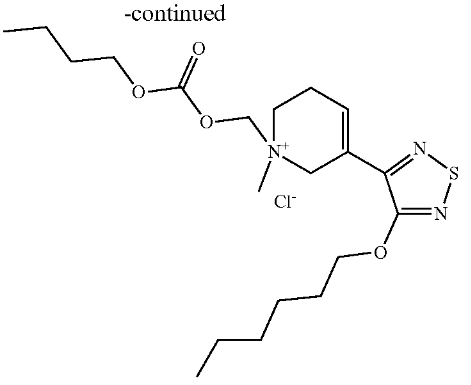

The reaction was carried out according to the general method using 0.15 g (0.63 mmol) of xanomeline. Product isolated (146 mg, 57%) as a solid. Retention time: 1.52 min; m/z=$[M]^+$ calculated for $C_{20}H_{34}N_3O_4S$ 412.2; found 412.2; $^1$H NMR (400 MHz, $CDCl_3$) δ 7.24 (d, J=4.1 Hz, 1H), 6.12 (d, J=8.4 Hz, 1H), 5.98 (d, J=8.4 Hz, 1H), 4.79-4.41 (m, 5H), 4.30-4.10 (m, 3H), 3.59 (s, 3H), 2.87 (s, 2H), 1.93-1.61 (m, 4H), 1.52-1.21 (m, 8H), 1.03-0.85 (m, 6H).

Example 25: Preparation of pentyl [5-(4-hexyloxy-1,2,5-thiadiazol-3-yl)-1-methyl-3,6-dihydro-2H-pyridin-1-ium-1-yl]methyl carbonate chloride aka [5-(4-hexyloxy-1,2,5-thiadiazol-3-yl)-1-methyl-3,6-dihydro-2H-pyridin-1-ium-1-yl]methyl pentyl carbonate chloride [Xanomeline methyl pentylcarbonate chloride prodrug] (Table 1 Compound 26)

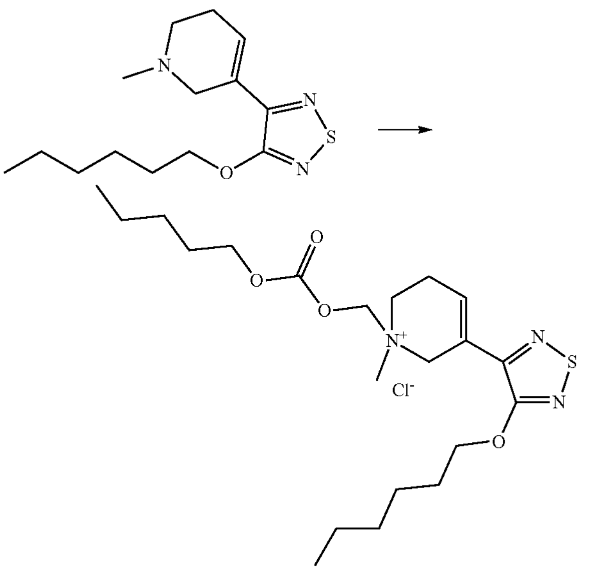

To a mixture of xanomeline (150 mg, 0.53 mmol) in MeCN (2 mL) at rt was added dropwise chloromethyl pentyl carbonate (289 mg, 1.6 mmol). The mixture was stirred at rt for 11 days, then concentrated in vacuo and the residue purified by column chromatography on silica gel (eluent: 0 to 15% MeOH in DCM) to afford the product (187 mg, 75%) as a solid. Retention time: 3.505 min; m/z=$[M]^+$ calculated for $C_{21}H_{36}N_3O_4S$ 426.2; found 426.2; $^1$H NMR (400 MHz, $CDCl_3$) δ 7.24 (td, J=4.0, 1.9 Hz, 1H), 6.17-5.95 (m, 2H), 4.82-4.60 (m, 2H), 4.58-4.40 (m, 3H), 4.29-4.12 (m, 3H), 3.60 (s, 3H), 2.88 (s, 2H), 1.85 (dq, J=8.4, 6.8 Hz, 2H), 1.77-1.62 (m, 2H), 1.54-1.22 (m, 10H), 1.00-0.84 (m, 6H).

Example 26: Preparation of [5-(4-hexyloxy-1,2,5-thiadiazol-3-yl)-1-methyl-3,6-dihydro-2H-pyridin-1-ium-1-yl]methyl hexyl carbonate chloride [Xanomeline methyl hexylcarbonate chloride prodrug] (Table 1 Compound 27)

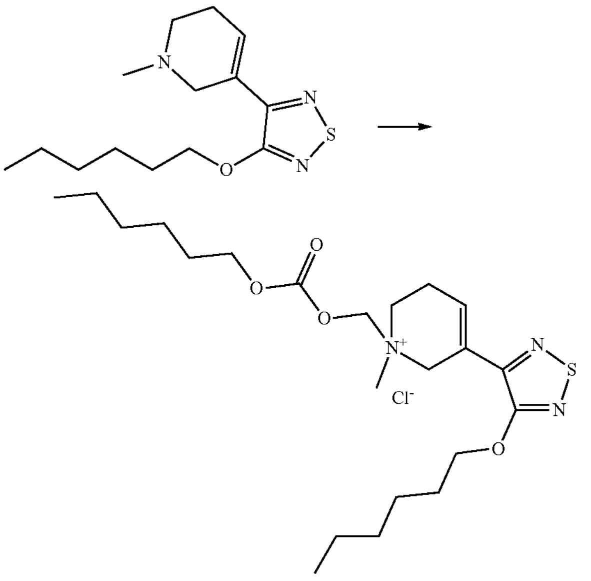

The reaction was carried out according to the general method using 0.15 g (0.63 mmol) of xanomeline. Product (111 mg, 33%) isolated as a solid. Retention time: 1.60 min; m/z=$[M]^+$ calculated for $C_{30}H_{54}N_3O_4S$ 440.3; found 440.2; $^1H$ NMR (400 MHz, $CDCl_3$) δ 7.24 (s, 1H), 6.10 (d, J=8.4 Hz, 1H), 5.96 (d, J=8.4 Hz, 1H), 4.73-4.60 (m, 2H), 4.53-4.45 (m, 3H), 4.25-4.15 (m, 3H), 3.58 (s, 3H), 2.87 (br. s, 2H), 1.90-1.66 (m, 4H), 1.48-1.32 (m, 12H), 0.94-0.85 (m, 6H).

Example 27: Preparation of heptyl [5-(4-hexyloxy-1,2,5-thiadiazol-3-yl)-1-methyl-3,6-dihydro-2H-pyridin-1-ium-1-yl]methyl carbonate chloride [Xanomeline methyl heptylcarbonate chloride prodrug] (Table 1 Compound 28)

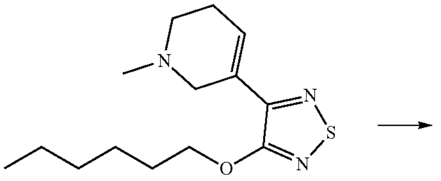

-continued

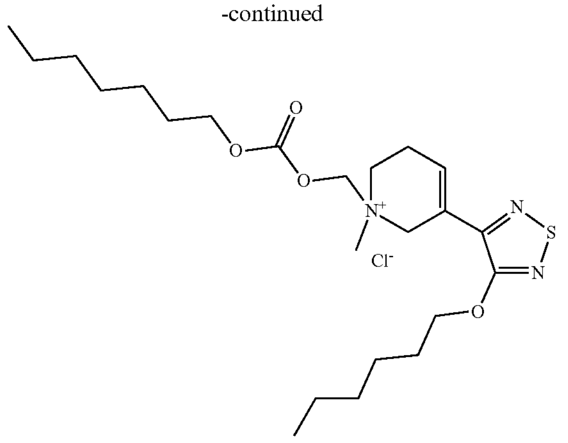

The reaction was carried out according to the general method using 0.15 g (0.63 mmol) of xanomeline. Product (207 mg, 85%) isolated as a solid. Retention time: 1.63 min; m/z=$[M]^+$ calculated for $C_{23}H_{40}N_3O_4S$ 454.3; found 454.2; $^1H$ NMR (400 MHz, $CDCl_3$) δ 7.24 (dd, J=3.8, 1.9 Hz, 1H), 6.10 (d, J=8.4 Hz, 1H), 5.97 (d, J=8.4 Hz, 1H), 4.78-4.41 (m, 5H), 4.29-4.09 (m, 3H), 3.58 (s, 3H), 2.87 (s, 2H), 1.93-1.62 (m, 4H), 1.52-1.21 (m, 14H), 0.98-0.82 (m, 6H).

Example 28: Preparation of [5-(4-hexyloxy-1,2,5-thiadiazol-3-yl)-1-methyl-3,6-dihydro-2H-pyridin-1-ium-1-yl]methyl octyl carbonate chloride [Xanomeline methyl octylcarbonate chloride prodrug] (Table 1 Compound 29)

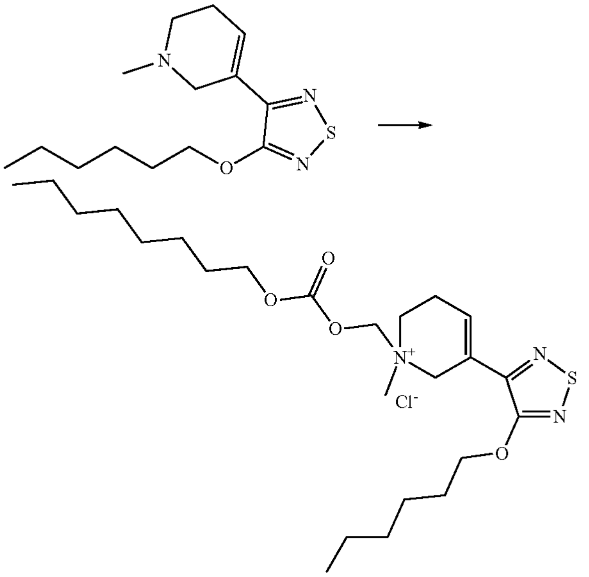

The reaction was carried out according to the general method using 0.15 g (0.63 mmol) of xanomeline. Product (127 mg, 47%) isolated as a solid. Retention time: 1.68 min; m/z=$[M]^+$ calculated for $C_{24}H_{42}N_3O_4S$ 468.3; found 468.2; $^1H$ NMR (400 MHz, $CDCl_3$) δ 7.32-7.18 (m, 1H), 6.11 (d, J=8.4 Hz, 1H), 5.96 (d, J=8.4 Hz, 1H), 4.78-4.57 (m, 2H), 4.57-4.41 (m, 3H), 4.30-4.11 (m, 3H), 3.58 (s, 3H), 2.87 (s, 2H), 1.85 (p, J=6.9 Hz, 2H), 1.78-1.62 (m, 3H), 1.52-1.21 (m, 16H), 0.98-0.82 (m, 6H).

Example 29: Preparation of [5-(4-hexyloxy-1,2,5-thiadiazol-3-yl)-1-methyl-3,6-dihydro-2H-pyridin-1-ium-1-yl]methyl nonyl carbonate chloride [Xanomeline methyl nonylcarbonate chloride prodrug] (Table 1 Compound 30)

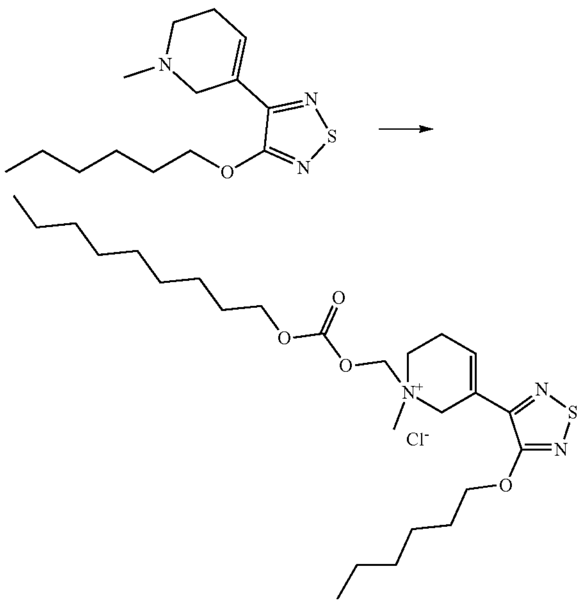

To a mixture of xanomeline (200 mg, 0.71 mmol) in MeCN (2 mL) at rt was added dropwise chloromethyl nonyl carbonate (505 mg, 2.13 mmol). The mixture was stirred at rt for 17 days, then concentrated in vacuo and the residue was purified by column chromatography on silica gel [Biotage system; 10 g cartridge, 2% MeOH in DCM (3 CVs), 2 to 20% MeOH in DCM (20 CVs), then 20% MeOH in DCM (10 CVS)] to give the product (322 mg, 87%) as a solid. Retention time: 1.718 min; m/z=[M]$^+$ calculated for $C_{25}H_{44}N_3O_4S$ 482.3; found 482.2; $^1$H NMR (400 MHz, $CDCl_3$) δ 7.24 (td, J=4.0, 1.9 Hz, 1H), 6.09 (d, J=8.4 Hz, 1H), 5.98 (d, J=8.4 Hz, 1H), 4.79-4.58 (m, 2H), 4.47 (t, J=6.8 Hz, 3H), 4.29-4.07 (m, 3H), 3.59 (s, 3H), 2.95-2.75 (m, 2H), 1.85 (ddd, J=13.0, 9.6, 6.8 Hz, 4H), 1.74-1.65 (m, 2H), 1.54-1.16 (m, 16H), 1.01-0.79 (m, 6H).

Example 30: Preparation of [5-(4-hexyloxy-1,2,5-thiadiazol-3-yl)-1-methyl-3,6-dihydro-2H-pyridin-1-ium-1-yl]methyl decyl carbonate chloride [Xanomeline methyl decylcarbonate chloride prodrug] (Table 1 Compound 31)

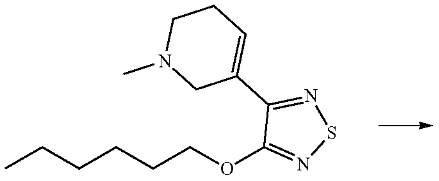

-continued

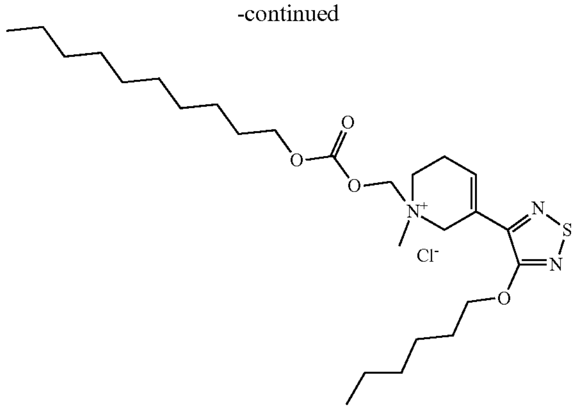

To a mixture of xanomeline (200 mg, 0.71 mmol) in MeCN (2 mL) at rt was added dropwise chloromethyl decyl carbonate (535 mg, 2.13 mmol). The mixture was stirred at rt for 7 days, then concentrated in vacuo and the residue was purified by column chromatography on silica gel [Biotage system; 10 g cartridge; 2% MeOH in DCM (3 CVs), 2 to 20% MeOH in DCM (20 CVs), then 20% MeOH in DCM (10 CVS)] to give the product (218 mg, 58%) as a solid. Retention time: 4.358 min; m/z=[M]$^+$ calculated for $C_{26}H_{46}N_3O_4S$ 496.3; found 496.2; $^1$H NMR (400 MHz, $CDCl_3$) δ 7.26-7.18 (m, 1H), 6.11 (d, J=8.4 Hz, 1H), 6.00 (d, J=8.4 Hz, 1H), 4.80-4.60 (m, 2H), 4.60-4.39 (m, 3H), 4.28-4.11 (m, 3H), 3.59 (s, 3H), 2.87 (s, 2H), 1.85 (p, J=6.8 Hz, 2H), 1.78-1.61 (m, 2H), 1.54-1.19 (m, 21H), 0.98-0.81 (m, 5H).

Example 31: Preparation of [5-(4-hexyloxy-1,2,5-thiadiazol-3-yl)-1-methyl-3,6-dihydro-2H-pyridin-1-ium-1-yl]methyl undecyl carbonate chloride [Xanomeline methyl undecylcarbonate chloride prodrug] (Table 1 Compound 32)

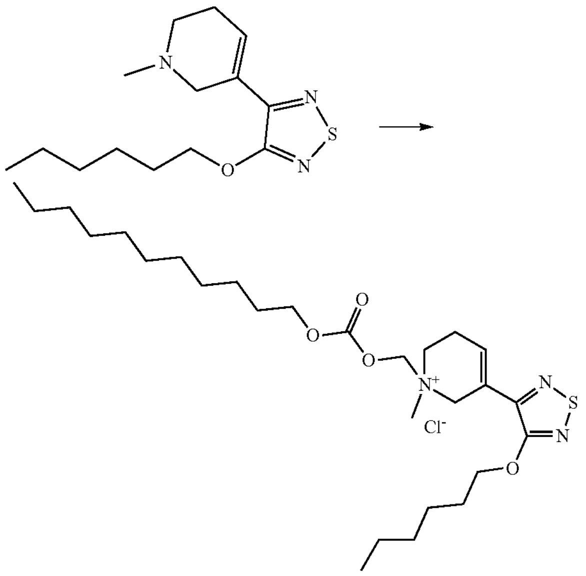

The reaction was carried out according to the general method using 0.15 g (0.63 mmol) of xanomeline. Product (131 mg, 48%) isolated as a solid. Retention time: 1.80 min;

m/z=[M]+ calculated for $C_{27}H_{48}N_3O_4S$ 510.3; found 510.2; $^1$H NMR (400 MHz, $CDCl_3$) δ 7.24 (d, J=4.3 Hz, 1H), 6.12 (d, J=8.4 Hz, 1H), 5.97 (d, J=8.4 Hz, 1H), 4.78-4.41 (m, 5H), 4.29-4.12 (m, 3H), 3.58 (s, 3H), 2.87 (s, 2H), 1.93-1.62 (m, 4H), 1.52-1.19 (m, 22H), 0.98-0.81 (m, 6H).

Example 32: Preparation of dodecyl [5-(4-hexyloxy-1,2,5-thiadiazol-3-yl)-1-methyl-3,6-dihydro-2H-pyridin-1-ium-1-yl]methyl carbonate chloride [Xanomeline methyl dodecylcarbonate chloride prodrug] (Table 1 Compound 33)

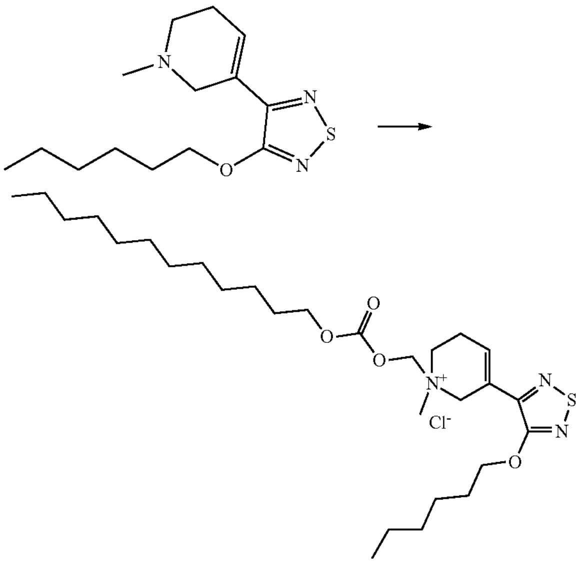

The reaction was carried out according to the general method using 0.15 g (0.63 mmol) of xanomeline. Product (91 mg, 31%) isolated as a solid. Retention time: 1.63 min; m/z=[M]+ calculated for $C_{28}H_{50}N_3O_4S$ 524.4; found 524.2; $^1$H NMR (400 MHz, $CDCl_3$) δ 7.26-7.21 (m, 1H), 6.11 (d, J=8.3 Hz, 1H), 5.98 (d, J=8.4 Hz, 1H), 4.79-4.58 (m, 2H), 4.58-4.39 (m, 3H), 4.29-4.13 (m, 3H), 3.59 (s, 3H), 2.87 (s, 2H), 2.12-1.78 (m, 2H), 1.78-1.61 (m, 2H), 1.54-1.18 (m, 24H), 1.02-0.67 (m, 6H).

Example 33: Preparation of [5-(4-hexyloxy-1,2,5-thiadiazol-3-yl)-1-methyl-3,6-dihydro-2H-pyridin-1-ium-1-yl]methyl tridecyl carbonate chloride [Xanomeline methyl decatriylcarbonate chloride prodrug] (Table 1 Compound 34)

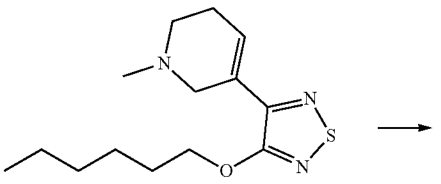

-continued

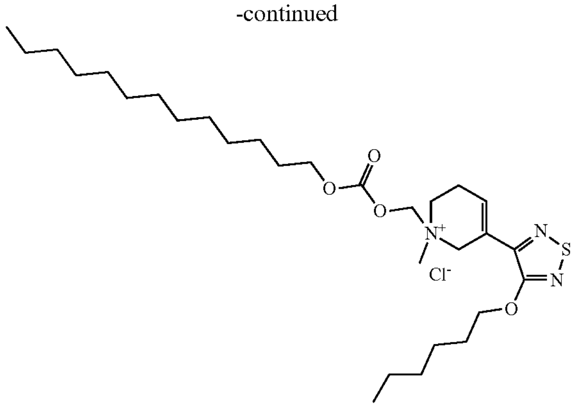

To a stirred mixture of 3-hexyloxy-4-(1-methyl-3,6-dihydro-2H-pyridin-5-yl)-1,2,5-thiadiazole [xanomeline] (175 mg, 0.62 mmol) in MeCN (3 mL) at rt was added chloromethyl tridecyl carbonate (546 mg, 1.87 mmol) in one portion. The mixture was heated to 45° C. and stirred for 48 h, then cooled to rt and concentrated in vacuo. The crude product was purified by column chromatography on silica gel (eluent: 1 to 15% MeOH in EtOAc gradient) to afford the product (104 mg, 29%) as an oil. Retention time: 1.887 min; m/z=[M]+ calculated for $C_{29}H_{52}N_3O_4S$ 538.4 found 538.3; $^1$H NMR (400 MHz, $CDCl_3$) δ 7.23 (d, J=4.1 Hz, 1H), 6.11 (d, J=8.4 Hz, 1H), 5.93 (d, J=8.5 Hz, 1H), 4.65 (q, J=16.4 Hz, 2H), 4.54-4.40 (m, 3H), 4.30-4.09 (m, 3H), 3.57 (s, 3H), 2.87 (s, 3H), 2.41 (s, 2H), 1.93-1.77 (m, 3H), 1.70 (p, J=6.8 Hz, 2H), 1.52-1.19 (m, 20H), 0.98-0.82 (m, 6H).

Example 34: Preparation of [5-(4-hexyloxy-1,2,5-thiadiazol-3-yl)-1-methyl-3,6-dihydro-2H-pyridin-1-ium-1-yl]methyl tetradecyl carbonate chloride aka [5-(4-hexyloxy-1,2,5-thiadiazol-3-yl)-1-methyl-3,6-dihydro-2H-pyridin-1-ium-1-yl]methyl tetradecane carbonate chloride [Xanomeline methyl decatettarylcarbonate chloride prodrug] (Table 1 Compound 35)

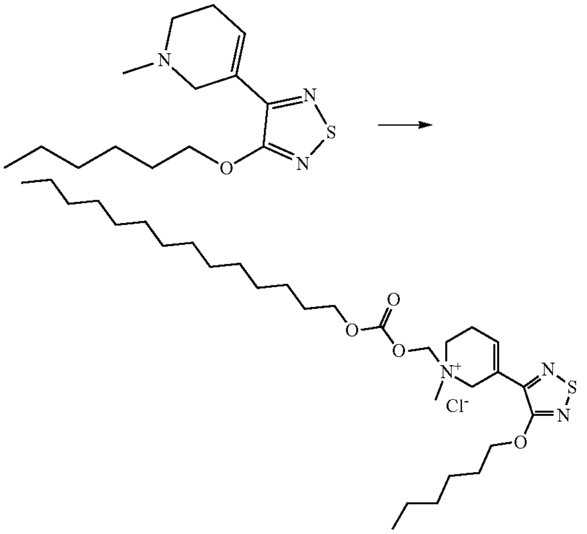

The reaction was carried out according to the general method using 0.15 g (0.63 mmol) of xanomeline. Product (72 mg, 23%) isolated as a solid. Retention time: 1.94 min; m/z=[M]+ calculated for $C_{30}H_{54}N_3O_4S$ 552.4; found 552.2; $^1$H NMR (400 MHz, $CDCl_3$) δ 7.24 (s, 1H), 6.10 (d, J=8.4 Hz, 1H), 5.95 (d, J=8.4 Hz, 1H), 4.73-4.60 (m, 2H), 4.53-4.45 (m, 3H), 4.24-4.15 (m, 3H), 3.57 (s, 3H), 2.87 (br. s, 2H), 1.90-1.66 (m, 7H), 1.52-1.22 (m, 25H), 0.94-0.85 (m, 6H).

Example 35: Preparation of [5-(4-hexyloxy-1,2,5-thiadiazol-3-yl)-1-methyl-3,6-dihydro-2H-pyridin-1-ium-1-yl]methyl pentadecyl carbonate chloride [Xanomeline methyl pentadecylcarbonate chloride prodrug] (Table 1 Compound 36)

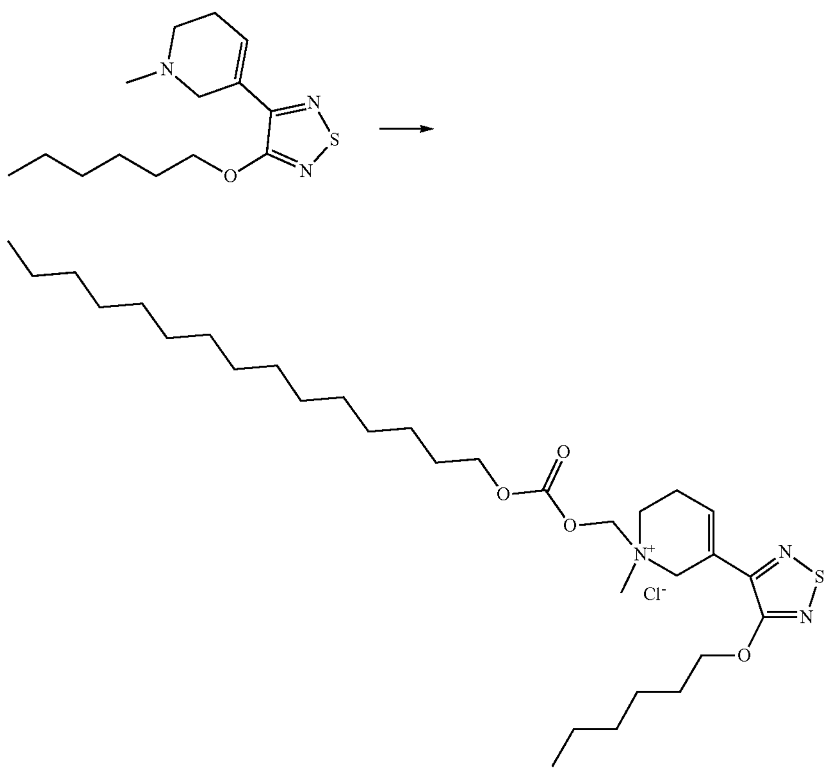

The reaction was carried out according to the general method using 0.15 g (0.63 mmol) of xanomeline. Product (220 mg, 51%) isolated as a solid. Retention time: 1.63 min; m/z=[M]$^+$ calculated for $C_{30}H_{54}N_3O_4S$ 566.4; found 566.2; $^1$H NMR (400 MHz, $CDCl_3$) δ 7.24 (dq, J=3.8, 2.1 Hz, 1H), 6.10 (d, J=8.4 Hz, 1H), 5.98 (d, J=8.4 Hz, 1H), 4.79-4.41 (m, 5H), 4.29-4.10 (m, 3H), 3.58 (s, 3H), 2.87 (s, 2H), 1.93-1.62 (m, 4H), 1.55-1.18 (m, 30H), 0.98-0.81 (m, 6H).

Example 36: Preparation of 1-methyl-5-[4-(hexyloxy)-1,2-5-thiadiazol-3-yl]-1-([(propan-2-yloxy)carbonyl]oxy)methyl-1,2,3,6-tetrahydropyridin-1-ium chloride [Xanomeline methyl isopropylcarbonate chloride prodrug] (Table 1 Compound 38)

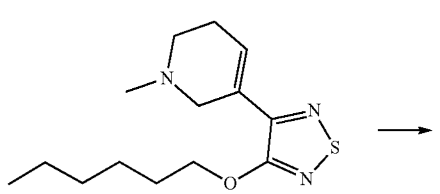

-continued

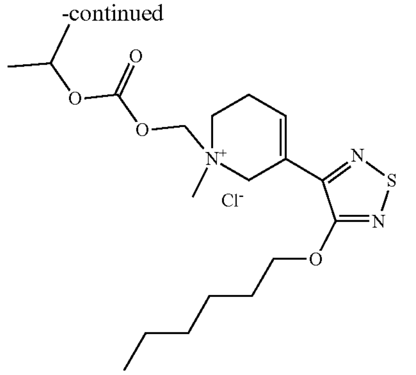

To a solution of xanomeline (150 mg, 0.53 mmol) in MeCN (2 mL) at rt was added dropwise chloromethyl isopropyl carbonate (244 mg, 1.6 mmol). The mixture was stirred at rt for 15 days, then concentrated in vacuo and the residue was purified by column chromatography on silica gel (eluent: 0 to 20% MeOH in DCM) to give the product (74 mg, 32%) as a solid. Retention time: 3.141 min; m/z=[M]$^+$ calculated for $C_{19}H_{32}N_3O_4S$ 398.2; found 398.2; $^1$H NMR (400 MHz, $CDCl_3$) δ 7.24 (tt, J=3.8, 1.7 Hz, 1H), 6.06 (d, J=8.4 Hz, 1H), 5.95 (d, J=8.4 Hz, 1H), 4.93 (hept, J=6.2 Hz, 1H), 4.79-4.57 (m, 2H), 4.57-4.40 (m, 3H), 4.18 (dt, J=13.0, 6.8 Hz, 1H), 3.58 (s, 3H), 2.96-2.80 (m, 1H), 1.95-1.77 (m, 2H), 1.53-1.21 (m, 13H), 0.98-0.85 (m, 3H).

Example 37: Preparation of 1-(([(tert-Butoxy)carbonyl]oxy)methyl)-1-methyl-5-[4-(hexyloxy)-1,2,5-thiadiazol-3-yl]-1,2,3,6-tetrahydropyridin-1-ium chloride [Xanomeline methyl tert-butylcarbonate chloride prodrug] (Table 1 Compound 37)

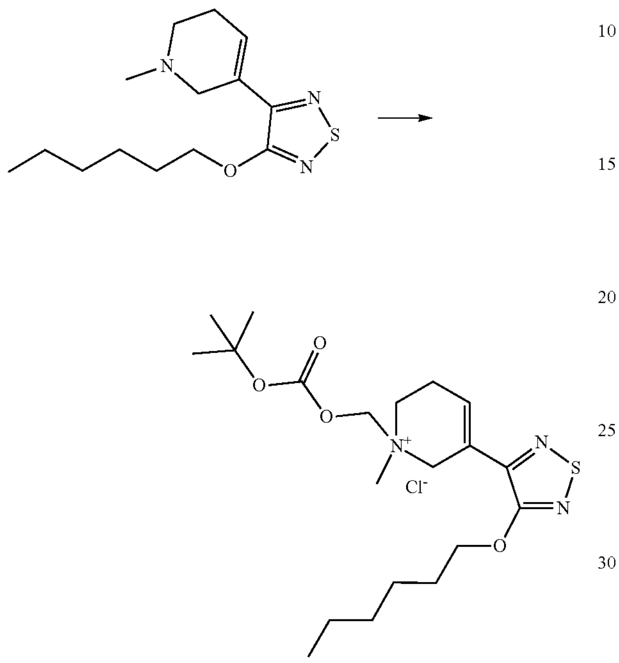

To a mixture of xanomeline (150 mg, 0.53 mmol) in MeCN (2 mL) at rt was added dropwise tert-butyl chloromethyl carbonate (266 mg, 1.6 mmol). The mixture was stirred at rt for 15 days, then concentrated in vacuo and the residue purified by column chromatography on silica gel (eluent: 0 to 20% MeOH in DCM) to give the product (80 mg, 33%) as a viscous oil. Retention time: 3.242 min; m/z=$[M]^+$ calculated for $C_{20}H_{34}N_3O_4S$ 398 412.2; found 412.2; $^1H$ NMR (400 MHz, $CDCl_3$) δ 7.24 (td, J=4.0, 1.9 Hz, 1H), 5.93 (d, J=8.5 Hz, 1H), 5.82 (d, J=8.5 Hz, 1H), 4.63 (dd, J=6.7, 2.0 Hz, 2H), 4.54-4.38 (m, 3H), 4.14 (dt, J=12.9, 6.7 Hz, 1H), 3.56 (s, 3H), 2.95-2.83 (m, 2H), 1.96-1.70 (m, 2H), 1.56-1.28 (m, 15H), 0.99-0.84 (m, 3H).

Example 38: Preparation of [5-(4-hexyloxy-1,2,5-thiadiazol-3-yl)-1-methyl-3,6-dihydro-2H-pyridin-1-ium-1-yl]methyl isobutyl carbonate chloride [Xanomeline methyl isobutylcarbonate chloride prodrug] (Table 1 Compound 39)

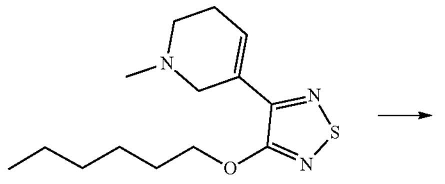

-continued

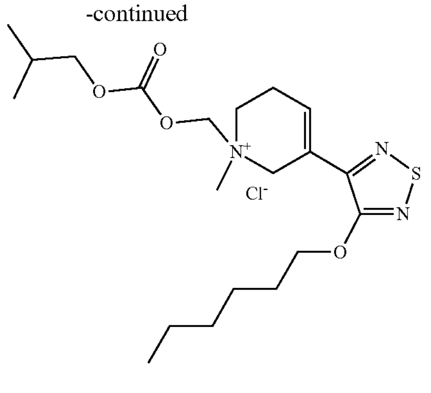

The reaction was carried out according to the general method using 0.15 g (0.63 mmol) of xanomeline. Product (146 mg, 57%) isolated as a solid. Retention time: 1.52 min; m/z=$[M]^+$ calculated for $C_{20}H_{34}N_3O_4S$ 398 412.2; found 412.2; $^1H$ NMR (400 MHz, $CDCl_3$) δ 7.24 (d, J=4.1 Hz, 1H), 6.11 (d, J=8.4 Hz, 1H), 5.98 (d, J=8.4 Hz, 1H), 4.76-4.63 (m, 2H), 4.64-4.43 (m, 3H), 4.23-4.12 (m, 1H), 4.01 (d, J=6.4 Hz, 2H), 3.59 (s, 3H), 2.87 (br. s, 2H), 2.05-1.88 (m, 5H), 1.47-1.34 (m, 6H), 0.97 (d, J=6.8 Hz, 7H), 0.91 (t, J=7.2 Hz, 3H).

Example 39: Preparation of 3-(4-hexyloxy-1,2,5-thiadiazol-3-yl)-1-methyl-piperidin-4-ol (mixture of isomers) (Table 1 Compound 41) Step 1: 3-(4-hexyloxy-1,2,5-thiadiazol-3-yl)-1-methyl-piperidine-3,4-diol

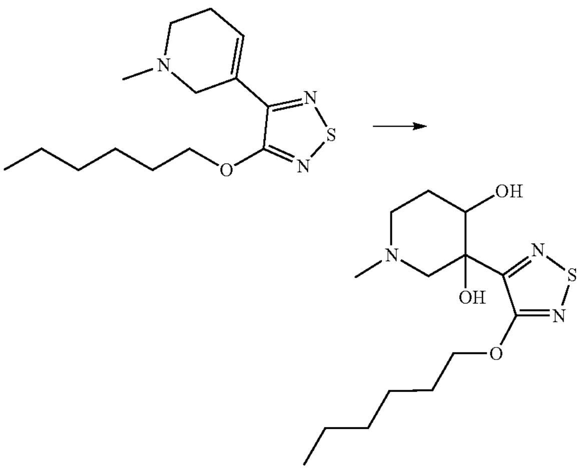

To a mixture of xanomeline (250 mg, 0.89 mmol) in acetone (10 mL) at rt was added dipotassium;dioxido(dioxo)osmium;dihydrate (1.31 mg, 0.00355 mmol), then a mixture of 4-N-methyl-morpholine-N-oxide (10.2 mol/L; 0.0958 mL, 0.977 mmol) in $H_2O$ (1 mL) was added dropwise, over 1 h. The mixture was stirred at rt for 48 h, then quenched with aqueous $NaSO_3H$ (240 mmol/L, 3.70 mL, 0.89 mmol) and extracted into EtOAc (3x5 mL). The combines organic layers were dried over $MgSO_4$, filtered and the filtrate was concentrated in vacuo. The crude product was purified by column chromatography silica gel (HC D Biotage column; 5 g; eluting with 0-10% MeOH in EtOAc) to give the product (82 mg, 29%). Retention time 1.223 min; m/z=[M+

H]+ calculated for $C_{14}H_{25}N_3O_3S$ 315.2; found 316.2; $^1H$ NMR (400 MHz, $CDCl_3$) δ 4.43 (t, J=6.5 Hz, 2H), 4.19-4.12 (m, 1H), 2.99 (dd, J=11.8, 2.5 Hz, 1H), 2.94-2.79 (m, 1H), 2.49 (d, J=11.8 Hz, 1H), 2.33 (s, 3H), 2.13 (td, J=11.4, 5.3 Hz, 2H), 2.00-1.73 (m, 4H), 1.56-1.28 (m, 4H), 1.01-0.80 (m, 6H).

Step 2: 1-(4-hexyloxy-1,2,5-thiadiazol-3-yl)-3-methyl-7-oxa-3-azabicyclo[4.1.0]heptane Table 1 Compound 40)

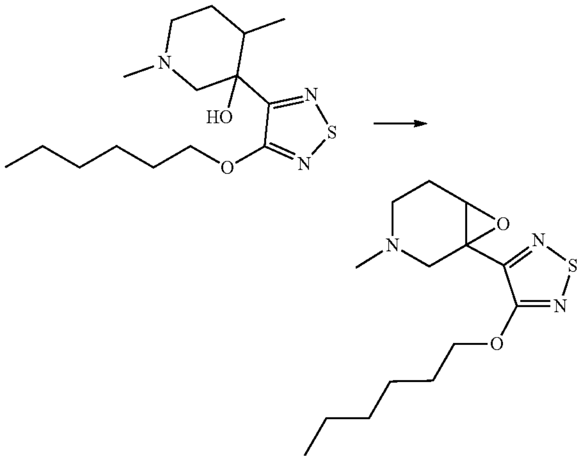

To a mixture of 3-(4-hexyloxy-1,2,5-thiadiazol-3-yl)-1-methyl-piperidine-3,4-diol (300 mg, 0.95 mmol) in pyridine (2 mL) was added MsCl (327 mg, 2.85 mmol), giving a fine precipitate. The mixture was stirred at rt for 1 h, then diluted with $H_2O$ (15 mL), giving an oily suspension, which was extracted with EtOAc (3x5 mL). The combined organic layers were washed with $H_2O$ (6x10 mL), dried over $MgSO_4$, filtered and the concentrate was concentrated in vacuo. The residue was triturated with hexane (5 mL) to give a solid, which was suspended in MeOH (2 mL) and THE (1 mL) in a microwave vial and KOH (160 mg, 2.85 mmol) added. The suspension was heated to 50° C. under microwave irradiation and the mixture was stirred for 1.5 h. $H_2O$ (5 mL) was added and the mixture was extracted with EtOAc (3x3 mL). The combined organic layers were washed with $H_2O$ (10 mL), dried over MgSO4, filtered, and the filtrate was concentrated in vacuo to give the product (130 mg, 46%) as an oil. Retention time 1.326 min; $^1H$ NMR (400 MHz, $CDCl_3$) δ 4.45 (t, J=6.7 Hz, 2H), 4.12 (dddd, J=12.8, 8.4, 6.5, 3.1 Hz, 1H), 2.99 (t, J=9.0 Hz, 1H), 2.78-2.65 (m, 2H), 2.53 (dt, J=9.1, 7.3 Hz, 1H), 2.37 (s, 3H), 2.28-2.09 (m, 2H), 1.95-1.73 (m, 2H), 1.57-1.29 (m, 6H), 1.01-0.80 (m, 3H).

Step 3: 3-(4-hexyloxy-1,2,5-thiadiazol-3-yl)-1-methyl-piperidin-4-ol (Table 1 Compound 41 and Table 1 Compound 42)

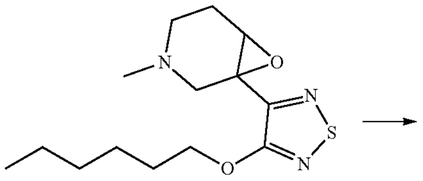

-continued

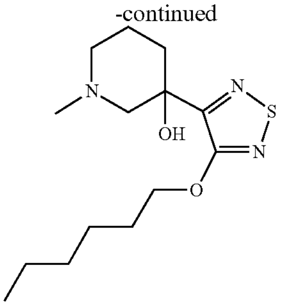

+

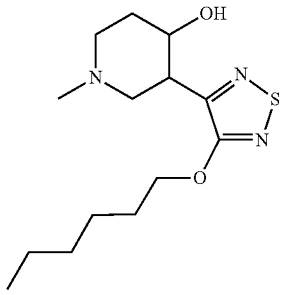

To a mixture of 1-(4-hexyloxy-1,2,5-thiadiazol-3-yl)-3-methyl-7-oxa-3-azabicyclo[4.1.0]heptane (0.13 g, 0.44 mmol) in THE (1 mL) at 0° C. under an atmosphere of $N_2$, was added 1M lithium triethylborohydride in THE (0.44 mL, 0.44 mmol). The mixture was stirred at 0° C. for 1 h, then quenched by dropwise addition of $H_2O$ (3 mL) and extracted with DCM (3x2 mL). The combined organic layers were dried over $MgSO_4$, filtered and the filtrate was concentrated in vacuo. The residue was purified by column chromatography on silica gel (HC D Biotage column; eluting with 0-5% 7M $NH_3$ in MeOH, in EtOAc) to give the products (60 mg). Retention time 1.287 min; $^1H$ NMR (400 MHz, $CDCl_3$) δ 5.00-4.65 (m, 1H), 4.40 (t, J=6.7 Hz, 2H), 3.02-2.42 (m, 4H), 2.35 (d, J=5.2 Hz, 3H), 2.32-2.22 (m, 2H), 1.85-1.75 (m, 2H), 1.50-1.29 (m, 6H), 0.95-0.85 (m, 3H). NMR consistent with a mixture of diastereoisomers.

Example 40: Preparation of Xanomeline hemi-pamoate (xanomeline:pamoate 2:1) (Table 1 Compound 594)

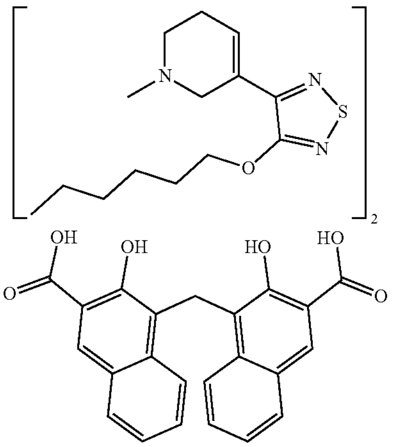

A solution of xanomeline (50 mg, 0.18 mmol, 1 equiv.) in pyridine (0.2 mL) was added to a solution of pamoic acid (35 mg, 0.09 mmol, 0.5 equiv.) in pyridine (0.4 mL) and the mixture was stirred at rt for 5 min. The mixture was concentrated and the residue was triturated with petrol (3×5 mL) to give xanomeline hemi-pamoate (62 mg, 72%) as a solid. $^{1}$H NMR (300 MHz, $CD_3OD$) δ 8.32 (s, 1H, 2×0.5ArH), 8.14 (d, 1H, J=8.4 Hz, 2×0.5ArH), 7.63 (d, 1H, J=8.7 Hz, 2×0.5ArH), 7.17 (t, 1H, J=6.9 Hz, 2×0.5ArH), 7.17 (m, 1H, C═CH), 7.07 (t, 1H, J=7.5 Hz, 2×0.5ArH), 4.84 (s, 1H, 2×0.5ArCH2), 4.41 (t, 2H, J=6.6 Hz, $CH_2O$), 4.16 (m, 2H, NCH2), 3.40 (m, 2H, CH2CH), 2.96 (s, 3H, NCH3), 2.68 (m, 2H, NCH2), 1.78 (m, 2H, CH2CH2O), 1.41 (m, 2H, CH2), 1.33 (m, 4H, 2×CH2), 0.91 (t, 3H, J=7.2 Hz, CH2CH3).

Example 41: Preparation of Xanomeline mono-pamoate (xanomeline:pamoate 1:1) (Table 1 Compound 595)

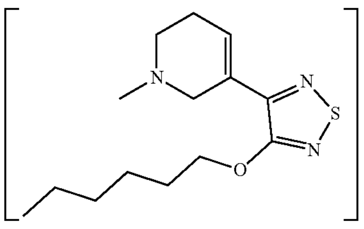

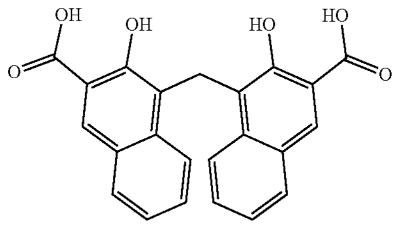

Xanomeline (33 mg, 0.12 mmol, 1.0 equiv.) and pamoic acid (46 mg, 0.12 mmol, 1.0 equiv.) were combined and dissolved in DMSO (0.2 mL) and stirred at rt for 5 min. $H_2O$ (10 mL) was added to the mixture and the resulting precipitate was collected by filtration, washed with $H_2O$ (2×5 mL) and dried in vacuo to give xanomeline mono-pamoate (71 mg, 88%) as a solid. $^{1}$H NMR (300 MHz, $CD_3OD$) δ 8.40 (s, 2H, 2×ArH), 8.20 (d, 2H, J=8.4 Hz, 2×ArH), 7.70 (d, 2H, J=8.7 Hz, 2×ArH), 7.24 (t, 2H, J=6.9 Hz, 2×ArH), 7.22 (m, 1H, C═CH), 7.13 (t, 2H, J=7.5 Hz, 2×ArH), 4.81 (s, 2H, ArCH2), 4.46 (t, 2H, J=6.6 Hz, CH2O), 4.24 (m, 2H, NCH2), 3.40 (m, 2H, CH2CH), 3.03 (s, 3H, NCH3), 2.73 (m, 2H, NCH2), 1.82 (m, 2H, CH2CH2O), 1.45 (m, 2H, CH2), 1.36 (m, 4H, 2×CH2), 0.92 (t, 3H, J=7.2 Hz, CH2CH3).

Example 42: Preparation of 5-(4-(Hexyloxy)-1,2,5-thiadiazol-3-yl)-1-methyl-1-(2-methyl-1-(propionyloxy)propyl)-1,2,3,6-tetrahydropyridin-1-ium chloride [Xanomeline oxyisobutyl propanoate chloride; NCT/2001](Table 1 Compound 373)

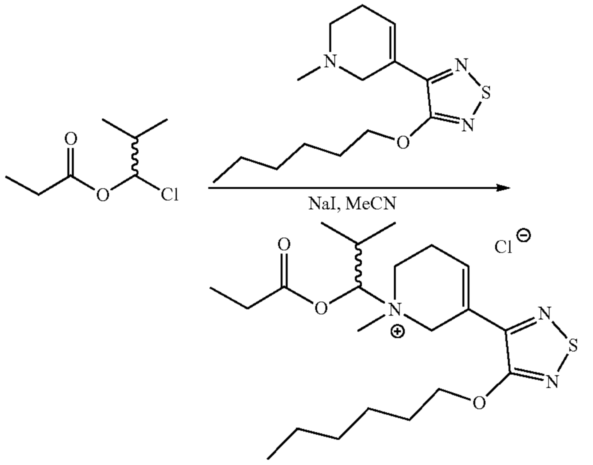

1-Chloro-2-methylpropyl propionate (175.5 mg, 170.40 μL, 1.07 mmol, 3.0 equiv.) was added to a mixture of xanomeline (100 mg, 0.36 mmol, 1.0 equiv.) and NaI (5.4 mg, 0.03 mmol, 0.1 equiv.) in MeCN (0.84 mL). The mixture was heated to 60° C. and stirred for 12 h, then concentrated under vacuum. The crude residue was purified by column chromatography on silica gel, eluting with a gradient of MeOH/DCM to afford the product (9 mg, 6%) as an oil.

LC-MS (+ve mode): m/z=410.30 $[M]^+$; $^{1}$H NMR (300 MHz, $CDCl_3$) δ 7.24 (m, 1H, C═CH), 5.90 (m, 1H, OCHN), 5.02 (m, 2H, $NCH_2$), 4.66 (br. s, 1H, NCHH), 4.47 (m, 2H, $OCH_2$), 4.34 (br. s, 1H, NCHH), 3.60 and 3.58 (s, 3H, $NCH_3$), 3.49 (m, 1H, $CH(CH_3)_2$), 2.68 (m, 4H, $CH_2C{=}O$ and $NCH_2CH_2$), 1.85 (m, 2H, $OCH_2CH_2$), 1.40 (m, 6H, $3{\times}CH_2$), 1.24 (m, 3H, $CH_2CH_3$), 1.15 and 1.05 (m, 6H, $CH(CH_3)_2$), 0.93 (m, 3H, $CH_2CH_3$).

Example 43: Preparation of 5-(4-(hexyloxy)-1,2,5-thiadiazol-3-yl)-1-methyl-1-(1-(pivaloyloxy)propyl)-1,2,3,6-tetrahydropyridin-1-ium iodide [Xanomeline oxypropyl pivalate iodide (NCT/2037)] (Table 1 Compound 596) 1-Iodopropyl pivalate

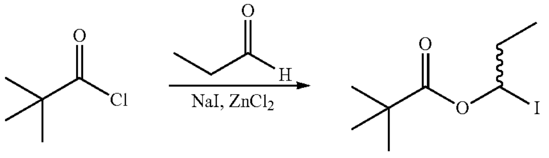

Trimethylacetyl chloride (1.00 g, 1.02 mL, 8.30 mmol, 1.0 equiv.) was added to NaI (1.49 g, 9.96 mmol, 1.2 equiv.) and catalytic $ZnCl_2$ (ca. 10 mg) at −10° C. Propionaldehyde (482 mg, 0.60 mL, 8.30 mmol, 1.0 equiv.) was added dropwise and the mixture was stirred at −10° C. for 1.5 h. The mixture was diluted in $H_2O$ (100 mL) and extracted with DCM (3×30 mL). The combined organic layers were washed with saturated aqueous sodium sulfite (30 mL), dried ($MgSO_4$) and concentrated to give 1-iodoethyl pivalate (1.41 g, 63%) as an oil, which was used without further purification. $^1$H NMR (300 MHz, $CDCl_3$) δ 6.77 (t, J=6.0 Hz, 1H, OCHI), 2.16 (m, 2H, $CH_2CH_3$), 1.19 (s, 9H, $3{\times}CH_3$), 1.01 (t, J=7.2 Hz, 3H, $CH_2CH_3$).

5-(4-(hexyloxy)-1,2,5-thiadiazol-3-yl)-1-methyl-1-(1-(pivaloyloxy)propyl)-1,2,3,6-tetrahydropyridin-1-ium iodide

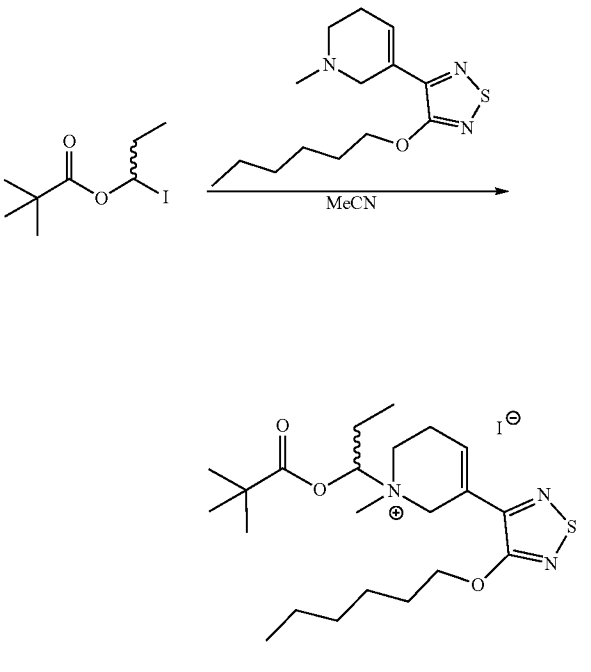

1-iodopropyl pivalate (1.73 g, 6.40 mmol, 3.0 equiv.) was added to a solution of xanomeline (600 mg, 2.14 mmol, 1.0 equiv.) in MeCN (6 mL). The mixture was heated to 60° C. and stirred for 18 h, then concentrated in vacuo. The residue was purified by column chromatography on silica gel, eluting with a gradient of MeOH/DCM. The appropriate fractions were combined and washed with sat. aq. sodium sulfite (100 mL), sat. aq. sodium iodide (100 mL), dried ($MgSO_4$) and concentrated to a glassy solid. Trituration with petrol (3×4 mL) with sonication afforded the product (110 mg). Additional product (387 mg), was obtained by trituration of the residue from concentration of the mixed fractions from the column (containing xanomeline starting material) with petrol (3×5 mL) and $Et_2O$ (3×5 mL), giving a total of 497 mg (42%). LC-MS (+ve mode): m/z=424.25 [M]$^+$; $^1$H NMR (300 MHz, $CDCl_3$) δ 7.28 (m, 1H, C═CH), 6.10 and 6.00 (dd, J=10.2, 2.4 Hz, 1H, OCHN), 4.47 (m, 2H, $OCH_2$), 4.70 and 4.27 (m, 3H, $2{\times}NCH_2$ and 1×NCHH), 3.86 and 3.44 (m, 1H, NCHH), 3.54 and 3.53 (s, 3H, $NCH_3$), 3.04 (m, 1H, NCHH), 2.78 (m, 1H, NCHH), 2.49 and 2.29 (m, 1H, CHH), 2.14 (m, 1H, CHH), 1.85 (m, 2H, $OCH_2CH_2$), 1.45 (m, 2H, $CH_2$), 1.36 (m, 4H, $2{\times}CH_2$), 1.34 and 1.31 (s, 9H, $CH(CH_3)_2$), 0.98 (m, 3H, $CHCH_2CH_3$), 0.91 (m, 3H, $CH_2CH_3$).

Example 44: 5-(4-(Hexyloxy)-1,2,5-thiadiazol-3-yl)-1-methyl-1-(phenyl(propionyloxy)methyl)-1,2,3,6-tetrahydropyridin-1-ium chloride [Xanomeline oxybenzyl propanoate chloride (NCT/1996)] (Table 1 Compound 447) Chloro(phenyl)methyl propionate

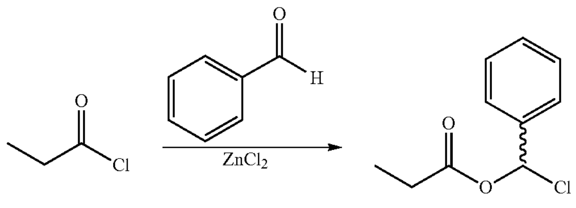

Benzaldehyde (0.50 g, 0.48 mL, 4.71 mmol, 1.0 equiv.) was added dropwise to neat propionyl chloride (0.74 g, 0.70 mL, 8.07 mmol, 1.7 equiv.) at −20° C. containing catalytic $ZnCl_2$ (ca. 5 mg). The mixture was stirred at −20° C. for 3 h, followed by 1 h at −10° C. A crystalline precipitate developed and the mixture was stored overnight to sediment at −20° C. The supernatant was removed and the solid residue was dissolved in $Et_2O$ (20 mL), washed with $H_2O$ (3×10 mL), dried ($MgSO_4$) and concentrated to give the product (697 mg, 75%) as an oil. $^1$H NMR (300 MHz, $CDCl_3$) δ 7.55 (m, 2H, 2×ArH), 7.42 (m, 4H, 3×ArH and CHPh), 2.48 (dq, J=7.5, 2.7 Hz, 2H, $CH_2$) 1.21 (t, J=7.5 Hz, 3H, $CH_3$).

5-(4-(Hexyloxy)-1,2,5-thiadiazol-3-yl)-1-methyl-1-(phenyl(propionyloxy)methyl)-1,2,3,6-tetrahydropyridin-1-ium chloride

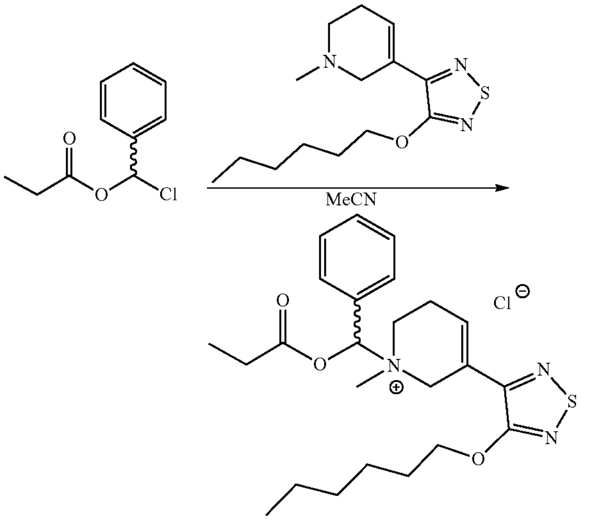

Chloro(phenyl)methyl propionate (118 mg, 0.93 mmol, 5.0 equiv.) was added to a mixture of xanomeline (50 mg, 0.18 mmol, 1.0 equiv.) in MeCN (0.5 mL). The mixture was heated to 60° C. and stirred for 3 h, then concentrated under vacuum. The crude residue was purified by column chromatography on silica gel, eluting with a gradient of MeOH/DCM to give the product (56 mg, 65%) as a glassy solid. LC-MS (+ve mode): m/z=444.20 [M]$^+$; $^1$H NMR (300 MHz, $CDCl_3$) δ 7.80 (m, 1H, CHPh), 7.52 (m, 4H, 4×ArH), 7.30

(m, 1H, ArH), 7.23 (m, 1H, C═CH), 4.79 (m, 2H, $NCH_2$), 4.48 (m, 2H, $OCH_2$), 3.55 and 3.43 (s, 3H, $NCH_3$), 2.97 (m, 2H, $NCH_2$), 2.74 (m, 2H, $NCH_2CH_2$), 1.85 (m, 2H, $O_2CCH_2$), 1.45 (m, 6H, 3×$CH_2$), 1.36 (m, 2H, $CH_2$), 1.20 (m, 3H, $O_2CCH_2CH_3$), 0.91 (m, 3H, $CH_2CH_3$).

Example 45: 5-(4-(Hexyloxy)-1,2,5-thiadiazol-3-yl)-1-methyl-1-(1-(pivaloyloxy)propyl)-1,2,3,6-tetrahydropyridin-1-ium chloride [Xanomeline oxypropyl pivalate chloride (NCT/1997)] (Table 1 Compound 352) 1-Chloropropyl pivalate

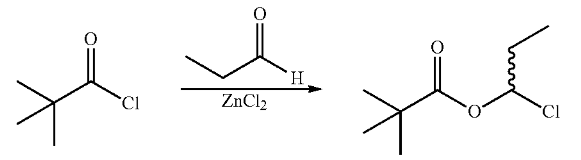

Trimethylacetyl chloride (1.0 g, 1.02 mL, 8.30 mmol, 1.0 equiv.) was added to propionaldehyde (0.48 g, 0.59 mL, 8.30 mmol, 1.0 equiv.) containing catalytic $ZnCl_2$ (ca. 5 mg) and $MgSO_4$ (70 mg, 0.58 mmol, 0.07 equiv.) at −20° C. The mixture was stirred at −10° C. to −20° C. for 4 h to give a colourless liquid. The material was used with no further purification. $^1$H NMR (300 MHz, $CDCl_3$) δ 6.31 (t, 1H, J=5.7 Hz, OCHCl), 1.97 (m, 1H, $CH_2CH_3$), 1.17 (s, 9H, 3×$CH_3$), 0.98 (t, 3H, J=7.4 Hz, $CH_3$).

5-(4-(Hexyloxy)-1,2,5-thiadiazol-3-yl)-1-methyl-1-(1-(pivaloyloxy)propyl)-1,2,3,6-tetrahydropyridin-1-ium chloride

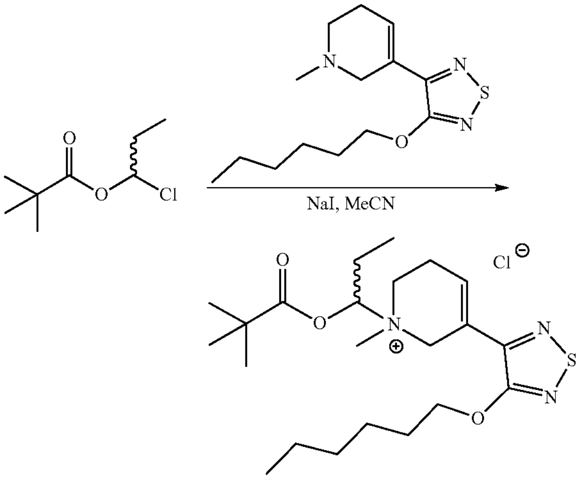

1-Chloropropyl pivalate (95 mg, 0.53 mmol, 3.0 equiv.) was added to a mixture of xanomeline (50 mg, 0.18 mmol, 1.0 equiv.) and NaI (2.7 mg, 0.02 mmol, 0.1 equiv.) in MeCN (0.42 mL). The mixture was heated to 60° C. and stirred for 12 h, then concentrated under vacuum. The residue was purified by column chromatography on silica gel, eluting with a gradient of MeOH/DCM to give a semi-solid (43.4 mg). This was combined with another batch (31.0 mg) and was further purified by reversed-phase chromatography on $C_{18}$ silica eluting with a gradient of MeCN in 0.02% hydrochloric acid. The fractions were partially concentrated and freeze-dried to afford the product (27.9 mg, 4%) as a semi-solid. LC-MS (+ve mode): m/z=424.30 $[M]^+$; $^1$H NMR (300 MHz, $CDCl_3$) δ 7.17 (m, 1H, C═CH), 5.97 (m, 1H, OCHN), 4.86 (br. s, 1H, NCHH), 4.82 (br. s, 1H, NCHH), 4.38 (br. s, 1H, NCHH), 4.40 (m, 2H, $OCH_2$), 3.50 (br. s, 1H, NCHH), 3.51 and 3.49 (s, 3H, $NCH_3$), 2.95 (m, 1H, CHH), 2.68 (m, 1H, CHH), 2.35 (m, 1H, CHH) 2.18 (m, 1H, CHH), 1.78 (m, 2H, $OCH_2CH_2$), 1.33 (m, 6H, 3×$CH_2$), 1.26 and 1.24 (s, 9H, $C(CH_3)_3$), 0.93 (m, 3H, $CH_2CH_3$), 0.86 (m, 3H, $CH_2CH_3$).

Example 46: 5-(4-(Hexyloxy)-1,2,5-thiadiazol-3-yl)-1-methyl-1-(1-(propionyloxy)propyl)-1,2,3,6-tetrahydropyridin-1-ium chloride [Xanomeline oxypropyl propanoate chloride (NCT/1994)] (Table 1 Compound 336) 1-Chloropropyl propionate

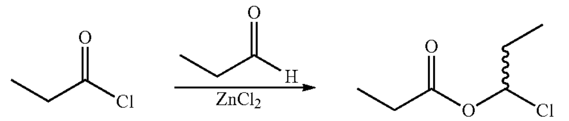

Propionaldehyde (0.64 g, 0.58 mL, 6.5 mmol, 1.0 equiv.) was added dropwise to neat propionyl chloride (0.60 g, 0.97 mL, 10.8 mmol, 1.7 equiv.) at −20° C. containing catalytic $ZnCl_2$ (ca. 5 mg). The mixture was stirred at −20° C. for 1 h, followed by rt for 1 h, then filtered through Celite, and the filter cake washed with petrol (5 mL). The filtrate was concentrated to give a an oil (778 mg, product: degradant ratio ~2:1). The material was used without further purification. $^1$H NMR (300 MHz, $CDCl_3$) δ 6.32 (t, 1H, J=5.7 Hz, OCHCl), 2.33 (q, 2H, J=7.5 Hz, $CH_2CO$), 1.97 (m, 2H, $CHCH_2$), 1.11 (t, 3H, J=7.5 Hz, $CH_3CH_2CO$), 0.98 (t, 3H, J=7.4 Hz, $CH_2CH_3$).

5-(4-(Hexyloxy)-1,2,5-thiadiazol-3-yl)-1-methyl-1-(1-(propionyloxy)propyl)-1,2,3,6-tetrahydropyridin-1-ium chloride

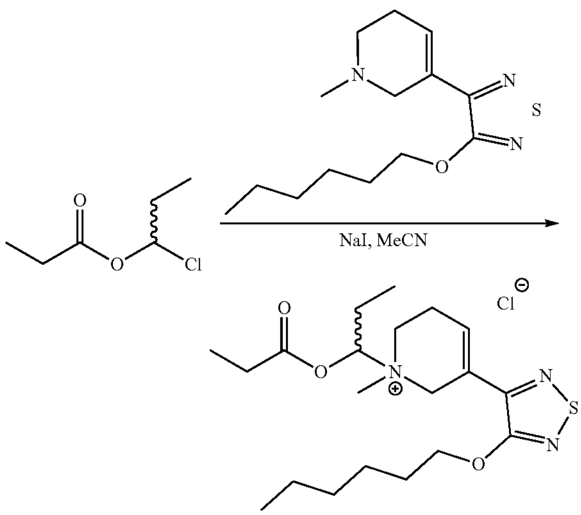

1-Chloropropyl propionate (160 mg, 0.71 mmol, 4.0 equiv.) was added to a mixture of xanomeline (50 mg, 0.18 mmol, 1.0 equiv.) and NaI (2.7 mg, 0.02 mmol, 0.1 equiv.) in MeCN (0.42 mL). The mixture was heated to 50° C. and stirred for 3 days, followed by stirring at 60° C. for 12 h. The mixture was concentrated under vacuum and the crude residue was purified by column chromatography on silica gel, eluting with a gradient of MeOH/DCM to afford the product (13 mg, 17%) as a semi-solid. LC-MS (+ve mode): m/z=396.20 $[M]^+$; $^1H$ NMR (300 MHz, $CDCl_3$) δ 7.18 (m, 1H, C=CH), 5.95 (t, 1H, J=10.2 Hz, OCHN), 4.78 (m, 2H, $NCH_2$), 4.38 (m, 1H, NCHH), 4.41 (m, 2H, $OCH_2$), 3.53 (m, 1H, NCHH), 3.51 (s, 3H, $NCH_3$), 2.99 (m, 1H, CHH), 261 (m, 3H, CHH and $CH_2$), 2.08 (m, 2H, $NCH_2CH_2$), 1.78 (m, 2H, $OCH_2CH_2$), 1.31 (m, 6H, $3\times CH_2$), 1.17 (m, 3H, $CH_3$), 0.92 (m, 3H, $CH_2CH_3$). 0.86 (m, 3H, $CH_2CH_3$).

Example 47: 5-(4-(Hexyloxy)-1,2,5-thiadiazol-3-yl)-1-methyl-1-(phenyl(pivaloyloxy)methyl)-1,2,3,6-tetrahydropyridin-1-ium chloride [Xanomeline oxybenzyl pivalate chloride (NCT/1995)] (Table 1 Compound 463) Chloro(phenyl)methylpivalate

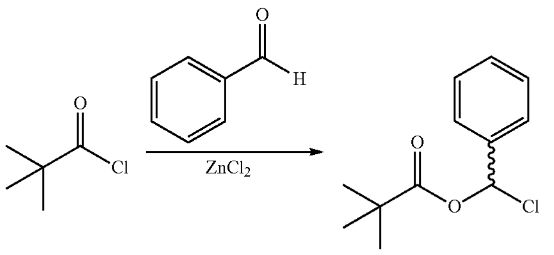

Benzaldehyde (0.5 g, 0.48 mL, 4.71 mmol, 1.0 equiv.) was added dropwise to trimethylacetyl chloride (0.97 g, 0.98 mL, 8.01 mmol, 1.7 equiv.) at −20° C. containing catalytic $ZnCl_2$ (ca. 5 mg). The mixture was stirred for 4 h, maintaining the temperature between −20° C. and −10° C. The resulting colourless liquid contained a 1:1 mixture of benzaldehyde to chloro(phenyl)methyl pivalate and was used without further purification. $^1H$ NMR (300 MHz, $CDCl_3$) δ 7.54 (m, 2H, ArH), 7.40 (m, 4H, 3×ArH and CHPh), 1.28 (s, 9H, $3\times CH_3$).

5-(4-(Hexyloxy)-1,2,5-thiadiazol-3-yl)-1-methyl-1-(phenyl(pivaloyloxy)methyl)-1,2,3,6-tetrahydropyridin-1-ium chloride

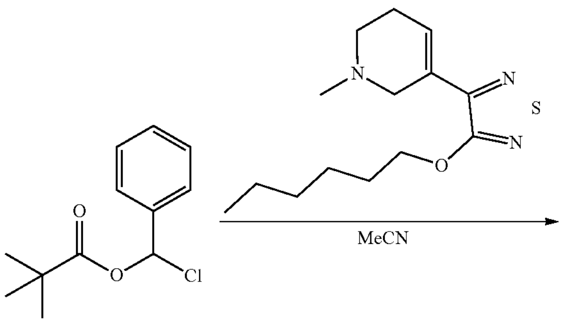

-continued

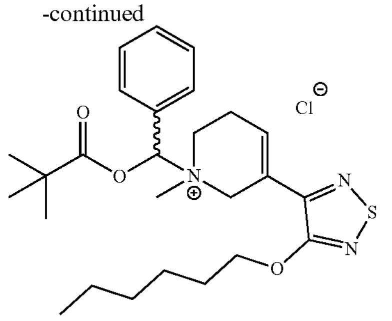

Chloro(phenyl)methyl pivalate (211 mg, 0.93 mmol, 5.0 equiv.) was added to a mixture of xanomeline (50 mg, 0.18 mmol, 1.0 equiv.) in MeCN (0.5 mL). The mixture was heated to 60° C. and stirred for 4.5 h, then cooled to rt and left overnight. The mixture was concentrated under vacuum and the crude residue was purified by column chromatography on silica gel, eluting with a gradient of MeOH in DCM to afford the product (8.5 mg, 9%) as a glassy solid. LC-MS (+ve mode): m/z=472.30 $[M]^+$; $^1H$ NMR (300 MHz, $CDCl_3$) δ 7.76 (m, 1H, CHPh), 7.60 (m, 2H, 2×ArH), 7.49 (m, 2H, 2×ArH), 7.30 (m, 1H, ArH), 7.11 (m, 1H, C=CH), 4.81 (m, 2H, $NCH_2$), 4.49 (m, 2H, $OCH_2$), 3.57 and 3.42 (br. s, 3H, $NCH_3$), 2.95 (m, 2H, $NCH_2$), 2.71 (m, 2H, $NCH_2CH_2$), 1.86 (m, 2H, $OCH_2CH_2$), 1.47 and 1.36 (m, 6H, $3\times CH_2$), 1.34 and 1.30 (s, 9H, $3\times CH_3$), 0.92 (m, 3H, $CH_2CH_3$).

Example 48

Improved Synthesis of Xanomeline:

3-(Hexyloxy)-4-(pyridin-3-yl)-1,2,5-thiadiazole

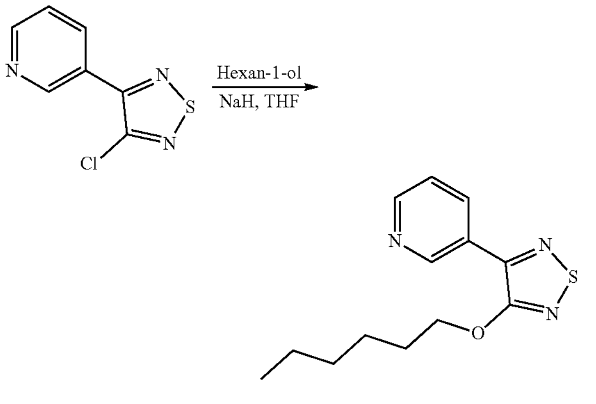

Hexan-1-ol (5.94 g, 7.24 mL, 58.1 mmol, 1.15 equiv.) was added to a mixture of 3-chloro-4-(pyridin-3-yl)-1,2,5-thiadiazole (10.0 g, 50.6 mmol) in anhydrous THF (100 mL). Sodium hydride (4.05 g as a 60% suspension in oil, 101.2 mmol, 2.0 equiv.) was added in portions and the mixture was stirred at rt for 18 h. The mixture was quenched with $H_2O$ (15 mL) and concentrated in vacuo. The residue was diluted with $H_2O$ (50 mL) and extracted with $Et_2O$ (3×25 mL). The combined organic layers were washed with sat. brine (30 mL), dried ($MgSO_4$) and concentrated in vacuo to give the product (15.4 g, quant.) as a solid. LC-MS (+ve mode): m/z=264.15 $[M+H]^+$; $^1H$ NMR (300 MHz, $CDCl_3$) δ 9.41 (dd, 1H, J=2.4, 0.9 Hz, ArH), 8.66 (dd, 1H, J=4.8, 1.5 Hz, ArH), 8.46 (m, 1H, ArH), 7.42 (ddd, 1H, J=8.1, 4.9, 0.9 Hz, ArH), 4.53 (t, 2H, J=6.6 Hz, $OCH_2$), 1.90 (m, 2H, $OCH_2CH_2$), 1.50 (m, 2H, $CH_2$), 1.36 (m, 4H, $2\times CH_2$), 0.91 (m, 3H, $CH_3$). 3-(4-(Hexyloxy)-1,2,5-thiadiazol-3-yl)-1-methylpyridin-1-ium iodide

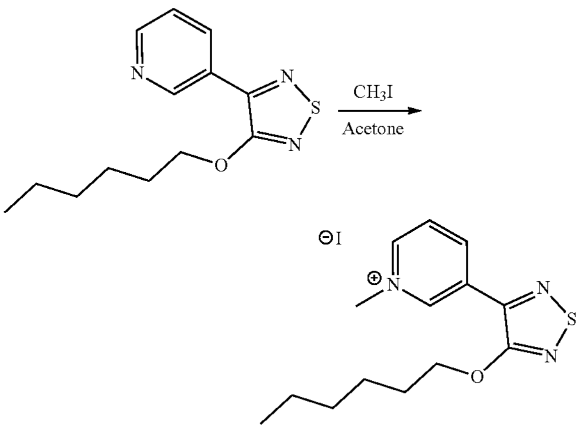

MeI (23.0 g, 10.1 mL, 161.9 mmol, 3.2 equiv.) was added to a mixture of 3-(hexyloxy)-4-(pyridin-3-yl)-1,2,5-thiadiazole (13.3 g, 50.6 mmol) in anhydrous acetone (100 mL) and the mixture was stirred at 30° C. for 18 h. The mixture was concentrated in vacuo and the residue stirred in $Et_2O$ (200 mL). The resulting precipitate was collected by filtration and air dried to give the product (19.8 g, 97%) as a solid. LC-MS (+ve mode): m/z=278.15 $[M]^+$; $^1H$ NMR (300 MHz, $CDCl_3$) δ 9.80 (d, 1H, J=6.1 Hz, ArH), 9.40 (s, 1H, ArH), 9.16 (d, 1H, J=8.3 Hz, ArH), 8.24 (dd, 1H, J=8.3, 6.0 Hz, ArH), 4.83 (s, 3H, $NCH_3$), 4.61 (t, 2H, J=6.9 Hz, $OCH_2$), 1.95 (m, 2H, $OCH_2CH_2$), 1.49 (m, 2H, $CH_2$), 1.38 (m, 4H, $2\times CH_2$), 0.92 (m, 3H, $CH_3$).

3-(Hexyloxy)-4-(1-methyl-1,2,5,6-tetrahydropyridin-3-yl)-1,2,5-thiadiazole (Xanomeline)

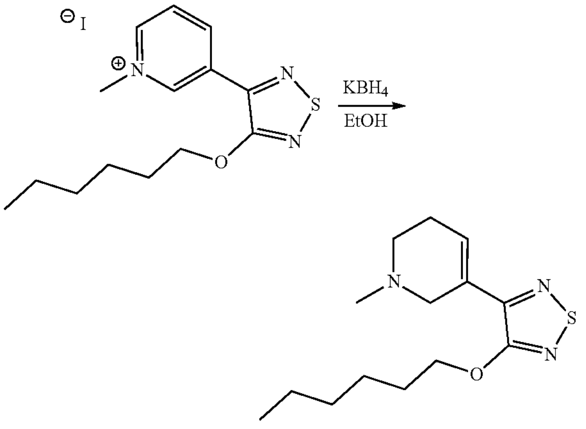

Potassium borohydride (3.55 g, 65.9 mmol, 1.5 equiv.) was added to a mixture of 3-(4-(hexyloxy)-1,2,5-thiadiazol-3-yl)-1-methylpyridin-1-ium iodide (17.8 g, 43.9 mmol) in anhydrous EtOH (175 mL) at −5° C. and the mixture was stirred at −5° C. for 4 h then left to warm to rt, and stirred overnight. The mixture was quenched with $H_2O$ (10 mL) and concentrated in vacuo. The residue was diluted with $H_2O$ (150 mL), extracted with $CH_2Cl_2$ (4×100 mL) and the combined extracts were dried ($MgSO_4$) and concentrated to an oil. The oil was taken up in petrol (200 mL), filtered through Celite and the filtrate was concentrated to give the product (11.1 g, 90%) as a semi-solid. LC-MS (+ve mode): m/z=282.20 $[M+H]^+$; $^1H$ NMR (300 MHz, $CDCl_3$) δ 7.07 (dt, 1H, J=4.1, 2.2 Hz, C═CH), 4.44 (t, 2H, J=6.6 Hz, $OCH_2$), 3.47 (m, 2H, $NCH_2$), 2.60 (t, 2H, J=5.8 Hz, $NCH_2$), 2.48 (s, 3H, $NCH_3$), 2.46 (m, 2H, $NCH_2CH_2$), 1.84 (m, 2H, $OCH_2CH_2$), 1.46 (m, 2H, $CH_2$), 1.35 (m, 4H, $2\times CH_2$), 0.90 (m, 3H, $CH_3$).

Reduction trials on 3-(4-(hexyloxy)-1,2,5-thiadiazol-3-yl)-1-methylpyridin-1-ium iodide

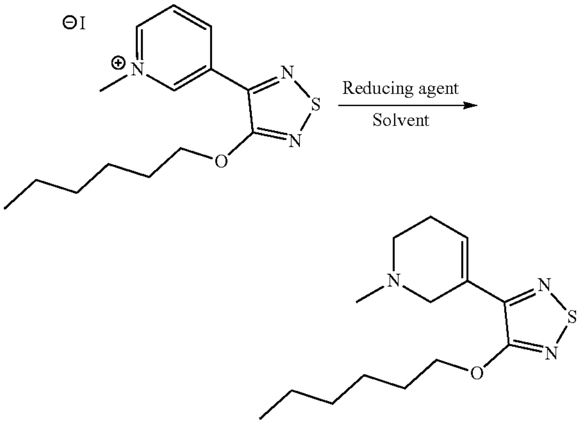

3-(4-(Hexyloxy)-1,2,5-thiadiazol-3-yl)-1-methylpyridin-1-ium iodide (0.5 g, 1.2 mmol) was dissolved in the appropriate solvent (5 mL) at −5° C. and the reducing agent (3.6 mmol, 3.0 equiv. or 1.8 mmol, 1.5 equiv.) was added portionwise. The mixture was stirred at −5° C. for 4 h, then warmed to rt and stirred overnight.

Aliquots were analysed by LC-MS from the reaction mixture after 2, 4 and 18 h: Xanomeline: m/z=282.20, $t_R$~5.9 min, starting material. m/z=278.15, $t_R$~5.6 min. The reaction mixture was diluted with $H_2O$ (30 mL) and extracted with $CH_2Cl_2$ (3×20 mL) The combined extracts were dried ($MgSO_4$) and concentrated. The residue was entrained with petrol (3×5 mL), combined and concentrated to give a semi-solid.

| Conditions (3.0 equiv. unless stated otherwise) | Results: product to starting material peak ratio by UV at 254 nm 2 h | 4 h | 18 h | Yield/Analysis |
|---|---|---|---|---|
| $NaBH_4$, EtOH | 2.8:1 | 2.8:1 | 3.2:1 | 289 mg (83%) |
| $NaBH_4$, MeOH | 1:1.1 | 1:1.2 | 1:1.2 | 219 mg (65%), 98.1 % by HPLC |
| $KBH_4$, EtOH | 5.8:1 | 10:1 | 11.7:1 | 321 mg (92%), 92.5 % by HPLC |
| $KBH_4$, MeOH | 2.6:1 | 2.1:1 | 2.0:1 | 273 mg (81%), 97.0 % by HPLC |
| $KBH_4$ (1.5 equiv.), EtOH | 3.9:1 | 9.3:1 | 16.4:1 | 331 mg (95%), 92.3 % by HPLC |

Synthesis of xanomeline via recycling of 3-chloro-4-(1-methyl-1,2,5,6-tetrahydropyridin-3-yl)-1,2,5-thiadiazole

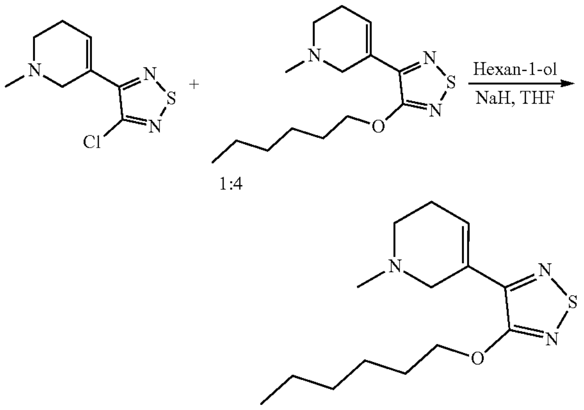

A mixture containing xanomeline and residual 3-chloro-4-(1-methyl-1,2,5,6-tetrahydropyridin-3-yl)-1,2,5-thiadiazole in a 4:1 molar ratio (10.9 g) was dissolved in anhydrous THF (100 mL). Hexan-1-ol (1.24 g, 1.47 mL, 12.17 mmol, 1.2 equiv.) was added followed by portion-wise addition of NaH (0.48 g as 60% suspension in oil, 20.1 mmol, 2.0 equiv.). The mixture was stirred at rt overnight, then quenched with $H_2O$ (10 mL) and concentrated in vacuo. The resulting solid was suspended in $H_2O$ (70 mL) and extracted with EtOAc (4×50 mL). The combined organic layers were washed with sat. brine (50 mL), dried ($MgSO_4$) and concentrated to afford the product (xanomeline) (11.2 g) as a solid.

| Literature comparison | |
|---|---|
| Source | Result |
| Sauerberg et al., *Journal of Medicinal Chemistry*, 1992, *Vol.* 35, No. 12, 2274-2283 | 38% yield over 3 steps |
| Kane et al., *Bioorg. Med. Chem.* 2008, 16 1376-1392 | 40% over 3 steps and conversion to HCl salt. |

Example 49: 5-(4-(Hexyloxy)-1,2,5-thiadiazol-3-yl)-1-methyl-1-(1-(pivaloyloxy)ethyl)-1,2,3,6-tetrahydropyridin-1-ium iodide (Table 1 Compound 190)

1-Iodoethyl pivalate

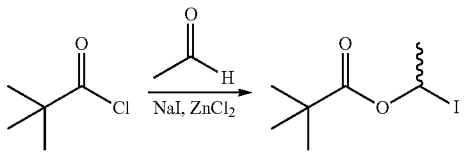

Trimethylacetyl chloride (1.00 g, 0.98 mL, 8.30 mmol, 1.0 equiv.) was added to NaI (1.49 g, 9.96 mmol, 1.2 equiv.) and catalytic $ZnCl_2$ (ca. 5 mg) at −10° C. Acetaldehyde (365 mg, 0.46 mL, 8.30 mmol, 1.0 equiv.) was added dropwise and the mixture was stirred at −10° C. for 1.5 h. The mixture was diluted with $H_2O$ (50 mL) and extracted with DCM (3×20 mL). The combined organic layers were washed with saturated aqueous sodium sulfite (20 mL), dried ($MgSO_4$) and concentrated to give the product (1.41 g, 66%) as an oil, which was used without further purification. $^1H$ NMR (300 MHz, $CDCl_3$) δ 6.78 (q, 1H, J=6.1 Hz, OCHI), 2.14 (d, 3H, J=6.1 Hz, $CH_3CH$), 1.13 (s, 9H, $C(CH_3)_3$).

5-(4-(Hexyloxy)-1,2,5-thiadiazol-3-yl)-1-methyl-1-(1-(pivaloyloxy)ethyl)-1,2,3,6-tetrahydropyridin-1-ium iodide

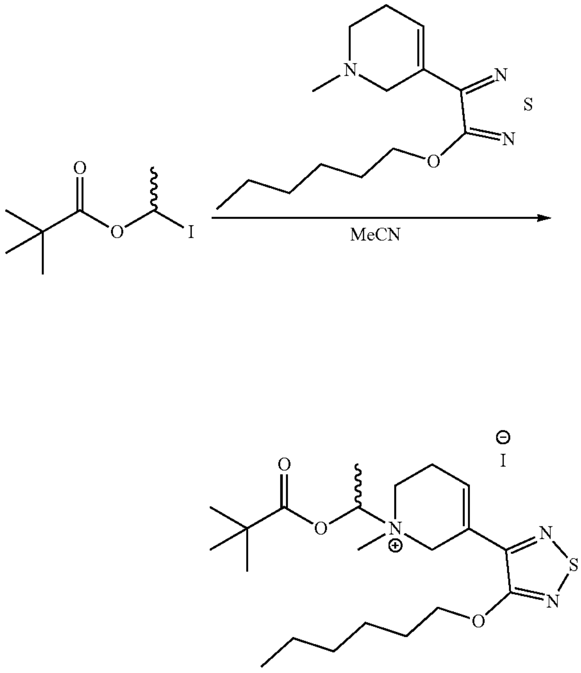

1-Iodoethyl pivalate (820 mg, 3.21 mmol, 3.0 equiv.) was added to a solution of xanomeline (300 mg, 1.07 mmol, 1.0 equiv.) in MeCN (3 mL). The reaction mixture was heated to 60° C. and stirred for 18 h. The mixture was concentrated under vacuum and the crude residue was dissolved in $CH_2Cl_2$ (50 mL), washed with saturated aqueous sodium sulfite (20 mL) followed by saturated aqueous NaI (20 mL), dried ($MgSO_4$) and concentrated. The residue was triturated with petrol (2×15 mL) and $Et_2O$ (3×15 mL) to give a solid. The solid was collected by filtration and washed with $Et_2O$ (4×5 mL) to give the product (421 mg, 73%) as a solid. LC-MS (+ve mode): m/z=410.30 $[M]^+$; $^1H$ NMR (300 MHz, $CDCl_3$) δ 7.19 (m, 1H, C=CH), 6.08 (m, 1H, OCHN), 4.84 (d, 1H, J=16.2 Hz, NCHH), 4.57 (m, 2H, 2×NCHH), 4.41 (m, 2H, $OCH_2$), 4.31 and 3.72 (m, 1H, NCHH), 3.50 and 3.48 (s, 3H, $NCH_3$), 3.00 (m, 1H, CHH), 2.68 (m, 1H, CHH), 1.75 (m, 5H, $OCH_2CH_2$ and $CHCH_3$), 1.31 (m, 6H, $3{\times}CH_2$), 1.25 and 1.23 (s, 9H, s, $C(CH_3)_3$), 0.86 (m, 3H, $CH_2CH_3$).

Example 50: 5-(4-(Hexyloxy)-1,2,5-thiadiazol-3-yl)-1-methyl-1-(1-(pivaloyloxy)ethyl)-1,2,3,6-tetrahydropyridin-1-ium pamoate [Xanomeline oxyethyl pivalate pamoate prodrug](Table 1 Compound 597)

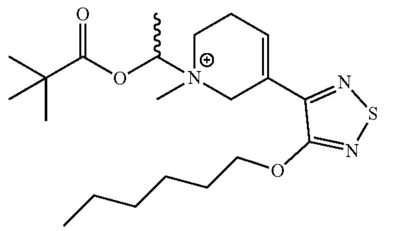

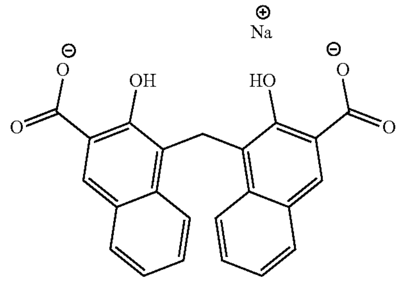

5-(4-(Hexyloxy)-1,2,5-thiadiazol-3-yl)-1-methyl-1-(1-(pivaloyloxy)ethyl)-1,2,3,6-tetrahydropyridin-1-ium iodide (100 mg, 0.19 mmol, 1 equiv.) and pamoic acid disodium salt (80.4 mg, 0.19 mmol, 1 equiv.) were suspended in anhydrous methanol (1.5 mL). The suspension became clear transiently before becoming cloudy. The mixture was stirred at room temperature for 2 h, centrifuged and the supernatant was concentrated to give a brown semi-solid (233 mg). The semi-solid was resuspended in MeOH (100 mL) and $H_2O$ (5 mL) was added and sonicated for 20 min. The supernatant removed and the solid residue was washed with $H_2O$ (5 mL) and the residue lyophilised. overnight to give xanomeline oxyethyl pivalate pamoate (119.4 mg, 78%) as a solid.

Alternative Procedure:

5-(4-(Hexyloxy)-1,2,5-thiadiazol-3-yl)-1-methyl-1-(1-(pivaloyloxy)ethyl)-1,2,3,6-tetrahydropyridin-1-ium iodide (88.0 mg, 0.16 mmol, 1 equiv.) and pamoic acid disodium salt (70.8 mg, 0.16 mmol, 1 equiv.) were suspended in anhydrous MeOH (1.3 mL). The suspension became clear transiently before becoming cloudy. The mixture was stirred at room temperature for 2 h, centrifuged and the supernatant was concentrated to give a brown semi-solid (158 mg). The solid residue was suspended in $H_2O$ (1.5 mL) and the resulting suspension was sonicated for 10 min. The supernatant was removed via syringe and the residue was washed with $H_2O$ (1 mL) and the solid was lyophilised overnight to give xanomeline oxyethyl pivalate pamoate (99 mg, 74%) as a solid. LC-MS (+ve mode): m/z=410.25 $[M]^+$; $^1H$ NMR (300 MHz, $CD_3OD$) δ 8.22 (s, 2H, 2×ArH), 8.12 (m, 2H, 2×ArH), 7.53 (m, 2H, 2×ArH), 7.14 (m, 1H, C═CH), 7.05 (m, 2H, 2×ArH), 6.94 (m, 2H, 2×ArH), 6.04 (m, 1H, OCHN), 4.74 (s, 2H, $ArCH_2Ar$), 4.33 (m, 4H, $OCH_2$ and 2×NCHH), 3.43 (m, 2H, 2×NCHH), 2.98 and 2.97 (s, 3H, $NCH_3$), 2.64 (m, 2H, $CH_2$), 1.72 (m, 2H, $OCH_2CH_2$), 1.60 and 1.57 (d, J=5.9 Hz, 3H, $CHCH_3$), 1.29 (m, 6H, $3×CH_2$), 1.20 and 1.18 (s, 9H, $C(CH_3)_3$), 0.83 (m, 3H, $CH_2CH_3$).

Example 51: 5-(4-(Hexyloxy)-1,2,5-thiadiazol-3-yl)-1-methyl-1-(1-(pivaloyloxy)ethyl)-1,2,3,6-tetrahydropyridin-1-ium hemi-pamoate [Xanomeline oxyethyl pivalate hemi-pamoate prodrug] (Table 1 Compound 598)

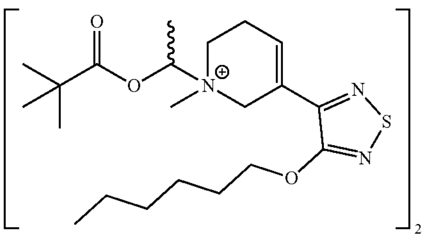

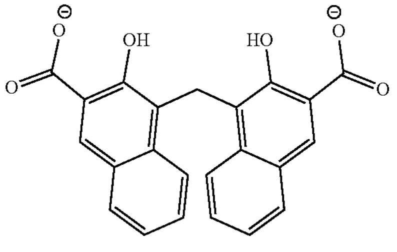

Xanomeline oxyethyl pivalate iodide (228 mg, 0.42 mmol, 1 equiv.) and pamoic acid disodium salt (56.3 mg, 0.13 mmol, 0.5 equiv.) were suspended in anhydrous MeOH (2 mL). The suspension became clear transiently before becoming cloudy. The mixture was stirred at room temperature for 2 h, centrifuged and the supernatant was concentrated to give a brown semi-solid (197 mg). The semi-solid was resuspended in MeOH (100 mL) and $H_2O$ (5 mL) was added and sonicated for 20 min. The supernatant removed and the solid residue was washed with $H_2O$ (5 mL) and the residue lyophilised. overnight to give xanomeline oxyethyl pivalate hemi-pamoate (132.4 mg, 84%) as a solid.

Alternative Procedure:

Xanomeline oxyethyl pivalate iodide (88.0 mg, 0.16 mmol, 1 equiv.) and pamoic acid disodium salt (35.4 mg, 0.081 mmol, 0.5 equiv.) were suspended in anhydrous MeOH (1.3 mL). The suspension became clear transiently before becoming cloudy. The mixture was stirred at room temperature for 2 h, centrifuged and the supernatant was removed to give a brown semi-solid (108 mg). The residue was suspended in $H_2O$ (1.5 mL) and the resulting suspension was sonicated for 10 min. The supernatant was removed via syringe and the residue was washed with $H_2O$ (1 mL) and the solid was lyophilised to give xanomeline oxyethyl pivalate hemi-pamoate (81 mg, 82%) as a solid. LC-MS (+ve mode): m/z=410.25 $[M]^+$; $^1H$ NMR (300 MHz, $CD_3OD$) δ 8.22 (s, 2H, 2×ArH), 8.12 (m, 2H, 2×ArH), 7.53 (m, 2H, 2×ArH), 7.17 (m, 2H, 2×C═CH), 7.05 (m, 2H, 2×ArH), 6.94 (m, 2H, 2×ArH), 6.07 (m, 2H, 2×OCHN), 4.73 (s, 2H, $ArCH_2$), 4.36 (m, 8H, $2×OCH_2$ and 4×NCHH), 3.48 (m, 4H, 4×NCHH), 3.02 and 3.01 (s, 6H, $2×NCH_3$), 2.68 (m, 4H, $2×CH_2$), 1.73 (m, 4H, $2×OCH_2CH_2$), 1.62 and 1.60 (d, 6H, J=5.9 Hz, $2×CHCH_3$), 1.29 (m, 12H, $6×CH_2$), 1.20 and 1.19 (s, 18H, $2×C(CH_3)_3$), 0.83 (m, 6H, $2×CH_2CH_3$).

Example 52: 5-(4-(Hexyloxy)-1,2,5-thiadiazol-3-yl)-1-methyl-1-(1-(pivaloyloxy)propyl)-1,2,3,6-tetrahydropyridin-1-ium pamoate [Xanomeline oxypropyl pivalate pamoate prodrug] (Table 1 Compound 599)

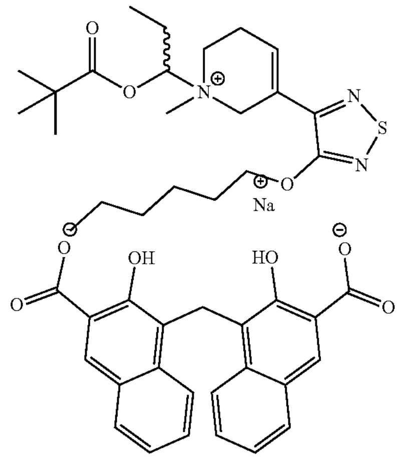

Xanomeline oxypropyl pivalate iodide (155 mg, 0.28 mmol) and disodium pamoate (121.5 mg, 0.28 mmol, 1.0 equiv.) were combined in MeOH (1 mL) and stirred at rt for 1 h. $H_2O$ (5 mL) was added and the resulting fine suspension was centrifuged and the solid was transferred with MeOH (ca. 2 mL) to a flask and concentrated to give a semi-solid, which was lyophilised to remove $H_2O$. To the resulting compound (162 mg) was added disodium pamoate (45 mg) and MeOH (0.5 mL). The resulting mixture was stirred for 1 h, then $H_2O$ (10 mL) was added and the solid was collected by centrifugation (3000 rpm for 20 min) and dried to give the product (169 mg, 72%) as a solid. LC-MS (+ve mode): m/z=424.30 $[M]^+$; $^1H$ NMR (300 MHz, $CD_3OD$) δ 8.32 (s, 2H, 2×ArH), 8.23 (m, 2H, 2×ArH), 7.63 (m, 2H, 2×ArH), 7.16 (m, 3H, C═CH and 2×ArH), 7.04 (m, 2H, 2×ArH), 6.07 and 6.00 (2×d, J=10.4, 2.5 and 10.7, 2.2 Hz, 1H, OCHN), 4.84 (s, 2H, $ArCH_2$), 4.43 (m, 3H, $OCH_2$ and NCHH), 4.23 (m, 1H, NCHH), 3.48 (m, 1H, NCHH), 3.40 (m, 1H, NCHH), 3.01 and 2.98 (s, 3H, $NCH_3$), 2.70 (m, 2H, $CH_2$), 2.10 (m, 2H, $OCHCH_2$), 1.80 (m, 2H, $OCH_2CH_2$), 1.44 and 1.35 (m, 6H, $3\times CH_2$), 1.31 and 1.28 (s, 9H, $C(CH_3)_3$), 0.94 (m, 6H, $2\times CH_2CH_3$).

Example 53: 5-(4-(Hexyloxy)-1,2,5-thiadiazol-3-yl)-1-methyl-1-(1-(pivaloyloxy)propyl)-1,2,3,6-tetrahydropyridin-1-ium hemi-pamoate [Xanomeline oxypropyl pivalate hemi-pamoate prodrug] (Table 1 Compound 600)

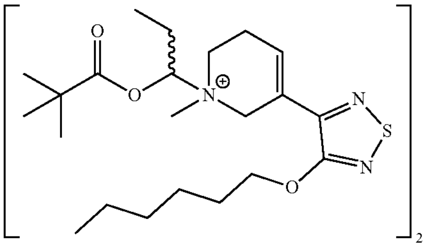

-continued

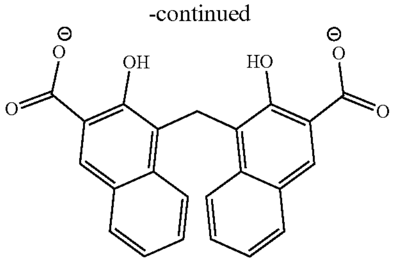

Xanomeline oxypropyl pivalate iodide (180 mg, 0.33 mmol) and disodium pamoate (70.5 mg, 0.17 mmol, 0.5 equiv.) were combined in MeOH (1 mL) and stirred at rt for 1 h. $H_2O$ (5 mL) was added and the resulting fine suspension was centrifuged and the solid was transferred with MeOH (ca. 2 mL) to a flask, and concentrated to give a semi-solid, which was lyophilised to give the hemi-pamoate (178 mg, 84%) as a solid. LC-MS (+ve mode): m/z=424.30 $[M]^+$; $^1H$ NMR (300 MHz, $CD_3OD$) δ 8.30 (s, 2H, 2×ArH), 8.24 (m, 2H, 2×ArH), 7.62 (m, 2H, 2×ArH), 7.21 (m, 2H, 2×C═CH), 7.15 (m, 2H, 2×ArH), 7.04 (m, 2H, 2×ArH), 6.08 (dd, 1H, J=10.5, 2.5, OCHN), 6.01 (dd, 1H, J=10.7, 2.2 Hz, OCHN) 4.81 (s, 2H, $ArCH_2$), 4.44 and 4.24 (m, 8H, $2\times OCH_2$ and 4×NCHH), 3.49 and 3.39 (m, 4H, 4×NCHH), 3.02 and 2.99 (s, 6H, $2\times NCH_3$), 2.70 (m, 4H, $2\times CH_2$), 2.12 (m, 4H, $2\times OCHCH_2$), 1.80 (m, 4H, $2\times OCH_2CH_2$), 1.44 and 1.35 (m, 12H, $6\times CH_2$), 1.31 and 1.29 (s, 18H, $2\times C(CH3)_3$), 0.95 (m, 6H, $2\times CH_2CH_3$), 0.90 (m, 6H, $2\times CH_2CH_3$).

Example 54: 5-(4-(Hexyloxy)-1,2,5-thiadiazol-3-yl)-1-methyl-1-(1-(propionyloxy)ethyl)-1,2,3,6-tetrahydropyridin-1-ium iodide [Xanomeline oxyethyl propanoate iodide prodrug](Table 1 Compound 601)

1-Iodoethyl propionate

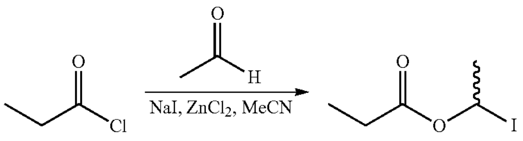

To a suspension of NaI (0.75 g, 4.98 mmol, 1.2 equiv.), propionyl chloride (384 mg, 362 μL, 4.15 mmol, 1 equiv.) and catalytic $ZnCl_2$ (5 mg, 0.037 mmol) in anhydrous MeCN (2 mL) at −10° C. under an atmosphere of N2 was added acetaldehyde (183 mg, 234 μL, 4.15 mmol, 1 equiv.) dropwise at −10° C. The mixture was stirred at −10° C. for 1.5 h before diluting with DCM (5 mL) and ice-cold $H_2O$ (20 mL). The layers were separated and the aqueous phase was extracted with DCM (2×5 mL). The combined organic layers were dried ($Na_2SO_4$), filtered and concentrated to give a semi-solid (0.95 g, quant.). This material was used without further purification. $^1H$ NMR (300 MHz, $CDCl_3$) δ 6.86 (q, 1H, J=6.1 Hz, OCH), 2.32 (m, 2H, $CH_2$), 2.20 (d, 3H, J=6.1 Hz, $CH_3$), 1.15 (t, 3H, J=7.5 Hz, $CH_3$).

5-(4-(Hexyloxy)-1,2,5-thiadiazol-3-yl)-1-methyl-1-(1-(propionyloxy)ethyl)-1,2,3,6-tetrahydropyridin-1-ium iodide

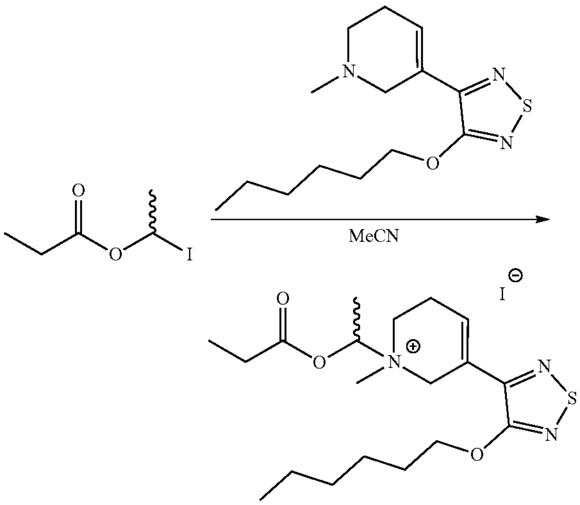

To xanomeline (50 mg, 0.18 mmol, 1 equiv.) in anhydrous MeCN (1.5 mL) at 50° C. under an atmosphere of $N_2$ was added a mixture of 1-iodoethyl propionate (250 mg, 1.1 mmol, 6 equiv.) in anhydrous MeCN (1 mL) dropwise. The resulting mixture was stirred at 50° C. for 2 h before cooling to rt. The mixture was concentrated and the residue was purified by column chromatography on silica gel, eluting with a gradient of MeOH/DCM to give the product (49.9 mg, 54%) as a semi-solid. LC-MS (+ve mode): m/z=382.25 $[M]^+$; $^1H$ NMR (300 MHz, $CDCl_3$) δ 7.30 (m, 1H, C=CH), 6.21 (m, 1H, $CHCH_3$), 4.49 (m, 5H, $OCH_2$, $NCH_2$ and 0.5×$NCH_2$), 3.76 (m, 1H, 0.5×$NCH_2$), 3.51 and 3.49 (s, 3H, $NCH_3$), 2.92 (partially obscured, 2H, $NCH_2CH_2$), 2.68 (m, 2H, $CO_2CH_2$), 1.85 (m, 5H, $CHCH_3$ and $CH_2$), 1.44 (m, 2H, $CH_2$), 1.36 (m, 4H, 2×$CH_2$), 1.22 (m, 3H, $CO_2CH_2CH_3$), 0.91 (m, 3H, $CH_2CH_3$).

Example 55: 5-(4-(Hexyloxy)-1,2,5-thiadiazol-3-yl)-1-methyl-1-(2-methyl-1-(pivaloyloxy)propyl)-1,2,3,6-tetrahydropyridin-1-ium chloride [Xanomeline oxyisobutyl pivalate chloride prodrug] (Table 1 Compound 389) 1-Iodo-2-methylpropyl pivalate

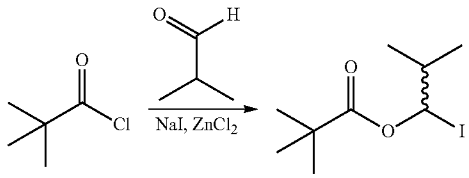

Trimethylacetyl chloride (0.50 g, 0.51 mL, 4.15 mmol, 1.0 equiv.) was added to a stirred suspension of NaI (746 mg, 4.98 mmol, 1.2 equiv.) and catalytic $ZnCl_2$ (ca. 5 mg) in MeCN (1 mL). Isobutyraldehyde (299 mg, 0.38 mL, 4.15 mmol, 1.0 equiv.) was added dropwise and the mixture was stirred at rt for 3 h. The mixture was diluted with DCM (50 mL) and washed with $H_2O$ (50 mL). The organic layer was dried ($MgSO_4$) and concentrated to give the product (1.08 g, 92%) as an oil. $^1H$ NMR (300 MHz, $CDCl_3$) δ 6.78 (m, 1H, OCHI), 1.79 (m, 1H, $CH(CH_3)_2$), 1.19 (s, 9H, 3×$CH_3$), 1.04 (m, 6H, 2×$CH_3$). 5-(4-(Hexyloxy)-1,2,5-thiadiazol-3-yl)-1-methyl-1-(2-methyl-1-(pivaloyloxy)propyl)-1,2,3,6-tetrahydropyridin-1-ium chloride

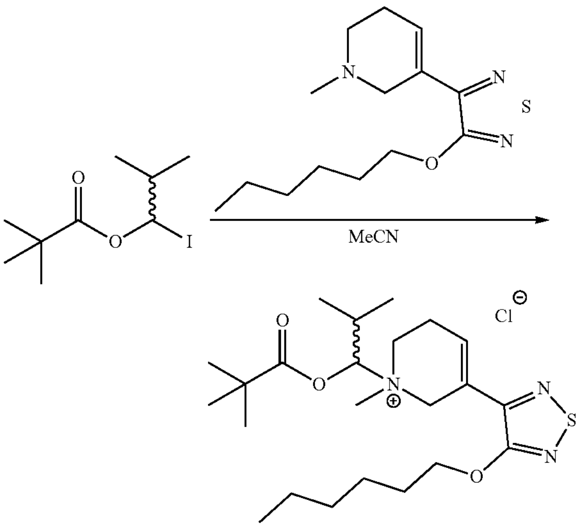

1-Iodo-2-methylpropyl pivalate (256 mg, 0.90 mmol, 5.0 equiv.) in MeCN (0.5 mL) was added in 0.1 mL portions at 30 min intervals to a solution of xanomeline (50 mg, 0.18 mmol, 1.0 equiv.) in MeCN (0.5 mL) at 60° C. After 3 h from the first addition, the mixture was concentrated under vacuum and the residue purified by column chromatography on silica gel eluting with a gradient of MeOH/DCM. The appropriate fractions were combined and washed with sat. aq. $NH_4Cl$ (30 mL), dried ($MgSO_4$) and concentrated to give the desired product (6.5 mg, 6%) as a solid. LC-MS (+ve mode): m/z=438.35 $[M]^+$; $^1H$ NMR (300 MHz, $CDCl_3$) δ 7.28 (m, 1H, C=CH), 5.92 and 5.87 (m, 1H, OCHN), 4.80 (m, 2H, $NCH_2$), 4.48 (m, 2H, $OCH_2$), 4.54 and 4.21 (m, 1H, CHH), 3.61 (m, 1H, CHH), 3.57 and 3.52 (s, 3H, $NCH_3$), 3.03 (m, 1H, CHH), 2.95 (m, 1H, CHH), 2.76 (m, 1H, $CH(CH_3)_2$), 1.86 (m, 2H, $OCH_2CH_2$), 1.44 (m, 4H, 2×$CH_2$), 1.36 and 1.35 (s, 9H, 3×$CH_3$), 1.25 (m, 2H, $CH_2$), 1.14 (m, 6H, $CH(CH_3)_2$), 0.91 (m, 3H, $CH_2CH_3$)

B. Biological Evaluation

Example A: Pharmacokinetics of Selected Compounds Following a Single Subcutaneous Administration in Rats A pharmacokinetic (PK) study was performed in three male Sprague-Dawley (SD) rats following subcutaneous (SC) administration of xanomeline or test compounds (prodrugs of xanomeline) at 1 mg/kg. Parent compound (xanomeline) was measured in plasma.

In Vivo Methods

Regulatory

All animal experiments were performed under UK Home Office Licenses and with local ethical committee clearance. All experiments were performed by technicians that have completed parts A and B of the Home Office Personal License course and hold a current personal license. All experiments were performed in dedicated Biohazard 2 facilities with full AAALAC accreditation.

TABLE A-1

| Protocol: Serial tail vein bleed PK study of Xanomeline Prodrugs in SD rats | |
|---|---|
| Protocol | SC Serial PK study at 1 dose level |
| Test Compound(s) | Xanomeline, Xanomeline Prodrugs |
| Dosing Route | SC |
| Overnight food withdrawal | No |
| Animals Type | rat |
| Strain | Sprague Dawley rats |
| Sex | male |
| Weight (g) | 250-300 g |
| N per cpd | 3 |
| Preparation | None |
| Cage | PK cages |
| Dose | 1 mg/kg of xanomeline |
| Dosing Soln. Conc. | 0.5 mg/mL |
| Dosing Volume | 2 mL/kg |
| Formulation checks required? | No |
| Vehicle | 10% DMSO/90% HPCD (20% in water) |
| Sampling time points (h) | 0.25, 0.5, 0.75, 1, 1.5, 2, 4 & 7 h |
| Blood sampling method | Serial via tail vein |
| Alternative method if required | n/a |
| Sample format required | >230 μL blood + 5 μL EDTA (93 mg/mL) to give 2 × 50 μL plasma |
| Sample processing | Centrifugation for plasma ASAP at 4° C. Place 110 μL plasma into Eppendorf tube on ice containing 11 μL 10% phosphoric acid. Gently mix before taking 2 × 50 μL aliquots into duplicate 96 well plates on dry ice. |
| Anticoagulant | EDTA (93 mg/mL): 5 μL per tube |
| Centrifugation | 10,000 rpm × 3 min at 4° C. |
| Additional samples | n/a |
| Perfusion/rinsing required | n/a |
| Euthanasia method | n/a |
| Plasma sample tubes | 96 well plates |
| Pre-freezer storage | Blood: ice (<30 min), Acidified Plasma: dry ice |
| Freezer storage | −80° C. |
| Dose formulation samples | 100 μL from vortex dose solution in Eppendorf |
| Number of samples per cpd at 1 dose level | 24 × acidified plasma (50 μL in duplicate), 1 dose soln |

Analysis

Samples were sent for method optimization and measurement of parent compound (xanomeline) via unique calibration lines and following acceptance QC's. Dose formulation concentrations were also measured, and PK parameters were determined (Cmax (ng/mL), Tmax (hr), Cl (ml/min/kg), Vdss (L/kg), t1/2(hr), AUCO-t (ng/mL*hr), AUCO-inf (ng/mL*hr), MRT (hr), Bioavailability (% F) where warranted) using WinNon Lin software. Data (including bioanalytical results and assay performance) were reported in a tabulated format Detailed Bioanalysis Standard Method for Xanomeline Analysis Calibrator and QC Preparation:

Step 1: A stock solution of the compound(s) were prepared to 1 mg/ml in DMSO

Step 2: A 10,000 ng/mL matched matrix standard was prepared using the stock solution(s)

Step 3: Calibration standards in matched matrix were prepared between 10,000 ng/ml and 0.5 ng/mL using serial dilution Step 4: QC samples were prepared in matched matrix at 4000, 800, 400, 40 and 10 ng/mL Calibration Standards:

| Standard name | Concentration |
|---|---|
| STD1 | 0.5 |
| STD2 | 1 |
| STD3 | 2.5 |
| STD4 | 5 |
| STD5 | 10 |
| STD6 | 25 |
| STD7 | 50 |
| STD8 | 100 |
| STD9 | 250 |
| STD10 | 500 |
| STD11 | 750 |
| STD12 | 1000 |
| STD13 | 2500 |
| STD14 | 5000 |
| STD15 | 10000 |

Internal Standard dilution preparation (internal standard used: Xanomeline-d3):

Step 1: A stock of the IS was diluted to 1 mg/ml in DMSO

Step 2: An ISY is made by diluting the stock to 10 μg/ml in DMSO

Step 3: An ISZ is made by diluting the ISY to 25 ng/ml in 0.1% formic acid in acetonitrile Extraction Procedure:

Step 1: Add 10 μL of the standards, QCs and samples to a 96-well plate (extraction plate)

Step 2: To each standard, QC and test sample, add 100 μL of ISZ

Step 3: Sonicate for 2 min then mix the plate for approximately 2 min at 1200 rpm on a plate shaker Step 4: Centrifuge the plate at 3000 rpm for 5 mins Step 5: Add 50 μL 0.1% Formic acid in UP H2O to wells of a new 96-well plate Step 6: Transfer 50 μL extracted sample to relevant position in second 96-well plate Step 7: Mix at 1200 rpm for 2 minutes Step 8: Heat seal and analyse on the LC-MS/MS system Instrument: Xevo TQ-D with CTC Autosampler

| LC Method: | |
|---|---|
| Mobile Phase A: | 0.1% Aqueous Formic Acid |
| Mobile Phase B: | 0.1% Mobile Phase B |
| Column temperature: | 50° C. |
| Column: | Acquity UPLC C18 BEH 1.7 μm 2.1 × 50 mm |
| Flow Rate: | 0.6 ml/min |

Gradient conditions:

| Time | % B | Curve |
|---|---|---|
| 0.00 | 10.0 | 6 |
| 0.20 | 10.0 | 6 |
| 1.00 | 95.0 | 6 |
| 2.60 | 95.0 | 6 |
| 2.70 | 10.0 | 6 |
| 3.00 | 10.0 | 6 |

| MS Source parameters: | |
|---|---|
| Capillary Voltage (kV) | 0.5 |
| Source Temperature (° C.) | 150 |

-continued

| MS Source parameters: | |
|---|---|
| Desolvation Temperature (° C.) | 650 |

| MRM methods: | | | | | |
|---|---|---|---|---|---|
| Mode | Compound | Parent (m/z) | Daughter (m/z) | Cone (V) | Collision (V) |
| ESI (+) | Xanomeline | 282.0 | 43.8 | 35 | 25 |
| ESI (+) | Xanomeline-d3 | 286.1 | 48.00 | 25 | 25 |

Sensitive method for Xanomeline analysis

Calibrator and QC Preparation

Step 1: A stock solution of the compound(s) were prepared to 1 mg/ml in DMSO

Step 2: A 10,000 ng/mL matched matrix standard was prepared using the stock solution(s)

Step 3: A 2,000 ng/ml matched matrix stock dilution was made from the 10,000 ng/ml stock dilution Step 4: Standards were prepared at a concentration of 200 ng/ml to 0.01 ng/ml in matched matrix via serial dilution from the second Stock diltuion Step 5: QC samples were prepared in matched matrix at 150, 40, 20, 4 and 0.4 ng/mL

| Calibration Standards: | |
|---|---|
| Standard name | Concentration |
| STD1 | 0.01 |
| STD2 | 0.05 |
| STD3 | 0.1 |
| STD4 | 0.5 |
| STD5 | 1 |
| STD6 | 2.5 |
| STD7 | 5 |
| STD8 | 10 |
| STD9 | 25 |
| STD10 | 50 |
| STD11 | 100 |
| STD12 | 200 |

Internal Standard Dilution Preparation (Internal Standard Used: Xanomeline-$d_3$):

Step 1: A stock of the IS was diluted to 1 mg/ml in DMSO

Step 2: An ISY is made by diluting the stock to 10 μg/ml in DMSO

Step 3: An ISZ is made by diluting the ISY to 25 ng/ml in 0.1% formic acid in acetonitrile Extraction Procedure Step 1: Add 10 μL of the standards, QCs and samples to a 96-well plate (extraction plate)

Step 2: To each standard, QC and test sample, add 100 μL of ISZ Step 3: Sonicate for 2 min then mix the plate for approximately 2 min at 1200 rpm on a plate shaker Step 4: Centrifuge the plate at 3000 rpm for 5 min Step 5: Add 50 μL 0.1% formic acid in UP $H_2O$ to wells of a new 96-well plate Step 6: Transfer 50 μL extracted sample to relevant position in second 96-well plate Step 7: Mix at 1200 rpm for 2 min Step 8: Heat seal and analyse on the LC-MS/MS system Instrument: Xevo TQ-Absolute UHPLC-MS/MS

| LC method: | |
|---|---|
| Mobile Phase A: | 0.1% Aqueous Formic Acid |
| Mobile Phase B: | 0.1% Mobile Phase B |
| Column temperature: | 50° C. |
| Column: | Acquity UPLC C18 BEH 1.7 μm 2.1 × 50 mm |
| Flow Rate: | 0.6 ml/min |

| Gradient conditions: | | |
|---|---|---|
| Time | % B | Curve |
| 0.00 | 10.0 | 6 |
| 0.20 | 10.0 | 6 |
| 1.00 | 95.0 | 6 |
| 2.60 | 95.0 | 6 |
| 2.70 | 10.0 | 6 |
| 3.00 | 10.0 | 6 |

| MS Source parameters: | |
|---|---|
| Capillary Voltage (kV) | 0.5 |
| Source Temperature (° C.) | 150 |
| Desolvation Temperature (° C.) | 650 |

| MRM methods: | | | | | |
|---|---|---|---|---|---|
| Mode | Compound | Parent (m/z) | Daughter (m/z) | Cone (V) | Collision (V) |
| ESI (+) | Xanomeline | 282.1 | 43.9 | 20 | 35 |
| ESI (+) | Xanomeline-d3 | 286.1 | 48.0 | 25 | 25 |

Calibrator and QC Preparation:

Step 1: A stock solution of the compound(s) were prepared to 1 mg/ml in DMSO

Step 2: A 10,000 ng/mL matched matrix standard was prepared using the stock solution(s)

Step 3: Calibration standards in matched matrix were prepared between 10,000 ng/ml and 0.5 ng/mL using serial dilution Step 4: QC samples were prepared in matched matrix at 4000, 800, 400, 40 and 10 ng/mL

| Calibration Standards: | |
|---|---|
| Standard name | Concentration |
| STD1 | 0.5 |
| STD2 | 1 |
| STD3 | 2.5 |
| STD4 | 5 |
| STD5 | 10 |
| STD6 | 25 |
| STD7 | 50 |
| STD8 | 100 |
| STD9 | 250 |

-continued

| Calibration Standards: | |
|---|---|
| Standard name | Concentration |
| STD10 | 500 |
| STD11 | 750 |
| STD12 | 1000 |
| STD13 | 2500 |
| STD14 | 5000 |
| STD15 | 10000 |

Internal Standard dilution preparation (internal standard used: Xanomeline-$d_3$):

| | |
|---|---|
| Step 1 | A stock of the IS was diluted to 1 mg/ml in DMSO |
| Step 2 | An ISY is made by diluting the stock to 10 μg/ml in DMSO |
| Step 3 | An ISZ is made by diluting the ISY to 25 ng/ml in 0.1% Formic acid in Acetonitrile |

Extraction Procedure

Step 1: Add 10 μL of the standards, QCs and samples to a 96-well plate (extraction plate)

Step 2: To each standard, QC and test sample, add 100 μL of ISZ

Step 3: Sonicate for 2 min then mix the plate for approximately 2 min at 1200 rpm on a plate shaker Step 4: Centrifuge the plate at 3000 rpm for 5 min Step 5: Add 50 μL 0.1% formic acid in UP $H_2O$ to wells of a new 96-well plate Step 6: Transfer 50 μL extracted sample to relevant position in second 96-well plate Step 7: Mix at 1200 rpm for 2 min Step 8: Heat seal and analyse on the LC-MS/MS system Instrument: Xevo TQ-D with CTC Autosampler

| LC method: | |
|---|---|
| Mobile Phase A: | 0.1% Aqueous Formic Acid |
| Mobile Phase B: | 0.1% Mobile Phase B |
| Column temperature: | 50° C. |
| Column: | Acquity UPLC C18 BEH 1.7 μm 2.1 × 50 mm |
| Flow Rate: | 0.6 ml/min |

| Gradient conditions: | | |
|---|---|---|
| Time | % B | Curve |
| 0.00 | 10.0 | 6 |
| 0.20 | 10.0 | 6 |
| 1.00 | 95.0 | 6 |
| 1.60 | 95.0 | 6 |
| 1.70 | 10.0 | 6 |
| 2.00 | 10.0 | 6 |

| MS source parameters: | |
|---|---|
| Capillary Voltage (kV) | 0.5 |
| Source Temperature (° C.) | 150 |
| Desolvation Temperature (° C.) | 650 |

| MRM methods: | | | | | |
|---|---|---|---|---|---|
| Mode | Compound | Parent (m/z) | Daughter (m/z) | Cone (V) | Collision (V) |
| ESI (+) | Xanomeline Oxypropyl Pivalate Chloride | 425.0 | 57.0 | 30 | 30 |
| ESI (+) | Xanomeline Oxyethyl Pivalate Chloride | 410.0 | 280.0 | 35 | 17 |
| ESI (+) | Xanomeline-d3 | 286.1 | 48.0 | 25 | 25 |

Additional Formulation Details for PK Study

Phosphoric acid. Diluted 85% phosphoric acid 8.5-fold to give a 10% solution.

Formulation for SC administration: For SC dosing, xanomeline and xanomeline prodrugs were formulated as solution in 10% DMSO/90% HPCD (20% in water) to a concentration of 0.5 mg free metabolite material/mL. This provided a dose of 1 mg free metabolite/kg when administered SC in 2 mL/kg dosing volumes.

Example A-1: Measurement of Concentration of Xanomeline after Subcutaneous (SC) Administration of Xanomeline Prodrugs In Vivo The pharmacokinetic properties of the synthesized xanomeline prodrugs after subcutaneous administration in a rat model were assessed. The concentration of xanomeline was measured in each rat at various sampling timepoints after subcutaneous administration of xanomeline or the synthesized xanomeline prodrugs to rats.

Dose formulations were made at equivalent concentrations of active compound (xanomeline) adjusted for molecular weight of the compounds. The synthesized xanomeline prodrugs were dosed at 1 mg/kg subcutaneous (SC) nominal dose. Nominal doses were used in PK parameter determinations. The parent compound (xanomeline) was dosed at 1 mg/kg subcutaneous (SC).

Example A-1-1: Xanomeline Parent Compound (SC)—Table 1 Compound 922

| | |
|---|---|
| Species | Rat |
| Dose Route: | SC |
| Nominal Dose Concentration: | 1 mg/kg |

Chemical name: Xanomeline

Structural class: parent

Mechanistic class: n/a—parent compound

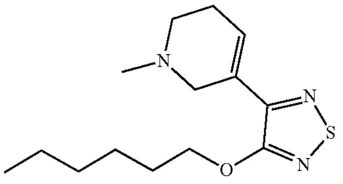 [SMILES: CCCCCCOc1nsnc1C1=CCCN(C)C1]

TABLE 3

| Xanomeline (SC) Pharmacokinetic Parameters | | | | | | | | |
|---|---|---|---|---|---|---|---|---|
| Analyte | Dose | Animal ID | T1/2 (h) | Cmax (ng/mL) | Tmax (h) | Tlast (h) | AUClast (ng/ml*hr) | AUCINF_obs (ng/ml*hr) |
| Xanomeline | SC | R1 | 2.30 | 15.9 | 0.250 | 7.00 | 40.1 | 46.0 |
| | | R2 | 1.66 | 15.1 | 0.250 | 7.00 | 40.0 | 42.9 |
| | | R3 | 1.58 | 12.3 | 0.250 | 7.00 | 34.9 | 37.0 |
| | | Mean | 1.85 | 14.4 | 0.250 | 7.00 | 38.3 | 42.0 |

FIG. 1 shows mean concentration-time profiles of xanomeline following SC dosing of xanomeline (1 mg/kg) to male Sprague Dawley (SD) rats.

Example A-1-2: Xanomeline Methyl Acetate Iodide Prodrug—Table 1 Compound 1

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl acetate iodide Structural class: acyloxymethyl Mechanistic class: presumed esterase+chemical breakdown

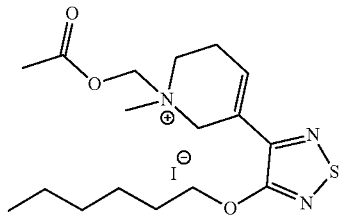 [SMILES: CCCCCCOc1nsnc1C1=CCC[N+](C)(COC(C)=O)C1 ; [I-]]

TABLE 4

| Xanomeline Pharmacokinetic Parameters | | | | | | | | |
|---|---|---|---|---|---|---|---|---|
| Analyte | Dose Route | Animal ID | T1/2 (h) | Tmax (hr) | Cmax (ng/mL) | Tlast (hr) | AUClast (ng/ml*hr) | AUCINF_obs (ng/ml*hr) |
| Xanomeline | SC | R1 | 4.34 | 0.250 | 8.53 | 7.00 | 27.4 | 41.8 |
| | | R2 | 2.54 | 0.250 | 9.44 | 7.00 | 28.9 | 35.0 |
| | | R3 | 2.03 | 0.250 | 11.1 | 7.00 | 26.3 | 29.7 |
| | | Mean | 2.97 | 0.250 | 9.69 | 7.00 | 27.5 | 35.5 |

Figure 2:
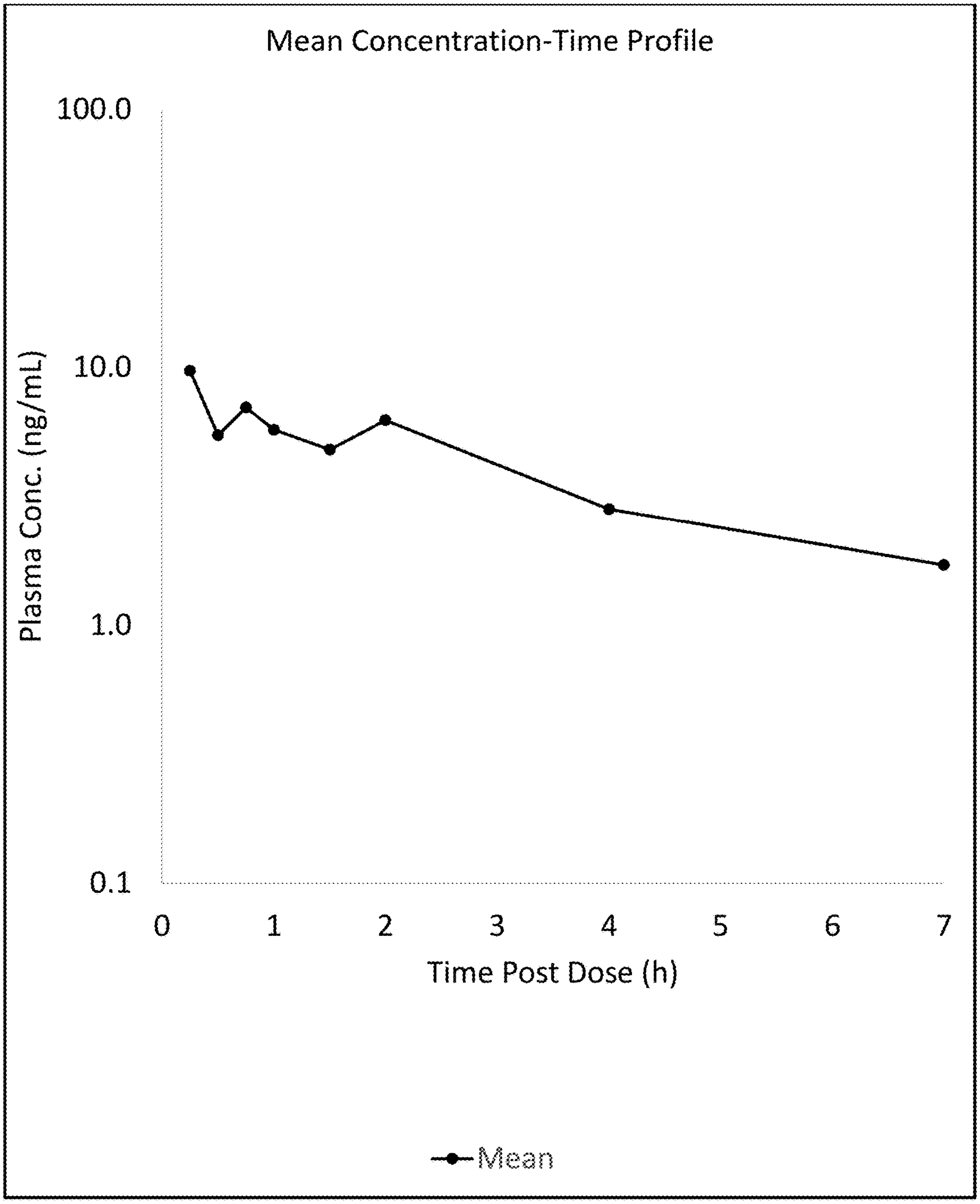
FIG. 2 shows mean concentration-time profiles of xanomeline following SC dosing of xanomeline methyl acetate iodide prodrug (1 mg/kg of xanomeline) to male SD rats.

FIG. 2 shows mean concentration-time profiles of xanomeline following SC dosing of xanomeline methyl acetate iodide prodrug (1 mg/kg of xanomeline) to male SD rats.

Example A-1-3: Xanomeline Methyl Heptanoate Chloride Prodrug—Table 1 Compound 6

| | |
|---|---|
| Species: | Rat |
| Dose Route: | SC |
| Dose Level (mg/kg) | 1 |

Chemical name: [5-(4-hexyloxy-,1,2,6-thiadiazol-3-yl)-1-methyl-3,6-dihydro-2H-pyriin-1-ium-1-yl]methyl heptanoate chloride

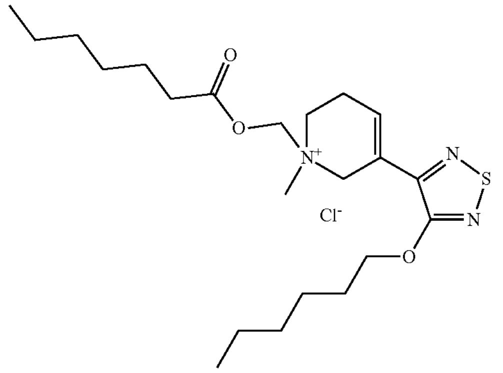 [SMILES: CCCCCCOc1nsnc1C1=CCC[N+](C)(COC(=O)CCCCCC)C1 ; [Cl-]]

TABLE 5

| Xanomeline Pharmacokinetic Parameters | | | | | | | | |
|---|---|---|---|---|---|---|---|---|
| Analyte | Dose Route | Animal ID | T1/2 (h) | Tmax (hr) | Cmax (ng/mL) | Tlast (hr) | AUClast (ng/ml*hr) | AUCINF_obs (ng/ml*hr) |
| Xanomeline | SC | R4 | 1.08 | 1.000 | 14.9 | 4.00 | 31.1 | 34.6 |
| | | R5 | 3.41 | 1.000 | 5.09 | 7.00 | 17.0 | 22.6 |
| | | R6 | 2.76 | 0.750 | 5.10 | 7.00 | 18.5 | 22.7 |
| | | Mean | 2.42 | 0.917 | 8.36 | 6.00 | 22.2 | 26.6 |

Figure 3:
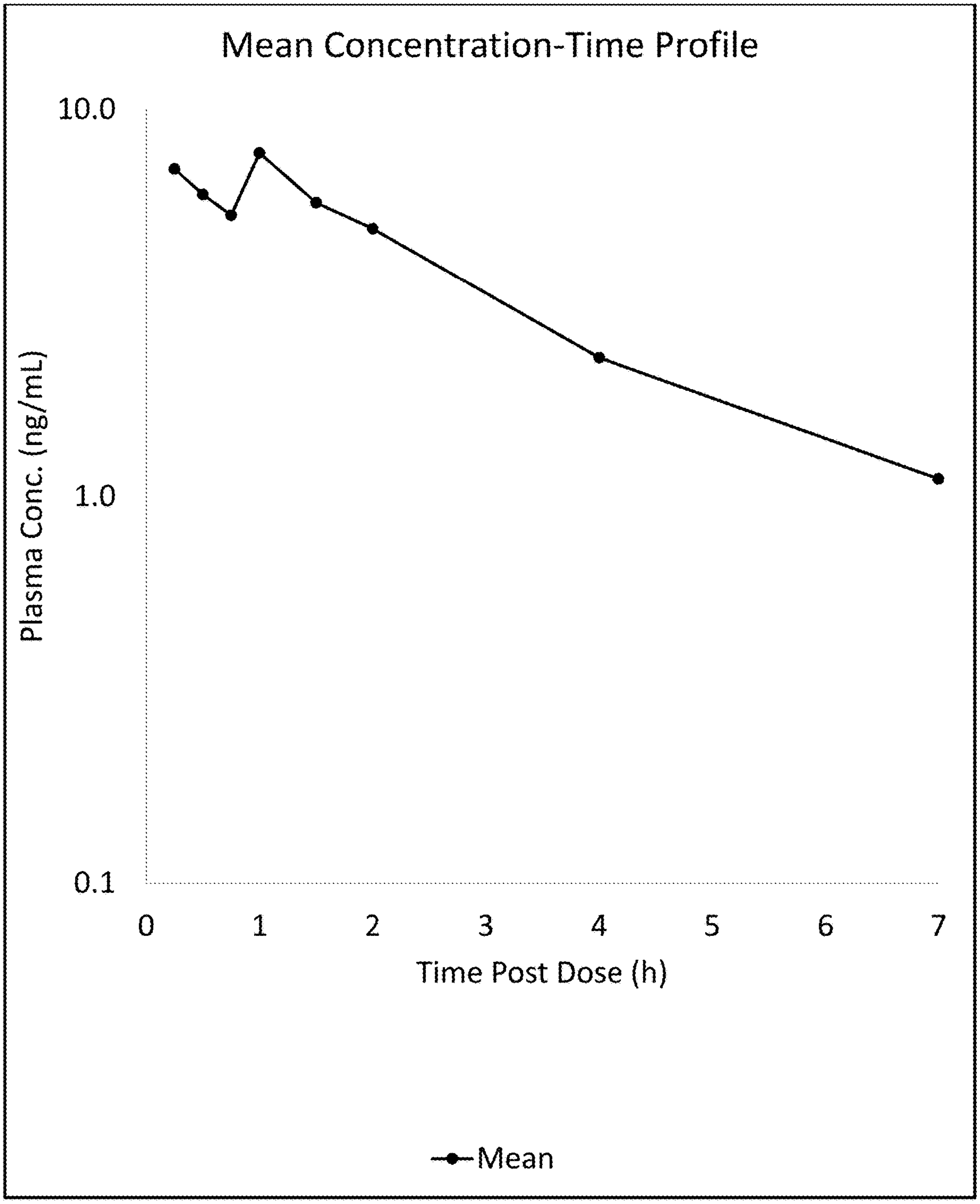
FIG. 3 shows mean concentration-time profiles of xanomeline following SC dosing of xanomeline methyl heptanoate chloride prodrug (1 mg/kg of xanomeline) to male SD rats.

FIG. 3 shows mean concentration-time profiles of xanomeline following SC dosing of xanomeline methyl heptanoate chloride prodrug (1 mg/kg of xanomeline) to male SD rats.

Example A-1-4: Xanomeline Methyl Undecanoate Chloride Prodrug—Table 1 Compound 10

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl undecanoate chloride Structural class: acyloxymethyl Mechanistic class: presumed esterase+chemical breakdown

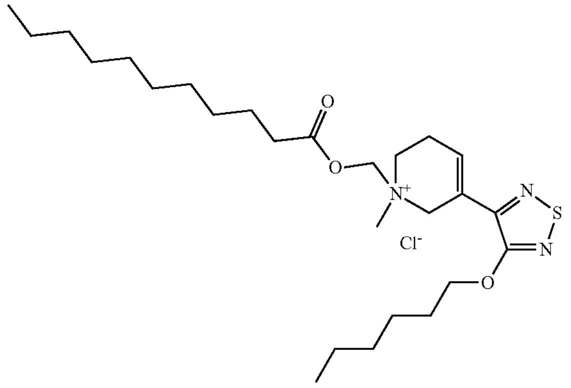 [SMILES: CCCCCCCCCCC(=O)OC[N+]1(C)CCC=C(c2nsnc2OCCCCCC)C1 ; [Cl-]]

TABLE 6

| Xanomeline Pharmacokinetic Parameters | | | | | | | | |
|---|---|---|---|---|---|---|---|---|
| Analyte | Dose Route | Animal ID | T1/2 (h) | Tmax (hr) | Cmax (ng/mL) | Tlast (hr) | AUClast (ng/ml*hr) | AUCINF_obs (ng/ml*hr) |
| Xanomeline | SC | R7 | 2.46 | 0.250 | 17.8 | 7.00 | 29.9 | 33.7 |
| | | R8 | 2.27 | 0.250 | 13.6 | 7.00 | 33.3 | 37.8 |
| | | R9 | 0.986 | 0.250 | 18.7 | 4.00 | 33.5 | 36.1 |
| | | Mean | 1.91 | 0.250 | 16.7 | 6.00 | 32.2 | 35.9 |

Figure 4:
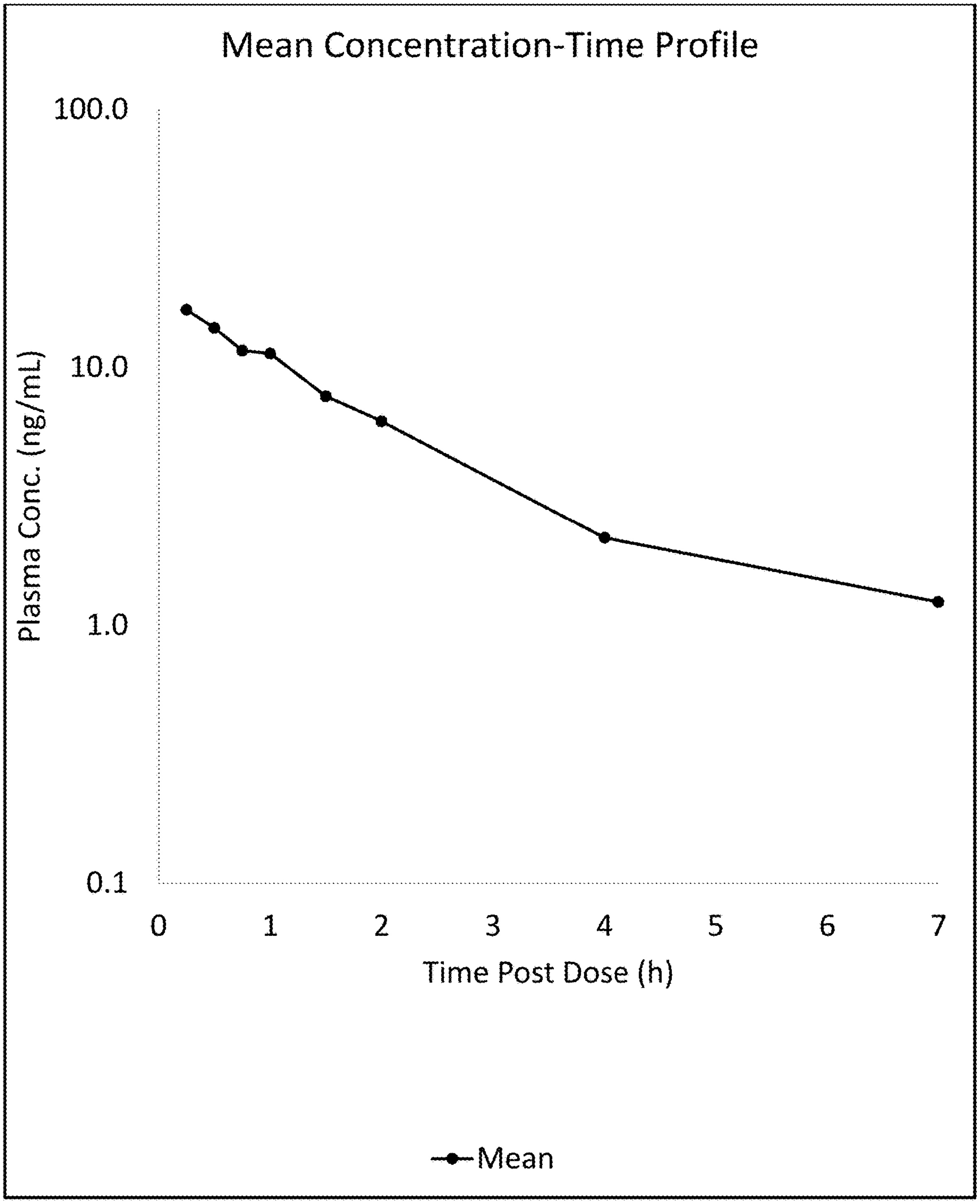
FIG. 4 shows mean concentration-time profiles of xanomeline following SC dosing of xanomeline methyl undecanoate chloride prodrug (1 mg/kg of xanomeline) to male SD rats.

FIG. 4 shows mean concentration-time profiles of xanomeline following SC dosing of xanomeline methyl undecanoate chloride prodrug (1 mg/kg of xanomeline) to male SD rats.

Example A-1-5: Xanomeline Methyl Hexadecanoate Chloride Prodrug—Table 1 Compound 15

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl hexadecanoate chloride Structural class: acyloxymethyl Mechanistic class: presumed esterase+chemical breakdown

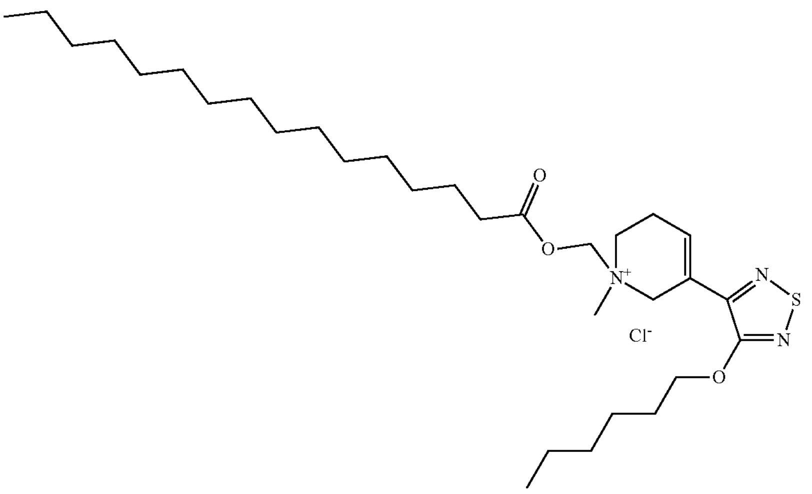 [SMILES: CCCCCCCCCCCCCCCC(=O)OC[N+]1(C)CCC=C(c2nsnc2OCCCCCC)C1 ; [Cl-]]

TABLE 7

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R10 | 2.12 | 0.250 | 10.6 | 7.00 | 30.0 | 33.6 |
| | | R11 | 1.36 | 0.500 | 10.0 | 4.00 | 26.5 | 31.5 |
| | | R12 | 1.49 | 0.500 | 7.68 | 4.00 | 21.9 | 27.0 |
| | | Mean | 1.66 | 0.417 | 9.43 | 5.00 | 26.1 | 30.7 |

Figure 5:
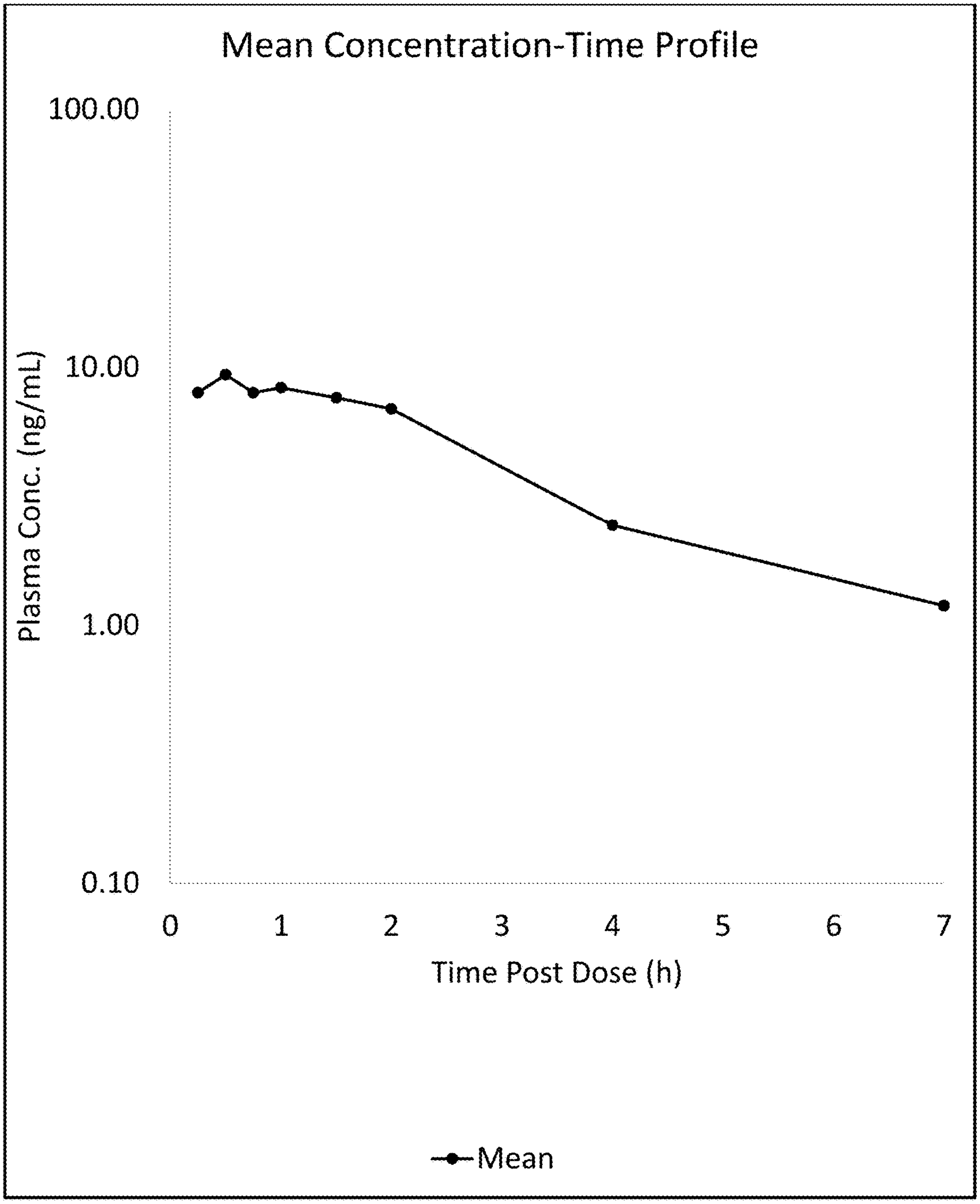
FIG. 5 shows mean concentration-time profiles of xanomeline following SC dosing of xanomeline methyl hexadecanoate chloride prodrug (1 mg/kg of xanomeline) to male SD rats.

FIG. 5 shows mean concentration-time profiles of xanomeline following SC dosing of xanomeline methyl hexadecanoate chloride prodrug (1 mg/kg of xanomeline) to male SD rats.

Example A-1-6: Xanomeline Oxyethyl Pivalate Chloride Prodrug—Table 1 Compound 19

| | |
|---|---|
| Species: | Rat |
| Dose Route: | SC |
| Dose Level (mg/kg) | 1 |

Chemical name: 1-[5-(4-hexyloxy-1,2,5-thiadiazol-3-yl)-1-methyl-3,6-dihydro-2H-pyridin-1-ium-1-yl]ethyl 2,2-dimethylpropanoate chloride Structural class: acyloxymethyl Mechanistic class: presumed esterase+chemical breakdown

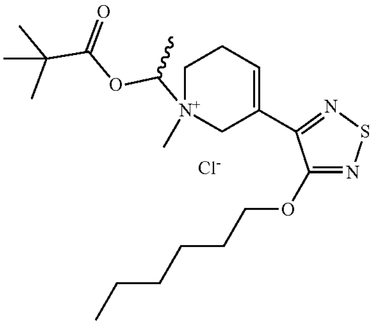 [SMILES: CCCCCCOc1nsnc1C1=CCC[N+](C)(C(C)OC(=O)C(C)(C)C)C1 ; [Cl-]]

Figure 6:
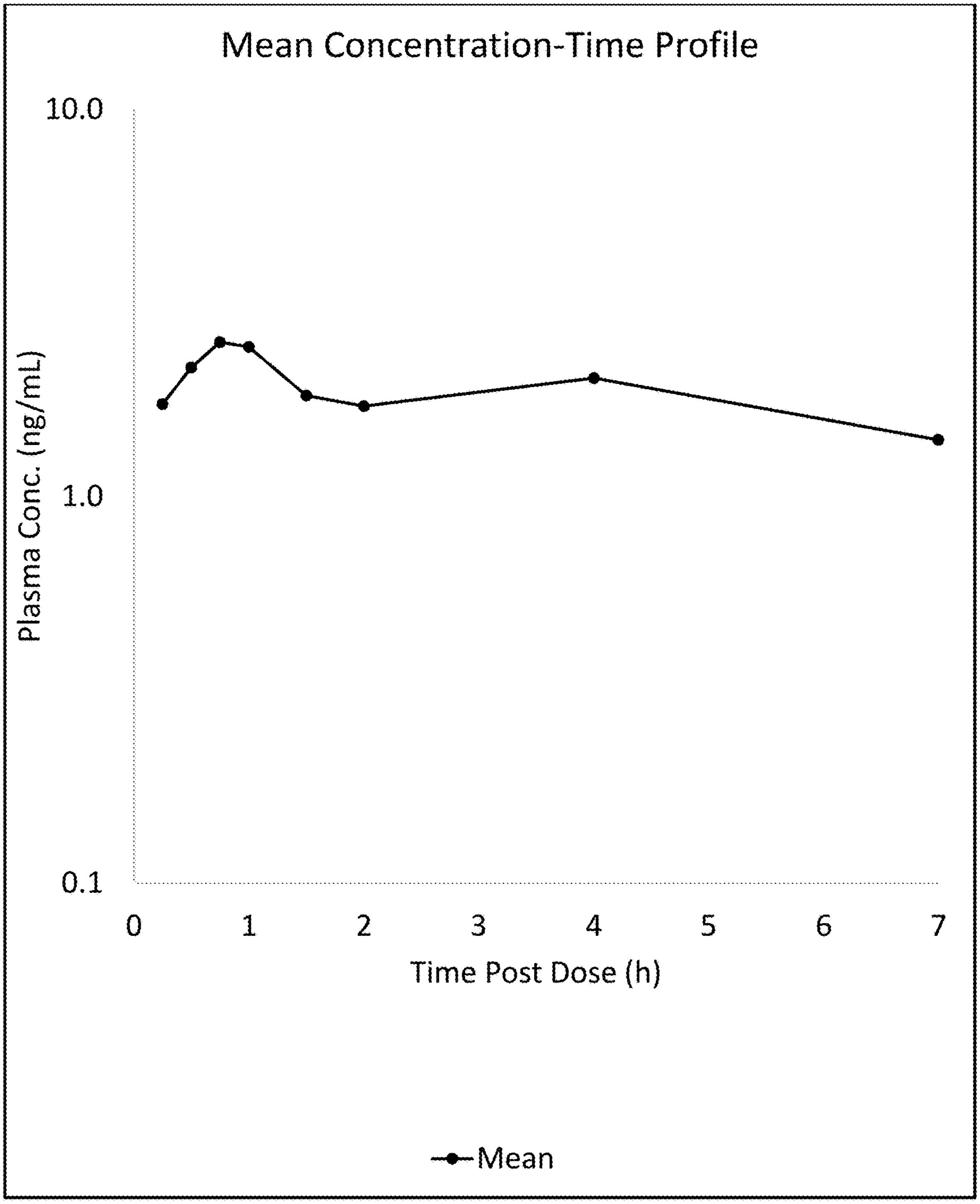
FIG. 6 shows mean concentration-time profiles of xanomeline following SC dosing of xanomeline oxyethyl pivalate chloride prodrug (1 mg/kg of xanomeline) to male SD rats.

FIG. 6 shows mean concentration-time profiles of xanomeline following SC dosing of xanomeline oxyethyl pivalate chloride prodrug (1 mg/kg of xanomeline) to male SD rats.

Example A-1-7: Xanomeline Methyl Propionate Chloride Prodrug—Table 1 Compound 2

| | |
|---|---|
| Species: | Rat |
| Dose Route: | SC |
| Dose Level (mg/kg) | 1 |

Chemical name: 1-methyl-5-[4-(hexyloxy)-1,2,5-thiadiazol-3-yl]-1-[(propanoyloxy)methyl]-1,2,3,6-tetrahydropyridin-1-ium chloride Structural class: acyloxymethyl Mechanistic class: presumed esterase+chemical breakdown

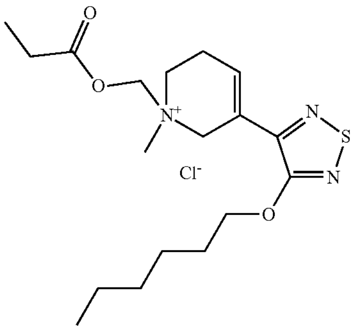 [SMILES: CCCCCCOc1nsnc1C1=CCC[N+](C)(COC(=O)CC)C1 ; [Cl-]]

TABLE 8

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R13 | 8.54 | 1.000 | 2.94 | 7.00 | 14.7 | 34.0 |
| | | R14 | NR | 0.750 | 2.34 | 7.00 | 10.6 | NR |
| | | R15 | 14.8 | 1.000 | 3.05 | 7.00 | 12.9 | 41.1 |
| | | Mean | 11.7 | 0.917 | 2.78 | 7.00 | 12.7 | 37.6 |

TABLE 9

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R1 | 3.28 | 0.500 | 31.1 | 7.00 | 58.8 | 74.2 |
| | | R2 | 1.64 | 0.500 | 32.4 | 7.00 | 60.0 | 63.1 |
| | | R3 | 1.24 | 0.500 | 37.9 | 4.00 | 52.7 | 57.9 |
| | | Mean | 2.05 | 0.500 | 33.8 | 6.00 | 57.2 | 65.1 |

Figure 7:
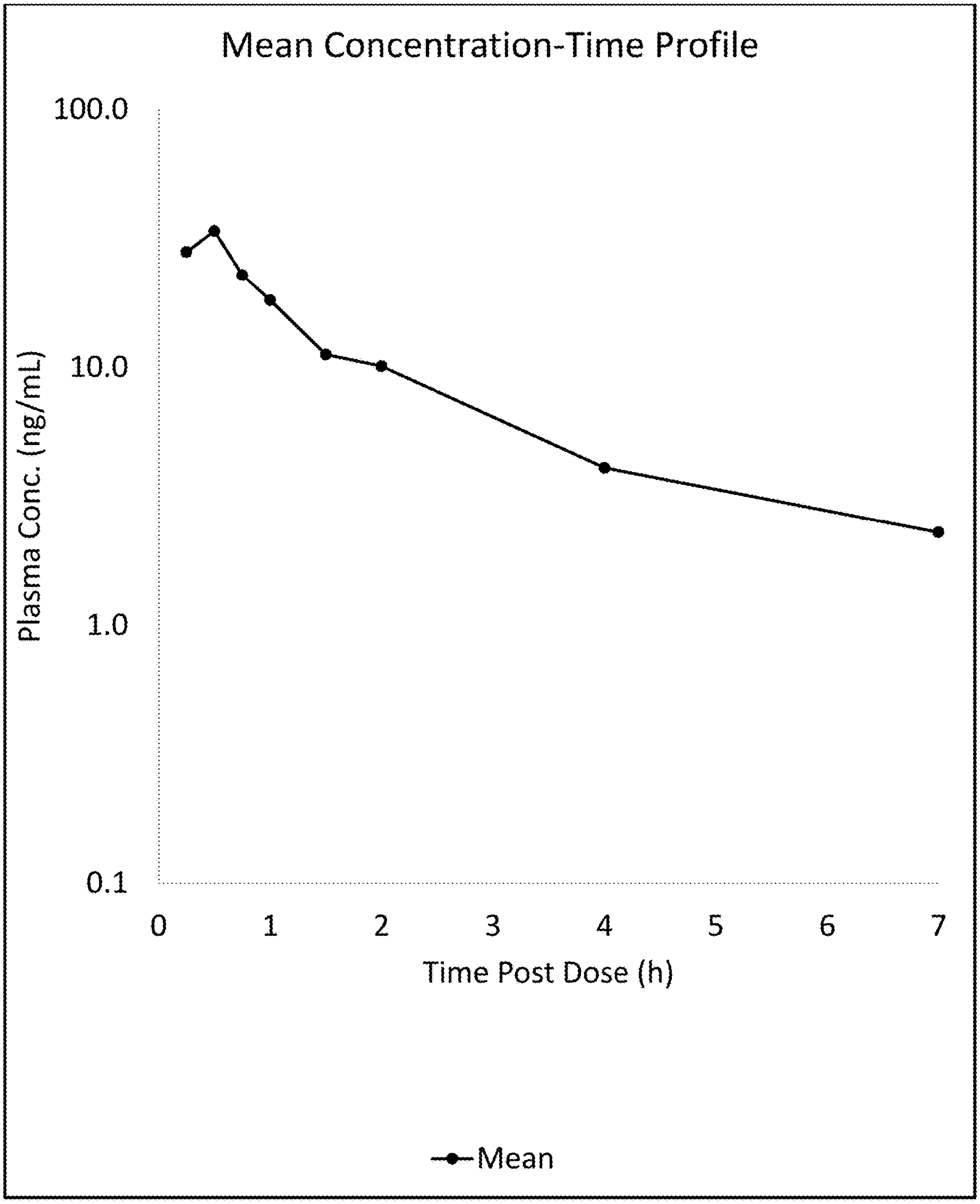
FIG. 7 shows mean concentration-time profiles of xanomeline following SC dosing of xanomeline methyl propionate chloride prodrug (1 mg/kg of xanomeline) to male SD rats.

FIG. 7 shows mean concentration-time profiles of xanomeline following SC dosing of xanomeline methyl propionate chloride prodrug (1 mg/kg of xanomeline) to male SD rats.

Example A-1-8: Xanomeline Methyl Pentanoate Chloride Prodrug—Table 1 Compound 4

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl pentanoate chloride Structural class: acyloxymethyl Mechanistic class: presumed esterase+chemical breakdown

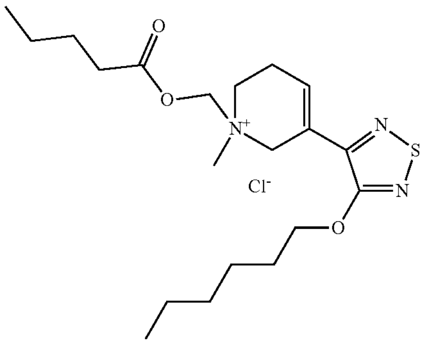 [SMILES: CCCCCCOc1nsnc1C1=CCC[N+](C)(COC(=O)CCCC)C1 ; [Cl-]]

TABLE 10

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R4 | 0.963 | 0.250 | 20.0 | 4.00 | 28.3 | 30.1 |
| | | R5 | 1.64 | 0.250 | 12.8 | 7.00 | 26.9 | 28.4 |
| | | R6 | 2.64 | 0.250 | 13.9 | 7.00 | 24.6 | 28.2 |
| | | Mean | 1.75 | 0.250 | 15.6 | 6.00 | 26.6 | 28.9 |

Figure 8:
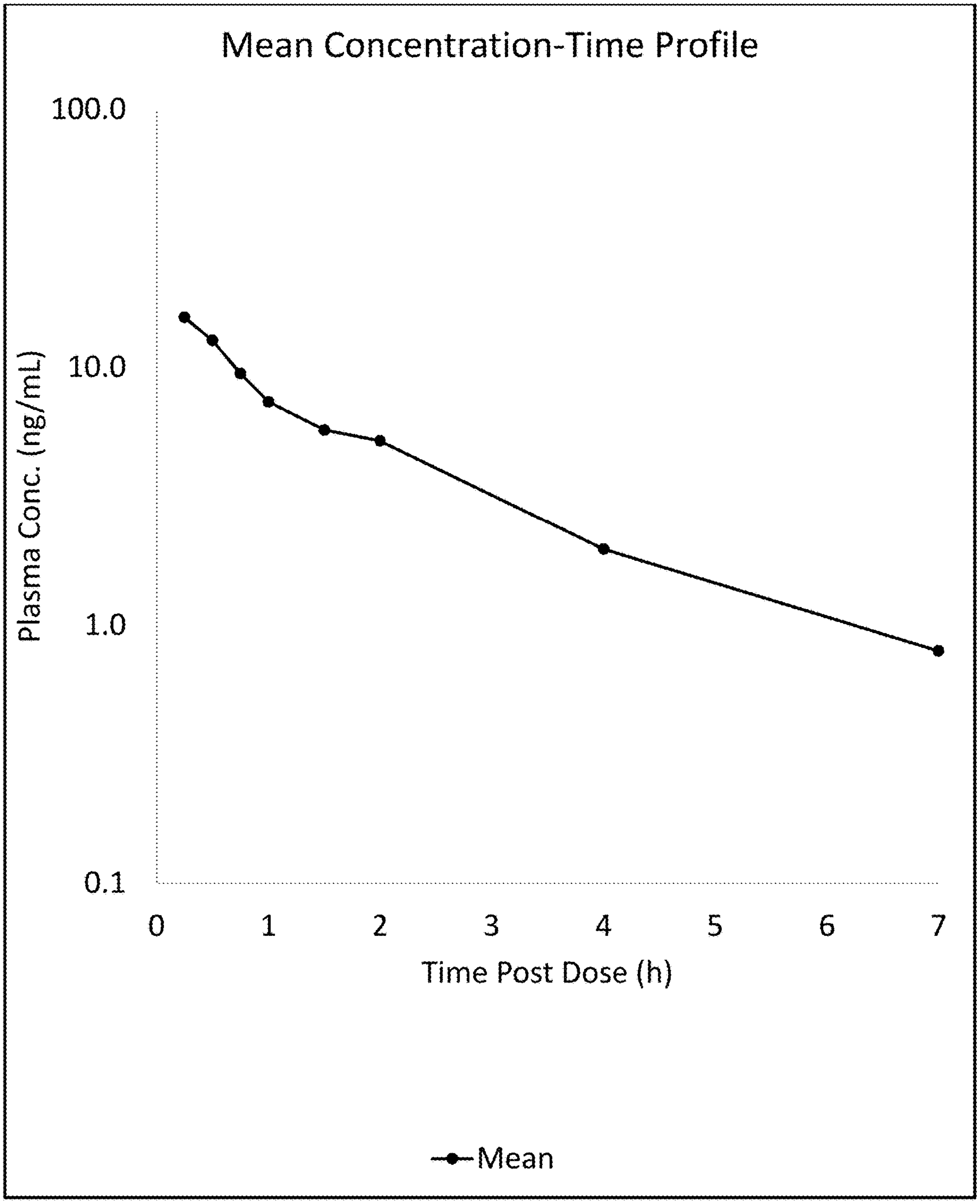
FIG. 8 shows mean concentration-time profiles of xanomeline following SC dosing of xanomeline methyl pentanoate chloride prodrug (1 mg/kg of xanomeline) to male SD rats.

FIG. 8 shows mean concentration-time profiles of xanomeline following SC dosing of xanomeline methyl pentanoate chloride prodrug (1 mg/kg of xanomeline) to male SD rats.

Example A-1-9: Xanomeline Methyl Hexanoate Chloride Prodrug—Table 1 Compound 5

| | |
|---|---|
| Species: | Rat |
| Dose Route: | SC |
| Dose Level (mg/kg) | 1 |

Chemical name: 1-[(hexanoyloxy)methyl]-1-methyl-5-[4-(hexyloxy-1,2,5-thiadiazol-3-yl)]-1,2,3,6-tetrahydropyridin-1-ium chloride Structural class: acyloxymethyl Mechanistic class: presumed estetase+chemical breakdown

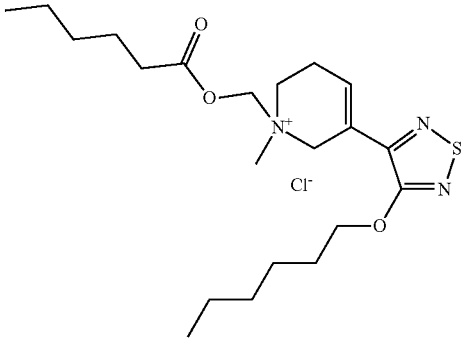 [SMILES: CCCCCCOc1nsnc1C1=CCC[N+](C)(COC(=O)CCCCC)C1 ; [Cl-]]

TABLE 11

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R7 | 1.77 | 0.500 | 18.9 | 7.00 | 28.4 | 30.2 |
| | | R8 | 1.02 | 0.250 | 24.0 | 4.00 | 29.7 | 31.6 |
| | | R9 | 1.41 | 0.250 | 25.5 | 4.00 | 28.7 | 32.4 |
| | | Mean | 1.40 | 0.333 | 22.8 | 5.00 | 28.9 | 31.4 |

Figure 9:
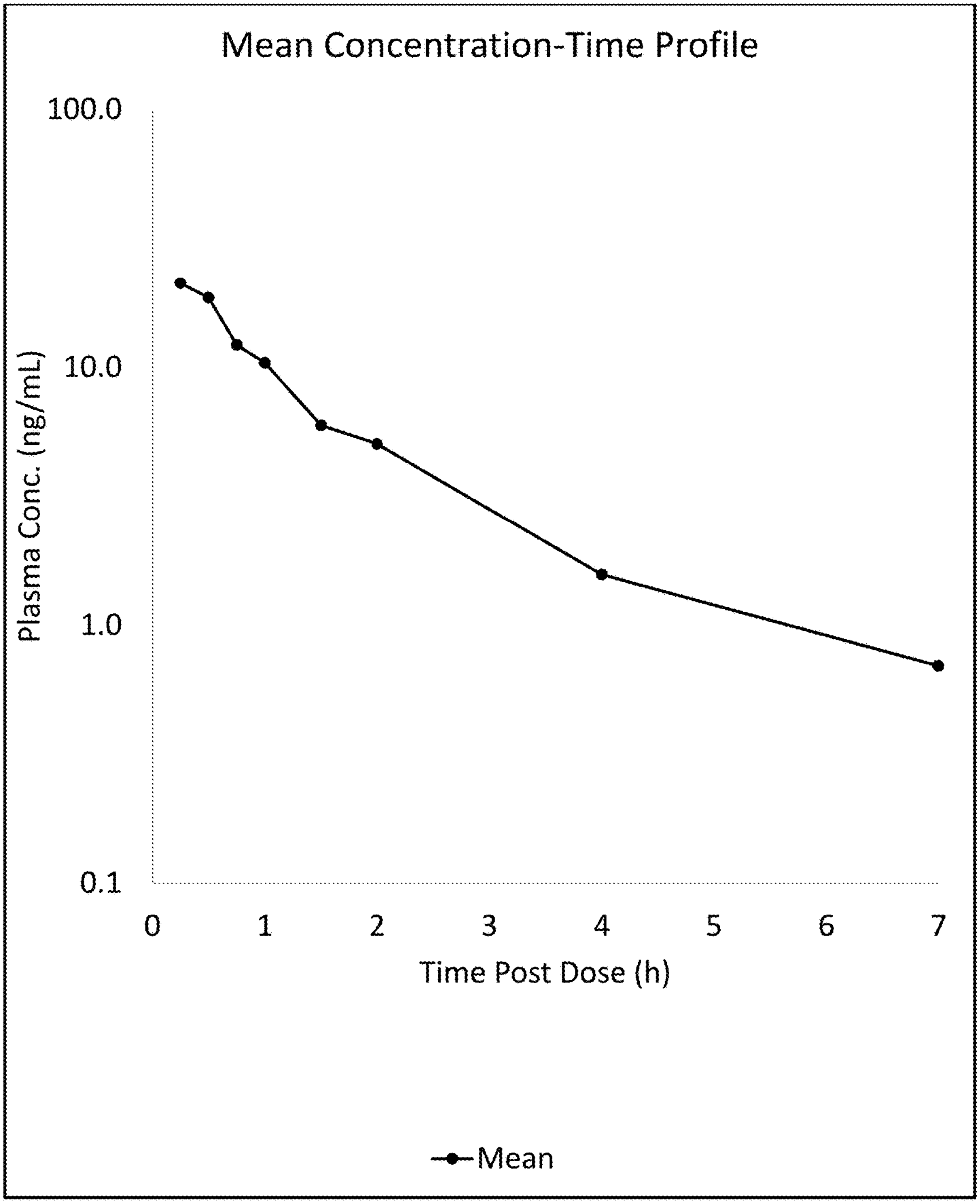
FIG. 9 shows mean concentration-time profiles of xanomeline following SC dosing of xanomeline methyl hexanoate chloride prodrug (1 mg/kg of xanomeline) to male SD rats.

FIG. 9 shows mean concentration-time profiles of xanomeline following SC dosing of xanomeline methyl hexanoate chloride prodrug (1 mg/kg of xanomeline) to male SD rats.

Example A-1-10: Xanomeline methyl octanoate chloride prodrug—Table 1 Compound 7

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl octanoate chloride Structural class: acyloxymethyl Mechanistic class: presumed esterase+chemical break-down

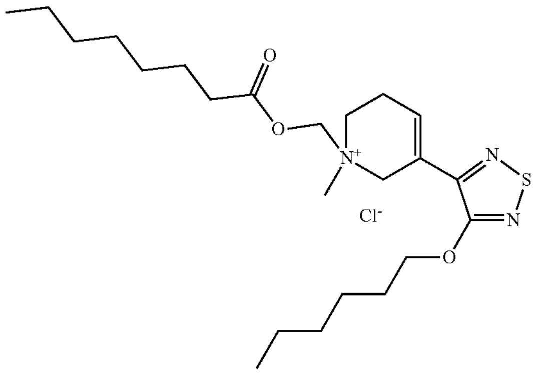 [SMILES: CCCCCCCC(=O)OC[N+]1(C)CCC=C(c2nsnc2OCCCCCC)C1 ; [Cl-]]

TABLE 12

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R10 | 1.52 | 0.250 | 20.4 | 4.00 | 22.3 | 24.9 |
| | | R11 | 1.12 | 0.500 | 18.7 | 4.00 | 30.8 | 33.6 |
| | | R12 | 1.61 | 0.500 | 16.9 | 4.00 | 26.9 | 32.6 |
| | | Mean | 1.42 | 0.417 | 18.7 | 4.00 | 26.7 | 30.4 |

Figure 10:
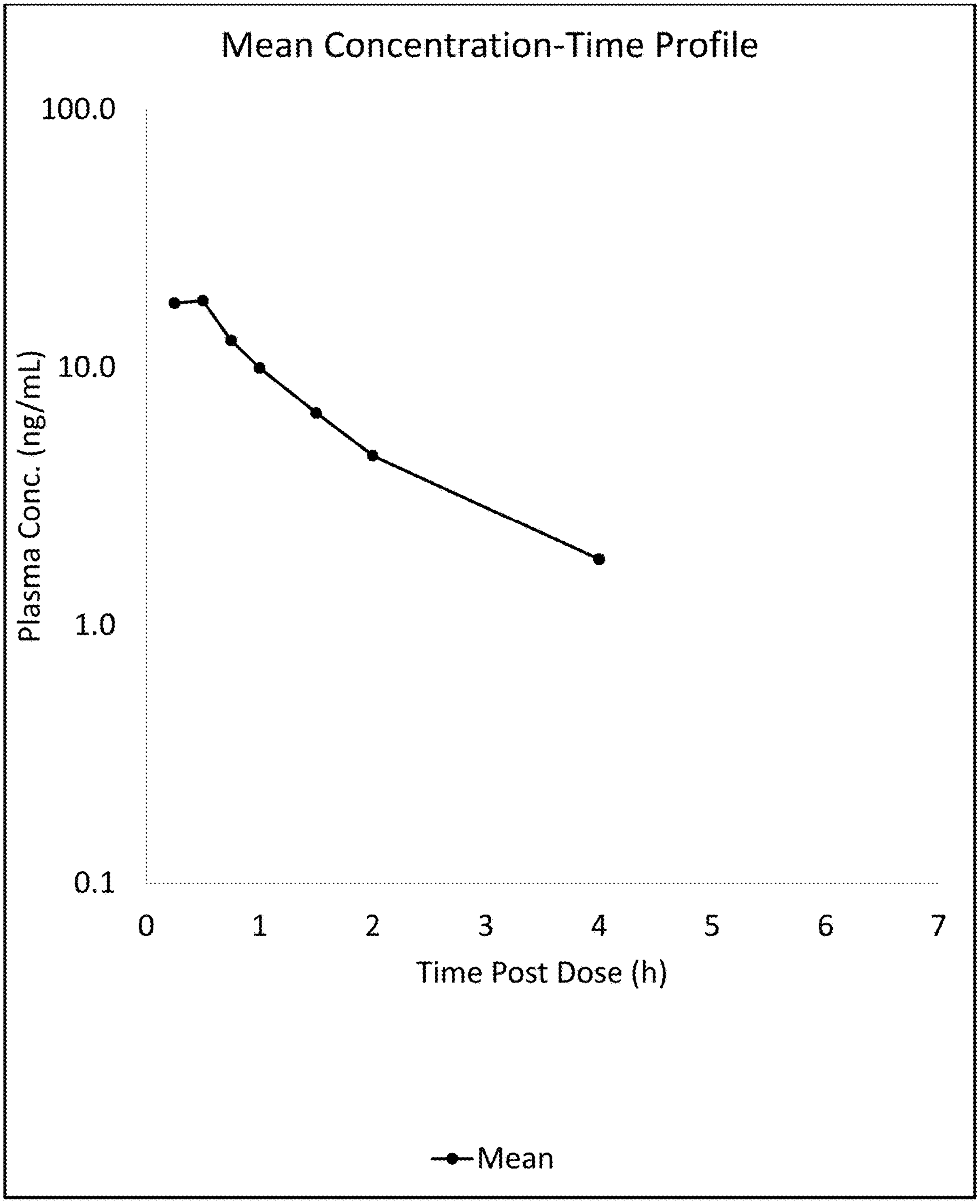
FIG. 10 shows mean concentration-time profiles of xanomeline following SC dosing of xanomeline methyl octanoate chloride prodrug (1 mg/kg of xanomeline) to male SD rats.

FIG. 10 shows mean concentration-time profiles of xanomeline following SC dosing of xanomeline methyl octanoate chloride prodrug (1 mg/kg of xanomeline) to male SD rats.

Example A-1-11: Xanomeline Methyl Nonanoate Chloride Prodrug—Table 1 Compound 8

| | |
|---|---|
| Species: | Rat |
| Dose Route: | SC |
| Dose Level (mg/kg | 1 |

Chemical name: [5-(4-hexyloxy-1,2,5-tiadiazol-3-yl)-1-methyl-3-ihydro-2-pyridin-1-ium-1-yl]methyl nonanoate chloride Structural class: acyloxymethyl Mechanistic class: presumed esterase+chemical break-down

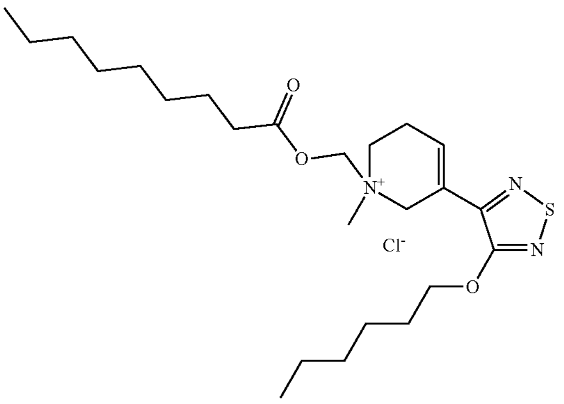 [SMILES: CCCCCCCCC(=O)OC[N+]1(C)CCC=C(c2nsnc2OCCCCCC)C1 ; [Cl-]]

TABLE 13

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R13 | 1.04 | 0.500 | 19.4 | 4.00 | 25.9 | 27.6 |
| | | R14 | 0.862 | 0.250 | 17.0 | 4.00 | 24.2 | 25.4 |
| | | R15 | 1.10 | 0.250 | 31.4 | 4.00 | 33.0 | 34.7 |
| | | Mean | 1.00 | 0.333 | 22.6 | 4.00 | 27.7 | 29.2 |

Figure 11:
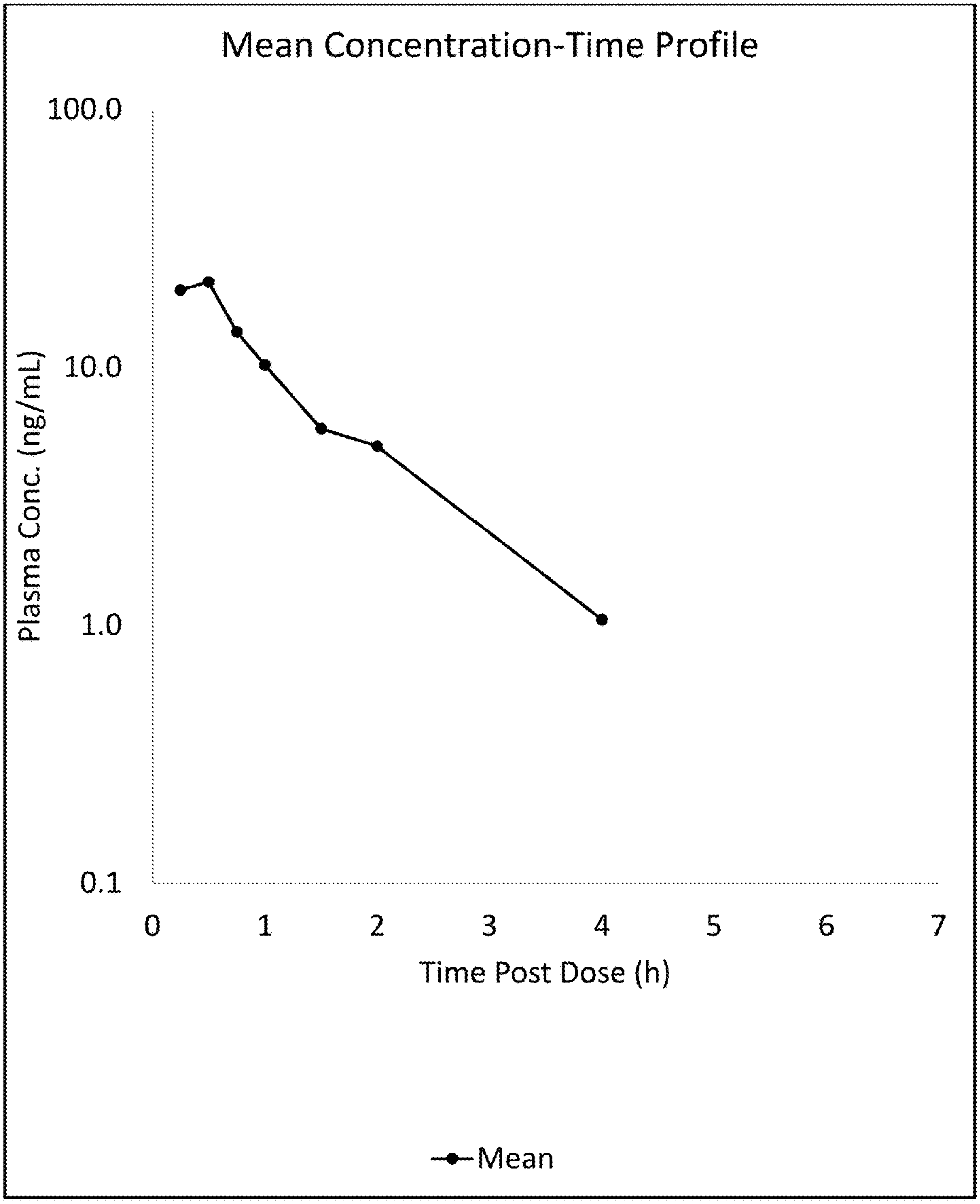
FIG. 11 shows mean concentration-time profiles of xanomeline following SC dosing of xanomeline methyl nonanoate chloride prodrug (1 mg/kg of xanomeline) to male SD rats.

FIG. 11 shows mean concentration-time profiles of xanomeline following SC dosing of xanomeline methyl nonanoate chloride prodrug (1 mg/kg of xanomeline) to male SD rats.

Example A-1-12: Xanomeline Methyl Decanoate Chloride Prodrug—Table 1 Compound 9

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl decanoate chloride Structural class: acyloxymethyl Mechanistic class: presumed esterase+chemical break-down

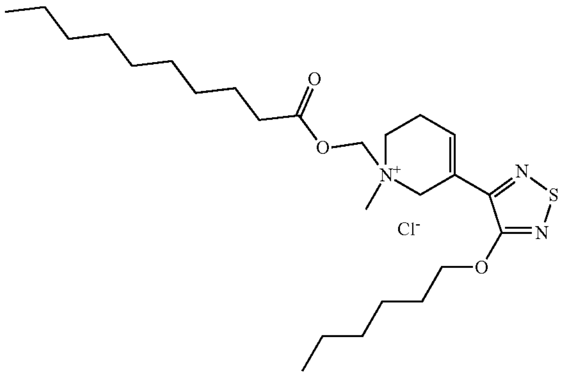 [SMILES: CCCCCCCCCC(=O)OC[N+]1(C)CCC=C(c2nsnc2OCCCCCC)C1 ; [Cl-]]

TABLE 14

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R16 | 0.986 | 0.500 | 21.4 | 4.00 | 25.5 | 27.0 |
| | | R17 | 0.833 | 0.250 | 24.9 | 4.00 | 32.4 | 33.6 |
| | | R18 | 1.70 | 0.250 | 27.4 | 7.00 | 33.3 | 34.7 |
| | | Mean | 1.17 | 0.333 | 24.6 | 5.00 | 30.4 | 31.8 |

Figure 12:
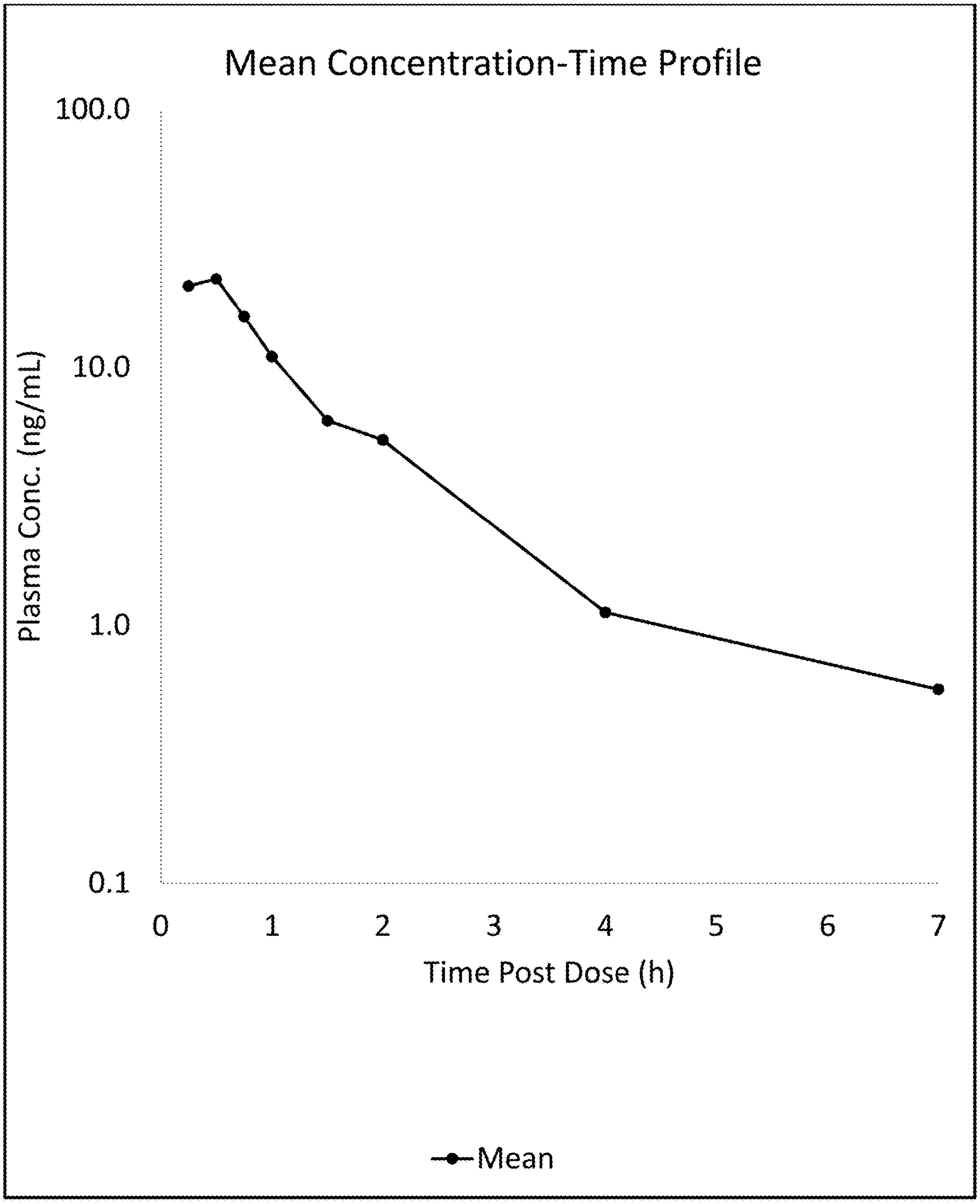
FIG. 12 shows mean concentration-time profiles of xanomeline following SC dosing of xanomeline methyl decanoate chloride prodrug (1 mg/kg of xanomeline) to male SD rats.

FIG. 12 shows mean concentration-time profiles of xanomeline following SC dosing of xanomeline methyl decanoate chloride prodrug (1 mg/kg of xanomeline) to male SD rats.

Example A-1-13: Xanomeline Methyl Dodecanoate Iodide Prodrug—Table 1 Compound 11

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl dodecanoate iodide Structural class: acyloxymethyl Mechanistic class: presumed esterase+chemical break-down

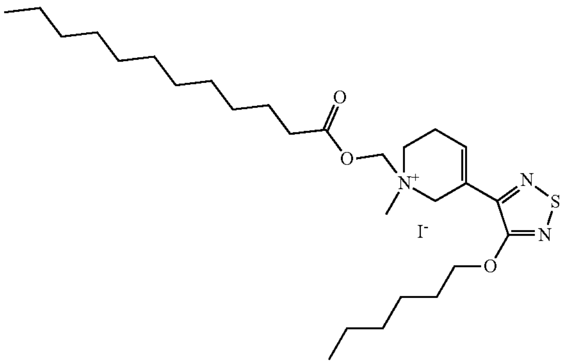 [SMILES: CCCCCCCCCCCC(=O)OC[N+]1(C)CCC=C(c2nsnc2OCCCCCC)C1 ; [I-]]

TABLE 15

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R19 | 0.851 | 0.500 | 19.4 | 4.00 | 27.4 | 28.5 |
| | | R20 | 1.10 | 0.500 | 25.2 | 4.00 | 35.9 | 38.4 |
| | | R21 | 0.952 | 0.500 | 11.4 | 4.00 | 19.3 | 20.5 |
| | | Mean | 0.968 | 0.500 | 18.7 | 4.00 | 27.5 | 29.1 |

Figure 13:
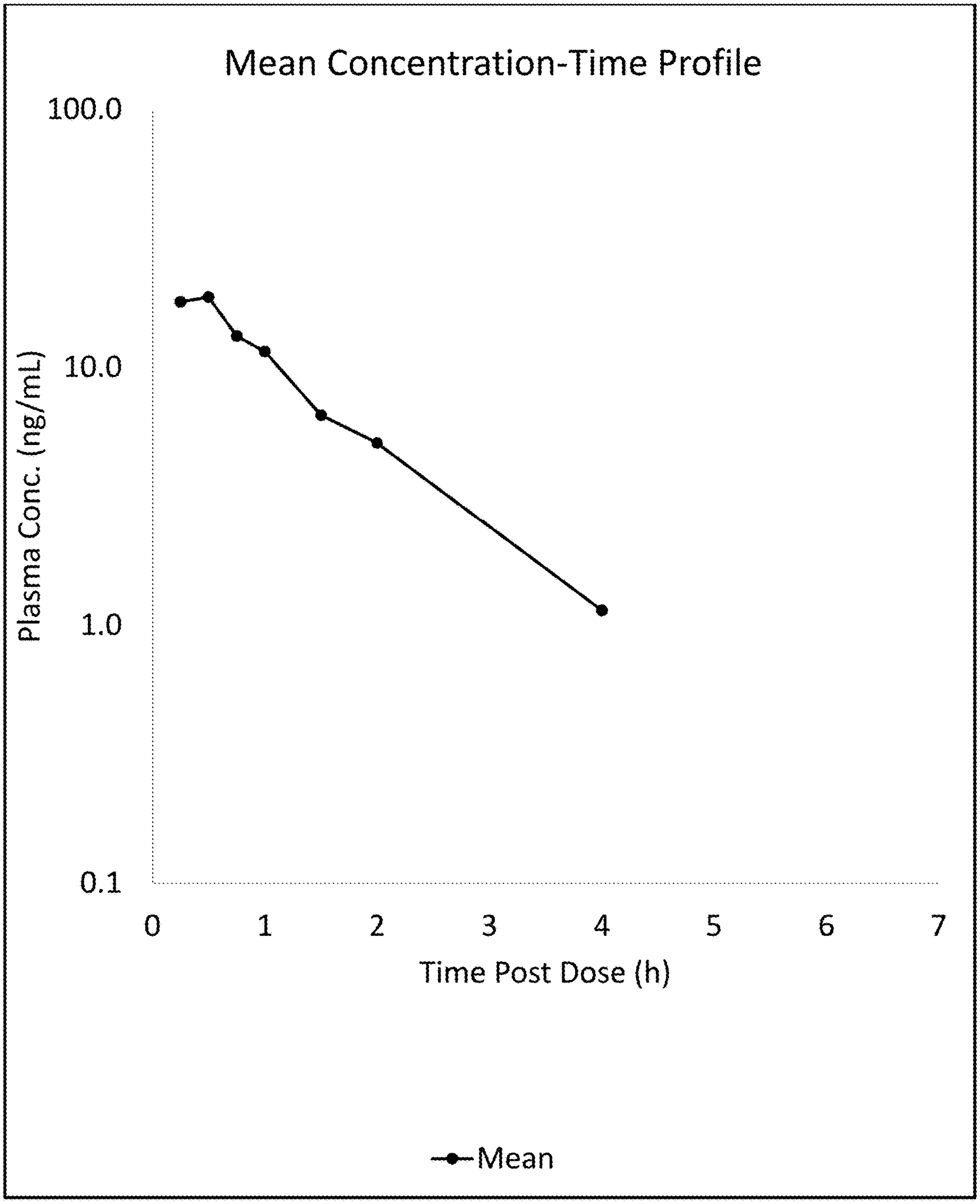
FIG. 13 shows mean concentration-time profiles of xanomeline following SC dosing of xanomeline methyl dodecanoate iodide prodrug (1 mg/kg of xanomeline) to male SD rats.

FIG. 13 shows mean concentration-time profiles of xanomeline following SC dosing of xanomeline methyl dodecanoate iodide prodrug (1 mg/kg of xanomeline) to male SD rats.

Example A-1-14: Xanomeline Methyl Decatriaoate Chloride Prodrug—Table 1 Compound 12

| | |
|---|---|
| Species: | Rat |
| Dose Route: | SC |
| Dose Level (mg/kg) | 1 |

Chemical name: 1-methyl-5-[4-(hexyloxy)-1,2,5-thiadiazol-3-yl]-1-[(tridecanoyloxy)methyl]-1,2,3,6-tetrahydropyridin-1-ium chloride Structural class: acyloxymethyl Mechanistic class: presumed esterase+chemical breakdown

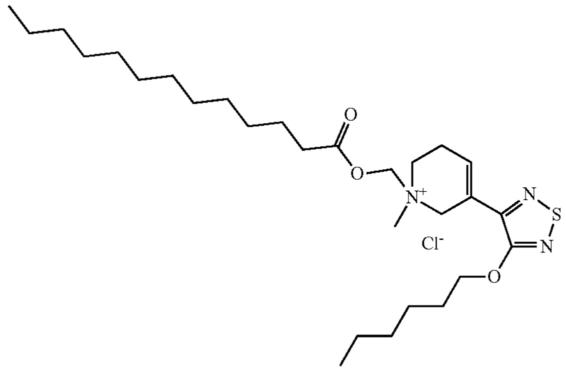 [SMILES: CCCCCCCCCCCCC(=O)OC[N+]1(C)CCC=C(c2nsnc2OCCCCCC)C1 ; [Cl-]]

TABLE 16

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R22 | 1.36 | 0.250 | 22.5 | 7.00 | 52.4 | 54.0 |
| | | R23 | 0.845 | 1.00 | 21.6 | 4.00 | 36.4 | 38.5 |
| | | R24 | 1.75 | 0.500 | 40.7 | 7.00 | 59.8 | 62.7 |
| | | Mean | 1.318 | 0.583 | 28.3 | 6.00 | 49.5 | 51.7 |

Figure 14:
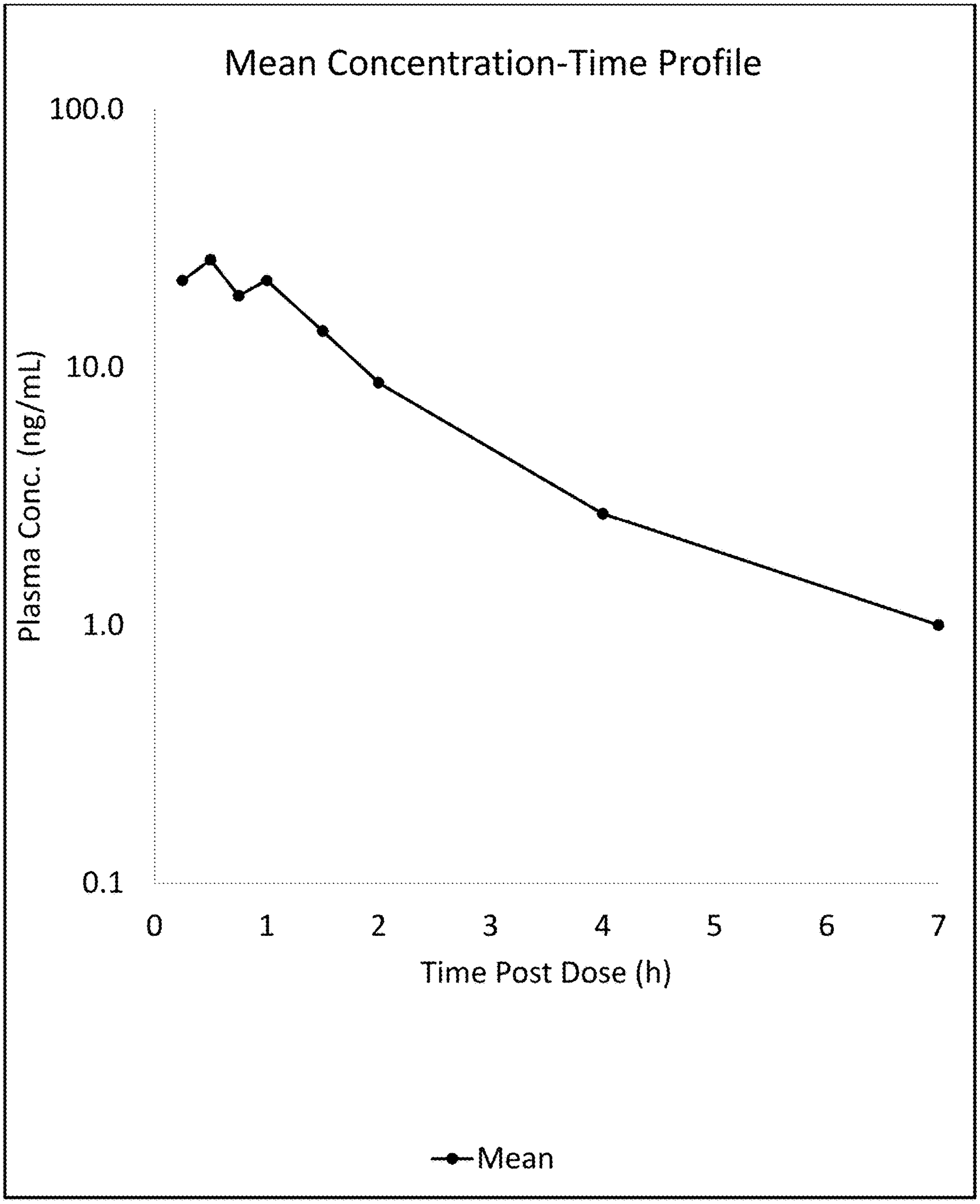
FIG. 14 shows mean concentration-time profiles of xanomeline following SC dosing of xanomeline methyl decatriaoate chloride prodrug (1 mg/kg of xanomeline) to male SD rats.

FIG. 14 shows mean concentration-time profiles of xanomeline following SC dosing of xanomeline methyl decatriaoate chloride prodrug (1 mg/kg of xanomeline) to male SD rats.

Example A-1-15: Xanomeline Methyl Decatettaraoate Chloride Prodrug—Table 1 Compound 13

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl tetradecanoate chloride Structural class: acyloxymethyl Mechanistic class: presumed esterase+chemical breakdown

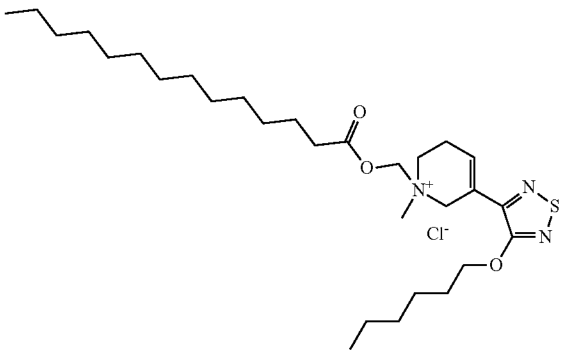 [SMILES: CCCCCCCCCCCCCC(=O)OC[N+]1(C)CCC=C(c2nsnc2OCCCCCC)C1 ; [Cl-]]

TABLE 17

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R25 | 1.89 | 0.250 | 11.4 | 7.00 | 27.8 | 30.4 |
| | | R26 | 1.57 | 0.250 | 23.1 | 7.00 | 57.8 | 60.6 |
| | | R27 | 1.41 | 0.500 | 23.1 | 7.00 | 33.0 | 34.1 |
| | | Mean | 1.62 | 0.333 | 19.2 | 7.00 | 39.5 | 41.7 |

Figure 15:
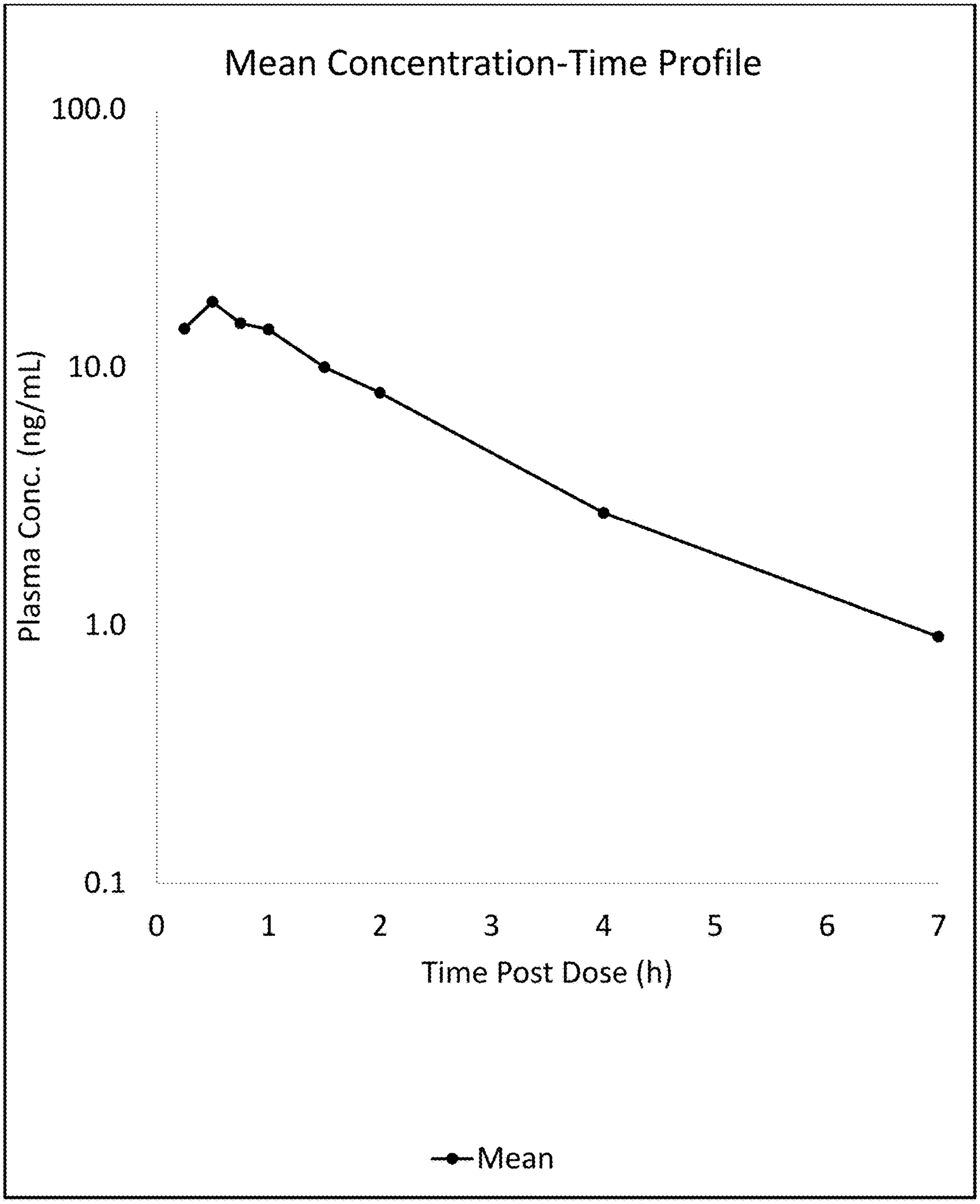
FIG. 15 shows mean concentration-time profiles of xanomeline following SC dosing of xanomeline methyl decatettaraoate chloride prodrug (1 mg/kg of xanomeline) to male SD rats.

FIG. 15 shows mean concentration-time profiles of xanomeline following SC dosing of xanomeline methyl decatettaraoate chloride prodrug (1 mg/kg of xanomeline) to male SD rats.

Example A-1-16: Xanomeline Methyl Pentadecanoate Chloride Prodrug—Table 1 Compound 14

| | |
|---|---|
| Species: | Rat |
| Dose Route: | SC |
| Dose Level (mg/kg) | 1 |

Chemical name: 1-methyl-1[((pentadecanoyloxy)methyl]-5-[4-(hexyloxy-1,2,5-thiadiazol-3-yl)]-1,2,3,6-tetrahydropyridin-1-ium chloride Structural class: acyloxymethyl Mechanistic class: presumed esterase+chemical breakdown

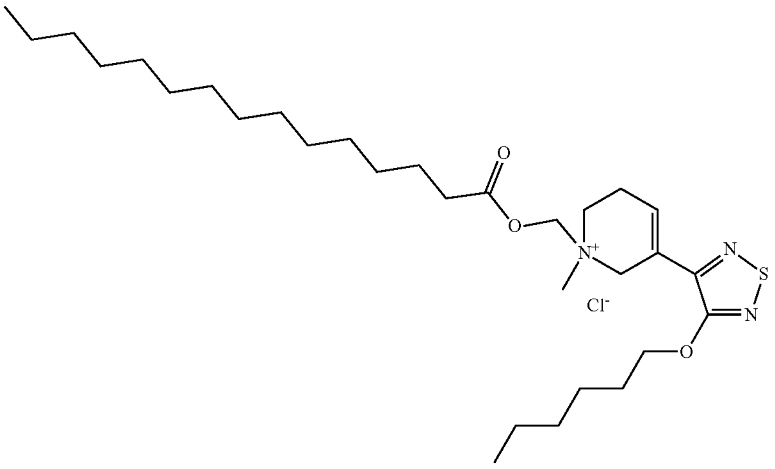 [SMILES: CCCCCCCCCCCCCCC(=O)OC[N+]1(C)CCC=C(c2nsnc2OCCCCCC)C1 ; [Cl-]]

TABLE 18

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R28 | 1.21 | 0.750 | 7.38 | 4.00 | 13.3 | 14.9 |
| | | R29 | 0.891 | 0.500 | 9.99 | 4.00 | 15.3 | 16.1 |
| | | R30 | 1.04 | 0.500 | 8.68 | 4.00 | 12.9 | 14.0 |
| | | Mean | 1.05 | 0.583 | 8.68 | 4.00 | 13.8 | 15.0 |

Figure 16:
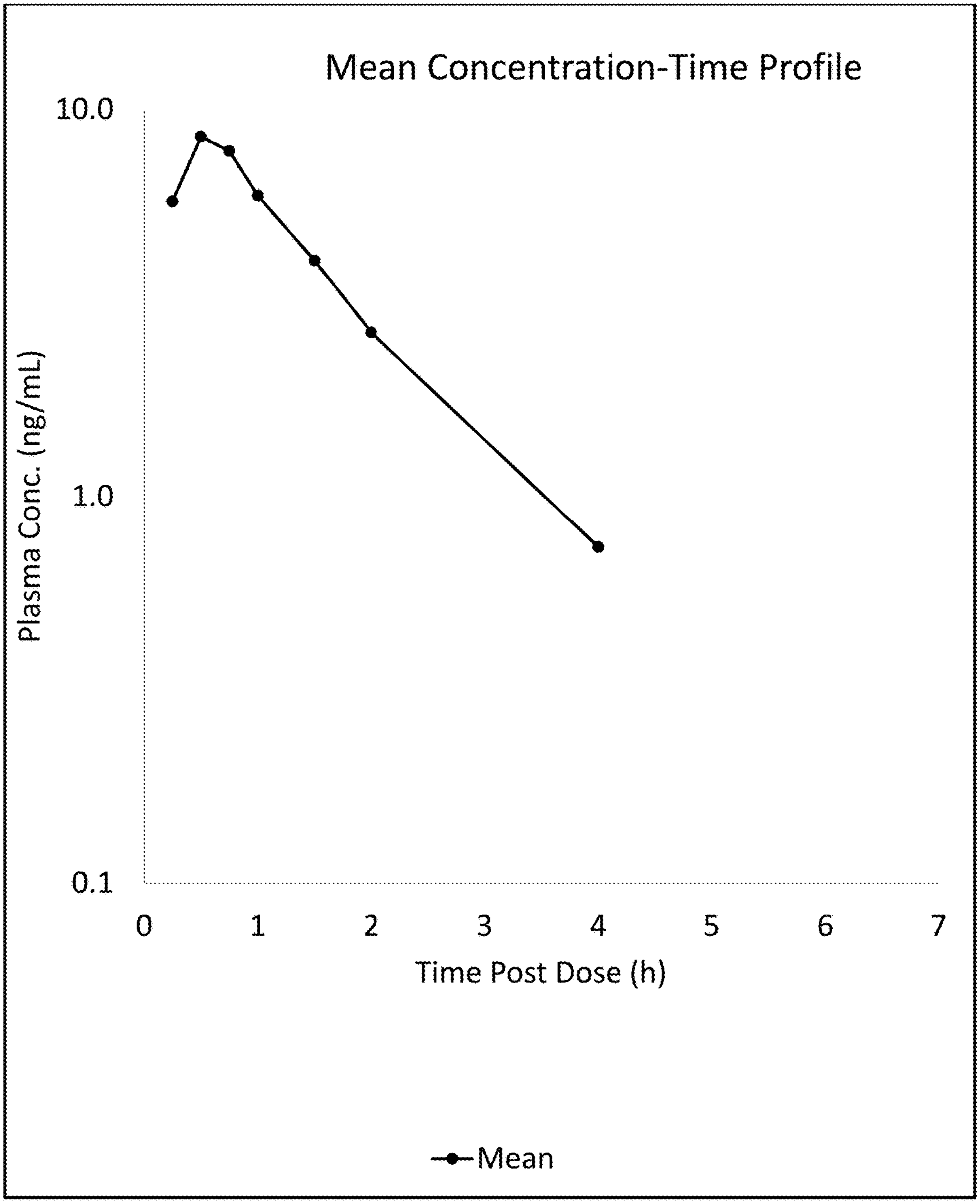
FIG. 16 shows mean concentration-time profiles of xanomeline following SC dosing of xanomeline methyl pentadecanoate chloride prodrug (1 mg/kg of xanomeline) to male SD rats.

FIG. 16 shows mean concentration-time profiles of xanomeline following SC dosing of xanomeline methyl pentadecanoate chloride prodrug (1 mg/kg of xanomeline) to male SD rats.

Example A-1-17: Xanomeline Methyl Isobutyrate Chloride Prodrug—Table 1 Compound 17

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl 2-methylpropanoate chloride Structural class: acyloxymethyl Mechanistic class: presumed esterase+chemical breakdown

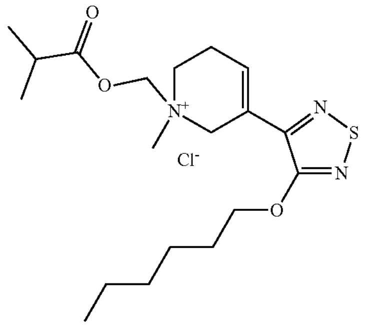 [SMILES: CCCCCCOc1nsnc1C1=CCC[N+](C)(COC(=O)C(C)C)C1 ; [Cl-]]

TABLE 19

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R31 | 1.32 | 0.500 | 85.5 | 4.00 | 36.6 | 39.2 |
| | | R32 | 1.17 | 0.250 | 18.6 | 4.00 | 29.3 | 32.2 |
| | | R33 | 1.18 | 0.250 | 19.0 | 4.00 | 34.1 | 37.5 |
| | | Mean | 1.22 | 0.333 | 41.0 | 4.00 | 33.3 | 36.3 |

Figure 17:
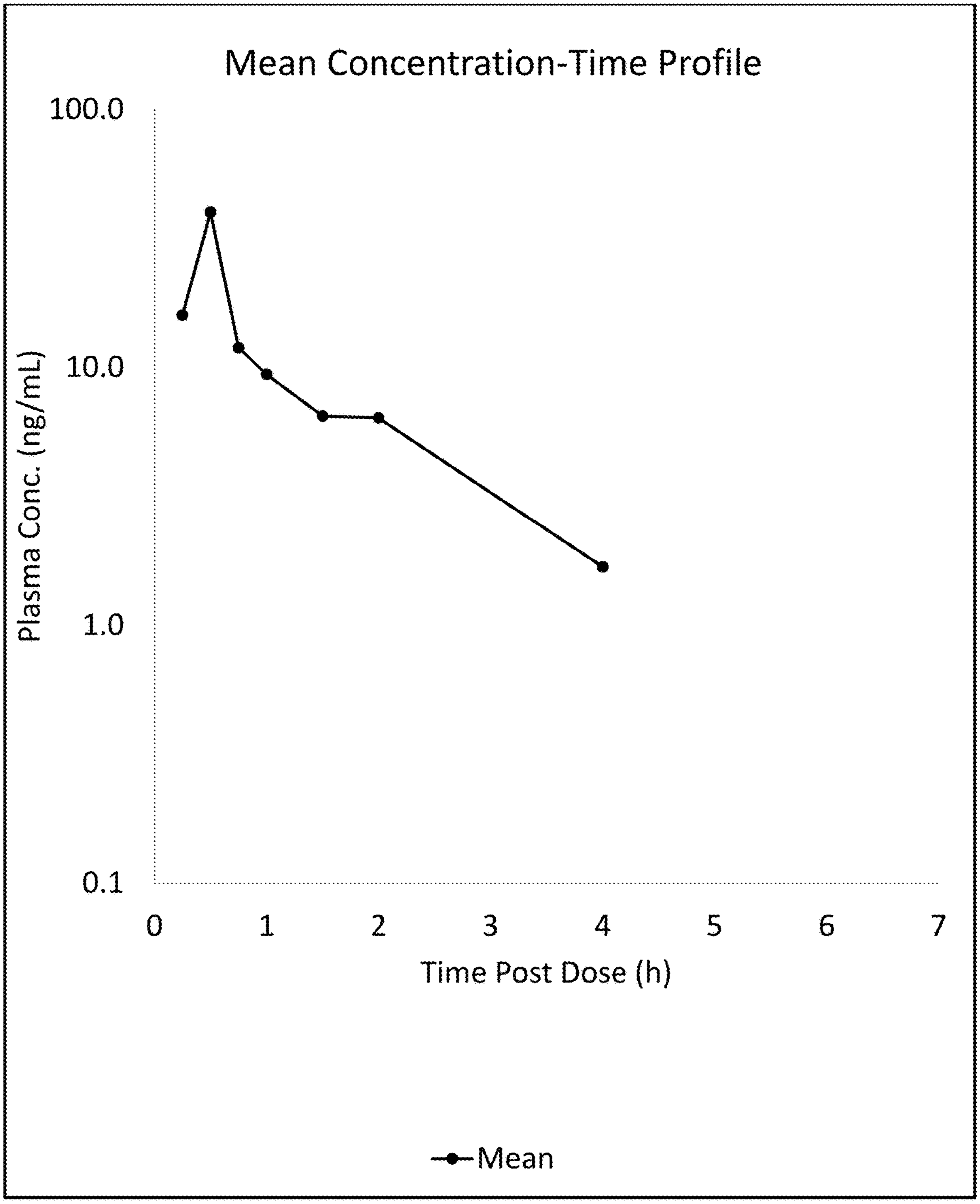
FIG. 17 shows mean concentration-time profiles of xanomeline following SC dosing of xanomeline methyl isobutyrate chloride prodrug (1 mg/kg of xanomeline) to male SD rats.

FIG. 17 shows mean concentration-time profiles of xanomeline following SC dosing of xanomeline methyl isobutyrate chloride prodrug (1 mg/kg of xanomeline) to male SD rats.

Example A-1-18: Xanomeline Methyl Neopentanoate Chloride Prodrug—Table 1 Compound 18

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl 3-methylbutanoate chloride Structural class: acyloxymethyl Mechanistic class: presumed esterase+chemical breakdown

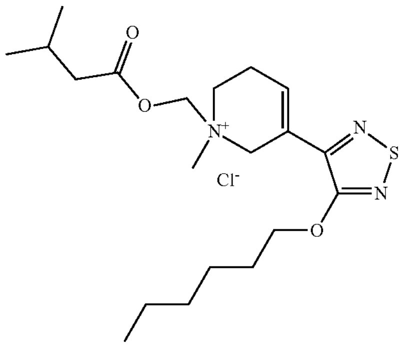 [SMILES: CCCCCCOc1nsnc1C1=CCC[N+](C)(COC(=O)CC(C)C)C1 ; [Cl-]]

TABLE 20

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R37 | 1.10 | 0.500 | 12.8 | 4.00 | 24.4 | 27.0 |
| | | R38 | NR | 1.50 | 12.1 | 4.00 | 18.1 | NR |
| | | R39 | 1.30 | 0.500 | 8.21 | 4.00 | 17.4 | 20.2 |
| | | Mean | 1.20 | 0.833 | 11.0 | 4.00 | 20.0 | 23.6 |

Figure 18:
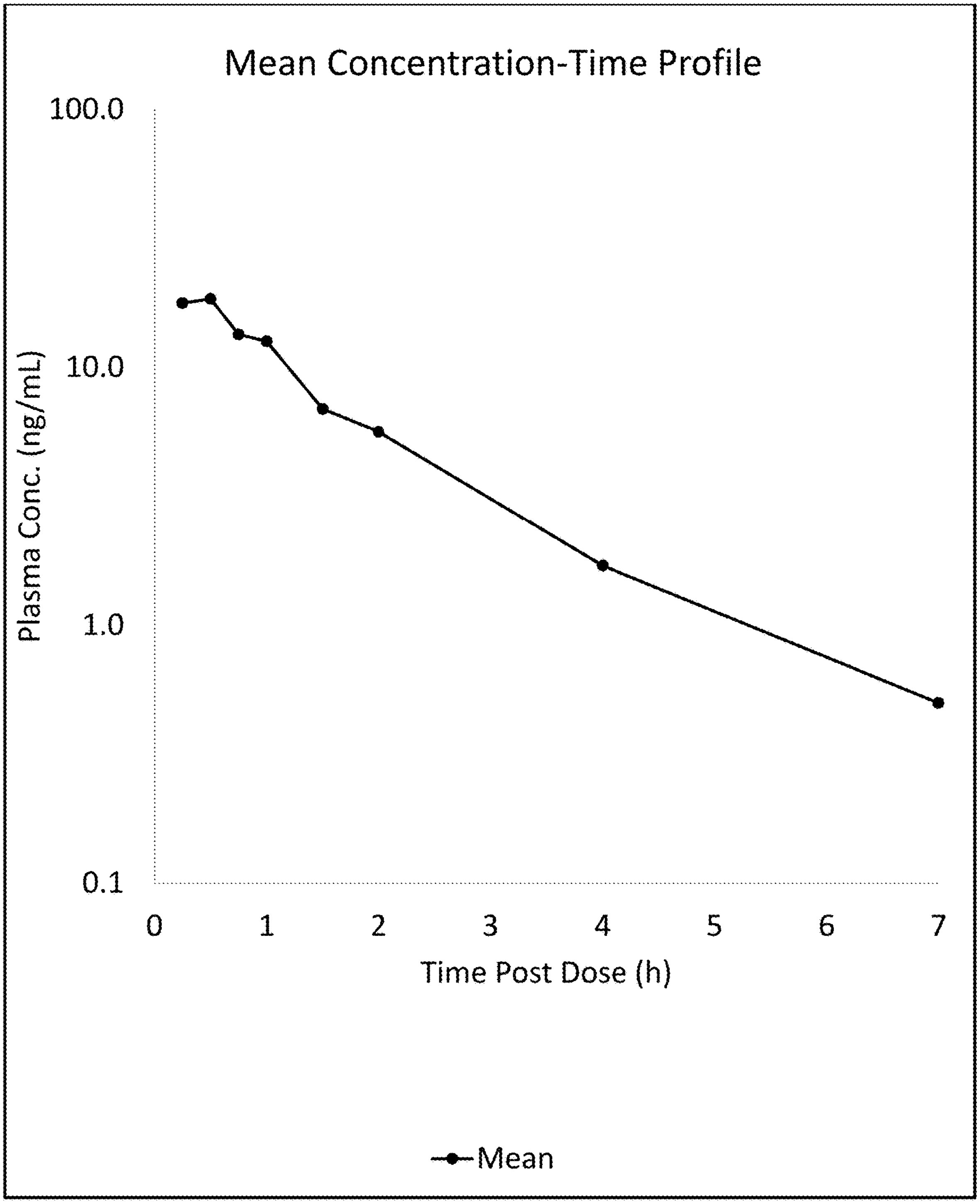
FIG. 18 shows mean concentration-time profiles of xanomeline following SC dosing of xanomeline methyl neopentanoate chloride prodrug (1 mg/kg of xanomeline) to male SD rats.

FIG. 18 shows mean concentration-time profiles of xanomeline following SC dosing of xanomeline methyl neopentanoate chloride prodrug (1 mg/kg of xanomeline) to male SD rats.

Example A-1-19: Xanomeline Methyl "Tert-Butanoate" Iodide Prodrug—Table 1 Compound 16

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl 2,2-dimethylpropanoate iodide Structural class: acyloxymethyl Mechanistic class: presumed esterase+chemical breakdown

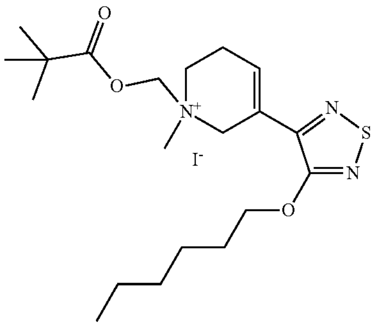 [SMILES: CCCCCCOc1nsnc1C1=CCC[N+](C)(COC(=O)C(C)(C)C)C1 ; [I-]]

TABLE 21

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | SC | R37 | 1.10 | 0.500 | 12.8 | 4.00 | 24.4 | 27.0 |
| | | R38 | NR | 1.50 | 12.1 | 4.00 | 18.1 | NR |
| | | R39 | 1.30 | 0.500 | 8.21 | 4.00 | 17.4 | 20.2 |
| | | Mean | 1.20 | 0.833 | 11.0 | 4.00 | 20.0 | 23.6 |

Figure 19:
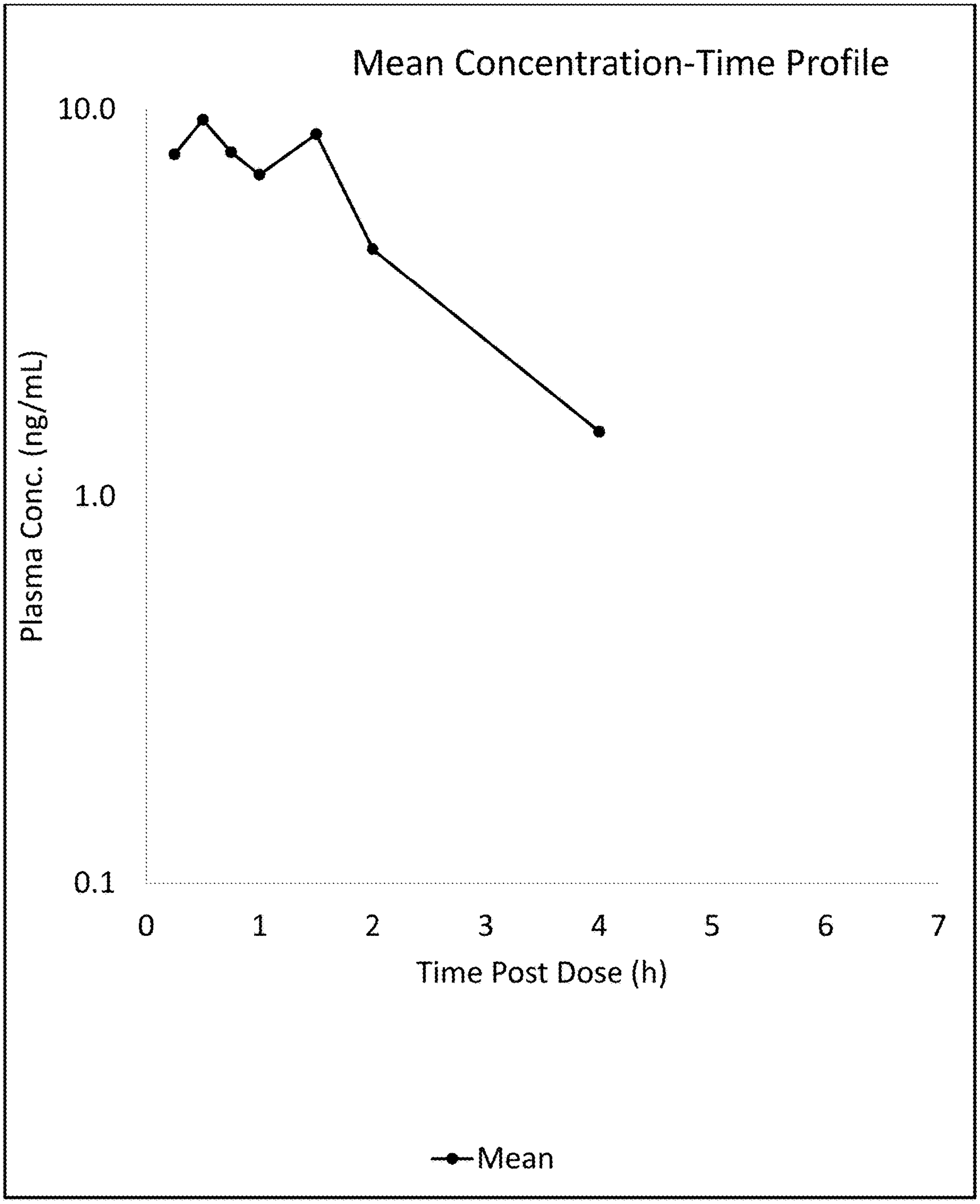
FIG. 19 shows mean concentration-time profiles of xanomeline following SC dosing of xanomeline methyl "tert-butanoate" iodide prodrug (1 mg/kg of xanomeline) to male SD rats.

FIG. 19 shows mean concentration-time profiles of xanomeline following SC dosing of xanomeline methyl "tert-butanoate" iodide prodrug (1 mg/kg of xanomeline) to male SD rats.

Example A-1-20: Xanomeline Methyl Ethylcarbonate Chloride Prodrug—Table 1 Compound 23

| | |
|---|---|
| Species: | Rat |
| Dose Route: | SC |
| Dose Level (mg/kg) | 1 |

Chemical name: ethyl [5-(4-hexyloxy-1,2,5-thiadiazol-3-yl)-1-methyl-3,6-dihydro-2H-pyridin-1-ium-1-yl] methyl carbonate chloride Structural class: alkoxycarbonyloxymethyl Mechanistic class: presumed esterase+chemical breakdown

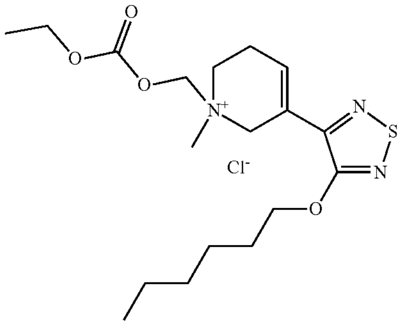

TABLE 22

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R40 | 2.99 | 0.500 | 21.8 | 7.00 | 40.6 | 48.0 |
| | | R41 | 1.20 | 0.250 | 22.9 | 7.00 | 43.1 | 44.1 |
| | | R42 | 1.26 | 0.250 | 19.8 | 4.00 | 31.5 | 35.6 |
| | | Mean | 1.82 | 0.333 | 21.5 | 6.00 | 38.4 | 42.6 |

Figure 20:
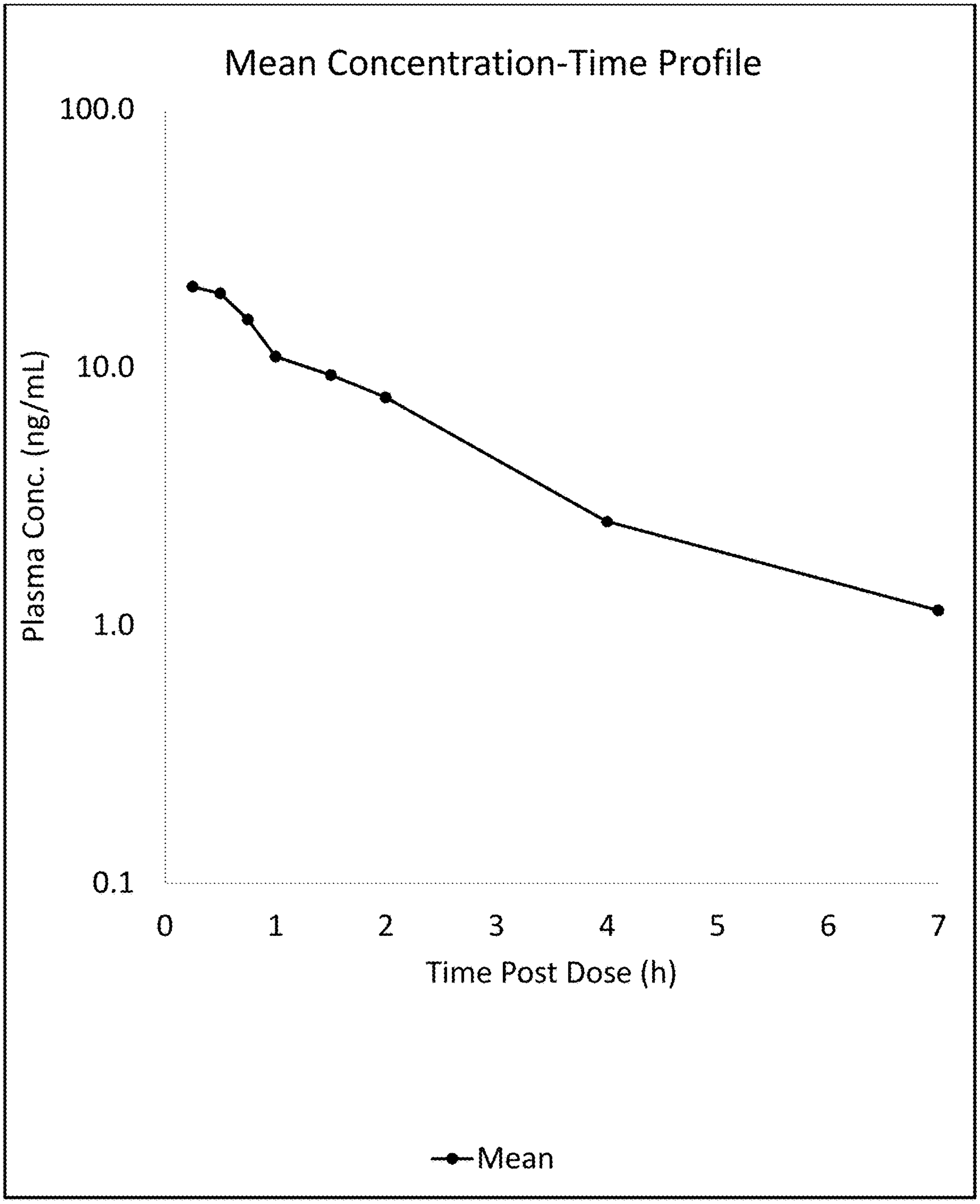
FIG. 20 shows mean concentration-time profiles of xanomeline following SC dosing of xanomeline methyl ethylcarbonate chloride prodrug (1 mg/kg of xanomeline) to male SD rats.

FIG. 20 shows mean concentration-time profiles of xanomeline following SC dosing of xanomeline methyl ethylcarbonate chloride prodrug (1 mg/kg of xanomeline) to male SD rats.

Example A-1-21: Xanomeline Methyl Propylcarbonate Chloride Prodrug—Table 1 Compound 24

| | |
|---|---|
| Species: | Rat |
| Dose Route: | SC |
| Dose Level (mg/kg | 1 |

Chemical name: [5-(4-hexyloxy-1,2,5-thiadiazol-3-yl)-1-methyl-3,6-dihydro-2H-pyridin-1-ium-1-yl]methyl propyl carbonate chloride Structural class: alkoxycarbonyloxymethyl Mechanistic class: presumed esterase+chemical breakdown

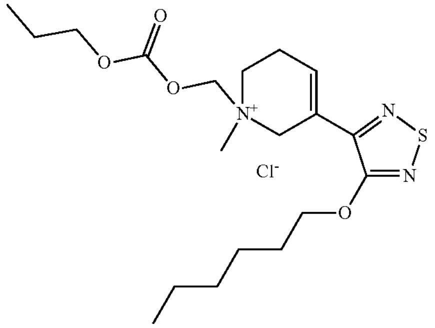 [SMILES: CCCCCCOc1nsnc1C1=CCC[N+](C)(COC(=O)OCCC)C1 ; [Cl-]]

TABLE 23

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R43 | 1.28 | 0.250 | 33.8 | 4.00 | 43.3 | 47.9 |
| | | R44 | 1.07 | 0.500 | 36.5 | 4.00 | 46.2 | 50.1 |
| | | R45 | 1.05 | 0.500 | 37.8 | 4.00 | 48.3 | 52.0 |
| | | Mean | 1.13 | 0.417 | 36.0 | 4.00 | 45.9 | 50.0 |

Figure 21:
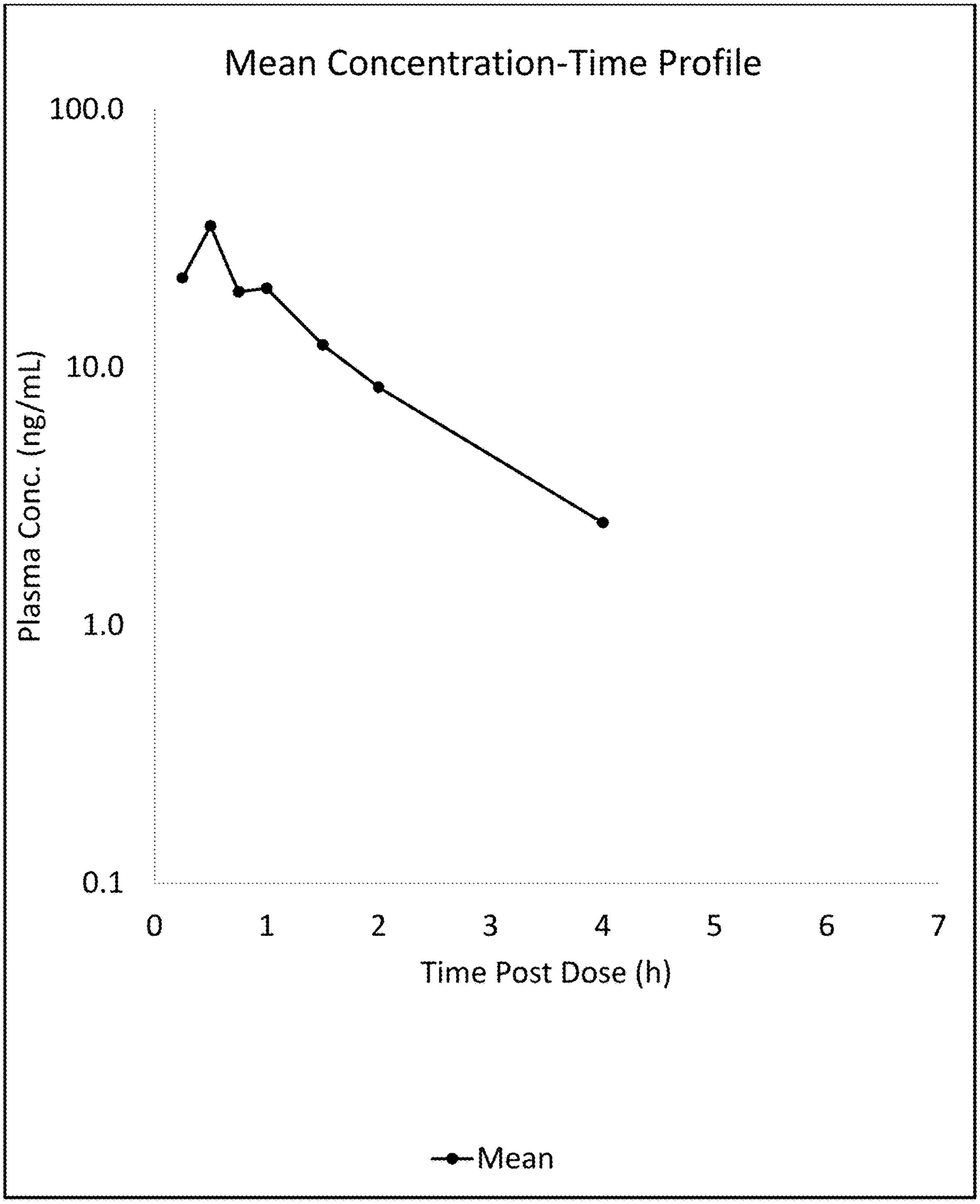
FIG. 21 shows mean concentration-time profiles of xanomeline following SC dosing of xanomeline methyl propylcarbonate chloride prodrug (1 mg/kg of xanomeline) to male SD rats.

FIG. 21 shows mean concentration-time profiles of xanomeline following SC dosing of xanomeline methyl propylcarbonate chloride prodrug (1 mg/kg of xanomeline) to male SD rats.

Example A-1-22: Xanomeline Methyl Butylcarbonate Chloride Prodrug—Table 1 Compound

| | |
|---|---|
| Species: | Rat |
| Dose Route: | SC |
| Dose Level (mg/kg) | 1 |

Chemical name: butyl [5-(4-hexyloxy-1,2,5-thiadiazol-3-yl)-1-methyl-3,6-dihydro-2H-pyridin-1-ium-1-yl] methyl carbonate chloride Structural class: alkoxycarbonyloxymethyl Mechanistic class: presumed esterase+chemical breakdown

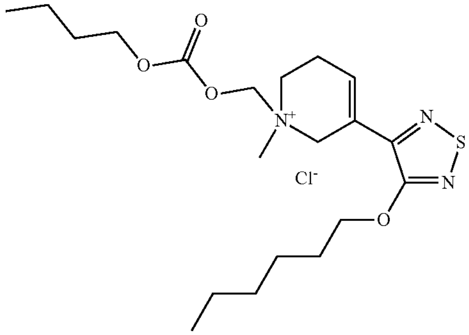 [SMILES: CCCCCCOc1nsnc1C1=CCC[N+](C)(COC(=O)OCCCC)C1 ; [Cl-]]

TABLE 24

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R46 | 1.41 | 0.500 | 41.0 | 4.00 | 46.6 | 51.6 |
| | | R47 | 1.17 | 0.500 | 35.5 | 4.00 | 45.0 | 48.7 |
| | | R48 | 1.79 | 0.250 | 23.0 | 4.00 | 27.5 | 33.6 |
| | | Mean | 1.46 | 0.417 | 33.2 | 4.00 | 39.7 | 44.6 |

Figure 22:
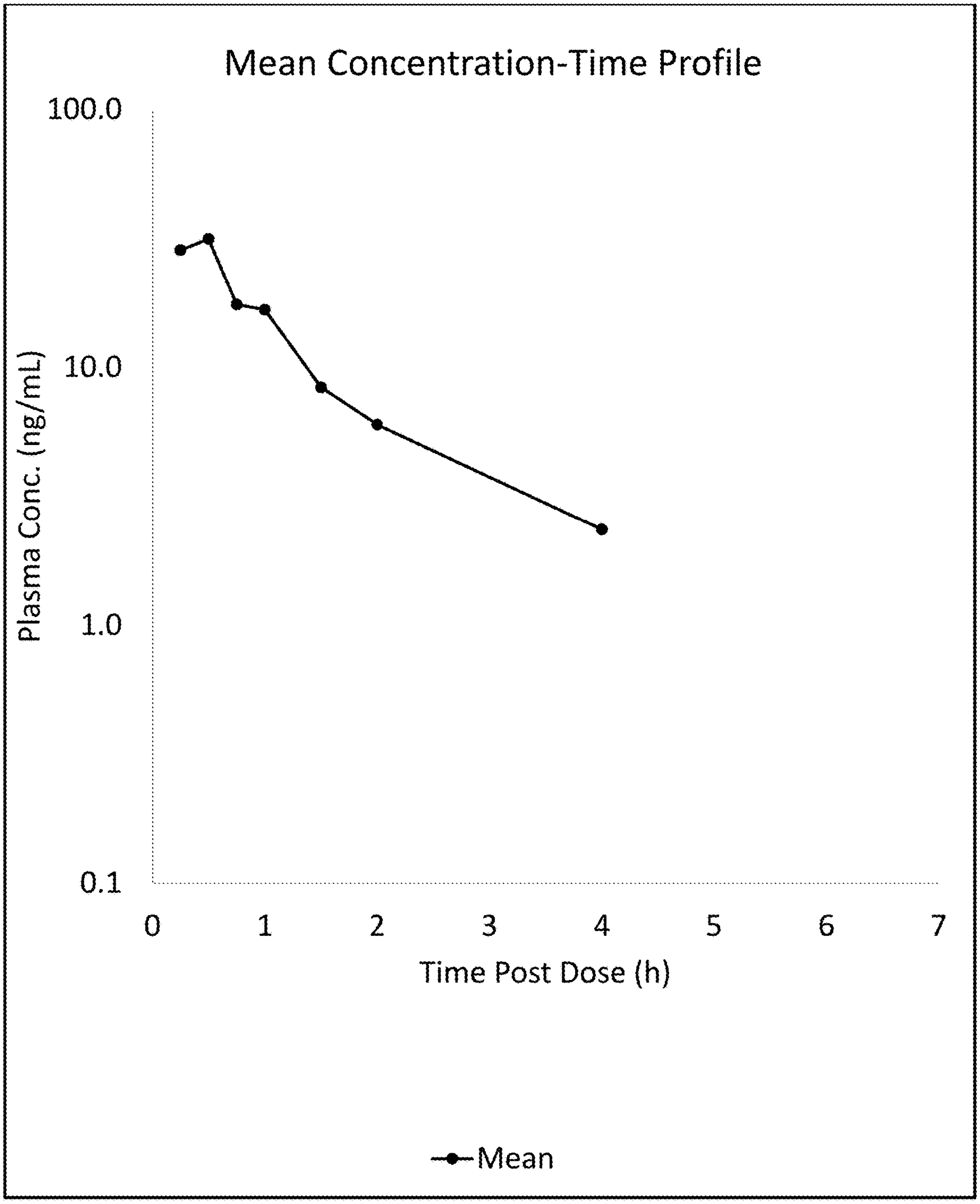
FIG. 22 shows mean concentration-time profiles of xanomeline following SC dosing of xanomeline methyl butylcarbonate chloride prodrug (1 mg/kg of xanomeline) to male SD rats.

FIG. 22 shows mean concentration-time profiles of xanomeline following SC dosing of xanomeline methyl butylcarbonate chloride prodrug (1 mg/kg of xanomeline) to male SD rats.

Example A-1-23: Xanomeline Methyl Pentylcarbonate Chloride Prodrug—Table 1 Compound 26

| | |
|---|---|
| Species: | Rat |
| Dose Route: | SC |
| Dose Level (mg/kg) | 1 |

Chemical name: penty [5-(4-hexyloxy-1,2,5-thiadiazol-3-yT)-1-methyl-3,6-dihydro-2H-pyridin-1-ium-1-yl] methyl carbonate chloride Structural class: alkoxycarbonyloxymethyl Mechanistic class: presumed esterase+chemical breakdown

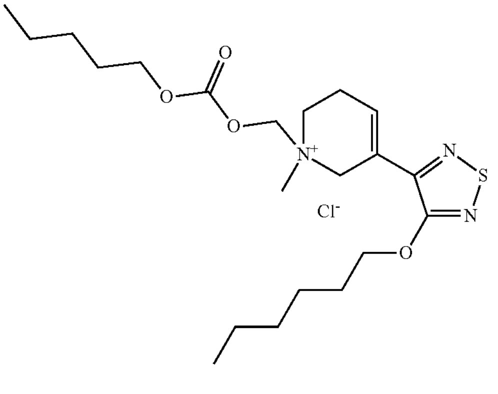 [SMILES: CCCCCCOc1nsnc1C1=CCC[N+](C)(COC(=O)OCCCCC)C1 ; [Cl-]]

TABLE 25

| Xanomeline Pharmacokinetic Parameters | | | | | | | | |
|---|---|---|---|---|---|---|---|---|
| Analyte | Dose Route | Ani-mal ID | T1/2 (hr) | Tmax (hr) | Cmax (ng/mL) | Tlast (hr) | AUClast (ng/ml*hr) | AUCINF_obs (ng/ml*hr) |
| Xano-meline | SC | R49 | 0.862 | 0.500 | 31.8 | 4.00 | 39.7 | 41.5 |
| | | R50 | 1.35 | 0.500 | 18.3 | 4.00 | 26.4 | 29.9 |
| | | R51 | 1.08 | 0.500 | 24.9 | 4.00 | 28.9 | 30.7 |
| | | Mean | 1.10 | 0.500 | 25.0 | 4.00 | 31.7 | 34.0 |

Figure 23:
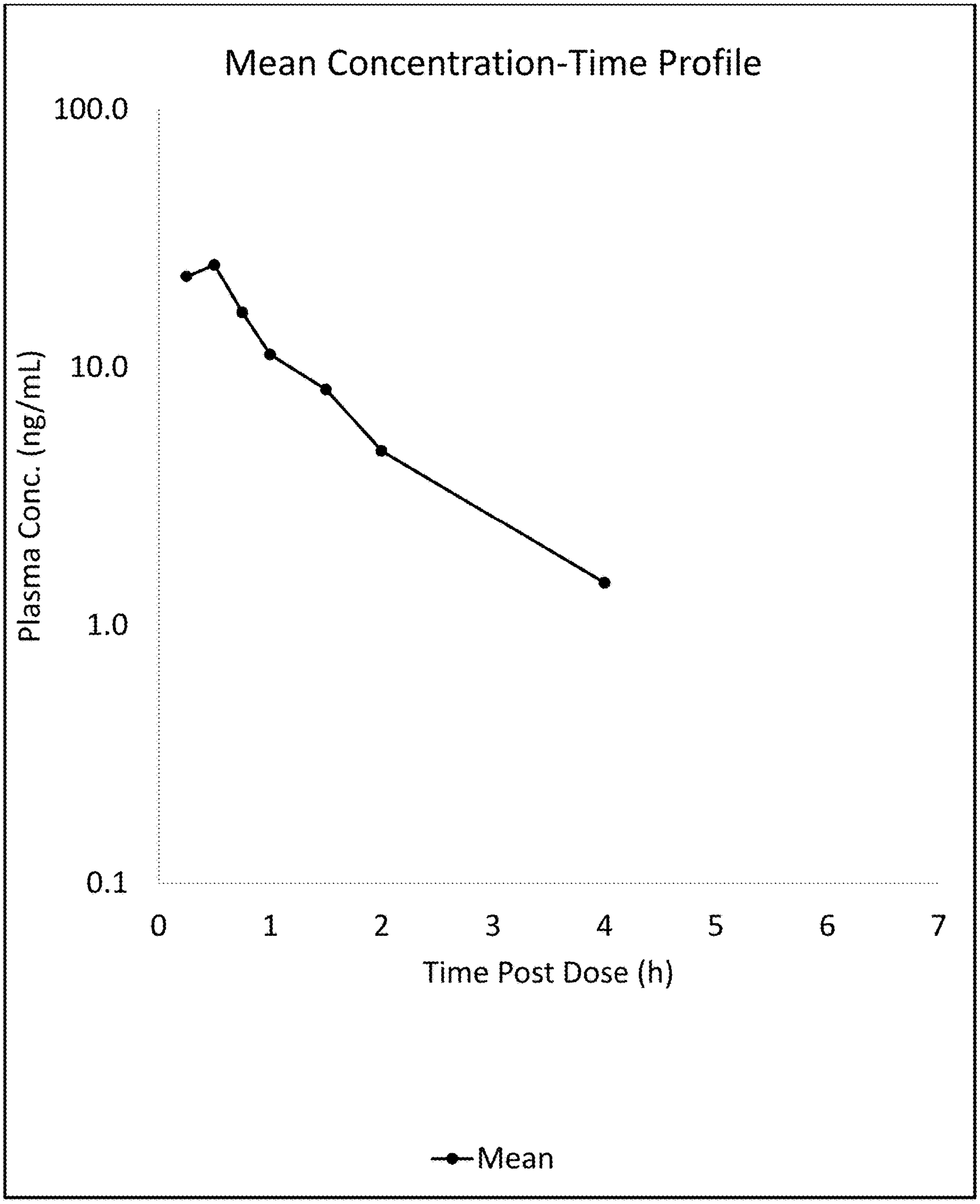
FIG. 23 shows mean concentration-time profiles of xanomeline following SC dosing of xanomeline methyl pentylcarbonate chloride prodrug (1 mg/kg of xanomeline) to male SD rats.

FIG. 23 shows mean concentration-time profiles of xanomeline following SC dosing of xanomeline methyl pentylcarbonate chloride prodrug (1 mg/kg of xanomeline) to male SD rats.

Example A-1-24: Xanomeline Methyl Hexylcarbonate Chloride Prodrug—Table 1 Compound 27

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl hexyl carbonate chloride Structural class: alkoxycarbonyloxymethyl Mechanistic class: presumed esterase+chemical breakdown

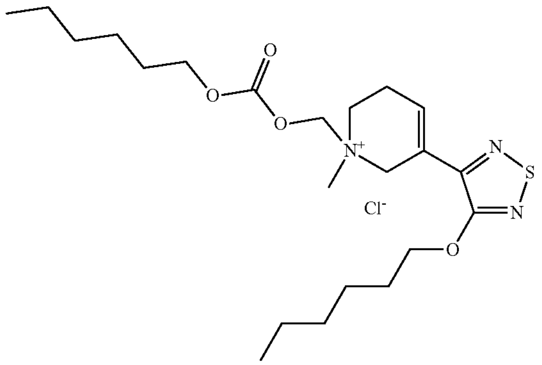 [SMILES: CCCCCCOC(=O)OC[N+]1(C)CCC=C(c2nsnc2OCCCCCC)C1 ; [Cl-]]

TABLE 26

| Xanomeline Pharmacokinetic Parameters | | | | | | | | |
|---|---|---|---|---|---|---|---|---|
| Analyte | Dose Route | Ani-mal ID | T1/2 (hr) | Tmax (hr) | Cmax (ng/mL) | Tlast (hr) | AUClast (ng/ml*hr) | AUCINF_obs (ng/ml*hr) |
| Xano-meline | SC | R52 | 0.911 | 0.500 | 37.5 | 4.00 | 41.2 | 43.2 |
| | | R53 | 1.01 | 0.500 | 30.9 | 4.00 | 31.5 | 33.4 |
| | | R54 | 1.07 | 0.500 | 47.2 | 4.00 | 36.9 | 39.2 |
| | | Mean | 0.997 | 0.500 | 38.5 | 4.00 | 36.5 | 38.6 |

Figure 24:
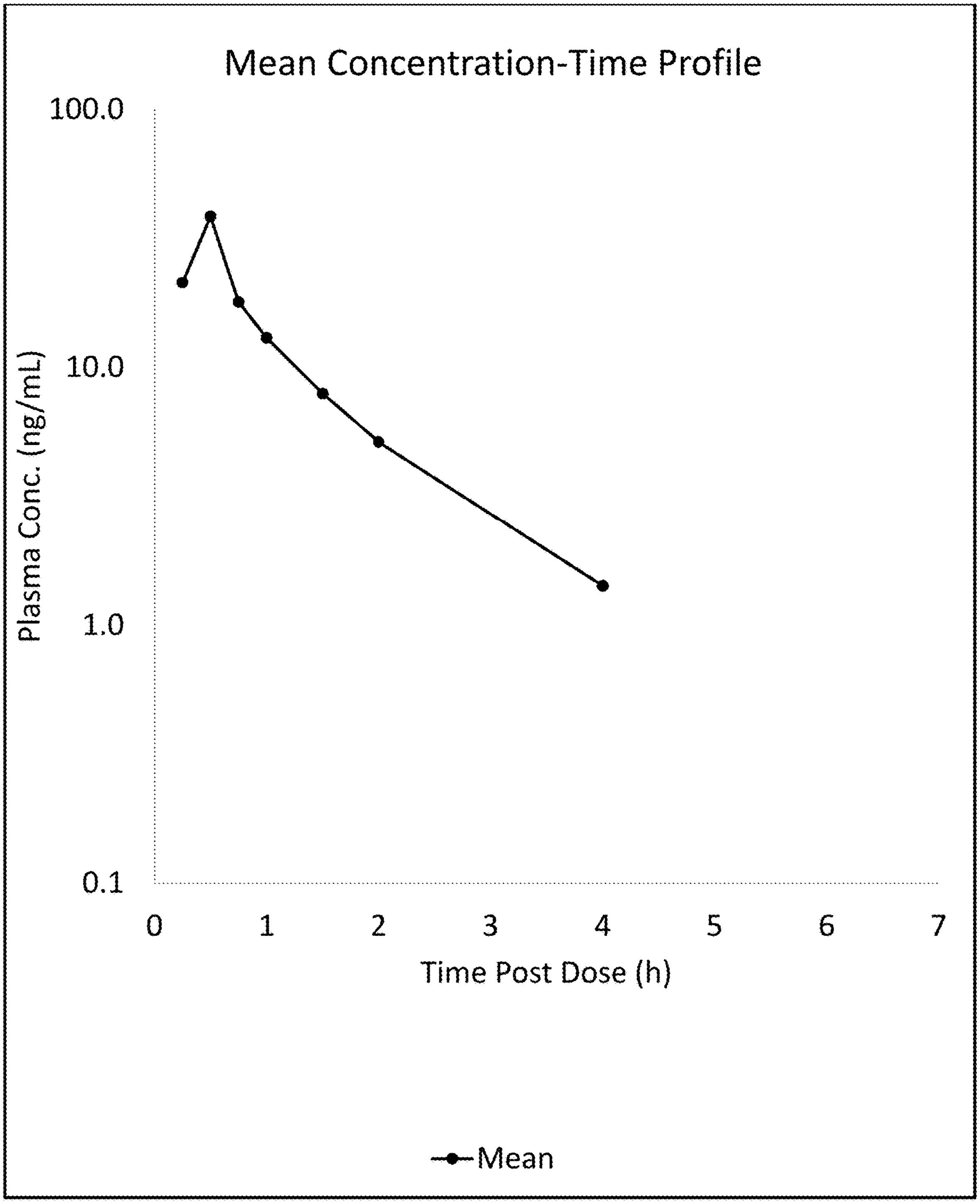
FIG. 24 shows mean concentration-time profiles of xanomeline following SC dosing of xanomeline methyl hexylcarbonate chloride prodrug (1 mg/kg of xanomeline) to male SD rats.

FIG. 24 shows mean concentration-time profiles of xanomeline following SC dosing of xanomeline methyl hexylcarbonate chloride prodrug (1 mg/kg of xanomeline) to male SD rats.

Example A-1-25: Xanomeline Methyl Heptylcarbonate Chloride Prodrug—Table 1 Compound 28

| | |
|---|---|
| Species: | Rat |
| Dose Route: | SC |
| Dose Level (mg/kg) | 1 |

Chemical name: heptyl [5-(4-hexyloxy-1,2,5-thiadiazol-3-yl)-1-methyl-3,6-dihydro-2H-pyridin-1-ium-1-yl] methyl carbonate chloride Structural class: alkoxycarbonyloxymethyl Mechanistic class: presumed esterase+chemical breakdown

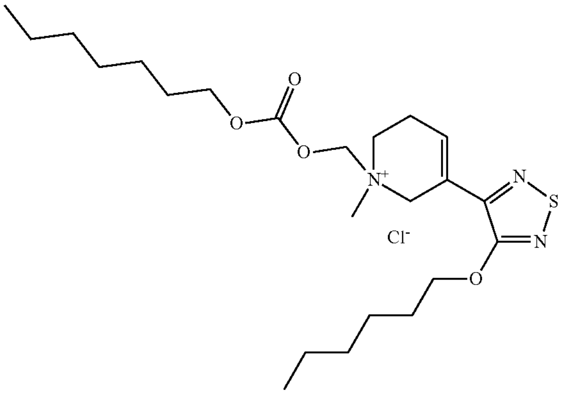 [SMILES: CCCCCCCOC(=O)OC[N+]1(C)CCC=C(c2nsnc2OCCCCCC)C1 ; [Cl-]]

TABLE 27

| Xanomeline Pharmacokinetic Parameters | | | | | | | | |
|---|---|---|---|---|---|---|---|---|
| Analyte | Dose Route | Ani-mal ID | T1/2 (hr) | Tmax (hr) | Cmax (ng/mL) | Tlast (hr) | AUClast (ng/ml*hr) | AUCINF_obs (ng/ml*hr) |
| Xano-meline | SC | R55 | 1.36 | 0.500 | 29.5 | 4.00 | 32.6 | 36.4 |
| | | R56 | 1.79 | 0.500 | 27.2 | 7.00 | 39.1 | 41.5 |
| | | R57 | 1.25 | 0.500 | 24.0 | 4.00 | 33.7 | 37.7 |
| | | Mean | 1.47 | 0.500 | 26.9 | 5.00 | 35.1 | 38.5 |

Figure 25:
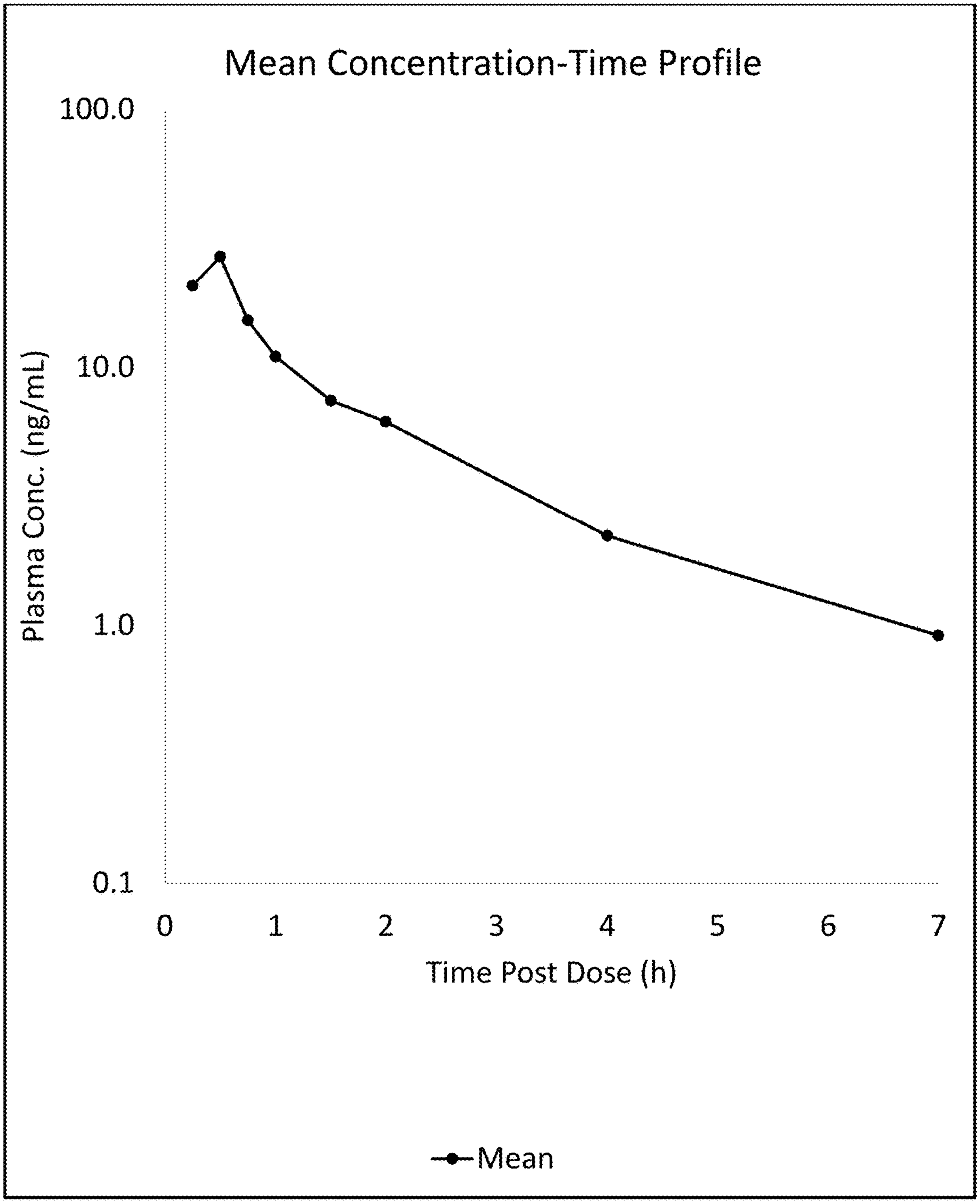
FIG. 25 shows mean concentration-time profiles of xanomeline following SC dosing of xanomeline methyl heptylcarbonate chloride prodrug (1 mg/kg of xanomeline) to male SD rats.

FIG. 25 shows mean concentration-time profiles of xanomeline following SC dosing of xanomeline methyl heptylcarbonate chloride prodrug (1 mg/kg of xanomeline) to male SD rats.

Example A-1-26: Xanomeline Methyl Octylcarbonate Chloride Prodrug—Table 1 Compound 29

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl octyl carbonate chloride Structural class: alkoxycarbonyloxymethyl Mechanistic class: presumed esterase+chemical breakdown

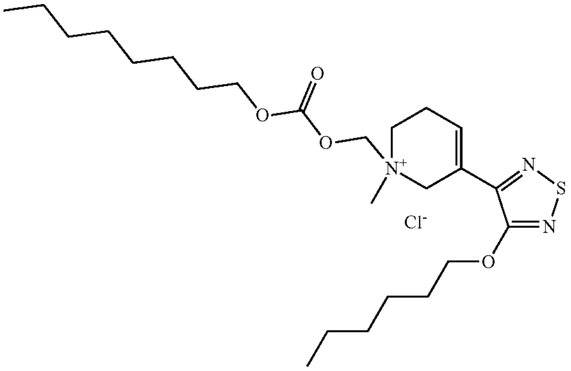 [SMILES: CCCCCCCCOC(=O)OC[N+]1(C)CCC=C(c2nsnc2OCCCCCC)C1 ; [Cl-]]

TABLE 28

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R58 | 1.85 | 0.500 | 27.1 | 7.00 | 41.3 | 43.5 |
| | | R59 | 1.20 | 0.250 | 28.1 | 4.00 | 39.5 | 43.6 |
| | | R60 | 1.33 | 0.500 | 36.7 | 7.00 | 51.3 | 52.4 |
| | | Mean | 1.46 | 0.417 | 30.6 | 6.00 | 44.0 | 46.5 |

Figure 26:
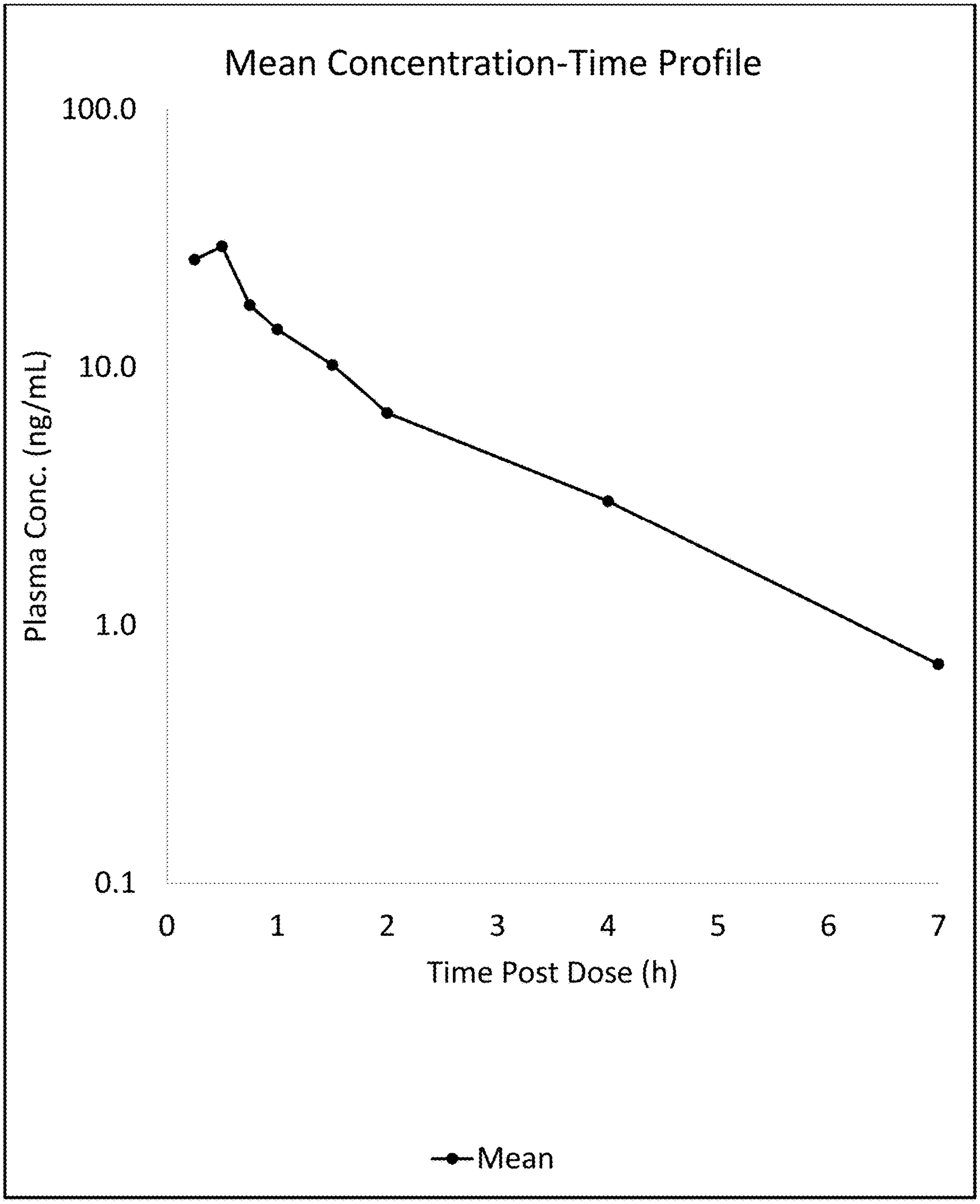
FIG. 26 shows mean concentration-time profiles of xanomeline following SC dosing of xanomeline methyl octylcarbonate chloride prodrug (1 mg/kg of xanomeline) to male SD rats.

FIG. 26 shows mean concentration-time profiles of xanomeline following SC dosing of xanomeline methyl octylcarbonate chloride prodrug (1 mg/kg of xanomeline) to male SD rats.

Example A-1-27: Xanomeline Methyl Nonylcarbonate Chloride Prodrug—Table 1 Compound 30

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl nonyl carbonate chloride Structural class: alkoxycarbonyloxymethyl Mechanistic class: presumed esterase+chemical breakdown

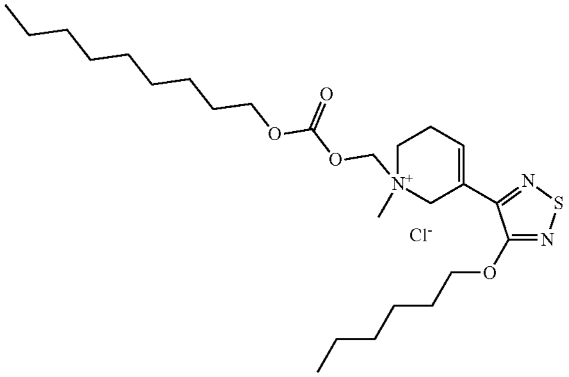 [SMILES: CCCCCCCCCOC(=O)OC[N+]1(C)CCC=C(c2nsnc2OCCCCCC)C1 ; [Cl-]]

TABLE 29

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R61 | 0.948 | 0.250 | 27.7 | 4.00 | 34.1 | 35.7 |
| | | R62 | 2.73 | 0.250 | 16.9 | 4.00 | 19.4 | 26.3 |
| | | R63 | 1.15 | 0.250 | 15.3 | 4.00 | 13.8 | 14.7 |
| | | Mean | 1.61 | 0.250 | 20.0 | 4.00 | 22.4 | 25.6 |

Figure 27:
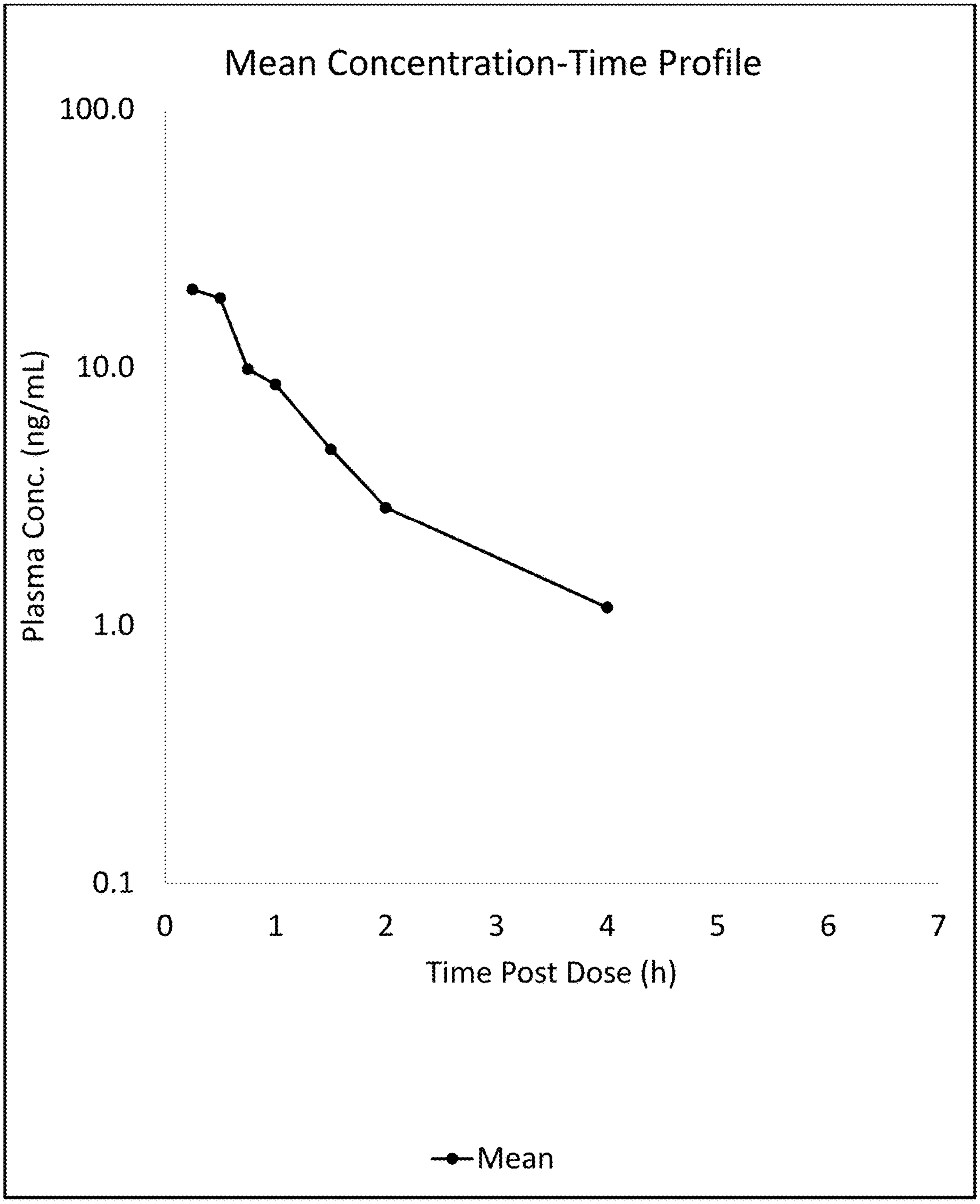
FIG. 27 shows mean concentration-time profiles of xanomeline following SC dosing of xanomeline methyl nonylcarbonate chloride prodrug (1 mg/kg of xanomeline) to male SD rats.

FIG. 27 shows mean concentration-time profiles of xanomeline following SC dosing of xanomeline methyl nonylcarbonate chloride prodrug (1 mg/kg of xanomeline) to male SD rats.

Example A-1-28: Xanomeline Methyl Decylcarbonate Chloride Prodrug—Table 1 Compound 31

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl decyl carbonate chloride Structural class: alkoxycarbonyloxymethyl Mechanistic class: presumed esterase+chemical breakdown

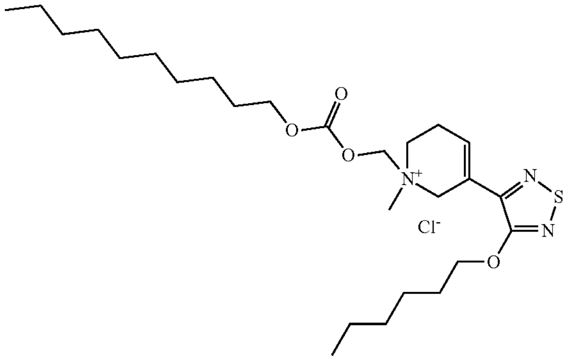 [SMILES: CCCCCCCCCCOC(=O)OC[N+]1(C)CCC=C(c2nsnc2OCCCCCC)C1 ; [Cl-]]

TABLE 30

Xanomeline Pharmacokinetic Parameters

| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
|---|---|---|---|---|---|---|---|---|
| Xanomeline | SC | R64 | 1.35 | 0.500 | 26.7 | 4.00 | 28.9 | 31.8 |
| | | R65 | 1.02 | 0.500 | 26.1 | 4.00 | 29.5 | 31.3 |
| | | R66 | 0.726 | 0.250 | 25.1 | 4.00 | 25.4 | 25.9 |
| | | Mean | 1.03 | 0.417 | 26.0 | 4.00 | 27.9 | 29.7 |

Figure 28:
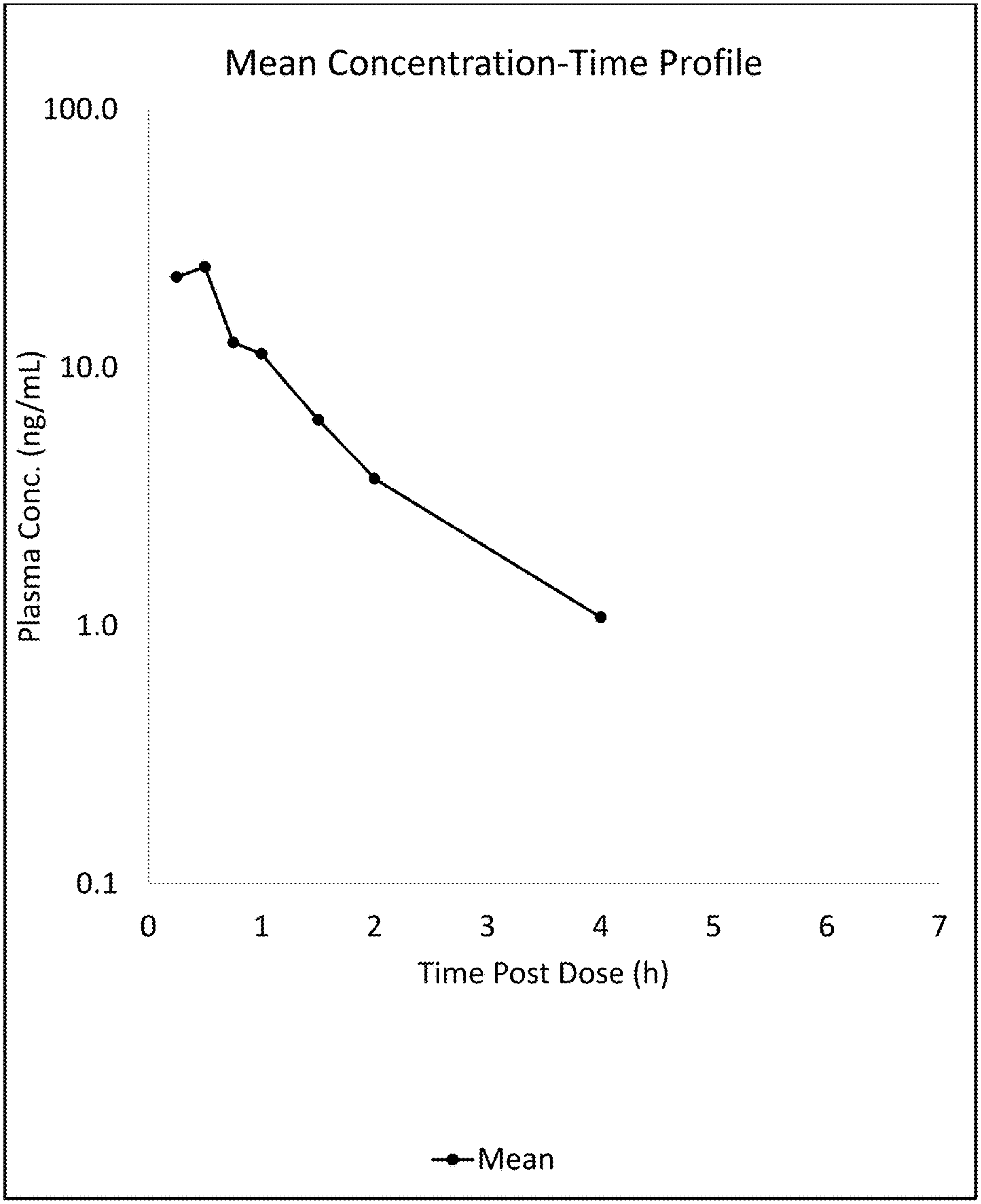
FIG. 28 shows mean concentration-time profiles of xanomeline following SC dosing of xanomeline methyl decylcarbonate chloride prodrug (1 mg/kg of xanomeline) to male SD rats.

FIG. 28 shows mean concentration-time profiles of xanomeline following SC dosing of xanomeline methyl decylcarbonate chloride prodrug (1 mg/kg of xanomeline) to male SD rats.

Example A-1-29: Xanomeline Methyl Undecylcarbonate Chloride Prodrug—Table 1 Compound 32

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl undecyl carbonate chloride Structural class: alkoxycarbonyloxymethyl Mechanistic class: presumed esterase+chemical breakdown

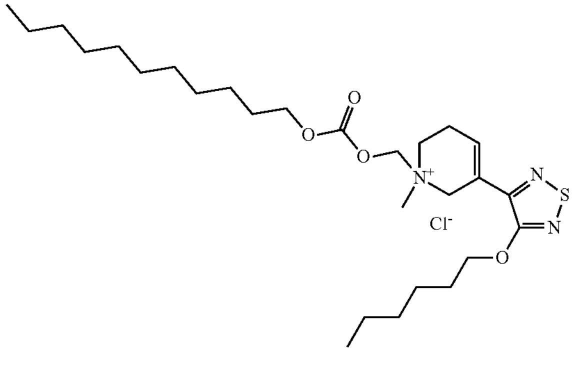 [SMILES: CCCCCCCCCCCOC(=O)OC[N+]1(C)CCC=C(c2nsnc2OCCCCCC)C1 ; [Cl-]]

TABLE 31

Xanomeline Pharmacokinetic Parameters

| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
|---|---|---|---|---|---|---|---|---|
| Xanomeline | SC | R67 | 1.03 | 0.250 | 12.9 | 4.00 | 14.3 | 15.3 |
| | | R68 | 1.09 | 0.250 | 14.1 | 4.00 | 15.8 | 16.8 |
| | | R69 | 0.708 | 0.250 | 13.3 | 2.00 | 12.2 | 14.4 |
| | | Mean | 0.943 | 0.250 | 13.4 | 3.33 | 14.1 | 15.5 |

Figure 29:
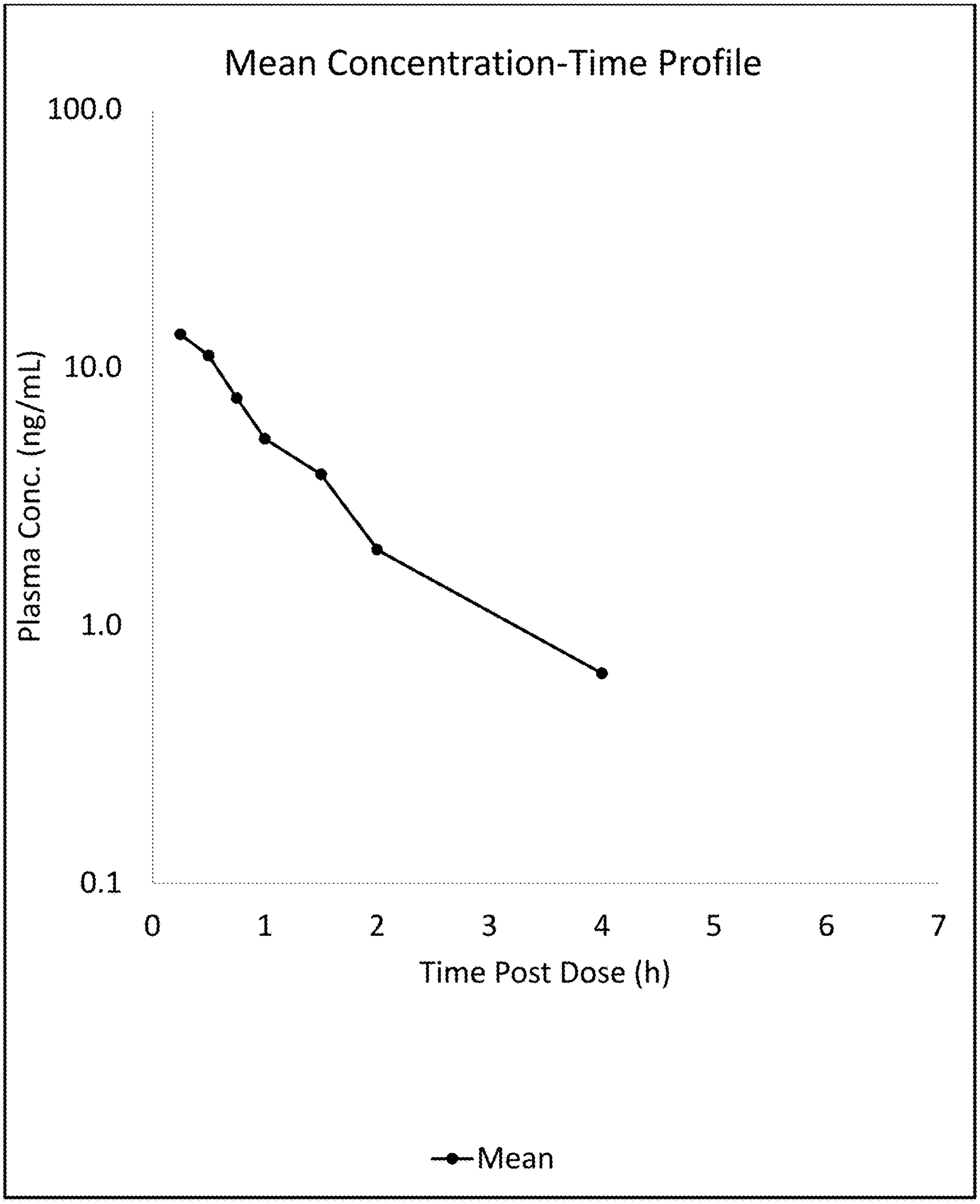
FIG. 29 shows mean concentration-time profiles of xanomeline following SC dosing of xanomeline methyl undecylcarbonate chloride prodrug (1 mg/kg of xanomeline) to male SD rats.

FIG. 29 shows mean concentration-time profiles of xanomeline following SC dosing of xanomeline methyl undecylcarbonate chloride prodrug (1 mg/kg of xanomeline) to male SD rats.

Example A-1-30: Xanomeline Methyl Dodecylcarbonate Chloride Prodrug—Table 1 Compound 33

| | |
|---|---|
| Species: | Rat |
| Dose Route: | SC |
| Dose Level (mg/kg) | 1 |

Chemical name: dodecyl [5-(4-hexyloxy-1,2,5-thiadiazol-3-yl)-1-methyl-3,6-dihydro-2H-pyridin-1-ium-1-yl]methyl carbonate chloride Structural class: alkoxycarbonyloxymethyl Mechanistic class: presumed esterase+chemical breakdown

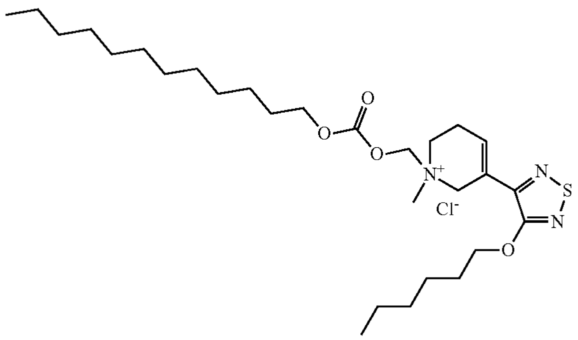 [SMILES: CCCCCCCCCCCCOC(=O)OC[N+]1(C)CCC=C(c2nsnc2OCCCCCC)C1 ; [Cl-]]

TABLE 32

Xanomeline Pharmacokinetic Parameters

| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
|---|---|---|---|---|---|---|---|---|
| Xanomeline | SC | R70 | 1.07 | 0.500 | 23.0 | 4.00 | 35.4 | 37.9 |
| | | R71 | 1.09 | 1.000 | 9.35 | 4.00 | 18.0 | 19.7 |
| | | R72 | 1.11 | 0.500 | 18.6 | 4.00 | 29.5 | 32.5 |
| | | Mean | 1.09 | 0.667 | 17.0 | 4.00 | 27.6 | 30.0 |

Figure 30:
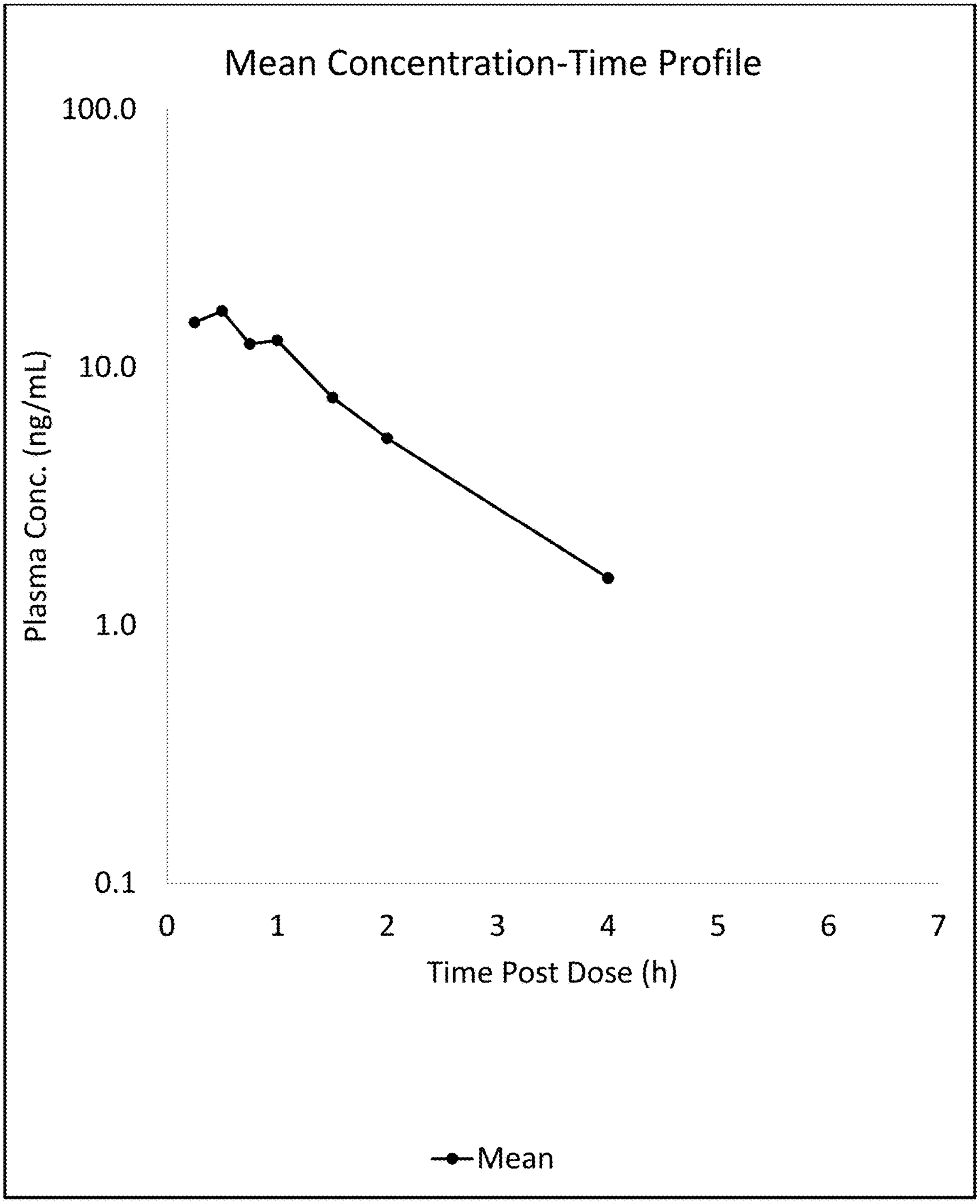
FIG. 30 shows mean concentration-time profiles of xanomeline following SC dosing of xanomeline methyl dodecylcarbonate chloride prodrug (1 mg/kg of xanomeline) to male SD rats.

FIG. 30 shows mean concentration-time profiles of xanomeline following SC dosing of xanomeline methyl dodecylcarbonate chloride prodrug (1 mg/kg of xanomeline) to male SD rats.

Example A-1-31: Xanomeline Methyl Decatriylcarbonate Chloride Prodrug—Table 1 Compound 34

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl tridecyl carbonate chloride Structural class: alkoxycarbonyloxymethyl Mechanistic class: presumed esterase+chemical breakdown

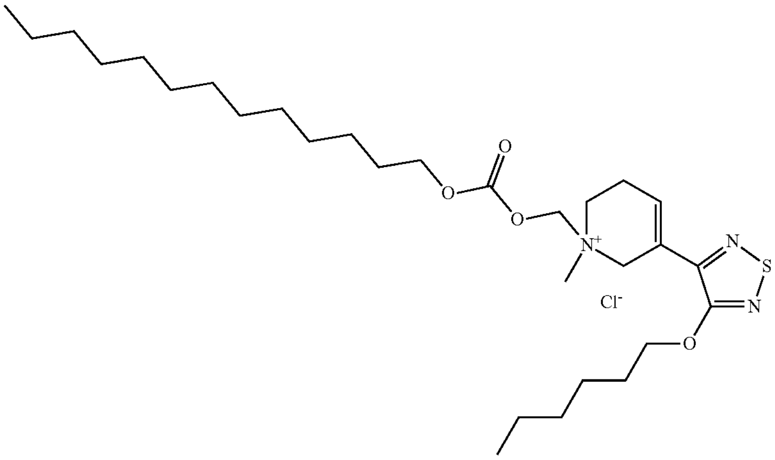 [SMILES: CCCCCCCCCCCCCOC(=O)OC[N+]1(C)CCC=C(c2nsnc2OCCCCCC)C1 ; [Cl-]]

TABLE 33

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R73 | 1.18 | 0.250 | 48.3 | 4.00 | 44.1 | 47.9 |
| | | R74 | 0.888 | 0.250 | 46.9 | 4.00 | 49.2 | 51.1 |
| | | R75 | 1.21 | 0.250 | 34.3 | 4.00 | 41.2 | 44.8 |
| | | Mean | 1.09 | 0.250 | 43.2 | 4.00 | 44.8 | 47.9 |

Figure 31:
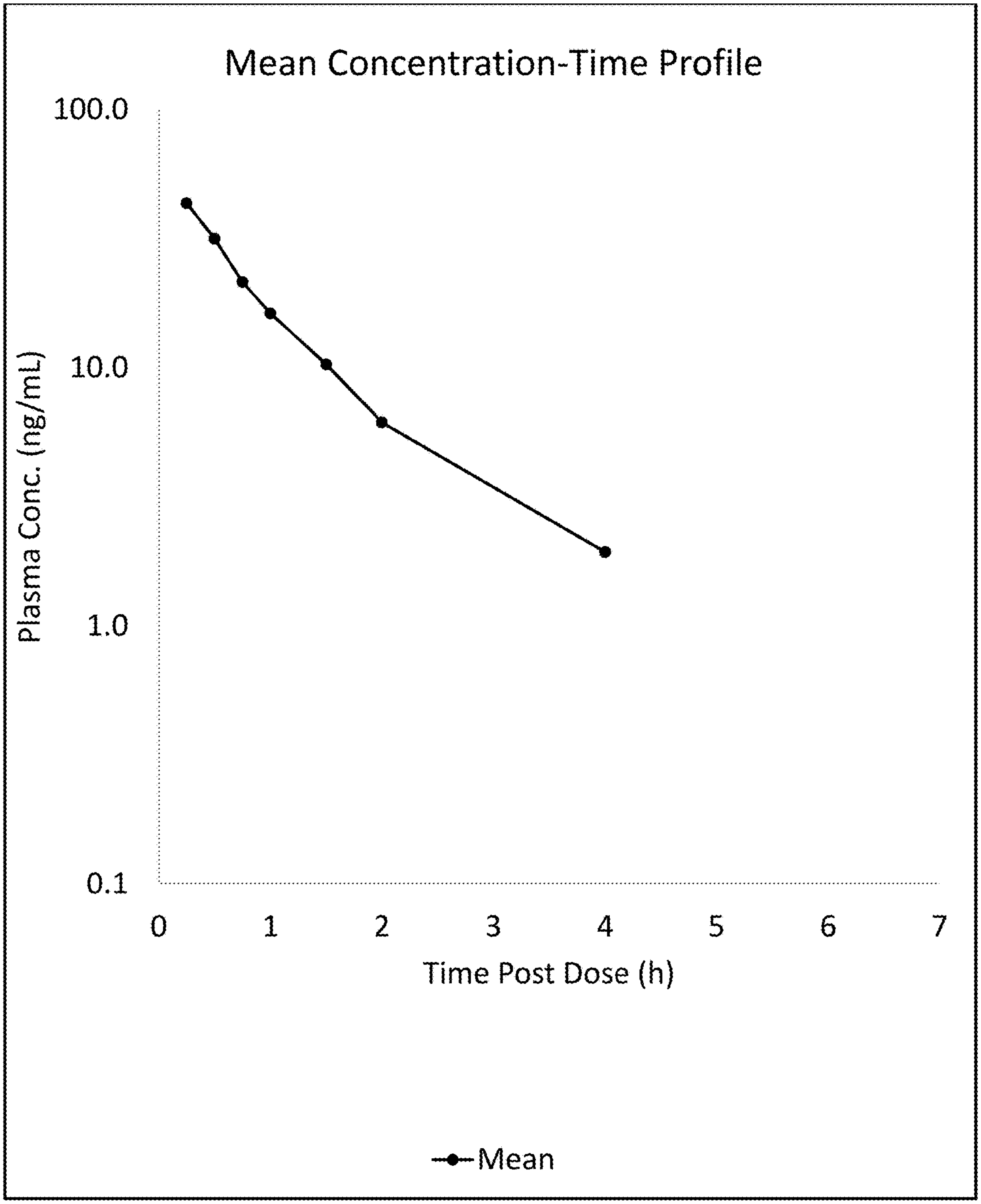
FIG. 31 shows mean concentration-time profiles of xanomeline following SC dosing of xanomeline methyl decatriylcarbonate chloride prodrug (1 mg/kg of xanomeline) to male SD rats.

FIG. 31 shows mean concentration-time profiles of xanomeline following SC dosing of xanomeline methyl decatriylcarbonate chloride prodrug (1 mg/kg of xanomeline) to male SD rats.

Example A-1-32: Xanomeline Methyl Decatettarylcarbonate Chloride Prodrug—Table 1 Compound 35

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl tetradecyl carbonate chloride Structural class: alkoxycarbonyloxymethyl Mechanistic class: presumed esterase+chemical breakdown

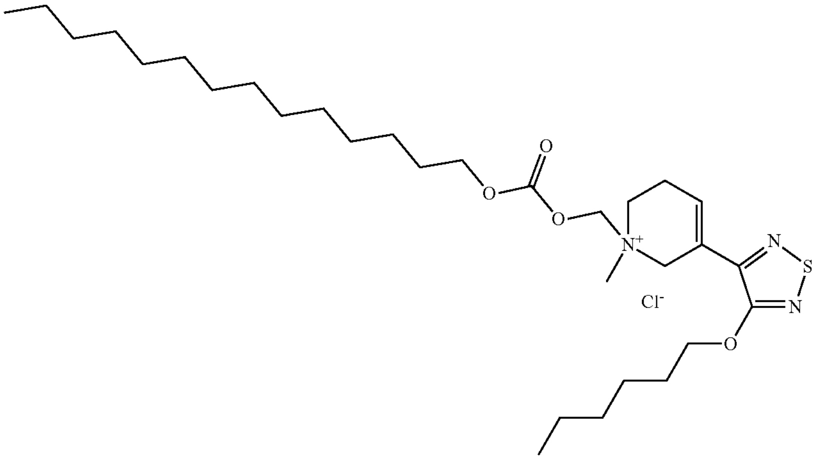 [SMILES: CCCCCCCCCCCCCCOC(=O)OC[N+]1(C)CCC=C(c2nsnc2OCCCCCC)C1 ; [Cl-]]

TABLE 34

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R1 | 3.41 | 0.500 | 12.5 | 7.00 | 32.1 | 40.0 |
| | | R2 | 1.36 | 1.00 | 7.43 | 4.00 | 16.9 | 19.9 |
| | | R3 | 1.53 | 0.250 | 13.2 | 7.00 | 26.3 | 27.5 |
| | | Mean | 2.10 | 0.583 | 11.0 | 6.00 | 25.1 | 29.1 |

Figure 32:
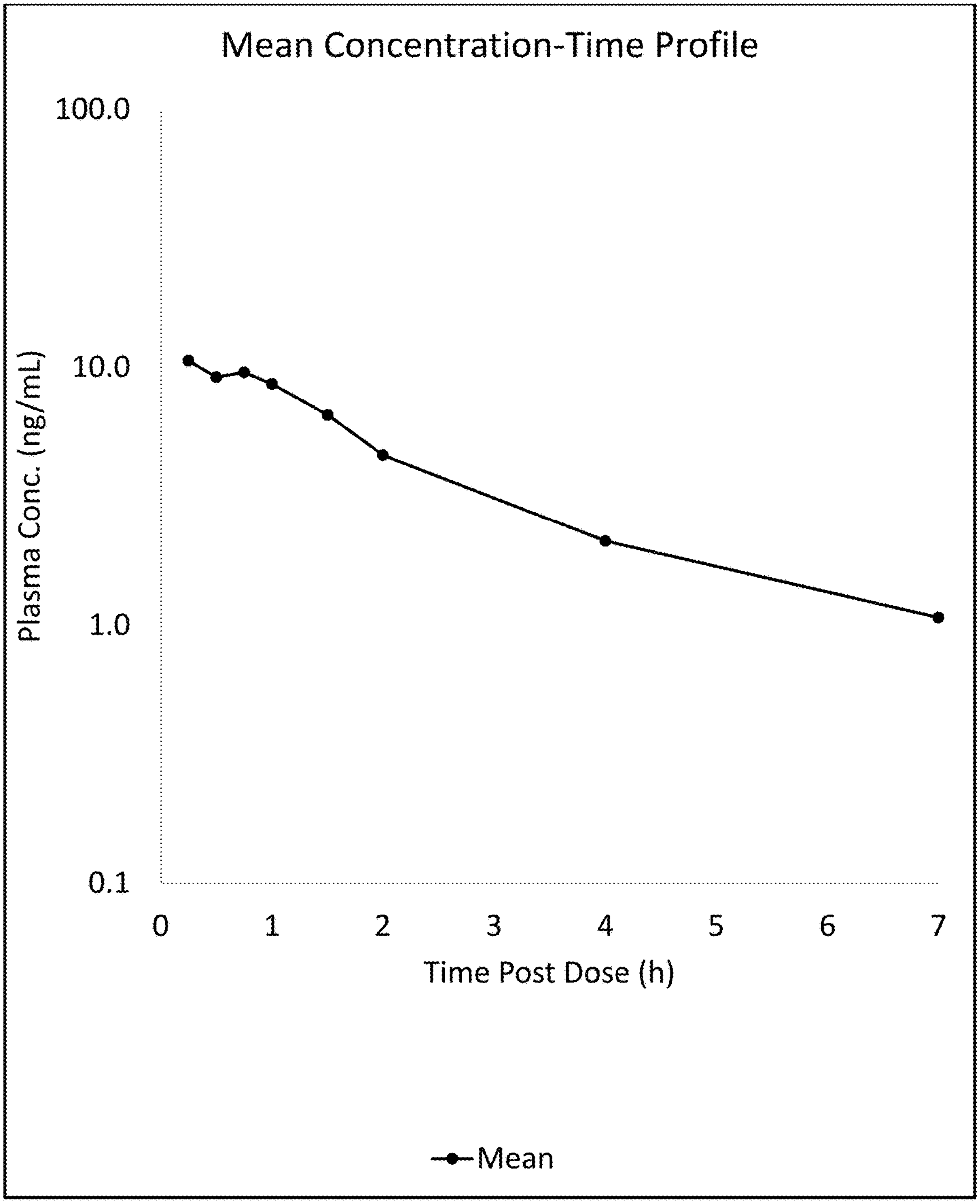
FIG. 32 shows mean concentration-time profiles of xanomeline following SC dosing of xanomeline methyl decatettarylcarbonate chloride prodrug (1 mg/kg of xanomeline) to male SD rats.

FIG. 32 shows mean concentration-time profiles of xanomeline following SC dosing of xanomeline methyl decatettarylcarbonate chloride prodrug (1 mg/kg of xanomeline) to male SD rats.

Example A-1-33: Xanomeline Methyl Pentadecylcarbonate Chloride Prodrug—Table 1 Compound 36

| | |
|---|---|
| Species: | Rat |
| Dose Route: | SC |
| Dose Level (mg/kg | 1 |

Chemical name: [5-(4-hexyloxy-1,2,5-thiadiazol-3-yl)-1-methyl-3,6-dihydro-2H-pyridin-1-ium-1-yl]methyl pentadecyl carbonate chloride Structural class: alkoxycarbonyloxymethyl Mechanistic class: presumed esterase+chemical breakdown

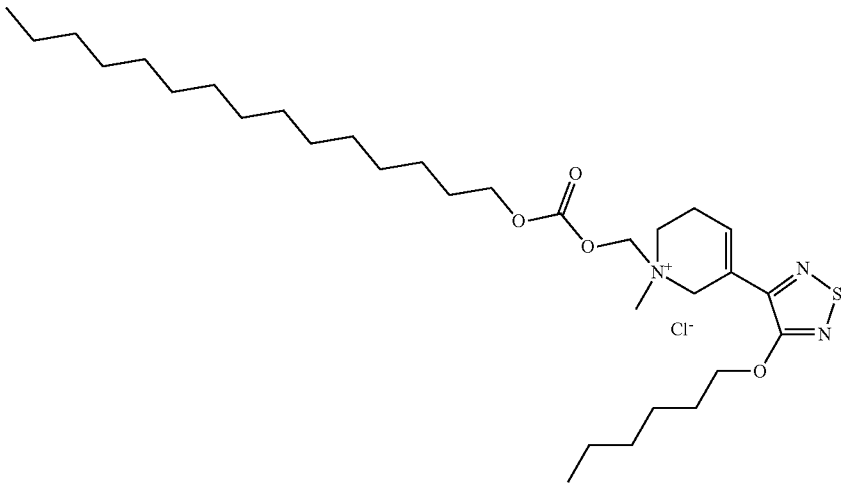 [SMILES: CCCCCCCCCCCCCCCOC(=O)OC[N+]1(C)CCC=C(c2nsnc2OCCCCCC)C1 ; [Cl-]]

TABLE 35

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R4 | 1.27 | 0.250 | 8.78 | 4.00 | 17.7 | 20.5 |
| | | R5 | 1.65 | 0.500 | 13.1 | 4.00 | 19.8 | 23.6 |
| | | R6 | 1.04 | 0.750 | 19.0 | 4.00 | 21.7 | 23.0 |
| | | Mean | 1.32 | 0.500 | 13.6 | 4.00 | 19.7 | 22.4 |

Figure 33:
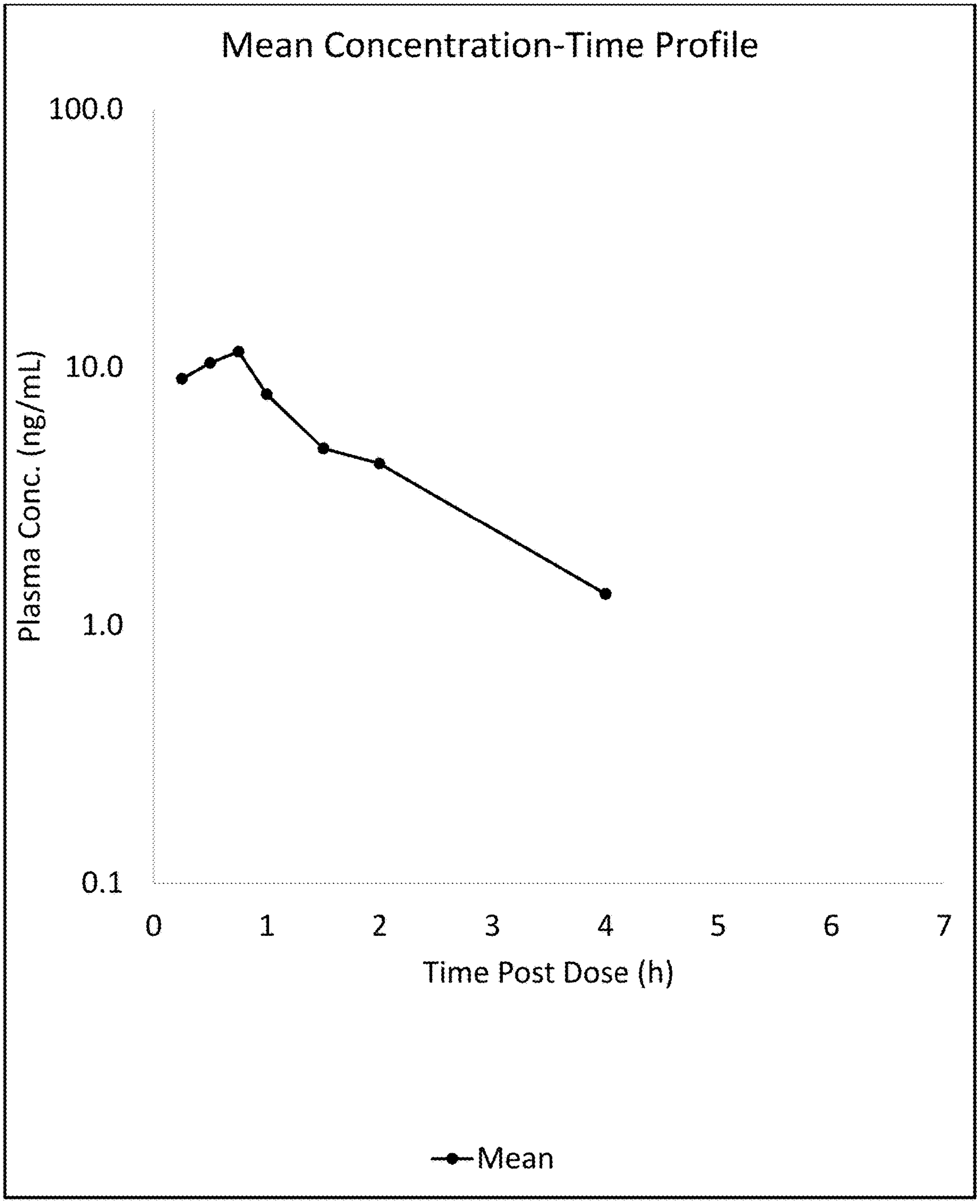
FIG. 33 shows mean concentration-time profiles of xanomeline following SC dosing of xanomeline methyl pentadecylcarbonate chloride prodrug (1 mg/kg of xanomeline) to male SD rats.

FIG. 33 shows mean concentration-time profiles of xanomeline following SC dosing of xanomeline methyl pentadecylcarbonate chloride prodrug (1 mg/kg of xanomeline) to male SD rats.

Example A-1-34: Xanomeline Methyl Isopropylcarbonate Chloride Prodrug—Table 1 Compound 38

| | |
|---|---|
| Species: | Rat |
| Dose Route: | SC |
| Dose Level (mg/kg) | 1 |

Chemical name: 1-methyl-5-[4-(hexyloxy)-1,2-5-thiadiazol-3-yl]-1-([(propan-2-yloxy)carbonyl]oxy)methyl-1,2,3,6-tetrahydropyridin-1-ium chloride Structural class: alkoxycarbonyloxymethyl Mechanistic class: presumed esterase+chemical breakdown

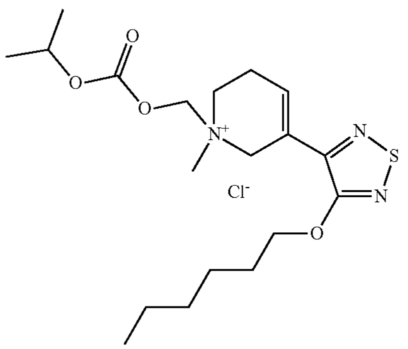 [SMILES: CCCCCCOc1nsnc1C1=CCC[N+](C)(COC(=O)OC(C)C)C1 ; [Cl-]]

TABLE 36

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R7 | 1.04 | 0.500 | 28.0 | 4.00 | 45.4 | 49.0 |
| | | R8 | 0.896 | 0.500 | 30.9 | 4.00 | 51.1 | 54.1 |
| | | R9 | 1.20 | 0.500 | 34.2 | 4.00 | 51.6 | 56.4 |
| | | Mean | 1.05 | 0.500 | 31.0 | 4.00 | 49.4 | 53.2 |

Figure 34:
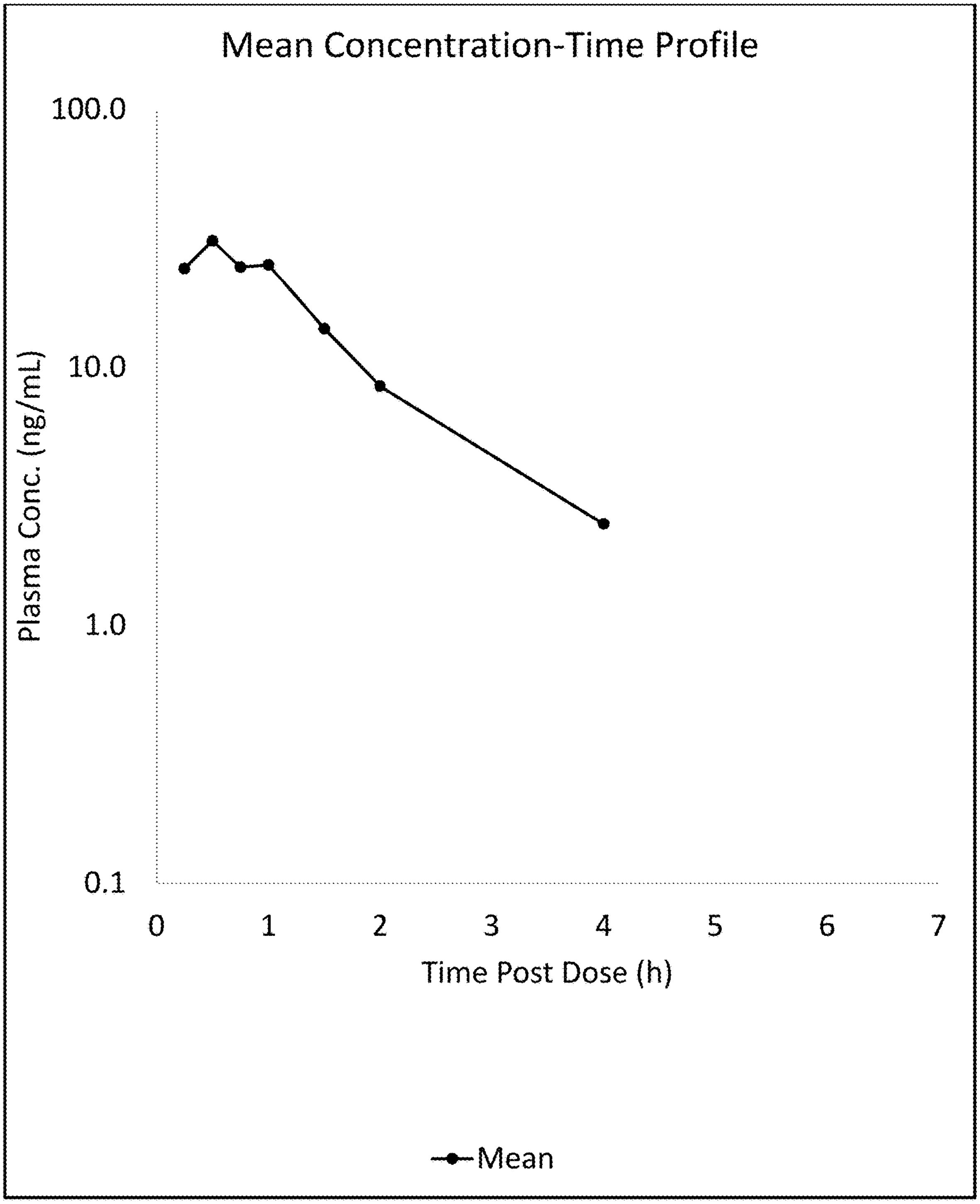
FIG. 34 shows mean concentration-time profiles of xanomeline following SC dosing of xanomeline methyl isopropylcarbonate chloride prodrug (1 mg/kg of xanomeline) to male SD rats.

FIG. 34 shows mean concentration-time profiles of xanomeline following SC dosing of xanomeline methyl isopropylcarbonate chloride prodrug (1 mg/kg of xanomeline) to male SD rats.

Example A-1-35: Xanomeline Methyl Isobutylcarbonate Chloride Prodrug—Table 1 Compound 39

| | |
|---|---|
| Species: | Rat |
| Dose Route: | SC |
| Dose Level (mg/kg) | 1 |

Chemical name: [I5-(4-hexyloxy-1,2,5-thiadiazol-3-yl)-1-methyl-3,6-dihydro-2H-pyridin-1-ium-1-yl]methyl isobutyl carbonate chloride Structural class: alkoxycarbonyloxymethyl Mechanistic class: presumed esterase+chemical breakdown

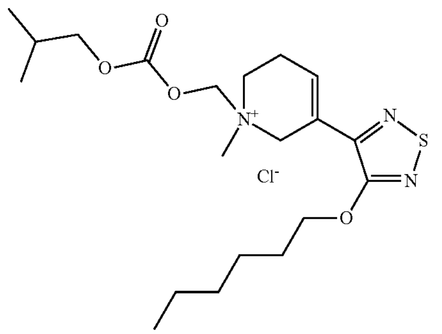 [SMILES: CCCCCCOc1nsnc1C1=CCC[N+](C)(COC(=O)OCC(C)C)C1 ; [Cl-]]

TABLE 37

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R10 | 0.814 | 0.500 | 22.9 | 4.00 | 40.6 | 42.7 |
| | | R11 | 0.964 | 0.500 | 19.9 | 4.00 | 34.9 | 37.7 |
| | | R12 | 0.922 | 0.500 | 19.3 | 4.00 | 37.3 | 39.5 |
| | | Mean | 0.900 | 0.500 | 20.7 | 4.00 | 37.6 | 40.0 |

Figure 35:
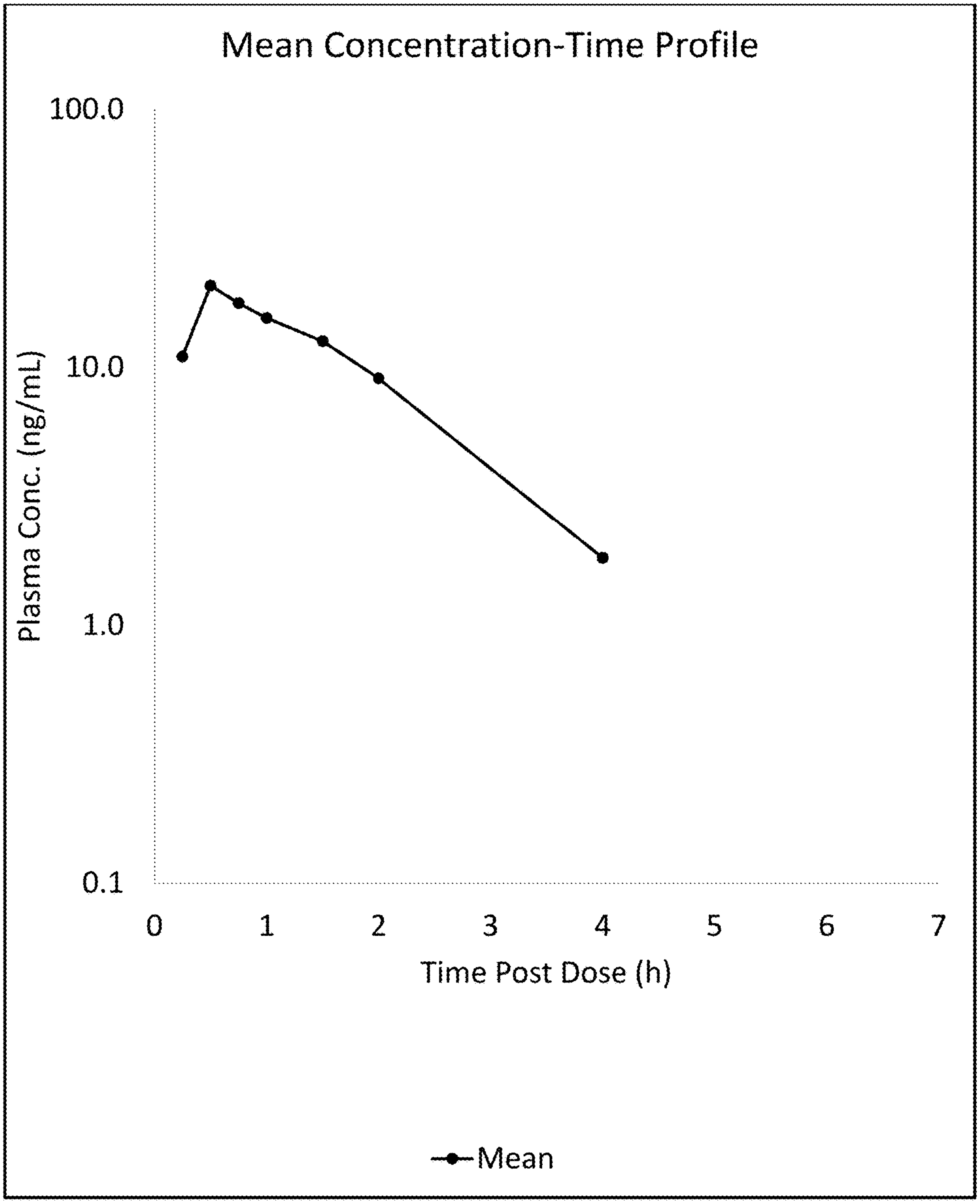
FIG. 35 shows mean concentration-time profiles of xanomeline following SC dosing of xanomeline methyl isobutylcarbonate chloride prodrug (1 mg/kg of xanomeline) to male SD rats.

FIG. 35 shows mean concentration-time profiles of xanomeline following SC dosing of xanomeline methyl isobutylcarbonate chloride prodrug (1 mg/kg of xanomeline) to male SD rats.

Example A-1-36: Xanomeline Methyl Tert-Butylcarbonate Chloride Prodrug—Table 1 Compound 37

| | |
|---|---|
| Species: | Rat |
| Dose Route: | SC |
| Dose Level (mg/kg) | 1 |

Chemical name: 1-((([(tert-Butoxy)carbonyl]oxy)methyl)-1-methyl-5-[4-(hexyloxy)-1,2,5-thiadiazol-3-yl]-1,2,3,6-tetrahydropyridin-1-ium chloride Structural class: alkoxycarbonyloxymethyl Mechanistic class presumed esterase+chemical breakdown

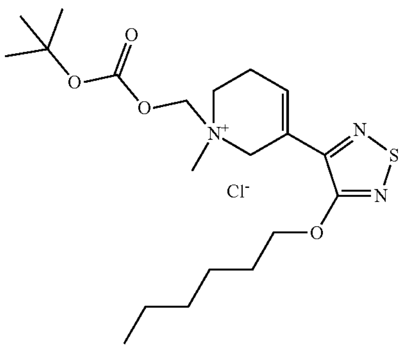 [SMILES: CCCCCCOc1nsnc1C1=CCC[N+](C)(COC(=O)OC(C)(C)C)C1 ; [Cl-]]

TABLE 38

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R13 | 0.764 | 0.250 | 21.6 | 4.00 | 26.0 | 26.7 |
| | | R14 | 0.708 | 0.250 | 20.5 | 4.00 | 30.2 | 31.0 |
| | | R15 | 0.734 | 0.250 | 24.5 | 4.00 | 32.5 | 33.3 |
| | | Mean | 0.735 | 0.250 | 22.2 | 4.00 | 29.6 | 30.3 |

Figure 36:
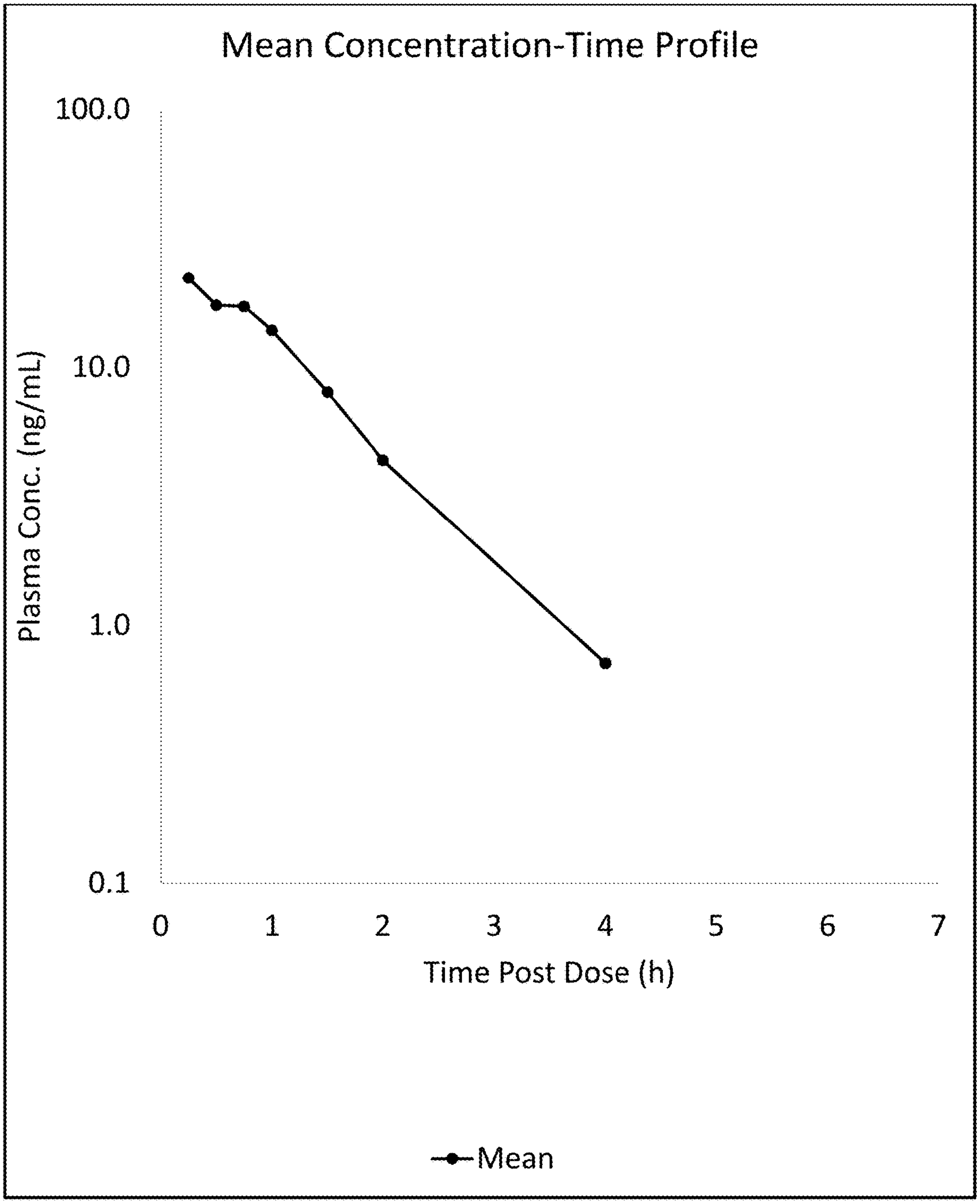
FIG. 36 shows mean concentration-time profiles of xanomeline following SC dosing of xanomeline methyl tert-butylcarbonate chloride prodrug (1 mg/kg of xanomeline) to male SD rats.

FIG. 36 shows mean concentration-time profiles of xanomeline following SC dosing of xanomeline methyl tert-butylcarbonate chloride prodrug (1 mg/kg of xanomeline) to male SD rats.

Example A-1-37: Xanomeline Methyl Tri-Isopropylsilyl Ether Chloride Prodrug—Table 1 Compound 20

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methoxy-triisopropyl-silane chloride Structural class: silyloxymethyl Mechanistic class: presumed chemical breakdown

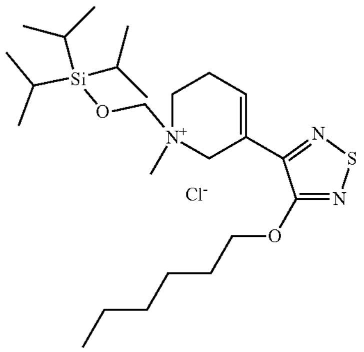 [SMILES: CCCCCCOc1nsnc1C1=CCC[N+](C)(CO[Si](C(C)C)(C(C)C)C(C)C)C1 ; [Cl-]]

Figure 37:
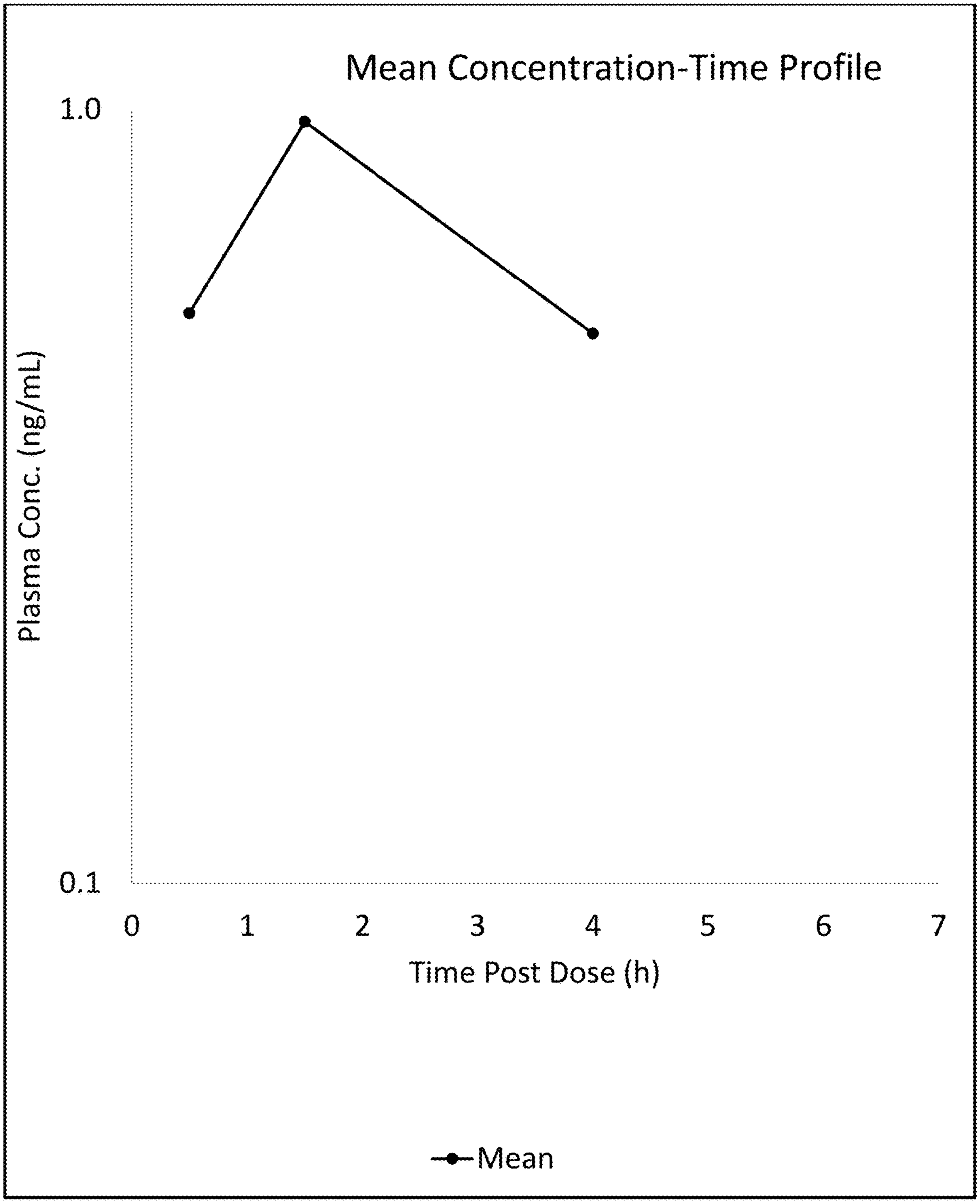
FIG. 37 shows mean concentration-time profiles of xanomeline following SC dosing of xanomeline methyl tri-isopropylsilyl ether chloride prodrug (1 mg/kg of xanomeline) to male SD rats.

FIG. 37 shows mean concentration-time profiles of xanomeline following SC dosing of xanomeline methyl tri-isopropylsilyl ether chloride prodrug (1 mg/kg of xanomeline) to male SD rats.

Example A-1-38: Xanomeline N-Oxide Prodrug—Table 1 Compound 21

| | |
|---|---|
| Species: | Rat |
| Dose Route: | SC |
| Dose Level (mg/kg) | 1 |

Chemical name: 3hexyloxy-4-(1-methyl-1-oxido-3,6-dihydro-2H-pyridin-1-ium-5-yl)-1,2,5-thiadiazole Structural class: N-oxide Mechanistic class: presumed reductase

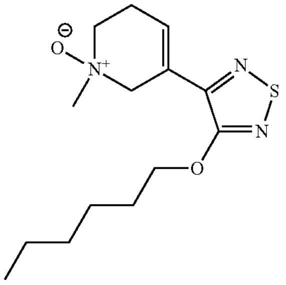 [SMILES: CCCCCCOc1nsnc1C1=CCC[N+](C)([O-])C1]

TABLE 39

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R16 | NR | 1.50 | 0.964 | 4.00 | 2.57 | NR |
| | | R17 | NR | NR | NR | NR | NR | NR |
| | | R18 | NR | 0.500 | 0.545 | 0.500 | 0.136 | NR |
| | | Mean | NR | 1.00 | 0.755 | 2.25 | 1.35 | NR |

TABLE 40

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R19 | NR | 1.50 | 0.747 | 2.00 | 1.06 | NR |
| | | R20 | NR | 0.25 | 1.09 | 1.00 | 0.691 | NR |
| | | R21 | NR | 0.50 | 0.947 | 1.50 | 0.901 | NR |
| | | Mean | NR | 0.75 | 0.928 | 1.50 | 0.884 | NR |

Figure 38:
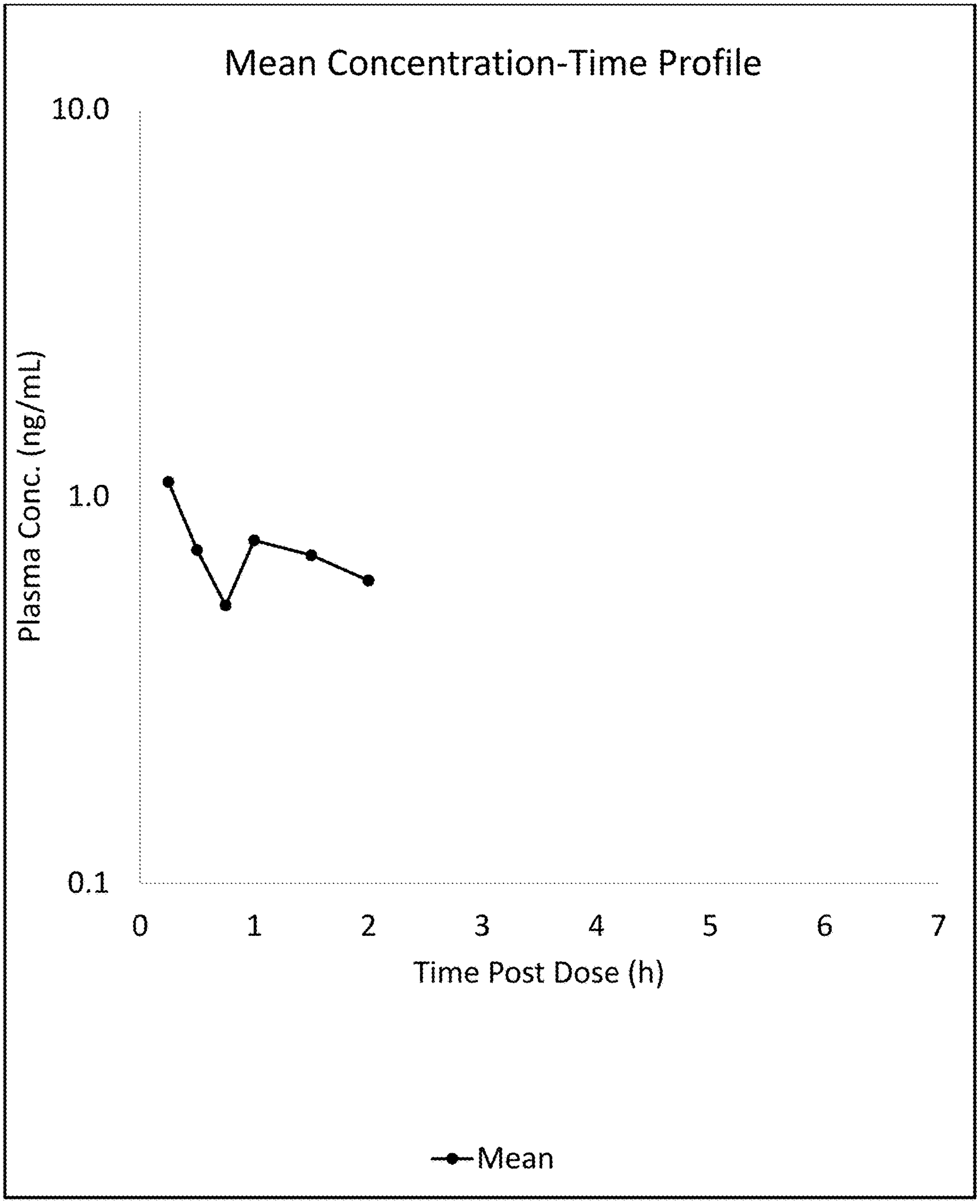
FIG. 38 shows mean concentration-time profiles of xanomeline following SC dosing of xanomeline N-oxide prodrug (1 mg/kg of xanomeline) to male SD rats.

FIG. 38 shows mean concentration-time profiles of xanomeline following SC dosing of xanomeline N-oxide prodrug (1 mg/kg of xanomeline) to male SD rats.

Example A-1-39: Xanomeline Methyl Butanoate Chloride Prodrug—Table 1 Compound 3

| | |
|---|---|
| Species: | Rat |
| Dose Route: | SC |
| Dose Level (mg/kg) | 1 |

Chemical name: [5-(4-hexyloxy-1,2,5-thiadiazol-3-yl)-1-methyl-3,6-dihydro-2H-pyridin-1-ium-1-yl]methyl butanoate chloride Structural class: acyloxymethyl Mechanistic class: presumed esterase+chemical breakdown

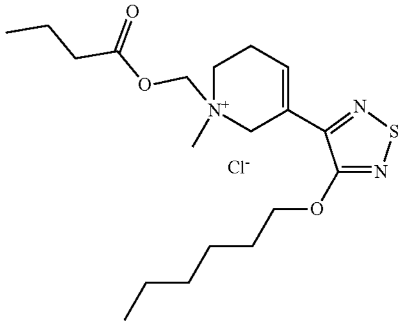 [SMILES: CCCCCCOc1nsnc1C1=CCC[N+](C)(COC(=O)CCC)C1 ; [Cl-]]

TABLE 41

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R22 | 0.959 | 0.500 | 23.8 | 4.00 | 35.6 | 37.7 |
| | | R23 | 1.49 | 0.500 | 18.2 | 7.00 | 32.2 | 33.5 |
| | | R24 | 1.25 | 0.500 | 18.0 | 4.00 | 31.5 | 36.1 |
| | | Mean | 1.23 | 0.500 | 20.0 | 5.00 | 33.1 | 35.8 |

Figure 39:
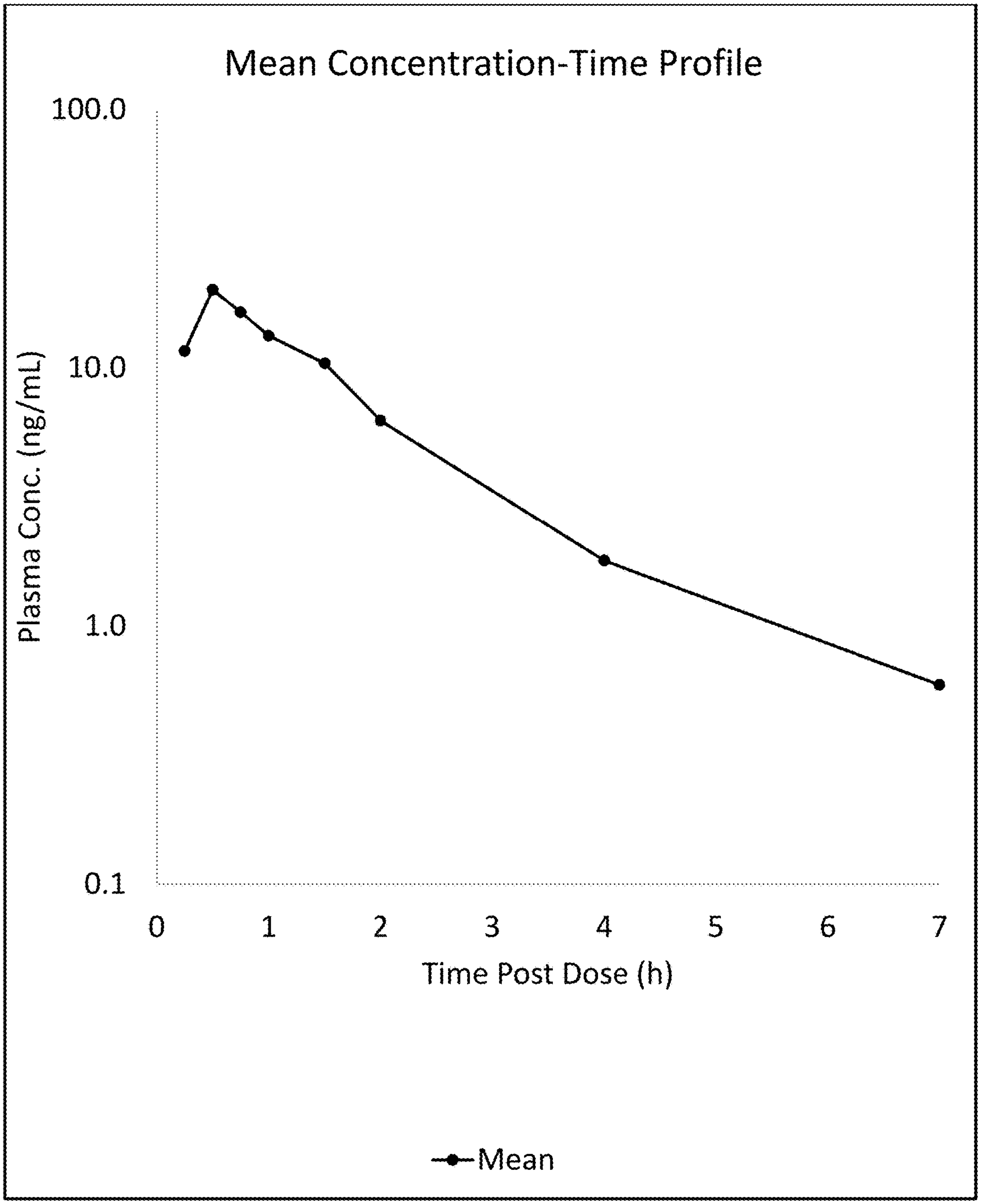
FIG. 39 shows mean concentration-time profiles of xanomeline following SC dosing of xanomeline methyl butanoate chloride prodrug (1 mg/kg of xanomeline) to male SD rats.

FIG. 39 shows mean concentration-time profiles of xanomeline following SC dosing of xanomeline methyl butanoate chloride prodrug (1 mg/kg of xanomeline) to male SD rats.

TABLE A-2

| Protocol: Serial tail vein bleed PK study of Xanomeline Prodrugs in SD rats | |
|---|---|
| Protocol | SC Serial PK study at 1 dose level |
| Test Compound(s) | Xanomeline, Xanomeline Prodrugs |
| Dosing Route | SC |
| Overnight food withdrawal | No |
| Animals Type | rat |
| Strain | Sprague Dawley rats |
| Sex | male |
| Weight (g) | 250-300 g |
| N per cpd | 3 |
| Preparation | None |
| Cage | PK cages |
| Dose | 5 mg/kg, 3.5 mg/kg of xanomeline |
| Dosing Soln. Conc. | 2.5 mg/mL, 1.75 mg/mL |
| Dosing Volume | 2 mL/kg |
| Formulation checks required? | No |
| Vehicle | 10% DMSO/90% HPCD (20% in water) |
| Sampling time points (h) | 0.5, 1, 2, 4, 8, 24, 31, 48, 72 & 96 h |
| Blood sampling method | Serial via tail vein |
| Alternative method if required | n/a |
| Sample format required | >230 μL blood + 5 μL EDTA (93 mg/mL) to give 2 × 50 μL plasma |
| Sample processing | Centrifugation for plasma ASAP at 4° C. Place 110 μL plasma into Eppendorf tube on ice containing 11 μL 10% phosphoric acid. Gently mix before taking 2 × 50 μL aliquots into duplicate 96 well plates on dry ice. |
| Anticoagulant | EDTA (93 mg/mL): 5 μL per tube |
| Centrifugation | 10,000 rpm × 3 min at 4° C. |
| Additional samples | n/a |
| Perfusion/rinsing required | n/a |
| Euthanasia method | n/a |
| Plasma sample tubes | 96 well plates |

TABLE A-2-continued

| Protocol: Serial tail vein bleed PK study of Xanomeline Prodrugs in SD rats | |
|---|---|
| Protocol | SC Serial PK study at 1 dose level |
| Pre-freezer storage | Blood: ice (<30 min), Acidified Plasma: dry ice |
| Freezer storage | −80° C. |
| Dose formulation samples | 100 µL from vortex dose solution in Eppendorf |
| Number of samples per cpd at 1 dose level | 30 × acidified plasma (50 µL in duplicate), 1 dose soln |

Analysis

Samples were sent for method optimization and measurement of parent compound (xanomeline) via unique calibration lines and following acceptance QC's. Dose formulation concentrations were also measured, and PK parameters were determined (Cmax (ng/mL), Tmax (hr), Cl (ml/min/kg), Vdss (L/kg), t1/2(hr), AUCO-t (ng/mL*hr), AUCO-inf (ng/mL*hr), MRT (hr), Bioavailability (% F) where warranted) using WinNon Lin software. Data (including bioanalytical results and assay performance) were reported in a tabulated format.

Example A-2-1: Xanomeline Parent Compound (SC)—Table 1 Compound 922

| | |
|---|---|
| Species | Rat |
| Dose Route: | SC |
| Nominal Dose Concentration: | 5 mg/kg |

Chemical name: Xanomeline

Structural class: parent

Mechanistic class: n/a—parent compound

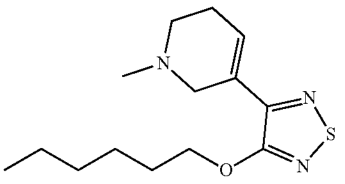 [SMILES: CCCCCCOc1nsnc1C1=CCCN(C)C1]

TABLE 42

| Xanomeline (SC) Pharmacokinetic Parameters | | | | | | | | |
|---|---|---|---|---|---|---|---|---|
| Analyte | Dose | Animal ID | T1/2 (h) | Cmax (ng/mL) | Tmax (h) | Tlast (h) | AUC0-last (h*ng/mL) | AUC0-inf (h*ng/ml) |
| Xanomeline | SC | R4 | 1.50 | 54.6 | 1.00 | 8.00 | 180 | 185 |
| | | R5 | NR | 30.0 | 0.50 | 96.0 | 213 | NR |
| | | R6 | 1.24 | 44.4 | 1.00 | 8.00 | 121 | 123 |
| | | Mean | 1.37 | 43.0 | 0.833 | 37.3 | 171 | 154 |

Additional Formulation Details for PK Study

Phosphoric acid. Diluted 85% phosphoric acid 8.5-fold to give a 10% solution.

Formulation for SC administration: For SC dosing, xanomeline and xanomeline prodrugs were formulated as solution in 10% DMSO/90% HPCD (20% in water) to a concentration of 2.5 mg free metabolite material/mL or 1.75 mg free metabolite material/mL. This provided a dose of 5 mg free metabolite/kg or 3.5 mg free metabolite/kg, respectively, when administered SC in 2 mL/kg dosing volumes.

Example A-2: Measurement of Concentration of Xanomeline after Subcutaneous (SC) Administration of Xanomeline Prodrugs In Vivo The pharmacokinetic properties of the synthesized xanomeline prodrugs after subcutaneous administration in a rat model were assessed. The concentration of xanomeline was measured in each rat at various sampling timepoints after subcutaneous administration of xanomeline or the synthesized xanomeline prodrugs to rats.

Dose formulations were made at equivalent concentrations of active compound (xanomeline) adjusted for molecular weight of the compounds. The synthesized xanomeline prodrugs were dosed at 5 mg/kg subcutaneous (SC) nominal dose except for xanomeline oxyisobutyl pivalate chloride prodrug and xanomeline oxypropyl pivalate chloride prodrug, which were dosed at 3.5 mg/kg subcutaneous. Nominal doses were used in PK parameter determinations. The parent compound (xanomeline) was dosed at 5 mg/kg subcutaneous (SC).

Figure 40:
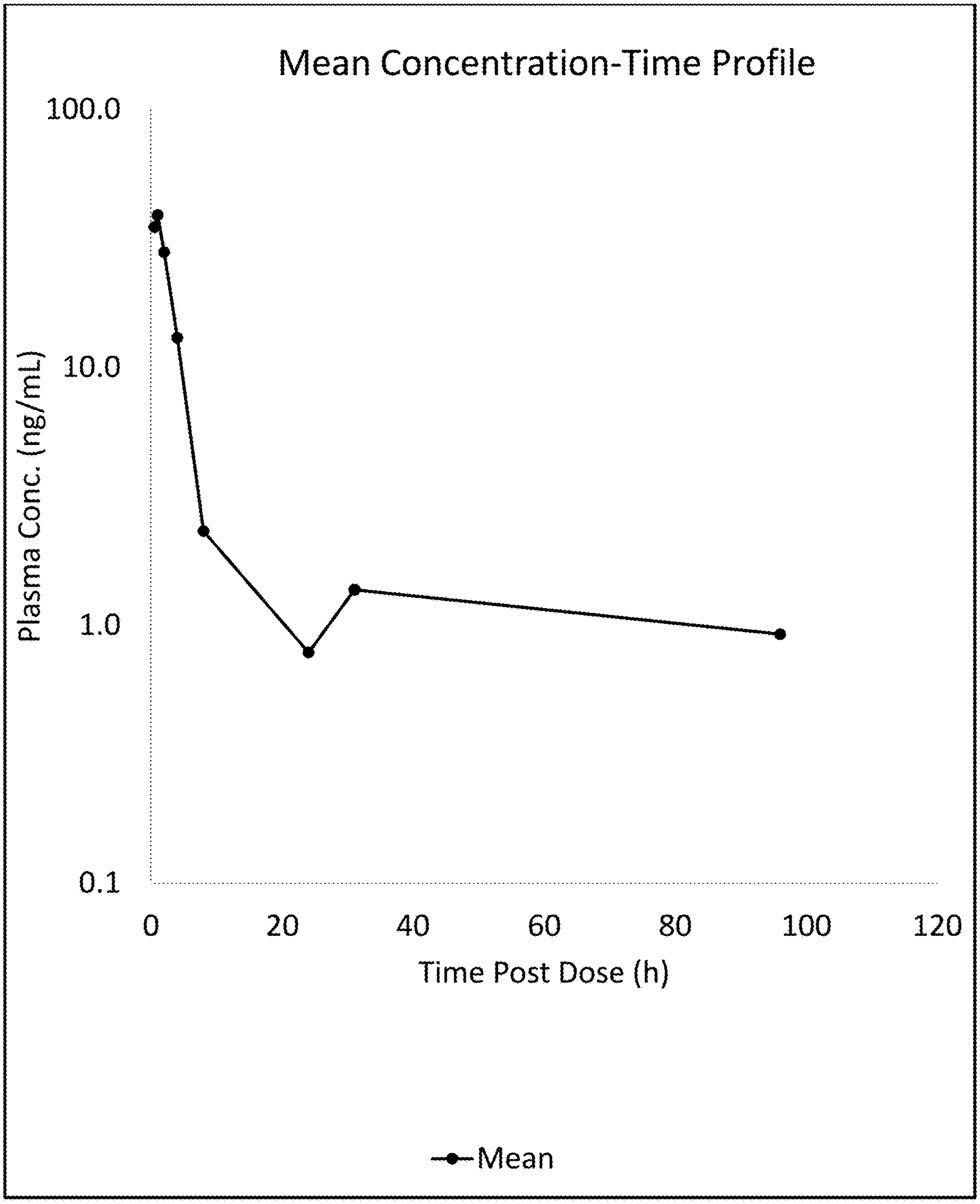
FIG. 40 shows mean concentration-time profiles of xanomeline following SC dosing of xanomeline (5 mg/kg of xanomeline) to male Sprague Dawley (SD) rats.

FIG. 40 shows mean concentration-time profiles of xanomeline following SC dosing of xanomeline (5 mg/kg) to male Sprague Dawley (SD) rats.

Example A-2-2: Xanomeline Oxyisobutyl Pivalate Chloride Prodrug—Table 1 Compound 389

| | |
|---|---|
| Species | Rat |
| Dose Route: | SC |
| Nominal Dose Concentration: | 3.5 mg/kg |

Chemical name: 5-(4-(Hexyloxy)-1,2,5-thiadiazol-3-yl)-1-methyl-1-(2-methyl-1-(pivaloyloxy)propyl)-1,2,3,6-tetrahydropyridin-1-ium chloride Structural class: acyloxymethyl Mechanistic class: presumed esterase+chemical breakdown

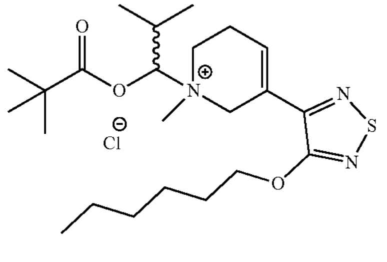 [SMILES: CCCCCCOc1nsnc1C1=CCC[N+](C)(C(OC(=O)C(C)(C)C)C(C)C)C1 ; [Cl-]]

TABLE 43

| Mean Concentration-Time Profile of Metabolite Xanomeline Following SC Dosing of Xanomeline Oxyisobutyl Pivalate Chloride Prodrug | | | | |
|---|---|---|---|---|
| Bioanalytical Data: | Plasma Concentrations (ng/mL) Following Subcutaneous Dosing Animal | | | |
| Time (h) | R7 | R8 | R9 | Mean |
| 0.500 | BLQ | BLQ | BLQ | BLQ |
| 1.00 | BLQ | BLQ | BLQ | BLQ |
| 2.00 | BLQ | BLQ | BLQ | BLQ |
| 4.00 | BLQ | BLQ | BLQ | BLQ |
| 8.00 | BLQ | BLQ | BLQ | BLQ |
| 24.0 | BLQ | BLQ | BLQ | BLQ |
| 31.0 | BLQ | BLQ | BLQ | BLQ |
| 48.0 | BLQ | BLQ | BLQ | BLQ |
| 72.0 | BLQ | BLQ | BLQ | BLQ |
| 96.0 | BLQ | BLQ | BLQ | BLQ |

BLQ: Below Lower Limit of Quantification (0.5 ng/mL)

Example A-2-3: Xanomeline Oxyisobutyl Propanoate Chloride Prodrug—Table 1 Compound

| | |
|---|---|
| Species: | Rat |
| Dose Route: | SC |
| Dose Level (mg/kg) | 5 mg/kg of xanomeline |

Chemical name: 5-(4-(Hexyloxy)-1,2,5-thiadiazol-3-yl)-1-methyl-1-(2-methyl-1-(propionyloxy)propyl)-1,2,3,6-tetrahydropyridin-1-ium chloride Structural class: acyloxymethyl Mechanistic class: presumed esterase+chemical breakdown

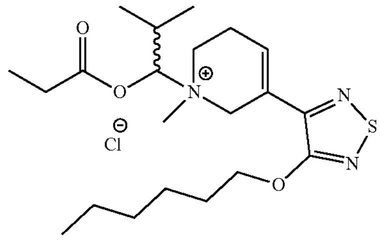 [SMILES: CCCCCCOc1nsnc1C1=CCC[N+](C)(C(OC(=O)CC)C(C)C)C1 ; [Cl-]]

TABLE 44

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R10 | 1.56 | 1.00 | 26.7 | 8.00 | 68.0 | 70.3 |
| | | R11 | 1.61 | 1.00 | 50.7 | 8.00 | 98.1 | 100 |
| | | R12 | 1.78 | 0.50 | 41.7 | 8.00 | 113 | 119 |
| | | Mean | 1.65 | 0.833 | 39.7 | 8.00 | 93.0 | 96.4 |

Figure 41:
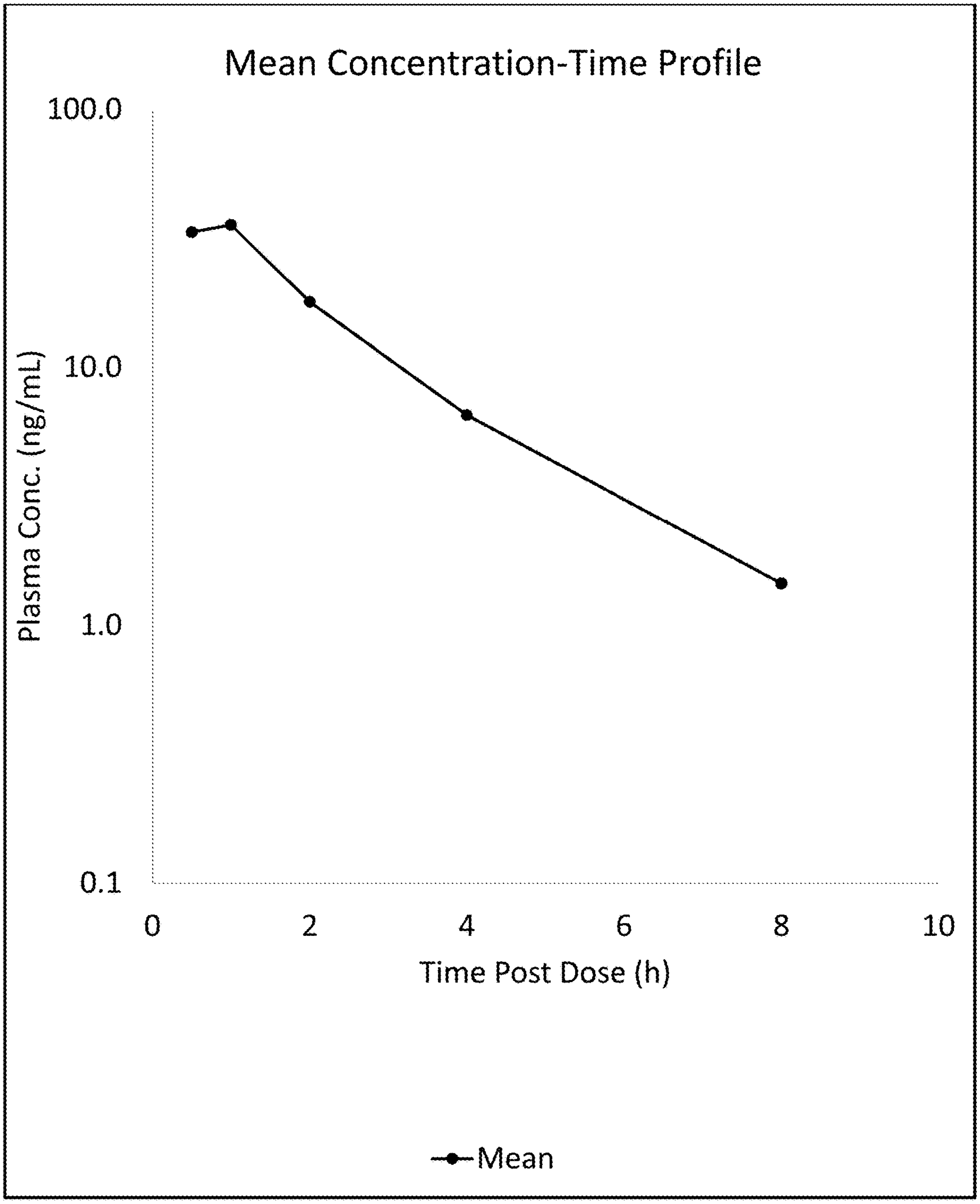
FIG. 41 shows mean concentration-time profiles of xanomeline following SC dosing of xanomeline oxyisobutyl propanoate chloride prodrug (5 mg/kg of xanomeline) to male SD rats.

FIG. 41 shows mean concentration-time profiles of xanomeline following SC dosing of xanomeline oxyisobutyl propanoate chloride prodrug (5 mg/kg of xanomeline) to male SD rats.

Example A-2-4: Xanomeline Oxyethyl Propanoate Iodide Prodrug—Table 1 Compound 601

| | |
|---|---|
| Species: | Rat |
| Dose Route: | SC |
| Dose Level (mg/kg | 5 mg/kg of xanomeline |

Chemical name: 5-(4-(Hexyloxy)-1,2,5-thiadiazol-3-yl)-1-methyl-1-(1-(propionyloxy)ethyl)-1,2,3,6-tetrahydropyridin-1-ium iodide Structural class: acyloxymethyl Mechanistic class: presumed esterase+chemical breakdown

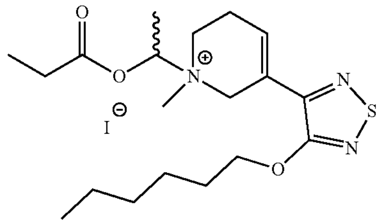 [SMILES: CCCCCCOc1nsnc1C1=CCC[N+](C)(C(C)OC(=O)CC)C1 ; [I-]]

TABLE 45

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R13 | NR | 1.00 | 13.9 | 4.00 | 24.0 | NR |
| | | R14 | NR | 1.00 | 32.2 | 8.00 | 80.4 | NR |
| | | R15 | NR | 2.00 | 30.3 | 8.00 | 112 | NR |
| | | Mean | NR | 1.33 | 25.5 | 6.67 | 72.1 | NR |

Figure 42:
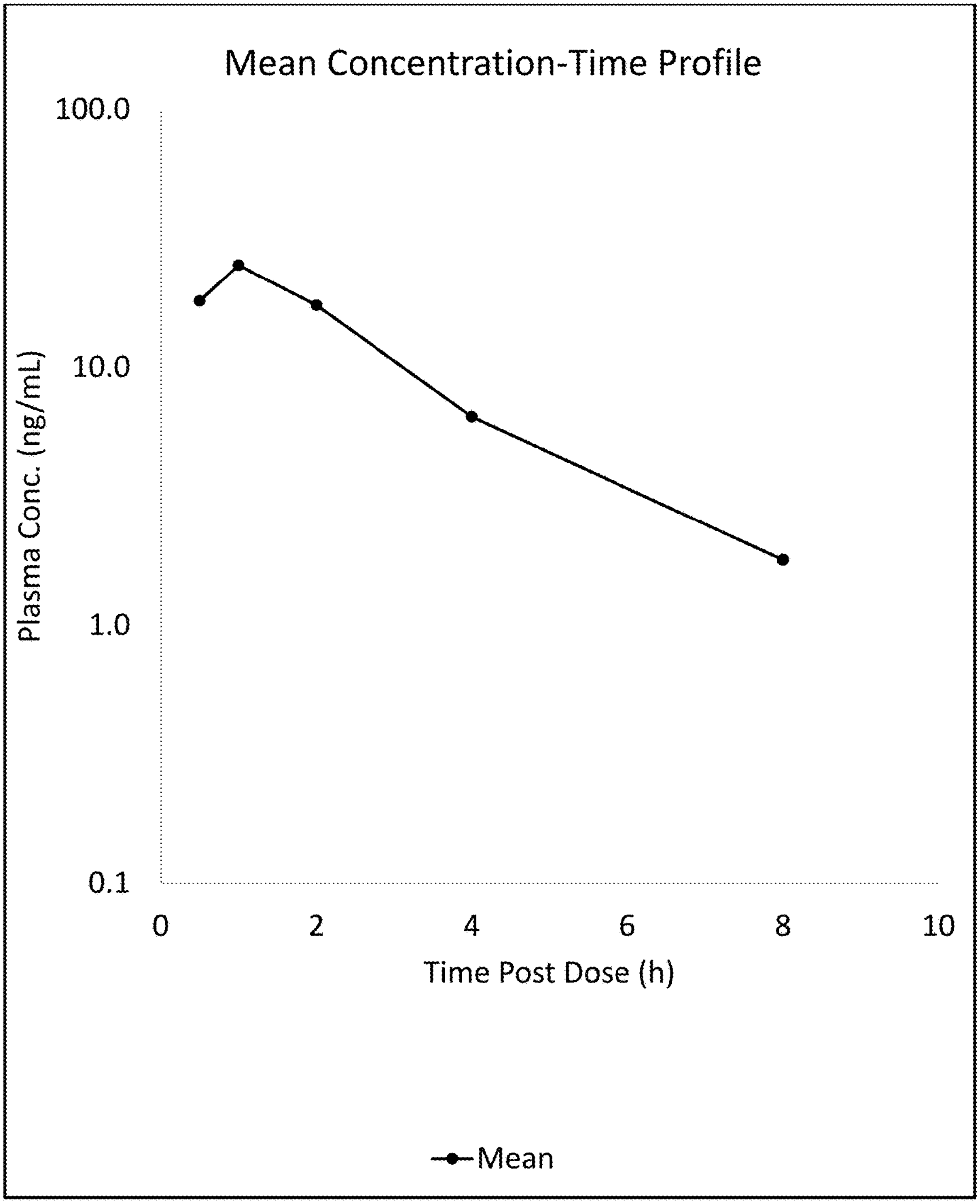
FIG. 42 shows mean concentration-time profiles of xanomeline following SC dosing of xanomeline oxyethyl propanoate iodide prodrug (5 mg/kg of xanomeline) to male SD rats.

FIG. 42 shows mean concentration-time profiles of xanomeline following SC dosing of xanomeline oxyethyl propanoate iodide prodrug (5 mg/kg of xanomeline) to male SD rats.

Example A-2-5: Xanomeline Oxyethyl Pivalate Chloride Prodrug—Table 1 Compound 19

| | |
|---|---|
| Species: | Rat |
| Dose Route: | SC |
| Dose Level (mg/kg) | 5 mg/kg of xanomeline |

Chemical name: 1-[5-(4-hexyloxy-1,2,5-thiadiazol-3-yl)-1-methyl-3,6-dihydro-2H-pyridin-1-ium-1-yl]ethyl 2,2-dimethylpropanoate chloride Structural class: acyloxymethyl Mechanistic class: presumed esterase+chemical breakdown

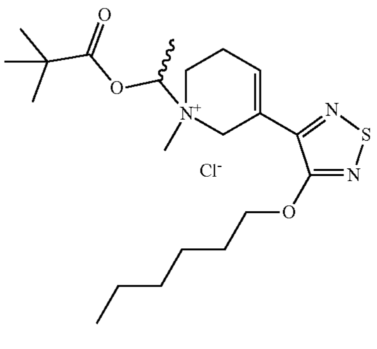 [SMILES: CCCCCCOc1nsnc1C1=CCC[N+](C)(C(C)OC(=O)C(C)(C)C)C1 ; [Cl-]]

TABLE 46

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R7 | 19.7 | 0.500 | 10.2 | 31.0 | 68.7 | 94.8 |
| | | R8 | 2.41 | 1.00 | 12.7 | 8.00 | 45.9 | 50.9 |
| | | R9 | 2.38 | 1.00 | 9.52 | 8.00 | 33.4 | 36.8 |
| | | Mean | 8.16 | 0.833 | 10.8 | 15.7 | 49.3 | 60.8 |

Figure 43:
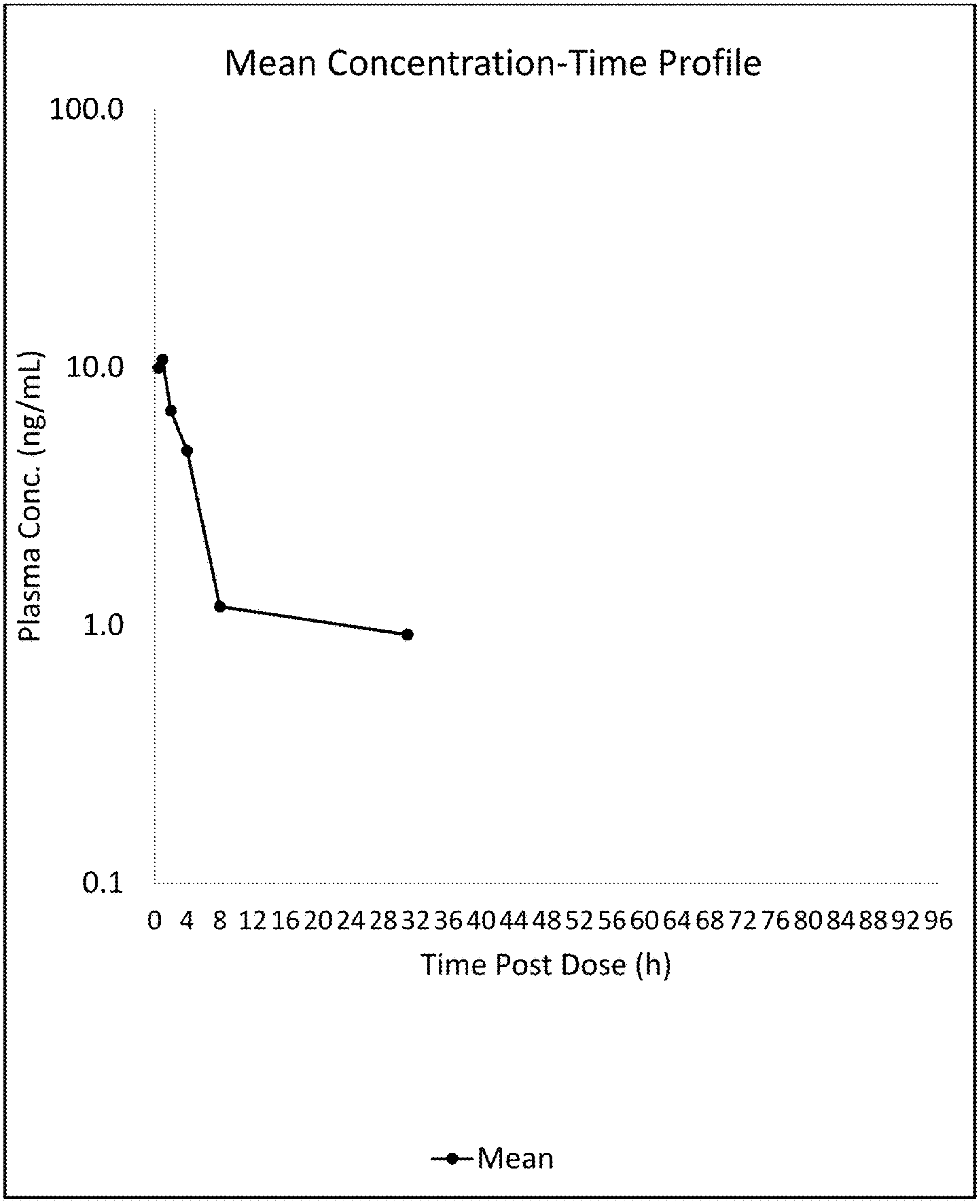
FIG. 43 shows mean concentration-time profiles of xanomeline following SC dosing of xanomeline oxyethyl pivalate chloride prodrug (5 mg/kg of xanomeline) to male SD rats.

FIG. 43 shows mean concentration-time profiles of xanomeline following SC dosing of xanomeline oxyethyl pivalate chloride prodrug (5 mg/kg of xanomeline) to male SD rats.

Example A-2-6: Xanomeline Oxybenzyl Propanoate Chloride Prodrug—Table 1 Compound

| | |
|---|---|
| Species: | Rat |
| Dose Route: | SC |
| Dose Level (mg/kg) | 5 mg/kg of xanomeline |

Chemical name: 5-(4-(Hexyloxy)-1,2,5-thiadiazol-3-yl)-1-methyl-1-(phenyl(propionyloxy)methyl)-1,2,3,6-tetrahydropyridin-1-ium chloride Structural class: acyloxymethyl Mechanistic class: presumed esterase+chemical breakdown

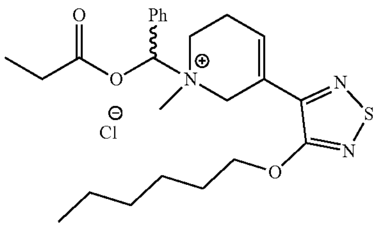 [SMILES: CCCCCCOc1nsnc1C1=CCC[N+](C)(C(OC(=O)CC)c2ccccc2)C1 ; [Cl-]]

TABLE 47

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R1 | NR | 0.50 | 108 | 96.0 | 495 | NR |
| | | R2 | 21.8 | 0.50 | 77.3 | 31.0 | 142 | 179 |
| | | R3 | 26.6 | 0.50 | 79.8 | 72.0 | 302 | 348 |
| | | Mean | 24.2 | 0.50 | 88.4 | 66.3 | 313 | 264 |

Figure 44:
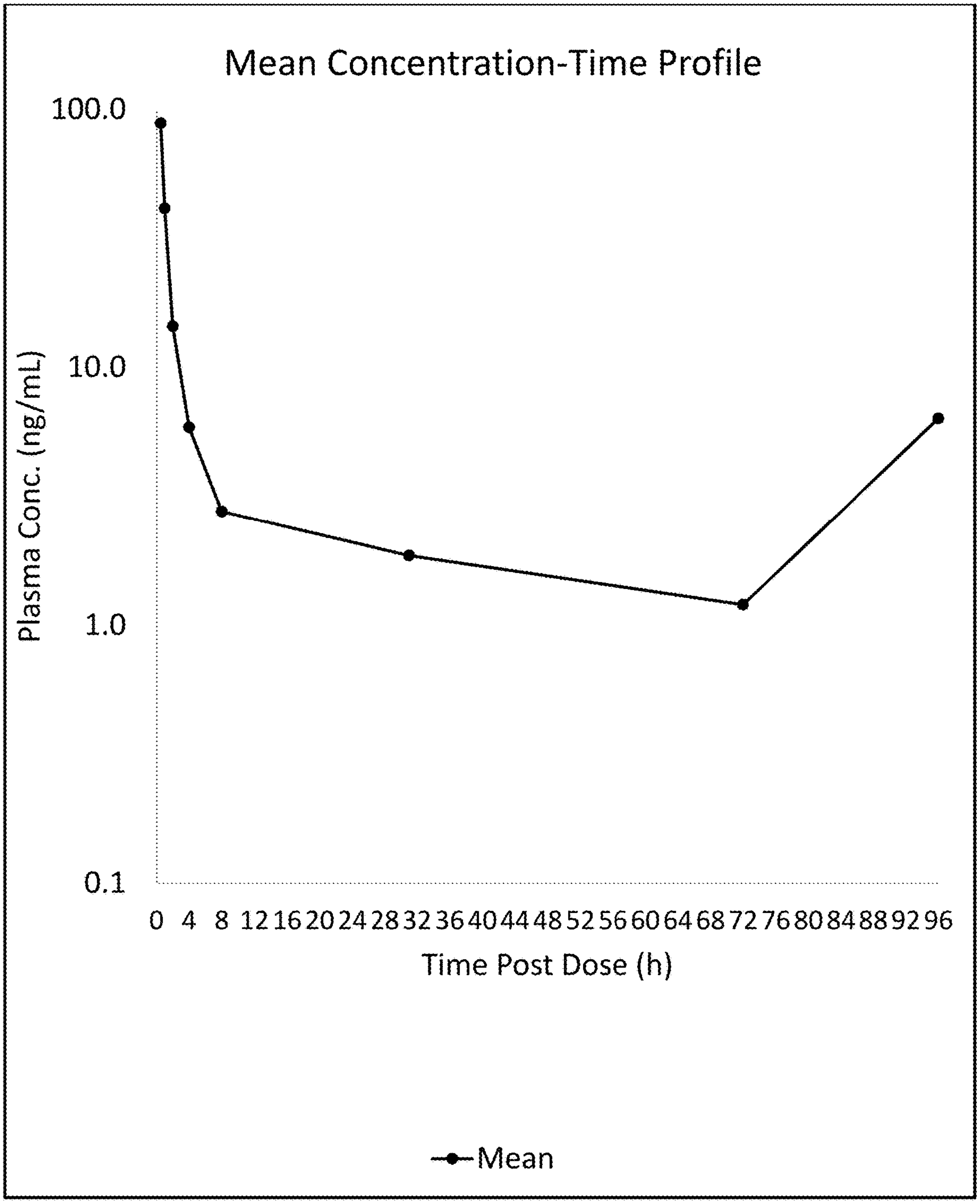
FIG. 44 shows mean concentration-time profiles of xanomeline following SC dosing of xanomeline oxybenzyl propanoate chloride prodrug (5 mg/kg of xanomeline) to male SD rats.

FIG. 44 shows mean concentration-time profiles of xanomeline following SC dosing of xanomeline oxybenzyl propanoate chloride prodrug (5 mg/kg of xanomeline) to male SD rats.

Example A-2-7: Xanomeline Oxypropyl Pivalate Chloride Prodrug—Table 1 Compound 352

| | |
|---|---|
| Species: | Rat |
| Dose Route: | SC |
| Dose Level (mg/kg) | 3.5 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium chloride Structural class: acyloxymethyl Mechanistic class: presumed esterase+chemical breakdown

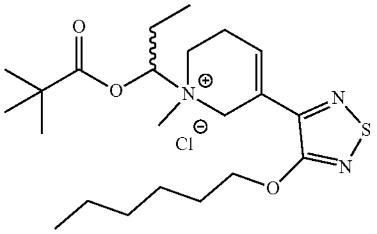 [SMILES: CCCCCCOc1nsnc1C1=CCC[N+](C)(C(CC)OC(=O)C(C)(C)C)C1 ; [Cl-]]

TABLE 48

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R4 | 86.7 | 36.0 | 6.82 | 96.0 | 251 | 486 |
| | | R5 | NR | 1.00 | 2.30 | 96.0 | 117 | NR |
| | | R6 | 47.1 | 0.500 | 1.25 | 24.0 | 14.8 | 54.1 |
| | | Mean | 66.9 | 12.5 | 3.46 | 72.0 | 128 | 270 |

Figure 45:
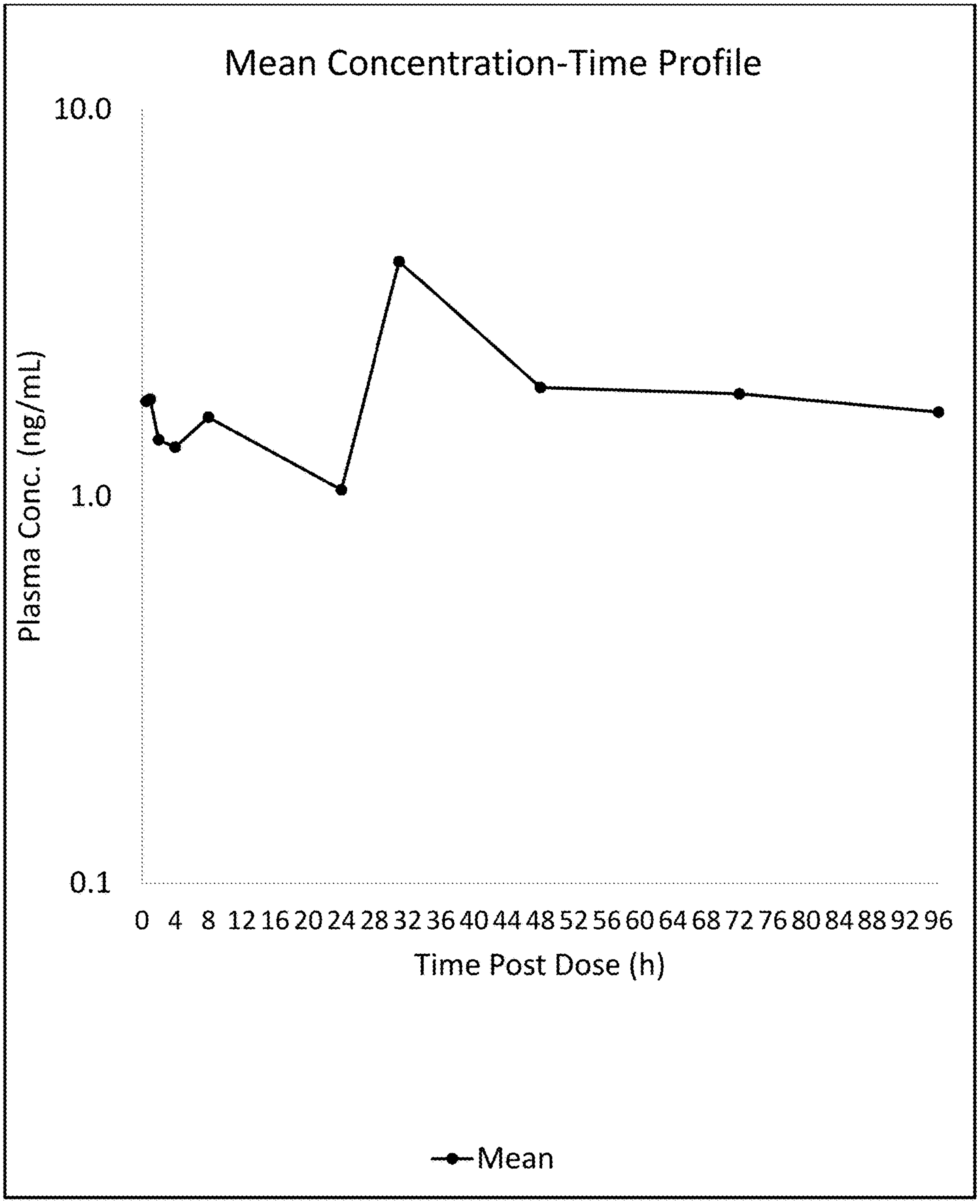
FIG. 45 shows mean concentration-time profiles of xanomeline following SC dosing of xanomeline oxypropyl pivalate chloride prodrug (3.5 mg/kg of xanomeline) to male SD rats.

FIG. 45 shows mean concentration-time profiles of xanomeline following SC dosing of xanomeline oxypropyl pivalate chloride prodrug (3.5 mg/kg of xanomeline) to male SD rats.

Example A-2-8: Xanomeline Oxypropyl Propanoate Chloride Prodrug—Table 1 Compound 336

| | |
|---|---|
| Species: | Rat |
| Dose Route: | SC |
| Dose Level (mg/kg) | 5 mg/kg of xanomeline |

Chemical name: 5-(4-(Hexyloxy)-1,2,5-thiadiazol-3-yl)-1-methyl-1-(1-(propionyloxy)propyl)-1,2,3,6-tetrahydropyridin-1-ium chloride Structural class: acyloxymethyl Mechanistic class: presumed esterase+chemical breakdown

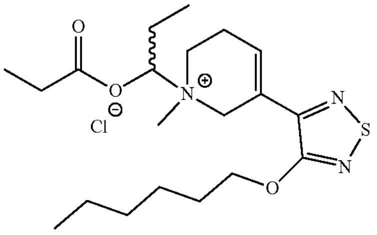 [SMILES: CCCCCCOc1nsnc1C1=CCC[N+](C)(C(CC)OC(=O)CC)C1 ; [Cl-]]

TABLE 49

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R10 | 1.23 | 0.500 | 20.8 | 4.00 | 41.2 | 46.4 |
| | | R11 | NR | 1.00 | 30.7 | 4.00 | 57.1 | NR |
| | | R12 | NR | 2.00 | 14.9 | 8.00 | 62.1 | NR |
| | | Mean | 1.23 | 1.17 | 22.1 | 5.33 | 53.5 | 46.4 |

Figure 46:
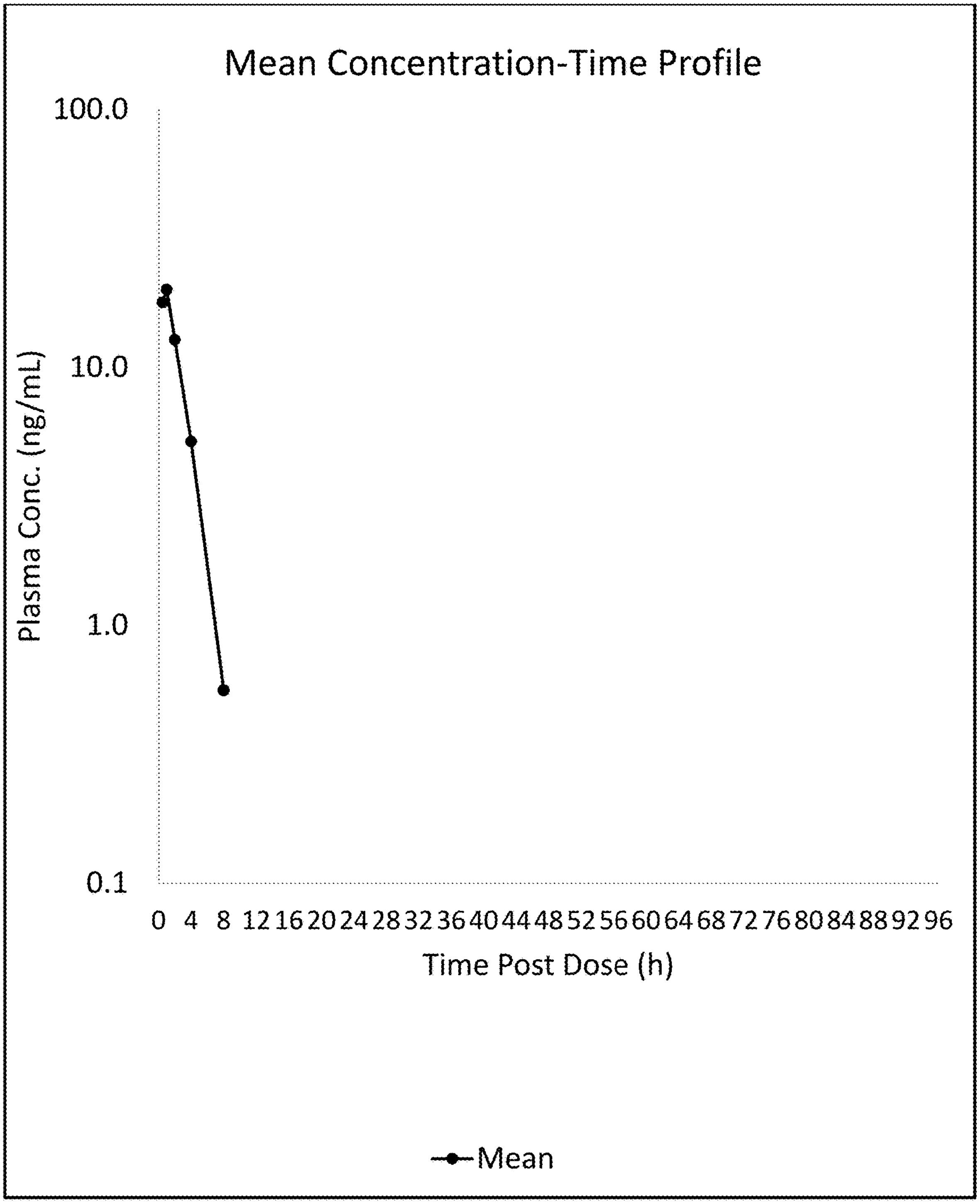
FIG. 46 shows mean concentration-time profiles of xanomeline following SC dosing of xanomeline oxypropyl propanoate chloride prodrug (5 mg/kg of xanomeline) to male SD rats.

FIG. 46 shows mean concentration-time profiles of xanomeline following SC dosing of xanomeline oxypropyl propanoate chloride prodrug (5 mg/kg of xanomeline) to male SD rats.

Example A-2-9: Xanomeline Oxybenzyl Pivalate Chloride Prodrug—Table 1 Compound 463

| | |
|---|---|
| Species: | Rat |
| Dose Route: | SC |
| Dose Level (mg/kg) | 5 mg/kg of xanomeline |

Chemical name: 5-(4-(Hexyloxy)-1,2,5-thiadiazol-3-yl)-1-methyl-1-(phenyl(pivaloyloxy)methyl)-1,2,3,6-tetrahydropyridin-1-ium chloride Structural class: acyloxymethyl Mechanistic class: presumed esterase+chemical breakdown

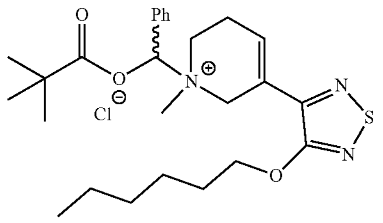

TABLE 50

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | SC | R13 | 1.80 | 1.00 | 8.69 | 8.00 | 33.8 | 35.5 |
| | | R14 | 4.45 | 0.50 | 7.31 | 8.00 | 31.0 | 43.4 |
| | | R15 | 1.88 | 0.50 | 9.64 | 8.00 | 32.3 | 33.9 |
| | | Mean | 2.71 | 0.667 | 8.55 | 8.00 | 32.4 | 37.6 |

Figure 47:
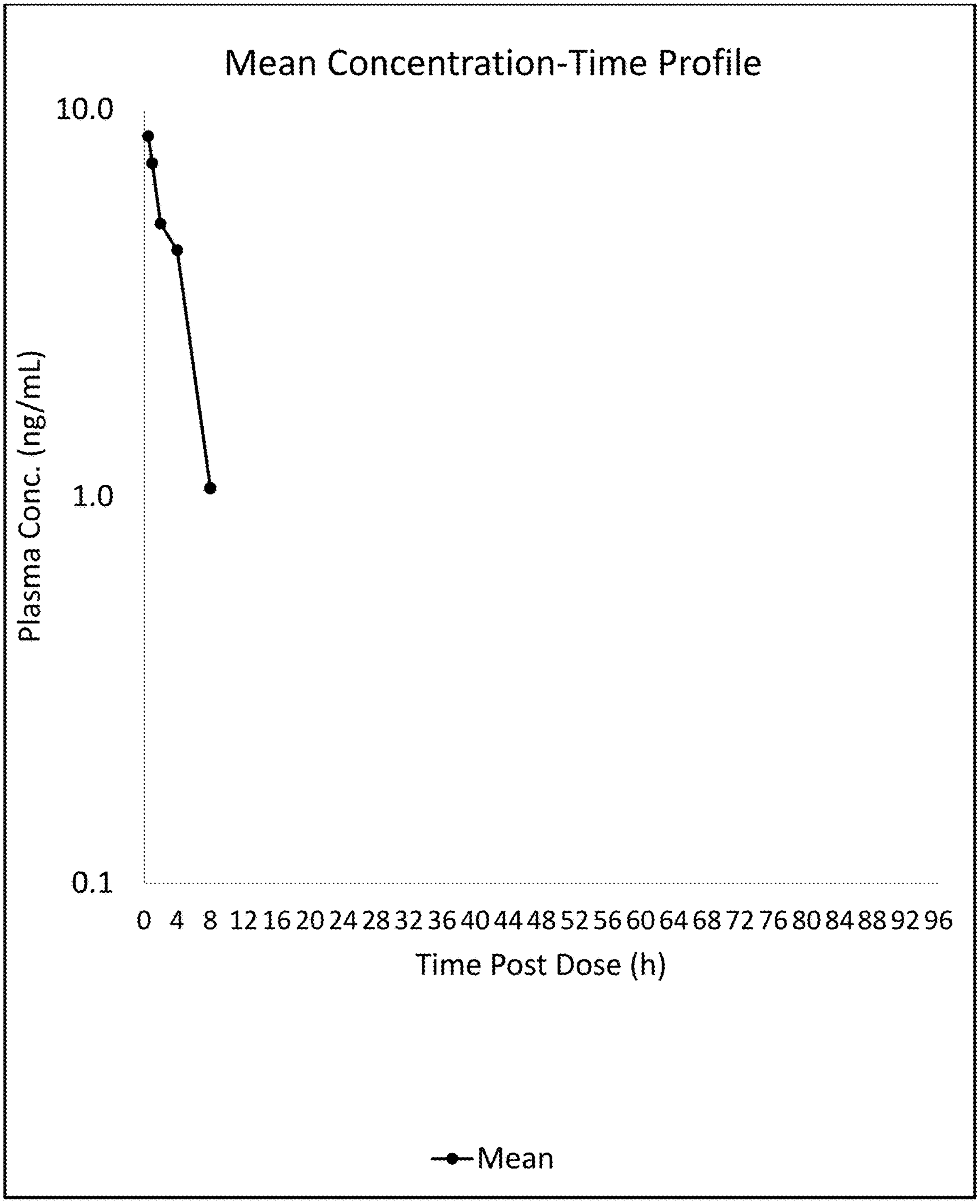
FIG. 47 shows mean concentration-time profiles of xanomeline following SC dosing of xanomeline oxybenzyl pivalate chloride prodrug (3.5 mg/kg of xanomeline) to male SD rats.

FIG. 47 shows mean concentration-time profiles of xanomeline following SC dosing of xanomeline oxybenzyl pivalate chloride prodrug (3.5 mg/kg of xanomeline) to male SD rats.

Example A-2-10: Xanomeline Mono-Pamoate—Table 1 Compound 595

| | |
|---|---|
| Species: | Rat |
| Dose Route: | SC |
| Dose Level (mg/kg) | 5 mg/kg of xanomeline |

Chemical name: Xanomeline mono-pamoate

Structural class: Pamoate salt

Mechanistic class: Parent with lower rate of dissolution

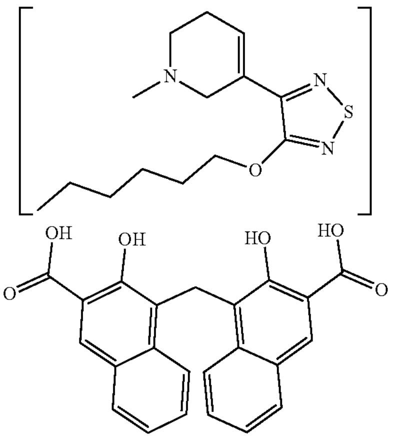

TABLE 51

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R13 | NR | 0.500 | 19.9 | 96.0 | 253 | NR |
| | | R14 | 3.25 | 1.00 | 23.7 | 8.00 | 83.3 | 103 |
| | | R15 | 2.49 | 0.500 | 29.5 | 8.00 | 57.3 | 62.3 |
| | | Mean | 2.87 | 0.667 | 24.4 | 37.3 | 131 | 82.7 |

Figure 48:
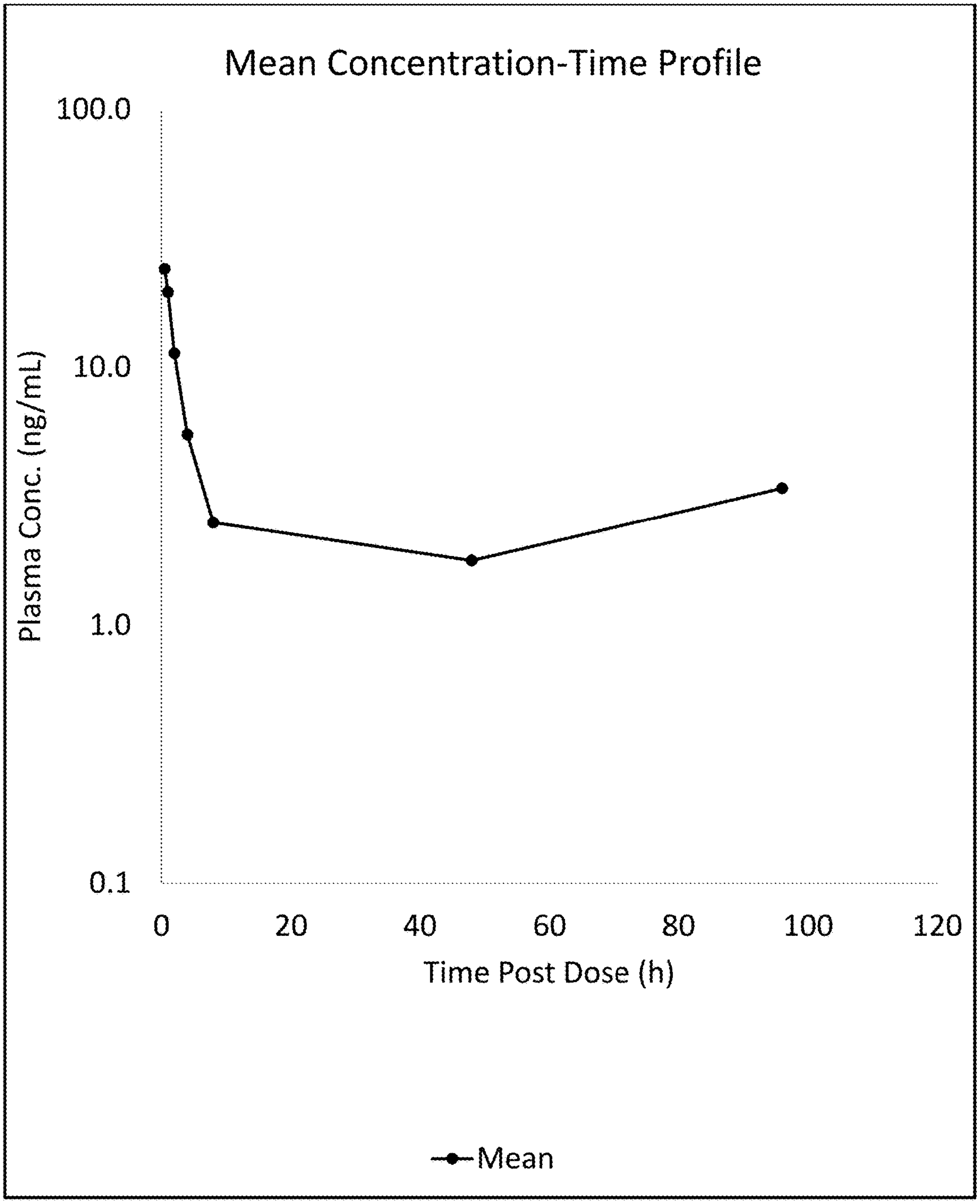
FIG. 48 shows mean concentration-time profiles of xanomeline following SC dosing of xanomeline mono-pamoate (5 mg/kg of xanomeline) to male SD rats.

FIG. 48 shows mean concentration-time profiles of xanomeline following SC dosing of xanomeline mono-pamoate (5 mg/kg of xanomeline) to male SD rats.

Example A-2-11: Xanomeline Hemi-Pamoate—Table 1 Compound 594

| | |
|---|---|
| Species: | Rat |
| Dose Route: | SC |
| Dose Level (mg/kg) | 5 mg/kg of xanomeline |

Chemical name: Xanomeline hemi-pamoate
Structural class: Pamoate salt
Mechanistic class: Parent with lower rate of dissolution

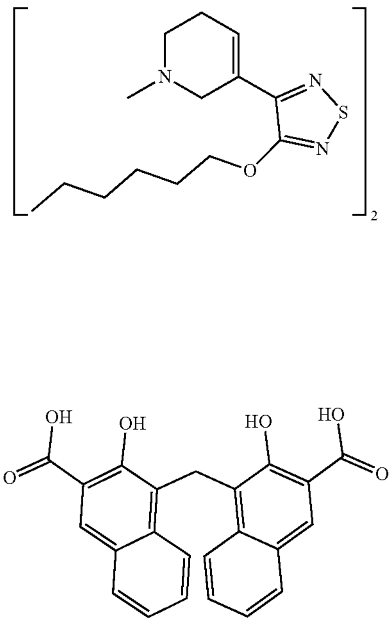

TABLE 52

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | SC | R16 | 2.08 | 0.500 | 27.4 | 8.00 | 55.8 | 59.7 |
| | | R17 | 1.85 | 1.00 | 34.1 | 8.00 | 104 | 111 |
| | | R18 | 1.54 | 0.500 | 46.6 | 8.00 | 137 | 141 |
| | | Mean | 1.82 | 0.667 | 36.0 | 8.00 | 98.9 | 104 |

Figure 49:
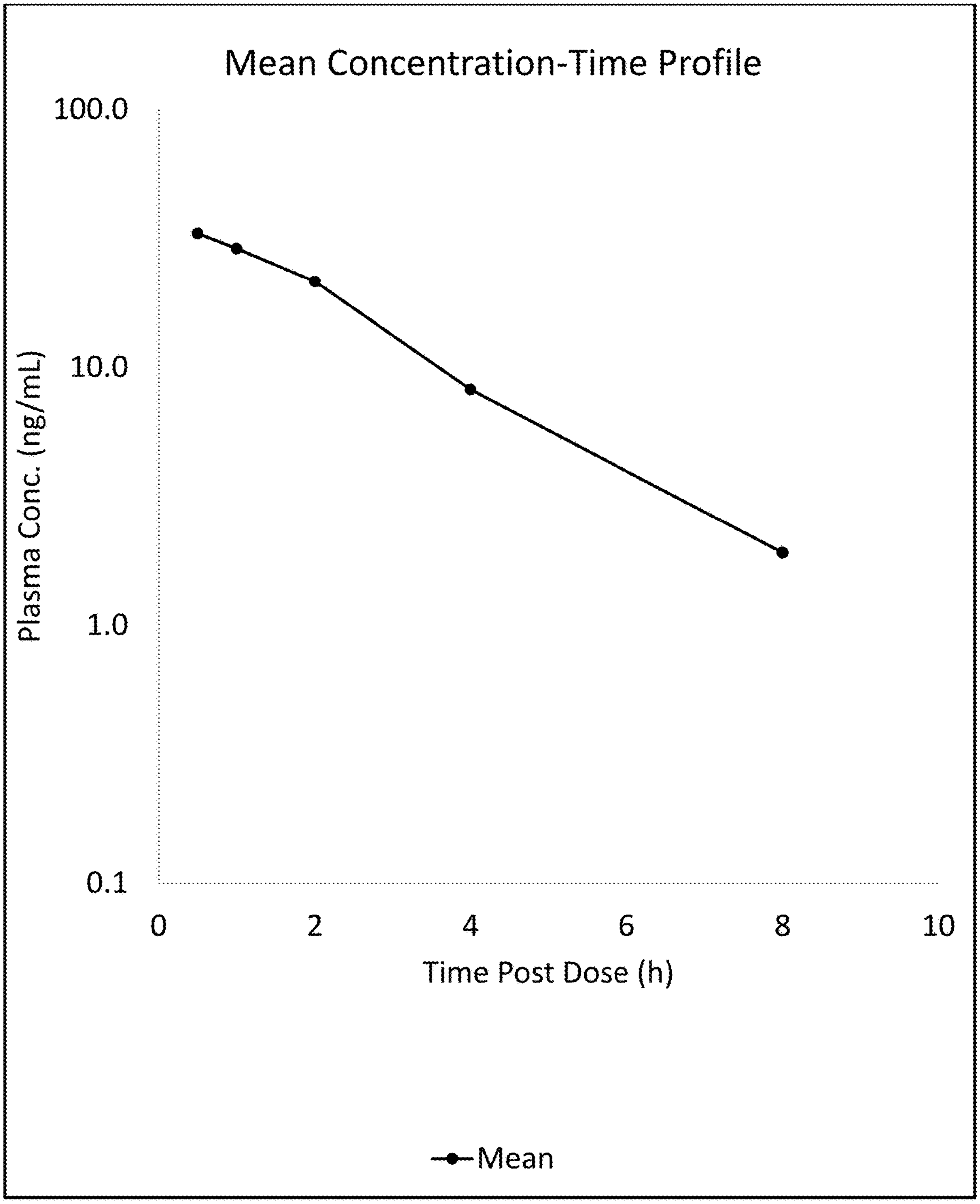
FIG. 49 shows mean concentration-time profiles of xanomeline following SC dosing of xanomeline hemi-pamoate (5 mg/kg of xanomeline) to male SD rats.

FIG. 49 shows mean concentration-time profiles of xanomeline following SC dosing of xanomeline hemi-pamoate (5 mg/kg of xanomeline) to male SD rats.

TABLE A-3

| Protocol: Serial tail vein bleed PK study of Xanomeline Prodrugs in SD rats | |
|---|---|
| Protocol | IM Serial PK study at 1 dose level |
| Test Compound(s) | Xanomeline, Xanomeline Prodrugs |
| Dosing Route | IM |
| Overnight food withdrawal | No |
| Animals Type | rat |
| Strain | Sprague Dawley rats |
| Sex | male |
| Weight (g) | 250-300 g |
| N per cpd | 3 |
| Preparation | None |
| Cage | PK cages |
| Dose | 5 mg/kg of xanomeline |
| Dosing Soln. Conc. | 12.5 mg/mL |
| Dosing Volume | 100 μL per 250 g (dose proportionately for rats <250 g) |
| Formulation checks required? | Yes |
| Vehicle | Saline |
| Sampling time points (h) | 0.5, 1, 2, 4, 8, 24, 31, 48, 72 & 96 h |
| Blood sampling method | Serial via tail vein |
| Alternative method if required | n/a |
| Sample format required | >230 μL blood + 5 μL EDTA (93 mg/mL) to give 2 × 50 μL plasma |
| Sample processing | Centrifugation for plasma ASAP at 4° C. Place 110 μL plasma into Eppendorf tube on ice containing 11 μL 10% phosphoric acid. Gently mix before taking 2 × 50 μL aliquots into duplicate 96 well plates on dry ice. |
| Anticoagulant | EDTA (93 mg/mL): 5 μL per tube |
| Centrifugation | 10,000 rpm × 3 min at 4° C. |
| Additional samples | n/a |
| Perfusion/rinsing required | n/a |
| Euthanasia method | n/a |
| Plasma sample tubes | 96 well plates |
| Pre-freezer storage | Blood: ice (<30 min), Acidified Plasma: dry ice |

TABLE A-3-continued

| Protocol: Serial tail vein bleed PK study of Xanomeline Prodrugs in SD rats | |
|---|---|
| Protocol | IM Serial PK study at 1 dose level |
| Freezer storage | −80° C. |
| Dose formulation samples | 100 μL from vortex dose solution in Eppendorf |
| Number of samples per cpd at 1 dose level | 30 × acidified plasma (50 μL in duplicate), 1 dose soln |

Analysis

Samples were sent for method optimization and measurement of parent compound (xanomeline) via unique calibration lines and following acceptance QC's. Dose formulation concentrations were also measured, and PK parameters were determined (Cmax (ng/mL), Tmax (hr), Cl (ml/min/kg), Vdss (L/kg), t1/2(hr), AUCO-t (ng/mL*hr), AUCO-inf (ng/mL*hr), MRT (hr), Bioavailability (% F) where warranted) using WinNon Lin software. Data (including bioanalytical results and assay performance) were reported in a tabulated format and QC'd.

Additional Formulation Details for PK Study

Phosphoric acid. Diluted 85% phosphoric acid 8.5-fold to give a 10% solution.

Formulation for IM administration: All compounds were formulated as solutions or fine suspensions in saline at 12.5 mg API/mL. This provided doses of 5 mg/kg (equivalent of xanomeline) when given to a 250 g rat in a 100 μL dosing volume.

Example A-3: Measurement of Concentration of Xanomeline after Intramuscular (IM) Administration of Xanomeline Prodrugs In Vivo The pharmacokinetic properties of the synthesized xanomeline prodrugs after intramuscular administration in a rat model were assessed. The concentration of xanomeline was measured in each rat at various sampling timepoints after intramuscular administration of xanomeline or the synthesized xanomeline prodrugs to rats.

Dose formulations were made at equivalent concentrations of active compound (xanomeline) adjusted for molecular weight of the compounds. The synthesized xanomeline prodrugs were dosed at 5 mg/kg intramuscular (IM) nominal dose. Nominal doses were used in PK parameter determinations. The parent compound (xanomeline) was dosed at 5 mg/kg intramuscular (IM).

Example A-3-1: Xanomeline Oxyethyl Pivalate Chloride Prodrug—Table 1 Compound 19

| | |
|---|---|
| Species: | Rat |
| Dose Route: | IM |
| Dose Level (mg/kg) | 5 mg/kg of xanomeline |

Chemical name: 1-[5-(4-hexyloxy-1,2,5-thiadiazol-3-yl)-1-methyl-3,6-dihydro-2H-pyridin-1-ium-1-yl]ethyl 2,2-dimethylpropanoate chloride Structural class: acyloxymethyl Mechanistic class: presumed esterase+chemical breakdown

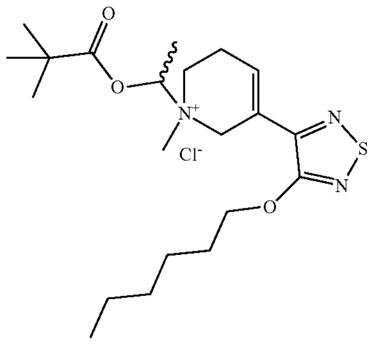 [SMILES: CCCCCCOc1nsnc1C1=CCC[N+](C)(C(C)OC(=O)C(C)(C)C)C1 ; [Cl-]]

TABLE 53

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IM | R1 | 38 | 0.50 | 9.62 | 72.0 | 132 | 175 |
| | | R2 | 110 | 0.50 | 5.93 | 48.0 | 78.8 | 194 |
| | | R3 | 3.48 | 0.50 | 6.50 | 8.00 | 32.6 | 41.1 |
| | | Mean | 50.5 | 0.50 | 7.35 | 42.7 | 81 | 137 |

Figure 50:
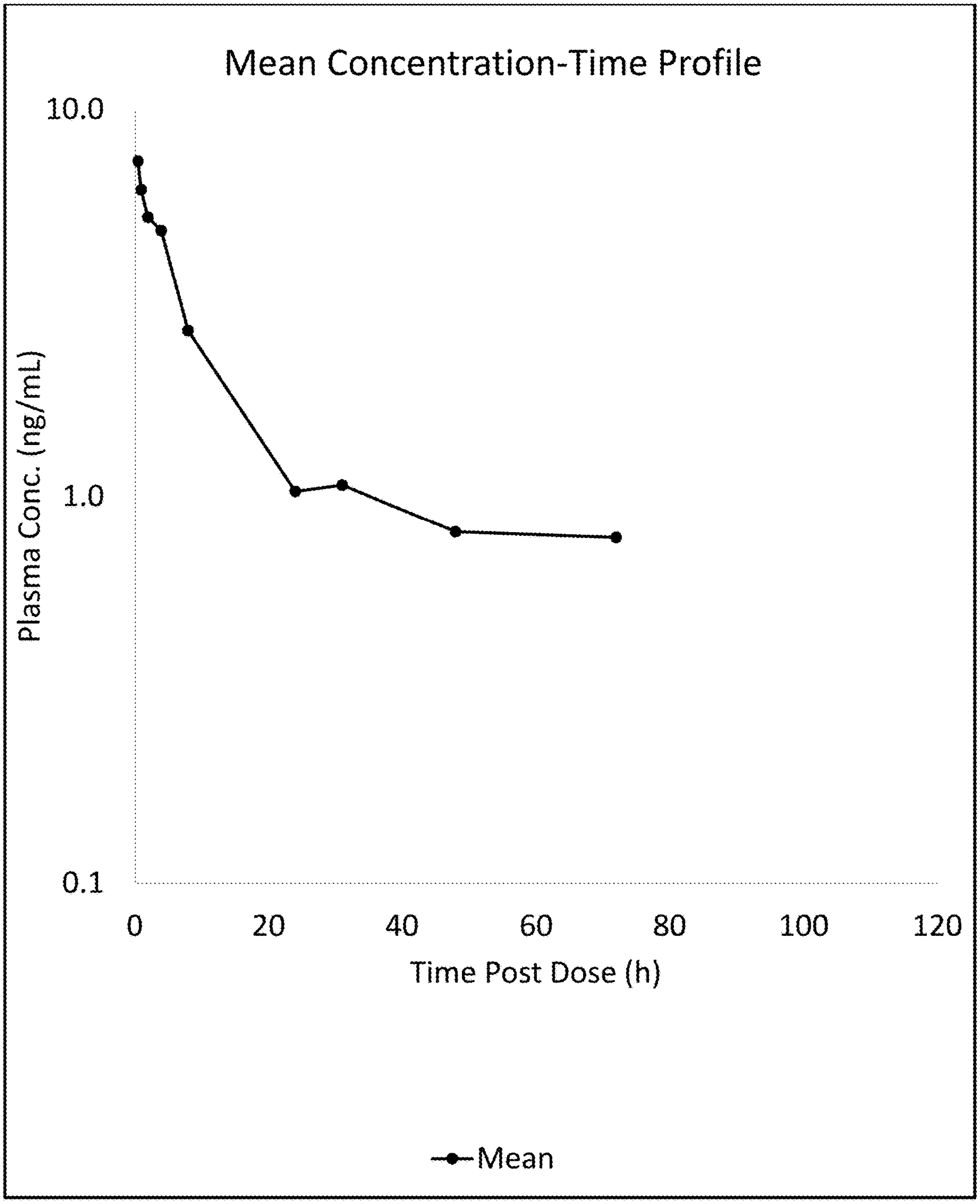
FIG. 50 shows mean concentration-time profiles of xanomeline following IM dosing of xanomeline oxyethyl pivalate chloride prodrug (5 mg/kg of xanomeline) to male SD rats.

FIG. 50 shows mean concentration-time profiles of xanomeline following IM dosing of xanomeline oxyethyl pivalate chloride prodrug (5 mg/kg of xanomeline) to male SD rats.

Example A-3-2: Xanomeline Oxypropyl Pivalate Chloride Prodrug—Table 1 Compound 352

| | |
|---|---|
| Species: | Rat |
| Dose Route: | IM |
| Dose Level (mg/kg) | 5 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium chloride Structural class: acyloxymethyl Mechanistic class: presumed esterase+chemical breakdown

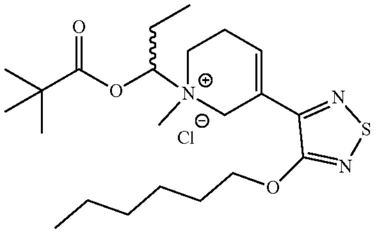 [SMILES: CCCCCCOc1nsnc1C1=CCC[N+](C)(C(CC)OC(=O)C(C)(C)C)C1 ; [Cl-]]

TABLE 54

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IM | R4 | 21.7 | 0.50 | 0.715 | 72.0 | 10.4 | 11.5 |
| | | R5 | 27.4 | 0.50 | 0.723 | 72.0 | 8.09 | 8.83 |
| | | R6 | 34.1 | 0.50 | 1.02 | 96.0 | 8.24 | 8.89 |
| | | Mean | 27.7 | 0.50 | 0.819 | 80.0 | 8.91 | 9.74 |

Figure 51:
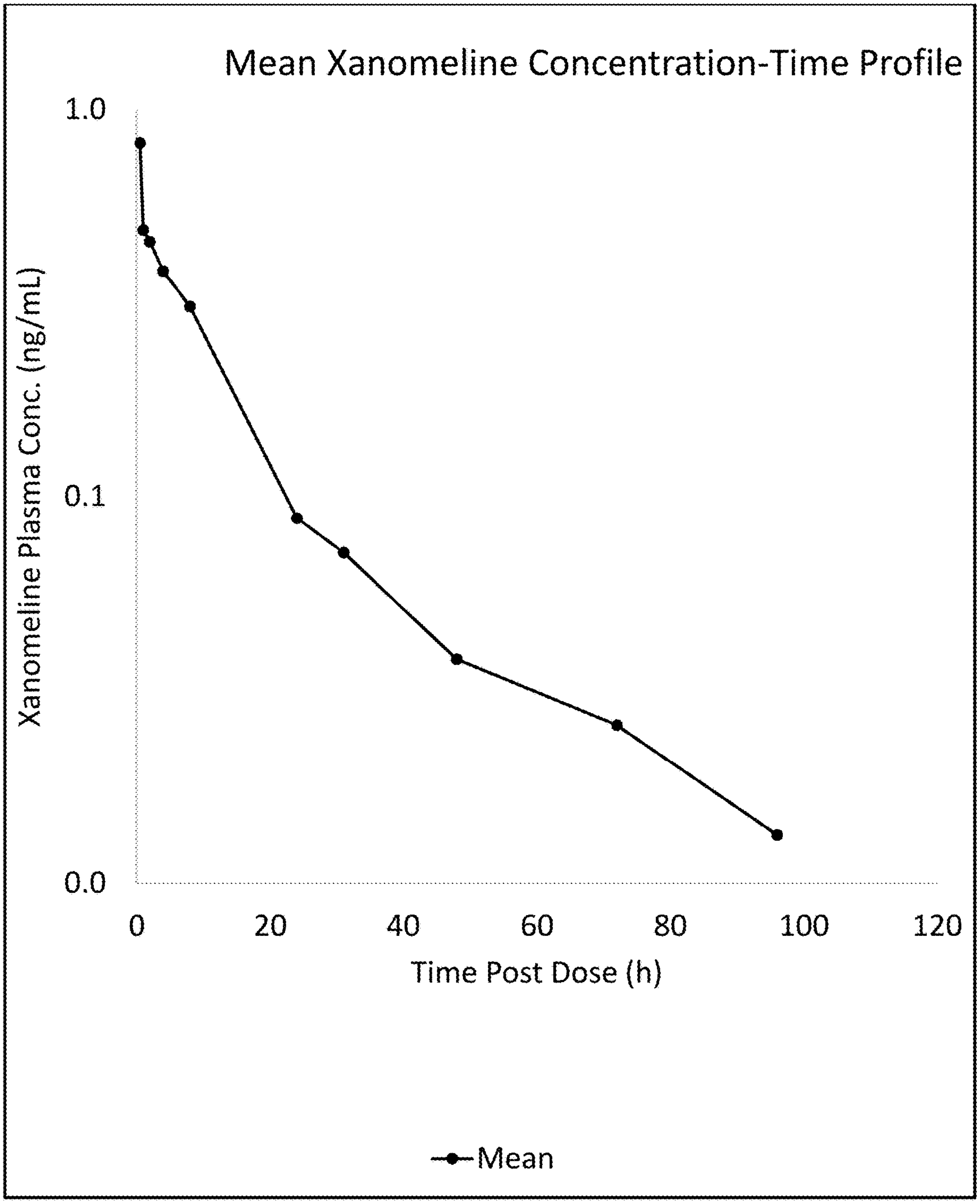
FIG. 51 shows mean concentration-time profiles of xanomeline following IM dosing of xanomeline oxypropyl pivalate chloride prodrug (5 mg/kg of xanomeline) to male SD rats.

FIG. 51 shows mean concentration-time profiles of xanomeline following IM dosing of xanomeline oxypropyl pivalate chloride prodrug (5 mg/kg of xanomeline) to male SD rats.

Example A-3-3: Xanomeline Oxypropyl Pivalate Iodide Prodrug—Table 1 Compound 596

| | |
|---|---|
| Species: | Rat |
| Dose Route: | IM |
| Dose Level (mg/kg) | 5 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium iodide Structural class: acyloxymethyl Mechanistic class: presumed esterase+chemical breakdown

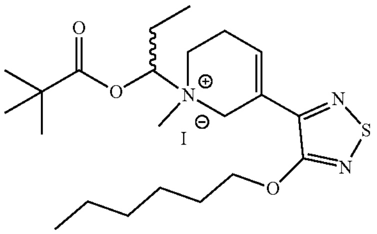 [SMILES: CCCCCCOc1nsnc1C1=CCC[N+](C)(C(CC)OC(=O)C(C)(C)C)C1 ; [I-]]

TABLE 55

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IM | R13 | 33.0 | 0.50 | 0.963 | 96.00 | 12.3 | 12.8 |
| | | R14 | 26.0 | 0.50 | 0.917 | 96.00 | 12.5 | 13.2 |
| | | R15 | 20.4 | 0.50 | 1.05 | 96.00 | 16.3 | 16.6 |
| | | Mean | 26.5 | 0.50 | 0.977 | 96.00 | 13.7 | 14.2 |

Figure 52:
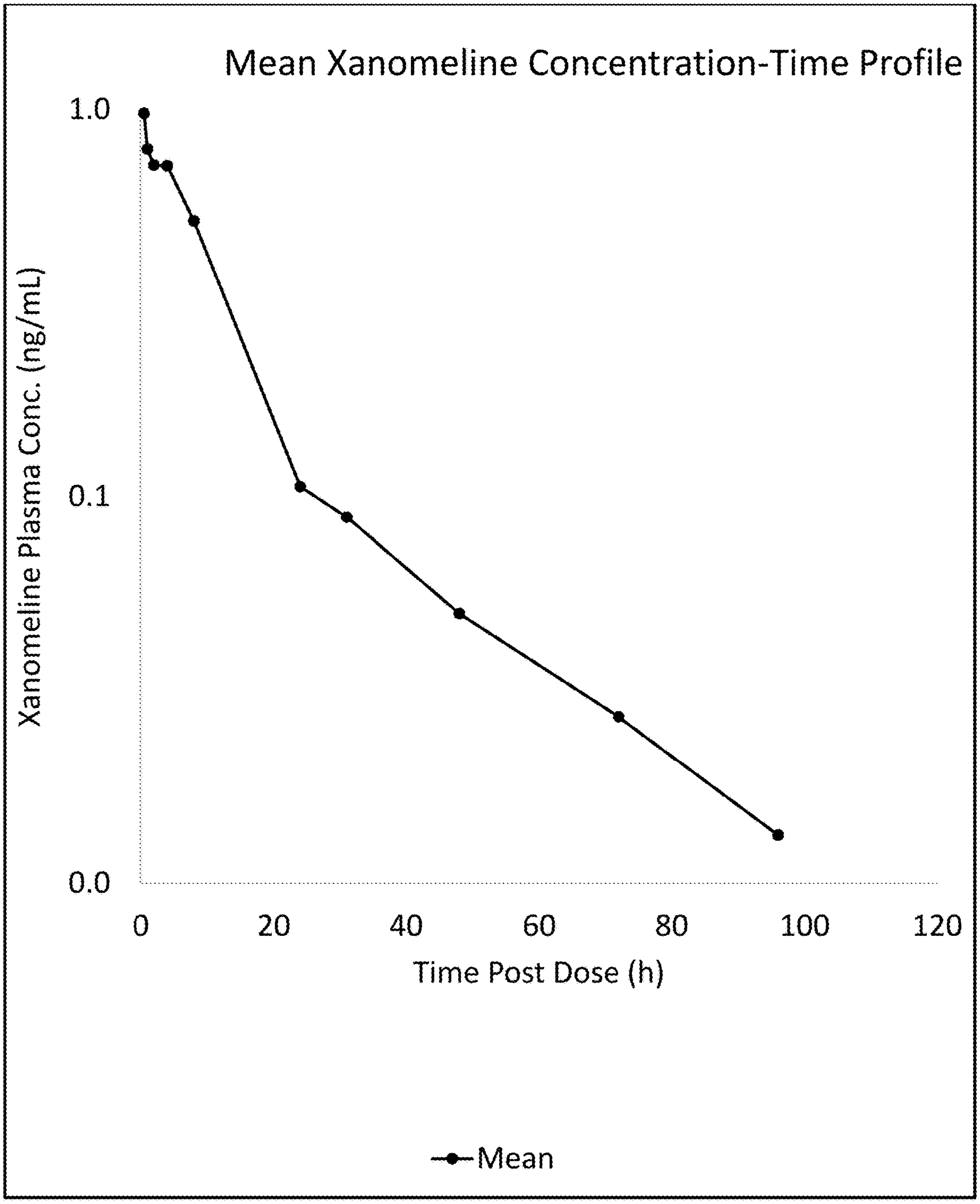
FIG. 52 shows mean concentration-time profiles of xanomeline following IM dosing of xanomeline oxypropyl pivalate iodide prodrug (5 mg/kg of xanomeline) to male SD rats.

FIG. 52 shows mean concentration-time profiles of xanomeline following IM dosing of xanomeline oxypropyl pivalate iodide prodrug (5 mg/kg of xanomeline) to male SD rats.

Example A-3-4: Xanomeline Oxyethyl Pivalate Pamoate Prodrug—Table 1 Compound 597

| | |
|---|---|
| Species: | Rat |
| Dose Route: | IM |
| Dose Level (mg/kg) | 5 mg/kg of xanomeline |

Chemical name: 5-(4-(Hexyloxy)-1,2,5-thiadiazol-3-yl)-1-methyl-1-(1-(pivaloyloxy)ethyl)-1,2,3,6-tetrahydropyridin-1-ium pamoate Structural class: acyloxymethyl Mechanistic class: presumed esterase+chemical breakdown

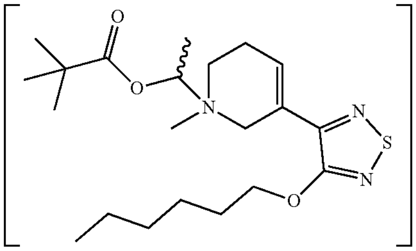

-continued

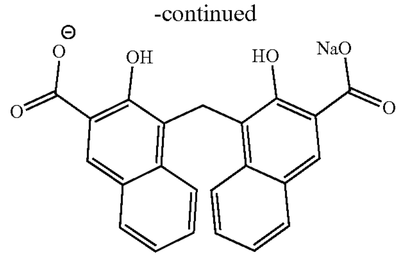

TABLE 56

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IM | R1 | 23.1 | 0.50 | 7.84 | 96.0 | 82.1 | 84.3 |
| | | R2 | 14.6 | 0.50 | 7.17 | 96.0 | 68.9 | 70.5 |
| | | R3 | 13.8 | 2.00 | 5.26 | 96.0 | 61.3 | 61.5 |
| | | Mean | 17.2 | 1.00 | 6.76 | 96.0 | 70.8 | 72.1 |

Figure 53:
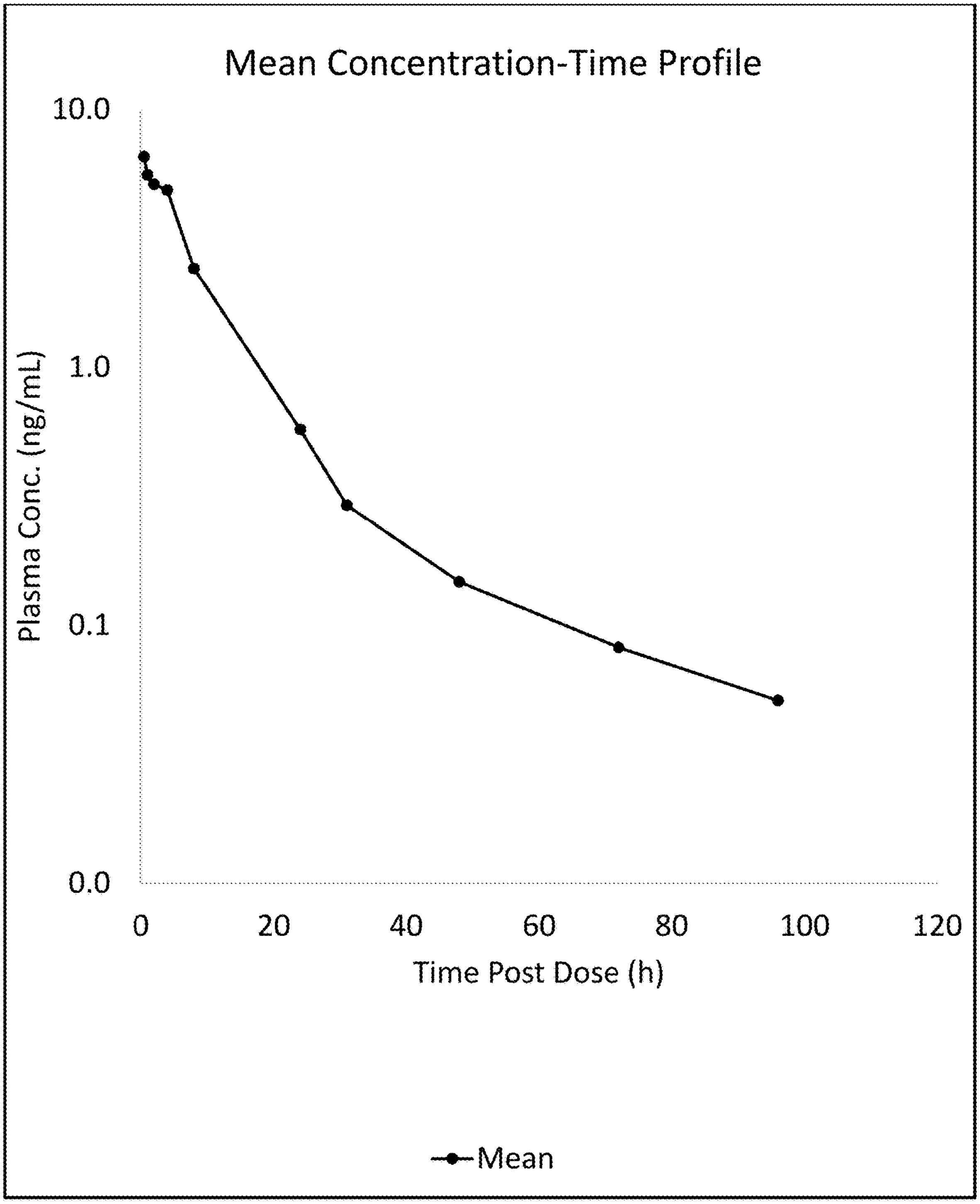
FIG. 53 shows mean concentration-time profiles of xanomeline following IM dosing of xanomeline oxyethyl pivalate pamoate prodrug (5 mg/kg of xanomeline) to male SD rats.

FIG. 53 shows mean concentration-time profiles of xanomeline following IM dosing of xanomeline oxyethyl pivalate pamoate prodrug (5 mg/kg of xanomeline) to male SD rats.

Example A-3-5: Xanomeline Oxyethyl Pivalate Hemi-Pamoate Prodrug—Table 1 Compound 598

| | |
|---|---|
| Species: | Rat |
| Dose Route: | IM |
| Dose Level (mg/kg) | 5 mg/kg of xanomeline |

Chemical name: 5-(4-(Hexyloxy)-1,2,5-thiadiazol-3-yl)-1-methyl-1-(1-(pivaloyloxy)ethyl)-1,2,3,6-tetrahydropyridin-1-ium hemi-pamoate Structural class: acyloxymethyl Mechanistic class: presumed esterase+chemical breakdown

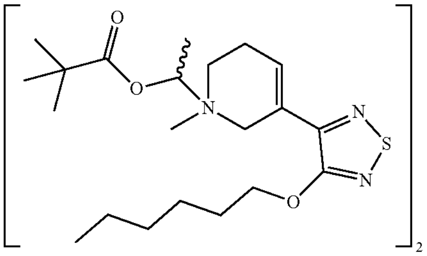

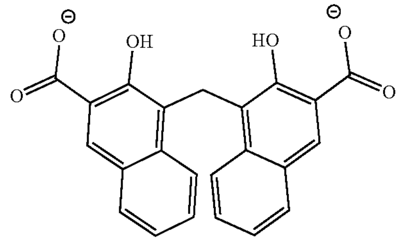

TABLE 57

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IM | R4 | 18.8 | 1.00 | 6.98 | 96.0 | 72.5 | 73.5 |
| | | R5 | 14.4 | 0.500 | 8.30 | 96.0 | 66.4 | 66.7 |
| | | R6 | 12.3 | 0.500 | 8.37 | 96.0 | 62.5 | 62.9 |
| | | Mean | 15.2 | 0.667 | 7.88 | 96.0 | 67.1 | 67.7 |

Figure 54:
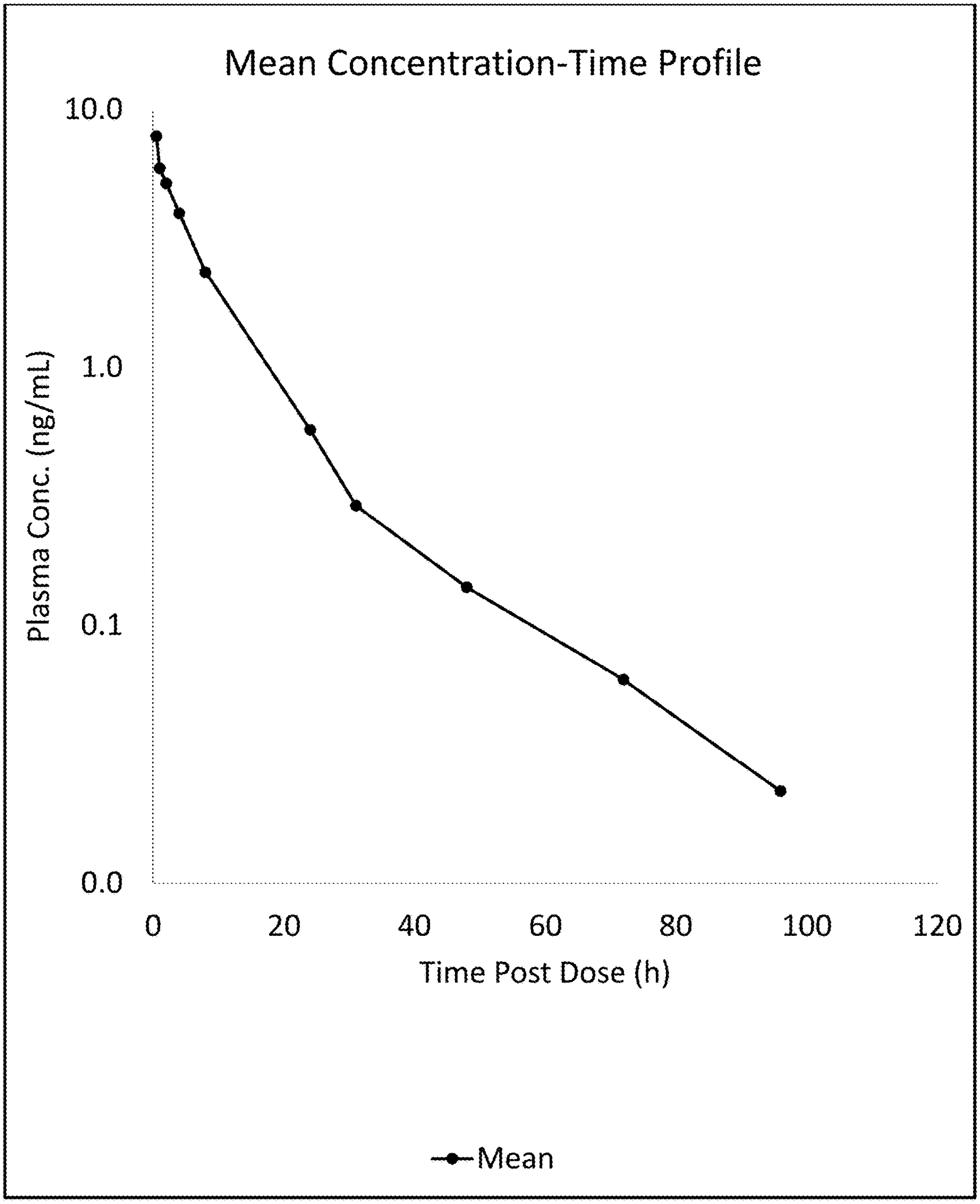
FIG. 54 shows mean concentration-time profiles of xanomeline following IM dosing of xanomeline oxyethyl pivalate hemi-pamoate prodrug (5 mg/kg of xanomeline) to male SD rats.

FIG. 54 shows mean concentration-time profiles of xanomeline following IM dosing of xanomeline oxyethyl pivalate hemi-pamoate prodrug (5 mg/kg of xanomeline) to male SD rats.

Example A-3-6: Xanomeline Oxypropyl Pivalate Pamoate Prodrug—Table 1 Compound 599

| | |
|---|---|
| Species: | Rat |
| Dose Route: | IM |
| Dose Level (mg/kg | 5 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium pamoate Structural class: acyloxymethyl Mechanistic class: presumed esterase+chemical breakdown

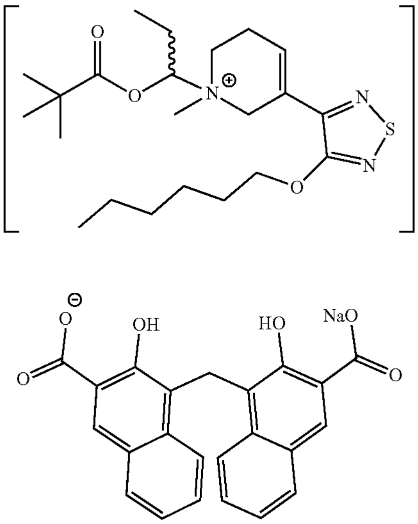

TABLE 58

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IM | R7 | 23.5 | 0.50 | 2.36 | 96.0 | 22.4 | 23.0 |
| | | R8 | 17.7 | 0.50 | 2.39 | 96.0 | 23.0 | 23.7 |
| | | R9 | 17.1 | 0.50 | 2.70 | 96.0 | 23.3 | 23.8 |
| | | Mean | 19.4 | 0.500 | 2.48 | 96.0 | 22.9 | 23.5 |

Figure 55:
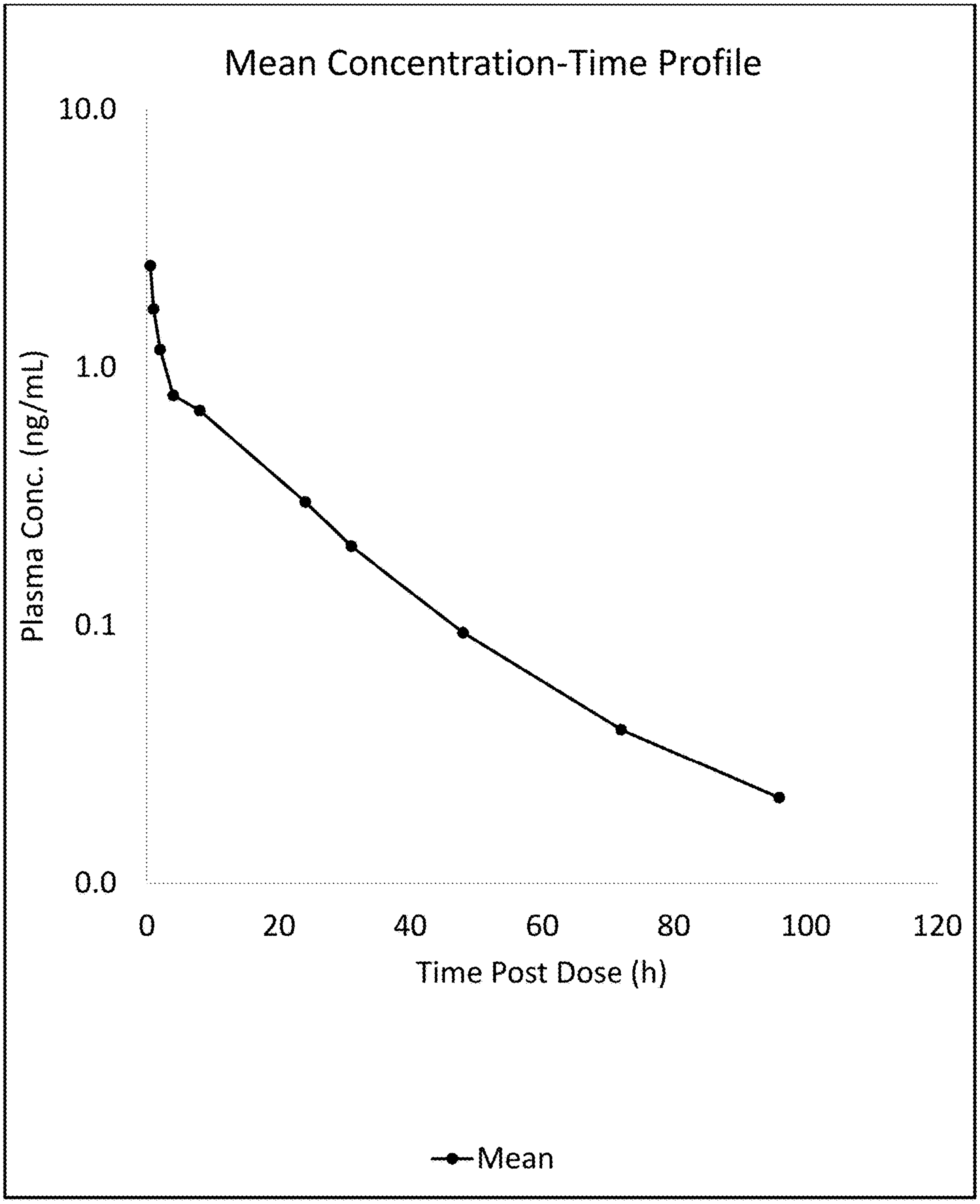
FIG. 55 shows mean concentration-time profiles of xanomeline following IM dosing of xanomeline oxypropyl pivalate pamoate prodrug (5 mg/kg of xanomeline) to male SD rats.

FIG. 55 shows mean concentration-time profiles of xanomeline following IM dosing of xanomeline oxypropyl pivalate pamoate prodrug (5 mg/kg of xanomeline) to male SD rats.

Example A-3-7: Xanomeline Oxypropyl Pivalate Hemi-Pamoate Prodrug—Table 1 Compound 600

| | |
|---|---|
| Species: | Rat |
| Dose Route: | IM |
| Dose Level (mg/kg) | 5 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium hemi-pamoate Structural class: acyloxymethyl Mechanistic class: presumed esterase+chemical breakdown

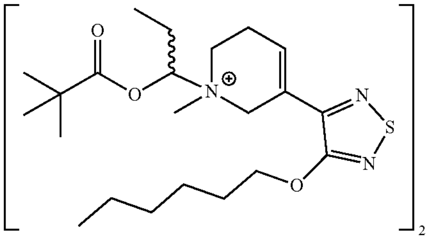

-continued

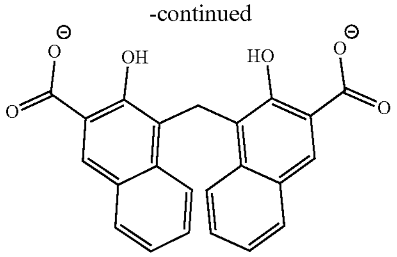

TABLE 59

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IM | R10 | 16.6 | 0.50 | 2.79 | 96.0 | 30.3 | 30.8 |
| | | R11 | 16.6 | 0.50 | 2.45 | 96.0 | 24.0 | 24.5 |
| | | R12 | 22.6 | 0.50 | 1.79 | 96.0 | 27.9 | 29.3 |
| | | Mean | 18.6 | 0.50 | 2.34 | 96.0 | 27.4 | 28.2 |

Figure 56:
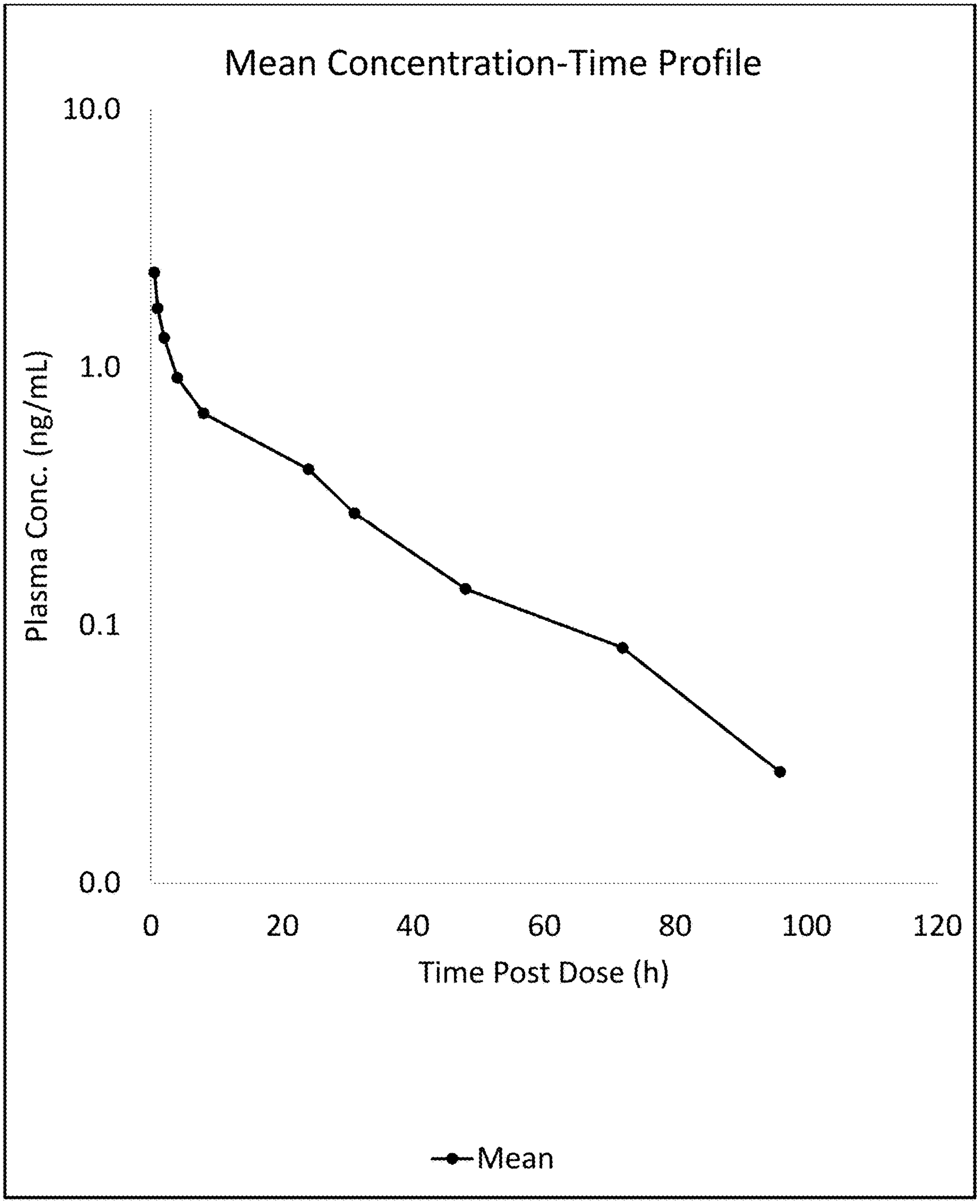
FIG. 56 shows mean concentration-time profiles of xanomeline following IM dosing of xanomeline oxypropyl pivalate hemi-pamoate prodrug (5 mg/kg of xanomeline) to male SD rats.

FIG. 56 shows mean concentration-time profiles of xanomeline following IM dosing of xanomeline oxypropyl pivalate hemi-pamoate prodrug (5 mg/kg of xanomeline) to male SD rats.

Example A-3-8: Xanomeline Parent Compound (IM)—Table 1 Compound 922

| | |
|---|---|
| Species: | Rat |
| Dose Route: | IM |
| Dose Level (mg/kg) | 5 mg/kg of xanomeline |

Chemical name: Xanomeline
Structural class: parent
Mechanistic class: n/a—parent compound

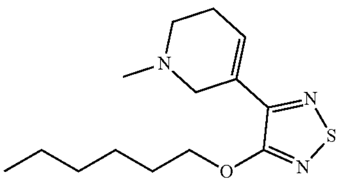 [SMILES: CCCCCCOc1nsnc1C1=CCCN(C)C1]

TABLE 60

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | IM | R13 | 12.3 | 0.50 | 82.1 | 96.0 | 179 | 179 |
| | | R14 | 16.9 | 0.50 | 127 | 96.0 | 207 | 207 |
| | | R15 | 10.4 | 0.50 | 119 | 72.0 | 188 | 189 |
| | | Mean | 13.2 | 0.50 | 109 | 88.0 | 191 | 192 |

Figure 57:
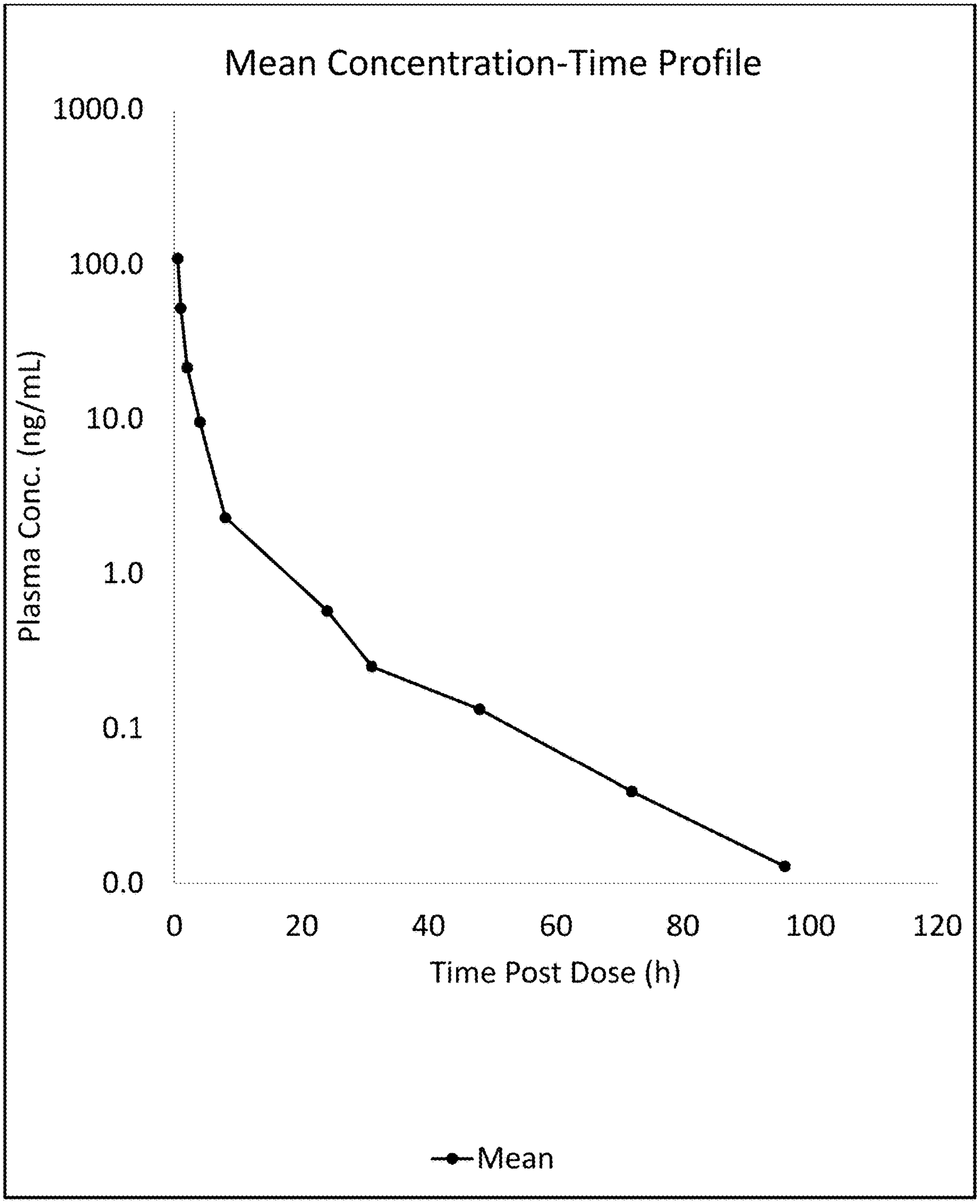
FIG. 57 shows mean concentration-time profiles of xanomeline following IM dosing of xanomeline (5 mg/kg of xanomeline) to male SD rats.

FIG. 57 shows mean concentration-time profiles of xanomeline following IM dosing of xanomeline (5 mg/kg of xanomeline) to male SD rats.

Example A-3-9: Xanomeline Mono-Pamoate—Table 1 Compound 595

| | |
|---|---|
| Species: | Rat |
| Dose Route: | IM |
| Dose Level (mg/kg) | 5 mg/kg of xanomeline |

Chemical name: Xanomeline mono-pamoate

Structural class: Pamoate salt

Mechanistic class: Parent with lower rate of dissolution

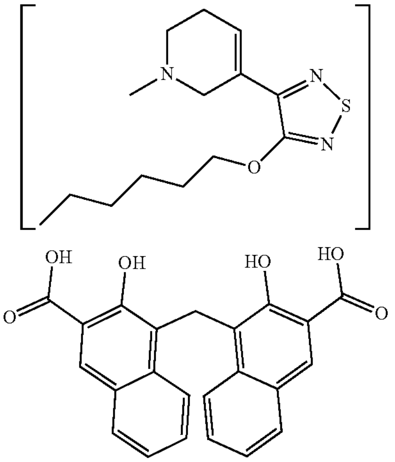

TABLE 61

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | IM | R16 | 4.78 | 0.50 | 58.9 | 36.0 | 69.4 | 69.4 |
| | | R17 | 5.91 | 0.50 | 44.7 | 36.0 | 73.0 | 73.5 |
| | | R18 | 7.55 | 0.50 | 54.2 | 48.0 | 64.3 | 64.4 |
| | | Mean | 6.08 | 0.50 | 52.6 | 40.0 | 68.9 | 69.1 |

Figure 58:
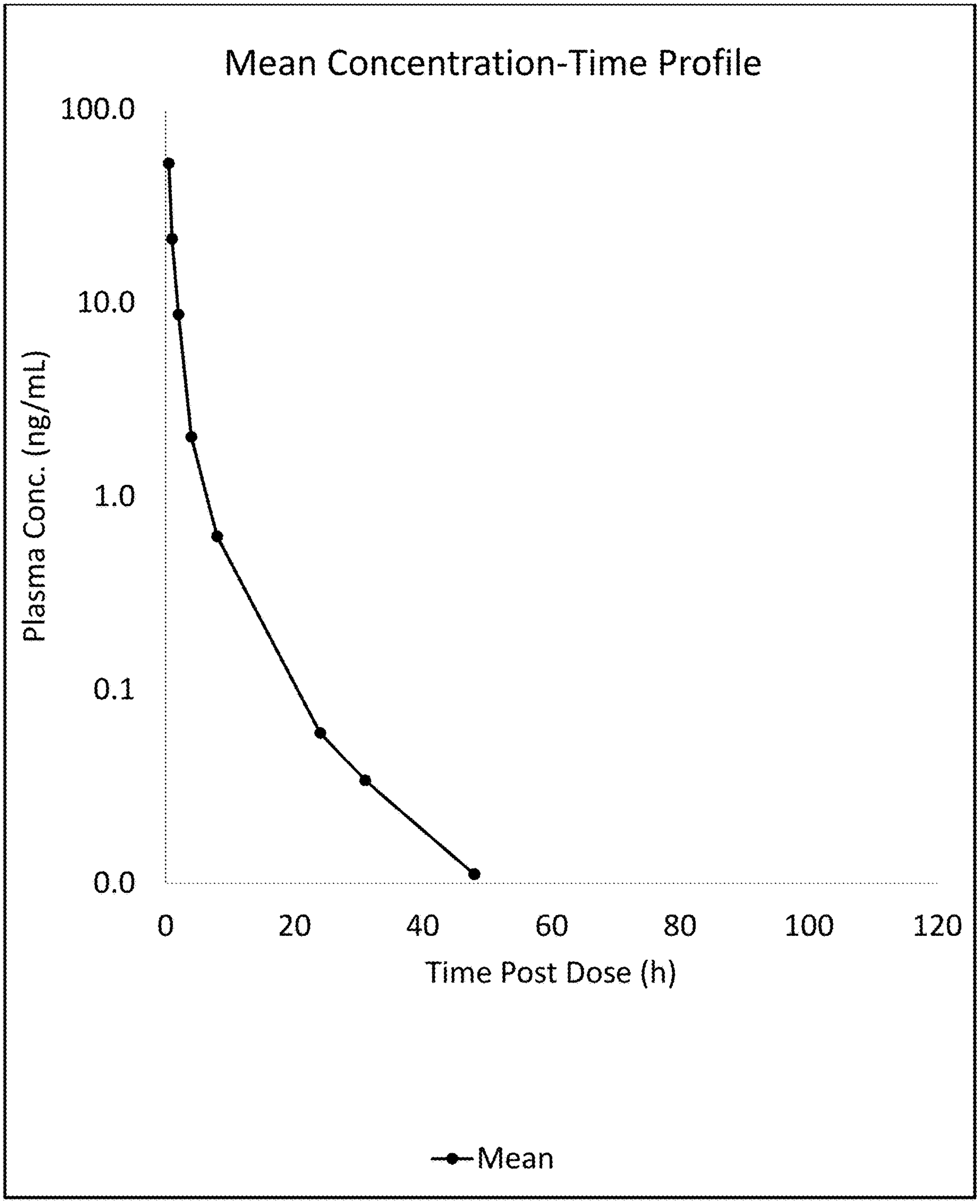
FIG. 58 shows mean concentration-time profiles of xanomeline following IM dosing of xanomeline mono-pamoate (5 mg/kg of xanomeline) to male SD rats.

FIG. 58 shows mean concentration-time profiles of xanomeline following IM dosing of xanomeline mono-pamoate (5 mg/kg of xanomeline) to male SD rats.

Example A-3-10: Xanomeline Hemi-Pamoate—Table 1 Compound 594

| | |
|---|---|
| Species: | Rat |
| Dose Route: | IM |
| Dose Level (mg/kg) | 5 mg/kg of xanomeline |

Chemical name: Xanomeline hemi-pamoate
Structural class: Pamoate salt
Mechanistic class: Parent with lower rate of dissolution

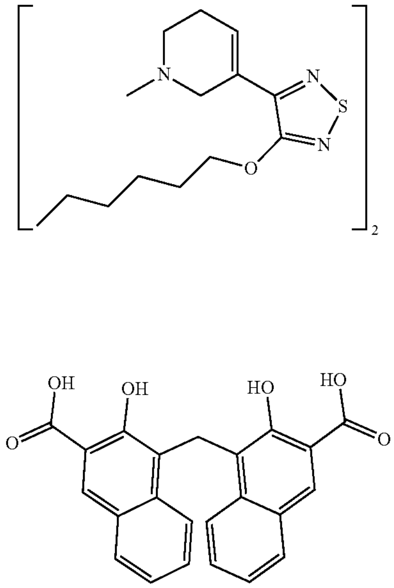

TABLE 62

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IM | R19 | 19.2 | 0.50 | 141 | 96.0 | 166 | 166 |
| | | R20 | 9.15 | 0.50 | 109 | 72.0 | 162 | 162 |
| | | R21 | 9.19 | 0.50 | 118 | 72.0 | 133 | 133 |
| | | Mean | 12.5 | 0.50 | 123 | 80.0 | 154 | 154 |

Figure 59:
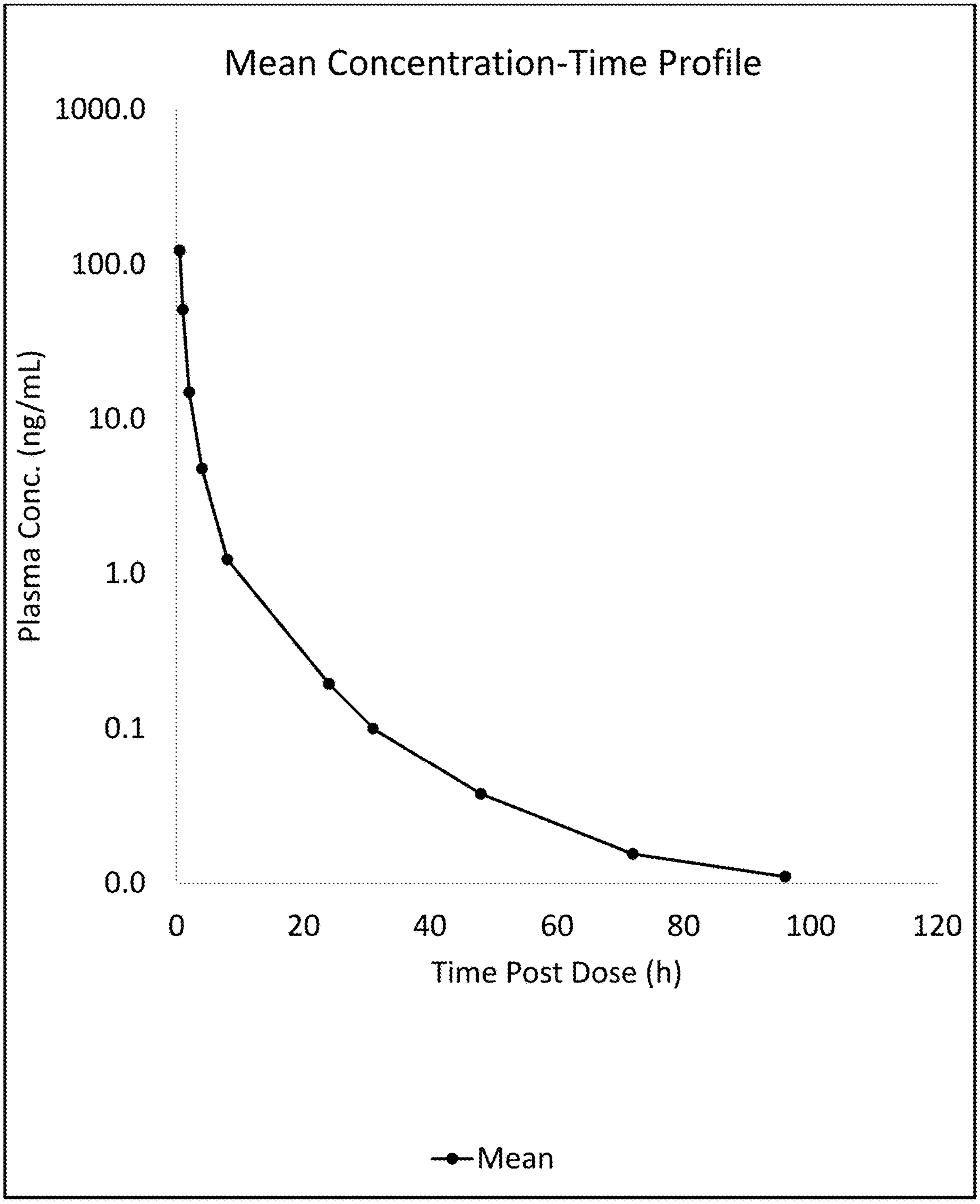
FIG. 59 shows mean concentration-time profiles of xanomeline following IM dosing of xanomeline hemi-pamoate (5 mg/kg of xanomeline) to male SD rats.

FIG. 59 shows mean concentration-time profiles of xanomeline following IM dosing of xanomeline hemi-pamoate (5 mg/kg of xanomeline) to male SD rats.

TABLE A-4

| Protocol: Serial tail vein bleed PK study of Xanomeline Prodrugs in SD rats | |
|---|---|
| Protocol | IM serial PK study at 1 dose level |
| Test Compound(s) | Xanomeline Prodrugs |
| Dosing Route | IM |
| Overnight food withdrawal | No |
| Animals Type | rat |
| Strain | Sprague Dawley rats |
| Sex | male |
| Weight (g) | 250-300 g |
| N per cpd | 3 |
| Preparation | None |
| Cage | PK cages |
| Dose | 5 mg/kg of xanomeline |
| Dosing Soln. Conc. | 12.5 mg/mL |
| Dosing Volume | 100 μL per 250 g (dose proportionately for rats <250 g) |
| Formulation checks required? | Yes |
| Vehicle | Saline |
| Sampling time points (h) | 0.5, 1, 2, 4, 8, 24, 31, 48, 72 & 96 h |
| Blood sampling method | Serial via tail vein |
| Alternative method if required | n/a |
| Sample format required | >230 μL blood + 5 μL EDTA (93 mg/mL) to give 2 × 50 μL plasma |
| Sample processing | Centrifugation for plasma ASAP at 4° C. Place 110 μL plasma into Eppendorf tube on ice containing 11 μL 10% phosphoric acid. Gently mix before taking 2 × 50 μL aliquots into duplicate 96 well plates on dry ice. |
| Anticoagulant | EDTA (93 mg/mL): 5 μL per tube |
| Centrifugation | 10,000 rpm × 3 min at 4° C. |
| Additional samples | n/a |
| Perfusion/rinsing required | n/a |
| Euthanasia method | n/a |
| Plasma sample tubes | 96 well plates |
| Pre-freezer storage | Blood: ice (<30 min), Acidified Plasma: dry ice |

TABLE A-4-continued

| Protocol: Serial tail vein bleed PK study of Xanomeline Prodrugs in SD rats | |
|---|---|
| Protocol | IM serial PK study at 1 dose level |
| Freezer storage | −80° C. |
| Dose formulation samples | 100 μL from vortex dose solution in Eppendorf |
| Number of samples per cpd at 1 dose level | 30 x acidified plasma (50 μL in duplicate), 1 dose soln |

Analysis

Samples were sent for method optimization and measurement of prodrug via unique calibration lines and following acceptance QC's. Dose formulation concentrations were also measured, and PK parameters were determined (Cmax (ng/mL), Tmax (hr), Cl (ml/min/kg), Vdss (L/kg), t1/2(hr), AUCO-t (ng/mL*hr), AUCO-inf (ng/mL*hr), MRT (hr), Bioavailability (% F) where warranted) using WinNon Lin software. Data (including bioanalytical results and assay performance) were reported in a tabulated format and QC'd.

Additional Formulation Details for PK Study

Phosphoric acid. Diluted 85% phosphoric acid 8.5-fold to give a 10% solution.

Formulation for IM administration: All compounds were formulated as solutions or fine suspensions in saline at 12.5 mg API/mL. This provided doses of 5 mg/kg (equivalent of xanomeline) when given to a 250 g rat in a 100 μL dosing volume.

Example A-4: Measurement of Concentration of Prodrug after Intramuscular (IM) Administration of Xanomeline Prodrugs In Vivo The pharmacokinetic properties of the synthesized xanomeline prodrugs after intramuscular administration in a rat model were assessed. The concentration of prodrug was measured in each rat at various sampling timepoints after intramuscular administration of the synthesized xanomeline prodrugs to rats.

Dose formulations were made at equivalent concentrations of active compound (xanomeline) adjusted for molecular weight of the compounds. The synthesized xanomeline prodrugs were dosed at 5 mg/kg intramuscular (IM) nominal dose. Nominal doses were used in PK parameter determinations.

Example A-4-1: Xanomeline Oxyethyl Pivalate Chloride Prodrug—Table 1 Compound 19

| | |
|---|---|
| Species: | Rat |
| Dose Route: | IM |
| Dose Level (mg/kg) | 5 mg/kg of xanomeline |

Chemical name: 1-[5-(4-hexyloxy-1,2,5-thiadiazol-3-yl)-1-methyl-3,6-dihydro-2H-pyridin-1-ium-1-yl]ethyl 2,2-dimethylpropanoate chloride Structural class: acyloxymethyl Mechanistic class: presumed esterase+chemical breakdown

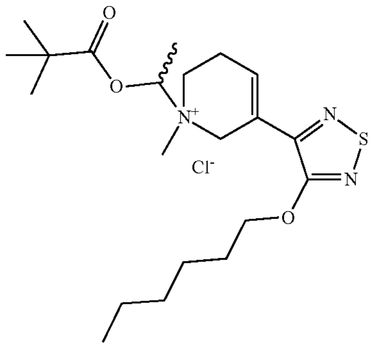 [SMILES: CCCCCCOc1nsnc1C1=CCC[N+](C)(C(C)OC(=O)C(C)(C)C)C1 ; [Cl-]]

TABLE 63

Prodrug Plasma Concentrations (ng/mL) Following Intramuscular Dosing

| Bioanalytical Data: Time (h) | Prodrug Plasma Concentrations (ng/ml) Following Intramuscular Dosing Animal R1 | R2 | R3 | Mean |
|---|---|---|---|---|
| 0.500 | 284 | 204 | 166 | 218 |
| 1.00 | 115 | 139 | 130 | 128 |
| 2.00 | 80.2 | 70.6 | 98.1 | 83.0 |
| 4.00 | 38.6 | 38.4 | 30.8 | 35.9 |
| 8.00 | 13.5 | 18.4 | 9.07 | 13.7 |
| 24.0 | 1.00 | 2.92 | 0.854 | 1.59 |
| 31.0 | 1.01 | 1.06 | BLQ | 1.04 |
| 48.0 | 0.775 | 0.556 | BLQ | 0.666 |
| 72.0 | BLQ | BLQ | BLQ | BLQ |
| 96.0 | 0.764 | BLQ | BLQ | 0.255 |

BLQ: Below Lower Limit of Quantification (0.5 ng/ml)

TABLE 64

Prodrug Pharmacokinetic Parameters

| Dose Route | Animal ID | HL_Lambda_z (hr) | Tmax (hr) | Cmax (ng/ml) | Tlast (hr) | AUClast (ng/ml*hr) | AUCINF_obs (ng/ml*hr) |
|---|---|---|---|---|---|---|---|
| Intramuscular | R1 | 203 | 0.50 | 284 | 96.0 | 667 | 891 |
| | R2 | 10.0 | 0.50 | 204 | 48.0 | 668 | 676 |
| | R3 | 4.07 | 0.50 | 166 | 24.0 | 518 | 523 |
| | Mean | 72.4 | 0.50 | 218 | 56.0 | 618 | 697 |

Figure 60:
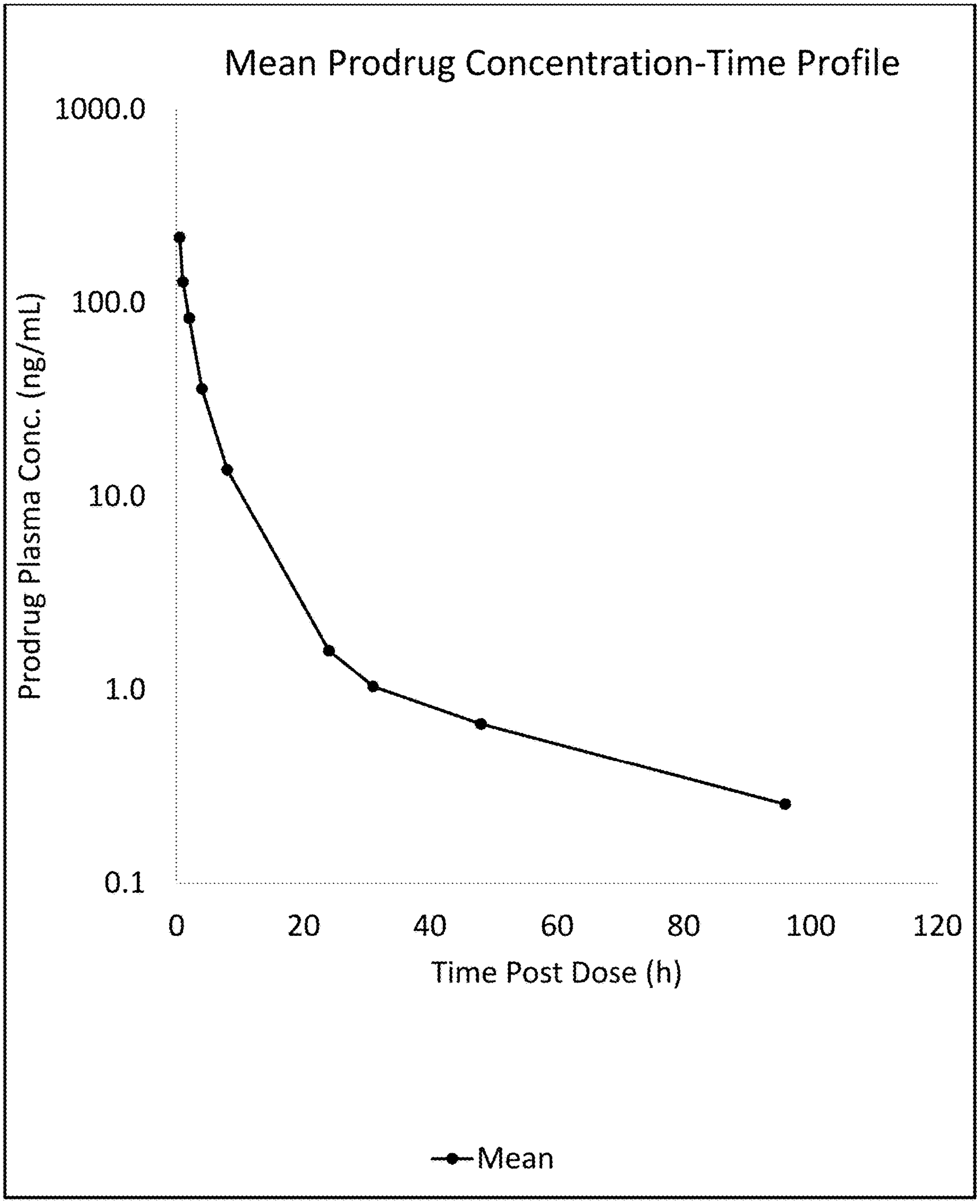
FIG. 60 shows mean concentration-time profiles of prodrug following IM dosing of xanomeline oxyethyl pivalate chloride prodrug (5 mg/kg of xanomeline) to male SD rats.

FIG. 60 shows mean concentration-time profiles of prodrug following IM dosing of xanomeline oxyethyl pivalate chloride prodrug (5 mg/kg of xanomeline) to male SD rats.

Example A-4-2: Xanomeline Oxypropyl Pivalate Chloride Prodrug—Table 1 Compound 352

| | |
|---|---|
| Species: | Rat |
| Dose Route: | IM |
| Dose Level (mg/kg) | 5 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium chloride Structural class: acyloxymethyl Mechanistic class: presumed esterase+chemical breakdown

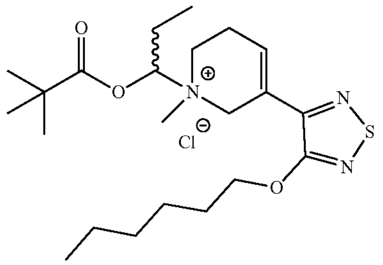 [SMILES: CCCCCCOc1nsnc1C1=CCC[N+](C)(C(CC)OC(=O)C(C)(C)C)C1 ; [Cl-]]

TABLE 65

Prodrug Plasma Concentrations (ng/mL) Following Intramuscular Dosing

| Time (h) | Bioanalytical Data: Prodrug Plasma Concentrations (ng/mL) Following Intramuscular Dosing Animal R4 | R5 | R6 | Mean |
|---|---|---|---|---|
| 0.500 | 130 | 99.2 | 210 | 146 |
| 1.00 | 61.0 | 68.3 | 134 | 87.8 |
| 2.00 | 55.0 | 63.4 | 95.6 | 71.3 |
| 4.00 | 34.7 | 30.1 | 35.5 | 33.4 |
| 8.00 | 15.3 | 14.9 | 25.6 | 18.6 |
| 24.0 | BLQ | BLQ | BLQ | BLQ |
| 31.0 | BLQ | BLQ | BLQ | BLQ |
| 48.0 | BLQ | BLQ | BLQ | BLQ |
| 72.0 | BLQ | BLQ | BLQ | BLQ |
| 96.0 | BLQ | BLQ | BLQ | BLQ |

BLQ: Below Lower Limit of Quantification (0.5 ng/mL)

TABLE 66

Prodrug Pharmacokinetic Parameters

| Dose Route | Animal ID | HL_Lambda_z (hr) | Tmax (hr) | Cmax (ng/mL) | Tlast (hr) | AUClast (ng/ml*hr) | AUCINF_obs (ng/ml*hr) |
|---|---|---|---|---|---|---|---|
| Intramuscular | R4 | 3.27 | 0.50 | 130 | 8.00 | 328 | 400 |
| | R5 | 2.99 | 0.50 | 99.2 | 8.00 | 316 | 380 |
| | R6 | 3.47 | 0.50 | 210 | 8.00 | 507 | 635 |
| | Mean | 3.24 | 0.50 | 146 | 8.00 | 384 | 472 |

Figure 61:
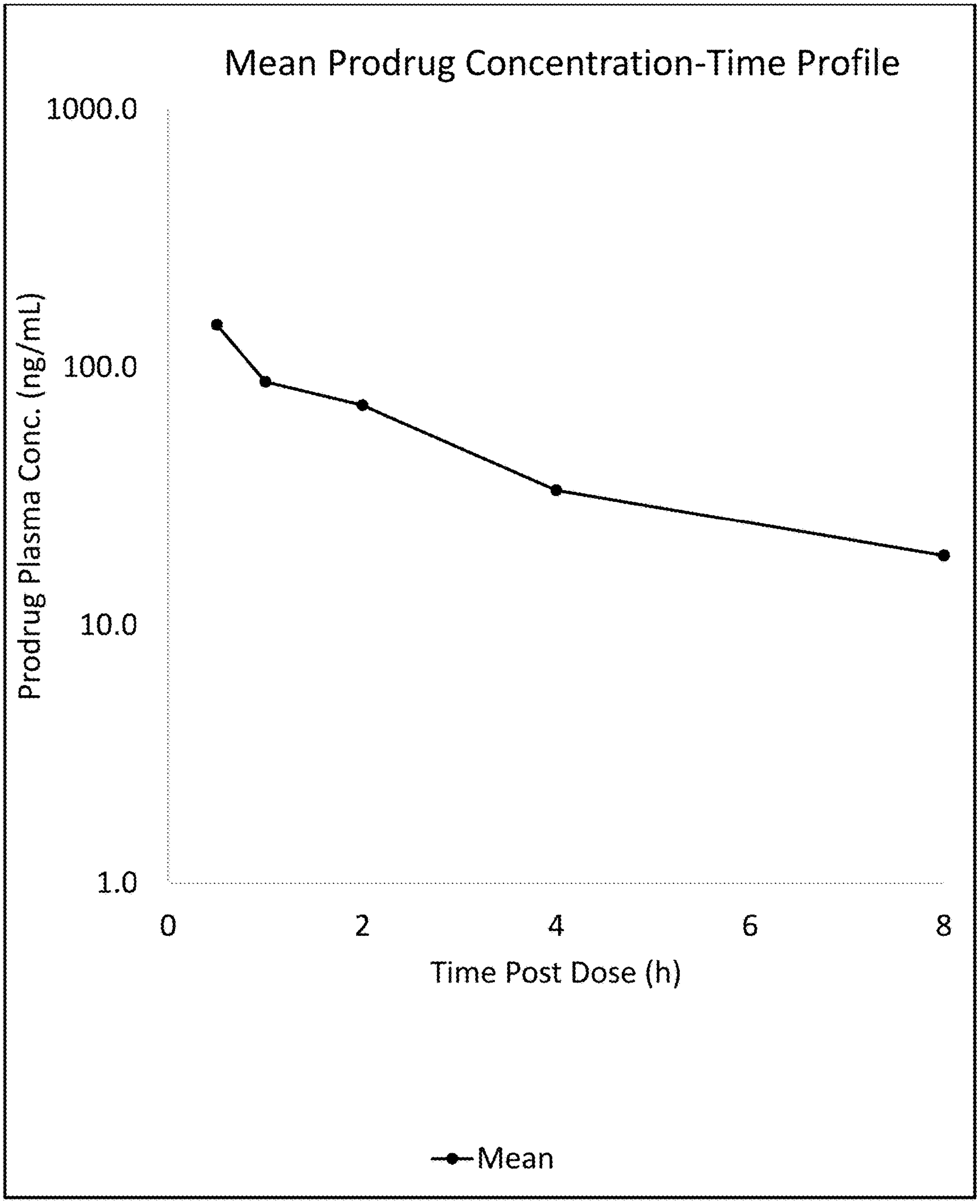
FIG. 61 shows mean concentration-time profiles of prodrug following IM dosing of xanomeline oxypropyl pivalate chloride prodrug (5 mg/kg of xanomeline) to male SD rats.

FIG. 61 shows mean concentration-time profiles of prodrug following IM dosing of xanomeline oxypropyl pivalate chloride prodrug (5 mg/kg of xanomeline) to male SD rats.

Example A-4-3: Xanomeline Oxypropyl Pivalate Iodide Prodrug—Table 1 Compound 596

| | |
|---|---|
| Species: | Rat |
| Dose Route: | IM |
| Dose Level (mg/kg) | 5 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium iodide Structural class: acyloxymethyl Mechanistic class: presumed esterase+chemical breakdown

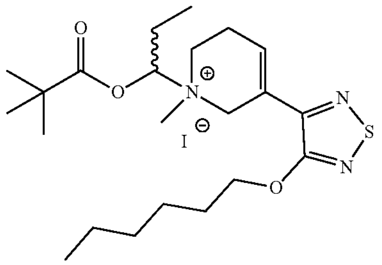 [SMILES: CCCCCCOc1nsnc1C1=CCC[N+](C)(C(CC)OC(=O)C(C)(C)C)C1 ; [I-]]

TABLE 67

Prodrug Plasma Concentrations (ng/mL) Following Intramuscular Dosing

| Time (h) | Bioanalytical Data: Prodrug Plasma Concentrations (ng/mL) Following Intramuscular Dosing Animal R13 | R14 | R15 | Mean |
|---|---|---|---|---|
| 0.500 | 348 | 422 | 512 | 427 |
| 1.00 | 196 | 214 | 356 | 255 |
| 2.00 | 105 | 159 | 149 | 138 |
| 4.00 | 48.6 | 46.6 | 74.3 | 56.5 |
| 8.00 | 31.3 | 33.8 | 31.3 | 32.1 |
| 24.0 | BLQ | BLQ | BLQ | BLQ |
| 31.0 | BLQ | BLQ | BLQ | BLQ |
| 48.0 | BLQ | BLQ | BLQ | BLQ |
| 72.0 | BLQ | BLQ | BLQ | BLQ |
| 96.0 | BLQ | BLQ | BLQ | BLQ |

BLQ: Below Lower Limit of Quantification (0.5 ng/mL)

TABLE 68

| Prodrug Pharmacokinetic Parameters | | | | | | | |
|---|---|---|---|---|---|---|---|
| Dose Route | Animal ID | HL_Lambda_z (hr) | Tmax (hr) | Cmax (ng/mL) | Tlast (hr) | AUClast (ng/ml*hr) | AUCINF_obs (ng/ml*hr) |
| Intramuscular | R13 | 3.67 | 0.50 | 348 | 8.00 | 687 | 853 |
| | R14 | 2.98 | 0.50 | 422 | 8.00 | 817 | 963 |
| | R15 | 2.73 | 0.50 | 512 | 8.00 | 1030 | 1160 |
| | Mean | 3.13 | 0.50 | 427 | 8.00 | 845 | 992 |

Figure 62:
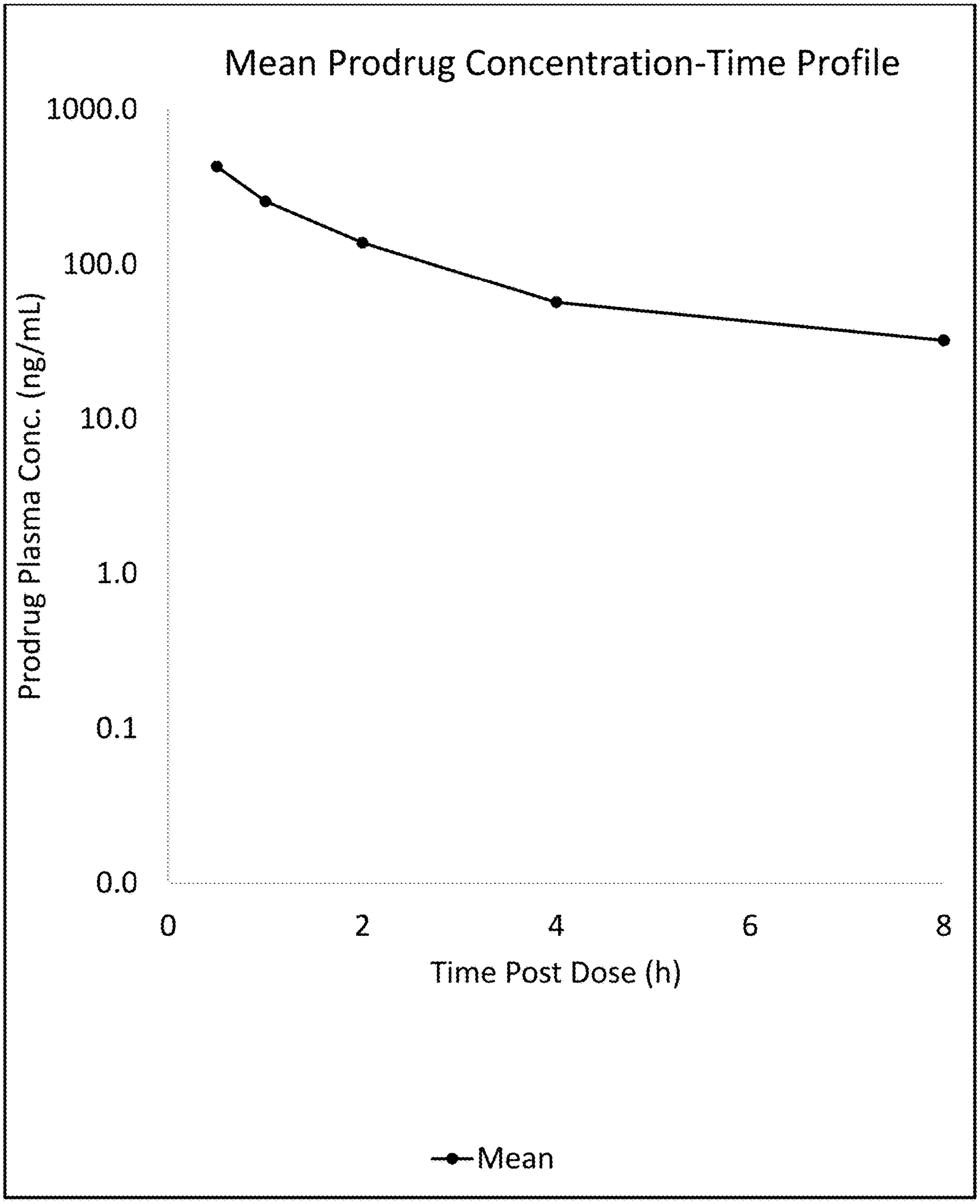
FIG. 62 shows mean concentration-time profiles of prodrug following IM dosing of xanomeline oxypropyl pivalate iodide prodrug (5 mg/kg of xanomeline) to male SD rats.

FIG. 62 shows mean concentration-time profiles of prodrug following IM dosing of xanomeline oxypropyl pivalate iodide prodrug (5 mg/kg of xanomeline) to male SD rats.

TABLE A-5

| Protocol: Serial tail vein bleed PK study of Xanomeline Prodrugs in SD rats | | |
|---|---|---|
| Protocol | | IV serial PK study of API & 2 prodrugs at 1 dose level |
| Test Compound(s) | | Xanomeline, Xanomeline Prodrugs |
| Dosing Route | | IV |
| Overnight food withdrawal | | No |
| Animals | Type | rat |
| | Strain | Sprague Dawley rats |
| | Sex | male |
| | Weight (g) | 250-300 g |
| | N per cpd | 3 |
| | Preparation | None |
| | Cage | PK cages |
| Dose | | 1 mg API/kg |
| Dosing Soln. Conc. | | 0.5 mg API/mL |
| Dosing Volume | | 2 mL/kg |
| Formulation checks required? | | No |
| Vehicle | | DMSO:HPCD (20%) [10:90] |
| Sampling time points (h) | | 0.25 0.5, 0.75, 1, 1.5, 2, 4, 7 h |
| Blood sampling method | | Serial via tail vein |
| Alternative method if required | | n/a |
| Sample format required | | >230 µL blood + 5 µL EDTA (93 mg/mL) to give 2 × 50 µL plasma |
| Sample processing | | Centrifugation for plasma ASAP at 4 deg C. Place 110 µL plasma into Eppendorf tube on ice containing 11 µL 10% phosphoric acid. Gently mix before taking 2 × 50 µL aliquots into duplicate 96 well plates on dry ice. |
| Anticoagulant | | EDTA (93 mg/mL): 5 µL per tube |
| Centrifugation | | 10,000 rpm × 3 min at 4 deg C. |
| Additional samples | | n/a |
| Perfusion/rinsing required | | n/a |
| Euthanasia method | | n/a |
| Plasma sample tubes | | 96 well plates |
| Pre-freezer storage | | Blood: ice (<30 min), Acidified Plasma: dry ice |
| Freezer storage | | −80° C. |
| Dose formulation samples | | 100 µL from vortex dose solution in Eppendorf |
| Number of samples per cpd at 1 dose level | | 24 × acidified plasma (50 µL in duplicate), 1 dose soln |

Analysis

Samples were sent for method optimization and measurement of parent compound (xanomeline) via unique calibration lines and following acceptance QC's. Dose formulation concentrations were also measured, and PK parameters were determined (Cmax (ng/mL), Tmax (hr), Cl (ml/min/kg), Vdss (L/kg), t1/2(hr), AUCO-t (ng/mL*hr), AUCO-inf (ng/mL*hr), MRT (hr), Bioavailability (% F) where warranted) using WinNon Lin software. Data (including bioanalytical results and assay performance) were reported in a tabulated format and QC'd.

Additional Formulation Details for PK Study

Compound was dissolved in DMSO:HPCD (20% w/v in water) [10:90] 0.5 mg API/mL to provide doses of 1 mg/kg when administered IV in a 2 mL/kg dosing volume.

Example A-5: Measurement of Concentration of Xanomeline after Intravenous (IV) Administration of Xanomeline or Xanomeline Prodrugs In Vivo The pharmacokinetic properties of the synthesized xanomeline prodrugs after intravenous administration in a rat model were assessed. The concentration of xanomeline was measured in each rat at various sampling timepoints after intravenous administration of xanomeline or the synthesized xanomeline prodrugs to rats.

Dose formulations were made at equivalent concentrations of active compound (xanomeline) adjusted for molecular weight of the compounds. The synthesized xanomeline prodrugs were dosed at 1 mg/kg intravenous (IV) nominal dose. Nominal doses were used in PK parameter determinations. The parent compound (xanomeline) was dosed at 1 mg/kg intravenously (IV).

Example A-5-1: Xanomeline Parent Compound (IV)—Table 1 Compound 922

| | |
|---|---|
| Species: | Rat |
| Dose Route: | IV |
| Dose Level (mg/kg) | 1 mg/kg of xanomeline |

Chemical name: Xanomeline

Structural class: parent

Mechanistic class: n/a—parent compound

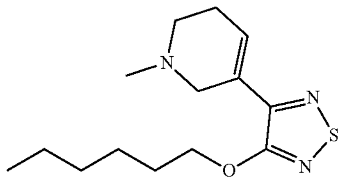 [SMILES: CCCCCCOc1nsnc1C1=CCCN(C)C1]

TABLE 69

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | IV | R10 | 1.86 | 0.25 | 45.2 | 4.00 | 44.6 | 51.8 |
| | | R11 | 0.454 | 0.25 | 25.0 | 2.00 | 20.2 | 21.0 |
| | | R12 | 1.38 | 0.25 | 42.7 | 4.00 | 40.1 | 42.7 |
| | | Mean | 1.23 | 0.25 | 37.6 | 3.33 | 35.0 | 38.5 |

Figure 63:
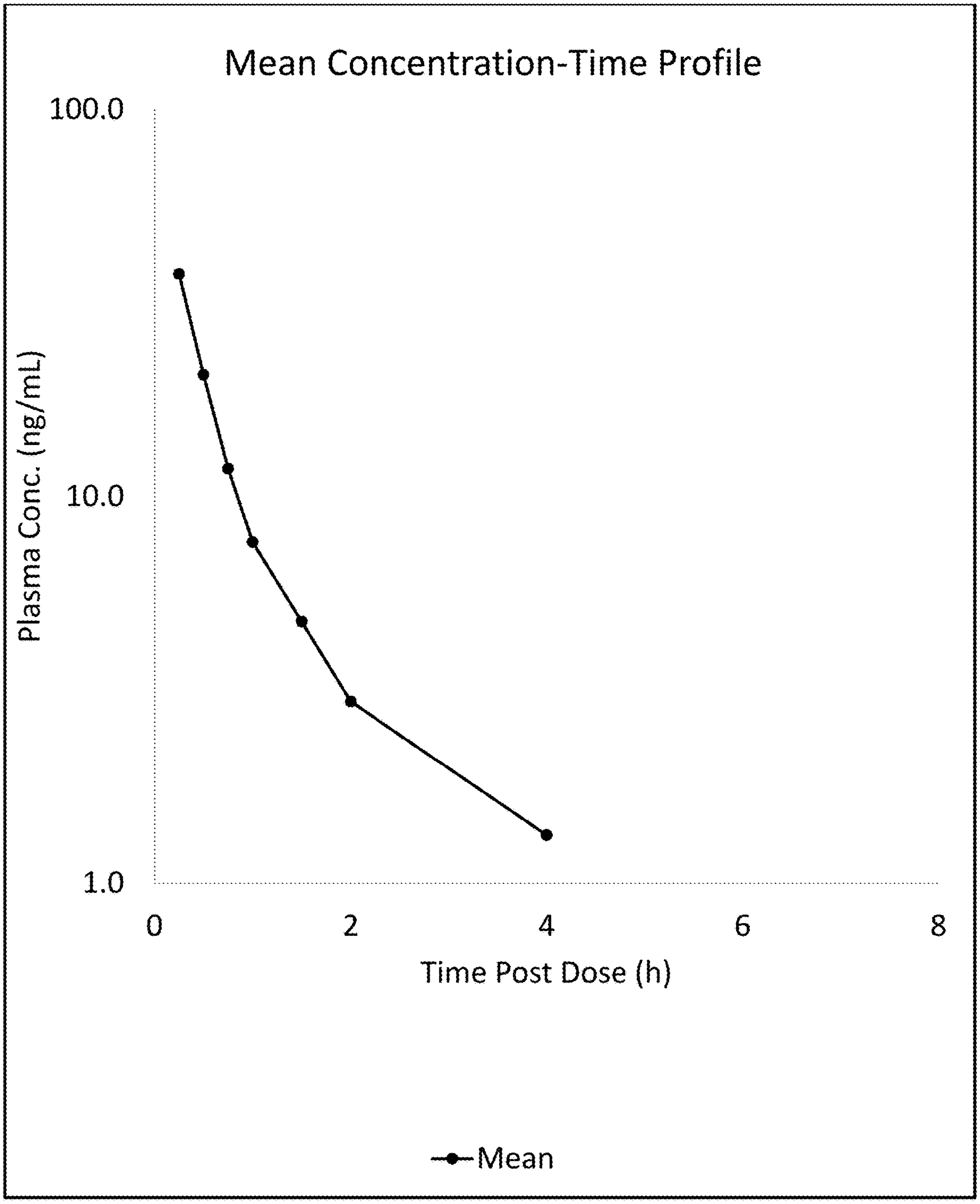
FIG. 63 shows mean concentration-time profiles of xanomeline following IV dosing of xanomeline (1 mg/kg of xanomeline) to male SD rats.

FIG. 63 shows mean concentration-time profiles of xanomeline following IV dosing of xanomeline (1 mg/kg of xanomeline) to male SD rats.

Example A-5-2: Xanomeline Oxypropyl Pivalate Chloride Prodrug—Table 1 Compound 352

| | |
|---|---|
| Species: | Rat |
| Dose Route: | IV |
| Dose Level (mg/kg) | 1 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium chloride Structural class: acyloxymethyl Mechanistic class: presumed esterase+chemical breakdown

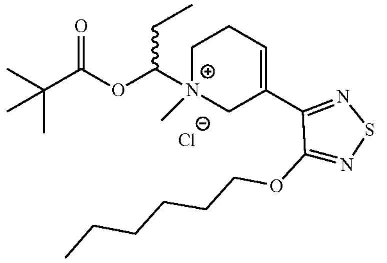 [SMILES: CCCCCCOc1nsnc1C1=CCC[N+](C)(C(CC)OC(=O)C(C)(C)C)C1 ; [Cl-]]

TABLE 70

Mean Concentration-Time Profile of Metabolite Xanomeline Following IV Dosing of Xanomeline Oxypropyl Pivalate Chloride Prodrug

| Time (h) | Bioanalytical Data: Plasma Concentrations (ng/mL) Following Intravenous Dosing Animal R13 | R14 | R15 | Mean |
|---|---|---|---|---|
| 0.250 | BLQ | BLQ | BLQ | BLQ |
| 0.500 | BLQ | BLQ | BLQ | BLQ |
| 0.750 | BLQ | BLQ | BLQ | BLQ |
| 1.00 | BLQ | BLQ | BLQ | BLQ |

TABLE 70-continued

Mean Concentration-Time Profile of Metabolite Xanomeline Following IV Dosing of Xanomeline Oxypropyl Pivalate Chloride Prodrug

| Time (h) | Bioanalytical Data: Plasma Concentrations (ng/mL) Following Intravenous Dosing Animal R13 | R14 | R15 | Mean |
|---|---|---|---|---|
| 1.50 | BLQ | BLQ | BLQ | BLQ |
| 2.00 | BLQ | BLQ | BLQ | BLQ |
| 4.00 | BLQ | BLQ | BLQ | BLQ |
| 7.00 | BLQ | BLQ | BLQ | BLQ |

BLQ: Below Lower Limit of Quantification (0.5 ng/mL)

Example A-5-3: Xanomeline Oxyethyl Pivalate Chloride Prodrug—Table 1 Compound 19

| | |
|---|---|
| Species: | Rat |
| Dose Route: | IV |
| Dose Level (mg/kg) | 1 mg/kg of xanomeline |

Chemical name: 1-[5-(4-hexyloxy-1,2,5-thiadiazol-3-yl)-1-methyl-3,6-dihydro-2H-pyridin-1-ium-1-yl]ethyl 2,2-dimethylpropanoate chloride Structural class: acyloxymethyl Mechanistic class: resumed esterase+chemical breakdown

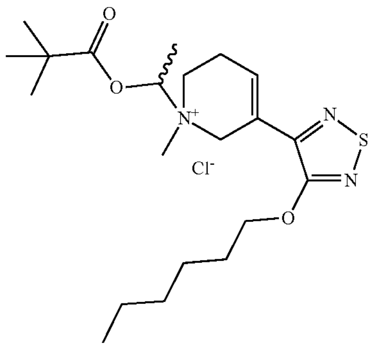 [SMILES: CCCCCCOc1nsnc1C1=CCC[N+](C)(C(C)OC(=O)C(C)(C)C)C1 ; [Cl-]]

TABLE 71

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | IV | R1 | 1.86 | 0.25 | 3.54 | 4.0 | 6.58 | 8.28 |
| | | R2 | 3.65 | 0.25 | 2.81 | 4.0 | 5.74 | 10.4 |
| | | R3 | 1.29 | 0.25 | 2.11 | 2.0 | 2.49 | 3.53 |
| | | Mean | 2.27 | 0.25 | 2.82 | 3.3 | 4.94 | 7.40 |

Figure 64:
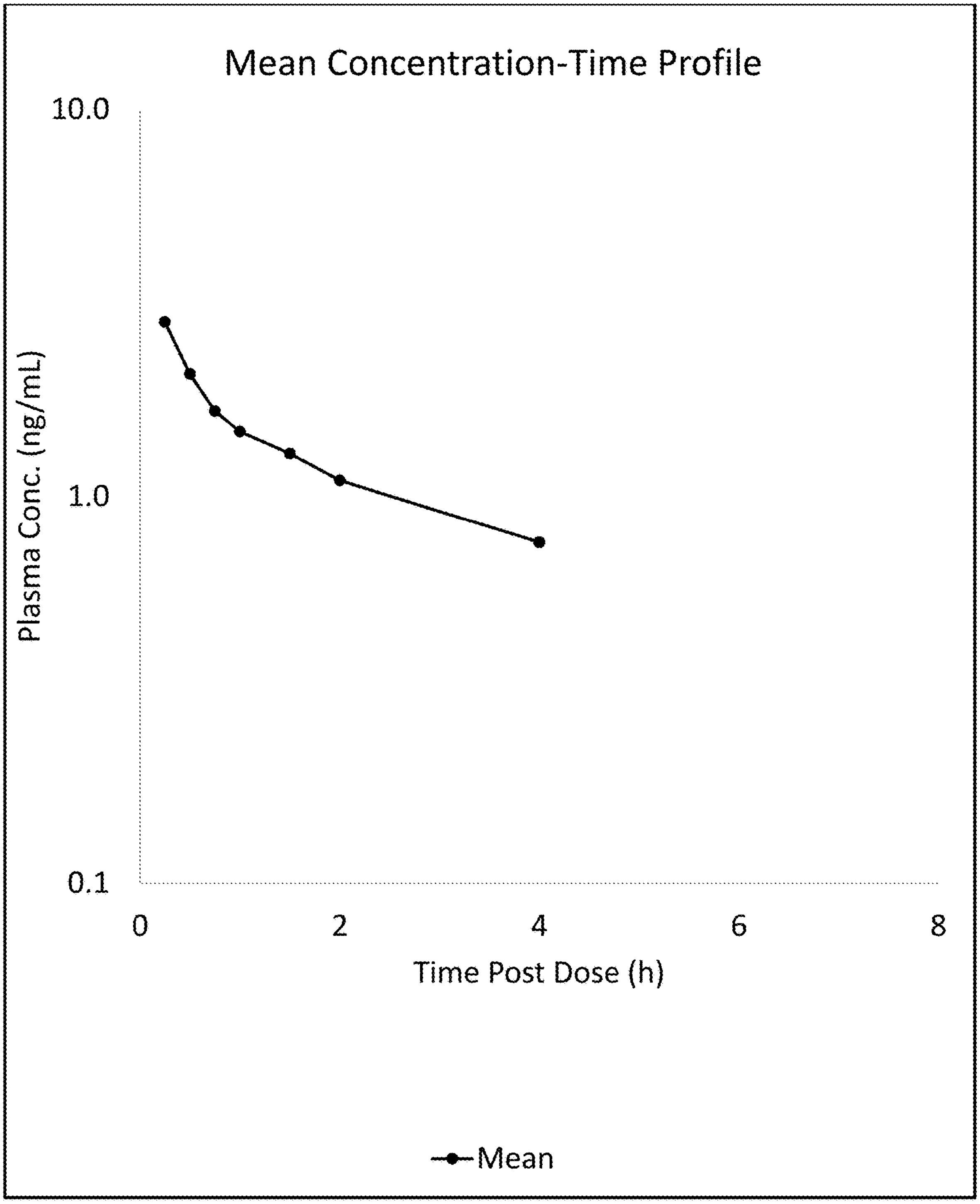
FIG. 64 shows mean concentration-time profiles of xanomeline following IV dosing of xanomeline oxyethyl pivalate chloride prodrug (1 mg/kg of xanomeline) to male SD rats.

FIG. 64 shows mean concentration-time profiles of xanomeline following IV dosing of xanomeline oxyethyl pivalate chloride prodrug (1 mg/kg of xanomeline) to male SD rats.

TABLE A-6

| Protocol: Serial tail vein bleed PK study of Xanomeline Prodrugs in SD rats | | |
|---|---|---|
| Protocol | | IV serial PK study of API & 2 prodrugs at 1 dose level |
| Test Compound(s) | | Xanomeline Prodrugs |
| Dosing Route | | IV |
| Overnight food withdrawal | | No |
| Animals | Type | rat |
| | Strain | Sprague Dawley rats |
| | Sex | male |
| | Weight (g) | 250-300 g |
| | N per cpd | 3 |
| | Preparation | None |
| | Cage | PK cages |
| Dose | | 1 mg API/kg |
| Dosing Soln. Conc. | | 0.5 mg API/mL |
| Dosing Volume | | 2 mL/kg |
| Formulation checks required? | | No |
| Vehicle | | DMSO:HPCD (20%) [10:90] |
| Sampling time points (h) | | 0.25 0.5, 0.75, 1, 1.5, 2, 4, 7 h |
| Blood sampling method | | Serial via tail vein |
| Alternative method if required | | n/a |
| Sample format required | | >230 μL blood + 5 μL EDTA (93 mg/mL) to give 2 × 50 μL plasma |
| Sample processing | | Centrifugation for plasma ASAP at 4 deg C. Place 110 μL plasma into Eppendorf tube on ice containing 11 μL 10% phosphoric acid. Gently mix before taking 2 × 50 μL aliquots into duplicate 96 well plates on dry ice. |
| Anticoagulant | | EDTA (93 mg/mL): 5 μL per tube |
| Centrifugation | | 10,000 rpm × 3 min at 4 deg C. |
| Additional samples | | n/a |
| Perfusion/rinsing required | | n/a |
| Euthanasia method | | n/a |
| Plasma sample tubes | | 96 well plates |
| Pre-freezer storage | | Blood: ice (<30 min), Acidified Plasma: dry ice |
| Freezer storage | | −80° C. |
| Dose formulation samples | | 100 μL from vortex dose solution in Eppendorf |
| Number of samples per cpd at 1 dose level | | 24 × acidified plasma (50 μL in duplicate), 1 dose soln |

Analysis

Samples were sent for method optimization and measurement of prodrug via unique calibration lines and following acceptance QC's. Dose formulation concentrations were also measured, and PK parameters were determined (Cmax (ng/mL), Tmax (hr), Cl (ml/min/kg), Vdss (L/kg), t1/2(hr), AUCO-t (ng/mL*hr), AUCO-inf (ng/mL*hr), MRT (hr), Bioavailability (% F) where warranted) using WinNon Lin software. Data (including bioanalytical results and assay performance) were reported in a tabulated format and QC'd.

Additional Formulation Details for PK Study

Compound was dissolved in DMSO:HPCD (20% w/v in water) [10:90] 0.5 mg API/mL to provide doses of 1 mg/kg when administered IV in a 2 mL/kg dosing volume.

Example A-6: Measurement of Concentration of Prodrug after Intravenous (IV) Administration of Xanomeline Prodrugs In Vivo The pharmacokinetic properties of the synthesized xanomeline prodrugs after intravenous administration in a rat model were assessed. The concentration of prodrug was measured in each rat at various sampling timepoints after intravenous administration of the synthesized xanomeline prodrugs to rats.

Dose formulations were made at equivalent concentrations of active compound (xanomeline) adjusted for molecular weight of the compounds. The synthesized xanomeline prodrugs were dosed at 1 mg/kg intravenous (IV) nominal dose. Nominal doses were used in PK parameter determinations.

Example A-6-1: Xanomeline Oxypropyl Pivalate Chloride Prodrug—Table 1 Compound 352

| | |
|---|---|
| Species: | Rat |
| Dose Route: | IV |
| Dose Level (mg/kg) | 1 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium chloride Structural class: acyloxymethyl Mechanistic class: presumed esterase+chemical breakdown

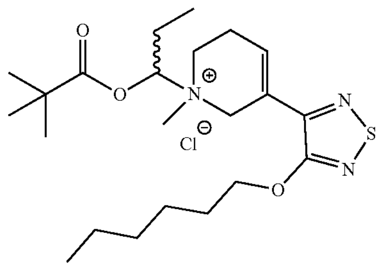 [SMILES: CCCCCCOc1nsnc1C1=CCC[N+](C)(C(CC)OC(=O)C(C)(C)C)C1 ; [Cl-]]

TABLE 72

Prodrug Plasma Concentrations (ng/mL) Following Intravenous Dosing

| | Bioanalytical Data: Prodrug Plasma Concentrations (ng/mL) Following Intravenous Dosing Animal | | | |
|---|---|---|---|---|
| Time (h) | R13 | R14 | R15 | Mean |
| 0.250 | 60.4 | 29.1 | 10.1 | 33.2 |
| 0.500 | 10.3 | 15.5 | BLQ | 12.9 |
| 0.750 | BLQ | 6.01 | BLQ | 6.01 |
| 1.00 | 5.58 | 5.15 | BLQ | 5.37 |
| 1.50 | BLQ | BLQ | BLQ | BLQ |
| 2.00 | BLQ | BLQ | BLQ | BLQ |
| 4.00 | BLQ | BLQ | BLQ | BLQ |
| 7.00 | BLQ | BLQ | BLQ | BLQ |

BLQ: Below Lower Limit of Quantification (0.5 ng/mL)

TABLE 73

Prodrug Pharmacokinetic Parameters

| Dose Route | Animal ID | HL_Lambda_z (hr) | Tmax (hr) | Cmax (ng/mL) | Tlast (hr) | AUClast (ng/ml * hr) | AUCINF_obs (ng/ml * hr) |
|---|---|---|---|---|---|---|---|
| Intravenous | R13 | 0.239 | 0.25 | 60.4 | 1.0 | 64.6 | 66.6 |
| | R14 | 0.282 | 0.25 | 29.1 | 1.0 | 20.1 | 22.2 |
| | R15 | NR | 0.25 | 10.1 | 0.25 | NR | NR |
| | Mean | 0.26 | 0.25 | 33.2 | 0.750 | 42.35 | 44.4 |

Figure 65:
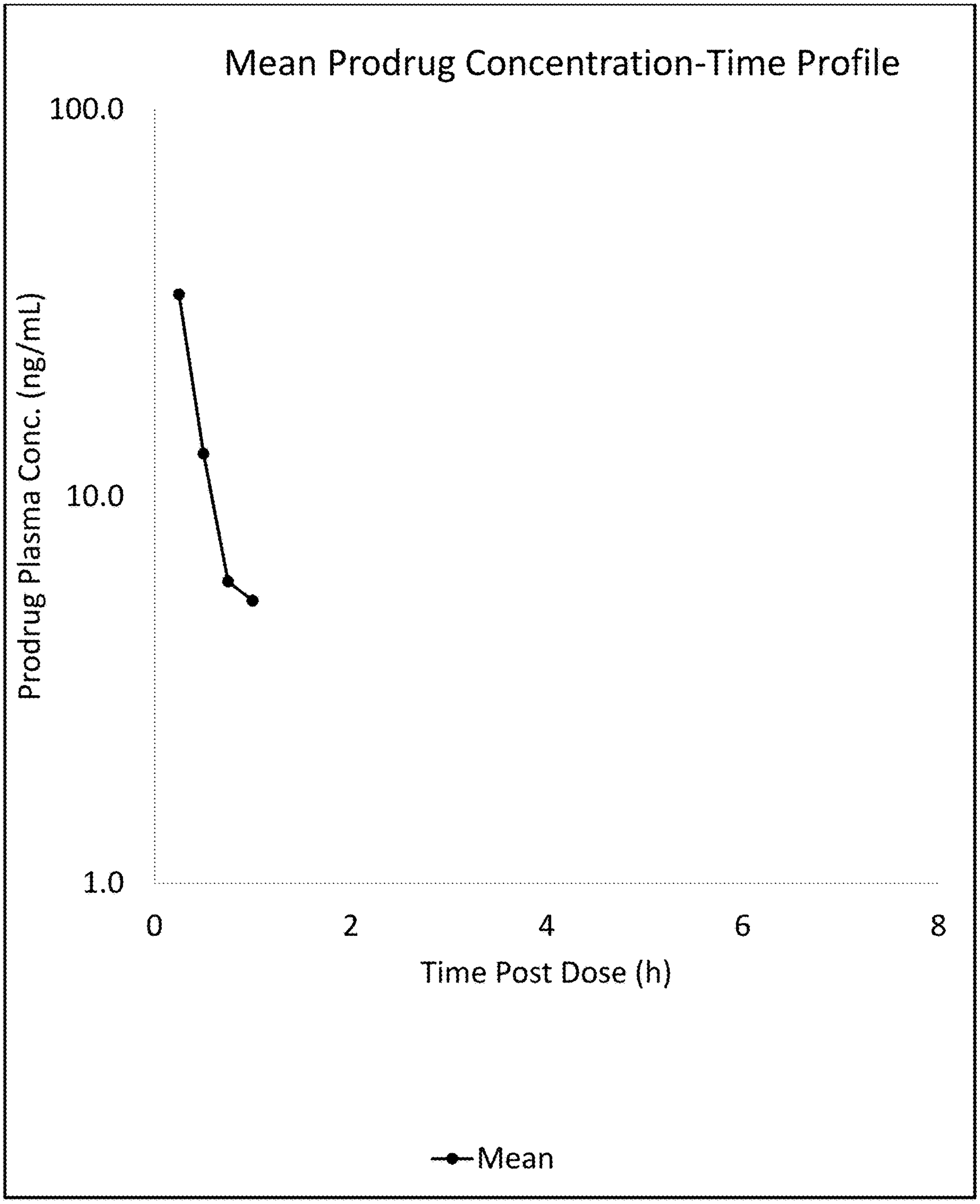
FIG. 65 shows mean concentration-time profiles of prodrug following IV dosing of xanomeline oxypropyl pivalate chloride prodrug (1 mg/kg of xanomeline) to male SD rats.

FIG. 65 shows mean concentration-time profiles of prodrug following IV dosing of xanomeline oxypropyl pivalate chloride prodrug (1 mg/kg of xanomeline) to male SD rats.

Example A-6-2: Xanomeline Oxyethyl Pivalate Chloride Prodrug—Table 1 Compound 19

| | |
|---|---|
| Species: | Rat |
| Dose Route: | IV |
| Dose Level (mg/kg) | 1 mg/kg of xanomeline |

Chemical name: 1-[5-(4-hexyloxy-1,2,5-thiadiazol-3-yl)-1-methyl-3,6-dihydro-2H-pyridin-1-ium-1-yl]ethyl 2,2-dimethypropanoate chloride Structural class: acyloxymethyl Mechanistic class: presumed esterase+chemical breakdown

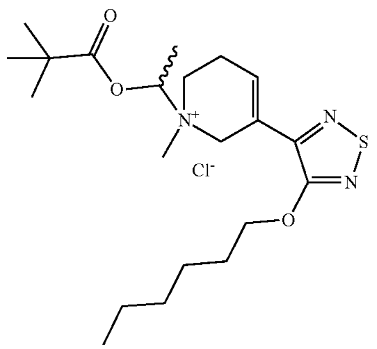 [SMILES: CCCCCCOc1nsnc1C1=CCC[N+](C)(C(C)OC(=O)C(C)(C)C)C1 ; [Cl-]]

TABLE 74

Prodrug Plasma Concentrations (ng/mL) Following Intravenous Dosing

| | Bioanalytical Data: Prodrug Plasma Concentrations (ng/mL) Following Intravenous Dosing Animal | | | |
|---|---|---|---|---|
| Time (h) | R16 | R17 | R18 | Mean |
| 0.250 | 35.4 | 25.1 | 21.1 | 27.2 |
| 0.500 | 15.2 | 11.4 | 8.82 | 11.8 |
| 0.750 | 8.62 | 5.57 | BLQ | 7.10 |
| 1.00 | BLQ | BLQ | BLQ | BLQ |
| 1.50 | BLQ | BLQ | BLQ | BLQ |

TABLE 74-continued

Prodrug Plasma Concentrations (ng/mL) Following Intravenous Dosing

| | Bioanalytical Data: Prodrug Plasma Concentrations (ng/mL) Following Intravenous Dosing Animal | | | |
|---|---|---|---|---|
| Time (h) | R16 | R17 | R18 | Mean |
| 2.00 | BLQ | BLQ | BLQ | BLQ |
| 4.00 | BLQ | BLQ | BLQ | BLQ |
| 7.00 | BLQ | BLQ | BLQ | BLQ |

BLQ: Below Lower Limit of Quantification (0.5 ng/mL)

TABLE 75

Prodrug Pharmacokinetic Parameters

| Dose Route | Animal ID | HL_Lambda_z (hr) | Tmax (hr) | Cmax (ng/mL) | Tlast (hr) | AUClast (ng/ml * hr) | AUCINF_obs (ng/ml * hr) |
|---|---|---|---|---|---|---|---|
| Intravenous | R16 | 0.245 | 0.25 | 35.4 | 0.750 | 24.0 | 27.1 |
| | R17 | 0.230 | 0.25 | 25.1 | 0.750 | 16.7 | 18.6 |
| | R18 | NR | 0.25 | 21.1 | 0.500 | 12.7 | NR |
| | Mean | 0.24 | 0.25 | 27.2 | 0.667 | 17.8 | 22.9 |

Figure 66:
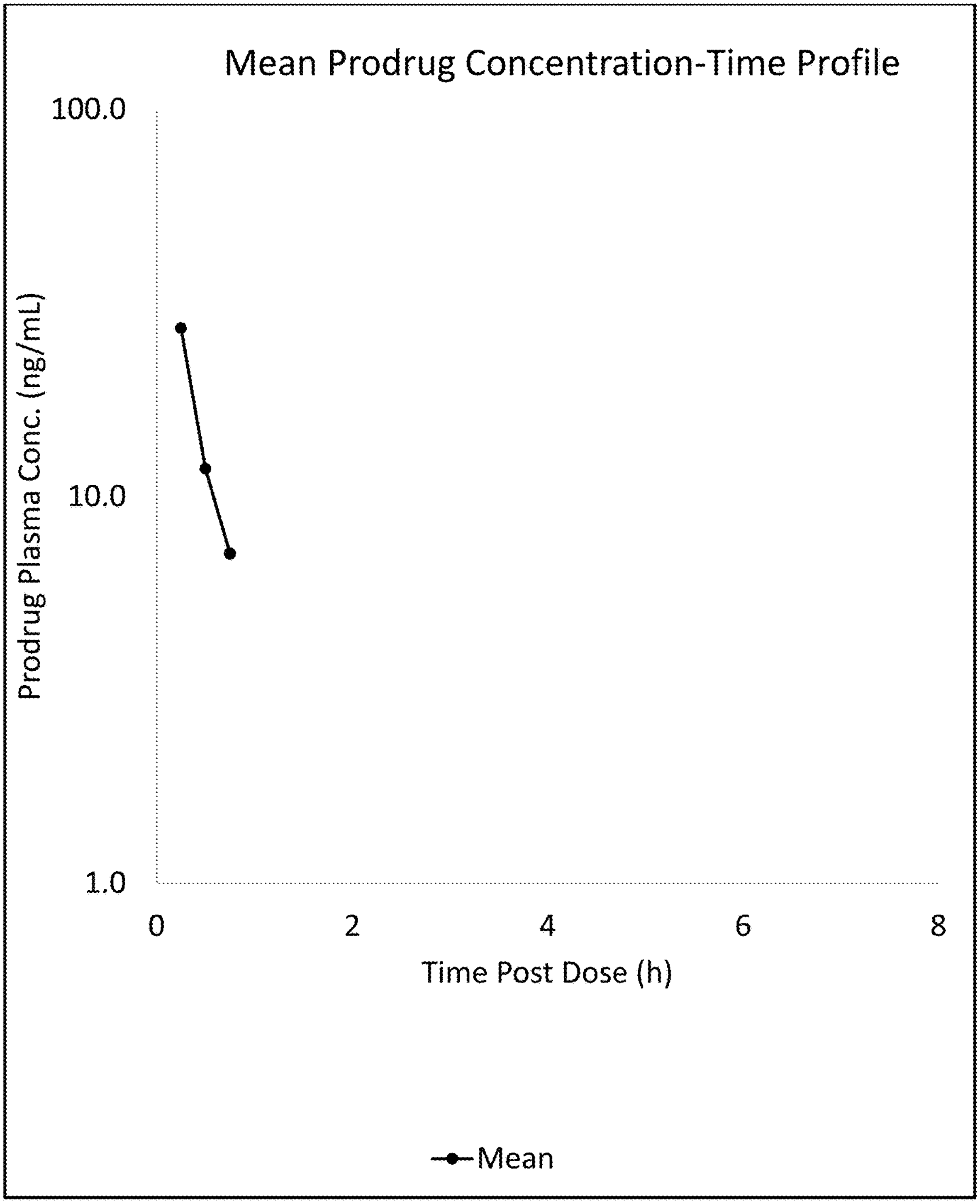
FIG. 66 shows mean concentration-time profiles of prodrug following IV dosing of xanomeline oxyethyl pivalate chloride prodrug (1 mg/kg of xanomeline) to male SD rats.

FIG. 66 shows mean concentration-time profiles of prodrug following IV dosing of xanomeline oxyethyl pivalate chloride prodrug (1 mg/kg of xanomeline) to male SD rats.

TABLE A-7

Protocol: Serial tail vein bleed PK study of orally dosed Xanomeline Prodrugs in SD rats

| Protocol | | PO serial PK study of 1 prodrug at 1 dose level |
|---|---|---|
| Test Compound(s) | | Xanomeline, Xanomeline Prodrugs |
| Dosing Route | | PO |
| Overnight food withdrawal | | No |
| Animals | Type | rat |
| | Strain | Sprague Dawley rats |
| | Sex | male |
| | Weight (g) | 250-300 g |
| | N per cpd | 3 |
| | Preparation | None |
| | Cage | PK cages |
| Dose | | 10 mg API/kg |
| Dosing Soln. Conc. | | PO: 2 mg API/mL |
| Dosing Volume | | PO: 5 mL/kg |
| Formulation checks required? | | No |
| Vehicle | | DMSO:HPCD (20%) [10:90] |
| Sampling time points (h) | | 1, 3, 7 & 24 h |
| Blood sampling method | | Serial via tail vein |
| Alternative method if required | | n/a |
| Sample format required | | >230 μL blood + 5 μL EDTA (93 mg/mL) to give 2 × 50 μL plasma |
| Sample processing | | Centrifugation for plasma ASAP at 4 deg C. Place 110 μL plasma into Eppendorf tube on ice containing 11 μL 10% phosphoric acid. Gently mix before taking 2 × 50 μL aliquots into duplicate 96 well plates on dry ice. |
| Anticoagulant | | EDTA (93 mg/mL): 5 μL per tube |
| Centrifugation | | 10,000 rpm × 3 min at 4 deg C. |
| Additional samples | | n/a |
| Perfusion/rinsing required | | n/a |
| Euthanasia method | | n/a |
| Plasma sample tubes | | 96 well plates |
| Pre-freezer storage | | Blood: ice (<30 min), Acidified Plasma: dry ice |
| Freezer storage | | −80° C. |
| Dose formulation samples | | 100 μL from vortex dose solution in Eppendorf |
| Number of samples per cpd at 1 dose level | | 12 × acidified plasma (50 μL in duplicate), 1 dose soln |

Analysis

Samples were sent for method optimization and measurement of parent compound (xanomeline) via unique calibration lines and following acceptance QC's. Dose formulation concentrations were also measured, and PK parameters were determined (Cmax (ng/mL), Tmax (hr), Cl (ml/min/kg), Vdss (L/kg), t1/2(hr), AUCO-t (ng/mL*hr), AUCO-inf (ng/mL*hr), MRT (hr), Bioavailability (% F) where warranted) using WinNon Lin software. Data (including bioanalytical results and assay performance) were reported in a tabulated format and QC'd.

Additional Formulation Details for PK Study

Compound was dissolved in DMSO:HPCD (20% w/v in water) [10:90] 2 mg API/mL to provide doses of 10 mg API/kg when administered PO in 5 mL/kg dosing volumes.

Example A-7: Measurement of Concentration of Xanomeline after Oral (PO) Administration of Xanomeline or Xanomeline Prodrugs In Vivo The pharmacokinetic properties of the synthesized xanomeline prodrugs after oral administration in a rat model were assessed. The concentration of xanomeline was measured in each rat at various sampling timepoints after oral administration of xanomeline or the synthesized xanomeline prodrugs to rats.

Dose formulations were made at equivalent concentrations of active compound (xanomeline) adjusted for molecular weight of the compounds. The synthesized xanomeline prodrugs were dosed at 10 mg/kg oral (PO) nominal dose. Nominal doses were used in PK parameter determinations. The parent compound (xanomeline) was dosed at 10 mg/kg oral (PO).

Example A-7-1: Xanomeline Parent Compound (PO)—Table 1 Compound 922

| | |
|---|---|
| Species: | Rat |
| Dose Route: | PO |
| Dose Level (mg/kg) | 10 mg/kg of xanomeline |

Chemical name: Xanomeline
Structural class: parent
Mechanistic class: n/a—parent compound

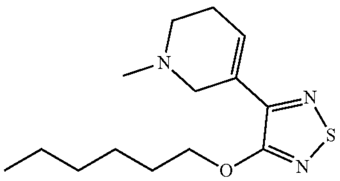 [SMILES: CCCCCCOc1nsnc1C1=CCCN(C)C1]

TABLE 76

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R10 | NR | 1.00 | 12.9 | 24.0 | 125 | NR |
| | | R11 | 8.05 | 1.00 | 11.2 | 24.0 | 94.5 | 108 |
| | | R12 | NR | 1.00 | 8.86 | 7.00 | 31.0 | NR |
| | | Mean | 2.68 | 1.00 | 11.0 | 18.33 | 83.5 | 36.0 |

Figure 67:
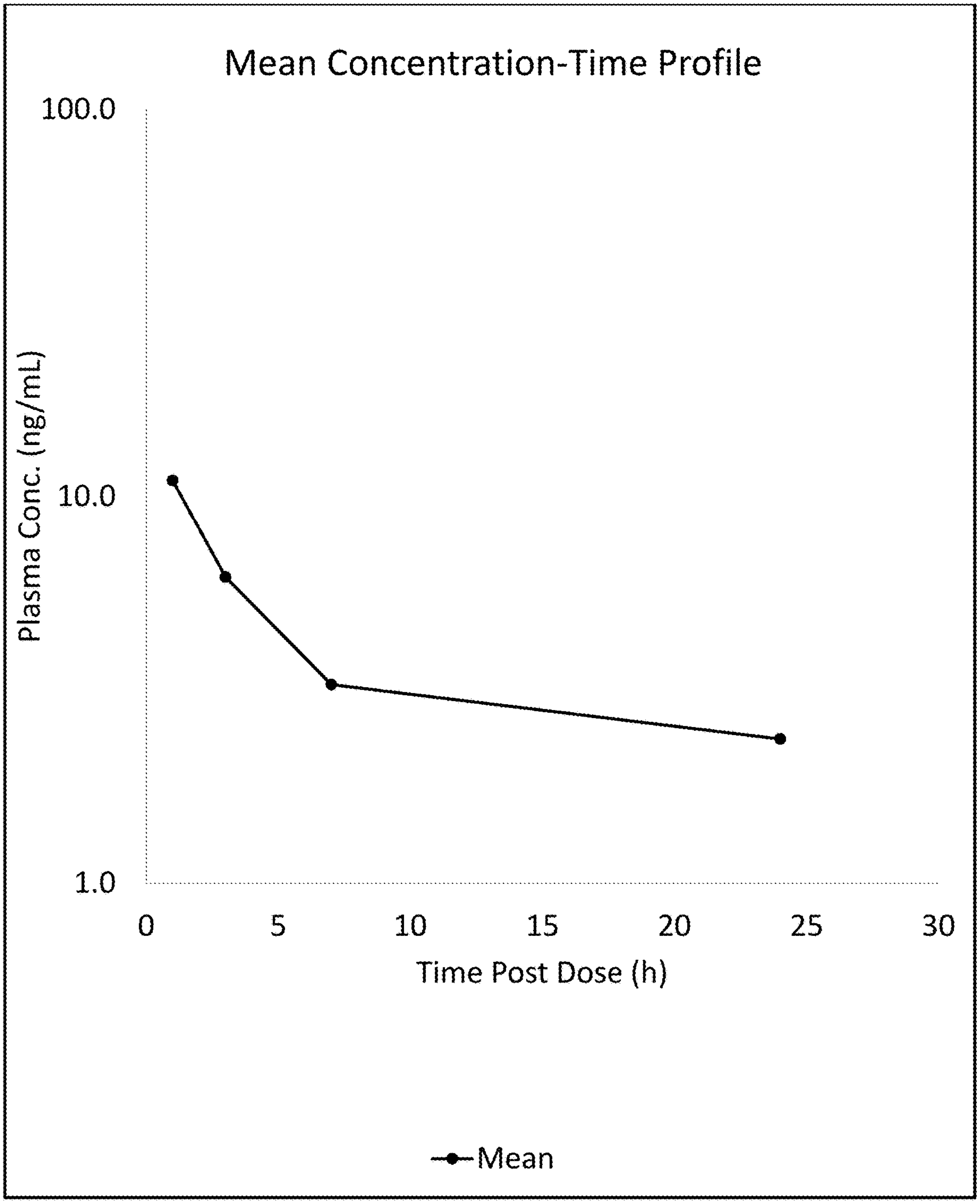
FIG. 67 shows mean concentration-time profiles of xanomeline following PO dosing of xanomeline (10 mg/kg of xanomeline) to male SD rats.

FIG. 67 shows mean concentration-time profiles of xanomeline following PO dosing of xanomeline (10 mg/kg of xanomeline) to male SD rats.

Example A-7-2: Xanomeline oxypropyl pivalate chloride prodrug—Table 1 Compound 352

| | |
|---|---|
| Species: | Rat |
| Dose Route: | PO |
| Dose Level (mg/kg) | 10 mg/kg of xanomeline |

Chemical name: 5-(4-(Hexyloxy)-1,2,5-thiadiazol-3-yl)-1-methyl-1-(1-(pivaloyloxy)propyl)-1,2,3,6-tetrahydropyridin-1-ium chloride Structural class: acyloxymethyl Mechanistic class: presumed esterase+chemical breakdown

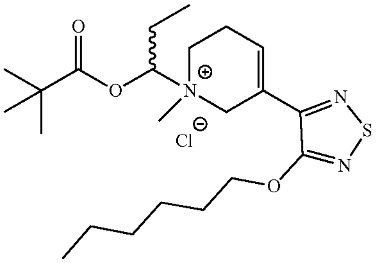 [SMILES: CCCCCCOc1nsnc1C1=CCC[N+](C)(C(CC)OC(=O)C(C)(C)C)C1 ; [Cl-]]

TABLE 77

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R13 | NR | 3.00 | 0.749 | 3.00 | 1.12 | NR |
| | | R14 | NR | 24.0 | 0.560 | 24.0 | 6.72 | NR |
| | | R15 | NR | NR | NR | NR | NR | NR |
| | | Mean | NR | 9.00 | 0.655 | 9.00 | 2.61 | NR |

Figure 68:
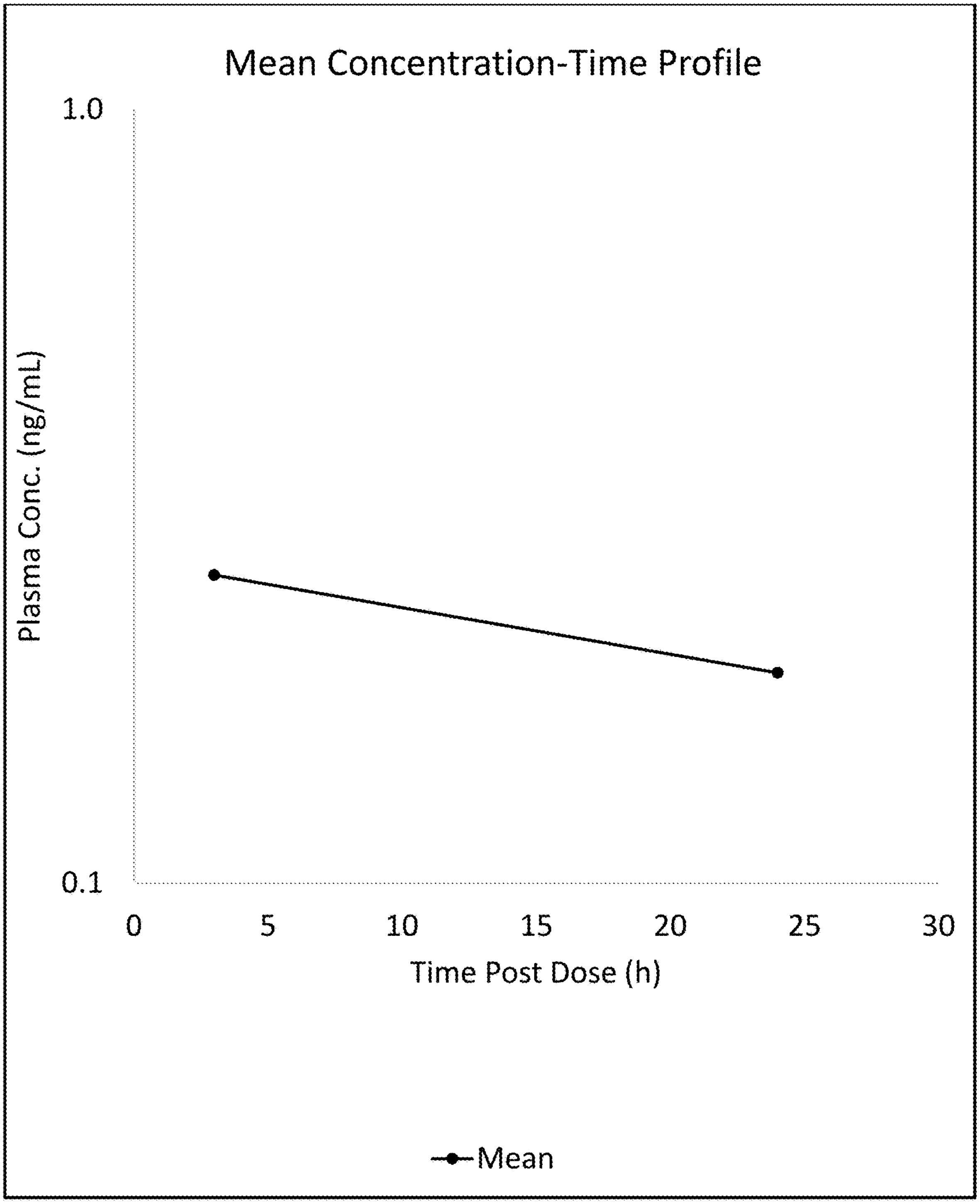
FIG. 68 shows mean concentration-time profiles of xanomeline following PO dosing of xanomeline oxypropyl pivalate chloride prodrug (10 mg/kg of xanomeline) to male SD rats.

FIG. 68 shows mean concentration-time profiles of xanomeline following PO dosing of xanomeline oxypropyl pivalate chloride prodrug (10 mg/kg of xanomeline) to male SD rats.

Example A-7-3: Xanomeline Oxyethyl Pivalate Chloride Prodrug—Table 1 Compound 19

| | |
|---|---|
| Species: | Rat |
| Dose Route: | PO |
| Dose Level (mg/kg) | 10 mg/kg of xanomeline |

Chemical name: 1-[5-(4-hexyloxy-1,2,5-thiadiazol-3-yl)-1-methyl-3,6-dihydro-2H-pyridin-1-ium-1-yl]ethyl 2,2-dimethylpropanoate chloride Structural class: acyloxymethyl Mechanistic class: presumed esterase+chemical breakdown

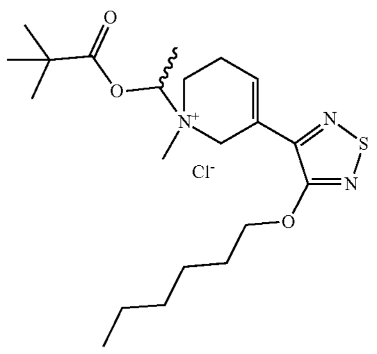 [SMILES: CCCCCCOc1nsnc1C1=CCC[N+](C)(C(C)OC(=O)C(C)(C)C)C1 ; [Cl-]]

TABLE 78

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R16 | NR | 7.00 | 1.24 | 7.0 | 6.79 | NR |
| | | R17 | NR | 3.00 | 1.30 | 7.0 | 6.69 | NR |
| | | R18 | NR | 7.00 | 1.60 | 7.0 | 7.93 | NR |
| | | Mean | NR | 5.67 | 1.38 | 7.0 | 7.14 | NR |

Figure 69:
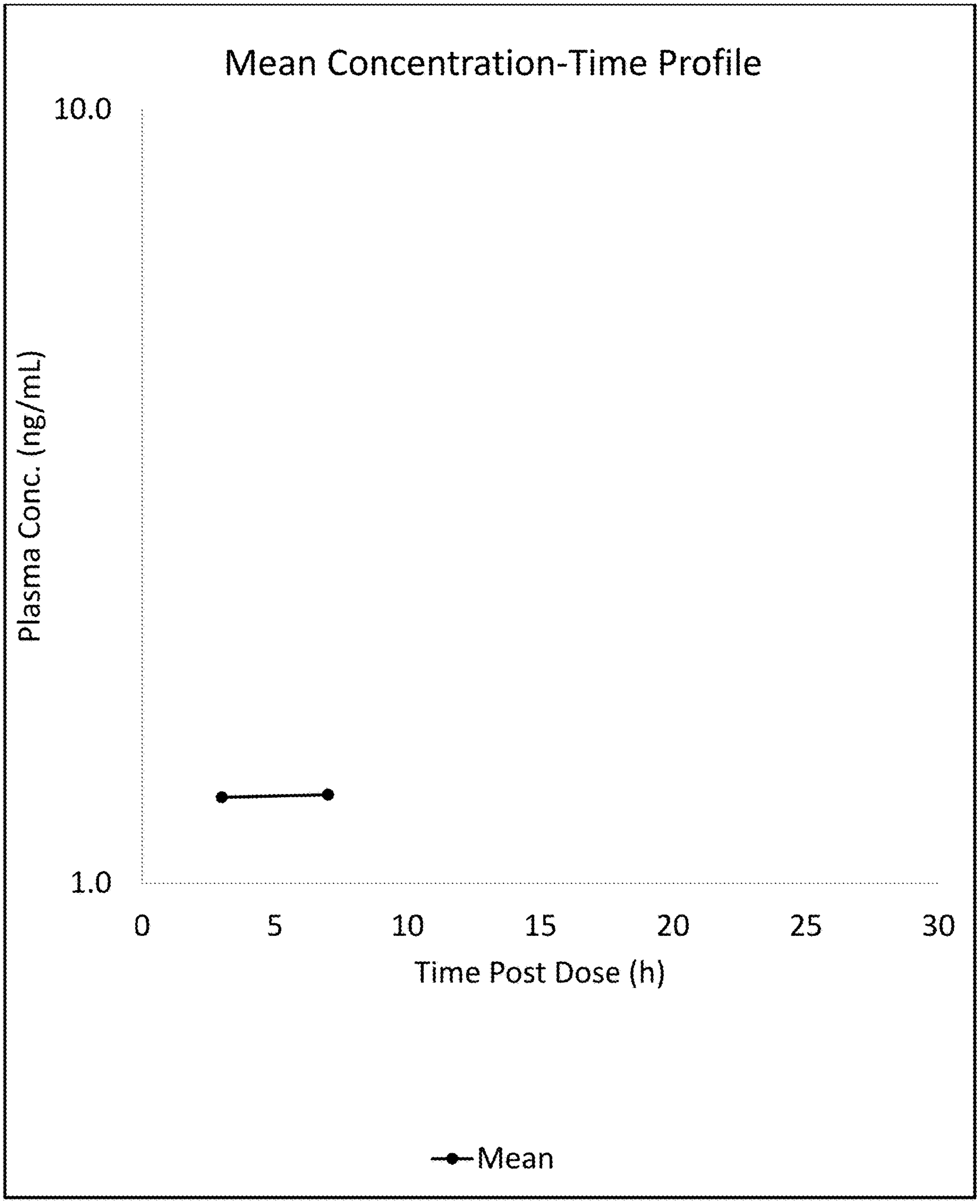
FIG. 69 shows mean concentration-time profiles of xanomeline following PO dosing of xanomeline oxyethyl pivalate chloride prodrug (10 mg/kg of xanomeline) to male SD rats.

FIG. 69 shows mean concentration-time profiles of xanomeline following PO dosing of xanomeline oxyethyl pivalate chloride prodrug (10 mg/kg of xanomeline) to male SD rats.

Example A-7-4: Xanomeline Methyl Hexadecanoate Chloride Prodrug—Table 1 Compound

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl hexadecanoate chloride Structural class: acyloxymethyl Mechanistic class: presumed esterase+chemical breakdown

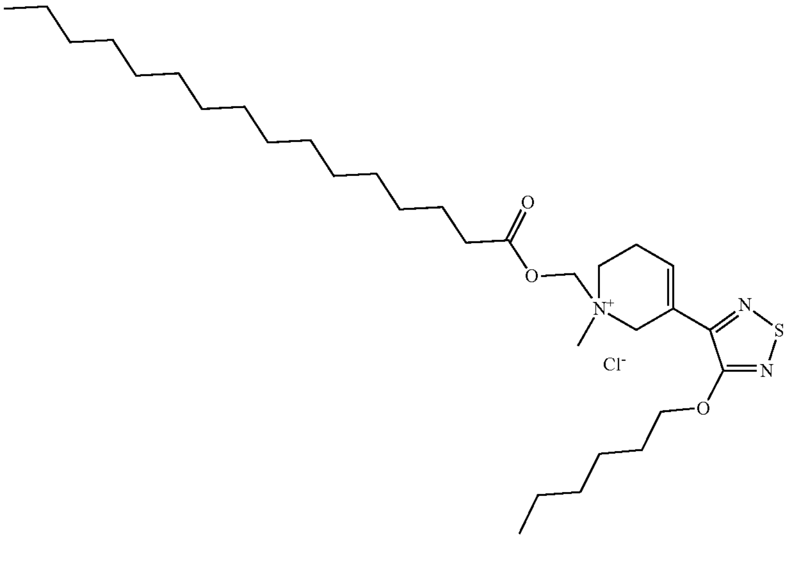 [SMILES: CCCCCCCCCCCCCCCC(=O)OC[N+]1(C)CCC=C(c2nsnc2OCCCCCC)C1 ; [Cl-]]

TABLE 79

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R19 | NR | 1.00 | 5.30 | 7.0 | 24.9 | NR |
| | | R20 | NR | 1.00 | 5.73 | 7.0 | 26.5 | NR |
| | | R21 | NR | 1.00 | 5.29 | 7.0 | 27.7 | NR |
| | | Mean | NR | 1.00 | 5.44 | 7.0 | 26.4 | NR |

Figure 70:
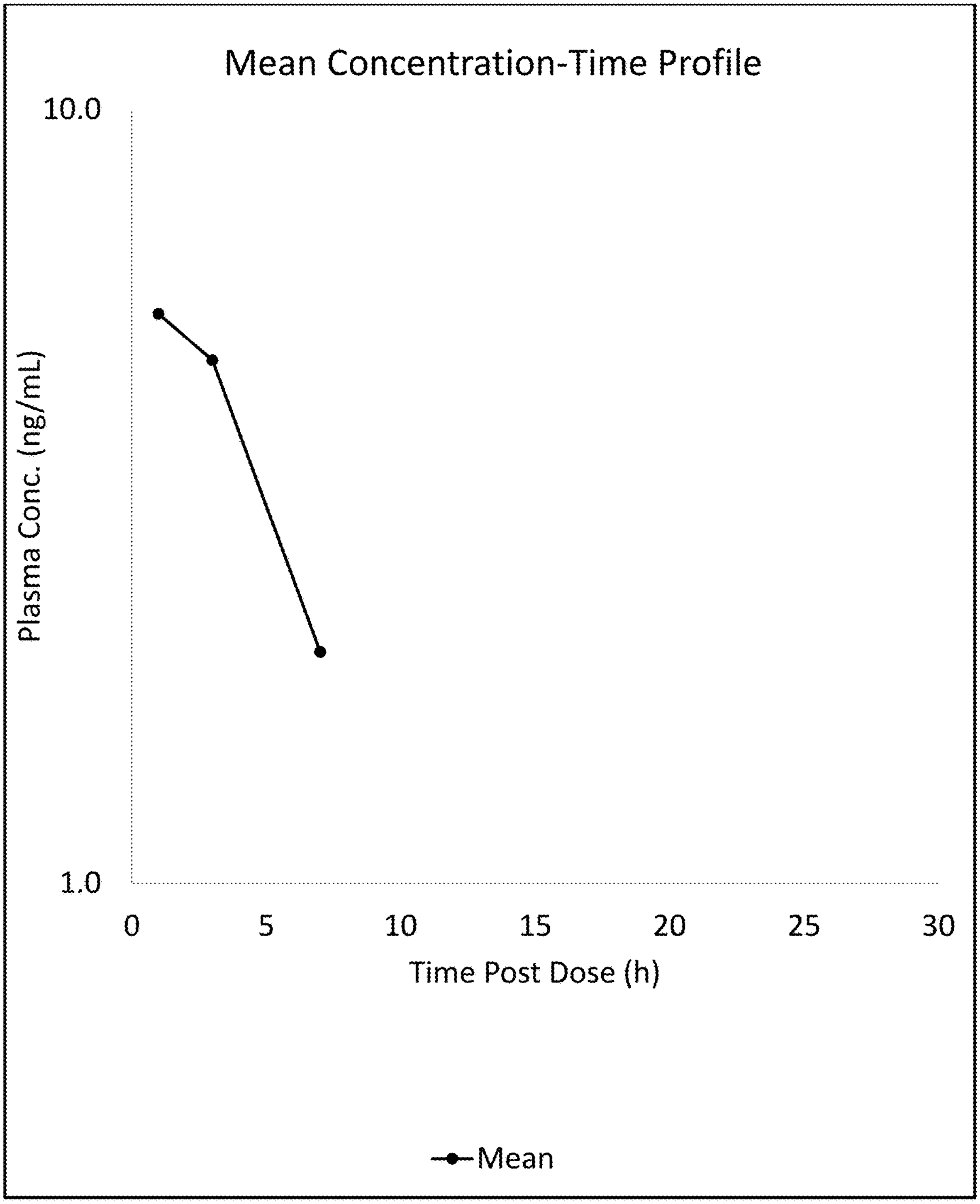
FIG. 70 shows mean concentration-time profiles of xanomeline following PO dosing of xanomeline methyl hexadecanoate chloride prodrug (10 mg/kg of xanomeline) to male SD rats.

FIG. 70 shows mean concentration-time profiles of xanomeline following PO dosing of xanomeline methyl hexadecanoate chloride prodrug (10 mg/kg of xanomeline) to male SD rats.

Example A-7-5: Xanomeline Methyl Decatriaoate Chloride Prodrug—Table 1 Compound 12

| | |
|---|---|
| Species: | Rat |
| Dose Route: | PO |
| Dose Level (mg/kg) | 10 mg/kg of xanomeline |

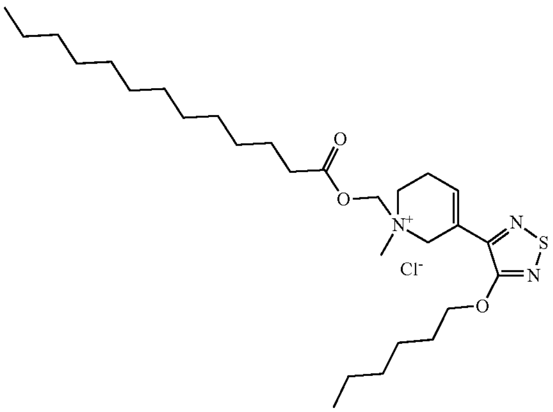 [SMILES: CCCCCCCCCCCCC(=O)OC[N+]1(C)CCC=C(c2nsnc2OCCCCCC)C1 ; [Cl-]]

Chemical name: 1-methyl-5-[4-(hexyloxy)-1,2,5-thiadiazol-3-yl]-1-[(tridecanoyloxy)methyl]-1,2,3,6-tetrahydropyridin-1-ium chloride Structural class: acyloxymethyl Mechanistic class: presumed esterase+chemical break-down

TABLE 80

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R22 | NR | 1.00 | 6.89 | 7.00 | 23.0 | NR |
| | | R23 | NR | 3.00 | 3.99 | 3.00 | 9.27 | NR |
| | | R24 | NR | 1.00 | 12.4 | 7.00 | 71.3 | NR |
| | | Mean | NR | 1.67 | 7.76 | 5.67 | 34.5 | NR |

Figure 71:
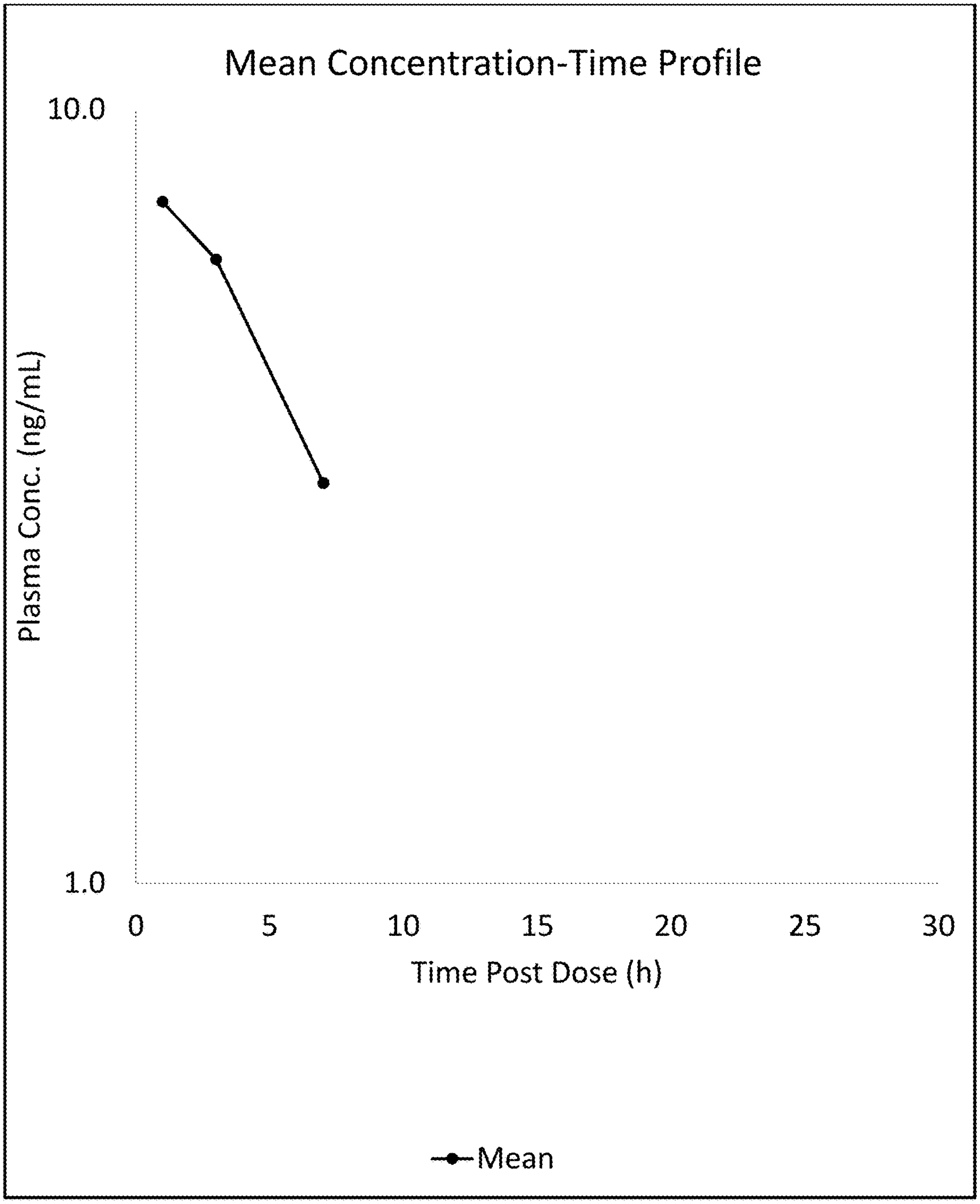
FIG. 71 shows mean concentration-time profiles of xanomeline following PO dosing of xanomeline methyl decatriaoate chloride prodrug (10 mg/kg of xanomeline) to male SD rats.

FIG. 71 shows mean concentration-time profiles of xanomeline following PG dosing of xanomeline methyl decatriaoate chloride prodrug (10 mg/kg of xanomeline) to male SD rats.

Example A-7-6: Xanomeline Methyl Nonanoate Chloride Prodrug—Table 1 Compound 8

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl nonanoate chloride Structural class: acyloxymethyl Mechanistic class: presumed esterase+chemical breakdown

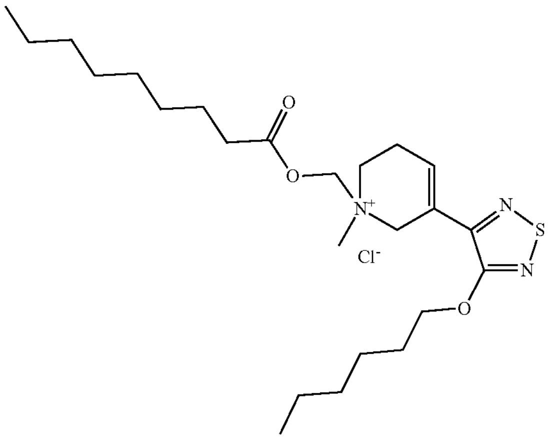 [SMILES: CCCCCCCCC(=O)OC[N+]1(C)CCC=C(c2nsnc2OCCCCCC)C1 ; [Cl-]]

TABLE 81

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R25 | NR | 1.00 | 5.41 | 7.00 | 17.9 | NR |
| | | R26 | NR | 3.00 | 4.26 | 7.00 | 24.4 | NR |
| | | R27 | NR | 1.00 | 5.01 | 7.00 | 24.5 | NR |
| | | Mean | NR | 1.67 | 4.89 | 7.00 | 22.3 | NR |

Figure 72:
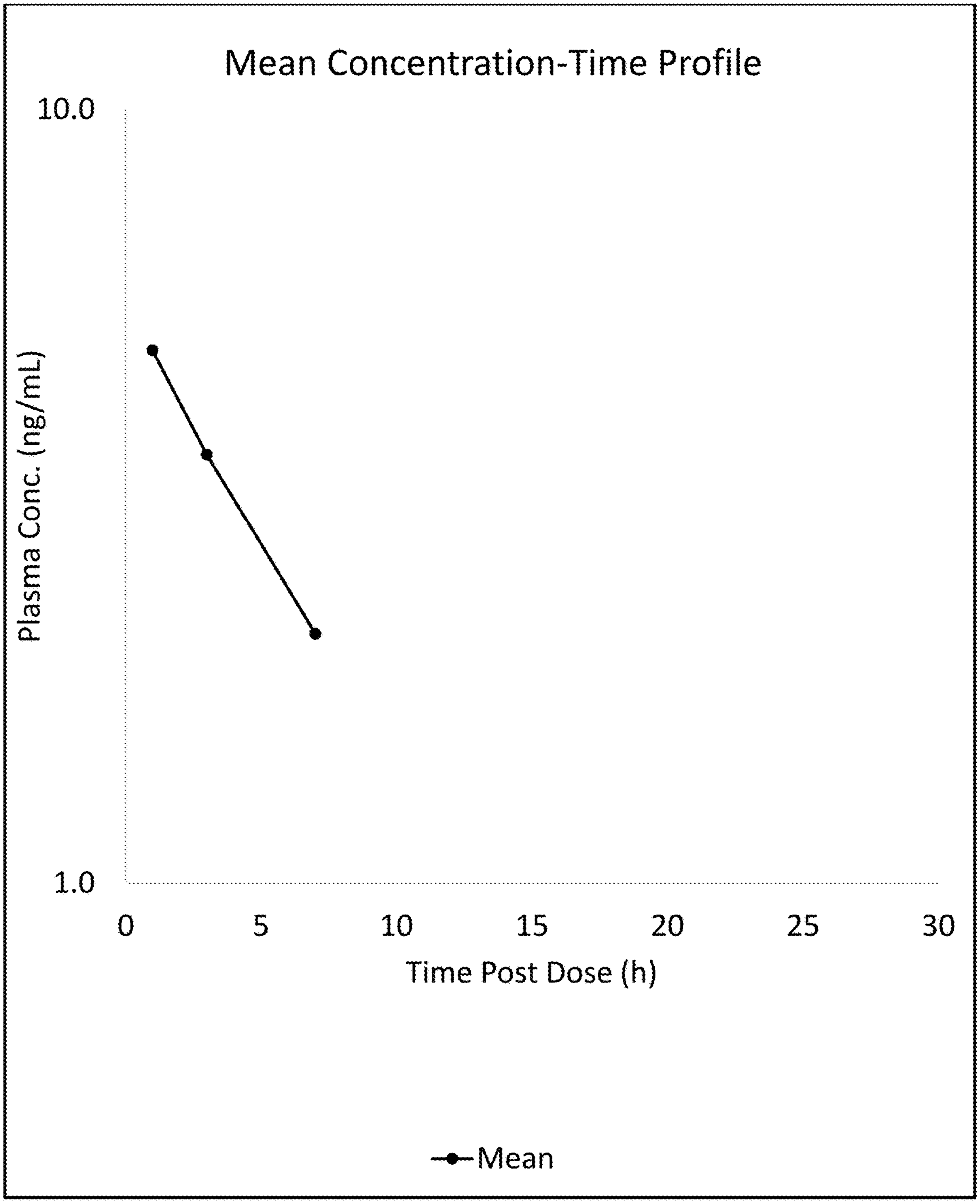
FIG. 72 shows mean concentration-time profiles of xanomeline following PO dosing of xanomeline methyl nonanoate prodrug (10 mg/kg of xanomeline) to male SD rats.

FIG. 72 shows mean concentration-time profiles of xanomeline following PO dosing of xanomeline methyl nonanoate chloride prodrug (10 mg/kg of xanomeline) to male SD rats.

Example A-7-7: Xanomeline Methyl Octylcarbonate Chloride Prodrug—Table 1 Compound

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl octyl carbonate chloride Structural class: alkoxycarbonyloxymethyl Mechanistic class: presumed esterase+chemical breakdown

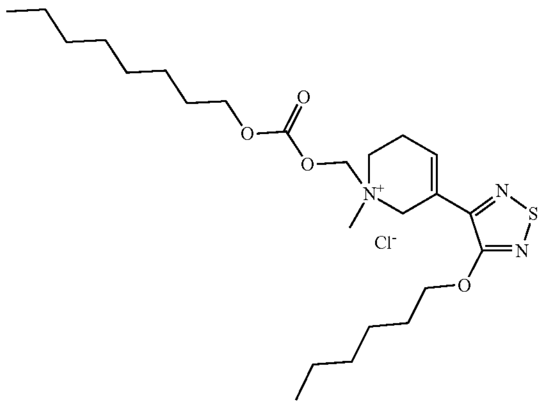 [SMILES: CCCCCCCCOC(=O)OC[N+]1(C)CCC=C(c2nsnc2OCCCCCC)C1 ; [Cl-]]

TABLE 82

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R28 | NR | 3.00 | 5.77 | 7.00 | 27.6 | NR |
| | | R29 | NR | 3.00 | 7.16 | 7.00 | 34.5 | NR |
| | | R30 | NR | 1.00 | 8.59 | 7.00 | 37.7 | NR |
| | | Mean | NR | 2.33 | 7.17 | 7.00 | 33.3 | NR |

Figure 73:
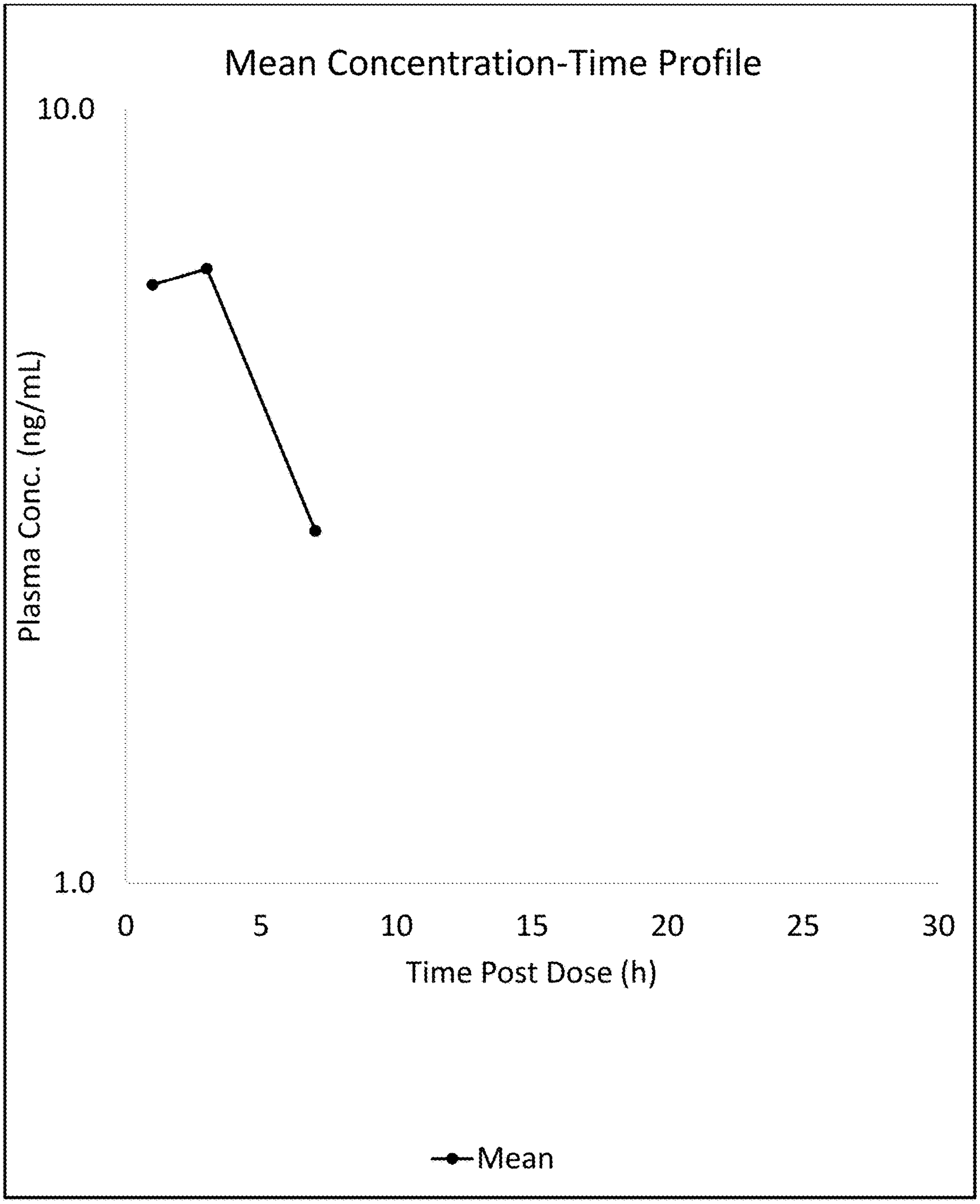
FIG. 73 shows mean concentration-time profiles of xanomeline following PO dosing of xanomeline methyl octylcarbonate chloride prodrug (10 mg/kg of xanomeline) to male SD rats.

FIG. 73 shows mean concentration-time profiles of xanomeline following PO dosing of xanomeline methyl octylcarbonate chloride prodrug (10 mg/kg of xanomeline) to male SD rats.

Example A-7-8: Xanomeline Methyl Dodecylcarbonate Chloride Prodrug—Table 1 Compound 33

| | |
|---|---|
| Species: | Rat |
| Dose Route: | PO |
| Dose Level (mg/kg) | 10 mg/kg of xanomeline |

Chemical name: dodecyl [5-(4-hexyloxy-1,2,5-thiadiazol-3-yl)-1-methyl-3,6-dihydro-2H-pyridin-1-ium-1-yl]methyl carbonate chloride Structural class: alkoxycarbonyloxymethyl Mechanistic class: presumed esterase+chemical break-down

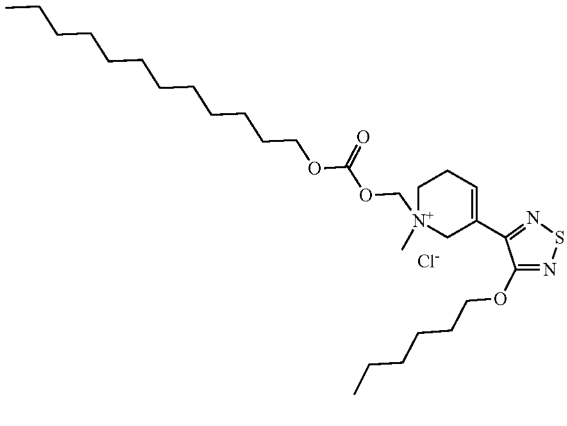 [SMILES: CCCCCCCCCCCCOC(=O)OC[N+]1(C)CCC=C(c2nsnc2OCCCCCC)C1 ; [Cl-]]

TABLE 83

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R31 | NR | 3.00 | 5.82 | 7.0 | 30.7 | NR |
| | | R32 | NR | 1.00 | 4.22 | 7.0 | 13.9 | NR |
| | | R33 | NR | 3.00 | 2.71 | 7.0 | 14.1 | NR |
| | | Mean | NR | 2.33 | 4.25 | 7.0 | 19.6 | NR |

Figure 74:
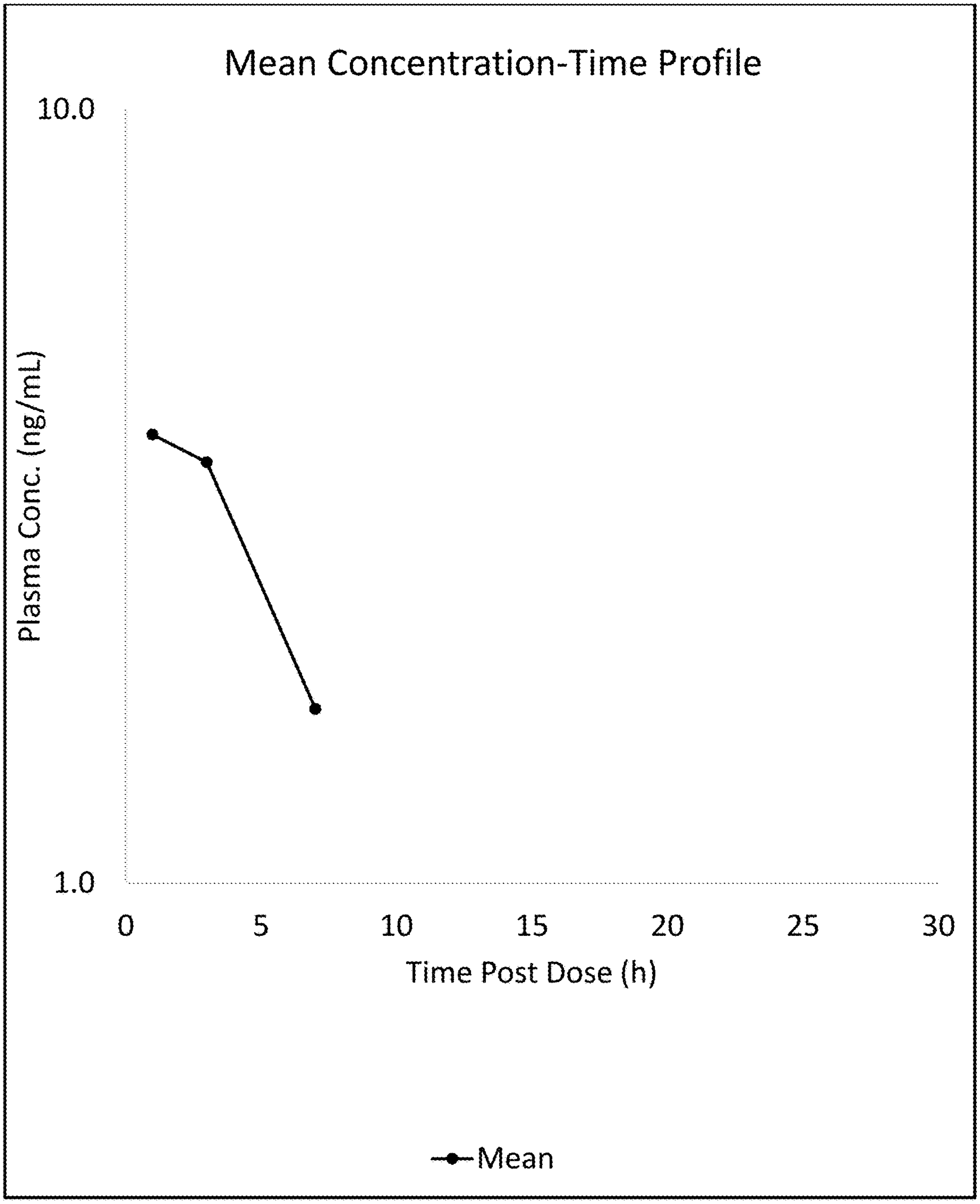
FIG. 74 shows mean concentration-time profiles of xanomeline following PO dosing of xanomeline methyl dodecylcarbonate chloride prodrug (10 mg/kg of xanomeline) to male SD rats.

FIG. 74 shows mean concentration-time profiles of xanomeline following PO dosing of xanomeline methyl dodecylcarbonate chloride prodrug (10 mg/kg of xanomeline) to male SD rats.

Example A-7-9: Xanomeline Methyl Pentadecylcarbonate Chloride Prodrug—Table 1 Compound 36

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl pentadecyl carbonate chloride Structural class: alkoxycarbonyloxymethyl Mechanistic class: presumed esterase+chemical break-down

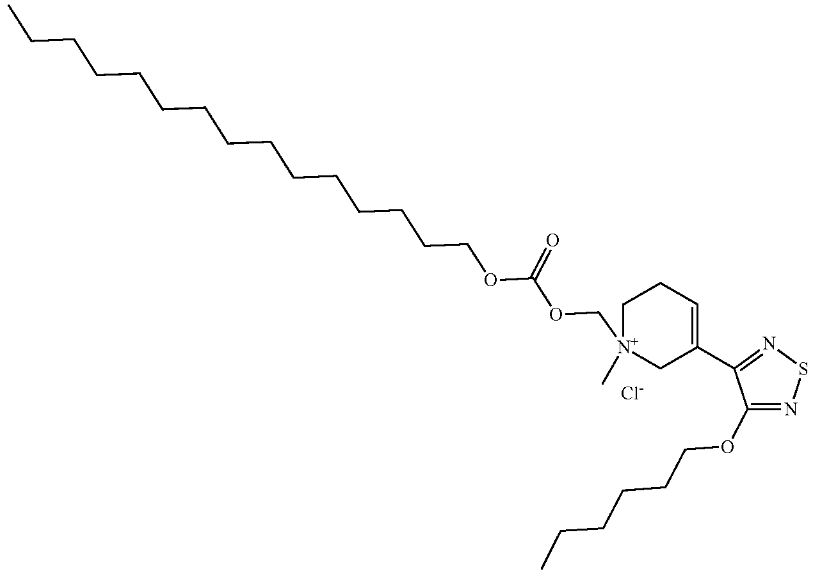 [SMILES: CCCCCCCCCCCCCCCOC(=O)OC[N+]1(C)CCC=C(c2nsnc2OCCCCCC)C1 ; [Cl-]]

TABLE 84

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R34 | NR | 1.00 | 6.59 | 7.00 | 22.5 | NR |
| | | R35 | NR | 3.00 | 4.21 | 7.00 | 22.3 | NR |
| | | R36 | NR | 3.00 | 4.74 | 7.00 | 24.0 | NR |
| | | Mean | NR | 2.33 | 5.18 | 7.00 | 22.9 | NR |

Figure 75:
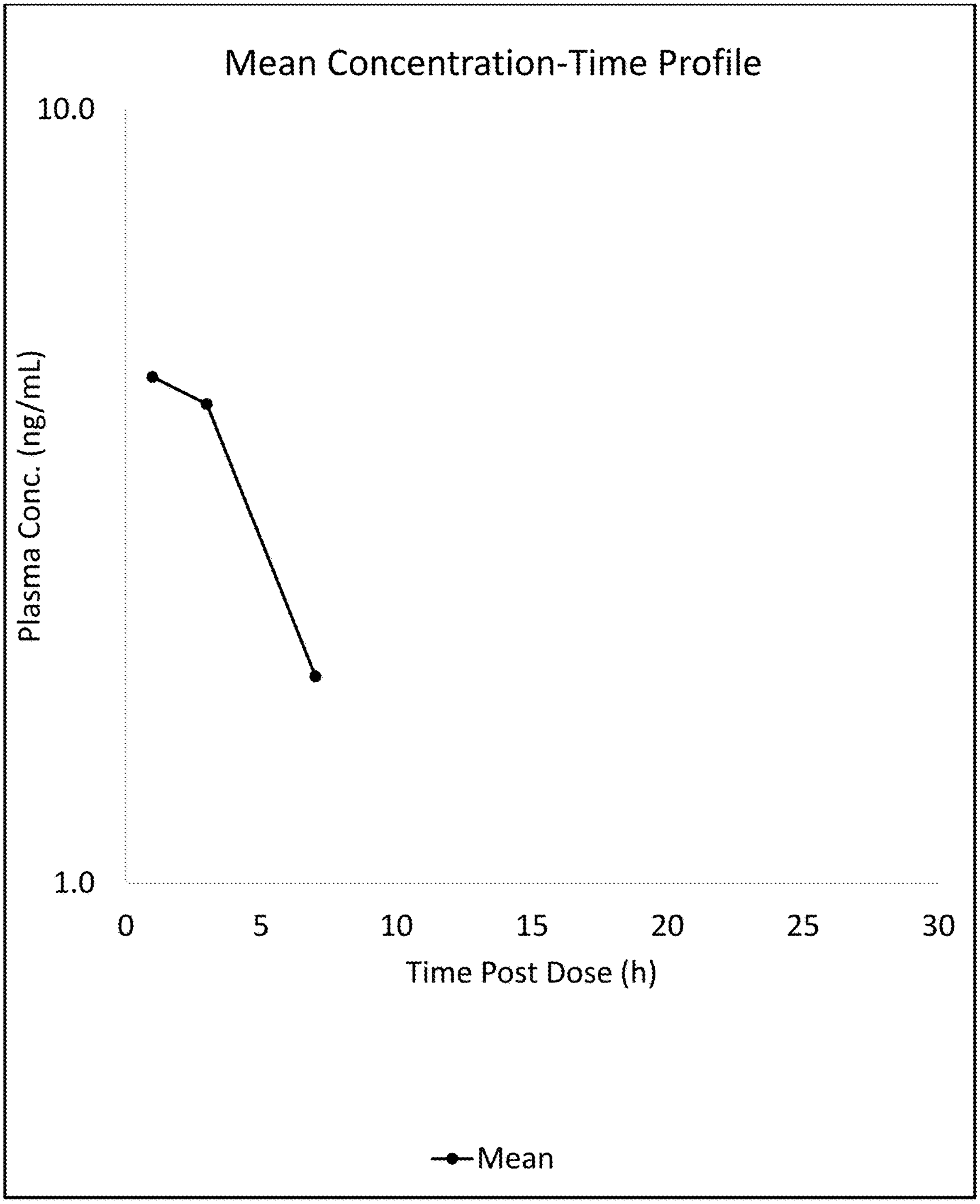
FIG. 75 shows mean concentration-time profiles of xanomeline following PO dosing of xanomeline methyl pentadecylcarbonate chloride prodrug (10 mg/kg of xanomeline) to male SD rats.

FIG. 75 shows mean concentration-time profiles of xanomeline following PO dosing of xanomeline methyl pentadecylcarbonate chloride prodrug (10 mg/kg of xanomeline) to male SD rats.

Example A-7-10: Xanomeline Methyl Octanoate Chloride Prodrug—Table 1 Compound 7

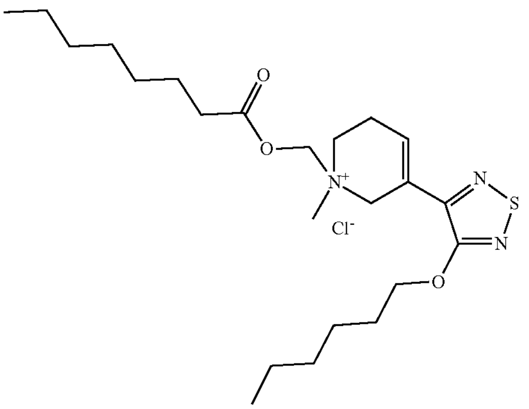 [SMILES: CCCCCCCC(=O)OC[N+]1(C)CCC=C(c2nsnc2OCCCCCC)C1 ; [Cl-]]

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl octanoate chloride Structural class: acyloxymethyl Mechanistic class: presumed esterase+chemical breakdown

TABLE 85

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R1 | 40.2 | 1.00 | 17.3 | 24.0 | 139 | 411 |
| | | R2 | NR | 3.00 | 8.38 | 7.00 | 36.1 | NR |
| | | R3 | NR | 1.00 | 6.20 | 7.00 | 21.5 | NR |
| | | Mean | 13.4 | 1.67 | 10.6 | 12.7 | 65.5 | 137 |

Figure 76:
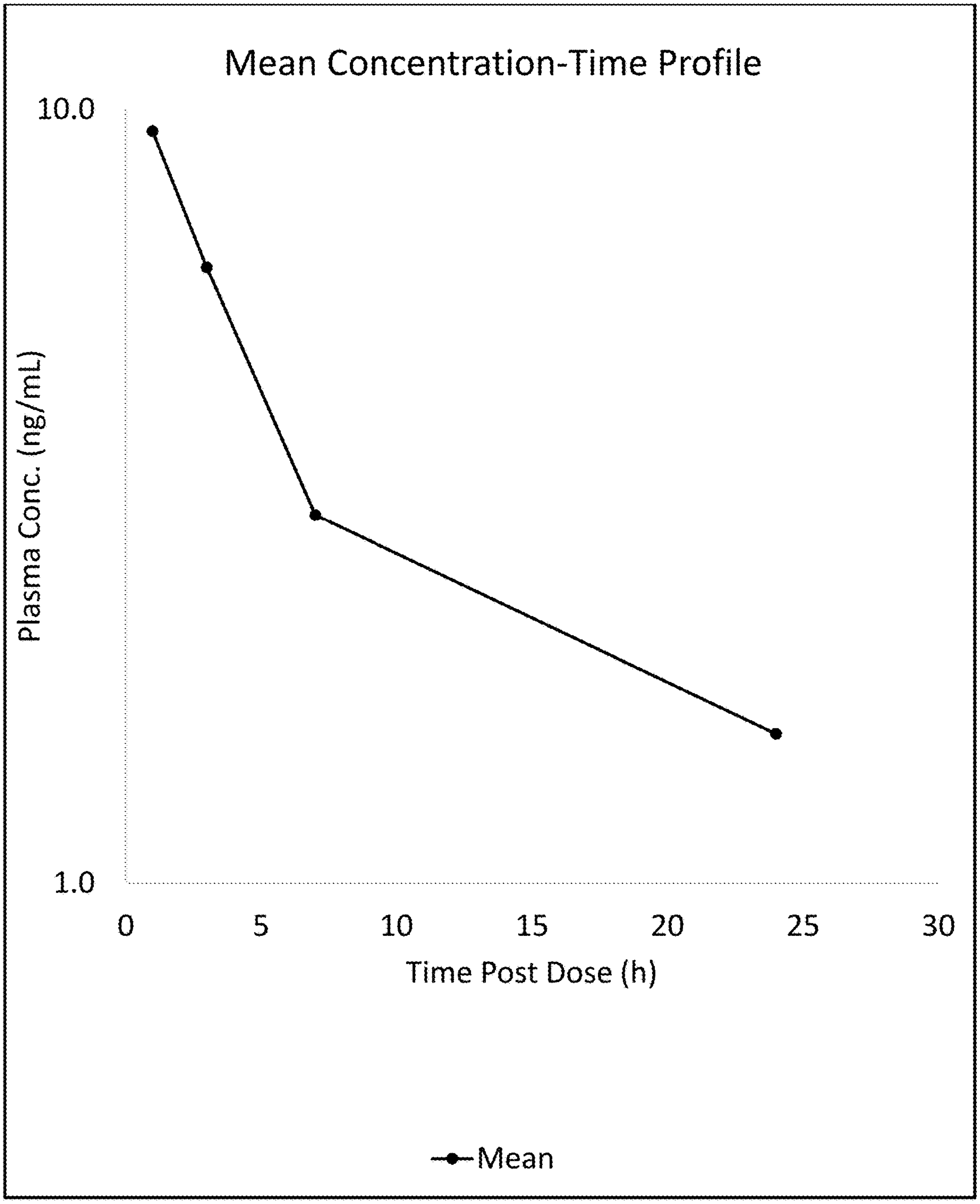
FIG. 76 shows mean concentration-time profiles of xanomeline following PO dosing of xanomeline methyl octanoate chloride prodrug (10 mg/kg of xanomeline) to male SD rats.

FIG. 76 shows mean concentration-time profiles of xanomeline following PO dosing of xanomeline methyl octanoate chloride prodrug (10 mg/kg of xanomeline) to male SD rats.

Example A-7-11: Xanomeline Methyl Decanoate Chloride Prodrug—Table 1 Compound 9

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl decanoate chloride Structural class: acyloxymethyl Mechanistic class: presumed esterase+chemical break-down

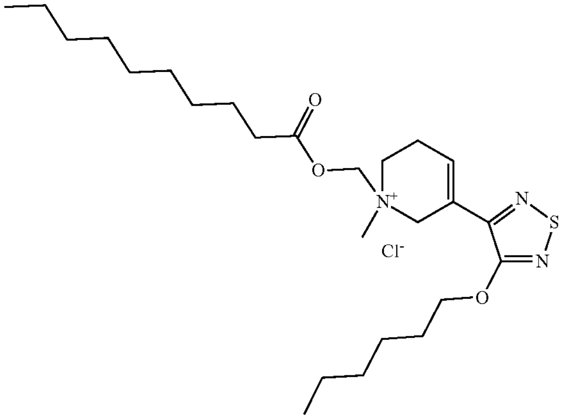 [SMILES: CCCCCCCCCC(=O)OC[N+]1(C)CCC=C(c2nsnc2OCCCCCC)C1 ; [Cl-]]

TABLE 86

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R4 | NR | 1.00 | 8.38 | 7.00 | 22.5 | NR |
| | | R5 | NR | 1.00 | 11.2 | 3.00 | 20.3 | NR |
| | | R6 | NR | 1.00 | 8.27 | 3.00 | 16.4 | NR |
| | | Mean | NR | 1.00 | 9.28 | 4.33 | 19.7 | NR |

Figure 77:
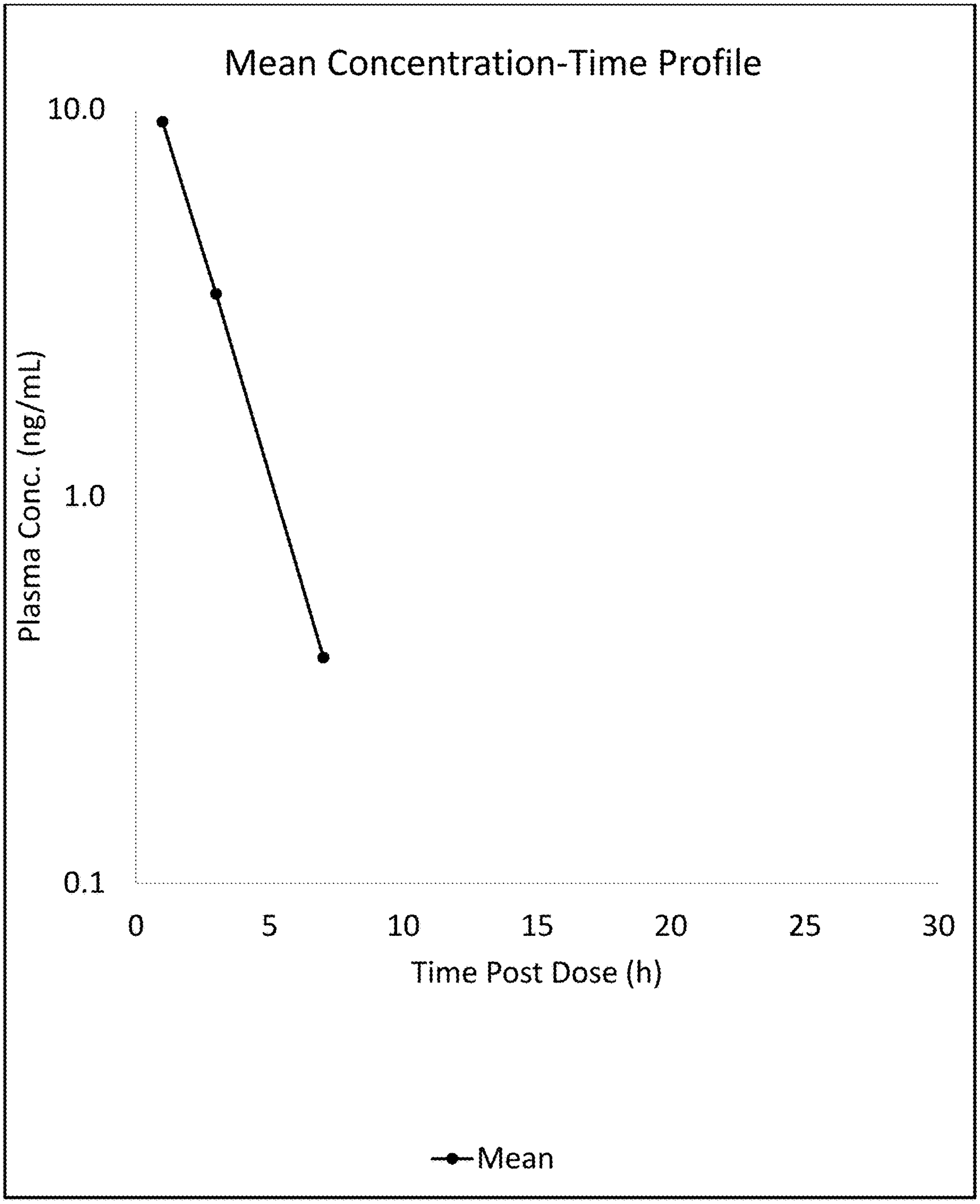
FIG. 77 shows mean concentration-time profiles of xanomeline following PO dosing of xanomeline methyl decanoate chloride prodrug (10 mg/kg of xanomeline) to male SD rats.

FIG. 77 shows mean concentration-time profiles of xanomeline following PO dosing of xanomeline methyl decanoate chloride prodrug (10 mg/kg of xanomeline) to male SD rats.

Example A-7-12: Xanomeline Methyl Undecanoate Chlorideprodrug—Table 1 Compound 10

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl undecanoate chloride Structural class: acyloxymethyl Mechanistic class: presumed esterase+chemical break-down

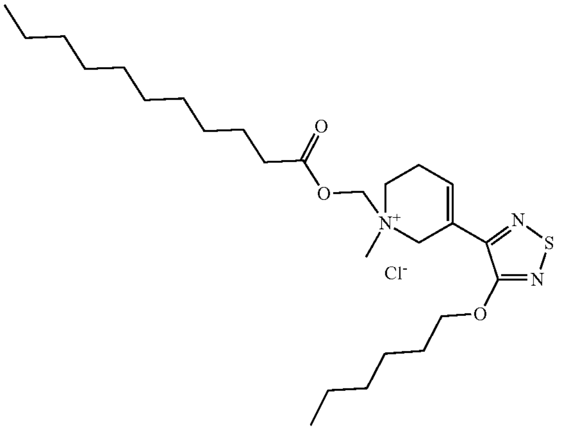 [SMILES: CCCCCCCCCCC(=O)OC[N+]1(C)CCC=C(c2nsnc2OCCCCCC)C1 ; [Cl-]]

TABLE 87

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R7 | NR | 1.00 | 16.8 | 3.00 | 28.4 | NR |
| | | R8 | NR | 1.00 | 15.1 | 3.00 | 28.3 | NR |
| | | R9 | NR | 1.00 | 4.49 | 7.00 | 15.1 | NR |
| | | Mean | NR | 1.00 | 12.1 | 4.33 | 23.9 | NR |

Figure 78:
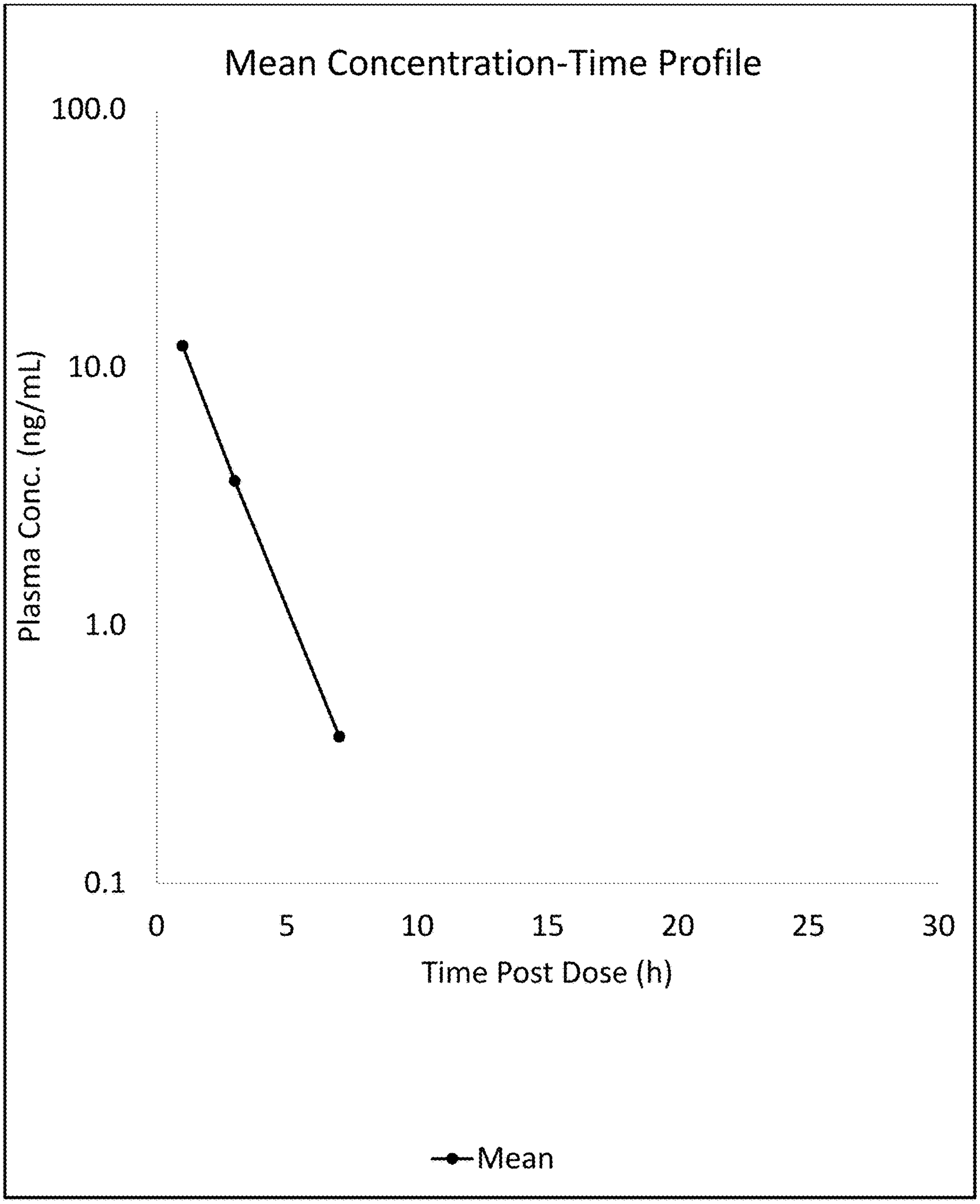
FIG. 78 shows mean concentration-time profiles of xanomeline following PO dosing of xanomeline methyl undecanoate chloride prodrug (10 mg/kg of xanomeline) to male SD rats.

FIG. 78 shows mean concentration-time profiles of xanomeline following PO dosing of xanomeline methyl undecanoate chloride prodrug (10 mg/kg of xanomeline) to male SD rats.

Example A-7-13: Xanomeline Methyl Dodecanoate Iodide Prodrug—Table 1 Compound 11

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl dodecanoate iodide Structural class: acyloxymethyl Mechanistic class: presumed esterase_+chemical breakdown

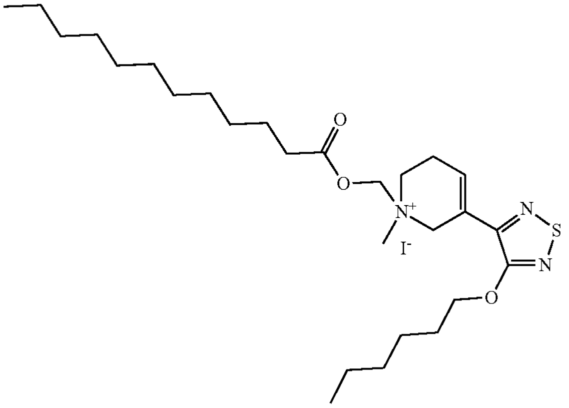 [SMILES: CCCCCCCCCCCC(=O)OC[N+]1(C)CCC=C(c2nsnc2OCCCCCC)C1 ; [I-]]

TABLE 88

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml * hr) | AUCINF_obs (ng/ml * hr) |
| Xanomeline | PO | R10 | NR | 1.00 | 3.41 | 3.00 | 6.15 | NR |
| | | R11 | NR | 1.00 | 5.03 | 3.00 | 8.70 | NR |
| | | R12 | NR | 1.00 | 10.5 | 3.00 | 17.6 | NR |
| | | Mean | NR | 1.00 | 6.31 | 3.00 | 10.8 | NR |

Figure 79:
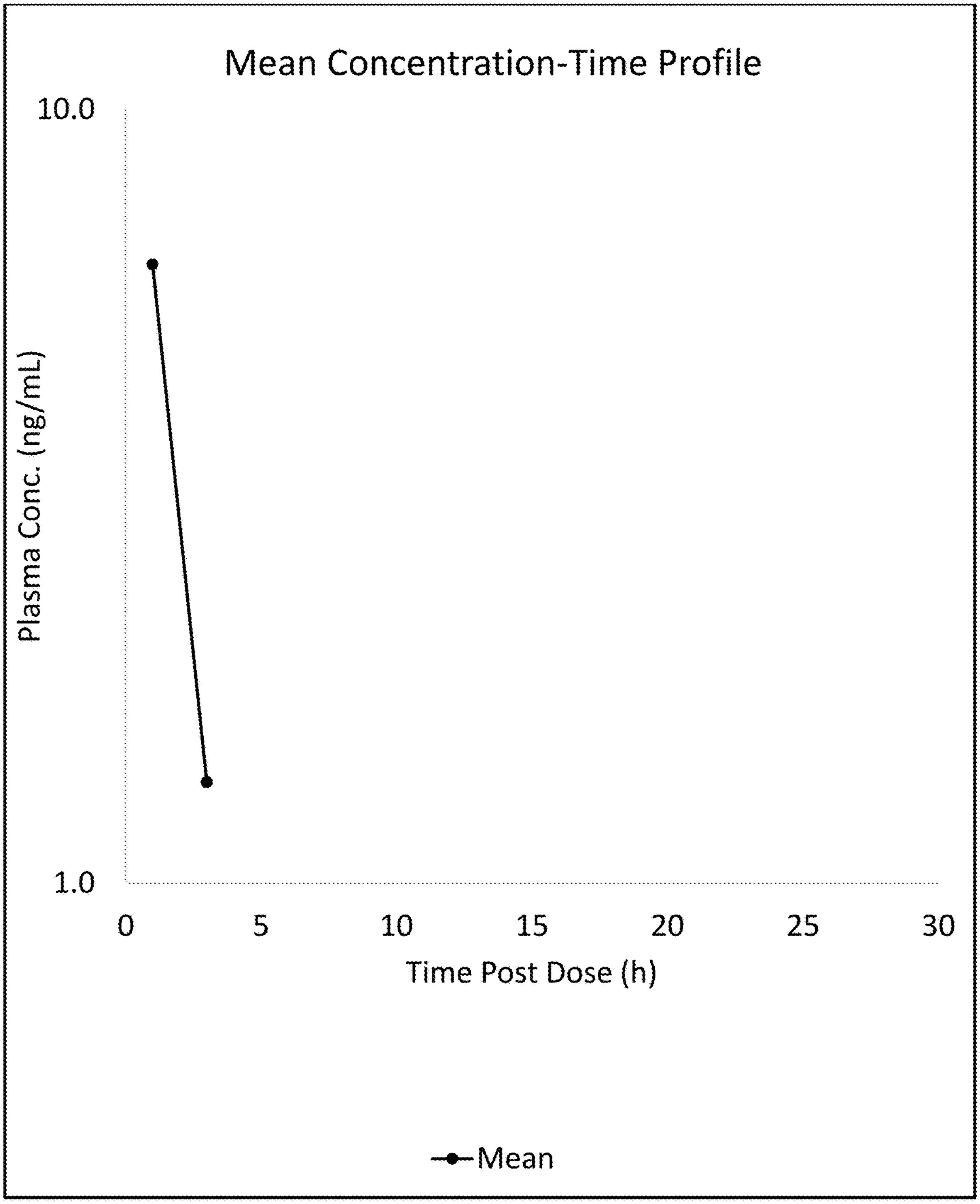
FIG. 79 shows mean concentration-time profiles of xanomeline following PO dosing of xanomeline methyl dodecanoate iodide prodrug (10 mg/kg of xanomeline) to male SD rats.

FIG. 79 shows mean concentration-time profiles of xanomeline following PG dosing of xanomeline methyl dodecanoate iodide prodrug (10 mg/kg of xanomeline) to male SD rats.

Example A-7-14: Xanomeline Methyl Decatettaraoate Chloride Prodrug—Table 1 Compound 13

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl tetradecanoate chloride Structural class: acyloxymethyl Mechanistic class: presumed esterase+chemical breakdown

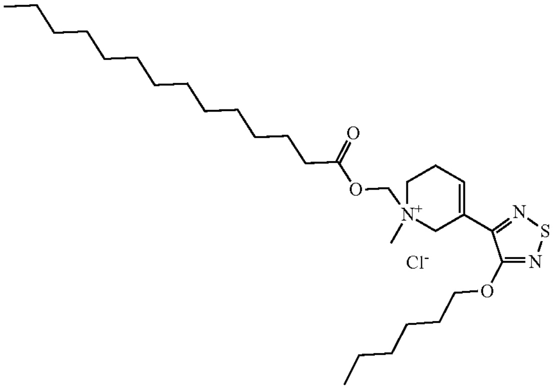 [SMILES: CCCCCCCCCCCCCC(=O)OC[N+]1(C)CCC=C(c2nsnc2OCCCCCC)C1 ; [Cl-]]

TABLE 89

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | PO | R13 | NR | 1.00 | 4.15 | 1.00 | 2.08 | NR |
| | | R14 | NR | 1.00 | 12.2 | 3.00 | 22.9 | NR |
| | | R15 | NR | 1.00 | 8.24 | 3.00 | 15.7 | NR |
| | | Mean | NR | 1.00 | 8.20 | 2.33 | 13.6 | NR |

Figure 80:
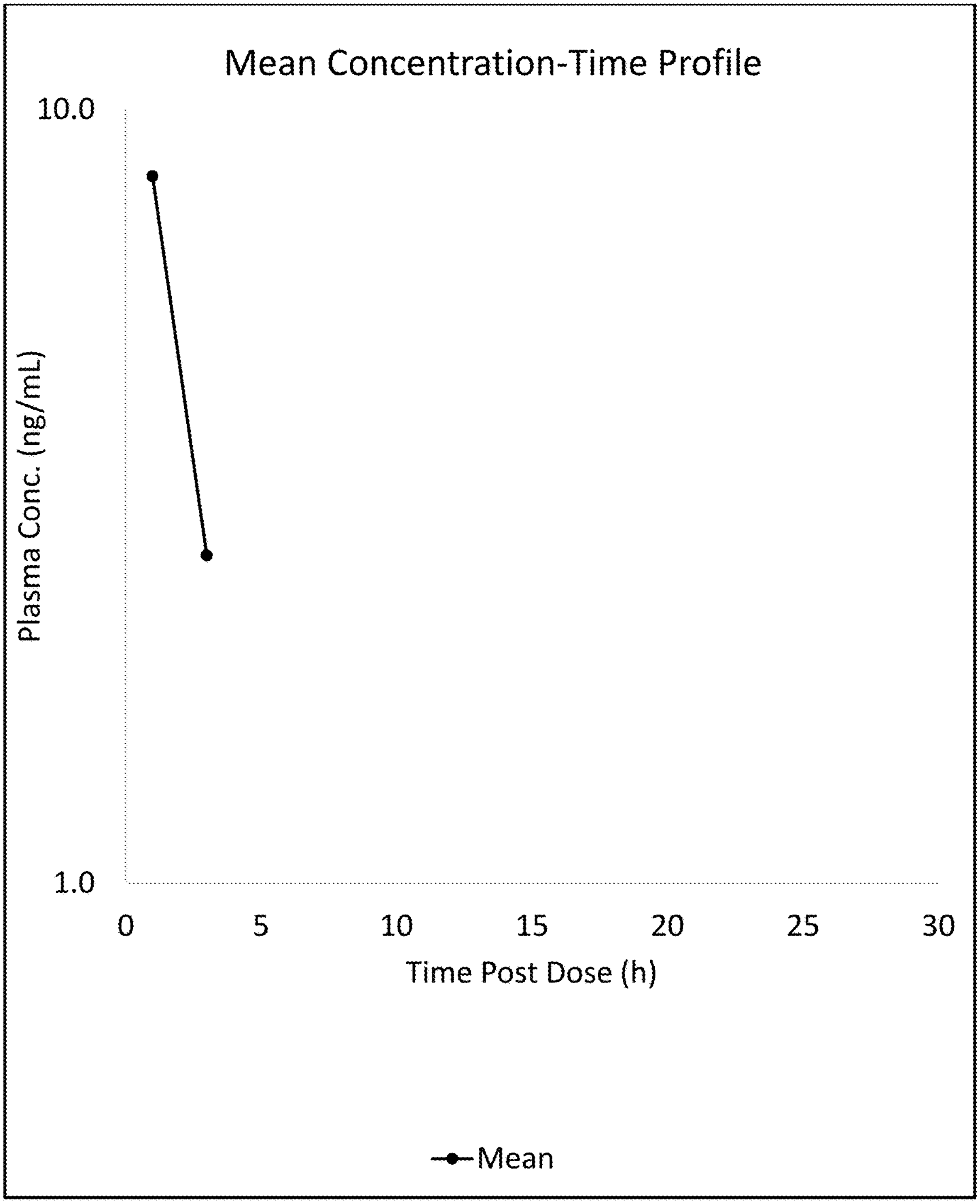
FIG. 80 shows mean concentration-time profiles of xanomeline following PO dosing of xanomeline methyl decatettaraoate chloride prodrug (10 mg/kg of xanomeline) to male SD rats.

FIG. 80 shows mean concentration-time profiles of xanomeline following PO dosing of xanomeline methyl decatettaraoate chloride prodrug (10 mg/kg of xanomeline) to male SD rats.

Example A-7-15: Xanomeline Methyl Hexylcarbonate Chloride Prodrug—Table 1 Compound 27

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl hexyl carbonate chloride Structural class: alkoxycarbonyloxymethyl Mechanistic class: presumed esterase+chemical breakdown

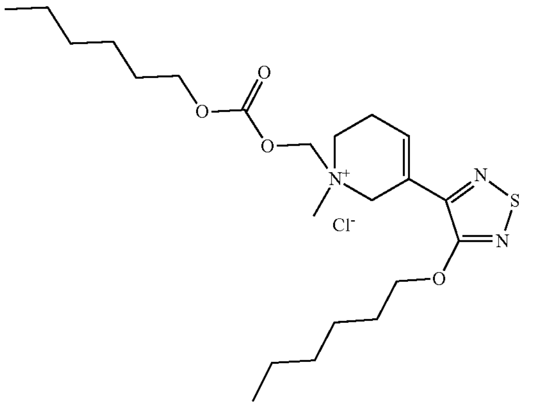 [SMILES: CCCCCCOC(=O)OC[N+]1(C)CCC=C(c2nsnc2OCCCCCC)C1 ; [Cl-]]

TABLE 90

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | PO | R1 | NR | 1.00 | 7.96 | 7.00 | 27.2 | NR |
| | | R2 | NR | 1.00 | 35.4 | 7.00 | 63.0 | NR |
| | | R3 | NR | 1.00 | 5.40 | 7.00 | 21.5 | NR |
| | | Mean | NR | 1.00 | 16.3 | 7.0 | 37.2 | NR |

Figure 81:
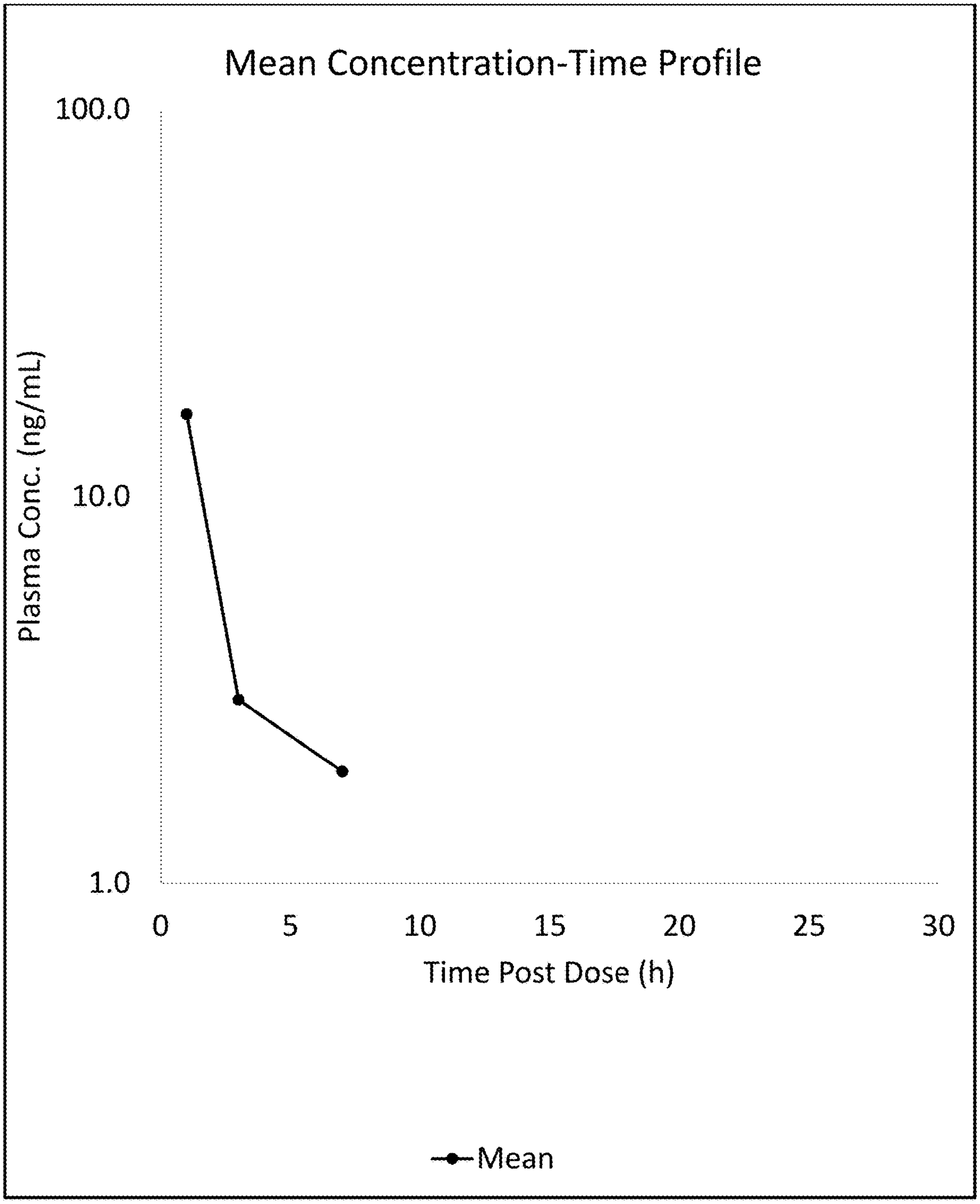
FIG. 81 shows mean concentration-time profiles of xanomeline following PO dosing of xanomeline methyl hexylcarbonate chloride prodrug (10 mg/kg of xanomeline) to male SD rats.

FIG. 81 shows mean concentration-time profiles of xanomeline following PO dosing of xanomeline methyl hexylcarbonate chloride prodrug (10 mg/kg of xanomeline) to male SD rats.

Example A-7-16: Xanomeline Methyl Heptylcarbonate Chloride Prodrug—Table 1 Compound 28

| | |
|---|---|
| Species: | Rat |
| Dose Route: | PO |
| Dose Level (mg/kg) | 10 mg/kg of xanomeline |

Chemical name: heptyl [5-(4-hexyloxy-1,2,5-thiadiazol-3-yl)-1-methyl-3,6-dihydro-2H-pyridin-1-ium-1-yl] methyl carbonate chloride Structural class: alkoxycarbonyloxymethyl Mechanistic class: presumed esterase+chemical breakdown

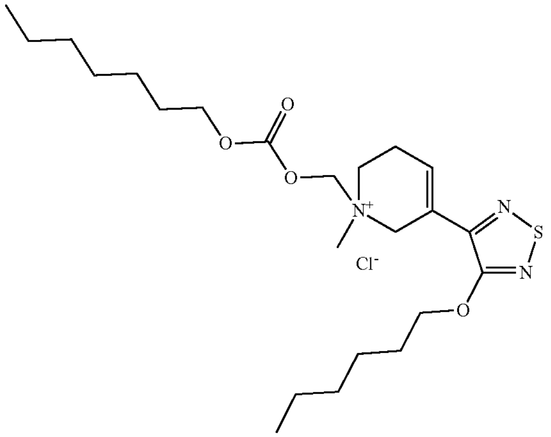 [SMILES: CCCCCCCOC(=O)OC[N+]1(C)CCC=C(c2nsnc2OCCCCCC)C1 ; [Cl-]]

TABLE 91

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R4 | NR | 1.00 | 4.05 | 7.00 | 16.6 | NR |
| | | R5 | NR | 1.00 | 3.64 | 7.00 | 13.9 | NR |
| | | R6 | NR | 1.00 | 5.27 | 3.00 | 9.85 | NR |
| | | Mean | NR | 1.00 | 4.32 | 5.67 | 13.5 | NR |

Figure 82:
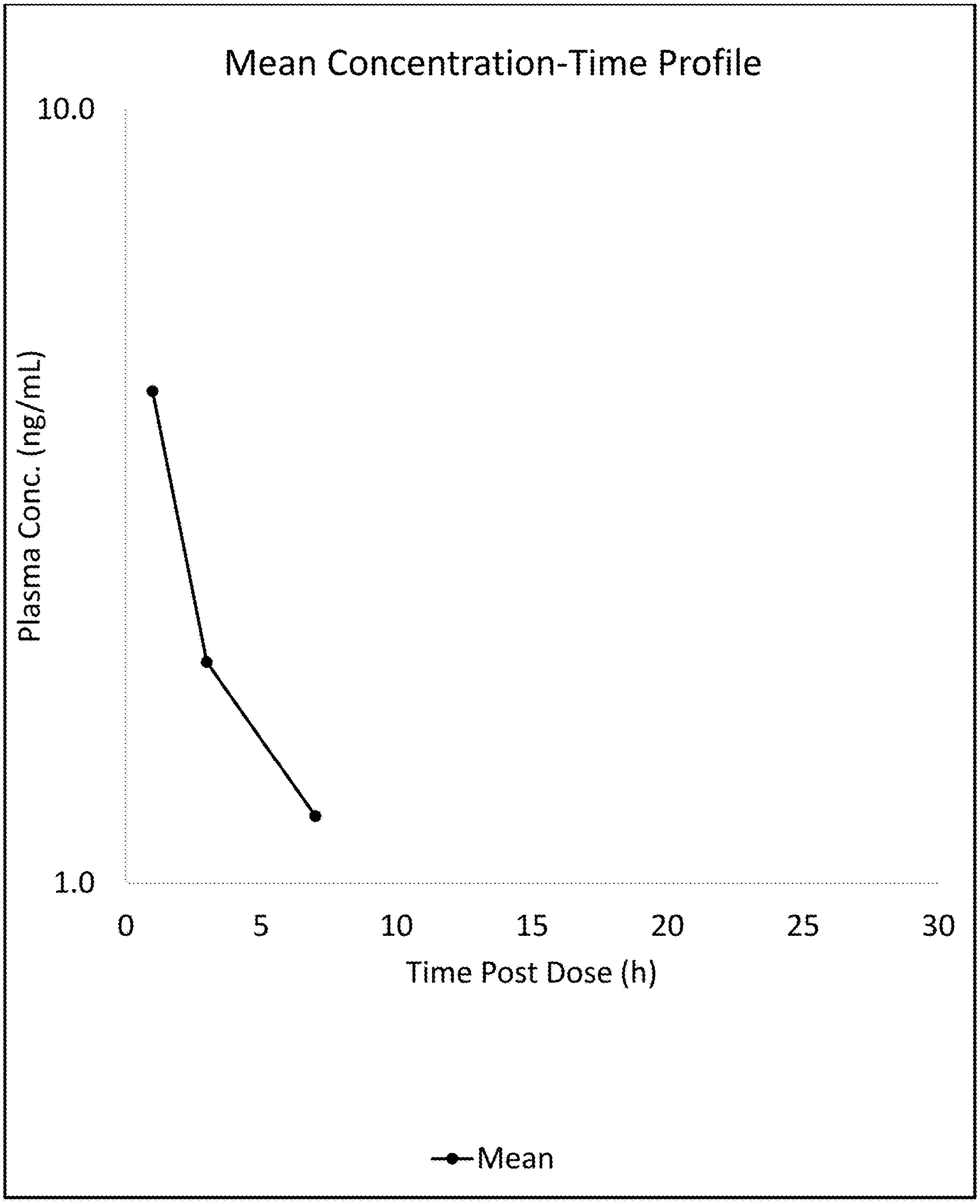
FIG. 82 shows mean concentration-time profiles of xanomeline following PO dosing of xanomeline methyl heptylcarbonate chloride prodrug (10 mg/kg of xanomeline) to male SD rats.

FIG. 82 shows mean concentration-time profiles of xanomeline following PO dosing of xanomeline methyl heptylcarbonate chloride prodrug (10 mg/kg of xanomeline) to male SD rats.

Example A-7-17: Xanomeline Methyl Undecylcarbonate Chloride Prodrug—Table 1 Compound 32

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl undecyl carbonate chloride Structural class: alkoxycarbonyloxymethyl Mechanistic class: presumed esterase+chemical breakdown

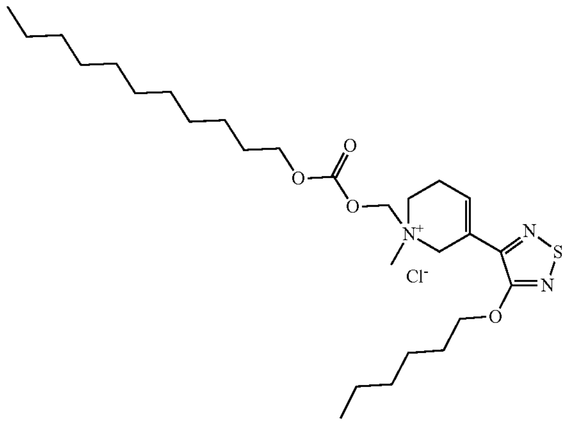 [SMILES: CCCCCCCCCCCOC(=O)OC[N+]1(C)CCC=C(c2nsnc2OCCCCCC)C1 ; [Cl-]]

TABLE 92

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R7 | NR | 1.00 | 3.46 | 7.00 | 15.5 | NR |
| | | R8 | NR | 1.00 | 4.40 | 7.00 | 12.4 | NR |
| | | R9 | NR | 1.00 | 4.03 | 7.00 | 14.5 | NR |
| | | Mean | NR | 1.00 | 4.0 | 7.00 | 14.1 | NR |

Figure 83:
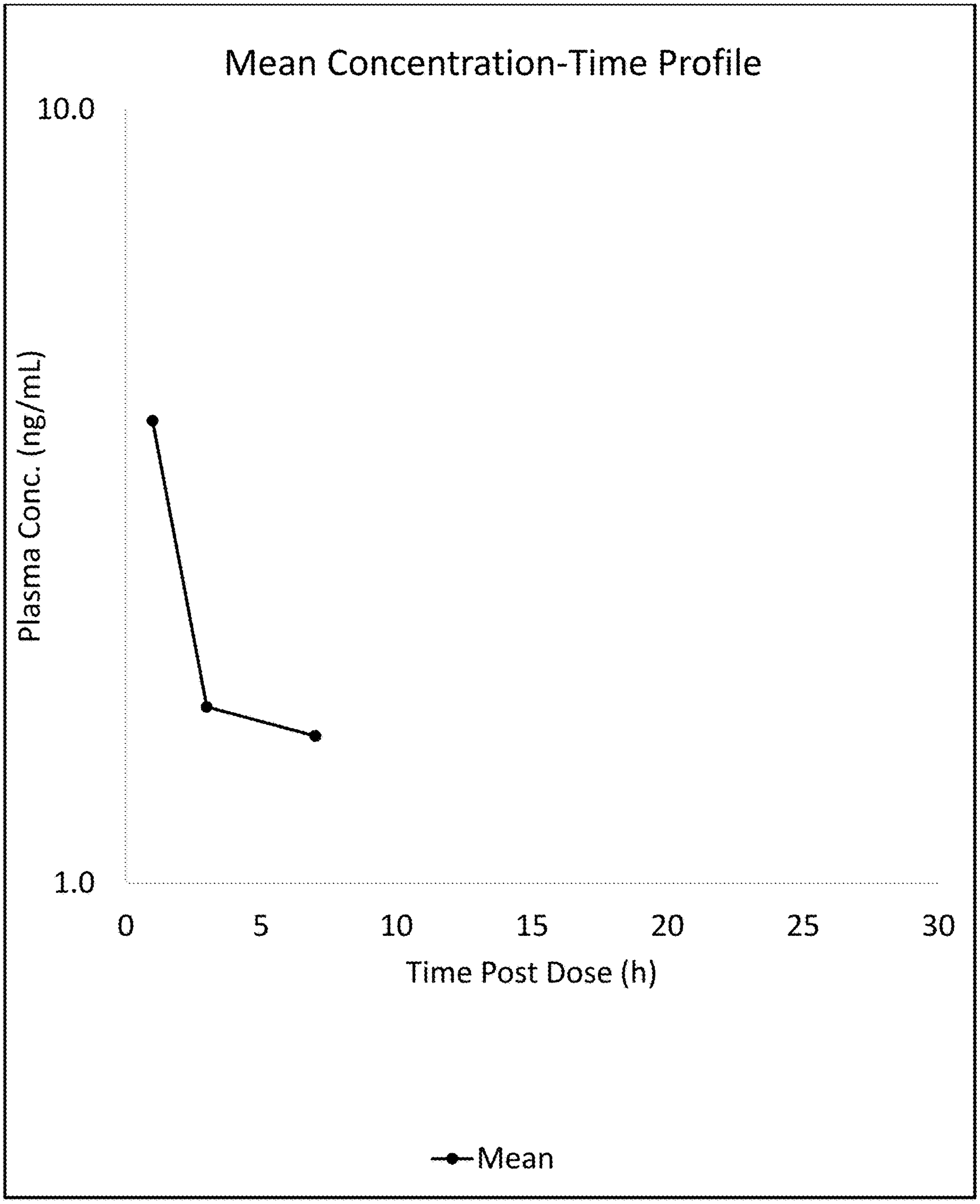
FIG. 83 shows mean concentration-time profiles of xanomeline following PO dosing of xanomeline methyl undecylcarbonate chloride prodrug (10 mg/kg of xanomeline) to male SD rats.

FIG. 83 shows mean concentration-time profiles of xanomeline following PO dosing of xanomeline methyl undecylcarbonate chloride prodrug (10 mg/kg of xanomeline) to male SD rats.

Example A-7-18: Xanomeline Methyl Pentanoate Chloride Prodrug—Table 1 Compound 4

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl pentanoate chloride Structural class: acyloxymethyl Mechanistic class: presumed esterase+chemical breakdown

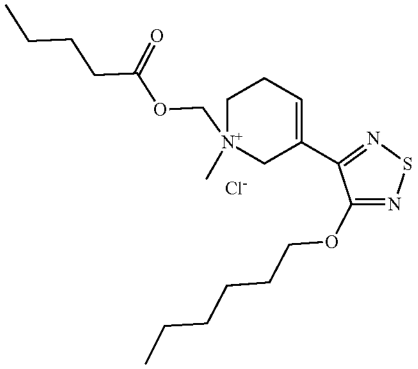 [SMILES: CCCCCCOc1nsnc1C1=CCC[N+](C)(COC(=O)CCCC)C1 ; [Cl-]]

TABLE 93

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R1 | NR | 1.00 | 9.75 | 3.00 | 21.9 | NR |
| | | R2 | NR | 1.00 | 15.0 | 1.00 | 7.50 | NR |
| | | R3 | NR | 1.00 | 2.13 | 1.00 | 1.07 | NR |
| | | Mean | NR | 1.00 | 8.96 | 1.67 | 10.2 | NR |

Figure 84:
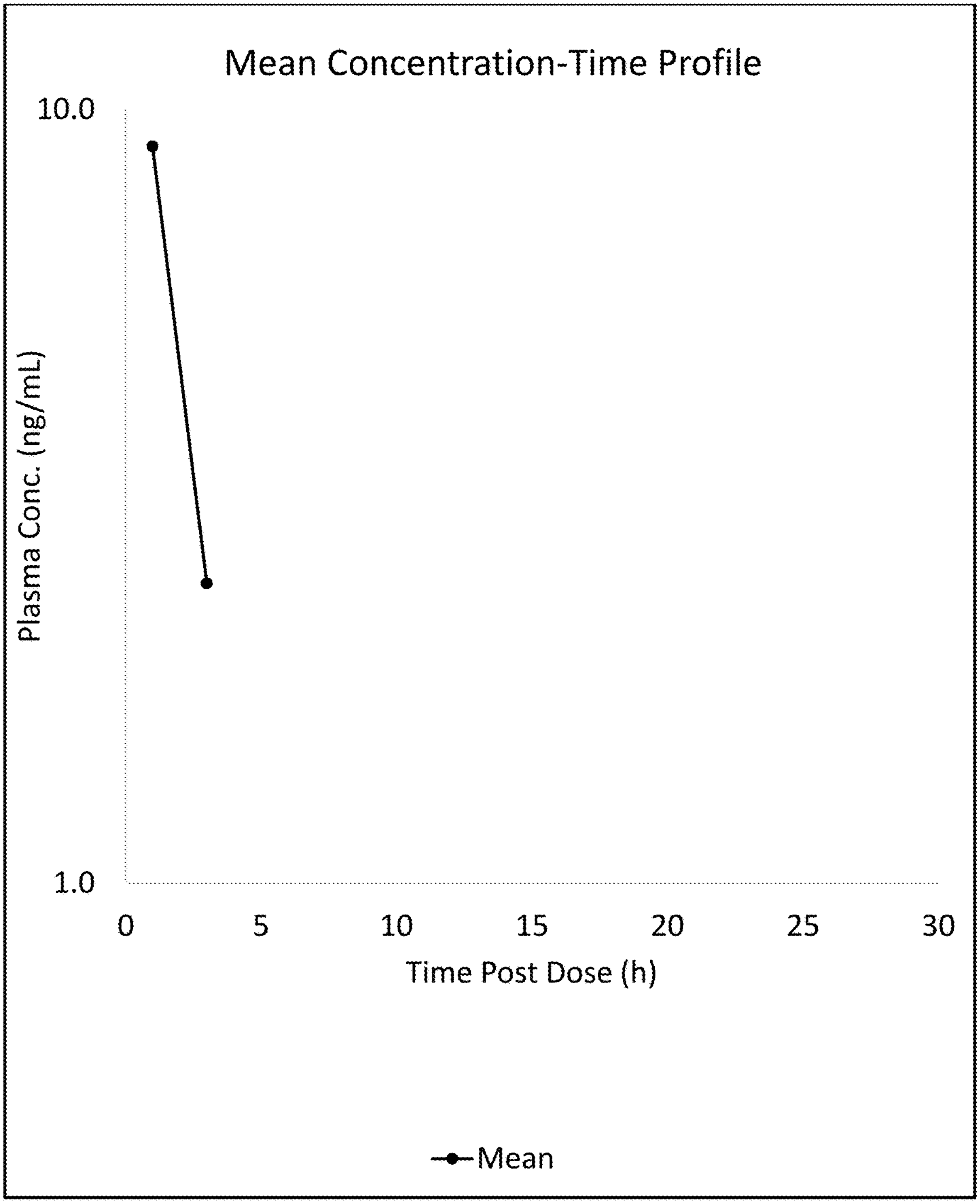
FIG. 84 shows mean concentration-time profiles of xanomeline following PO dosing of xanomeline methyl pentanoate chloride prodrug (10 mg/kg of xanomeline) to male SD rats.

FIG. 84 shows mean concentration-time profiles of xanomeline following PO dosing of xanomeline methyl pentanoate chloride prodrug (10 mg/kg of xanomeline) to male SD rats.

Example A-7-19: Xanomeline Methyl Hexanoate Chloride Prodrug—Table 1 Compound 5

| | |
|---|---|
| Species: | Rat |
| Dose Route: | PO |
| Dose Level (mg/kg) | 10 mg/kg of xanomeline |

Chemical name: 1-[(hexanoyloxy)methyl]-1-methyl-5-[4-(hexyloxy-1,2,5-thiadiazol-3-yl)]-1,2,3,6-tetrahydropyridin-1-ium chloride Structural class: acyloxymethyl Mechanistic class: presumed esterase+chemical breakdown

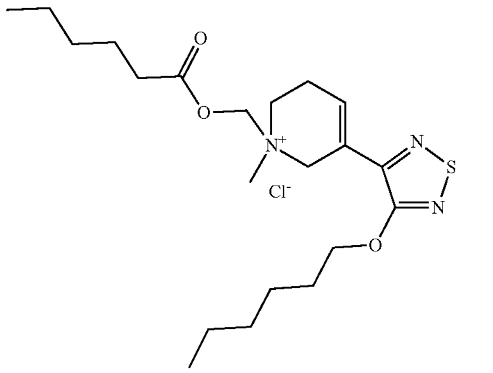 [SMILES: CCCCCCOc1nsnc1C1=CCC[N+](C)(COC(=O)CCCCC)C1 ; [Cl-]]

TABLE 94

| Xanomeline Pharmacokinetic Parameters | | | | | | | | | |
|---|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R4 | NR | 1.00 | 7.12 | 1.00 | 3.56 | NR |
| | | R5 | NR | 1.00 | 14.7 | 24.0 | 7.35 | NR |
| | | R6 | NR | 1.00 | 7.41 | 1.00 | 3.71 | NR |
| | | Mean | NR | 1.00 | 9.74 | 8.67 | 4.87 | NR |

Figure 85:
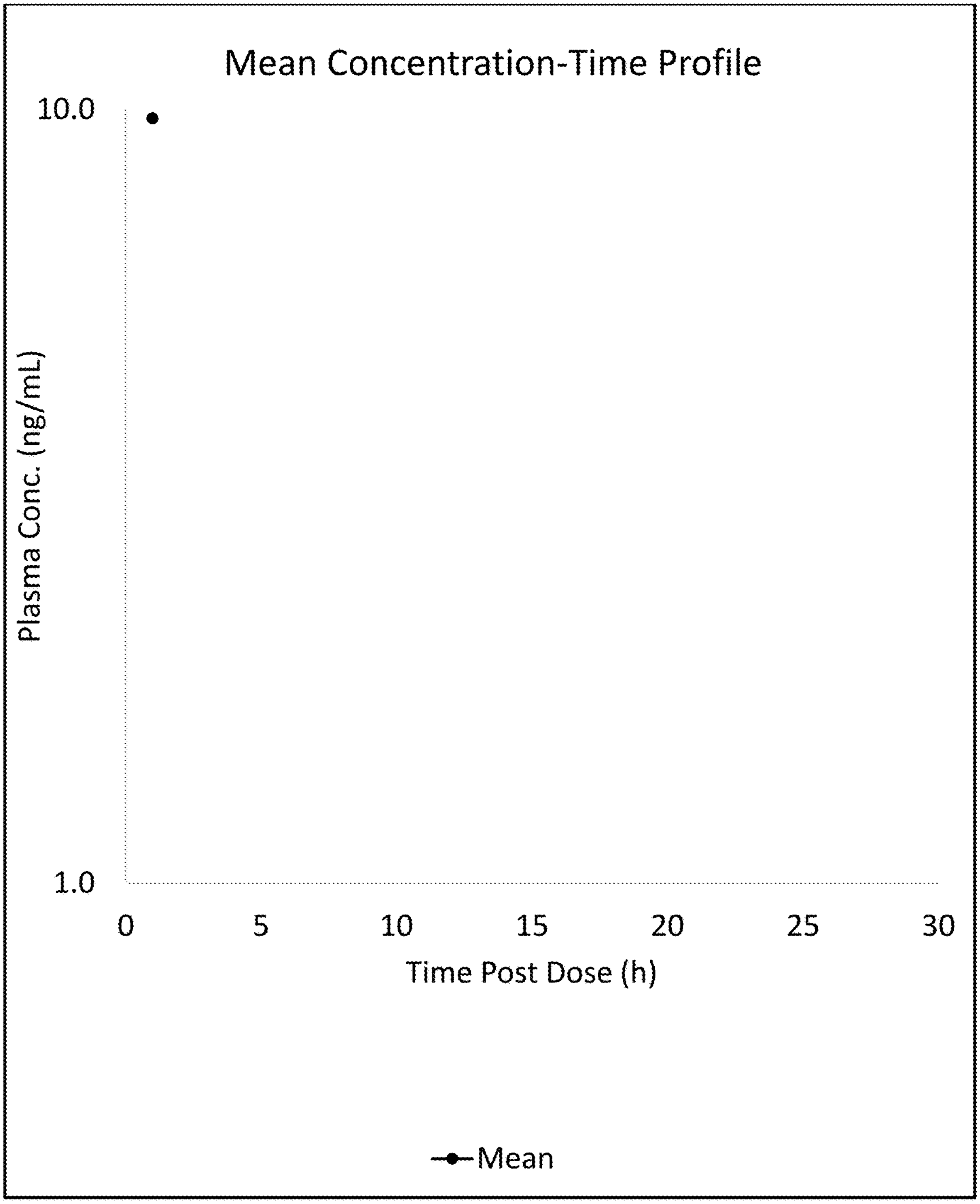
FIG. 85 shows mean concentration-time profiles of xanomeline following PO dosing of xanomeline methyl hexanoate chloride prodrug (10 mg/kg of xanomeline) to male SD rats.

FIG. 85 shows mean concentration-time profiles of xanomeline following PO dosing of xanomeline methyl hexanoate chloride prodrug (10 mg/kg of xanomeline) to male SD rats.

Example A-7-20: Xanomeline Methyl Pentadecanoate Chloride Prodrug—Table 1 Compound 14

| | |
|---|---|
| Species: | Rat |
| Dose Route: | PO |
| Dose Level (mg/kg) | 10 mg/kg of xanomeline |

Chemical name: 1-methyl-1[(pentadecanoyloxy)methyl]-5-4-(hexyloxy-1,2,5-thiadiazol-3-yl)-1,2,3,6-tetrahydropyridin-1-ium chloride Structural class: acyloxymethyl Mechanistic class: presumed esterase+chemical breakdown

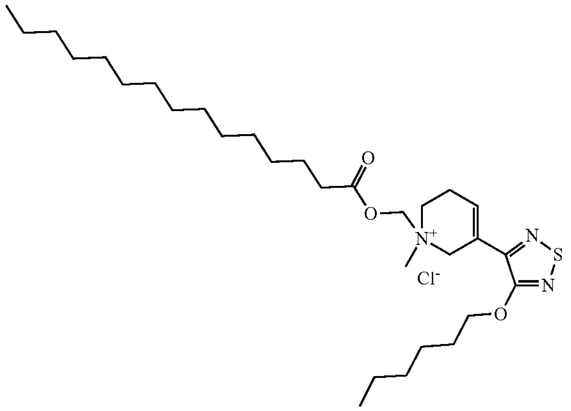 [SMILES: CCCCCCCCCCCCCCC(=O)OC[N+]1(C)CCC=C(c2nsnc2OCCCCCC)C1 ; [Cl-]]

TABLE 95

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R7 | NR | 3.00 | 3.71 | 3.00 | 5.57 | NR |
| | | R8 | NR | NR | NR | NR | NR | NR |
| | | R9 | NR | 1.00 | 4.41 | 3.00 | 7.26 | NR |
| | | Mean | NR | 1.33 | 2.71 | 2.00 | 4.28 | NR |

Figure 86:
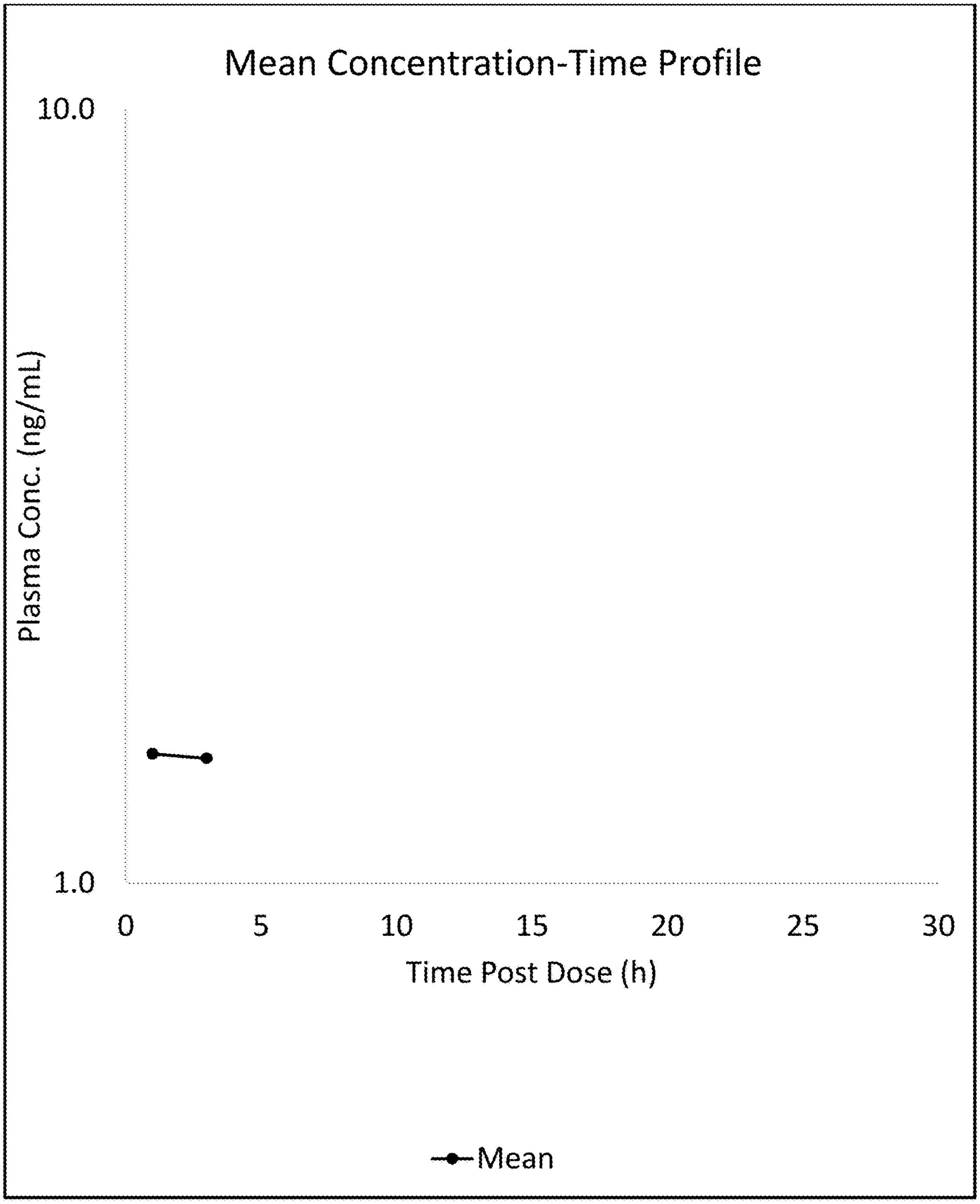
FIG. 86 shows mean concentration-time profiles of xanomeline following PO dosing of xanomeline methyl pentadecanoate chloride prodrug (10 mg/kg of xanomeline) to male SD rats.

FIG. 86 shows mean concentration-time profiles of xanomeline following PO dosing of xanomeline methyl pentadecanoate chloride prodrug (10 mg/kg of xanomeline) to male SD rats.

Example A-7-21: Xanomeline Methyl Neopentanoate Chloride Prodrug—Table 1 Compound 18

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl 3-methylbutanoate chloride Structural class: acyloxymethyl Mechanistic class: presumed esterase+chemical breakdown

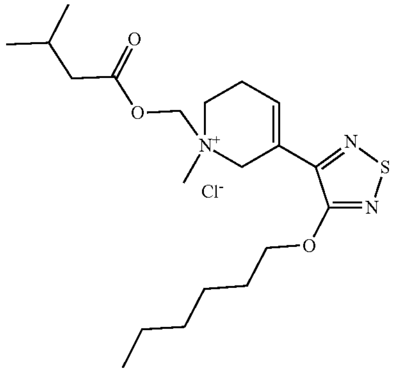 [SMILES: CCCCCCOc1nsnc1C1=CCC[N+](C)(COC(=O)CC(C)C)C1 ; [Cl-]]

TABLE 96

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | PO | R10 | NR | 1.00 | 2.24 | 1.00 | 1.12 | NR |
| | | R11 | NR | 1.00 | 1.04 | 1.00 | 0.520 | NR |
| | | R12 | NR | 1.00 | 3.06 | 3.00 | 5.73 | NR |
| | | Mean | NR | 1.00 | 2.11 | 1.67 | 2.46 | NR |

Figure 87:
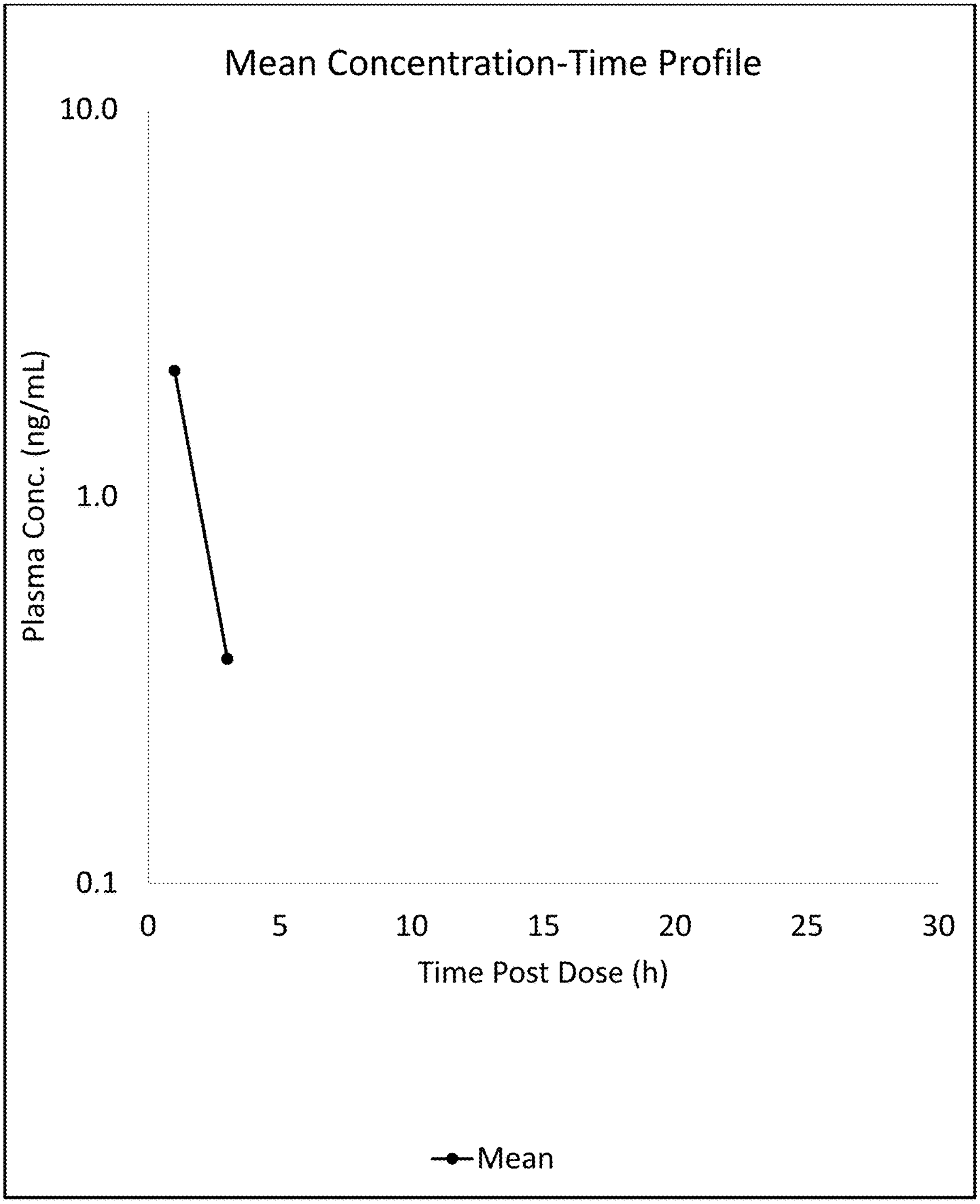
FIG. 87 shows mean concentration-time profiles of xanomeline following PO dosing of xanomeline methyl neopentanoate chloride prodrug (10 mg/kg of xanomeline) to male SD rats.

FIG. 87 shows mean concentration-time profiles of xanomeline following PG dosing of xanomeline methyl neopentanoate chloride prodrug (10 mg/kg of xanomeline) to male SD rats.

Example A-7-22: Xanomeline Methyl "Tert-Butanoate" Iodide Prodrug—Table 1 Compound 16

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl 2,2-dimethylpropanoate iodide Structural class: acyloxymethyl Mechanistic class: presumed esterase+chemical breakdown

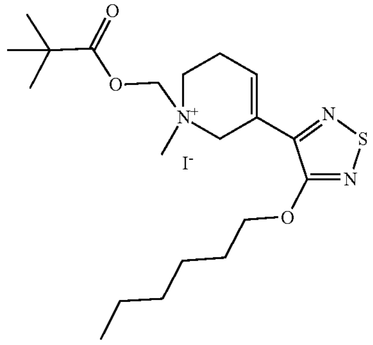 [SMILES: CCCCCCOc1nsnc1C1=CCC[N+](C)(COC(=O)C(C)(C)C)C1 ; [I-]]

TABLE 97

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R13 | NR | NR | NR | NR | NR | NR |
| | | R14 | NR | NR | NR | NR | NR | NR |
| | | R15 | NR | 1.00 | 0.732 | 1.00 | 0.366 | NR |
| | | Mean | NR | 0.333 | 0.244 | 0.333 | 0.122 | NR |

Figure 88:
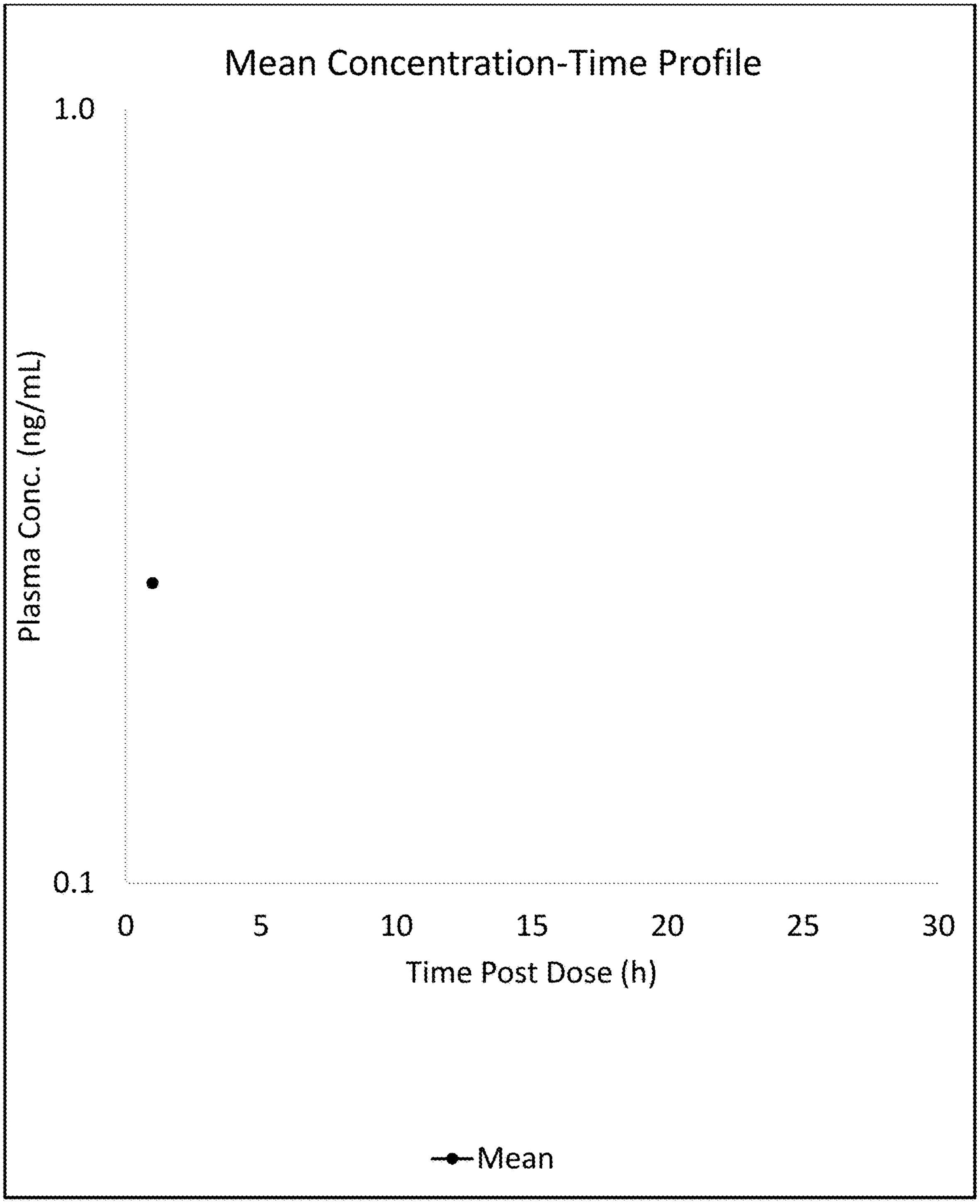
FIG. 88 shows mean concentration-time profiles of xanomeline following PO dosing of xanomeline methyl "tert-butanoate" iodide prodrug (10 mg/kg of xanomeline) to male SD rats.

FIG. 88 shows mean concentration-time profiles of xanomeline following PO dosing of xanomeline methyl “tert-butanoate” iodide prodrug (10 mg/kg of xanomeline) to male SD rats.

Example A-7-23: Xanomeline Methyl Propylcarbonate Chloride Prodrug—Table 1 Compound 24

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl propyl carbonate chloride Structural class: alkoxycarbonyloxymethyl Mechanistic class: presumed esterase+chemical breakdown

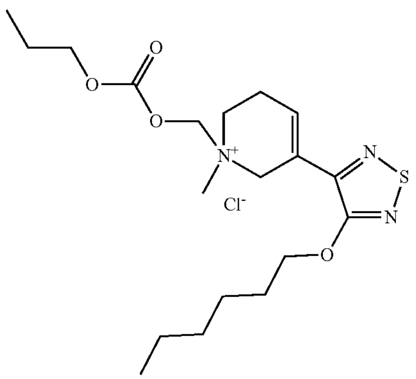 [SMILES: CCCCCCOc1nsnc1C1=CCC[N+](C)(COC(=O)OCCC)C1 ; [Cl-]]

TABLE 98

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | PO | R16 | NR | 3.00 | 13.6 | 7.00 | 56.5 | NR |
| | | R17 | NR | 1.00 | 5.75 | 3.00 | 10.7 | NR |
| | | R18 | NR | 1.00 | 3.34 | 3.00 | 5.72 | NR |
| | | Mean | NR | 1.67 | 7.56 | 4.33 | 24.3 | NR |

Figure 89:
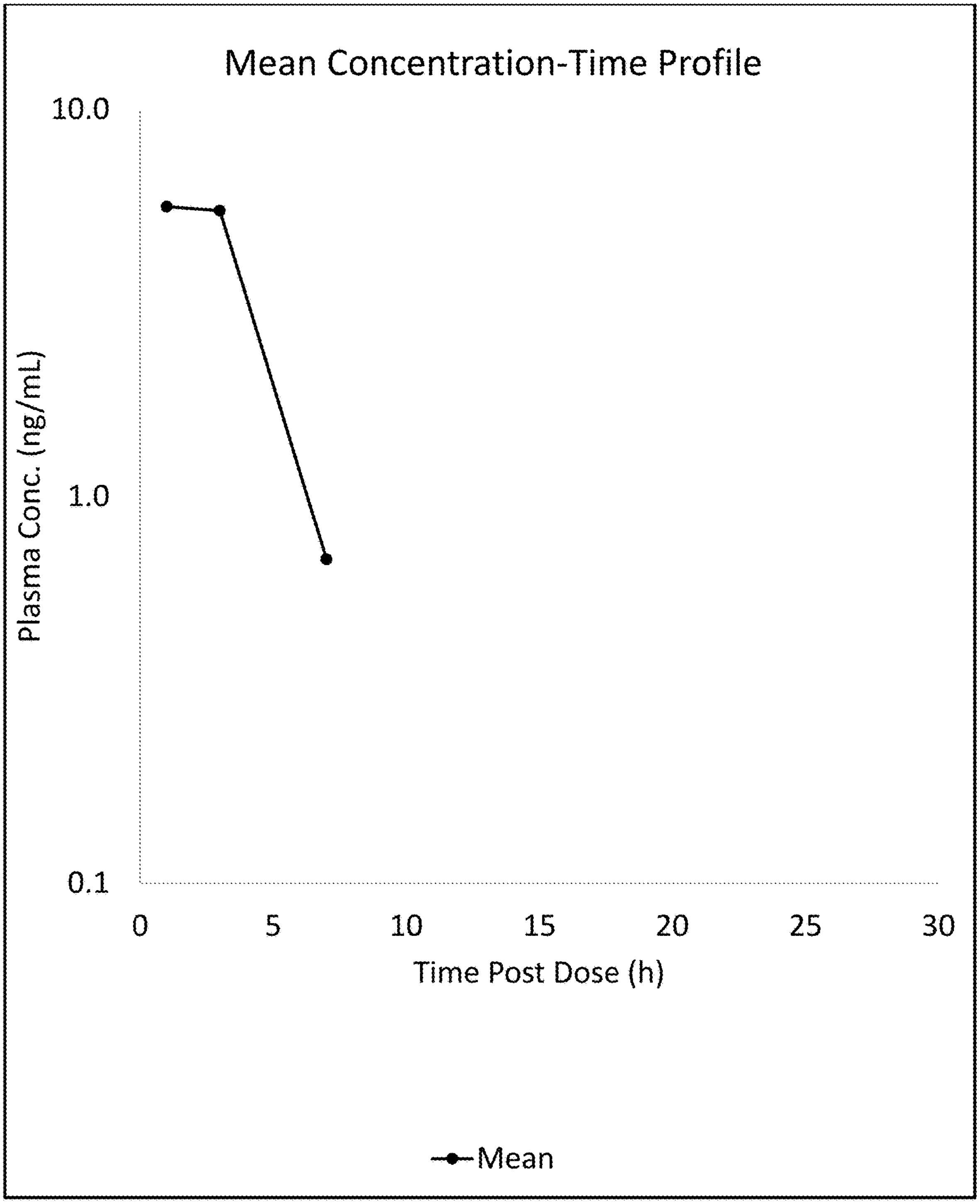
FIG. 89 shows mean concentration-time profiles of xanomeline following PO dosing of xanomeline methyl propylcarbonate chloride prodrug (10 mg/kg of xanomeline) to male SD rats.

FIG. 89 shows mean concentration-time profiles of xanomeline following PO dosing of xanomeline methyl propylcarbonate chloride prodrug (10 mg/kg of xanomeline) to male SD rats.

Example A-7-24: Xanomeline Methyl Butylcarbonate Chloride Prodrug—Table 1 Compound

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl butyl carbonate chloride Structural class: alkoxycarbonyloxymethyl Mechanistic class: presumed esterase+chemical breakdown

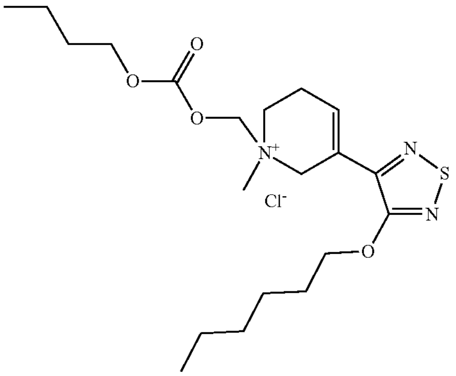 [SMILES: CCCCCCOc1nsnc1C1=CCC[N+](C)(COC(=O)OCCCC)C1 ; [Cl-]]

TABLE 99

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R19 | NR | 1.00 | 6.35 | 1.00 | 3.18 | NR |
| | | R20 | 10.60 | 1.00 | 4.05 | 24.00 | 63.5 | 77.3 |
| | | R21 | NR | 1.00 | 5.27 | 1.00 | 2.64 | NR |
| | | Mean | 3.53 | 1.00 | 5.22 | 8.67 | 23.1 | 25.8 |

Figure 90:
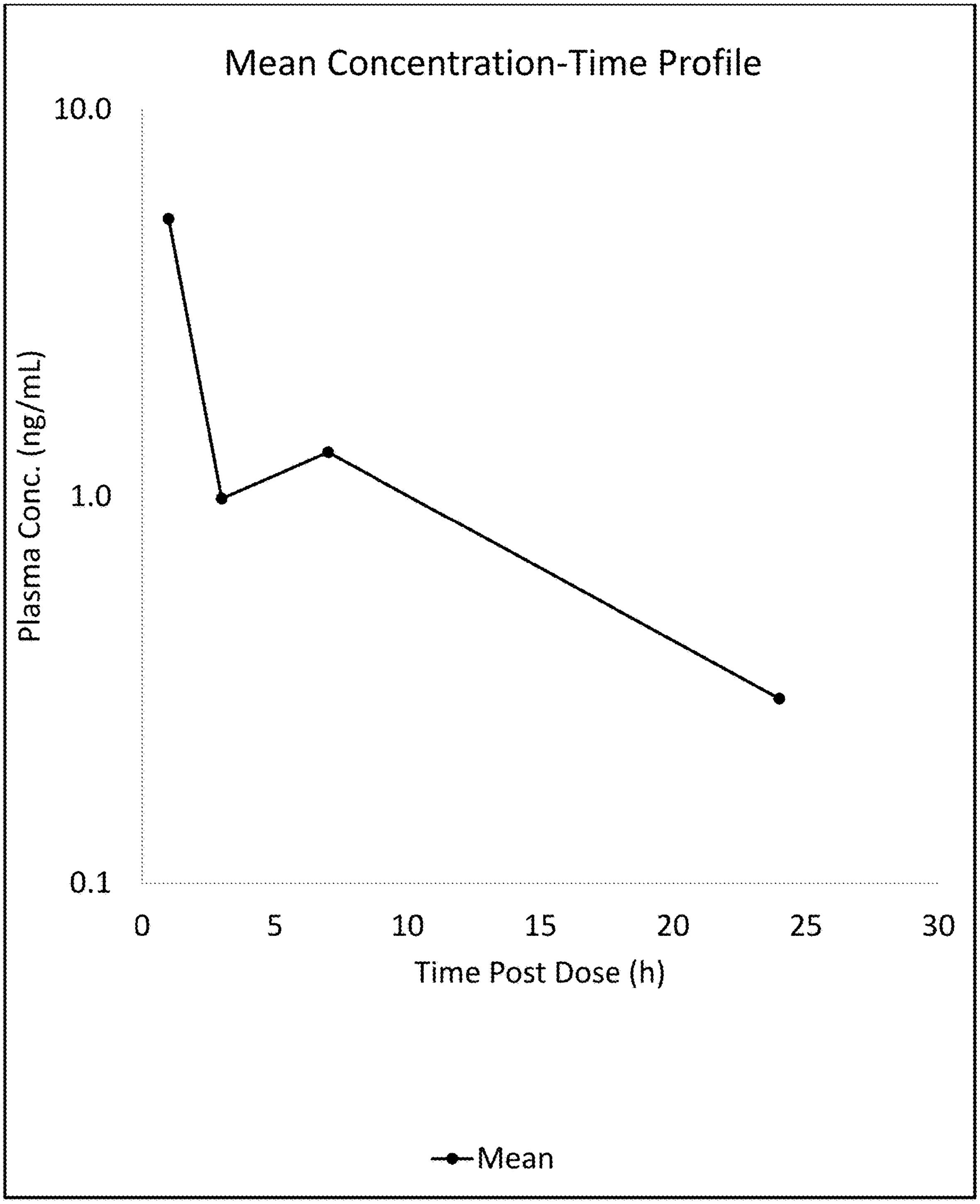
FIG. 90 shows mean concentration-time profiles of xanomeline following PO dosing of xanomeline methyl butylcarbonate chloride prodrug (10 mg/kg of xanomeline) to male SD rats.

FIG. 90 shows mean concentration-time profiles of xanomeline following PO dosing of xanomeline methyl butylcarbonate chloride prodrug (10 mg/kg of xanomeline) to male SD rats.

Example A-7-25: Xanomeline Methyl Pentylcarbonate Chloride Prodrug—Table 1 Compound 26

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl pentyl carbonate chloride Structural class: alkoxycarbonyloxymethyl Mechanistic class: presumed esterase+chemical breakdown

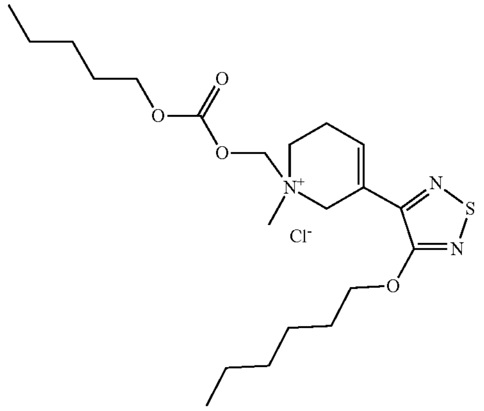 [SMILES: CCCCCCOc1nsnc1C1=CCC[N+](C)(COC(=O)OCCCCC)C1 ; [Cl-]]

TABLE 100

| Mean Concentration-Time Profile of Metabolite Xanomeline Following PO Dosing of Xanomeline Pentylmethylene Carbonate Chloride Prodrug | | | | |
|---|---|---|---|---|
| Bioanalytical Data: | Plasma Concentrations (ng/mL) Following Oral Dosing Animal | | | |
| Time (h) | R22 | R23 | R24 | Mean |
| 1.00 | BLQ | BLQ | BLQ | BLQ |
| 3.00 | BLQ | BLQ | BLQ | BLQ |

TABLE 100-continued

| Mean Concentration-Time Profile of Metabolite Xanomeline Following PO Dosing of Xanomeline Pentylmethylene Carbonate Chloride Prodrug | | | | |
|---|---|---|---|---|
| Bioanalytical Data: | Plasma Concentrations (ng/mL) Following Oral Dosing Animal | | | |
| Time (h) | R22 | R23 | R24 | Mean |
| 7.00 | BLQ | BLQ | BLQ | BLQ |
| 24.0 | BLQ | BLQ | BLQ | BLQ |

BLQ: Below Lower Limit of Quantification (0.5 ng/mL)

Example A-7-26: Xanomeline Methyl Hexylcarbonate Chloride Prodrug—Table 1 Compound

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl hexyl carbonate chloride Structural class: alkoxycarbonyloxymethyl Mechanistic class. presumed esterase+chemical breakdown

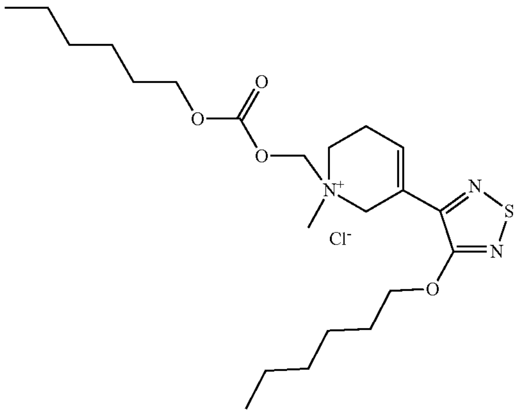 [SMILES: CCCCCCOC(=O)OC[N+]1(C)CCC=C(c2nsnc2OCCCCCC)C1 ; [Cl-]]

TABLE 101

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | PO | R25 | NR | 1.00 | 1.66 | 1.00 | 0.830 | NR |
| | | R26 | NR | NR | NR | NR | NR | NR |
| | | R27 | NR | 1.00 | 5.57 | 7.00 | 25.3 | NR |
| | | Mean | NR | 0.667 | 2.41 | 2.67 | 8.71 | NR |

Figure 91:
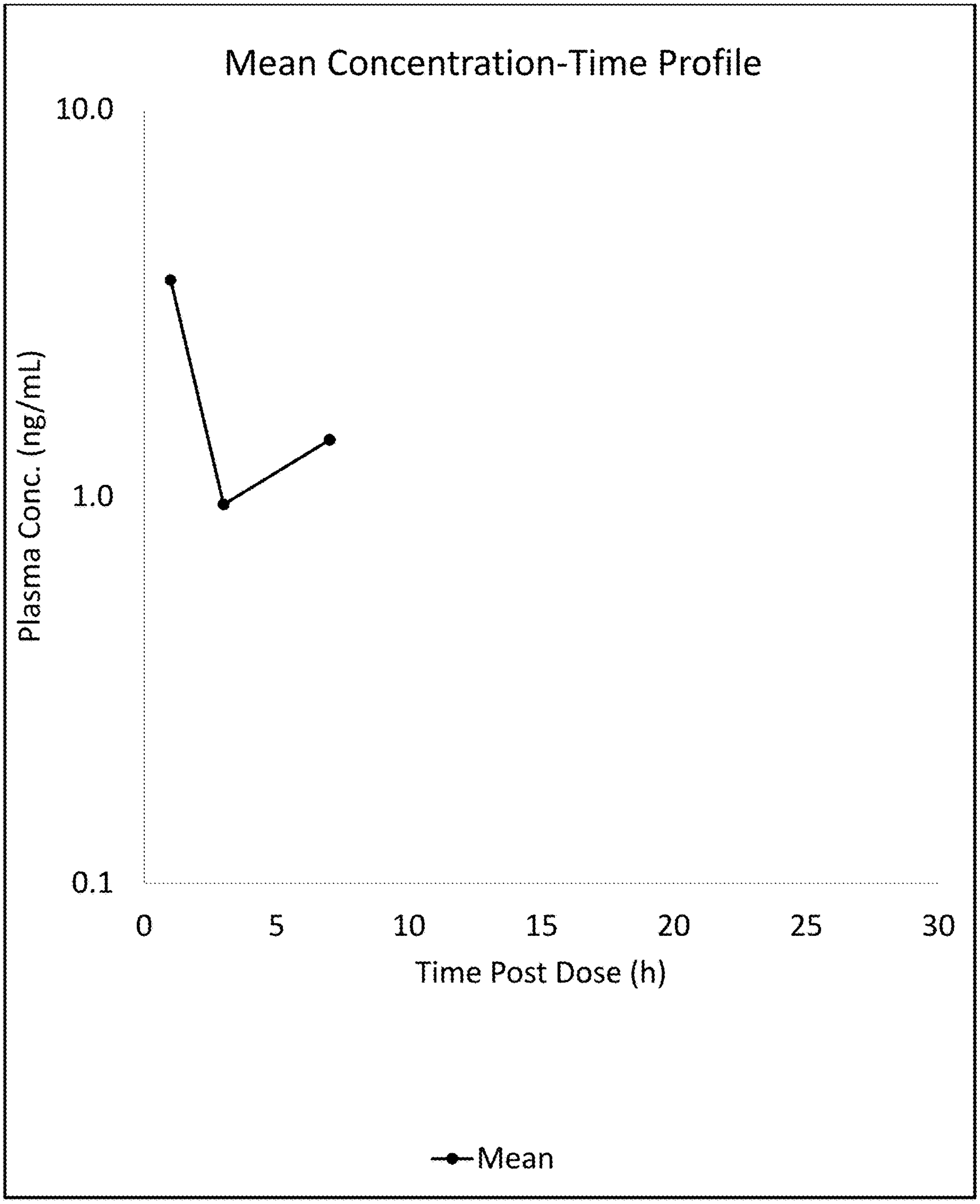
FIG. 91 shows mean concentration-time profiles of xanomeline following PO dosing of xanomeline methyl hexylcarbonate chloride prodrug (10 mg/kg of xanomeline) to male SD rats.

FIG. 91 shows mean concentration-time profiles of xanomeline following PO dosing of xanomeline methyl hexylcarbonate chloride prodrug (10 mg/kg of xanomeline) to male SD rats.

Example A-7-27: Xanomeline Methyl Decatettarylcarbonate Chloride Prodrug—Table 1 Compound 35

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl tetradecane carbonate chloride Structural class: alkoxycarbonyloxymethyl Mechanistic class: presumed esterase+chemical breakdown

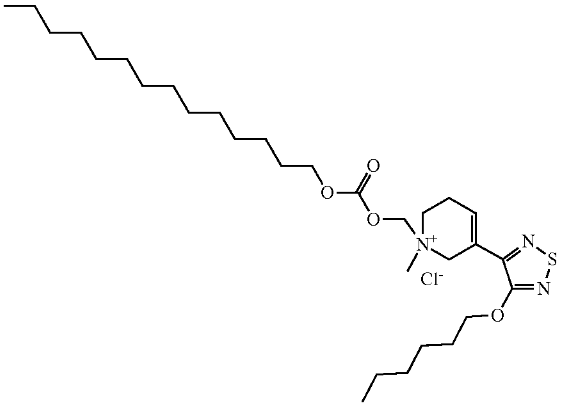 [SMILES: CCCCCCCCCCCCCCOC(=O)OC[N+]1(C)CCC=C(c2nsnc2OCCCCCC)C1 ; [Cl-]]

TABLE 102

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/ml) | Tlast (hr) | AUClast (ng/ml*hr) | AUCINF_obs (ng/ml*hr) |
| Xanomeline | PO | R28 | NR | NR | NR | NR | NR | NR |
| | | R29 | NR | 1.00 | 3.60 | 1.00 | 1.80 | NR |
| | | R30 | NR | NR | NR | NR | NR | NR |
| | | Mean | NR | 0.333 | 1.20 | 0.333 | 0.600 | NR |

Figure 92:
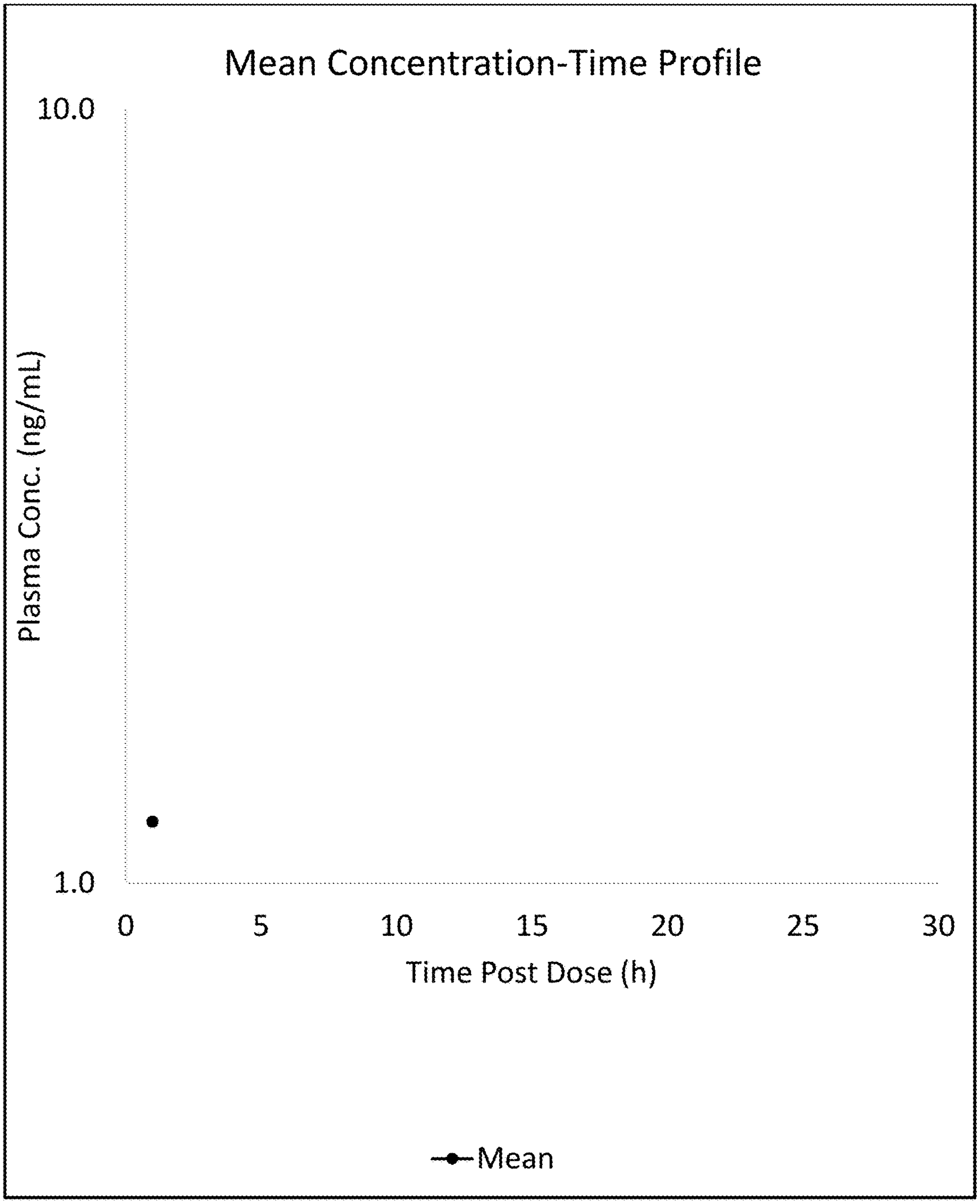
FIG. 92 shows mean concentration-time profiles of xanomeline following PO dosing of xanomeline methyl decatettarylcarbonate chloride prodrug (10 mg/kg of xanomeline) to male SD rats.

FIG. 92 shows mean concentration-time profiles of xanomeline following PO dosing of xanomeline methyl decatettarylcarbonate chloride prodrug (10 mg/kg of xanomeline) to male SD rats.

Example A-7-28: Xanomeline Methyl Isopropylcarbonate Chloride Prodrug—Table 1 Compound 38

| | |
|---|---|
| Species: | Rat |
| Dose Route: | PO |
| Dose Level (mg/kg) | 10 mg/kg of xanomeline |

Chemical name: 1-methyl-5-[4-(hexyloxy)-1,2-5-thiadiazol-3-yl]-1-([(propan-2-yloxy)carbonyl]oxy)methyl-1,2,3,6-tetrahydropyridin-1-ium chloride Structural class: alkoxycarbonyloxymethyl Mechanistic class: presumed esterase+chemical breakdown

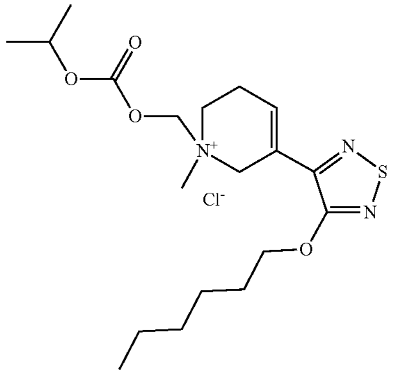 [SMILES: CCCCCCOc1nsnc1C1=CCC[N+](C)(COC(=O)OC(C)C)C1 ; [Cl-]]

TABLE 103

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R31 | NR | 1.00 | 0.653 | 1.00 | 0.327 | NR |
| | | R32 | NR | 1.00 | 4.73 | 1.00 | 2.37 | NR |
| | | R33 | NR | 1.00 | 9.45 | 1.00 | 4.73 | NR |
| | | Mean | NR | 1.00 | 4.94 | 1.00 | 2.48 | NR |

Figure 93:
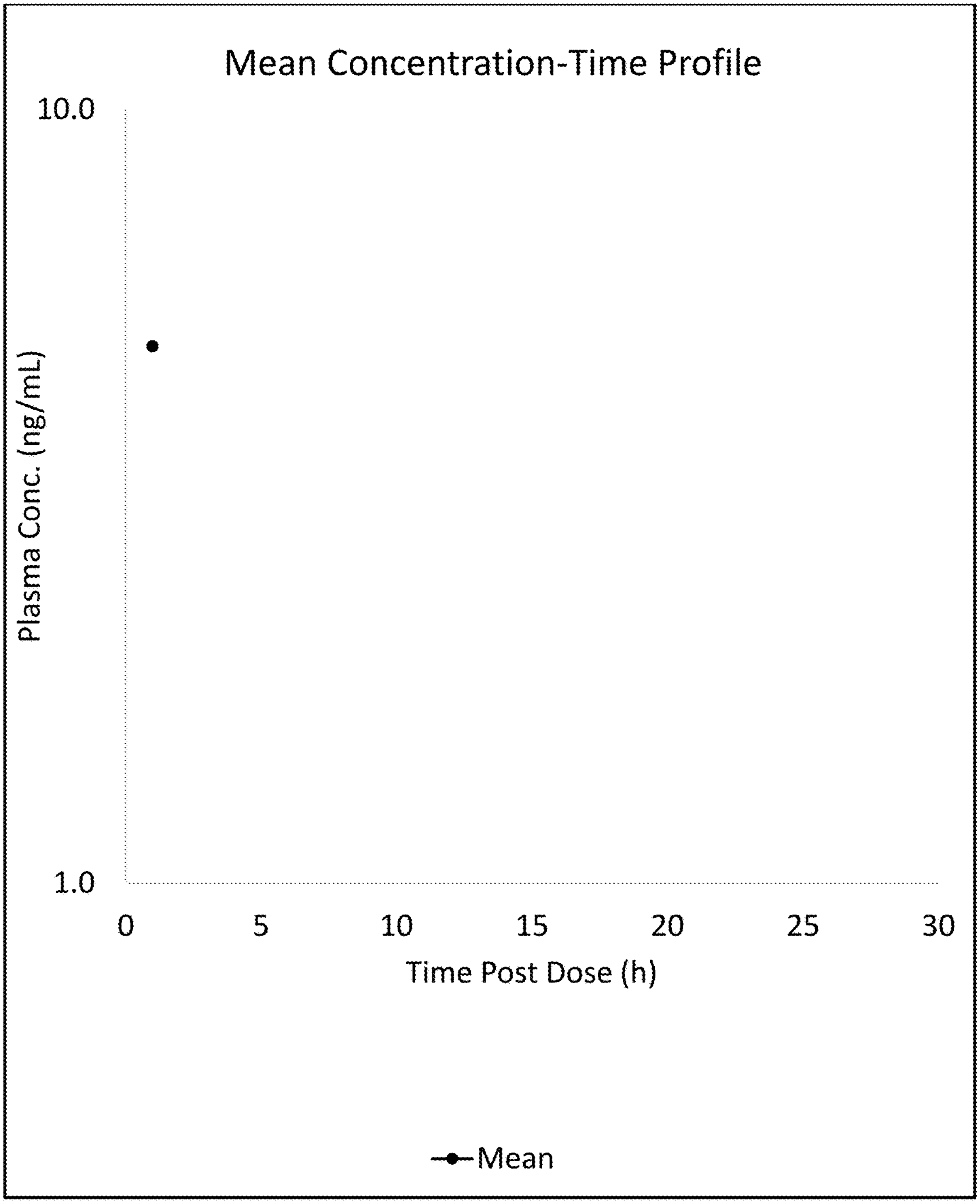
FIG. 93 shows mean concentration-time profiles of xanomeline following PO dosing of xanomeline methyl isopropylcarbonate chloride prodrug (10 mg/kg of xanomeline) to male SD rats.

FIG. 93 shows mean concentration-time profiles of xanomeline following PO dosing of xanomeline methyl isopropylcarbonate chloride prodrug (10 mg/kg of xanomeline) to male SD rats.

Example A-7-29: Xanomeline methyl isobutylcarbonate chloride prodrug—Table 1 Compound 39

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methyl isobutyl carbonate chloride Structural class: alkoxycarbonyloxymethyl Mechanistic class: presumed esterase+chemical breakdown

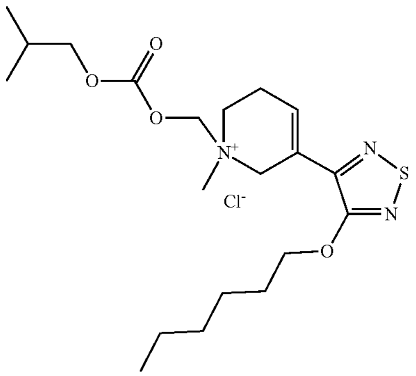 [SMILES: CCCCCCOc1nsnc1C1=CCC[N+](C)(COC(=O)OCC(C)C)C1 ; [Cl-]]

TABLE 104

| Xanomeline Pharmacokinetic Parameters | | | | | | | | |
|---|---|---|---|---|---|---|---|---|
| Analyte | Dose Route | Animal ID | T1/2 (hr) | Tmax (hr) | Cmax (ng/mL) | Tlast (hr) | AUClast (ng/ml*hr) | AUCINF_obs (ng/ml*hr) |
| Xanomeline | PO | R34 | NR | NR | NR | NR | NR | NR |
| | | R35 | NR | 1.00 | 3.89 | 3.00 | 7.47 | NR |
| | | R36 | NR | NR | NR | NR | NR | NR |
| | | Mean | NR | 0.333 | 1.30 | 1.00 | 2.49 | NR |

Figure 94:
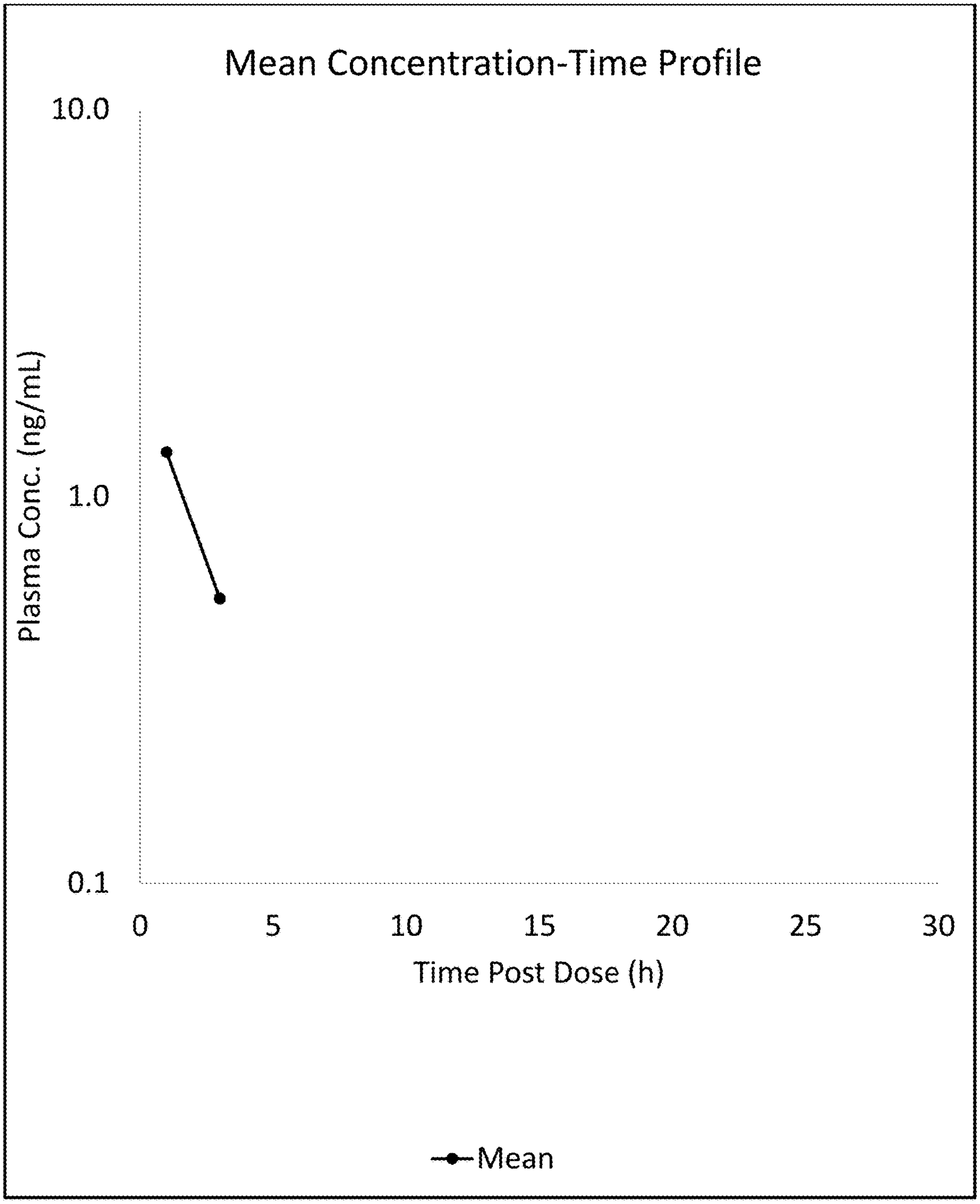
FIG. 94 shows mean concentration-time profiles of xanomeline following PO dosing of xanomeline methyl isobutylcarbonate chloride prodrug (10 mg/kg of xanomeline) to male SD rats.
Figure 95:
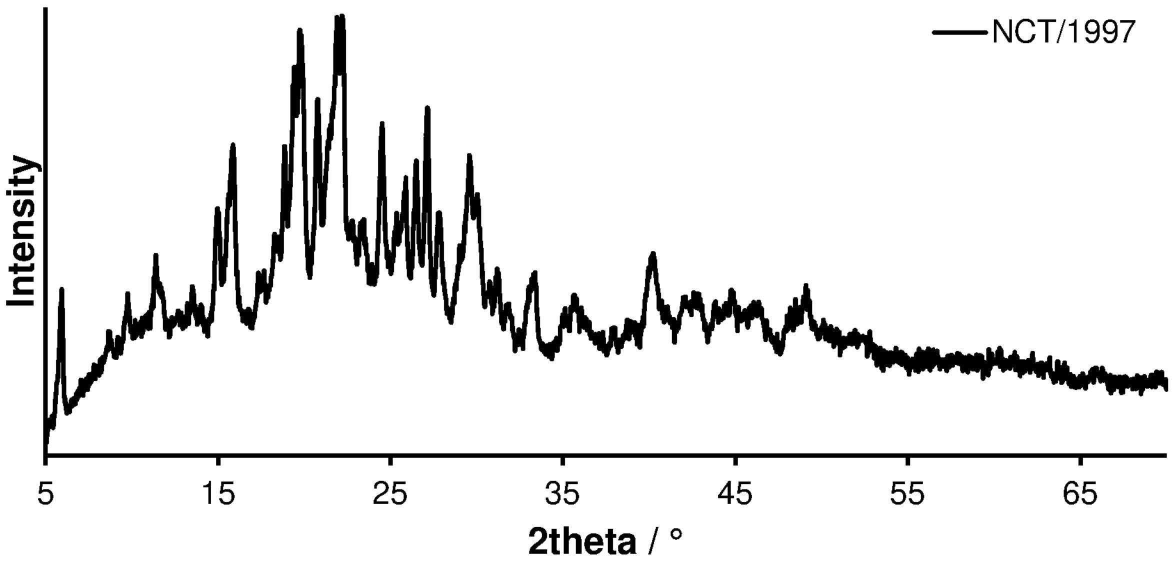
FIG. 95 shows an XRPD of xanomeline oxypropyl pivalate chloride prodrug in the 2theta range of 5-70°.
Figure 96:
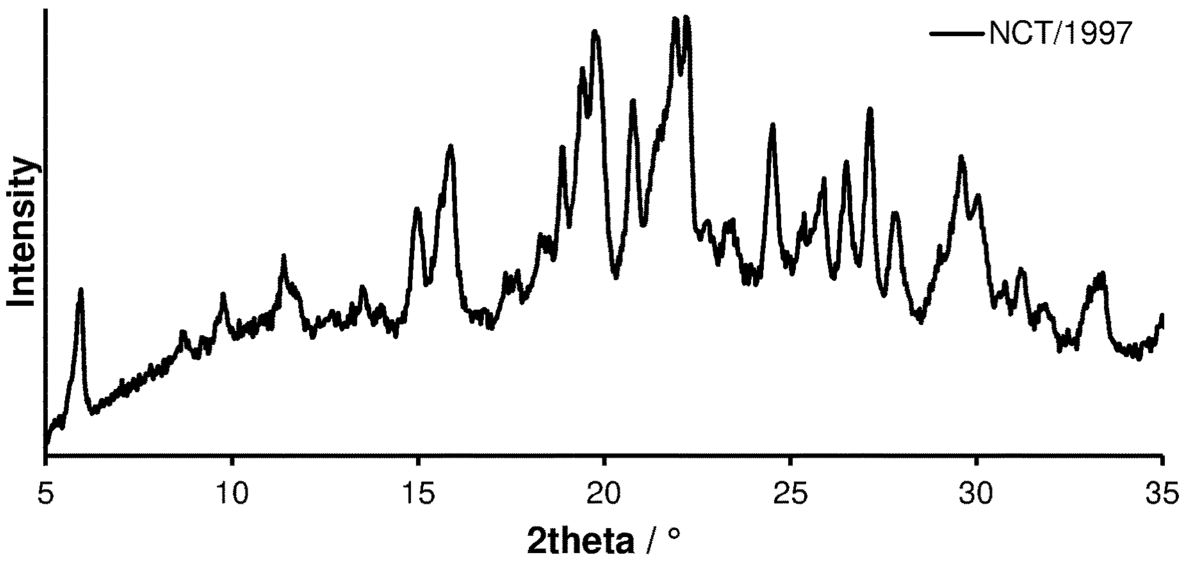
FIG. 96 shows an XRPD of xanomeline oxypropyl pivalate chloride prodrug in the 2theta range of 5-35°.
Figure 97:
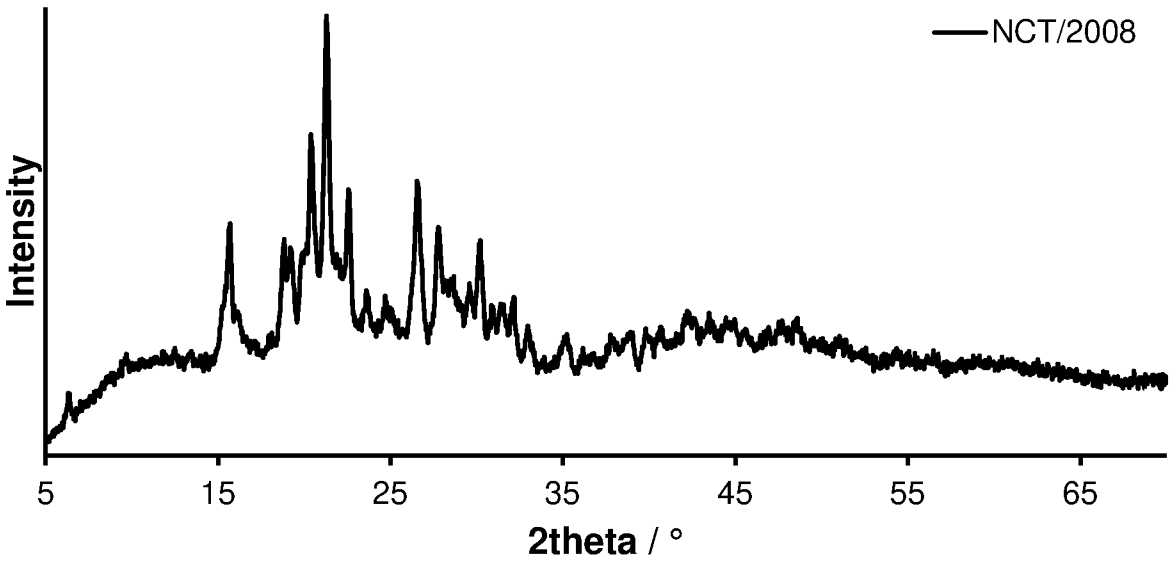
FIG. 97 shows an XRPD of xanomeline oxyethyl pivalate chloride prodrug in the 2theta range of 5-70°.
Figure 98:
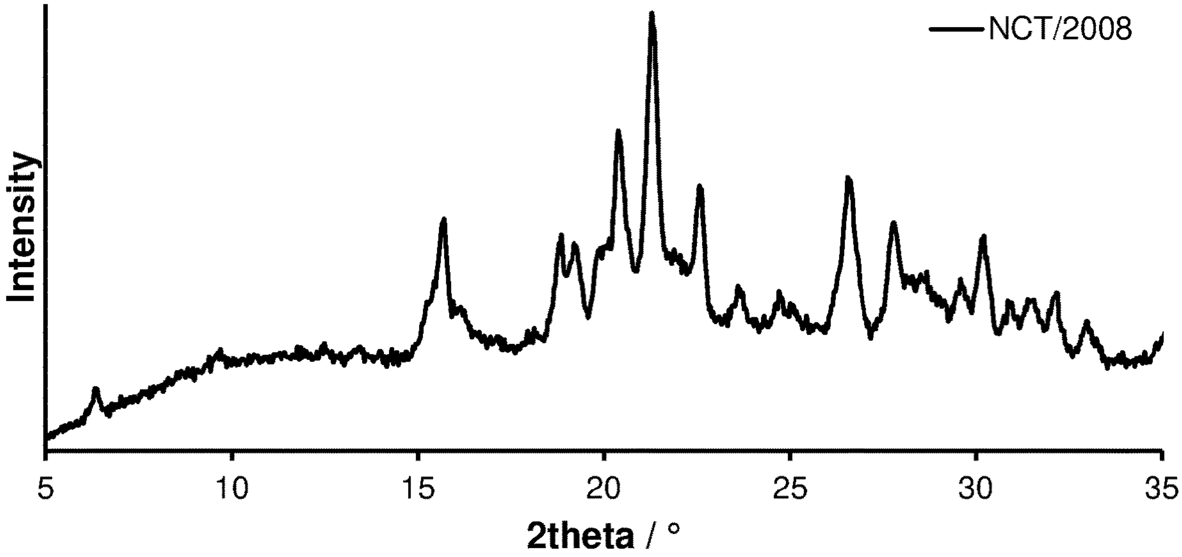
FIG. 98 shows an XRPD of xanomeline oxyethyl pivalate chloride prodrug in the 2theta range of 5-35°.

FIG. 94 shows mean concentration-time profiles of xanomeline following PG dosing of xanomeline methyl isobutylcarbonate chloride prodrug (10 mg/kg of xanomeline) to male SD rats.

Example A-7-30: Xanomeline Methyl Tri-Isopropylsilyl Ether Chloride Prodrug—Table 1 Compound 20

| | |
|---|---|
| Species: | Rat |
| Dose Route: | PO |
| Dose Level (mg/kg) | 10 mg/kg of xanomeline |

Chemical name: [5-(4-hexyloxy-1,2,5-thiadiazol-3-yl)-1-methyl-3,6-dihydro-2H-pyridin-1-ium-1-yl]methoxy-triisopropyl-silane chloride Structural class: silyloxymethyl Mechanistic class: presumed chemical breakdown

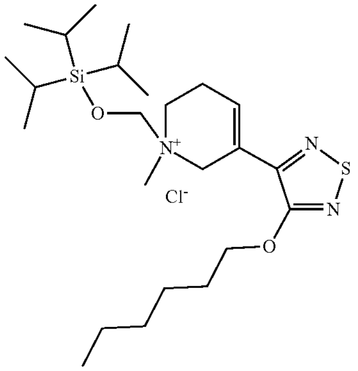 [SMILES: CCCCCCOc1nsnc1C1=CCC[N+](C)(CO[Si](C(C)C)(C(C)C)C(C)C)C1 ; [Cl-]]

TABLE 105

| Mean Concentration-Time Profile of Metabolite Xanomeline Following PO Dosing of Xanomeline Methyl Tri-Isopropylsilyl Ether Chloride Prodrug | | | | |
|---|---|---|---|---|
| Bioanalytical Data: | Plasma Concentrations (ng/mL) Following Oral Dosing Animal | | | |
| Time (h) | R37 | R38 | R39 | Mean |
| 1.00 | BLQ | BLQ | BLQ | BLQ |
| 3.00 | BLQ | BLQ | BLQ | BLQ |
| 7.00 | BLQ | BLQ | BLQ | BLQ |
| 24.0 | BLQ | BLQ | BLQ | BLQ |

BLQ: Below Lower Limit of Quantification (0.5 ng/mL)

Example B: Evaluation of Metabolic Stability in Human Liver Microsomes

Microsomal Assay: Human liver microsomes (20 mg/mL) are obtained. β-nicotinamide adenine dinucleotide phosphate, reduced form (NADPH), magnesium chloride ($MgCl_2$), and dimethyl sulfoxide (DMSO) are purchased.

Determination of Metabolic Stability: 7.5 mM stock solutions of test compounds of the above structural formula (e.g., of an embodiment or aspect of embodiment thereof described herein), or pharmaceutically acceptable salt thereof, are prepared in DMSO.

The 7.5 mM stock solutions are diluted to 12.5-50 μM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 μL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 4.0 mg/mL human liver microsomes, 0.25 μM test compound, and 2 mM NADPH in 0.1 M potassium phosphate buffer, pH 7.4, and 3 mM $MgCl_2$. The reaction mixtures are incubated at 37° C., and 50 pL aliquots are removed at 0, 5, 10, 20, and 30 minutes and added to shallow-well 96-well plates which contain 50 μL of ice-cold ACN (acetonitrile) with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-enriched counterpart of the compound and the positive control, 7-ethoxycoumarin (1 ptM). Testing is done in triplicate.

Data analysis: The in vitro T/s for test compounds are calculated from the slopes of the linear regression of % parent remaining (In) vs incubation time relationship.

$$\text{in vitro } T_{1/2}=0.693/k$$

k=−[slope of linear regression of % parent remaining (In) vs incubation time]

The apparent intrinsic clearance is calculated using the following equation: $CL_{int}$ (mL/min/kg)=(0.693/in vitro T) (Incubation Volume/mg of microsomes) (45 mg microsomes/gram of liver) (20 gm of liver/kg b.w.)

Data analysis is performed using Microsoft Excel Software.

In these experiments, values equal to or more than a 15% increase in half-life are considered to be a significant difference if the apparent intrinsic clearance ratio (prodrug of xanomeline or of an isotopically enriched analog of xanomeline/xanomeline) is >1.15 or <0.85, then there is considered to be significant differentiation.

What is claimed is:

1. A compound according to the following formula:

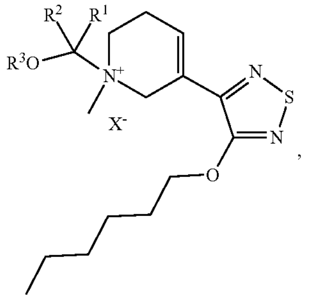

wherein:

$R^1$ and $R^2$ are independently selected from hydrogen and $C_{1-6}$ alkyl;

$R^3$ is —C(O)$R^5$;

$R^5$ is $C_{1-14}$ alkyl; and $X^-$ is a pharmaceutically acceptable counterion.

2. The compound of claim 1, wherein $R^1$ is H.

3. The compound of claim 1, wherein $R^2$ is $C_{1-2}$ alkyl.

4. The compound of claim 1, wherein:

(i) $R^1$ is H, and $R^2$ is $C_{1-2}$ alkyl; or (ii) $R^1$ is H, and $R^2$ is H.

5. The compound of claim 1, wherein $R^5$ is $C_{4-12}$ alkyl.

6. The compound of claim 1, wherein $R^5$ is $C_4$ alkyl, $C_7$ alkyl, or $C_{12}$ alkyl.

7. The compound of claim 1, wherein:

(i) $R^1$ is H, $R^2$ is H, and $R^5$ is $C_7$ alkyl or $C_{12}$ alkyl; or (ii) $R^1$ is H, $R^2$ is $C_{1-2}$ alkyl, and $R^5$ is $C_4$ alkyl.

8. The compound of claim 1, wherein the compound

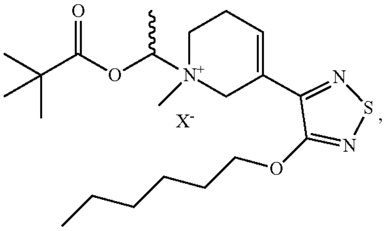

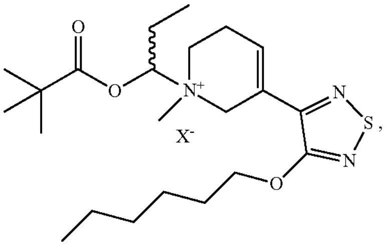

-continued
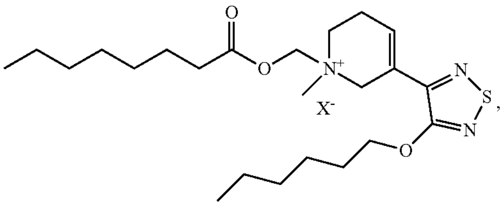
or
-continued
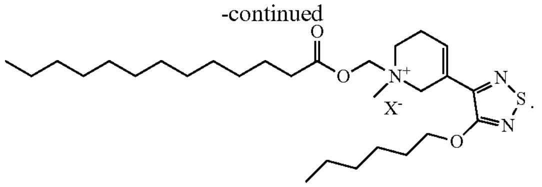
9. A pharmaceutical composition comprising the compound of claim 8 and a pharmaceutically acceptable excipient.
10. The compound of claim 1, wherein the compound is
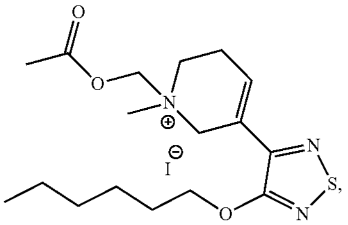
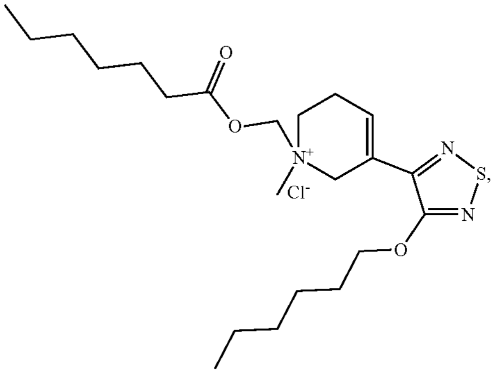
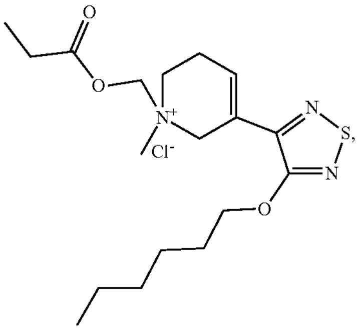
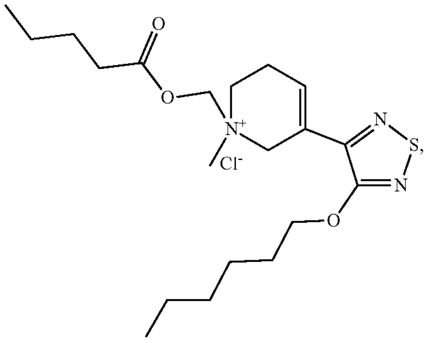
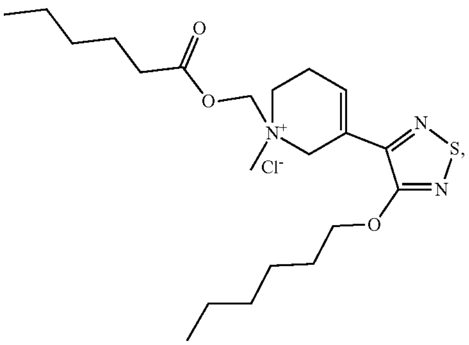
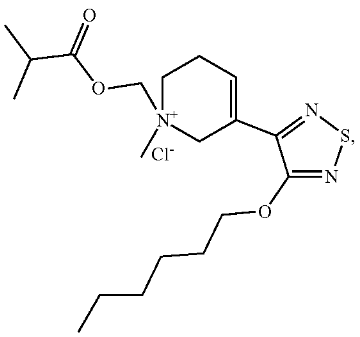

-continued
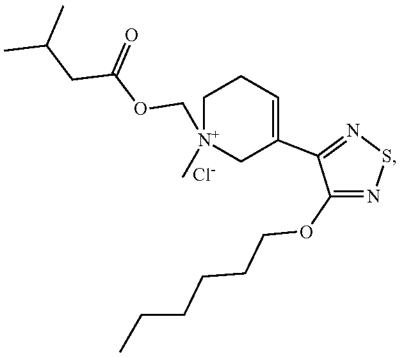
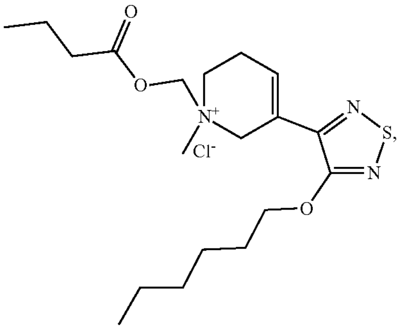
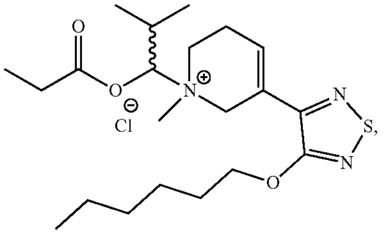
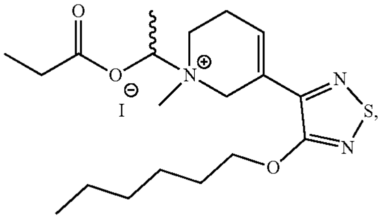
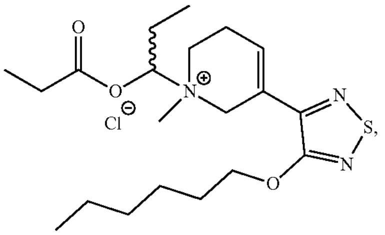
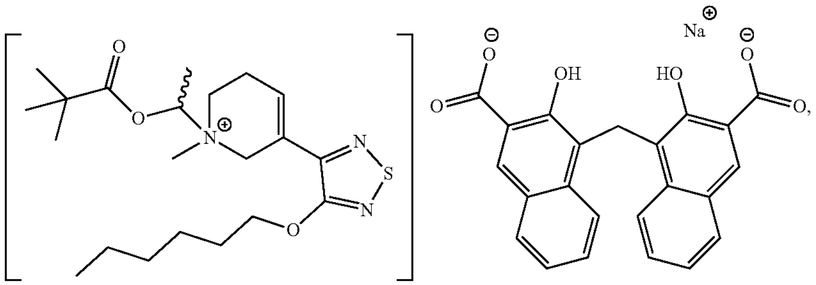
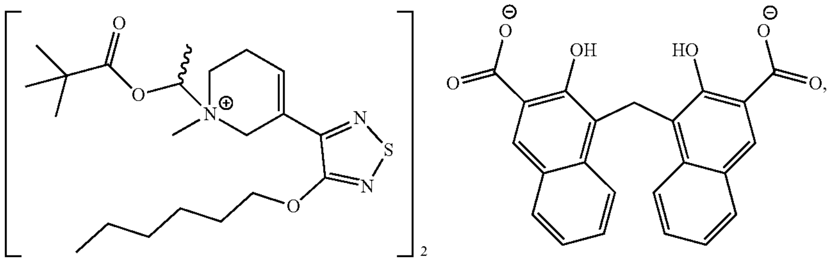

-continued

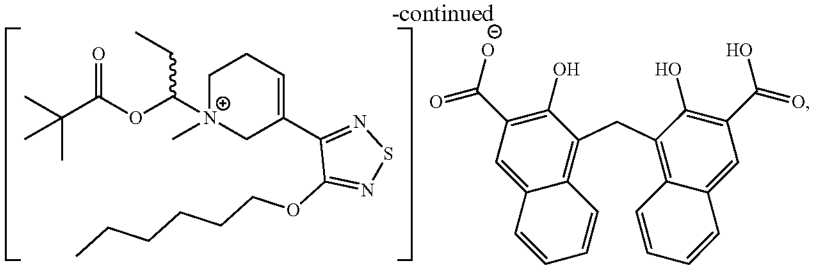

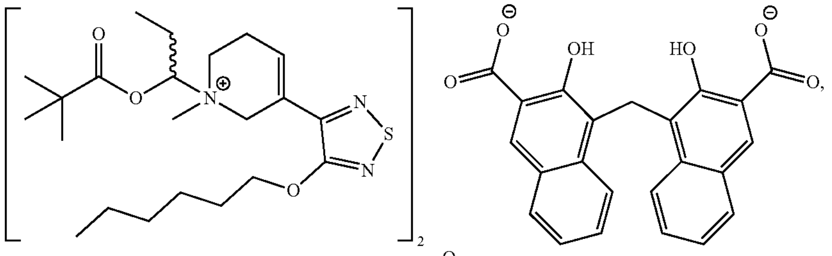

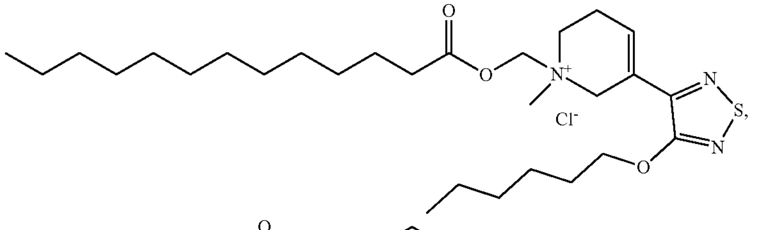

or

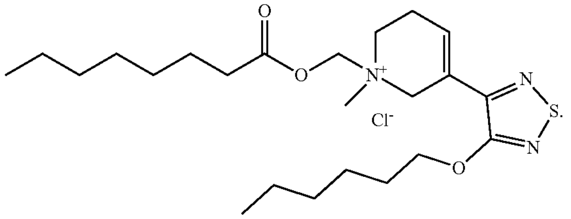

11. A pharmaceutical composition comprising the compound of claim 3 and a pharmaceutically acceptable excipient.

12. A method for treating a neuropsychiatric disease in a subject in need thereof, comprising administering an effective amount of the compound of claim 10 to the subject.

13. A method for treating a neuropsychiatric disease in a subject in need thereof, comprising administering an effective amount of the pharmaceutical composition of claim 11 to the subject.

14. The compound of claim 10, wherein the compound is

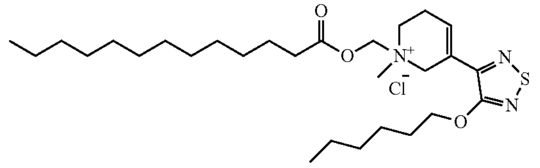

or

-continued

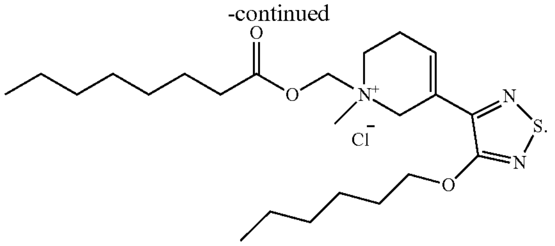

15. The compound of claim 14, wherein the compound is:

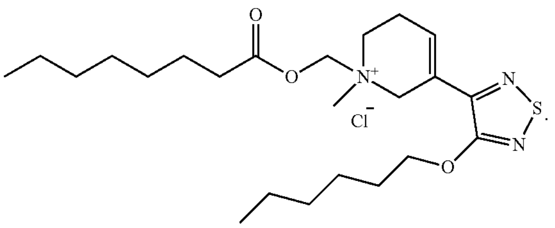 [SMILES: CCCCCCCC(=O)OC[N+]1(C)CCC=C(c2nsnc2OCCCCCC)C1 ; [Cl-]]

16. A pharmaceutical composition comprising the compound of claim 15 and a pharmaceutically acceptable excipient.

17. A method for treating a neuropsychiatric disease, in a subject in need thereof, comprising administering an effective amount of the compound of claim 15 to the subject.

18. A method for treating a neuropsychiatric disease in a subject in need thereof, comprising administering an effective amount of the pharmaceutical composition of claim 16 to the subject.

19. The compound of claim 14, wherein the compound is:

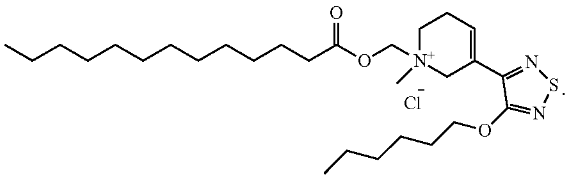 [SMILES: CCCCCCCCCCCCC(=O)OC[N+]1(C)CCC=C(c2nsnc2OCCCCCC)C1 ; [Cl-]]

20. A pharmaceutical composition comprising the compound of claim 19 and a pharmaceutically acceptable excipient.

21. A method for treating a neuropsychiatric disease in a subject in need thereof, comprising administering an effective amount of the compound of claim 19 to the subject.

22. A method for treating a neuropsychiatric disease in a subject in need thereof, comprising administering an effective amount of the pharmaceutical composition of claim 20 to the subject.

23. The compound of claim 1, wherein the compound is

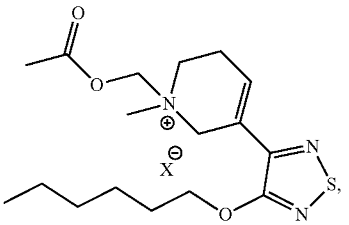

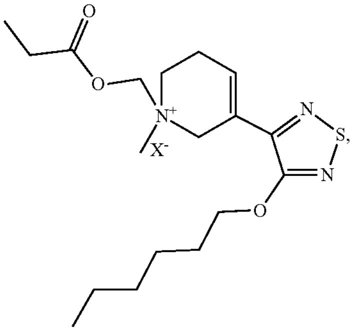

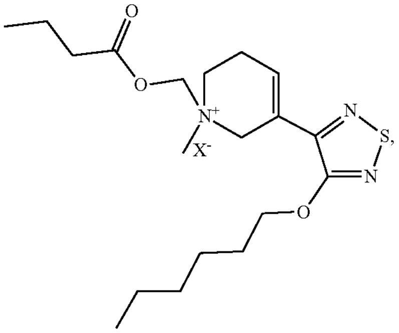

-continued

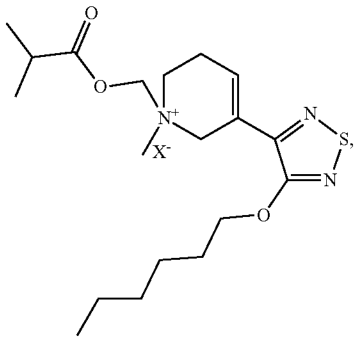

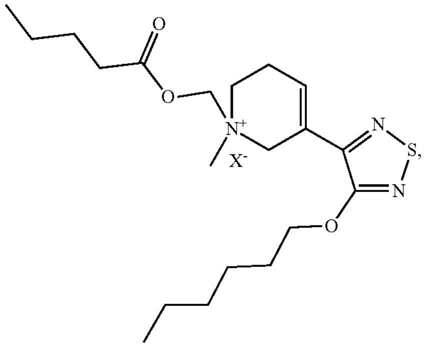

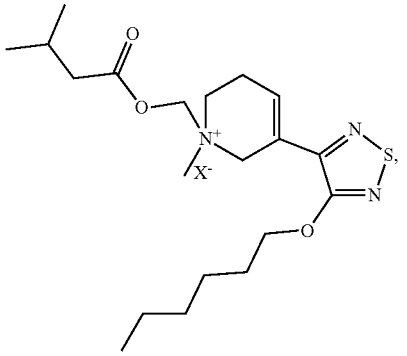

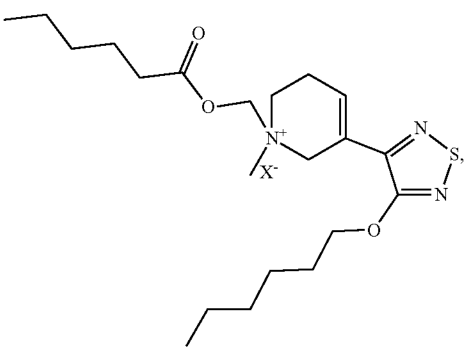

-continued

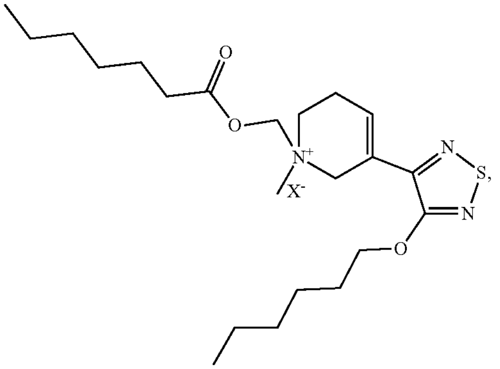

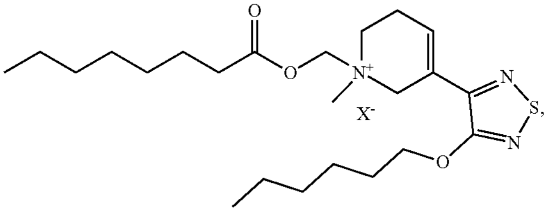

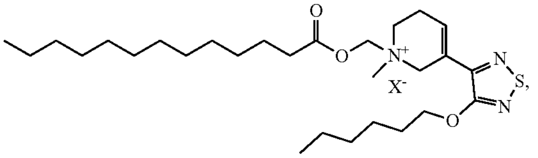

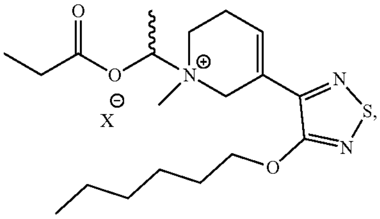

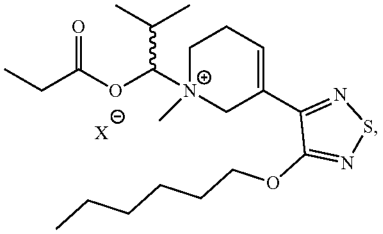

or

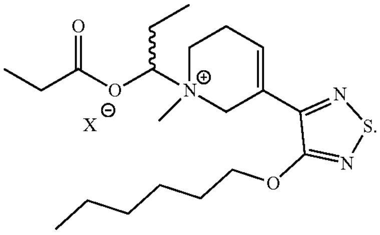

24. A pharmaceutical composition comprising the compound of claim 23 and a pharmaceutically acceptable excipient.

25. A method for treating a neuropsychiatric disease in a subject in need thereof, comprising administering an effective amount of the compound of claim 23 to the subject.

26. The compound of claim 1, wherein $R^5$ is $C_1$-$C_5$ alkyl.

27. The compound of claim 26, wherein $R^1$ is H and $R^2$ is H.

28. The compound of claim 23, wherein the compound is

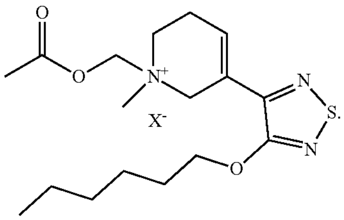

29. The compound of claim 28, wherein the compound is

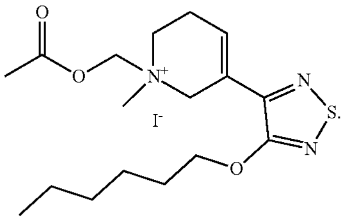 [SMILES: CCCCCCOc1nsnc1C1=CCC[N+](C)(COC(C)=O)C1 ; [I-]]

30. A pharmaceutical composition comprising the compound of claim 28 and a pharmaceutically acceptable excipient.

31. A method for treating a neuropsychiatric disease in a subject in need thereof, comprising administering an effective amount of the compound of claim 28 to the subject.

32. A method for treating a neuropsychiatric disease in a subject in need thereof, comprising administering an effective amount of the pharmaceutical composition of claim 30 to the subject.

33. The compound of claim 23, wherein the compound is

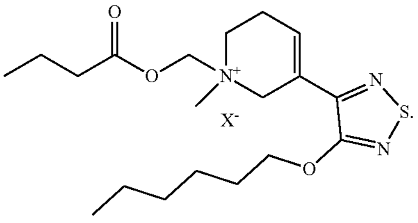

34. The compound of claim 33, wherein the compound is

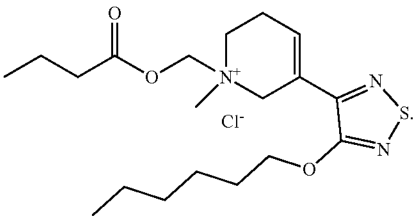 [SMILES: CCCCCCOc1nsnc1C1=CCC[N+](C)(COC(=O)CCC)C1 ; [Cl-]]

35. A pharmaceutical composition comprising the compound of claim 33 and a pharmaceutically acceptable excipient.

36. A method for treating a neuropsychiatric disease in a subject in need thereof, comprising administering an effective amount of the compound of claim 33 to the subject.

37. A method for treating a neuropsychiatric disease in a subject in need thereof, comprising administering an effective amount of the pharmaceutical composition of claim 35 to the subject.

38. The compound of claim 23, wherein the compound is

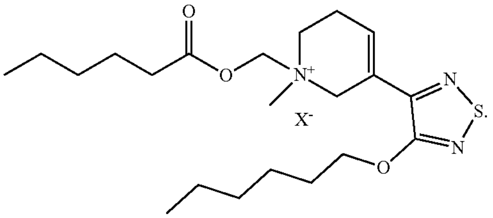

39. The compound of claim 38, wherein the compound is

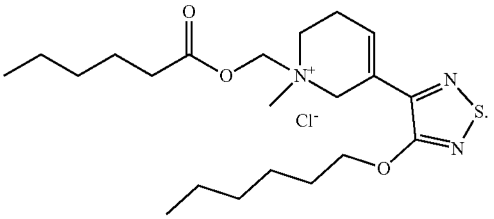

40. A pharmaceutical composition comprising the compound of claim 38 and a pharmaceutically acceptable excipient.

41. A method for treating a neuropsychiatric disease in a subject in need thereof, comprising administering an effective amount of the compound of claim 38 to the subject.

42. A method for treating a neuropsychiatric disease in a subject in need thereof, comprising administering an effective amount of the pharmaceutical composition of claim 40 to the subject.

* * * * *

UNITED STATES PATENT AND TRADEMARK OFFICE

CERTIFICATE OF CORRECTION

PATENT NO. : 12,269,818 B2
APPLICATION NO. : 18/444450
DATED : April 8, 2025
INVENTOR(S) : Samuel Clark et al.

It is certified that error appears in the above-identified patent and that said Letters Patent is hereby corrected as shown below:

In the Claims

At Column 870, Claim number 8, Line number 46:
"the compound"
Should read:
– the compound is –

Signed and Sealed this
Nineteenth Day of August, 2025

Coke Morgan Stewart
*Acting Director of the United States Patent and Trademark Office*